(12) United States Patent
Klar et al.

(10) Patent No.: US 9,255,100 B2
(45) Date of Patent: Feb. 9, 2016

(54) SUBSTITUTED IMIDAZOPYRIDAZINES

(75) Inventors: Ulrich Klar, Berlin (DE); Marcus Koppitz, Berlin (DE); Rolf Jautelat, Haan (DE); Dirk Kosemund, Berlin (DE); Rolf Bohlmann, Berlin (DE); Philip Lienau, Berlin (DE); Gerhard Siemeister, Berlin (DE); Antje Margret Wengner, Berlin (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 0 days.

(21) Appl. No.: 13/822,175

(22) PCT Filed: Sep. 6, 2011

(86) PCT No.: PCT/EP2011/065368
§ 371 (c)(1),
(2), (4) Date: Jun. 11, 2013

(87) PCT Pub. No.: WO2012/032031
PCT Pub. Date: Mar. 15, 2012

(65) Prior Publication Data
US 2013/0338133 A1    Dec. 19, 2013

(30) Foreign Application Priority Data

| Sep. 10, 2010 | (EP) | 10176134 |
| Feb. 4, 2011 | (EP) | 11075022 |
| Jun. 21, 2011 | (EP) | 11170771 |
| Jun. 21, 2011 | (EP) | 11170775 |

(51) Int. Cl.
C07D 487/04 (2006.01)
A61K 31/5025 (2006.01)
A61K 31/506 (2006.01)
A61K 31/5377 (2006.01)
A61K 45/06 (2006.01)
C07D 471/04 (2006.01)

(52) U.S. Cl.
CPC ............ *C07D 487/04* (2013.01); *A61K 31/506* (2013.01); *A61K 31/5025* (2013.01); *A61K 31/5377* (2013.01); *A61K 45/06* (2013.01); *C07D 471/04* (2013.01)

(58) Field of Classification Search
CPC ............... C07D 487/04; C07D 471/04; A61K 31/5025; A61K 31/5377
USPC .......................................... 544/236; 514/248
See application file for complete search history.

(56) References Cited

U.S. PATENT DOCUMENTS

2008/0045536 A1  2/2008  Vaccaro et al.
2012/0059162 A1  3/2012  Kusakabe et al.

FOREIGN PATENT DOCUMENTS

| CA | 2407573 A1 | 8/2001 |
| WO | 9808847 A1 | 3/1998 |
| WO | 0183481 A1 | 8/2001 |
| WO | 2005007658 A2 | 1/2005 |
| WO | 2005080355 A1 | 9/2005 |
| WO | 2005097052 A1 | 10/2005 |
| WO | 2007025090 A2 | 3/2007 |
| WO | 2007038314 A2 | 4/2007 |
| WO | 2009060197 A1 | 5/2009 |
| WO | 2009100375 A1 | 8/2009 |
| WO | 2010042699 A1 | 4/2010 |
| WO | 2010088518 A2 | 8/2010 |
| WO | 2010124826 A1 | 11/2010 |
| WO | 2011013729 A1 | 3/2011 |
| WO | 2011026579 A1 | 3/2011 |
| WO | 2011063907 A1 | 6/2011 |
| WO | 2011063908 A1 | 6/2011 |
| WO | 2011064328 A1 | 6/2011 |
| WO | 2011113862 A1 | 9/2011 |
| WO | 2011151259 A1 | 12/2011 |
| WO | 2012032031 A1 | 3/2012 |
| WO | 2012080228 A1 | 6/2012 |
| WO | 2012080229 A1 | 6/2012 |
| WO | 2012080230 A1 | 6/2012 |
| WO | 2012080232 A1 | 6/2012 |
| WO | 2012080234 A1 | 6/2012 |
| WO | 2012080236 A1 | 6/2012 |

OTHER PUBLICATIONS

Vippagunta et al (2001).*
Dorer et al., "A Small-Molecule Inhibitor of Mps1 Blocks the Spindle-Checkpoint Response to a Lack of Tension on Mitotic Chromosomes," Current Biology, Jun. 7, 2005, 15:1070-1076.
Jelluma et al., "Chromosomal Instability by Inefficient Mps1 Auto-Activation Due to a Weakened Mitotic Checkpoint and Lagging Chromosomes," PLoS ONE, Jun. 2008, e2415, 3:1-6.

(Continued)

*Primary Examiner* — Paul V Ward

(57) ABSTRACT

The present invention relates to substituted imidazopyridazine compounds of general formula (I), which are Mps-1 (Monopolar Spindle 1) Kinase inhibitors (also known as Tyrosine Threonine Kinase, TTK) in which $R^3$, $R^5$, and A are as defined in the claims, to methods of preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

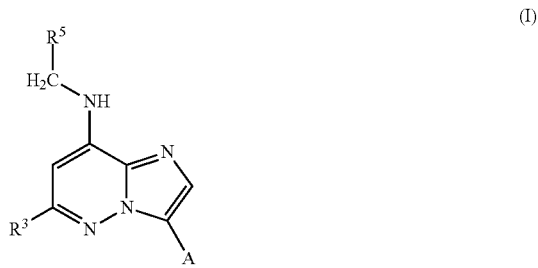

14 Claims, No Drawings

(56) References Cited

OTHER PUBLICATIONS

Jones et al., "Chemical Genetics Reveals a Role for Mps1 Kinase in Kinetochore Attachment during Mitosis," Current Biology, Jan. 26, 2005, 15:160-165.

Kops et al., "On the Road to Cancer: Aneuploidy and the Mitotic Checkpoint," Nature Reviews/Cancer, Oct. 2005, 5:773-785.

Musacchio et al., "The spindle-assembly checkpoint in space and time," Nature Reviews/Molecular Cell Biology, May 2007, 8:379-393.

Schmidt et al., "Exploiting the Compromised Spindle Assembly Checkpoint Function of Tumor Cells," Cell Cycle, Jan. 16, 2006, 5(2):159-163.

Schmidt et al., "Mitotic drug targets and the development of novel anti-mitotic anticancer drugs," Drug Resistance Updates, 2007, 10:162-181.

Schmidt et al., "Ablation of the spindle assembly checkpoint by a compound targeting Mps1," EMBO Reports, Jul. 29, 2005, 6(9):866-872.

Suijkerbuijk et al., "Preventing aneuploidy: The contribution of mitotic checkpoint proteins," Biochimica et Biophysica Acta, 2008, 1786:24-31.

Weaver et al., "Aneuploidy: Instigator and Inhibitor of Tumorigenesis," Cancer Research, Nov. 1, 2007, 67 (21)10103-10105.

Yuan et al., "Increased Expression of Mitotic Checkpoint Genes in Breast Cancer Cells with Chromosomal Instability," Clin. Cancer Res., Jan. 16, 2006, 12(2):405-410.

\* cited by examiner

SUBSTITUTED IMIDAZOPYRIDAZINES

The present invention relates to substituted imidazopyridazine compounds of general formula I as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, TTK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumourigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Established anti-mitotic drugs such as vinca alkaloids, taxanes or epothilones activate the SAC inducing a mitotic arrest either by stabilising or destabilising microtubule dynamics. This arrest prevents separation of sister chromatids to form the two daughter cells. Prolonged arrest in mitosis forces a cell either into mitotic exit without cytokinesis or into mitotic catastrophe leading to cell death.

In contrast, inhibitors of Mps-1 induce a SAC inactivation that accelerates progression of cells through mitosis resulting in severe chromosomal missegregation and finally in cell death.

These findings suggest that Mps-1 inhibitors should be of therapeutic value for the treatment of proliferative disorders associated with enhanced uncontrolled proliferative cellular processes such as, for example, cancer, inflammation, arthritis, viral diseases, neurodegenerative diseases such as Alzheimer's disease, cardiovascular diseases, or fungal diseases in a warm-blooded animal such as man. Therefore, inhibitors of Mps-1 represent valuable compounds that should complement therapeutic options either as single agents or in combination with other drugs.

Different compounds have been disclosed in prior art which show an inhibitory effect on Mps-1 kinase. WO2010/124826A1 discloses substituted imidazoquinoxaline compounds as inhibitors of Mps-1 kinase or TTK. WO2011/026579A1 discloses substituted aminoquinoxalines as Mps-1 inhibitors. WO2011/063908A1, WO2011/064328A1 as well as WO2011/063907A1 disclose triazolopyridine derivates as inhibitors of Mps-1 kinase.

Imidazopyridazine derivates have been disclosed for the treatment or prophylaxis of different diseases:

WO 2007/038314 A2 (Bristol-Myers Squibb Company) relates to fused heterocyclic compounds useful as kinase modulators, including MK2 modulation. In particular, WO 2007/038314 A2 relates to imidazo[1,2-b]pyridazines.

US patent application publication US 2008/0045536 A1 (Bristol-Myers Squibb Company) similarly relates to fused heterocyclic compounds useful as kinase modulators, including MK2 modulation. In particular, it relates to imidazo[1,2-b]pyridazines.

WO 2010/042699 A1 (Bristol-Myers Squibb Company) relates to fused heterocyclic compounds useful as kinase modulators, particularly CK2 modulation. In particular, WO 2010/042699 A1 relates to imidazo[1,2-b]pyridazines which are substituted with a nitrite group in position 3.

WO 2007/025090 A2 (Kalypsis, Inc.) relates to heterocyclic compounds useful as inhibitors of MEK kinase. In particular, WO 2007/025090 A2 relates inter alia to imidazo[1,2-b]pyridazines.

WO 1998/08847 A1 (Pfizer, Inc.) relates to heterocyclic compounds useful as corticotropin releasing factor (hormone) CRF (CRH) antagonists. In particular, WO 1998/08847 A1 relates inter alia to imidazo[1,2-b]pyridazines.

WO 20111013729A1 discloses fused imidazole derivatives as Mps-1 inhibitors. Among the disclosed fused imidazole derivates there are also imidazo[1,2-b]pyridazines. For example, WO 2011/013729A1 discloses compounds of formula C1:

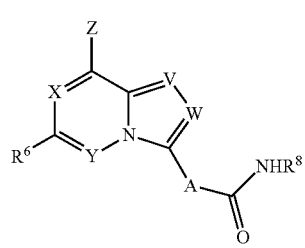

C1 in which (X, Y, V, W) is (—N═, ═CR$^1$—, ═N—, —CR$^7$═), (—CR$^2$═, ═N—, ═N—, —CR$^7$═), (—N═, αCR$^1$—, ═N—, —N═) or (—N═, ═CR$^1$—, —O—, —N═);

R$^8$ is substituted or unsubstituted cycloalkyl;

Z is a group represented by formula —NR$^3$R$^4$ or a group represented by formula —OR$^5$;

A is substituted or unsibstituted aromatic hydrocarbon ring, substituted or unsibstituted aromatic heterocyclic ring, substituted or unsibstituted non-aromatic hydrocarbon ring or substituted or unsibstituted non-aromatic heterocyclic ring;

$R^1$, $R^3$, $R^4$, $R^5$, and $R^6$ represent a large variety of substituents (see WO 2011/013729A1, e.g. claim 1).

The inventors of the present invention surprisingly observed that compounds of general formula I as described and defined herein show a high activity in Mps-1 inhibition and show a high metabolic stability.

The state of the art described above does not describe the imidazopyridazine compounds of claims 1 to 8, or a stereoisomer, a tautomer, an N-oxide, a hydrate, a solvate, or a salt thereof, or a mixture of same, as described and defined herein, and as hereinafter referred to as "compounds of the present invention", or their pharmacological activity and stability. It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula I:

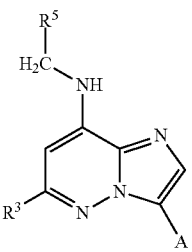

I in which:
A represents a

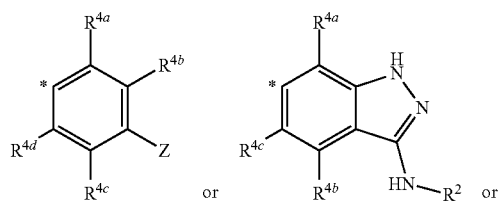

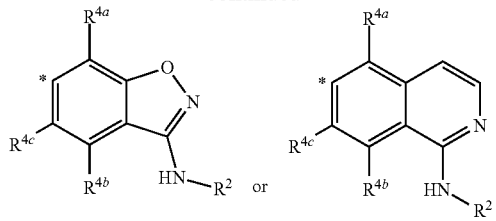

-group;
wherein * indicates the point of attachment of said groups with the rest of the molecule;

Z represents a —C(=O)N(H)$R^2$ or —C(=S)N(H)$R^2$ group, or a group selected from

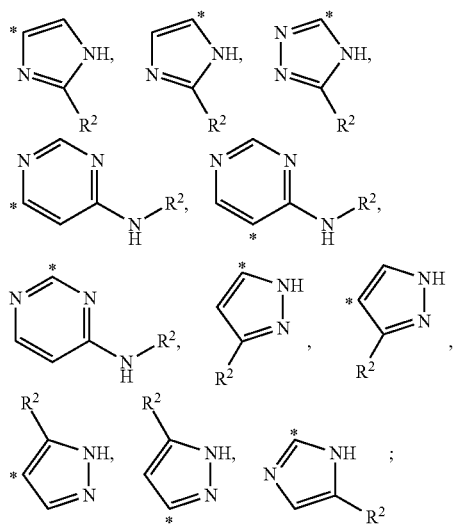

wherein * indicates the point of attachment of said groups with the rest of the molecule;

$R^2$ represents a hydrogen atom, or a $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;
wherein said $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-, halo-$C_1$-$C_6$-alkyl-;

$R^3$ represents a hydrogen atom or a halogen atom, or a —CN, $C_1$-$C_6$-alkyl-, $C_1$-$C_6$-alkoxy-, —(CH$_2$)$_m$—$C_2$-$C_6$-alkenyl, —(CH$_2$)$_m$—$C_4$-$C_8$-cycloalkenyl, —(CH$_2$)$_m$—$C_2$-$C_6$-alkynyl, —(CH$_2$)$_m$—$C_3$-$C_6$-cycloalkyl, —(CH$_2$)$_m$-(3- to 7-membered heterocycloalkyl), —(CH$_2$)$_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, $C_1$-$C_6$-alkyl-X—, —X—(CH$_2$)$_m$—$C_2$-$C_6$-alkenyl, —X—(CH$_2$)$_m$—$C_4$-$C_8$-cycloalkenyl, —X—(CH$_2$)$_m$—$C_2$-$C_6$-alkynyl, —X—(CH$_2$)$_m$—$C_3$-$C_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(═O)R$^6$, —C(═O)N(H)R$^{6a}$, —C(═O)N(R$^{6a}$)R$^{6b}$, —C(═O)O—R$^6$, —N(R$^{6a}$)R$^{6b}$, —NO$_2$, —N(H)C(═O)R$^6$, —OR$^6$, —SR$^6$, —S(═O)R$^6$, —S(═O)$_2$R$^6$, —S(═O)(═NR$^{6a}$)R$^{6b}$, —S(═O)$_2$N(R$^{6b}$)R$^{6c}$, —S—(CH$_2$)$_n$—N(R$^{6a}$)R$^{6b}$ or —S—(CH$_2$)$_n$-(3- to 7-membered heterocycloalkyl) group;

wherein said C$_1$-C$_6$-alkyl-, C$_1$-C$_6$-alkoxy-, —(CH$_2$)$_m$—C$_2$-C$_6$-alkenyl, —(CH$_2$)$_m$—C$_2$-C$_6$-alkynyl, —(CH$_2$)$_m$—C$_3$-C$_6$-cycloalkyl, aryl-C$_1$-C$_6$-alkyl-, heteroaryl-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl or heteroaryl-group is optionally substituted, identically or differently, with 1, 2, 3, 4 or 5 R$^7$ groups;

R$^{4a}$, R$^{4b}$, R$^{4c}$, R$^{4d}$ represent, independently from each other, a hydrogen or halogen atom, or a —CN, C$_1$-C$_6$-alkyl-, C$_1$-C$_6$-alkoxy-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, —C(═O)R$^6$, —C(═O)N(H)R$^{6a}$, —C(═O)N(R$^{6a}$)R$^{6b}$, —C(═O)O—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —S(═O)R$^6$, —S(═O)N(H)R$^6$, —S(═O)N(R$^{6a}$)R$^{6b}$, —S(═O)$_2$R$^6$, —S(═O)$_2$N(H)R$^{6a}$, —S(═O)$_2$N(R$^{6a}$)R$^{6b}$, —S(═O)(═NR$^{6c}$)R$^6$ group;

R$^5$ represents a hydrogen atom, or a C$_1$-C$_6$-alkyl-, —(CH$_2$)$_n$—C$_2$-C$_6$-alkenyl, —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl- or heteroaryl-group;

wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group is optionally substituted, identically or differently, with 1, 2, 3 or 4 R$^8$ groups;

R$^6$, R$^{6a}$, R$^{6b}$, R$^{6c}$ represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl- or heteroaryl-C$_1$-C$_6$-alkyl-group;

R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl-, aryl-, heteroaryl-, —C(═O)R$^6$, —C(═O)N(H)R$^{6a}$, —C(═O)N(R$^{6a}$)R$^{6b}$, —C(═O)O—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —S(═O)R$^6$, —S(═O)N(H)R$^6$, —S(═O)N(R$^{6a}$)R$^{6b}$, —S(═O)$_2$R$^6$, —S(═O)$_2$N(H)R$^6$, —S(═O)$_2$N(R$^{6a}$)R$^{6b}$ or —S(═O)(═NR$^{6c}$)R$^6$ group;

wherein said C$_1$-C$_6$-alkoxy-, aryl- or heteroaryl-group is optionally substituted, identically or differently, with 1, 2 or 3 C$_1$-C$_6$-alkyl-, C$_1$-C$_6$-alkoxy-, halo-C$_1$-C$_6$-alkoxy-, —C(═O)O—R$^6$ or —OH groups; or when 2 R$^7$ groups are present ortho to each other on an aryl- or heteroaryl-ring, said 2 R$^7$ groups together form a bridge:

*O(CH$_2$)$_2$O*, *O(CH$_2$)O*, *NH(C(═O))NH*, wherein * represent the point of attachment to said aryl- or heteroaryl-ring;

R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, 3- to 7-membered heterocycloalkyl-, aryl-, heteroaryl-, —C(═O)R$^6$, —C(═O)N(H)R$^{6a}$, —C(═O)N(R$^{6a}$)R$^{6b}$, —C(═O)O—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —S(═O)R$^6$, —S(═O)N(H)R$^6$, —S(═O)N(R$^{6a}$)R$^{6b}$, —S(═O)$_2$R$^6$, —S(═O)$_2$N(H)R$^6$, —S(═O)$_2$N(R$^{6a}$)R$^{6b}$, —S(═O)(═NR$^{6c}$)R$^6$ or —S(═O)$_2$-(3- to 7-membered heterocycloalkyl) group;

wherein said 3- to 7-membered heterocycloalkyl- or heteroaryl-group is optionally substituted, identically or differently, with 1, 2, 3 or 4 C$_1$-C$_6$-alkyl-groups;

m is an integer of 0, 1, 2, 3, 4, 5 or 6;

n is an integer of 0, 1, 2, 3, 4 or 5;

X represents S(═O)$_p$, O, NR$^6$, CR$^{6a}$R$^{6b}$ or C═CR$^{6a}$R$^{6b}$;

p is an integer of 0, 1 or 2;

or a stereoisomer, a tautomer, an N-oxide, a hydrate, a solvate, or a salt thereof, or a mixture of same.

The present invention also relates to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom, preferably a fluorine, chlorine, bromine or iodine atom.

The term "C$_1$-C$_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O—$C_1$-$C_6$-alkyl, in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is/are replaced, in identically or differently, by one or more halogen atoms. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is/are replaced, in identically or differently, by one or more halogen atoms. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "$C_3$-$C_6$-cycloalkyl" is to be understood as meaning a saturated, monovalent, mono-, or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl, or cyclohexyl or a bicyclic hydrocarbon ring.

The term "$C_4$-$C_8$-cycloalkenyl" is to be understood as preferably meaning a monovalent, mono-, or bicyclic hydrocarbon ring which contains 4, 5, 6, 7 or 8 carbon atoms and one, two, three or four double bonds, in conjugation or not, as the size of said cycloalkenyl ring allows. Said $C_4$-$C_8$-cycloalkenyl group is for example, a monocyclic hydrocarbon ring, e.g. a cyclobutenyl, cyclopentenyl, or cyclohexenyl or a bicyclic hydrocarbon ring, e.g. a cylooctadienyl ring.

The term "3- to 7-membered heterocycloalkyl", is to be understood as meaning a saturated, monovalent, mono- or bicyclic hydrocarbon ring which contains 2, 3, 4, 5, or 6 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl-group; it being possible for said heterocycloalkyl group to be attached to the rest of the molecule via any one of the carbon atoms or, if present, the nitrogen atom.

Particularly, said 3- to 7-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl) ring, or a 5,6-membered bicyclic ring, e.g. a hexahydropyrrolo[1,2-a]pyrazin-2(1H)-yl ring, or for example.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "4- to 8-membered heterocycloalkenyl", is to be understood as meaning an unsaturated, monovalent, mono- or bicyclic hydrocarbon ring which contains 4, 5, 6, 7 or 8 carbon atoms, and one or more heteroatom containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group, or, it may be benzo fused.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

In accordance with a first aspect, the present invention is directed to compounds of general formula I:

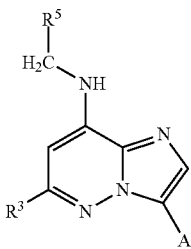

in which:
A represents a

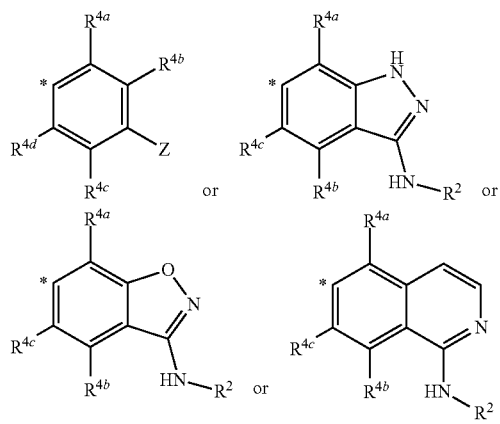

-group;
wherein * indicates the point of attachment of said groups with the rest of the molecule;

Z represents a —C(=O)N(H)R$^2$ or —C(=S)N(H)R$^2$ group, or a group selected from

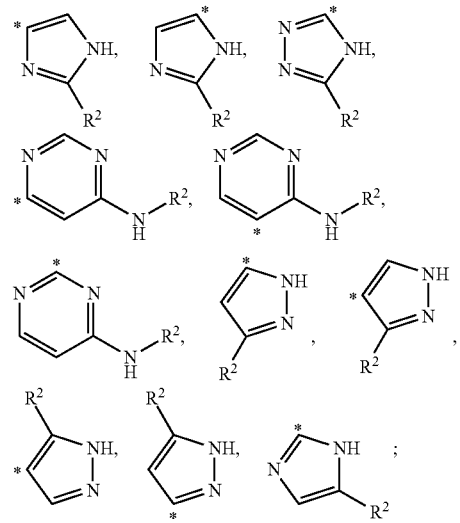

wherein * indicates the point of attachment of said groups with the rest of the molecule;

R$^2$ represents a hydrogen atom, or a C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl- or C$_3$-C$_6$-cycloalkyl-group;
wherein said C$_3$-C$_6$-cycloalkyl-group is optionally substituted, identically or differently, with 1, 2, 3 or 4 groups selected from: halogen, —OH, —CN, C$_1$-C$_6$-alkyl-, C$_1$-C$_6$-alkoxy-, halo-C$_1$-C$_6$-alkyl-;

R$^3$ represents a hydrogen atom or a halogen atom, or a —CN, C$_1$-C$_6$-alkyl-, C$_1$-C$_6$-alkoxy-, —(CH$_2$)$_m$—C$_2$-C$_6$-alkenyl, —(CH$_2$)$_m$—C$_4$-C$_8$-cycloalkenyl, —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, —C$_1$-C$_6$-alkyl-aryl, —C$_1$-C$_6$-alkyl-heteroaryl, heteroaryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —OR$^6$, —SR$^6$, —S(=O)R$^6$, —S(=O)$_2$R$^6$, —S(=O)(=NR$^{6a}$)R$^{6b}$, —S(=O)$_2$N(R$^{6b}$)R$^{6c}$, —S—(CH$_2$)$_m$—N(R$^{6a}$)R$^{6b}$ or —S—(CH$_2$)$_m$-(3- to 7-membered heterocycloalkyl) group;
wherein said C$_1$-C$_6$-alkyl-, C$_1$-C$_6$-alkoxy-, —(CH$_2$)$_m$—C$_2$-C$_6$-alkenyl, —(CH$_2$)$_m$—C$_2$-C$_6$-alkynyl, —(CH$_2$)$_m$—C$_3$-C$_6$-cycloalkyl, aryl-C$_1$-C$_6$-alkyl-, heteroaryl-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X—(CH$_2$)$_m$—C$_4$-

$C_8$-cycloalkenyl, $-X-(CH_2)_m-C_2-C_6$-alkynyl, $-X-(CH_2)_m-C_3-C_6$-cycloalkyl, $-X-(CH_2)_m$-(3- to 7-membered heterocycloalkyl), $-X-(CH_2)_m$-(4- to 8-membered heterocycloalkenyl), aryl-X—, heteroaryl-X—, $-C_1-C_6$-alkyl-aryl, $-C_1-C_6$-alkyl-heteroaryl or heteroaryl-group is optionally substituted, identically or differently, with 1, 2, 3, 4 or 5 $R^7$ groups;

$R^{4a}$, $R^{4b}$, $R^{4c}$, $R^{4d}$
represent, independently from each other, a hydrogen or halogen atom, or a $-CN$, $C_1-C_6$-alkyl-, $C_1-C_6$-alkoxy-, halo-$C_1-C_6$-alkyl-, $R^{6a}(R^{6b})N-C_1-C_6$-alkyl-, $HO-C_1-C_6$-alkyl-, $C_1-C_6$-alkoxy-$C_1-C_6$-alkyl-, halo-$C_1-C_6$-alkoxy-$C_1-C_6$-alkyl-, $-C(=O)R^6$, $-C(=O)N(H)R^{6a}$, $-C(=O)N(R^{6a})R^{6b}$, $-C(=O)O-R^6$, $-N(R^{6a})R^{6b}$, $-NO_2$, $-N(H)C(=O)R^6$, $-N(R^{6c})C(=O)R^6$, $-N(H)C(=O)N(R^{6a})R^{6b}$, $-N(R^{6c})C(=O)N(R^{6a})R^{6b}$, $-N(H)C(=O)OR^6$, $-N(R^{6c})C(=O)OR^6$, $-N(H)S(=O)R^6$, $-N(R^{6c})S(=O)R^6$, $-N(H)S(=O)_2R^6$, $-N(R^{6c})S(=O)_2R^6$, $-N=S(=O)(R^{6a})R^{6b}$, $-OR^6$, $-O(C=O)R^6$, $-O(C=O)N(R^{6a})R^{6b}$, $-O(C=O)OR^6$, $-SR^6$, $-S(=O)R^6$, $-S(=O)N(H)R^6$, $-S(=O)N(R^{6a})R^{6b}$, $-S(=O)_2R^6$, $-S(=O)_2N(H)R^{6a}$, $-S(=O)_2N(R^{6a})R^{6b}$, $-S(=O)(=NR^{6c})R^6$ group;

$R^5$ represents a hydrogen atom, or a $C_1-C_6$-alkyl-, $-(CH_2)_n-C_2-C_6$-alkenyl, $-(CH_2)_n-C_2-C_6$-alkynyl, $-(CH_2)_m-C_3-C_6$-cycloalkyl, $-(CH_2)_m$-(3- to 7-membered heterocycloalkyl), aryl-$C_1-C_6$-alkyl-, heteroaryl-$C_1-C_6$-alkyl-, halo-$C_1-C_6$-alkyl-, $R^{6a}(R^{6b})N-C_1-C_6$-alkyl-, $HO-C_1-C_6$-alkyl-, $-C_1-C_6$-alkyl-CN, $C_1-C_6$-alkoxy-$C_1-C_6$-alkyl-, halo-$C_1-C_6$-alkoxy-$C_1-C_6$-alkyl-, $C_3-C_6$-cycloalkyl-, 3- to 7-membered heterocycloalkyl-, $C_2-C_6$-alkenyl-, $C_4-C_8$-cycloalkenyl-, $C_2-C_6$-alkynyl-, aryl- or heteroaryl-group;
wherein said $C_1-C_6$-alkyl-, $-(CH_2)_n-C_2-C_6$-alkenyl, $-(CH_2)_n-C_2-C_6$-alkynyl, $-(CH_2)_m-C_3-C_6$-cycloalkyl, $-(CH_2)_m$-(3- to 7-membered heterocycloalkyl), aryl-$C_1-C_6$-alkyl-, heteroaryl-$C_1-C_6$-alkyl-, halo-$C_1-C_6$-alkyl-, $R^{6a}(R^{6b})N-C_1-C_6$-alkyl-, $HO-C_1-C_6$-alkyl-, $-C_1-C_6$-alkyl-CN, $C_1-C_6$-alkoxy-$C_1-C_6$-alkyl-, halo-$C_1-C_6$-alkoxy-$C_1-C_6$-alkyl-, $C_3-C_6$-cycloalkyl-, 3- to 7-membered heterocycloalkyl-, $C_4-C_8$-cycloalkenyl-, aryl- or heteroaryl-group is optionally substituted, identically or differently, with 1, 2, 3 or 4 $R^8$ groups;

$R^6$, $R^{6a}$, $R^{6b}$, $R^{6c}$
represent, independently from each other, a hydrogen atom, or a $C_1-C_6$-alkyl-, $HO-C_1-C_6$-alkyl-, $C_3-C_6$-cycloalkyl-, $C_2-C_6$-alkenyl-, 3- to 7-membered heterocycloalkyl-, aryl-, heteroaryl-, aryl-$C_1-C_6$-alkyl- or heteroaryl-$C_1-C_6$-alkyl-group;

$R^7$ represents a hydrogen or halogen atom, or a $HO-$, $-CN$, $C_1-C_6$-alkoxy-, $C_1-C_6$-alkyl-, halo-$C_1-C_6$-alkyl-, $R^{6a}(R^{6b})N-C_1-C_6$-alkyl-, $HO-C_1-C_6$-alkyl-, $C_1-C_6$-alkoxy-$C_1-C_6$-alkyl-, halo-$C_1-C_6$-alkoxy-$C_1-C_6$-alkyl-, $C_2-C_6$-alkenyl, 3- to 7-membered heterocycloalkyl-, aryl-, heteroaryl-, $-C(=O)R^6$, $-C(=O)N(H)R^{6a}$, $-C(=O)N(R^{6a})R^{6b}$, $-C(=O)O-R^6$, $-N(R^{6a})R^{6b}$, $-NO_2$, $-N(H)C(=O)R^6$, $-N(R^{6c})C(=O)R^6$, $-N(H)C(=O)N(R^{6a})R^{6b}$, $-N(R^{6c})C(=O)N(R^{6a})R^{6b}$, $-N(H)C(=O)OR^6$, $-N(R^{6c})C(=O)OR^6$, $-N(H)S(=O)R^6$, $-N(R^{6c})S(=O)R^6$, $-N(H)S(=O)_2R^6$, $-N(R^{6c})S(=O)_2R^6$, $-N=S(=O)(R^{6a})R^{6b}$, $-OR^6$, $-O(C=O)R^6$, $-O(C=O)OR^6$, $-SR^6$, $-O(C=O)N(R^{6a})R^{6b}$, $-S(=O)R^6$, $-S(=O)N(H)R^6$, $-S(=O)N(R^{6a})R^{6b}$, $-S(=O)_2R^6$, $-S(=O)_2N(H)R^6$, $-S(=O)_2N(R^{6a})R^{6b}$ or $-S(=O)(=NR^{6c})R^6$ group;

wherein said $C_1-C_6$-alkoxy-, aryl- or heteroaryl-group is optionally substituted, identically or differently, with 1, 2 or 3 $C_1-C_6$-alkyl-, $C_1-C_6$-alkoxy-, halo-$C_1-C_6$-alkoxy-, $-C(=O)O-R^6$ or $-OH$ groups; or
when 2 $R^7$ groups are present ortho to each other on an aryl- or heteroaryl-ring, said 2 $R^7$ groups together form a bridge:
*$O(CH_2)_2O$*, *$O(CH_2)O$*, *$NH(C(=O))NH$*, wherein * represent the point of attachment to said aryl- or heteroaryl-ring;

$R^8$ represents a hydrogen or halogen atom, or a $-CN$, $C_1-C_6$-alkoxy-, $C_1-C_6$-alkyl-, halo-$C_1-C_6$-alkyl-, $R^{6a}(R^{6b})N-C_1-C_6$-alkyl-, $HO-C_1-C_6$-alkyl-, $C_1-C_6$-alkoxy-$C_1-C_6$-alkyl-, halo-$C_1-C_6$-alkoxy-$C_1-C_6$-alkyl-, $C_2-C_6$-alkenyl-, 3- to 7-membered heterocycloalkyl-, aryl-, heteroaryl-, $-C(=O)R^6$, $-C(=O)N(H)R^{6a}$, $-C(=O)N(R^{6a})R^{6b}$, $-C(=O)O-R^6$, $-N(R^{6a})R^{6b}$, $-NO_2$, $-N(H)C(=O)R^6$, $-N(R^{6c})C(=O)R^6$, $-N(H)C(=O)N(R^{6a})R^{6b}$, $-N(R^{6c})C(=O)N(R^{6a})R^{6b}$, $-N(H)C(=O)OR^6$, $-N(R^{6c})C(=O)OR^6$, $-N(H)S(=O)R^6$, $-N(R^{6c})S(=O)R^6$, $-N(H)S(=O)_2R^6$, $-N(R^{6c})S(=O)_2R^6$, $-N=S(=O)(R^{6a})R^{6b}$, $-OR^6$, $-O(C=O)R^6$, $-O(C=O)N(R^{6a})R^{6b}$, $-O(C=O)OR^6$, $-SR^6$, $-S(=O)R^6$, $-S(=O)N(H)R^6$, $-S(=O)N(R^{6a})R^{6b}$, $-S(=O)_2R^6$, $-S(=O)_2N(H)R^6$, $-S(=O)_2N(R^{6a})R^{6b}$, $-S(=O)(=NR^{6c})R^6$ or $-S(=O)_2$-(3- to 7-membered heterocycloalkyl) group;
wherein said 3- to 7-membered heterocycloalkyl- or heteroaryl-group is optionally substituted, identically or differently, with 1, 2, 3 or 4 $C_1-C_6$-alkyl-groups;

m is an integer of 0, 1, 2, 3, 4, 5 or 6;
n is an integer of 0, 1, 2, 3, 4 or 5;
X represents $S(=O)_p$, O, $NR^6$, $CR^{6a}R^{6b}$ or $C=CR^{6a}R^{6b}$; and
p is an integer of 0, 1 or 2.

As defined supra, A represents a

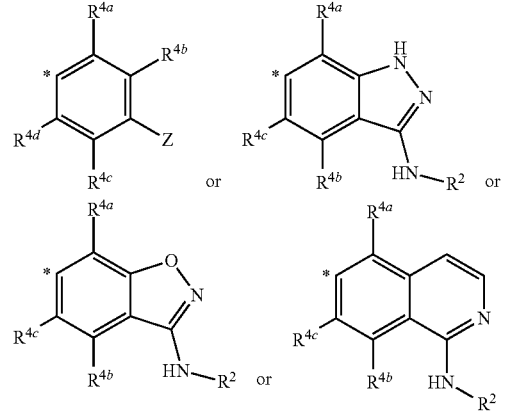

-group;
wherein * indicates the point of attachment of said groups with the rest of the molecule.

In a preferred embodiment A represents a

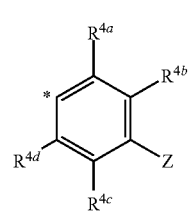

-group.

In another preferred embodiment A represents a

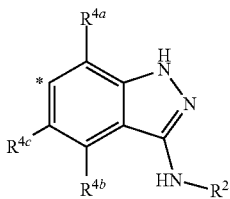

-group.

In another preferred embodiment, the invention relates to compounds of formula I, supra, wherein A is selected from the group consisting of:

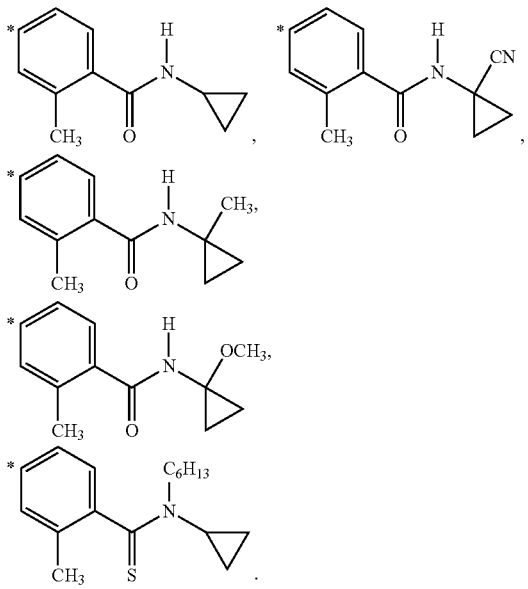

As defined supra, $R^2$ represents a hydrogen atom, or a $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;
wherein said $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-, halo-$C_1$-$C_6$-alkyl-.

In a preferred embodiment, the invention relates to compounds of formula I, wherein:
$R^2$ represents a $C_3$-$C_6$-cycloalkyl-group;
wherein said $C_3$-$C_6$-cycloalkyl-group is optionally substituted, identically or differently, with 1, 2, 3 or 4 groups selected from: halogen, —OH, —CN, $C_1$-$C_6$-alkyl-, $C_1$-$C_6$-alkoxy-, halo-$C_1$-$C_6$-alkyl-.

In another preferred embodiment, the invention relates to compounds of formula I, wherein:
$R^2$ represents a $C_3$-$C_6$-cycloalkyl-group;
wherein said $C_3$-$C_6$-cycloalkyl-group is optionally substituted, identically or differently, with 1, 2, or 3 groups selected from:
halogen, —OH, —CN, —$C_1$-$C_6$-alkyl, —$C_1$-$C_6$-alkoxy.
Preferably, the $C_3$-$C_6$-cycloalkyl-group is a cyclopropyl-group.

In another preferred embodiment, the invention relates to compounds of formula I, wherein:
$R^2$ represents a $C_3$-$C_6$-cycloalkyl-group;
wherein said $C_3$-$C_6$-cycloalkyl-group is optionally substituted, identically or differently, with 1 or 2 groups selected from:
—CN, —$C_1$-$C_3$-alkyl, —$C_1$-$C_3$-alkoxy.
Preferably, the $C_3$-$C_6$-cycloalkyl-group is a cyclopropyl-group.

In another preferred embodiment, the invention relates to compounds of formula I, wherein:
$R^2$ represents a cyclopropyl-group;
wherein said cyclopropyl-group is optionally substituted, identically or differently, with 1, 2, 3, or 4 groups selected from:
halogen, —OH, —CN, —$C_1$-$C_6$-alkyl, —$C_1$-$C_6$-alkoxy.

In another preferred embodiment, the invention relates to compounds of formula I, wherein:
$R^2$ represents a cyclopropyl-group;
wherein said cyclopropyl-group is optionally substituted, identically or differently, with 1 or 2 groups selected from:
halogen, —OH, —CN, —$C_1$-$C_6$-alkyl, —$C_1$-$C_6$-alkoxy.

In another preferred embodiment, the invention relates to compounds of formula I, wherein:
$R^2$ represents a cyclopropyl-group;
wherein said cyclopropyl-group is substituted, identically or differently, with 1 or 2 groups selected from:
halogen, —CN, —$C_1$-$C_3$-alkyl, —$C_1$-$C_3$-alkoxy.

In another preferred embodiment, the invention relates to compounds of formula I, wherein:
$R^2$ represents a halo-$C_1$-$C_6$-alkyl-group.

In another preferred embodiment, the invention relates to compounds of formula I, wherein:
$R^2$ represents a $C_1$-$C_6$-alkyl-group;
wherein said $C_1$-$C_6$-alkyl-group is optionally substituted, identically or differently, with 1, 2, 3 or 4 groups selected from:
halogen, —OH, —CN, $C_1$-$C_6$-alkoxy-.

In another preferred embodiment, the invention relates to compounds of formula I, wherein:
$R^2$ represents a $C_1$-$C_4$-alkyl-group;
wherein said $C_1$-$C_4$-alkyl-group is optionally substituted, identically or differently, with 1, 2 or 3 groups selected from:
halogen, —OH, —CN, —$C_1$-$C_4$-alkoxy.

In another preferred embodiment, the invention relates to compounds of formula I, wherein:
$R^2$ represents a methyl- or ethyl-group;
wherein said methyl- or ethyl-group is optionally substituted, identically or differently, with 1, 2 or 3 groups selected from:
halogen, —OH, —CN.

In another preferred embodiment, the invention relates to compounds of formula I, wherein:
$R^2$ represents $CH_3$ or $C_2H_5$.

In another preferred embodiment, the invention relates to compounds of formula I, wherein:
$R^2$ represents a $C_1$-$C_3$-alkyl-group;
wherein said $C_1$-$C_3$-alkyl-group is optionally substituted, identically or differently, with 1, 2 or 3 groups selected from:
halogen, —OH, —CN, —$C_1$-$C_3$-alkoxy.

The invention relates to compounds of formula I, wherein:
$R^3$ represents a hydrogen atom or a halogen atom, or a —CN, $C_1$-$C_6$-alkyl-, $C_1$-$C_6$-alkoxy-, —$(CH_2)_m$—$C_2$-$C_6$-alkenyl, —$(CH_2)_m$—$C_4$-$C_8$-cycloalkenyl, —$(CH_2)_m$—$C_2$-$C_6$- alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_3$-cycloalkenyl-, C$_2$-C$_6$-alkynyl-, aryl-, —C$_1$-C$_6$-alkyl-aryl, —C$_1$-C$_6$-alkyl-heteroaryl, heteroaryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —OR$^6$, —SR$^6$, —S(=O)R$^6$, —S(=O)$_2$R$^6$, —S(=O)(=NR$^{6a}$)R$^{6b}$, —S(=O)$_2$N(R$^{6b}$)R$^{6c}$, —S—(CH$_2$)$_n$—N(R$^{6a}$)R$^{6b}$ or —S—(CH$_2$)$_n$-(3- to 7-membered heterocycloalkyl) group;

wherein said C$_1$-C$_6$-alkyl-, C$_1$-C$_6$-alkoxy-, —(CH$_2$)$_m$, —C$_2$-C$_6$-alkenyl, —(CH$_2$)$_m$, —C$_2$-C$_6$-alkynyl, —(CH$_2$)$_m$, —C$_3$-C$_6$-cycloalkyl, aryl-C$_1$-C$_6$-alkyl-, heteroaryl-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X—(CH$_2$)$_m$, —C$_4$-C$_8$-cycloalkenyl, —X—(CH$_2$)$_m$, —C$_2$-C$_6$-alkynyl, —X—(CH$_2$)$_m$, —C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl or heteroaryl-group is optionally substituted, identically or differently, with 1, 2, 3, 4 or 5 R$^7$ groups.

In a preferred embodiment, the invention relates to compounds of formula I, supra, wherein:

R$^3$ represents a

C$_1$-C$_6$-alkyl-X—, —X—(CH$_2$)$_m$—C$_2$-C$_6$-alkenyl, —X—(CH$_2$)$_n$, —C$_4$-C$_8$-cycloalkenyl, —X—(CH$_2$)$_n$, —C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-, heteroaryl-, aryl-X— or heteroaryl-X— group;

wherein said C$_1$-C$_6$-alkyl-X—, —X—(CH$_2$)$_m$, —C$_2$-C$_6$-alkenyl, —X—(CH$_2$)$_m$, —C$_4$-C$_8$-cycloalkenyl, —X—(CH$_2$)$_m$, —C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-, heteroaryl-, aryl-X— or heteroaryl-X— group is optionally substituted, identically or differently, with 1, 2, 3, or 4 R$^7$ groups.

In another preferred embodiment, the invention relates to compounds of formula I, supra, wherein:

R$^3$ represents a hydrogen atom or a halogen atom, or a C$_1$-C$_6$-alkoxy-, —(CH$_2$)$_m$, —C$_2$-C$_6$-alkenyl, aryl-, aryl-X—, heteroaryl-X—, heteroaryl-, —(CH$_2$)$_m$, —C$_4$-C$_8$-cycloalkenyl, —(CH$_2$)$_m$, —C$_3$-C$_6$-cycloalkyl, —(CH$_2$)$_m$-(4- to 8-membered heterocycloalkenyl), aryl-, —C(=O)N(H)R$^{6a}$, —OR$^6$, —SR$^6$, —S(=O)R$^6$, —S(=O)$_2$R$^6$, —S—(CH$_2$)$_n$—N(R$^{6a}$)R$^{6b}$ or —S—(CH$_2$)$_n$-(3- to 7-membered heterocycloalkyl) group;

wherein said C$_1$-C$_6$-alkoxy-, aryl-, aryl-X—, heteroaryl-X— or heteroaryl-group is optionally substituted, identically or differently, with 1, 2, 3, 4 or 5 R$^7$ groups.

In another preferred embodiment, the invention relates to compounds of formula I, supra, wherein:

R$^3$ represents a hydrogen atom or a halogen atom, or a —(CH$_2$)$_m$, —C$_2$-C$_6$-alkenyl, —(CH$_2$)$_m$—C$_4$-C$_8$-cycloalkenyl —(CH$_2$)$_m$—C$_3$-C$_6$-cycloalkyl, —(CH$_2$)$_m$-(4- to 8-membered heterocycloalkenyl), aryl-, heteroaryl-, aryl-X—, heteroaryl-X—, —C(=O)N(H)R$^{6a}$, —OR$^6$, —SR$^6$, —S(=O)R$^6$, —S(=O)$_2$R$^6$, —S—(CH$_2$), —N(R$^{6a}$)R$^{6b}$, or —S—(CH$_2$)$_n$-(3- to 7-membered heterocycloalkyl) group;

wherein said aryl-, aryl-X—, heteroaryl-X— or heteroaryl-group is optionally substituted, identically or differently, with 1, 2, 3, or 4 R$^7$ groups.

In another preferred embodiment, the invention relates to compounds of formula I, supra, wherein:

R$^3$ represents an aryl-, —C$_1$-C$_6$-alkyl-aryl, aryl-X—, heteroaryl-X—, heteroaryl-, —C$_1$-C$_6$-alkyl-heteroaryl, heteroaryl-group; wherein said aryl-, aryl-X—, heteroaryl-X—, heteroaryl-, —C$_1$-C$_6$-alkyl-aryl or —C$_1$-C$_6$-alkyl-heteroaryl-group is optionally substituted, identically or differently, with 1, 2, 3 or 4 R$^7$ groups.

In another preferred embodiment, the invention relates to compounds of formula I, supra, wherein:

R$^3$ represents a substituted or unsubstituted aryl-X— group, or a substituted or unsubstituted heteroaryl-X— group.

A preferred aryl-X— group is phenyl-X—.

Preferred heteroaryl-X— groups are quinolinyl-X—, pyridyl-X—, thienyl-X—, pyrazinyl-X—, imidazyl-X—, triazyl-X— and pyrazyl-X—.

R$^3$ is optionally substituted, identically or differently, with 1, 2, 3, 4 or 5 R$^7$ groups. In a preferred embodiment, the invention relates to compounds of formula I, wherein R$^3$ is optionally substituted, identically or differently, with 1 or 2 R$^7$ groups.

In another preferred embodiment, the invention relates to compounds of formula I, wherein R$^3$ is selected from the group consisting of:

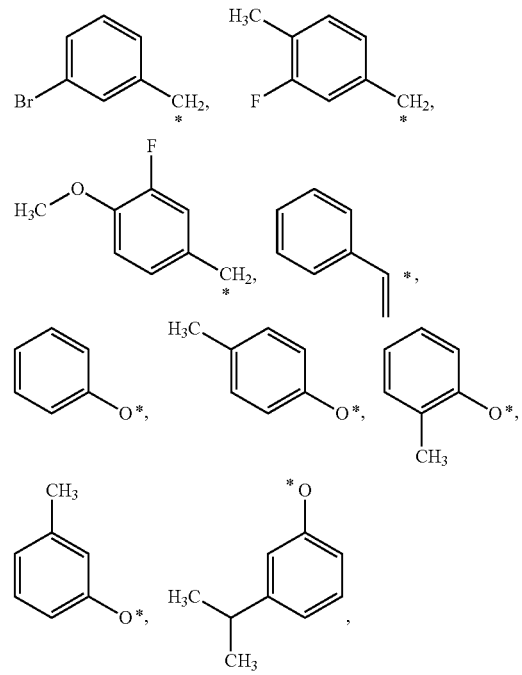

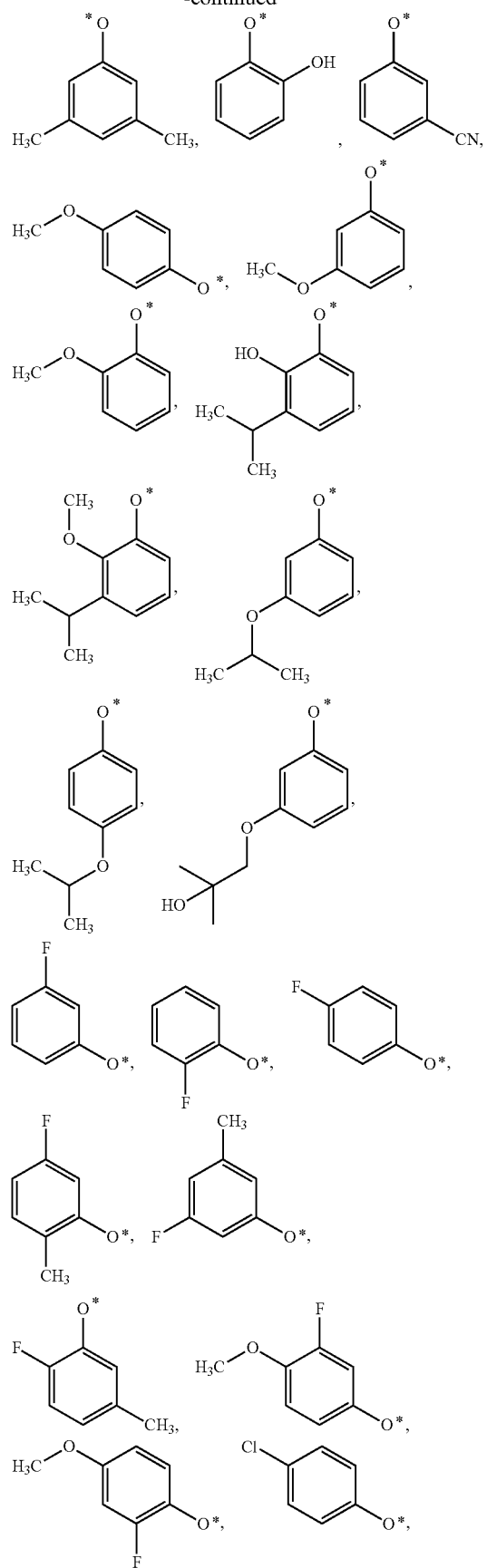
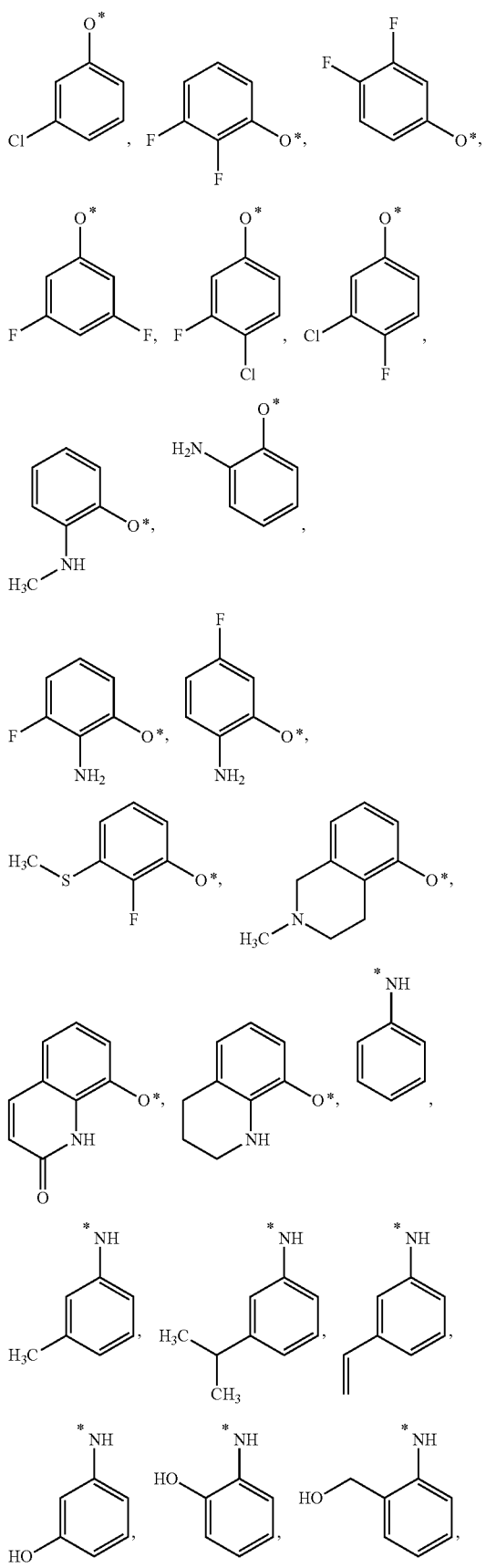

-continued
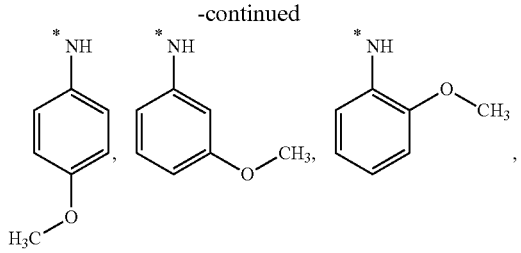
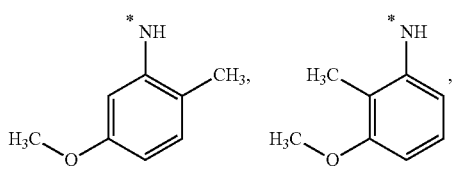
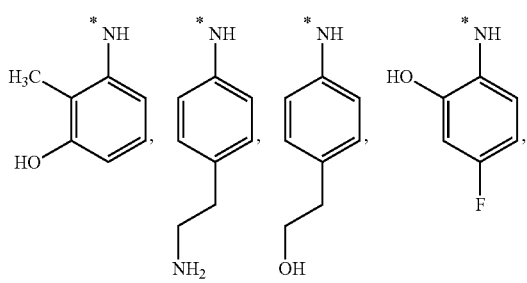
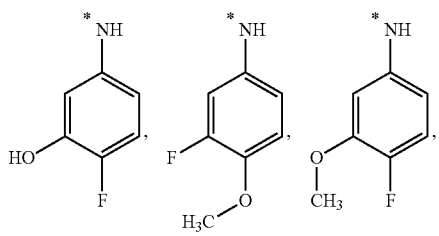
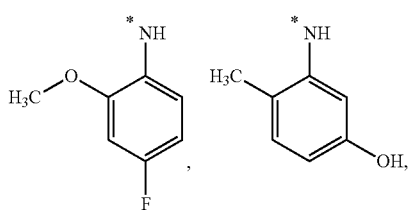
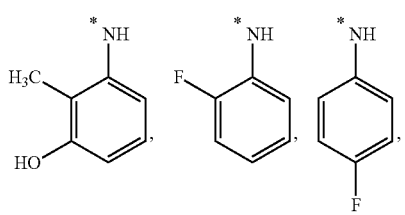
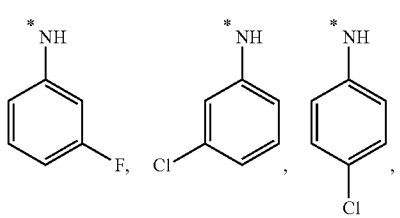
-continued
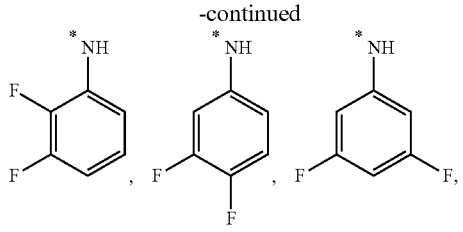
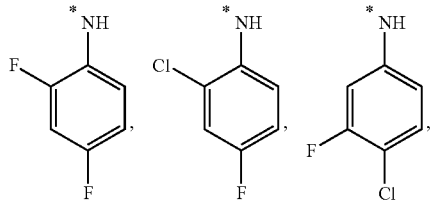
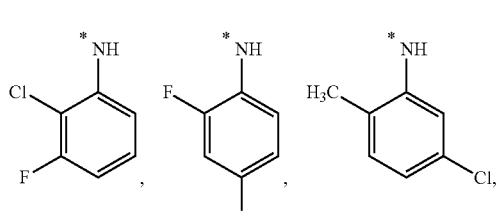
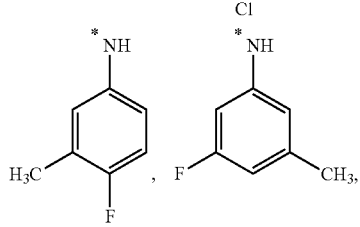
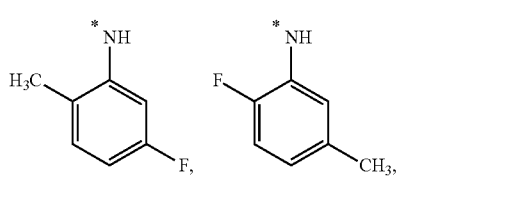
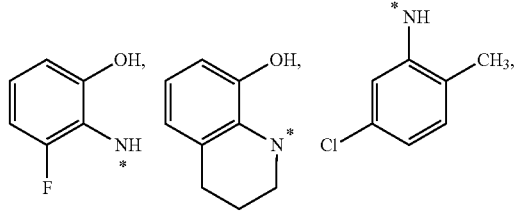
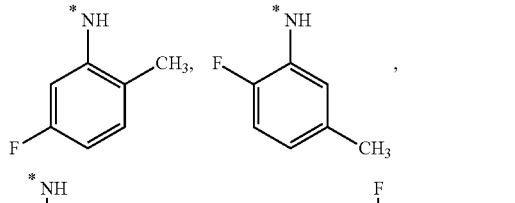
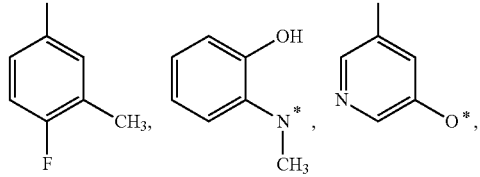

-continued
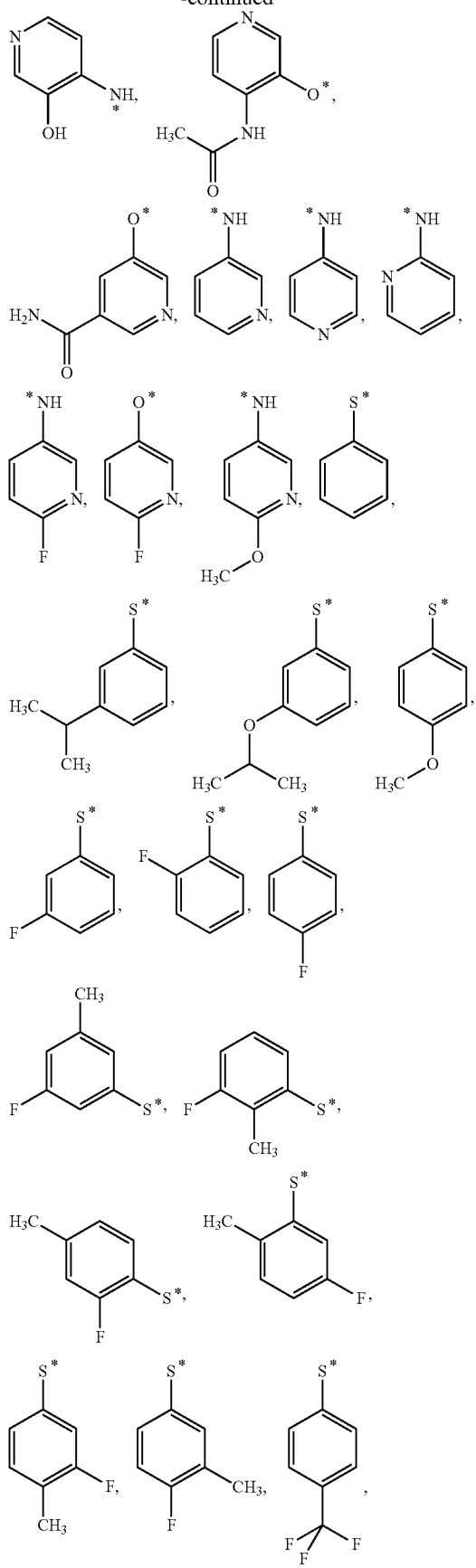
-continued
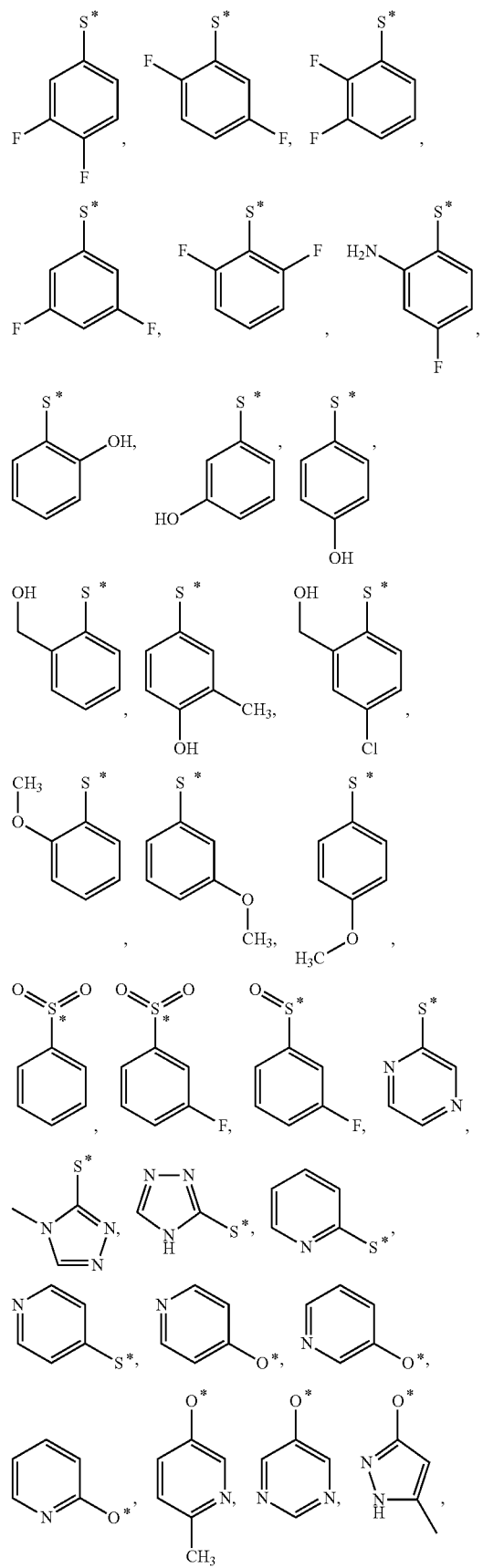

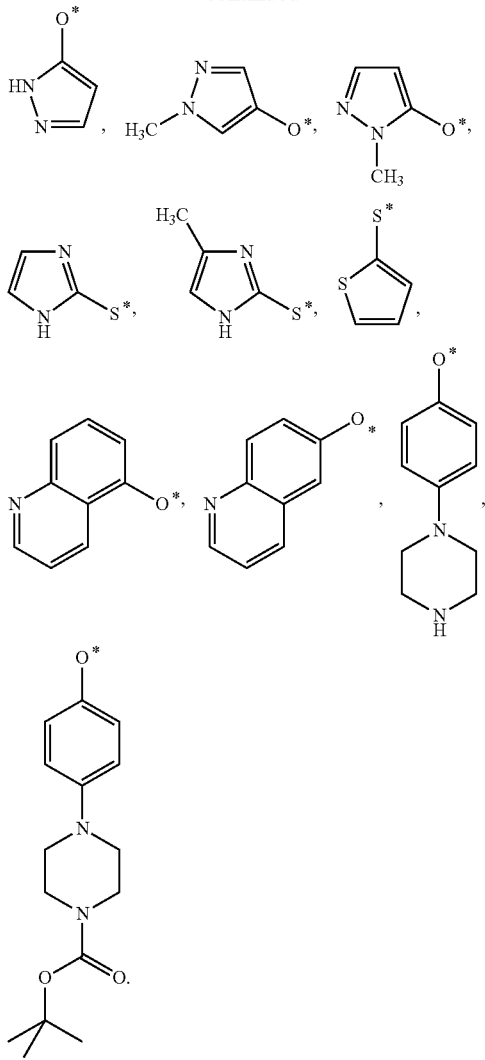

The invention relates to compounds of formula I, supra, wherein:

$R^{4a}, R^{4b}, R^{4c}, R^{4d}$ represent, independently from each other, a hydrogen or halogen atom, or a —CN, $C_1$-$C_6$-alkyl-, $C_1$-$C_6$-alkoxy-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^{6a}$, —S(=O)$_2$N($R^{6a}$)$R^{6b}$, —S(=O)(=N$R^{6c}$)$R^6$ group.

In a preferred embodiment, the invention relates to compounds of formula I, supra, wherein:
$R^{4a}, R^{4c}, R^{4d}$ represent a hydrogen atom, and
$R^{4b}$ represents a hydrogen atom, halogen atom or a $C_1$-$C_6$-alkyl-group.

In another preferred embodiment, the invention relates to compounds of formula I, supra, wherein:
$R^{4b}, R^{4c}, R^{4d}$ represent a hydrogen atom, and
$R^{4a}$ represents a halogen atom, $C_1$-$C_6$-alkyl-, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$$R^{6b}$, —S(=O)$_2$$R^6$, —S(=O)$_2$N(H)$R^{6a}$, —S(=O)$_2$N($R^{6a}$)$R^{6b}$, or —S(=O)(=N$R^{6c}$)$R^6$ group.

In another preferred embodiment, the invention relates to compounds of formula I, supra, wherein:
$R^{4b}, R^{4c}, R^{4d}$ represent a hydrogen atom, and
$R^{4a}$ represents a halogen atom, $C_1$-$C_6$-alkyl- or —O$R^6$ group.

In another preferred embodiment, the invention relates to compounds of formula I, supra, wherein:
$R^{4a}, R^{4b}, R^{4c}$, and $R^{4d}$ represent, independently from each other, a hydrogen or halogen atom, or a —CN, —OH, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-group; with the proviso that at least one of the groups $R^{4b}$ and $R^{4c}$ is not a hydrogen atom.

In another preferred embodiment of the present invention $R^{4a}$ and $R^{4d}$ represent, independently from each other, a hydrogen or halogen atom, or a —CN, $C_1$-$C_6$-alkyl-, $C_1$-$C_6$-alkoxy-, halo-$C_1$-$C_6$-alkyl- or a halo-$C_1$-$C_6$-alkoxy-group.

In another preferred embodiment of the present invention $R^{4a}$ and $R^{4d}$ represent, independently from each other, a hydrogen or halogen atom, or a $C_1$-$C_6$-alkyl-, $C_1$-$C_6$-alkoxy-, or a halo-$C_1$-$C_6$-alkyl-group.

In another preferred embodiment of the present invention $R^{4a}$ and $R^{4d}$ represent hydrogen.

In another preferred embodiment of the present invention $R^{4b}$ and $R^{4c}$ represent independently from each other, a hydrogen or halogen atom, or a —CN, —OH, $C_1$-$C_6$-alkyl-, $C_1$-$C_6$-alkoxy-group; with the proviso that at least one of the groups $R^{4b}$ and $R^{4c}$ is not a hydrogen atom.

In another preferred embodiment of the present invention $R^{4b}$ and $R^{4c}$ represent independently from each other, a hydrogen or a $C_1$-$C_6$-alkyl-group; with the proviso that at least one of the groups Rob and $R^{4c}$ is not a hydrogen atom.

In another preferred embodiment of the present invention $R^{4b}$ and $R^{4c}$ represent independently from each other, a hydrogen or a $C_1$-$C_4$-alkyl-group; with the proviso that at least one of the groups Rob and $R^{4c}$ is not a hydrogen atom.

In another preferred embodiment of the present invention one of the groups $R^{4b}$ and $R^{4c}$ represents a hydrogen atom while the other one represents a group selected from: halo-, —CN, —OH, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})N$—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, and halo-$C_1$-$C_6$-alkoxy-$C_1$-$C_6$-alkyl-.

In another preferred embodiment of the present invention one of the groups $R^{4b}$ and $R^{4c}$ represents a hydrogen atom while the other one represents a group selected from: halo-, —CN, —OH, $C_1$-$C_6$-alkyl- and $C_1$-$C_6$-alkoxy-.

In another preferred embodiment of the present invention either: $R^{4b}$=$C_1$-$C_4$-alkyl- and $R^{4c}$=hydrogen;
or: $R^{4b}$=hydrogen and $R^{4c}$=$C_1$-$C_4$-alkyl-.

In another preferred embodiment, the invention relates to compounds of formula I, wherein:

A represents a

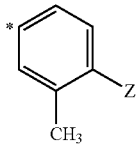

group wherein * indicates the point of attachment of said groups with the rest of the molecule; and Z represents a —C(=O)N(H)R² or a —C(=S)N(H)R² group.

Preferably Z represents a —C(=O)N(H)R² group.

In another preferred embodiment, the invention relates to compounds of formula I, supra, wherein the following compounds (which are specifically disclosed in WO 2011/013729A1) are excluded:

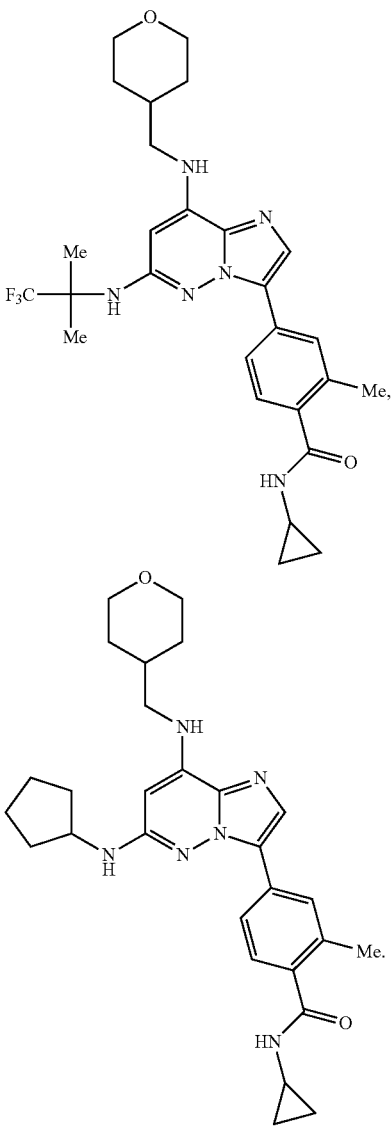 [SMILES: Cc1cc(-c2cnc3c(NCC4CCOCC4)cc(NC(C)(C)C(F)(F)F)nn23)ccc1C(=O)NC1CC1 ; Cc1cc(-c2cnc3c(NCC4CCOCC4)cc(NC4CCCC4)nn23)ccc1C(=O)NC1CC1]

The invention relates to compounds of formula I, supra, wherein:

$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl-group;

wherein said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3 or 4 $R^8$ groups.

In a preferred embodiment, the invention relates to compounds of formula I, supra, wherein:

$R^5$ represents a hydrogen atom, or a $C_1$-$C_6$-alkyl-, —(CH$_2$)$_m$-(3- to 7-membered heterocycloalkyl), aryl- or heteroaryl-group;

wherein said $C_1$-$C_6$-alkyl-, —(CH$_2$)$_m$-(3- to 7-membered heterocycloalkyl), aryl-, or heteroaryl-group is optionally substituted, identically or differently, with 1, 2, 3 or 4 $R^8$ groups.

In another preferred embodiment, the invention relates to compounds of formula I, supra, wherein:

$R^5$ represents a $C_1$-$C_6$-alkyl-, —(CH$_2$)$_m$-(3- to 7-membered heterocycloalkyl), aryl- or heteroaryl-group;

wherein said $C_1$-$C_6$-alkyl-, —(CH$_2$)$_m$-(3- to 7-membered heterocycloalkyl), aryl-, heteroaryl-group is optionally substituted, identically or differently, with 1, 2, 3 or 4 $R^8$ groups.

In another preferred embodiment, the invention relates to compounds of formula I, wherein $R^5$ is selected from the group consisting of:

H, (CH$_3$)$_2$CH—, CHF$_2$—, CF$_3$—, CF$_3$—CH$_2$—, CF$_3$—CH$_2$—CH$_2$—, CF$_3$—CH(OH)—, HO—CH$_2$—, HO—C(CH$_3$)$_2$—, HO—C(CH$_3$)$_2$CH$_2$—, HO—CH$_2$—CH(OH)—, H$_3$C—O—CH$_2$—, H$_2$N—CH$_2$—CH$_2$—, H$_2$N—C(CH$_3$)$_2$—, (CH$_3$)$_2$N—CH$_2$—, (CH$_3$)$_2$N—CH$_2$—CH$_2$—, (CH$_3$)$_2$N—CH$_2$—CH$_2$—CH$_2$—, (CH$_3$)$_2$N—C(CH$_3$)$_2$—, H$_3$C—S(=O)$_2$—CH$_2$—, H$_3$C—S(=O)$_2$—CH$_2$—CH$_2$—, HO—S(=O)$_2$—CH$_2$—, HO—S(=O)$_2$—CH$_2$—CH$_2$—, NC—CH$_2$—, H$_3$C—C(=O)—N(H)—CH$_2$, H$_3$C—C(=O)—N(H)—CH$_2$—CH$_2$—, H$_2$N—C(=O)—CH$_2$—, (CH$_3$)$_2$N—C(=O)—CH$_2$—, H$_3$C—N(H)—C(=O)—N(CH$_3$)—CH$_2$—CH$_2$—,

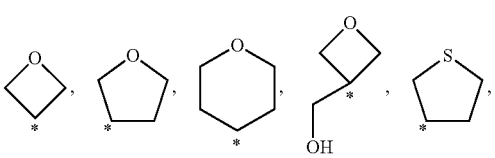

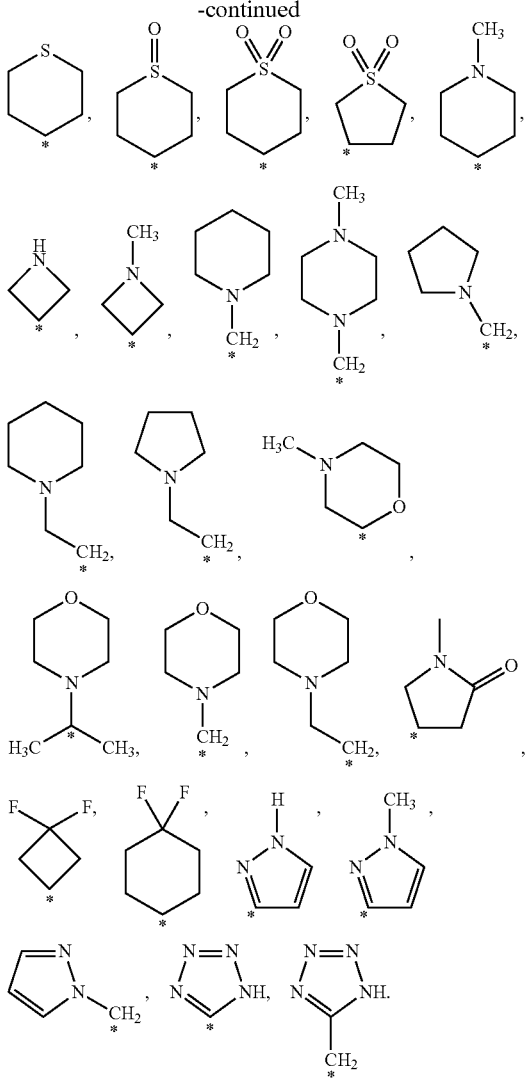

In another preferred embodiment, with respect to compounds of formula I, supra, $R^5$ represents a 1,1,1-trifluoroethyl group.

The invention relates to compounds of formula I, supra, wherein:

$R^6$, $R^{6a}$, $R^{6b}$ and $R^{6c}$ represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group.

In a preferred embodiment, the invention relates to compounds of formula I, supra, wherein:

$R^6$, $R^{6a}$, $R^{6b}$, $R^{6c}$, represent, independently from each other, a hydrogen atom, or a $C_1$-$C_6$-alkyl-, HO—$C_1$-$C_6$-alkyl-, $C_3$-$C_6$-cycloalkyl- or aryl-group.

In another preferred embodiment, the invention relates to compounds of formula I, wherein $R^6$, $R^{6a}$, $R^{6b}$, and $R^{6c}$ represent, independently from each other, a hydrogen atom, or a $C_1$-$C_6$-alkyl-group.

The invention relates to compounds of formula I, supra, wherein:

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$ or —S(=O)(=N$R^{6c}$)$R^6$ group;

wherein said $C_1$-$C_6$-alkoxy-, aryl- or heteroaryl-group is optionally substituted, identically or differently, with 1, 2 or 3 $C_1$-$C_6$-alkyl-, $C_1$-$C_6$-alkoxy-, halo-$C_1$-$C_6$-alkoxy-, —C(=O)O—$R^6$ or —OH groups;

or when 2 $R^7$ groups are present ortho to each other on an aryl- or heteroaryl-ring, said 2 $R^7$ groups together form a bridge:

*O(CH$_2$)$_2$O*, *O(CH$_2$)O*, *NH(C(=O))NH*, wherein * represent the point of attachment to said aryl- or heteroaryl-ring.

In a preferred embodiment, the invention relates to compounds of formula I, wherein $R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, H$_2$N—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, or —S(=O)(=N$R^{6c}$)$R^6$ group;

wherein said $C_1$-$C_6$-alkoxy-, aryl-, 3- to 7-membered heterocycloalkyl- or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups.

In another preferred embodiment, the invention relates to compounds of formula I, supra, wherein:

$R^7$ represents a hydrogen or halogen atom, or an HO—, —CN, $C_1$-$C_6$-alkoxy-, $C_1$-$C_6$-alkyl-, halo-$C_1$-$C_6$-alkyl-, HO—$C_1$-$C_6$-alkyl-, aryl-, heteroaryl-, —C(=O)N($R^{6a}$)$R^{6b}$, —N(H)C(=O)$R^6$, —N(H)C(=O)N($R^{6a}$)$R^{6b}$, —O$R^6$, —S(=O)$R^6$ or —S(=O)$_2R^6$, group;

wherein said $C_1$-$C_6$-alkoxy- or heteroaryl-group is optionally substituted, identically or differently, with a $C_1$-$C_4$-alkyl-, halo-$C_1$-$C_6$-alkoxy-, —C(=O)O—$R^6$ or —OH group;

or when 2 R' groups are present ortho- to each other on an aryl- or heteroaryl-ring, said 2 $R^7$ groups together form a bridge:

*O(CH$_2$)$_2$O*, *O(CH$_2$)O*, *NH(C(=O))NH*, wherein * represent the point of attachment to said aryl- or heteroaryl-ring.

In another preferred embodiment, the invention relates to compounds of formula I, supra, wherein:

R$^7$ represents a hydrogen or halogen atom, or an HO—, —CN, C$_1$-C$_6$-alkoxy-, C$_1$-C$_6$-alkyl-, halo-C$_1$-C$_6$-alkyl-, HO—C$_1$-C$_6$-alkyl-, aryl-, heteroaryl-, —C(=O)N(R$^{6a}$)R$^{6b}$, —N(H)C(=O)R$^6$, —N(H)C(=O)N(R$^{6a}$)R$^{6b}$, —OR$^6$, —S(=O)R$^6$, or —S(=O)$_2$R$^6$, group;

wherein said C$_1$-C$_6$-alkoxy- or heteroaryl-group is optionally substituted, identically or differently, with a C$_1$-C$_4$-alkyl-, halo-C$_1$-C$_6$-alkoxy-, —C(=O)O—R$^6$ or —OH group.

In another preferred embodiment, the invention relates to compounds of formula I, supra, wherein:

R$^7$ represents a hydrogen or halogen atom, or an HO—, —CN, C$_1$-C$_6$-alkoxy-, C$_1$-C$_6$-alkyl-, halo-C$_1$-C$_6$-alkyl-, HO—C$_1$-C$_6$-alkyl-, aryl-, heteroaryl-, —C(=O)N(R$^{6a}$)R$^{6b}$, —N(H)C(=O)R$^6$, —N(H)C(=O)N(R$^{6a}$)R$^{6b}$, —OR$^6$, —S(=O)R$^6$, or —S(=O)$_2$R$^6$ group;

wherein said heteroaryl-group is optionally substituted with a C$_1$-C$_4$-alkyl group;

or when 2 R$^7$ groups are present ortho- to each other on an aryl- or heteroaryl-ring, said 2 R$^7$ groups together form a bridge:

*O(CH$_2$)$_2$O*, *O(CH$_2$)O*, *NH(C(=O))NH*, wherein * represent the point of attachment to said aryl- or heteroaryl-ring.

In another preferred embodiment, the invention relates to compounds of formula I, wherein R$^7$ represents a halogen atom, or a HO—, —CN, C$_1$-C$_6$-alkoxy-, C$_1$-C$_6$-alkyl-, halo-C$_1$-C$_6$-alkyl-, HO—C$_1$-C$_6$-alkyl-, H$_2$N—C$_1$-C$_6$-alkyl-, C$_2$-C$_6$-alkenyl, 3- to 7-membered heterocycloalkyl, —C(=O)N(H)R$^{6a}$, —N(R$^{6a}$)R$^{6b}$, —N(H)C(=O)R$^6$, or —SR$^6$ group;

wherein said C$_1$-C$_6$-alkoxy-, or 3- to 7-membered heterocycloalkyl-group is optionally substituted, identically or differently, with 1, 2, or 3 C$_1$-C$_6$-alkyl-, C$_1$-C$_6$-alkoxy-, halo-C$_1$-C$_6$-alkoxy-, —C(=O)O—R$^6$ or —OH groups.

In another preferred embodiment, the invention relates to compounds of formula I, wherein R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, H$_2$N—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, or —S(=O)(=NR$^{6c}$)R$^6$ group;

wherein said C$_1$-C$_6$-alkoxy-, aryl-, 3- to 7-membered heterocycloalkyl, or heteroaryl-group is optionally substituted, identically or differently, with 1 C$_1$-C$_6$-alkyl-, C$_1$-C$_6$-alkoxy-, halo-C$_1$-C$_6$-alkoxy-, —C(=O)O—R$^6$ or —OH group.

In another preferred embodiment, the invention relates to compounds of formula I, wherein R$^7$ represents a hydrogen or halogen atom, or a HO—, —CN, C$_1$-C$_6$-alkoxy-, C$_1$-C$_6$-alkyl-, halo-C$_1$-C$_6$-alkyl-, HO—C$_1$-C$_6$-alkyl-, H$_2$N—C$_1$-C$_6$-alkyl-, C$_2$-C$_6$-alkenyl, 3- to 7-membered heterocycloalkyl, —C(=O)N(H)R$^{6a}$, —N(R$^{6a}$)R$^{6b}$, —N(H)C(=O)R$^6$ or —SR$^6$ group;

wherein said C$_1$-C$_6$-alkoxy- or 3- to 7-membered heterocycloalkyl-group is optionally substituted, identically or differently, with one —C(=O)O—R$^6$ or —OH group.

In another preferred embodiment, the invention relates to compounds of formula I, supra, wherein 2 R$^7$ groups are present ortho to each other on the aryl- or heteroaryl-ring of the R$^3$ group;

said 2 R$^7$ groups together form a bridge:
*O(CH$_2$)$_2$O*, *O(CH$_2$)O*, *CH$_2$(CH$_2$)$_2$NH*, *CH$_2$CH$_2$N(R$^{6a}$)CH$_2$*, *NH(C(=O))NH*, *C(H)=C(H)—C(=O)—N(H)*, wherein * represent the point of attachment to said aryl- or heteroaryl-ring.

Preferably the 2 R$^7$ groups together form a bridge selected from:
*CH$_2$(CH$_2$)$_2$NH*, *CH$_2$CH$_2$N(R$^{6a}$)CH$_2$*, *C(H)=C(H)—C(=O)—N(H)*.

The invention relates to compounds of formula I, supra, wherein

R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;

wherein said 3- to 7-membered heterocycloalkyl- or heteroaryl-group is optionally substituted, identically or differently, with 1, 2, 3 or 4 C$_1$-C$_6$-alkyl-groups.

In a preferred embodiment, the invention relates to compounds of formula I, supra, wherein:

R$^8$ represents a halogen atom, or a —CN, —OH, C$_1$-C$_6$-alkoxy-, C$_1$-C$_6$-alkyl-, HO—C$_1$-C$_6$-alkyl, —C(=O)N(R$^{6a}$)R$^{6b}$, —N(R$^{6a}$)R$^{6b}$, —N(H)C(=O)R$^6$, —N(R$^{6c}$)C(=O)N(R$^{6a}$)R$^{6b}$, —S(=O)$_2$R$^6$ or —S(=O)$_2$OH group.

In another preferred embodiment, the invention relates to compounds of formula I, supra, wherein:

R$^8$ represents a halogen atom, a —CN, —N(R$^{6a}$)R$^{6b}$, or —OR$^6$ group.

Preferably, R$^8$ represents a halogen atom, a —N(R$^{6a}$)R$^{6b}$ or a —OR$^6$ group.

The invention relates to compounds of formula I, wherein m is an integer of 0, 1, 2, 3, 4, 5 or 6.

In a preferred embodiment, with respect to compounds of formula I, supra, m is 0.

In another preferred embodiment, with respect to compounds of formula I, supra, m is 1.

The invention relates to compounds of formula I, wherein n is an integer of 0, 1, 2, 3, 4 or 5.

In a preferred embodiment, with respect to compounds of formula I, supra, n is 1.

The invention relates to compounds of formula I, wherein X is S, S(=O), S(=O)$_2$, O, NR$^6$, CR$^{6a}$R$^{6b}$ or C=CR$^{6a}$R$^{6b}$.

In a preferred embodiment, the invention relates to compounds of formula I, wherein X is S.

In another preferred embodiment, the invention relates to compounds of formula I, wherein X is S(=O).

In another preferred embodiment, the invention relates to compounds of formula I, wherein X is S(=O)$_2$.

In another preferred embodiment, the invention relates to compounds of formula I, wherein X is O.

In another preferred embodiment, the invention relates to compounds of formula I, wherein X is NR$^6$. Preferably, X is NH or N(CH$_3$). Most preferably, X is NH.

It should be noted that in a group of e.g. formula aryl-NR$^6$— or heteroaryl-NR$^6$— the substituent R$^6$ optionally can be attached to the aryl- or heteroaryl-ring, thereby—together with the N-atom—forming a heterocyclic ring fused to the aryl- or heteroaryl-ring. An example of such a fused ring system is the group:

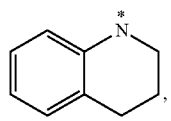

in which * indicates the point of attachment of said group with the rest of the molecule. In other words, a group with the formula

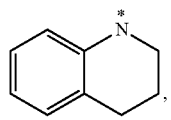

in which * indicates the point of attachment of said group with the rest of the molecule, is an example of an aryl-X— group.

In another preferred embodiment, the invention relates to compounds of formula I, wherein X is CR$^{6a}$R$^{6b}$. Preferably, X is CH$_2$.

It should be noted that in a group of e.g. formula aryl-CR$^{6a}$R$^{6b}$— or heteroaryl-CR$^{6a}$R$^{6b}$— the substituents R$^{6a}$ and/or R$^{6b}$ option ally can be attached to the aryl- or heteroaryl-ring, thereby forming one or more carbocyclic rings fused to the aryl- or heteroaryl-ring. An example of such a fused ring system is the group

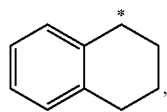

in which * indicates the point of attachment of said group with the rest of the molecule. In other words, a group with the formula

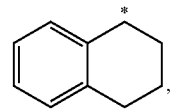

in which * indicates the point of attachment of said group with the rest of the molecule, is an example of an aryl-X— group.

In another preferred embodiment, the invention relates to compounds of formula I, wherein X is C=CR$^{6a}$R$^{6b}$. Preferably, X is C=CH$_2$.

The invention relates to compounds of formula I, wherein Z represents a —C(=O)N(H)R$^2$ or —C(=S)N(H)R$^2$ group, or a group selected from

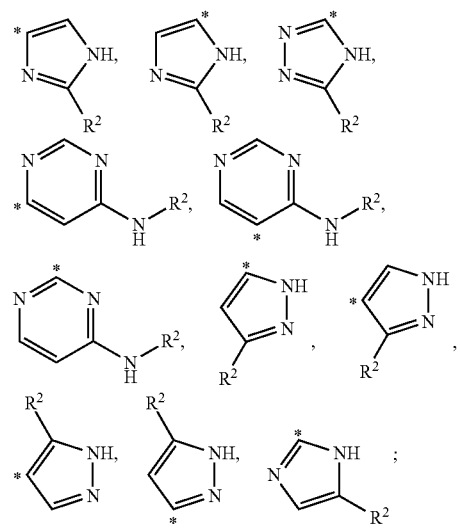

wherein * indicates the point of attachment of said groups with the rest of the molecule.

In a preferred embodiment Z represents a —C(=O)N(H)R$^2$ group.

In another preferred embodiment Z represents a —C(=S)N(H)R$^2$ group.

In another preferred embodiment Z represents a

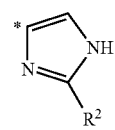

group.

In an embodiment of the above-mentioned aspects, the invention relates to compounds of formula I, according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of general formula I, supra, in which:

A represents a

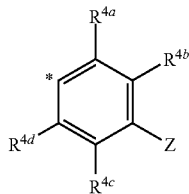

-group;
wherein * indicates the point of attachment of said groups with the rest of the molecule;

Z represents a —C(=O)N(H)R$^2$ or —C(=S)N(H)R$^2$ group, or a group selected from

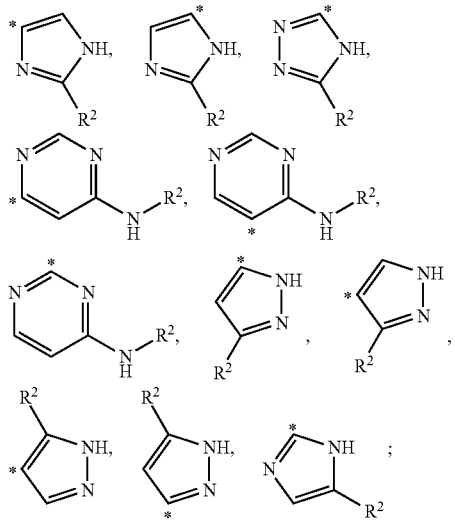

wherein * indicates the point of attachment of said groups with the rest of the molecule;

R$^2$ represents a hydrogen atom, or a C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl- or C$_3$-C$_6$-cycloalkyl-group;
wherein said C$_3$-C$_6$-cycloalkyl-group is optionally substituted, identically or differently, with 1, 2, 3 or 4-groups selected from: halogen, OH, —CN, C$_1$-C$_6$-alkyl, —C$_1$-C$_6$-alkoxy, halo-C$_1$-C$_6$-alkyl-;

R$^3$ represents a hydrogen atom or a halogen atom, or a —CN, C$_1$-C$_6$-alkyl-, —(CH$_2$)$_m$—, —C$_2$-C$_6$-alkenyl —(CH$_2$)$_m$—, —C$_4$-C$_8$-cycloalkenyl —(CH$_2$)$_m$—, —C$_2$-C$_6$-alkynyl, —(CH$_2$)$_m$—, —C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, a 3- to 7-membered heterocycloalkyl, C$_2$-C$_6$-alkenyl-, C$_4$-C$_8$-cycloalkenyl-, C$_2$-C$_6$-alkynyl-, aryl-, —C$_1$-C$_6$-alkyl-aryl, —C$_1$-C$_6$-alkyl-heteroaryl, heteroaryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —OR$^6$, —SR$^6$, —S(=O)R$^6$, —S(=O)$_2$R$^6$, —S(=O)(=NR$^{6a}$)R$^{6b}$, —S(=O)$_2$N(R$^{6b}$)R$^{6c}$, —S—(CH$_2$)$_n$—N(R$^{6a}$)R$^{6b}$, or —S—(CH$_2$)$_m$-(3- to 7-membered heterocycloalkyl) group;
wherein said C$_1$-C$_6$-alkyl-, —(CH$_2$)$_m$—C$_2$-C$_6$-alkenyl, —(CH$_2$)$_m$—C$_2$-C$_6$-alkynyl, —(CH$_2$)$_m$—C$_3$-C$_6$-cycloalkyl, aryl-C$_1$-C$_6$-alkyl-, heteroaryl-C$_1$-C$_6$-alkyl-, C$_3$-C$_6$-cycloalkyl-, a 3- to 7-membered heterocycloalkyl, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X—(CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl or heteroaryl-group is optionally substituted, identically or differently, with 1, 2, 3, or 4 R$^7$ groups;

R$^{4a}$, R$^{4b}$, R$^{4c}$, R$^{4d}$
represent, independently from each other, a hydrogen or halogen atom, or a —CN, C$_1$-C$_6$-alkyl-, C$_1$-C$_6$-alkoxy-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^{6a}$, —S(=O)$_2$N(R$^{6a}$)R$^{6b}$ or —S(=O)(=NR$^{6c}$)R$^6$ group.

R$^5$ represents a hydrogen atom, or a C$_1$-C$_6$-alkyl-, —(CH$_2$)$_n$—, —C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl- or heteroaryl group;
wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl-group is optionally substituted, identically or differently, with 1, 2, 3, or 4 R$^8$ groups;

R$^6$, R$^{6a}$, R$^{6b}$, R$^{6c}$,
represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl, 3- to 7-membered heterocycloalkyl-, aryl-, heteroaryl-, aryl-C$_1$-C$_6$-alkyl-, or heteroaryl-C$_1$-C$_6$-alkyl-group;

R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)

N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$), —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group;

wherein said aryl- or heteroaryl-group is optionally substituted, identically or differently, with 1, 2, or 3 $C_1$-$C_6$-alkyl groups;

or when 2 $R^7$ groups are present ortho- to each other on an aryl-ring, said 2 $R^7$ groups together form a bridge: *O($CH_2$)$_2$O*, *O($CH_2$)O*, *NH(C(=O))NH*, wherein * represent the point of attachment to said aryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group or —S(=O)$_2$-(3- to 7-membered heterocycloalkyl);

wherein said 3- to 7-membered heterocycloalkyl- or heteroaryl-group is optionally substituted, identically or differently, with 1, 2, 3, or 4 $C_1$-$C_6$-alkyl-groups;

m is an integer of 0, 1, 2, 3, 4, 5 or 6;

n is an integer of 0, 1, 2, 3, 4 or 5;

X is S, S(=O), S(=O)$_2$, O, N$R^6$;

or a stereoisomer, a tautomer, an N-oxide, a hydrate, a solvate, or a salt thereof, or a mixture of same.

In another preferred embodiment, the invention relates to compounds of general formula I, supra, in which:

A represents a

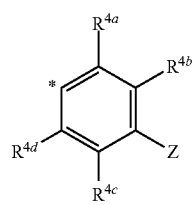

-group;

wherein * indicates the point of attachment of said groups with the rest of the molecule;

Z represents a —C(=O)N(H)$R^2$ or —C(=S)N(H)$R^2$ group, or a group selected from

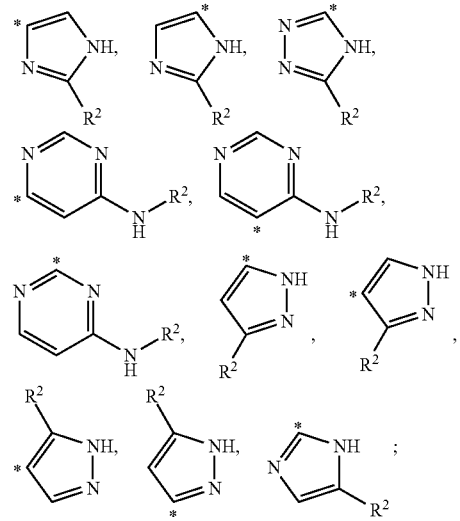

wherein * indicates the point of attachment of said groups with the rest of the molecule;

$R^2$ represents a hydrogen atom, or a $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;

wherein said $C_3$-$C_6$-cycloalkyl-group is optionally substituted, identically or differently, with 1, 2, 3, or 4-groups selected from: halogen, OH, —CN, $C_1$-$C_6$-alkyl, —$C_1$-$C_6$-alkoxy, halo-$C_1$-$C_6$-alkyl-;

$R^3$ represents a hydrogen atom or a halogen atom, or a —CN, $C_1$-$C_6$-alkyl-, —($CH_2$)$_m$—$C_2$-$C_6$-alkenyl-, —($CH_2$)$_m$—$C_4$-$C_8$-cycloalkenyl, —($CH_2$)$_m$, —$C_2$-$C_6$-alkynyl, —($CH_2$)$_m$, —$C_3$-$C_6$-cycloalkyl, —($CH_2$)$_m$-(3- to 7-membered heterocycloalkyl), —($CH_2$)$_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, $C_1$-$C_6$-alkyl-X—, —X—($CH_2$)$_m$—$C_2$-$C_6$-alkenyl, —X—($CH_2$)$_m$—$C_4$-$C_8$-cycloalkenyl, —X—($CH_2$)$_m$—$C_2$-$C_6$-alkynyl, —X—($CH_2$)$_m$—$C_3$-$C_6$-cycloalkyl, —X—($CH_2$)$_m$-(3- to 7-membered heterocycloalkyl), —X—($CH_2$)$_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —O$R^6$, —S$R^6$, —S(=O)$R^6$, —S(=O)$_2$$R^6$, —S(=O)(=N$R^{6a}$)$R^{6b}$, —S(=O)$_2$N($R^{6b}$)$R^{6c}$, —S—($CH_2$)$_n$—N($R^{6a}$)$R^{6b}$, or —S—($CH_2$)$_n$-(3- to 7-membered heterocycloalkyl) group;

wherein said $C_1$-$C_6$-alkyl-, —($CH_2$)$_m$—$C_2$-$C_6$-alkenyl, —($CH_2$)$_m$—$C_2$-$C_6$-alkynyl, —($CH_2$)$_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—($CH_2$)$_m$—$C_2$-$C_6$-alkenyl, —X—($CH_2$)$_m$—$C_4$-$C_8$-cycloalkenyl, —X—($CH_2$)$_m$—$C_2$-$C_6$-alkynyl, —X—($CH_2$)$_m$—$C_3$-$C_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl, or heteroaryl-group is optionally substituted, identically or differently, with 1, 2, 3 or 4 R$^7$ groups;

either

R$^{4a}$, R$^{4c}$, R$^{4d}$ represent a hydrogen atom, and

R$^{4b}$ represents a hydrogen atom or a halogen atom or a C$_1$-C$_6$-alkyl-group;

or

R$^{4b}$, R$^{4c}$, R$^{4d}$ represent a hydrogen atom, and

R$^{4a}$ represents a halogen atom or an C$_1$-C$_6$-alkyl-, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^{6a}$, —S(=O)$_2$N(R$^{6a}$)R$^{6b}$ or —S(=O)(=NR$^{6c}$)R$^6$ group;

R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—, —C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, a 3- to 7-membered heterocycloalkyl, C$_2$-C$_6$-alkenyl-, C$_4$-C$_8$-cycloalkenyl-, C$_2$-C$_6$-alkynyl-, aryl- or heteroaryl-group;

wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_4$-C$_8$-cycloalkenyl-, aryl- or heteroaryl-group is optionally substituted, identically or differently, with 1, 2, 3, or 4 R$^8$ groups;

R$^6$, R$^{6a}$, R$^{6b}$, R$^{6c}$, represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl-, or heteroaryl-C$_1$-C$_6$-alkyl-group;

R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, or —S(=O)(=NR$^{6c}$)R$^6$ group;

wherein said aryl- or heteroaryl-group is optionally substituted, identically or differently, with 1, 2, or 3 C$_1$-C$_6$-alkyl-groups;

or when 2 R$^7$ groups are present ortho to each other on an aryl-ring, said 2 R$^7$ groups together form a bridge:

*O(CH$_2$)$_2$O*, *O(CH$_2$)O*, *NH(C(=O))NH*, wherein * represent the point of attachment to said aryl-ring;

R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;

wherein said 3- to 7-membered heterocycloalkyl- or heteroaryl-group is optionally substituted, identically or differently, with 1, 2, 3, or 4 C$_1$-C$_6$-alkyl-groups;

m is an integer of 0, 1, 2, 3, 4, 5 or 6;

n is an integer of 0, 1, 2, 3, 4 or 5;

X is S, S(=O), S(=O)$_2$, O, NR$^6$;

or a stereoisomer, a tautomer, an N-oxide, a hydrate, a solvate, or a salt thereof, or a mixture of same.

In another preferred embodiment, the invention relates to compounds of general formula I, supra, in which:

A represents a

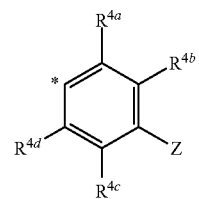

-group;

wherein * indicates the point of attachment of said groups with the rest of the molecule;

Z represents a —C(=O)N(H)R$^2$ or —C(=S)N(H)R$^2$ group, or a group selected from

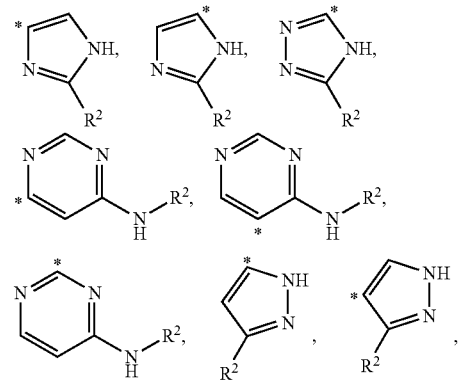

-continued

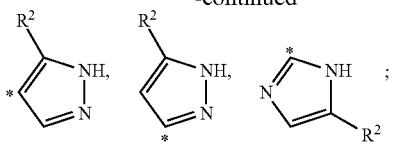

wherein * indicates the point of attachment of said groups with the rest of the molecule;

$R^2$ represents a hydrogen atom, or a $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;

wherein said $C_3$-$C_6$-cycloalkyl-group is optionally substituted, identically or differently, with 1, 2, 3, or 4-groups selected from: halogen, OH, —CN, $C_1$-$C_6$-alkyl, —$C_1$-$C_6$-alkoxy, halo-$C_1$-$C_6$-alkyl-;

$R^3$ represents a hydrogen atom or a halogen atom, or a —CN, $C_1$-$C_6$-alkyl-, —$(CH_2)_m$—$C_2$-$C_6$-alkenyl-, —$(CH_2)_m$—$C_4$-$C_8$-cycloalkenyl —$(CH_2)_m$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —$C_1$-$C_6$-alkyl-aryl, —$C_1$-$C_6$-alkyl-heteroaryl, heteroaryl-, $C_1$-$C_6$-alkyl-X—, —X—$(CH_2)_m$—$C_7$-$C_6$-alkenyl, —X—$(CH_7)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —O$R^6$, —S$R^6$, —S(=O)$R^6$, —S(=O)$_2R^6$, —S(=O)(=N$R^{6a}$)$R^{6b}$, —S(=O)$_2$N($R^{6b}$)$R^{6c}$, —S—$(CH_2)_n$—N($R^{6a}$)$R^{6b}$, or —S—$(CH_2)_n$-(3- to 7-membered heterocycloalkyl) group;

wherein said $C_1$-$C_6$-alkyl-, —$(CH_2)_m$—$C_2$-$C_6$-alkenyl, —$(CH_2)_n$, —$C_2$-$C_6$-alkynyl, —$(CH_2)_n$, —$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)$, —$C_4$-$C_8$-cycloalkenyl, —X—$(CH_2)$, —$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$(4- to 8-membered heterocycloalkenyl), aryl-X—, heteroaryl-X—, —$C_1$-$C_6$-alkyl-aryl, —$C_1$-$C_6$-alkyl-heteroaryl, or heteroaryl-group is optionally substituted, identically or differently, with 1, 2, 3, or 4 $R^7$ groups;

either
$R^{4a}$, $R^{4c}$, $R^{4d}$ represent a hydrogen atom, and
$R^{4b}$ represents a hydrogen atom or a halogen atom or a $C_1$-$C_6$-alkyl group;
or
$R^{4b}$, $R^{4c}$, $R^{4d}$ represent a hydrogen atom, and
$R^{4a}$ represents a halogen atom or a $C_1$-$C_6$-alkyl-, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^{6a}$, —S(=O)$_2$N($R^{6a}$)$R^{6b}$, or —S(=O)(=N$R^{6c}$)$R^6$ group;

$R^5$ represents a hydrogen atom, or a $C_1$-$C_6$-alkyl-, —$(CH_2)_m$-(3- to 7-membered heterocycloalkyl), aryl- or heteroaryl-group;

wherein said $C_1$-$C_6$-alkyl-, —$(CH_2)_m$-(3- to 7-membered heterocycloalkyl), aryl- or heteroaryl-group is optionally substituted, identically or differently, with 1, 2, 3, or 4 $R^8$ groups;

$R^6$, $R^{6a}$, $R^{6b}$, $R^{6c}$ represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-C1-C6-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ group;

wherein said aryl-, heteroaryl- is optionally substituted, identically or differently, with 1, 2, or 3 $C_1$-$C_6$-alkyl groups;
or
when 2 $R^7$ groups are present ortho- to each other on an aryl-ring, said 2 $R^7$ groups together form a bridge:
*O(CH$_2$)$_2$O*, *O(CH$_2$)O*, *NH(C(=O))NH*, wherein * represent the point of attachment to said aryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —$NO_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ group, —S(=O)$_2$-(3- to 7-membered heterocycloalkyl);

wherein said 3- to 7-membered heterocycloalkyl- or heteroaryl- is optionally substituted, identically or differently, with 1, 2, 3 or 4 $C_1$-$C_6$-alkyl-groups;

m is an integer of 0, 1, 2, 3, 4, 5 or 6;
n is an integer of 0, 1, 2, 3, 4 or 5;
X is S, S(=O), S(=O)$_2$, O, N$R^6$;
or a stereoisomer, a tautomer, an N-oxide, a hydrate, a solvate, or a salt thereof, or a mixture of same.

In another preferred embodiment, the invention relates to compounds of general formula I, supra, in which:

A represents a

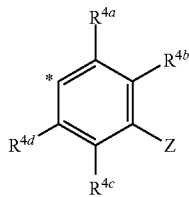

-group;
wherein * indicates the point of attachment of said groups with the rest of the molecule;

Z represents a —C(=O)N(H)R² or —C(=S)N(H)R² group, or a group selected from

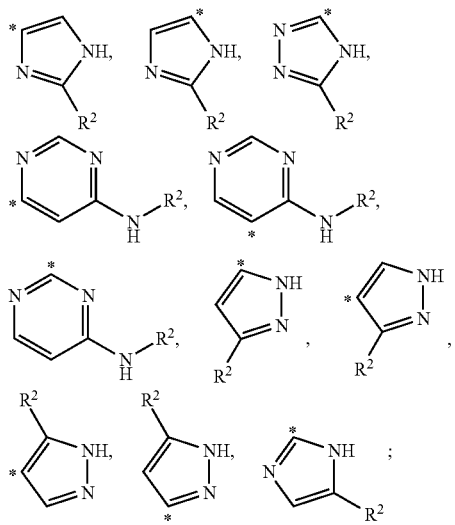

wherein * indicates the point of attachment of said groups with the rest of the molecule;

R² represents a hydrogen atom, or a $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;
wherein said $C_3$-$C_6$-cycloalkyl-group is optionally substituted, identically or differently, with 1, 2, 3, or 4 groups selected from: halogen, OH, —CN, $C_1$-$C_6$-alkyl, $C_1$-$C_6$-alkoxy-, halo-$C_1$-$C_6$-alkyl-;

R³ represents a hydrogen atom or a halogen atom, or a —CN, $C_1$-$C_6$-alkyl-, —$(CH_2)_m$—$C_2$-$C_6$-alkenyl —$(CH_2)_m$—$C_4$-$C_8$-cycloalkenyl —$(CH_2)_m$—$C_2$-$C_6$-alkynyl-, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)R⁶, —C(=O)N(H)R⁶ᵃ, —C(=O)N($R^{6a}$)$R^{6b}$, —C(=O)O—R⁶, —N($R^{6a}$)$R^{6b}$, —NO₂, —N(H)C(=O)R⁶, —OR⁶, —SR⁶, —S(=O)R⁶, —S(=O)₂R⁶, —S(=O)(=N$R^{6a}$)$R^{6b}$, —S(=O)₂N($R^{6b}$)$R^{6c}$, —S—$(CH_2)_n$—N($R^{6a}$)$R^{6b}$, or —S—$(CH_2)_n$-(3- to 7-membered heterocycloalkyl) group;
wherein said $C_1$-$C_6$-alkyl-, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl, or heteroaryl-group is optionally substituted, identically or differently, with 1, 2, 3, or 4 R' groups;

either
$R^{4a}$, $R^{4c}$, $R^{4d}$ represent a hydrogen atom, and
$R^{4b}$ represents a hydrogen atom or a halogen atom or a $C_1$-$C_6$-alkyl group;
or
$R^{4b}$, $R^{4c}$, $R^{4d}$ represent a hydrogen atom, and
$R^{4a}$ represents a halogen atom or a $C_1$-$C_6$-alkyl-, —OR⁶, —O(C=O)R⁶, —O(C=O)N($R^{6a}$)$R^{6b}$, —O(C=O)OR⁶, —SR⁶, —S(=O)R⁶, —S(=O)N(H)R⁶, —S(=O)N($R^{6a}$)$R^{6b}$, —S(=O)₂R⁶, —S(=O)₂N(H)$R^{6a}$, —S(=O)₂N($R^{6a}$)$R^{6b}$, —S(=O)(=N$R^{6c}$)R⁶ group;

R⁵ represents a hydrogen atom, or a $C_1$-$C_6$-alkyl-, —$(CH_2)_m$-(3- to 7-membered heterocycloalkyl), aryl- or heteroaryl group;
said $C_1$-$C_6$-alkyl-, —$(CH_2)_m$-(3- to 7-membered heterocycloalkyl), aryl- or heteroaryl-group is optionally substituted, identically or differently, with 1, 2, 3, or 4 R⁸ groups;

R⁶, $R^{6a}$, $R^{6b}$, $R^{6c}$, represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

R⁷ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)R⁶, —C(=O)N(H)R⁶ᵃ, —C(=O)N($R^{6a}$)$R^{6b}$, —C(=O)O—R⁶, —N($R^{6a}$)$R^{6b}$, —NO₂, —N(H)C(=O)R⁶, —N($R^{6c}$)C(=O)R⁶, —N(H)C(=O)N($R^{6a}$)$R^{6b}$, —N($R^{6c}$)C(=O)N($R^{6a}$)$R^{6b}$, —N(H)C(=O)OR⁶, —N($R^{6c}$)C(=O)OR⁶, —N(H)S(=O)R⁶, —N($R^{6c}$)S(=O)R⁶, —N(H)S(=O)₂R⁶, —N($R^{6c}$)S(=O)₂R⁶, —N=S(=O)($R^{6a}$)$R^{6b}$, —OR⁶, —O(C=O)R⁶, —O(C=O)N($R^{6a}$)$R^{6b}$, —O(C=O)OR⁶, —SR⁶, —S(=O)R⁶, —S(=O)N(H)R⁶, —S(=O)N($R^{6a}$)$R^{6b}$, —S(=O)₂R⁶, —S(=O)₂N(H)R⁶, —S(=O)₂N($R^{6a}$)$R^{6b}$, —S(=O)(=N$R^{6c}$)R⁶ group;
wherein said aryl- or heteroaryl-group is optionally substituted, identically or differently, with 1, 2, or 3 $C_1$-$C_6$-alkyl groups;
or
when 2 R⁷ groups are present ortho- to each other on an aryl ring, said 2 R⁷ groups together form a bridge:

*O(CH$_2$)$_2$O*, *O(CH$_2$)O*, *NH(C(=O))NH*, wherein * represent the point of attachment to said aryl ring;
R$^8$ represents a halogen atom, an —N(R$^{6a}$)R$^{6b}$ or —OR$^6$ group;
m is an integer of 0, 1, 2, 3, 4, 5 or 6;
n is an integer of 0, 1, 2, 3, 4 or 5;
X is S, S(=O), S(=O)$_2$, O, NR$^6$;
or a stereoisomer, a tautomer, an N-oxide, a hydrate, a solvate, or a salt thereof, or a mixture of same.

In another preferred embodiment, the invention relates to compounds of general formula I, supra, in which:
A represents a

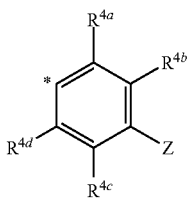

-group;
wherein * indicates the point of attachment of said groups with the rest of the molecule;
Z represents a —C(=O)N(H)R$^2$ or —C(=S)N(H)R$^2$ group, or a

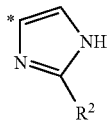

group;
wherein * indicates the point of attachment of said groups with the rest of the molecule;
R$^2$ represents a hydrogen atom, or a C$_1$-C$_6$-alkyl- or C$_3$-C$_6$-cycloalkyl-group;
R$^3$ represents a hydrogen atom or a halogen atom, or a —(CH$_2$)$_m$—C$_2$-C$_6$-alkenyl, —(CH$_2$)$_m$—C$_4$-C$_8$-cycloalkenyl —(CH$_2$)$_m$—C$_3$-C$_6$-cycloalkyl, —(CH$_2$)$_m$-(4- to 8-membered heterocycloalkenyl), aryl-, aryl-X—, heteroaryl-X—, heteroaryl-, —C(=O)N(H)R$^{6a}$, —OR$^6$, —SR$^6$, —S(=O)R$^6$, —S(=O)$_2$R$^6$, —S—(CH$_2$)$_n$—N(R$^{6a}$)R$^{6b}$, or —S—(CH$_2$)$_n$-(3- to 7-membered heterocycloalkyl) group;
wherein said aryl-, aryl-X—, heteroaryl-X— or heteroaryl-group is optionally substituted, identically or differently, with 1, 2, 3, or 4 R$^7$ groups;
either
R$^{4a}$, R$^{4c}$, R$^{4d}$ represent a hydrogen atom, and
R$^{4b}$ represents a hydrogen atom or a halogen atom or a C$_1$-C$_6$-alkyl group;
or
R$^{4b}$, R$^{4c}$, R$^{4d}$ represent a hydrogen atom, and
R$^{4a}$ represents a halogen atom or a C$_1$-C$_6$-alkyl-, or —OR$^6$ group;
R$^5$ represents a C$_1$-C$_6$-alkyl-, —(CH$_2$)$_m$-(3- to 7-membered heterocycloalkyl), aryl- or heteroaryl-group;
said C$_1$-C$_6$-alkyl-, —(CH$_2$)$_m$-(3- to 7-membered heterocycloalkyl), aryl- or heteroaryl-group is optionally substituted, identically or differently, with 1, 2, 3 or 4 R$^8$ groups;

R$^6$, R$^{6a}$, R$^{6b}$, R$^{6c}$,
represent, independently from each other, a hydrogen atom, or a C$_1$-C$_6$-alkyl-, HO—C$_1$-C$_6$-alkyl-, C$_3$-C$_6$-cycloalkyl- or aryl-group;
R$^7$ represents a hydrogen or halogen atom, or an HO—, —CN, C$_1$-C$_6$-alkoxy-, C$_1$-C$_6$-alkyl-, halo-C$_1$-C$_6$-alkyl-, HO—C$_1$-C$_6$-alkyl-, aryl-, heteroaryl-, —C(=O)N(R$^{6a}$)R$^{6b}$), —N(H)C(=O)R$^6$, —N(H)C(=O)N(R$^{6a}$)R$^{6b}$, —OR$^6$, —S(=O)R$^6$, or —S(=O)$_2$R$^6$ group; wherein said heteroaryl-group is optionally substituted with a C$_1$-C$_4$-alkyl group;
or
when 2 R$^7$ groups are present ortho- to each other on an aryl ring, said 2 R$^7$ groups together form a bridge:
*O(CH$_2$)$_2$O*, *O(CH$_2$)O*, *NH(C(=O))NH*, wherein * represent the point of attachment to said aryl ring;
R$^8$ represents a halogen atom, a —N(R$^{6a}$)R$^{6b}$, or —OR$^6$ group;
m is an integer of 0, 1, 2, 3, 4, 5 or 6;
X is S, S(=O), S(=O)$_2$, O, NR$^6$;
or a stereoisomer, a tautomer, an N-oxide, a hydrate, a solvate, or a salt thereof, or a mixture of same.

In another preferred embodiment, the invention relates to compounds of general formula I, supra, in which:
A represents a

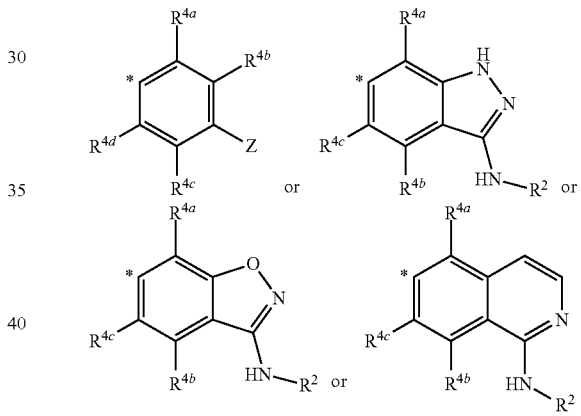

-group;
wherein * indicates the point of attachment of said groups with the rest of the molecule;
Z represents a —C(=O)N(H)R$^2$ or —C(=S)N(H)R$^2$ group, or a group selected from

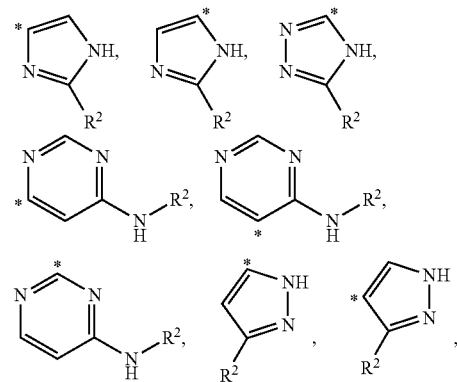

-continued

[Three pyrazole/imidazole structures with R² substituents and * attachment points]

wherein * indicates the point of attachment of said groups with the rest of the molecule;

$R^2$ represents a hydrogen atom, or a $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;

wherein said $C_3$-$C_6$-cycloalkyl-group is optionally substituted, identically or differently, with 1, 2, 3, or 4-groups selected from: halogen, OH, —CN, $C_1$-$C_6$-alkyl, —$C_1$-$C_6$-alkoxy, halo-$C_1$-$C_6$-alkyl-;

$R^3$ represents a hydrogen atom or a halogen atom, or a —CN, $C_1$-$C_6$-alkyl-, —$C_1$-$C_6$-alkoxy, —$(CH_2)_m$—$C_2$-$C_6$-alkenyl —$(CH_2)_m$—$C_4$-$C_8$-cycloalkenyl —$(CH_2)_m$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —OR$^6$, —SR$^6$, —S(=O)$R^6$, —S(=O)$_2R^6$, —S(=O)(=NR$^{6a}$)$R^{6b}$, —S(=O)$_2$N($R^{6b}$)$R^{6c}$, —S—$(CH_2)_n$—N($R^{6a}$)$R^{6b}$, or —S—$(CH_2)_n$-(3- to 7-membered heterocycloalkyl) group;

said $C_1$-$C_6$-alkyl-, —$C_1$-$C_6$-alkoxy, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group is optionally substituted, identically or differently, with 1, 2, 3, 4 or 5 $R^7$ groups;

$R^{4a}$, $R^{4b}$, $R^{4c}$, $R^{4d}$ represent, independently from each other, a hydrogen or halogen atom, or a —CN, $C_1$-$C_6$-alkyl-, $C_1$-$C_6$-alkoxy-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —OR$^6$, —O(C=O)$R^6$, —O(C=O)N($R^{6a}$)$R^{6b}$, —O(C=O)OR$^6$, —SR$^6$, —S(=O)$R^6$, —S(=O)N(H)$R^6$, —S(=O)N($R^{6a}$)$R^{6b}$, —S(=O)$_2R^6$, —S(=O)$_2$N(H)$R^{6a}$, —S(=O)$_2$N($R^{6a}$)$R^{6b}$, —S(=O)(=NR$^{6c}$)$R^6$ group;

$R^5$ represents a hydrogen atom, or a $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl-group;

wherein said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$, —$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_4$-$C_8$-cycloalkenyl-, aryl- or heteroaryl-group is optionally substituted, identically or differently, with 1, 2, 3, or 4 $R^8$ groups;

$R^6$, $R^{6a}$, $R^{6b}$, $R^{6c}$, represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —OR$^6$, —O(C=O)$R^6$, —O(C=O)N($R^{6a}$)$R^{6b}$, —O(C=O)OR$^6$, —SR$^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=NR$^{6c}$)$R^6$ group;

wherein said $C_1$-$C_6$-alkoxy-, aryl- or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups; or when 2 $R^7$ groups are present ortho- to each other on an aryl ring, said 2 $R^7$ groups together form a bridge:

*O$(CH_2)_2$O*, *O$(CH_2)$O*, *NH(C(=O))NH*, wherein * represent the point of attachment to said aryl ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ or —S(=O)$_2$-(3- to 7-membered heterocycloalkyl) group;

wherein said 3- to 7-membered heterocycloalkyl- or heteroaryl-group is optionally substituted, identically or differently, with 1, 2, 3, or 4 C$_1$-C$_6$-alkyl-groups;

m is an integer of 0, 1, 2, 3, 4, 5 or 6;

n is an integer of 0, 1, 2, 3, 4 or 5;

X is S, S(=O), S(=O)$_2$, O, NR$^6$;

or a stereoisomer, a tautomer, an N-oxide, a hydrate, a solvate, or a salt thereof, or a mixture of same.

In another preferred embodiment, the invention relates to compounds of general formula I, supra, in which:

A represents a

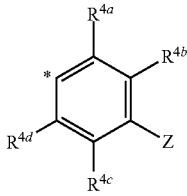

-group;

wherein * indicates the point of attachment of said groups with the rest of the molecule;

Z represents a —C(=O)N(H)R$^2$ or —C(=S)N(H)R$^2$ group, or a group selected from

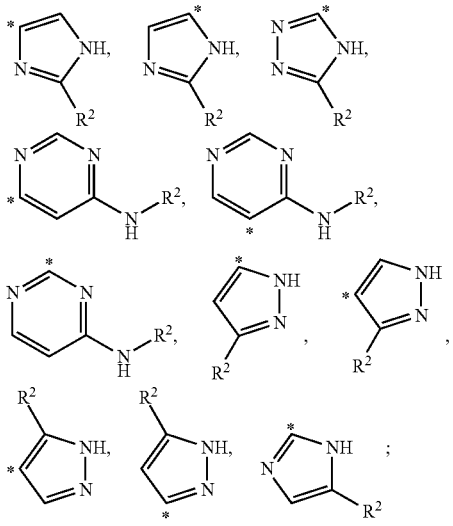

wherein * indicates the point of attachment of said groups with the rest of the molecule;

R$^2$ represents a hydrogen atom, or a C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl- or C$_3$-C$_6$-cycloalkyl-group;

wherein said C$_3$-C$_6$-cycloalkyl-group is optionally substituted, identically or differently, with 1, 2, 3, or 4-groups selected from: halogen, OH, —CN, C$_1$-C$_6$-alkyl, —C$_1$-C$_6$-alkoxy, halo-C$_1$-C$_6$-alkyl-;

R$^3$ represents a hydrogen atom or a halogen atom, or a —CN, C$_1$-C$_6$-alkyl-, —C$_1$-C$_6$-alkoxy, —(CH$_2$)$_m$—C$_2$-C$_6$-alkenyl, —(CH$_2$)$_m$—C$_4$-C$_8$-cycloalkenyl, —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, —C1-C6-alkyl-aryl, —C1-C6-alkyl-heteroaryl, heteroaryl-, C$_1$-C$_6$-alkyl-X—, —X— (CH$_2$)$_m$—C$_2$-C$_6$-alkenyl, —X— (CH$_2$)$_m$—C$_4$-C$_8$-cycloalkenyl, —X— (CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —OR$^6$, —SR$^6$, —S(=O)R$^6$, —S(=O)$_2$R$^6$, —S(=O)(=NR$^{6a}$)R$^{6b}$, —S(=O)$_2$N(R$^{6b}$)R$^{6c}$, —S—(CH$_2$)$_n$—N(R$^{6a}$)R$^{6b}$, or —S—(CH$_2$)$_n$-(3- to 7-membered heterocycloalkyl) group;

wherein said C$_1$-C$_6$-alkyl-, —C$_1$-C$_6$-alkoxy, —(CH$_2$)$_m$—C$_2$-C$_6$-alkenyl, —(CH$_2$)$_m$—C$_2$-C$_6$-alkynyl, —(CH$_2$)$_m$—C$_3$-C$_6$-cycloalkyl, aryl-C$_1$-C$_6$-alkyl-, heteroaryl-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, C$_1$-C$_6$-alkyl-X—, —X—(CH$_2$)$_m$—C$_2$-C$_6$-alkenyl, —X— (CH$_2$)$_m$—C$_4$-C$_8$-cycloalkenyl, —X—(CH$_2$)$_m$—C$_2$-C$_6$-alkynyl, —X—(CH$_2$)$_m$—C$_3$-C$_6$-cycloalkyl, —X—(CH$_2$)$_m$-(3- to 7-membered heterocycloalkyl), —X—(CH$_2$)$_m$-(4- to 8-membered heterocycloalkenyl), aryl-X—, heteroaryl-X—, —C$_1$-C$_6$-alkyl-aryl, —C$_1$-C$_6$-alkyl-heteroaryl or heteroaryl-group is optionally substituted, identically or differently, with 1, 2, 3, 4 or 5 R$^7$ groups;

R$^{4a}$, R$^{4b}$, R$^{4c}$, R$^{4d}$ represent, independently from each other, a hydrogen or halogen atom, or a —CN, C$_1$-C$_6$-alkyl-, C$_1$-C$_6$-alkoxy-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^{6a}$, —S(=O)$_2$N(R$^{6a}$)R$^{6b}$, —S(=O)(=NR$^{6c}$)R$^6$ group;

R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, a 3- to 7-membered heterocycloalkyl, C$_2$-C$_6$-alkenyl-, C$_4$-C$_8$-cycloalkenyl-, C$_2$-C$_6$-alkynyl-, aryl- or heteroaryl group;

wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl, a 3- to 7-membered heterocycloalkyl, C$_4$-C$_8$-cycloalkenyl-, aryl- or heteroaryl-group is optionally substituted, identically or differently, with 1, 2, 3, or 4 R$^8$ groups;

R$^6$, R$^{6a}$, R$^{6b}$, R$^{6c}$
represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl-, or heteroaryl-C$_1$-C$_6$-alkyl-group;

R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)$_2$R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$ or —S(=O)(=NR$^{6c}$)R$^6$ group;

wherein said C$_1$-C$_6$-alkoxy-, aryl- or heteroaryl-group is optionally substituted, identically or differently, with 1, 2, or 3 C$_1$-C$_6$-alkyl-, C$_1$-C$_6$-alkoxy-, halo-C$_1$-C$_6$-alkoxy-, —C(=O)O—R$^6$ or —OH groups;

or
when 2 R$^7$ groups are present ortho- to each other on an aryl ring, said 2 R$^7$ groups together form a bridge:
*O(CH$_2$)$_2$O*, *O(CH$_2$)O*, *NH(C(=O))NH*, wherein * represent the point of attachment to said aryl group;

R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ group, —S(=O)$_2$-(3- to 7-membered heterocycloalkyl);

wherein said 3- to 7-membered heterocycloalkyl- or heteroaryl-, is optionally substituted, identically or differently, with 1, 2, 3, or 4 C$_1$-C$_6$-alkyl-groups;

m is an integer of 0, 1, 2, 3, 4, 5 or 6;
n is an integer of 0, 1, 2, 3, 4 or 5;
X is S, S(=O), S(=O)$_2$, O, NR$^6$;
or a stereoisomer, a tautomer, an N-oxide, a hydrate, a solvate, or a salt thereof, or a mixture of same.

In another preferred embodiment, the invention relates to compounds of general formula I, supra, in which:
A represents a

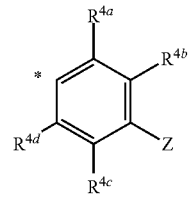

-group;
wherein * indicates the point of attachment of said groups with the rest of the molecule;
Z represents a —C(=O)N(H)R$^2$ or —C(=S)N(H)R$^2$ group, or a group selected from

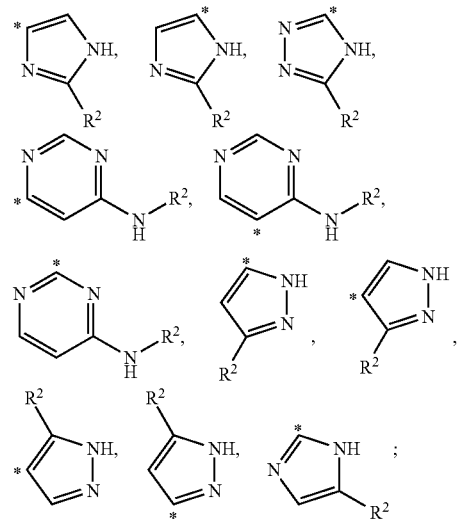

wherein * indicates the point of attachment of said groups with the rest of the molecule;

R$^2$ represents a hydrogen atom, or a C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl- or C$_3$-C$_6$-cycloalkyl-group;

wherein said C$_3$-C$_6$-cycloalkyl-group is optionally substituted, identically or differently, with 1, 2, 3, or 4-groups selected from: halogen, OH, —CN, C$_1$-C$_6$-alkyl, —C$_1$-C$_6$-alkoxy, halo-C$_1$-C$_6$-alkyl-;

R$^3$ represents a hydrogen atom or a halogen atom, or a —CN, C$_1$-C$_6$-alkyl-, C$_1$-C$_6$-alkoxy-, —(CH$_2$)$_m$—C$_2$-C$_6$-alkenyl, —(CH$_2$)$_m$—C$_4$-C$_8$-cycloalkenyl —(CH$_2$)$_m$—C$_2$-C$_6$-alkynyl, —(CH$_2$)$_m$—C$_3$-C$_6$-cycloalkyl, —(CH$_2$)$_m$-(3- to 7-membered heterocycloalkyl), —(CH$_2$)$_m$-(4- to 8-membered heterocycloalkenyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl-, —C1-C6-alkyl-aryl, —C1-C6-alkyl-heteroaryl, heteroaryl-, C$_1$-C$_6$-alkyl-X—, —X— (CH$_2$)$_m$—C$_2$-C$_6$-alkenyl, —X— (CH$_2$)$_m$—C$_4$-C$_8$-cycloalkenyl, —X—

$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —O$R^6$, —S$R^6$, —S(=O)$R^6$, —S(=O)$_2R^6$, —S(=O)(=N$R^{6a}$)$R^{6b}$, —S(=O)$_2$N($R^{6b}$)$R^{6c}$, —S—$(CH_2)_n$—N($R^{6a}$)$R^{6b}$, or —S—$(CH_2)_n$-(3- to 7-membered heterocycloalkyl) group;

wherein said $C_1$-$C_6$-alkyl-, —$C_1$-$C_6$-alkoxy, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group is optionally substituted, identically or differently, with 1, 2, 3, 4 or 5 $R^7$ groups;

either $R^{4a}$, $R^{4c}$, $R^{4d}$ represent a hydrogen atom, and $R^{4b}$ represents a hydrogen atom or a halogen atom or a $C_1$-$C_6$-alkyl group;

or $R^{4b}$, $R^{4c}$, $R^{4d}$ represent a hydrogen atom, and $R^{4a}$ represents a halogen atom or an $C_1$-$C_6$-alkyl-, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^{6a}$, —S(=O)$_2$N($R^{6a}$)$R^{6b}$, —S(=O)(=N$R^{6c}$)$R^6$ group;

$R^5$ represents a hydrogen atom, or a $C_1$-$C_6$-alkyl-, —$(CH_2)_n$—$C_2$-$C_6$-alkenyl, —$(CH_2)_n$—$C_2$-$C_6$-alkynyl, —$(CH_2)$, —$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl- or heteroaryl group;

wherein said $C_1$-$C_6$-alkyl-, —$(CH_2)_n$—$C_2$-$C_6$-alkenyl, —$(CH_2)_n$—$C_2$-$C_6$-alkynyl, —$(CH_2)_n$, —$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_4$-$C_8$-cycloalkenyl-, aryl- or heteroaryl-group is optionally substituted, identically or differently, with 1, 2, 3, or 4 $R^8$ groups;

$R^6$, $R^{6a}$, $R^{6b}$, $R^{6c}$, represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ group;

wherein said $C_1$-$C_6$-alkoxy-, aryl- or heteroaryl-group is optionally substituted, identically or differently, with 1, 2 or 3 $C_1$-$C_6$-alkyl-, $C_1$-$C_6$-alkoxy-, halo-$C_1$-$C_6$-alkoxy-, —C(=O)O—$R^6$ or —OH groups;

or when 2 $R^7$ groups are present ortho- to each other on an aryl ring, said 2 $R^7$ groups together form a bridge:

*O(CH$_2$)$_2$O*, *O(CH$_2$)O*, *NH(C(=O))NH*, wherein * represent the point of attachment to said aryl ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ group, —S(=O)$_2$-(3- to 7-membered heterocycloalkyl);

wherein said 3- to 7-membered heterocycloalkyl- or heteroaryl-group is optionally substituted, identically or differently, with 1, 2, 3 or 4 $C_1$-$C_6$-alkyl-groups;

m is an integer of 0, 1, 2, 3, 4, 5 or 6;

n is an integer of 0, 1, 2, 3, 4 or 5;

X is S, S(=O), S(=O)$_2$, O, N$R^6$;

or a stereoisomer, a tautomer, an N-oxide, a hydrate, a solvate, or a salt thereof, or a mixture of same.

In another preferred embodiment, the invention relates to compounds of general formula I, supra, in which:

A represents a

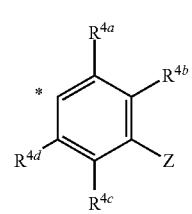

-group;

wherein * indicates the point of attachment of said groups with the rest of the molecule;

Z represents a —C(=O)N(H)R² or —C(=S)N(H)R² group, or a group selected from

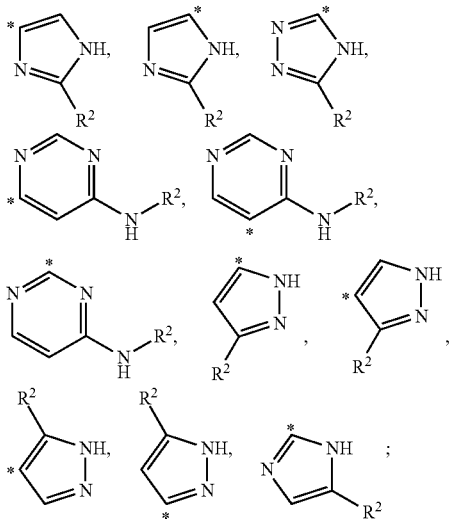

wherein * indicates the point of attachment of said groups with the rest of the molecule;

R² represents a hydrogen atom, or a $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-group;

wherein said $C_3$-$C_6$-cycloalkyl-group is optionally substituted, identically or differently, with 1, 2, 3, or 4-groups selected from: halogen, OH, —CN, $C_1$-$C_6$-alkyl, —$C_1$-$C_6$-alkoxy, halo-$C_1$-$C_6$-alkyl-;

R³ represents a hydrogen atom or a halogen atom, or a —CN, $C_1$-$C_6$-alkyl-, —$C_1$-$C_6$-alkoxy, —$(CH_2)_n$—, —$C_2$-$C_6$-alkenyl —$(CH_2)_n$—, —$C_4$-$C_8$-cycloalkenyl —$(CH_2)_m$—, —$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, $C_1$-$C_6$-alkyl-X—, —X—$(CH_2)_m$—$C_2$-$C_6$-alkenyl, —X—$(CH_2)_n$, —$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —C(=O)R⁶, —C(=O)N(H)$R^{6a}$, —C(=O)N($R^{6a}$)$R^{6b}$, —C(=O)O—R⁶, —N($R^{6a}$)$R^{6b}$, —NO₂, —N(H)C(=O)R⁶, —OR⁶, —SR⁶, —S(=O)R⁶, —S(=O)₂R⁶, —S(=O)(=$NR^{6a}$)$R^{6b}$, —S(=O)₂N($R^{6b}$)$R^{6c}$, —S—$(CH_2)_n$—N($R^{6a}$)$R^{6b}$, or —S—$(CH_2)_n$-(3- to 7-membered heterocycloalkyl) group;

wherein said $C_1$-$C_6$-alkyl-, —$C_1$-$C_6$-alkoxy, —$(CH_2)_m$—$C_2$-$C_6$-alkenyl, —$(CH_2)_m$—$C_2$-$C_6$-alkynyl, —$(CH_2)_m$—$C_3$-$C_6$-cycloalkyl, aryl-$C_1$-$C_6$-alkyl-, heteroaryl-$C_1$-$C_6$-alkyl-, $C_3$-$C_6$-cycloalkyl-, 3- to 7-membered heterocycloalkyl-, $C_2$-$C_6$-alkenyl-, $C_4$-$C_8$-cycloalkenyl-, $C_2$-$C_6$-alkynyl-, aryl-, $C_1$-$C_6$-alkyl-X—, —X—$(CH_2)_m$—$C_2$-$C_6$-alkenyl, —X—$(CH_2)_m$—$C_4$-$C_8$-cycloalkenyl, —X—$(CH_2)_m$—$C_2$-$C_6$-alkynyl, —X—$(CH_2)_m$—$C_3$-$C_6$-cycloalkyl, —X—$(CH_2)_m$-(3- to 7-membered heterocycloalkyl), —X—$(CH_2)_m$-(4- to 8-membered heterocycloalkenyl), aryl-X—, heteroaryl-X—, —$C_1$-$C_6$-alkyl-aryl, —$C_1$-$C_6$-alkyl-heteroaryl or heteroaryl-group is optionally substituted, identically or differently, with 1, 2, 3, 4 or 5 R⁷ groups;

either $R^{4a}$, $R^{4c}$, $R^{4d}$ represent a hydrogen atom, and $R^{4b}$ represents a hydrogen atom or a halogen atom or a $C_1$-$C_6$-alkyl group;

or $R^{4b}$, $R^{4c}$, $R^{4d}$ represent a hydrogen atom, and $R^{4a}$ represents a halogen atom or an $C_1$-$C_6$-alkyl-, or —$OR^6O)R^6$, —O(C=O)N($R^{6a}$)$R^{6b}$, —O(C=O)OR⁶, —SR⁶, —S(=O)R⁶, —S(=O)N(H)R⁶, —S(=O)N($R^{6a}$)$R^{6b}$, —S(=O)₂R⁶, —S(=O)₂N(H)$R^{6a}$, —S(=O)₂N($R^{6a}$)$R^{6b}$, —S(=O)(=$NR^{6c}$)R⁶ group;

R⁵ represents a hydrogen atom, or a $C_1$-$C_6$-alkyl-, —$(CH_2)_m$-(3- to 7-membered heterocycloalkyl), aryl- or heteroaryl group;

said $C_1$-$C_6$-alkyl-, —$(CH_2)_m$-(3- to 7-membered heterocycloalkyl), aryl- or heteroaryl-group is optionally substituted, identically or differently, with 1, 2, 3, or 4 R⁸ groups;

R⁶, $R^{6a}$, $R^{6b}$, $R^{6C}$, represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-C1-C6-alkyl-group;

R⁷ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)R⁶, —C(=O)N(H)$R^{6a}$, —C(=O)N($R^{6a}$)$R^{6b}$, —C(=O)O—R⁶, —N($R^{6a}$)$R^{6b}$, —NO₂, —N(H)C(=O)R⁶, —N($R^{6c}$)C(=O)R⁶, —N(H)C(=O)N($R^{6a}$)$R^{6b}$, —N($R^{6c}$)C(=O)N($R^{6a}$)$R^{6b}$, —N(H)C(=O)OR⁶, —N($R^{6c}$)C(=O)OR⁶, —N(H)S(=O)R⁶, —N($R^{6c}$)S(=O)R⁶, —N(H)S(=O)₂R⁶, —N($R^{6c}$)S(=O)₂R⁶, —N=S(=O)($R^{6a}$)$R^{6b}$, —OR⁶, —O(C=O)R⁶, —O(C=O)N($R^{6a}$)$R^{6b}$, —O(C=O)OR⁶, —SR⁶, —S(=O)R⁶, —S(=O)N(H)R⁶, —S(=O)N($R^{6a}$)$R^{6b}$, —S(=O)₂R⁶, —S(=O)₂N(H)R⁶, —S(=O)₂N($R^{6a}$)$R^{6b}$, —S(=O)(=$NR^{6c}$)R⁶ group;

wherein said $C_1$-$C_6$-alkoxy-, aryl- or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—R⁶ or —OH groups;

or when 2 R⁷ groups are present ortho- to each other on an aryl ring, said 2 R⁷ groups together form a bridge:
*O(CH₂)₂O*, *O(CH₂)O*, *NH(C(=O))NH*, wherein * represent the point of attachment to said aryl ring;

R⁸ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)R⁶, —C(=O)N(H)$R^{6a}$, —C(=O)N($R^{6a}$)$R^{6b}$, —C(=O)O—R⁶, —N($R^{6a}$)$R^{6b}$, —NO₂, —N(H)C(=O)R⁶, —N($R^{6c}$)C(=O)R⁶, —N(H)C(=O)N($R^{6a}$)$R^{6b}$, —N($R^{6c}$)C(=O)N($R^{6a}$)$R^{6b}$, —N(H)C(=O)OR⁶, —N($R^{6c}$)C(=O)OR⁶, —N(H)S(=O)R⁶, —N($R^{6c}$)S(=O)R⁶, —N(H)S(=O)₂R⁶, —N($R^{6c}$)S(=O)₂R⁶, —N=S(=O)($R^{6a}$)$R^{6b}$, —OR⁶, —O(C=O)R⁶, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, —S(=O)(=NR$^{6c}$)R$^6$ group, —S(=O)$_2$-(3- to 7-membered heterocycloalkyl);

wherein said 3- to 7-membered heterocycloalkyl- or heteroaryl-group is optionally substituted, identically or differently, with 1, 2, 3, or 4 C$_1$-C$_6$-alkyl-groups;

m is an integer of 0, 1, 2, 3, 4, 5 or 6;

n is an integer of 0, 1, 2, 3, 4 or 5;

X is S, S(=O), S(=O)$_2$, O, NR$^6$;

or a stereoisomer, a tautomer, an N-oxide, a hydrate, a solvate, or a salt thereof, or a mixture of same.

WO 2011/013729A1 discloses IC$_{50}$ values for the inhibition of Mps-1 (TTK) for a couple of compounds of formula C1, supra. However, WO 2011/013729A1 does not disclose any information about the metabolic stability of the compounds.

The inventors of the present invention surprisingly observed that compounds of general formula I, supra, in which R$^3$ is an aryl-X— or heteroaryl-X— group, and in which at least one of the groups R$^{4c}$ and R$^{4b}$ is not a hydrogen atom show a high inhibitory activity as well as a high metabolic stability.

Hence, in another preferred embodiment, the invention relates to compounds of general formula I:

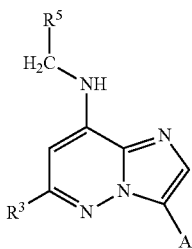

I in which:

A represents

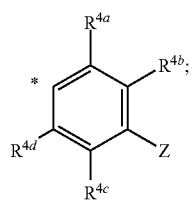

wherein * indicates the point of attachment of said groups with the rest of the molecule;

Z represents a —C(=O)N(H)R$^2$ or a —C(=S)N(H)R$^2$ group;

R$^2$ represents a hydrogen atom, or a C$_1$-C$_6$-alkyl- or C$_3$-C$_6$-cycloalkyl-group;

wherein said C$_1$-C$_6$-alkyl- or C$_3$-C$_6$-cycloalkyl-group is optionally substituted, identically or differently, with 1, 2, 3, or 4 groups selected from:

halogen, —OH, —CN, —C$_1$-C$_6$-alkyl, —C$_1$-C$_6$-alkoxy;

R$^3$ represents an aryl-X— or a heteroaryl-X— group, or a

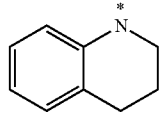

group, in which * indicates the point of attachment of said group with the rest of the molecule;

wherein said aryl-X—, heteroaryl-X— or

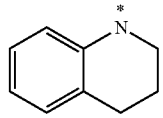

group is optionally substituted, identically or differently, with 1, 2, 3, 4 or 5 R$^7$ groups;

R$^{4a}$, R$^{4b}$, R$^{4c}$, R$^{4d}$ represent, independently from each other, a hydrogen or halogen atom, or a —CN, —OH, C$_1$-C$_6$-alkyl-, C$_1$-C$_6$-alkoxy-, halo-C$_1$-C$_6$-alkyl-, halo-C$_1$-C$_6$-alkoxy-, R$^{6a}$(R$^{6b}$)N—C$_1$-C$_6$-alkyl-, HO—C$_1$-C$_6$-alkyl-, NC—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-group;

with the proviso that at least one of the groups R$^{4b}$ and R$^{4c}$ is not a hydrogen atom;

R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_2$-C$_6$-alkenyl-, C$_4$-C$_3$-cycloalkenyl-, C$_2$-C$_6$-alkynyl-, aryl- or heteroaryl-group;

said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_4$-C$_8$-cycloalkenyl-, aryl- or heteroaryl-group is optionally substituted, identically or differently, with 1, 2, 3, or 4 R$^8$ groups;

R$^6$, R$^{6a}$, R$^{6b}$, R$^{6c}$, represent, independently from each other, a hydrogen atom, or a C$_1$-C$_6$-alkyl, HO—C$_1$-C$_6$-alkyl-, C$_3$-C$_6$-cycloalkyl, C$_2$-C$_6$-alkenyl, 3- to 7-membered heterocycloalkyl, aryl, heteroaryl, aryl-C$_1$-C$_6$-alkyl-, or heteroaryl-C$_1$-C$_6$-alkyl-group;

R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, H$_2$N—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)

$R^{6b}$, —S(=O)$_2$R$^6$, —S(=O)$_2$N(H)R$^6$, —S(=O)$_2$N(R$^{6a}$)R$^{6b}$, or —S(=O)(=NR$^{6c}$)R$^6$ group;

wherein said C$_1$-C$_6$-alkoxy-, aryl-, 3- to 7-membered heterocycloalkyl, or heteroaryl-group is optionally substituted, identically or differently, with 1, 2, or 3 C$_1$-C$_6$-alkyl-, C$_1$-C$_6$-alkoxy-, halo-C$_1$-C$_6$-alkoxy-, —C(=O)O—R$^6$ or —OH groups;

or when 2 R$^7$ groups are present ortho to each other on an aryl or heteroaryl ring, said 2 R$^7$ groups together form a bridge:
*O(CH$_2$)$_2$O*, *O(CH$_2$)O*, *CH$_2$(CH$_2$)$_2$NH*, *CH$_2$CH$_2$N(R$^{6a}$)CH$_2$*, *NH(C(=O))NH*, *C(H)=C(H)—C(=O)—N(H)*, wherein * represent the point of attachment to said aryl or heteroaryl ring;

R$^8$ represents a hydrogen or halogen atom, or a —CN, —OH, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$OH, —S(=O)$_2$N(H)R$^6$, —S(=O)$_2$N(R$^{6a}$)R$^{6b}$, —S(=O)(=NR$^{6c}$)R$^6$ group, —S(=O)$_2$-(3- to 7-membered heterocycloalkyl);

wherein said 3- to 7-membered heterocycloalkyl- or heteroaryl-group is optionally substituted, identically or differently, with 1, 2, 3, or 4 C$_1$-C$_6$-alkyl-groups;

m is an integer of 0, 1, 2, 3, 4, 5 or 6;
n is an integer of 0, 1, 2, 3, 4 or 5; and
X is S, S(=O), S(=O)$_2$, O, NR$^6$, CR$^{6a}$R$^{6b}$, C=CR$^{6a}$R$^{6b}$.

In another preferred embodiment, the invention relates to compounds of formula I

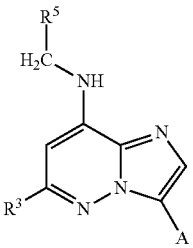

I in which:
A represents

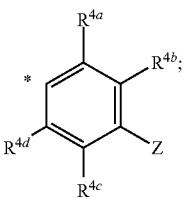

wherein * indicates the point of attachment of said groups with the rest of the molecule;
Z represents a —C(=O)N(H)R$^2$ or a —C(=S)N(H)R$^2$ group;
R$^2$ represents a hydrogen atom, or a C$_1$-C$_6$-alkyl- or C$_3$-C$_6$-cycloalkyl-group;

wherein said C$_1$-C$_6$-alkyl- or C$_3$-C$_6$-cycloalkyl-group is optionally substituted, identically or differently, with 1, 2, 3, or 4 groups selected from:
halogen, —OH, —CN, —C$_1$-C$_6$-alkyl, —C$_1$-C$_6$-alkoxy;
R$^3$ represents an aryl-X— or a heteroaryl-X— group, or a

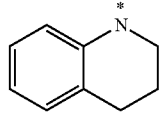

group, in which * indicates the point of attachment of said group with the rest of the molecule;
wherein said aryl-X—, heteroaryl-X— or

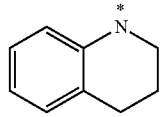

group
is optionally substituted, identically or differently, with 1, 2, 3, 4 or 5 R$^7$ groups;
R$^{4a}$ represents hydrogen;
R$^{4d}$ represents hydrogen;
one of the groups R$^{4b}$ and R$^{4c}$ represents a hydrogen atom while the other one represents a group selected from: halo-, —CN, —OH, C$_1$-C$_6$-alkyl- and C$_1$-C$_6$-alkoxy-;
R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_2$-C$_6$-alkenyl-, C$_4$-C$_8$-cycloalkenyl-, C$_2$-C$_6$-alkynyl-, aryl- or heteroaryl-group;
said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_4$-C$_8$-cycloalkenyl-, aryl- or heteroaryl-group
is optionally substituted, identically or differently, with 1, 2, 3, or 4 R$^8$ groups;
R$^6$, R$^{6a}$, R$^{4b}$, R$^{4c}$,
represent, independently from each other, a hydrogen atom, or a C$_1$-C$_6$-alkyl, HO—C$_1$-C$_6$-alkyl-, C$_3$-C$_6$-cycloalkyl, C$_2$-C$_6$-alkenyl, 3- to 7-membered heterocycloalkyl, aryl, heteroaryl, aryl-C$_1$-C$_6$-alkyl-, or heteroaryl-C$_1$-C$_6$-alkyl-group;
R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, H$_2$N—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, or —S(=O)(=N$R^{6c}$)$R^6$ group;

wherein said $C_1$-$C_6$-alkoxy-, aryl-, 3- to 7-membered heterocycloalkyl, or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups;

or when 2 $R^7$ groups are present ortho to each other on an aryl or heteroaryl ring, said 2 R' groups together form a bridge:

*O(CH$_2$)$_2$O*, *O(CH$_2$)O*, *CH$_2$(CH$_2$)$_2$NH*, *CH$_2$CH$_2$N($R^{6a}$)CH$_2$*, *NH(C(=O))NH*, *C(H)=C(H)—C(=O)—N(H)*, wherein * represent the point of attachment to said aryl or heteroaryl ring;

$R^8$ represents a hydrogen or halogen atom, or a —CN, —OH, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$OH, —S(=O)$_2$N(H)$R^6$, —S(=O)$_2$N($R^{6a}$)$R^{6b}$, —S(=O)(=N$R^{6c}$)$R^6$ group, —S(=O)$_2$-(3- to 7-membered heterocycloalkyl);

wherein said 3- to 7-membered heterocycloalkyl- or heteroaryl-group is optionally substituted, identically or differently, with 1, 2, 3, or 4 $C_1$-$C_6$-alkyl-groups;

m is an integer of 0, 1, 2, 3, 4, 5 or 6;

n is an integer of 0, 1, 2, 3, 4 or 5; and

X is S, S(=O), S(=O)$_2$, O, N$R^6$, C$R^{6a}$$R^{6b}$, C=C$R^{6a}$$R^{6b}$.

In another preferred embodiment, the invention relates to compounds of formula I

I in which:

A represents wherein * indicates the point of attachment of said groups with the rest of the molecule;

Z represents a —C(=O)N(H)$R^2$ or a —C(=S)N(H)$R^2$ group;

$R^2$ represents a $C_1$-$C_3$-alkyl- or $C_3$-$C_6$-cycloalkyl-group;

wherein said $C_1$-$C_3$-alkyl- or $C_3$-$C_6$-cycloalkyl-group is optionally substituted, identically or differently, with 1, 2 or 3 groups selected from:

halogen, —OH, —CN, —$C_1$-$C_6$-alkyl, —$C_1$-$C_6$-alkoxy;

$R^3$ represents an aryl-X— or a heteroaryl-X— group, or a group, in which * indicates the point of attachment of said group with the rest of the molecule;

wherein said aryl-X—, heteroaryl-X— or group is optionally substituted, identically or differently, with 1, 2, 3, 4 or 5 $R^7$ groups;

$R^{4a}$ represents hydrogen;

$R^{4d}$ represents hydrogen;

one of the groups $R^{4b}$ and $R^{4c}$ represents a hydrogen atom while the other one represents a group selected from: halo-, —CN, —OH, $C_1$-$C_6$-alkyl- and $C_1$-$C_6$-alkoxy-;

$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl, $C_2$-$C_6$-alkenyl-, $C_4$-$C_8$-cycloalkenyl-, $C_2$-$C_6$-alkynyl-, aryl- or heteroaryl-group;

said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to to 7-membered heterocycloalkyl, $C_4$-$C_8$-cycloalkenyl-, aryl- or heteroaryl-group is optionally substituted, identically or differently, with 1, 2, 3, or 4 $R^8$ groups;

$R^6$, $R^{6a}$, $R^{6b}$, $R^{6c}$, represent, independently from each other, a hydrogen atom, or a $C_1$-$C_6$-alkyl, HO—$C_1$-$C_6$-alkyl-, $C_3$-$C_6$-cycloalkyl, $C_2$-$C_6$-alkenyl, 3- to 7-membered heterocycloalkyl, aryl, heteroaryl, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, H$_2$N—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)

$R^{6b}$, —S(=O)$_2$R$^6$, —S(=O)$_2$N(H)R$^6$, —S(=O)$_2$N(R$^{6a}$)R$^{6b}$, or —S(=O)(=NR$^{6c}$)R$^6$ group;
  wherein said C$_1$-C$_6$-alkoxy-, aryl-, 3- to 7-membered heterocycloalkyl, or heteroaryl-group is optionally substituted, identically or differently, with 1, 2, or 3 C$_1$-C$_6$-alkyl-, C$_1$-C$_6$-alkoxy-, halo-C$_1$-C$_6$-alkoxy-, —C(=O)O—R$^6$ or —OH groups;
or
when 2 R$^7$ groups are present ortho to each other on an aryl or heteroaryl ring, said 2 R$^7$ groups together form a bridge:
  *O(CH$_2$)$_2$O*, *O(CH$_2$)O*, *CH$_2$(CH$_2$)$_2$NH*, *CH$_2$CH$_2$N(R$^{6a}$)CH$_2$*, *NH(C(=O))NH*, *C(H)=C(H)—C(=O)—N(H)*,
  wherein * represent the point of attachment to said aryl or heteroaryl ring;
R$^8$ represents a hydrogen or halogen atom, or a —CN, —OH, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$OH, —S(=O)$_2$N(H)R$^6$, —S(=O)$_2$N(R$^{6a}$)R$^{6b}$, —S(=O)(=NR$^{6c}$)R$^6$ group, —S(=O)$_2$-(3- to 7-membered heterocycloalkyl);
  wherein said 3- to 7-membered heterocycloalkyl- or heteroaryl-group is optionally substituted, identically or differently, with 1, 2, 3, or 4 C$_1$-C$_6$-alkyl-groups;
m is an integer of 0, 1, 2, 3, 4, 5 or 6;
n is an integer of 0, 1, 2, 3, 4 or 5; and
X is S, S(=O), S(=O)$_2$, O, NR$^6$, CR$^{6a}$R$^{6b}$, C=CR$^{6a}$R$^{6b}$.

In another preferred embodiment, the invention relates to compounds of formula I

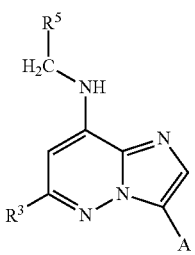

I in which:
A represents

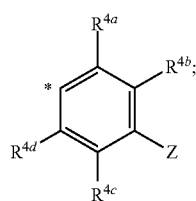

wherein * indicates the point of attachment of said groups with the rest of the molecule;

Z represents a —C(=O)N(H)R$^2$ or a —C(=S)N(H)R$^2$ group;
R$^2$ represents a C$_1$-C$_3$-alkyl- or C$_3$-C$_6$-cycloalkyl-group;
  wherein said C$_1$-C$_3$-alkyl- or C$_3$-C$_6$-cycloalkyl-group is optionally substituted, identically or differently, with 1, 2 or 3 groups selected from:
  halogen, —OH, —CN, —C$_1$-C$_6$-alkyl, —C$_1$-C$_6$-alkoxy;
R$^3$ represents a group selected from:
  phenyl-X, quinolinyl-X—, pyridyl-X—, thienyl-X—, pyrazinyl-X—, imidazyl-X—, triazyl-X—, pyrazyl-X— and

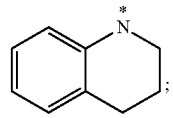

wherein said group is optionally substituted, identically or differently, with 1, 2, 3, 4 or 5 R$^7$ groups;
R$^{4a}$ represents hydrogen;
R$^{4d}$ represents hydrogen;
one of the groups R$^{ob}$ and R$^{4c}$ represents a hydrogen atom while the other one represents halo- or a C$_1$-C$_6$-alkyl-group;
R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_2$-C$_6$-alkenyl-, C$_4$-C$_8$-cycloalkenyl-, C$_2$-C$_6$-alkynyl-, aryl- or heteroaryl-group;
said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl, C$_4$-C$_8$-cycloalkenyl-, aryl- or heteroaryl-group
is optionally substituted, identically or differently, with 1, 2, 3, or 4 R$^8$ groups;
R$^6$, R$^{6a}$, R$^{6b}$, R$^{4c}$
represent, independently from each other, a hydrogen atom, or a C$_1$-C$_6$-alkyl, HO—C$_1$-C$_6$-alkyl-, C$_3$-C$_6$-cycloalkyl, C$_2$-C$_6$-alkenyl, 3- to 7-membered heterocycloalkyl, aryl, heteroaryl, aryl-C$_1$-C$_6$-alkyl-, or heteroaryl-C$_1$-C$_6$-alkyl-group;
R$^1$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, H$_2$N—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, —NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$, or —S(=O)(=NR$^{6c}$)R$^6$ group;
  wherein said C$_1$-C$_6$-alkoxy-, aryl-, 3- to 7-membered heterocycloalkyl, or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups;
or
when 2 $R^7$ groups are present ortho to each other on an aryl or heteroaryl ring, said 2 $R^7$ groups together form a bridge:
*O(CH$_2$)$_2$O*, *O(CH$_2$)O*, *CH$_2$(CH$_2$)$_2$NH*, *CH$_2$CH$_2$N(R$^{6a}$)CH$_2$*, *NH(C(=O))NH*, *C(H)=C(H)—C(=O)—N(H)*,
wherein * represent the point of attachment to said aryl or heteroaryl ring;
$R^8$ represents a hydrogen or halogen atom, or a —CN, —OH, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —OR$^6$, —O(C=O)$R^6$, —O(C=O)N($R^{6a}$)$R^{6b}$, —O(C=O)OR$^6$, —SR$^6$, —S(=O)$R^6$, —S(=O)N(H)$R^6$, —S(=O)N($R^{6a}$)$R^{6b}$, —S(=O)$_2$$R^6$, —S(=O)$_2$OH, —S(=O)$_2$N(H)$R^6$, —S(=O)$_2$N($R^{6a}$)$R^{6b}$, —S(=O)(=NR$^{6c}$)$R^6$ group, —S(=O)$_2$-(3- to 7-membered heterocycloalkyl);
wherein said 3- to 7-membered heterocycloalkyl- or heteroaryl-group is optionally substituted, identically or differently, with 1, 2, 3, or 4 $C_1$-$C_6$-alkyl-groups;
m is an integer of 0, 1, 2, 3, 4, 5 or 6;
n is an integer of 0, 1, 2, 3, 4 or 5; and
X is S, S(=O), S(=O)$_2$, O, NR$^6$, CR$^{6a}$R$^{6b}$, C=CR$^{6a}$R$^{6b}$.
In another preferred embodiment, the invention relates to compounds of formula I

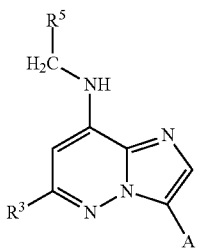

I in which:
A represents

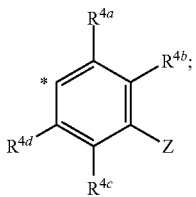

wherein * indicates the point of attachment of said groups with the rest of the molecule;
Z represents a —C(=O)N(H)$R^2$ or a —C(=S)N(H)$R^2$ group;
$R^2$ represents a $C_1$-$C_3$-alkyl- or $C_3$-$C_6$-cycloalkyl-group;
wherein said $C_1$-$C_3$-alkyl- or $C_3$-$C_6$-cycloalkyl-group is optionally substituted, identically or differently, with 1, 2 or 3 groups selected from:
halogen, —OH, —CN, —$C_1$-$C_6$-alkyl, —$C_1$-$C_6$-alkoxy;

$R^3$ represents a group selected from:
phenyl-X, quinolinyl-X—, pyridyl-X—, thienyl-X—, pyrazinyl-X—, imidazyl-X—, triazyl-X—, pyrazyl-X— and

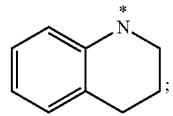

wherein said group is optionally substituted, identically or differently, with 1, 2, 3, 4 or 5 $R^7$ groups;
$R^{4a}$ represents hydrogen;
$R^{4d}$ represents hydrogen;
one of the groups $R^{4b}$ and $R^{4c}$ represents a hydrogen atom while the other one represents a $C_1$-$C_4$-alkyl-group;
$R^5$ represents a hydrogen atom, or a $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, or heteroaryl-group;
said $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, heteroaryl-group is optionally substituted, identically or differently, with 1, 2, 3, or 4 $R^8$ groups;
$R^6$, $R^{6a}$, $R^{6b}$, $R^{4c}$,
represent, independently from each other, a hydrogen atom, or a $C_1$-$C_6$-alkyl, HO—$C_1$-$C_6$-alkyl-, $C_3$-$C_6$-cycloalkyl, $C_2$-$C_6$-alkenyl, 3- to 7-membered heterocycloalkyl, aryl, heteroaryl, aryl-$C_1$-$C_6$-alkyl-, or heteroaryl-$C_1$-$C_6$-alkyl-group;
$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, H$_2$N—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —OR$^6$, —O(C=O)$R^6$, —O(C=O)N($R^{6a}$)$R^{6b}$, —O(C=O)OR$^6$, —SR$^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$^2$N($R^{6a}$)$R^{6b}$, or —S(=O)(=NR$^{6c}$)$R^6$ group;
wherein said $C_1$-$C_6$-alkoxy-, aryl-, 3- to 7-membered heterocycloalkyl, or heteroaryl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups;
or
when 2 $R^7$ groups are present ortho to each other on an aryl or heteroaryl ring, said 2 $R^7$ groups together form a bridge:
*O(CH$_2$)$_2$O*, *O(CH$_2$)O*, *CH$_2$(CH$_2$)$_2$NH*, *CH$_2$CH$_2$N(R$^{6a}$)CH$_2$*, *NH(C(=O))NH*, *C(H)=C(H)—C(=O)—N(H)*,
wherein * represent the point of attachment to said aryl or heteroaryl ring;
$R^8$ represents a hydrogen or halogen atom, or a —CN, —OH, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)OR$^6$, —N($R^{6c}$)C(=O)OR$^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)(R⁶ᵃ)R⁶ᵇ, —OR⁶, —O(C=O)R⁶, —O(C=O)N(R⁶ᵃ)R⁶ᵇ, —O(C=O)OR⁶, —SR⁶, —S(=O)R⁶, —S(=O)N(H)R⁶, —S(=O)N(R⁶ᵃ)R⁶ᵇ, —S(=O)₂R⁶, —S(=O)₂OH, —S(=O)₂N(H)R⁶, —S(=O)₂N(R⁶ᵃ)R⁶ᵇ, —S(=O)(=NR⁶ᶜ)R⁶ group, —S(=O)₂-(3- to 7-membered heterocycloalkyl);
wherein said 3- to 7-membered heterocycloalkyl- or heteroaryl-group is optionally substituted, identically or differently, with 1, 2, 3, or 4 $C_1$-$C_6$-alkyl-groups;
m is an integer of 0, 1, 2, 3, 4, 5 or 6;
n is an integer of 0, 1, 2, 3, 4 or 5; and
X is S, S(=O), S(=O)₂, O, NR⁶, CR⁶ᵃR⁶ᵇ, C=CR⁶ᵃR⁶ᵇ.

In another preferred embodiment, the invention relates to compounds of formula I in which:
A represents a group;
wherein * indicates the point of attachment of said groups with the rest of the molecule;
Z represents a —C(=O)N(H)R² or a —C(=S)N(H)R² group;
R² represents a $C_1$-$C_3$-alkyl- or $C_3$-$C_6$-cycloalkyl-group;
wherein said $C_1$-$C_3$-alkyl- or $C_3$-$C_6$-cycloalkyl-group is optionally substituted, identically or differently, with 1, 2 or 3 groups selected from:
halogen, —OH, —CN, —$C_1$-$C_6$-alkyl, —$C_1$-$C_6$-alkoxy;
R³ represents a group selected from:
phenyl-X, quinolinyl-X—, pyridyl-X—, thienyl-X—, pyrazinyl-X—, imidazyl-X—, triazyl-X—, pyrazyl-X— and wherein said group is optionally substituted, identically or differently, with 1, 2, 3, 4 or 5 R⁷ groups;
R⁵ represents a hydrogen atom, or a $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, or heteroaryl-group;
said $C_1$-$C_6$-alkyl-, halo-$C_1$-$C_6$-alkyl-, HO—$C_1$-$C_6$-alkyl-, $C_3$-$C_6$-cycloalkyl, 3- to 7-membered heterocycloalkyl, heteroaryl-group is optionally substituted, identically or differently, with 1, 2, 3, or 4 R⁸ groups;
R⁶, R⁶ᵃ, R⁶ᵇ, R⁶ᶜ,
represent, independently from each other, a hydrogen atom, or a $C_1$-$C_6$-alkyl, HO—$C_1$-$C_6$-alkyl-, $C_3$-$C_6$-cycloalkyl, $C_2$-$C_6$-alkenyl, 3- to 7-membered heterocycloalkyl, aryl, heteroaryl, aryl-$C_1$-$C_6$-alkyl-, or heteroaryl-$C_1$-$C_6$-alkyl-group;

R⁷ represents a halogen atom, or a HO—, —CN, $C_1$-$C_6$-alkoxy-, $C_1$-$C_6$-alkyl-, halo-$C_1$-$C_6$-alkyl-, HO—$C_1$-$C_6$-alkyl-, H₂N—$C_1$-$C_6$-alkyl-, $C_2$-$C_6$-alkenyl, 3- to 7-membered heterocycloalkyl, —C(=O)N(H)R⁶ᵃ, —N(R⁶ᵃ)R⁶ᵇ), —N(H)C(=O)R⁶, or —SR⁶ group;
wherein said $C_1$-$C_6$-alkoxy-, or 3- to 7-membered heterocycloalkyl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—R⁶ or —OH groups;
or
when 2 R⁷ groups are present ortho to each other on an aryl or heteroaryl ring, said 2 R⁷ groups together form a bridge:
*CH₂(CH₂)₂NH*, *CH₂CH₂N(R⁶ᵃ)CH₂*, *C(H)=C(H)—C(=O)—N(H)*,
wherein * represent the point of attachment to said aryl or heteroaryl ring;
R⁸ represents a hydrogen or halogen atom, or a —CN, —OH, $C_1$-$C_6$-alkoxy-, $C_1$-$C_6$-alkyl-, halo-$C_1$-$C_6$-alkyl-, R⁶ᵃ(R⁶ᵇ)N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R⁶, —C(=O)N(H)R⁶ᵃ, —C(=O)N(R⁶ᵃ)R⁶ᵇ, —C(=O)O—R⁶, —N(R⁶ᵃ)R⁶ᵇ, —NO₂, —N(H)C(=O)R⁶, —N(R⁶ᶜ)C(=O)R⁶, —N(H)C(=O)N(R⁶ᵃ)R⁶ᵇ, —N(R⁶ᶜ)C(=O)N(R⁶ᵃ)R⁶ᵇ, —N(H)C(=O)OR⁶, —N(R⁶ᶜ)C(=O)OR⁶, —N(H)S(=O)R⁶, —N(R⁶ᶜ)S(=O)R⁶, —N(H)S(=O)₂R⁶, —N(R⁶ᶜ)S(=O)₂R⁶, —N=S(=O)(R⁶ᵃ)R⁶ᵇ, —OR⁶, —O(C=O)R⁶, —O(C=O)N(R⁶ᵃ)R⁶ᵇ, —O(C=O)OR⁶, —SR⁶, —S(=O)R⁶, —S(=O)N(H)R⁶, —S(=O)N(R⁶ᵃ)R⁶ᵇ, —S(=O)₂R⁶, —S(=O)₂OH, —S(=O)₂N(H)R⁶, —S(=O)₂N(R⁶ᵃ)R⁶ᵇ, —S(=O)(=NR⁶ᶜ)R⁶ group, —S(=O)₂-(3- to 7-membered heterocycloalkyl);
wherein said 3- to 7-membered heterocycloalkyl- or heteroaryl-group is optionally substituted, identically or differently, with 1, 2, 3, or 4 $C_1$-$C_6$-alkyl-groups;
m is an integer of 0, 1, 2, 3, 4, 5 or 6;
n is an integer of 0, 1, 2, 3, 4 or 5; and
X is S, S(=O), S(=O)₂, O, NR⁶, CR⁶ᵃR⁶ᵇ, C=CR⁶ᵃR⁶ᵇ.

In another preferred embodiment, the invention relates to compounds of formula I in which:
A represents a group;
wherein * indicates the point of attachment of said groups with the rest of the molecule;

Z represents a —C(=O)N(H)R² or a —C(=S)N(H)R² group;

R² represents a $C_1$-$C_3$-alkyl- or $C_3$-$C_6$-cycloalkyl-group;
wherein said $C_1$-$C_3$-alkyl- or $C_3$-$C_6$-cycloalkyl-group is optionally substituted, identically or differently, with 1, 2 or 3 groups selected from:
halogen, —OH, —CN, —$C_1$-$C_6$-alkyl, —$C_1$-$C_6$-alkoxy;

R³ represents a group selected from:
phenyl-X—, quinolinyl-X—, pyridyl-X—, thienyl-X—, pyrazinyl-X—, imidazyl-X—, triazyl-X—, pyrazyl-X— and

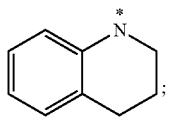

wherein said group is optionally substituted, identically or differently, with 1, 2, 3, 4 or 5 R⁷ groups;

R⁵ represents a hydrogen atom, or a $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, or heteroaryl-group;
said $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, heteroaryl-group is optionally substituted, identically or differently, with 1, 2, 3, or 4 R⁸ groups;

R⁶, $R^{6a}$, $R^{6b}$, $R^{4c}$,
represent, independently from each other, a hydrogen atom, or a $C_1$-$C_6$-alkyl-group;

R⁷ represents a halogen atom, or a HO—, —CN, $C_1$-$C_6$-alkoxy-, $C_1$-$C_6$-alkyl-, halo-$C_1$-$C_6$-alkyl-, HO—$C_1$-$C_6$-alkyl-, $H_2N$—$C_1$-$C_6$-alkyl-, $C_2$-$C_6$-alkenyl, 3- to 7-membered heterocycloalkyl, —C(=O)N(H)$R^{6a}$, —N($R^{6a}$)$R^{6b}$, —N(H)C(=O)R⁶, or —SR⁶ group;
wherein said $C_1$-$C_6$-alkoxy-, or 3- to 7-membered heterocycloalkyl-group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—R⁶ or —OH groups;
or
when 2 R⁷ groups are present ortho to each other on an aryl or heteroaryl ring, said 2 R⁷ groups together form a bridge:
*$CH_2(CH_2)_2NH$*, *$CH_2CH_2N(R^{6a})CH_2$*, *C(H)=C(H)—C(=O)—N(H)*,
wherein * represent the point of attachment to said aryl or heteroaryl ring;

R⁸ represents a hydrogen or halogen atom, or a —CN, —OH, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R⁶, —C(=O)N(H)$R^{6a}$, —C(=O)N($R^{6a}$)$R^{6b}$, —C(=O)O—R⁶, —N($R^{6a}$)$R^{6b}$, —NO₂, —N(H)C(=O)R⁶, —N($R^{6c}$)C(=O)R⁶, —N(H)C(=O)N($R^{6a}$)$R^{6b}$, —N($R^{6c}$)C(=O)N($R^{6a}$)$R^{6b}$, —N(H)C(=O)OR⁶, —N($R^{6c}$)C(=O)OR⁶, —N(H)S(=O)R⁶, —N($R^{6c}$)S(=O)R⁶, —N(H)S(=O)₂R⁶, —N($R^{6c}$)S(=O)₂R⁶, —N=S(=O)($R^{6a}$)$R^{6b}$, —OR⁶, —O(C=O)R⁶, —O(C=O)N($R^{6a}$)$R^{6b}$, —O(C=O)OR⁶, —SR⁶, —S(=O)R⁶, —S(=O)N(H)R⁶, —S(=O)N($R^{6a}$)$R^{6b}$, —S(=O)₂R⁶, —S(=O)₂OH, —S(=O)₂N(H)R⁶, —S(=O)₂N($R^{6a}$)$R^{6b}$, —S(=O)(=N$R^{6c}$)R⁶ group, —S(=O)₂-(3- to 7-membered heterocycloalkyl);

wherein said 3- to 7-membered heterocycloalkyl- or heteroaryl-group is optionally substituted, identically or differently, with 1, 2, 3, or 4 $C_1$-$C_6$-alkyl-groups;

m is an integer of 0, 1, 2, 3, 4, 5 or 6;
n is an integer of 0, 1, 2, 3, 4 or 5; and
X is S, S(=O), S(=O)₂, O, NR⁶, $CR^{6a}R^{6b}$, C=$CR^{6a}R^{6b}$.

WO 2011/013729 A1 teaches that compounds of formula C1, supra, in which R⁸ represents a cyclopropyl-group are preferred because they tendentially show higher activity in Mps-1 inhibition than compounds of formula C1 in which R⁸ does not represent a cyclopropyl-group.

The inventors of the present invention surprisingly observed that compounds of formula C1 in which R⁸ is a non-cyclic group rather than a cycloalkyl-group show higher metabolic stability. The inventors of the present invention surprisingly observed that compounds of formula C1 show especially high inhibitory effect on Mps-1 kinase if R⁶ represents an aryl-X— or a heteroaryl-X— group in which X is defined as for compounds of formula I, supra.

So the combination of R⁸ being a non-cyclic group with R⁶ being an aryl-X— or a heteroaryl-X— group, results in compounds of superior inhibitory and metabolic properties.

Hence, in another preferred embodiment, the invention relates to compounds of formula I

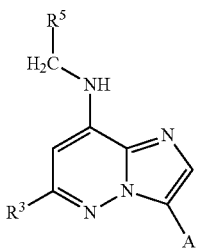

I in which:
A represents

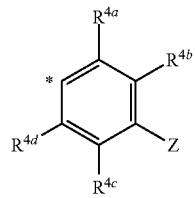

wherein * indicates the point of attachment of said group with the rest of the molecule;

Z represents a —C(=O)N(H)R² or —C(=S)N(H)R² group;
R² represents a hydrogen atom, or a $C_1$-$C_6$-alkyl-group;
wherein said $C_1$-$C_6$-alkyl-group is optionally substituted, identically or differently, with 1, 2, 3 or 4 groups selected from: halogen, —OH, —CN, $C_1$-$C_6$-alkyl-, $C_1$-$C_6$-alkoxy-;

R³ represents an aryl-X— or a heteroaryl-X— group, wherein said aryl-X— or heteroaryl-X— group is optionally substituted, identically or differently, with 1, 2, 3, 4 or 5 R⁷ groups;

$R^{4a}$, $R^{4b}$, $R^{4c}$, $R^{4d}$
represent, independently from each other, a hydrogen or halogen atom, or a —CN, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})$N—

$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-group;

$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;

$R^6$, $R^{6a}$, $R^{6b}$, $R^{6c}$,
represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl- or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group;
wherein said aryl- or heteroaryl-group is optionally substituted, identically or differently, with 1, 2 or 3 $C_1$-$C_6$-alkyl-groups;
or
when 2 $R^7$ groups are present ortho- to each other on an aryl- or heteroaryl-ring, said 2 $R^7$ groups together form a bridge:
*O(CH$_2$)$_2$O*, *O(CH$_2$)O*, *NH(C(=O))NH*, wherein * represent the point of attachment to said aryl- or heteroaryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)

$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;
wherein said 3- to 7-membered heterocycloalkyl- or heteroaryl-group, is optionally substituted, identically or differently, with 1, 2, 3 or 4 $C_1$-$C_6$-alkyl-groups m is an integer of 0, 1, 2, 3, 4, 5 or 6;
n is an integer of 0, 1, 2, 3, 4 or 5; and
X is selected from: S, S(=O), S(=O)$_2$, O, N$R^6$, C$R^{6a}R^{6b}$;
or a stereoisomer, a tautomer, an N-oxide, a hydrate, a solvate, or a salt thereof, or a mixture of same.

In another preferred embodiment, the invention relates to compounds of general formula I:

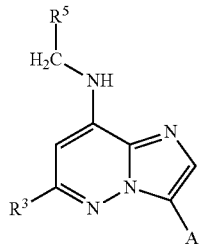

I in which:
A represents

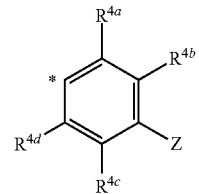

wherein * indicates the point of attachment of said groups with the rest of the molecule;
Z represents a —C(=O)N(H)$R^2$ or —C(=S)N(H)$R^2$ group;
wherein * indicates the point of attachment of said groups with the rest of the molecule;
$R^2$ represents a hydrogen atom, or a $C_1$-$C_6$-alkyl-group;
wherein said $C_1$-$C_6$-alkyl-group is optionally substituted, identically or differently, with 1, 2, 3, or 4 groups selected from: halogen, OH, —CN, $C_1$-$C_6$-alkyl-, $C_1$-$C_6$-alkoxy-;
$R^3$ represents an aryl-X— or a heteroaryl-X— group, wherein said aryl-X— or heteroaryl-X— group is optionally substituted, identically or differently, with 1, 2, 3, 4 or 5 $R^7$ groups;
$R^{4a}$, $R^{4b}$, $R^{4c}$, $R^{4d}$
are selected, independently from each other, from hydrogen, halogen, —CN, $C_1$-$C_6$-alkyl-, $C_1$-$C_6$-alkoxy-, halo-$C_1$-$C_6$-alkyl-, halo-$C_1$-$C_6$-alkoxy-;
$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;
said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;

$R^6$, $R^{6a}$, $R^{6b}$, $R^{6c}$,
represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O$_2$)$R^6$, —S(=O)$_2$N(H)$R^6$, —S(=O)$_2$N($R^{6a}$)$R^{6b}$, —S(=O)(=N$R^{6c}$)$R^6$ group;
wherein said aryl- or heteroaryl-group is optionally substituted, identically or differently, with 1, 2 or 3 $C_1$-$C_6$-alkyl-groups;
or
when 2 $R^7$ groups are present ortho- to each other on an aryl- or heteroaryl-ring, said 2 R' groups together form a bridge:
*O(CH$_2$)$_2$O*, *O(CH$_2$)O*, *NH(C(=O))NH*, wherein * represent the point of attachment to said aryl- or heteroaryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group, —S(=O)$_2$-(3- to 7-membered heterocycloalkyl);
wherein said 3- to 7-membered heterocycloalkyl- or heteroaryl-group, is optionally substituted, identically or differently, with 1, 2, 3 or 4 $C_1$-$C_6$-alkyl-groups;

m is an integer of 0, 1, 2, 3, 4, 5 or 6;
n is an integer of 0, 1, 2, 3, 4 or 5; and
X is S, S(=O), S(=O)$_2$, O, N$R^6$ or C$R^{6a}$$R^{6b}$.

In another preferred embodiment, the invention relates to compounds of general formula I:

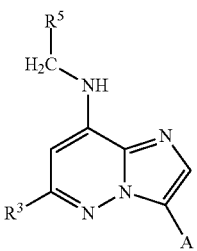

in which:
A represents

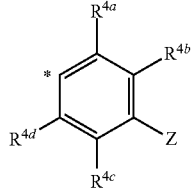

wherein * indicates the point of attachment of said groups with the rest of the molecule;
Z represents a —C(=O)N(H)$R^2$ or —C(=S)N(H)$R^2$ group;
$R^2$ represents a $C_1$-$C_4$-alkyl-group;
wherein said $C_1$-$C_4$-alkyl-group is optionally substituted, identically or differently, with 1 or 2 groups selected from: halogen, —OH, —CN, $C_1$-$C_3$-alkyl-, $C_1$-$C_4$-alkoxy-;
$R^3$ represents an aryl-X— or a heteroaryl-X— group, wherein said aryl-X— or heteroaryl-X— group is optionally substituted, identically or differently, with 1, 2, 3, 4 or 5 $R^7$ groups;

$R^{4a}$, $R^{4b}$, $R^{4c}$, $R^{4d}$
are selected, independently from each other, from hydrogen, halogen, —CN, $C_1$-$C_6$-alkyl-, $C_1$-$C_6$-alkoxy-, halo-$C_1$-$C_6$-alkyl-, halo-$C_1$-$C_6$-alkoxy-;

$R^5$ represents a hydrogen atom, or a $C_1$-$C_6$-alkyl-, —(CH$_2$), —$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;
said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;

$R^6$, $R^{6a}$, $R^{6b}$, $R^{6c}$,
represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group;

wherein said aryl- or heteroaryl-group is optionally substituted, identically or differently, with 1, 2, or 3 $C_1$-$C_6$-alkyl-groups;

or when 2 $R^7$ groups are present ortho- to each other on an aryl- or heteroaryl-ring, said 2 $R^7$ groups together form a bridge:

*O(CH$_2$)$_2$O*, *O(CH$_2$)O*, *NH(C(=O))NH*, wherein * represent the point of attachment to said aryl- or heteroaryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;

wherein said 3- to 7-membered heterocycloalkyl- or heteroaryl-group, is optionally substituted, identically or differently, with 1, 2, 3, or 4 $C_1$-$C_6$-alkyl-groups;

m is an integer of 0, 1, 2, 3, 4, 5 or 6;
n is an integer of 0, 1, 2, 3, 4 or 5; and
X is S, S(=O), S(=O)$_2$, O, N$R^6$ or C$R^{6a}$$R^{6b}$.

In another preferred embodiment, the invention relates to compounds of general formula I:

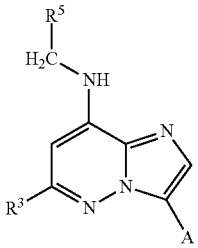

in which:
A represents

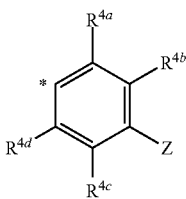

wherein * indicates the point of attachment of said groups with the rest of the molecule;

Z represents a —C(=O)N(H)$R^2$ or —C(=S)N(H)$R^2$ group;
$R^2$ represents a methyl- or ethyl-group;
  wherein said methyl- or ethyl-group is optionally substituted, identically or differently, with 1 or 2 groups selected from: halogen, —OH, —CN, $C_1$-$C_3$-alkoxy-;
$R^3$ represents an aryl-X— or a heteroaryl-X— group, wherein said aryl-X— or heteroaryl-X— group is optionally substituted, identically or differently, with 1, 2, 3, 4 or 5 $R^7$ groups;
$R^{4a}$, $R^{4b}$, $R^{4c}$, $R^{4d}$
  are selected, independently from each other, from hydrogen, halogen, —CN, $C_1$-$C_6$-alkyl-, $C_1$-$C_6$-alkoxy-, halo-$C_1$-$C_6$-alkyl-, halo-$C_1$-$C_6$-alkoxy-;
$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_n$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;
  said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;
$R^6$, $R^{6a}$, $R^{6b}$, $R^{6c}$,
  represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;
$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group;

wherein said aryl- or heteroaryl-group is optionally substituted, identically or differently, with 1, 2 or 3 $C_1$-$C_6$-alkyl-groups;

or when 2 $R^7$ groups are present ortho- to each other on an aryl- or heteroaryl-ring, said 2 $R^7$ groups together form a bridge:

*O(CH$_2$)$_2$O*, *O(CH$_2$)O*, *NH(C(=O))NH*, wherein * represent the point of attachment to said aryl- or heteroaryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$ $R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2$$R^6$, —S(=O)$_2$N(H)$R^6$, —S(=O)$_2$N($R^{6a}$)$R^{6b}$, —S(=O)(=N$R^{6c}$)$R^6$ group, —S(=O)$_2$-(3- to 7-membered heterocycloalkyl);

wherein said 3- to 7-membered heterocycloalkyl- or heteroaryl-group, is optionally substituted, identically or differently, with 1, 2, 3, or 4 $C_1$-$C_6$-alkyl-groups;

m is an integer of 0, 1, 2, 3, 4, 5 or 6;
n is an integer of 0, 1, 2, 3, 4 or 5; and
X is S, S(=O), S(=O)$_2$, O, N$R^6$ or C$R^{6a}R^{6b}$.

In another preferred embodiment, the invention relates to compounds of general formula I:

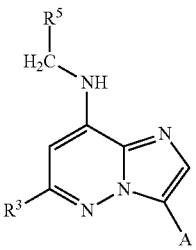

I in which:
A represents

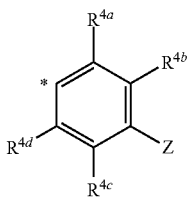

wherein * indicates the point of attachment of said groups with the rest of the molecule;
Z represents a —C(=O)N(H)$R^2$ or —C(=S)N(H)$R^2$ group;
$R^2$ represents a $C_1$-$C_4$-alkyl-group;
wherein said $C_1$-$C_4$-alkyl-group is optionally substituted, identically or differently, with 1 or 2 groups selected from: halogen, OH, —CN, $C_1$-$C_3$-alkyl-, $C_1$-$C_4$-alkoxy-;
$R^3$ represents an aryl-X— or heteroaryl-X— group; wherein said aryl-X— or heteroaryl-X— group is optionally substituted, identically or differently, with 1 or 2 $R^7$ groups;
$R^{4a}$, $R^{4b}$, $R^{4c}$, $R^{4d}$
are selected, independently from each other, from hydrogen, halogen, —CN, $C_1$-$C_6$-alkyl-, $C_1$-$C_6$-alkoxy-, halo-$C_1$-$C_6$-alkyl-, halo-$C_1$-$C_6$-alkoxy-;

$R^5$ represents a hydrogen atom, or a $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group;

said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups;

$R^6$, $R^{6a}$, $R^{6b}$, $R^{6c}$,
represent, independently from each other, a hydrogen atom, or a $C_1$-$C_6$-alkyl-, HO—$C_1$-$C_6$-alkyl-, $C_3$-$C_6$-cycloalkyl-, $C_2$-$C_6$-alkenyl-, 3- to 7-membered heterocycloalkyl-, aryl-, heteroaryl-, aryl-$C_1$-$C_6$-alkyl-, or heteroaryl-$C_1$-$C_6$-alkyl-group;

$R^7$ represents a hydrogen or halogen atom, or a HO—, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O$_2$)$R^6$, —S(=O)$_2$N(H)$R^6$, —S(=O)$_2$N($R^{6a}$)$R^{6b}$, —S(=O)(=N$R^{6c}$)$R^6$ group;

wherein said aryl- or heteroaryl-group is optionally substituted, identically or differently, with 1, 2 or 3 $C_1$-$C_6$-alkyl-groups;
or
when 2 $R^7$ groups are present ortho- to each other on an aryl- or heteroaryl-ring, said 2 $R^7$ groups together form a bridge:
*O(CH$_2$)$_2$O*, *O(CH$_2$)O*, *NH(C(=O))NH*, wherein * represent the point of attachment to said aryl- or heteroaryl-ring;

$R^8$ represents a hydrogen or halogen atom, or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$ $R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)₂R⁶, —S(=O)₂N(H)R⁶, —S(=O)₂N(R⁶ᵃ)R⁶ᵇ, —S(=O)(=NR⁶ᶜ)R⁶ group, —S(=O)₂-(3- to 7-membered heterocycloalkyl);
wherein said 3- to 7-membered heterocycloalkyl- or heteroaryl-group, is optionally substituted, identically or differently, with 1, 2, 3 or 4 C₁-C₆-alkyl-groups;

m is an integer of 0, 1, 2, 3, 4, 5 or 6;
n is an integer of 0, 1, 2, 3, 4 or 5; and
X is S, S(=O), S(=O)₂, O, NR⁶ or CR⁶ᵃR⁶ᵇ.

In another preferred embodiment, the invention relates to compounds of general formula I:

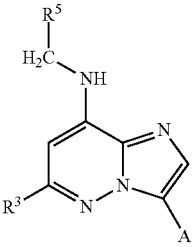

I in which:
A represents

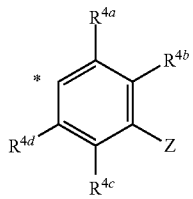

wherein * indicates the point of attachment of said groups with the rest of the molecule;
Z represents a —C(=O)N(H)R² or —C(=S)N(H)R² group;
R² represents a C₁-C₄-alkyl-group;
wherein said C₁-C₄-alkyl-group is optionally substituted, identically or differently, with 1 or 2 groups selected from: halogen, —OH, —CN, C₁-C₃-alkyl-, C₁-C₄-alkoxy-;
R³ is selected from aryl-X— or heteroaryl-X—; wherein said aryl-X— or heteroaryl-X— group is optionally substituted, identically or differently, with 1 or 2 R⁷ groups;
R⁴ᵃ, R⁴ᵇ, R⁴ᶜ, R⁴ᵈ
are selected, independently from each other, from hydrogen, halogen, —CN, C₁-C₆-alkyl-, C₁-C₆-alkoxy-, halo-C₁-C₆-alkyl-, or halo-C₁-C₆-alkoxy-;
R⁵ represents a hydrogen atom, C₁-C₆-alkyl-, —(CH₂)ₘ-(3- to 7-membered heterocycloalkyl), aryl- or heteroaryl-group;
wherein said C₁-C₆-alkyl-, —(CH₂)ₘ-(3- to 7-membered heterocycloalkyl), aryl- or heteroaryl-group is optionally substituted, identically or differently, with 1, 2, 3 or 4 R⁸ groups;
R⁶, R⁶ᵃ, R⁶ᵇ, R⁶ᶜ,
represent, independently from each other, a hydrogen atom, or a C₁-C₆-alkyl-, HO—C₁-C₆-alkyl-, C₃-C₆-cycloalkyl-, C₂-C₆-alkenyl-, 3- to 7-membered heterocycloalkyl-, aryl-, heteroaryl-, aryl-C₁-C₆-alkyl-, or heteroaryl-C₁-C₆-alkyl-group;
R⁷ represents a hydrogen or halogen atom, or a HO—, —CN, C₁-C₆-alkoxy-, C₁-C₆-alkyl-, halo-C₁-C₆-alkyl-, R⁶ᵃ(R⁶ᵇ)N—C₁-C₆-alkyl-, HO—C₁-C₆-alkyl-, C₁-C₆-alkoxy-C₁-C₆-alkyl-, halo-C₁-C₆-alkoxy-C₁-C₆-alkyl-, C₂-C₆-alkenyl-, C₂-C₆-alkynyl-, 3- to 7-membered heterocycloalkyl-, aryl-, heteroaryl-, —C(=O)R⁶, —C(=O)N(H)R⁶ᵃ, —C(=O)N(R⁶ᵃ)R⁶ᵇ, —C(=O)O—R⁶, —N(R⁶ᵃ)R⁶ᵇ, —NO₂, —N(H)C(=O)R⁶, —N(R⁶ᶜ)C(=O)R⁶, —N(H)C(=O)N(R⁶ᵃ)R⁶ᵇ, —N(R⁶ᶜ)C(=O)N(R⁶ᵃ)R⁶ᵇ, —N(H)C(=O)OR⁶, —N(R⁶ᶜ)C(=O)OR⁶, —N(H)S(=O)R⁶, —N(R⁶ᶜ)S(=O)R⁶, —N(H)S(=O)₂R⁶, —N(R⁶ᶜ)S(=O)₂R⁶, —N=S(=O)(R⁶ᵃ)R⁶ᵇ, —OR⁶, —O(C=O)R⁶, —O(C=O)N(R⁶ᵃ)R⁶ᵇ, —O(C=O)OR⁶, —SR⁶, —S(=O)R⁶, —S(=O)N(H)R⁶, —S(=O)N(R⁶ᵃ)R⁶ᵇ, —S(=O)₂R⁶, —S(=O)₂N(H)R⁶, —S(=O)₂N(R⁶ᵃ)R⁶ᵇ, —S(=O)(=NR⁶ᶜ)R⁶ group;
wherein said aryl- or heteroaryl-group is optionally substituted, identically or differently, with 1, 2 or 3 C₁-C₆-alkyl-groups;
or
when 2 R⁷ groups are present ortho- to each other on an aryl- or heteroaryl-ring, said 2 R⁷ groups together form a bridge:
*O(CH₂)₂O*, *O(CH₂)O*, *NH(C(=O))NH*, wherein * represent the point of attachment to said aryl- or heteroaryl-ring;
R⁸ represents a hydrogen or halogen atom, or a —CN, C₁-C₆-alkoxy-, C₁-C₆-alkyl-, halo-C₁-C₆-alkyl-, R⁶ᵃ(R⁶ᵇ)N—C₁-C₆-alkyl-, HO—C₁-C₆-alkyl-, C₁-C₆-alkoxy-C₁-C₆-alkyl-, halo-C₁-C₆-alkoxy-C₁-C₆-alkyl-, C₂-C₆-alkenyl-, C₂-C₆-alkynyl-, 3- to 7-membered heterocycloalkyl-, aryl-, heteroaryl-, —C(=O)R⁶, —C(=O)N(H)R⁶ᵃ, —C(=O)N(R⁶ᵃ)R⁶ᵇ, —C(=O)O—R⁶, —N(R⁶ᵃ)R⁶ᵇ, —NO₂, —N(H)C(=O)R⁶, —N(R⁶ᶜ)C(=O)R⁶, —N(H)C(=O)N(R⁶ᵃ)R⁶ᵇ, —N(R⁶ᶜ)C(=O)N(R⁶ᵃ)R⁶ᵇ, —N(H)C(=O)OR⁶, —N(R⁶ᶜ)C(=O)OR⁶, —N(H)S(=O)R⁶, —N(R⁶ᶜ)S(=O)R⁶, —N(H)S(=O)₂R⁶, —N(R⁶ᶜ)S(=O)₂ R⁶, —N=S(=O)(R⁶ᵃ)R⁶ᵇ, —OR⁶, —O(C=O)R⁶, —O(C=O)N(R⁶ᵃ)R⁶ᵇ, —O(C=O)OR⁶, —SR⁶, —S(=O)R⁶, —S(=O)N(H)R⁶, —S(=O)N(R⁶ᵃ)R⁶ᵇ, —S(=O)₂R⁶, —S(=O)₂N(H)R⁶, —S(=O)₂N(R⁶ᵃ)R⁶ᵇ, —S(=O)(=NR⁶ᶜ)R⁶ group, —S(=O)₂-(3- to 7-membered heterocycloalkyl);
wherein said 3- to 7-membered heterocycloalkyl- or heteroaryl-group is optionally substituted, identically or differently, with 1, 2, 3 or 4 C₁-C₆-alkyl-groups;
m is an integer of 0, 1, 2, 3, 4, 5 or 6;
n is an integer of 0, 1, 2, 3, 4 or 5; and
X is S, S(=O), S(=O)₂, O, NR⁶ or CR⁶ᵃR⁶ᵇ.

In another preferred embodiment, the invention relates to compounds of general formula I:

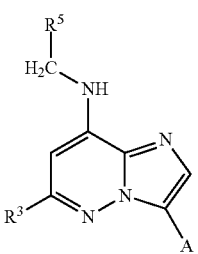

I in which:
A represents

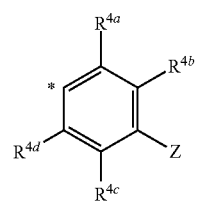

wherein * indicates the point of attachment of said groups with the rest of the molecule;

Z represents a —C(═O)N(H)R$^2$ or —C(═S)N(H)R$^2$ group;
R$^2$ represents a C$_1$-C$_4$-alkyl-group;
  wherein said C$_1$-C$_4$-alkyl-group is optionally substituted, identically or differently, with 1 or 2 groups selected from: halogen, OH, —CN, C$_1$-C$_3$-alkyl-, C$_1$-C$_4$-alkoxy-;
R$^3$ represent an aryl-X— or heteroaryl-X— group; wherein said aryl-X— or heteroaryl-X— group is optionally substituted, identically or differently, with 1 or 2 R$^7$ groups;
R$^{4a}$, R$^{4b}$, R$^{4c}$, R$^{4d}$
  are selected, independently from each other, from hydrogen, halogen, —CN, C$_1$-C$_6$-alkyl-, C$_1$-C$_6$-alkoxy-, halo-C$_1$-C$_6$-alkyl-, halo-C$_1$-C$_6$-alkoxy-;
R$^5$ represents a hydrogen atom, C$_1$-C$_6$-alkyl-, —(CH$_2$)$_m$-(3- to 7-membered heterocycloalkyl), aryl- or heteroaryl-group;
  wherein said C$_1$-C$_6$-alkyl-, —(CH$_2$)$_m$-(3- to 7-membered heterocycloalkyl), aryl- or heteroaryl-group is optionally substituted, identically or differently, with 1, 2, 3 or 4 R$^8$ groups;
R$^6$, R$^{6a}$, R$^{6b}$, R$^{6c}$,
  represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl-, or heteroaryl-C$_1$-C$_6$-alkyl-group;
R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl-, 3- to 7-membered heterocycloalkyl-, aryl-, heteroaryl-, —C(═O)R$^6$, —C(═O)N(H)R$^{6a}$, —C(═O)N(R$^{6a}$)R$^{6b}$, —C(═O)O—R$^6$, —N(R$^{6a}$)R$^{6b}$, —NO$_2$, —N(H)C(═O)R$^6$, —N(R$^{6c}$)C(═O)R$^6$, —N(H)C(═O)N(R$^{6a}$)R$^{6b}$, —N(R$^{6c}$)C(═O)N(R$^{6a}$)R$^{6b}$, —N(H)C(═O)OR$^6$, —N(R$^{6c}$)C(═O)OR$^6$, —N(H)S(═O)R$^6$, —N(R$^{6c}$)S(═O)R$^6$, —N(H)S(═O)$_2$R$^6$, —N(R$^{6c}$)S(═O)$_2$R$^6$, —N═S(═O)(R$^{6a}$)R$^{6b}$, —OR$^6$, —O(C═O)R$^6$, —O(C═O)N(R$^{6a}$)R$^{6b}$, —O(C═O)OR$^6$, —SR$^6$, —S(═O)R$^6$, —S(═O)N(H)R$^6$, —S(═O)N(R$^{6a}$)R$^{6b}$, —S(═O$_2$)R$^6$, —S(═O)$_2$N(H)R$^6$, —S(═O)$_2$N(R$^{6a}$)R$^{6b}$, —S(═O)(═NR$^{6c}$)R$^6$ group;
  wherein said aryl- or heteroaryl-group is optionally substituted, identically or differently, with 1, 2 or 3 C$_1$-C$_6$-alkyl-groups;
  or
  when 2 R$^7$ groups are present ortho- to each other on an aryl- or heteroaryl-ring, said 2 R$^7$ groups together form a bridge:
  *O(CH$_2$)$_2$O*, *O(CH$_2$)O*, *NH(C(═O))NH*, wherein * represent the point of attachment to said aryl- or heteroaryl-ring;
R$^8$ represents a halogen atom, a —CN, —N(R$^{6a}$)R$^{6b}$, or —OR$^6$ group;
m is an integer of 0, 1, 2, 3, 4, 5 or 6;
n is an integer of 0, 1, 2, 3, 4 or 5; and
X is S, S(═O), S(═O)$_2$, O, NR$^6$ or CR$^{6a}$R$^{6b}$.

It is to be understood that the present invention relates to any sub-combination within any embodiment or aspect of the present invention of compounds of general formula I, supra.

More particularly still, the present invention covers compounds of general formula I which are disclosed in the Experimental Section of this text, infra.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

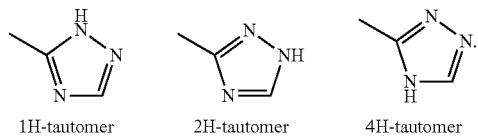

1H-tautomer   2H-tautomer   4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

Furthermore, the present invention includes all possible crystalline forms, or polymorphs, of the compounds of the present invention, either as single polymorphs, or as a mixture of more than one polymorph, in any ratio.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

In an embodiment of the above-mentioned aspects, the invention relates to compounds of formula I, according to any of the above-mentioned embodiments, in the form of or a stereoisomer, a tautomer, an N-oxide, a hydrate, a solvate, or a salt thereof, or a mixture of same.

The compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Therefore, the compounds of formula I, supra, are expected to be valuable as therapeutic agents.

Accordingly, in another embodiment, the present invention is directed to a compound of general formula I, supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In another embodiment, the present invention provides a method of treating disorders associated with enhanced uncontrolled proliferative cellular processes in a patient in need of such treatment, comprising administering to the patient an effective amount of a compound of formula I.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The terms "cell proliferative disorder" or "disorder associated with enhanced uncontrolled proliferative cellular processes" include disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

In another embodiment, the present invention is directed to a compound of general formula I, or a stereoisomer, a tautomer, an N-oxide, a hydrate, a solvate, or a salt thereof, particularly a pharmaceutically acceptable salt thereof, or a mixture of same, for use in the treatment or prophylaxis of a disease, wherein said disease is a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the mitogen-activated protein kinase (MEK-ERK) pathway, more particularly in which the disease of uncontrolled cell growth, proliferation and/or survival, inappropriate cellular immune response, or inappropriate cellular inflammatory response is a haemotological tumour, a solid tumour and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The present invention also relates to useful forms of the compounds as disclosed herein, such as metabolites, hydrates, solvates, prodrugs, salts, in particular pharmaceutically acceptable salts, in vivo hydrolysable esters, and co-precipitates.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Compounds of formula I may be administered as the sole pharmaceutical agent or in combination with one or more additional therapeutic agents where the combination causes no unacceptable adverse effects. This combination therapy includes administration of a single pharmaceutical dosage formulation which contains a compound of formula I and one or more additional therapeutic agents, as well as administration of the compound of formula I and each additional therapeutic agent in its own separate pharmaceutical dosage formulation. For example, a compound of formula I and a therapeutic agent may be administered to the patient together in a single oral dosage composition such as a tablet or capsule, or each agent may be administered in separate dosage formulations.

Where separate dosage formulations are used, the compound of formula I and one or more additional therapeutic agents may be administered at essentially the same time (e.g., concurrently) or at separately staggered times (e.g., sequentially).

In another aspect, the invention provides a pharmaceutical composition comprising a compound of general formula I, or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Preferably, the pharmaceutical combination comprises:
 one or more compounds of general formula I, or a stereoisomer, a tautomer, an N-oxide, a hydrate, a solvate, or a salt thereof, particularly a pharmaceutically acceptable salt thereof, or a mixture of same; and
 one or more agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2"-deoxyadenosine; Thioguanine; an anti-androgen, such as Flutamide, Cyproterone acetate, or Bicalutamide; Bortezomib; a platinum derivative, such as Cisplatin, or Carboplatin; Chlorambucil; Methotrexate; and Rituximab.

In still another aspect, the invention provides a process for preparing a pharmaceutical composition. The process includes the step of combining at least one compound of formula I as defined above with at least one pharmaceutically acceptable carrier, and bringing the resulting combination into a suitable administration form.

In still another aspect, the invention provides use of a compound of formula I as defined above for manufacturing a pharmaceutical composition for the treatment or prevention of a cell proliferative disorder. In certain embodiments, the cell proliferative disorder is cancer.

The active component of formula I can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Regardless of the route of administration selected, the compounds of the invention, which may be used in a suitable hydrated form, and/or the pharmaceutical compositions of the present invention, are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient.

In accordance with another aspect, the present invention covers methods of preparing compounds of the present invention.

In accordance with a first embodiment, the present invention relates to a method of preparing a compound of general formula I, supra, said method comprising the step of allowing an intermediate compound of general formula IV:

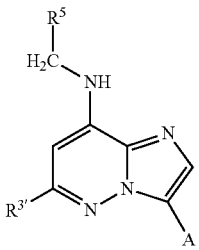

IV in which A, and $R^5$ are as defined for general formula I, supra, and $R^{3'}$ is a leaving group;
to react with a compound of general formula IVa:

R³—Y  IVa in which $R^3$ is as defined for general formula I, supra, and Y is a substituent which is displaced in a coupling reaction, such as a hydrogen atom, or a boronic acid group, or a boronic ester group, for example;
thereby giving a compound of general formula I:

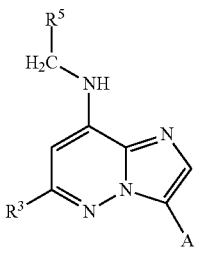

I in which A, $R^3$, and $R^5$ are as defined for general formula I, supra.

In accordance with a second embodiment, the present invention also relates to a method of preparing a compound of general formula I, supra, said method comprising the step of allowing an intermediate compound of general formula Ia:

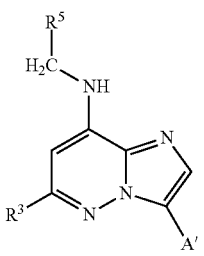

Ia in which $R^3$ and $R^5$ are as defined for general formula I, supra; and A' is

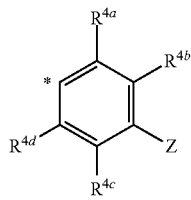

wherein * indicates the point of attachment of said group with the rest of the molecule; $R^{4a}$, $R^{4b}$, $R^{4c}$ and $R^{4d}$ are as defined for general formula I, supra, and Z' represents a group selected from:
—C(=O)OH, —C(=S)OH, —C(=O)O—($C_1$-$C_6$-alkyl) or —C(=S)O—($C_1$-$C_6$-alkyl);
to react with a compound of general formula Ib:

$H_2NR^2$  Ib in which $R^2$ is as defined as for general formula I, supra, thereby giving, upon optional deprotection, a compound of general formula I:

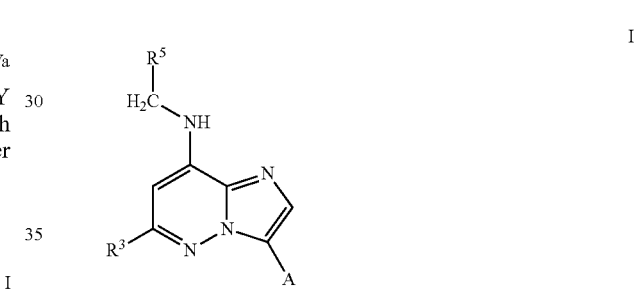

I in which $R^3$, $R^5$ and A are as defined for general formula I, supra.

In accordance with a third embodiment, the present invention also relates to a method of preparing a compound of general formula I, supra, said method comprising the step of allowing an intermediate compound of general formula II:

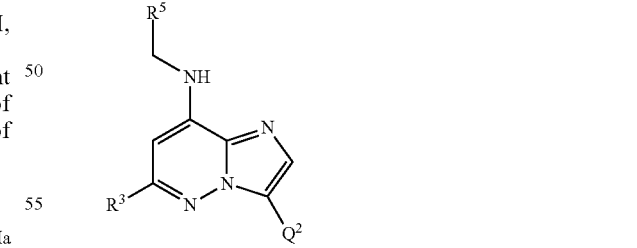

II in which $R^3$ and $R^5$ are as defined for general formula I, supra, and $Q^2$ is a leaving group, preferably $Q^2$ is a halogen atom;
to react with a compound of general formula IIa:

A-Y  IIa in which A is as defined for general formula I, supra, and Y is a substituent which is displaced in a coupling reaction, such as a boronic acid group, or an ester of a boronic acid group, for example, thereby giving, upon optional deprotection, a compound of general formula I:

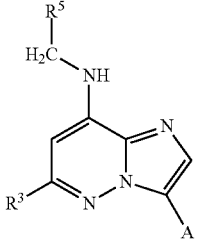

in which $R^3$, $R^5$ and A are as defined for general formula I, supra.

In accordance with a fourth embodiment, the present invention also relates to a method of preparing a compound of general formula I, supra, said method comprising the step of allowing an intermediate compound of general formula VII:

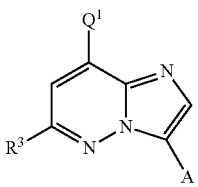

in which $R^3$ and A are as defined for general formula I, supra, and $Q^1$ is a leaving group, for example a halogen atom, to react with a compound of general formula VIIIa:

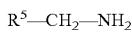  VIIa in which $R^5$ is as defined for general formula I, supra, thereby giving, upon optional deprotection, a compound of general formula I:

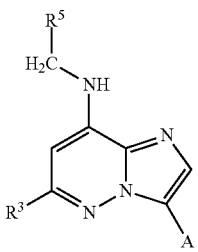

in which $R^3$, $R^5$ and A are as defined for general formula I, supra.

In accordance with a forth embodiment, the present invention also relates to a method of preparing a compound of general formula I, supra, said method comprising the step of allowing an intermediate compound of general formula VII:

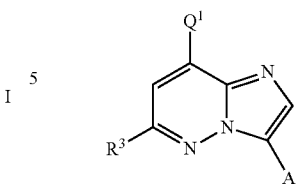

in which $R^3$ and A are as defined for general formula I, supra, and $Q^1$ is an optionally protected $NH_2$-group to react with a compound of general formula VIIb:

$O=CHR^5$  VIIb in which $R^5$ is as defined for general formula I, supra, thereby giving, upon optional deprotection, a compound of general formula I:

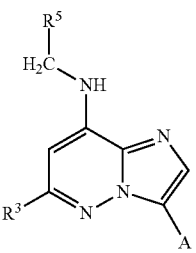

in which $R^3$, $R^5$ and A are as defined for general formula I, supra.

In accordance with a further aspect, the present invention covers intermediate compounds which are useful in the preparation of compounds of the present invention of general formula I, particularly in the method described herein.

In particular, the present invention covers intermediate compounds of general formula Ia:

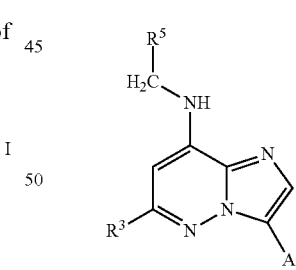

in which $R^3$ and $R^5$ are as defined for general formula I, supra; and A' is

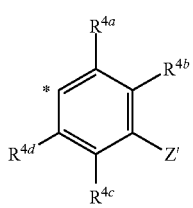

wherein * indicates the point of attachment of said group with the rest of the molecule; $R^{4a}$, $R^{4b}$, $R^{4c}$ and $R^{4d}$ are as defined for general formula I, supra, and Z' represents a group selected from:

—C(=O)OH, —C(=S)OH, —C(=O)O—($C_1$-$C_6$-alkyl) or —C(=S)O—($C_1$-$C_6$-alkyl).

In accordance with yet another aspect, the present invention covers the use of the intermediate compounds of general formula Ia:

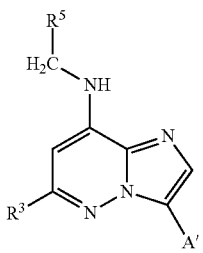

in which $R^3$ and $R^5$ are as defined for general formula I, supra; and A' is

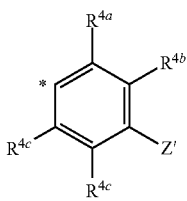

wherein * indicates the point of attachment of said group with the rest of the molecule; $R^{4a}$, $R^{4b}$, $R^{4c}$ and $R^{4d}$ are as defined for general formula I, supra, and Z' represents a group selected from:

—C(=O)OH, —C(=S)OH, —C(=O)O—($C_1$-$C_6$-alkyl) or —C(=S)O—($C_1$-$C_6$-alkyl);

for the preparation of a compound of general formula I as defined supra.

In accordance with yet another aspect, the present invention covers intermediate compounds of general formula II:

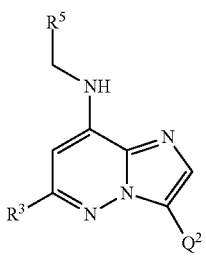

in which $R^3$ and $R^5$ are as defined for general formula I, supra, and $Q^2$ is a leaving group, preferably $Q^2$ is a halogen atom.

In accordance with yet another aspect, the present invention covers the use of the intermediate compounds of general formula II:

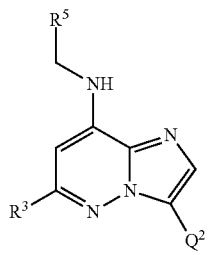

in which $R^3$ and $R^5$ are as defined for general formula I, supra, and $Q^2$ is a leaving group, preferably $Q^2$ is a halogen atom; for the preparation of a compound of general formula I as defined supra.

In accordance with yet another aspect, the present invention covers intermediate compounds of general formula IV:

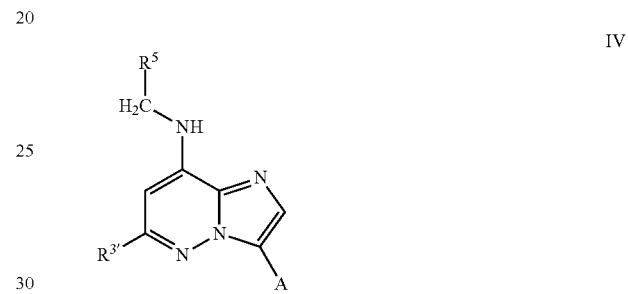

in which A, and $R^5$ are as defined for general formula I, supra, and $R^{3'}$ is a leaving group.

In accordance with yet another aspect, the present invention covers the use of the intermediate compounds of general formula IV:

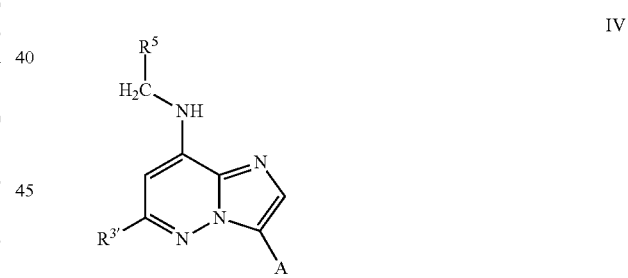

in which A, and $R^5$ are as defined for general formula I, supra, and $R^{3'}$ is a leaving group, for the preparation of a compound of general formula I as defined supra.

In accordance with a further aspect, the present invention covers intermediate compounds of general formula VII:

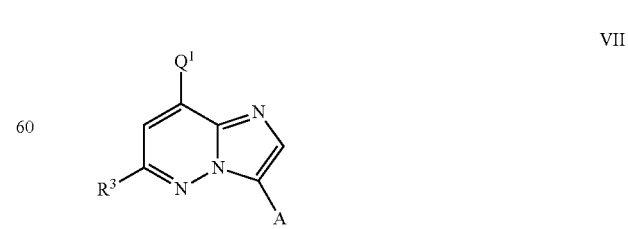

in which A, and $R^3$ are as defined for general formula I, supra, and $Q^1$ represents an optionally protected $NH_2$-group or a leaving group.

In accordance with yet another aspect, the present invention covers the use of the intermediate compounds of general formula VII:

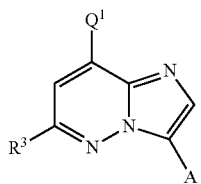
VII in which A, and $R^3$ are as defined for general formula I, supra, and $Q^1$ represents an optionally protected $NH_2$-group or a leaving group;
for the preparation of a compound of general formula I as defined supra.

EXPERIMENTAL SECTION

The following Table lists the abbreviations used in this paragraph, and in the Examples section.

| Abbreviation | Meaning |
|---|---|
| EDC | 1-Ethyl-3-(3-dimethylaminopropyl)carbodiimide |
| DIPEA | N,N-diisopropylethylamine |
| DMF | N,N-Dimethylformamide |
| DMSO | Dimethyl sulfoxide |
| Pd(dppf)Cl$_2$ | Dichloro[1,1'-bis(diphenylphosphino)ferrocene]palladium(II) |
| NMR | nuclear magnetic resonance spectroscopy |
| Rt | Room temperature |
| RT | Retention time in minutes |
| MW | molecular weight |
| NMP | N-methylpyrrolidinone |
| Oxone | Potassium peroxymonosulfate |
| UPLC | ultra performance liquid chromatography |

Synthesis of Compounds of General Formula I of the Present Invention

Compounds of general formula I can be synthesized as depicted in the Scheme, with A, $R^3$, $R^5$ having the meaning as given for general formula I, supra;
$R^{3'}$, $Q^2$ representing leaving groups; and
$Q^1$ represents an optionally protected $NH_2$-group or a leaving group.

Examples for typical leaving groups include but are not limited to halogen atoms like a chlorine, bromine or iodine atom, or $S(O)_pR^6$-groups (wherein p is 0, 1, or 2, and $R^6$ is as defined for general formula I, supra) like a methylsulfonyl-group, or a triflate- or nonaflate-group.

Scheme

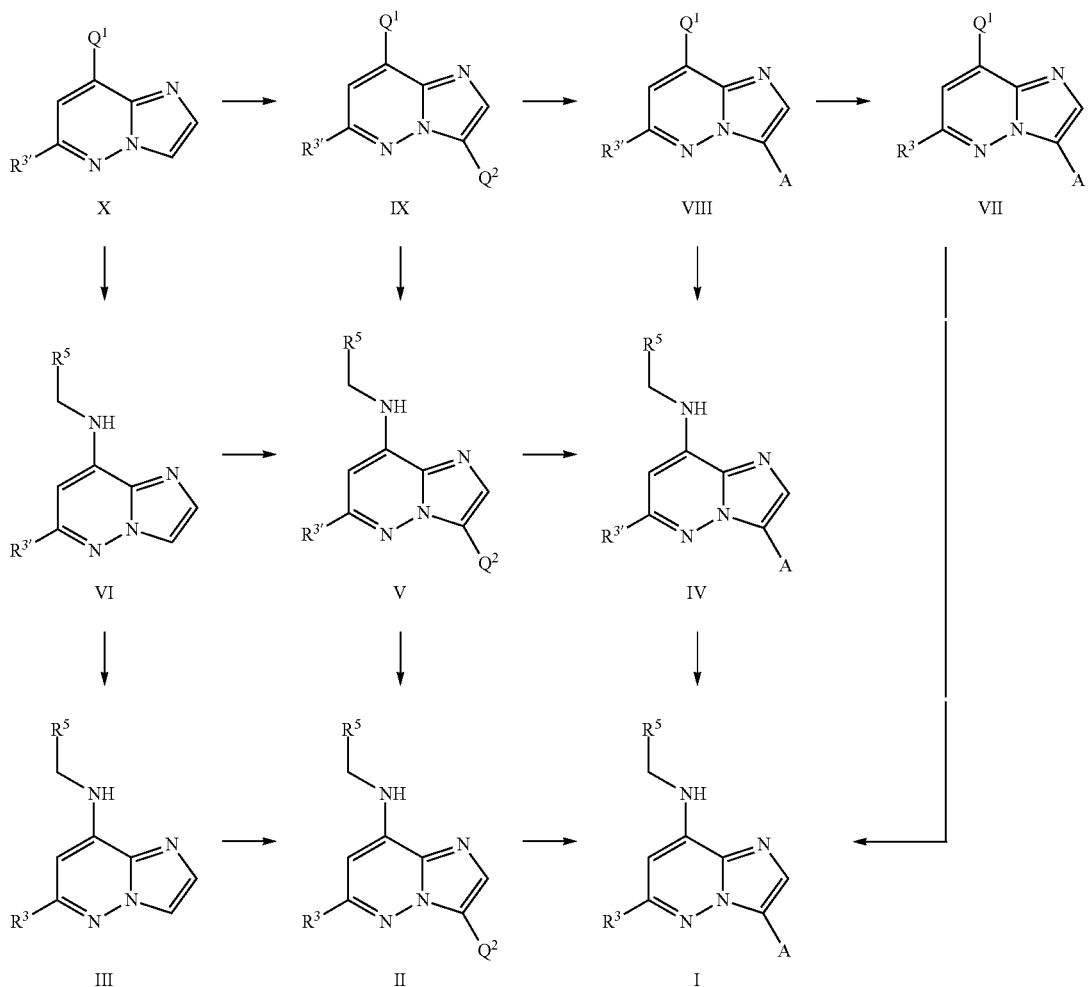

The Scheme exemplifies routes that allow variations for $R^3$, $R^{3'}$, $R^5$, $Q^1$, $Q^2$ and A during the synthesis. Functional moieties in $R^3$, $R^{3'}$, $R^5$, $Q^1$, $Q^2$ and A can be converted at every suitable stage of the synthesis.

However, also other routes were used for synthesis of the target compounds. Compounds of formula X may be commercially available or can be synthesized according to procedures known to persons skilled in the art, for example applying procedures described in WO2007/38314A2.

A leaving group $Q^2$ can be introduced in compounds of general formula X, VI or III by procedures known to persons skilled in the art to give compounds of general formula IX, V or II. As an example, halogens can be introduced using halogenation reagents like N-iodosuccinimide (NIS), N-bromosuccinimide (NBS), or N-chlorosuccinimide (NCS), in an inert solvent like N,N-dimethylformamide or 1-methylpyrrolidin-2-one, for example, at temperatures ranging from room temperature to the boiling point of the solvent, for example.

Compounds of general formula I, IV or VIII can be obtained from compounds of general formula II, V or IX via a coupling reaction between a reagent of formula Y-A, in which A is defined supra and Y represents a suitable functional group by which the group A can be transferred to the Q-group bearing carbon atom of compounds of formula II, V or IX. Examples of suitable functional groups for Y in A-Y include boronic acids $A-B(OH)_2$, or esters of boronic acids $A-B(OC_1-C_6-alkyl)_2$. Said coupling reactions are performed in the presence of suitable catalysts, such as, for example, palladium based catalysts like, for example, Palladium (II) acetate, tetrakis(triphenylphosphine)palladium (0), bis(triphenylphosphine)-palladium (II) chloride or (1,1,-bis(diphenylphosphino) ferrocene)-dichloropalladium (II) and optionally suitable additives such as, for example, phosphines like, for example, $P(oTol)_3$ or triphenylphosphine and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran. Examples of such coupling reactions may be found in the textbook entitled "Metal-Catalyzed Cross-Coupling Reactions", Armin de Meijere (Editor), Francois Diederich (Editor) September 2004, Wiley Interscience ISBN: 978-3-527-30518-6.

Compounds of general formula I, II, III or VII can be obtained from compounds of general formula IV, V, VI or VIII via a coupling reaction using a reagent of formula Y—$R^3$ in which $R^3$ is defined supra and Y represents a suitable functional group by which the group $R^3$ can be transferred to the $R^{3'}$ bearing carbon atom of compounds of formula IV, V, VI or VIII. Examples of suitable functional groups Y for the use in coupling reactions are given supra for the preparation of compounds of general formula I, IV or VIII from compounds of general formula II, V or IX.

The coupling reactions include metal catalyzed coupling reactions like Sonogashira coupling reactions with alkynes for alkyne introduction, Heck coupling reactions with alkenes for alkene introduction, Hartwig Buchwald coupling reactions with amines for amine introduction.

Y in Y—$R^3$ may also represent an acidic hydrogen that can be removed by suitable bases, for example sodium hydride, in a suitable solvent, such as DMSO or tetrahydrofuran at temperatures ranging from rt to the boiling point. The resulting nucleophiles, like, for example, primary or secondary amines, alkoxides, thiolates or carbon anion bearing groups can be used to replace $R^{3'}$ in compounds of general formula IV, V, VI or VIII to add secondary or tertiary amines, ethers, thioethers or carbon-atom attached groups to give compounds of general formula I, II, III or VII.

Compounds of general formula I, II, III or VII containing primary or secondary amines, ethers or thioether can also be build by Ullmann-type coupling reactions in the presence of suitable catalysts, such as, for example, copper based catalysts like copper(II)diacetate in presence of a suitable base, like for example, caesium carbonate staring from compounds of general formula IV, V, VI or VIII in which $R^{3'}$ represents a leaving group such as, for example, an iodine, bromine or chlorine atom. Optionally, suitable ligands like N,N-dimethylglycine or phenyl hydrogen pyrrolidin-2-ylphosphonate can be added.

In the case $Q^1$ represents a leaving group, the introduction of a $R^5$—$CH_2$-group can be achieved by nucleophilic substitution of $Q^1$ in compounds of formula VII, VIII, IX or X i.e. by a reaction with suitable amines $R^5$—$CH_2$—$NH_2$ in the presence of a suitable base, such as, for example DIPEA in a suitable solvent such as N,N-dimethylformamide or 1-methylpyrrolidin-2-one, at temperatures ranging from room temperature to the boiling point of the solvent to give amines of general formula I, IV, V or VI.

In the case $Q^1$ represents a leaving group, the introduction of a $R^5$—$CH_2$-group can also be achieved in a coupling reaction in which $Q^1$ in compounds of formula VII, VIII, IX or X is reacted with suitable amines $R^5$—$CH_2$—$NH_2$ optionally in the presence of a suitable catalyst, such as $Pd_2$ $dba_3$ and BINAP for example, and optionally with a suitable base, such as, for example, sodium tert-butylate in a suitable solvent, such as, for example, N,N-dimethylformamide or 1-methylpyrrolidin-2-one to give amines of general formula I, IV, V or VI.

In the case $Q^1$ represents an optionally protected $NH_2$-group the introduction of a $R^5$—$CH_2$-group, after deprotection to a $NH_2$-group, can be achieved by a reductive amination reaction using an aldehyde of formula $O=CHR^5$, a suitable reducing agent, for example sodium tris(acetato-kappaO)(hydrido)borate or sodium cyanoborohydride in a suitable solvent like, for example, acetic acid at reaction temperatures ranging from room temperature to the boiling point of the solvent.

Residues in compounds of formula I, II, III, IV, V, VI, VII, VIII, IX or X can be optionally modified. For example, thioethers can be oxidized using oxidation reagents like 3-chlorobenzenecarboperoxoic acid, oxone or dimethyldioxirane in inert solvents like dichloromethane or acetone, respectively. Depending on the stoichiometric ratio of oxidation reagent to the afore mentioned compounds sulfoxides or sulfones or mixtures thereof will be obtained.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH2 silica gel in combination with a suitable chromatographic system such as a Flashmaster II (Separtis) or an Isolera system (Biotage) and eluents such as, for example, gradients of hexane/EtOAc or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

EXAMPLES

Analytical UPLC-MS was performed as follows:

Method A: System: UPLC Acquity (Waters) with PDA Detector and Waters ZQ mass spectrometer; Column: Acquity BEH C18 1.7 µm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 µl (0.1 mg-1 mg/mL sample concentration); Detection: PDA scan range 210-400 nm-Fixed and ESI (+), scan range 170-800 m/z General:

All reactions were run under an atmosphere of argon in degassed solvents unless stated otherwise.

Example 1

1-({6-[(2E/Z)-But-2-en-2-yl]-3-[4-(2-cyclopropyl-1H-imidazol-5-yl)phenyl]imidazo[1,2-b]pyridazin-8-yl}amino)-2-methylpropan-2-ol

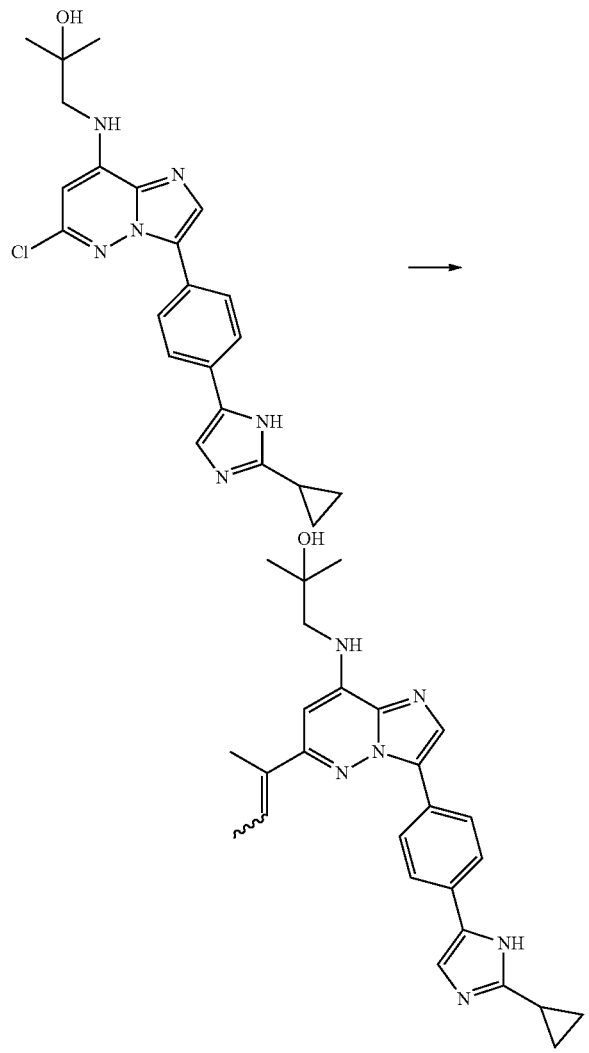

A mixture of 47.5 mg (112 µmol) 1-({6-chloro-3-[4-(2-cyclopropyl-1H-imidazol-5-yl)phenyl]imidazo[1,2-b]pyridazin-8-yl}amino)-2-methylpropan-2-ol which was prepared according to intermediate example 1a, 47.3 mg (2E/Z)-but-2-en-2-ylboronic acid, 1.6 mL n-propanol, 228 µL 1-methylpyrrolidin-2-one, 168 µL of an aqueous 2M potassium carbonate solution, 1.47 mg triphenylphosphine, and 7.9 mg bis(triphenylphosphine)palladium (II) chloride was stirred at 120° C. for 2 hours under microwave irradiation. Solvent was removed and the residue was purified by chromatography to give 20.7 mg (40%) of the title compounds.

$^1$H-NMR (DMSO-d6): δ=0.81-0.91 (4H), 1.15 (6H), 1.72 (3H), 1.93 (1H), 2.05 (3H), 3.13+3.26 (2H), 4.75+4.77 (1H), 5.73 (1H), 6.16+6.18 (1H), 6.75 (1H), 7.19+7.45 (1H), 7.65+7.76 (2H), 7.90+7.95 (1H), 8.06+8.14 (2H), 11.79+12.09 (1H) ppm.

Intermediate Example 1a 1-({6-Chloro-3-[4-(2-cyclopropyl-1H-imidazol-5-yl)phenyl]imidazo[1,2-b]pyridazin-8-yl}amino)-2-methylpropan-2-ol

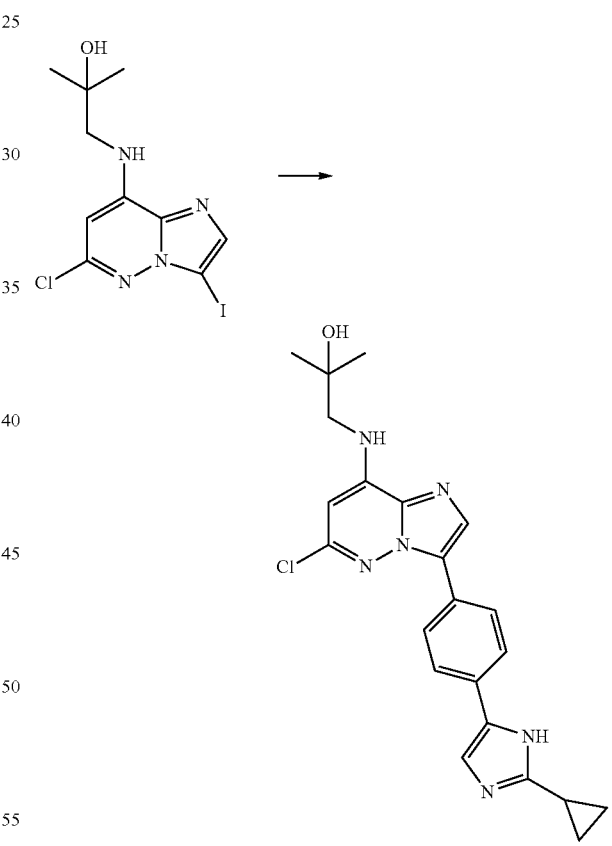

A mixture comprising 700 mg (1.91 mmol) 1-[(6-chloro-3-iodoimidazo[1,2-b]pyridazin-8-yl)amino]-2-methylpropan-2-ol which was prepared according to intermediate example 1b, 610 mg [4-(2-cyclopropyl-1H-imidazol-5-yl)phenyl]boronic acid, which was prepared according to intermediate example 1d, 156 mg (1,1,-bis(diphenylphosphino)ferrocene)-dichloropalladium (II), 2.86 mL aqueous 2M tribasic potassium phosphate solution and 8.2 mL tetrahydrofuran was stirred at 45° C. for 12 hours. Water was added and the mixture was extracted with ethyl acetate and methanol.

The organic layer was washed with brine and dried over sodium sulfate. After filtration and removal of the solvent the residue was purified by chromatography to give 345 mg (43%) of the title compound.

Intermediate Example 1b

1-[(6-Chloro-3-iodoimidazo[1,2-b]pyridazin-8-yl)amino]-2-methylpropan-2-ol

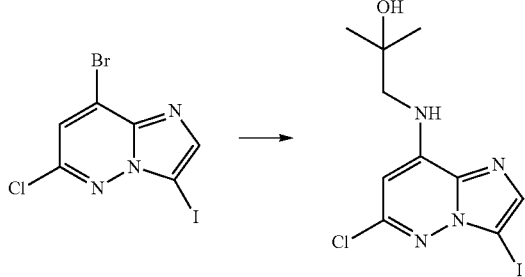 [SMILES: Clc1cc(Br)c2ncc(I)n2n1 ; CC(C)(O)CNc1cc(Cl)nn2c(I)cnc12]

To a solution of 1.20 g (3.35 mmol) 8-bromo-6-chloro-3-iodoimidazo[1,2-b]pyridazine which was prepared according to intermediate example 1c in 24 mL N,N-dimethylformamide were added 895 mg 1-amino-2-methylpropan-2-ol and the mixture was stirred at 40° C. overnight. Water was added and the mixture was extracted with dichloromethane and methanol. The organic phase was washed with water and dried over sodium sulfate. After filtration and removal of solvent the residue was purified by chromatography to give 798 mg (65%) of the title compound.

Intermediate Example 1c

8-Bromo-6-chloro-3-iodoimidazo[1,2-b]pyridazine

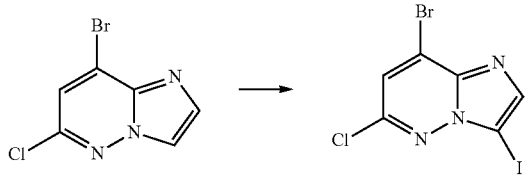 [SMILES: Clc1cc(Br)c2nccn2n1 ; Clc1cc(Br)c2ncc(I)n2n1]

A mixture comprising 100 g (430 mmol) 8-bromo-6-chloroimidazo[1,2-b]pyridazine which was prepared according to a procedure described in US2007/78136 (WO2007/38314), 145 g N-iodosuccinimide, 5 percent per weight conc. hydrochloric acid and 1 L trichloromethane was heated at reflux for 6 hours. 20 g N-iodosuccinimide were added and heating was continued for additional 3 hours. The precipitate was removed and the filtrate was washed with 1N sodium hydroxide solution, brine and dried over sodium sulfate. After filtration and removal of solvent diisopropyl ether was added and the residue was stirred at 23° C. overnight. The precipitate was filtered off and dried to give 66.6 g (43%) of the title compound.

Intermediate Example 1d

2-Cyclopropyl-5-[4-(4,4,5,5-tetramethyl-1,3,2-dioxaborolan-2-yl)phenyl]-1H-imidazole

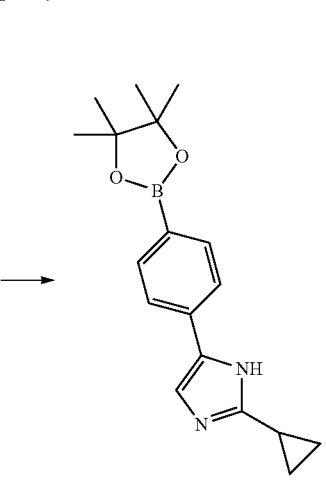

A mixture comprising 42.1 g (160 mmol) 5-(4-bromophenyl)-2-cyclopropyl-1H-imidazole which was prepared according to intermediate example 1e, 60.9 g 4,4,4',4',5,5,5',5'-octamethyl-2,2'-bi-1,3,2-dioxaborolane, 3.05 g dicyclohexyl(2',4',6'-triisopropylbiphenyl-2-yl)phosphine, 1.46 g tris-(dibenzylidenacetone)-dipalladium(0), 23.5 g potassium acetate and 267 mL 1,4-dioxane was stirred at 110° C. for 4 hours. After cooling to 23° C., ethyl acetate and 1M hydrochloric acid were added and the pH was adjusted to 8.0 by adding 5% sodium hydroxide solution. The mixture was extracted with ethyl acetate. The organic layer was washed with brine and dried over sodium sulfate. After filtration and removal of the solvent the residue was purified by crystallisation to give 33.5 g (67%) of the title compound.

Intermediate Example 1e 5-(4-Bromophenyl)-2-cyclopropyl-1H-imidazole

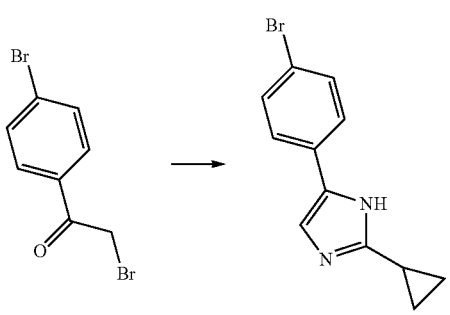 [SMILES: O=C(CBr)c1ccc(Br)cc1 ; Brc1ccc(-c2cnc(C3CC3)[nH]2)cc1]

To a solution of 89.0 g (320 mmol) 2-bromo-1-(4-bromophenyl)ethanone in 2.0 L N,N-dimethylformamide were added cyclopropanecarboximidamide hydrochloride, 132.8 g potassium carbonate and the mixture was stirred at 23° C. overnight. After removal of the solvent, water was added and the mixture was extracted with ethyl acetate. The organic layer was washed with brine and dried over sodium sulfate. After filtration and removal of the solvent the residue was purified by crystallisation to give 42.1 g (50%) of the title compound.

101
Example 2

1-({3-[4-(2-Cyclopropyl-1H-imidazol-5-yl)phenyl]-6-[(1E/Z)-prop-1-en-1-yl]imidazo[1,2-b]pyridazin-8-yl}amino)-2-methylpropan-2-ol

102
Example 3

3-[4-(2-Cyclopropyl-1H-imidazol-5-yl)phenyl]-N-isobutyl-6-(pyridin-4-yl) imidazo[1,2-b]pyridazin-8-amine

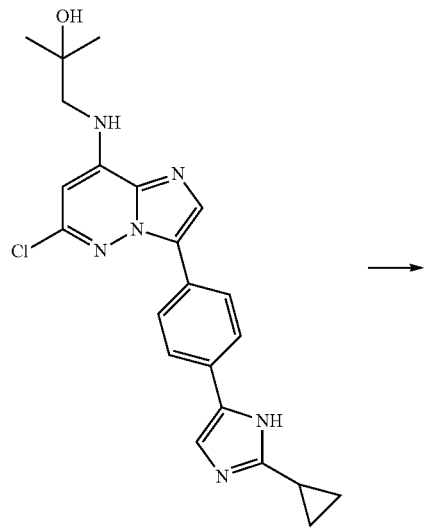

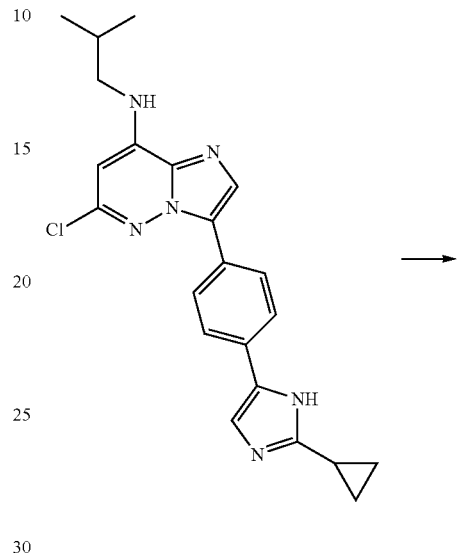

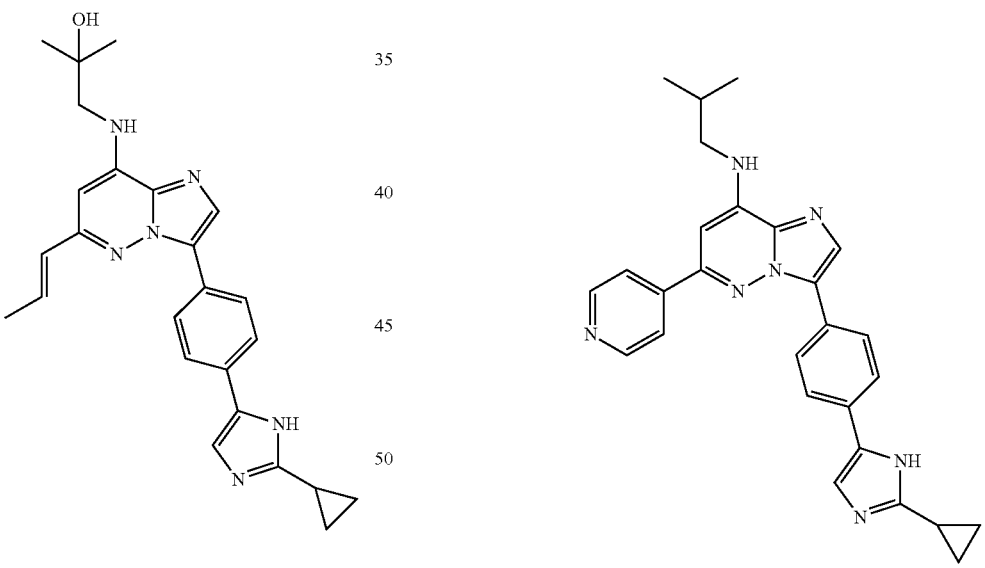

47.5 mg (112 μmol) 1-({6-chloro-3-[4-(2-cyclopropyl-1H-imidazol-5-yl)phenyl]imidazo[1,2-b]pyridazin-8-yl}amino)-2-methylpropan-2-ol which was prepared according to intermediate example 1a were transformed in analogy to example 1 using (1E/Z)-prop-1-en-1-ylboronic acid to give after working up and purification 34.1 mg (71%) of the title compounds.

¹H-NMR (DMSO-d6): δ=0.81-0.93 (4H), 1.16 (6H), 1.83-1.98 (4H), 3:13+3.26 (2H), 4.76 (1H), 6.34-6.46 (2H), 6.59-6.78 (2H), 7.19+7.45 (1H), 7.66+7.76 (2H), 7.85+7.91 (1H), 8.08+8.15 (2H), 11.79+12.11 (1H) ppm.

50 mg (123 μmol) 6-chloro-3-[4-(2-cyclopropyl-1H-imidazol-5-yl)phenyl]-N-isobutylimidazo[1,2-b]pyridazin-8-amine which was prepared according to intermediate example 3a were transformed in analogy to example 1 using pyridin-4-ylboronic acid to give after working up and purification 10.9 mg (20%) of the title compound.

¹H-NMR (DMSO-d6): δ=0.82-0.91 (4H), 0.94 (6H), 1.94 (1H), 2.04 (1H), 3.26 (2H), 6.74 (1H), 7.49 (1H), 7.68 (1H), 7.82 (2H), 7.98 (1H), 8.05 (2H), 8.16 (2H), 8.72 (2H), 11.82+12.13 (1H) ppm.

Intermediate Example 3a

6-Chloro-3-[4-(2-cyclopropyl-1H-imidazol-5-yl)phenyl]-N-isobutylimidazo[1,2-b]pyridazin-8-amine

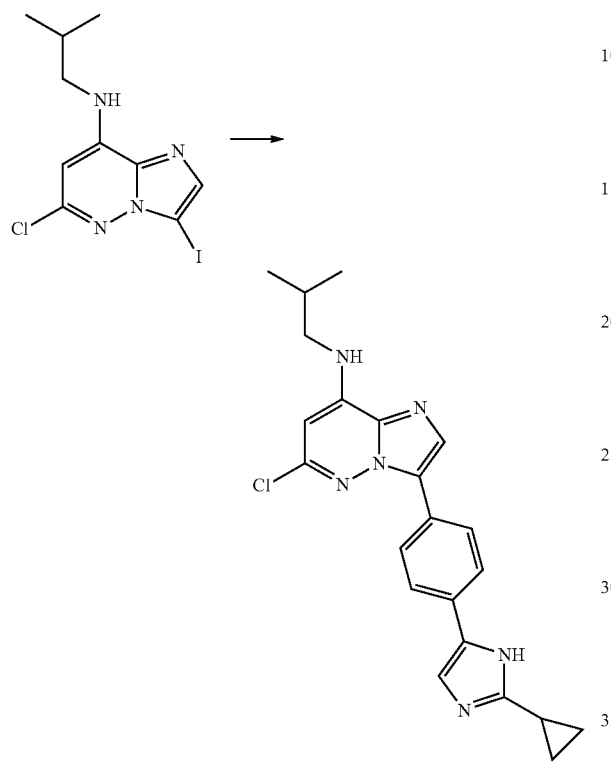

200 mg (570 μmol) 6-chloro-3-iodo-N-isobutylimidazo[1,2-b]pyridazin-8-amine which was prepared according to intermediate example 3b were transformed in analogy to intermediate example 1a to give after working up and purification 114 mg (49%) of the title compound.

Intermediate Example 3b

6-Chloro-3-iodo-N-isobutylimidazo[1,2-b]pyridazin-8-amine

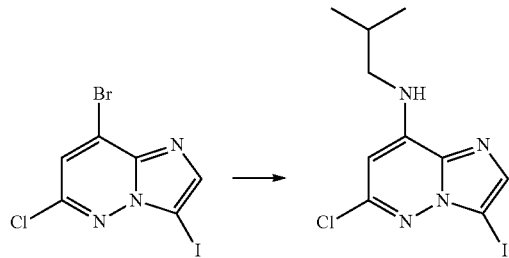 [SMILES: Clc1cc(Br)c2ncc(I)n2n1 ; CC(C)CNc1cc(Cl)nn2c(I)cnc12]

200 mg (558 μmol) 8-bromo-6-chloro-3-iodoimidazo[1,2-b]pyridazine which was prepared according to intermediate example 1c were transformed in analogy to intermediate example 1b using 2-methylpropan-1-amine to give after working up and purification 188 mg (96%) of the title compound.

Example 4

3-[4-(2-Cyclopropyl-1H-imidazol-5-yl)phenyl]-6-(pyridin-4-yl)-N-[(2S)-tetrahydrofuran-2-ylmethyl]imidazo[1,2-b]pyridazin-8-amine

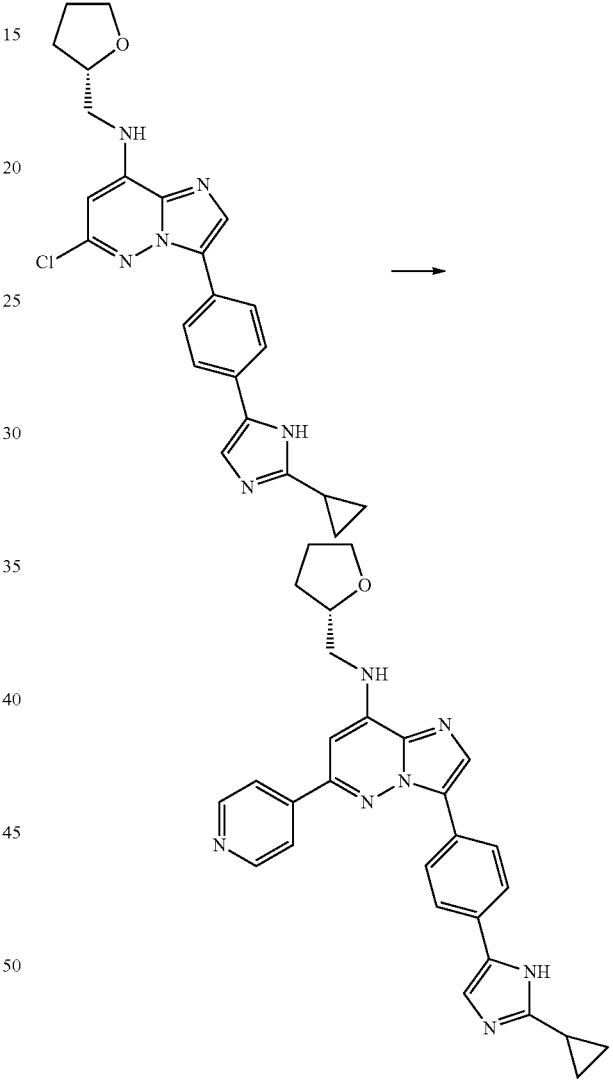

50 mg (115 μmol) 6-chloro-3-[4-(2-cyclopropyl-1H-imidazol-5-yl)phenyl]-N-[(2S)-tetrahydrofuran-2-yl methyl] imidazo[1,2-b]pyridazin-8-amine which was prepared according to intermediate example 4a were transformed in analogy to example 1 using pyridin-4-ylboronic acid to give after working up and purification 4.4 mg (8%) of the title compound.

$^1$H-NMR (CDCl$_3$): δ=1.01-1.12 (4H), 1.73 (1H), 1.95 (2H), 2.09 (2H), 3.44 (1H), 3.53 (1H), 3.78 (1H), 3.92 (1H), 4.21 (1H), 6.50 (1H), 7.21 (1H), 7.70 (2H), 7.74 (2H), 7.85 (2H), 8.07 (2H), 8.17 (1H), 8.63 (2H) ppm.

Intermediate Example 4a

6-Chloro-3-[4-(2-cyclopropyl-1H-imidazol-5-yl)phenyl]-N-[(2S)-tetrahydrofuran-2-yl methyl]imidazo[1,2-b]pyridazin-8-amine

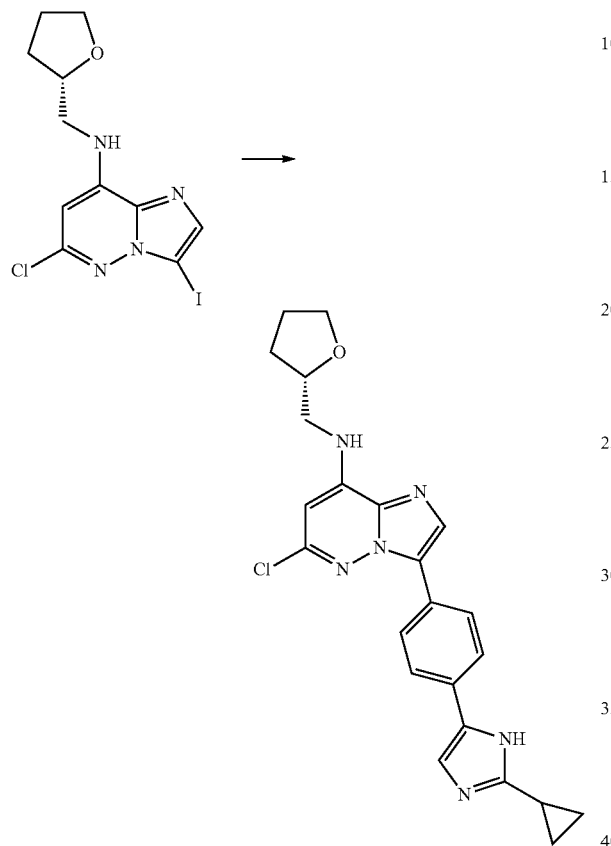

232 mg (613 µmol) 6-chloro-3-iodo-N-[(2S)-tetrahydrofuran-2-ylmethyl]imidazo[1,2-b]pyridazin-8-amine which was prepared according to intermediate example 4b were transformed in analogy to intermediate example 1a to give after working up and purification 118 mg (44%) of the title compound.

Intermediate Example 4b

6-Chloro-3-iodo-N-[(2S)-tetrahydrofuran-2-ylmethyl]imidazo[1,2-b]pyridazin-8-amine

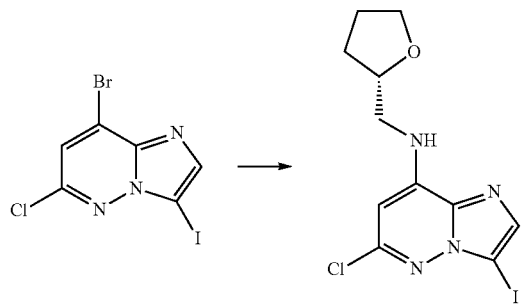 [SMILES: Clc1cc(Br)c2ncc(I)n2n1 ; Clc1cc(NC[C@@H]2CCCO2)c2ncc(I)n2n1]

500 mg (1.40 mmol) 8-bromo-6-chloro-3-iodoimidazo[1,2-b]pyridazine which was prepared according to intermediate example 1c were transformed in analogy to intermediate example 1b using 1[(2S)-tetrahydrofuran-2-yl]methanamine to give after working up and purification 497 mg (94%) of the title compound.

Example 5

3-[4-(2-Cyclopropyl-1H-imidazol-5-yl)phenyl]-6-(pyridin-4-yl)-N-[(2R)-tetrahydrofuran-2-ylmethyl]imidazo[1,2-b]pyridazin-8-amine

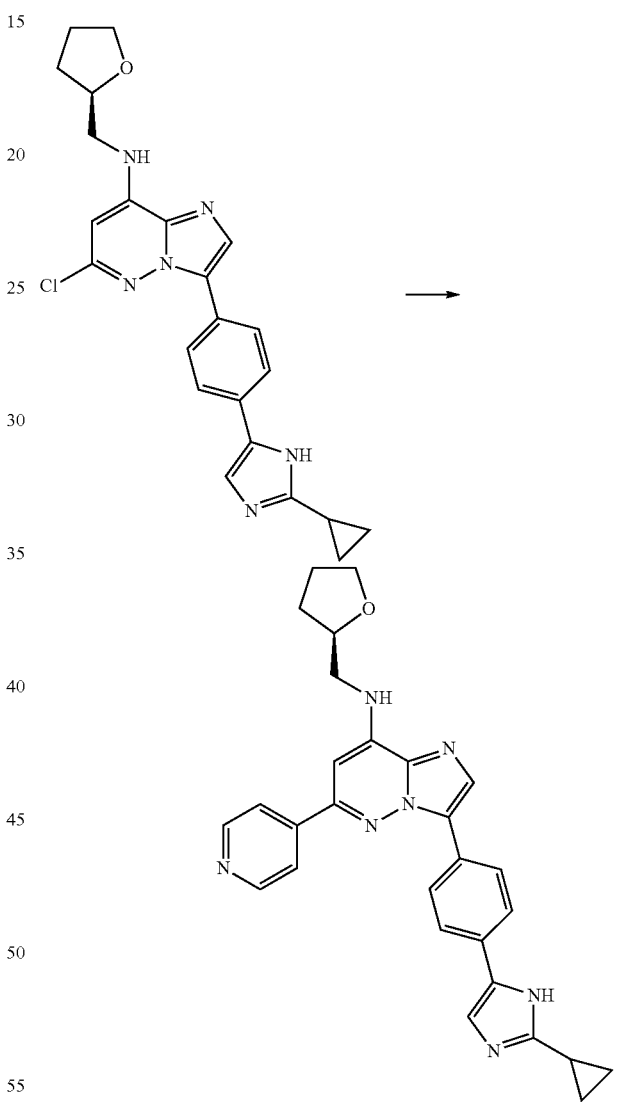

50 mg (115 µmol) 6-chloro-3-[4-(2-cyclopropyl-1H-imidazol-5-yl)phenyl]-N-[(2R)-tetrahydrofuran-2-yl methyl]imidazo[1,2-b]pyridazin-8-amine which was prepared according to intermediate example 5a were transformed in analogy to example 1 using pyridin-4-ylboronic acid to give after working up and purification 6.1 mg (11%) of the title compound.

$^1$H-NMR (CDCl$_3$): δ=1.01-1.12 (4H), 1.73 (1H), 1.95 (2H), 2.09 (2H), 3.44 (1H), 3.53 (1H), 3.78 (1H), 3.92 (1H), 4.21 (1H), 6.50 (1H), 7.21 (1H), 7.70 (2H), 7.74 (1H), 7.85 (2H), 8.07 (2H), 8.17 (1H), 8.63 (2H) ppm.

Intermediate Example 5a

6-Chloro-3-[4-(2-cyclopropyl-1H-imidazol-5-yl)phenyl]-N-[(2R)-tetrahydrofuran-2-yl methyl]imidazo[1,2-b]pyridazin-8-amine

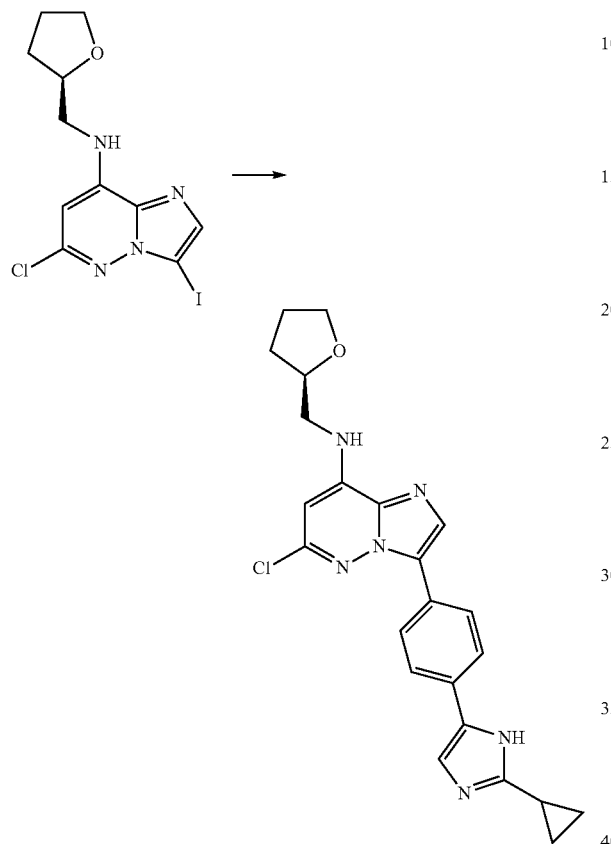

247 mg (652 µmol) 6-chloro-3-iodo-N-[(2R)-tetrahydrofuran-2-ylmethyl]imidazo[1,2-b]pyridazin-8-amine which was prepared according to intermediate example 5b were transformed in analogy to intermediate example 1a to give after working up and purification 112 mg (39%) of the title compound.

Intermediate Example 5b

6-Chloro-3-iodo-N-[(2R)-tetrahydrofuran-2-ylmethyl]imidazo[1,2-b]pyridazin-8-amine

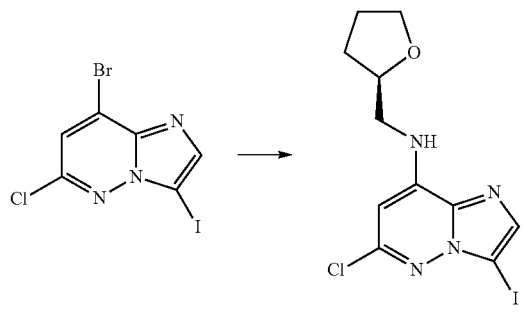 [SMILES: Clc1cc(Br)c2ncc(I)n2n1 ; Clc1cc(NC[C@H]2CCCO2)c2ncc(I)n2n1]

500 mg (1.40 mmol) 8-bromo-6-chloro-3-iodoimidazo[1,2-b]pyridazine which was prepared according to intermediate example 1c were transformed in analogy to intermediate example 1b using 1-[(2R)-tetrahydrofuran-2-yl]methanamine to give after working up and purification 513 mg (97%) of the title compound.

Example 6

3-[4-(2-Cyclopropyl-1H-imidazol-5-yl)phenyl]-6-(4-fluorophenyl)-N-(3,3,3-trifluoropropyl)imidazo[1,2-b]pyridazin-8-amine

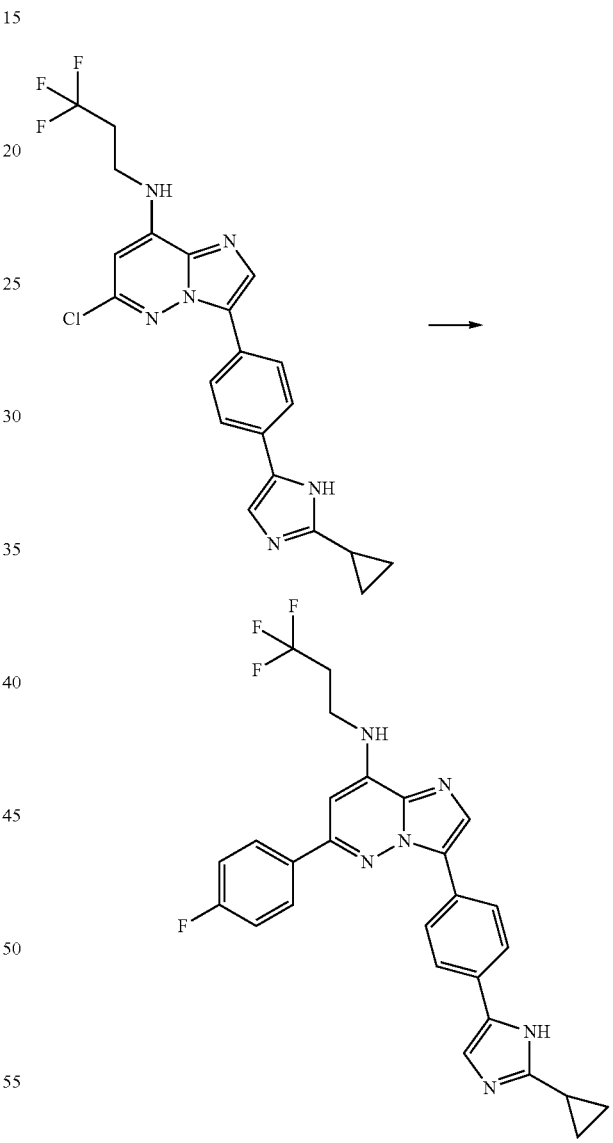

40 mg (90 µmol) 6-chloro-3-[4-(2-cyclopropyl-1H-imidazol-5-yl)phenyl]-N-(3,3,3-trifluoropropyl)imidazo[1,2-b]pyridazin-8-amine which was prepared according to intermediate example 6a were transformed in analogy to example 1 using (4-fluorophenyl)boronic acid to give after working up and purification 3.6 mg (7%) of the title compound.

$^1$H-NMR (CDCl$_3$): δ=0.97-1.09 (4H), 2.00 (2H), 2.59 (2H), 3.73 (2H), 5.97 (1H), 6.37 (1H), 7.14-7.26 (3H), 7.75-7.84 (3H), 7.96 (2H), 8.13 (2H) ppm.

Intermediate Example 6a

6-Chloro-3-[4-(2-cyclopropyl-1H-imidazol-5-yl)phenyl]-N-(3,3,3-trifluoropropyl) imidazo[1,2-b]pyridazin-8-amine

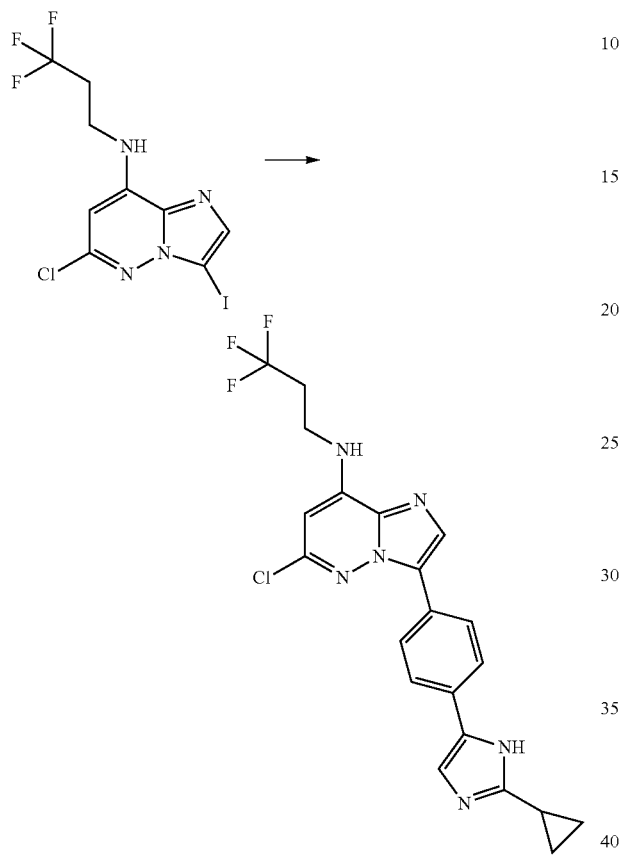

330 mg (845 µmol) 6-chloro-3-iodo-N-(3,3,3-trifluoropropyl)imidazo[1,2-b]pyridazin-8-amine which was prepared according to intermediate example 6b were transformed in analogy to intermediate example 1a to give after working up and purification 220 mg (58%) of the title compound.

Intermediate Example 6b

6-Chloro-3-iodo-N-(3,3,3-trifluoropropyl)imidazo[1,2-b]pyridazin-8-amine

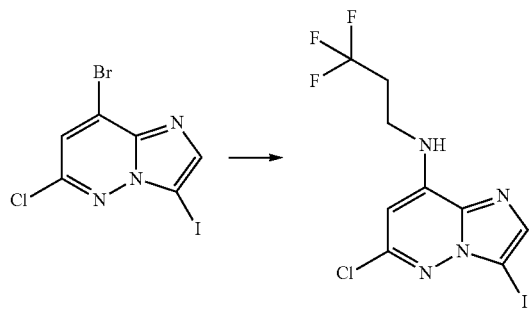 [SMILES: Clc1cc(Br)c2ncc(I)n2n1 ; FC(F)(F)CCNc1cc(Cl)nn2c(I)cnc12]

1.96 g (5.46 mmol) 8-bromo-6-chloro-3-iodoimidazo[1,2-b]pyridazine which was prepared according to intermediate example 1c were transformed in analogy to intermediate example 1b using 3,3,3-trifluoropropan-1-amine to give after working up and purification 1.58 g (74%) of the title compound.

Example 7

N-cyclopropyl-4-{6-(4-fluorophenyl)-8-[(2-hydroxy-2-methylpropyl)amino]imidazo[1,2-b]pyridazin-3-yl}-2-methylbenzamide

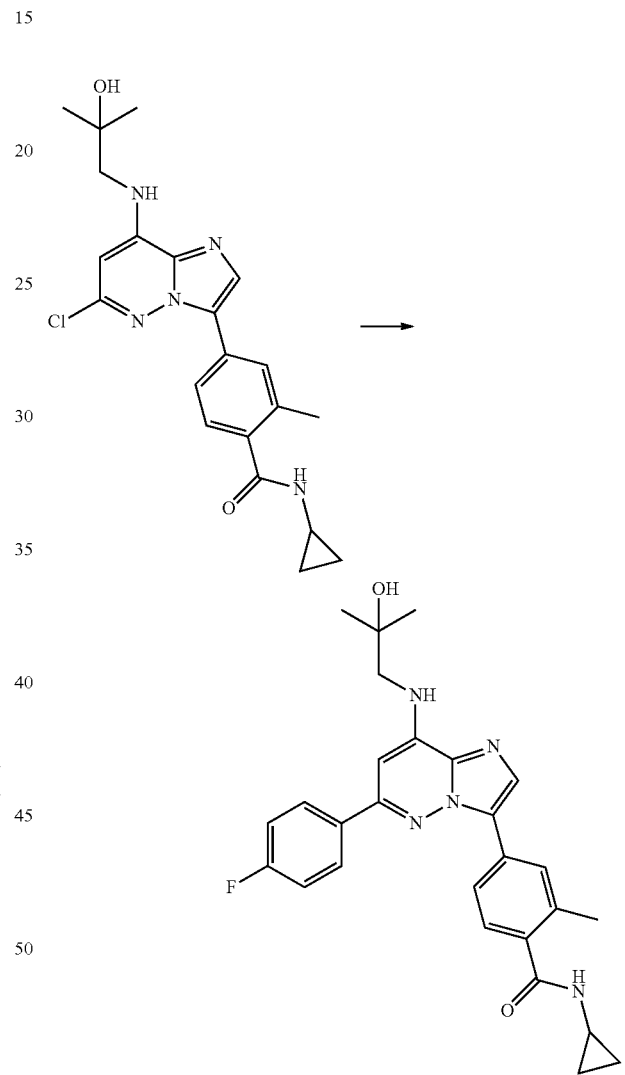

76 mg (184 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using (4-fluorophenyl)boronic acid to give after working up and purification 25.7 mg (30%) of the title compound.

$^1$H-NMR (CDCl$_3$/CD$_3$OD): δ=0.61 (2H), 0.86 (2H), 1.37 (6H), 2.47 (3H), 2.88 (1H), 3.33 (2H), 6.38 (1H), 7.13 (2H), 7.39 (1H), 7.69 (1H), 7.83-7.91 (3H), 7.94 (1H) ppm.

Intermediate Example 7a

4-{6-Chloro-8-[(2-hydroxy-2-methylpropyl)amino]imidazo[1,2-b]pyridazin-3-yl}-N-cyclopropyl-2-methylbenzamide

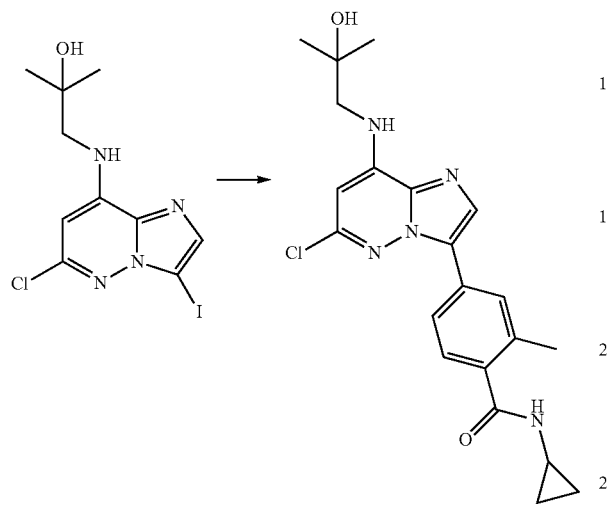

700 mg (1.91 mmol) 1-[(6-chloro-3-iodoimidazo[1,2-b]pyridazin-8-yl)amino]-2-methylpropan-2-ol which was prepared according to intermediate example 1b were transformed in analogy to intermediate example 1a using N-cyclopropyl-2-methyl-4-(4,4,5,5-tetramethyl-1,3,2-dioxaborolan-2-yl)benzamide which was prepared according to intermediate example 7b to give after working up and purification 360 mg (46%) of the title compound.

Intermediate Example 7b

N-cyclopropyl-2-methyl-4-(4,4,5,5-tetramethyl-1,3,2-dioxaborolan-2-yl)benzamide

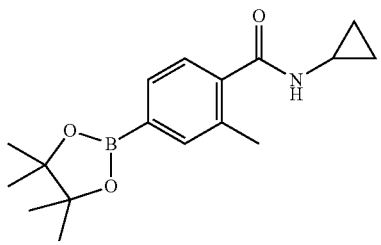 [SMILES: Cc1cc(B2OC(C)(C)C(C)(C)O2)ccc1C(=O)NC1CC1]

To a solution of 260 g (1.02 mol) 4-bromo-N-cyclopropyl-2-methylbenzamide which was prepared according to intermediate example 7c in 2 L dioxane at 23° C. were added 390 g bis-(pinacolato)-diboron, 19.5 g 2-dicyclohexylphosphino-2',4',6'-triisopropylbiphenyl, 150 .g potassium acetate and 9.37 g tris-(dibenzylidenaceton)-dipalladium(0) and the mixture was refluxed for 6 h. After cooling to 23° C., water and ethyl acetate were added and the mixture stirred for 15 min. The organic phase was washed with water, dried over sodium sulfate, filtered and evaporated. The residue was purified by chromatography to give 308 g (56%) of the title compound.

$^1$H-NMR (300 MHz, CDCl$_3$): δ=0.59 (2H), 0.85 (2H), 1.33 (6H), 2.41 (3H), 2.87 (1H), 5.94 (1H), 7.28 (1H), 7.60 (1H), 7.63 (1H) ppm.

Intermediate Example 7c

4-Bromo-N-cyclopropyl-2-methylbenzamide

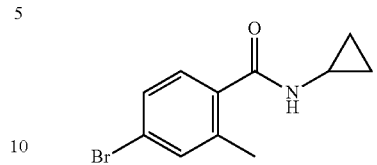

To a stirred solution of 300 g (1.4 mol) 4-bromo-2-methylbenzoic acid in 8.4 L dichloromethane at 23° C. were added 79.6 g cyclopropanamine and 320.9 g EDC. After stirring overnight, the solution was washed with water and the aqueous phase was extracted with dichloromethane. The combined organic phases were dried over sodium sulfate, filtered and evaporated. The remaining solid was triturated with diisopropyl ether, filtered, washed and dried in vaccuo to yield 260 g (73%) of the title compound.

Example 8

1-({3-[4-(2-Cyclopropyl-1H-imidazol-5-yl)phenyl]-6-(4-fluorophenyl)imidazo[1,2-b]pyridazin-8-yl}amino)-2-methylpropan-2-ol

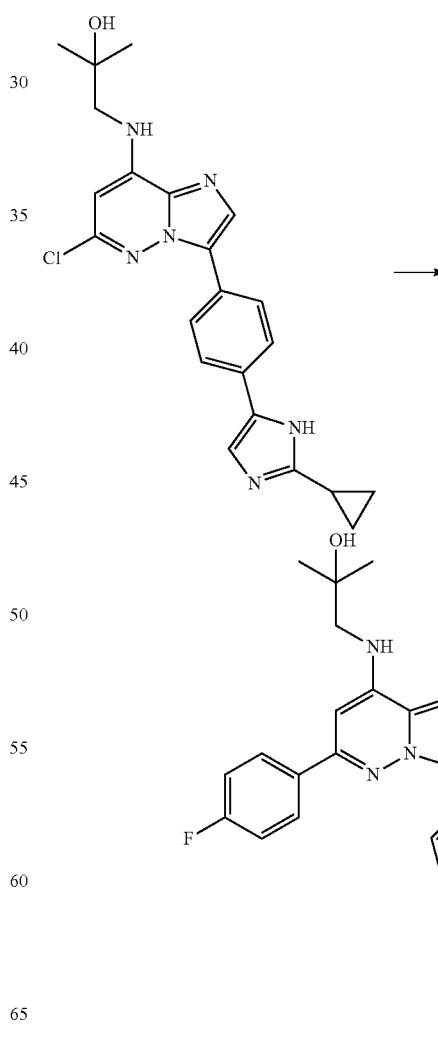

70 mg (166 μmol) 1-({6-chloro-3-[4-(2-cyclopropyl-1H-imidazol-5-yl)phenyl]imidazo[1,2-b]pyridazin-8-yl}amino)-2-methylpropan-2-ol which was prepared according to intermediate example 1a were transformed in analogy to example 1 using (4-fluorophenyl)boronic acid to give after working up and purification 4.9 mg (6%) of the title compound.

$^1$H-NMR (DMSO-d6): δ=0.80-0.94 (4H), 1.18 (6H), 1.93 (1H), 3.39 (2H), 4.79 (1H), 6.77 (1H), 6.86 (1H), 7.21+7.48 (1H), 7.85 (2H), 7.70+7.81 (2H), 7.94+7.99 (1H), 8.06-8.24 (4H), 11.81+12.12 (1H) ppm.

Example 9

1-({3-[4-(2-Cyclopropyl-1H-imidazol-5-yl)phenyl]-6-(pyridin-4-yl)imidazo[1,2-b]pyridazin-8-yl}amino)-2-methylpropan-2-ol

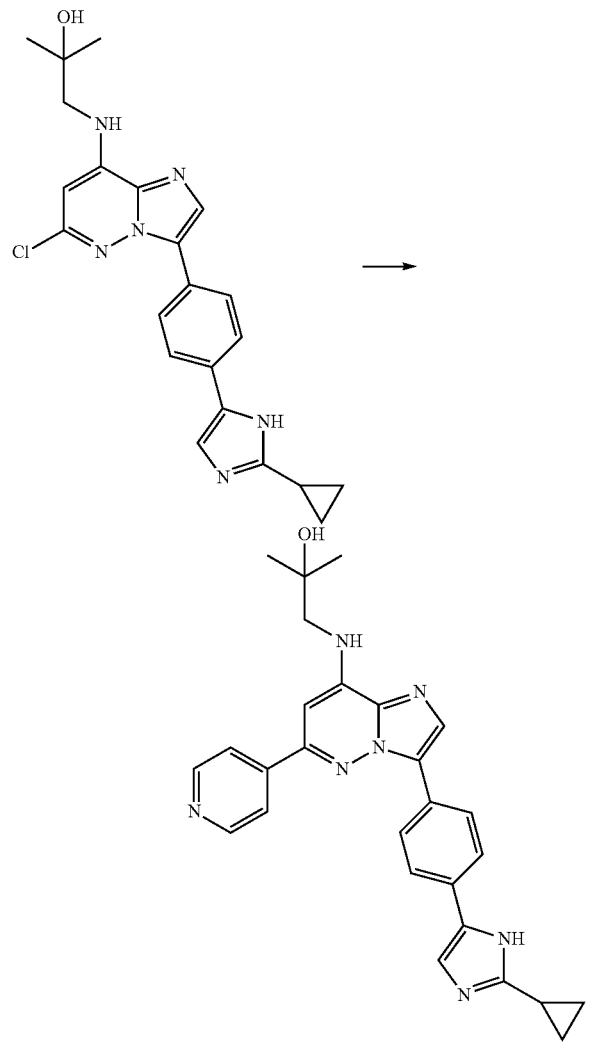

47.5 mg (112 μmol) 1-({6-chloro-3-[4-(2-cyclopropyl-1H-imidazol-5-yl)phenyl]imidazo[1,2-b]pyridazin-8-yl}amino)-2-methylpropan-2-ol which was prepared according to intermediate example 1a were transformed in analogy to example 1 using pyridin-4-ylboronic acid to give after working up and purification 12.5 mg (23%) of the title compound.

$^1$H-NMR (DMSO-d6): δ=0.82-0.92 (4H), 1.19 (6H), 1.93 (1H), 3.42 (2H), 4.79 (1H), 6.89 (1H), 7.01 (1H), 7.22+7.49 (1H), 7.72+7.83 (2H), 7.97-8.08 (3H), 8.15+8.23 (2H), 8.73 (2H), 7.82+12.13 (1H) ppm.

Example 10

N-cyclopropyl-2-methyl-4-{6-(1-methyl-1H-pyrazol-5-yl)-8-[(3,3,3-trifluoropropyl)amino]imidazo[1,2-b]pyridazin-3-yl}benzamide

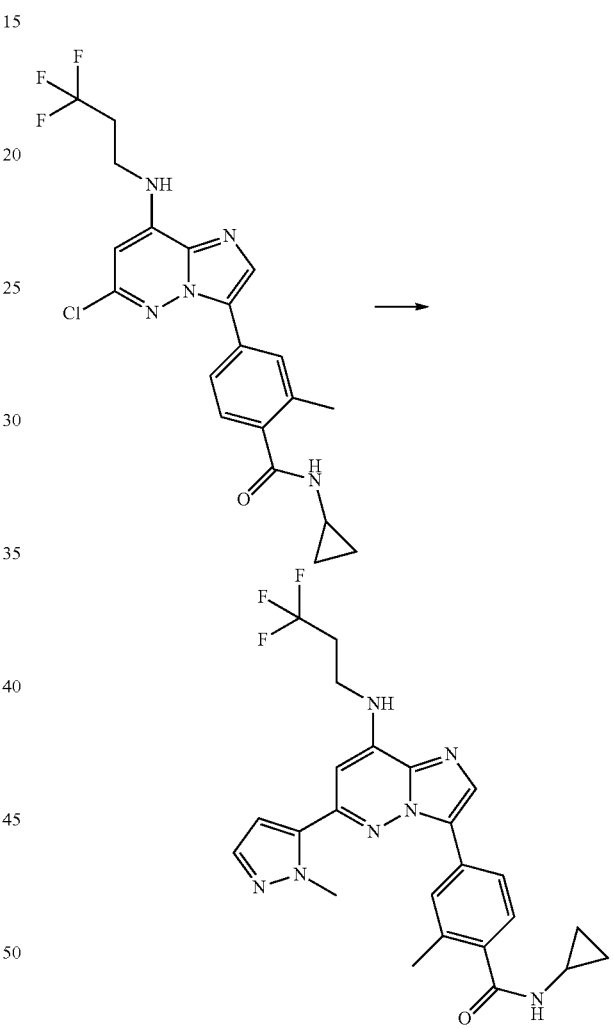

40 mg (91 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using 1-methyl-5-(4,4,5,5-tetramethyl-1,3,2-dioxaborolan-2-yl)-1H-pyrazole to give after working up and purification 7.2 mg (16%) of the title compound.

$^1$H-NMR (CDCl$_3$): δ=0.64 (2H), 0.90 (2H), 2.52 (3H), 2.58 (2H), 2.93 (1H), 3.72 (2H), 4.20 (3H), 5.95 (1H), 6.01 (1H), 6.28 (1H), 6.66 (1H), 7.42 (1H), 7.55 (1H), 7.79 (1H), 7.85 (1H), 7.89 (1H) ppm.

Intermediate Example 10a

4-{6-Chloro-8-[(3,3,3-trifluoropropyl)amino]imidazo[1,2-b]pyridazin-3-yl}-N-cyclopropyl-2-methylbenzamide

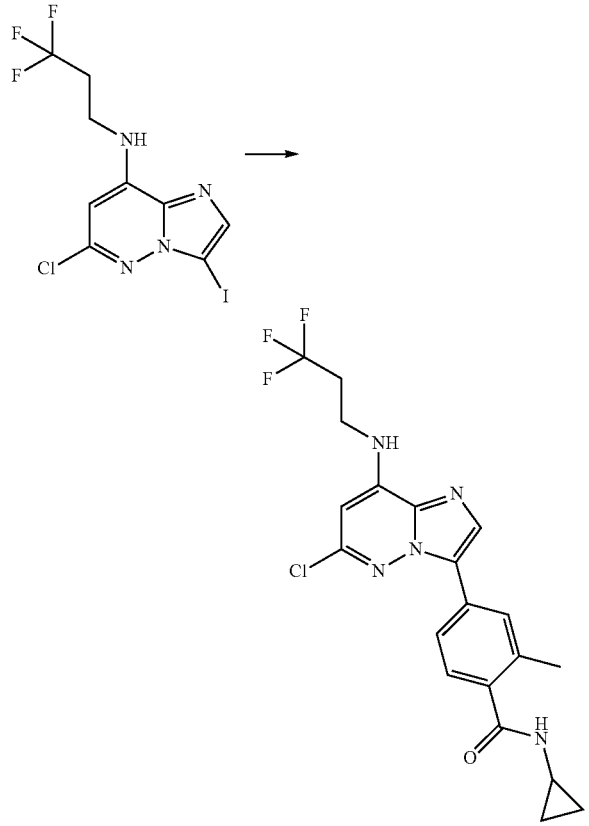

500 mg (1.28 mmol) 6-chloro-3-iodo-N-(3,3,3-trifluoropropyl)imidazo[1,2-b]pyridazin-8-amine which was prepared according to intermediate example 6b were transformed in analogy to intermediate example 1a using N-cyclopropyl-2-methyl-4-(4,4,5,5-tetramethyl-1,3,2-dioxaborolan-2-yl)benzamide to give after working up and purification 139 mg (25%) of the title compound.

Example 11

3-(3-Amino-1H-indazol-6-yl)-N-isobutyl-6-phenylimidazo[1,2-b]pyridazin-8-amine

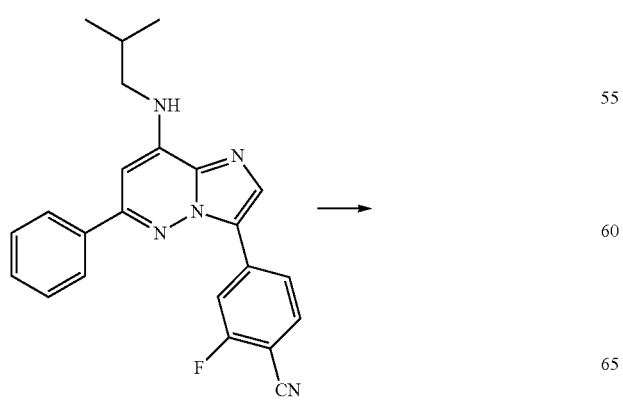

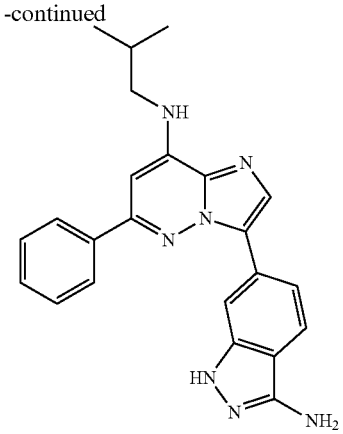

To a solution of 46 mg (119 µmol) 2-fluoro-4-[8-(isobutylamino)-6-phenylimidazo[1,2-b]pyridazin-3-yl]benzonitrile which was prepared according to intermediate example 11a in 2.5 mL n-butanol were added 232 µL hydrazine hydrate and the mixture was heated at 120° C. overnight. The precipitate was filtered, washed with 2-propanol and dried to give 26.5 mg (53%) of the title compound.

¹H-NMR (DMSO-d6): δ=0.94 (6H), 2.04 (1H), 3.26 (2H), 5.33 (2H), 6.63 (1H), 7.46-7.58 (5H), 7.74 (1H), 8.00 (1H), 8.07 (2H), 8.38 (1H), 11.53 (1H) ppm.

Intermediate Example 11a

2-Fluoro-4-[8-(isobutylamino)-6-phenylimidazo[1,2-b]pyridazin-3-yl]benzonitrile

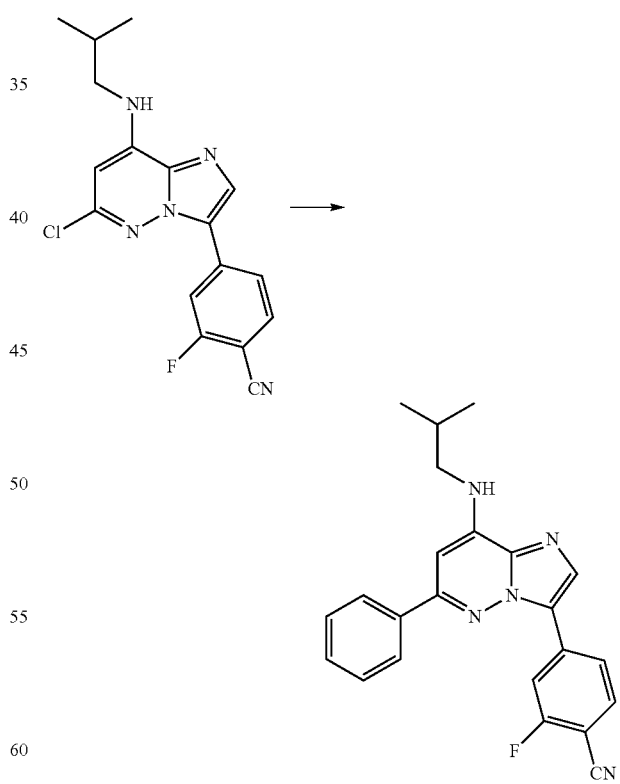

100 mg (291 µmol) 4-[6-chloro-8-(isobutylamino)imidazo[1,2-b]pyridazin-3-yl]-2-fluorobenzonitrile which was prepared according to intermediate example 11b were transformed in analogy to example 1 using phenylboronic acid to give after working up and purification 49 mg (44%) of the title compound.

Intermediate Example 11b

4-[6-Chloro-8-(isobutylamino)imidazo[1,2-b]pyridazin-3-yl]-2-fluorobenzonitrile

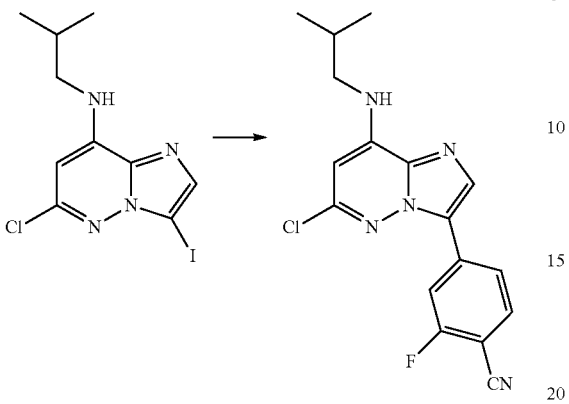

500 mg (1.43 mmol) 6-Chloro-3-iodo-N-isobutylimidazo[1,2-b]pyridazin-8-amine which was prepared according to intermediate example 3b were transformed in analogy to intermediate example 1a using (4-cyano-3-fluorophenyl)boronic acid to give after working up and purification 217 mg (44%) of the title compound.

Example 12

N-cyclopropyl-4-{8-[(2-hydroxy-2-methylpropyl)amino]-6-phenylimidazo[1,2-b]pyridazin-3-yl}-2-methylbenzamide

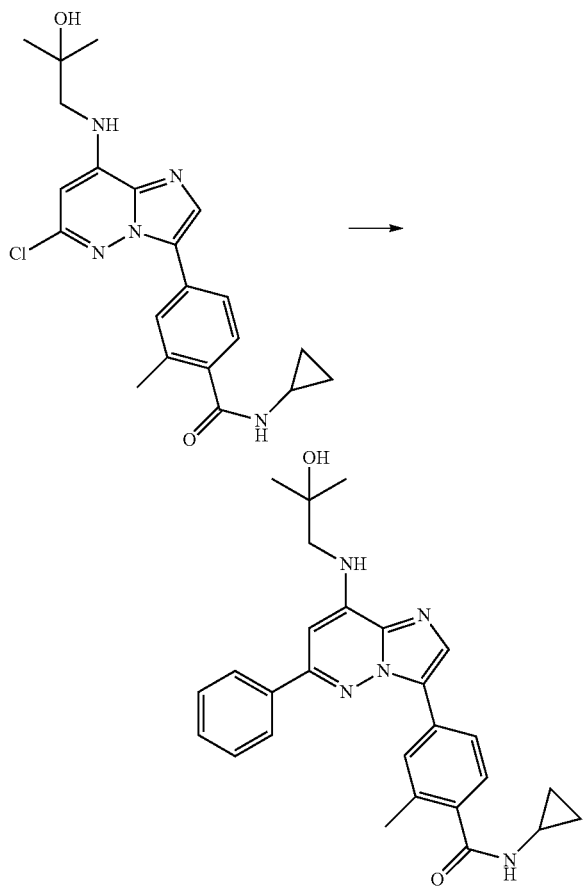

250 mg (604 μmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using phenylboronic acid to give after working up and purification 48 mg (17%) of the title compound.

$^1$H-NMR (DMSO-d6): δ=0.51 (2H), 0.66 (2H), 1.18 (6H), 2.39 (3H), 2.81 (1H), 3.39 (2H), 4.78 (1H), 6.80 (1H), 6.90 (1H), 7.40 (1H), 7.46-7.55 (3H), 8.00-8.07 (4H), 8.13 (1H), 8.30 (1H) ppm.

Example 13

N-cyclopropyl-4-[8-(isobutylamino)-6-(pyridin-4-yl)imidazo[1,2-b]pyridazin-3-yl]benzenecarbothioamide

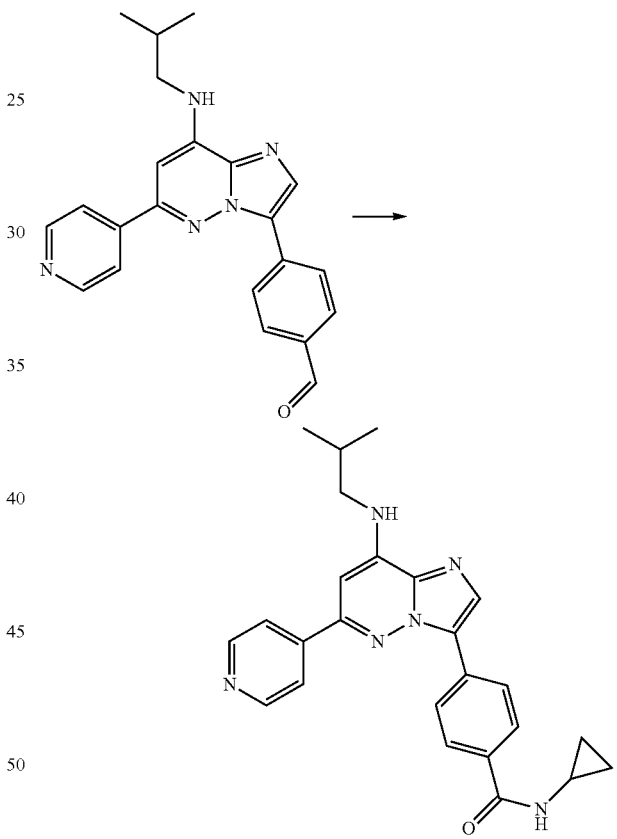

A mixture of 40 mg (108 μmol) 4-[8-(isobutylamino)-6-(pyridin-4-yl)imidazo[1,2-b]pyridazin-3-yl]benzaldehyde which was prepared according to intermediate example 13a, 3.45 mg sulfur, 37 μL cyclopropanamine and 250 μL dimethyl sulfoxide were heated at 100° C. under microwave irradiation for 4 hours. The mixture was stirred at 90° C. overnight, the solvent was evaporated and the residue purified by chromatography to give 4.8 mg (10%) of the title compound.

$^1$H-NMR (CDCl$_3$/CD$_3$OD): δ=0.80 (2H), 1.03 (2H), 1.08 (6H), 2.08 (1H), 3.21 (2H), 3.40 (1H), 6.40 (1H), 7.78-7.89 (5H), 8.12 (2H), 8.69 (2H) ppm.

Intermediate Example 13a

4-[8-(Isobutylamino)-6-(pyridin-4-yl)imidazo[1,2-b]pyridazin-3-yl]benzaldehyde

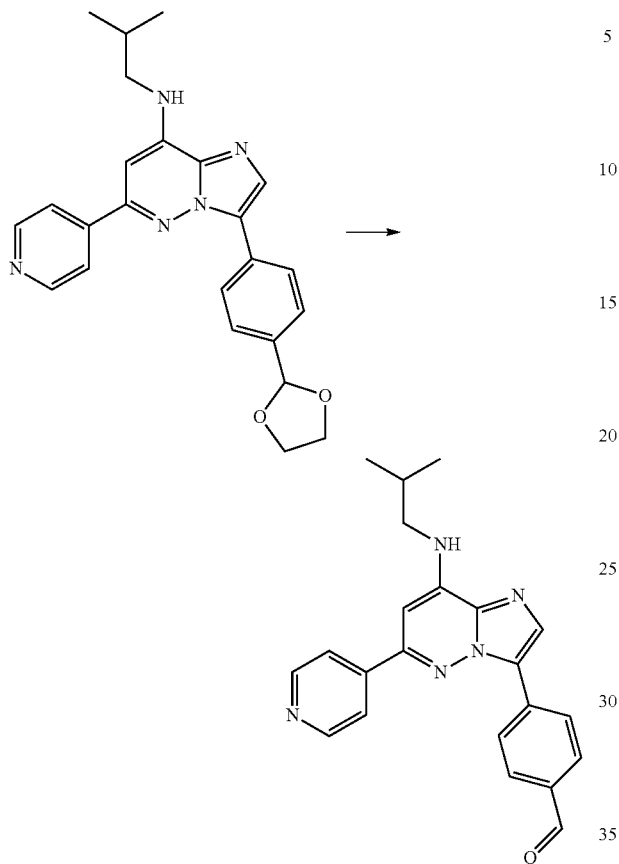

To a solution of 63 mg (152 μmol) 3-[4-(1,3-dioxolan-2-yl)phenyl]-N-isobutyl-6-(pyridin-4-yl)imidazo[1,2-b]pyridazin-8-amine which was prepared according to intermediate example 13b, in 2.8 mL acetone were added 190 μL 4N hydrochloric acid and the mixture was stirred at 23° C. for 2 hours. Saturated hydrogen carbonate solution was added and the mixture was extracted with dichloromethane. The organic phase was dried over sodium sulfate. After filtration and removal of solvent the residue was purified by chromatography to give 41 mg (73%) of the title compound.

Intermediate Example 13b

3-[4-(1,3-Dioxolan-2-yl)phenyl]-N-isobutyl-6-(pyridin-4-yl)imidazo[1,2-b]pyridazin-8-amine

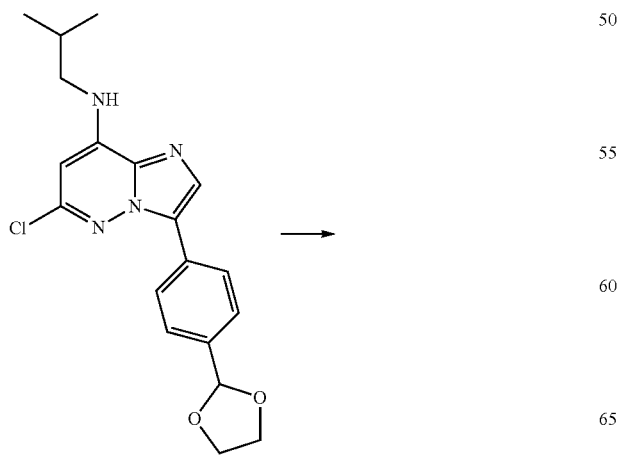

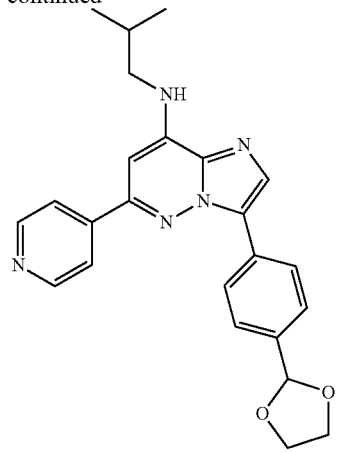

105 mg (282 μmol) 6-chloro-3-[4-(1,3-dioxolan-2-yl)phenyl]-N-isobutylimidazo[1,2-b]pyridazin-8-amine which was prepared according to intermediate example 13c were transformed in analogy to example 1 using pyridin-4-ylboronic acid to give after working up and purification 64 mg (55%) of the title compound.

Intermediate Example 13c

6-Chloro-3-[4-(1,3-dioxolan-2-yl)phenyl]-N-isobutylimidazo[1,2-b]pyridazin-8-amine

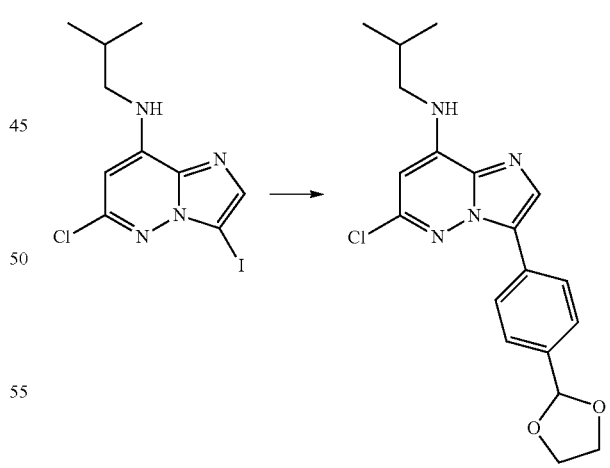

500 mg (1.43 mmol) 6-Chloro-3-iodo-N-isobutylimidazo[1,2-b]pyridazin-8-amine which was prepared according to intermediate example 3b were transformed in analogy to intermediate example 1a using 2-[4-(1,3-dioxolan-2-yl)phenyl]-4,4,5,5-tetramethyl-1,3,2-dioxaborolane to give after working up and purification 314 mg (47%) of the title compound.

Example 14

N-cyclopropyl-4-{8-[(2-hydroxy-2-methylpropyl)amino]-6-phenylimidazo[1,2-b]pyridazin-3-yl}benzamide

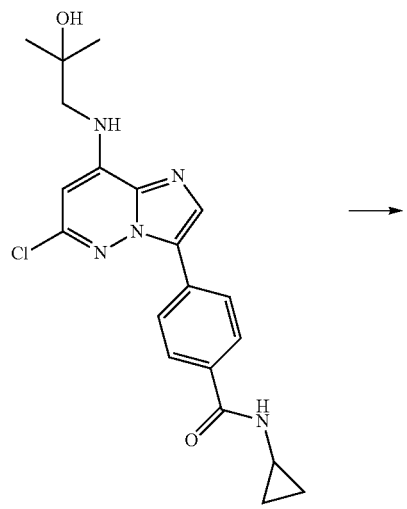

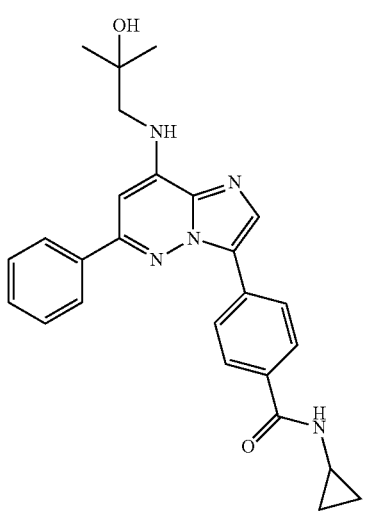

176 mg (440 μmol) which 4-{6-chloro-8-[(2-hydroxy-2-methylpropyl)amino]imidazo[1,2-b]pyridazin-3-yl}-N-cyclopropylbenzamide was prepared according to intermediate example 14a were transformed in analogy to example 1 using phenylboronic acid to give after working up and purification 42 mg (21%) of the title compound.

$^1$H-NMR (DMSO-d6): δ=0.56 (2H), 0.67 (2H), 1.19 (6H), 2.85 (1H), 3.40 (2H), 4.78 (1H), 6.82 (1H), 6.93 (1H), 7.46-7.55 (3H), 7.93 (2H), 8.05 (2H), 8.09 (1H), 8.33 (2H), 8.45 (1H) ppm.

Intermediate Example 14a

4-{6-Chloro-8-[(2-hydroxy-2-methylpropyl)amino]imidazo[1,2-b]pyridazin-3-yl}-N-cyclopropylbenzamide

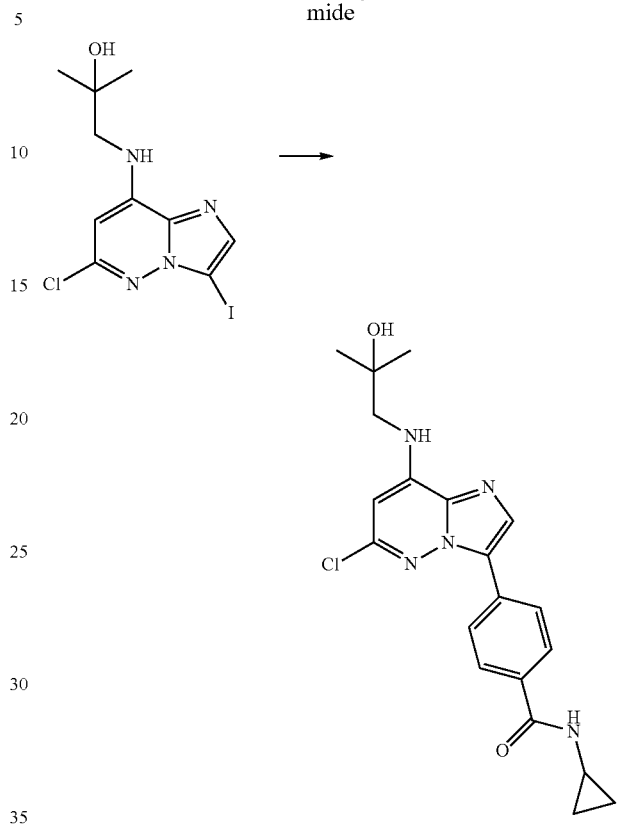

976 mg (2.66 mmol) 1-[(6-chloro-3-iodoimidazo[1,2-b]pyridazin-8-yl)amino]-2-methylpropan-2-ol which was prepared according to intermediate example 1b were transformed in analogy to intermediate example 1a using [4-(cyclopropylcarbamoyl)phenyl]boronic acid to give after working up and purification 602 mg (57%) of the title compound.

Example 15

N-cyclopropyl-4-{8-[(2-hydroxy-2-methylpropyl)amino]-6-(methylsulfanyl)imidazo[1,2-b]pyridazin-3-yl}-2-methylbenzamide

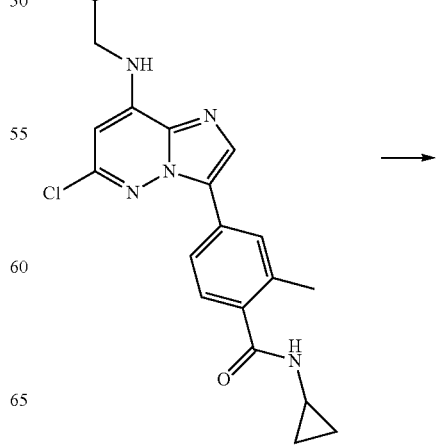

123

-continued

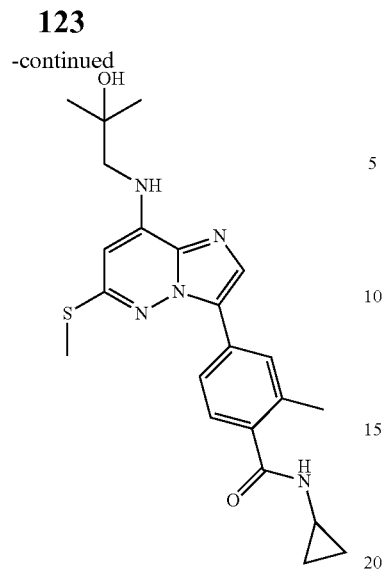

To a solution of 83 mg (201 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a in 1.0 mL dimethyl sulfoxide were added 70 mg sodium methanethiolate and the mixture was heated under microwave irradiation at 70° C. for 1 hour. The mixture was poured into water and extracted with dichloromethane and methanol. The organic layer was washed with brine and dried over sodium sulfate. After filtration and removal of the solvent the residue was purified by recrystallisation to give 46.7 mg (55%) of the title compound.

Example 16

3-[4-(2-Cyclopropyl-1H-imidazol-5-yl)phenyl]-6-[(1E)-prop-1-en-1-yl]-N-(3,3,3-trifluoropropyl)imidazo[1,2-b]pyridazin-8-amine

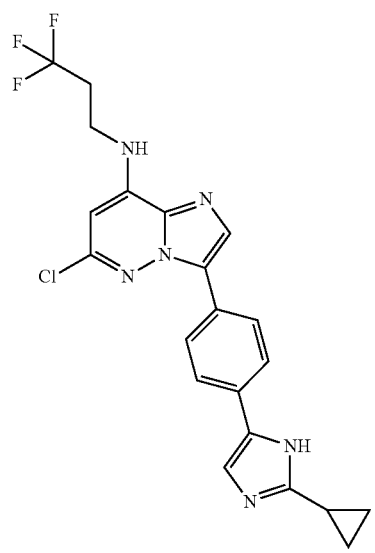

124

-continued

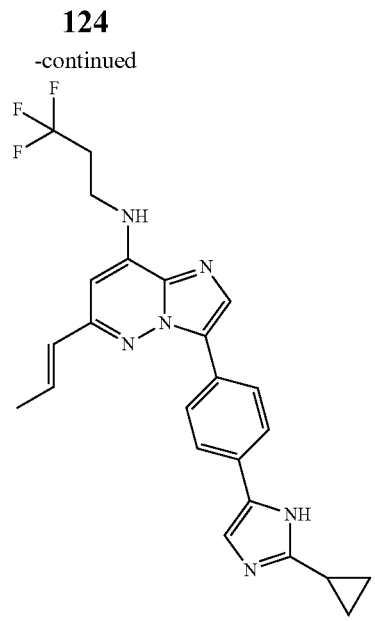

35 mg (78 μmol) 6-chloro-3-[4-(2-cyclopropyl-1H-imidazol-5-yl)phenyl]-N-(3,3,3-trifluoropropyl)imidazo[1,2-b]pyridazin-8-amine which was prepared according to intermediate example 6a were transformed in analogy to example 1 using (1E)-prop-1-en-1-ylboronic acid to give after working up and purification 3.6 mg (10%) of the title compound.

$^1$H-NMR (CDCl$_3$): δ=0.95-1.04 (4H), 1.95 (3H), 2.00 (1H), 2.55 (2H), 3.62 (2H), 6.10 (1H), 6.46 (1H), 6.61 (1H), 7.16 (1H), 7.67 (1H), 7.70 (2H), 8.05 (2H) ppm.

Example 17

N-cyclopropyl-4-{8-[(2-methoxy-2-methylpropyl)amino]-6-(pyridin-4-yl) imidazo[1,2-b]pyridazin-3-yl}-2-methylbenzamide

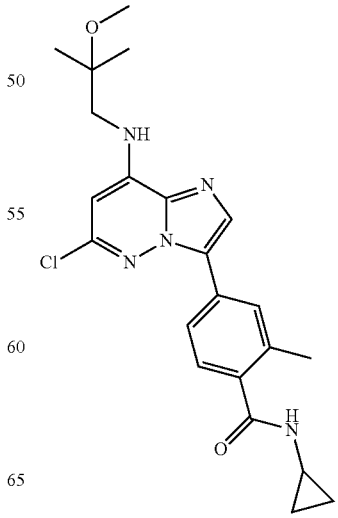

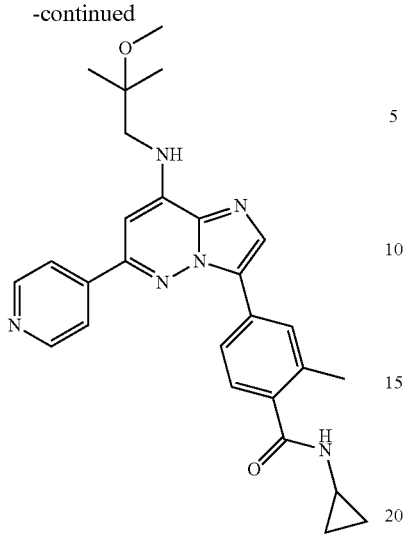

60 mg (140 μmol) 4-{6-Chloro-8-[(2-methoxy-2-methylpropyl)amino]imidazo[1,2-b]pyridazin-3-yl}-N-cyclopropyl-2-methylbenzamide which was prepared according to intermediate example 17a were transformed in analogy to example 1 using pyridin-4-ylboronic acid to give after working up and purification 18.7 mg (28%) of the title compound.

$^1$H-NMR (CDCl$_3$): δ=0.64 (2H), 0.90 (2H), 1.33 (6H), 2.54 (3H), 2.93 (1H), 3.28 (3H), 3.38 (2H), 6.11 (1H), 6.18 (1H), 6.42 (1H), 7.44 (1H), 7.80-7.85 (3H), 7.92 (1H), 8.00 (1H), 8.71 (2H) ppm.

Intermediate Example 17a

4-{6-Chloro-8-[(2-methoxy-2-methylpropyl)amino]imidazo[1,2-b]pyridazin-3-yl}-N-cyclopropyl-2-methylbenzamide

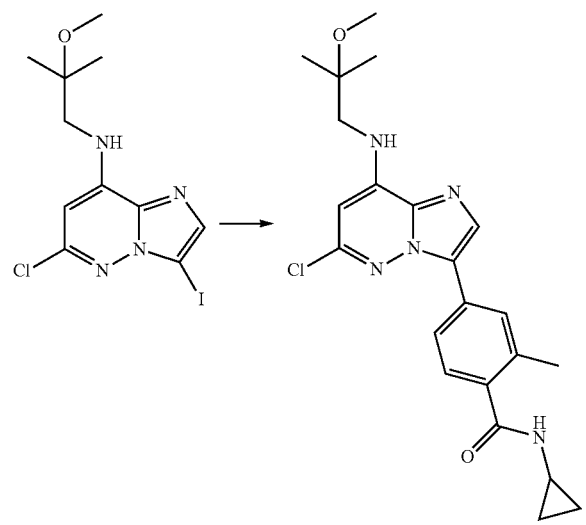 [SMILES: COC(C)(C)CNc1cc(Cl)nn2c(I)cnc12 ; COC(C)(C)CNc1cc(Cl)nn2c(-c3ccc(C(=O)NC4CC4)c(C)c3)cnc12]

145 mg (380 μmol) 6-chloro-3-iodo-N-(2-methoxy-2-methylpropyl)imidazo[1,2-b]pyridazin-8-amine which was prepared according to intermediate example 17b were transformed in analogy to intermediate example 1a using N-cyclopropyl-2-methyl-4-(4,4,5,5-tetramethyl-1,3,2-dioxaborolan-2-yl)benzamide to give after working up and purification 131 mg (81%) of the title compound.

Intermediate Example 17b

6-Chloro-3-iodo-N-(2-methoxy-2-methylpropyl)imidazo[1,2-b]pyridazin-8-amine

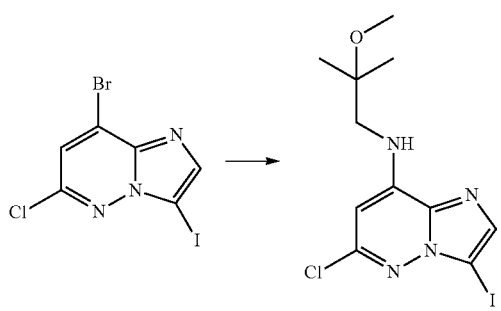 [SMILES: Clc1cc(Br)c2ncc(I)n2n1 ; COC(C)(C)CNc1cc(Cl)nn2c(I)cnc12]

250 mg (698 μmol) 8-bromo-6-chloro-3-iodoimidazo[1,2-b]pyridazine which was prepared according to intermediate example 1c were transformed in analogy to intermediate example 1b using 2-methoxy-2-methylpropan-1-amine to give after working up and purification 260 mg (98%) of the title compound.

Example 18

N-cyclopropyl-4-{8-[(2-hydroxy-2-methylpropyl)amino]-6-(methylsulfonyl)imidazo[1,2-b]pyridazin-3-yl}-2-methylbenzamide

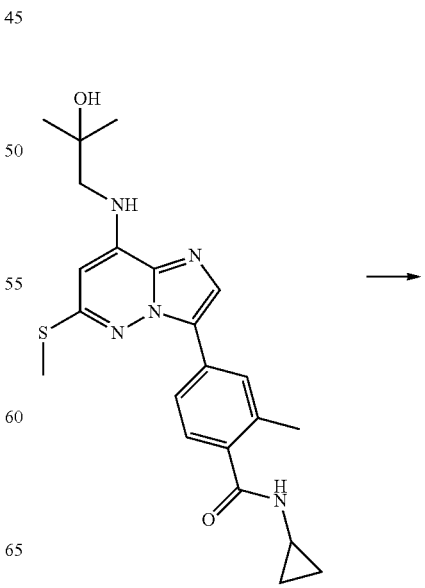

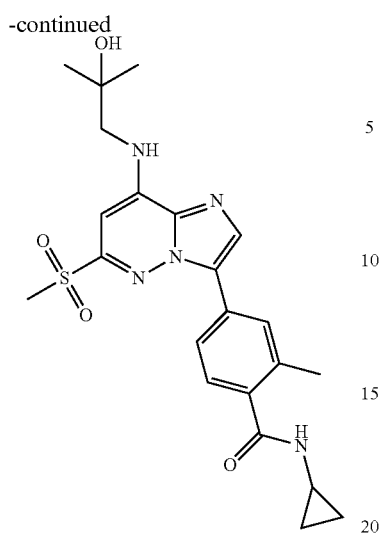

To a solution of 38.7 mg (91 μmol) N-cyclopropyl-4-{8-[(2-hydroxy-2-methylpropyl)amino]-6-(methylsulfanyl)imidazo[1,2-b]pyridazin-3-yl}-2-methylbenzamide which was prepared according to intermediate example 15 in 1.2 mL N,N-dimethylformamide were added 168 mg Oxone and the mixture was stirred at 23° C. for 2.5 days. Water was added and the mixture was extracted with dichloromethane. The organic phase was washed with water and dried over sodium sulfate. After filtration and removal of solvent the residue was purified by chromatography to give 18.5 mg (39%) of the title compound.

$^1$H-NMR (DMSO-d6): δ=0.50 (2H), 0.65 (2H), 1.15 (6H), 2.37 (3H), 2.80 (1H), 3.34 (2H), 3.38 (3H), 4.79 (1H), 6.76 (1H), 7.40 (1H), 7.71 (1H), 7.95 (1H), 7.99 (1H), 8.16 (1H), 8.32 (1H) ppm.

Example 19

N-cyclopropyl-4-{6-(4-fluorophenyl)-8-[(2-hydroxy-2-methylpropyl)amino]imidazo[1,2-b]pyridazin-3-yl}benzamide

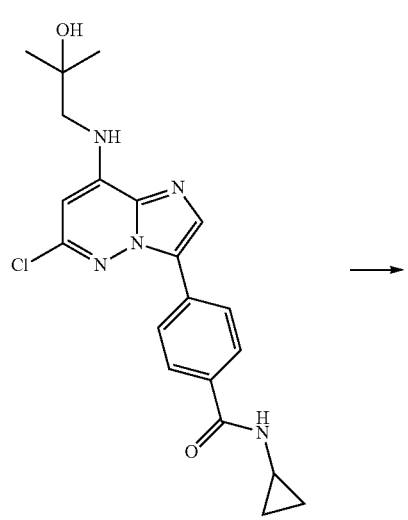

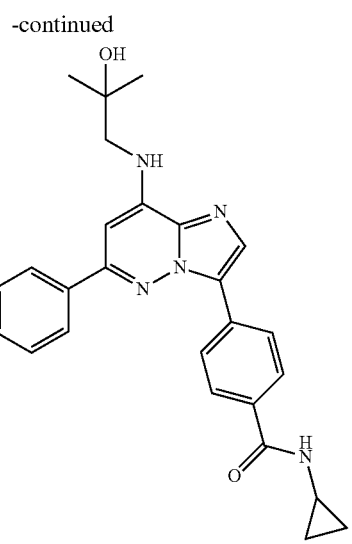

200 mg (500 μmol) 4-{6-chloro-8-[(2-hydroxy-2-methylpropyl)amino]imidazo[1,2-b]pyridazin-3-yl}-N-cyclopropylbenzamide which was prepared according to intermediate example 14a were transformed in analogy to example 1 using (4-fluorophenyl)boronic acid to give after working up and purification 136 mg (59%) of the title compound.

$^1$H-NMR (DMSO-d6): δ=0.56 (2H), 0.68 (2H), 1.18 (6H), 2.85 (1H), 3.39 (2H), 4.79 (1H), 6.81 (1H), 6.94 (1H), 7.35 (2H), 7.93 (2H), 8.09 (1H), 8.11 (2H), 8.31 (2H), 8.46 (1H) ppm.

Example 20

N-cyclopropyl-4-{6-[2-(hydroxymethyl)phenyl]-8-[(3,3,3-trifluoropropyl)amino]imidazo[1,2-b]pyridazin-3-yl}-2-methylbenzamide

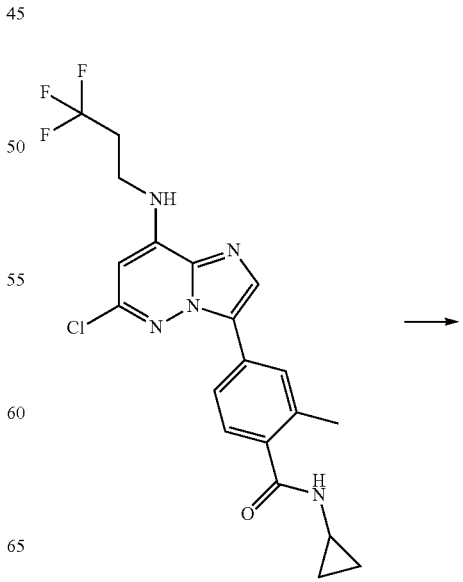

-continued

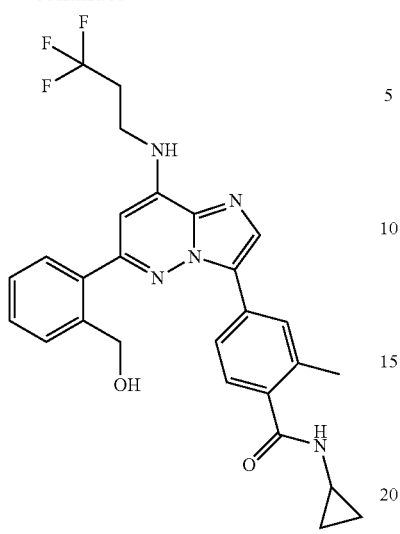

172 mg (393 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using [2-(hydroxymethyl)phenyl]boronic acid to give after working up and purification 29.1 mg (14%) of the title compound.

$^1$H-NMR (CDCl$_3$): δ=0.58 (2H), 0.85 (2H), 2.48 (3H), 2.58 (2H), 2.88 (1H), 3.72 (2H), 3.96 (1H), 4.41 (2H), 6.16 (1H), 6.19 (1H), 6.24 (1H), 7.38 (1H), 7.45-7.52 (3H), 7.60 (1H), 7.61 (1H), 7.70 (1H), 7.72 (1H) ppm.

Example 21

N-cyclopropyl-4-{8-[(2-hydroxy-2-methylpropyl)amino]-6-(1-methyl-1H-pyrazol-5-yl)imidazo[1,2-b]pyridazin-3-yl}-2-methylbenzamide

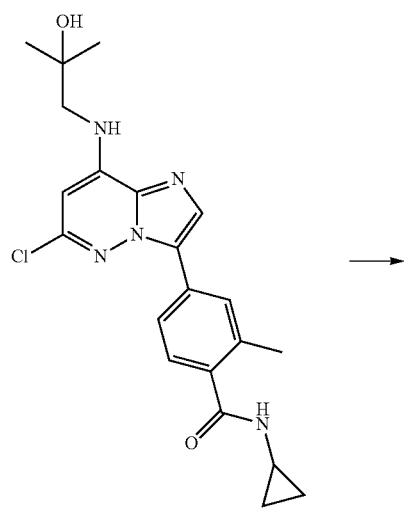

-continued

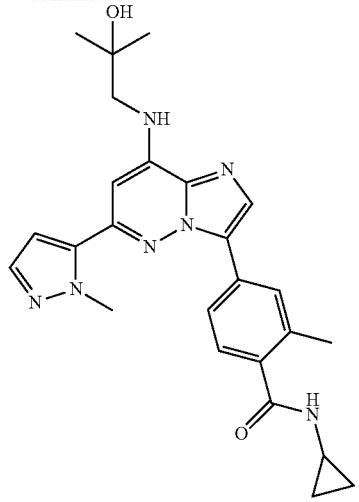

100 mg (242 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using 1-methyl-5-(4,4,5,5-tetramethyl-1,3,2-dioxaborolan-2-yl)-1H-pyrazole to give after working up and purification 35.9 mg (31%) of the title compound.

$^1$H-NMR (DMSO-d6): δ=0.50 (2H), 0.65 (2H), 1.17 (6H), 2.35 (3H), 2.80 (1H), 3.35 (2H), 4.13 (3H), 4.76 (1H), 6.62 (1H), 6.89 (1H), 7.00 (1H), 7.37 (1H), 7.51 (1H), 7.93 (1H), 7.97 (1H), 7.98 (1H), 8.30 (1H) ppm.

Example 22

3-[4-(2-Cyclopropyl-1H-imidazol-5-yl)phenyl]-6-ethenyl-N-(3,3,3-trifluoropropyl)imidazo[1,2-b]pyridazin-8-amine

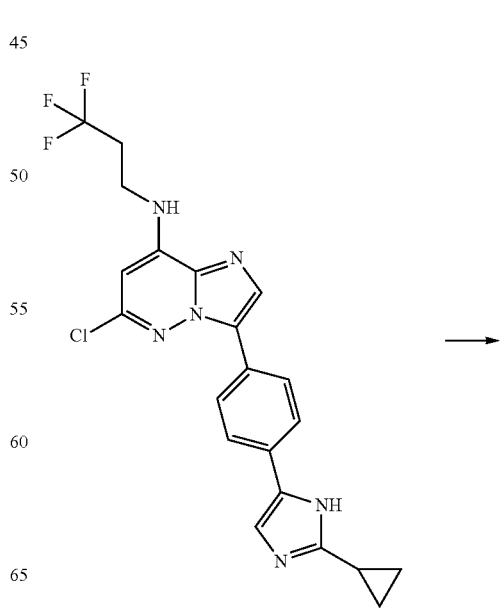

131
-continued

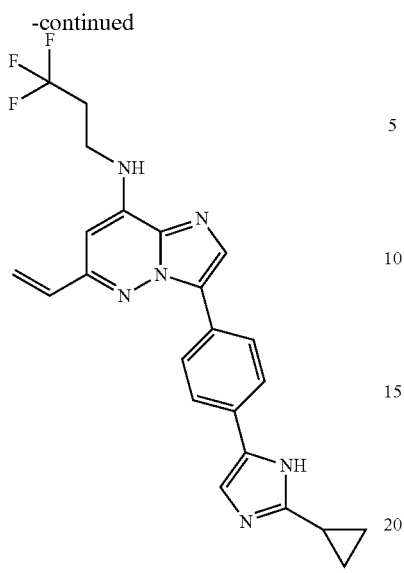

55 mg (123 µmol) 6-chloro-3-[4-(2-cyclopropyl-1H-imidazol-5-yl)phenyl]-N-(3,3,3-trifluoropropyl)imidazo[1,2-b]pyridazin-8-amine which was prepared according to intermediate example 6a were transformed in analogy to example 1 using 4,4,5,5-tetramethyl-2-vinyl-1,3,2-dioxaborolane to give after working up and purification 3.2 mg (6%) of the title compound.

¹H-NMR (CDCl₃): δ=0.95-1.03 (4H), 1.99 (1H), 2.56 (2H), 3.64 (2H), 5.58 (1H), 6.07 (1H), 6.18 (1H), 6.76 (1H), 7.16 (1H), 7.68-7.74 (3H), 8.05 (2H) ppm.

Example 23

N-cyclopropyl-2-methyl-4-{6-[(1E/Z)-prop-1-en-1-yl]-8-[(3,3,3-trifluoropropyl)amino]imidazo[1,2-b]pyridazin-3-yl}benzamide

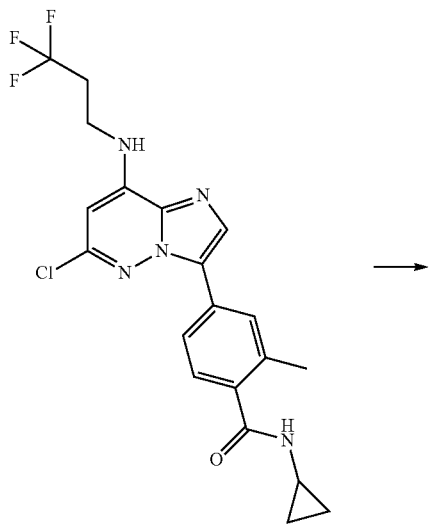

132
-continued

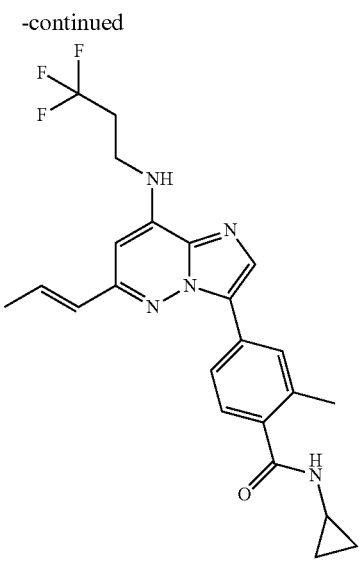

75 mg (171 µmol) 4-{6-Chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using (1E)-prop-1-en-1-ylboronic acid to give after working up and purification 3.0 mg (4%) of the title compound.

¹H-NMR (CDCl₃): δ=0.63 (2H), 0.90 (2H), 1.98 (3H), 2.47-2.65 (2H), 2.54 (3H), 2.92 (1H), 3.67 (2H), 5.91 (1H), 5.98 (1H), 6.46 (1H), 6.60+6.66 (1H), 7.25 (1H), 7.43 (1H), 7.73 (1H), 7.90 (1H), 7.96 (1H) ppm.

Example 24

N-cyclopropyl-4-{8-[(2-hydroxy-2-methylpropyl)amino]-6-[(1E/Z)-prop-1-en-1-yl]imidazo[1,2-b]pyridazin-3-yl}-2-methylbenzamide

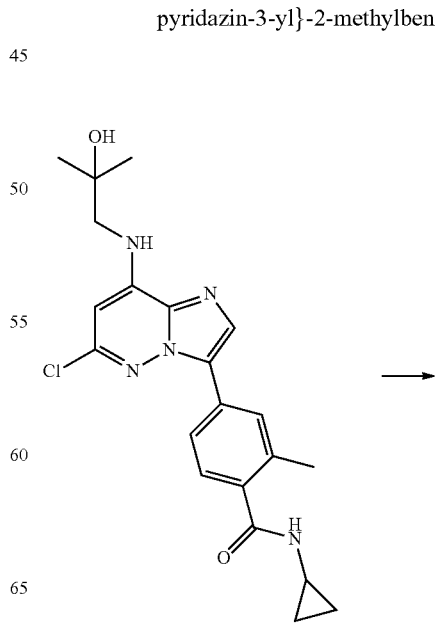

133

-continued

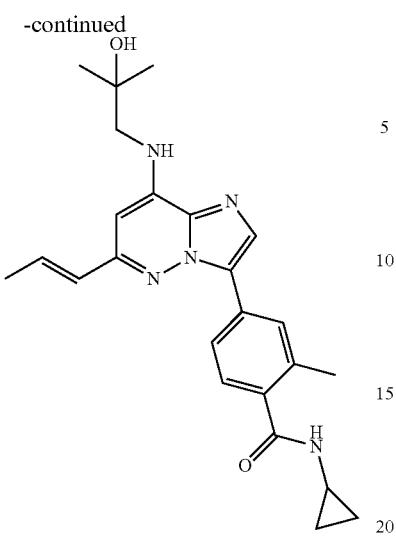

75 mg (181 µmol) 4-{6-Chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 1 using (1E)-prop-1-en-1-ylboronic acid to give after working up and purification 22 mg (29%) of the title compound.

¹H-NMR (CDCl₃): δ=0.63 (2H), 0.89 (2H), 1.43 (6H), 1.95+2.16 (3H), 2.51 (3H), 2.92 (1H), 3.32 (2H), 4.33 (1H), 5.99 (1H), 6.07+6.14 (1H), 6.37 (1H), 6.41 (1H), 6.57+6.63 (1H), 7.39 (1H), 7.66+7.70 (1H), 7.84+7.87 (1H), 7.94 (1H) ppm.

Example 25

4-{6-[(2E)-But-2-en-2-yl]-8-[(2-hydroxy-2-methyl-propyl)amino]imidazo[1,2-b]pyridazin-3-yl}-N-cyclopropyl-2-methylbenzamide

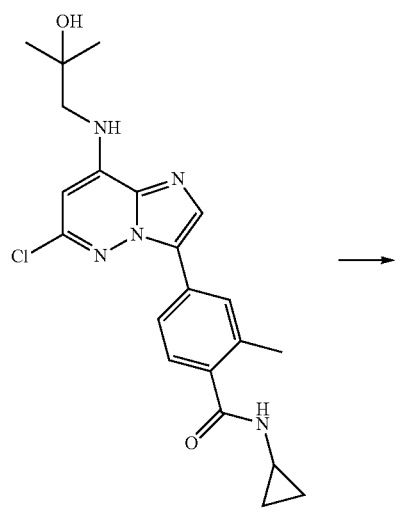

134

-continued

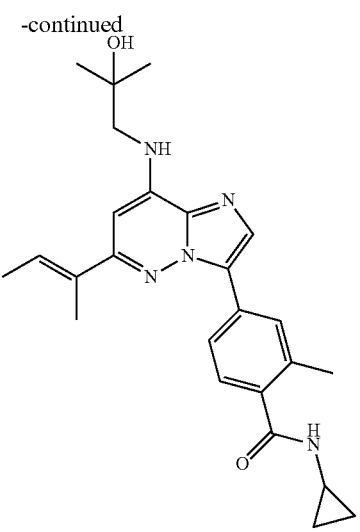

75 mg (181 µmol) 4-{6-Chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 1 to give after working up and purification 7.0 mg (8%) of the title compound.

¹H-NMR (CDCl₃): δ=0.62 (2H), 0.88 (2H), 1.45 (6H), 1.79 (3H), 2.11 (3H), 2.50 (3H), 2.91 (1H), 3.32 (2H), 5.02 (1H), 5.77 (1H), 5.97 (1H), 6.00 (1H), 6.50 (1H), 7.38 (1H), 7.70 (1H), 7.89 (1H), 7.91 (1H) ppm.

Example 26

3-[4-(2-Cyclopropyl-1H-imidazol-5-yl)phenyl]-6-(pyridin-4-yl)-N-(3,3,3-trifluoropropyl)imidazo[1,2-b]pyridazin-8-amine

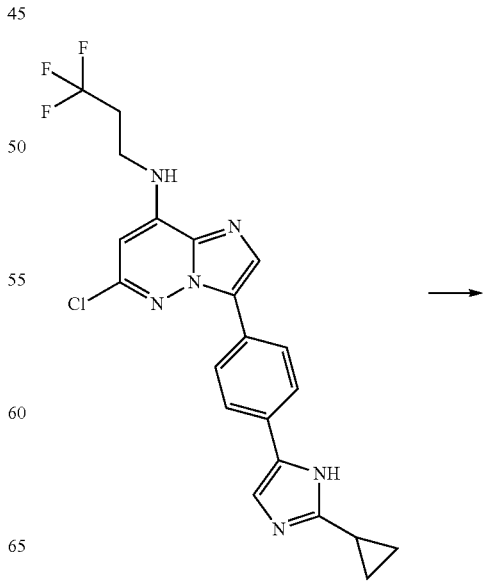

-continued

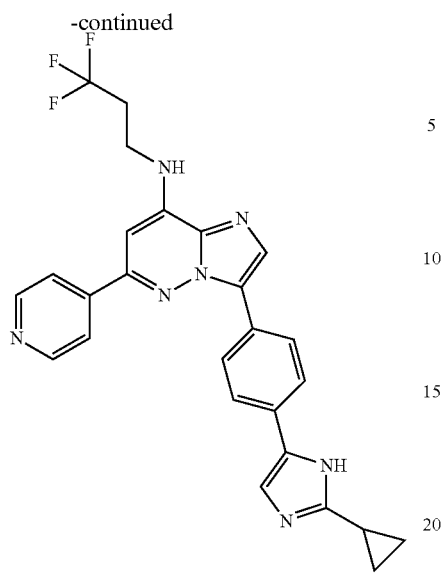

70 mg (157 µmol) 6-Chloro-3-[4-(2-cyclopropyl-1H-imidazol-5-yl)phenyl]-N-(3,3,3-trifluoropropyl)imidazo[1,2-b]pyridazin-8-amine which was prepared according to intermediate example 6a were transformed in analogy to example 1 using pyridin-4-ylboronic acid to give after working up and purification 3.2 mg (4%) of the title compound.

¹H-NMR (CDCl₃): δ=0.92-0.98 (4H), 1.98 (1H), 2.58 (2H), 3.32 (2H), 3.69 (2H), 6.42 (1H), 7.15 (1H), 7.72 (2H), 7.75 (1H), 7.87 (2H), 8.04 (2H), 8.65 (2H) ppm.

-continued

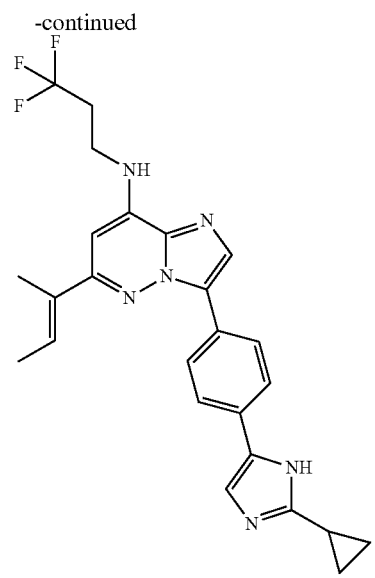

50 mg (112 µmol) 6-Chloro-3-[4-(2-cyclopropyl-1H-imidazol-5-yl)phenyl]-N-(3,3,3-trifluoropropyl)imidazo[1,2-b]pyridazin-8-amine which was prepared according to intermediate example 6a were transformed in analogy to example 1 to give after working up and purification 3.0 mg (5%) of the title compound.

¹H-NMR (CDCl₃): δ=0.95-1.02 (4H), 1.78 (3H), 1.99 (1H), 2.12 (3H), 2.46-2.63 (2H), 3.62 (2H), 5.78 (1H), 5.96 (1H), 7.16 (1H), 7.69 (2H), 7.73 (1H), 8.05 (2H) ppm.

Example 27

6-[(2E)-But-2-en-2-yl]-3-[4-(2-cyclopropyl-1H-imidazol-5-yl)phenyl]-N-(3,3,3-trifluoropropyl)imidazo[1,2-b]pyridazin-8-amine

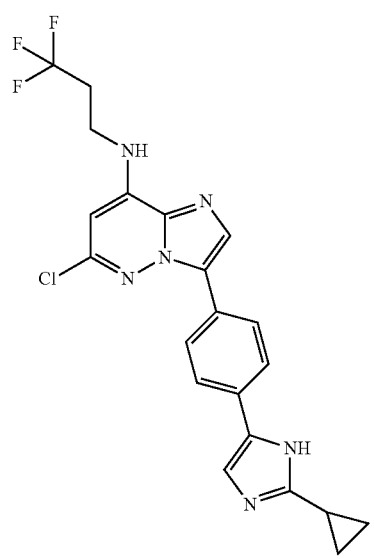

Example 28

N-cyclopropyl-4-{6-(4-fluorophenyl)-8-[(3,3,3-trifluoropropyl)amino]imidazo[1,2-b]pyridazin-3-yl}-2-methylbenzamide

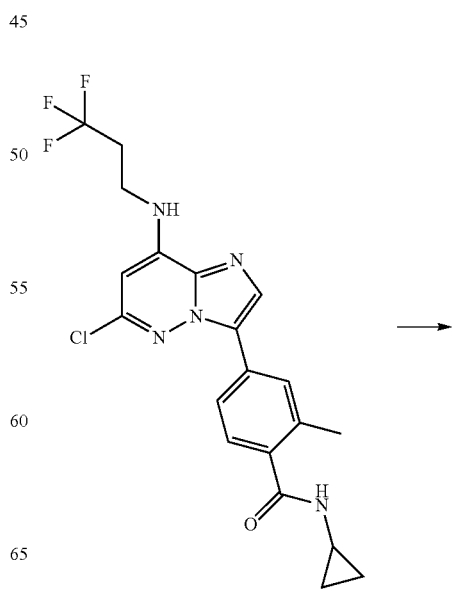

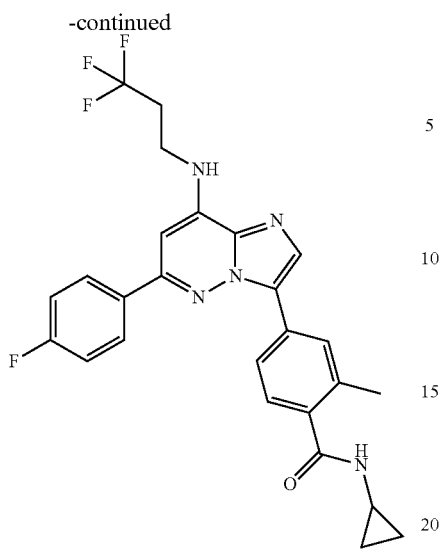

50 mg (114 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using (4-fluorophenyl)boronic acid to give after working up and purification 5.4 mg (9%) of the title compound.

$^1$H-NMR (CDCl$_3$/CD$_3$OD): δ=0.59 (2H), 0.86 (2H), 2.48 (3H), 2.58 (2H), 2.86 (1H), 3.68 (2H), 6.36 (1H), 7.16 (2H), 7.41 (1H), 7.74 (1H), 7.85-8.03 (4H) ppm.

Example 29

(RS) 3-[4-(2-Cyclopropyl-1H-imidazol-5-yl)phenyl]-6-(pyridin-4-yl)-N-(tetrahydro-2H-pyran-2-ylmethyl)imidazo[1,2-b]pyridazin-8-amine

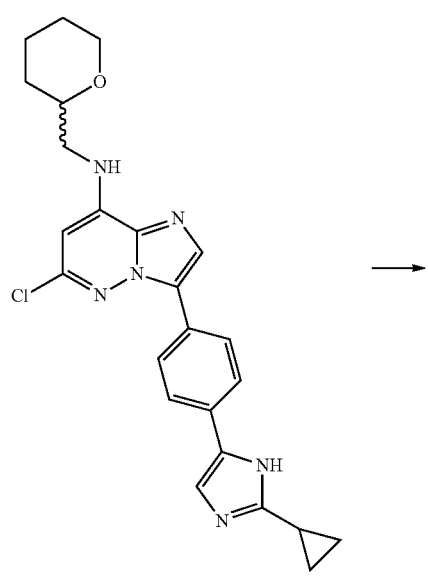

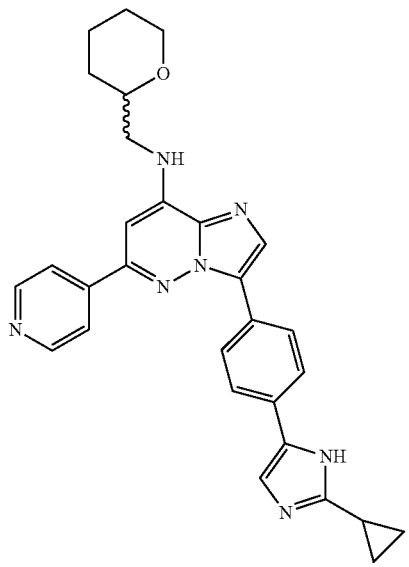

53 mg (118 μmol) (RS)-6-Chloro-3-[4-(2-cyclopropyl-1H-imidazol-4-yl)phenyl]-N(tetrahydro-2H-pyran-2-ylmethyl)imidazo[1,2-b]pyridazin-8-amine which was prepared according to intermediate example 29a were transformed in analogy to example 1 using pyridin-4-ylboronic acid to give after working up and purification 6.2 mg (10%) of the title compound.

$^1$H-NMR (CDCl$_3$): δ=0.99-1.09 (4H), 1.45-2.07 (7H), 3.34-3.55 (3H), 3.67 (1H), 4.06 (1H), 6.26 (1H), 6.44 (1H), 7.24 (1H), 7.79 (2H), 7.83 (1H), 7.88 (2H), 8.13 (2H), 8.74 (2H) ppm.

Intermediate Example 29a (RS)-6-Chloro-3-[4-(2-cyclopropyl-1H-imidazol-4-yl)phenyl]-N(tetrahydro-2H-pyran-2-ylmethyl)imidazo[1,2-b]pyridazin-8-amine

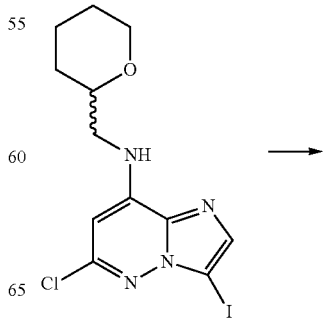

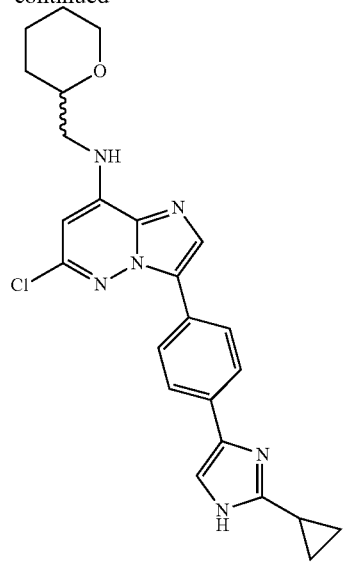

105 mg (267 µmol) (RS)-6-chloro-3-iodo-N-(tetrahydro-2H-pyran-2-ylmethyl)imidazo[1,2-b]pyridazin-8-amine which was prepared according to intermediate example 29b were transformed in analogy to intermediate example 1a to give after working up and purification 61 mg (51%) of the title compound.

Intermediate Example 29b (RS)-6-Chloro-3-iodo-N-(tetrahydro-2H-pyran-2-ylmethyl)imidazo[1,2-b]pyridazin-8-amine

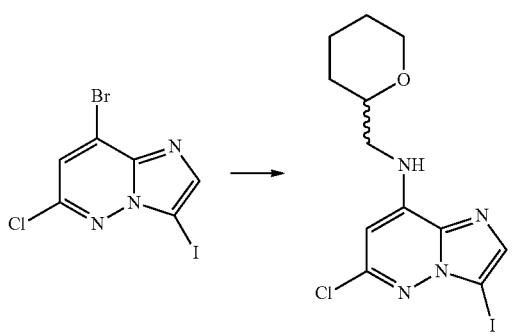 [SMILES: Clc1cc(Br)c2ncc(I)n2n1 ; Clc1cc(NCC2CCCCO2)c2ncc(I)n2n1]

530 mg (1.48 mmol) 8-bromo-6-chloro-3-iodoimidazo[1,2-b]pyridazine which was prepared according to intermediate example 1c were transformed in analogy to intermediate example 1b using 1-[(2RS)-tetrahydro-2H-pyran-2-yl]methanamine to give after working up and purification 214 mg (37%) of the title compound.

Example 30

(RS)—N-cyclopropyl-2-methyl-4-[8-{[(2-methyltetrahydrofuran-2-yl)methyl]amino}-6-(pyridin-4-yl)imidazo[1,2-b]pyridazin-3-yl]benzamide

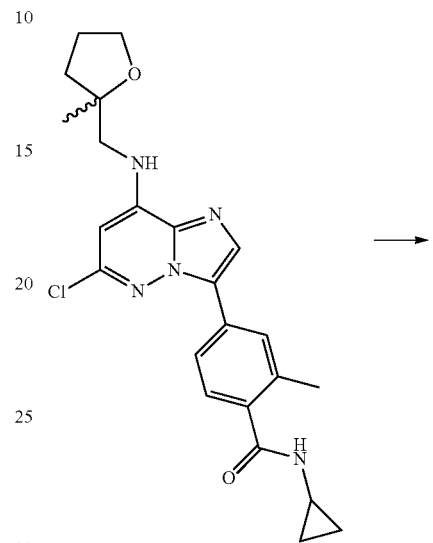

50 mg (114 µmol) (RS)-4-(6-Chloro-8-{[(2-methyltetrahydrofuran-2-yl)methyl]amino}imidazo[1,2-b]pyridazin-3-yl)-N-cyclopropyl-2-methylbenzamide which was prepared according to intermediate example 30a were transformed in analogy to example 1 using pyridin-4-ylboronic acid to give after working up and purification 12.5 mg (22%) of the title compound.

$^1$H-NMR (CDCl$_3$): δ=0.64 (2H), 0.89 (2H), 1.35 (3H), 1.81 (1H), 1.91-2.10 (3H), 2.54 (3H), 2.93 (1H), 3.45 (2H), 3.93 (2H), 6.10 (1H), 6.20 (1H), 6.50 (1H), 7.44 (1H), 7.79-7.84 (3H), 7.92 (1H), 7.99 (1H), 8.71 (2H) ppm.

Intermediate Example 30a (RS)-4-(6-Chloro-8-{[(2-methyltetrahydrofuran-2-yl)methyl]amino}imidazo[1,2-b]pyridazin-3-yl)-N-cyclopropyl-2-methylbenzamide

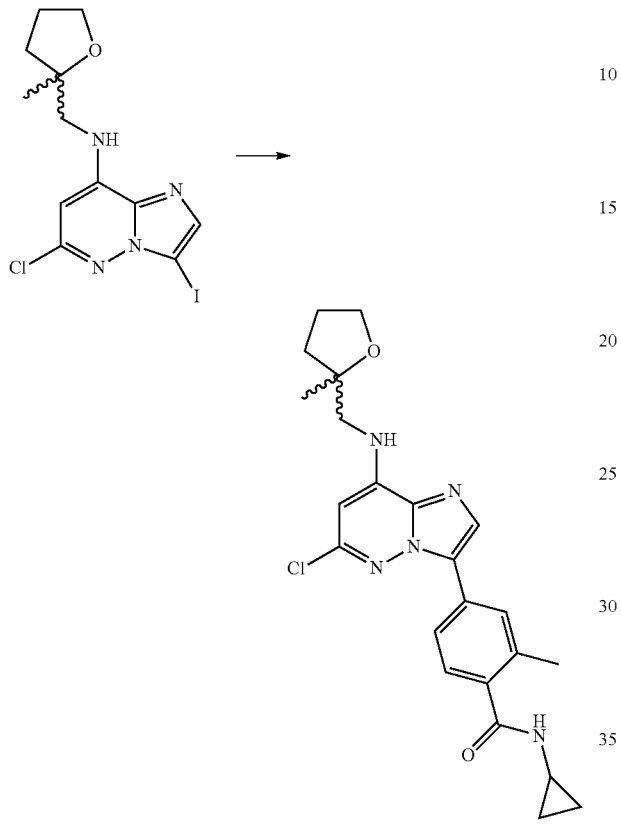

150 mg (382 μmol) (RS)-6-chloro-3-iodo-N-[(2-methyltetrahydrofuran-2-yl)methyl]imidazo[1,2-b]pyridazin-8-amine which was prepared according to intermediate example 30b were transformed in analogy to intermediate example 1a using N-cyclopropyl-2-methyl-4-(4,4,5,5-tetramethyl-1,3,2-dioxaborolan-2-yl)benzamide to give after working up and purification 110 mg (65%) of the title compound.

Intermediate Example 30b (RS) 6-Chloro-3-iodo-N-[(2-methyltetrahydrofuran-2-yl)methyl]imidazo[1,2-b]pyridazin-8-amine

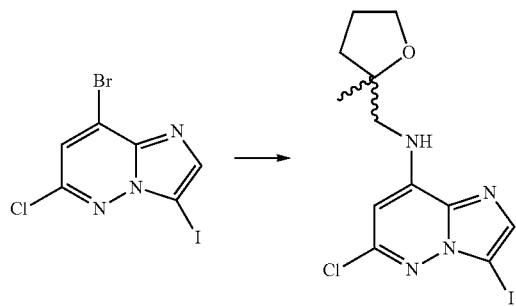

250 mg (698 μmol) 8-bromo-6-chloro-3-iodoimidazo[1,2-b]pyridazine which was prepared according to intermediate example 1c were transformed in analogy to intermediate example 1b using 1-[(2RS)-2-methyltetrahydrofuran-2-yl]methanamine to give after working up and purification 262 mg (96%) of the title compound.

Example 31

N-cyclopropyl-2-methyl-4-[6-(pyridin-4-yl)-8-{[(2S)-tetrahydrofuran-2-ylmethyl]amino}imidazo[1,2-b]pyridazin-3-yl]benzamide

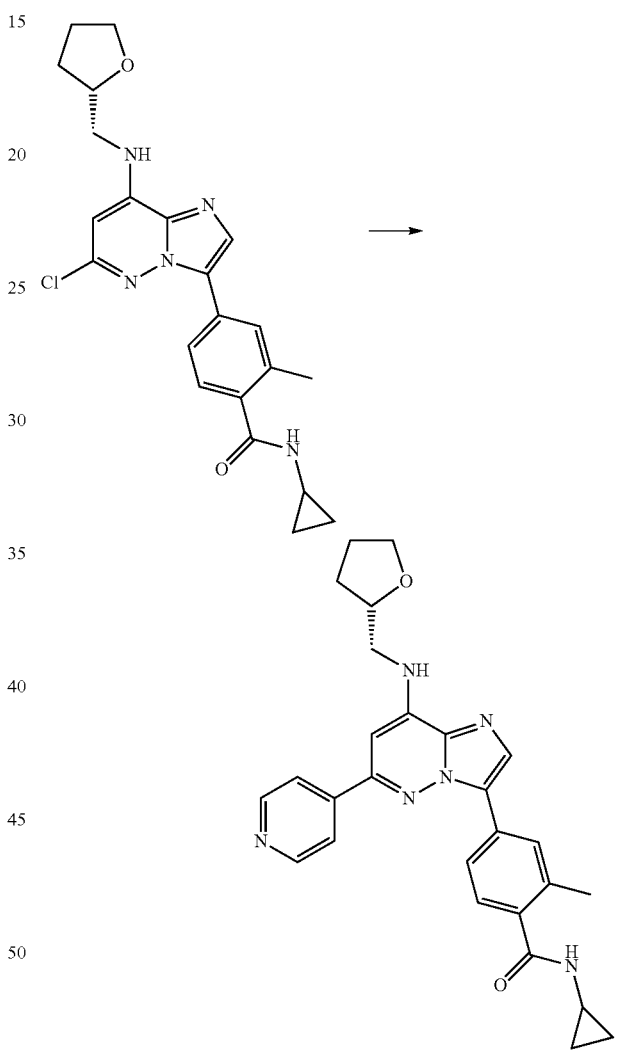

49 mg (115 μmol) 4-(6-Chloro-8-{[(2S)-tetrahydrofuran-2-ylmethyl]amino}imidazo[1,2-b]pyridazin-3-yl)-N-cyclopropyl-2-methylbenzamide which was prepared according to intermediate example 31a were transformed in analogy to example 1 using pyridin-4-ylboronic acid to give after working up and purification 3.6 mg (6%) of the title compound.

$^1$H-NMR (CDCl$_3$): δ=0.64 (2H), 0.90 (2H), 1.75 (1H), 1.98 (2H), 2.11 (1H), 2.55 (3H), 2.93 (1H), 3.46 (1H), 3.60 (1H), 3.82 (1H), 3.96 (1H), 4.24 (1H), 6.01 (1H), 6.23 (1H), 6.50 (1H), 7.45 (1H), 7.83 (1H), 7.84 (2H), 7.93 (1H), 8.00 (1H), 8.74 (2H) ppm.

143

Intermediate Example 31a 4-(6-Chloro-8-{[(2S)-tetrahydrofuran-2-ylmethyl]amino}imidazo[1,2-b]pyridazin-3-yl)-N-cyclopropyl-2-methylbenzamide

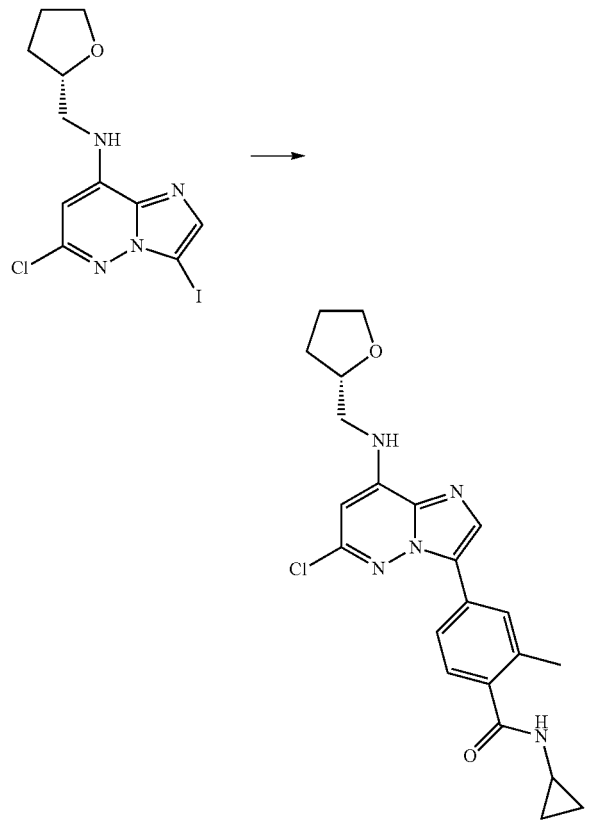 [SMILES: Clc1cc(NC[C@@H]2CCCO2)c2ncc(I)n2n1 ; Cc1cc(-c2cnc3c(NC[C@@H]4CCCO4)cc(Cl)nn23)ccc1C(=O)NC1CC1]

232 mg (613 µmol) 6-chloro-3-iodo-N-[(2S)-tetrahydrofuran-2-ylmethyl]imidazo[1,2-b]pyridazin-8-amine which was prepared according to intermediate example 4b were transformed in analogy to intermediate example 1a using N-cyclopropyl-2-methyl-4-(4,4,5,5-tetramethyl-1,3,2-dioxaborolan-2-yl)benzamide to give after working up and purification 98 mg (38%) of the title compound.

Example 32

N-cyclopropyl-4-{6-(4-fluorophenyl)-8-[(2-hydroxy-2-methylpropyl)amino]imidazo[1,2-b]pyridazin-3-yl}benzenecarbothioamide

144

-continued

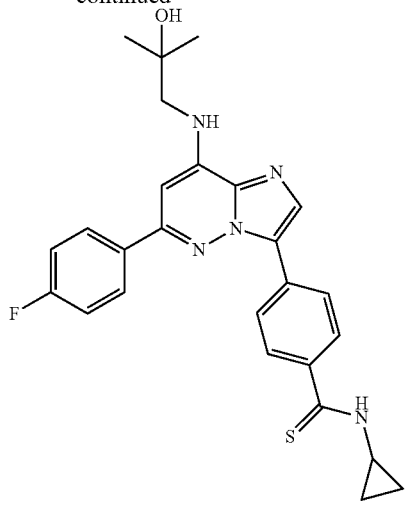

33 mg (82 µmol) 4-{6-(4-fluorophenyl)-8-[(2-hydroxy-2-methylpropyl)amino]imidazo[1,2-b]pyridazin-3-yl}benzaldehyde which was prepared according to intermediate example 32a were transformed in analogy to example 13 to give after working up and purification 3.3 mg (8%) of the title compound.

$^1$H-NMR (DMSO-d6): δ=0.75-0.88 (4H), 1.18 (6H), 3.40 (2H), 3.47 (1H), 4.78 (1H), 6.81 (1H), 6.95 (1H), 7.35 (2H), 7.84 (2H), 8.07 (1H), 8.11 (2H), 8.26 (2H), 10.16 (1H) ppm.

Intermediate Example 32a

4-{6-(4-Fluorophenyl)-8-[(2-hydroxy-2-methylpropyl)amino]imidazo[1,2-b]pyridazin-3-yl}benzaldehyde

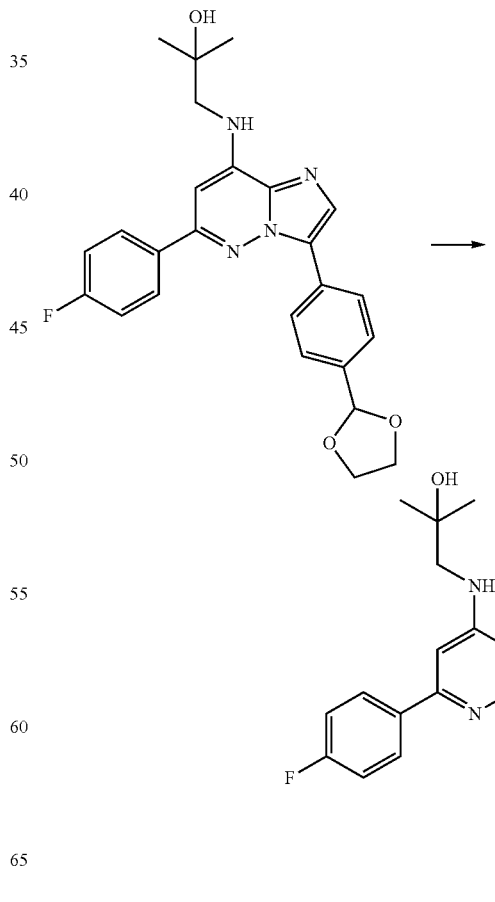

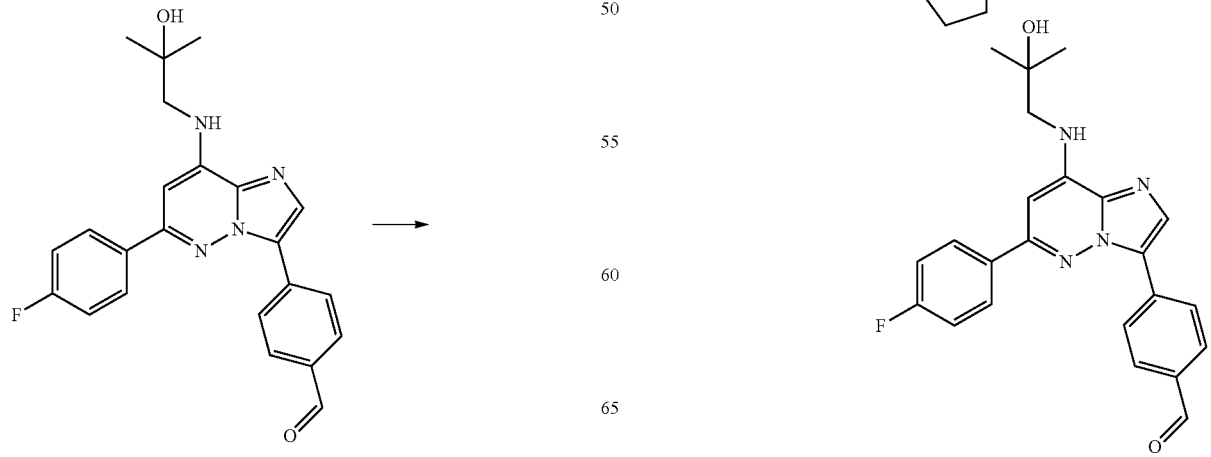

145

48 mg (107 µmol) 1-({3-[4-(1,3-dioxolan-2-yl)phenyl]-6-(4-fluorophenyl)imidazo[1,2-b]pyridazin-8-yl}amino)-2-methylpropan-2-ol which was prepared according to intermediate example 32b were transformed in analogy to intermediate example 13a to give after working up and purification 34.6 mg (76%) of the title compound.

Intermediate Example 32b 1-({3-[4-(1,3-Dioxolan-2-yl)phenyl]-6-(4-fluorophenyl)imidazo[1,2-b]pyridazin-8-yl}amino)-2-methylpropan-2-ol

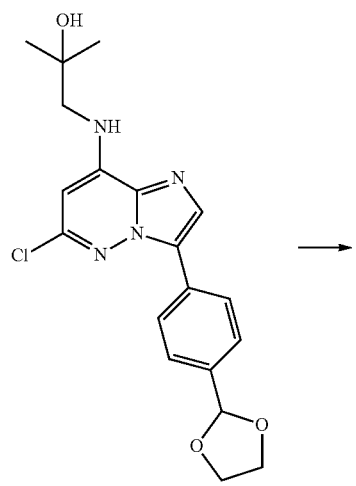

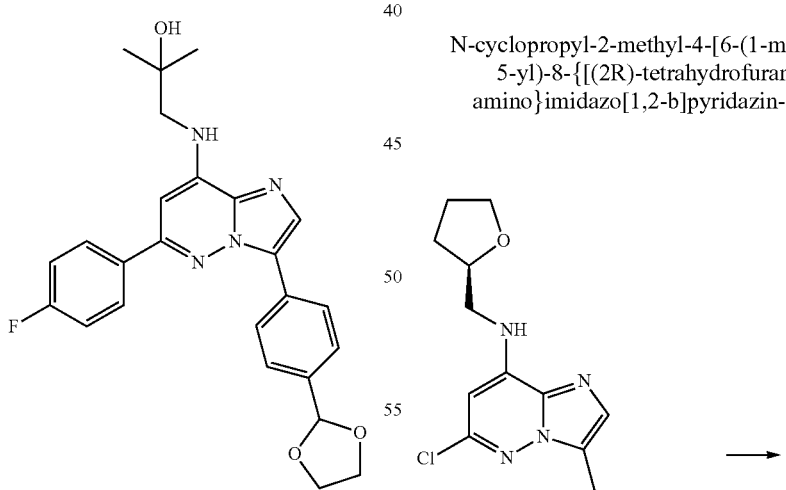

100 mg (257 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 1 using (4-fluorophenyl)boronic acid to give after working up and purification 50.0 mg (43%) of the title compound.

146

Intermediate Example 32c 1-({3-[4-(1,3-Dioxolan-2-yl)phenyl]-6-(4-fluorophenyl)imidazo[1,2-b]pyridazin-8-yl}amino)-2-methylpropan-2-ol

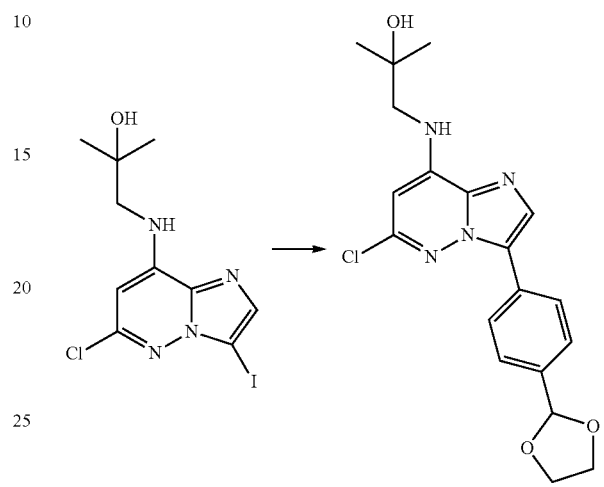

2.65 g (7.2 mmol) 1-[(6-chloro-3-iodoimidazo[1,2-b]pyridazin-8-yl)amino]-2-methylpropan-2-ol which was prepared according to intermediate example 1b were transformed in analogy to intermediate example 1a using 2-[4-(1,3-dioxolan-2-yl)phenyl]-4,4,5,5-tetramethyl-1,3,2-dioxaborolane to give after working up and purification 1.36 g (48%) of the title compound.

Example 33

N-cyclopropyl-2-methyl-4-[6-(1-methyl-1H-pyrazol-5-yl)-8-{[(2R)-tetrahydrofuran-2-ylmethyl]amino}imidazo[1,2-b]pyridazin-3-yl]benzamide

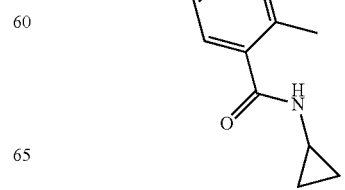

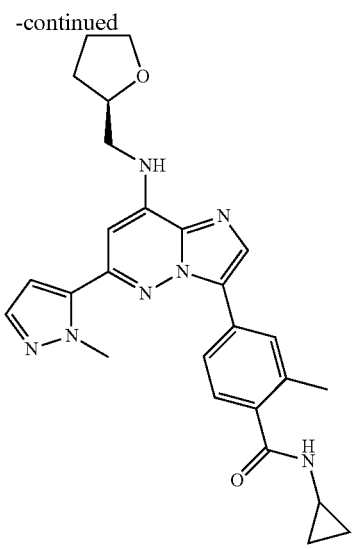

63 mg (148 μmol) 4-(6-chloro-8-{[(2R)-tetrahydrofuran-2-ylmethyl]amino}imidazo[1,2-b]pyridazin-3-yl)-N-cyclopropyl-2-methylbenzamide which was prepared according to intermediate example 33a were transformed in analogy to example 1 using 1-methyl-5-(4,4,5,5-tetramethyl-1,3,2-dioxaborolan-2-yl)-1H-pyrazole to give after working up and purification 10.6 mg (14%) of the title compound.

$^1$H-NMR (CDCl$_3$): δ=0.64 (2H), 0.89 (2H), 1.72 (1H), 1.97 (2H), 2.09 (1H), 2.50 (3H), 2.92 (1H), 3.40 (1H), 3.53 (1H), 3.81 (1H), 3.95 (1H), 4.17 (3H), 4.21 (1H), 6.05 (1H), 6.17 (1H), 6.30 (1H), 6.63 (1H), 7.39 (1H), 7.52 (1H), 7.76 (1H), 7.83 (1H), 7.88 (1H) ppm.

Intermediate Example 33a 4-(6-Chloro-8-{[(2R)-tetrahydrofuran-2-ylmethyl]amino}imidazo[1,2-b]pyridazin-3-yl)-N-cyclopropyl-2-methylbenzamide

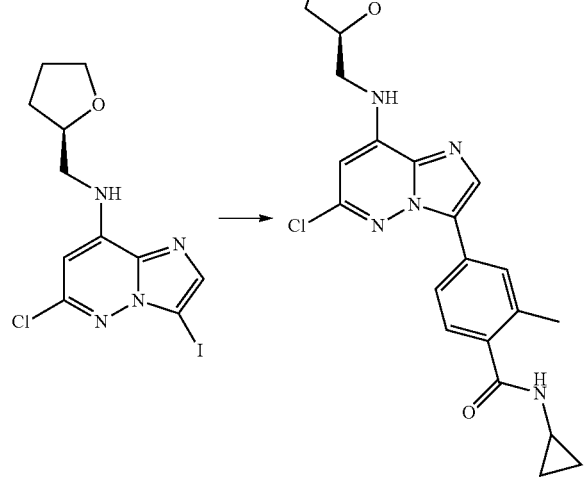

247 mg (652 μmol) 6-chloro-3-iodo-N-[(2R)-tetrahydrofuran-2-ylmethyl]imidazo[1,2-b]pyridazin-8-amine which was prepared according to intermediate example 5b were transformed in analogy to intermediate example 1a using N-cyclopropyl-2-methyl-4-(4,4,5,5-tetramethyl-1,3,2-dioxaborolan-2-yl)benzamide to give after working up and purification 127 mg (46%) of the title compound.

Example 34

N-cyclopropyl-2-methyl-4-[6-(1-methyl-1H-pyrazol-5-yl)-8-{[(2S)-tetrahydrofuran-2-ylmethyl]amino}imidazo[1,2-b]pyridazin-3-yl]benzamide

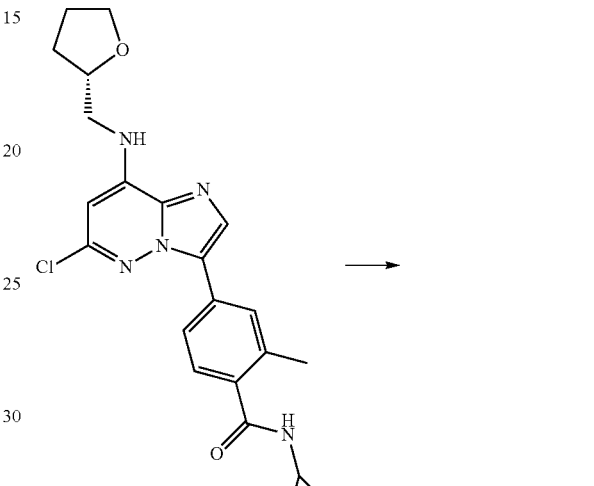

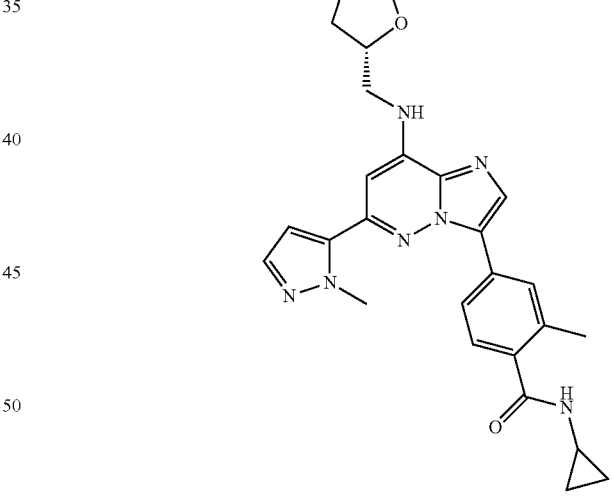

49 mg (115 μmol) 4-(6-chloro-8-{[(2S)-tetrahydrofuran-2-ylmethyl]amino}imidazo[1,2-b]pyridazin-3-yl)-N-cyclopropyl-2-methylbenzamide which was prepared according to intermediate example 31a were transformed in analogy to example 1 using 1-methyl-5-(4,4,5,5-tetramethyl-1,3,2-dioxaborolan-2-yl)-1H-pyrazole to give after working up and purification 8.5 mg (15%) of the title compound.

$^1$H-NMR (CDCl$_3$): δ=0.64 (2H), 0.89 (2H), 1.72 (1H), 1.97 (2H), 2.09 (1H), 2.50 (3H), 2.92 (1H), 3.40 (1H), 3.53 (1H), 3.81 (1H), 3.95 (1H), 4.17 (3H), 4.21 (1H), 6.05 (1H), 6.17 (1H), 6.30 (1H), 6.63 (1H), 7.39 (1H), 7.52 (1H), 7.76 (1H), 7.83 (1H), 7.88 (1H) ppm.

149
Example 35

N-cyclopropyl-2-methyl-4-[6-(pyridin-4-yl)-8-{[(2R)-tetrahydrofuran-2-ylmethyl]amino}imidazo[1,2-b]pyridazin-3-yl]benzamide

150
Example 36

(RS)—N-cyclopropyl-4-{8-[(1,4-dioxan-2-ylmethyl)amino]-6-(pyridin-4-yl)imidazo[1,2-b]pyridazin-3-yl}-2-methylbenzamide

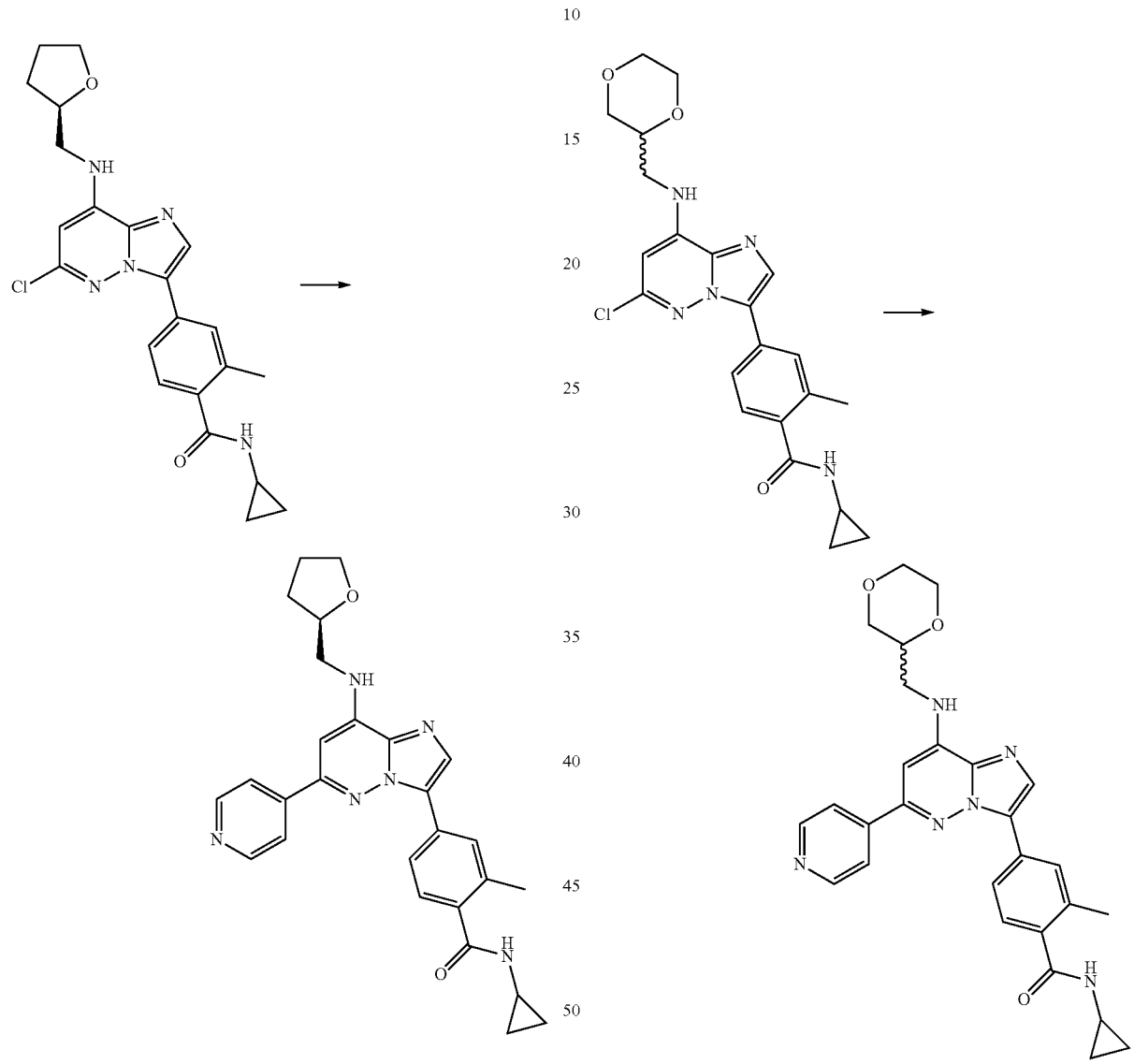

63 mg (148 µmol) 4-(6-chloro-8-{[(2R)-tetrahydrofuran-2-ylmethyl]amino}imidazo[1,2-b]pyridazin-3-yl)-N-cyclopropyl-2-methylbenzamide which was prepared according to intermediate example 33a were transformed in analogy to example 1 using pyridin-4-ylboronic acid to give after working up and purification 4.2 mg (6%) of the title compound.

$^1$H-NMR (CDCl$_3$): δ=0.64 (2H), 0.90 (2H), 1.75 (1H), 1.98 (2H), 2.11 (1H), 2.55 (3H), 2.93 (1H), 3.46 (1H), 3.59 (1H), 3.82 (1H), 3.96 (1H), 4.24 (1H), 6.02 (1H), 6.20 (1H), 6.49 (1H), 7.45 (1H), 7.83 (1H), 7.84 (2H), 7.93 (1H), 8.01 (1H), 8.73 (2H) ppm.

88 mg (199 µmol) (RS)-4-{6-chloro-8-[(1,4-dioxan-2-ylmethyl)amino]imidazo[1,2-b]pyridazin-3-yl}-N-cyclopropyl-2-methylbenzamide which was prepared according to intermediate example 36a were transformed in analogy to example 1 using pyridin-4-ylboronic acid to give after working up and purification 2.9 mg (3%) of the title compound.

$^1$H-NMR (CDCl$_3$): δ=0.62 (2H), 0.88 (2H), 2.52 (3H), 2.90 (1H), 3.36-4.01 (9H), 6.06 (1H), 6.23 (1H), 6.46 (1H), 7.44 (1H), 7.80 (1H), 7.84 (2H), 7.90 (1H), 7.98 (1H), 8.70 (2H) ppm.

Intermediate Example 36a (RS)-4-{6-Chloro-8-[(1,4-dioxan-2-ylmethyl)amino]imidazo[1,2-b]pyridazin-3-yl}-N-cyclopropyl-2-methylbenzamide

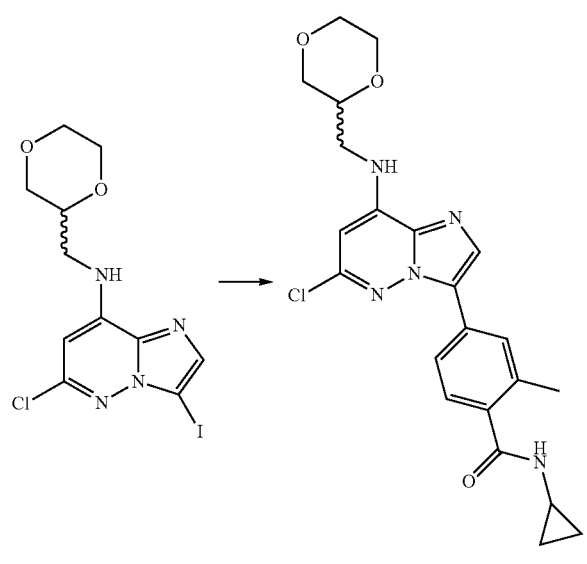 [SMILES: Clc1cc(NCC2COCCO2)c2ncc(I)n2n1 ; Cc1cc(-c2cnc3c(NCC4COCCO4)cc(Cl)nn23)ccc1C(=O)NC1CC1]

200 mg (507 µmol) (RS)-6-chloro-N-(1,4-dioxan-2-ylmethyl)-3-iodoimidazo[1,2-b]pyridazin-8-amine which was prepared according to intermediate example 36b were transformed in analogy to intermediate example 1a using N-cyclopropyl-2-methyl-4-(4,4,5,5-tetramethyl-1,3,2-dioxaborolan-2-yl)benzamide to give after working up and purification 93.6 mg (42%) of the title compound.

Intermediate Example 36b (RS)-6-Chloro-N-(1,4-dioxan-2-ylmethyl)-3-iodoimidazo[1,2-b]pyridazin-8-amine

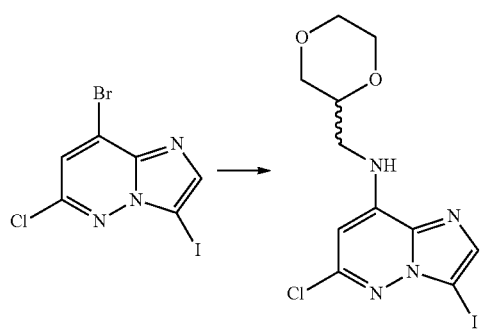 [SMILES: Clc1cc(Br)c2ncc(I)n2n1 ; Clc1cc(NCC2COCCO2)c2ncc(I)n2n1]

500 mg (1.40 mmol) 8-bromo-6-chloro-3-iodoimidazo[1,2-b]pyridazine which was prepared according to intermediate example 1c were transformed in analogy to intermediate example 1b using 1-[(2RS)-1,4-dioxan-2-yl]methanamine to give after working up and purification 520 mg (94%) of the title compound.

Example 37

(RS)—N-cyclopropyl-2-methyl-4-{6-(pyridin-4-yl)-8-[(tetrahydro-2H-pyran-2-ylmethyl)amino]imidazo[1,2-b]pyridazin-3-yl}benzamide

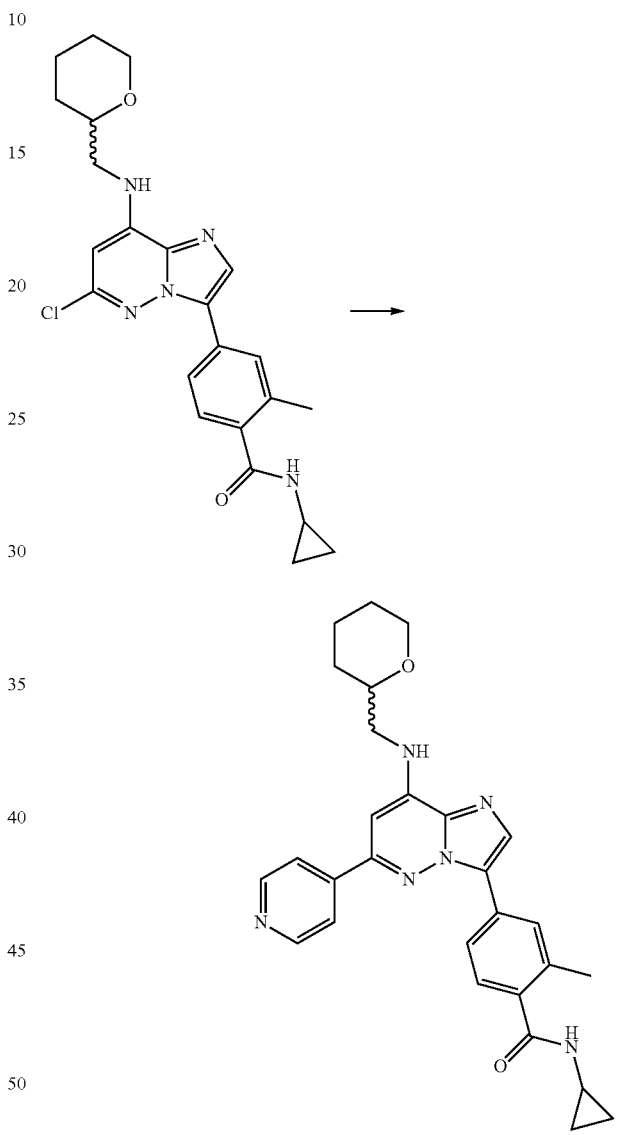

63 mg (143 µmol) which (RS)-4-{6-chloro-8-[(tetrahydro-2H-pyran-2-ylmethyl)amino]imidazo[1,2-b]pyridazin-3-yl}-N-cyclopropyl-2-methylbenzamide was prepared according to intermediate example 37a were transformed in analogy to example 1 using pyridin-4-ylboronic acid to give after working up and purification 4.0 mg (5%) of the title compound.

$^{1}$H-NMR (CDCl$_{3}$): δ=0.63 (2H), 0.88 (2H), 1.40-2.03 (6H), 2.53 (3H), 2.91 (1H), 3.33-3.55 (3H), 3.66 (1H), 4.05 (1H), 6.18 (1H), 6.43 (1H), 6.47 (1H), 7.44 (1H), 7.80 (1H), 7.83 (2H), 7.91 (1H), 7.98 (1H), 8.70 (2H) ppm.

Intermediate Example 37a (RS)-4-{6-Chloro-8-[(tetrahydro-2H-pyran-2-ylmethyl)amino]imidazo[1,2-b]pyridazin-3-yl}-N-cyclopropyl-2-methylbenzamide

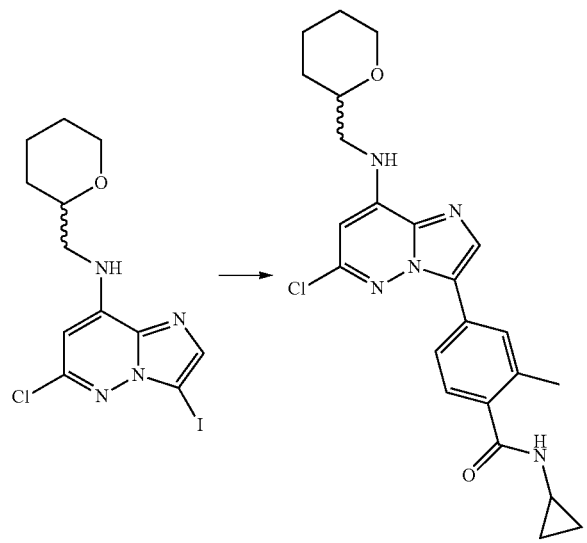 [SMILES: Clc1cc(NCC2CCCCO2)c2ncc(I)n2n1 ; Cc1cc(-c2cnc3c(NCC4CCCCO4)cc(Cl)nn23)ccc1C(=O)NC1CC1]

100 mg (255 µmol) 6-chloro-3-iodo-N-(tetrahydro-2H-pyran-2-ylmethyl)imidazo[1,2-b]pyridazin-8-amine which was prepared according to intermediate example 29b were transformed in analogy to intermediate example 1a using N-cyclopropyl-2-methyl-4-(4,4,5,5-tetramethyl-1,3,2-dioxaborolan-2-yl)benzamide to give after working up and purification 68 mg (61%) of the title compound.

Example 38

N-cyclopropyl-4-{6-[2-(hydroxymethyl)phenyl]-8-[(2-methoxy-2-methylpropyl)amino]imidazo[1,2-b]pyridazin-3-yl}-2-methylbenzamide

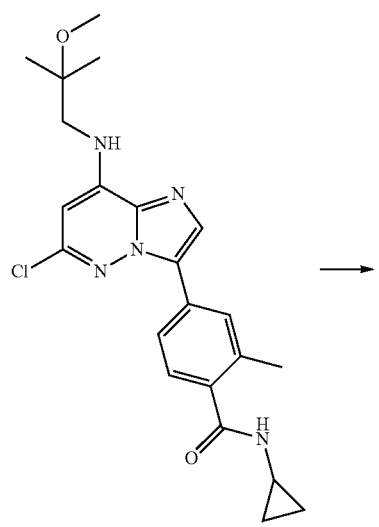

-continued

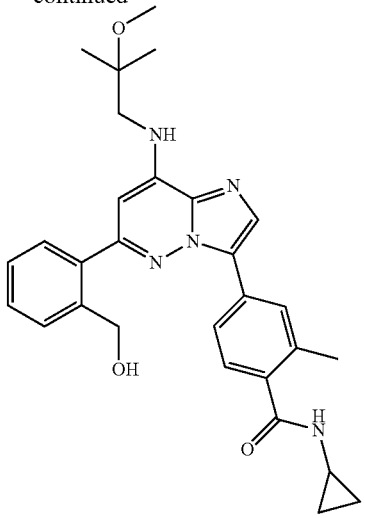

62 mg (145 µmol) 4-{6-chloro-8-[(2-methoxy-2-methylpropyl)amino]imidazo[1,2-b]pyridazin-3-yl}-N-cyclopropyl-2-methylbenzamide which was prepared according to intermediate example 17a were transformed in analogy to example 1 using [2-(hydroxymethyl)phenyl]boronic acid to give after working up and purification 24.8 mg (33%) of the title compound.

$^1$H-NMR (CDCl$_3$): δ=0.58 (2H), 0.84 (2H), 1.31 (6H), 2.47 (3H), 2.87 (1H), 3.28 (3H), 3.34 (2H), 4.13 (1H), 4.38 (2H), 6.19 (1H), 6.21 (1H), 6.25 (1H), 7.36 (1H), 7.42-7.49 (3H), 7.59 (1H), 7.61 (1H), 7.70 (1H), 7.72 (1H) ppm.

Example 39

N-cyclopropyl-4-{8-[(2-methoxy-2-methylpropyl)amino]-6-(1-methyl-1H-pyrazol-5-yl)imidazo[1,2-b]pyridazin-3-yl}-2-methylbenzamide

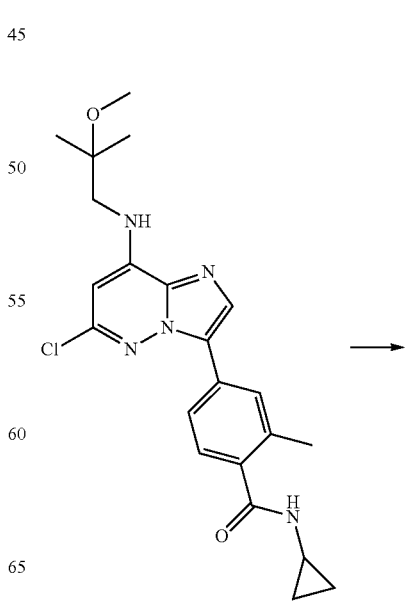

-continued

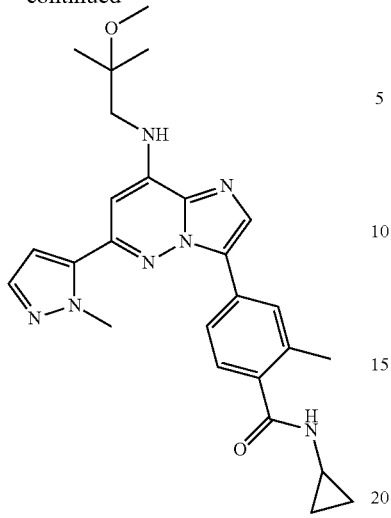

-continued

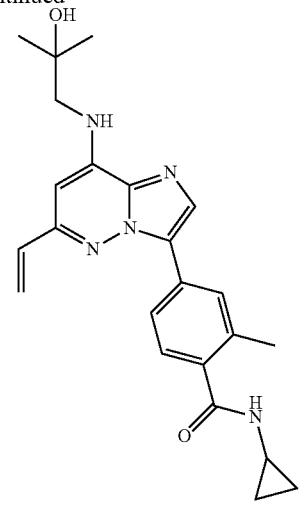

70 mg (164 μmol) 4-{6-chloro-8-[(2-methoxy-2-methylpropyl)amino]imidazo[1,2-b]pyridazin-3-yl}-N-cyclopropyl-2-methylbenzamide which was prepared according to intermediate example 17a were transformed in analogy to example 1 using 1-methyl-5-(4,4,5,5-tetramethyl-1,3,2-dioxaborolan-2-yl)-1H-pyrazole to give after working up and purification 30 mg (37%) of the title compound.

$^1$H-NMR (CDCl$_3$): δ=0.63 (2H), 0.89 (2H), 1.31 (6H), 2.50 (3H), 2.91 (1H), 3.27 (3H), 3.32 (2H), 4.16 (3H), 6.10 (1H), 6.17 (1H), 6.25 (1H), 6.62 (1H), 7.38 (1H), 7.51 (1H), 7.76 (1H), 7.83 (1H), 7.87 (1H) ppm.

100 mg (242 μmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using 4,4,5,5-tetramethyl-2-vinyl-1,3,2-dioxaborolane to give after working up and purification 13 mg (12%) of the title compound.

$^1$H-NMR (CDCl$_3$): δ=0.63 (2H), 0.89 (2H), 1.43 (6H), 2.52 (3H), 2.92 (1H), 3.35 (2H), 5.56 (1H), 5.97 (1H), 6.07 (1H), 6.22 (1H), 6.37 (1H), 6.73 (1H), 7.40 (1H), 7.71 (1H), 7.50 (1H), 7.94 (1H) ppm.

Example 40

N-cyclopropyl-4-{8-[(2-hydroxy-2-methylpropyl)amino]-6-vinylimidazo[1,2-b]pyridazin-3-yl}-2-methylbenzamide Example 41

N-cyclopropyl-2-methyl-4-{8-[(3,3,3-trifluoropropyl)amino]-6-vinylimidazo[1,2-b]pyridazin-3-yl}benzamide

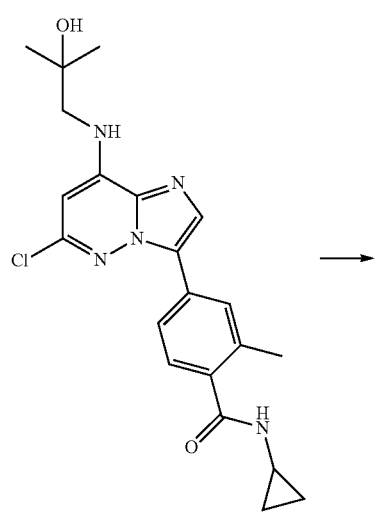

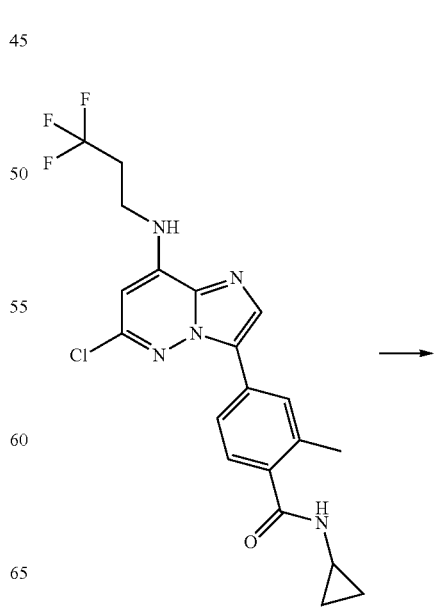

157

-continued

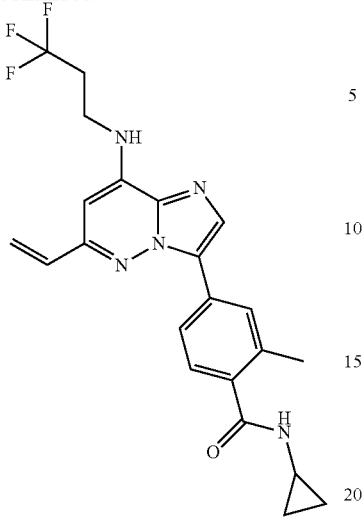

100 mg (228 µmol) 4-{6-Chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using 4,4,5,5-tetramethyl-2-vinyl-1,3,2-dioxaborolane to give after working up and purification 11.4 mg (10%) of the title compound.

$^1$H-NMR (CDCl$_3$): δ=0.62 (2H), 0.89 (2H), 2.52 (3H), 2.56 (2H), 2.92 (1H), 3.69 (2H), 5.60 (1H), 5.92 (1H), 5.95 (1H), 6.09 (1H), 6.20 (1H), 6.77 (1H), 7.42 (1H), 7.75 (1H), 7.91 (1H), 7.95 (1H) ppm.

Example 42

N-cyclopropyl-4-{8-[(2-hydroxy-2-methylpropyl)amino]-6-(1,2,3,6-tetrahydropyridin-4-yl)imidazo[1,2-b]pyridazin-3-yl}-2-methylbenzamide

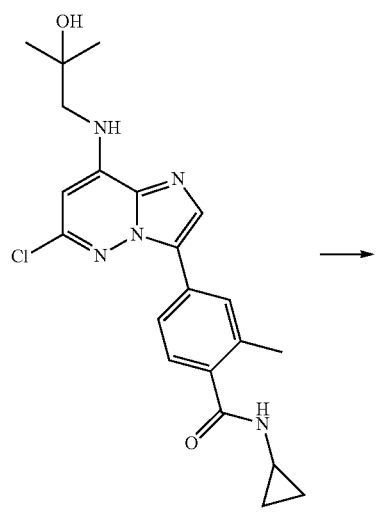

158

-continued

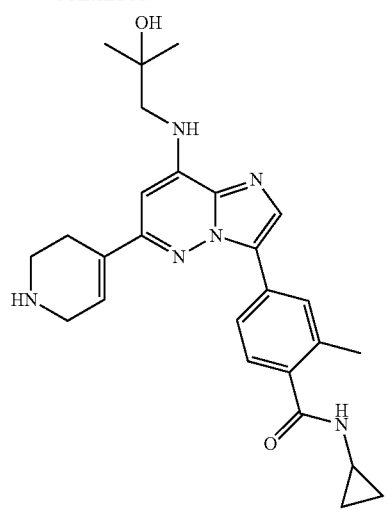

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using 4-(4,4,5,5-tetramethyl-1,3,2-dioxaborolan-2-yl)-1,2,3,6-tetrahydropyridine to give after working up and purification 10.5 mg (18%) of the title compound.

$^1$H-NMR (DMSO-d6): δ=0.50 (2H), 0.65 (2H), 1.16 (6H), 2.37 (3H), 2.61 (2H), 2.80 (1H), 3.05 (2H), 3.31 (2H), 3.56 (1H), 6.54 (1H), 6.66-6.74 (2H), 7.35 (1H), 7.97 (1H), 8.03 (1H), 8.04 (1H), 8.26 (1H), 8.28 (1H) ppm.

Example 43

4-{6-(Cyclohex-1-en-1-yl)-8-[(2-hydroxy-2-methylpropyl)amino]imidazo[1,2-b]pyridazin-3-yl}-N-cyclopropylbenzenecarbothioamide

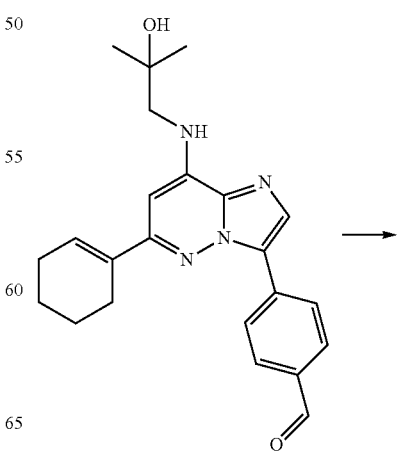

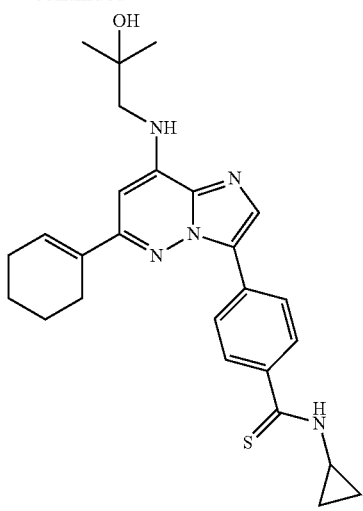

20.6 mg (53 µmol) 4-{6-(cyclohex-1-en-1-yl)-8-[(2-hydroxy-2-methylpropyl)amino]imidazo[1,2-b]pyridazin-3-yl}benzaldehyde which was prepared according to intermediate example 43a were transformed in analogy to example 13 to give after working up and purification 3.2 mg (13%) of the title compound.

¹H-NMR (DMSO-d6): δ=0.75-0.85 (4H), 1.15 (6H), 1.61 (2H), 1.71 (2H), 2.22 (2H), 2.52 (2H), 3.13 (2H), 3.49 (1H), 4.77 (1H), 6.51 (1H), 6.63 (1H), 6.68 (1H), 7.83 (2H), 8.01 (1H), 8.21 (2H), 10.12 (1H) ppm.

Intermediate Example 43a

4-{6-(Cyclohex-1-en-1-yl)-8-[(2-hydroxy-2-methylpropyl)amino]imidazo[1,2-b]pyridazin-3-yl}benzaldehyde

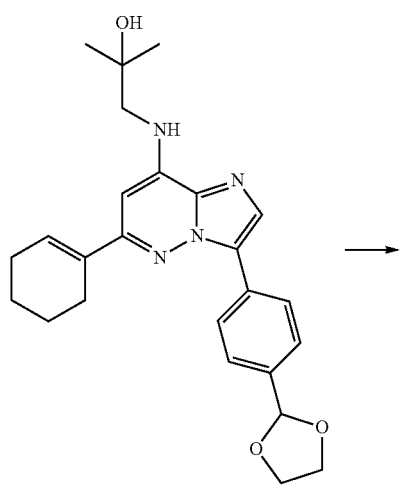

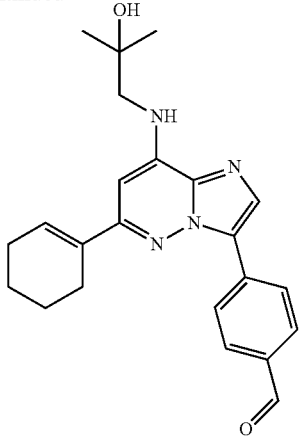

97 mg (223 µmol) 1-({6-(cyclohex-1-en-1-yl)-3-[4-(1,3-dioxolan-2-yl)phenyl]imidazo[1,2-b]pyridazin-8-yl}amino)-2-methylpropan-2-ol which was prepared according to intermediate example 43b were transformed in analogy to intermediate example 13a to give after working up and purification 24 mg (25%) of the title compound.

Intermediate Example 43b 1-({6-(Cyclohex-1-en-1-yl)-3-[4-(1,3-dioxolan-2-yl)phenyl]imidazo[1,2-b]pyridazin-8-yl}amino)-2-methylpropan-2-ol

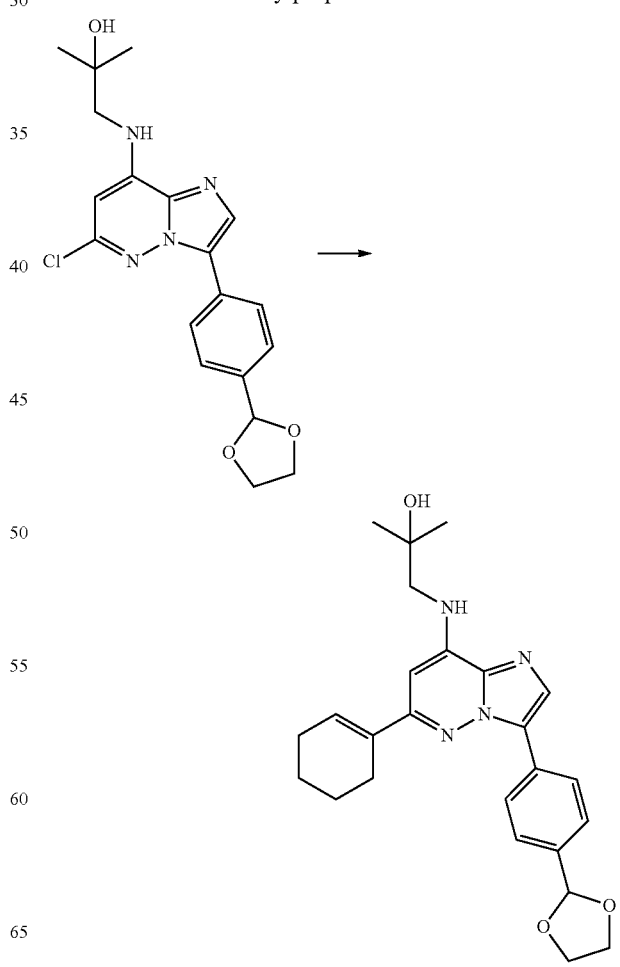

100 mg (257 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 1 using cyclohex-1-en-1-ylboronic acid to give after working up and purification 97 mg (87%) of the title compound.

Example 44

N-cyclopropyl-4-{6-[2-(hydroxymethyl)phenyl]-8-[(3,3,3-trifluoropropyl)amino]imidazo[1,2-b]pyridazin-3-yl}benzenecarbothioamide

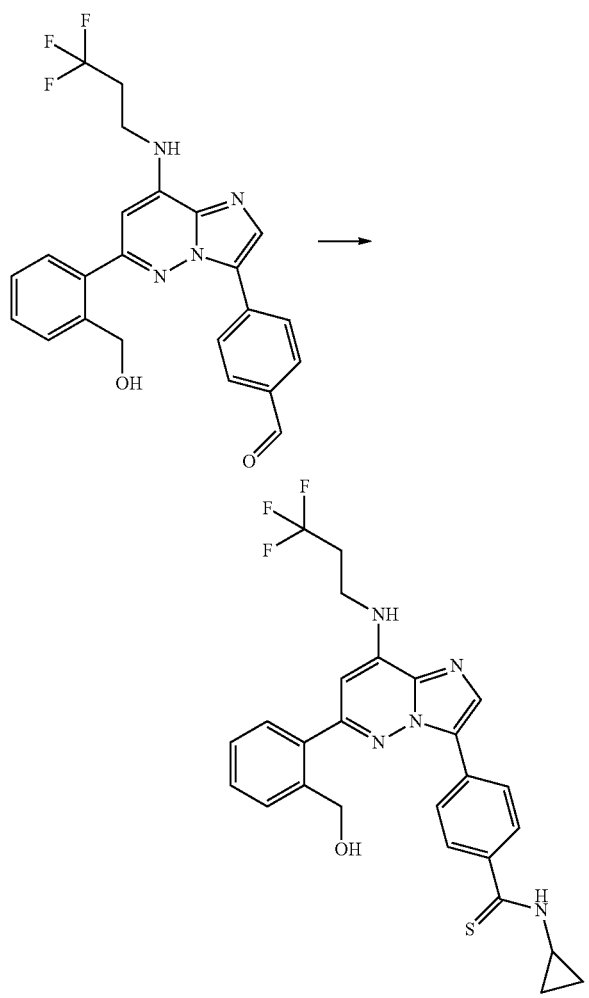

72.3 mg (164 µmol) 4-{6-[2-(hydroxymethyl)phenyl]-8-[(3,3,3-trifluoropropyl)amino]imidazo[1,2-b]pyridazin-3-yl}benzaldehyde which was prepared according to intermediate example 44a were transformed in analogy to example 13 to give after working up and purification 6.6 mg (7%) of the title compound.

$^1$H-NMR (CDCl$_3$): δ=0.76 (2H), 1.00 (2H), 2.58 (2H), 3.37 (1H), 3.72 (2H), 3.96 (1H), 4.40 (2H), 6.16 (1H), 6.25 (1H), 7.46-7.51 (3H), 7.59 (1H), 7.76 (1H), 7.77 (2H), 7.84 (2H), 7.89 (1H) ppm.

Intermediate Example 44a

4-{6-[2-(Hydroxymethyl)phenyl]-8-[(3,3,3-trifluoropropyl)amino]imidazo[1,2-b]pyridazin-3-yl}benzaldehyde

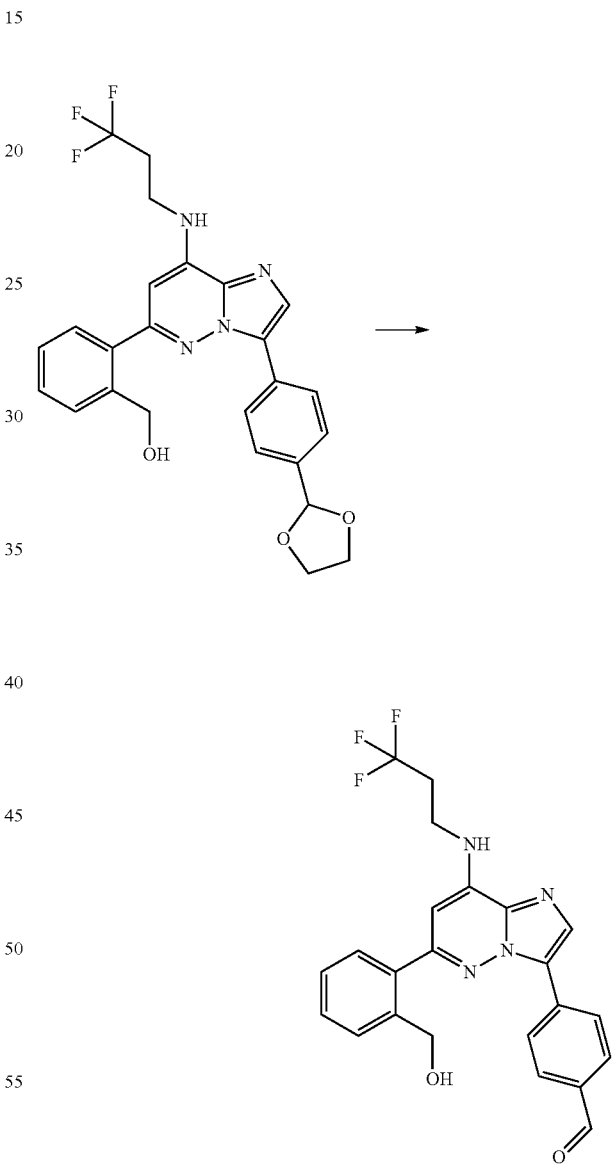

52 mg (107 µmol) (2-{3-[4-(1,3-dioxolan-2-yl)phenyl]-8-[(3,3,3-trifluoropropyl)amino]imidazo[1,2-b]pyridazin-6-yl}phenyl)methanol which was prepared according to intermediate example 44b were transformed in analogy to intermediate example 13a to give after working up and purification 72.3 mg (76%) of the title compound.

Intermediate Example 44b (2-{3-[4-(1,3-Dioxolan-2-yl)phenyl]-8-[(3,3,3-trifluoropropyl)amino]imidazo[1,2-b]pyridazin-6-yl}phenyl)methanol

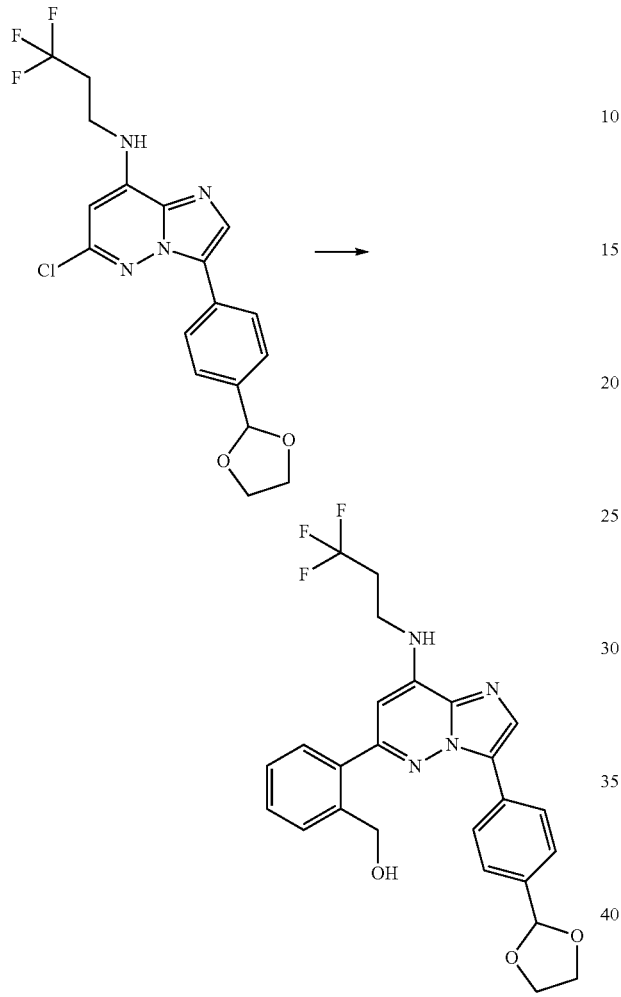

100 mg (242 µmol) 6-chloro-3-[4-(1,3-dioxolan-2-yl)phenyl]-N-(3,3,3-trifluoropropyl)imidazo[1,2-b]pyridazin-8-amine which was prepared according to intermediate example 44c were transformed in analogy to example 1 using [2-(hydroxymethyl)phenyl]boronic acid to give after working up and purification 52 mg (44%) of the title compound.

Intermediate Example 44c

6-Chloro-3-[4-(1,3-dioxolan-2-yl)phenyl]-N-(3,3,3-trifluoropropyl)imidazo[1,2-b]pyridazin-8-amine

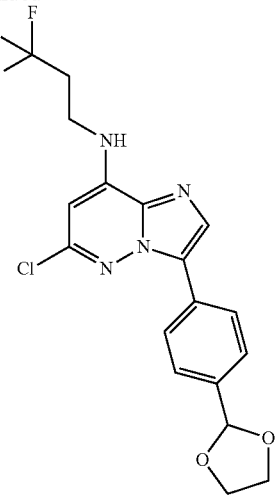

800 mg (2.05 Mmol) 6-chloro-3-iodo-N-(3,3,3-trifluoropropyl)imidazo[1,2-b]pyridazin-8-amine which was prepared according to intermediate example 6b were transformed in analogy to intermediate example 1a using 2-[4-(1,3-dioxolan-2-yl)phenyl]-4,4,5,5-tetramethyl-1,3,2-dioxaborolane to give after working up and purification 332 mg (35%) of the title compound.

Example 45

N-cyclopropyl-4-{6-(1-methyl-1H-pyrazol-5-yl)-8-[(3,3,3-trifluoropropyl)amino]imidazo[1,2-b]pyridazin-3-yl}benzenecarbothioamide

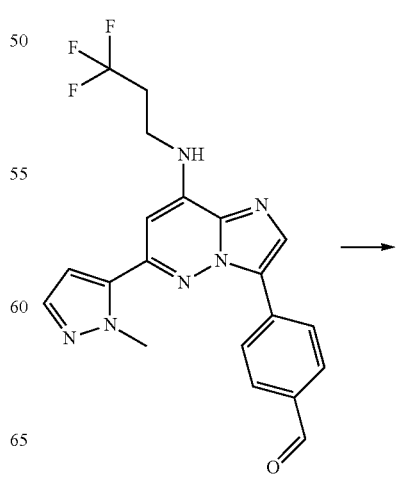

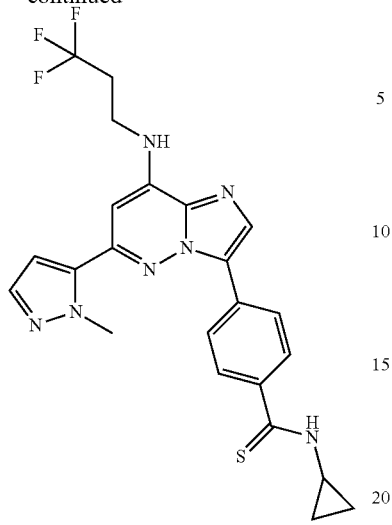

27 mg (65 µmol) 4-{6-(1-methyl-1H-pyrazol-5-yl)-8-[(3,3,3-trifluoropropyl)amino]imidazo[1,2-b]pyridazin-3-yl}benzaldehyde which was prepared according to intermediate example 45a were transformed in analogy to example 13 to give after working up and purification 1.8 mg (5%) of the title compound.

$^1$H-NMR (CDCl$_3$): δ=0.82 (2H), 1.07 (2H), 2.59 (2H), 3.42 (1H), 3.73 (2H), 4.19 (3H), 6.08 (1H), 6.29 (1H), 6.66 (1H), 7.56 (1H), 7.64 (1H), 7.84 (2H), 7.85 (1H), 8.07 (2H) ppm.

Intermediate Example 45a

4-{6-(1-Methyl-1H-pyrazol-5-yl)-8-[(3,3,3-trifluoropropyl)amino]imidazo[1,2-b]pyridazin-3-yl}benzaldehyde

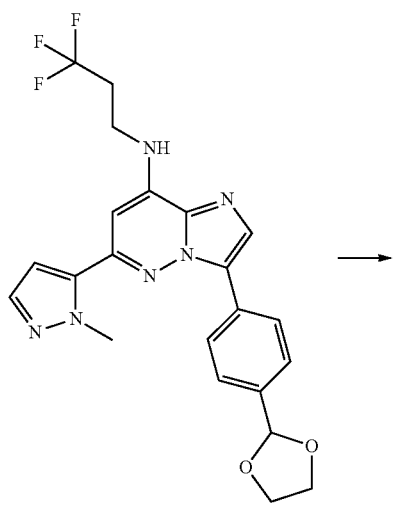

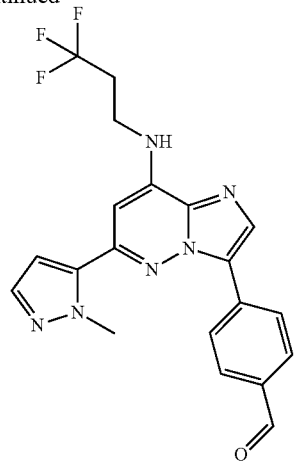

73 mg (159 µmol) 3-[4-(1,3-dioxolan-2-yl)phenyl]-6-(1-methyl-1H-pyrazol-5-yl)-N-(3,3,3-trifluoropropyl)imidazo[1,2-b]pyridazin-8-amine which was prepared according to intermediate example 45b were transformed in analogy to intermediate example 13a to give after working up and purification 27 mg (41%) of the title compound.

Intermediate Example 45b

3-[4-(1,3-Dioxolan-2-yl)phenyl]-6-(1-methyl-1H-pyrazol-5-yl)-N-(3,3,3-trifluoropropyl)imidazo[1,2-b]pyridazin-8-amine

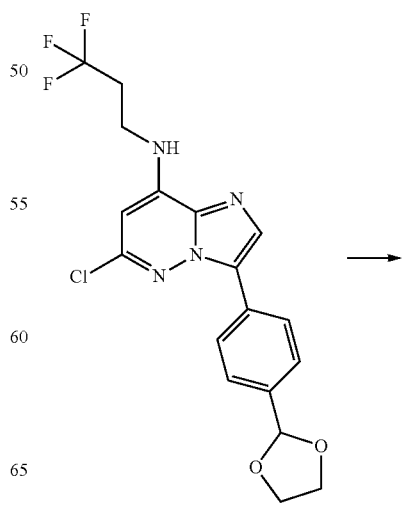

167

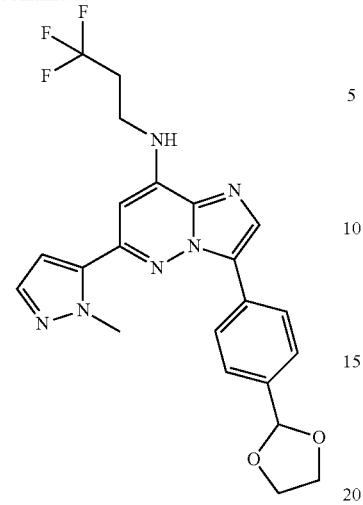

100 mg (242 µmol) 6-chloro-3-[4-(1,3-dioxolan-2-yl)phenyl]-N-(3,3,3-trifluoropropyl)imidazo[1,2-b]pyridazin-8-amine which was prepared according to intermediate example 44c were transformed in analogy to example 1 using 1-methyl-5-(4,4,5,5-tetramethyl-1,3,2-dioxaborolan-2-yl)-1H-pyrazole to give after working up and purification 73 mg (66%) of the title compound.

Example 46

N-cyclopropyl-4-{6-[3-(hydroxymethyl)phenyl]-8-[(3,3,3-trifluoropropyl)amino]imidazo[1,2-b]pyridazin-3-yl}benzenecarbothioamide

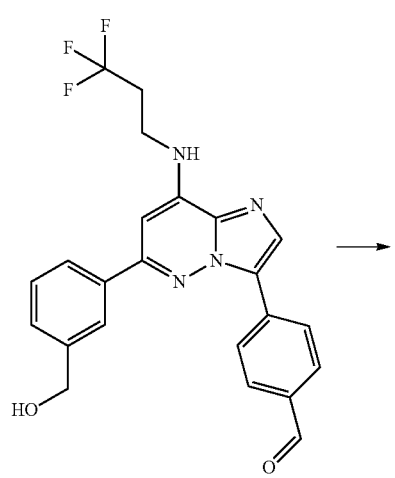

168

39.1 mg (89 µmol) 4-{6-[3-(hydroxymethyl)phenyl]-8-[(3,3,3-trifluoropropyl)amino]imidazo[1,2-b]pyridazin-3-yl}benzaldehyde which was prepared according to intermediate example 46a were transformed in analogy to example 13 to give after working up and purification 2.0 mg (4%) of the title compound.

$^1$H-NMR (CDCl$_3$): δ=0.83 (2H), 1.07 (2H), 2.56 (2H), 3.43 (1H), 3.68 (2H), 4.82 (2H), 6.00 (1H), 6.40 (1H), 7.50 (2H), 7.71 (1H), 7.79-7.90 (5H), 8.15 (2H) ppm.

Intermediate Example 46a

4-{6-[3-(Hydroxymethyl)phenyl]-8-[(3,3,3-trifluoropropyl)amino]imidazo[1,2-b]pyridazin-3-yl}benzaldehyde

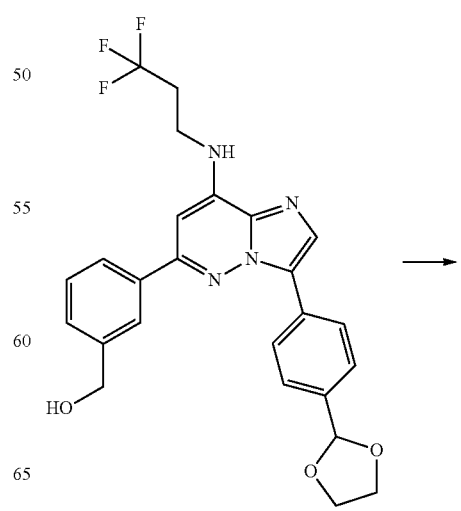

169
-continued

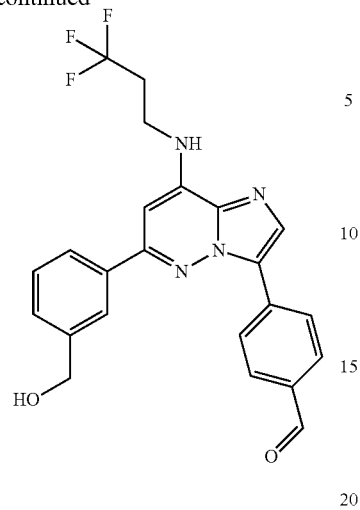

167 mg (µmol) (3-{3-[4-(1,3-dioxolan-2-yl)phenyl]-8-[(3,3,3-trifluoropropyl)amino]imidazo[1,2-b]pyridazin-6-yl}phenyl)methanol which was prepared according to intermediate example 46b were transformed in analogy to intermediate example 13a to give after working up and purification 39.1 mg (37%) of the title compound.

Intermediate Example 46b (3-{3-[4-(1,3-Dioxolan-2-yl)phenyl]-8-[(3,3,3-trifluoropropyl)amino]imidazo[1,2-b]pyridazin-6-yl}phenyl)methanol

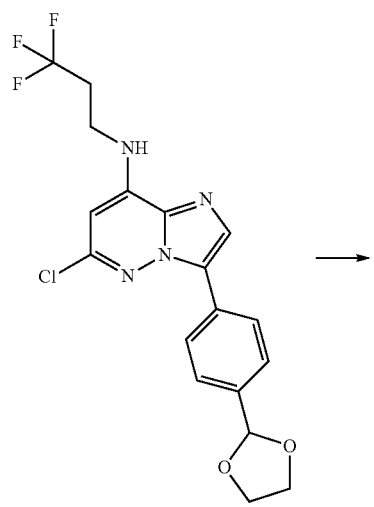

170
-continued 100 mg (242 µmol) 6-chloro-3-[4-(1,3-dioxolan-2-yl)phenyl]-N-(3,3,3-trifluoropropyl)imidazo[1,2-b]pyridazin-8-amine which was prepared according to intermediate example 44c were transformed in analogy to example 1 using [3-(hydroxymethyl)phenyl]boronic acid to give after working up and purification 83.5 mg (71%) of the title compound.

Example 47

N-cyclopropyl-4-{8-[(2-hydroxy-2-methylpropyl)amino]-6-(pyridin-4-yl)imidazo[1,2-b]pyridazin-3-yl}benzenecarbothioamide

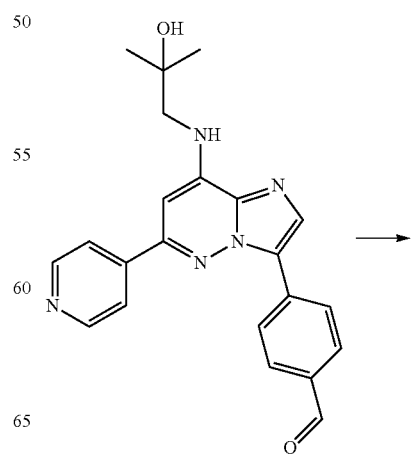

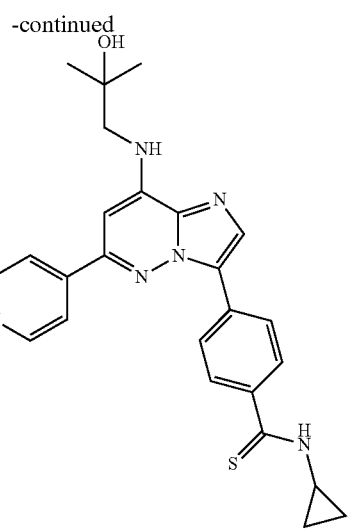

48 mg (124 µmol) 4-{8-[(2-hydroxy-2-methylpropyl)amino]-6-(pyridin-4-yl)imidazo[1,2-b]pyridazin-3-yl}benzaldehyde which was prepared according to intermediate example 47a were transformed in analogy to example 13 to give after working up and purification 4.7 mg (6%) of the title compound.

$^1$H-NMR (DMSO-d6): δ=0.76-0.88 (4H), 1.18 (6H), 3.38-3.52 (3H), 4.79 (1H), 6.93 (1H), 7.09 (1H), 7.86 (2H), 8.04 (2H), 8.12 (1H), 8.27 (2H), 8.73 (2H), 10.16 (1H) ppm.

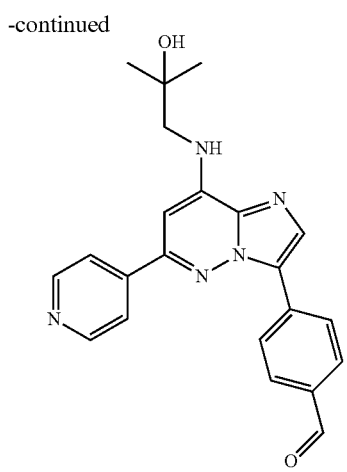

69 mg (160 µmol) 1-({3-[4-(1,3-dioxolan-2-yl)phenyl]-6-(pyridin-4-yl)imidazo[1,2-b]pyridazin-8-yl}amino)-2-methylpropan-2-ol which was prepared according to intermediate example 47b were transformed in analogy to intermediate example 13a to give after working up and purification 51.5 mg (83%) of the title compound.

Intermediate Example 47a

4-{8-[(2-Hydroxy-2-methylpropyl)amino]-6-(pyridin-4-yl)imidazo[1,2-b]pyridazin-3-yl}benzaldehyde

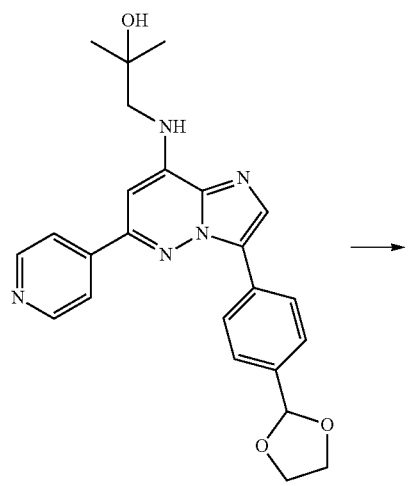 →

Intermediate Example 47b 1-({3-[4-(1,3-Dioxolan-2-yl)phenyl]-6-(pyridin-4-yl)imidazo[1,2-b]pyridazin-8-yl}amino)-2-methylpropan-2-ol

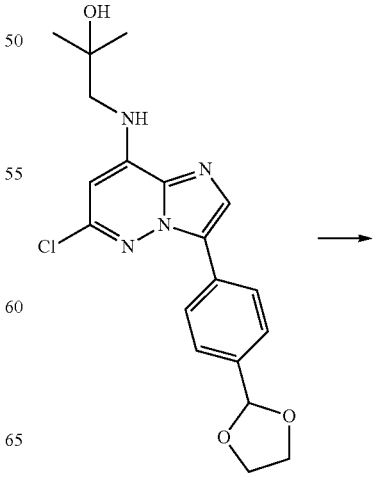 →

-continued

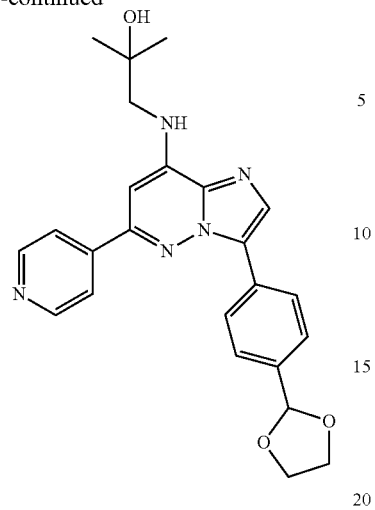

200 mg (514 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 1 using pyridin-4-ylboronic acid to give after working up and purification 51.5 mg (23%) of the title compound.

Example 48

N-cyclopropyl-4-{6-cyclopropyl-8-[(3,3,3-trifluoropropyl)amino]imidazo[1,2-b]pyridazin-3-yl}-2-methylbenzamide

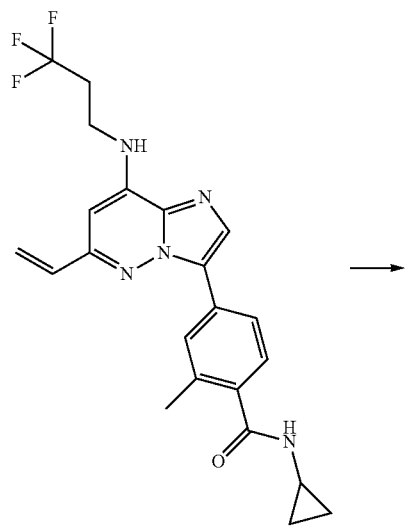

-continued

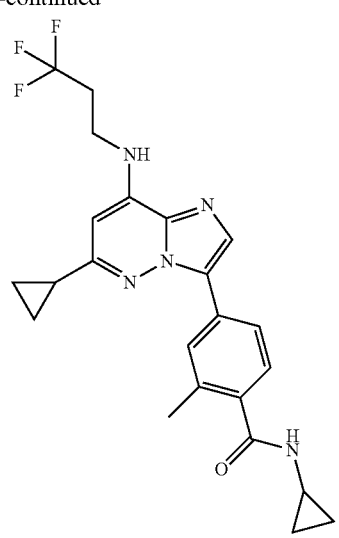

A solution of 31 mg (72 µmol) N-cyclopropyl-2-methyl-4-{8-[(3,3,3-trifluoropropyl)amino]-6-vinylimidazo[1,2-b]pyridazin-3-yl}benzamide which was prepared according to example 41 in 3.5 mL tetrahydrofuran was cooled to 3° C., 5 mL of diazomethane solution in diethyl ether was added followed by 0.81 mg palladium(II) diacetate and the mixture was stirred for 1 hour. The solvents were removed and the residue was purified by chromatography to give 5.8 mg (18%) of the title compound.

$^1$H-NMR (CDCl$_3$): δ=0.63 (2H), 0.89 (2H), 1.00-1.11 (4H), 2.00 (1H), 2.53 (3H), 2.47-2.61 (2H), 2.92 (1H), 3.65 (2H), 5.78 (1H), 5.91 (1H), 5.93 (1H), 7.41 (1H), 7.73 (1H), 7.91 (1H), 7.92 (1H) ppm.

Example 49

N-cyclopropyl-4-{6-(4-fluorophenyl)-8-[(2-hydroxy-2-methylpropyl)amino]imidazo[1,2-b]pyridazin-3-yl}-3-methoxybenzamide

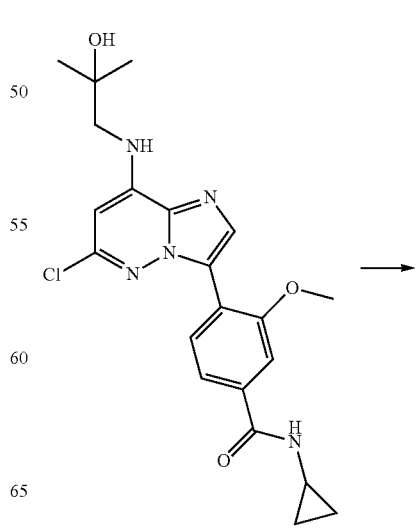

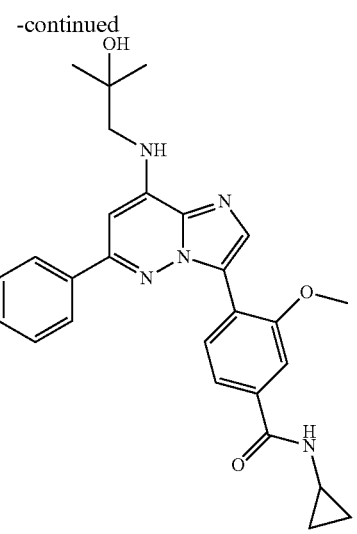

75 mg (174 μmol) 4-{6-chloro-8-[(2-hydroxy-2-methylpropyl)amino]imidazo[1,2-b]pyridazin-3-yl}-N-cyclopropyl-3-methoxybenzamide which was prepared according to intermediate example 49a were transformed in analogy to example 1 using (4-fluorophenyl)boronic acid to give after working up and purification 18.5 mg (22%) of the title compound.

$^1$H-NMR (DMSO-d6): δ=0.57 (2H), 0.69 (2H), 1.19 (6H), 2.85 (1H), 3.39 (2H), 3.89 (3H), 4.78 (1H), 6.77 (1H), 6.87 (1H), 7.31 (2H), 7.54 (1H), 7.56 (1H), 7.87 (1H), 8.03 (2H), 8.25 (1H), 8.51 (1H) ppm.

Example 49a

4-{6-Chloro-8-[(2-hydroxy-2-methylpropyl)amino]imidazo[1,2-b]pyridazin-3-yl}-N-cyclopropyl-3-methoxybenzamide

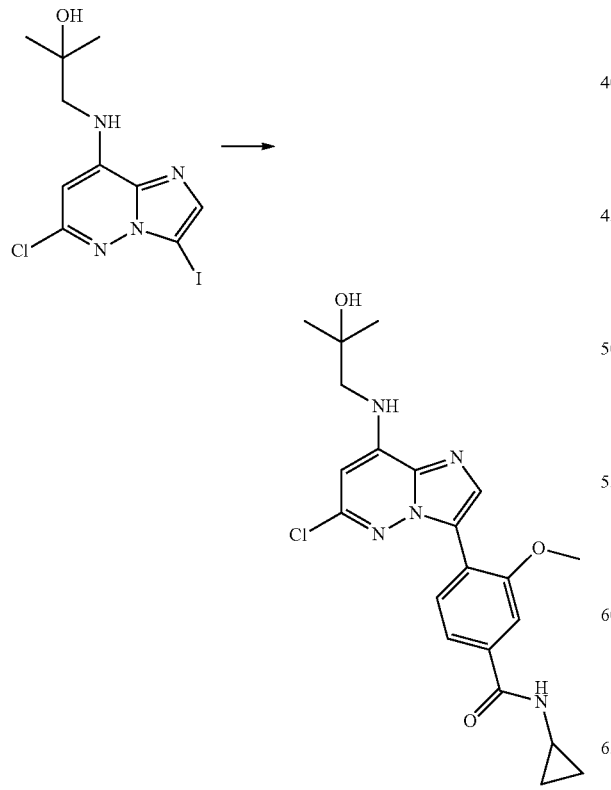

1.0 g (2.73 mmol) 1-[(6-Chloro-3-iodoimidazo[1,2-b]pyridazin-8-yl)amino]-2-methylpropan-2-ol which was prepared according to intermediate example 1b were transformed in analogy to intermediate example 1a using [4-(cyclopropylcarbamoyl)-2-methoxyphenyl]boronic acid which was prepared according to intermediate example 49b to give after working up and purification 741 mg (60%) of the title compound.

Example 49b

[4-(Cyclopropylcarbamoyl)-2-methoxyphenyl]boronic acid

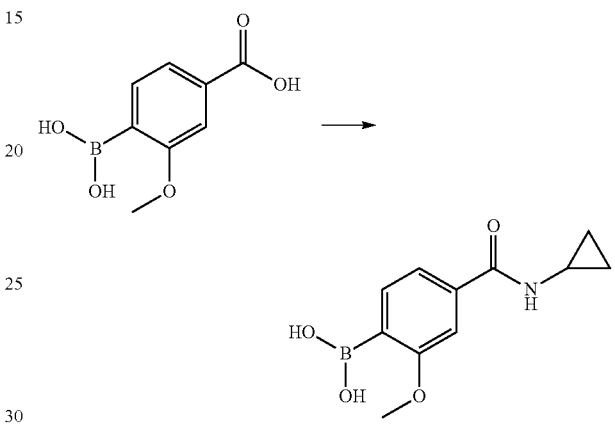

A suspension of 3.0 g (15.3 mmol) 4-(dihydroxyboryl)-3-methoxybenzoic acid, 874 mg cyclopropanamine and 3.5 g N-[3-(dimethylamino)propyl]-N'-ethylcarbodiimide in 93 mL dichloromethane was stirred overnight at 23° C.

Water was added and the mixture was extracted with dichloromethane. The organic layer was washed with brine and dried over sodium sulfate. After filtration and removal of the solvent the residue was purified by chromatography to give 2.60 g (72%) of the title compound.

Example 50

N-cyclopropyl-4-{8-[(2-hydroxy-2-methylpropyl)amino]-6-(1-methyl-1H-pyrazol-5-yl)imidazo[1,2-b]pyridazin-3-yl}-3-methoxybenzamide

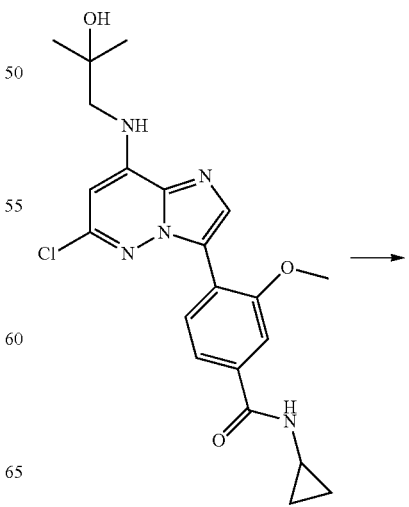

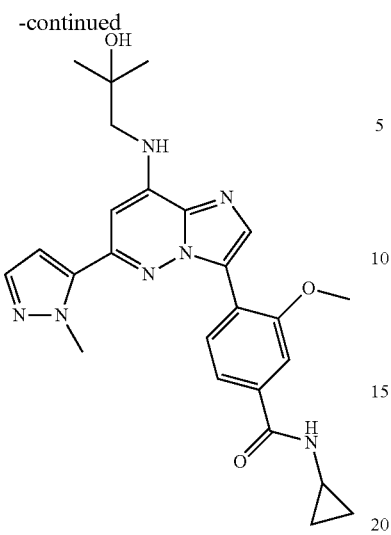

75 mg (174 μmol) 4-{6-chloro-8-[(2-hydroxy-2-methylpropyl)amino]imidazo[1,2-b]pyridazin-3-yl}-N-cyclopropyl-3-methoxybenzamide which was prepared according to intermediate example 49a were transformed in analogy to example 1 using 1-methyl-5-(4,4,5,5-tetramethyl-1,3,2-dioxaborolan-2-yl)-1H-pyrazole to give after working up and purification 14.8 mg (18%) of the title compound.

$^1$H-NMR (DMSO-d6): δ=0.57 (2H), 0.69 (2H), 1.17 (6H), 2.83 (1H), 3.35 (2H), 3.85 (3H), 4.01 (3H), 4.77 (1H), 6.59 (1H), 6.85 (1H), 6.95 (1H), 7.47 (1H), 7.51 (1H), 7.53 (1H), 7.81 (1H), 8.03 (1H), 8.49 (1H) ppm.

Example 51

N-cyclopropyl-4-{8-[(2-hydroxy-2-methylpropyl)amino]-6-(phenylsulfanyl) imidazo[1,2-b]pyridazin-3-yl}-3-methoxybenzamide (A) and N-cyclopropyl-3-hydroxy-4-{8-[(2-hydroxy-2-methylpropyl)amino]-6-(phenylsulfanyl)imidazo[1,2-b]pyridazin-3-yl}benzamide (B)

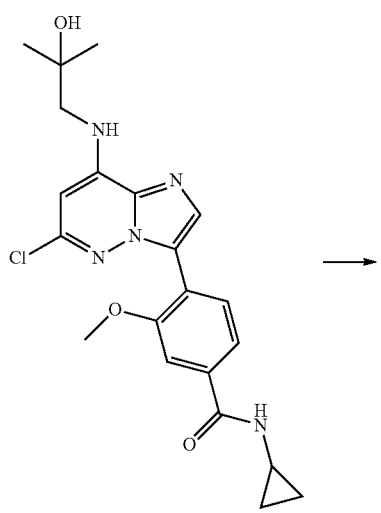

→

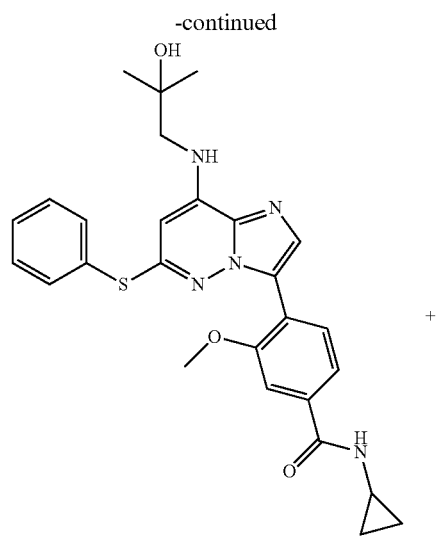

(A)

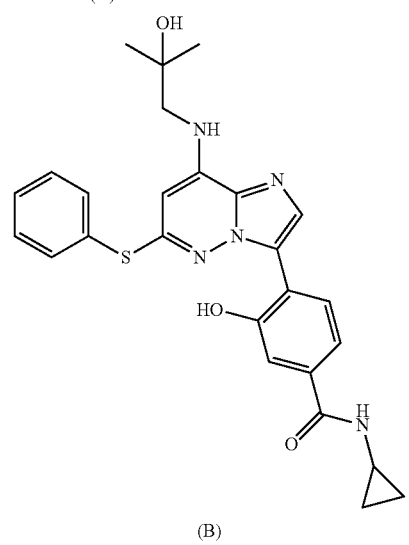

(B)

To a solution of 76.9 mg benzenethiol in 1.0 mL dimethyl sulfoxide were added 27.9 mg sodium hydride (60%) and the mixture was stirred at 23° C. for 1 hour. Then 50 mg (116 μmol) 4-{6-chloro-8-[(2-hydroxy-2-methylpropyl)amino]imidazo[1,2-b]pyridazin-3-yl}-N-cyclopropyl-3-methoxybenzamide which was prepared according to intermediate example 49a were added and the mixture was heated at 120° C. using microwave irradiation for 1 hour. Water was added and the mixture was extracted with dichloromethane and methanol. The organic layer was washed with brine and dried over sodium sulfate. After filtration and removal of the solvent the residue was purified by chromatography to give 8.0 mg (18%) of the title compound A and 15.3 mg (27%) of the title compound B.

$^1$H-NMR (DMSO-d6) of A: δ=0.56 (2H), 0.69 (2H), 1.10 (6H), 2.82 (1H), 3.19 (2H), 3.27 (3H), 4.70 (1H), 6.19 (1H), 6.97 (1H), 7.22 (1H), 7.41-7.47 (4H), 7.53-7.58 (2H), 7.85 (1H), 7.86 (1H), 8.44 (1H) ppm.

$^1$H-NMR (DMSO-d6) of B: δ=0.54 (2H), 0.66 (2H), 1.10 (6H), 2.80 (1H), 3.18 (2H), 4.70 (1H), 6.17 (1H), 6.98 (1H), 7.04 (1H), 7.33 (1H), 7.42-7.48 (3H), 7.55-7.61 (2H), 7.87 (1H), 7.95 (1H), 8.33 (1H), 10.13 (1H) ppm.

Example 52

N-cyclopropyl-4-{6-(4-fluorophenyl)-8-[(3,3,3-trifluoropropyl)amino]imidazo[1,2-b]pyridazin-3-yl}-3-methoxybenzamide

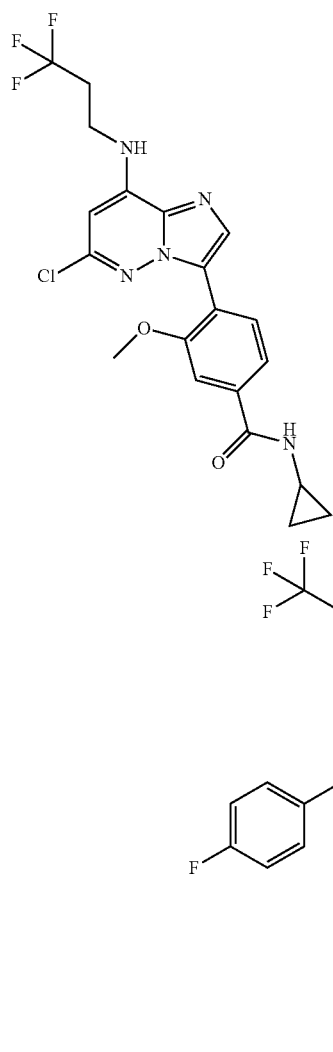

65 mg (143 µmol) 4-{6-chloro-8-[(3,3,3-trifluoropropyl)amino]imidazo[1,2-b]pyridazin-3-yl}-N-cyclopropyl-3-methoxybenzamide which was prepared according to intermediate example 52a were transformed in analogy to example 1 using (4-fluorophenyl)boronic acid to give after working up and purification 14.3 mg (18%) of the title compound.

$^1$H-NMR (CDCl$_3$): δ=0.66 (2H), 0.91 (2H), 2.59 (2H), 2.95 (1H), 3.75 (2H), 3.97 (3H), 6.00 (1H), 6.32 (1H), 6.39 (1H), 7.17 (2H), 7.33 (1H), 7.58 (1H), 7.90 (2H), 8.01 (1H), 8.37 (1H) ppm.

Intermediate Example 52a

4-{6-Chloro-8-[(3,3,3-trifluoropropyl)amino]imidazo[1,2-b]pyridazin-3-yl}-N-cyclopropyl-3-methoxybenzamide

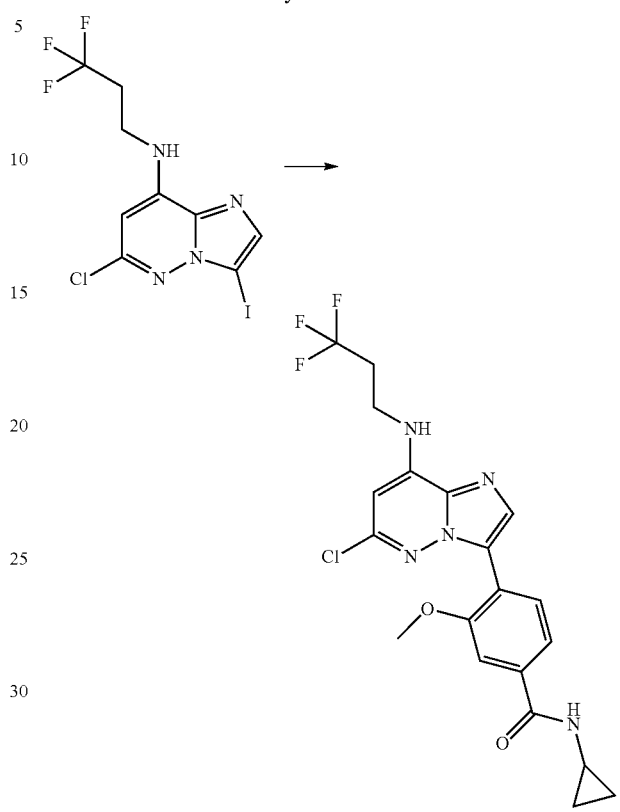

484 mg (1.24 mmol) 6-chloro-3-iodo-N-(3,3,3-trifluoropropyl)imidazo[1,2-b]pyridazin-8-amine which was prepared according to intermediate example 6b were transformed in analogy to intermediate example 1a using [4-(cyclopropylcarbamoyl)-2-methoxyphenyl]boronic acid which was prepared according to intermediate example 49b to give after working up and purification 163 mg (29%) of the title compound.

Example 53

N-cyclopropyl-3-methoxy-4-{6-(1-methyl-1H-pyrazol-5-yl)-8-[(3,3,3-trifluoropropyl)amino]imidazo[1,2-b]pyridazin-3-yl}benzamide

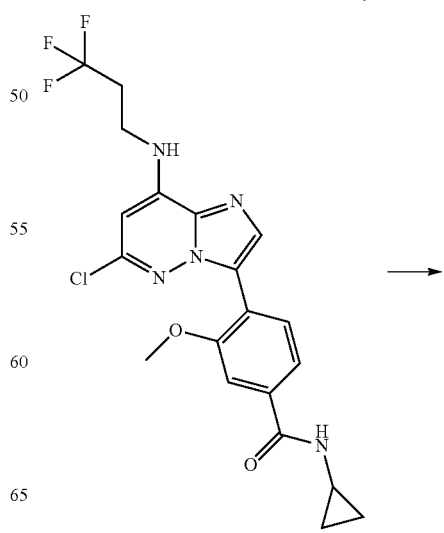

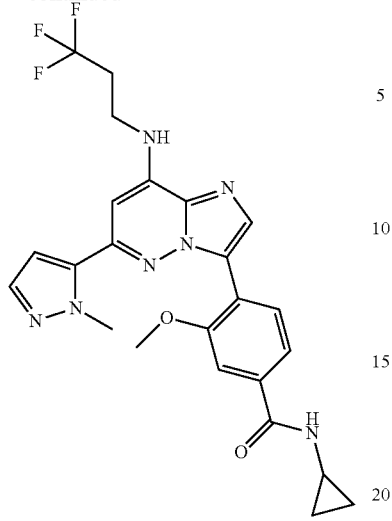

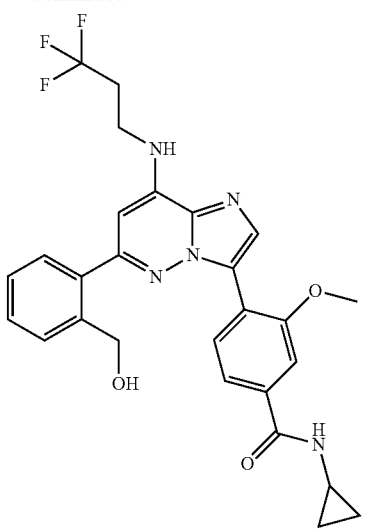

65 mg (143 μmol) 4-{6-chloro-8-[(3,3,3-trifluoropropyl)amino]imidazo[1,2-b]pyridazin-3-yl}-N-cyclopropyl-3-methoxybenzamide which was prepared according to intermediate example 52a were transformed in analogy to example 1 using 1-methyl-5-(4,4,5,5-tetramethyl-1,3,2-dioxaborolan-2-yl)-1H-pyrazole to give after working up and purification 3.6 mg (5%) of the title compound.

$^1$H-NMR (CDCl$_3$): δ=0.66 (2H), 0.91 (2H), 2.58 (2H), 2.94 (1H), 3.72 (2H), 3.94 (3H), 4.11 (3H), 6.04 (1H), 6.27 (1H), 6.31 (1H), 6.64 (1H), 7.27 (1H), 7.53 (1H), 7.58 (1H), 7.95 (1H), 8.13 (1H) ppm.

50 mg (110 μmol) 4-{6-chloro-8-[(3,3,3-trifluoropropyl)amino]imidazo[1,2-b]pyridazin-3-yl}-N-cyclopropyl-3-methoxybenzamide which was prepared according to intermediate example 52a were transformed in analogy to example 1 using [2-(hydroxymethyl)phenyl]boronic acid to give after working up and purification 11.8 mg (18%) of the title compound.

$^1$H-NMR (CDCl$_3$): δ=0.60 (2H), 0.85 (2H), 2.58 (2H), 2.88 (1H), 3.73 (2H), 3.90 (3H), 4.39 (2H), 5.12 (1H), 6.13 (1H), 6.24 (1H), 6.34 (1H), 7.22 (1H), 7.43-7.49 (3H), 7.55 (1H), 7.58 (1H), 7.79 (1H), 7.84 (1H) ppm.

Example 54

N-cyclopropyl-4-{6-[2-(hydroxymethyl)phenyl]-8-[(3,3,3-trifluoropropyl)amino]imidazo[1,2-b]pyridazin-3-yl}-3-methoxybenzamide Example 55

N-cyclopropyl-4-{6-[(2-methoxyphenyl)sulfanyl]-8-[(3,3,3-trifluoropropyl)amino]imidazo[1,2-b]pyridazin-3-yl}-2-methylbenzamide

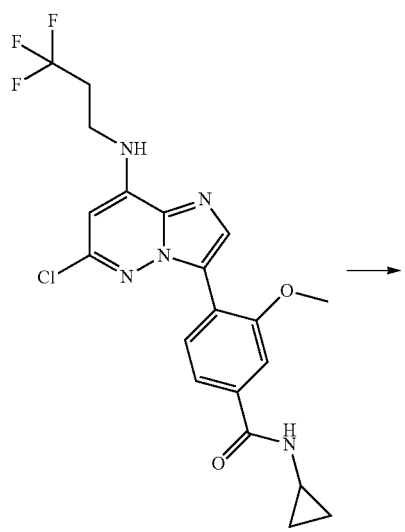

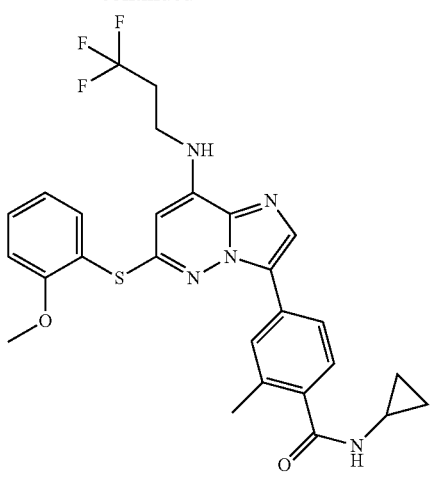

50 mg (114 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 2-methoxybenzenethiol to give after working up and purification 9.2 mg (14%) of the title compound.

$^1$H-NMR (CDCl$_3$): δ=0.61 (2H), 0.88 (2H), 2.36 (3H), 2.47 (2H), 2.89 (1H), 3.52 (2H), 3.77 (3H), 5.88 (1H), 6.01 (1H), 6.28 (1H), 6.97-7.07 (2H), 7.16 (1H), 7.48 (1H), 7.57-7.65 (3H), 7.67 (1H) ppm.

75 mg (165 μmol) (RS)-4-(6-chloro-8-{[(4-methylmorpholin-2-yl)methyl]amino}imidazo[1,2-b]pyridazin-3-yl)-N-cyclopropyl-2-methylbenzamide which was prepared according to intermediate example 56a were transformed in analogy to example 51 using benzenethiol to give after working up and purification 21.6 mg (25%) of the title compound.

$^1$H-NMR (DMSO-d6): δ=0.49 (2H), 0.65 (2H), 1.70 (1H), 1.93 (1H), 2.13 (3H), 2.20 (3H), 2.53 (1H), 2.64 (1H), 2.79 (1H), 3.25-3.34 (2H), 3.43 (1H), 3.62 (1H), 3.73 (1H), 6.10 (1H), 7.10 (1H), 7.42 (1H), 7.45-7.51 (3H), 7.59-7.67 (3H), 7.71 (1H), 7.92 (1H), 8.23 (1H) ppm.

Example 56

(RS)—N-cyclopropyl-2-methyl-4-[8-{[(4-methylmorpholin-2-yl)methyl]amino}-6-(phenylsulfanyl)imidazo[1,2-b]pyridazin-3-yl]benzamide

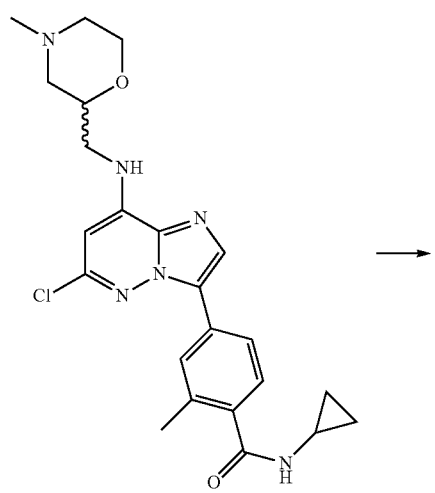

Intermediate Example 56a (RS)-4-(6-Chloro-8-{[(4-methylmorpholin-2-yl)methyl]amino}imidazo[1,2-b]pyridazin-3-yl)-N-cyclopropyl-2-methylbenzamide

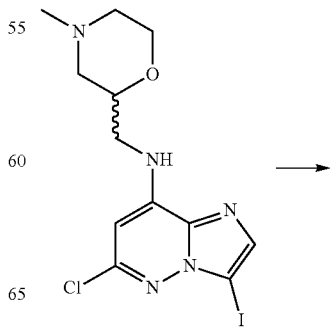

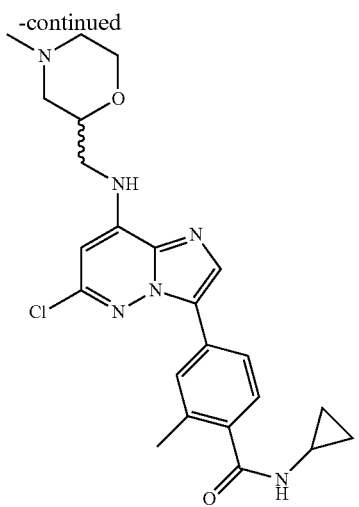

352 mg (864 µmol) (RS)-6-chloro-3-iodo-N-[(4-methylmorpholin-2-yl)methyl]imidazo[1,2-b]pyridazin-8-amine which was prepared according to intermediate example 56b were transformed in analogy to intermediate example 1a using N-cyclopropyl-2-methyl-4-(4,4,5,5-tetramethyl-1,3,2-dioxaborolan-2-yl)benzamide to give after working up and purification 372 mg (95%) of the title compound.

Intermediate Example 56b (RS)-6-Chloro-3-iodo-N-[(4-methylmorpholin-2-yl)methyl]imidazo[1,2-b]pyridazin-8-amine

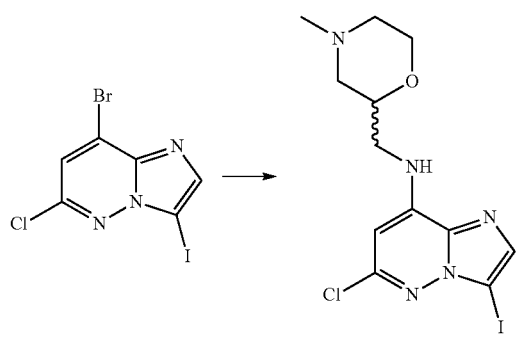 [SMILES: Clc1cc(Br)c2ncc(I)n2n1 ; CN1CCOC(CNc2cc(Cl)nn3c(I)cnc23)C1]

370 mg (1.03 mmol) 8-bromo-6-chloro-3-iodoimidazo[1,2-b]pyridazine which was prepared according to intermediate example 1c were transformed in analogy to intermediate example 1b using 1-[(2RS)-4-methylmorpholin-2-yl]methanamine to give after working up and purification 359 mg (85%) of the title compound.

Example 57

4-{8-[(2-Amino-2-methylpropyl)amino]-6-(4-fluorophenyl)imidazo[1,2-b]pyridazin-3-yl}-N-cyclopropyl-2-methylbenzamide

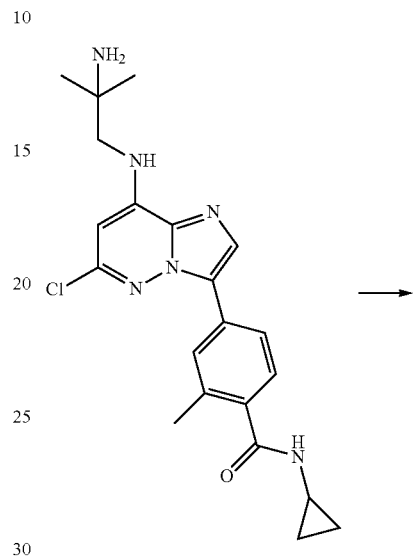

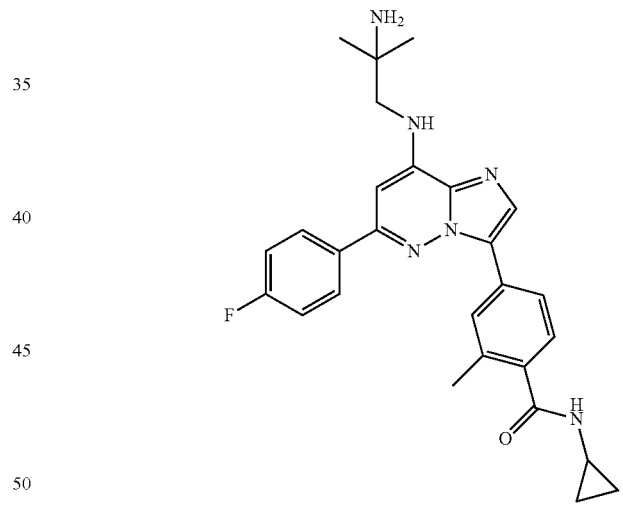

100 mg (242 µmol) 4-{8-[(2-amino-2-methylpropyl)amino]-6-chloroimidazo[1,2-b]pyridazin-3-yl}-N-cyclopropyl-2-methylbenzamide which was prepared according to intermediate example 57a were transformed in analogy to example 1 using (4-fluorophenyl)boronic acid to give after working up and purification 17.9 mg (14%) of the title compound.

$^1$H-NMR (CDCl$_3$): δ=0.63 (2H), 0.90 (2H), 1.25 (2H), 1.29 (6H), 2.55 (3H), 2.93 (1H), 3.27 (2H), 5.94 (1H), 6.34 (1H), 6.41 (1H), 7.17 (2H), 7.45 (1H), 7.81 (1H), 7.91-7.98 (3H), 8.04 (1H) ppm.

Intermediate Example 57a

4-{8-[(2-Amino-2-methylpropyl)amino]-6-chloroimidazo[1,2-b]pyridazin-3-yl}-N-cyclopropyl-2-methylbenzamide

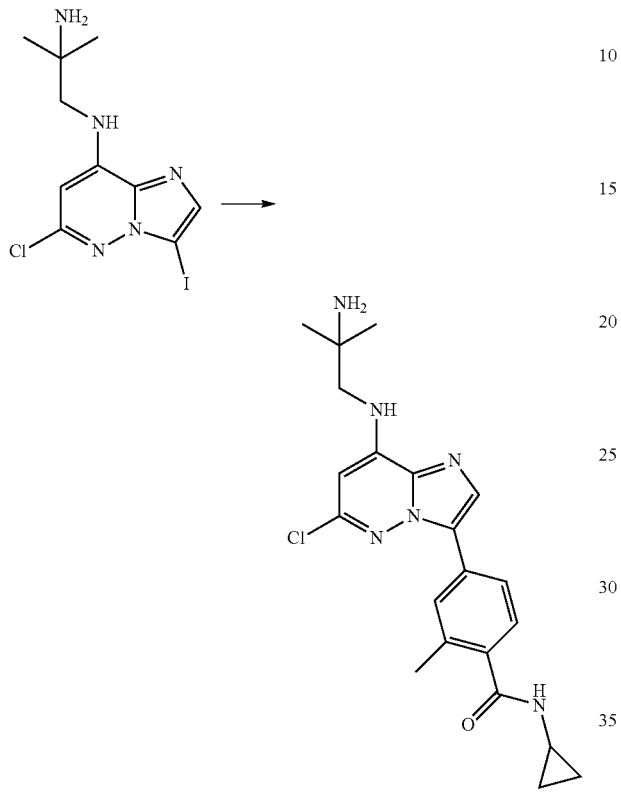

1.07 g (2.93 mmol) N$^1$-(6-chloro-3-iodoimidazo[1,2-b]pyridazin-8-yl)-2-methylpropane-1,2-diamine which was prepared according to intermediate example 57b were transformed in analogy to intermediate example 1a using N-cyclopropyl-2-methyl-4-(4,4,5,5-tetramethyl-1,3,2-dioxaborolan-2-yl)benzamide to give after working up and purification 809 mg (64%) of the title compound.

Intermediate Example 57b

N$^1$-(6-chloro-3-iodoimidazo[1,2-b]pyridazin-8-yl)-2-methylpropane-1,2-diamine

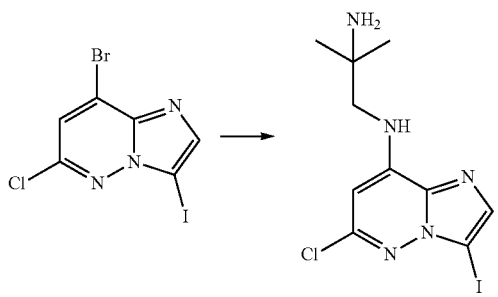 [SMILES: Clc1cc(Br)c2ncc(I)n2n1 ; CC(C)(N)CNc1cc(Cl)nn2c(I)cnc12]

2.00 g (5.58 mmol) 8-bromo-6-chloro-3-iodoimidazo[1,2-b]pyridazine which was prepared according to intermediate example 1c were transformed in analogy to intermediate example 1b using 2-methylpropane-1,2-diamine to give after working up and purification 1.08 g (53%) of the title compound.

Example 58

4-{8-[(2-Amino-2-methylpropyl)amino]-6-(1-methyl-1H-pyrazol-5-yl)imidazo[1,2-b]pyridazin-3-yl}-N-cyclopropyl-2-methylbenzamide

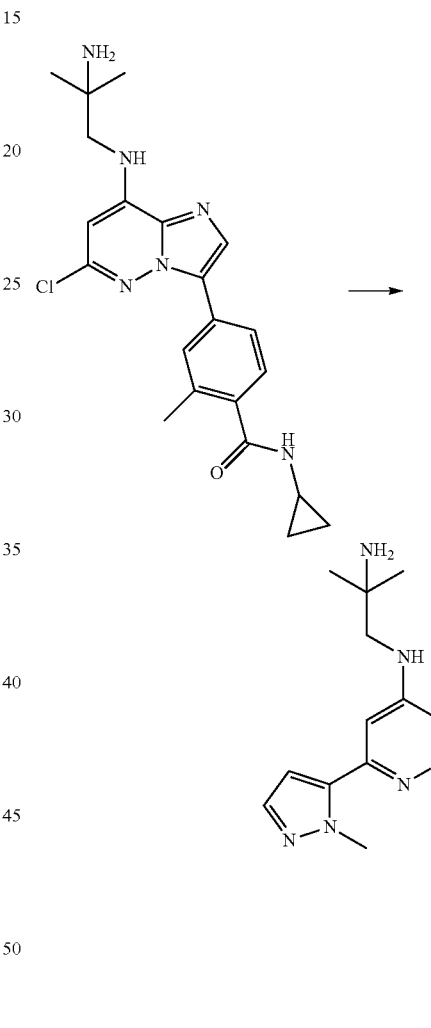

100 mg (242 μmol) 4-{8-[(2-amino-2-methylpropyl)amino]-6-chloroimidazo[1,2-b]pyridazin-3-yl}-N-cyclopropyl-2-methylbenzamide which was prepared according to intermediate example 57a were transformed in analogy to example 1 using 1-methyl-5-(4,4,5,5-tetramethyl-1,3,2-dioxaborolan-2-yl)-1H-pyrazole to give after working up and purification 27.5 mg (22%) of the title compound.

$^1$H-NMR (CDCl$_3$): δ=0.64 (2H), 0.90 (2H), 1.25 (2H), 1.28 (6H), 2.52 (3H), 2.93 (1H), 3.23 (2H), 4.20 (3H), 5.97 (1H), 6.29 (1H), 6.42 (1H), 6.64 (1H), 7.41 (1H), 7.53 (1H), 7.79 (1H), 7.86 (1H), 7.90 (1H) ppm.

Example 59

4-{8-[(2-Amino-2-methylpropyl)amino]-6-[2-(hydroxymethyl)phenyl]imidazo[1,2-b]pyridazin-3-yl}-N-cyclopropyl-2-methylbenzamide

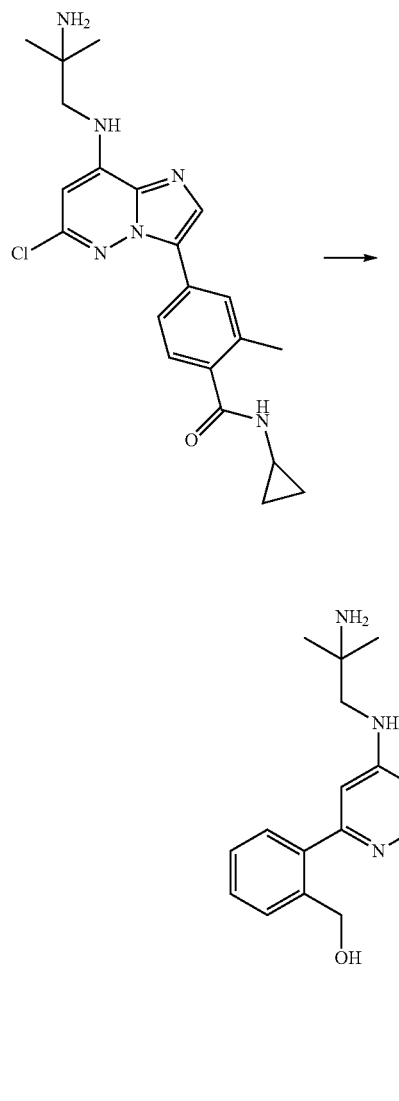

100 mg (242 µmol) 4-{8-[(2-amino-2-methylpropyl)amino]-6-chloroimidazo[1,2-b]pyridazin-3-yl}-N-cyclopropyl-2-methylbenzamide which was prepared according to intermediate example 57a were transformed in analogy to example 1 using [2-(hydroxymethyl)phenyl]boronic acid to give after working up and purification 30.0 mg (23%) of the title compound.

$^1$H-NMR (CDCl$_3$): δ=0.59 (2H), 0.85 (2H), 1.25 (2H), 1.28 (6H), 2.49 (3H), 2.89 (1H), 3.25 (2H), 4.40 (2H), 5.30 (1H), 6.07 (1H), 6.30 (1H), 6.47 (1H), 7.38 (1H), 7.43-7.50 (3H), 7.60 (1H), 7.64 (1H), 7.73 (1H), 7.74 (1H) ppm.

Example 60

N-cyclopropyl-4-{8-[(2-hydroxy-2-methylpropyl)amino]-6-[(4-hydroxyphenyl)sulfanyl]imidazo[1,2-b]pyridazin-3-yl}-2-methylbenzamide (A) and N-cyclopropyl-4-{8-[(2-hydroxy-2-methylpropyl)amino]-6-[(4-methoxyphenyl)sulfanyl]imidazo[1,2-b]pyridazin-3-yl}-2-methylbenzamide (B)

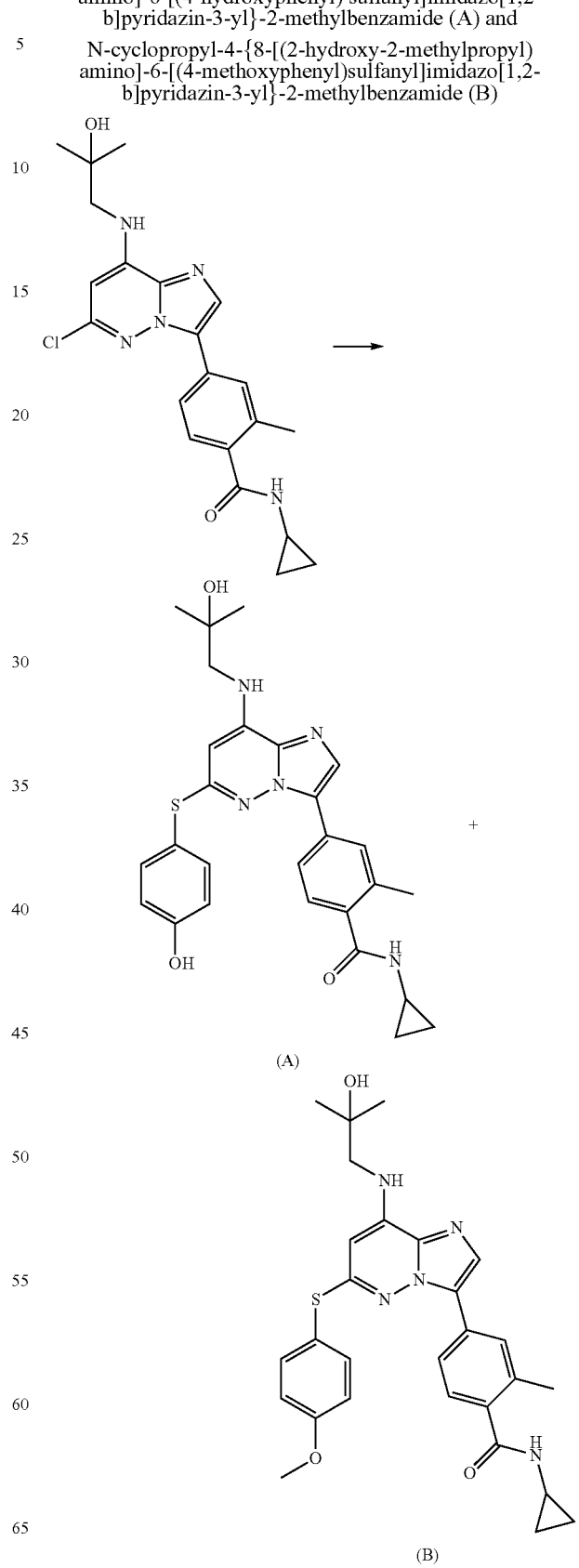

75 mg (181 μmol) 4-{6-chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 51 using 4-methoxybenzenethiol to give after working up and purification 50 mg (43%) of the title compound A and 8.8 mg (5%) of the title compound B.

$^1$H-NMR (DMSO-d6) of A: δ=0.49 (2H), 0.65 (2H), 1.11 (6H), 2.21 (3H), 2.79 (1H), 3.19 (2H), 4.72 (1H), 6.12 (1H), 6.82-6.91 (3H), 7.12 (1H), 7.42 (2H), 7.65 (1H), 7.70 (1H), 7.91 (1H), 8.22 (1H), 10.04 (1H) ppm.

$^1$H-NMR (CDCl$_3$) of B: δ=0.64 (2H), 0.90 (2H), 1.39 (6H), 2.37 (3H), 2.92 (1H), 3.24 (2H), 3.88 (3H), 4.09 (1H), 5.30 (1H), 5.92 (1H), 5.97 (1H), 6.36 (1H), 6.96 (2H), 7.12 (1H), 7.50-7.58 (3H), 7.61 (1H) ppm.

Example 61

N-cyclopropyl-4-{8-[(2-hydroxy-2-methylpropyl)amino]-6-[(3-hydroxyphenyl) sulfanyl]imidazo[1,2-b]pyridazin-3-yl}-2-methylbenzamide (A) and N-cyclopropyl-4-{8-[(2-hydroxy-2-methylpropyl)amino]-6-[(3-methoxyphenyl)sulfanyl]imidazo[1,2-b]pyridazin-3-yl}-2-methylbenzamide (B)

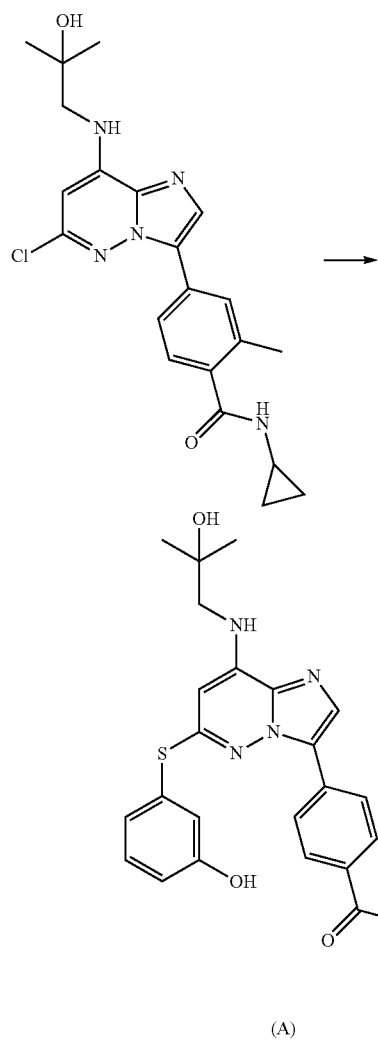

(A)

-continued

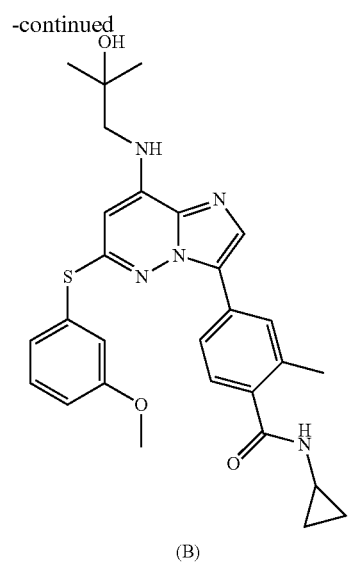

(B)

75 mg (181 μmol) 4-{6-chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 51 using 3-methoxybenzenethiol to give after working up and purification 26.9 mg (21%) of the title compound A and 14.9 mg (15%) of the title compound B.

$^1$H-NMR (DMSO-d6) of A: δ=0.49 (2H), 0.65 (2H), 1.11 (6H), 2.22 (3H), 2.79 (1H), 3.20 (2H), 4.71 (1H), 6.21 (1H), 6.85 (1H), 6.94-7.02 (3H), 7.15 (1H), 7.25 (1H), 7.73 (1H), 7.74 (1H), 7.94 (1H), 8.23 (1H), 9.73 (1H) ppm.

$^1$H-NMR (CDCl$_3$) of B: δ=0.63 (2H), 0.90 (2H), 1.40 (6H), 2.37 (3H), 2.92 (1H), 3.23 (2H), 3.73 (3H), 5.94 (1H), 6.02 (1H), 6.50 (1H), 6.97 (1H), 7.13-7.20 (3H), 7.22 (1H), 7.33 (1H), 7.56-7.63 (3H) ppm.

Example 62

N-cyclopropyl-4-{6-[(3-fluorophenyl)sulfanyl]-8-[(2-hydroxy-2-methylpropyl)amino]imidazo[1,2-b]pyridazin-3-yl}-3-hydroxybenzamide (A) and N-cyclopropyl-4-{6-[(3-fluorophenyl)sulfanyl]-8-[(2-hydroxy-2-methylpropyl)amino]imidazo[1,2-b]pyridazin-3-yl}-3-methoxybenzamide (B)

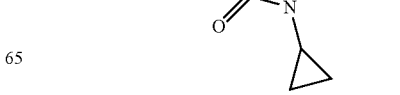

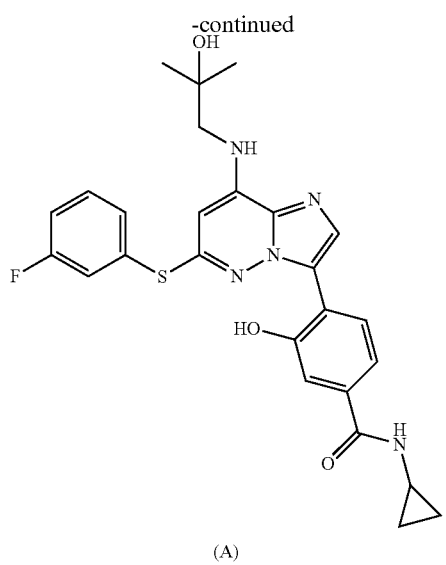

(A)

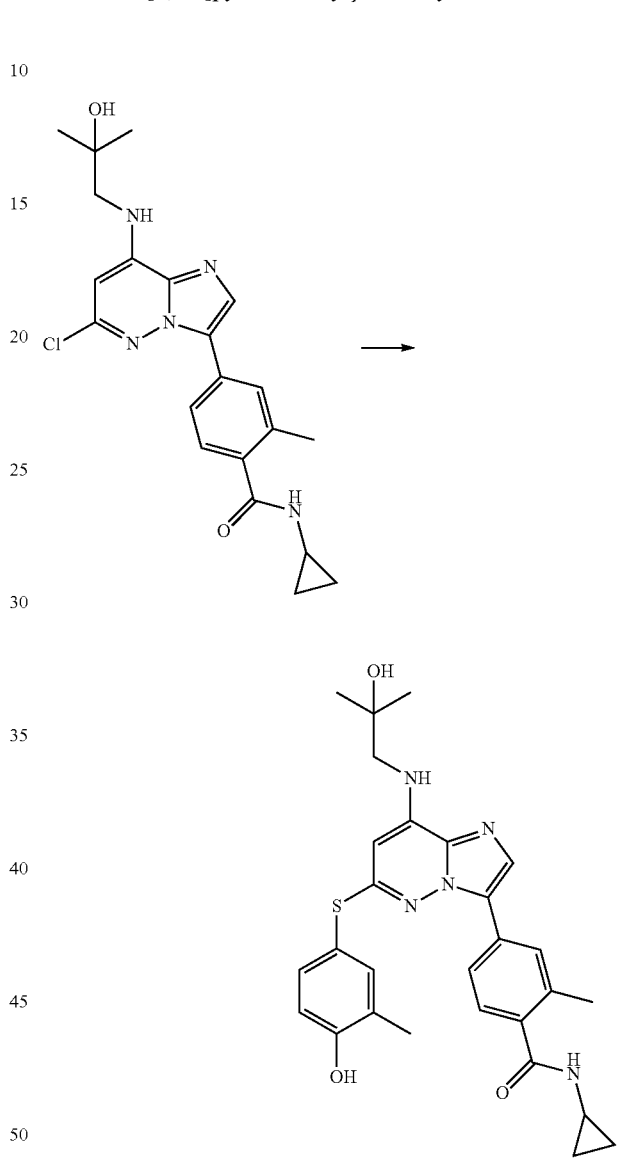

Example 63

N-cyclopropyl-4-{6-[(4-hydroxy-3-methylphenyl)sulfanyl]-8-[(2-hydroxy-2-methylpropyl)amino]imidazo[1,2-b]pyridazin-3-yl}-2-methylbenzamide (B)

150 mg (349 µmol) 4-{6-chloro-8-[(2-hydroxy-2-methylpropyl)amino]imidazo[1,2-b]pyridazin-3-yl}-N-cyclopropyl-3-methoxybenzamide which was prepared according to intermediate example 49a were transformed in analogy to example 51 using 3-fluorobenzenethiol to give after working up and purification 3.3 mg (2%) of the title compound A and 2.5 mg (1%) of the title compound B.

$^1$H-NMR (DMSO-d6) of A: δ=0.53 (2H), 0.66 (2H), 1.11 (6H), 2.80 (1H), 3.21 (2H), 4.71 (1H), 6.24 (1H), 7.06 (2H), 7.26 (1H), 7.33-7.52 (4H), 7.86 (1H), 7.94 (1H), 8.33 (1H), 10.18 (1H) ppm.

$^1$H-NMR (DMSO-d6) of B: δ=0.55 (2H), 0.69 (2H), 1.11 (6H), 2.82 (1H), 3.22 (2H), 3.84 (3H), 4.70 (1H), 6.26 (1H), 7.04 (1H), 7.21-7.30 (2H), 7.36 (1H), 7.39-7.49 (3H), 7.84 (1H), 7.85 (1H), 8.44 (1H) ppm.

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2-methyl-4-sulfanylphenol to give after working up and purification 27.6 mg (28%) of the title compound.

$^1$H-NMR (DMSO-d6): δ=0.49 (2H), 0.65 (2H), 1.11 (6H), 2.10 (3H), 2.20 (3H), 2.79 (1H), 3.18 (2H), 4.70 (1H), 6.11 (1H), 6.86 (1H), 6.88 (1H), 7.10 (1H), 7.25 (1H), 7.32 (1H), 7.67 (1H), 7.71 (1H), 7.92 (1H), 8.21 (1H), 9.87 (1H) ppm.

Example 64

N-cyclopropyl-4-{6-[(5-fluoro-2-methylphenyl)sulfanyl]-8-[(2-hydroxy-2-methylpropyl)amino]imidazo[1,2-b]pyridazin-3-yl}-2-methylbenzamide

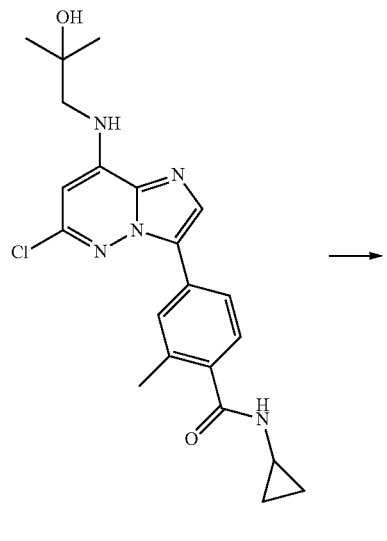

Example 65

N-cyclopropyl-4-{6-[(4-fluoro-3-methylphenyl)sulfanyl]-8-[(2-hydroxy-2-methylpropyl)amino]imidazo[1,2-b]pyridazin-3-yl}-2-methylbenzamide

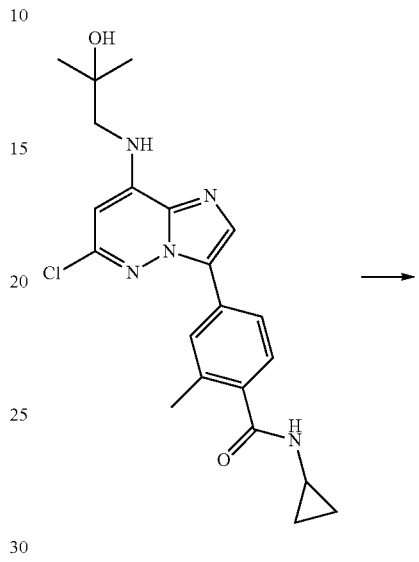

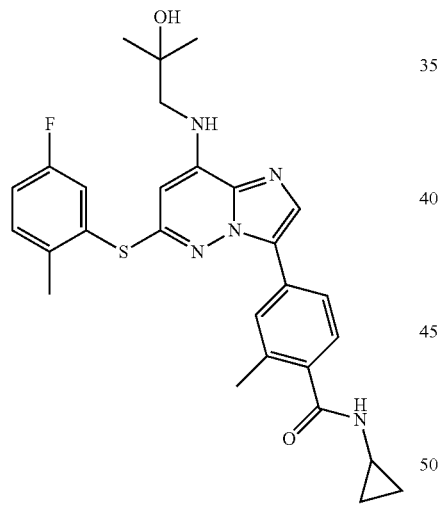

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 5-fluoro-2-methylbenzenethiol to give after working up and purification 47.7 mg (48%) of the title compound.

$^1$H-NMR (DMSO-d6): δ=0.48 (2H), 0.65 (2H), 1.12 (6H), 2.19 (3H), 2.31 (3H), 2.79 (1H), 3.23 (2H), 4.71 (1H), 6.27 (1H), 7.01 (1H), 7.06 (1H), 7.29 (1H), 7.42-7.49 (2H), 7.57 (1H), 7.67 (1H), 7.94 (1H), 8.23 (1H) ppm.

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 4-fluoro-3-methylbenzenethiol to give after working up and purification 25.9 mg (26%) of the title compound.

$^1$H-NMR (DMSO-d6): δ=0.48 (2H), 0.65 (2H), 1.11 (6H), 2.18 (3H), 2.22 (3H), 2.79 (1H), 3.22 (2H), 4.71 (1H), 6.22 (1H), 6.97 (1H), 7.08 (1H), 7.25 (1H), 7.48 (1H), 7.59 (2H), 7.67 (1H), 7.93 (1H), 7.23 (1H) ppm.

Example 66

N-cyclopropyl-4-{6-[(3-fluoro-4-methylphenyl)sulfanyl]-8-[(2-hydroxy-2-methylpropyl)amino]imidazo[1,2-b]pyridazin-3-yl}-2-methylbenzamide

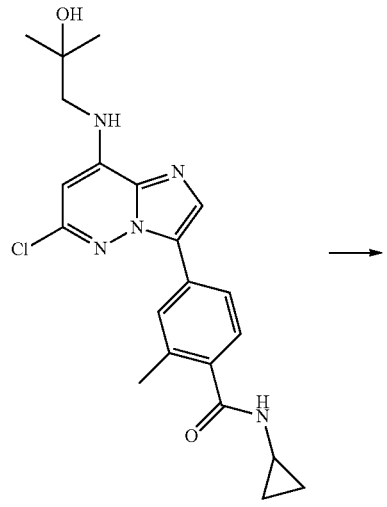

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-fluoro-4-methylbenzenethiol to give after working up and purification 41.7 mg (42%) of the title compound.

$^1$H-NMR (DMSO-d6): δ=0.48 (2H), 0.65 (2H), 1.12 (6H), 2.19 (3H), 2.28 (3H), 2.79 (1H), 3.23 (2H), 4.72 (1H), 6.27 (1H), 6.99 (1H), 7.07 (1H), 7.34 (1H), 7.39 (1H), 7.44 (1H), 7.63 (1H), 7.69 (1H), 7.94 (1H), 8.25 (1H) ppm.

Example 67

N-cyclopropyl-4-{6-[(3-fluoro-5-methylphenyl)sulfanyl]-8-[(2-hydroxy-2-methylpropyl)amino]imidazo[1,2-b]pyridazin-3-yl}-2-methylbenzamide

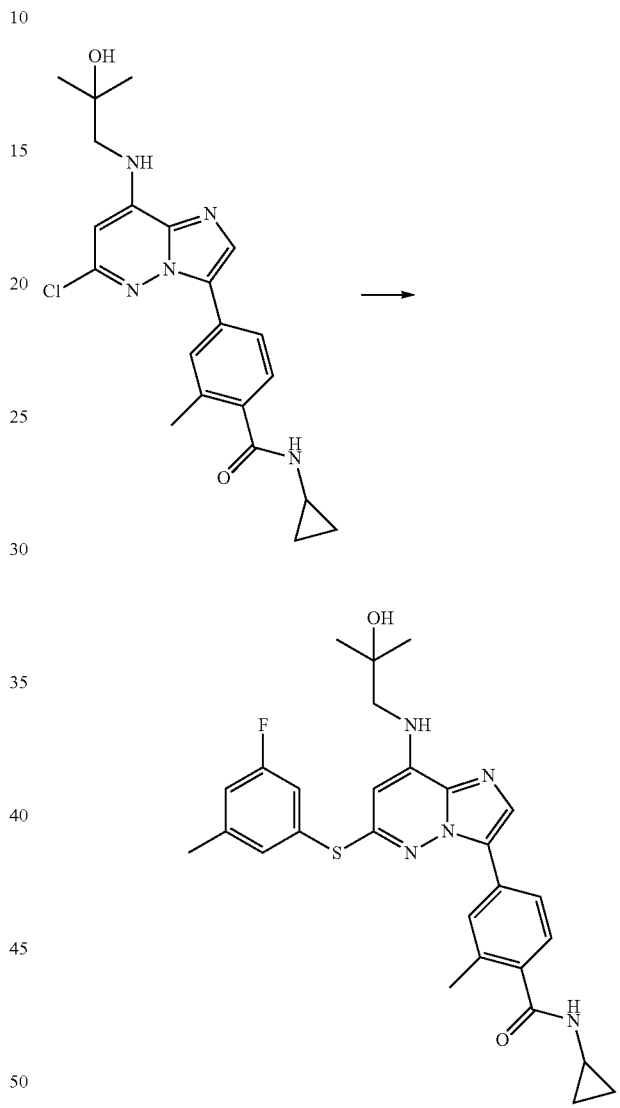

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-fluoro-5-methylbenzenethiol to give after working up and purification 33 mg (33%) of the title compound.

$^1$H-NMR (DMSO-d6): δ=0.49 (2H), 0.65 (2H), 1.12 (6H), 2.21 (3H), 2.30 (3H), 2.79 (1H), 3.22 (2H), 4.70 (1H), 6.27 (1H), 7.05 (1H), 7.13 (1H), 7.16 (1H), 7.26 (1H), 7.27 (1H), 7.70 (1H), 7.73 (1H), 7.95 (1H), 8.24 (1H) ppm.

Example 68

N-cyclopropyl-4-{6-[(3,5-difluorophenyl)sulfanyl]-8-[(2-hydroxy-2-methylpropyl)amino]imidazo[1,2-b]pyridazin-3-yl}-2-methylbenzamide

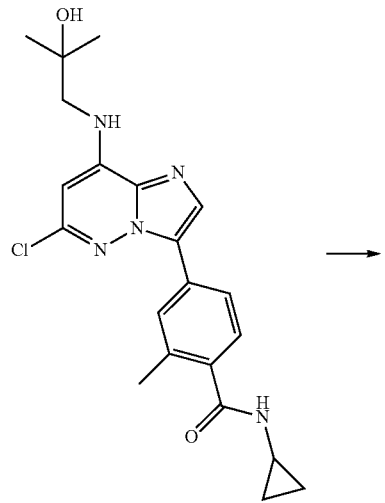

→

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3,5-difluorobenzenethiol to give after working up and purification 5.7 mg (6%) of the title compound.

$^1$H-NMR (DMSO-d6): δ=0.49 (2H), 0.65 (2H), 1.12 (6H), 2.22 (3H), 2.79 (1H), 3.24 (2H), 4.71 (1H), 6.34 (1H), 7.12 (1H), 7.16 (1H), 7.35-7.40 (3H), 7.71 (1H), 7.74 (1H), 7.96 (1H), 8.25 (1H) ppm.

Example 69

N-cyclopropyl-4-{6-[(4-fluoro-2-methylphenyl)sulfanyl]-8-[(2-hydroxy-2-methylpropyl)amino]imidazo[1,2-b]pyridazin-3-yl}-2-methylbenzamide

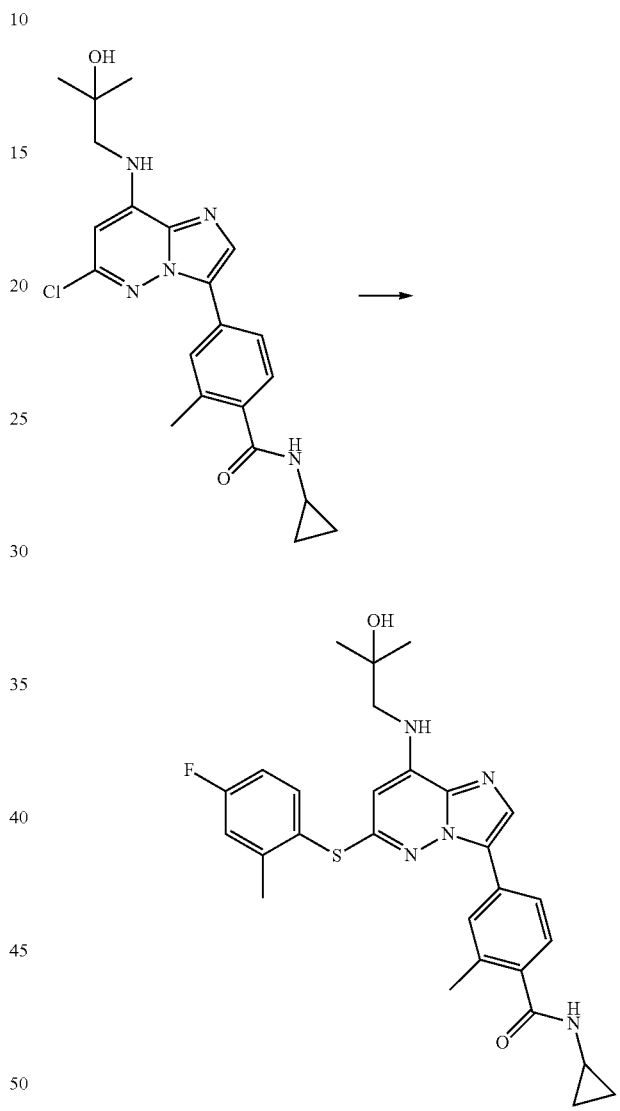

75 mg (181 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 4-fluoro-3-methylbenzenethiol to give after working up and purification 32.1 mg (32%) of the title compound.

$^1$H-NMR (DMSO-d6): δ=0.48 (2H), 0.65 (2H), 1.12 (6H), 2.18 (3H), 2.35 (3H), 2.79 (1H), 3.22 (2H), 4.72 (1H), 6.23 (1H), 6-95 (1H), 7.05 (1H), 7.15 (1H), 7.34 (1H), 7.53 (1H), 7.63 (1H), 7.65 (1H), 7.92 (1H), 8.23 (1H) ppm.

201
Example 70

N-cyclopropyl-4-{6-[(2-fluorophenyl)sulfanyl]-8-[(2-hydroxy-2-methylpropyl)amino]imidazo[1,2-b]pyridazin-3-yl}-2-methylbenzamide

202
Example 71

N-cyclopropyl-4-{6-[(4-fluorophenyl)sulfanyl]-8-[(2-hydroxy-2-methylpropyl)amino]imidazo[1,2-b]pyridazin-3-yl}-2-methylbenzamide

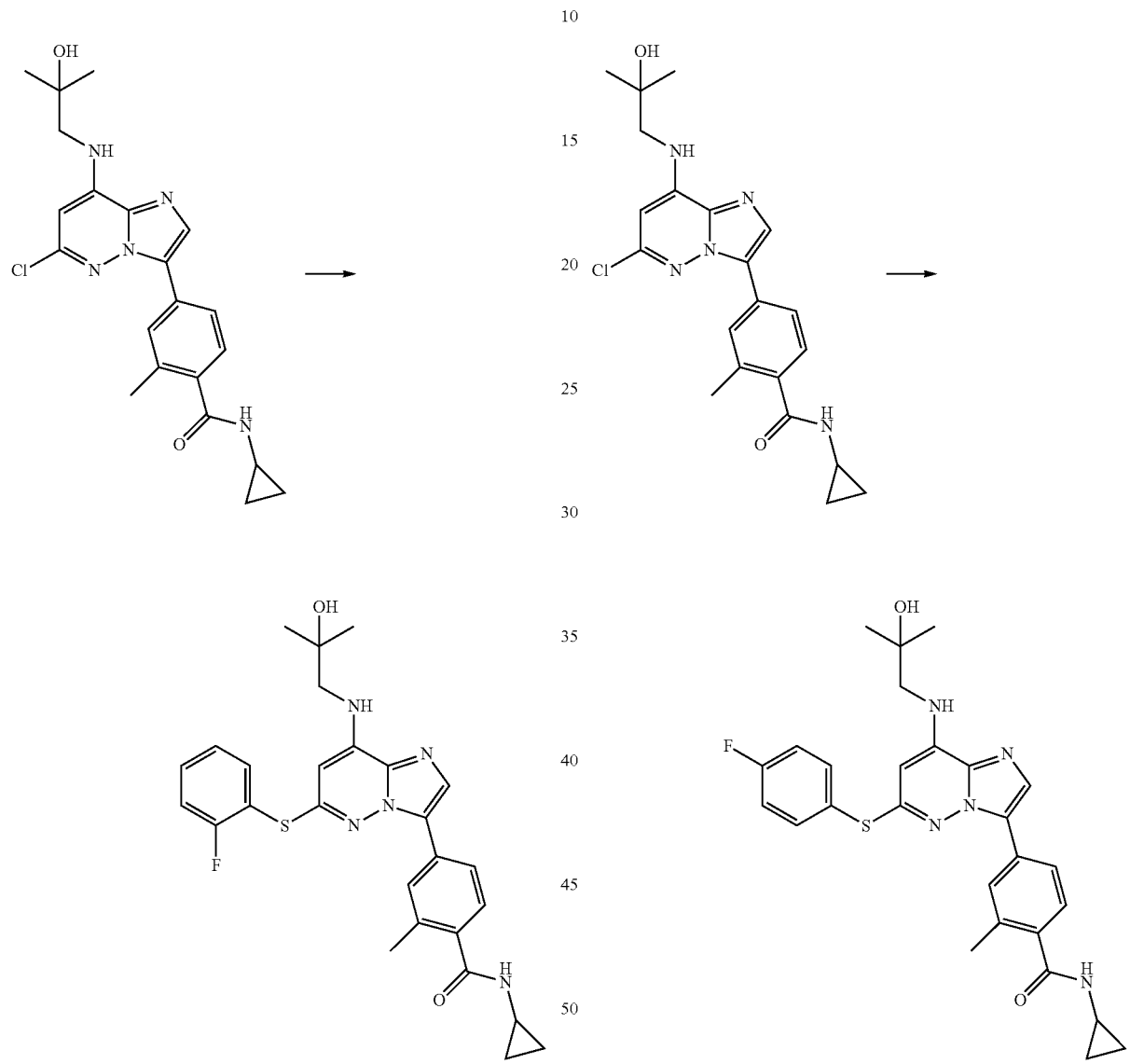

75 mg (181 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2-fluorobenzenethiol to give after working up and purification 36.8 mg (38%) of the title compound.

$^1$H-NMR (DMSO-d6): δ=0.49 (2H), 0.65 (2H), 1.13 (6H), 2.18 (3H), 2.78 (1H), 3.24 (2H), 4.72 (1H), 6.31 (1H), 7.00 (1H), 7.03 (1H), 7.32 (1H), 7.40 (1H), 7.53 (1H), 7.61 (1H), 7.64 (1H), 7.69 (1H), 7.93 (1H), 8.22 (1H) ppm.

75 mg (181 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 4-fluorobenzenethiol to give after working up and purification 31.6 mg (33%) of the title compound.

$^1$H-NMR (DMSO-d6): δ=0.48 (2H), 0.65 (2H), 1.12 (6H), 2.19 (3H), 2.79 (1H), 3.22 (2H), 4.72 (1H), 6.24 (1H), 6.97 (1H), 7.08 (1H), 7.33 (2H), 7.58 (1H), 7.64-7.71 (3H), 7.92 (1H), 8.23 (1H) ppm.

Example 72

4-{6-[(2E)-But-2-en-2-yl]-8-[(2-hydroxy-2-methyl-propyl)amino]imidazo[1,2-b]pyridazin-3-yl}-N-cyclopropyl-3-methoxybenzamide

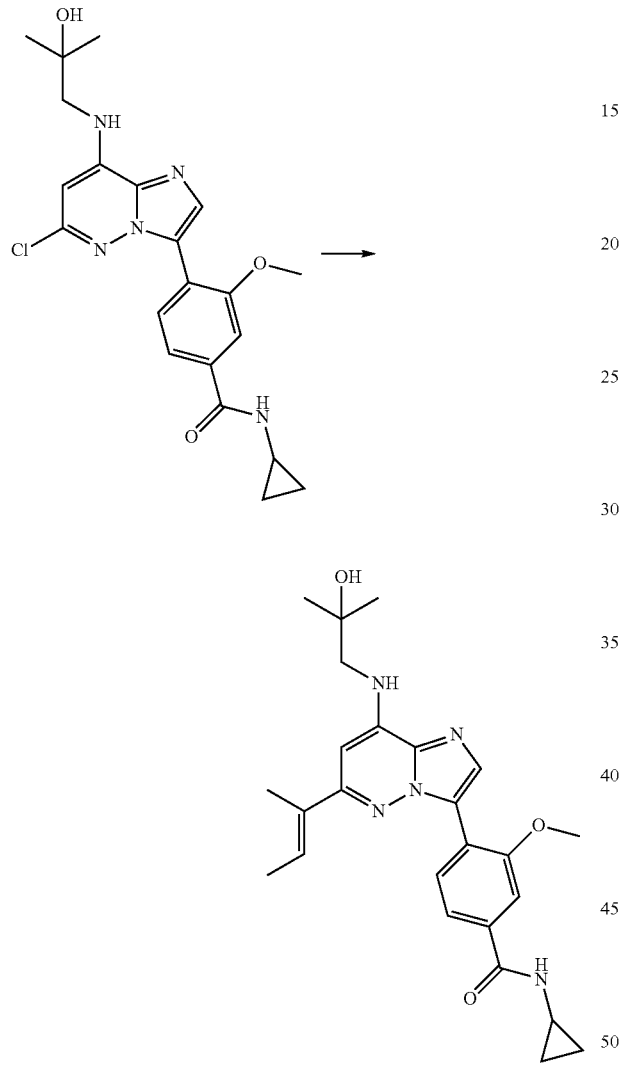

75 mg (174 µmol) 4-{6-chloro-8-[(2-hydroxy-2-methylpropyl)amino]imidazo[1,2-b]pyridazin-3-yl}-N-cyclopropyl-3-methoxybenzamide which was prepared according to intermediate example 49a were transformed in analogy to example 1 using (2Z)-but-2-en-2-ylboronic acid to give after working up and purification 26.9 mg (33%) of the title compound.

$^1$H-NMR (DMSO-d6): δ=0.57 (2H), 0.68 (2H), 1.16 (6H), 1.81 (3H), 1.99 (3H), 2.84 (1H), 3.28 (2H), 3.89 (3H), 4.75 (1H), 6.40 (1H), 6.48 (1H), 6.58 (1H), 7.51 (1H), 7.53 (1H), 7.85 (1H), 8.32 (1H), 8.47 (1H) ppm.

Example 73

N-cyclopropyl-4-{8-[(2-hydroxy-2-methylpropyl)amino]-6-[(2-hydroxyphenyl)sulfanyl]imidazo[1,2-b]pyridazin-3-yl}-2-methylbenzamide (A) and N-cyclopropyl-4-{8-[(2-hydroxy-2-methylpropyl)amino]-6-[(2-methoxyphenyl)sulfanyl]imidazo[1,2-b]pyridazin-3-yl}-2-methylbenzamide (B)

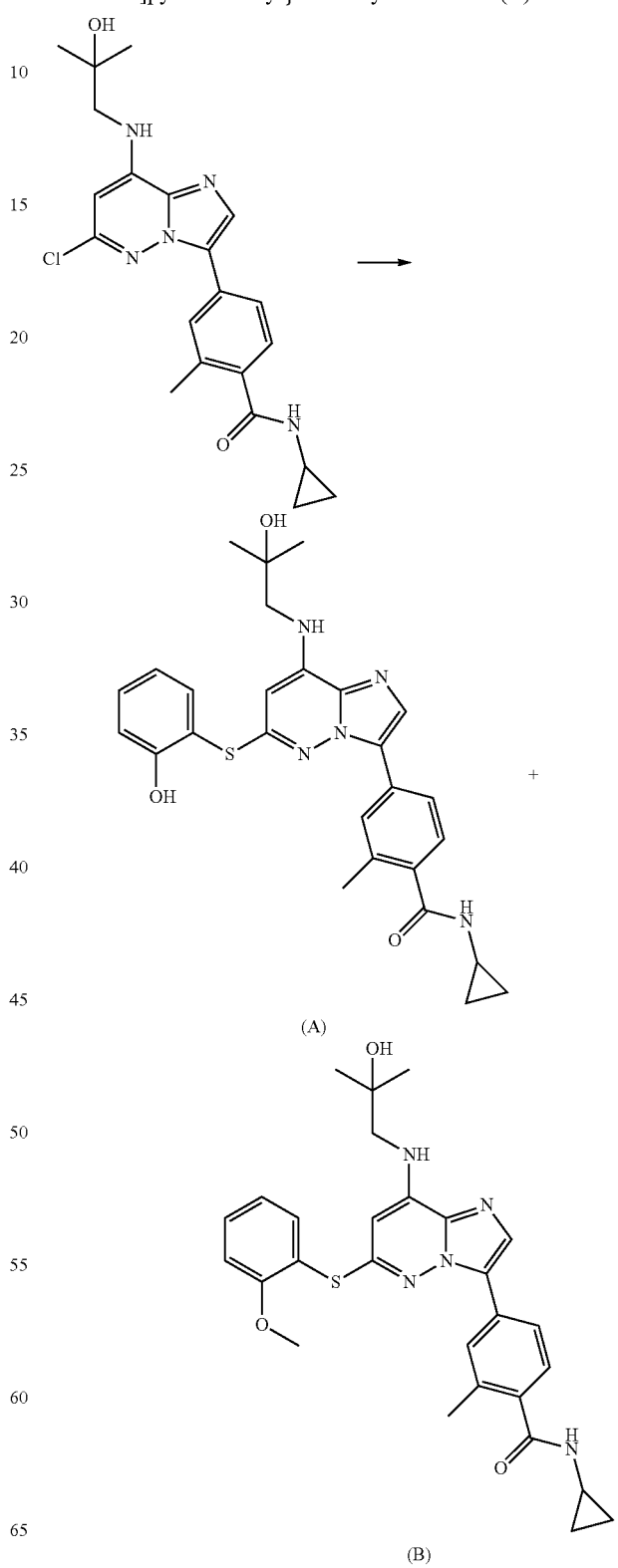

100 mg (242 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2-methoxybenzenethiol to give after working up and purification 43.1 mg (35%) of the title compound A and 5.8 mg (4%) of the title compound B.

¹H-NMR (DMSO-d6) of A: δ=0.49 (2H), 0.65 (2H), 1.11 (6H), 2.20 (3H), 2.78 (1H), 3.19 (2H), 4.72 (1H), 6.14 (1H), 6.82-6.90 (2H), 6.97 (1H), 7.07 (1H), 7.33 (1H), 7.44 (1H), 7.66 (1H), 7.71 (1H), 7.91 (1H), 8.22 (1H), 9.96 (1H) ppm.

¹H-NMR (CDCl₃) of B: δ=0.63 (2H), 0.89 (2H), 1.39 (6H), 2.35 (3H), 2.91 (1H), 3.23 (2H), 3.77 (3H), 4.62 (1H), 5.92 (1H), 5.97 (1H), 6.42 (1H), 6.99 (1H), 7.03 (1H), 7.13 (1H), 7.47 (1H), 7.56-7.64 (4H) ppm.

Example 74

N-cyclopropyl-3-hydroxy-4-{6-(phenylsulfanyl)-8-[(3,3,3-trifluoropropyl)amino]imidazo[1,2-b]pyridazin-3-yl}benzamide

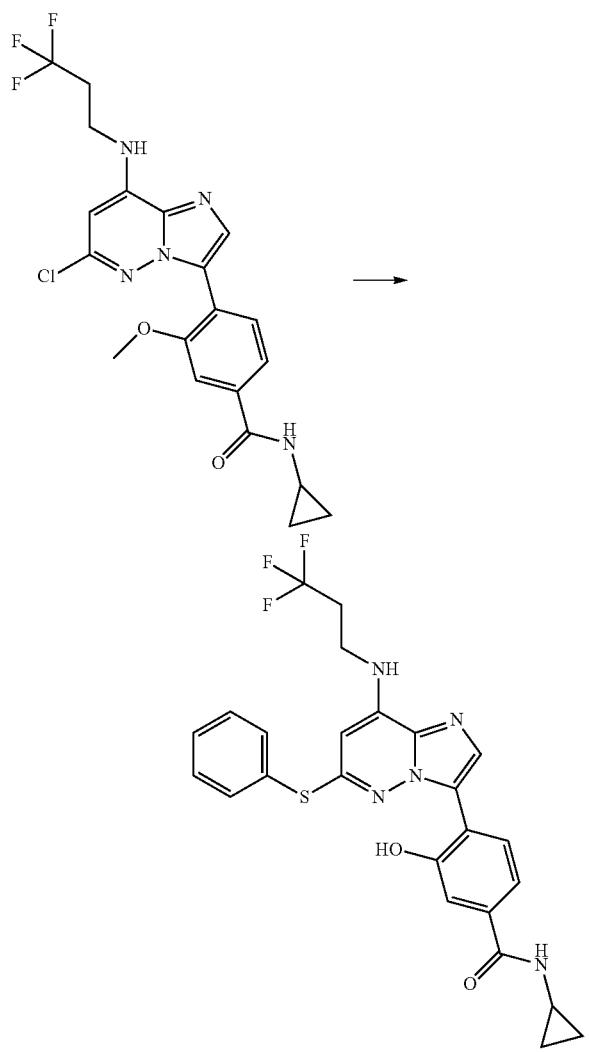

29.5 mg (67 µmol) 4-{6-chloro-8-[(3,3,3-trifluoropropyl)amino]imidazo[1,2-b]pyridazin-3-yl}-N-cyclopropyl-3-methoxybenzamide which was prepared according to intermediate example 52a were transformed in analogy to example 51 using benzenethiol to give after working up and purification 19 mg (52%) of the title compound.

¹H-NMR (CDCl₃): δ=0.63 (2H), 0.88 (2H), 2.44 (2H), 2.92 (1H), 3.55 (2H), 5.81 (1H), 6.12 (1H), 6.22 (1H), 7.22 (1H), 7.33 (1H), 7.41-7.54 (4H), 7.58-7.66 (3H), 9.01 (1H) ppm.

Example 75

N-cyclopropyl-4-{6-(3-fluorophenoxy)-8-[(2-hydroxy-2-methylpropyl)amino]imidazo[1,2-b]pyridazin-3-yl}-2-methylbenzamide

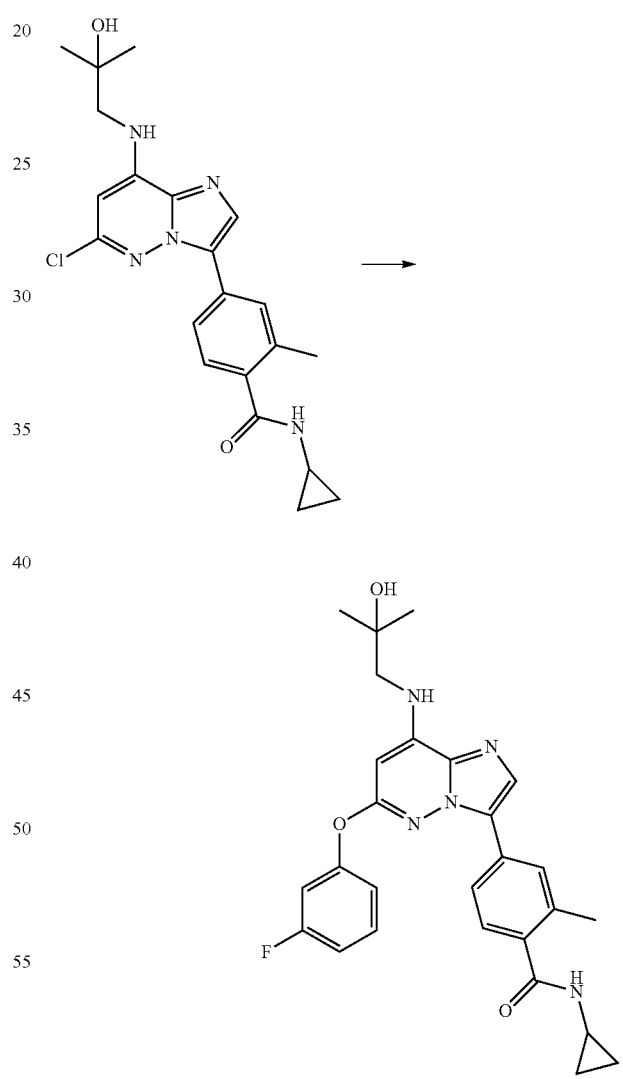

50 mg (121 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-fluorophenol to give after working up and purification 13.9 mg (22%) of the title compound.

207

¹H-NMR (DMSO-d6): δ=0.47 (2H), 0.63 (2H), 1.16 (6H), 2.14 (3H), 2.76 (1H), 3.27 (2H), 4.74 (1H), 6.18 (1H), 7.02 (1H), 7.08-7.14 (2H), 7.16 (1H), 7.24 (1H), 7.47 (1H), 7.67 (1H), 7.77 (1H), 7.92 (1H), 8.21 (1H) ppm.

Example 76

N-cyclopropyl-4-{8-[(2-hydroxy-2-methylpropyl)amino]-6-phenoxyimidazo[1,2-b]pyridazin-3-yl}-2-methylbenzamide

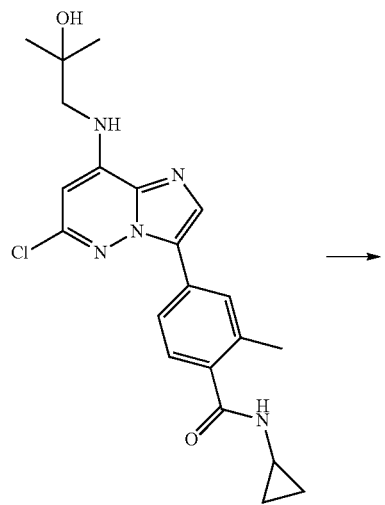

50 mg (121 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using phenol to give after working up and purification 15.1 mg (25%) of the title compound.

208

¹H-NMR (CDCl₃): δ=0.59 (2H), 0.86 (2H), 1.38 (6H), 2.26 (3H), 2.86 (1H), 3.29 (2H), 3.74 (1H), 5.91 (1H), 6.02 (1H), 6.42 (1H), 7.19 (2H), 7.23 (2H), 7.41 (2H), 7.57 (1H), 7.66 (1H), 7.70 (1H) ppm.

Example 77

N-cyclopropyl-2-methyl-4-{6-phenoxy-8-[(3,3,3-trifluoropropyl)amino]imidazo[1,2-b]pyridazin-3-yl}benzamide

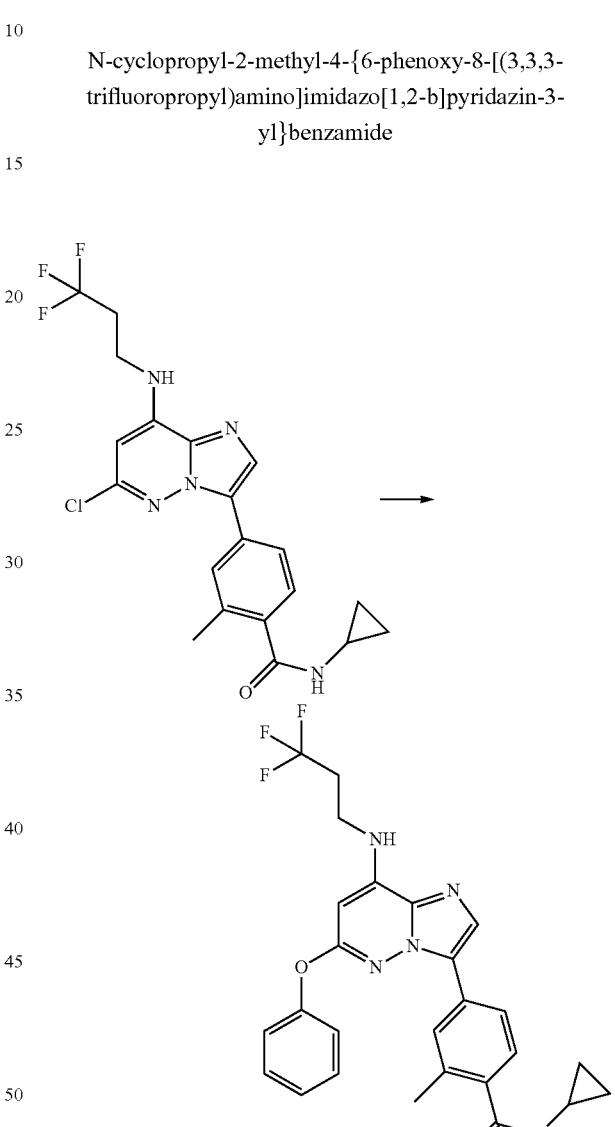

50 mg (114 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using phenol to give after working up and purification 5.7 mg (9%) of the title compound.

¹H-NMR (CDCl₃): δ=0.60 (2H), 0.87 (2H), 2.29 (3H), 2.57 (2H), 2.88 (1H), 1.97 (2H), 5.84 (1H), 5.90 (1H), 5.97 (1H), 7.20-7.30 (4H), 7.44 (2H), 7.60 (1H), 7.73 (1H), 7.74 (1H) ppm.

Example 78

4-{8-[(2-Amino-2-methylpropyl)amino]-6-[(3-fluorophenyl)sulfanyl]imidazo[1,2-b]pyridazin-3-yl}-N-cyclopropyl-2-methylbenzamide

Example 79

N-cyclopropyl-4-{6-[(3-fluoro-5-methylphenyl)sulfanyl]-8-[(3,3,3-trifluoropropyl)amino]imidazo[1,2-b]pyridazin-3-yl}-2-methylbenzamide

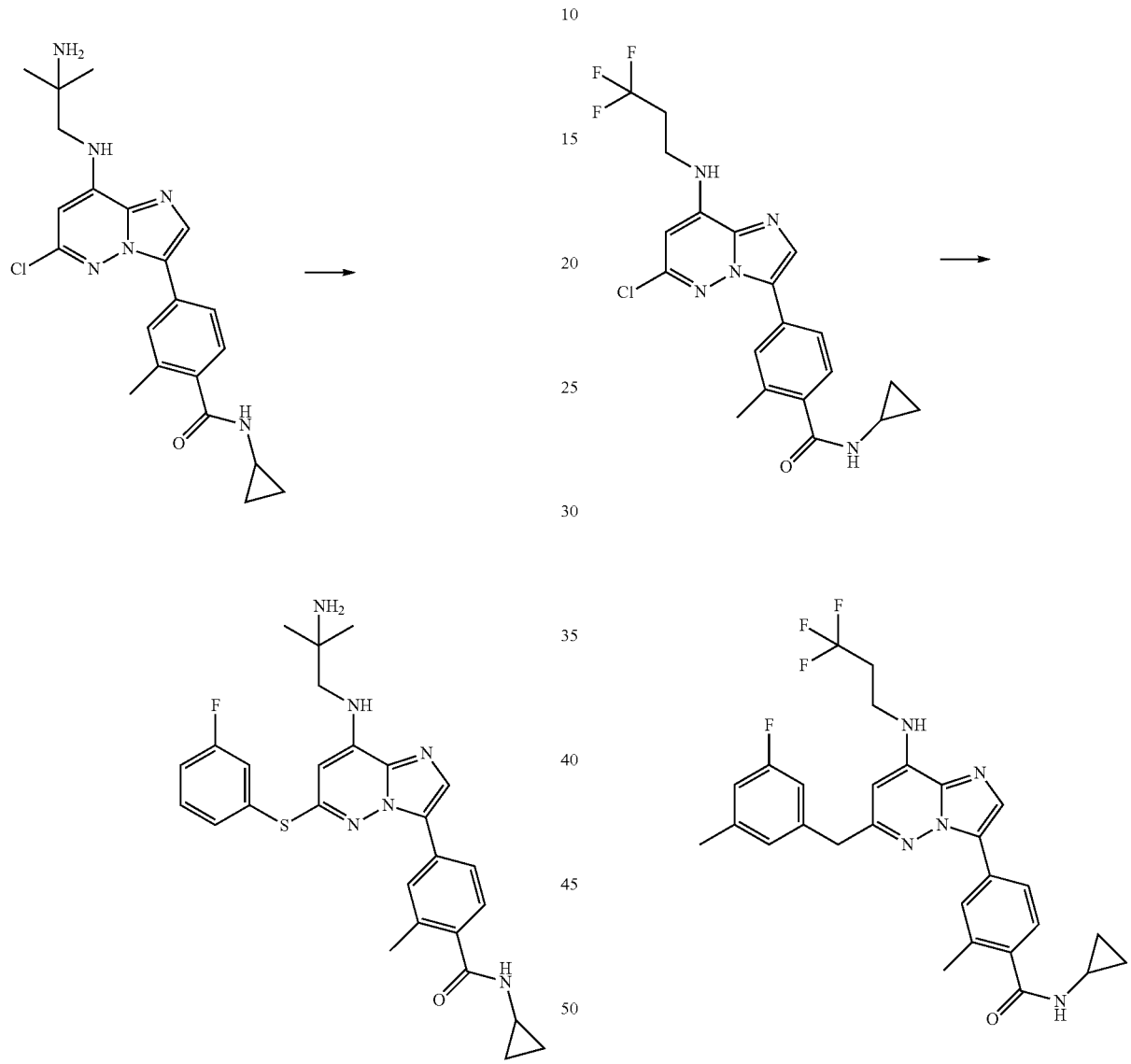

250 mg (605 µmol) 4-{8-[(2-amino-2-methylpropyl)amino]-6-chloroimidazo[1,2-b]pyridazin-3-yl}-N-cyclopropyl-2-methylbenzamide which was prepared according to intermediate example 57a were transformed in analogy to example 51 using 3-fluorobenzenethiol to give after working up and purification 9.8 mg (3%) of the title compound.

$^1$H-NMR (CDCl$_3$): δ=0.63 (2H), 0.89 (2H), 1.24 (6H), 1.80 (2H), 2.39 (3H), 2.91 (1H), 3.14 (2H), 5.91 (1H), 5.97 (1H), 6.34 (1H), 7.12 (1H), 7.22 (1H), 7.32-7.42 (3H), 7.62 (1H), 7.64 (1H), 7.69 (1H) ppm.

50 mg (114 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3-fluoro-5-methylbenzenethiol to give after working up and purification 6.9 mg (11%) of the title compound.

$^1$H-NMR (CDCl$_3$+CD$_3$OD): δ=0.61 (2H), 0.88 (2H), 2.35 (3H), 2.39 (3H), 2.48 (2H), 2.89 (1H), 3.54 (2H), 5.89 (1H), 6.07 (1H), 6.46 (1H), 6.96 (1H), 7.17 (1H), 7.21 (1H), 7.23 (1H), 7.63 (1H), 7.66 (1H), 7.68 (1H) ppm.

211
Example 80

N-cyclopropyl-4-{6-(3-fluorophenoxy)-8-[(3,3,3-trifluoropropyl)amino]imidazo[1,2-b]pyridazin-3-yl}-2-methylbenzamide

212
Example 81

N-cyclopropyl-4-{6-(2-fluoro-5-methylphenoxy)-8-[(2-hydroxy-2-methylpropyl)amino]imidazo[1,2-b]pyridazin-3-yl}-2-methylbenzamide

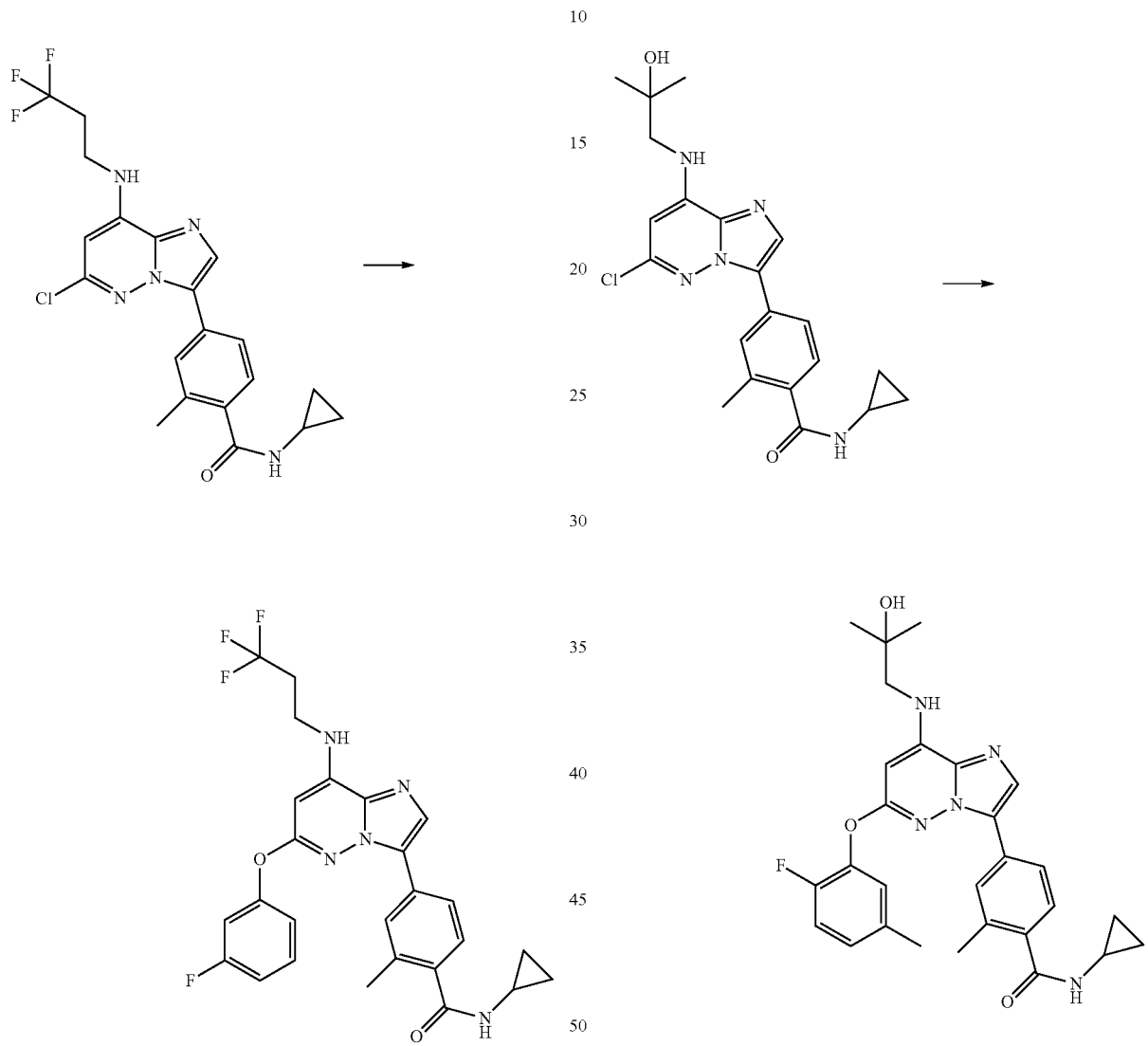

50 mg (114 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3-fluorophenol to give after working up and purification 9.1 mg (15%) of the title compound.

$^1$H-NMR (CDCl$_3$): δ=0.60 (2H), 0.87 (2H), 2.32 (3H), 2.57 (2H), 2.89 (1H), 3.67 (2H), 5.87 (1H), 5.89 (1H), 6.12 (1H), 6.94-7.08 (3H), 7.25 (1H), 7.39 (1H), 7.60 (1H), 7.72 (2H) ppm.

50 mg (121 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2-fluoro-5-methylphenol to give after working up and purification 5.2 mg (8%) of the title compound.

$^1$H-NMR (DMSO-d6): δ=0.46 (2H), 0.63 (2H), 1.17 (6H), 2.09 (3H), 2.29 (3H), 2.76 (1H), 3.29 (2H), 4.75 (1H), 6.23 (1H), 7.02 (1H), 7.10-7.16 (2H), 7.23 (1H), 7.27 (1H), 7.62 (1H), 7.70 (1H), 7.92 (1H), 8.21 (1H) ppm.

Example 82

4-{6-(3-Cyanophenoxy)-8-[(2-hydroxy-2-methylpropyl)amino]imidazo[1,2-b]pyridazin-3-yl}-N-cyclopropyl-2-methylbenzamide

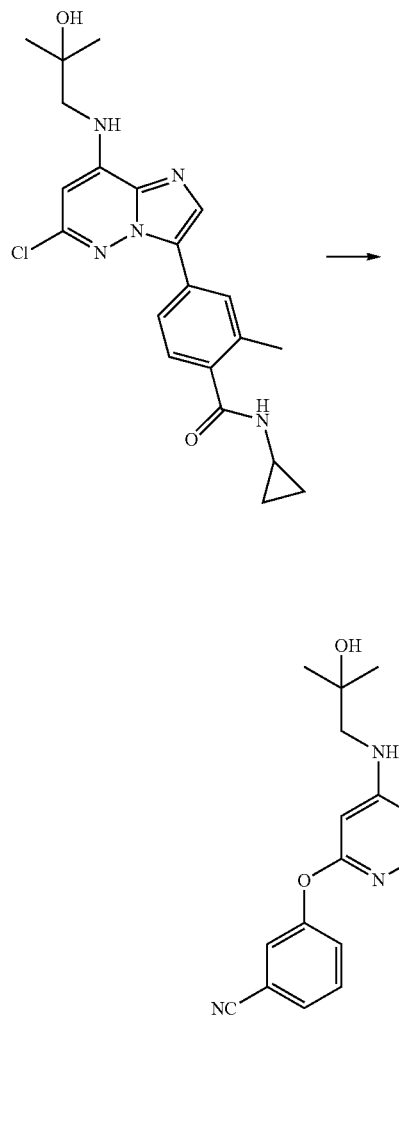

Example 83

N-cyclopropyl-4-{6-[(3-fluorophenyl)sulfonyl]-8-[(3,3,3-trifluoropropyl)amino]imidazo[1,2-b]pyridazin-3-yl}-2-methylbenzamide (A) and (RS)—N-cyclopropyl-4-{6-[(3-fluorophenyl)sulfinyl]-8-[(3,3,3-trifluoropropyl)amino]imidazo[1,2-b]pyridazin-3-yl}-2-methylbenzamide (B)

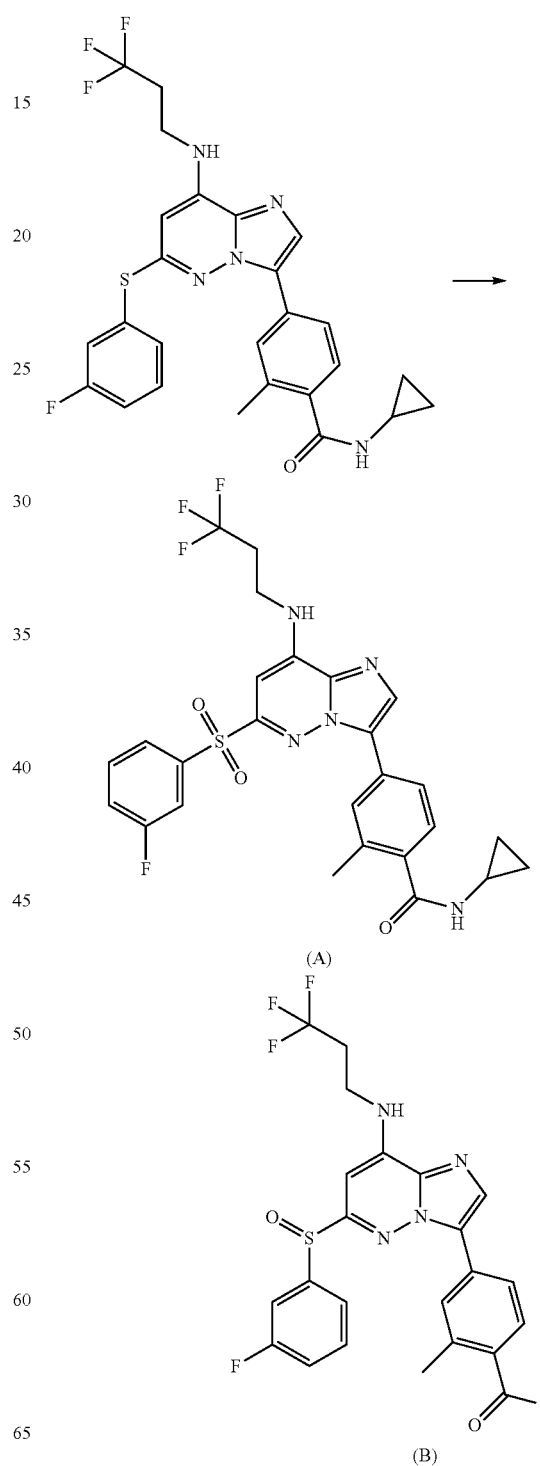

50 mg (121 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-hydroxybenzonitrile to give after working up and purification 5.8 mg (9%) of the title compound.

$^1$H-NMR (CDCl$_3$+CD$_3$OD): δ=0.63 (2H), 0.86 (2H), 1.42 (6H), 2.35 (3H), 2.90 (1H), 3.32 (2H), 5.88 (1H), 6.26 (1H), 6.66 (1H), 7.30 (1H), 7.46 (1H), 7.49-7.60 (4H), 7.65 (1H), 7.72 (1H) ppm.

To a solution of 50 mg (121 µmol) N-cyclopropyl-4-{6-[(3-fluorophenyl) sulfanyl]-8-[(3,3,3-trifluoropropyl)amino]imidazo[1,2-b]pyridazin-3-yl}-2-methylbenzamide, which was prepared according to intermediate example 209 in 1.0 mL dichloromethane were added 0.71 mg methyl(trioxo)rhenium, 1.77 mg isonicotinonitrile and 58 µL aqueous hydrogen peroxide (30%). The mixture was stirred for two days at 23° C., poured into sodium thiosulfate solution and extracted with dichloromethane. The organic phase was dried over sodium sulfate. After filtration and removal of solvent the residue was purified by chromatography to give 14.9 mg (53%) of the title compound A and 4.5 mg (8%) of the title compound B.

$^1$H-NMR (CDCl$_3$+CD$_3$OD) of A: δ=0.65 (2H), 0.90 (2H), 2.47 (3H), 2.59 (2H), 2.92 (1H), 3.75 (2H), 6.08 (1H), 6.76 (1H), 6.77 (1H), 7.33 (1H), 7.38 (1H), 7.53-7.65 (3H), 7.81 (1H), 7.82 (1H), 7.88 (1H) ppm.

$^1$H-NMR (CDCl$_3$) of B: δ=0.65 (2H), 0.92 (2H), 2.55 (5H), 2.94 (1H), 3.73 (2H), 5.98 (1H), 6.37 (1H), 6.60 (1H), 7.17 (1H), 7.46 (1H), 7.50 (1H), 7.56 (1H), 7.60 (1H), 7.74-7.84 (3H) ppm.

Example 84

N-cyclopropyl-2-methyl-4-{6-(phenylsulfanyl)-8-[(3,3,3-trifluoropropyl)amino]imidazo[1,2-b]pyridazin-3-yl}benzenecarbothioamide

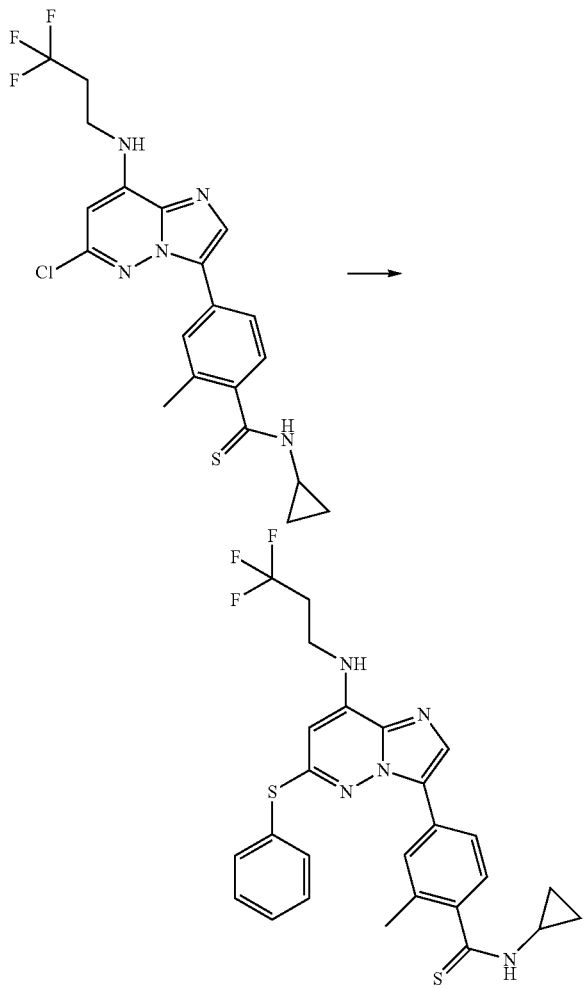

59.1 mg (130 µmol) 4-{6-chloro-8-[(3,3,3-trifluoropropyl)amino]imidazo[1,2-b]pyridazin-3-yl}-N-cyclopropyl-2-methylbenzenecarbothioamide which was prepared according to intermediate example 84a were transformed in analogy to example 51 using benzenethiol to give after working up and purification 7.1 mg (9%) of the title compound.

$^1$H-NMR (CDCl$_3$): δ=0.75 (2H), 1.05 (2H), 2.30 (3H), 2.47 (2H), 3.41 (1H), 3.56 (2H), 5.87 (2H), 7.16 (1H), 7.27 (1H), 7.41-7.50 (3H), 7.57-7.71 (5H) ppm.

Intermediate Example 84a

4-{6-Chloro-8-[(3,3,3-trifluoropropyl)amino]imidazo[1,2-b]pyridazin-3-yl}-N-cyclopropyl-2-methyl-benzenecarbothioamide

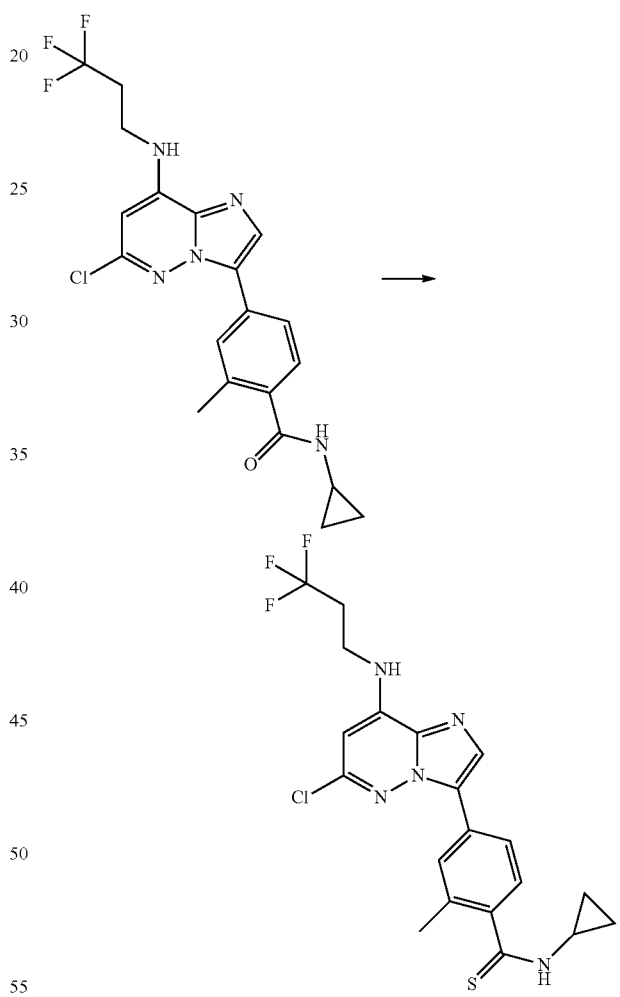

A mixture comprising 100 mg (228 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a, 25.4 mg phosphorus pentasulfide and 0.47 mL pyridine were heated at 115° C. for 4 hours. Water and brine were added and the mixture was extracted several times with ethyl acetate. The combined organic layers were dried over sodium sulfate. After filtration and removal of the solvent the residue was purified by chromatography to give 65.7 mg (63%) of the title compound.

217

Example 85

4-{6-(3-Chlorophenoxy)-8-[(2-hydroxy-2-methyl-propyl)amino]imidazo[1,2-b]pyridazin-3-yl}-N-cyclopropyl-2-methylbenzamide

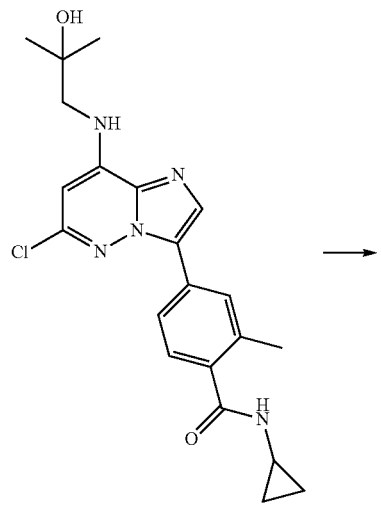

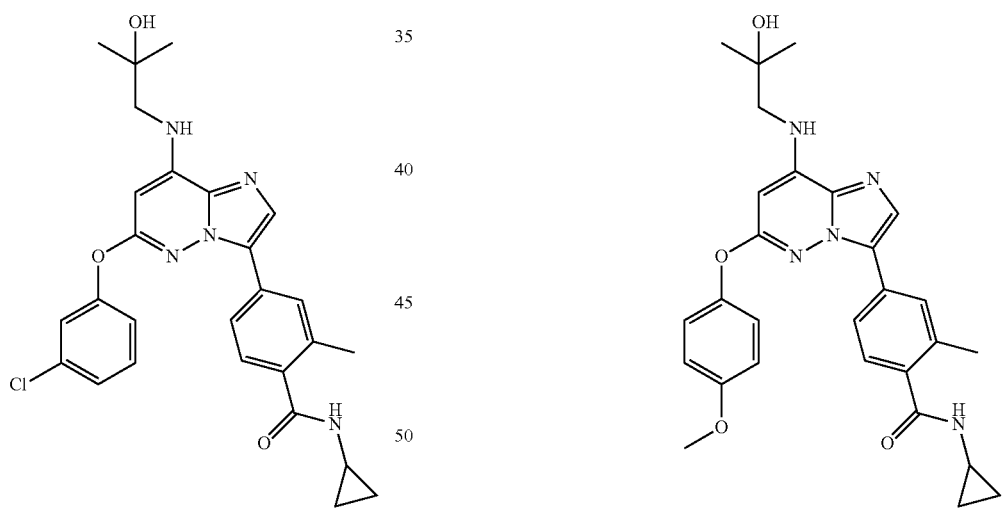

50 mg (121 μmol) 4-{6-Chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 51 using 3-chlorophenol to give after working up and purification 9.3 mg (14%) of the title compound.

$^1$H-NMR (DMSO-d6): 0.3=0.47 (2H), 0.63 (2H), 1.16 (6H), 2.14 (3H), 2.77 (1H), 3.29 (2H), 4.74 (1H), 6.18 (1H), 7.03 (1H), 7.17 (1H), 7.25 (1H), 7.33 (1H), 7.44 (1H), 7.47 (1H), 7.67 (1H), 7.74 (1H), 7.93 (1H), 8.22 (1H) ppm.

218

Example 86

N-cyclopropyl-4-{8-[(2-hydroxy-2-methylpropyl)amino]-6-(4-methoxyphenoxy) imidazo[1,2-b]pyridazin-3-yl}-2-methylbenzamide

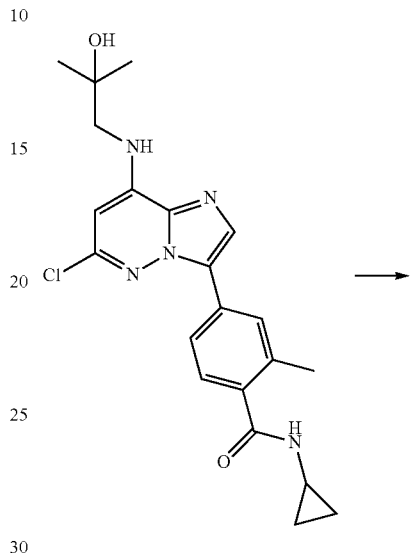

50 mg (121 μmol) 4-{6-Chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 51 using 4-methoxyphenol to give after working up and purification 22.5 mg (35%) of the title compound.

$^1$H-NMR (DMSO-d6): δ=0.47 (2H), 0.63 (2H), 1.16 (6H), 2.11 (3H), 2.77 (1H), 3.27 (2H), 3.75 (3H), 4.75 (1H), 6.13 (1H), 6.91 (1H), 6.98 (2H), 7.15 (1H), 7.18 (2H), 7.65 (1H), 7.77 (1H), 7.91 (1H), 8.21 (1H) ppm.

Example 87

N-cyclopropyl-4-{6-(3-fluoro-5-methylphenoxy)-8-[(2-hydroxy-2-methylpropyl)amino]imidazo[1,2-b]pyridazin-3-yl}-2-methylbenzamide

Example 88

N-cyclopropyl-4-{6-(3-fluoro-5-methylphenoxy)-8-[(3,3,3-trifluoropropyl)amino]imidazo[1,2-b]pyridazin-3-yl}-2-methylbenzamide

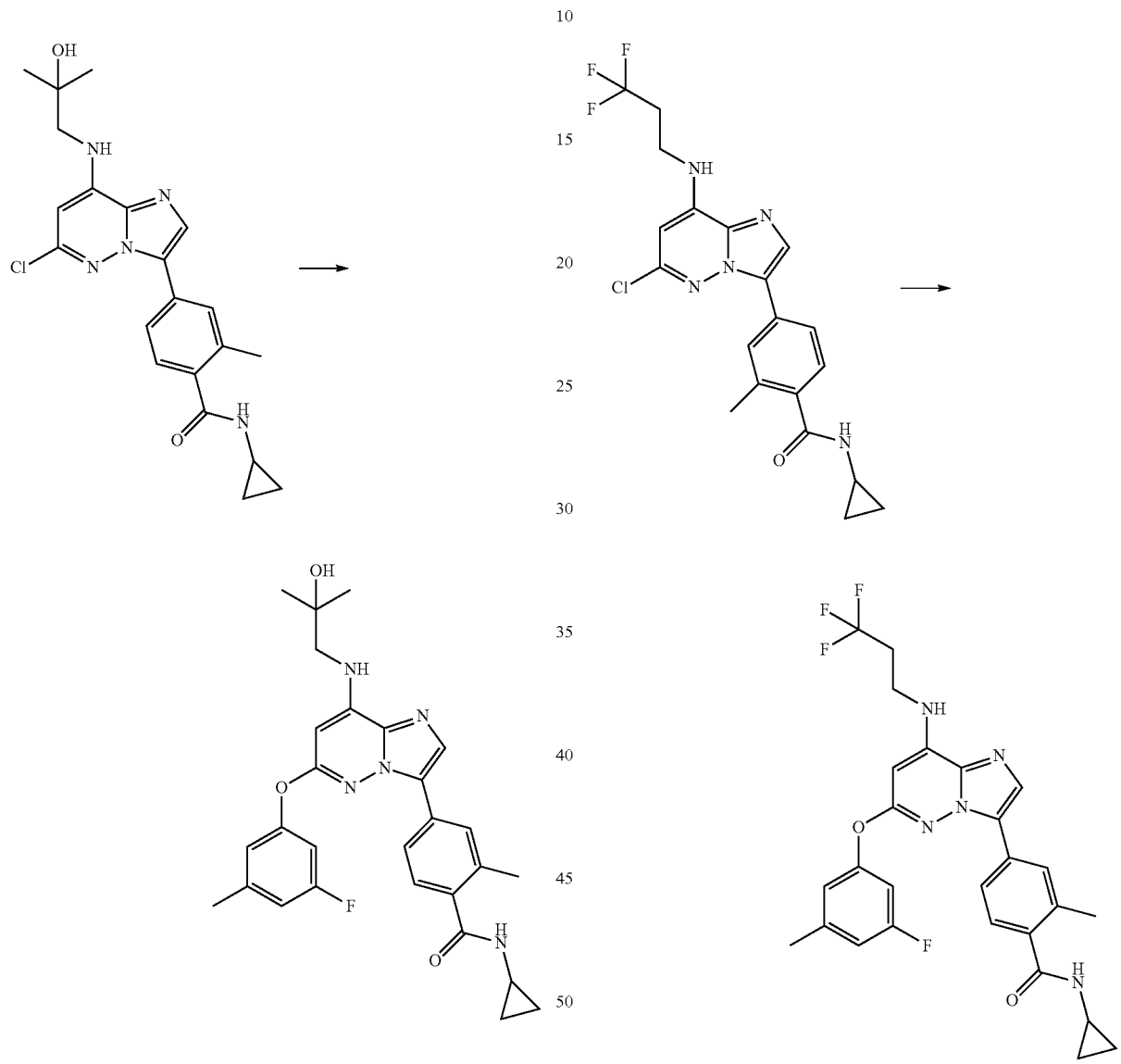

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-fluoro-5-methylphenol to give after working up and purification 12.0 mg (19%) of the title compound.

$^1$H-NMR (DMSO-d6): δ=0.47 (2H), 0.63 (2H), 1.15 (6H), 2.15 (3H), 2.31 (3H), 2.77 (1H), 3.27 (2H), 4.73 (1H), 6.16 (1H), 6.90-7.06 (4H), 7.17 (1H), 7.69 (1H), 7.78 (1H), 7.92 (1H), 8.22 (1H) ppm.

50 mg (114 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3-fluoro-5-methylphenol to give after working up and purification 7.6 mg (12%) of the title compound.

$^1$H-NMR (DMSO-d6): δ=0.47 (2H), 0.63 (2H), 2.15 (3H), 2.32 (3H), 2.67 (2H), 2.77 (1H), 3.59 (2H), 6.11 (1H), 6.95 (2H), 7.03 (1H), 7.17 (1H), 7.65-7.75 (2H), 7.78 (1H), 7.93 (1H), 8.22 (1H) ppm.

221
Example 89

N-cyclopropyl-4-{6-[(3-fluorophenyl)sulfanyl]-8-[(2-hydroxy-2-methylpropyl)amino]imidazo[1,2-b]pyridazin-3-yl}-2-methylbenzamide

222
Example 90

4-{6-(4-Chlorophenoxy)-8-[(2-hydroxy-2-methylpropyl)amino]imidazo[1,2-b]pyridazin-3-yl}-N-cyclopropyl-2-methylbenzamide

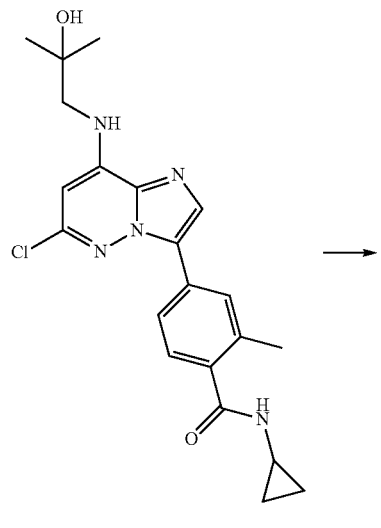
→

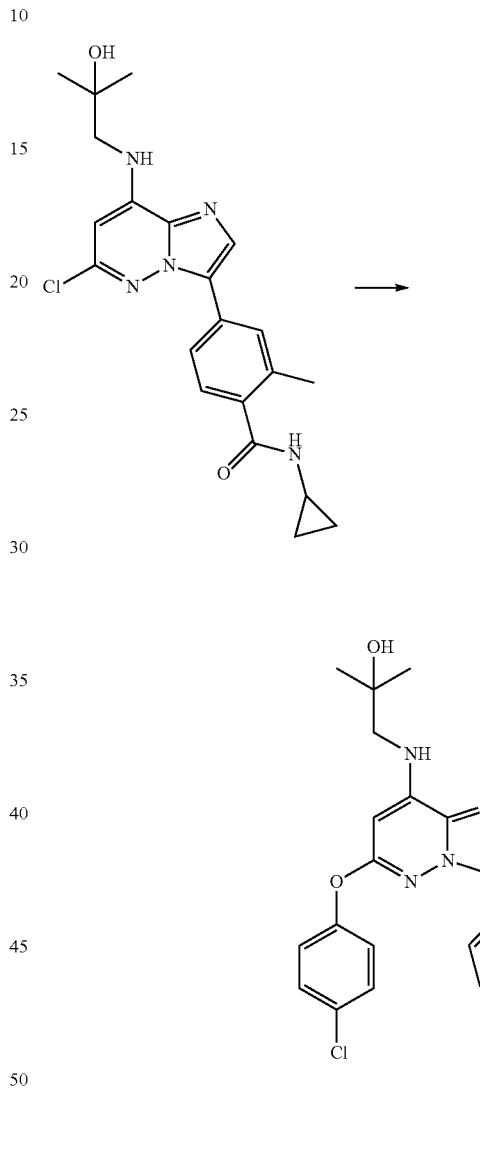

300 mg (725 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-fluorobenzenethiol to give after working up and purification 27.9 mg (7%) of the title compound.

$^1$H-NMR (DMSO-d6): δ=0.49 (2H), 0.65 (2H), 1.12 (6H), 2.20 (3H), 2.79 (1H), 3.23 (2H), 4.71 (1H), 6.29 (1H), 7.04 (1H), 7.12 (1H), 7.33 (1H), 7.43 (1H), 7.46-7.53 (2H), 7.66 (1H), 7.71 (1H), 7.94 (1H), 8.23 (1H) ppm.

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 4-chlorophenol to give after working up and purification 14.5 mg (23%) of the title compound.

$^1$H-NMR (DMSO-d6): δ=0.47 (2H), 0.64 (2H), 1.16 (6H), 2.13 (3H), 2.77 (1H), 3.28 (2H), 4.74 (1H), 6.18 (1H), 7.00 (1H), 7.17 (1H), 7.30 (2H), 7.50 (2H), 7.64 (1H), 7.73 (1H), 7.92 (1H), 8.22 (1H) ppm.

Example 91

4-{6-(3-Chloro-4-fluorophenoxy)-8-[(2-hydroxy-2-methylpropyl)amino]imidazo[1,2-b]pyridazin-3-yl}-N-cyclopropyl-2-methylbenzamide

Example 92

N-cyclopropyl-4-{6-(2,3-difluorophenoxy)-8-[(2-hydroxy-2-methylpropyl)amino]imidazo[1,2-b]pyridazin-3-yl}-2-methylbenzamide

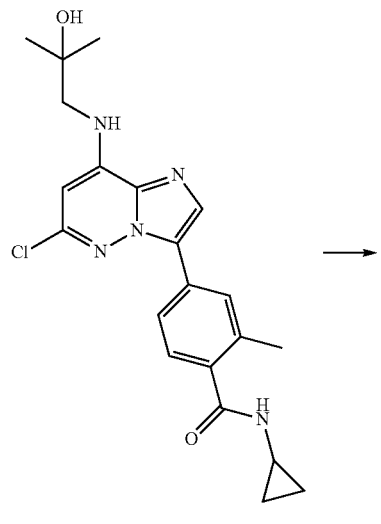

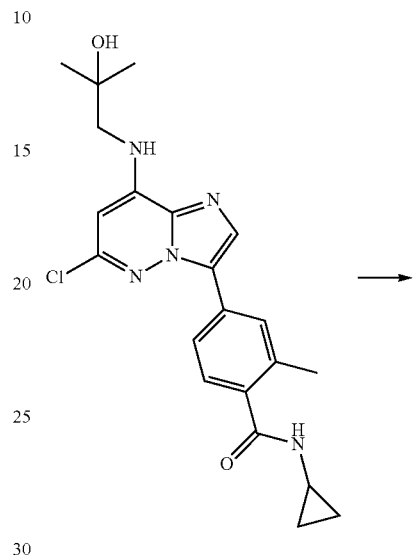

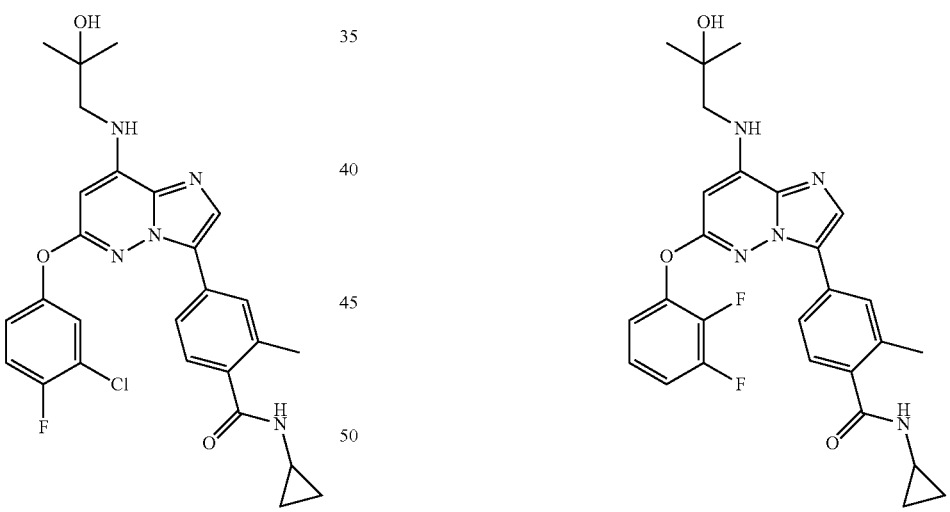

50 mg (121 μmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-chloro-4-fluorophenol to give after working up and purification 16.2 mg (24%) of the title compound.

$^1$H-NMR (DMSO-d6): δ=0.47 (2H), 0.64 (2H), 1.16 (6H), 2.13 (3H), 2.77 (1H), 3.28 (2H), 4.74 (1H), 6.18 (1H), 7.02 (1H), 7.18 (1H), 7.32 (1H), 7.51 (1H), 7.66 (2H), 7.72 (1H), 7.93 (1H), 8.22 (1H) ppm.

50 mg (121 μmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2,3-difluorophenol to give after working up and purification 5.8 mg (9%) of the title compound.

$^1$H-NMR (CDCl$_3$+CD$_3$OD): δ=0.59 (2H), 0.85 (2H), 1.38 (6H), 2.24 (3H), 2.86 (1H), 3.31 (2H), 5.98 (1H), 6.16 (1H), 6.53 (1H), 7.02-7.14 (3H), 7.17 (1H), 7.47 (1H), 7.61 (2H), ppm.

225

Example 93

N-cyclopropyl-4-{6-(2-fluorophenoxy)-8-[(2-hydroxy-2-methylpropyl)amino]imidazo[1,2-b]pyridazin-3-yl}-2-methylbenzamide

226

Example 94

N-cyclopropyl-4-{8-[(2-hydroxy-2-methylpropyl)amino]-6-(3-isopropylphenoxy) imidazo[1,2-b]pyridazin-3-yl}-2-methylbenzamide

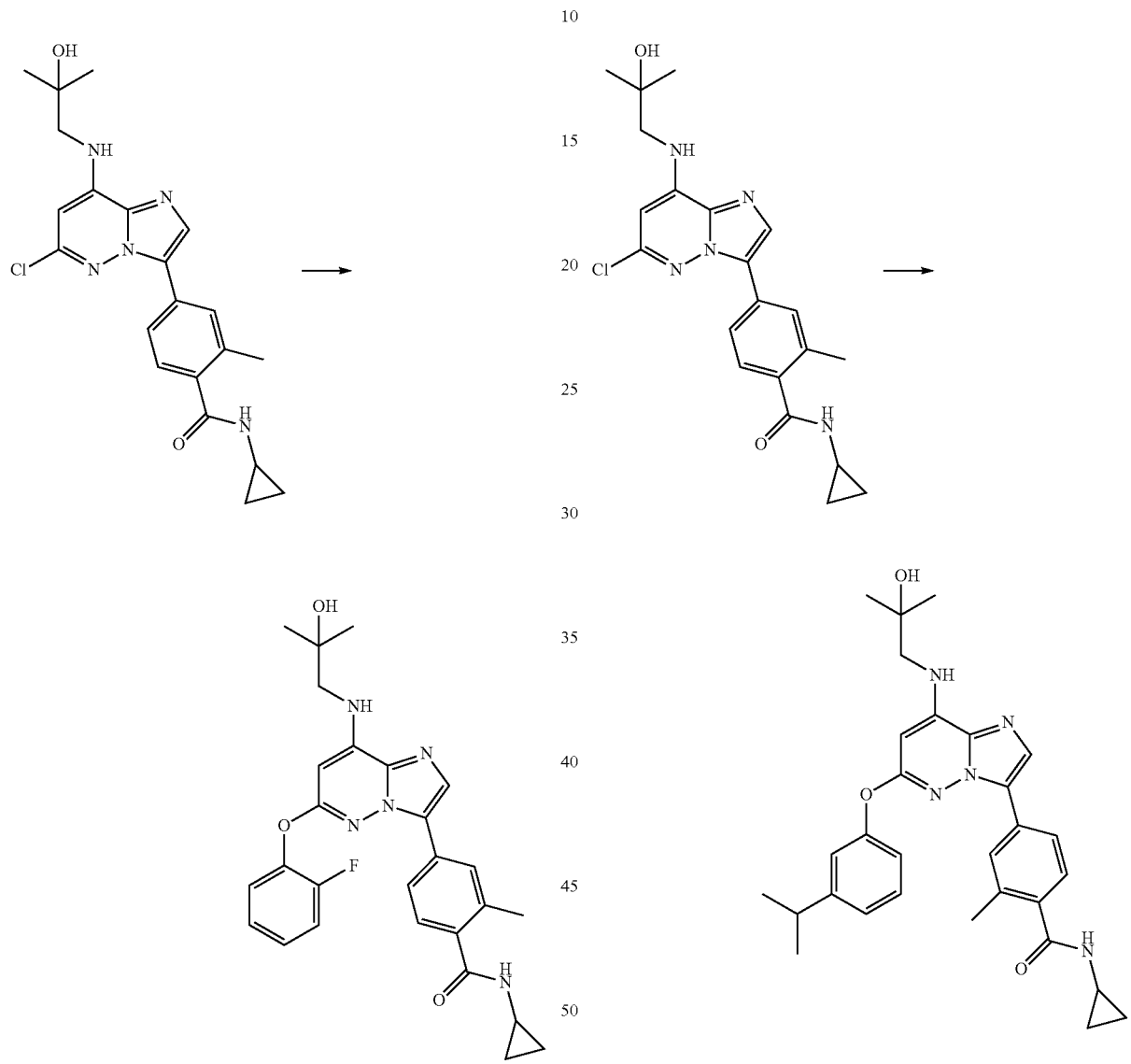

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2-fluorophenol to give after working up and purification 4.2 mg (7%) of the title compound.

$^1$H-NMR (DMSO-d6): 0.3=0.46 (2H), 0.63 (2H), 1.17 (6H), 2.08 (3H), 2.46 (2H), 2.76 (1H), 4.75 (1H), 6.25 (1H), 7.03 (1H), 7.11 (1H), 7.24-7.45 (4H), 7.59 (1H), 7.67 (1H), 7.92 (1H), 8.21 (1H) ppm.

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3-isopropylphenol to give after working up and purification 9.0 mg (14%) of the title compound.

$^1$H-NMR (CDCl$_3$+CD$_3$OD): δ=0.58 (2H), 0.84 (2H), 1.22 (6H), 1.36 (6H), 2.24 (3H), 2.33 (1H), 2.85 (1H), 2.89 (1H), 3.27 (2H), 5.88 (1H), 6.15 (1H), 6.44 (1H), 7.02 (1H), 7.03 (1H), 7.10 (1H), 7.17 (1H), 7.31 (1H), 7.59 (1H), 7.64 (1H), 7.68 (1H) ppm.

Example 95

4-{6-(4-Chloro-3-fluorophenoxy)-8-[(2-hydroxy-2-methylpropyl)amino]imidazo[1,2-b]pyridazin-3-yl}-N-cyclopropyl-2-methylbenzamide

Example 96

N-cyclopropyl-4-{6-(3,5-dimethylphenoxy)-8-[(2-hydroxy-2-methylpropyl)amino]imidazo[1,2-b]pyridazin-3-yl}-2-methylbenzamide

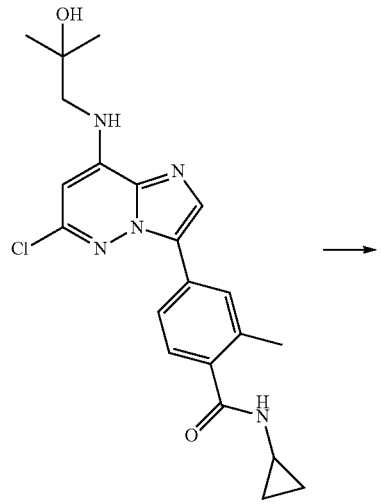

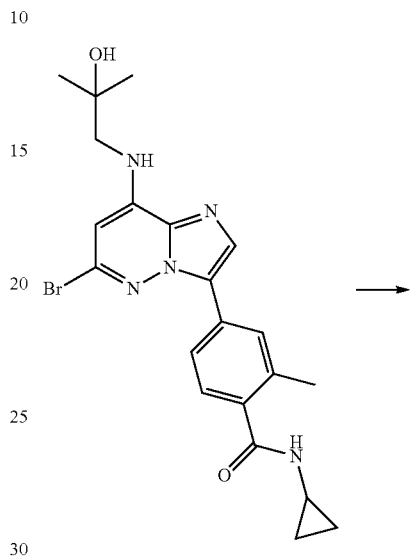

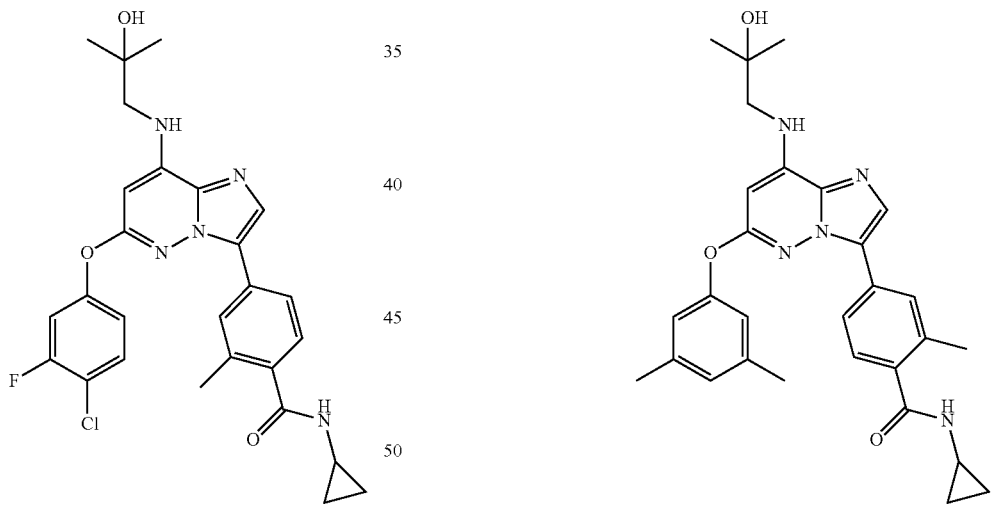

50 mg (121 µmol) 4-{6-Chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 4-chloro-3-fluorophenol to give after working up and purification 4.0 mg (6%) of the title compound.

$^{1}$H-NMR (CDCl$_{3}$+CD$_{3}$OD): δ=0.60 (2H), 086 (2H), 1.37 (6H), 2.31 (3H), 2.34 (1H), 2.87 (1H), 3.29 (2H), 5.89 (1H), 6.09 (1H), 6.57 (1H), 6.98 (1H), 7.09 (1H), 7.15 (1H), 7.42 (1H), 7.55 (1H), 7.67 (2H) ppm.

50 mg (109 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3,5-dimethylphenol to give after working up and purification 14.6 mg (27%) of the title compound.

$^{1}$H-NMR (CDCl$_{3}$): δ=0.61 (2H), 0.87 (2H), 1.45 (6H), 2.28 (3H), 2.33 (6H), 2.89 (1H), 3.31 (2H), 3.83 (1H), 5.86 (1H), 5.92 (1H), 6.59 (1H), 6.83 (2H), 6.87 (1H), 7.21 (1H), 7.63 (1H), 7.65 (1H), 7.73 (1H) ppm.

Intermediate Example 96a

4-{6-bromo-8-[(2-hydroxy-2-methylpropyl)amino]imidazo[1,2-b]pyridazin-3-yl}-N-cyclopropyl-2-methylbenzamide

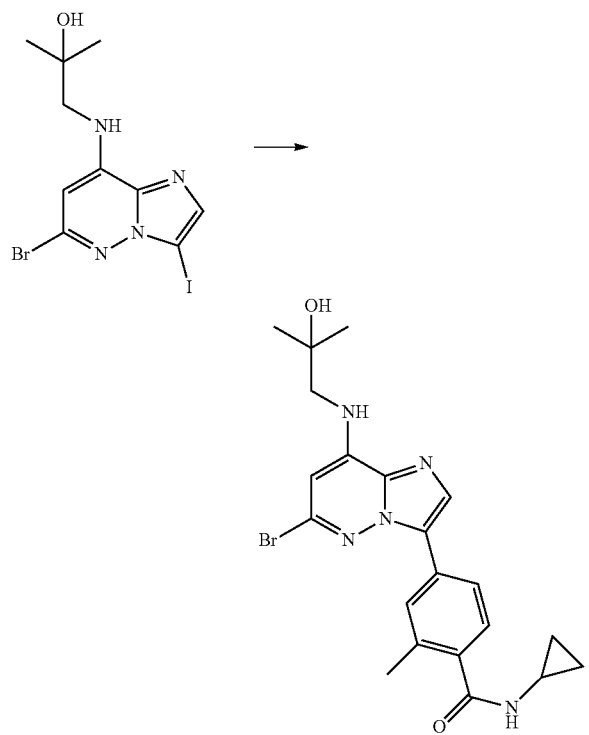

809 mg (1.97 mmol) 1-[(6-bromo-3-iodoimidazo[1,2-b]pyridazin-8-yl)amino]-2-methylpropan-2-ol which was prepared according to intermediate example 96b were transformed in analogy to intermediate example 1a using N-cyclopropyl-2-methyl-4-(4,4,5,5-tetramethyl-1,3,2-dioxaborolan-2-yl)benzamide to give after working up and purification 659 mg (73%) of the title compound.

Intermediate Example 96b

1-[(6-bromo-3-iodoimidazo[1,2-b]pyridazin-8-yl)amino]-2-methylpropan-2-ol

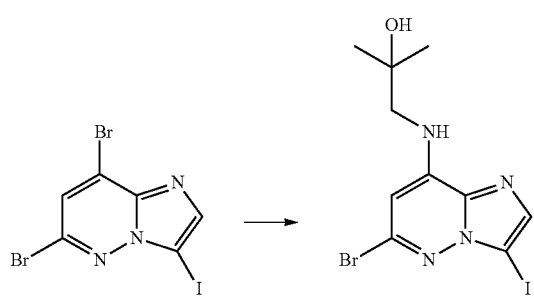 [SMILES: Brc1cc(Br)c2ncc(I)n2n1 ; CC(C)(O)CNc1cc(Br)nn2c(I)cnc12]

1.0 g (2.48 mmol) 6,8-dibromo-3-iodoimidazo[1,2-b]pyridazine which was prepared according to intermediate example 96c were transformed in analogy to intermediate example 1b using 1-amino-2-methylpropan-2-ol to give after working up and purification 915 mg (90%) of the title compound.

Intermediate Example 96c 6,8-dibromo-3-iodoimidazo[1,2-b]pyridazine

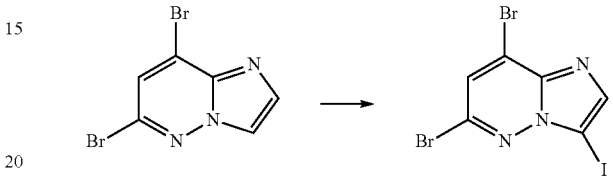

A mixture comprising 3.64 g (10.5 mmol) 6,8-dibromoimidazo[1,2-b]pyridazine which was prepared according to intermediate example 96d, 2.8 g N-iodosuccinimide, 72.6 mL N,N-dimethylformamide was heated at 60° C. for 3 hours. 1.4 g N-iodosuccinimide were added and heating was continued for additional 4 hours. Most of the solvent was removed, water was added and the mixture was extracted with dichloromethane. The organic phase was washed with water, sodium thiosulfate solution and dried over sodium sulfate. After filtration and removal of solvent the residue was purified by chromatography to give 3.64 g (86%) of the title compound.

Intermediate Example 96d 6,8-dibromoimidazo[1,2-b]pyridazine

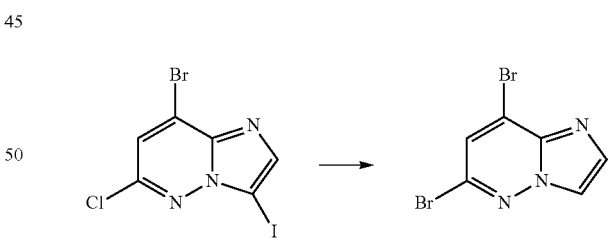

A mixture of 5.0 (14.0 mmol) 8-bromo-6-chloro-3-iodoimidazo[1,2-b]pyridazine which was prepared according to intermediate example 1c, 30 mL of hydrogen bromide solution in acetic acid (33%) was stirred at 120° C. for 1 hour under microwave irradiation. The mixture was poured into water and extracted with dichloromethane. The organic phase was washed with sodium thiosulfate and sodium hydrogencarbonate solution and dried over sodium sulfate. After filtration and removal of solvent the residue was purified by chromatography to give 3.0 g (78%) of the title compound.

Example 97

N-cyclopropyl-4-{8-[(2-hydroxy-2-methylpropyl)amino]-6-(3-methylphenoxy)imidazo[1,2-b]pyridazin-3-yl}-2-methylbenzamide

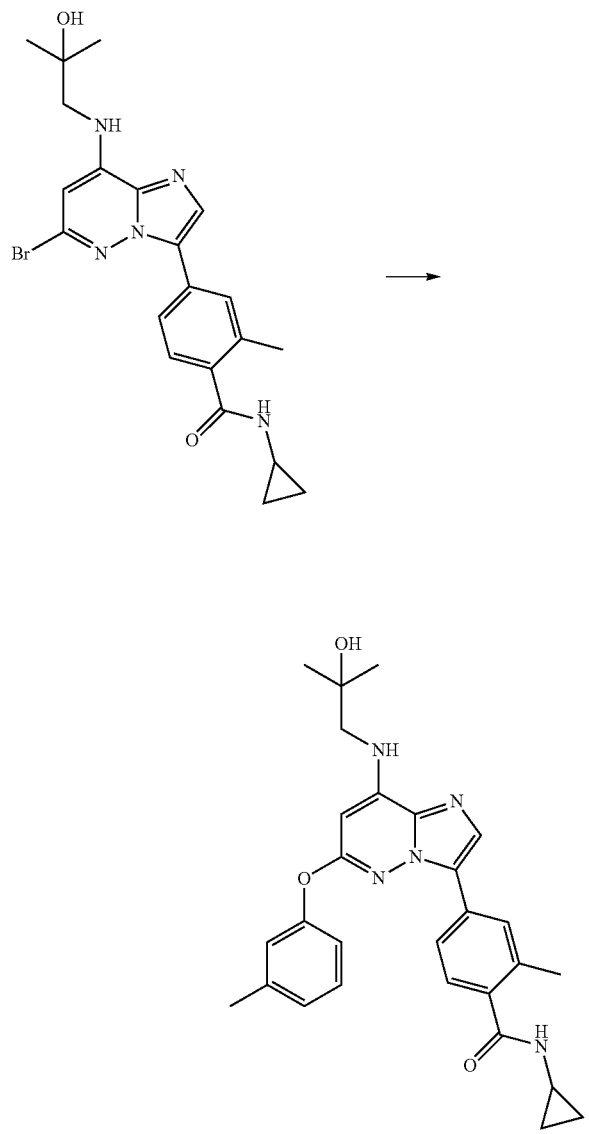 [SMILES: Cc1cc(-c2cnc3c(NCC(C)(C)O)cc(Br)nn23)ccc1C(=O)NC1CC1 ; Cc1cccc(Oc2cc(NCC(C)(C)O)c3ncc(-c4ccc(C(=O)NC5CC5)c(C)c4)n3n2)c1]

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3-methylphenol to give after working up and purification 17.1 mg (32%) of the title compound.

$^1$H-NMR (CDCl$_3$): δ=0.61 (2H), 0.87 (2H), 1.46 (6H), 2.26 (3H), 2.37 (3H), 2.89 (1H), 3.31 (2H), 5.87 (1H), 5.94 (1H), 6.61 (1H), 6.98-7.09 (3H), 7.19 (1H), 7.29 (1H), 7.59 (1H), 7.63 (1H), 7.70 (1H) ppm.

Example 98

4-{6-Chloro-8-[(2-sulfamoylethyl)amino]imidazo[1,2-b]pyridazin-3-yl}-N-cyclopropylbenzamide

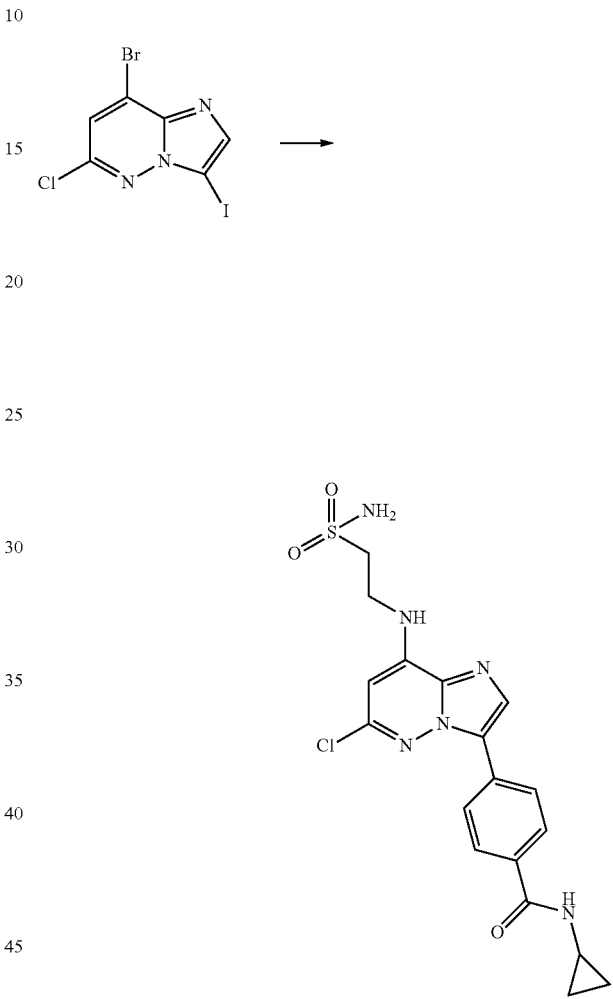

8-Bromo-6-chloro-3-iodoimidazo[1,2-b]pyridazine (0.3 mmol) which was prepared according to intermediate example 1c, 2-aminoethanesulfonamide hydrochloride (1:1) (0.3 mmol, 1.0 eq)) and DIPEA (3 eq, 157 μL) were combined with 3 mL NMP in a sealed vial and heated at 160° C. under microwave irradiation for 30 min. After cooling, [4-(cyclopropylcarbamoyl)phenyl]boronic acid (1.2 eq, 74 mg), Pd(dppf)Cl$_2$ (0.2 eq, 49 mg) and potassium carbonate (3 eq, 900 μL, 1M in water) were added and the mixture was heated at 80° C. overnight. After cooling, the solution was filtered and subjected to preparative HPLC to give 4-{6-chloro-8-[(2-sulfamoylethyl)amino]imidazo[1,2-b]pyridazin-3-yl}-N-cyclopropyl benzamide (45 mg, 35%): UPLC-MS: RT=–0.92 min; m/z (ES+) 435.9 [MH+]; required MW=434.9.

Intermediate Example 99

4-{6-Chloro-8-[(2-methylpropyl)amino]imidazo[1,2-b]pyridazin-3-yl}-N-cyclopropyl-2-methylbenzamide

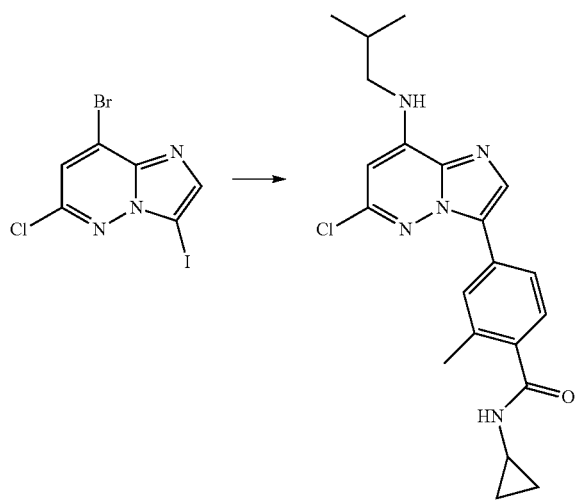 [SMILES: Clc1cc(Br)c2ncc(I)n2n1 ; Cc1cc(-c2cnc3c(NCC(C)C)cc(Cl)nn23)ccc1C(=O)NC1CC1]

6 g (16.7 mmol) 8-Bromo-6-chloro-3-iodoimidazo[1,2-b]pyridazine which was prepared according to intermediate example 1c were transformed in analogy to example 98 using 2-methylpropan-1-amine and N-cyclopropyl-2-methyl-4-(4,4,5,5-tetramethyl-1,3,2-dioxaborolan-2-yl)benzamide to give after working up and purification 1.27 g (19%) of the title compound.

UPLC-MS: RT=1.32 min; m/z (ES+) 398.9 [MH+]; required MW=397.9.

$^1$H-NMR (DMSO-d6): δ=0.50 (2H), 0.65 (2H), 0.90 (6H), 1.96 (1H), 2.35 (3H), 2.80 (1H), 3.12 (2H), 6.29 (1H), 7.36 (1H), 7.84 (1H), 7.91 (1H), 7.96 (1H), 7.99 (1H), 8.29 (1H) ppm.

Example 100

N-cyclopropyl-4-{8-[(2-methylpropyl)amino]imidazo[1,2-b]pyridazin-3-yl}benzamide

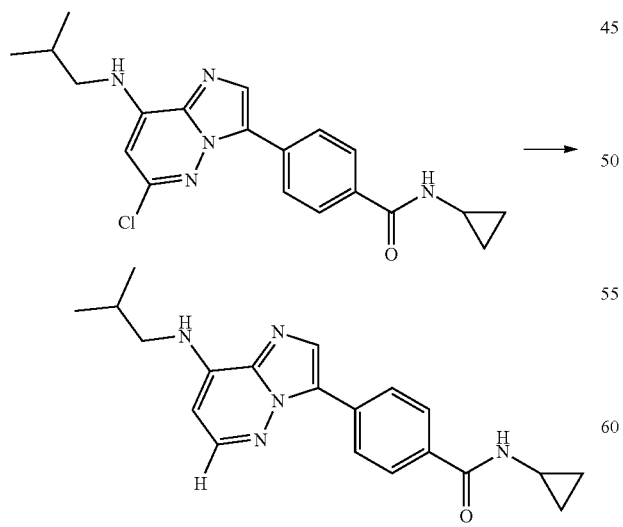

100 mg (260 μmol) 4-{6-chloro-8-[(2-methylpropyl) amino]imidazo[1,2-b]pyridazin-3-yl}-N-cyclopropylbenzamide which was prepared according to intermediate example 100a were dissolved in 50 mL ethanol and subjected to flow hydrogenation using an H-Cube with cartridge Pd/C 10% CATCART 30 at 30° C., 10 bar and 0.8 mL/min flow. Purification by RP-HPLC yielded 21.1 mg (23%) of the title compound.

UPLC-MS: RT=1.13 min; m/z (ES+) 350.4 [MH+]; required MW=349.4.

$^1$H-NMR (DMSO-d6): δ=0.56 (2H), 0.67 (2H), 0.90 (6H), 1.96 (1H), 2.82 (1H), 3.11 (2H), 6.15 (1H), 7.54 (1H), 7.87 (2H), 8.04 (1H), 8.12 (1H), –8.21 (2H), 8.43 (1H) ppm.

Intermediate Example 100a

4-{6-chloro-8-[(2-methylpropyl)amino]imidazo[1,2-b]pyridazin-3-yl}-N-cyclopropylbenzamide

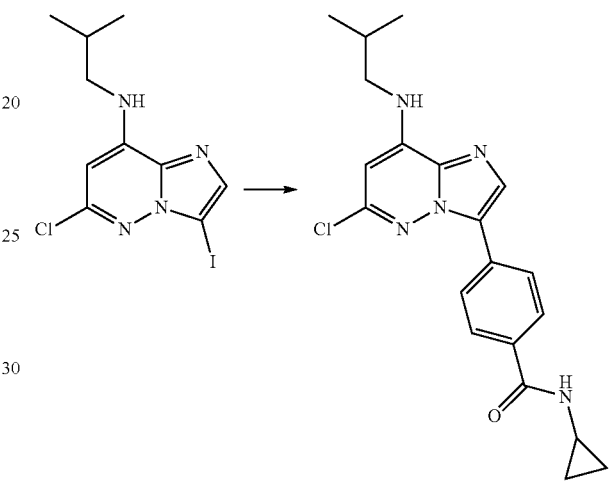

1 mmol 6-chloro-3-iodo-N-(2-methylpropyl)imidazo[1,2-b]pyridazin-8-amine (10 mL, 0.1 M in NMP), which was prepared according to intermediate example 100b, 1.5 mmol [4-(cyclopropylcarbamoyl)phenyl]boronic acid, 0.2 mmol Pd(dppf)Cl$_2$ and 3 mmol potassium carbonate (3 mL, 1M in water, 3 eq) were combined in a sealed vial and heated at 150° C. for 180 min. After cooling, the mixture was treated with water and extracted with ethyl acetate, the combined organic layers were dried and concentrated, purified by flash silica gel column chromatography (Ethyl acetate:Petroleum ether 1:5) give 115 mg (30%) of the title compound.

UPLC-MS: RT=1.29 min; m/z (ES+) 384.9 [MH+]; required MW 383.9.

$^1$H-NMR (DMSO-d6): δ=0.60 (2H), 0.72 (2H), 0.93 (6H), 2.0 (1H), 2.87 (1H), 3.34 (2H), 6.33 (1H), 7.92 (1H), 8.07 (2H), 8.16 (2H), 8.48 (1H) ppm.

Intermediate Example 100b 6-chloro-3-iodo-N-(2-methylpropyl)imidazo[1,2-b]pyridazin-8-amine

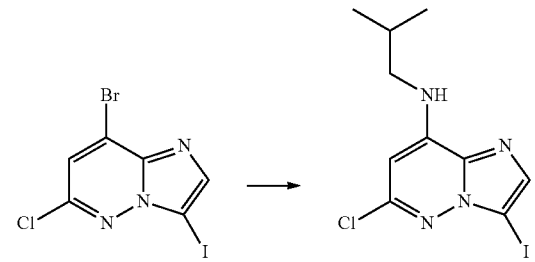 [SMILES: Clc1cc(Br)c2ncc(I)n2n1 ; CC(C)CNc1cc(Cl)nn2c(I)cnc12]

235

To a solution of 200 mg (0.558 mmol) 8-bromo-6-chloro-3-iodoimidazo[1,2-b]pyridazine which was prepared according to intermediate example 1c in 4 mL N,N-dimethylformamide were added 122 mg 2-methylpropan-1-amine and the mixture was stirred at rt overnight. Water was added and the mixture was extracted with dichloromethane and methanol. The organic phase was washed with water and dried over sodium sulfate. After filtration and removal of solvent the residue was purified by chromatography to give 188 mg (96%) of the title compound.

UPLC-MS: RT=1.36 min; m/z (ES+) 351.6 [MH+]; required MW 350.6.

$^1$H-NMR (DMSO-d6): δ=1.04 (6H), 2.00 (1H), 3.13 (2H), 6.00 (1H), 7.27 (1H), 7.53 (1H) ppm.

Example 101

3-[4-(2-Cyclopropyl-1H-imidazol-5-yl)phenyl]-6-ethenyl-N-(3,3,3-trifluoropropyl)imidazo[1,2-b]pyridazin-8-amine

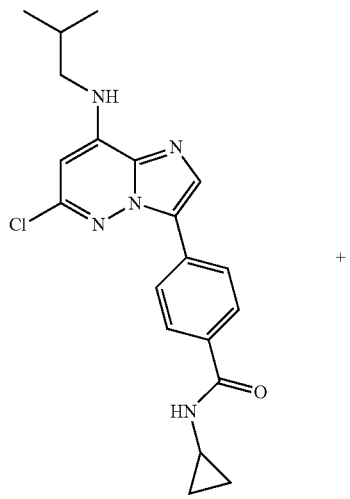

+

0.1 mmol 4-{6-chloro-8-[(2-methylpropyl)amino]imidazo[1,2-b]pyridazin-3-yl}-N-cyclopropylbenzamide (1 mL, 0.1 M in NMP), which was prepared according to intermediate example 100a, 0.4 mmol 2,3-dihydro-1,4-benzodioxin-6-ylboronic acid (0.8 mL, 0.5 M in NMP, 4 eq), 0.02 mmol Pd(dppf)Cl$_2$ (0.3 eq, 800 µL, 0.0375 M in NMP) and 0.3 mmol potassium carbonate (0.3 mL, 1M in water, 3 eq) were combined in a sealed vial and heated at 150° C. under microwave irradiation for 90 min. After cooling, the solution was filtered and subjected to preparative HPLC to give 4.2 mg (8%) of the title compound.

UPLC-MS: RT=1.34 min; m/z (ES+) 484.6 [MH+]; required MW=483.6.

The following compound examples were prepared analogously to the procedure described above using the appropriate intermediate and the appropriate boronic acid building block [LC-MS data such as retention time (RT in min) or observed mass peak were collected using LC-MS Method A unless explicitly stated]:

| Example | Structure | Name | Analytical Data |
|---|---|---|---|
| 102 | 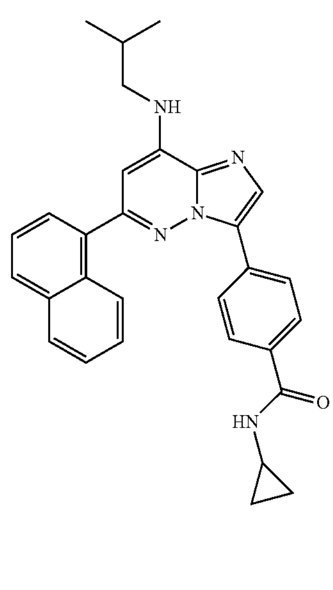 [SMILES: CC(C)CNc1cc(-c2cccc3ccccc23)nn2c(-c3ccc(C(=O)NC4CC4)cc3)cnc12] | N-cyclopropyl-4-{8-[(2-methylpropyl)amino]-6-(naphthalen-1-yl)imidazo[1,2-b]pyridazin-3-yl}benzamide | RT = 1.47<br>MWfound = 476.6<br>MWcalc = 475.6 |

| Example | Structure | Name | Analytical Data |
|---|---|---|---|
| 103 | 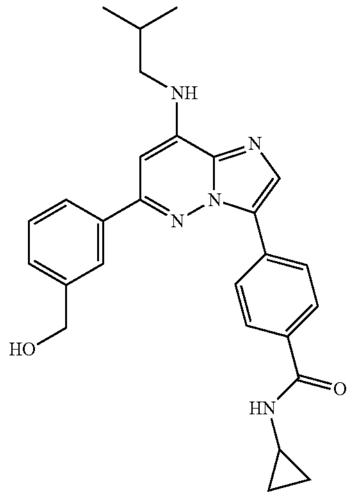 [SMILES: CC(C)CNc1cc(-c2cccc(CO)c2)nn2c(-c3ccc(C(=O)NC4CC4)cc3)cnc12] | N-cyclopropyl-4-{6-[3-(hydroxymethyl)phenyl]-8-[(2-methylpropyl)amino]imidazo[1,2-b]pyridazin-3-yl}benzamide | RT = 1.18<br>MWfound = 456.6<br>MWcalc = 455.6 |
| 104 | 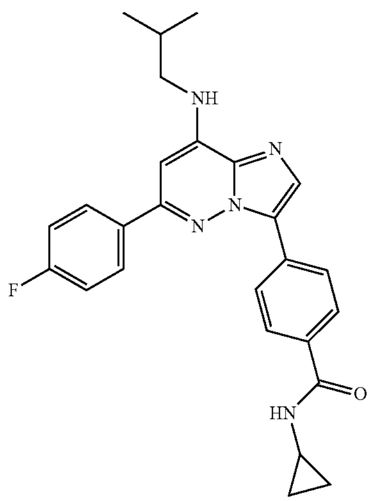 [SMILES: CC(C)CNc1cc(-c2ccc(F)cc2)nn2c(-c3ccc(C(=O)NC4CC4)cc3)cnc12] | N-cyclopropyl-4-{6-(4-fluorophenyl)-8-[(2-methylpropyl)amino]imidazo[1,2-b]pyridazin-3-yl}benzamide | RT = 1.39<br>MWfound = 444.5<br>MWcalc = 443.5 |
| 105 | 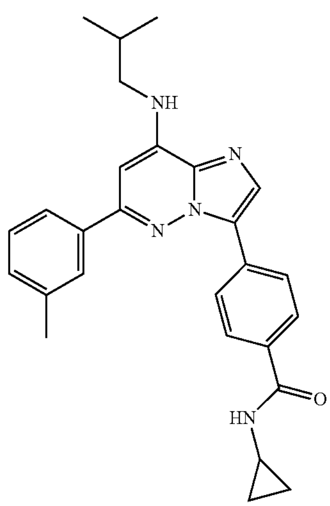 [SMILES: Cc1cccc(-c2cc(NCC(C)C)c3ncc(-c4ccc(C(=O)NC5CC5)cc4)n3n2)c1] | N-cyclopropyl-4-{6-(3-methylphenyl)-8-[(2-methylpropyl)amino]imidazo[1,2-b]pyridazin-3-yl}benzamide | RT = 1.44<br>MWfound = 440.6<br>MWcalc = 439.6 |

| Example | Structure | Name | Analytical Data |
| --- | --- | --- | --- |
| 106 | 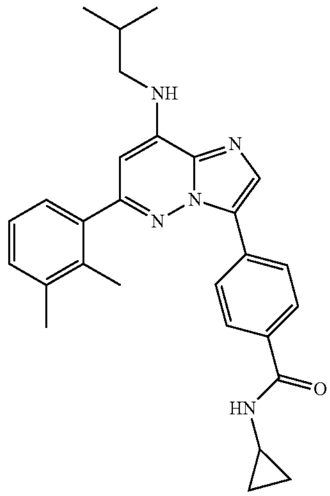 [SMILES: Cc1cccc(-c2cc(NCC(C)C)c3ncc(-c4ccc(C(=O)NC5CC5)cc4)n3n2)c1C] | N-cyclopropyl-4-{6-(2,3-dimethylphenyl)-8-[(2-methylpropyl)amino]imidazo[1,2-b]pyridazin-3-yl}benzamide | RT = 1.46<br>MWfound = 454.6<br>MWcalc = 453.6 |
| 107 | 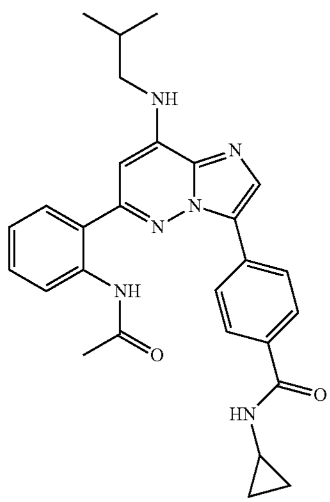 [SMILES: CC(=O)Nc1ccccc1-c1cc(NCC(C)C)c2ncc(-c3ccc(C(=O)NC4CC4)cc3)n2n1] | 4-{6-[2-(Acetylamino)phenyl]-8-[(2-methylpropyl)amino]imidazo[1,2-b]pyridazin-3-yl}-N-cyclopropylbenzamide | RT = 1.22<br>MWfound = 483.6<br>MWcalc = 482.6 |
| 108 | 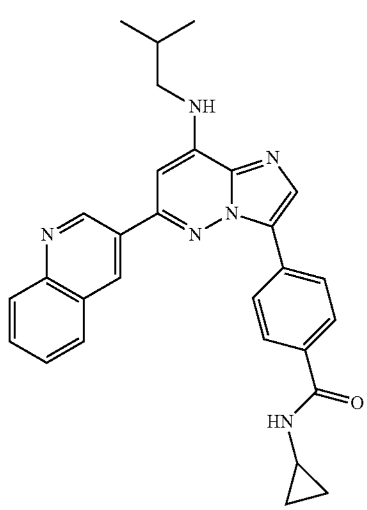 [SMILES: CC(C)CNc1cc(-c2cnc3ccccc3c2)nn2c(-c3ccc(C(=O)NC4CC4)cc3)cnc12] | N-cyclopropyl-4-{8-[(2-methylpropyl)amino]-6-(quinolin-3-yl)imidazo[1,2-b]pyridazin-3-yl}benzamide | RT = 1.32<br>MWfound = 477.6<br>MWcalc = 476.6 |

| Example | Structure | Name | Analytical Data |
|---|---|---|---|
| 109 | 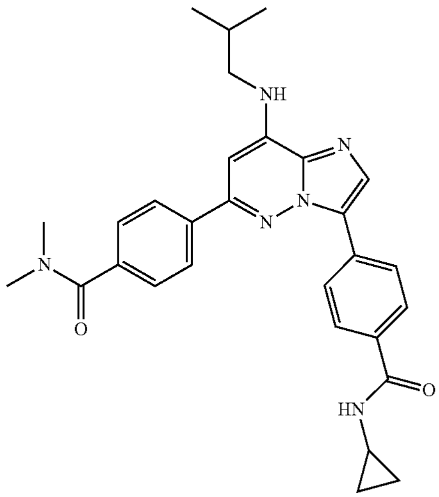 [SMILES: CC(C)CNc1cc(-c2ccc(C(=O)N(C)C)cc2)nn2c(-c3ccc(C(=O)NC4CC4)cc3)cnc12] | 4-{3-[4-(Cyclopropylcarbamoyl)phenyl]-8-[(2-methylpropyl)amino]imidazo[1,2-b]pyridazin-6-yl}-N,N-dimethylbenzamide | RT = 1.19<br>MWfound = 497.6<br>MWcalc = 496.6 |
| 110 | 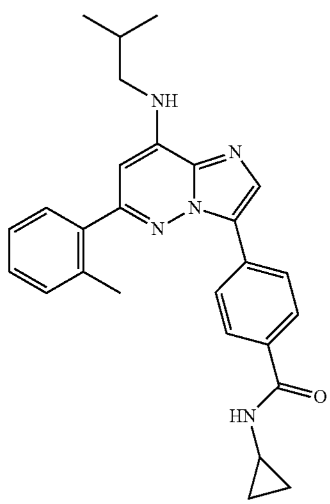 [SMILES: Cc1ccccc1-c1cc(NCC(C)C)c2ncc(-c3ccc(C(=O)NC4CC4)cc3)n2n1] | N-cyclopropyl-4-{6-(2-methylphenyl-8-[(2-methylpropyl)amino]imidazo[1,2-b]pyridazin-3-yl}benzamide | RT = 1.41<br>MWfound = 440.6<br>MWcalc = 439.6 |
| 111 | 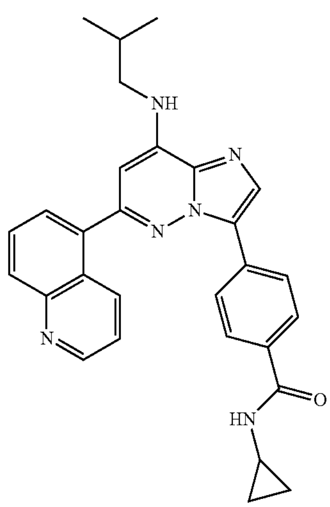 [SMILES: CC(C)CNc1cc(-c2cccc3ncccc23)nn2c(-c3ccc(C(=O)NC4CC4)cc3)cnc12] | N-cyclopropyl-4-{8-[(2-methylpropyl)amino]-6-(quinolin-5-yl)imidazo[1,2-b]pyridazin-3-yl}benzamide | RT = 1.18<br>MWfound = 477.6<br>MWcalc = 476.6 |

| Example | Structure | Name | Analytical Data |
|---|---|---|---|
| 112 | 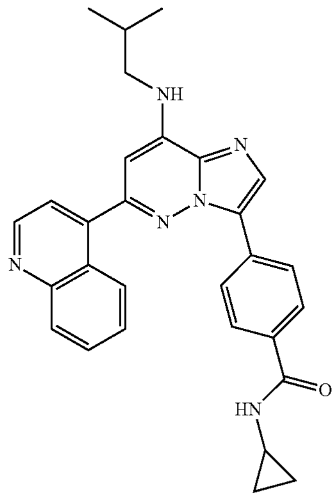 [SMILES: CC(C)CNc1cc(-c2ccnc3ccccc23)nn2c(-c3ccc(C(=O)NC4CC4)cc3)cnc12] | N-cyclopropyl-4-{8-[(2-methylpropyl)amino]-6-(quinolin-4-yl)imidazol[1,2-b]pyridazin-3-yl}benzamide | RT = 1.23<br>MW found = 477.6<br>MW calc = 476.6 |
| 113 | 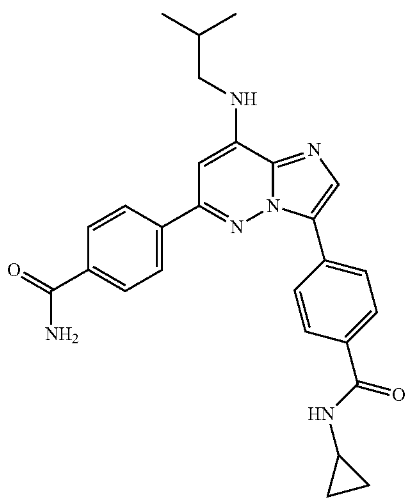 [SMILES: CC(C)CNc1cc(-c2ccc(C(N)=O)cc2)nn2c(-c3ccc(C(=O)NC4CC4)cc3)cnc12] | 4-{6-(4-Carbamoylphenyl)-8-[(2-methylpropyl)amino]imidazo[1,2-b]pyridazin-3-yl}-N-cyclopropylbenzamide | RT = 1.10<br>MW found = 469.6<br>MW calc = 468.6 |
| 114 | 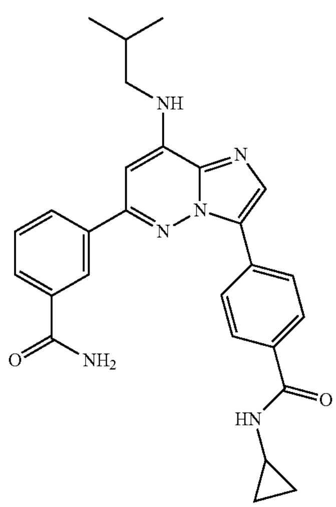 [SMILES: CC(C)CNc1cc(-c2cccc(C(N)=O)c2)nn2c(-c3ccc(C(=O)NC4CC4)cc3)cnc12] | 4-{6-(3-Carbamoylphenyl)-8-[(2-methylpropyl)amino]imidazo[1,2-b]pyridazin-3-yl}-N-cyclopropylbenzamide | RT = 1.11<br>MW found = 469.6<br>MW calc = 468.6 |

-continued

| Example | Structure | Name | Analytical Data |
|---|---|---|---|
| 115 | 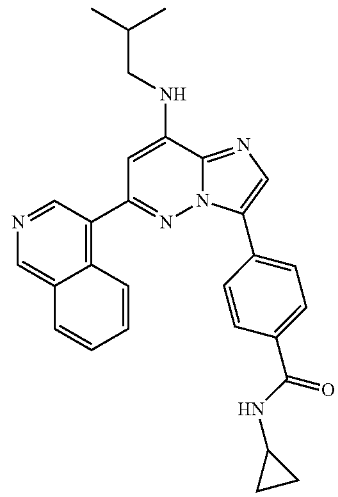 [SMILES: CC(C)CNc1cc(-c2cncc3ccccc23)nn2c(-c3ccc(C(=O)NC4CC4)cc3)cnc12] | N-cyclopropyl-4-{6-(isoquinolin-4-yl)-8-[(2-methylpropyl)amino]imidazo[1,2-b]pyridazin-3-yl}benzamide | RT = 1.21<br>MWfound = 477.6<br>MWcalc = 476.6 |
| 116 | 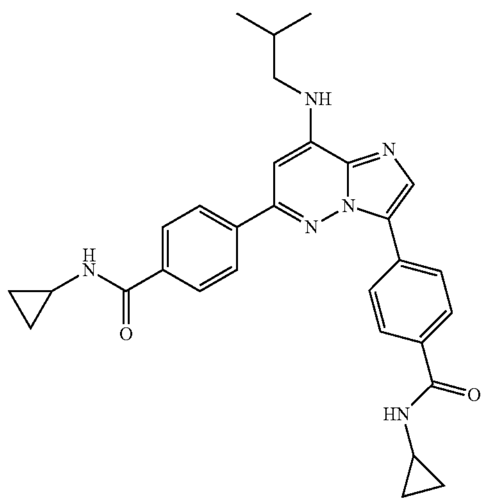 [SMILES: CC(C)CNc1cc(-c2ccc(C(=O)NC3CC3)cc2)nn2c(-c3ccc(C(=O)NC4CC4)cc3)cnc12] | 4,4'-{8-[(2-Methylpropyl)amino]imidazo[1,2-b]pyridazine-3,6-diyl}bis(N-cyclopropylbenzamide) | RT = 1.21<br>MWfound = 509.6<br>MWcalc = 508.6 |
| 117 | 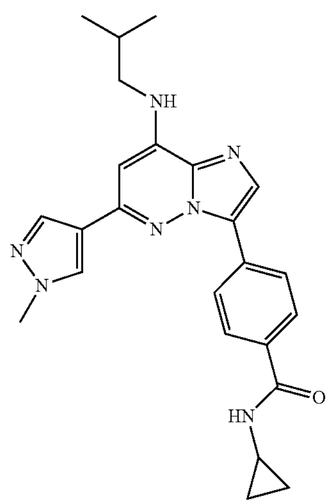 [SMILES: CC(C)CNc1cc(-c2cnn(C)c2)nn2c(-c3ccc(C(=O)NC4CC4)cc3)cnc12] | N-cyclopropyl-4-{8-[(2-methylpropyl)amino]-6-(1-methyl-1H-pyrazol-4-yl)imidazo[1,2-b]pyridazin-3-yl}benzamide | RT = 1.12<br>MWfound = 430.5<br>MWcalc = 429.5 |

| Example | Structure | Name | Analytical Data |
|---|---|---|---|
| 118 | 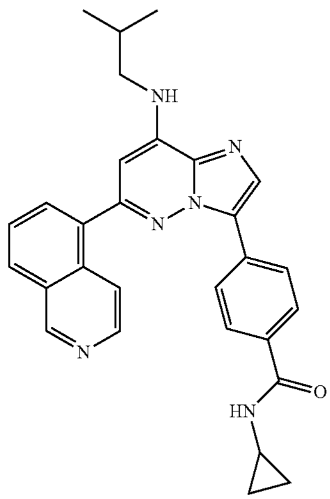 [SMILES: CC(C)CNc1cc(-c2cccc3cnccc23)nn2c(-c3ccc(C(=O)NC4CC4)cc3)cnc12] | N-cyclopropyl-4-{6-(isoquinolin-5-yl)-8-[(2-methylpropyl)amino]imidazo[1,2-b]pyridazin-3-yl}benzamide | RT = 1.09<br>MW found = 477.6<br>MW calc = 476.6 |
| 119 | 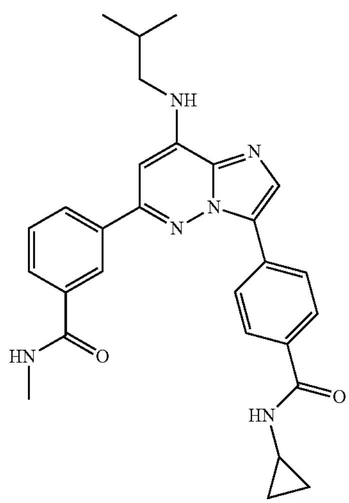 [SMILES: CNC(=O)c1cccc(-c2cc(NCC(C)C)c3ncc(-c4ccc(C(=O)NC5CC5)cc4)n3n2)c1] | 3-{3-[4-(Cyclopropylcarbamoyl)phenyl]-8-[(2-methylpropyl)amino]imidazo[1,2-b]pyridazin-6-yl}-N-methylbenzamide | RT = 1.16<br>MW found = 483.6<br>MW calc = 482.6 |
| 120 | 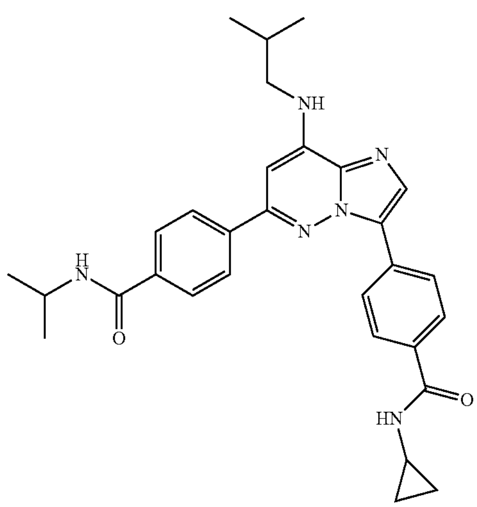 [SMILES: CC(C)CNc1cc(-c2ccc(C(=O)NC(C)C)cc2)nn2c(-c3ccc(C(=O)NC4CC4)cc3)cnc12] | 4-{3-[4-(Cyclopropylcarbamoyl)phenyl]-8-[(2-methylpropyl)amino]imidazo[1,2-b]pyridazin-6-yl}-N-(propan-2-yl)benzamide | RT = 1.25<br>MW found = 511.6<br>MW calc = 510.6 |

| Example | Structure | Name | Analytical Data |
|---|---|---|---|
| 121 | 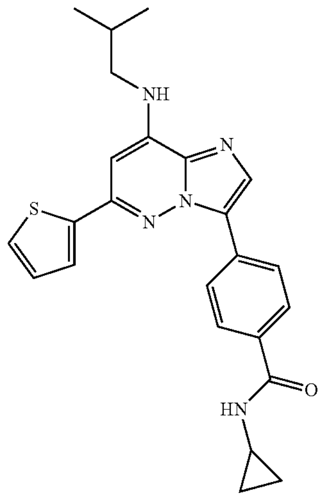 [SMILES: CC(C)CNc1cc(-c2cccs2)nn2c(-c3ccc(C(=O)NC4CC4)cc3)cnc12] | N-cyclopropyl-4-{8-[(2-methylpropyl)amino]-6-(thiophen-2-yl)imidazo[1,2-b]pyridazin-3-yl}benzamide | RT = 1.36<br>MWfound = 432.6<br>MWcalc = 431.6 |
| 122 | 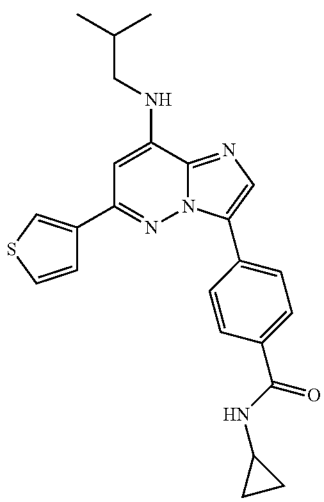 [SMILES: CC(C)CNc1cc(-c2ccsc2)nn2c(-c3ccc(C(=O)NC4CC4)cc3)cnc12] | N-cyclopropyl-4-{8-[(2-methylpropyl)amino]-6-(thiophen-3-yl)imidazo[1,2-b]pyridazin-3-yl}benzamide | RT = 1.35<br>MWfound = 432.6<br>MWcalc = 431.6 |
| 123 | 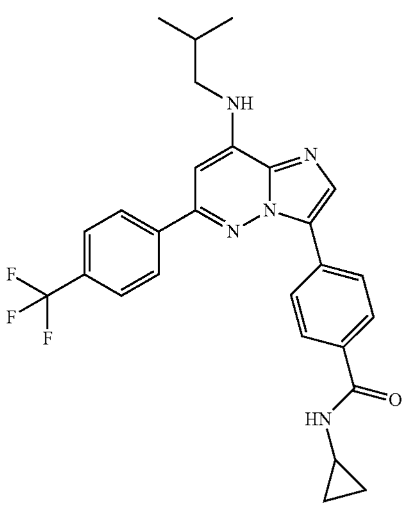 [SMILES: CC(C)CNc1cc(-c2ccc(C(F)(F)F)cc2)nn2c(-c3ccc(C(=O)NC4CC4)cc3)cnc12] | N-cyclopropyl-4-{8-[(2-methylpropyl)amino]-6-[4-(trifluoromethyl)phenyl]imidazo[1,2-b]pyridazin-3-yl}benzamide | RT = 1.49<br>MWfound = 494.5<br>MWcalc = 493.5 |

| Example | Structure | Name | Analytical Data |
|---|---|---|---|
| 124 | 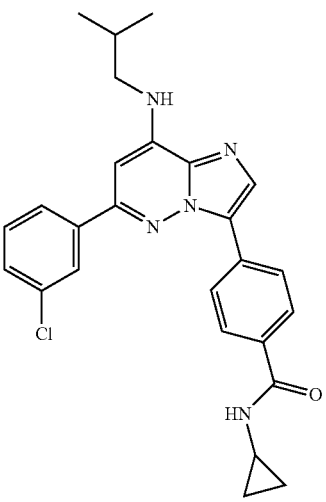 | 4-{6-(3-Chlorophenyl)-8-[(2-methylpropyl)amino]imidazo[1,2-b]pyridazin-3-yl}-N-cyclopropylbenzamide | RT = 1.48<br>MWfound = 461.0<br>MWcalc = 460.0 |
| 125 | 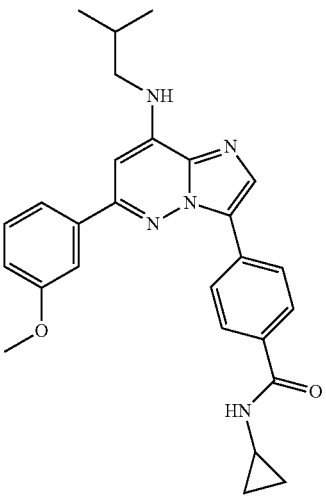 [SMILES: COc1cccc(-c2cc(NCC(C)C)c3ncc(-c4ccc(C(=O)NC5CC5)cc4)n3n2)c1] | N-cyclopropyl-4-{6-(3-methoxyphenyl)-8-[(2-methylpropyl)amino]imidazo[1,2-b]pyridazin-3-yl}benzamide | RT = 1.38<br>MWfound = 456.6<br>MWcalc = 455.6 |
| 126 | 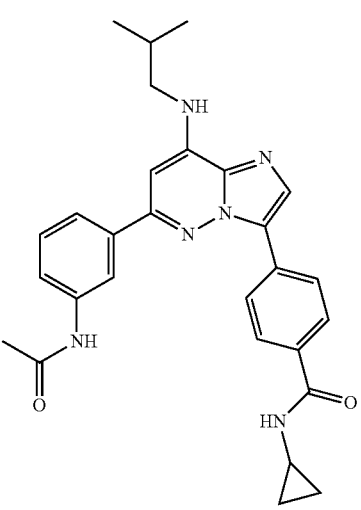 [SMILES: CC(=O)Nc1cccc(-c2cc(NCC(C)C)c3ncc(-c4ccc(C(=O)NC5CC5)cc4)n3n2)c1] | 4-{6-[3-(Acetylamino)phenyl]-8-[(2-methylpropyl)amino]imidazo[1,2-b]pyridazin-3-yl}-N-cyclopropylbenzamide | RT = 1.19<br>MWfound = 483.6<br>MWcalc = 482.6 |

-continued

| Example | Structure | Name | Analytical Data |
|---|---|---|---|
| 127 | 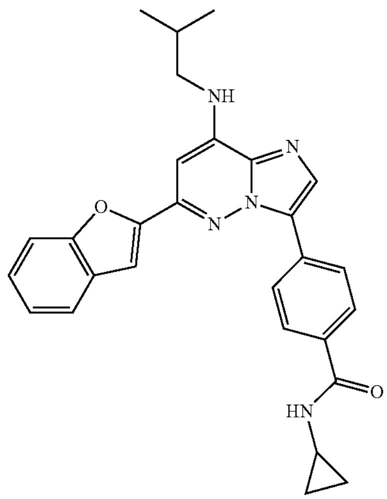 [SMILES: CC(C)CNc1cc(-c2cc3ccccc3o2)nn2c(-c3ccc(C(=O)NC4CC4)cc3)cnc12] | 4-{6-(1-Benzofuran-2-yl)-8-[(2-methylpropyl)amino]imidazo[1,2-b]pyridazin-3-yl}-N-cyclopropylbenzamide | RT = 1.48<br>MW found = 466.5<br>MW calc = 465.5 |
| 128 | 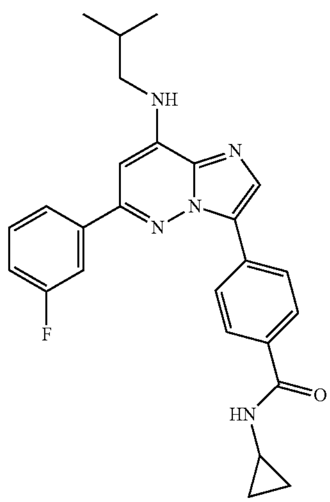 | N-cyclopropyl-4-{6-(3-fluorophenyl)-8-[(2-methylpropyl)amino]imidazo[1,2-b]pyridazin-3-yl}benzamide | RT = 1.40<br>MW found = 444.5<br>MW calc = 443.5 |
| 129 | 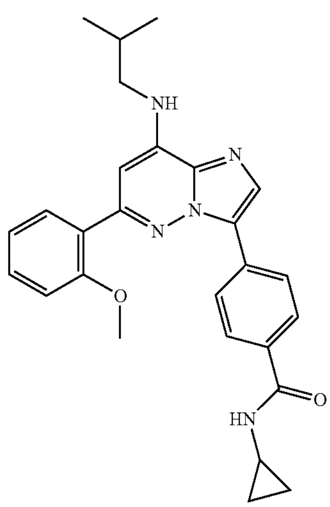 [SMILES: COc1ccccc1-c1cc(NCC(C)C)c2ncc(-c3ccc(C(=O)NC4CC4)cc3)n2n1] | N-cyclopropyl-4-{6-(2-methoxyphenyl)-8-[(2-methylpropyl)amino]imidazo[1,2-b]pyridazin-3-yl}benzamide | RT = 1.34<br>MW found = 456.6<br>MW calc = 455.6 |

-continued

| Example | Structure | Name | Analytical Data |
|---|---|---|---|
| 130 | 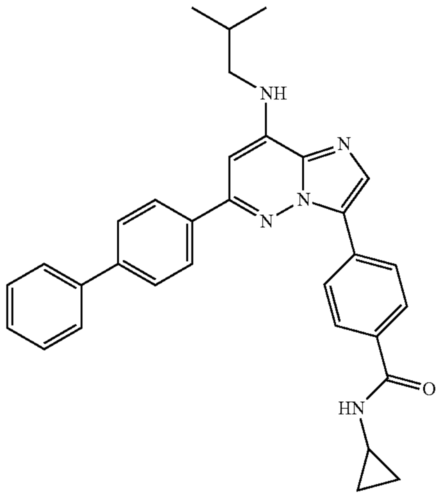 [SMILES: CC(C)CNc1cc(-c2ccc(-c3ccccc3)cc2)nn2c(-c3ccc(C(=O)NC4CC4)cc3)cnc12] | 4-{6-(Biphenyl-4-yl)-8-[(2-methylpropyl)amino]imidazo[1,2-b]pyridazin-3-yl}-N-cyclopropylbenzamide | RT = 1.56<br>MWfound = 502.6<br>MWcalc = 501.6 |
| 131 | 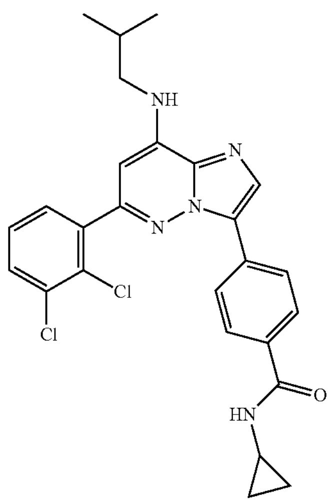 [SMILES: CC(C)CNc1cc(-c2cccc(Cl)c2Cl)nn2c(-c3ccc(C(=O)NC4CC4)cc3)cnc12] | N-cyclopropyl-4-{6-(2,3-dichlorophenyl)-8-[(2-methylpropyl)amino]imidazo[1,2-b]pyridazin-3-yl}benzamide | RT = 1.49<br>MWfound = 495.4<br>MWcalc = 494.4 |
| 132 | 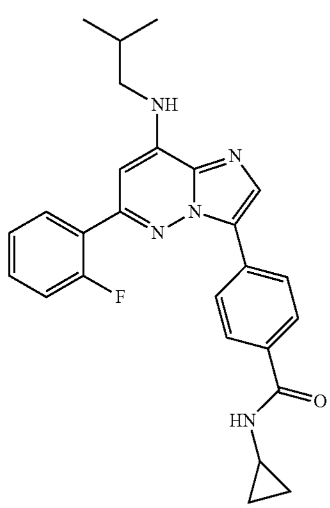 [SMILES: CC(C)CNc1cc(-c2ccccc2F)nn2c(-c3ccc(C(=O)NC4CC4)cc3)cnc12] | N-cyclopropyl-4-{6-(2-fluorophenyl)-8-[(2-methylpropyl)amino]imidazo[1,2-b]pyridazin-3-yl}benzamide | RT = 1.38<br>MWfound = 444.5<br>MWcalc = 443.5 |

-continued

| Example | Structure | Name | Analytical Data |
|---|---|---|---|
| 133 | 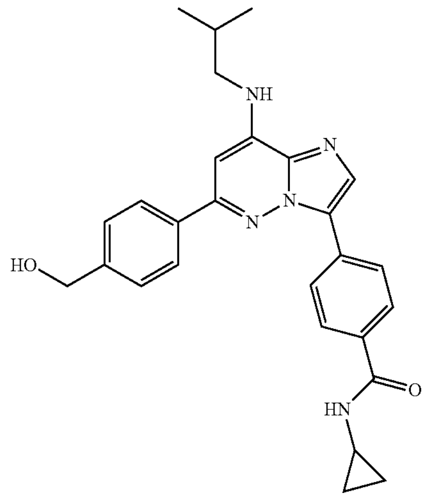 [SMILES: CC(C)CNc1cc(-c2ccc(CO)cc2)nn2c(-c3ccc(C(=O)NC4CC4)cc3)cnc12] | N-cyclopropyl-4-{6-[4-(hydroxymethyl)phenyl]-8-[(2-methylpropyl)amino]imidazo[1,2-b]pyridazin-3-yl}benzamide | RT = 1.17<br>MWfound = 456.6<br>MWcalc = 455.6 |
| 134 | 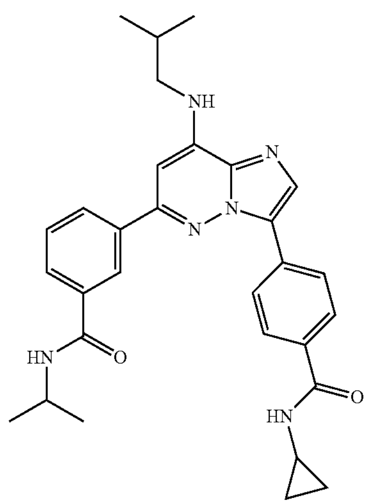 [SMILES: CC(C)CNc1cc(-c2cccc(C(=O)NC(C)C)c2)nn2c(-c3ccc(C(=O)NC4CC4)cc3)cnc12] | 3-{3-[4-(Cyclopropylcarbamoyl)phenyl]-8-[(2-methylpropyl)amino]imidazo[1,2-b]pyridazin-6-yl}-N-(propan-2-yl)benzamide | RT = 1.26<br>MWfound = 511.6<br>MWcalc = 510.6 |
| 135 | 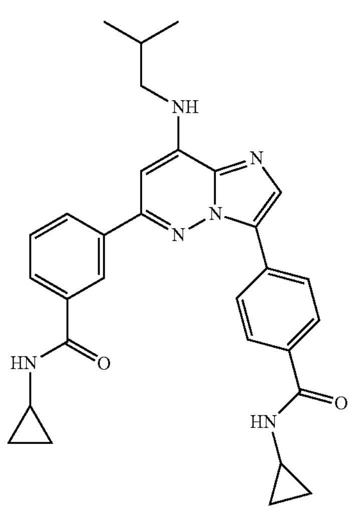 [SMILES: CC(C)CNc1cc(-c2cccc(C(=O)NC3CC3)c2)nn2c(-c3ccc(C(=O)NC4CC4)cc3)cnc12] | N-cyclopropyl-3-{3-[4-(cyclopropylcarbamoyl)phenyl]-8-[(2-methylpropyl)amino]imidazo[1,2-b]pyridazin-6-yl}benzamide | RT = 1.21<br>MWfound = 509.6<br>MWcalc = 508.6 |

| Example | Structure | Name | Analytical Data |
|---|---|---|---|
| 136 | 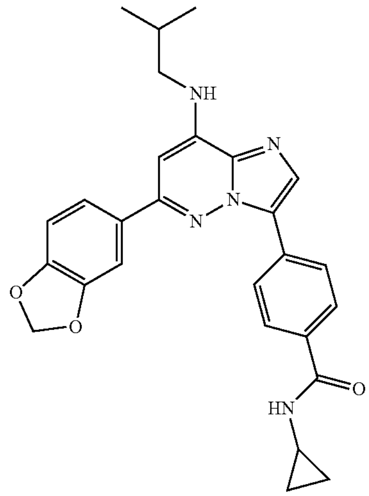 [SMILES: CC(C)CNc1cc(-c2ccc3c(c2)OCO3)nn2c(-c3ccc(C(=O)NC4CC4)cc3)cnc12] | 4-{6-(1,3-Benzodioxol-5-yl)-8-[(2-methylpropyl)amino]imidazo[1,2-b]pyridazin-3-yl}-N-cyclopropylbenzamide | RT = 1.34<br>MW found = 470.5<br>MW calc = 469.5 |
| 137 | 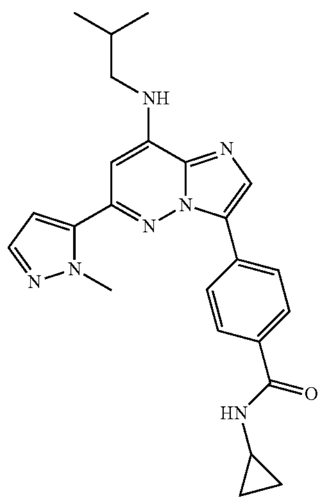 [SMILES: CC(C)CNc1cc(-c2ccnn2C)nn2c(-c3ccc(C(=O)NC4CC4)cc3)cnc12] | N-cyclopropyl-4-{8-[(2-methylpropyl)amino]-6-(1-methyl-1H-pyrazol-5-yl)imidazo[1,2-b]pyridazin-3-yl}benzamide | RT = 1.19<br>MW found = 430.5<br>MW calc = 429.5 |
| 138 | 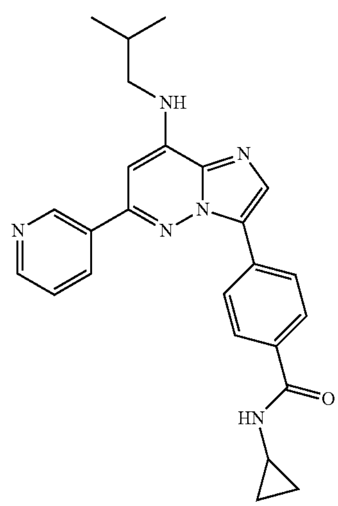 [SMILES: CC(C)CNc1cc(-c2cccnc2)nn2c(-c3ccc(C(=O)NC4CC4)cc3)cnc12] | N-cyclopropyl-4-{8-[(2-methylpropyl)amino]-6-(pyridin-3-yl)imidazo[1,2-b]pyridazin-3-yl}benzamide | RT = 1.11<br>MW found = 427.5<br>MW calc = 426.5 |

-continued

| Example | Structure | Name | Analytical Data |
|---|---|---|---|
| 139 | 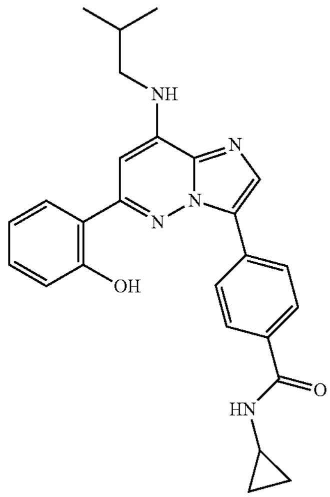 [SMILES: CC(C)CNc1cc(-c2ccccc2O)nn2c(-c3ccc(C(=O)NC4CC4)cc3)cnc12] | N-cyclopropyl-4-{6-(2-hydroxyphenyl)-8-[(2-methylpropyl)amino]imidazo[1,2-b]pyridazin-3-yl}benzamide | RT = 1.35<br>MWfound = 442.5<br>MWcalc = 441.5 |
| 140 | 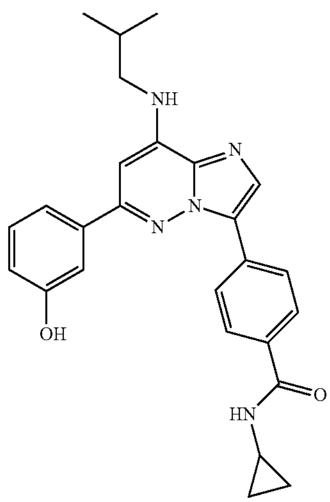 [SMILES: CC(C)CNc1cc(-c2cccc(O)c2)nn2c(-c3ccc(C(=O)NC4CC4)cc3)cnc12] | N-cyclopropyl-4-{6-(3-hydroxyphenyl)-8-[(2-methylpropyl)amino]imidazo[1,2-b]pyridazin-3-yl}benzamide | RT = 1.21<br>MWfound = 442.5<br>MWcalc = 441.5 |
| 141 | 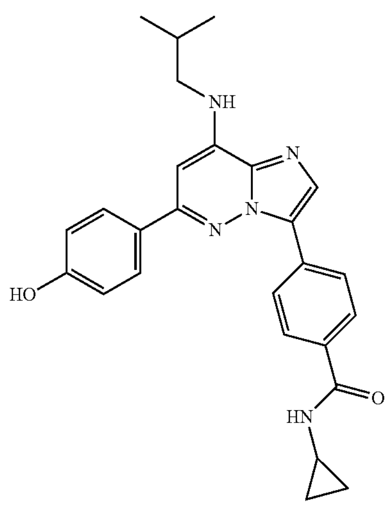 [SMILES: CC(C)CNc1cc(-c2ccc(O)cc2)nn2c(-c3ccc(C(=O)NC4CC4)cc3)cnc12] | N-cyclopropyl-4-{6-(4-hydroxyphenyl)-8-[(2-methylpropyl)amino]imidazo[1,2-b]pyridazin-3-yl}benzamide | RT = 1.18<br>MWfound = 442.5<br>MWcalc = 441.5 |

| Example | Structure | Name | Analytical Data |
|---|---|---|---|
| 142 | 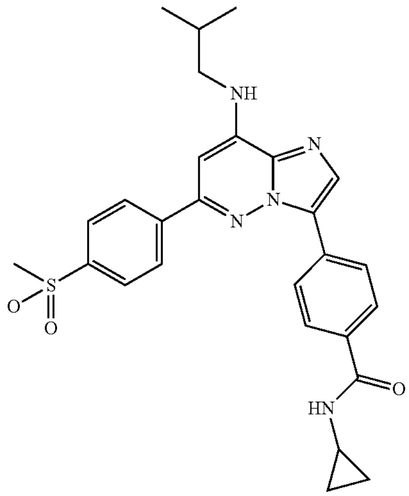 | N-cyclopropyl-4-{8-[(2-methylpropyl)amino]-6-[4-(methylsulfonyl)phenyl]imidazo[1,2-b]pyridazin-3-yl}benzamide | RT = 1.21<br>MWfound = 504.6<br>MWcalc = 503.6 |
| 143 | 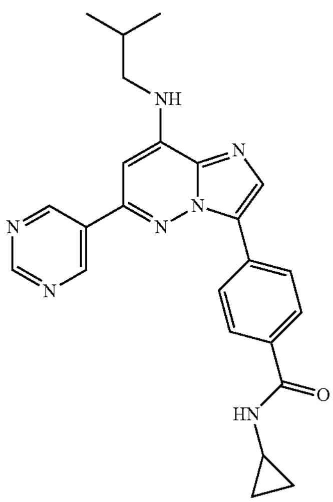 [SMILES: CC(C)CNc1cc(-c2cncnc2)nn2c(-c3ccc(C(=O)NC4CC4)cc3)cnc12] | N-cyclopropyl-4-{8-[(2-methylpropyl)amino]-6-(pyrimidin-5-yl)imidazo[1,2-b]pyridazin-3-yl}benzamide | RT = 1.13<br>MWfound = 428.5<br>MWcalc = 427.5 |
| 144 | 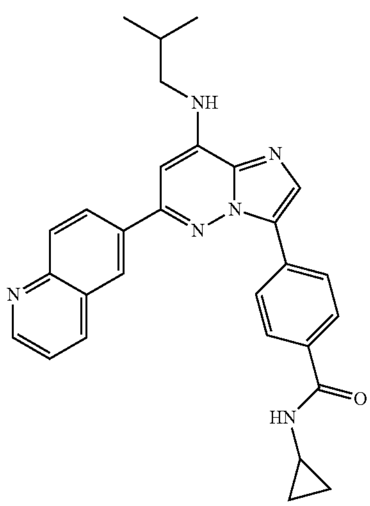 [SMILES: CC(C)CNc1cc(-c2ccc3ncccc3c2)nn2c(-c3ccc(C(=O)NC4CC4)cc3)cnc12] | N-cyclopropyl-4-{8-[(2-methylpropyl)amino]-6-(quinolin-6-yl)imidazo[1,2-b]pyridazin-3-yl}benzamide | RT = 1.21<br>MWfound = 477.6<br>MWcalc = 476.6 |

| Example | Structure | Name | Analytical Data |
|---|---|---|---|
| 145 | 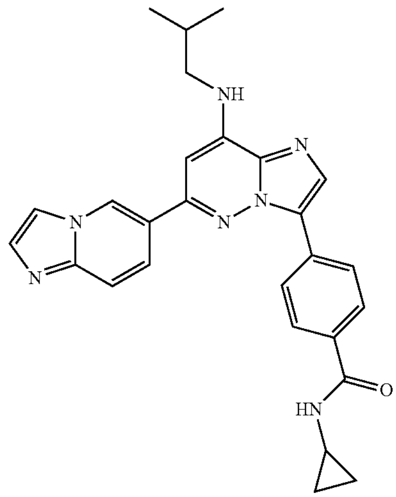 [SMILES: CC(C)CNc1cc(-c2ccc3nccn3c2)nn2c(-c3ccc(C(=O)NC4CC4)cc3)cnc12] | N-cyclopropyl-4-{6-(imidazo[1,2-a]pyridin-6-yl)-8-[(2-methylpropyl)amino]imidazo[1,2-b]pyridazin-3-yl}benzamide | RT = 0.84<br>MWfound = 466.5<br>MWcalc = 465.5 |
| 146 | 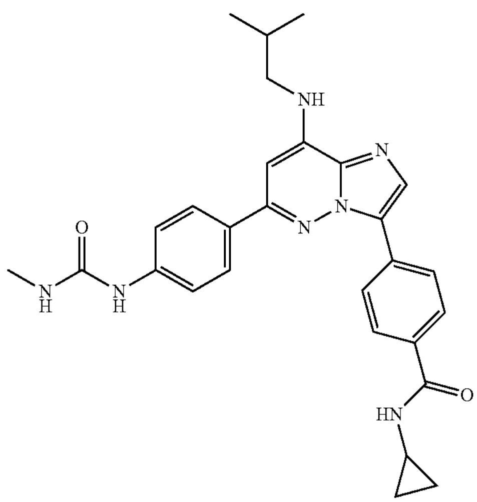 [SMILES: CNC(=O)Nc1ccc(-c2cc(NCC(C)C)c3ncc(-c4ccc(C(=O)NC5CC5)cc4)n3n2)cc1] | N-cyclopropyl-4-(6-{4-[(methylcarbamoyl)amino]phenyl}-8-[(2-methylpropyl)amino]imidazo[1,2-b]pyridazin-3-yl)benzamide | RT = 1.13<br>MWfound = 498.6<br>MWcalc = 497.6 |
| 147 | 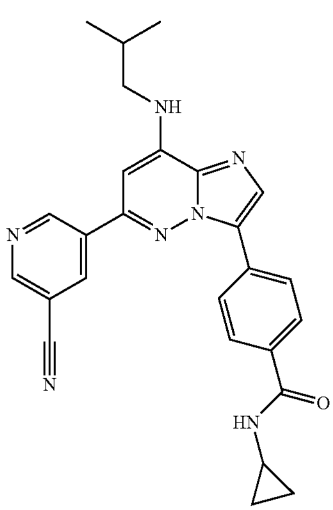 [SMILES: CC(C)CNc1cc(-c2cncc(C#N)c2)nn2c(-c3ccc(C(=O)NC4CC4)cc3)cnc12] | 4-{6-(5-Cyanopyridin-3-yl)-8-[(2-methylpropyl)amino]imidazo[1,2-b]pyridazin-3-yl}-N-cyclopropylbenzamide | RT = 1.23<br>MWfound = 452.5<br>MWcalc = 451.5 |

| Example | Structure | Name | Analytical Data |
|---|---|---|---|
| 148 | 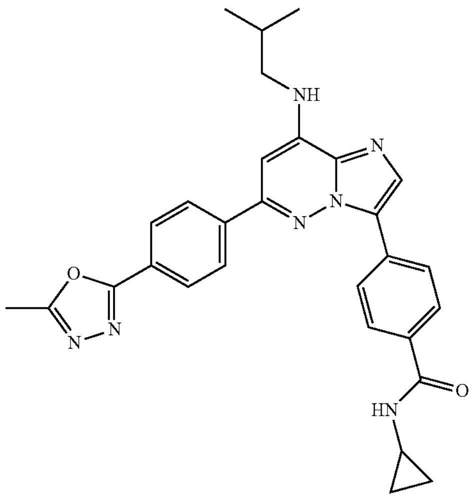 [SMILES: Cc1nnc(-c2ccc(-c3cc(NCC(C)C)c4ncc(-c5ccc(C(=O)NC6CC6)cc5)n4n3)cc2)o1] | N-cyclopropyl-4-{6-[4-(5-methyl-1,3,4-oxadiazol-2-yl)phenyl]-8-[(2-methylpropyl)amino]imidazo[1,2-b]pyridazin-3-yl}benzamide | RT = 1.26<br>MW found = 508.6<br>MW calc = 507.6 |
| 149 | 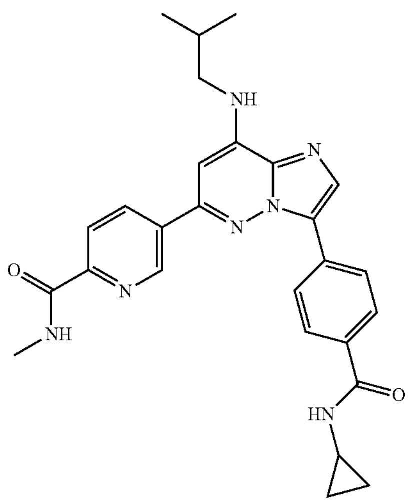 [SMILES: CNC(=O)c1ccc(-c2cc(NCC(C)C)c3ncc(-c4ccc(C(=O)NC5CC5)cc4)n3n2)cn1] | 5-{3-[4-(Cyclopropylcarbamoyl)phenyl]-8-[(2-methylpropyl)amino]imidazo[1,2-b]pyridazin-6-yl}-N-methylpyridine-2-carboxamide | RT = 1.18<br>MW found = 484.6<br>MW calc = 483.6 |
| 150 | 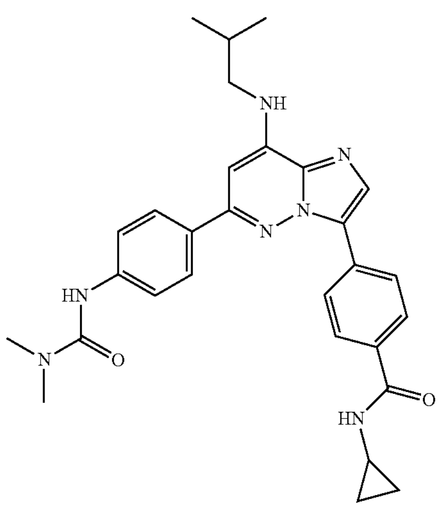 [SMILES: CC(C)CNc1cc(-c2ccc(NC(=O)N(C)C)cc2)nn2c(-c3ccc(C(=O)NC4CC4)cc3)cnc12] | N-cyclopropyl-4-(6-{4-[(dimethylcarbamoyl)amino]phenyl}-8-[(2-methylpropyl)amino]imidazo[1,2-b]pyridazin-3-yl)benzamide | RT = 1.18<br>MW found = 512.6<br>MW calc = 511.6 |

| Example | Structure | Name | Analytical Data |
|---|---|---|---|
| 151 | 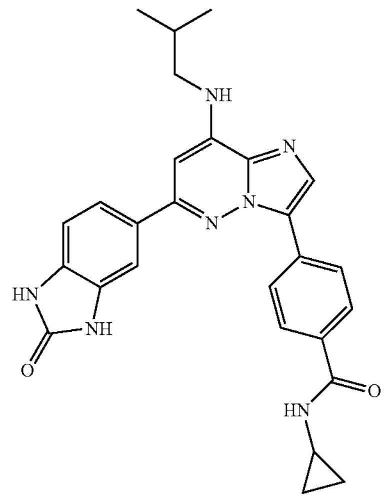 [SMILES: CC(C)CNc1cc(-c2ccc3[nH]c(=O)[nH]c3c2)nn2c(-c3ccc(C(=O)NC4CC4)cc3)cnc12] | N-cyclopropyl-4-{8-[(2-methylpropyl)amino]-6-(2-oxo-2,3-dihydro-1H-benzimidazol-5-yl)imidazo[1,2-b]pyridazin-3-yl}benzamide | RT = 1.07<br>MWfound = 482.5<br>MWcalc = 481.5 |
| 152 | 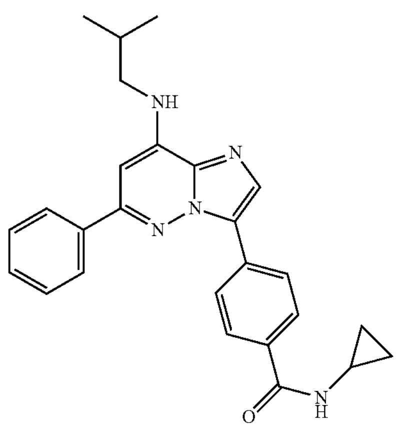 [SMILES: CC(C)CNc1cc(-c2ccccc2)nn2c(-c3ccc(C(=O)NC4CC4)cc3)cnc12] | N-cyclopropyl-4-{8-[(2-methylpropyl)amino]-6-phenylimidazo[1,2-b]pyridazin-3-yl}benzamide | RT = 1.39<br>MWfound = 426.5<br>MWcalc = 425.5 |
| 153 | 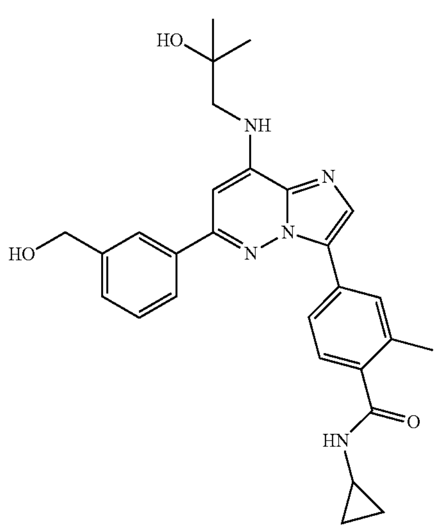 [SMILES: Cc1cc(-c2cnc3c(NCC(C)(C)O)cc(-c4cccc(CO)c4)nn23)ccc1C(=O)NC1CC1] | N-cyclopropyl-4-{6-[3-(hydroxymethyl)phenyl]-8-[(2-hydroxy-2-methylpropyl)amino]imidazo[1,2-b]pyridazin-3-yl}-2-methylbenzamide | RT = 1.00<br>MWfound = 486.6<br>MWcalc = 485.6 |

-continued

| Example | Structure | Name | Analytical Data |
|---|---|---|---|
| 154 | 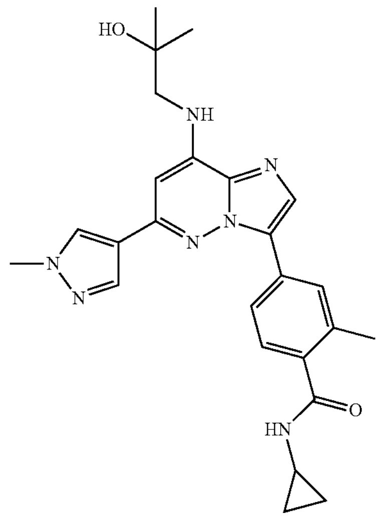 | N-cyclopropyl-4-{8-[(2-hydroxy-2-methylpropyl)amino]-6-(1-methyl-1H-pyrazol-4-yl)imidazo[1,2-b]pyridazin-3-yl}-2-methylbenzamide | RT = 0.93<br>MW found = 460.5<br>MW calc = 459.5 |
| 155 | 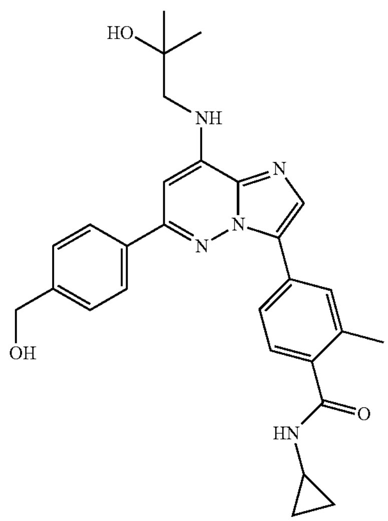 [SMILES: Cc1cc(-c2cnc3c(NCC(C)(C)O)cc(-c4ccc(CO)cc4)nn23)ccc1C(=O)NC1CC1] | N-cyclopropyl-4-{6-[4-(hydroxymethyl)phenyl]-8-[(2-hydroxy-2-methylpropyl)amino]imidazo[1,2-b]pyridazin-3-yl}-2-methylbenzamide | RT = 0.97<br>MW found = 486.6<br>MW calc = 485.6 |
| 156 | 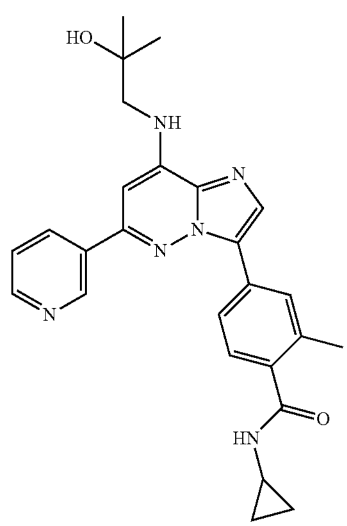 [SMILES: Cc1cc(-c2cnc3c(NCC(C)(C)O)cc(-c4cccnc4)nn23)ccc1C(=O)NC1CC1] | N-cyclopropyl-4-{8-[(2-hydroxy-2-methylpropyl)amino]-6-(pyridin-3-yl)imidazo[1,2-b]pyridazin-3-yl}-2-methylbenzamide | RT = 0.91<br>MW found = 457.5<br>MW calc = 456.5 |

-continued

| Example | Structure | Name | Analytical Data |
|---|---|---|---|
| 157 | 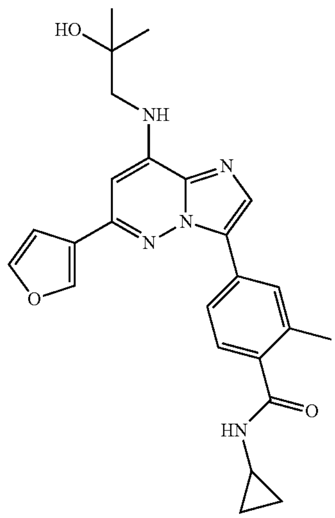 [SMILES: Cc1cc(-c2cnc3c(NCC(C)(C)O)cc(-c4ccoc4)nn23)ccc1C(=O)NC1CC1] | N-cyclopropyl-4-{6-(furan-3-yl)-8-[(2-hydroxy-2-methylpropyl)amino]imidazo[1,2-b]pyridazin-3-yl}-2-methylbenzamide | RT = 1.09<br>MWfound = 446.5<br>MWcalc = 445.5 |
| 158 | 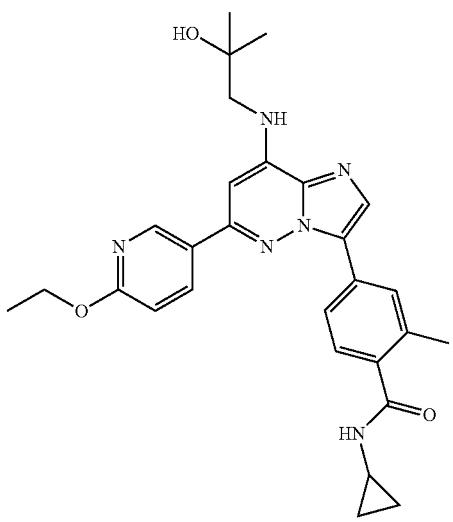 [SMILES: CCOc1ccc(-c2cc(NCC(C)(C)O)c3ncc(-c4ccc(C(=O)NC5CC5)c(C)c4)n3n2)cn1] | N-cyclopropyl-4-{6-(6-ethoxypyridin-3-yl)-8-[(2-hydroxy-2-methylpropyl)amino]imidazo[1,2-b]pyridazin-3-yl}-2-methylbenzamide | RT = 1.20<br>MWfound = 501.6<br>MWcalc = 500.6 |
| 159 | 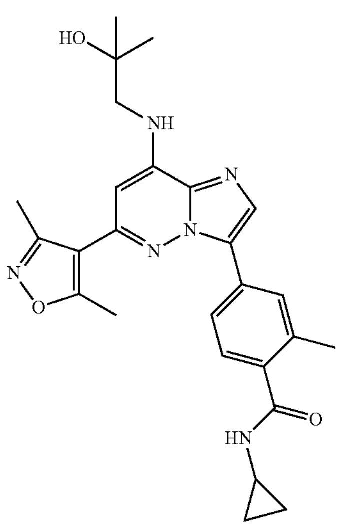 [SMILES: Cc1cc(-c2cnc3c(NCC(C)(C)O)cc(-c4c(C)noc4C)nn23)ccc1C(=O)NC1CC1] | N-cyclopropyl-4-{6-(3,5-dimethyl-1,2-oxazol-4-yl)-8-[(2-hydroxy-2-methylpropyl)amino]imidazo[1,2-b]pyridazin-3-yl}-2-methylbenzamide | RT = 1.06<br>MWfound = 475.6<br>MWcalc = 474.6 |

-continued

| Example | Structure | Name | Analytical Data |
|---|---|---|---|
| 160 | 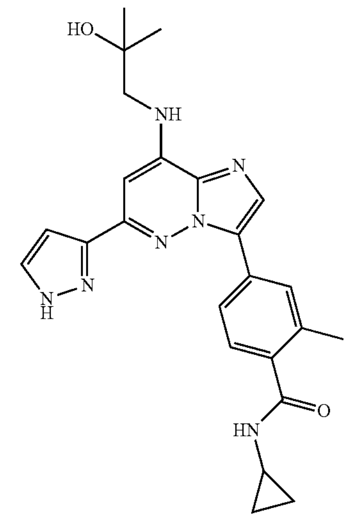 [SMILES: Cc1cc(-c2cnc3c(NCC(C)(C)O)cc(-c4cc[nH]n4)nn23)ccc1C(=O)NC1CC1] | N-cyclopropyl-4-{8-[(2-hydroxy-2-methylpropyl)amino]-6-(1H-pyrazol-3-yl)imidazo[1,2-b]pyridazin-3-yl}-2-methylbenzamide | RT = 0.90<br>MWfound = 446.5<br>MWcalc = 445.5 |
| 161 | 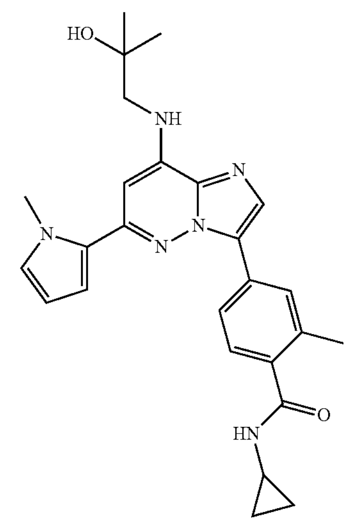 [SMILES: Cc1cc(-c2cnc3c(NCC(C)(C)O)cc(-c4cccn4C)nn23)ccc1C(=O)NC1CC1] | N-cyclopropyl-4-{8-[(2-hydroxy-2-methylpropyl)amino]-6-(1-methyl-1H-pyrrol-2-yl)imidazo[1,2-b]pyridazin-3-yl}-2-methylbenzamide | RT = 1.12<br>MWfound = 459.6<br>MWcalc = 458.6 |
| 162 | 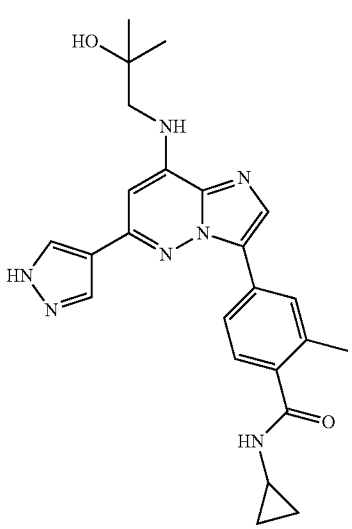 [SMILES: Cc1cc(-c2cnc3c(NCC(C)(C)O)cc(-c4cn[nH]c4)nn23)ccc1C(=O)NC1CC1] | N-cyclopropyl-4-{8-[(2-hydroxy-2-methylpropyl)amino]-6-(1H-pyrazol-4-yl)imidazo[1,2-b]pyridazin-3-yl}-2-methylbenzamide | RT = 0.84<br>MWfound = 446.5<br>MWcalc = 445.5 |

-continued

| Example | Structure | Name | Analytical Data |
|---|---|---|---|
| 163 | 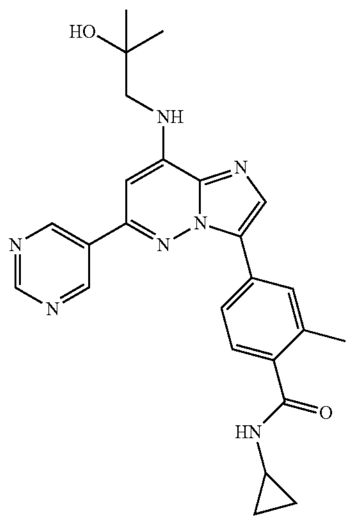 [SMILES: Cc1cc(-c2cnc3c(NCC(C)(C)O)cc(-c4cncnc4)nn23)ccc1C(=O)NC1CC1] | N-cyclopropyl-4-{8-[(2-hydroxy-2-methylpropyl)amino]-6-(pyrimidin-5-yl)imidazo[1,2-b]pyridazin-3-yl}-2-methylbenzamide | RT = 0.94<br>MWfound = 458.5<br>MWcalc = 457.5 |
| 164 | 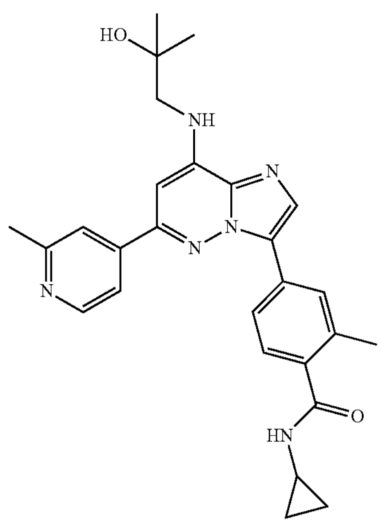 | N-cyclopropyl-4-{8-[(2-hydroxy-2-methylpropyl)amino]-6-(2-methylpyridin-4-yl)imidazo[1,2-b]pyridazin-3-yl}-2-methylbenzamide | RT = 0.80<br>MWfound = 471.6<br>MWcalc = 470.6 |
| 165 | 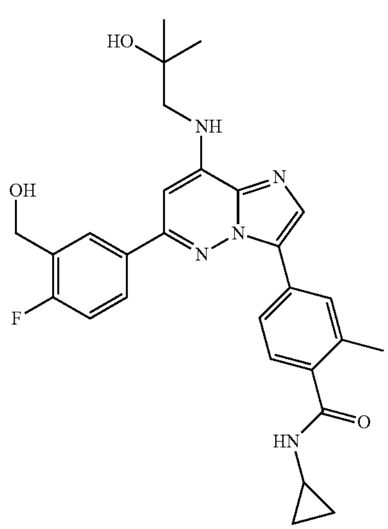 [SMILES: Cc1cc(-c2cnc3c(NCC(C)(C)O)cc(-c4ccc(F)c(CO)c4)nn23)ccc1C(=O)NC1CC1] | N-cyclopropyl-4-{6-[4-fluoro-3-(hydroxymethyl)phenyl]-8-[(2-hydroxy-2-methylpropyl)amino]imidazo[1,2-b]pyridazin-3-yl}-2-methylbenzamide | RT = 1.04<br>MWfound = 504.6<br>MWcalc = 503.6 |

| Example | Structure | Name | Analytical Data |
|---|---|---|---|
| 166 | 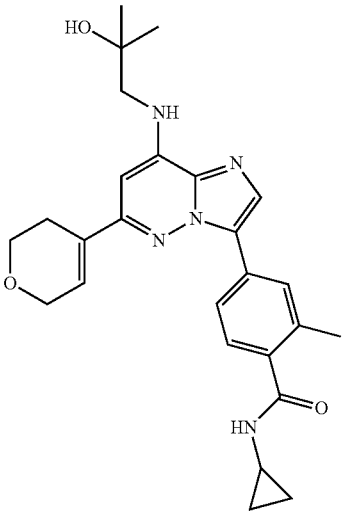 [SMILES: Cc1cc(-c2cnc3c(NCC(C)(C)O)cc(C4=CCOCC4)nn23)ccc1C(=O)NC1CC1] | N-cyclopropyl-4-{6-(3,6-dihydro-2H-pyran-4-yl)-8-[(2-hydroxy-2-methylpropyl)amino]imidazo[1,2-b]pyridazin-3-yl}-2-methylbenzamide | RT = 1.06<br>MWfound = 462.6<br>MWcalc = 461.6 |

The following compound examples were prepared analogously to the procedure described for example 51 using the appropriate alcohol or thiol building block [LC-MS data such as retention time (RT in min) or observed mass peak were collected using LC-MS Method A unless explicitly stated]:

| Example | Structure | Name | Analytical Data |
|---|---|---|---|
| 167 | 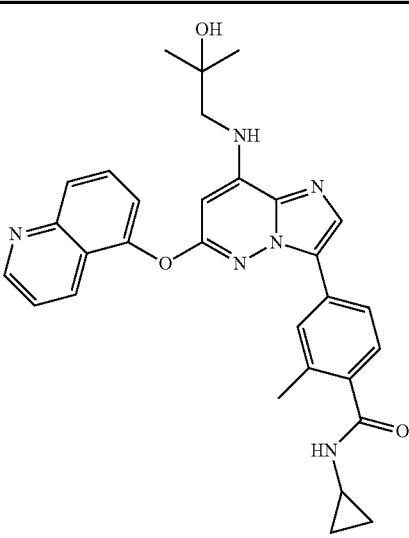 | N-cyclopropyl-4-{8-[(2-hydroxy-2-methylpropyl)amino]-6-(quinolin-5-yloxy)imidazo[1,2-b]pyridazin-3-yl}-2-methylbenzamide | RT = 1.03<br>$MW_{found}$ = 523.6<br>$MW_{calc}$ = 522.6 |

| Example | Structure | Name | Analytical Data |
|---|---|---|---|
| 168 | 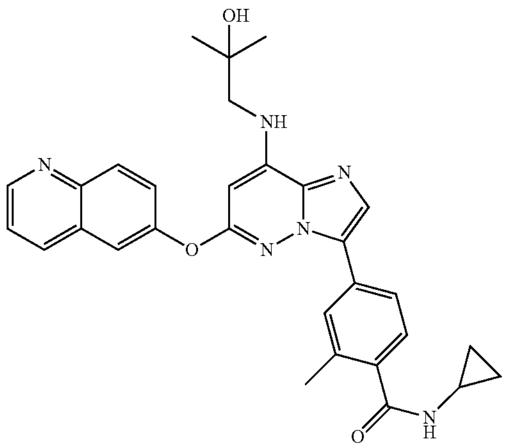 [SMILES: Cc1cc(-c2cnc3c(NCC(C)(C)O)cc(Oc4ccc5ncccc5c4)nn23)ccc1C(=O)NC1CC1] | N-cyclopropyl-4-{8-[(2-hydroxy-2-methylpropyl)amino]-6-(quinolin-6-yloxy)imidazo[1,2-b]pyridazin-3-yl}-2-methylbenzamide | RT = 0.99<br>$MW_{found}$ = 523.6<br>$MW_{calc}$ = 522.6 |
| 169 | 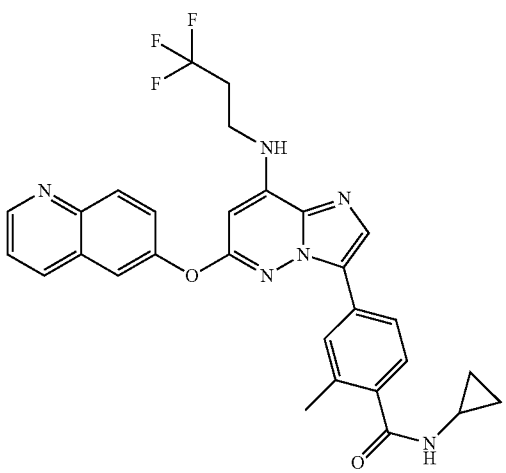 [SMILES: Cc1cc(-c2cnc3c(NCCC(F)(F)F)cc(Oc4ccc5ncccc5c4)nn23)ccc1C(=O)NC1CC1] | N-cyclopropyl-2-methyl-4-{6-(quinolin-6-yloxy)-8-[(3,3,3-trifluoropropyl)amino]imidazo[1,2-b]pyridazin-3-yl}benzamide | RT = 1.17<br>$MW_{found}$ = 547.6<br>$MW_{calc}$ = 546.6 |
| 170 | 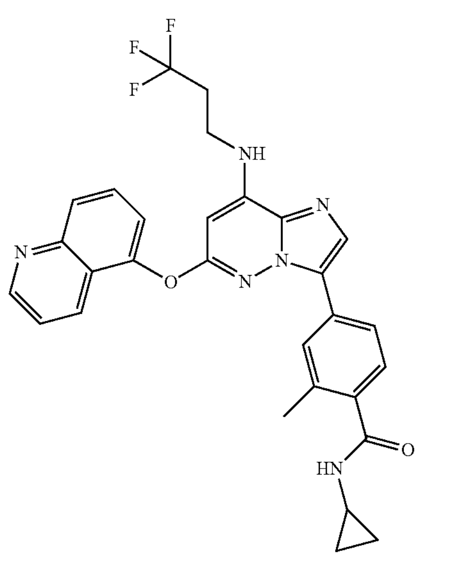 [SMILES: Cc1cc(-c2cnc3c(NCCC(F)(F)F)cc(Oc4cccc5ncccc45)nn23)ccc1C(=O)NC1CC1] | N-cyclopropyl-2-methyl-4-{6-(quinolin-5-yloxy)-8-[(3,3,3-trifluoropropyl)amino]imidazo[1,2-b]pyridazin-3-yl}benzamide | RT = 1.20<br>$MW_{found}$ = 547.6<br>$MW_{calc}$ = 546.6 |

| Example | Structure | Name | Analytical Data |
|---|---|---|---|
| 171 | 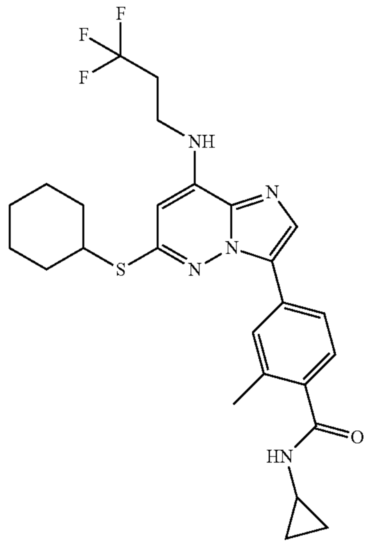 [SMILES: Cc1cc(-c2cnc3c(NCCC(F)(F)F)cc(SC4CCCCC4)nn23)ccc1C(=O)NC1CC1] | 4-{6-(cyclohexylsulfanyl)-8-[(3,3,3-trifluoropropyl)amino]imidazo[1,2-b]pyridazin-3-yl}-N-cyclopropyl-2-methylbenzamide | RT = 1.51<br>$MW_{found}$ = 518.6<br>$MW_{calc}$ = 517.6 |
| 172 | 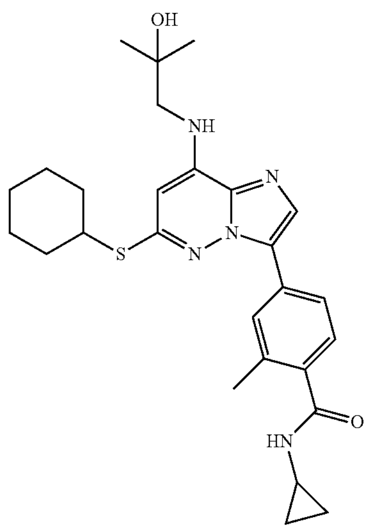 [SMILES: Cc1cc(-c2cnc3c(NCC(C)(C)O)cc(SC4CCCCC4)nn23)ccc1C(=O)NC1CC1] | 4-{6-(cyclohexylsulfanyl)-8-[(2-hydroxy-2-methylpropyl)amino]imidazo[1,2-b]pyridazin-3-yl}-N-cyclopropyl-2-methylbenzamide | RT = 1.36<br>$MW_{found}$ = 494.7<br>$MW_{calc}$ = 493.7 |
| 173 | 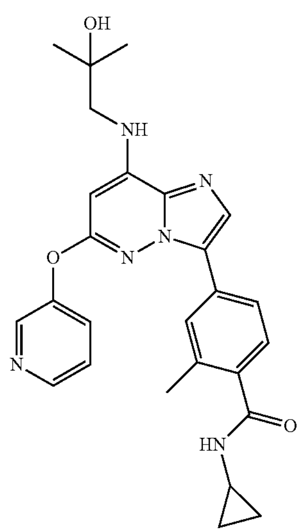 [SMILES: Cc1cc(-c2cnc3c(NCC(C)(C)O)cc(Oc4cccnc4)nn23)ccc1C(=O)NC1CC1] | N-cyclopropyl-4-{8-[(2-hydroxy-2-methylpropyl)amino]-6-(pyridin-3-yloxy)imidazo[1,2-b]pyridazin-3-yl}-2-methylbenzamide | RT = 0.96<br>$MW_{found}$ = 473.6<br>$MW_{calc}$ = 472.6 |

| Example | Structure | Name | Analytical Data |
|---|---|---|---|
| 174 | 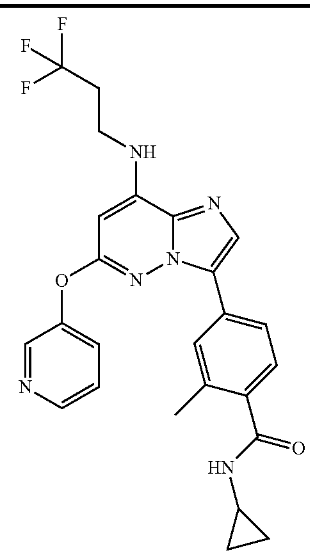 | N-cyclopropyl-2-methyl-4-{6-(pyridin-3-yloxy)-8-[(3,3,3-trifluoropropyl)amino]imidazo[1,2-b]pyridazin-3-yl}benzamide | RT = 1.14<br>$MW_{found}$ = 497.5<br>$MW_{calc}$ = 496.5 |

Example 175

3-[4-(2-Cyclopropyl-1H-imidazol-5-yl)phenyl]-6-ethenyl-N-(3,3,3-trifluoropropyl)imidazo[1,2-b]pyridazin-8-amine

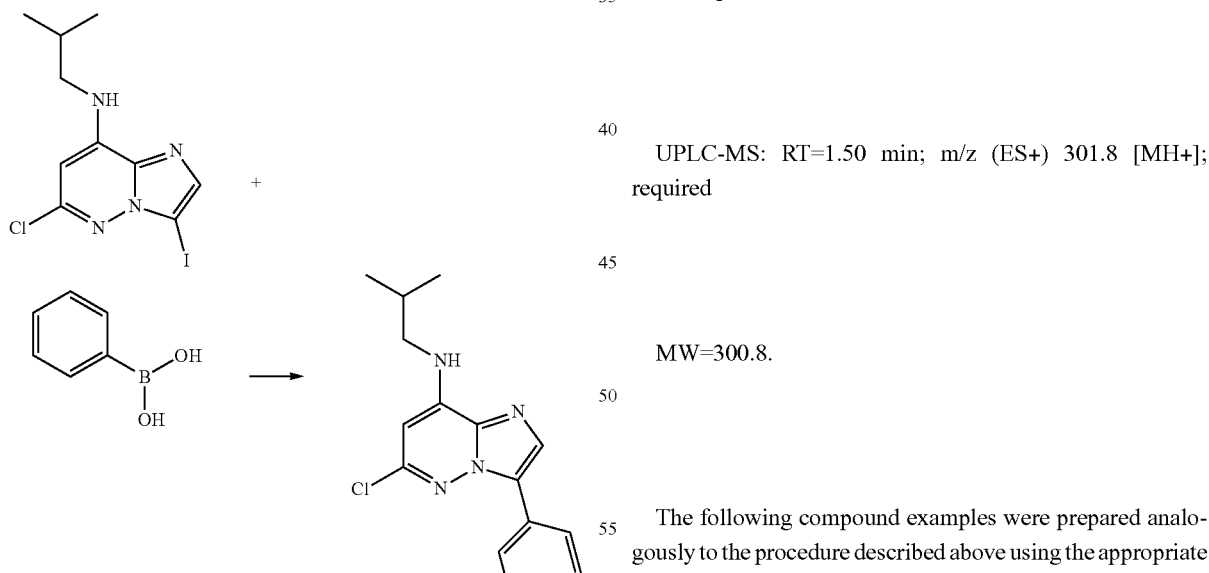

52 mg (150 μmol) 6-chloro-3-iodo-N-(2-methylpropyl)imidazo[1,2-b]pyridazin-8-amine which was prepared according to intermediate example 100b were transformed in analogy to intermediate example 1a using phenylboronic acid to give after working up and purification 7.4 mg (17%) of the title compound.

UPLC-MS: RT=1.50 min; m/z (ES+) 301.8 [MH+]; required

MW=300.8.

The following compound examples were prepared analogously to the procedure described above using the appropriate boronic acid building block [LC-MS data such as retention time (RT in min) or observed mass peak were collected using LC-MS Method A unless explicitly stated]:

| Example | Structure | Name | Analytical Data |
|---|---|---|---|
| 176 | 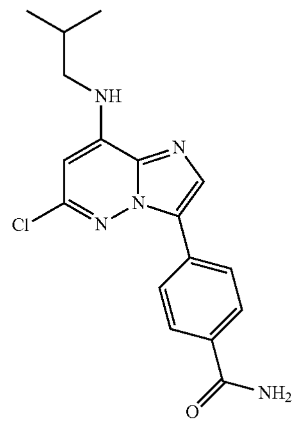 [SMILES: CC(C)CNc1cc(Cl)nn2c(-c3ccc(C(N)=O)cc3)cnc12] | 4-{6-Chloro-8-[(2-methylpropyl)amino]imidazo[1,2-b]pyridazin-3-yl}benzamide | RT = 1.17<br>$MW_{found}$ = 344.8<br>$MW_{calc}$ = 343.8 |
| 177 | 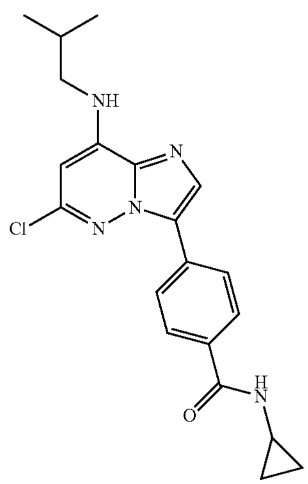 [SMILES: CC(C)CNc1cc(Cl)nn2c(-c3ccc(C(=O)NC4CC4)cc3)cnc12] | 4-{6-Chloro-8-[(2-methylpropyl)amino]imidazo[1,2-b]pyridazin-3-yl}-N-cyclopropylbenzamide | RT = 1.29<br>$MW_{found}$ = 384.9<br>$MW_{calc}$ = 383.9 |
| 178 | 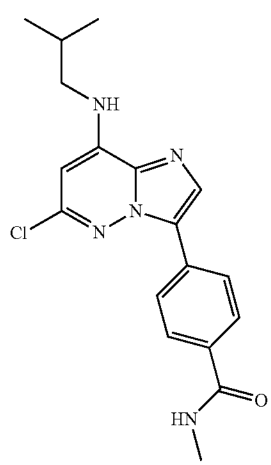 [SMILES: CNC(=O)c1ccc(-c2cnc3c(NCC(C)C)cc(Cl)nn23)cc1] | 4-{6-Chloro-8-[(2-methylpropyl)amino]imidazo[1,2-b]pyridazin-3-yl}-N-methylbenzamide | RT = 1.22<br>$MW_{found}$ = 358.8<br>$MW_{calc}$ = 357.8 |

-continued

| Example | Structure | Name | Analytical Data |
|---|---|---|---|
| 179 | 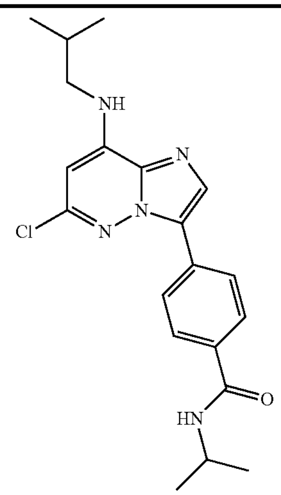 | 4-{6-Chloro-8-[(2-methylpropyl)amino]imidazo[1,2-b]pyridazin-3-yl}-N-(propan-2-yl)benzamide | RT = 1.34<br>$MW_{found}$ = 386.9<br>$MW_{calc}$ = 385.9 |
| 180 | 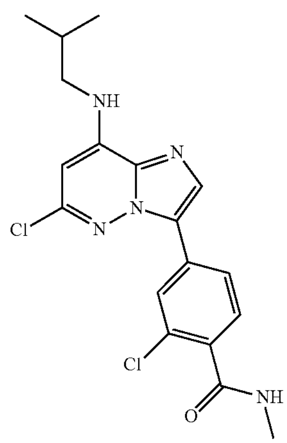 [SMILES: CNC(=O)c1ccc(-c2cnc3c(NCC(C)C)cc(Cl)nn23)cc1Cl] | 2-Chloro-4-{6-chloro-8-[(2-methylpropyl)amino]imidazo[1,2-b]pyridazin-3-yl}-N-methylbenzamide | RT = 1.27<br>$MW_{found}$ = 393.3<br>$MW_{calc}$ = 392.3 |
| 181 | 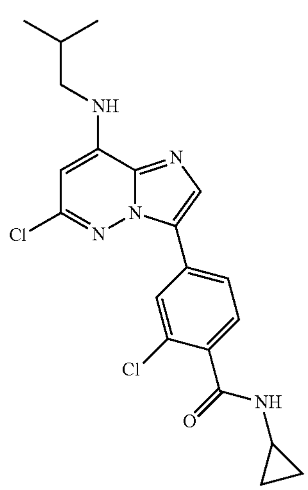 [SMILES: CC(C)CNc1cc(Cl)nn2c(-c3ccc(C(=O)NC4CC4)c(Cl)c3)cnc12] | 2-Chloro-4-{6-chloro-8-[(2-methylpropyl)amino]imidazo[1,2-b]pyridazin-3-yl}-N-cyclopropylbenzamide | RT = 1.34<br>$MW_{found}$ = 419.3<br>$MW_{calc}$ = 418.3 |

| Example | Structure | Name | Analytical Data |
|---|---|---|---|
| 182 | 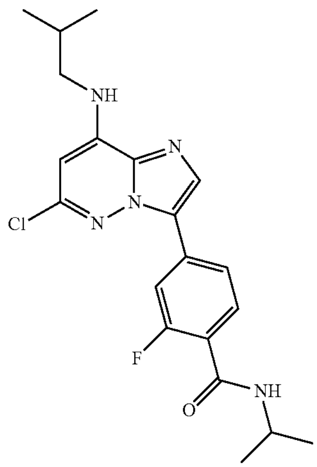 [SMILES: CC(C)CNc1cc(Cl)nn2c(-c3ccc(C(=O)NC(C)C)c(F)c3)cnc12] | 4-{6-Chloro-8-[(2-methylpropyl)amino]imidazo[1,2-b]pyridazin-3-yl}-2-fluoro-N-(propan-2-yl)benzamide | RT = 1.42<br>$MW_{found}$ = 404.9<br>$MW_{calc}$ = 403.9 |
| 183 | 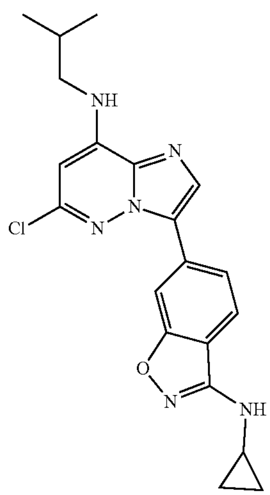 [SMILES: CC(C)CNc1cc(Cl)nn2c(-c3ccc4c(NC5CC5)noc4c3)cnc12] | 6-Chloro-3-[3-(cyclopropylamino)-1,2-benzoxazol-6-yl]-N-(2-methylpropyl)imidazo[1,2-b]pyridazin-8-amine | RT = 1.40<br>$MW_{found}$ = 397.9<br>$MW_{calc}$ = 396.9 |
| 184 | 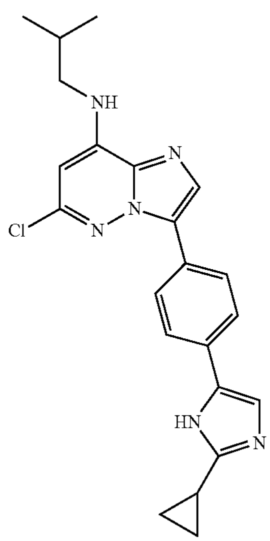 [SMILES: CC(C)CNc1cc(Cl)nn2c(-c3ccc(-c4cnc(C5CC5)[nH]4)cc3)cnc12] | 6-Chloro-3-[4-(2-cyclopropyl-1H-imidazol-5-yl)phenyl]-N-(2-methylpropyl)imidazo[1,2-b]pyridazin-8-amine | RT = 0.95<br>$MW_{found}$ = 407.9<br>$MW_{calc}$ = 406.9 |

Example 185

4-{6-Chloro-8-[(thiophen-2-ylmethyl)amino]imidazo[1,2-b]pyridazin-3-yl}-N,N-dimethylbenzamide

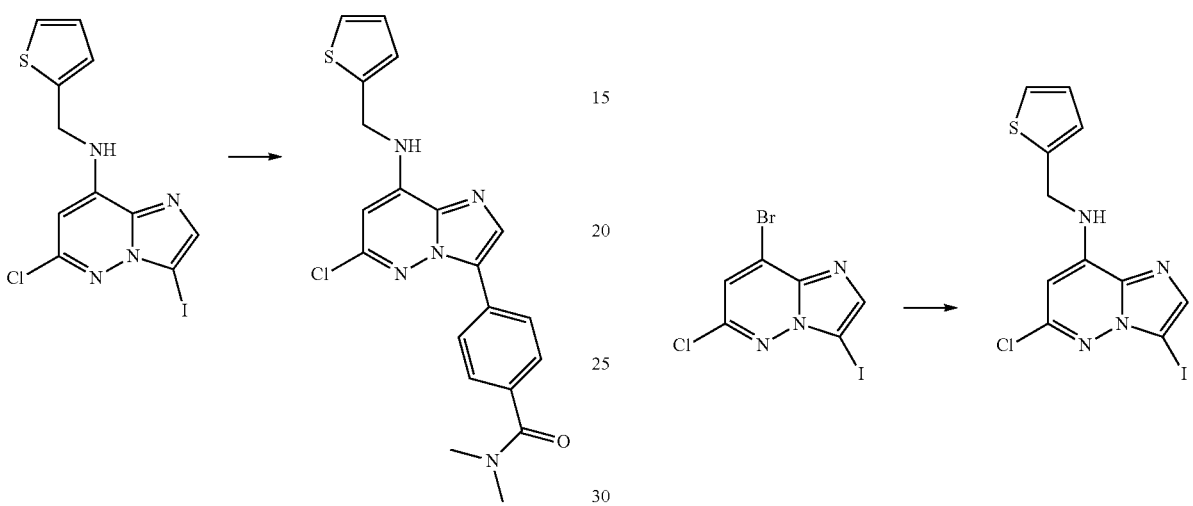

117 mg (300 µmol) 6-chloro-3-iodo-N-(thiophen-2-ylmethyl)imidazo[1,2-b]pyridazin-8-amine which was prepared according to intermediate example 185a were transformed in analogy to intermediate example 100a using [4-(dimethylcarbamoyl)phenyl]boronic acid to give after working up and purification 15 mg (12%) of the title compound.

UPLC-MS: RT=1.25 min; m/z (ES$^+$) 412.9 [MH+]; required MW 411.9.

Intermediate Example 185a 6-chloro-3-iodo-N-(thiophen-2-ylmethyl)imidazo[1,2-b]pyridazin-8-amine 6-chloro-3-iodo-N-(thiophen-2-ylmethyl)imidazo[1,2-b]pyridazin-8-amine was prepared in analogy to example 100b using 1-(thiophen-2-yl)methanamine which was prepared according to intermediate example 1c to give after working up and purification 80% of the title compound.

The following compound examples were prepared analogously to the procedure described for example 185 using the appropriate boronic acid building block [LC-MS data such as retention time (RT in min) or observed mass peak were collected using LC-MS Method A unless explicitly stated]:

| Example | Structure | Name | Analytical Data |
|---|---|---|---|
| 186 | 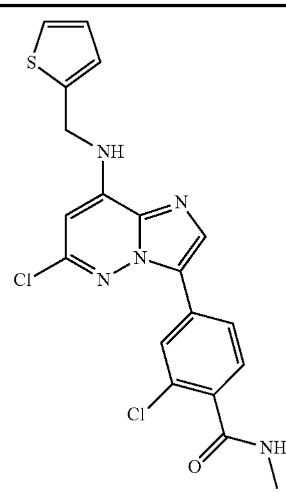 | 2-Chloro-4-{6-chloro-8-[(thiophen-2-ylmethyl)amino]imidazo[1,2-b]pyridazin-3-yl}-N-methylbenzamide | RT = 1.24<br>MW$_{found}$ = 433.3<br>MW$_{calc}$ = 432.3 |

-continued

| Example | Structure | Name | Analytical Data |
|---|---|---|---|
| 187 | 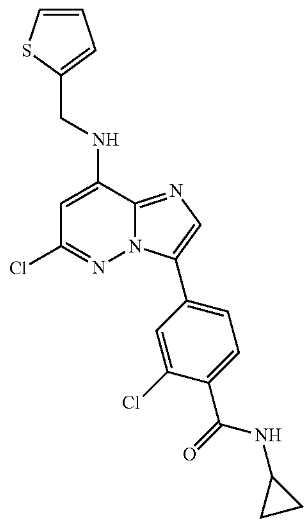 [SMILES: O=C(NC1CC1)c1ccc(-c2cnc3c(NCc4cccs4)cc(Cl)nn23)cc1Cl] | 2-Chloro-4-{6-chloro-8-[(thiophen-2-ylmethyl)amino]imidazo[1,2-b]pyridazin-3-yl}-N-cyclopropyl-benzamide | RT = 1.31<br>$MW_{found}$ = 459.4<br>$MW_{calc}$ = 458.4 |
| 188 | 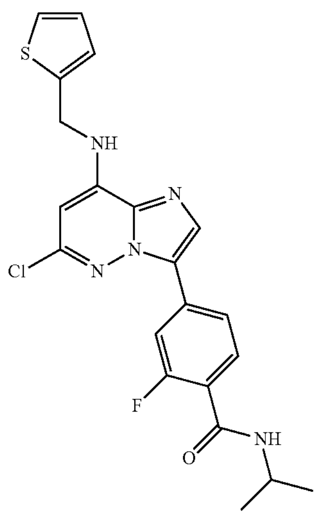 [SMILES: CC(C)NC(=O)c1ccc(-c2cnc3c(NCc4cccs4)cc(Cl)nn23)cc1F] | 4-{6-Chloro-8-[(thiophen-2-ylmethyl)amino]imidazo[1,2-b]pyridazin-3-yl}-2-fluoro-N-(propan-2-yl)benzamide | RT = 1.40<br>$MW_{found}$ = 444.9<br>$MW_{calc}$ = 443.9 |
| 189 | 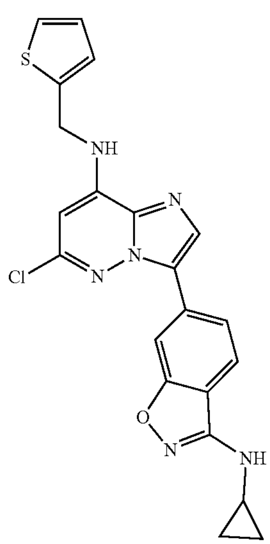 [SMILES: Clc1cc(NCc2cccs2)c2ncc(-c3ccc4c(NC5CC5)noc4c3)n2n1] | 6-Chloro-3-[3-(cyclopropylamino)-1,2-benzoxazol-6-yl]-N-(thiophen-2-ylmethyl)imidazo[1,2-b]pyridazin-8-amine | RT = 1.37<br>$MW_{found}$ = 437.9<br>$MW_{calc}$ = 436.9 |

-continued

| Example | Structure | Name | Analytical Data |
|---|---|---|---|
| 190 | 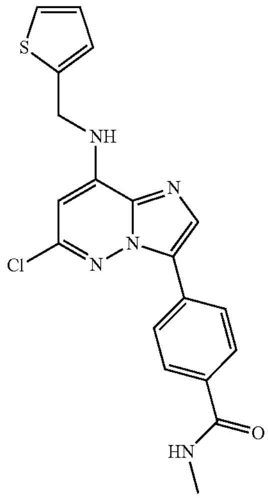 [SMILES: CNC(=O)c1ccc(-c2cnc3c(NCc4cccs4)cc(Cl)nn23)cc1] | 4-{6-Chloro-8-[(thiophen-2-yl-methyl)amino]imidazo[1,2-b]pyridazin-3-yl}-N-methylbenzamide | RT = 1.45<br>$MW_{found}$ = 398.9<br>$MW_{calc}$ = 397.9 |
| 191 | 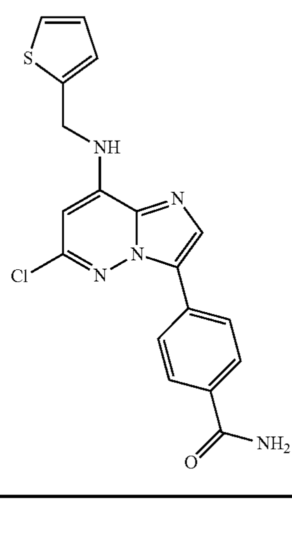 | 4-{6-Chloro-8-[(thiophen-2-yl-methyl)amino]imidazol[1,2-b]pyridazin-3-yl}benzamide | RT = 1.14<br>$MW_{found}$ = 384.9<br>$MW_{calc}$ = 383.9 |

Example 192

N-cyclopropyl-4-[8-({(2S)-2-[(4R)-2,2-dimethyl-1,3-dioxolan-4-yl]-2-hydroxyethyl}amino)-6-(1-methyl-1H-pyrazol-5-yl)imidazo[1,2-b]pyridazin-3-yl]benzamide

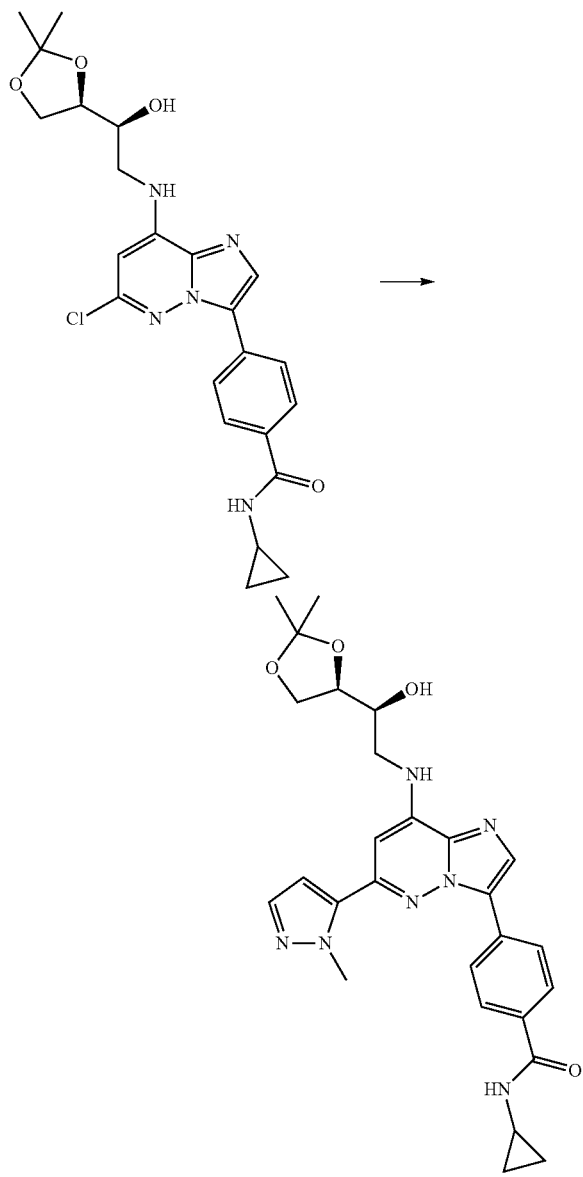

To a mixture of 52 mg (94 mot) 4-[6-chloro-8-({(2S)-2-[(4R)-2,2-dimethyl-1,3-dioxolan-4-yl]-2-hydroxyethyl}amino)imidazo[1,2-b]pyridazin-3-yl]-N-cyclopropylbenzamide which was prepared according to intermediate example 192a, 33 mg 1-methyl-1H-pyrazol-5-yl) boronic acid, 6.5 mg tetrakis(triphenylphosphin)palladium in 1 mL of ethanol and 1 mL of toluene was added 0.26 mL of an aqueous 10% sodiumbicarbonate solution and the mixture was stirred at 120° C. for 2 hours under microwave irradiation. Then the mixture was filtered, the solvent was removed and the residue was purified by chromatography to give 36 mg of the title compounds.

1H-NMR (DMSO-d6): δ=0.49-0.68 (4H), 1.24 (3H), 1.32 (3H), 2.62 (1H), 3.31-3.95 (3H), 3.60-4.05 (3H), 4.12 (3H), 6.54 (1H), 6.85 (1H), 7.31 (1H) 7.90 (2H), 8.07 (1H), 8.18 (2H), 8.45 (1H), ppm.

Intermediate Example 192a

4-[6-chloro-8-({(2S)-2-[(4R)-2,2-dimethyl-1,3-dioxolan-4-yl]-2-hydroxyethyl}amino) imidazo[1,2-b]pyridazin-3-yl]-N-cyclopropylbenzamide

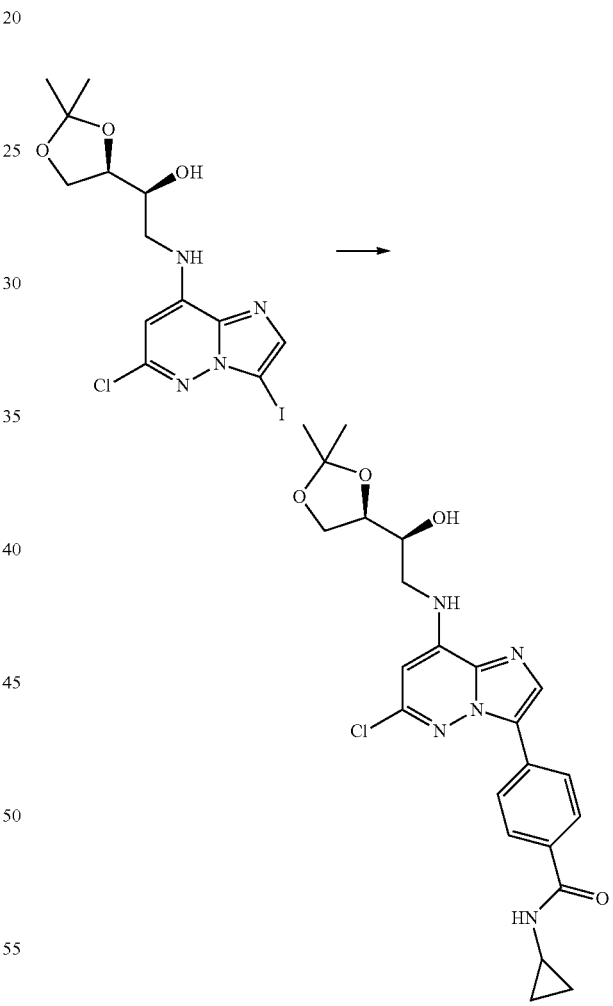

300 mg (684 μmol) (1S)-2-[(6-chloro-3-iodoimidazo[1,2-b]pyridazin-8-yl)amino]-1-[(4R)-2,2-dimethyl-1,3-dioxolan-4-yl]ethanol which was prepared according to intermediate example 192b were transformed in analogy to intermediate example 1a using [4-(cyclopropylcarbamoyl)phenyl]boronic acid to give after working up and purification 17 mg (5%) of the title compound.

Intermediate Example 192b (1S)-2-[(6-chloro-3-iodoimidazo[1,2-b]pyridazin-8-yl)amino]-1-[(4R)-2,2-dimethyl-1,3-dioxolan-4-yl]ethanol

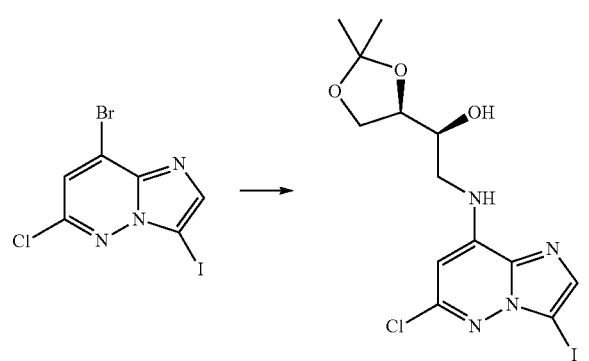 [SMILES: Clc1cc(Br)c2ncc(I)n2n1 ; CC1(C)OC[C@H]([C@@H](O)CNc2cc(Cl)nn3c(I)cnc23)O1]

700 mg (1.95 mmol) 8-bromo-6-chloro-3-iodoimidazo[1,2-b]pyridazine which was prepared according to intermediate example 1c were transformed in analogy to intermediate example 1b using (1S)-2-amino-1-[(4R)-2,2-dimethyl-1,3-dioxolan-4-yl]ethanol to give after working up and purification 512 mg (60%) of the title compound.

Example 193

N-cyclopropyl-4-{8-[(2-methylpropyl)amino]-6-(methylsulfanyl)imidazo[1,2-b]pyridazin-3-yl}benzamide

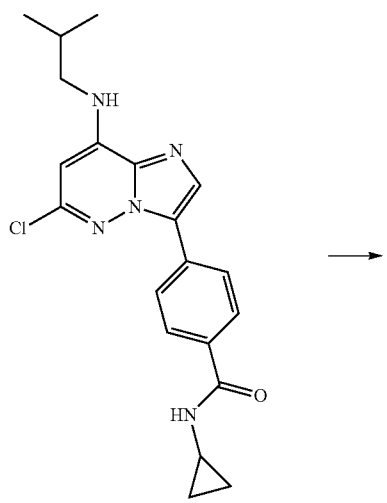

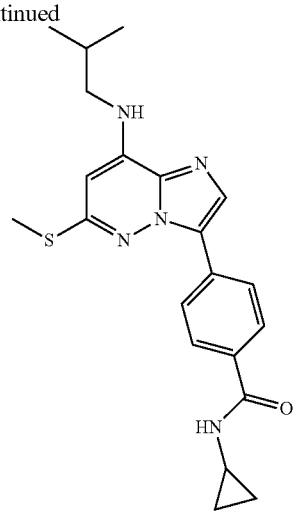

A solution of 450 mg (1172 μmol) of 4-[6-chloro-8-(isobutylamino)imidazo[1,2-b]pyridazin-3-yl]-N-cyclopropylbenzamide, which was prepared according to intermediate example 100a, and 330 mg (4690 μmol) sodiummethylsulfide in 8 mL of dimethylsulfoxide was heated for 60 min at 70° C. in the microwave. Then the mixture was poured onto water and the precipitate was collected and dried under vacuum to yield 460 mg of the title compound as a white solid.

¹H-NMR (DMSO-d6): δ=0.52-0.71 (4H), 0.88 (6H), 1.94 (1H), 2.56 (3H), 2.84 (1H), 3.08 (2H), 6.08 (1H), 7.49 (1H), 7.88 (2H), 7.97 (1H), 8.22 (2H), 8.43 (1H) ppm.

Example 194

(RS)—N-cyclopropyl-2-methyl-4-{8-[(2-methylpropyl)amino]-6-[(tetrahydrofuran-2-ylmethyl)sulfanyl]imidazo[1,2-b]pyridazin-3-yl}benzamide

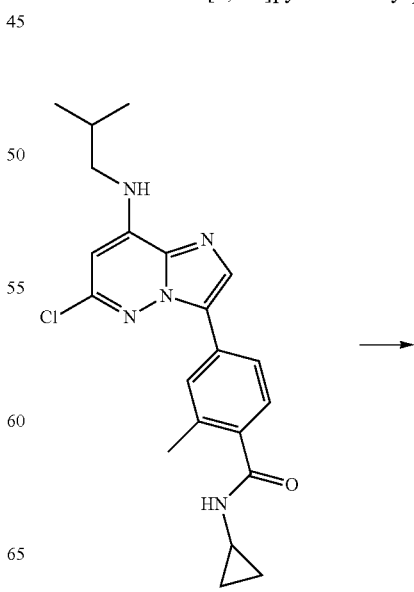

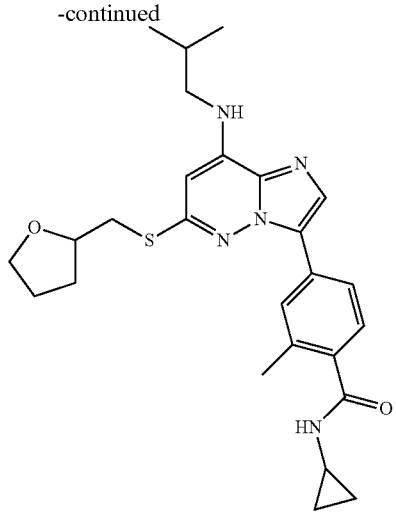

A solution of 45 mg (377 µmol) of (RS)-tetrahydrofuran-2-ylmethanethiol in 1 mL of dimethylsulfoxide was treated with 14 mg (350 µmol) of sodium hydride and stirred at room temperature for 2 hours. Then 100 mg (251 µmol) of 4-[6-chloro-8-(isobutylamino)imidazo[1,2-b]pyridazin-3-yl]-N-cyclopropyl-2-methylbenzamide, which was prepared according to intermediate example 194a, was added and the mixture was heated for 2 hours at 70° C. Then the mixture was purified by reversed phase chromatography to yield 12 mg of the title compound.

$^1$H-NMR (DMSO-d6): δ=0.48-0.68 (4H), 0.88 (6H), 1.63-1.99 (4H), 2.36 (3H), 2.81 (1H), 3.08 (2H), 3.22-3.36 (2H), 3.62 (1H), 3.76 (1H), 4.12 (1H), 6.04 (1H), 7.32 (1H), 7.50 (1H), 7.90 (1H), 7.93 (1H), 8.04 (1H), 8.29 (1H) ppm.

Intermediate Example 194a

4-[6-chloro-8-(isobutylamino)imidazo[1,2-b]pyridazin-3-yl]-N-cyclopropyl-2-methylbenzamide

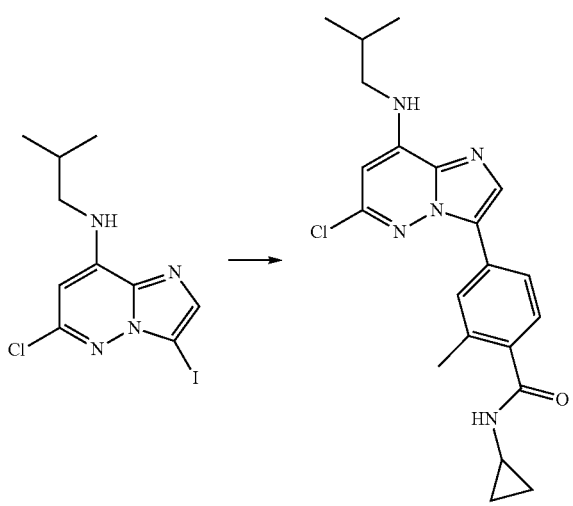 [SMILES: CC(C)CNc1cc(Cl)nn2c(I)cnc12 ; Cc1cc(-c2cnc3c(NCC(C)C)cc(Cl)nn23)ccc1C(=O)NC1CC1]

3.54 g (10.1 mmol) 6-Chloro-3-iodo-N-isobutylimidazo[1,2-b]pyridazin-8-amine which was prepared according to intermediate example 3b were transformed in analogy to intermediate example 1a using [4-(cyclopropylcarbamoyl)-3-methylphenyl]boronic acid to give after working up and purification 1.79 g (45%) of the title compound.

Example 195

N-cyclopropyl-2-methyl-4-{8-[(2-methylpropyl)amino]-6-(1H-pyrazol-5-yl) imidazo[1,2-b]pyridazin-3-yl}benzamide

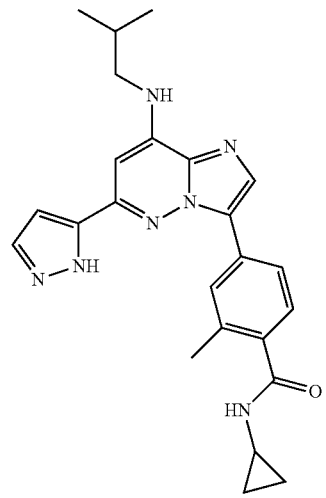

To a mixture of 125 mg (314 µmol) 4-[6-chloro-8-(isobutylamino)imidazo[1,2-b]pyridazin-3-yl]-N-cyclopropyl-2-methylbenzamide, which was prepared according to example 194a, 111 mg (942 µmol) 1H-pyrazol-5-yl boronic acid, 44 mg Tetrakis(triphenylphosphin)palladium in 2 mL of ethanol and 2 mL of toluene was added 0.63 mL of an aqueous 10% sodiumbicarbonate solution and the mixture was stirred at 120° C. for 2 hours under microwave irradiation. Then the mixture was filtered and concentrated and purified by chromatography to give 41 mg of the title compound.

$^1$H-NMR (DMSO-d6): δ=0.48-0.69 (4H), 0.91 (6H), 2.02 (1H), 2.39 (3H), 2.82 (1H), 3.17 (2H), 6.72 (1H), 6.78 (1H), 7.39 (1H), 7.85 (1H), 8.00 (1H), 8.10-8.17 (2H), 8.29 (1H), ppm.

305

Example 196

N-cyclopropyl-2-methyl-4-{8-[(2-methylpropyl)amino]-6-(methylsulfanyl) imidazo[1,2-b]pyridazin-3-yl}benzamide

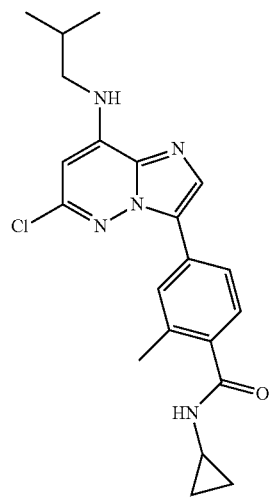

A solution of 50 mg (126 µmol) of 4-[6-chloro-8-(isobutylamino)imidazo[1,2-b]pyridazin-3-yl]-N-cyclopropyl-2-methylbenzamide, which was prepared according to example 194a, and 35 mg (503 µmol) sodiummethylsulfide in 1 mL of dimethylsulfoxide was heated for 30 min at 70° C. in the microwave. Then the mixture was poured onto water and the precipitate was collected and dried under vacuum to yield 26 mg of the title compound as a yellow solid.

¹H-NMR (DMSO-d6): δ=0.47-0.68 (4H), 0.88 (6H), 1.94 (1H), 2.35 (3H), 2.55 (3H) 2.80 (1H), 3.08 (2H), 6.06 (1H), 7.32 (1H), 7.47 (1H), 7.90 (1H), 7.98 (1H), 8.05 (1H), 8.29 (1H), ppm.

306

Example 197

N-cyclopropyl-2-methyl-4-{8-[(2-methylpropyl)amino]-6-(phenylsulfanyl) imidazo[1,2-b]pyridazin-3-yl}benzamide

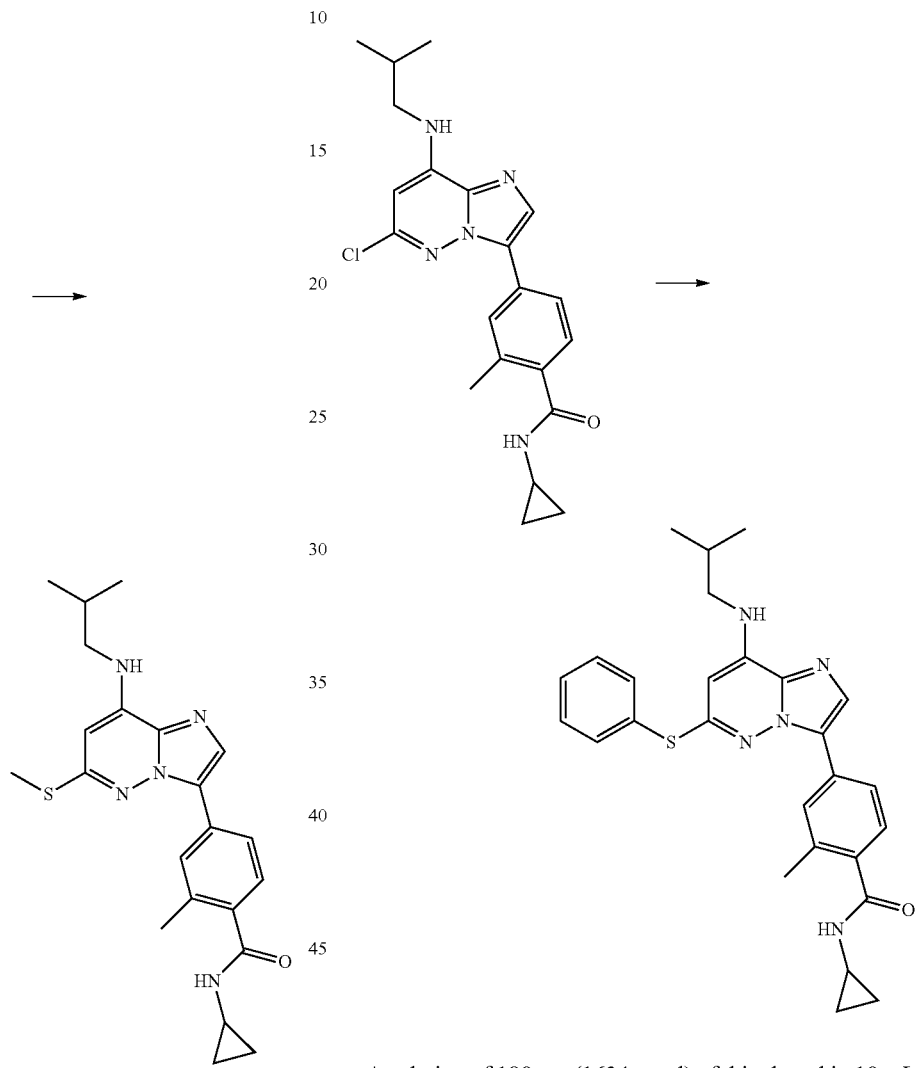

A solution of 180 mg (1634 µmol) of thiophenol in 10 mL of dimethylsulfoxide was treated with 64 mg (1608 µmol) of sodium hydride and stirred at room temperature for 2 hours. Then 100 mg (251 µmol) of 4-[6-chloro-8-(isobutylamino)imidazo[1,2-b]pyridazin-3-yl]-N-cyclopropyl-2-methylbenzamide, which was prepared according to intermediate example 194a, was added and the mixture was heated for 1.5 hours at 140° C. Then the mixture poured onto ice water and the precipitate was collected and subsequently purified by normal phase chromatography to yield 112 mg of the title compound.

¹H-NMR (DMSO-d6): δ=0.48-0.69 (4H), 0.84 (6H), 1.87 (1H), 2.21 (3H), 2.79 (1H), 3.03 (2H), 5.99 (1H), 7.10 (1H), 7.49 (3H), 7.61-7.71 (5H), 7.92 (1H), 8.24 (1H), ppm.

307

Example 198

N-cyclopropyl-2-methyl-4-{8-[(2-methylpropyl)amino]-6-(phenylsulfonyl) imidazo[1,2-b]pyridazin-3-yl}benzamide

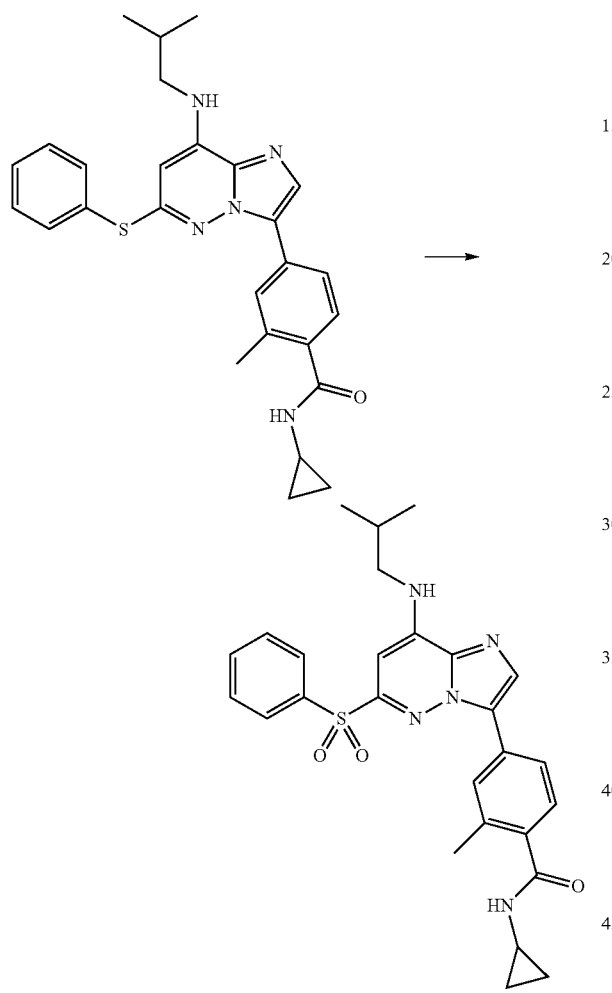

To a solution of 105 mg (223 μmol) of N-cyclopropyl-2-methyl-4-{8-[(2-methylpropyl)amino]-6-(phenylsulfanyl) imidazo[1,2-b]pyridazin-3-yl}benzamide, which was prepared according to example 197, in 15 mL of DMF was added and 684 mg (1113 μmol) OXONE (potassium peroxymonosulfate) in small portions. The mixture was stirred over night, then cooled to 0° C. and poured onto 200 mL of cold water. The precipitate was collected and purified with normal phase chromatography to yield 97 mg of the title compound as a yellow solid.

$^1$H-NMR (DMSO-d6): δ=0.50-0.69 (4H), 0.91 (6H), 1.99 (1H), 2.30 (3H), 2.56 (1H), 3.41 (2H), 4.31 (1H), 6.71 (1H), 7.28 (1H), 7.66-7.81 (5H), 8.03 (2H), 8.12 (1H), 8.31 (1H), 8.43 (1H) ppm.

308

Example 199

3-[4-(Cyclopropylcarbamoyl)-3-methylphenyl]-N-(2-hydroxyethyl)-8-[(2-methylpropyl)amino]imidazo[1,2-b]pyridazine-6-carboxamide

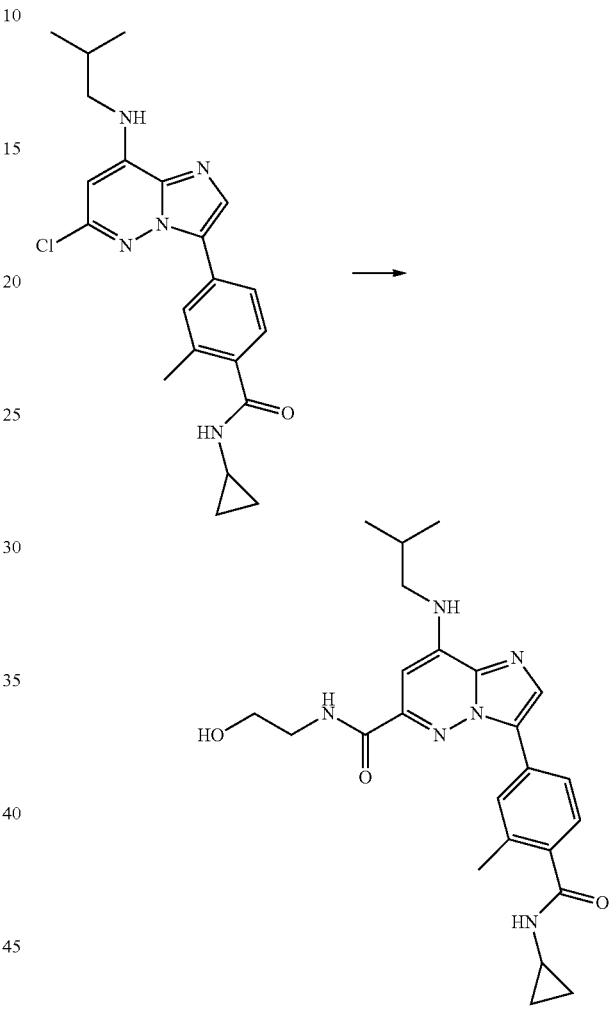

A solution of 100 mg (251 μmol) of 4-[6-chloro-8-(isobutylamino)imidazo[1,2-b]pyridazin-3-yl]-N-cyclopropyl-2-methylbenzamide, which was prepared according to example 194a, 46 mg (754 μmol) aminoethanol, 66 mg (251 μmol) molybdonhexacarbonyl, 80 mg (754 μmol) sodiumbicarbonate, 5.6 mg (25 μmol) palladium(II) acetate and 7.3 mg (25 μmol) tri-tert-butylphosphine tetrafluorborate in 3 mL of dioxane was heated in the microwave for 2 hours at 140° C. Then the mixture was directly submitted to reversed phase chromatography to yield 13 mg of the title compound.

$^1$H-NMR (DMSO-d6): δ=0.48-0.69 (4H), 0.91 (6H), 1.99 (1H), 2.38 (3H), 2.81 (1H), 3.17 (2H), 3.38 (3H), 3.53 (2H), 5.99 (1H), 6.61 (1H), 7.36 (1H), 7.84 (1H), 8.00-8.09 (3H), 8.16 (1H), 8.29 (1H), ppm.

Example 200

N-cyclopropyl-4-{8-[(2-methylpropyl)amino]-6-(methylsulfonyl)imidazo[1,2-b]pyridazin-3-yl}benzamide

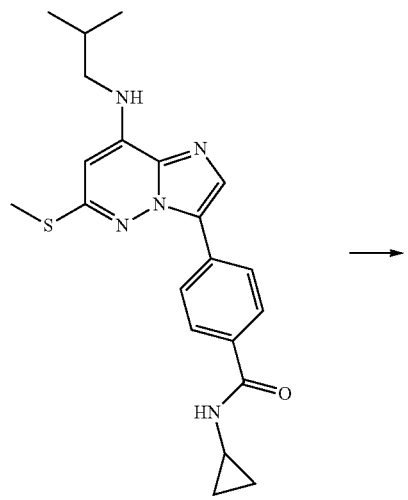

To a solution of 410 mg (1037 µmol) of N-cyclopropyl-4-{8-[(2-methylpropyl)amino]-6-(methylsulfanyl)imidazo[1,2-b]pyridazin-3-yl}benzamide, which was prepared according to example 193, in 15 mL of DMF was added and 1912 mg (3110 µmol) OXONE (potassium peroxymonosulfate) in small portions. The mixture was stirred over night, then cooled to 0° C. and poured onto 200 mL of cold water. The precipitate was collected and dried under vacuum to yield 291 mg of the title compound as a yellow solid.

$^{1}$H-NMR (DMSO-d6): δ=0.53-0.71 (4H), 0.91 (6H), 2.00 (1H), 2.84 (1H), 3.20 (2H), 3.38 (3H), 6.58 (1H), 7.92 (2H), 8.19-8.23 (3H), 8.37 (1H), 8.46 (1H), ppm.

Example 201

N-cyclopropyl-2-methyl-4-{8-[(2-methylpropyl)amino]-6-(propylsulfanyl) imidazo[1,2-b]pyridazin-3-yl}benzamide

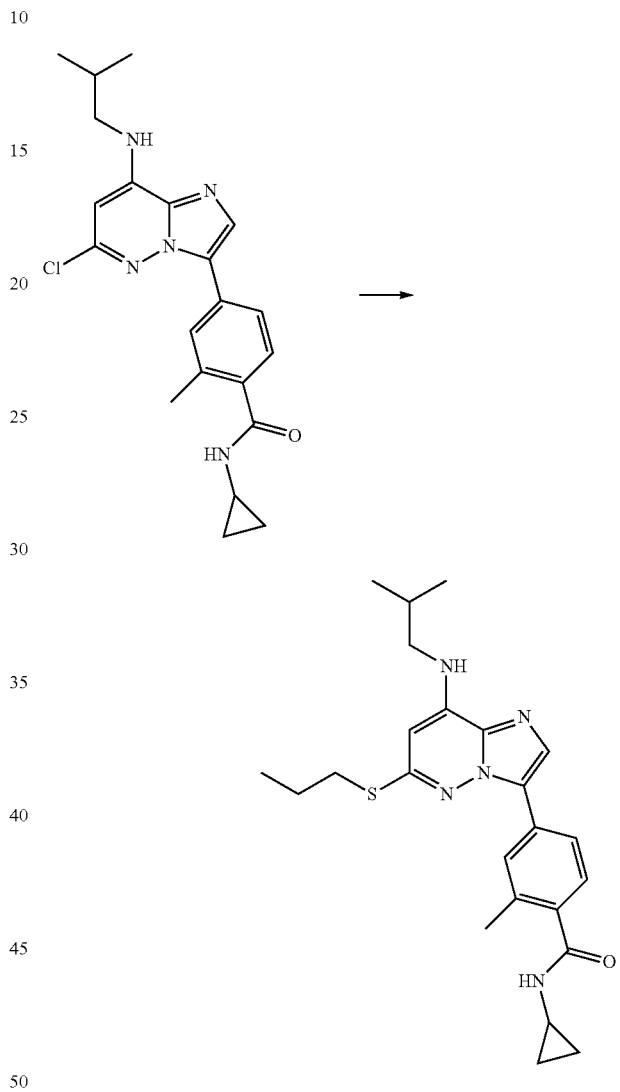

A solution of 100 mg (251 µmol) of 4-[6-chloro-8-(isobutylamino)imidazo[1,2-b]pyridazin-3-yl]-N-cyclopropyl-2-methylbenzamide, which was prepared according to example 194a, and 49 mg (503 µmol) sodium propane-1-thiolate in 1 mL of dimethylsulfoxide was heated for 60 min at 70° C. in the microwave. Then the mixture was purified by reversed phase chromatography to yield 18.5 mg of the title compound.

$^{1}$H-NMR (DMSO-d6): δ=0.49-0.66 (4H), 0.88 (6H), 1.00 (3H), 1.74 (2H), 1.94 (1H), 2.36 (3H), 2.79 (1H), 3.05-3.15 (4H), 6.02 (1H), 7.33 (1H), 7.47 (1H), 7.90 (1H), 7.96 (1H), 8.03 (1H), 8.29 (1H) ppm.

311

Example 202

N-cyclopropyl-2-methyl-4-{8-[(2-methylpropyl)amino]-6-(1-methyl-1H-pyrazol-5-yl)imidazo[1,2-b]pyridazin-3-yl}benzamide

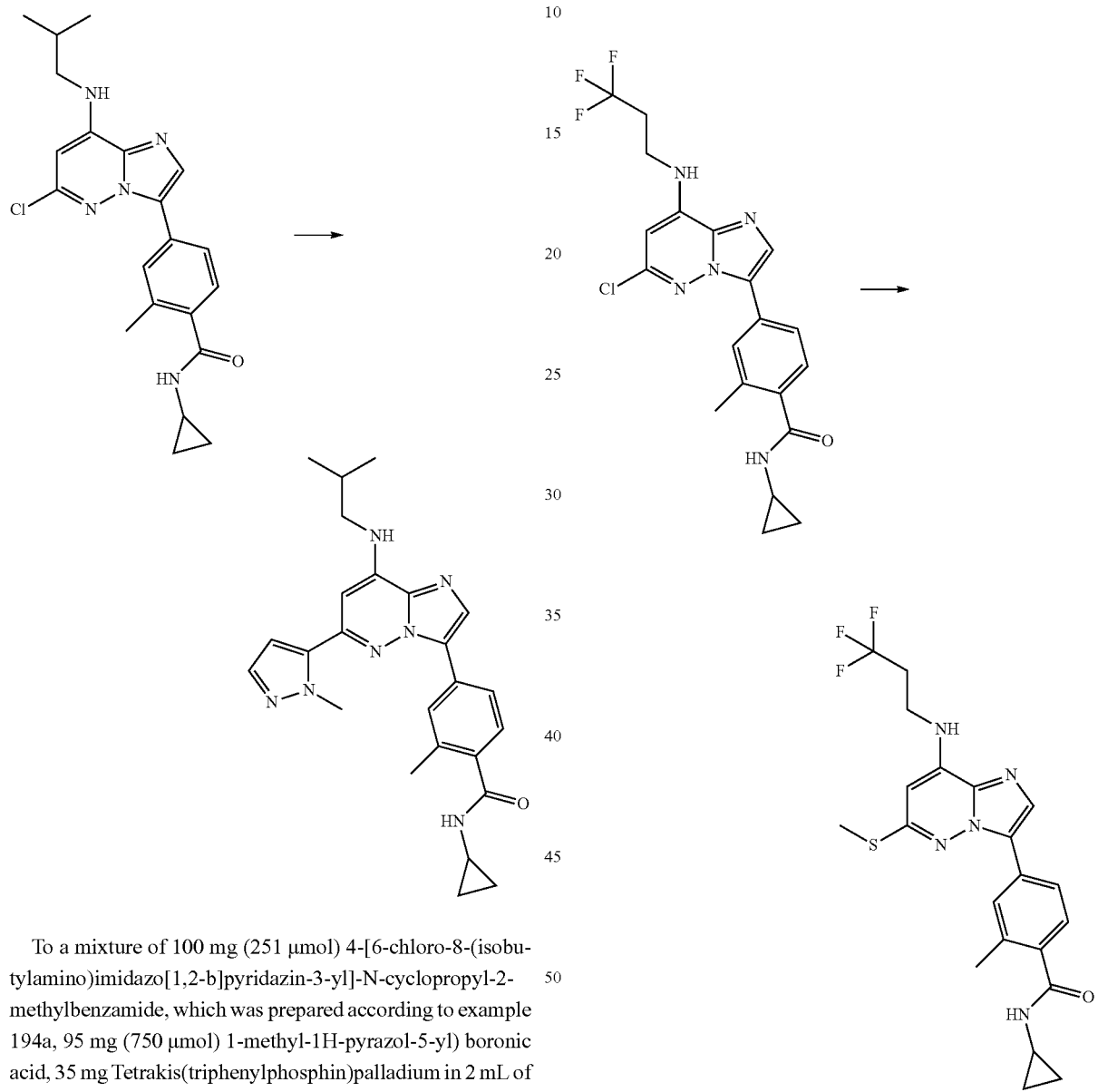

To a mixture of 100 mg (251 μmol) 4-[6-chloro-8-(isobutylamino)imidazo[1,2-b]pyridazin-3-yl]-N-cyclopropyl-2-methylbenzamide, which was prepared according to example 194a, 95 mg (750 μmol) 1-methyl-1H-pyrazol-5-yl) boronic acid, 35 mg Tetrakis(triphenylphosphin)palladium in 2 mL of ethanol and 2 mL of toluene was added 0.5 mL of an aqueous 10% sodiumbicarbonate solution and the mixture was stirred at 120° C. for 2 hours under microwave irradiation. Then water and was added and the organic layer was washed with water and brine, concentrated and purified by chromatography to give 99 mg of the title compound.

¹H-NMR (DMSO-d6): δ=0.49-0.67 (4H), 0.93 (6H), 2.00 (1H), 2.36 (3H), 2.80 (1H), 3.21 (3H), 4.13 (3H), 6.46 (1H), 6.90 (1H), 7.37 (1H), 7.50 (1H), 7.65 (1H), 7.92-7.97 (3H), 8.29 (1H) ppm.

312

Example 203

N-cyclopropyl-2-methyl-4-{6-(methylsulfanyl)-8-[(3,3,3-trifluoropropyl)amino]imidazo[1,2-b]pyridazin-3-yl}benzamide The title compound was prepared according to the procedure described for example 193 employing 4-{6-chloro-8-[(3,3,3-trifluoropropyl)amino]imidazo[1,2-b]pyridazin-3-yl}-N-cyclopropyl-2-methylbenzamide, which was prepared according to intermediate example 10a.

¹H-NMR (DMSO-d6): δ=0.48-0.70 (4H), 2.36 (3H), 2.54-2.70 (6H), 2.82 (1H), 3.54 (2H), 6.16 (1H), 7.35 (1H), 7.51 (1H), 7.92 (1H), 7.97 (1H), 8.05 (1H), 8.28 (1H), ppm.

Example 204

N-cyclopropyl-4-{6-[(2-hydroxyethyl)sulfanyl]-8-[(3,3,3-trifluoropropyl)amino]imidazo[1,2-b]pyridazin-3-yl}-2-methylbenzamide

Intermediate Example 205

(RS)-4-{6-Chloro-8-[(3,3,3-trifluoro-2-hydroxypropyl)amino]imidazo[1,2-b]pyridazin-3-yl}-N-cyclopropyl-2-methylbenzamide

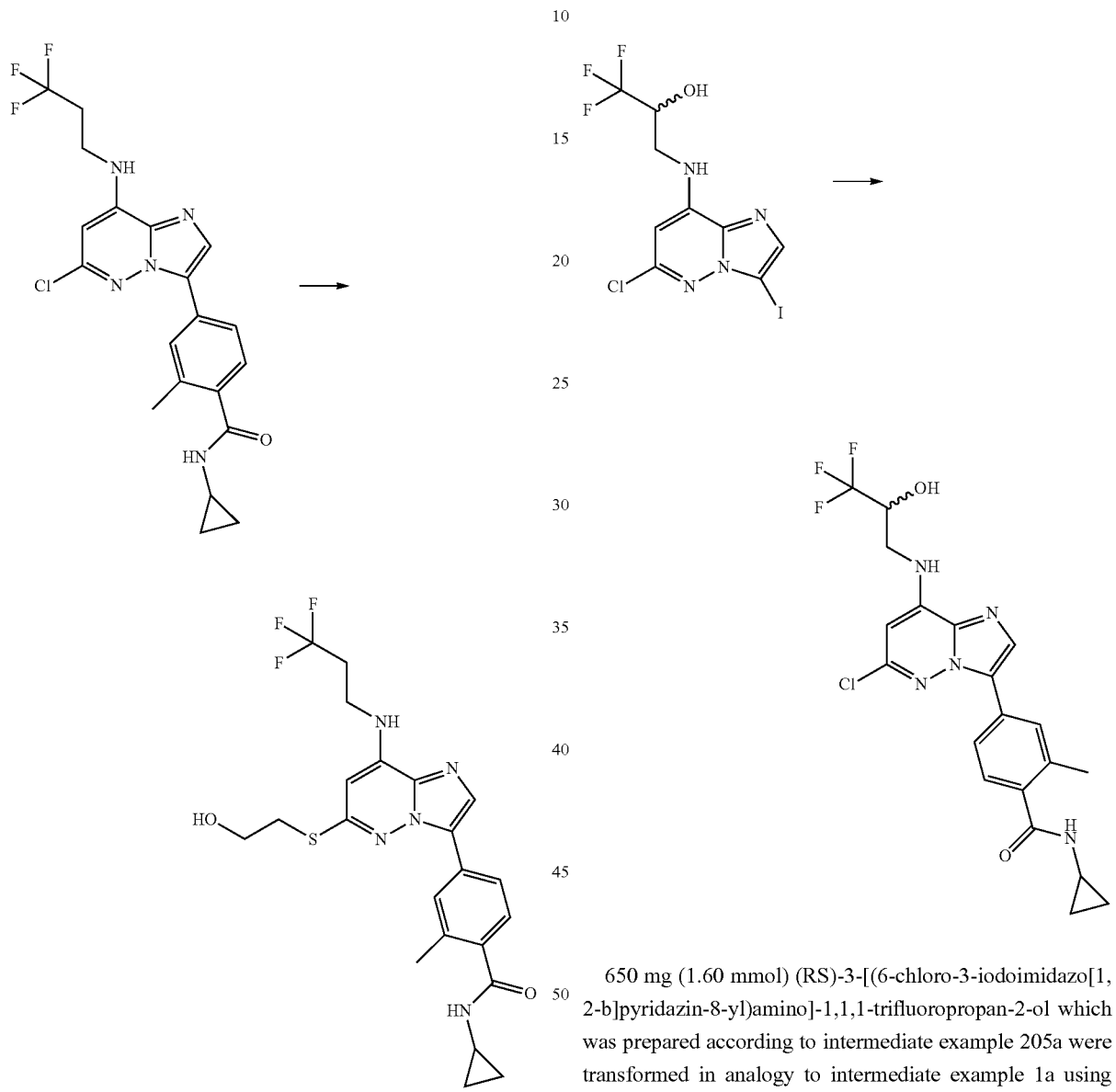

The title compound was prepared according to the procedure described for example 194 employing 4-{6-chloro-8-[(3,3,3-trifluoropropyl)amino]imidazo[1,2-b]pyridazin-3-yl}-N-cyclopropyl-2-methylbenzamide, which was prepared according to intermediate example 10a.

$^1$H-NMR (DMSO-d6): δ=0.47-0.70 (4H), 2.36 (3H), 2.53-2.70 (4H), 2.81 (1H), 3.52 (2H), 3.71 (2H), 4.97 (1H), 6.13 (1H), 7.33 (1H), 7.53 (1H), 7.92 (1H), 8.02 (1H), 8.29 (1H), ppm.

650 mg (1.60 mmol) (RS)-3-[(6-chloro-3-iodoimidazo[1,2-b]pyridazin-8-yl)amino]-1,1,1-trifluoropropan-2-ol which was prepared according to intermediate example 205a were transformed in analogy to intermediate example 1a using N-cyclopropyl-2-methyl-4-(4,4,5,5-tetramethyl-1,3,2-dioxaborolan-2-yl)benzamide which was prepared according to intermediate example 7b to give after working up and purification 430 mg (59%) of the title compound.

$^1$H-NMR (DMSO-d6): δ=0.48-0.68 (4H), 2.36 (3H), 2.81 (1H), 3.45-3.62 (2H), 4.31 (1H), 6.40 (2H), 6.58 (1H), 7.37 (1H), 7.81 (1H), 7.85 (1H), 7.90 (1H), 8.00 (1H), 8.29 (1H), ppm.

Intermediate Example 205a (RS)-3-[(6-chloro-3-iodoimidazo[1,2-b]pyridazin-8-yl)amino]-1,1,1-trifluoropropan-2-ol

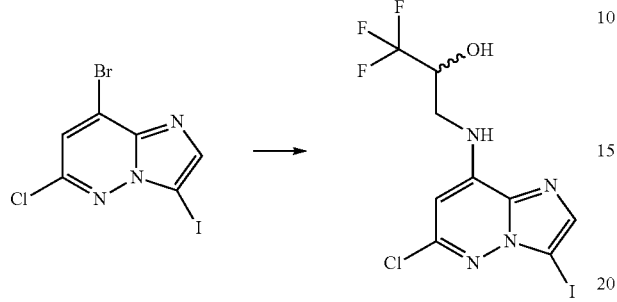

8-bromo-6-chloro-3-iodoimidazo[1,2-b]pyridazine which was prepared according to intermediate example 1c was transformed in analogy to intermediate example 1b using (RS)-(3,3,3-trifluoro-2-hydroxypropyl)amine to provide the title compound.

Example 206

(RS)N-cyclopropyl-2-methyl-4-{6-(methylsulfanyl)-8-[(3,3,3-trifluoro-2-hydroxypropyl)amino]imidazo[1,2-b]pyridazin-3-yl}benzamide

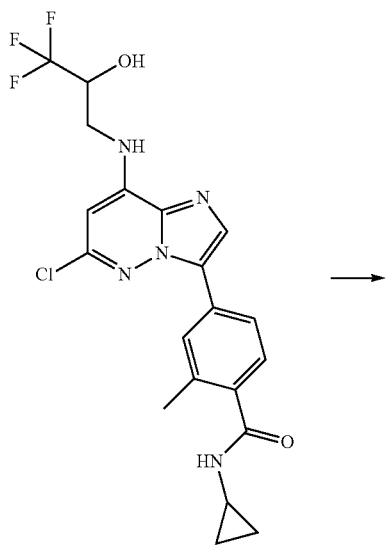

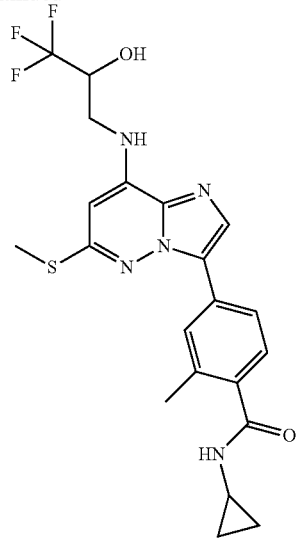

The title compound was prepared according to the procedure described for example 193 employing (RS)-4-{6-chloro-8-[(3,3,3-trifluoro-2-hydroxypropyl)amino]imidazo[1,2-b]pyridazin-3-yl}-N-cyclopropyl-2-methylbenzamide, which was prepared according to example 205.

$^1$H-NMR (DMSO-d6): δ=0.48-0.70 (4H), 2.36 (3H), 2.56 (3H), 2.80 (1H), 3.47 (1H), 3.58 (1H), 4.30 (1H), 6.19 (1H), 6.56 (1H), 7.29 (1H), 7.35 (1H), 7.93 (1H), 7.97 (1H), 8.06 (1H), 8.28 (1H), ppm.

Example 207

N-cyclopropyl-2-methyl-4-{6-(phenylsulfanyl)-8-[(3,3,3-trifluoropropyl)amino]imidazo[1,2-b]pyridazin-3-yl}benzamide -continued

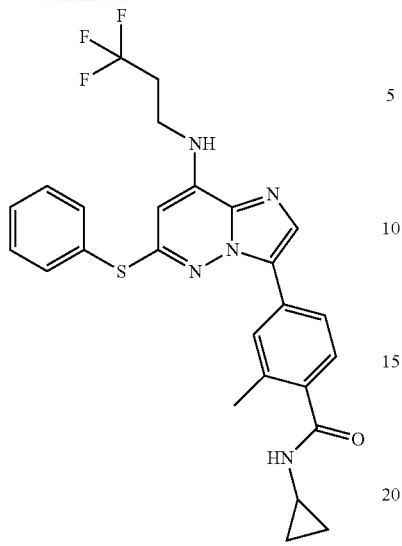

The title compound was prepared according to the procedure described for example 197 employing 4-{6-chloro-8-[(3,3,3-trifluoropropyl)amino]imidazo[1,2-b]pyridazin-3-yl}-N-cyclopropyl-2-methylbenzamide, which was prepared according to intermediate example 10a.

¹H-NMR (DMSO-d6): δ=0.48-0.70 (4H), 2.20 (3H), 2.54-2.70 (4H), 2.82 (1H), 3.50 (2H), 6.13 (1H), 7.09 (1H), 7.46-7.70 (8H), 7.94 (1H), 8.22 (1H), ppm.

Example 208

(RS)—N-cyclopropyl-2-methyl-4-{6-(1-methyl-1H-pyrazol-5-yl)-8-[(3,3,3-trifluoro-2-hydroxypropyl)amino]imidazo[1,2-b]pyridazin-3-yl}benzamide

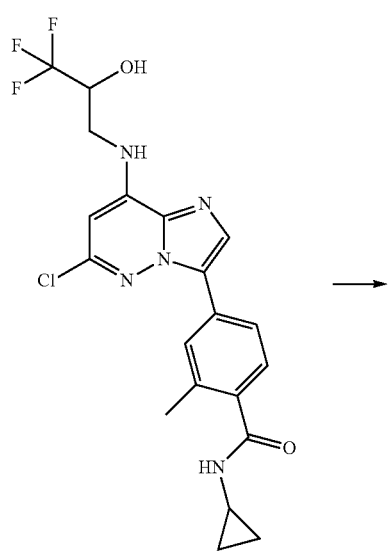

-continued

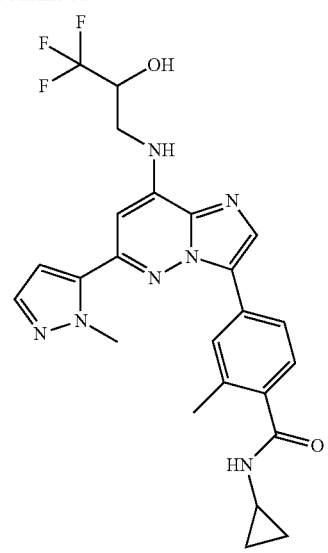

The title compound was prepared according to the procedure described for example 211 employing (RS)-4-{6-chloro-8-[(3,3,3-trifluoro-2-hydroxypropyl)amino]imidazo[1,2-b]pyridazin-3-yl}-N-cyclopropyl-2-methylbenzamide, which was prepared according to example 205.

¹H-NMR (DMSO-d6): δ=0.48-0.67 (4H), 2.36 (3H), 2.80 (1H), 3.47 (1H), 3.58 (1H), 4.32 (1H), 6.58 (2H), 6.90 (1H), 7.37 (1H), 7.48 (1H), 7.51 (1H), 7.91-8.00 (3H), 8.29 (1H), ppm.

Example 209

N-cyclopropyl-4-{6-[(3-fluorophenyl)sulfanyl]-8-[(3,3,3-trifluoropropyl)amino]imidazo[1,2-b]pyridazin-3-yl}-2-methylbenzamide

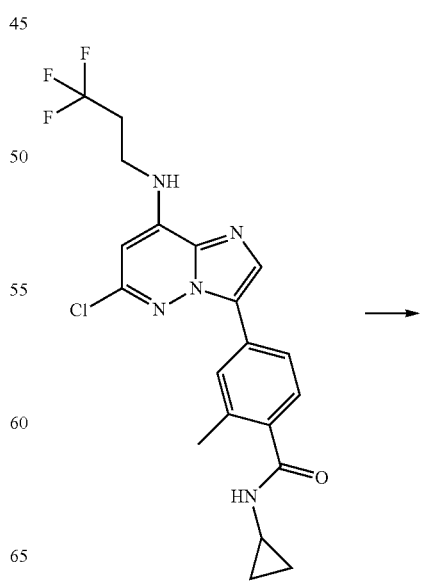

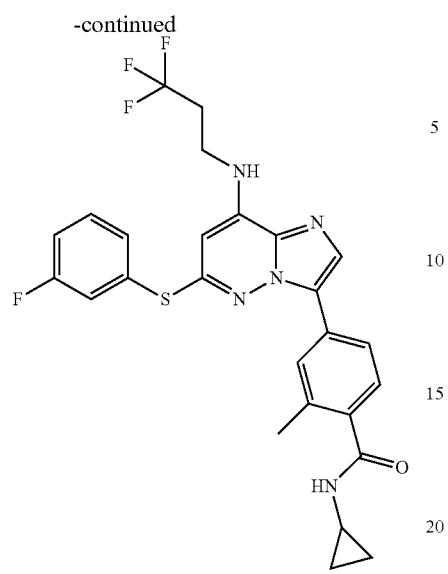

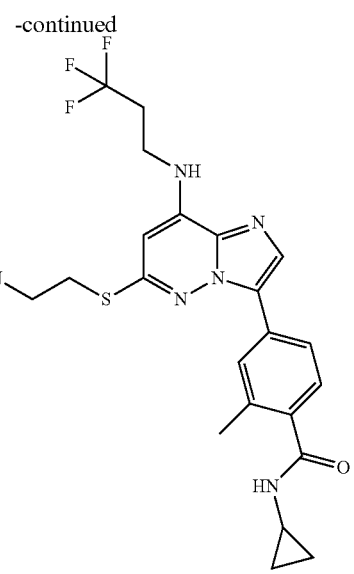

The title compound was prepared according to the procedure described for example 194 employing 4-{6-chloro-8-[(3,3,3-trifluoropropyl)amino]imidazo[1,2-b]pyridazin-3-yl}-N-cyclopropyl-2-methylbenzamide, which was prepared according to intermediate example 10a.

¹H-NMR (DMSO-d6): δ=0.49-0.66 (4H), 2.20 (3H), 2.53-2.70 (4H), 2.78 (1H), 3.54 (2H), 6.20 (1H), 7.12 (1H), 7.34 (1H), 7.43-7.71 (6H), 7.95 (1H), 8.23 (1H), ppm.

The title compound was prepared according to the procedure described for example 194 employing 4-{6-chloro-8-[(3,3,3-trifluoropropyl)amino]imidazo[1,2-b]pyridazin-3-yl}-N-cyclopropyl-2-methylbenzamide, which was prepared according to intermediate example 10a.

¹H-NMR (DMSO-d6): δ=0.50 (2H), 0.65 (2H), 0.86 (6H), 2.36 (3H), 2.59-2.71 (4H), 2.79 (1H), 3.23-3.33 (multiple H, overlaps with water peak), 3.54 (2H), 6.13 (1H), 7.32 (1H), 7.52 (1H), 7.91 (1H), 7.95 (1H), 8.02 (1H) 8.28 (1H), ppm.

Example 210

N-cyclopropyl-4-(6-{[2-(diethylamino)ethyl]sulfanyl}-8-[(3,3,3-trifluoropropyl)amino]imidazo[1,2-b]pyridazin-3-yl)-2-methylbenzamide Example 211

N-cyclopropyl-4-{8-[(3-hydroxypropyl)amino]-6-(1-methyl-1H-pyrazol-5-yl) imidazo[1,2-b]pyridazin-3-yl}-2-methylbenzamide

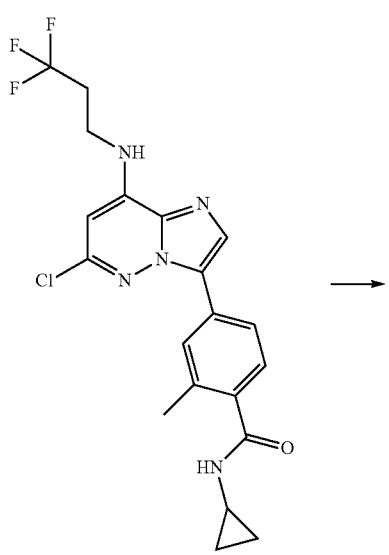

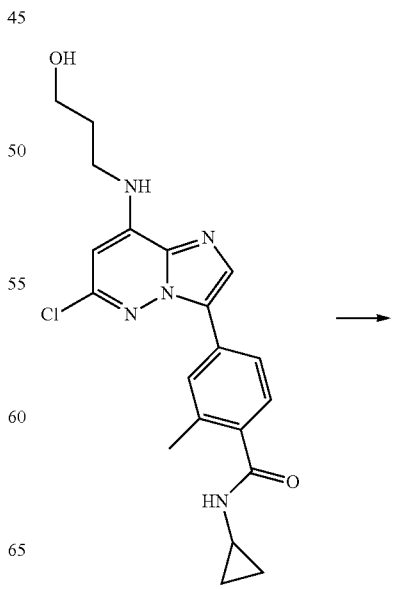

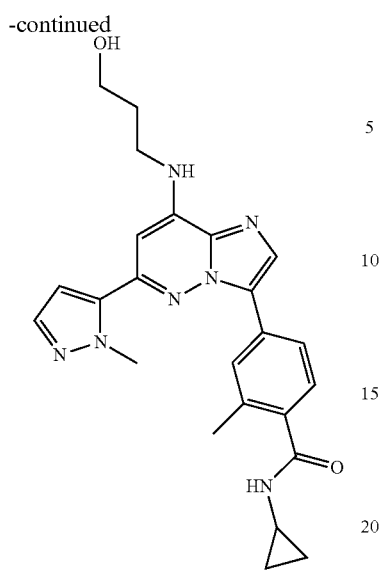

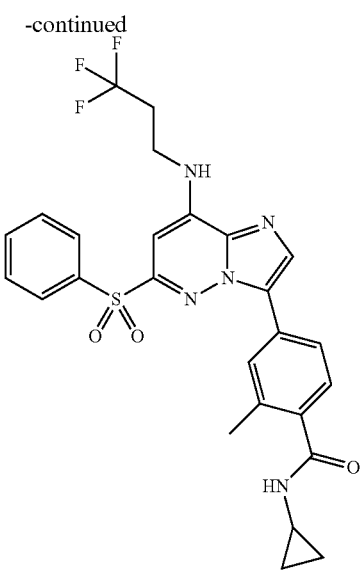

To a mixture of 51 mg (128 mot) 4-{6-chloro-8-[(3-hydroxypropyl)amino]imidazo[1,2-b]pyridazin-3-yl}-N-cyclopropyl-2-methylbenzamide, which was prepared in analogy to example 205 employing 3-hydroxy-n-propylamine, 80 mg (380 μmol) 1-methyl-1H-pyrazol-5-yl) boronic acid pinacol ester, 18 mg Tetrakis(triphenylphosphin)palladium in 1 mL of ethanol and 1 mL of toluene was added 0.27 mL of an aqueous 10% sodiumbicarbonate solution and the mixture was stirred at 120° C. for 2 hours under microwave irradiation. Then water and ethyl acetate was added and the organic layer was washed with water and brine, concentrated and treated with dichloromethane. The remaining undissolved solid yielded 25 mg of the title compound.

¹H-NMR (DMSO-d6): δ=0.50 (2H), 0.66 (2H), 1.78 (2H), 2.35 (3H), 2.80 (1H), 3.41-3.51 (4H), 6.47 (1H), 6.88 (1H), 7.36 (1H), 7.51 (1H), 7.62 (1H), 7.91-7.97 (3H), (1H), 8.29 (1H), ppm.

50 mg (98 μmol) N-cyclopropyl-2-methyl-4-{6-(phenylsulfanyl)-8-[(3,3,3-trifluoropropyl)amino]imidazo[1,2-b]pyridazin-3-yl}benzamide which was prepared according to example 207 were transformed in analogy to example 18 to give after working up and purification 30.2 mg (57%) of the title compound.

¹H-NMR (DMSO-d6): δ=0.51 (2H), 0.67 (2H), 2.31 (3H), 2.70 (2H), 2.81 (1H), 3.29 (2H), 6.81 (1H), 7.28 (1H), 7.65-7.82 (5H), 8.03 (1H), 8.06 (1H), 8.15 (1H), 8.30 (1H), 8.36 (1H) ppm.

Example 212

N-cyclopropyl-2-methyl-4-{6-(phenylsulfonyl)-8-[(3,3,3-trifluoropropyl)amino]imidazo[1,2-b]pyridazin-3-yl}benzamide Example 213

4-{6-(5-Cyanopyridin-3-yl)-8-(isobutylamino)imidazo[1,2-b]pyridazin-3-yl}-N-cyclopropyl-2-methylbenzamide

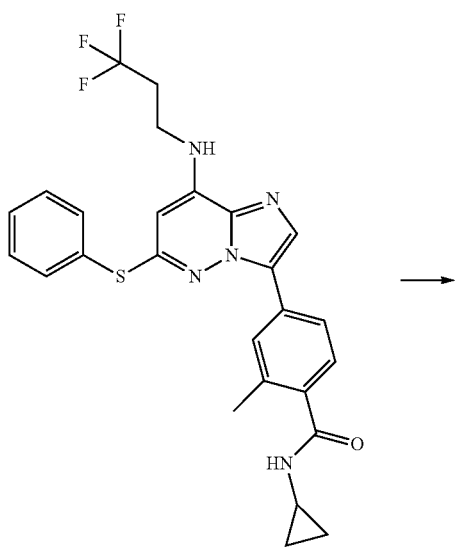

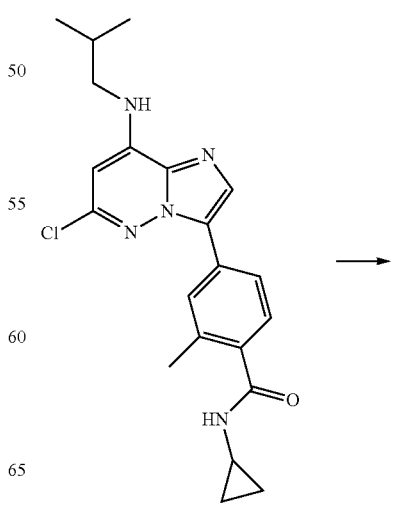

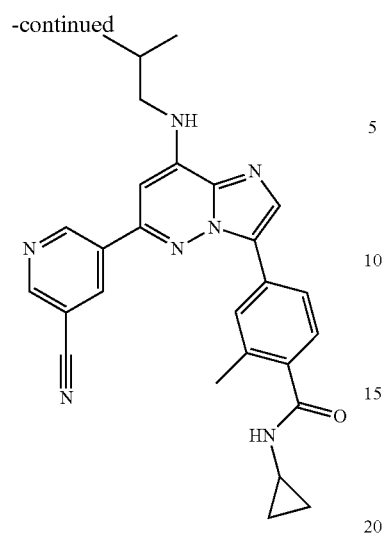

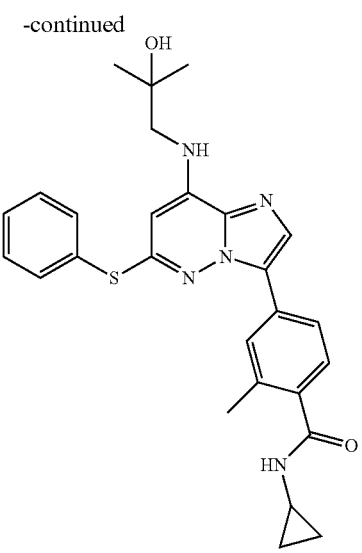

200 mg (503 µmol) 4-[6-chloro-8-(isobutylamino)imidazo[1,2-b]pyridazin-3-yl]-N-cyclopropyl-2-methylbenzamide which was prepared according to intermediate example 194a were transformed in analogy to example 202 using 5-cyanopyridin-3-yl boronic acid to give after working up and purification 80.9 mg (33%) of the title compound.

$^1$H-NMR (DMSO-d6): δ=0.51 (2H), 0.62 (2H), 0.92 (6H), 2.04 (1H), 2.39 (3H), 2.81 (1H), 3.26 (2H), 6.83 (1H), 7.41 (1H), 7.76 (1H), 8.01-8.10 (3H), 8.30 (1H), 8.93 (1H), 9.10 (1H), 9.49 (1H), ppm.

100 mg (242 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 55 using benzenethiol to give after working up and purification 113.5 mg (96%) of the title compound.

$^1$H-NMR (DMSO-d6): δ=0.49 (2H), 0.65 (2H), 1.11 (6H), 2.19 (3H), 2.79 (1H), 3.21 (2H), 4.71 (1H), 6.23 (1H), 6.97 (1H), 7.08 (1H), 7.44-7.52 (3H), 7.58-7.65 (3H), 7.70 (1H), 7.93 (1H), 8.22 (1H) ppm.

Example 214

N-cyclopropyl-4-{8-[(2-hydroxy-2-methylpropyl)amino]-6-(phenylsulfanyl) imidazo[1,2-b]pyridazin-3-yl}-2-methylbenzamide Example 215

N-cyclopropyl-2-methyl-4-(6-{[2-(morpholin-4-yl)ethyl]sulfanyl}-8-[(3,3,3-trifluoropropyl)amino]imidazo[1,2-b]pyridazin-3-yl)benzamide

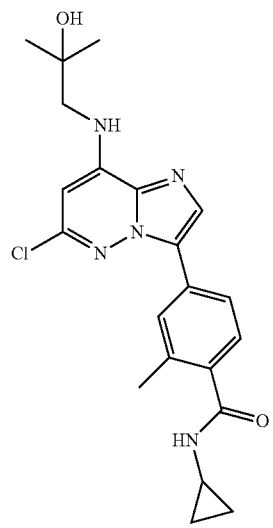

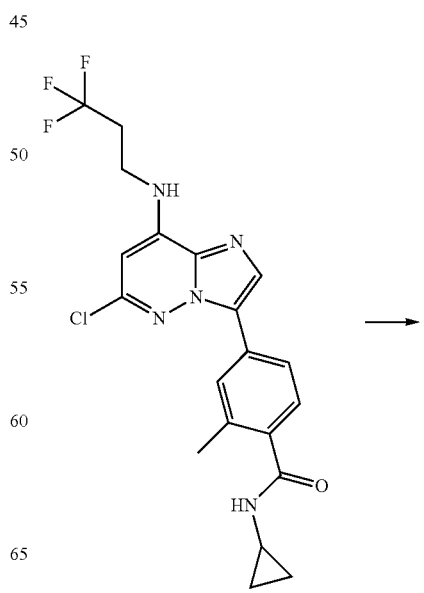

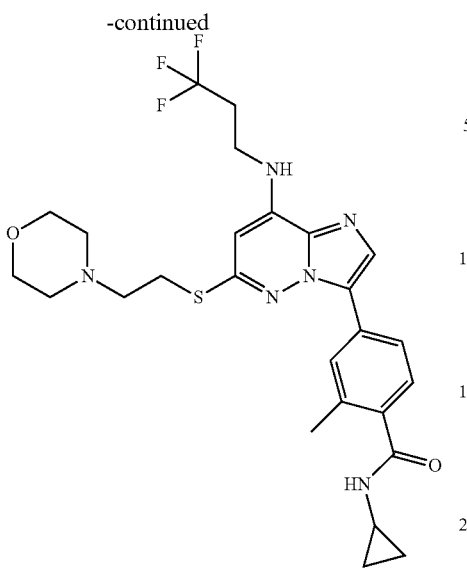

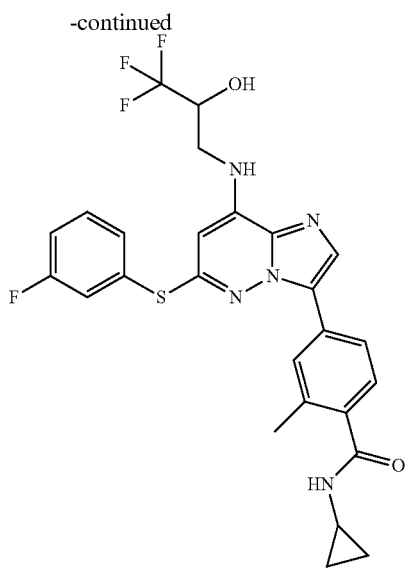

100 mg (228 µmol) 4-{6-Chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 55 using 2-(morpholin-4-yl)ethanethiol to give after working up and purification 78.2 mg (59%) of the title compound.

$^1$H-NMR (DMSO-d6): δ=0.49 (2H), 0.65 (2H), 2.30-2.39 (4H), 2.37 (3H), 2.57-2.71 (4H), 2.80 (1H), 3.28 (2H), 3.47-3.57 (6H), 6.13 (1H), 7.33 (1H), 7.53 (1H), 7.90 (1H), 7.96 (1H), 7.98 (1H), 8.29 (1H) ppm.

Example 216

(RS)—N-cyclopropyl-4-{6-[(3-fluorophenyl)sulfanyl]-8-[(3,3,3-trifluoro-2-hydroxypropyl)amino]imidazo[1,2-b]pyridazin-3-yl}-2-methylbenzamide 95 mg (191 µmol) (RS)-4-{6-chloro-8-[(3,3,3-trifluoro-2-hydroxypropyl)amino]imidazo[1,2-b]pyridazin-3-yl}-N-cyclopropyl-2-methylbenzamide which was prepared according to intermediate example 205 were transformed in analogy to example 194 using 3-fluorobenzenethiol to give after working up and purification 54 mg (49%) of the title compound.

$^1$H-NMR (DMSO-d6): δ=0.49 (2H), 0.65 (2H), 2.20 (3H), 2.79 (1H), 3.45-3.62 (2H), 4.26 (1H), 6.24 (1H), 6.56 (1H), 7.13 (1H), 7.35 (1H), 7.50 (1H), 7.51-7.56 (3H), 7.65 (1H), 7.71 (1H), 7.97 (1H), 8.25 (1H), ppm.

Example 217

N-cyclopropyl-4-{6-[(3,3-dimethylbutyl)sulfanyl]-8-[(2-hydroxy-2-methylpropyl)amino]imidazo[1,2-b]pyridazin-3-yl}-2-methylbenzamide

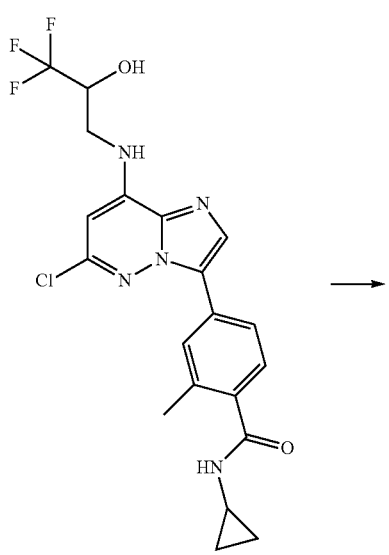

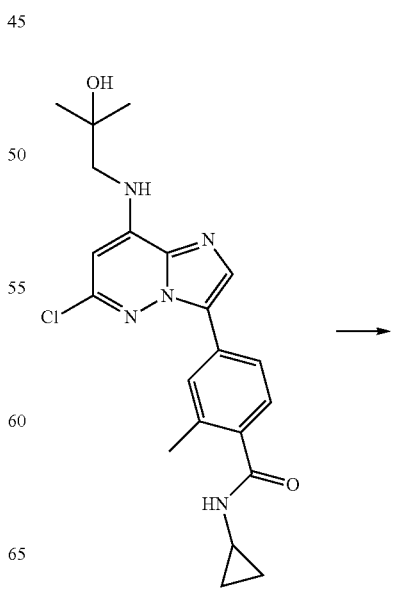

327

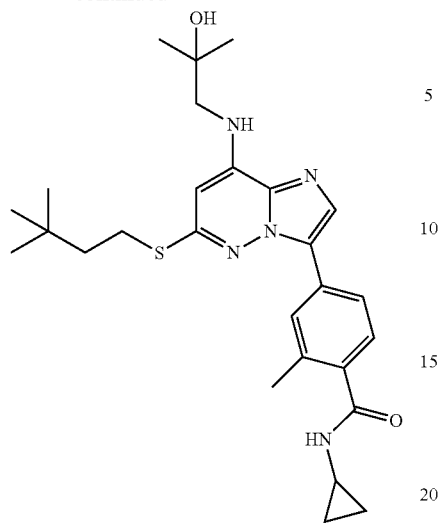

75 mg (181 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 3,3-dimethylbutane-1-thiol to give after working up and purification 29.2 mg (31%) of the title compound.

$^1$H-NMR (DMSO-d6): δ=0.49 (2H), 0.65 (2H), 0.89 (9H), 1.13 (6H), 1.54 (2H), 2.35 (3H), 2.79 (1H), 3.13 (2H), 3.21 (2H), 4.72 (1H), 6.17 (1H), 6.81 (1H), 7.29 (1H), 7.91 (1H), 7.98 (1H), 7.99 (1H), 8.28 (1H) ppm.

Example 218

N-cyclopropyl-4-{6-[(2,6-difluorophenyl)sulfanyl]-8-[(2-hydroxy-2-methylpropyl)amino]imidazo[1,2-b]pyridazin-3-yl}-2-methylbenzamide

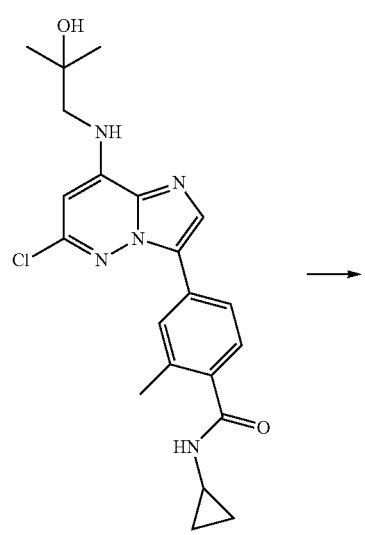

328

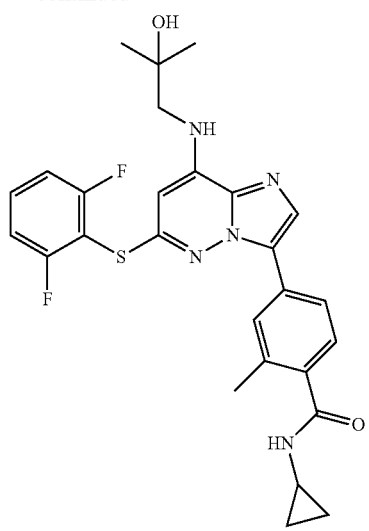

75 mg (181 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2,6-difluorobenzenethiol to give after working up and purification 6.5 mg (6%) of the title compound.

$^1$H-NMR (CDCl$_3$): δ=0.63 (2H), 0.89 (2H), 1.40 (6H), 2.33 (3H), 2.91 (1H), 3.29 (2H), 5.96 (1H), 6.05 (1H), 6.55 (1H), 7.00-7.11 (3H), 7.41-7.53 (3H), 7.57 (1H) ppm.

Example 219

N-cyclopropyl-4-{6-[(3-fluorophenyl)sulfanyl]-8-[(3,3,3-trifluoropropyl)amino]imidazo[1,2-b]pyridazin-3-yl}-3-hydroxybenzamide

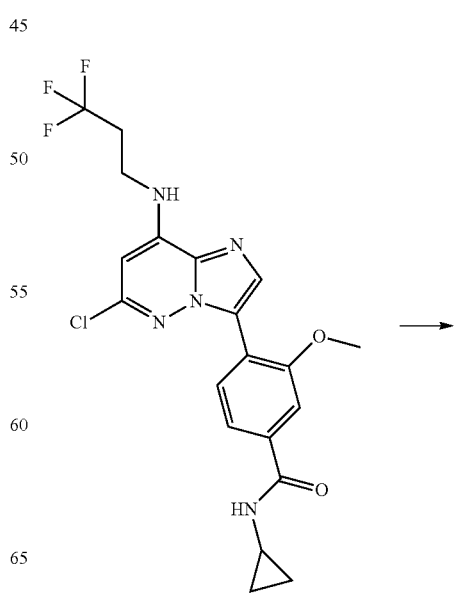

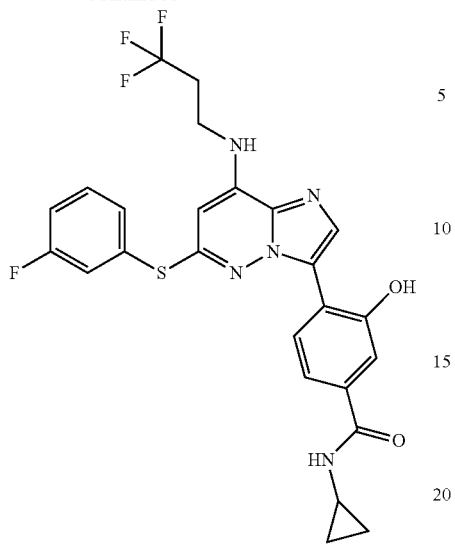

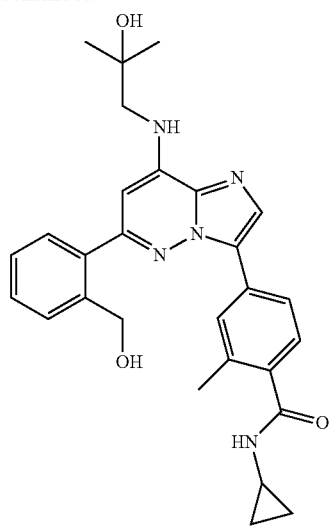

75 mg (165 μmol) 4-{6-chloro-8-[(3,3,3-trifluoropropyl)amino]imidazo[1,2-b]pyridazin-3-yl}-N-cyclopropyl-3-methoxybenzamide which was prepared according to intermediate example 52a were transformed in analogy to intermediate example 51 using 3-fluorobenzenethiol to give after working up and purification 24.0 mg (27%) of the title compound.

¹H-NMR (DMSO-d6): δ=0.54 (2H), 0.66 (2H), 2.60 (2H), 2.80 (1H), 3.52 (2H), 6.13 (1H), 7.07 (1H), 7.28 (1H), 7.34 (1H), 7.38-7.53 (3H), 7.71 (1H), 7.85 (1H), 7.94 (1H), 8.34 (1H), 10.12 (1H) ppm.

5.25 g (12.7 mmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using [2-(hydroxymethyl)phenyl]boronic acid to give after working up and purification 4.90 g (80%) of the title compound.

¹H-NMR (DMSO-d6): δ=0.51 (2H), 0.66 (2H), 1.18 (6H), 2.36 (3H), 2.82 (1H), 3.32 (2H), 4.66 (2H), 4.75 (1H), 5.13 (1H), 6.45 (1H), 6.95 (1H), 7.35 (1H), 7.39 (1H), 7.45-7.52 (2H), 7.66 (1H), 7.95 (1H), 8.00 (1H), 8.01 (1H), 8.26 (1H) ppm.

Example 220

N-cyclopropyl-4-{6-[2-(hydroxymethyl)phenyl]-8-[(2-hydroxy-2-methylpropyl)amino]imidazo[1,2-b]pyridazin-3-yl}-2-methylbenzamide Example 221

4-{6-[(2E)-but-2-en-2-yl]-8-[(3,3,3-trifluoropropyl)amino]imidazo[1,2-b]pyridazin-3-yl}-N-cyclopropyl-2-methylbenzamide

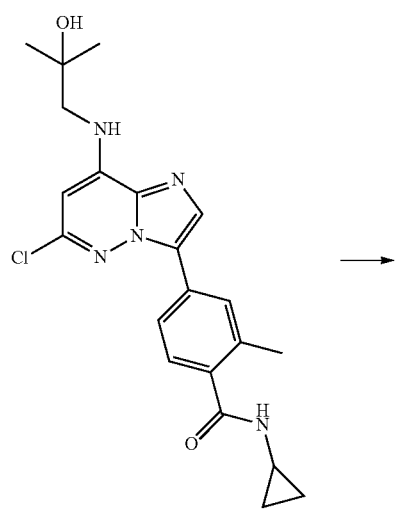

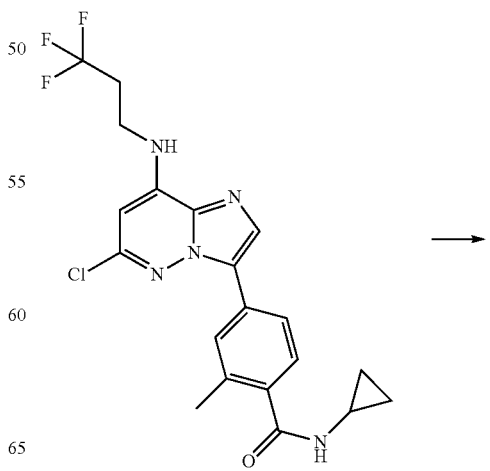

-continued

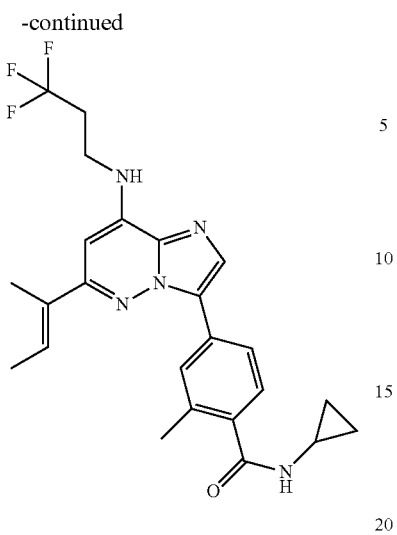

115 mg (262 µmol) 4-{6-chloro-8-[(3,3,3-trifluoropropyl) amino]imidazo[1,2-b]pyridazin-3-yl}-N-cyclopropyl-2-methylbenzamide which was prepared according to intermediate example 10a were transformed in analogy to example 1 using (2Z)-but-2-en-2-ylboronic acid to give after working up and purification 7.2 mg (6%) of the title compound.

$^1$H-NMR (DMSO-d6): δ=0.50 (2H), 0.65 (2H), 1.84 (3H), 2.07 (3H), 2.36 (3H), 2.67 (2H), 2.80 (1H), 3.61 (2H), 6.43 (1H), 6.49 (1H), 7.32 (1H), 7.35 (1H), 7.97 (1H), 8.03 (1H), 8.07 (1H), 8.27 (1H) ppm.

Example 222

N-cyclopropyl-4-{6-[2-(fluoromethyl)phenyl]-8-[(2-hydroxy-2-methylpropyl)amino]imidazo[1,2-b]pyridazin-3-yl}-2-methylbenzamide

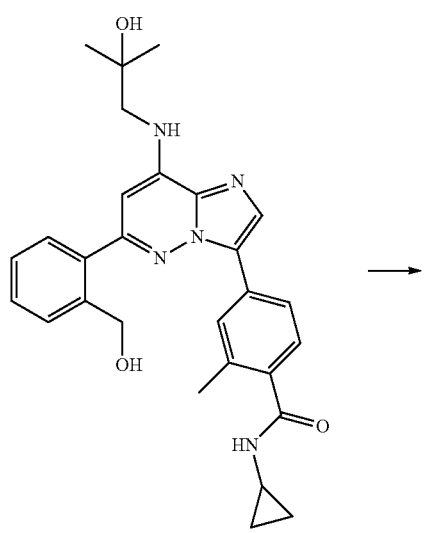

-continued

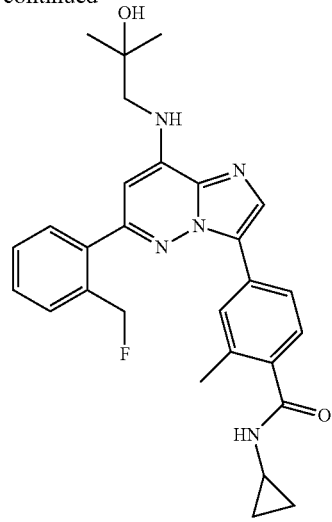

To a solution of 329 mg (677 µmol) N-cyclopropyl-4-{6-[2-(hydroxymethyl)phenyl]-8-[(2-hydroxy-2-methylpropyl) amino]imidazo[1,2-b]pyridazin-3-yl}-2-methylbenzamide which was prepared according to example 220 in 13 mL dichloromethane at 3° C. were added 98 µL N-ethyl-N-(trifluoro-lambda$^4$-sulfanyl)ethanamine. After stirring for 10 minutes, the solution was poured into water and the aqueous phase was extracted with dichloromethane. The combined organic phases were washed with sodium hydrogencarbonate solution and dried over sodium sulfate. After filtration and removal of solvent the residue was purified by chromatography to give 28.6 mg (8%) of the title compound.

$^1$H-NMR (CDCl$_3$): δ=0.61 (2H), 0.87 (2H), 1.47 (6H), 2.48 (3H), 2.90 (1H), 3.36 (2H), 5.21 (1H), 5.58 (2H), 5.97 (1H), 6.26 (1H), 6.71 (1H), 7.37 (1H), 7.46 (1H), 7.51 (1H), 7.58 (1H), 7.64 (1H), 7.74 (1H), 7.81 (1H), 7.88 (1H) ppm.

Example 223

N-cyclopropyl-4-{6-(2-methoxyphenoxy)-8-[(3,3,3-trifluoropropyl)amino]imidazo[1,2-b]pyridazin-3-yl}-2-methylbenzamide

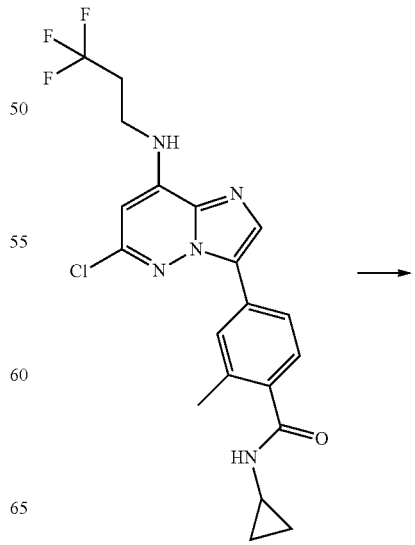

333
-continued

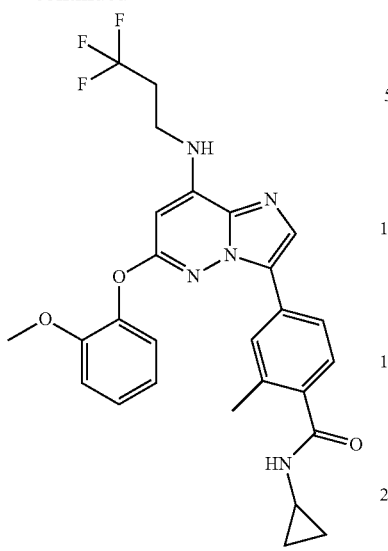

150 mg (343 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 2-methoxyphenol to give after working up and purification 8.1 mg (5%) of the title compound.

$^1$H-NMR (CDCl$_3$): δ=0.60 (2H), 0.88 (2H), 2.26 (3H), 2.57 (2H), 2.89 (1H), 3.68 (2H), 3.78 (3H), 5.82 (1H), 5.94 (1H), 5.98 (1H), 7.01 (1H), 7.05 (1H), 7.18 (1H), 7.22 (1H), 7.27 (1H), 7.55 (1H), 7.70 (1H), 7.72 (1H) ppm.

Example 224

N-cyclopropyl-4-{6-[(2-hydroxyphenyl)sulfanyl]-8-[(3,3,3-trifluoropropyl)amino]imidazo[1,2-b]pyridazin-3-yl}-2-methylbenzamide

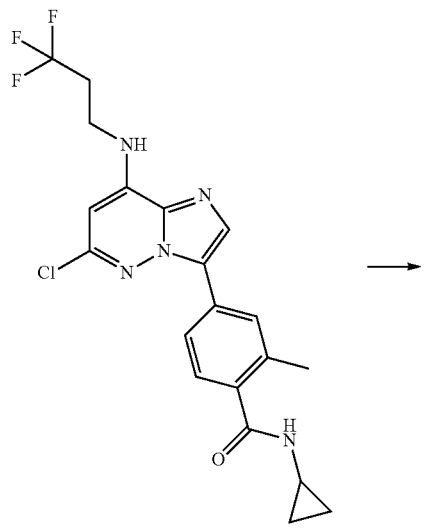

334
-continued

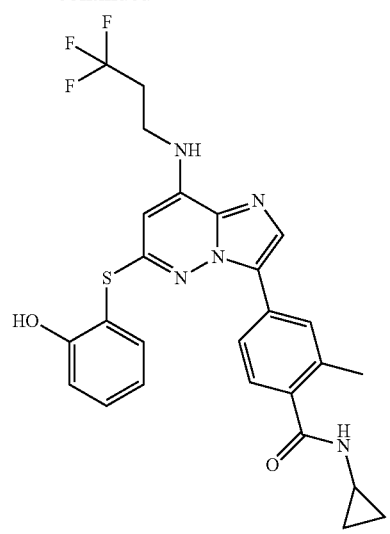

100 mg (228 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 2-methoxybenzenethiol to give after working up and purification 5.1 mg (4%) of the title compound.

$^1$H-NMR (DMSO-d6): δ=0.49 (2H), 0.65 (2H), 2.21 (3H), 2.59 (2H), 2.79 (1H), 3.49 (2H), 6.05 (1H), 6.87 (1H), 6.98 (1H), 7.07 (1H), 7.34 (1H), 7.46 (1H), 7.56 (1H), 7.67 (1H), 7.72 (1H), 7.93 (1H), 8.23 (1H), 9.96 (1H) ppm.

Example 225

N-cyclopropyl-4-{6-(3-methoxyphenoxy)-8-[(3,3,3-trifluoropropyl)amino]imidazo[1,2-b]pyridazin-3-yl}-2-methylbenzamide

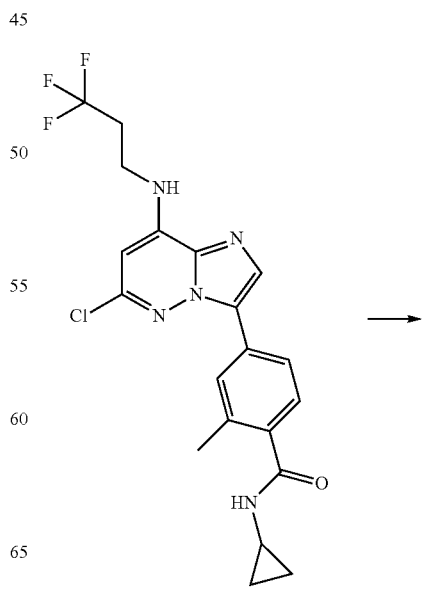

335

-continued

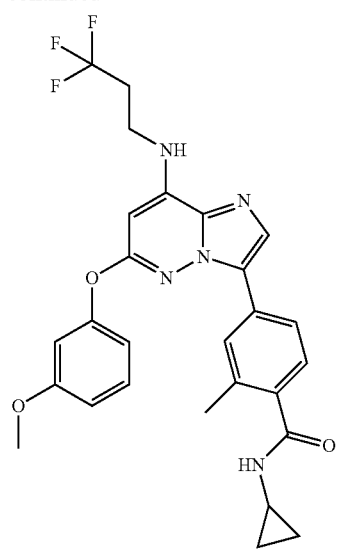

150 mg (343 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3-methoxyphenol to give after working up and purification 5.1 mg (3%) of the title compound.

$^1$H-NMR (CDCl$_3$): δ=0.60 (2H), 0.87 (2H), 2.31 (3H), 2.56 (2H), 2.89 (1H), 3.66 (2H), 3.80 (3H), 5.85 (1H), 5.88 (1H), 6.03 (1H), 6.79-6.88 (3H), 7.24 (1H), 7.33 (1H), 7.63 (1H), 7.73 (1H), 7.79 (1H) ppm.

Example 226

N-cyclopropyl-4-{6-[(3,3-dimethylbutyl)sulfanyl]-8-[(3,3,3-trifluoropropyl)amino]imidazo[1,2-b]pyridazin-3-yl}-2-methylbenzamide

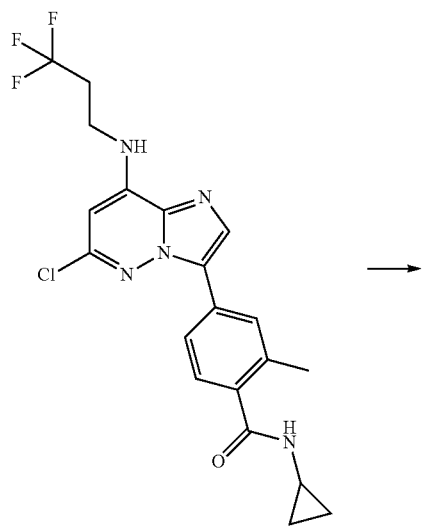

336

-continued

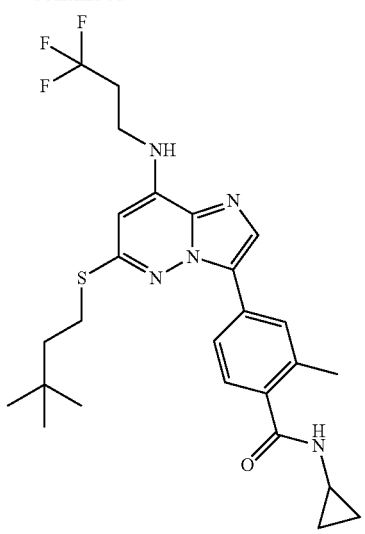

100 mg (228 µmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3,3-dimethylbutane-1-thiol to give after working up and purification 3.6 mg (3%) of the title compound.

$^1$H-NMR (CDCl$_3$): δ=0.63 (2H), 0.90 (2H), 0.94 (9H), 1.62 (2H), 2.51 (3H), 2.52 (2H), 2.92 (1H), 3.19 (2H), 3.61 (2H), 5.84-5.93 (3H), 7.37 (1H), 7.69 (1H), 7.88 (1H), 7.91 (1H) ppm.

Example 227

N-cyclopropyl-4-{6-[(4-methoxyphenyl)sulfanyl]-8-[(3,3,3-trifluoropropyl)amino]imidazo[1,2-b]pyridazin-3-yl}-2-methylbenzamide

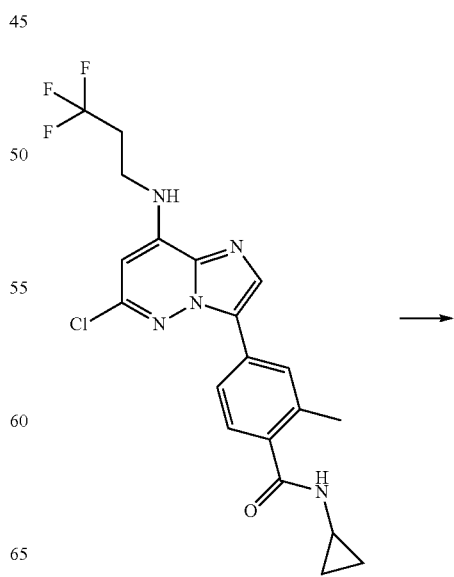

337

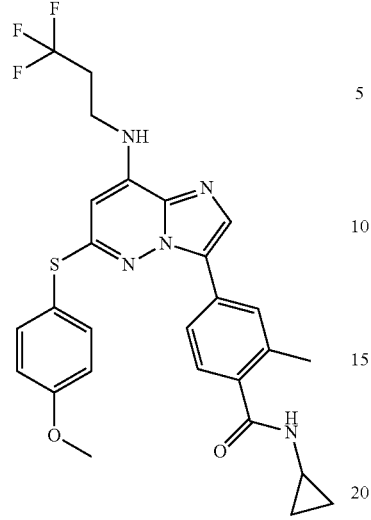

100 mg (228 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 4-methoxybenzenethiol to give after working up and purification 16.8 mg (13%) of the title compound.

$^1$H-NMR (CDCl$_3$): δ=0.63 (2H), 0.90 (2H), 2.40 (3H), 2.47 (2H), 2.92 (1H), 3.57 (2H), 3.88 (3H), 5.82-5.93 (3H), 6.98 (2H), 7.17 (1H), 7.54-7.63 (4H), 7.69 (1H) ppm.

Example 228

N-cyclopropyl-2-methyl-4-{6-(pyridin-4-yl)-8-[(3,3,3-trifluoropropyl)amino]imidazo[1,2-b]pyridazin-3-yl}benzamide

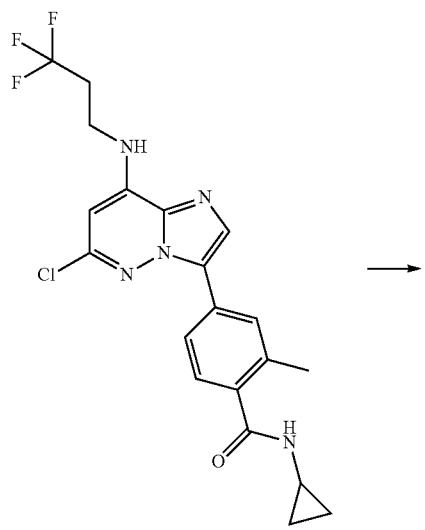

338

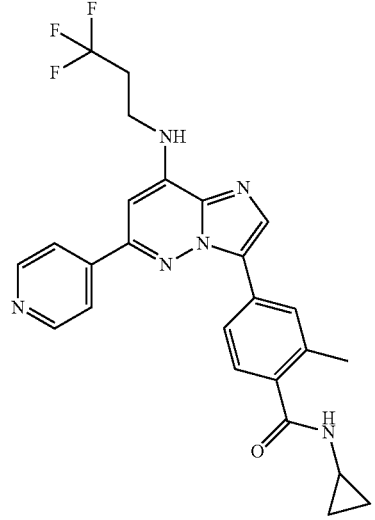

250 mg (571 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 1 using pyridin-4-ylboronic acid to give after working up and purification 6.7 mg (2%) of the title compound.

$^1$H-NMR (CDCl$_3$): δ=0.63 (2H), 0.89 (2H), 2.53 (3H), 2.61 (2H), 2.91 (1H), 3.72 (2H), 6.20 (1H), 6.43 (1H), 6.67 (1H), 7.44 (1H), 7.80 (1H), 7.82 (2H), 7.89 (1H), 7.96 (1H), 8.72 (2H) ppm.

Example 229

(RS)—N-cyclopropyl-4-[6-(4-fluorophenyl)-8-{[(4-methylmorpholin-2-yl)methyl]amino}imidazo[1,2-b]pyridazin-3-yl]-2-methylbenzamide

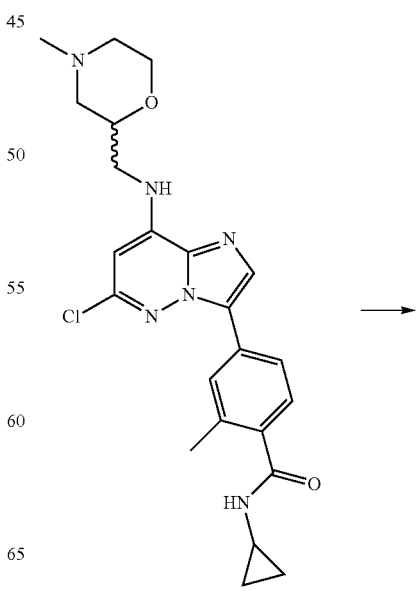

-continued

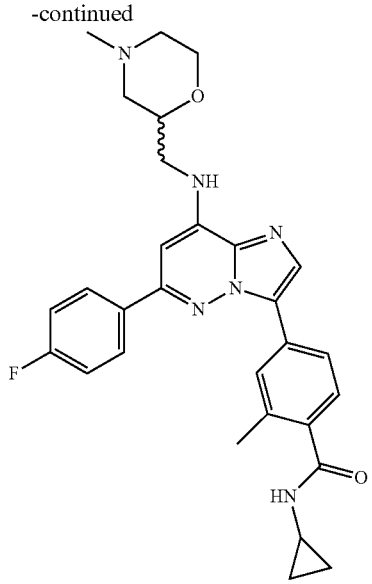

50 mg (110 μmol) (RS)-4-[6-chloro-8-({[(2S)-4-methyl-morpholin-2-yl]methyl}amino)imidazo[1,2-b]pyridazin-3-yl]-N-cyclopropyl-2-methylbenzamide which was prepared according to intermediate example 56a were transformed in analogy to example 1 using (4-fluorophenyl)boronic acid to give after working up and purification 12.2 mg (22%) of the title compound.

¹H-NMR (DMSO-d6): δ=0.51 (2H), 0.66 (2H), 1.80 (1H), 1.96 (1H), 2.14 (3H), 2.39 (3H), 2.54 (1H), 2.74 (1H), 2.81 (1H), 3.45-3.55 (3H), 3.72-3.80 (2H), 6.72 (1H), 7.34 (2H), 7.39 (2H), 8.00 (1H), 8.03 (1H), 8.06-8.12 (3H), 8.30 (1H), ppm.

Example 230

N-cyclopropyl-4-{8-[(2-hydroxy-2-methylpropyl)amino]-6-(pyridin-4-yl)imidazo[1,2-b]pyridazin-3-yl}-2-methylbenzamide

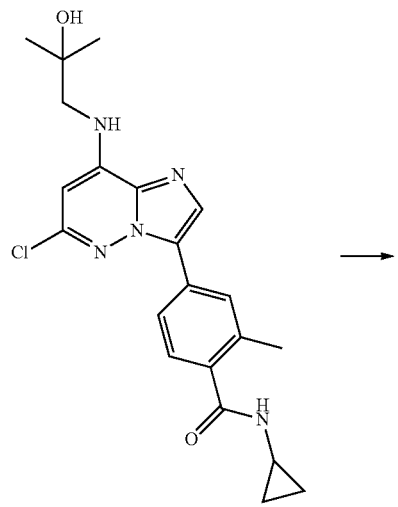

-continued

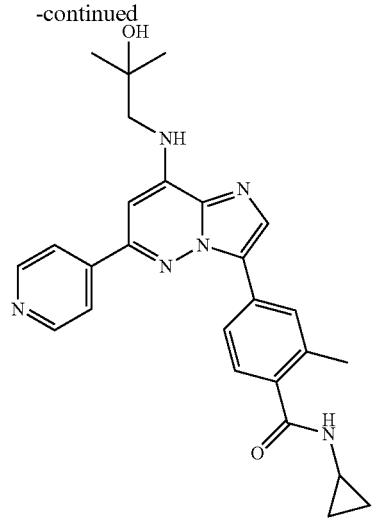

200 mg (483 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using pyridin-4-ylboronic acid to give after working up and purification 28.3 mg (12%) of the title compound.

¹H-NMR (DMSO-d6): δ=0.69 (2H), 0.91 (2H), 1.49 (6H), 2.46 (3H), 2.96 (1H), 3.33 (2H), 4.99 (1H), 6.23 (1H), 6.53 (1H), 6.58 (1H), 7.29 (1H), 7.66 (2H), 7.70 (1H), 7.76 (1H), 7.82 (1H), 8.57 (2H) ppm.

Example 231

N-cyclopropyl-2-methyl-4-[6-(methylsulfanyl)-8-{[2-(morpholin-4-ylsulfonyl)ethyl]amino}imidazo[1,2-b]pyridazin-3-yl]benzamide

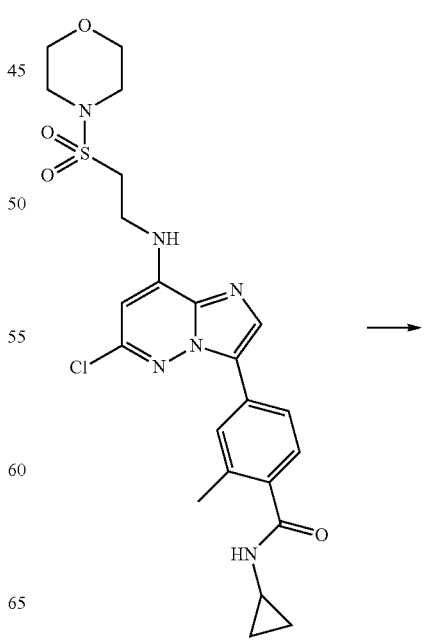

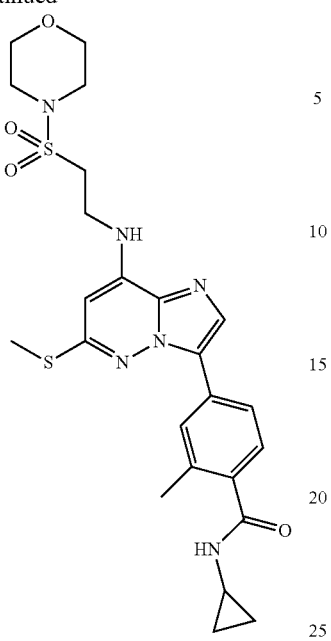

46 mg (89 μmol) 4-(6-chloro-8-{[2-(morpholin-4-ylsulfonyl)ethyl]amino}imidazo[1,2-b]pyridazin-3-yl)-N-cyclopropyl-2-methylbenzamide which was prepared according to intermediate example 231a were transformed in analogy to example 51 using sodium methanethiolate to give after working up and purification 12 mg (25%) of the title compound.

¹H-NMR (DMSO-d6): δ=0.50 (2H), 0.65 (2H), 2.36 (3H), 2.57 (3H), 2.80 (1H), 3.14 (4H), 3.44 (2H), 3.60 (4H), 3.69 (2H), 6.15 (1H), 7.35 (1H), 7.43 (1H), 7.93 (1H), 7.98 (1H), 8.06 (1H), 8.28 (1H) ppm.

Intermediate Example 231a 4-(6-chloro-8-{[2-(morpholin-4-ylsulfonyl)ethyl]amino}imidazo[1,2-b]pyridazin-3-yl)-N-cyclopropyl-2-methylbenzamide

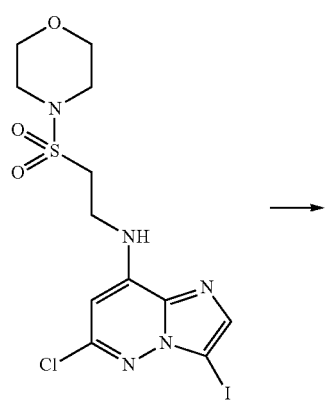

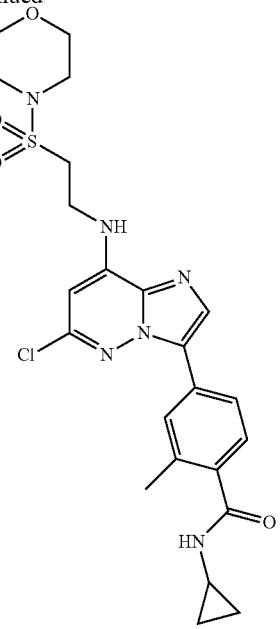

650 mg (1.38 mmol) 6-chloro-3-iodo-N-[2-(morpholin-4-ylsulfonyl)ethyl]imidazo[1,2-b]pyridazin-8-amine which was prepared according to intermediate example 231b were transformed in analogy to intermediate example 1a using N-cyclopropyl-2-methyl-4-(4,4,5,5-tetramethyl-1,3,2-dioxaborolan-2-yl)benzamide to give after working up and purification 102 mg (14%) of the title compound.

Intermediate Example 231b 6-chloro-3-iodo-N-[2-(morpholin-4-ylsulfonyl)ethyl]imidazo[1,2-b]pyridazin-8-amine

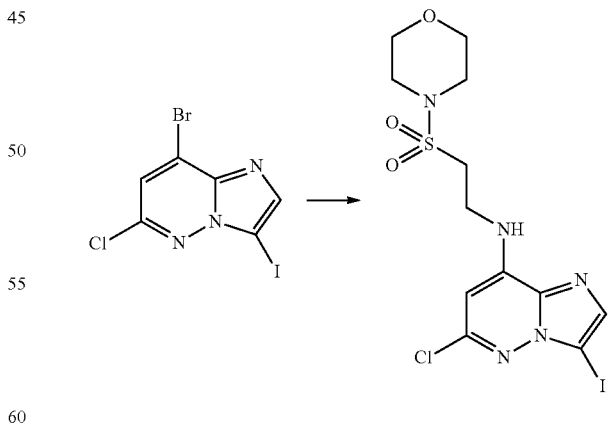

1.00 g (2.79 mmol) 8-bromo-6-chloro-3-iodoimidazo[1,2-b]pyridazine which was prepared according to intermediate example 1c were transformed in analogy to intermediate example 1b using 2-(morpholin-4-ylsulfonyl)ethanamine to give after working up and purification 650 mg (49%) of the title compound.

Example 232

N-cyclopropyl-4-{6-(4-fluoro-2-methylphenyl)-8-[(2-hydroxy-2-methylpropyl)amino]imidazo[1,2-b]pyridazin-3-yl}-2-methylbenzamide

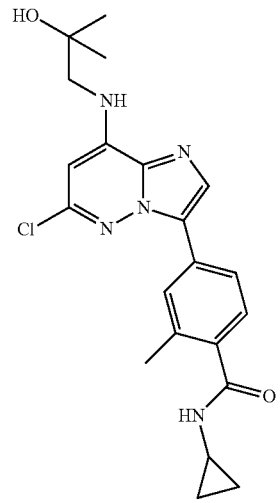

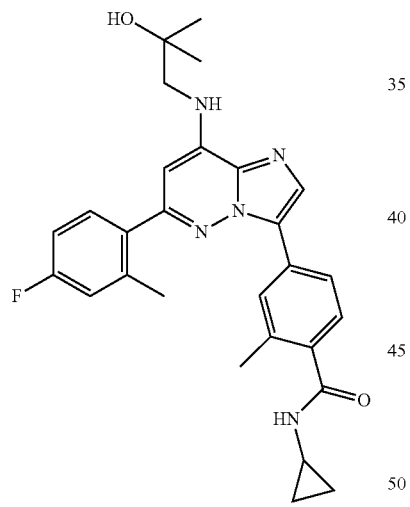

100 mg (242 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using (4-fluoro-2-methylphenyl)boronic acid to give after working up and purification 19.0 mg (15%) of the title compound.

$^1$H-NMR (DMSO-d6): δ=0.47 (2H), 0.64 (2H), 1.15 (6H), 2.33 (3H), 2.38 (3H), 2.78 (1H), 3.31 (2H), 4.71 (1H), 6.36 (1H), 6.95 (1H), 7.12 (1H), 7.19 (1H), 7.32 (1H), 7.47 (1H), 7.92 (1H), 7.98 (1H), 7.99 (1H), 8.24 (1H) ppm.

Example 233

N-cyclopropyl-4-{6-(2-fluorophenyl)-8-[(2-hydroxy-2-methylpropyl)amino]imidazo[1,2-b]pyridazin-3-yl}-2-methylbenzamide

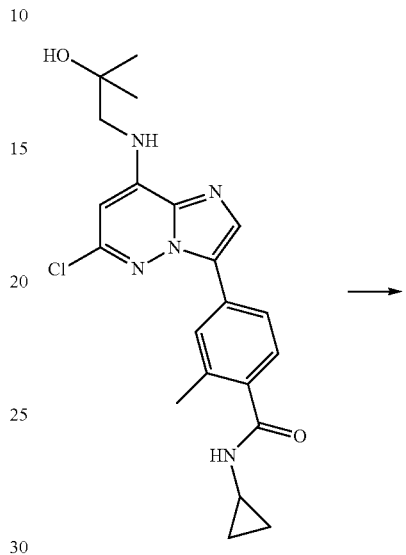

100 mg (242 μmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 1 using (2-fluorophenyl)boronic acid to give after working up and purification 10.0 mg (8%) of the title compound.

$^1$H-NMR (DMSO-d6): δ=0.49 (2H), 0.64 (2H), 1.16 (6H), 2.36 (3H), 2.79 (1H), 3.31 (2H), 4.74 (1H), 6.57 (1H), 7.00 (1H), 7.31-7.40 (3H), 7.52 (1H), 7.78 (1H), 8.01 (1H), 8.03 (1H), 8.06 (1H), 8.26 (1H) ppm.

Example 234

4-{6-(5-cyanopyridin-3-yl)-8-[(2-hydroxy-2-methyl-propyl)amino]imidazo[1,2-b]pyridazin-3-yl}-N-cyclopropyl-2-methylbenzamide

Example 235

N-cyclopropyl-4-{8-[(2-hydroxy-2-methylpropyl)amino]-6-[1-methyl-3-(trifluoromethyl)-1H-pyrazol-5-yl]imidazo[1,2-b]pyridazin-3-yl}-2-methylbenzamide

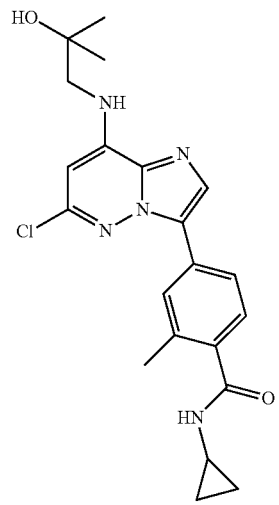

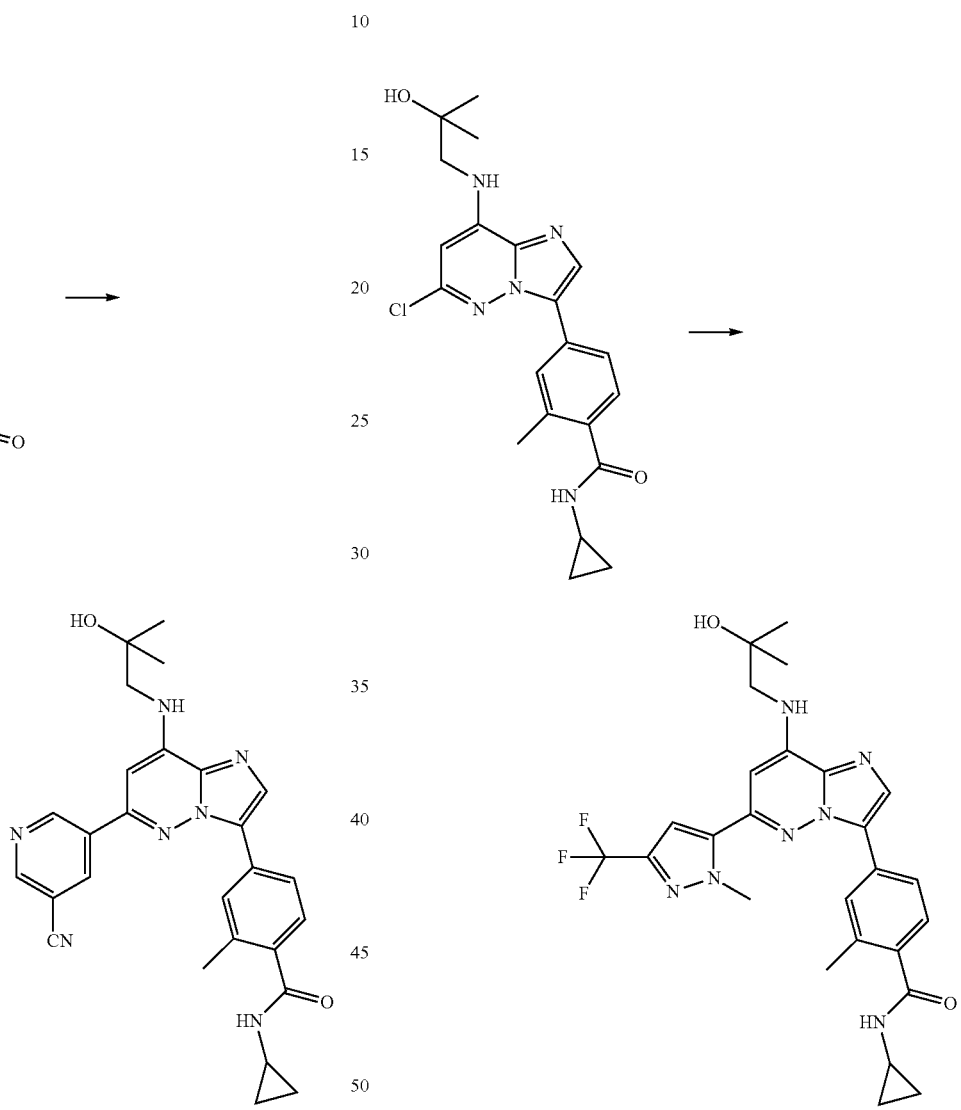

200 mg (483 µmol) 4-{6-chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 1 using (5-cyanopyridin-3-yl)boronic acid to give after working up and purification 19.0 mg (8%) of the title compound.

$^1$H-NMR (DMSO-d6): δ=0.51 (2H), 0.66 (2H), 1.19 (6H), 2.39 (3H), 2.81 (1H), 3.42 (2H), 4.79 (1H), 6.96 (1H), 7.08 (1H), 7.41 (1H), 8.01 (1H), 8.04 (1H), 8.10 (1H), 8.31 (1H), 8.91 (1H), 9.11 (1H), 9.50 (1H) ppm.

100 mg (242 µmol) 4-{6-chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 1 using [1-methyl-3-(trifluoromethyl)-1H-pyrazol-5-yl]boronic acid to give after working up and purification 25 mg (19%) of the title compound.

$^1$H-NMR (DMSO-d6): δ=0.50 (2H), 0.65 (2H), 1.17 (6H), 2.36 (3H), 2.80 (1H), 3.37 (2H), 4.22 (3H), 4.77 (1H), 6.73 (1H), 7.07 (1H), 7.37 (1H), 7.46 (1H), 7.91 (1H), 7.94 (1H), 8.00 (1H), 8.30 (1H) ppm.

347

Example 236

(RS)-4-{6-(cyclohex-1-en-1-yl)-8-[(3,3,3-trifluoro-2-hydroxypropyl)amino]imidazo[1,2-b]pyridazin-3-yl}-N-cyclopropyl-2-methylbenzamide

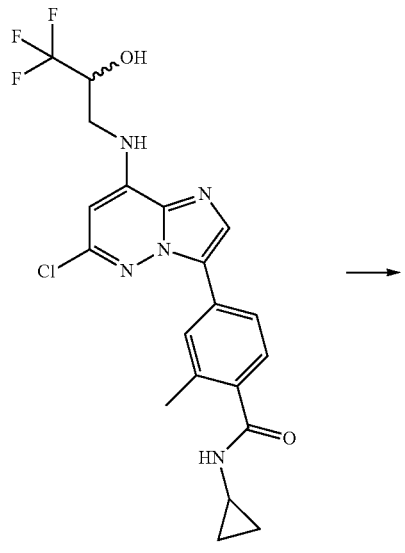

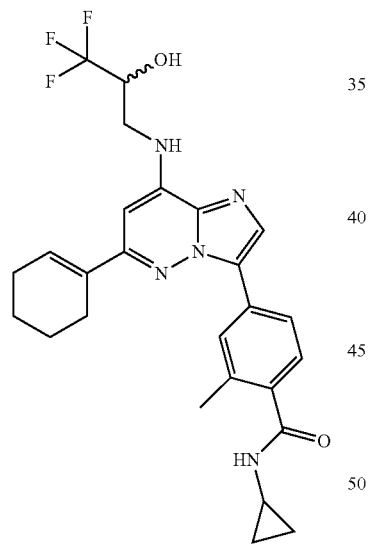

85 mg (187 µmol) (RS)-4-{6-chloro-8-[(3,3,3-trifluoro-2-hydroxypropyl)amino]imidazo[1,2-b]pyridazin-3-yl}-N-cyclopropyl-2-methylbenzamide which was prepared according to example 205 were transformed in analogy to intermediate example 1 using cyclohex-1-en-1-ylboronic acid to give after working up and purification 4.0 mg (4%) of the title compound.

$^1$H-NMR (DMSO-d6): δ=0.48 (2H), 0.62 (2H), 1.58 (2H), 1.68 (2H), 2.20 (2H), 2.34 (3H), 2.49 (2H), 2.77 (1H), 3.48 (1H), 3.64 (1H), 4.28 (1H), 6.46 (1H), 6.54 (1H), 6.65 (1H), 7.05 (1H), 7.33 (1H), 7.94 (1H), 8.01 (1H), 8.02 (1H), 8.23 (1H) ppm.

348

Example 237

N-cyclopropyl-2-methyl-4-[8-{[(1-methyl-1H-pyrazol-5-yl)methyl]amino}-6-(methylsulfanyl)imidazo[1,2-b]pyridazin-3-yl]benzamide

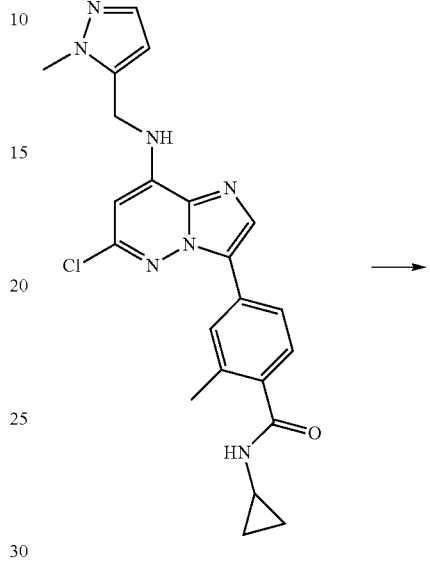

100 mg (229 µmol) 4-(6-chloro-8-{[(1-methyl-1H-pyrazol-5-yl)methyl]amino}imidazo[1,2-b]pyridazin-3-yl)-N-cyclopropyl-2-methylbenzamide which was prepared according to intermediate example 237a were transformed in analogy to example 51 using sodium methanethiolate to give after working up and purification 75 mg (72%) of the title compound.

$^1$H-NMR (DMSO-d6): δ=0.49 (2H), 0.65 (2H), 2.35 (3H), 2.53 (3H), 2.80 (1H), 3.79 (3H), 4.58 (2H), 6.14 (2H), 7.25 (1H), 7.34 (1H), 7.92-8.02 (3H), 8.05 (1H), 8.28 (1H) ppm.

Intermediate Example 237a 4-(6-chloro-8-{[(1-methyl-1H-pyrazol-5-yl)methyl]amino}imidazo[1,2-b]pyridazin-3-yl)-N-cyclopropyl-2-methylbenzamide

500 mg (1.29 mmol) 6-chloro-3-iodo-N-[(1-methyl-1H-pyrazol-5-yl)methyl]imidazo[1,2-b]pyridazin-8-amine which was prepared according to intermediate example 237b were transformed in analogy to intermediate example 1a using N-cyclopropyl-2-methyl-4-(4,4,5,5-tetramethyl-1,3,2-dioxaborolan-2-yl)benzamide to give after working up and purification 277 mg (47%) of the title compound.

Intermediate Example 237b 6-chloro-3-iodo-N-[(1-methyl-1H-pyrazol-5-yl)methyl]imidazo[1,2-b]pyridazin-8-amine

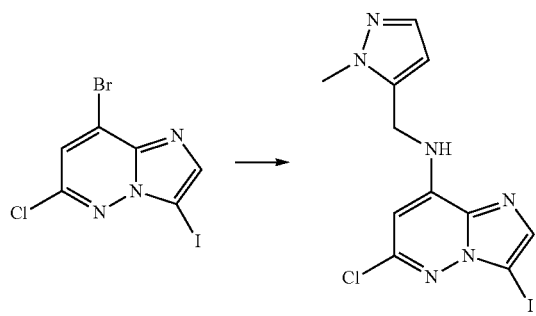 [SMILES: Clc1cc(Br)c2ncc(I)n2n1 ; Cn1nccc1CNc1cc(Cl)nn2c(I)cnc12]

1.00 g (2.79 mmol) 8-bromo-6-chloro-3-iodoimidazo[1,2-b]pyridazine which was prepared according to intermediate example 1c were transformed in analogy to intermediate example 1b using 1-(1-methyl-1H-pyrazol-5-yl)methanamine to give after working up and purification 1.00 g (92%) of the title compound.

Example 238

N-cyclopropyl-4-{6-[(3-hydroxyphenyl)sulfanyl]-8-[(3,3,3-trifluoropropyl)amino]imidazo[1,2-b]pyridazin-3-yl}-2-methylbenzamide

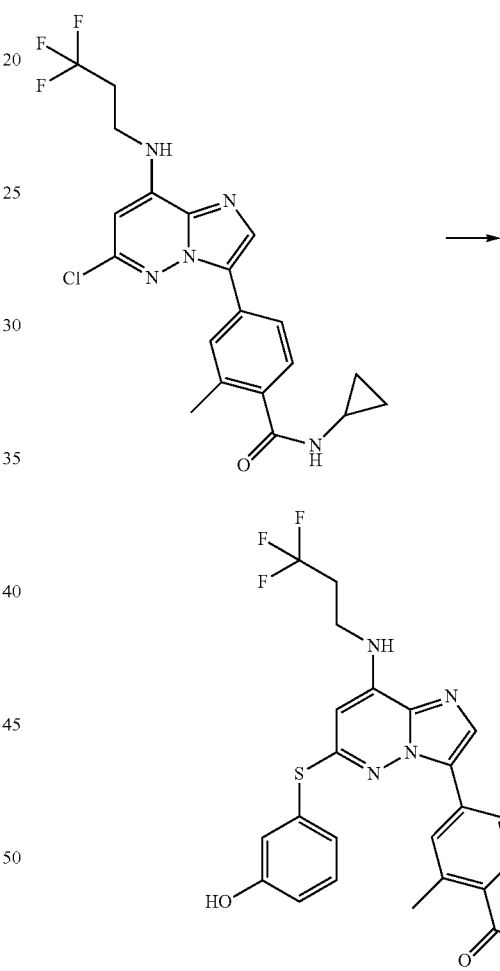

100 mg (228 μmol) 4-{6-chloro-8-[(3,3,3-trifluoropropyl)amino]imidazo[1,2-b]pyridazin-3-yl}-N-cyclopropyl-2-methylbenzamide which was prepared according to intermediate example 10a were transformed in analogy to example 51 using 3-methoxybenzenethiol to give after working up and purification 68 mg (65%) of the title compound.

$^1$H-NMR (DMSO-d6): δ=0.49 (2H), 0.65 (2H), 2.23 (3H), 2.60 (2H), 2.79 (1H), 3.52 (2H), 6.11 (1H), 6.86 (1H), 6.98 (1H), 7.01 (1H), 7.15 (1H), 7.26 (1H), 7.63 (1H), 7.73 (1H), 7.74 (1H), 7.94 (1H), 8.21 (1H), 9.69 (1H) ppm.

351
Example 239

N-cyclopropyl-4-(8-[(2-hydroxy-2-methylpropyl)
amino]-6-{[2-(morpholin-4-yl)ethyl]
sulfanyl}imidazo[1,2-b]pyridazin-3-yl)-2-methyl-
benzamide

352
Example 240

(RS)—N-cyclopropyl-4-{6-[(2,2-difluorocyclopro-
pyl)methoxy]-8-[(2-hydroxy-2-methylpropyl)amino]
imidazo[1,2-b]pyridazin-3-yl}-2-methylbenzamide

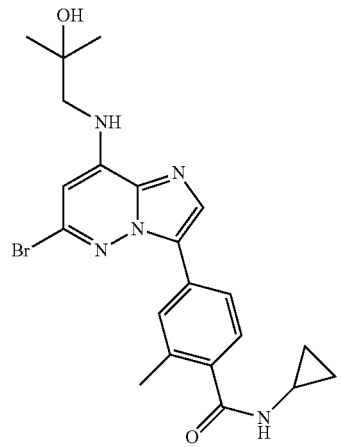

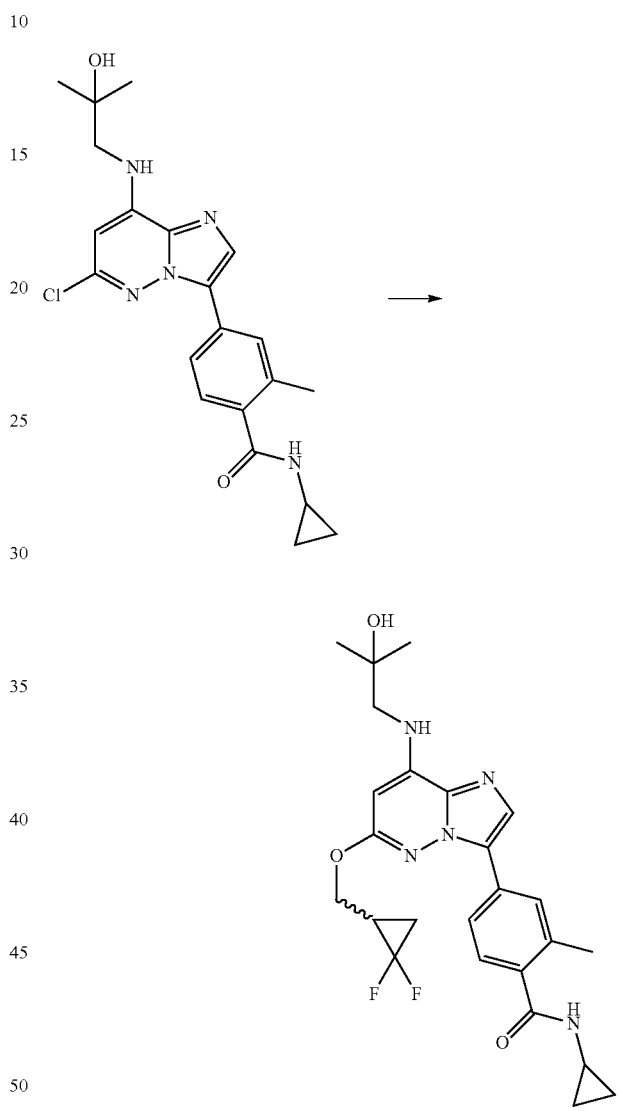

75 mg (164 µmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using 2-(morpholin-4-yl)ethanethiol to give after working up and purification 45.4 mg (50%) of the title compound.

$^1$H-NMR (DMSO-d6): δ=0.49 (2H), 0.65 (2H), 1.13 (6H), 2.30-2.40 (4H), 2.37 (3H), 2.61 (2H), 2.80 (1H), 3.22 (2H), 3.27 (2H), 3.51 (4H), 4.71 (1H), 6.18 (1H), 6.81 (1H), 7.33 (1H), 7.89 (1H), 7.96 (1H), 7.98 (1H), 8.28 (1H) ppm.

325 mg (785 µmol) 4-{6-chloro-8-[(2-hydroxy-2-methyl-propyl)amino]imidazo[1,2-b]pyridazin-3-yl}-N-cyclopropyl-2-methylbenzamide which was prepared according to intermediate example 7a were transformed in analogy to example 51 using [(1RS)-2,2-difluorocyclopropyl]methanol to give after working up and purification 12.3 mg (3%) of the title compound.

$^1$H-NMR (CDCl$_3$): δ=0.64 (2H), 0.89 (2H), 1.29 (1H), 1.43 (6H), 1.56 (1H), 2.15 (1H), 2.49 (3H), 2.92 (1H), 3.27 (2H), 4.34 (2H), 4.78 (1H), 5.70 (1H), 6.01 (1H), 6.42 (1H), 7.38 (1H), 7.60 (1H), 7.80 (1H), 7.83 (1H) ppm.

Example 241

N-cyclopropyl-4-{8-[(2-hydroxy-2-methylpropyl)amino]-6-(2,2,3,3-tetrafluoro-4-hydroxybutoxy)imidazo[1,2-b]pyridazin-3-yl}-2-methylbenzamide (A) and N-cyclopropyl-4-(8-[(2-hydroxy-2-methylpropyl)amino]-6-{[(1E)-2,3,3-trifluoro-4-hydroxybut-1-en-1-yl]oxy}imidazo[1,2-b]pyridazin-3-yl)-2-methylbenzamide

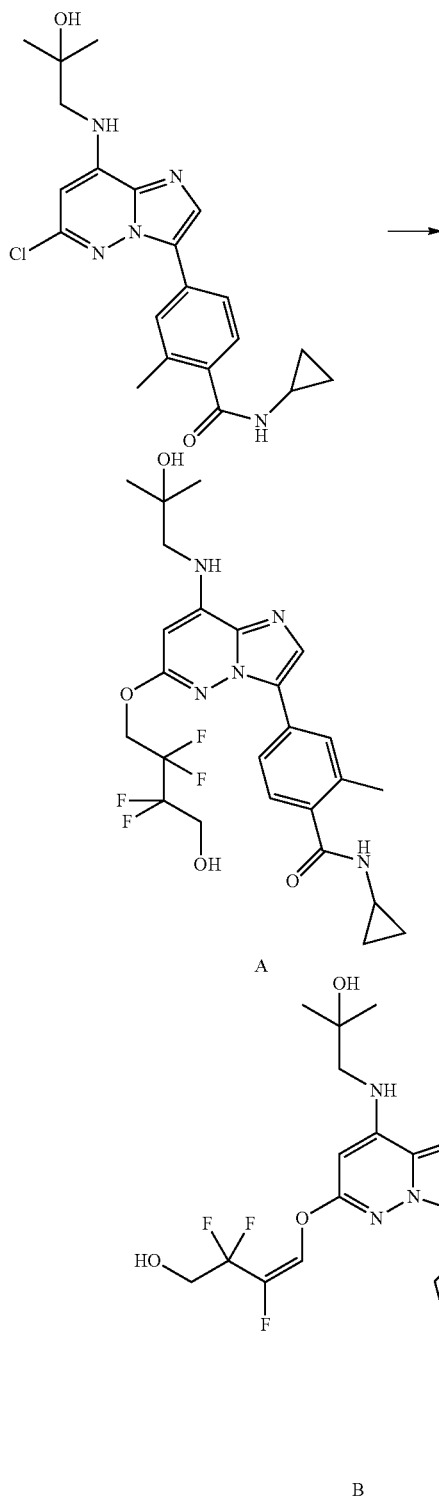

250 mg (604 µmol) 4-{6-chloro-8-[(2-hydroxy-2-methylpropyl)amino]imidazo[1,2-b]pyridazin-3-yl}-N-cyclopropyl-2-methylbenzamide which was prepared according to intermediate example 7a were transformed in analogy to example 51 using 2,2,3,3-tetrafluorobutane-1,4-diol to give after working up and purification 38.3 mg (12%) of the title compound A and 88.7 mg (28%) of the title compound B.

$^{1}$H-NMR (DMSO-d6) of A: δ=0.50 (2H), 0.65 (2H), 1.14 (6H), 2.35 (3H), 2.80 (1H), 3.26 (2H), 3.90 (2H), 4.71 (1H), 4.89 (2H), 6.01 (2H), 6.89 (1H), 7.33 (1H), 7.90 (1H), 7.93 (1H), 7.97 (1H), 7.28 (1H) ppm.

$^{1}$H-NMR (DMSO-d6) of B: δ=0.50 (2H), 0.65 (2H), 1.14 (6H), 2.35 (3H), 2.80 (1H), 3.26 (2H), 3.85 (2H), 4.70 (1H), 5.93 (1H), 6.18 (1H), 7.17 (1H), 7.33 (1H), 7.70 (1H), 7.89 (1H), 7.96 (1H), 8.02 (1H), 8.29 (1H) ppm.

Example 242

N-cyclopropyl-4-(8-[(2-hydroxy-2-methylpropyl)amino]-6-{[4-(trifluoromethyl)phenyl]sulfanyl}imidazo[1,2-b]pyridazin-3-yl)-2-methylbenzamide

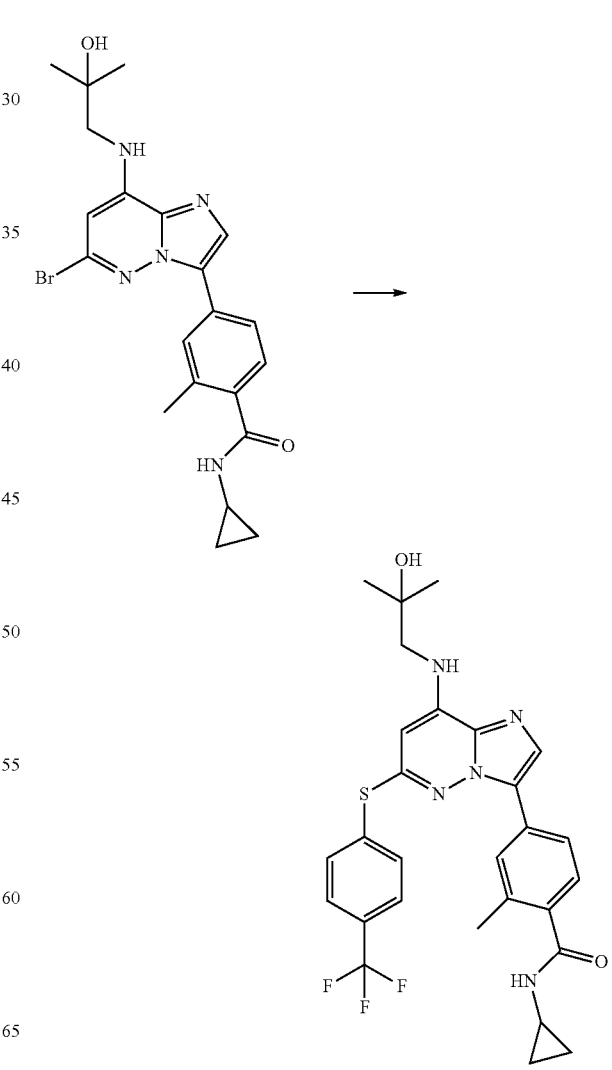

50 mg (109 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using 4-(trifluoromethyl)benzenethiol to give after working up and purification 23 mg (36%) of the title compound.

$^1$H-NMR (DMSO-d6): δ=0.47 (2H), 0.65 (2H), 1.13 (6H), 2.17 (3H), 2.78 (1H), 3.25 (2H), 4.70 (1H), 6.37 (1H), 7.04-7.10 (2H), 7.59 (1H), 7.69 (1H), 7.79 (4H), 7.95 (1H), 8.18 (1H) ppm.

Example 243

N-cyclopropyl-4-{8-[(2-hydroxy-2-methylpropyl)amino]-6-phenoxyimidazo[1,2-b]pyridazin-3-yl}benzenecarbothioamide

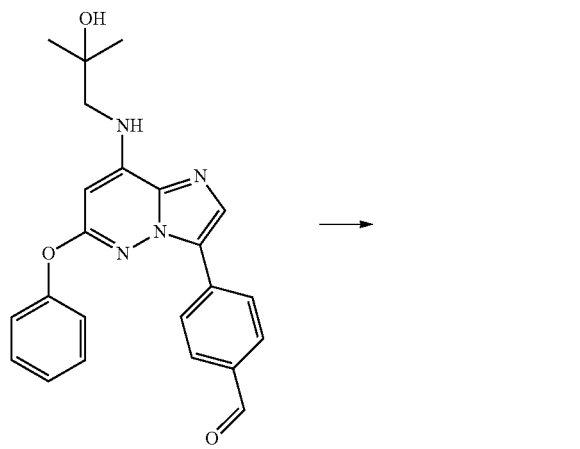

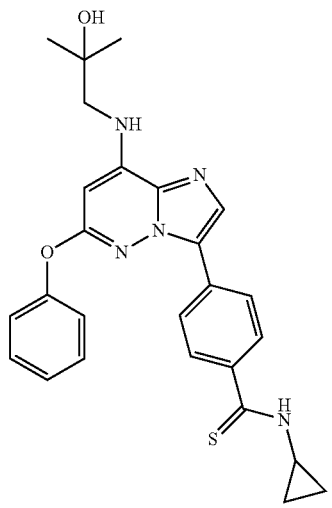

127 mg (316 μmol) 4-{8-[(2-hydroxy-2-methylpropyl)amino]-6-phenoxyimidazo[1,2-b]pyridazin-3-yl}benzaldehyde which was prepared according to intermediate example 243a were transformed in analogy to example 13 to give after working up and purification 47 mg (30%) of the title compound.

$^1$H-NMR (DMSO-d6): δ=0.71-0.87 (4H), 1.16 (6H), 3.26 (2H), 3.41 (1H), 4.72 (1H), 6.16 (1H), 6.99 (1H), 7.21-7.30 (3H), 7.44 (2H), 7.57 (2H), 7.91 (2H), 7.99 (1H), 10.05 (1H) ppm.

Intermediate Example 243a

4-{8-[(2-hydroxy-2-methylpropyl)amino]-6-phenoxyimidazo[1,2-b]pyridazin-3-yl}benzaldehyde

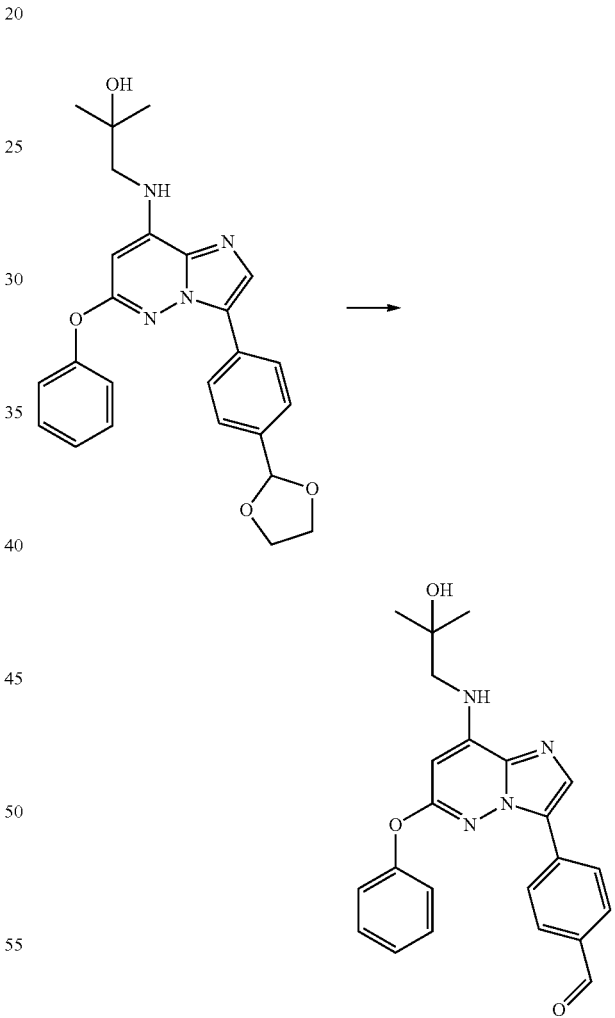

152 mg (340 μmol) 1-({3-[4-(1,3-dioxolan-2-yl)phenyl]-6-phenoxyimidazo[1,2-b]pyridazin-8-yl}amino)-2-methyl-propan-2-ol which was prepared according to intermediate example 243b were transformed in analogy to intermediate example 13a to give after working up and purification 132 mg (96%) of the title compound.

Intermediate Example 243b 1-({3-[4-(1,3-dioxolan-2-yl)phenyl]-6-phenoxyimidazo[1,2-b]pyridazin-8-yl}amino)-2-methylpropan-2-ol

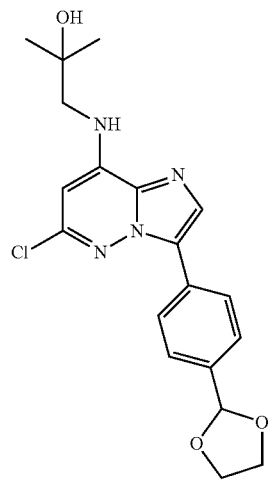

250 mg (643 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 51 using phenol to give after working up and purification 157 mg (55%) of the title compound.

Example 244

N-cyclopropyl-4-{6-(3-fluorophenoxy)-8-[(2-hydroxy-2-methylpropyl)amino]imidazo[1,2-b]pyridazin-3-yl}benzenecarbothioamide

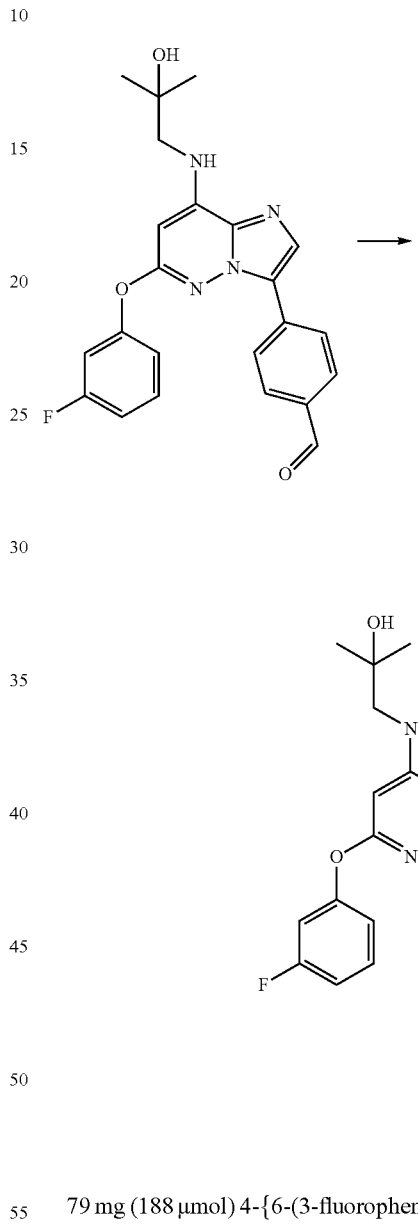

79 mg (188 µmol) 4-{6-(3-fluorophenoxy)-8-[(2-hydroxy-2-methylpropyl)amino]imidazo[1,2-b]pyridazin-3-yl}benzaldehyde which was prepared according to intermediate example 244a were transformed in analogy to example 13 to give after working up and purification 22 mg (22%) of the title compound.

$^1$H-NMR (DMSO-d6): δ=0.72-0.86 (4H), 1.15 (6H), 3.41 (2H), 3.49 (1H), 4.72 (1H), 6.18 (1H), 7.03-7.15 (3H), 7.21 (1H), 7.47 (1H), 7.60 (2H), 7.92 (2H), 8.00 (1H), 10.07 (1H) ppm.

Intermediate Example 244a

4-{6-(3-fluorophenoxy)-8-[(2-hydroxy-2-methylpropyl)amino]imidazo[1,2-b]pyridazin-3-yl}benzaldehyde

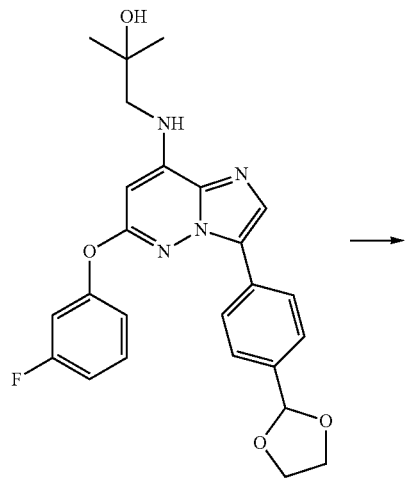

Intermediate Example 244b 1-({3-[4-(1,3-dioxolan-2-yl)phenyl]-6-(3-fluorophenoxy)imidazo[1,2-b]pyridazin-8-yl}amino)-2-methylpropan-2-ol

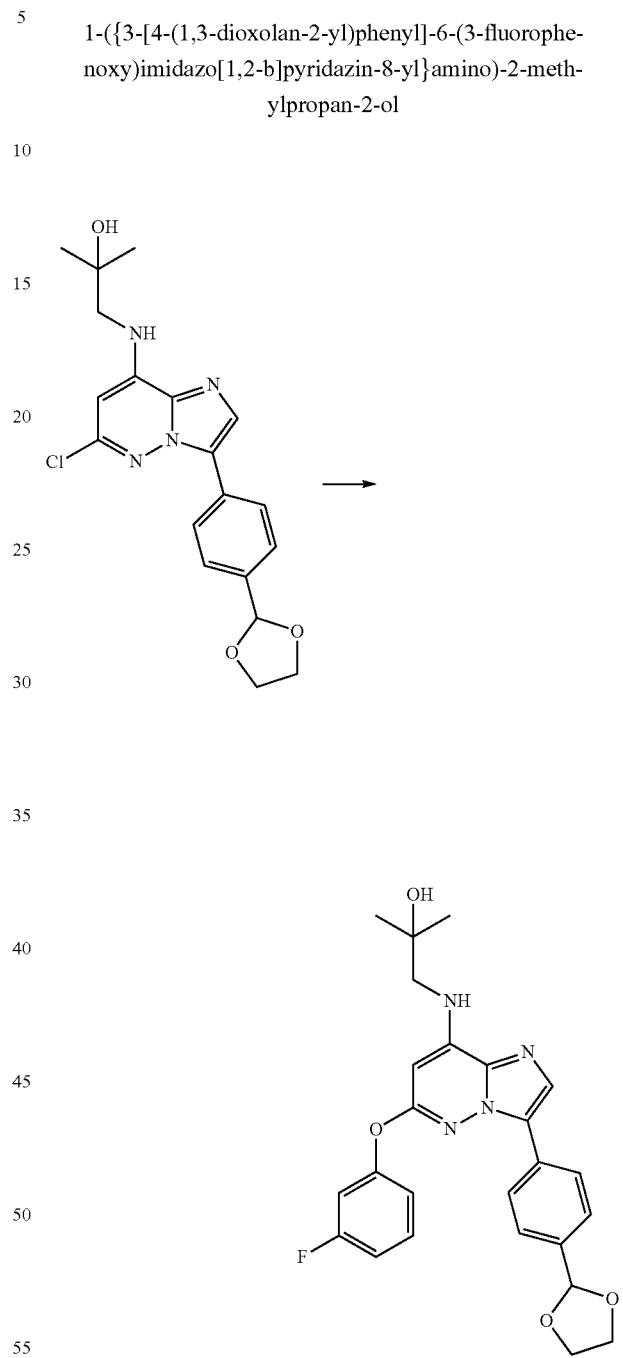

92 mg (198 µmol) 1-({3-[4-(1,3-dioxolan-2-yl)phenyl]-6-(3-fluorophenoxy)imidazo[1,2-b]pyridazin-8-yl}amino)-2-methylpropan-2-ol which was prepared according to intermediate example 244b were transformed in analogy to intermediate example 13a to give after working up and purification 80 mg (96%) of the title compound.

250 mg (643 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 51 using 3-fluorophenol to give after working up and purification 94.2 mg (32%) of the title compound.

Example 245

N-cyclopropyl-4-{8-[(2-hydroxy-2-methylpropyl)amino]-6-(phenylsulfanyl) imidazo[1,2-b]pyridazin-3-yl}benzenecarbothioamide

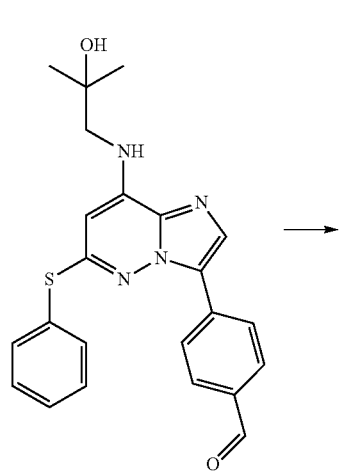

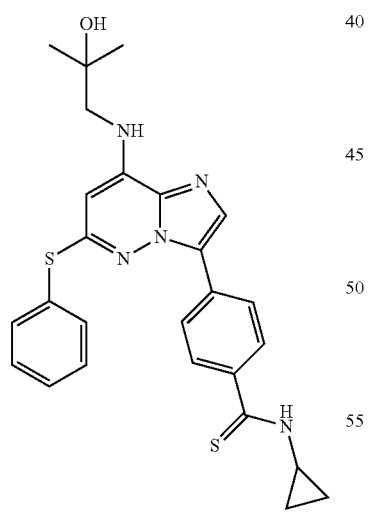

105 mg (251 μmol) 4-{8-[(2-hydroxy-2-methylpropyl)amino]-6-(phenylsulfanyl)imidazo[1,2-b]pyridazin-3-yl}benzaldehyde which was prepared according to intermediate example 245a were transformed in analogy to example 13 to give after working up and purification 27.3 mg (21%) of the title compound.

Intermediate Example 245a

4-{8-[(2-hydroxy-2-methylpropyl)amino]-6-(phenylsulfanyl)imidazo[1,2-b]pyridazin-3-yl}benzaldehyde

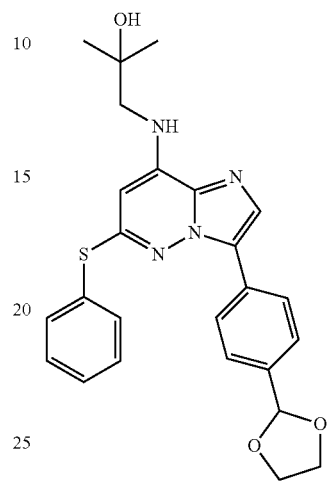

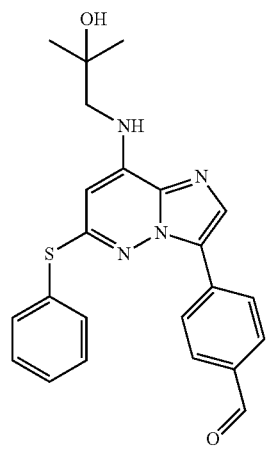

155 mg (335 μmol) 1-({3-[4-(1,3-dioxolan-2-yl)phenyl]-6-(phenylsulfanyl)imidazo[1,2-b]pyridazin-8-yl}amino)-2-methylpropan-2-ol which was prepared according to intermediate example 245b were transformed in analogy to intermediate example 13a to give after working up and purification 109 mg (78%) of the title compound.

Intermediate Example 245b 1-({3-[4-(1,3-dioxolan-2-yl)phenyl]-6-(phenylsulfanyl)imidazo[1,2-b]pyridazin-8-yl}amino)-2-methyl-propan-2-ol

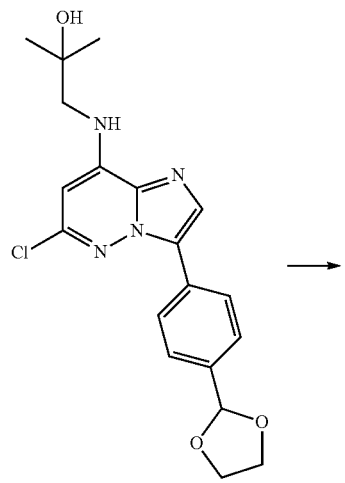

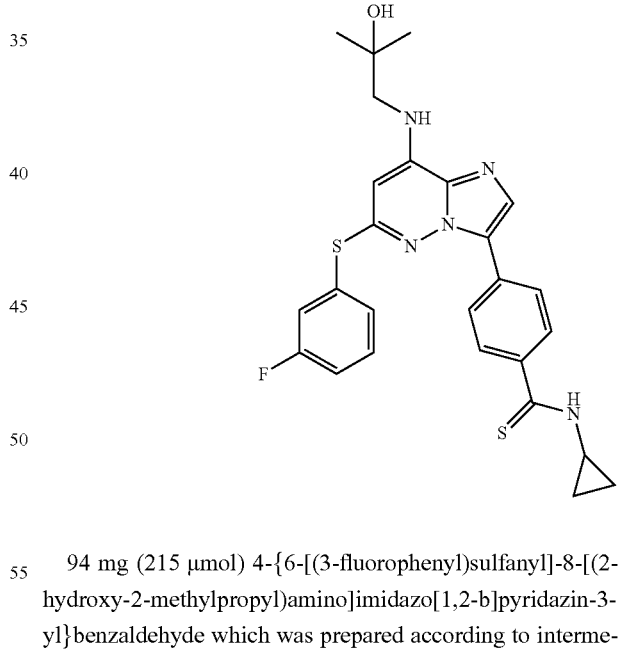

250 mg (643 μmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 51 using benzenethiol to give after working up and purification 154 mg (52%) of the title compound.

Example 246

N-cyclopropyl-4-{6-[(3-fluorophenyl)sulfanyl]-8-[(2-hydroxy-2-methylpropyl)amino]imidazo[1,2-b]pyridazin-3-yl}benzenecarbothioamide

94 mg (215 μmol) 4-{6-[(3-fluorophenyl)sulfanyl]-8-[(2-hydroxy-2-methylpropyl)amino]imidazo[1,2-b]pyridazin-3-yl}benzaldehyde which was prepared according to intermediate example 246a were transformed in analogy to example 13 to give after working up and purification 9.2 mg (8%) of the title compound.

$^1$H-NMR (DMSO-d6): δ=0.75-0.87 (4H), 1.12 (6H), 3.23 (2H), 3.44 (1H), 4.71 (1H), 6.31 (1H), 7.07 (1H), 7.35 (1H), 7.44 (1H), 7.48-7.55 (2H), 7.58 (2H), 7.85 (2H), 8.01 (1H), 10.10 (1H) ppm.

Intermediate Example 246a

4-{6-[(3-fluorophenyl)sulfanyl]-8-[(2-hydroxy-2-methylpropyl)amino]imidazo[1,2-b]pyridazin-3-yl}benzaldehyde

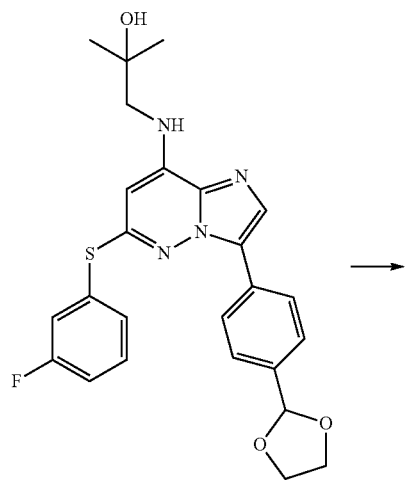

Intermediate Example 246b 1-({3-[4-(1,3-dioxolan-2-yl)phenyl]-6-[(3-fluorophenyl)sulfanyl]imidazo[1,2-b]pyridazin-8-yl}amino)-2-methylpropan-2-ol

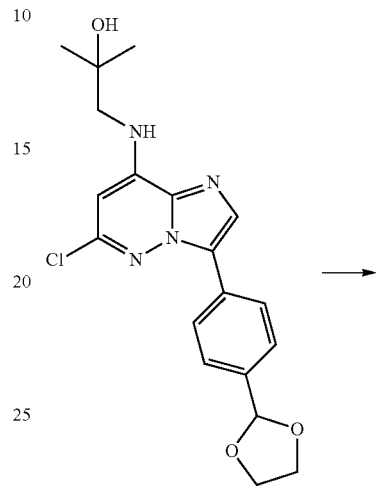

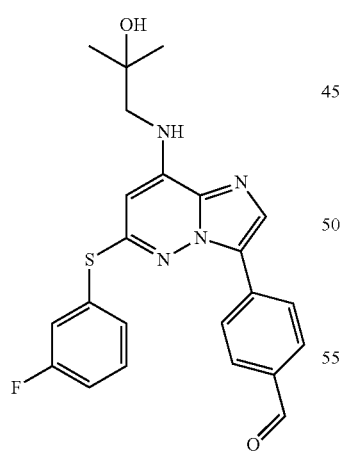

108 mg (225 µmol) 1-({3-[4-(1,3-dioxolan-2-yl)phenyl]-6-[(3-fluorophenyl)sulfanyl]imidazo[1,2-b]pyridazin-8-yl}amino)-2-methylpropan-2-ol which was prepared according to intermediate example 246b were transformed in analogy to intermediate example 13a to give after working up and purification 95 mg (97%) of the title compound.

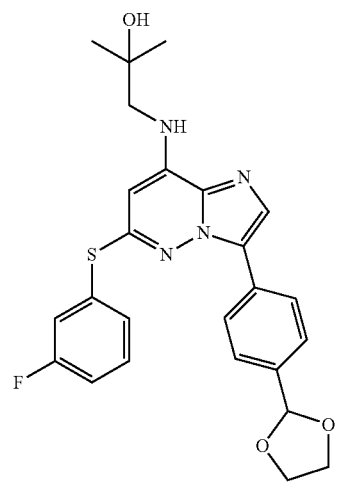

250 mg (643 µmol) 1-({6-chloro-3-[4-(1,3-dioxolan-2-yl)phenyl]imidazo[1,2-b]pyridazin-8-yl}amino)-2-methylpropan-2-ol which was prepared according to intermediate example 32c were transformed in analogy to example 51 using 3-fluorobenzenethiol to give after working up and purification 103.2 mg (33%) of the title compound.

Example 247

N-cyclopropyl-2-methyl-4-(6-{[4-(trifluoromethyl)phenyl]sulfanyl}-8-[(3,3,3-trifluoropropyl)amino]imidazo[1,2-b]pyridazin-3-yl)benzamide

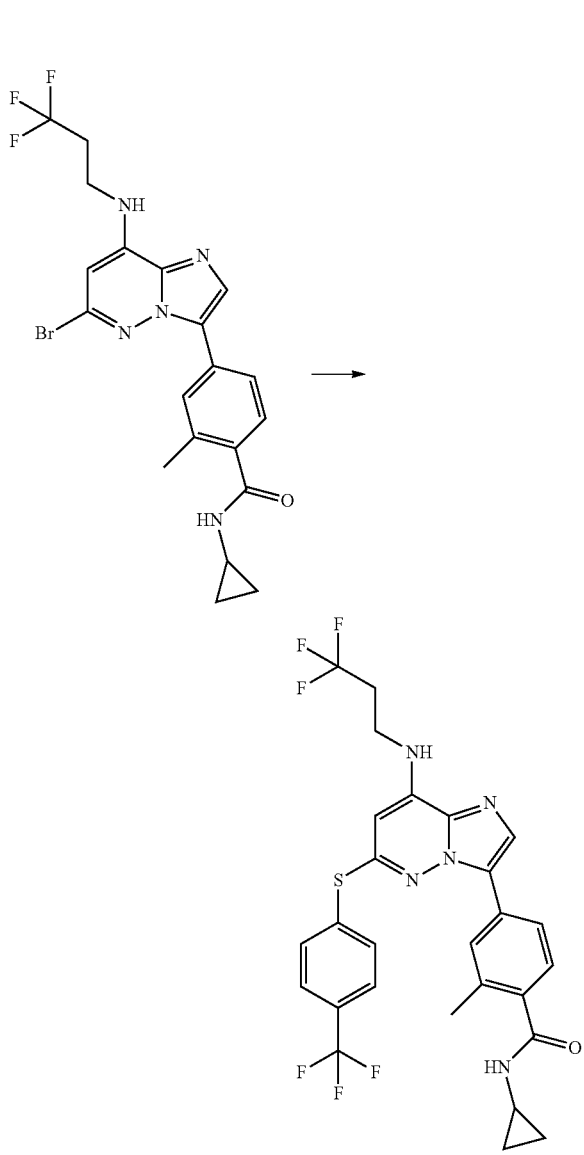

50 mg (104 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 4-(trifluoromethyl)benzenethiol to give after working up and purification 20.2 mg (32%) of the title compound.

$^1$H-NMR (CDCl$_3$): δ=0.60 (2H), 0.86 (2H), 2.37 (3H), 2.51 (2H), 2.87 (1H), 3.57 (2H), 5.95 (1H), 6.04 (1H), 6.54 (1H), 7.08 (1H), 7.48 (1H), 7.55 (1H), 7.66 (2H), 7.68 (1H), 7.73 (2H) ppm.

Intermediate Example 247a

4-{6-bromo-8-[(3,3,3-trifluoropropyl)amino]imidazo[1,2-b]pyridazin-3-yl}-N-cyclopropyl-2-methylbenzamide

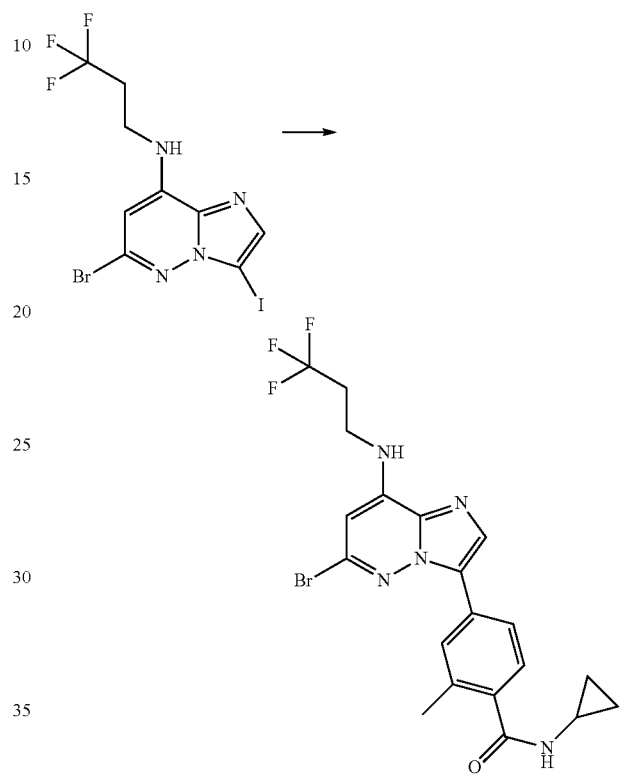

1.00 g (2.3 mmol) 6-bromo-3-iodo-N-(3,3,3-trifluoropropyl)imidazo[1,2-b]pyridazin-8-amine which was prepared according to intermediate example 247b were transformed in analogy to intermediate example 1a using N-cyclopropyl-2-methyl-4-(4,4,5,5-tetramethyl-1,3,2-dioxaborolan-2-yl)benzamide which was prepared according to intermediate example 7b to give after working up and purification 580 mg (52%) of the title compound.

Intermediate Example 247b 6-bromo-3-iodo-N-(3,3,3-trifluoropropyl)imidazo[1,2-b]pyridazin-8-amine

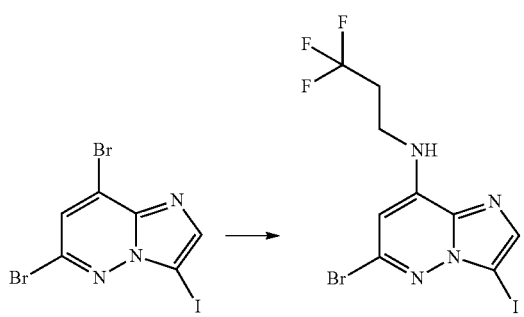 [SMILES: Brc1cc(Br)c2ncc(I)n2n1 ; FC(F)(F)CCNc1cc(Br)nn2c(I)cnc12]

2.30 g (5.71 mmol) 6,8-dibromo-3-iodoimidazo[1,2-b]pyridazine which was prepared according to intermediate example 96c were transformed in analogy to intermediate example 1b using 3,3,3-trifluoropropan-1-amine to give after working up and purification 2.0 g (81%) of the title compound.

Example 248

N-cyclopropyl-4-{6-[(2,5-difluorophenyl)sulfanyl]-8-[(2-hydroxy-2-methylpropyl)amino]imidazo[1,2-b]pyridazin-3-yl}-2-methylbenzamide

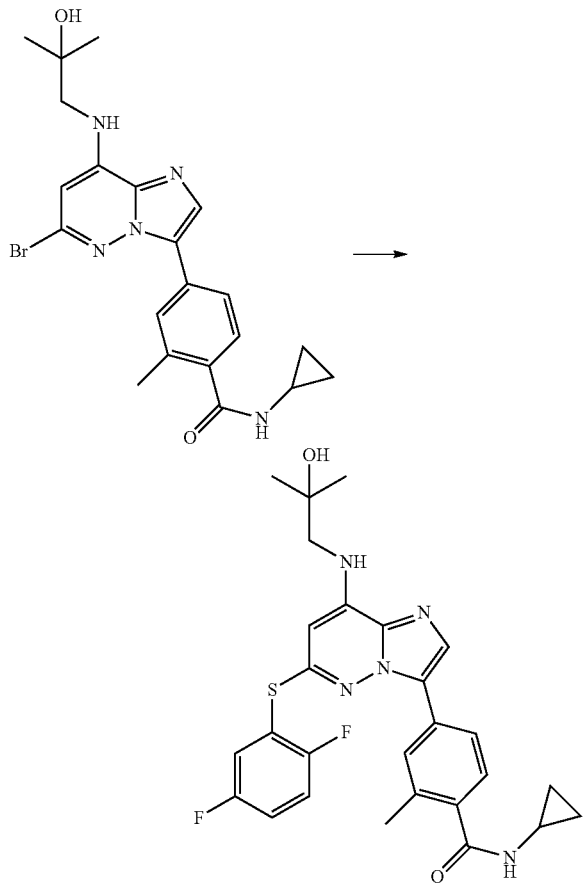

50 mg (109 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 2,5-difluorobenzenethiol to give after working up and purification 10.4 mg (17%) of the title compound.

$^1$H-NMR (DMSO-d6): δ=0.49 (2H), 0.65 (2H), 1.14 (6H), 2.20 (3H), 2.79 (1H), 3.25 (2H), 4.71 (1H), 6.35 (1H), 7.04 (1H), 7.08 (1H), 7.42-7.51 (2H), 7.57 (1H), 7.62 (1H), 7.66 (1H), 7.94 (1H), 8.22 (1H) ppm.

Example 249

N-cyclopropyl-4-{6-[(3,4-difluorophenyl)sulfanyl]-8-[(3,3,3-trifluoropropyl)amino]imidazo[1,2-b]pyridazin-3-yl}-2-methylbenzamide

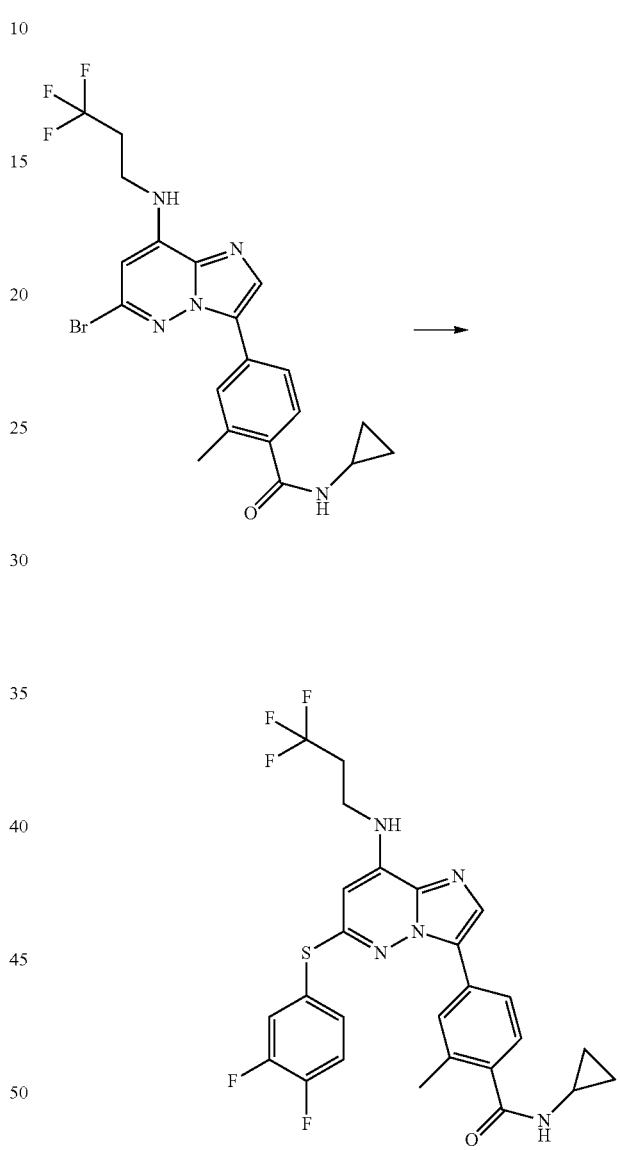

50 mg (104 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3,4-difluorobenzenethiol to give after working up and purification 5.0 mg (8%) of the title compound.

$^1$H-NMR (CDCl$_3$): δ=0.64 (2H), 0.90 (2H), 2.42 (3H), 2.52 (2H), 2.93 (1H), 3.61 (2H), 5.88 (1H), 8.90 (1H), 5.94 (1H), 7.20-7.28 (2H), 7.39 (1H), 7.51 (1H), 7.56 (1H), 7.57 (1H), 7.70 (1H) ppm.

371

Example 250

N-cyclopropyl-4-{6-[(4-fluorophenyl)sulfanyl]-8-[(3,3,3-trifluoropropyl)amino]imidazo[1,2-b]pyridazin-3-yl}-2-methylbenzamide

372

Example 251

N-cyclopropyl-4-{6-[(3,5-difluorophenyl)sulfanyl]-8-[(3,3,3-trifluoropropyl)amino]imidazo[1,2-b]pyridazin-3-yl}-2-methylbenzamide

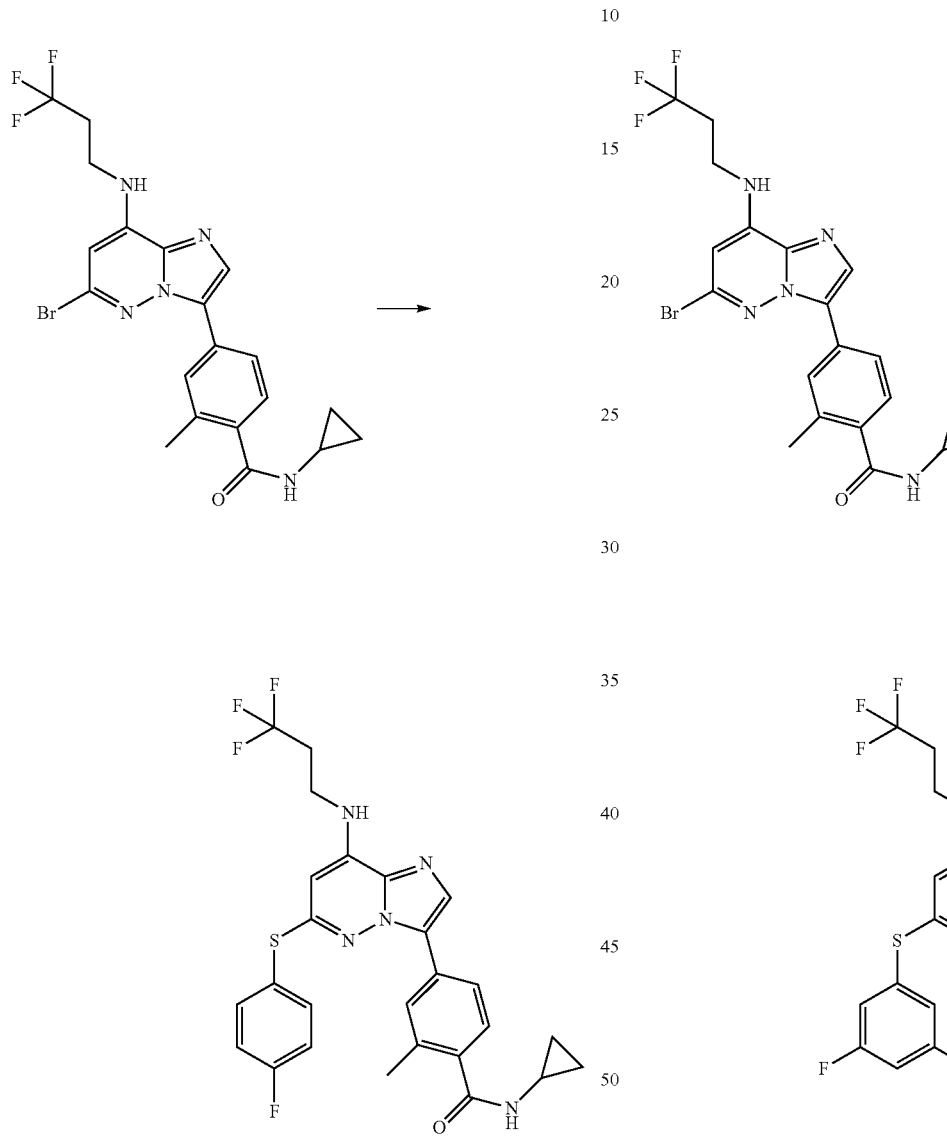

50 mg (104 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 4-fluorobenzenethiol to give after working up and purification 3.8 mg (7%) of the title compound.

$^1$H-NMR (CDCl$_3$): δ=0.64 (2H), 0.90 (2H), 2.41 (3H), 2.50 (2H), 2.93 (1H), 3.59 (2H), 5.87 (1H), 5.88 (1H), 5.96 (1H), 7.15 (2H), 7.19 (1H), 7.55 (1H), 7.59 (1H), 7.64 (2H), 7.70 (1H) ppm.

50 mg (104 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3,5-difluorobenzenethiol to give after working up and purification 2.9 mg (5%) of the title compound.

$^1$H-NMR (CDCl$_3$): δ=0.63 (2H), 0.90 (2H), 2.43 (3H), 2.52 (2H), 2.93 (1H), 3.62 (2H), 5.86 (1H), 5.96 (1H), 6.00 (1H), 6.88 (1H), 7.18 (2H), 7.29 (1H), 7.65 (1H), 7.69 (1H), 7.73 (1H) ppm.

373

Example 252

N-cyclopropyl-4-{6-[(2,3-difluorophenyl)sulfanyl]-8-[(3,3,3-trifluoropropyl)amino]imidazo[1,2-b]pyridazin-3-yl}-2-methylbenzamide

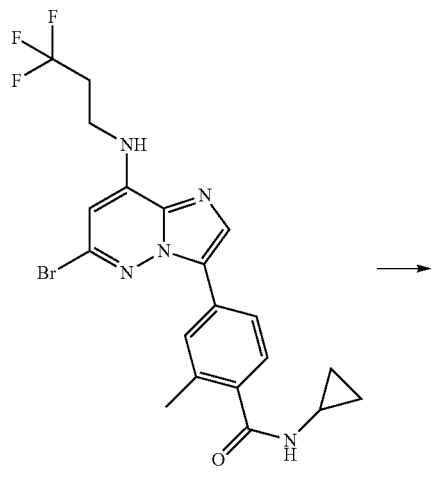

374

Example 253

N-cyclopropyl-4-{6-(4-fluorophenoxy)-8-[(2-hydroxy-2-methylpropyl)amino]imidazo[1,2-b]pyridazin-3-yl}-2-methylbenzamide

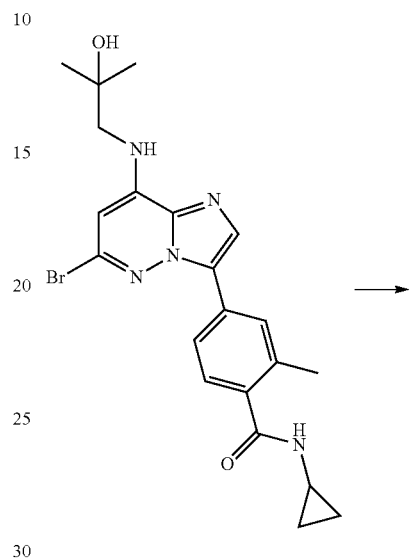

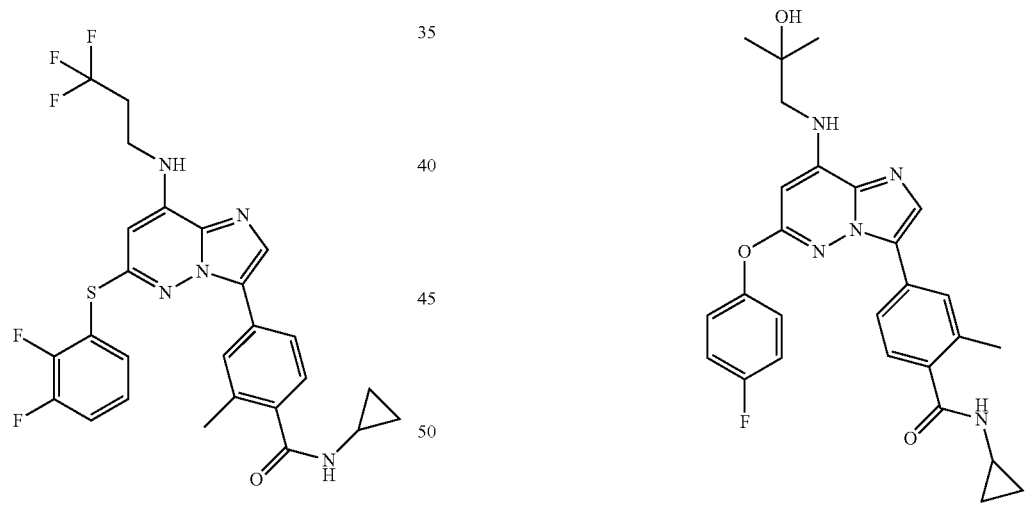

50 mg (104 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2,3-difluorobenzenethiol to give after working up and purification 1.6 mg (3%) of the title compound.

$^1$H-NMR (CDCl$_3$): δ=0.63 (2H), 0.90 (2H), 2.39 (3H), 2.54 (2H), 2.93 (1H), 3.62 (2H), 5.85 (1H), 5.97 (1H), 6.10 (1H), 7.16 (1H), 7.20 (1H), 7.33 (1H), 7.41 (1H), 7.56 (1H), 7.57 (1H), 7.69 (1H) ppm.

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 4-fluorophenol to give after working up and purification 27.5 mg (49%) of the title compound.

$^1$H-NMR (DMSO-d6): δ=0.47 (2H), 0.63 (2H), 1.16 (6H), 2.13 (3H), 2.77 (1H), 3.27 (2H), 4.73 (1H), 6.16 (1H), 6.95 (1H), 7.16 (1H), 7.24-7.34 (4H), 7.64 (1H), 7.73 (1H), 7.91 (1H), 8.19 (1H) ppm.

Example 254

N-cyclopropyl-4-{6-(3,4-difluorophenoxy)-8-[(2-hydroxy-2-methylpropyl)amino]imidazo[1,2-b]pyridazin-3-yl}-2-methylbenzamide

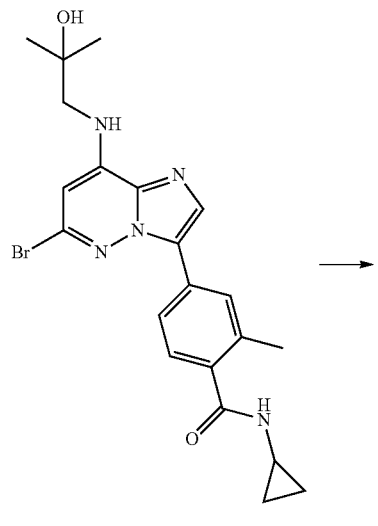

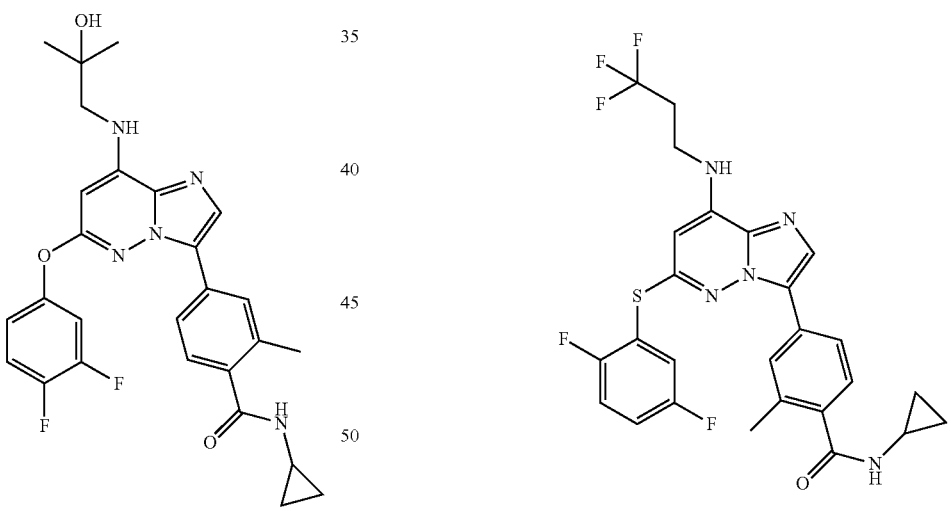

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3,4-difluorophenol to give after working up and purification 18.1 mg (31%) of the title compound.

$^1$H-NMR (DMSO-d6): δ=0.47 (2H), 0.64 (2H), 1.16 (6H), 2.14 (3H), 2.77 (1H), 3.27 (2H), 4.73 (1H), 6.17 (1H), 7.00 (1H), 7.13 (1H), 7.18 (1H), 7.51 (1H), 7.56 (1H), 7.65 (1H), 7.75 (1H), 7.91 (1H), 8.21 (1H) ppm.

Example 255

N-cyclopropyl-4-{6-[(2,5-difluorophenyl)sulfanyl]-8-[(3,3,3-trifluoropropyl)amino]imidazo[1,2-b]pyridazin-3-yl}-2-methylbenzamide

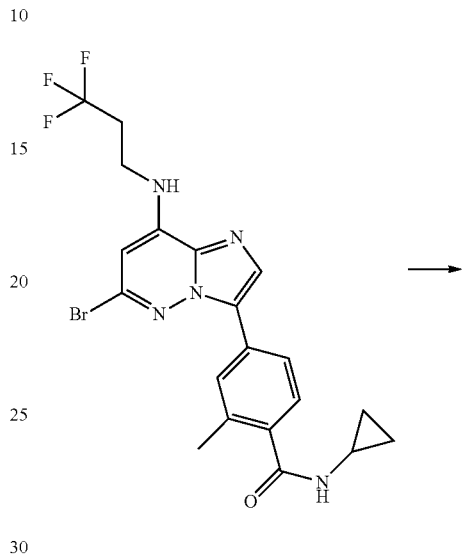

50 mg (104 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2,5-difluorobenzenethiol to give after working up and purification 13.3 mg (22%) of the title compound.

$^1$H-NMR (CDCl$_3$): δ=0.62 (2H), 0.90 (2H), 2.39 (3H), 2.53 (2H), 2.92 (1H), 3.62 (2H), 5.87 (1H), 5.97 (1H), 6.06 (1H), 7.14-7.23 (3H), 7.39 (1H), 7.57 (1H), 7.59 (1H), 7.70 (1H) ppm.

377
Example 256

N-cyclopropyl-4-{8-[(2-hydroxy-2-methylpropyl)amino]-6-(4-isopropoxyphenoxy)imidazo[1,2-b]pyridazin-3-yl}-2-methylbenzamide

378
Example 257

N-cyclopropyl-4-{6-(4-isopropoxyphenoxy)-8-[(3,3,3-trifluoropropyl)amino]imidazo[1,2-b]pyridazin-3-yl}-2-methylbenzamide

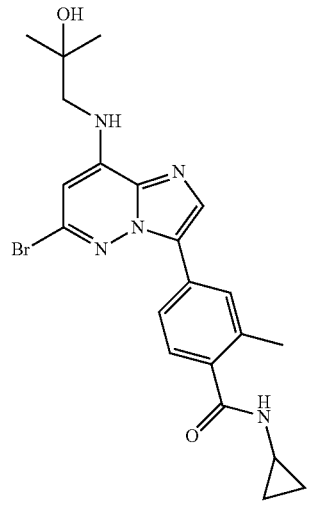
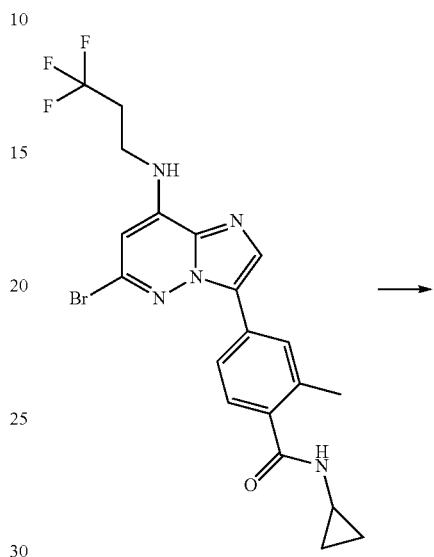
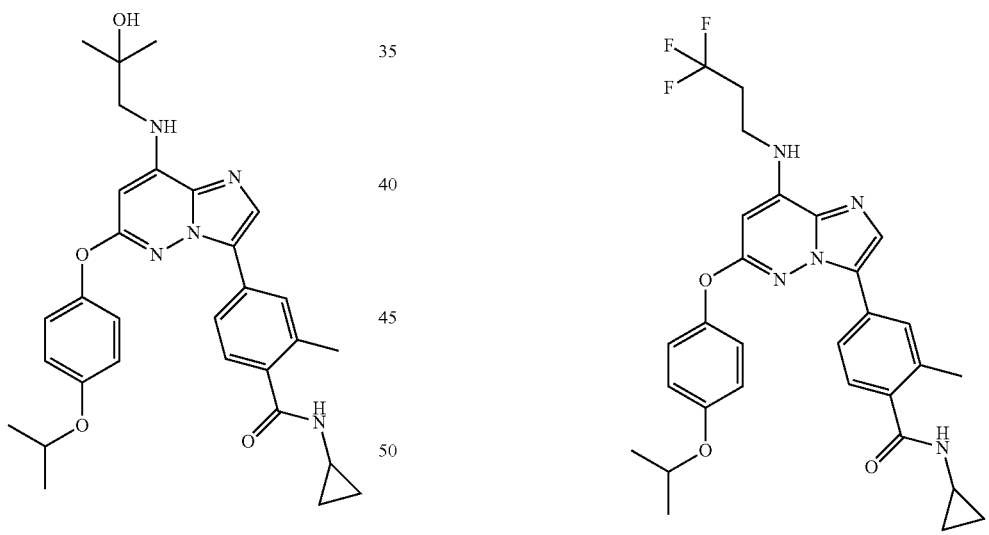

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 4-isopropoxyphenol to give after working up and purification 13.7 mg (15%) of the title compound.

$^1$H-NMR (CDCl$_3$): δ=0.60 (2H), 0.87 (2H), 1.36 (6H), 1.44 (6H), 2.30 (3H), 2.89 (1H), 3.31 (2H), 4.52 (1H), 5.87 (1H), 5.93 (1H), 6.52 (1H), 6.91 (2H), 7.11 (2H), 7.19 (1H), 7.58 (1H), 7.64 (1H), 7.74 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 4-isopropoxyphenol to give after working up and purification 9.3 mg (10%) of the title compound.

$^1$H-NMR (CDCl$_3$): δ=0.59 (2H), 0.88 (2H), 1.37 (6H), 2.32 (3H), 2.56 (2H), 2.88 (1H), 3.66 (2H), 4.53 (1H), 5.84 (1H), 5.88 (1H), 5.91 (1H), 6.93 (2H), 7.14 (2H), 7.22 (1H), 7.62 (1H), 7.73 (1H), 7.79 (1H) ppm.

379

Example 258

N-cyclopropyl-4-{6-(2,3-difluorophenoxy)-8-[(3,3,3-trifluoropropyl)amino]imidazo[1,2-b]pyridazin-3-yl}-2-methylbenzamide

380

Example 259

N-cyclopropyl-4-{6-(2-fluoro-5-methylphenoxy)-8-[(3,3,3-trifluoropropyl)amino]imidazo[1,2-b]pyridazin-3-yl}-2-methylbenzamide

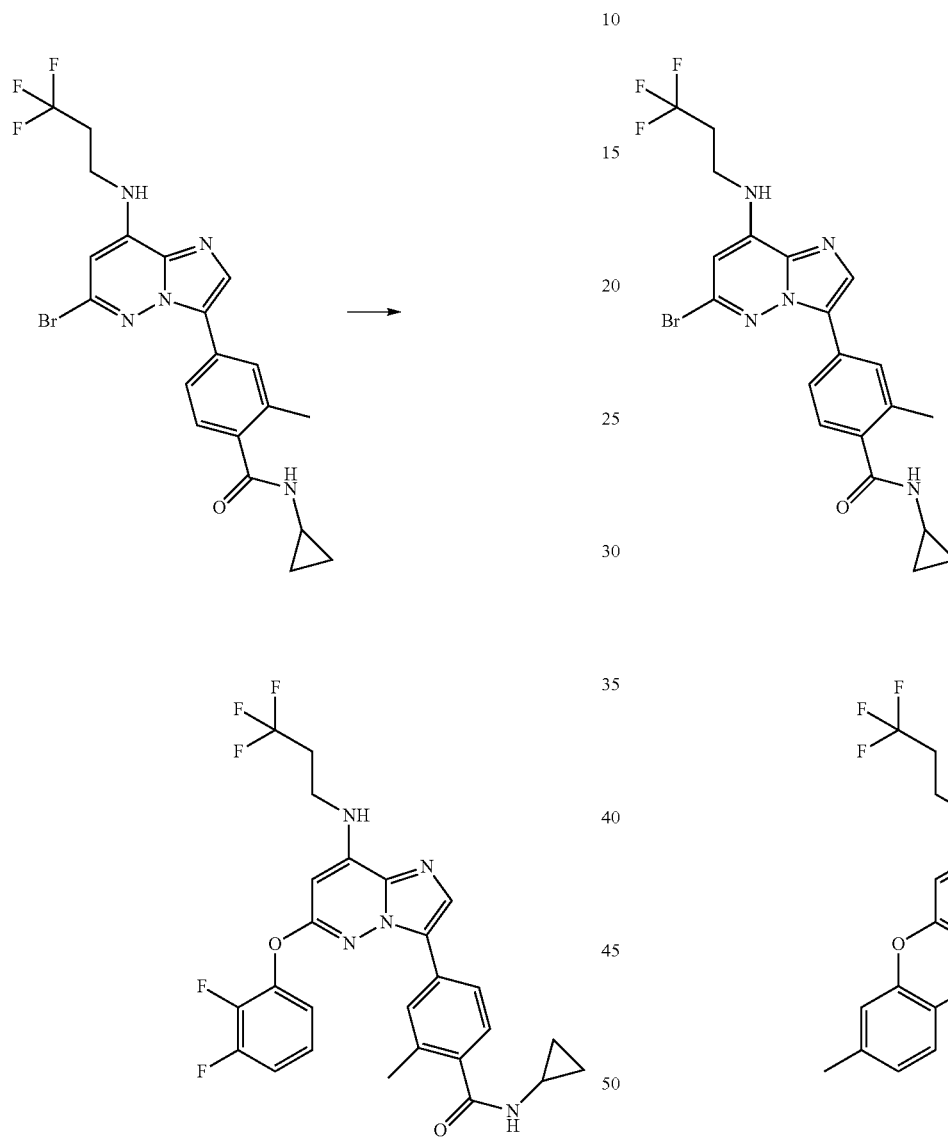

100 mg (207 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2,3-difluorophenol to give after working up and purification 22 mg (19%) of the title compound.

$^{1}$H-NMR (CDCl$_{3}$): δ=0.60 (2H), 0.88 (2H), 2.29 (3H), 2.58 (2H), 2.89 (1H), 3.70 (2H), 5.86 (1H), 5.96 (1H), 6.07 (1H), 7.06-7.17 (3H), 7.22 (1H), 7.53 (1H), 7.66 (1H), 7.71 (1H) ppm.

100 mg (207 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-fluoro-5-methylphenol to give after working up and purification 23 mg (20%) of the title compound.

$^{1}$H-NMR (CDCl$_{3}$): δ=0.60 (2H), 0.88 (2H), 2.27 (3H), 2.35 (3H), 2.58 (2H), 2.89 (1H), 3.68 (2H), 5.84 (1H), 5.95 (1H), 6.11 (1H), 7.00-7.16 (3H), 7.21 (1H), 7.55 (1H), 7.71 (2H) ppm.

381

Example 260

N-cyclopropyl-4-{6-(3,4-difluorophenoxy)-8-[(3,3,3-trifluoropropyl)amino]imidazo[1,2-b]pyridazin-3-yl}-2-methylbenzamide

382

Example 261

N-cyclopropyl-4-{8-[(2-hydroxy-2-methylpropyl)amino]-6-(2-thienylsulfanyl) imidazo[1,2-b]pyridazin-3-yl}-2-methylbenzamide

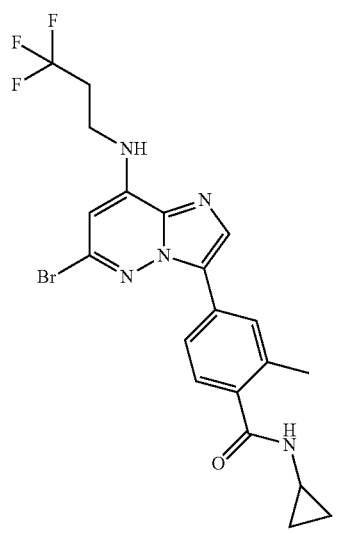

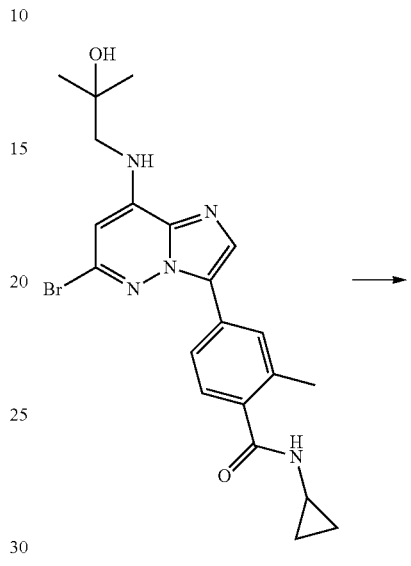

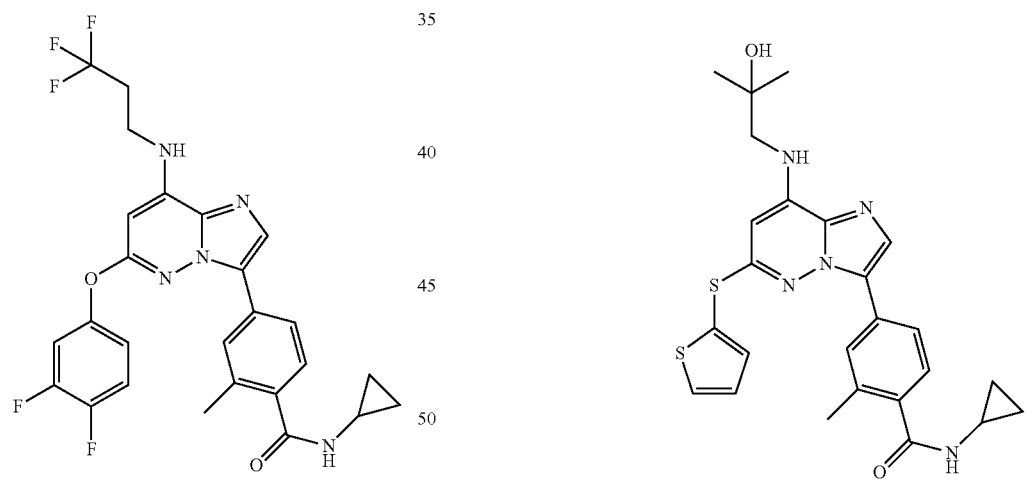

100 mg (207 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3,4-difluorophenol to give after working up and purification 36 mg (31%) of the title compound.

¹H-NMR (CDCl₃): δ=0.61 (2H), 0.88 (2H), 2.34 (3H), 2.57 (2H), 2.90 (1H), 3.68 (2H), 5.86 (1H), 5.87 (1H), 6.04 (1H), 6.99 (1H), 7.11-7.29 (3H), 7.59 (1H), 7.71 (1H), 7.72 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using thiophene-2-thiol to give after working up and purification 34 mg (41%) of the title compound.

¹H-NMR (DMSO-d6): δ=0.50 (2H), 0.65 (2H), 1.12 (6H), 2.26 (3H), 2.80 (1H), 1.64 (2H), 4.70 (1H), 6.21 (1H), 7.01 (1H), 7.17 (1H), 7.23 (1H), 7.47 (1H), 7.71 (1H), 7.76 (1H), 7.94 (2H), 8.23 (1H) ppm.

Example 262

N-cyclopropyl-4-{6-(3,5-difluorophenoxy)-8-[(2-hydroxy-2-methylpropyl)amino]imidazo[1,2-b]pyridazin-3-yl}-2-methylbenzamide

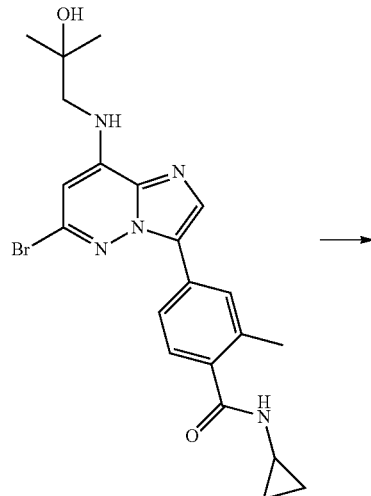

Example 263

N-cyclopropyl-4-(8-[(2-hydroxy-2-methylpropyl)amino]-6-{[(3S)-2-oxopyrrolidin-3-yl]oxy}imidazo[1,2-b]pyridazin-3-yl)-2-methylbenzamide

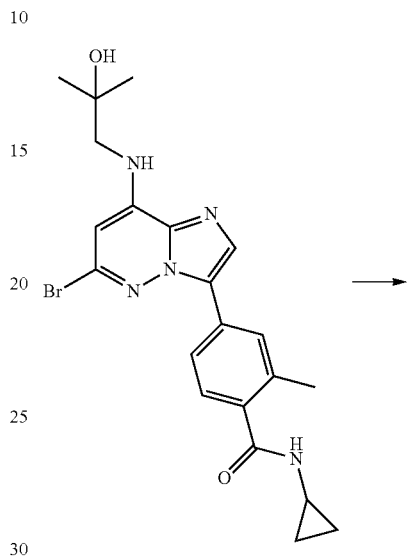

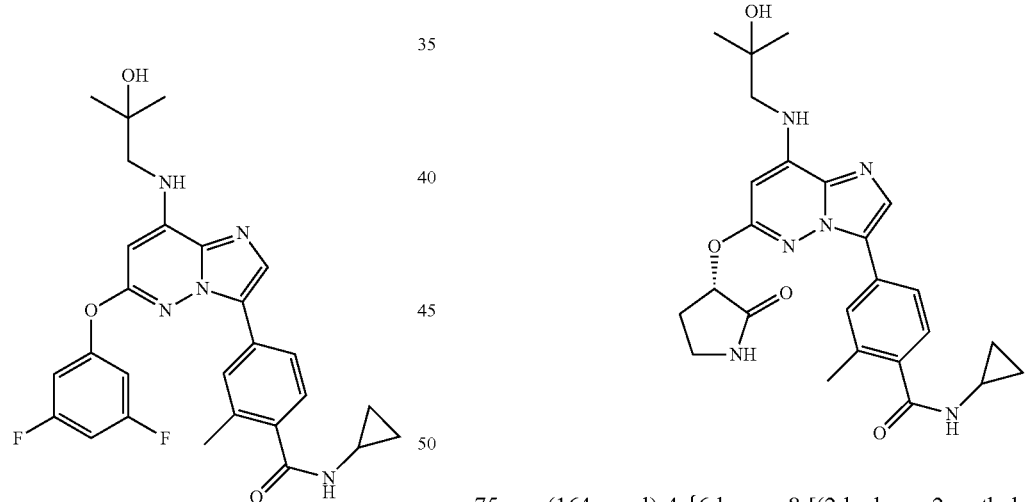

200 mg (436 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3,5-difluorophenol to give after working up and purification 34.6 mg (15%) of the title compound.

$^1$H-NMR (DMSO-d6): δ=0.47 (2H), 0.63 (2H), 1.15 (6H), 2.17 (3H), 2.77 (1H), 3.27 (2H), 4.74 (1H), 6.19 (1H), 7.08 (1H), 7.12-7.22 (4H), 7.68 (1H), 7.79 (1H), 7.93 (1H), 8.23 (1H) ppm.

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using (3S)-3-hydroxypyrrolidin-2-one to give after working up and purification 3.2 mg (4%) of the title compound.

$^1$H-NMR (CDCl$_3$): δ=0.64 (2H), 0.89 (2H), 1.40 (6H), 2.20 (1H), 2.49 (3H), 2.80 (1H), 2.92 (1H), 3.27 (2H), 3.37-3.51 (2H), 4.04 (1H), 5.33 (1H), 5.82 (1H), 6.09 (1H), 6.18 (1H), 6.34 (1H), 7.38 (1H), 7.57 (1H), 7.74 (1H), 7.80 (1H) ppm.

385

Example 264

N-cyclopropyl-4-{8-[(2-hydroxy-2-methylpropyl)amino]-6-[(6-methylpyridin-3-yl)oxy]imidazo[1,2-b]pyridazin-3-yl}-2-methylbenzamide

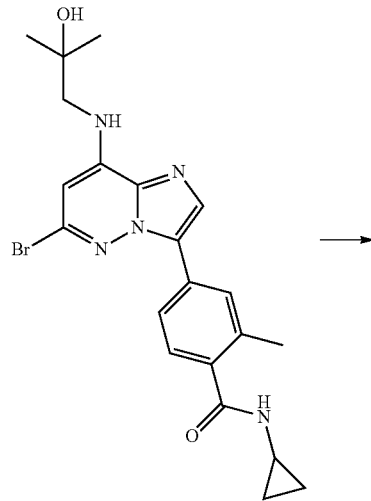

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 6-methylpyridin-3-ol to give after working up and purification 24.5 mg (30%) of the title compound.

$^1$H-NMR (DMSO-d6): δ=0.50 (2H), 0.66 (2H), 1.19 (6H), 2.14 (3H), 2.51 (3H), 2.80 (1H), 3.32 (2H), 4.76 (1H), 6.23 (1H), 7.02 (1H), 7.19 (1H), 7.37 (1H), 7.64 (1H), 7.68 (1H), 7.73 (1H), 7.94 (1H), 8.22 (1H), 8.43 (1H) ppm.

386

Example 265

N-cyclopropyl-4-{8-[(2-hydroxy-2-methylpropyl)amino]-6-(pyrimidin-5-yloxy) imidazo[1,2-b]pyridazin-3-yl}-2-methylbenzamide

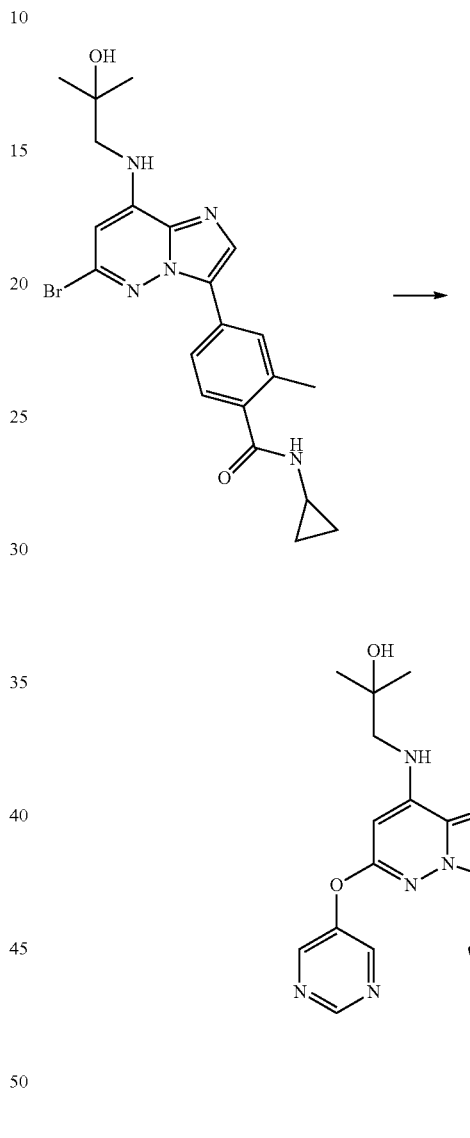

200 mg (436 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using pyrimidin-5-ol to give after working up and purification 34.6 mg (15%) of the title compound.

$^1$H-NMR (CDCl$_3$): δ=0.64 (2H), 0.89 (2H), 1.48 (6H), 2.30 (3H), 2.92 (1H), 3.35 (2H), 4.81 (1H), 5.87 (1H), 6.41 (1H), 6.62 (1H), 7.23 (1H), 7.45 (1H), 7.51 (1H), 7.58 (1H), 8.52 (2H), 9.05 (1H) ppm.

Example 266

4-{6-(3-chlorophenoxy)-8-[(3,3,3-trifluoropropyl)amino]imidazo[1,2-b]pyridazin-3-yl}-N-cyclopropyl-2-methylbenzamide

Example 267

4-{6-(4-chlorophenoxy)-8-[(3,3,3-trifluoropropyl)amino]imidazo[1,2-b]pyridazin-3-yl}-N-cyclopropyl-2-methylbenzamide

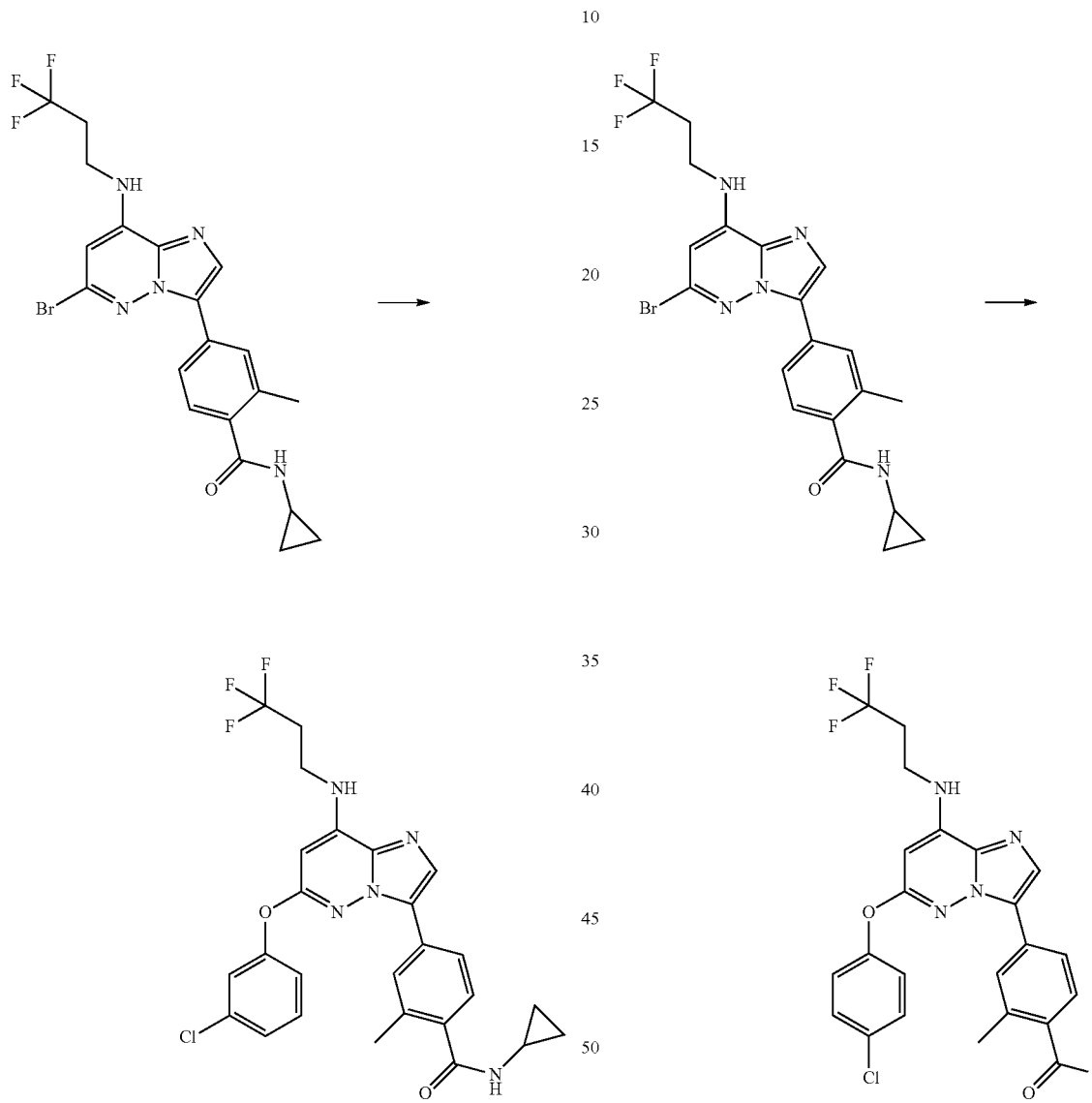

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3-chlorophenol to give after working up and purification 13.9 mg (17%) of the title compound.

$^1$H-NMR (CDCl$_3$): δ=0.61 (2H), 0.88 (2H), 2.34 (3H), 2.58 (2H), 2.90 (1H), 3.68 (2H), 5.82 (1H), 5.89 (1H), 5.97 (1H), 7.15 (1H), 7.25 (1H), 7.27 (1H), 7.31 (1H), 7.36 (1H), 7.63 (1H), 7.72 (1H), 7.74 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 4-chlorophenol to give after working up and purification 12.6 mg (12.6%) of the title compound.

$^1$H-NMR (CDCl$_3$): δ=0.61 (2H), 0.88 (2H), 2.33 (3H), 2.57 (2H), 2.90 (1H), 3.68 (2H), 5.83 (1H), 5.89 (1H), 5.96 (1H), 7.19 (2H), 7.25 (1H), 7.40 (2H), 7.58 (1H), 7.72 (1H), 7.73 (1H) ppm.

Example 268

N-cyclopropyl-4-{6-[(2-fluorophenyl)sulfanyl]-8-[(3,3,3-trifluoropropyl)amino]imidazo[1,2-b]pyridazin-3-yl}-2-methylbenzamide

Example 269

N-cyclopropyl-4-{6-[(5-fluoro-2-methylphenyl)sulfanyl]-8-[(3,3,3-trifluoropropyl)amino]imidazo[1,2-b]pyridazin-3-yl}-2-methylbenzamide

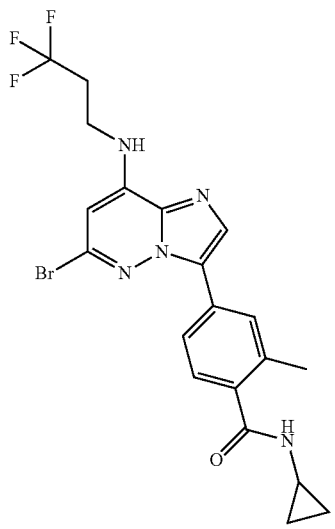

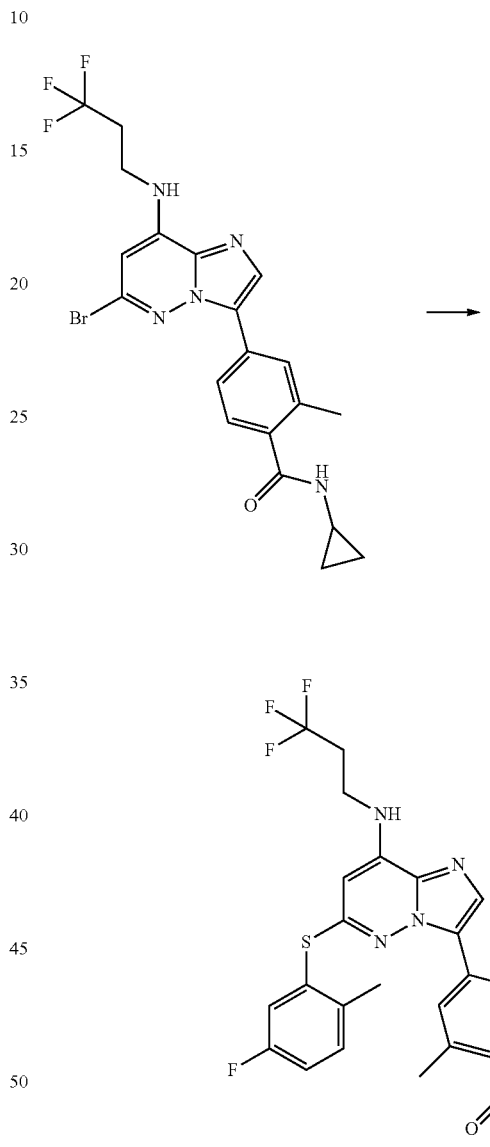

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-fluorobenzenethiol to give after working up and purification 31.8 mg (39%) of the title compound.

$^1$H-NMR (CDCl$_3$): δ=0.62 (2H), 0.90 (2H), 2.37 (3H), 2.51 (2H), 2.92 (1H), 3.60 (2H), 5.83 (1H), 5.89 (1H), 5.94 (1H), 7.16 (1H), 7.20 (1H), 7.25 (1H), 7.51 (1H), 7.56 (1H), 7.59 (1H), 7.66 (1H), 7.70 (1H) ppm.

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 5-fluoro-2-methylbenzenethiol to give after working up and purification 6.1 mg (7%) of the title compound.

$^1$H-NMR (CDCl$_3$): δ=0.63 (2H), 0.90 (2H), 2.39 (3H), 2.40 (3H), 2.50 (2H), 2.92 (1H), 3.59 (2H), 5.86 (1H), 5.89 (1H), 5.93 (1H), 7.10 (1H), 7.19 (1H), 7.31 (1H), 7.38 (1H), 7.57 (1H), 7.60 (1H), 7.71 (1H) ppm.

Example 270

N-cyclopropyl-4-(6-{[2-(hydroxymethyl)phenyl]
sulfanyl}-8-[(3,3,3-trifluoropropyl)amino]imidazo[1,
2-b]pyridazin-3-yl)-2-methylbenzamide

Example 271

N-cyclopropyl-4-{8-[(2-hydroxy-2-methylpropyl)
amino]-6-[(3-methoxyphenyl)sulfanyl]imidazo[1,2-
b]pyridazin-3-yl}-2-methylbenzamide

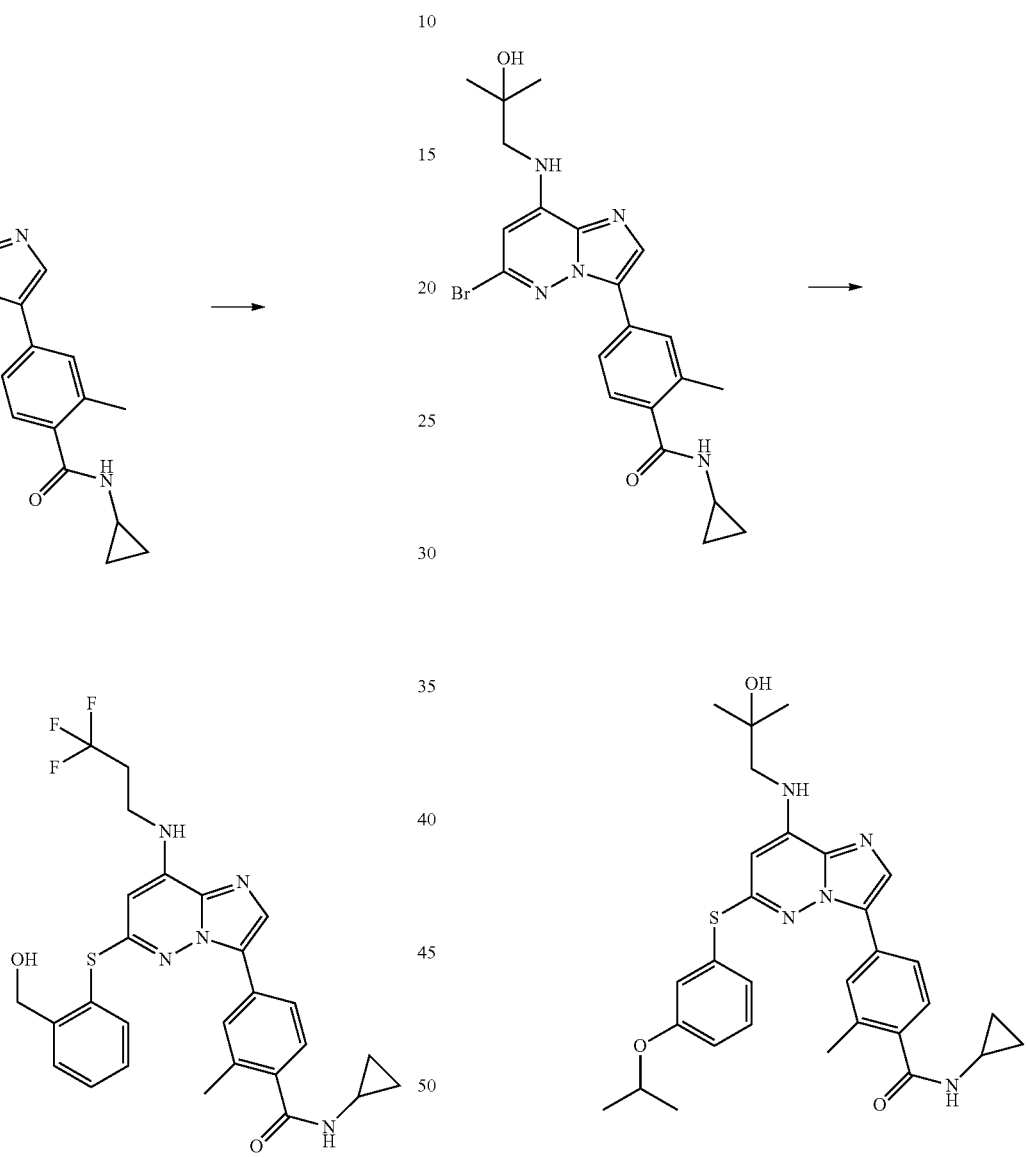

75 mg (156 μmol) 4-{6-bromo-8-[(3,3,3-trifluoropropyl) amino]imidazo[1,2-b]pyridazin-3-yl}-N-cyclopropyl-2-methylbenzamide which was prepared according to intermediate example 247a were transformed in analogy to example 51 using (2-sulfanylphenyl)methanol to give after working up and purification 12.3 mg (15%) of the title compound.

$^1$H-NMR (CDCl$_3$): δ=0.63 (2H), 0.90 (2H), 2.34 (3H), 2.51 (2H), 2.92 (1H), 3.61 (2H), 4.83 (2H), 5.86 (1H), 5.89 (1H), 5.94 (1H), 7.14 (1H), 7.41 (1H), 7.42 (1H), 7.50 (1H), 7.57 (1H), 7.65 (1H), 7.68 (1H), 7.70 (1H) ppm.

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3-isopropoxybenzenethiol to give after working up and purification 18.5 mg (20%) of the title compound.

$^1$H-NMR (DMSO-d6): δ=0.48 (2H), 0.65 (2H), 1.11 (6H), 1.18 (6H), 2.21 (3H), 2.78 (1H), 3.20 (2H), 4.58 (1H), 4.71 (1H), 6.21 (1H), 6.95-7.05 (2H), 7.08-7.16 (3H), 7.34 (1H), 7.71 (1H), 7.73 (1H), 7.94 (1H), 8.23 (1H) ppm.

Example 272

(RS)—N-cyclopropyl-4-{8-[(2-hydroxy-2-methyl-propyl)amino]-6-(pyrrolidin-3-ylamino)imidazo[1,2-b]pyridazin-3-yl}-2-methylbenzamide

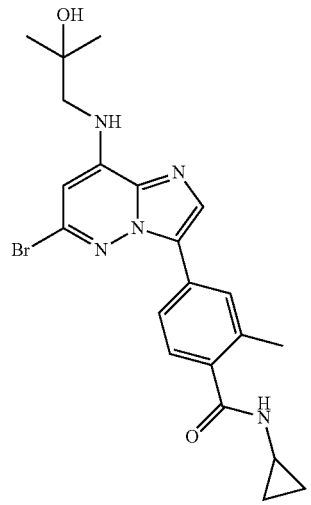

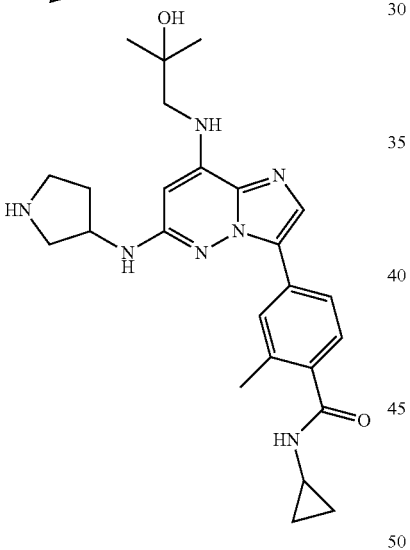

50 mg (109 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using (RS)-pyrrolidin-3-amine to give after working up and purification 18 mg (36%) of the title compound.

$^1$H-NMR (DMSO-d6): δ=0.50 (2H), 0.65 (2H), 1.16 (6H), 1.86 (1H), 2.15 (1H), 2.36 (3H), 2.80 (1H), 3.21 (2H), 3.28 (1H), 3.45 (1H), 3.53-3.65 (2H), 3.71 (1H), 4.27 (1H), 5.68 (1H), 6.36 (1H), 7.31 (1H), 7.78 (1H), 8.07 (1H), 8.10 (1H), 8.26 (1H), 8.29 (1H) ppm.

Example 273

N-cyclopropyl-4-{8-[(2-hydroxy-2-methylpropyl)amino]-6-[(3-isopropylphenyl)sulfanyl]imidazo[1,2-b]pyridazin-3-yl}-2-methylbenzamide

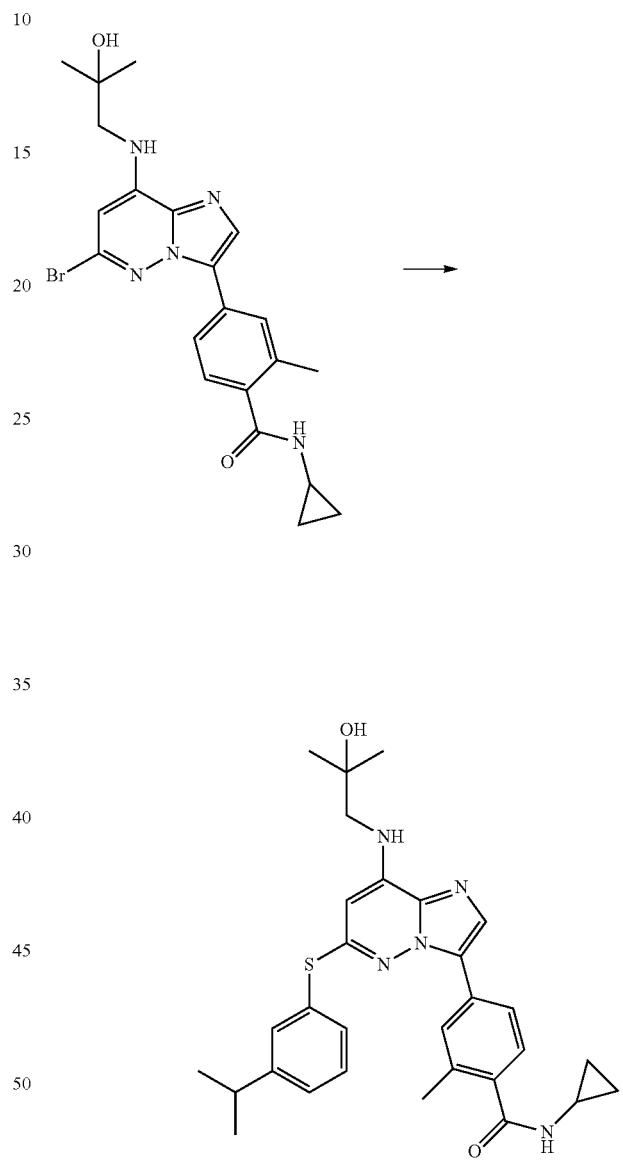

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using 3-isopropylbenzenethiol to give after working up and purification 14.0 mg (15%) of the title compound.

$^1$H-NMR (DMSO-d6): δ=0.48 (2H), 0.64 (2H), 1.10 (6H), 1.14 (6H), 2.18 (3H), 2.78 (1H), 2.88 (1H), 3.18 (2H), 4.71 (1H), 6.18 (1H), 6.98 (1H), 7.08 (1H), 7.34-7.43 (3H), 7.45 (1H), 7.64 (1H), 7.71 (1H), 7.94 (1H), 8.22 (1H) ppm.

395

Example 274

N-cyclopropyl-4-{8-[(2-hydroxy-2-methylpropyl)amino]-6-(pyridin-2-yloxy) imidazo[1,2-b]pyridazin-3-yl}-2-methylbenzamide

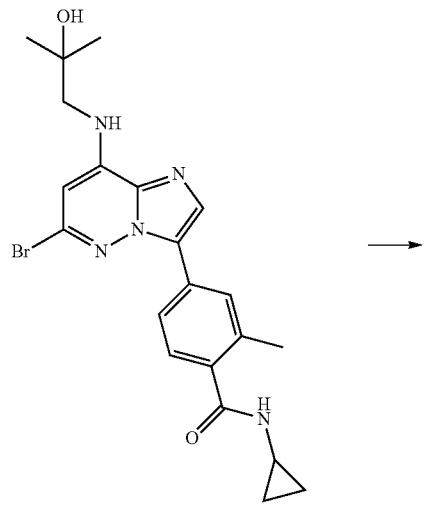

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using pyridin-2-ol to give after working up and purification 11.0 mg (14%) of the title compound.

$^1$H-NMR (DMSO-d6): δ=0.48 (2H), 0.64 (2H), 1.14 (6H), 2.33 (3H), 2.79 (1H), 3.27 (2H), 4.73 (1H), 6.33 (1H), 6.47 (1H), 6.48 (1H), 7.21 (1H), 7.33 (1H), 7.54 (1H), 7.79 (1H), 7.82 (1H), 7.91 (1H), 8.03 (1H), 8.24 (1H) ppm.

396

Example 275

N-cyclopropyl-4-{6-[3-(2-hydroxy-2-methylpropoxy)phenoxy]-8-[(2-hydroxy-2-methylpropyl)amino]imidazo[1,2-b]pyridazin-3-yl}-2-methylbenzamide

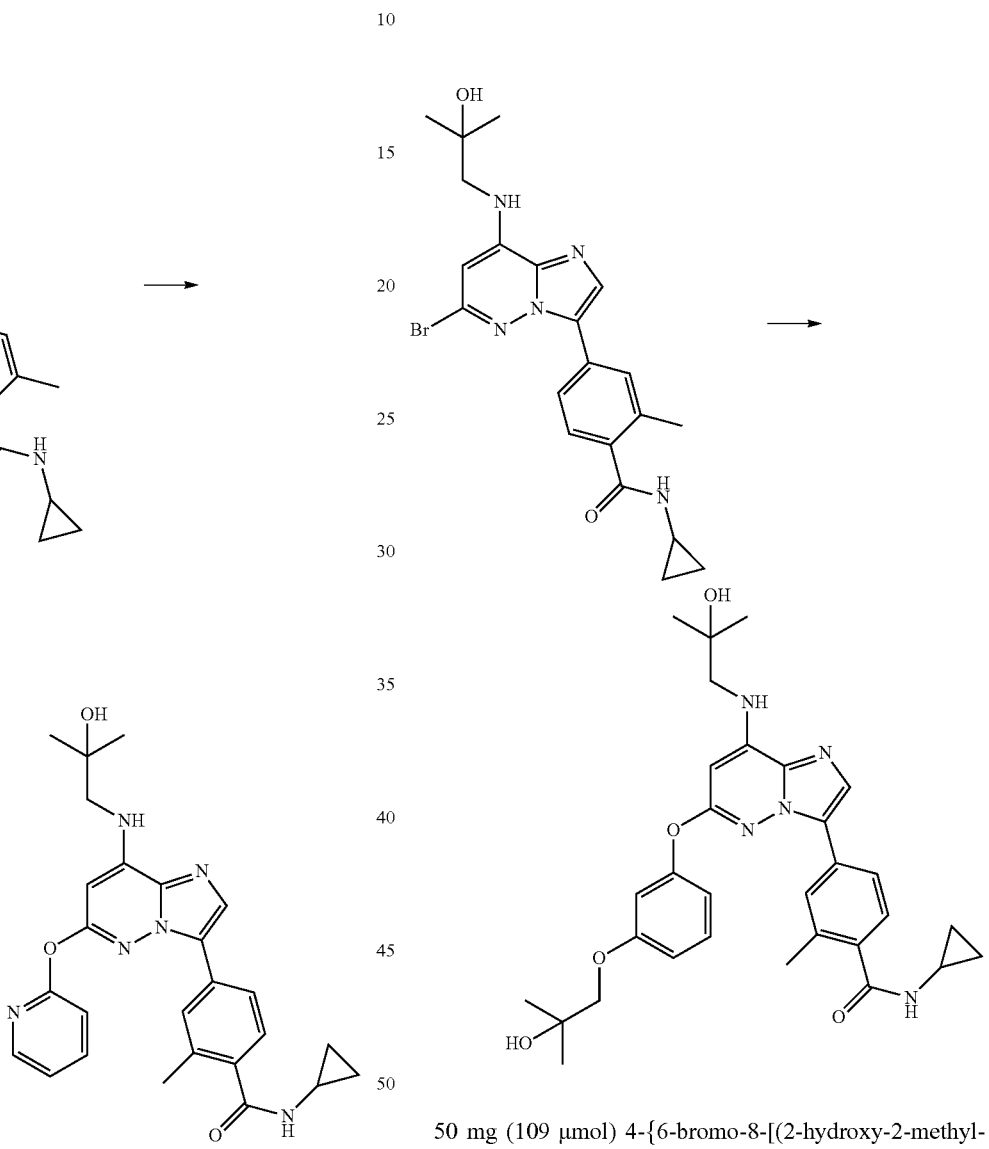

50 mg (109 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3-{2-methyl-2-[(triisopropylsilyl)oxy]propoxy}phenol to give after working up and purification 2.3 mg (4%) of the title compound.

$^1$H-NMR (DMSO-d6): δ=0.46 (2H), 0.63 (2H), 1.14 (6H), 1.15 (6H), 2.14 (3H), 2.76 (1H), 3.27 (2H), 3.66 (2H), 4.59 (1H), 4.74 (1H), 6.14 (1H), 6.76-6.86 (3H), 6.97 (1H), 7.16 (1H), 7.31 (1H), 7.70 (1H), 7.79 (1H), 7.92 (1H), 8.21 (1H) ppm.

Example 276

N-cyclopropyl-4-{6-[(3-fluorophenyl)sulfanyl]-8-[(2-hydroxyethyl)amino]imidazo[1,2-b]pyridazin-3-yl}-2-methylbenzamide

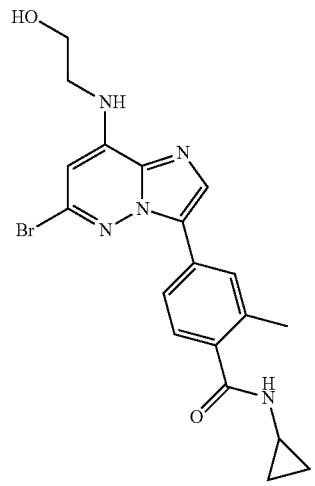

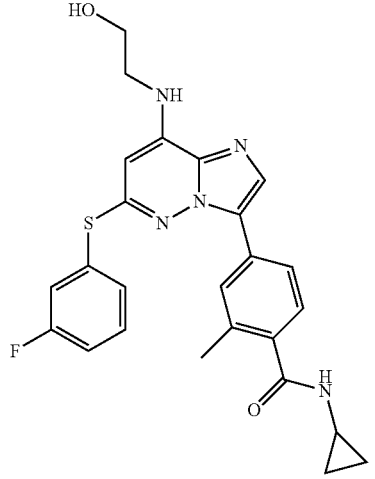

75 mg (174 μmol) 4-{6-bromo-8-[(2-hydroxyethyl)amino]imidazo[1,2-b]pyridazin-3-yl}-N-cyclopropyl-2-methylbenzamide which was prepared according to intermediate example 276a were transformed in analogy to example 51 using 3-fluorobenzenethiol to give after working up and purification 14.5 mg (17%) of the title compound.

$^1$H-NMR (DMSO-d6): δ=0.48 (2H), 0.65 (2H), 2.20 (3H), 2.78 (1H), 3.33 (2H), 3.57 (2H), 4.82 (1H), 6.19 (1H), 7.12 (1H), 7.33 (1H), 7.38-7.54 (4H), 7.66 (1H), 7.71 (1H), 7.94 (1H), 8.23 (1H) ppm.

Intermediate Example 276a

4-{6-bromo-8-[(2-hydroxyethyl)amino]imidazo[1,2-b]pyridazin-3-yl}-N-cyclopropyl-2-methylbenzamide

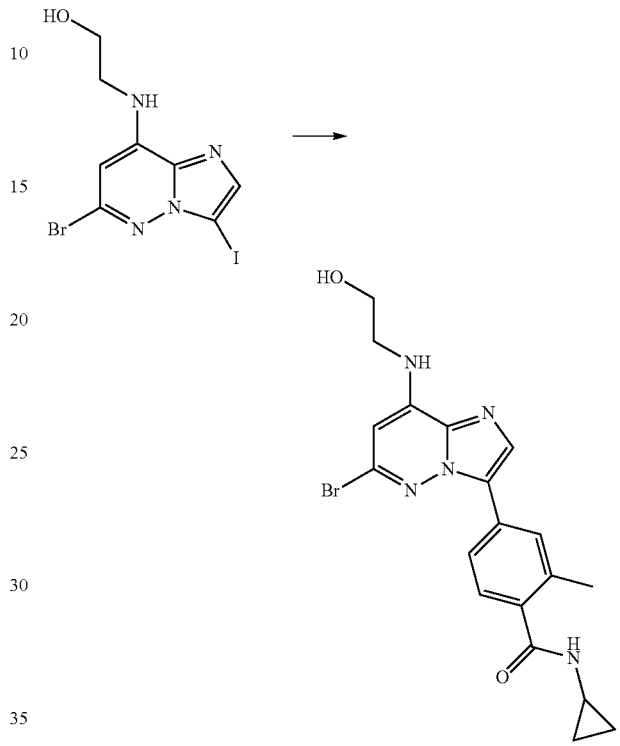

1.98 g (5.17 mmol) 2-[(6-bromo-3-iodoimidazo[1,2-b]pyridazin-8-yl)amino]ethanol which was prepared according to intermediate example 276b were transformed in analogy to intermediate example 1a using N-cyclopropyl-2-methyl-4-(4,4,5,5-tetramethyl-1,3,2-dioxaborolan-2-yl)benzamide to give after working up and purification 1.27 g (51%) of the title compound.

Intermediate Example 276b

2-[(6-bromo-3-iodoimidazo[1,2-b]pyridazin-8-yl)amino]ethanol 2.50 g (6.21 mmol) 6,8-dibromo-3-iodoimidazo[1,2-b]pyridazine which was prepared according to intermediate example 96c were transformed in analogy to intermediate example 1b using 2-aminoethanol to give after working up and purification 1.99 g (81%) of the title compound.

Example 277

N-cyclopropyl-4-{6-(3-fluorophenoxy)-8-[(2-hydroxyethyl)amino]imidazo[1,2-b]pyridazin-3-yl}-2-methylbenzamide

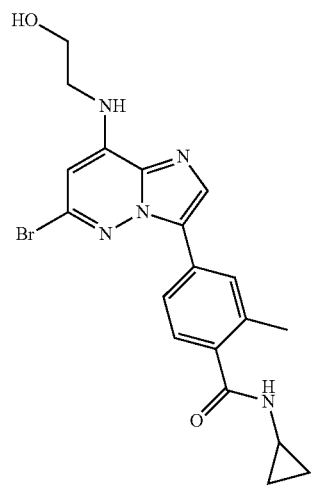

75 mg (174 µmol) 4-{6-bromo-8-[(2-hydroxyethyl)amino]imidazo[1,2-b]pyridazin-3-yl}-N-cyclopropyl-2-methylbenzamid which was prepared according to intermediate example 276a were transformed in analogy to example 51 using 3-fluorophenol to give after working up and purification 17.2 mg (21%) of the title compound.

$^1$H-NMR (DMSO-d6): δ=0.46 (2H), 0.63 (2H), 2.14 (3H), 2.76 (1H), 3.38 (2H), 3.62 (2H), 4.84 (1H), 6.08 (1H), 7.07-7.20 (3H), 7.24 (1H), 7.41 (1H), 7.48 (1H), 7.66 (1H), 7.76 (1H), 7.92 (1H), 8.21 (1H) ppm.

Example 278

N-cyclopropyl-2-methyl-4-{6-(2,2,3,3-tetrafluoro-4-hydroxybutoxy)-8-[(3,3,3-trifluoropropyl)amino]imidazo[1,2-b]pyridazin-3-yl}benzamide (A) and N-cyclopropyl-2-methyl-4-(6-{[(1E)-2,3,3-trifluoro-4-hydroxybut-1-en-1-yl]oxy}-8-[(3,3,3-trifluoropropyl)amino]imidazo[1,2-b]pyridazin-3-yl)benzamide

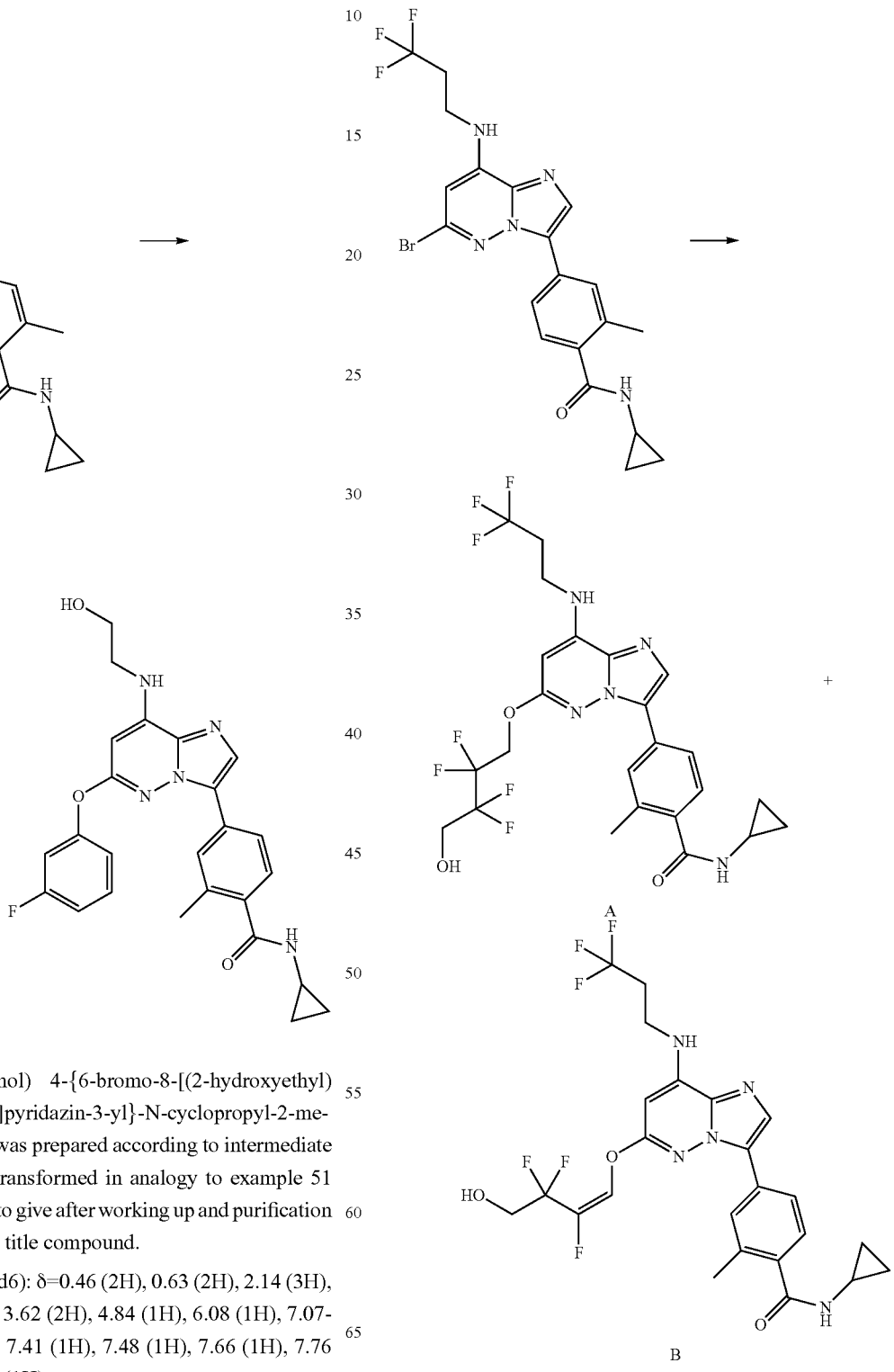

100 mg (207 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2,2,3,3-tetrafluorobutane-1,4-diol to give after working up and purification 5.2 mg (4%) of the title compound A and 5.3 mg (4%) of the title compound B.

$^1$H-NMR (DMSO-d6) of A: δ=0.50 (2H), 0.65 (2H), 2.35 (3H), 2.65 (2H), 2.80 (1H), 3.56 (2H), 3.91 (2H), 4.91 (2H), 5.97 (1H), 6.00 (1H), 7.33 (1H), 7.60 (1H), 7.90 (1H), 7.92 (1H), 7.97 (1H), 8.27 (1H) ppm.

$^1$H-NMR (DMSO-d6) of B: δ=0.50 (2H), 0.66 (2H), 2.35 (3H), 2.66 (2H), 2.80 (1H), 3.59 (2H), 3.86 (2H), 5.92 (1H), 6.14 (1H), 7.33 (1H), 7.70 (1H), 7.84 (1H), 7.89 (1H), 7.97 (1H), 8.02 (1H), 8.28 (1H) ppm.

Example 279

2-{3-[4-(cyclopropylcarbamoyl)-3-methylphenyl]-8-[(2-hydroxy-2-methylpropyl)amino]imidazo[1,2-b]pyridazin-6-yl}-5-fluoro-benzoic acid methyl ester

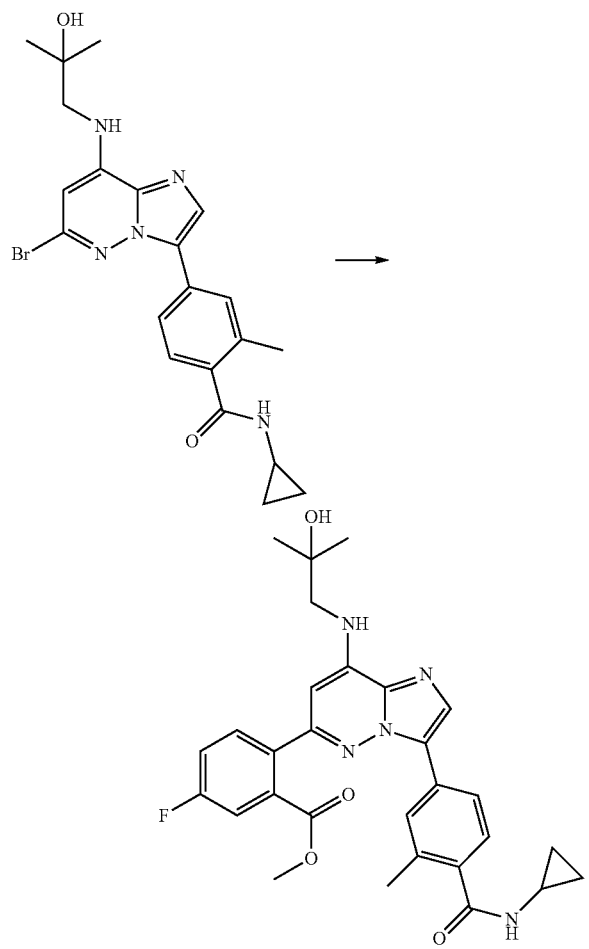

600 mg (1.31 mmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 1 using [4-fluoro-2-(methoxycarbonyl)phenyl]boronic acid. After working up 19 mL tetrahydrofuran were added to the crude product and the suspension was cooled to 3° C. 21.8 mL of a freshly prepared diazomethane solution in diethyl ether were added in portions over 2 hours. The solvent was removed and the residue purified by chromatography to give 52.7 mg (9%) of the title compound.

$^1$H-NMR (DMSO-d6): δ=0.50 (2H), 0.65 (2H), 1.17 (6H), 2.36 (3H), 2.80 (1H), 3.33 (2H), 3.47 (3H), 4.75 (1H), 6.52 (1H), 6.96 (1H), 7.30 (1H), 7.51-7.59 (2H), 7.78 (1H), 7.92 (1H), 7.97 (1H), 8.04 (1H), 8.23 (1H) ppm.

Example 280

N-cyclopropyl-4-{6-(2-hydroxyphenoxy)-8-[(3,3,3-trifluoropropyl)amino]imidazo[1,2-b]pyridazin-3-yl}-2-methylbenzamide

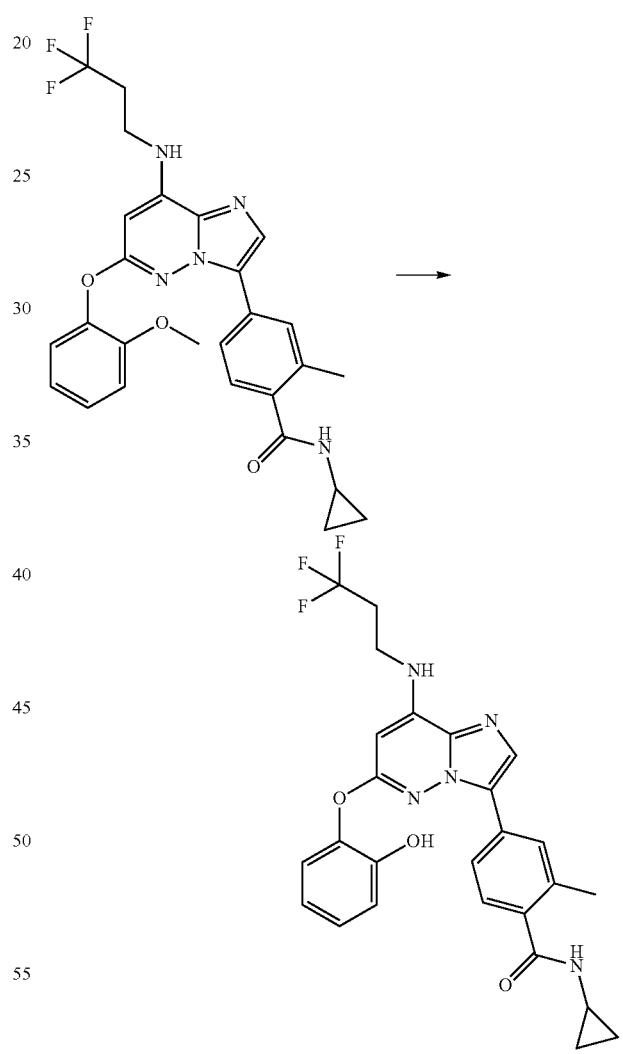

A mixture of 28.0 mg (53 μmol) N-cyclopropyl-4-{6-(2-methoxyphenoxy)-8-[(3,3,3-trifluoropropyl)amino]imidazo[1,2-b]pyridazin-3-yl}-2-methylbenzamide which was prepared according to example 223, 44.8 mg sodium methanethiolate and 350 μL N,N-dimethylformamide was heated under microwave irradiation for 30 minutes at 120° C. The mixture was poured into water, the pH was adjusted between 7 and 8 by addition of ammonium chloride and extracted with a mixture of dichloromethane and methanol. The combined organic phases were dried over sodium sulfate. After filtration and removal of solvent the residue was purified by chromatography to give 11.5 mg (40%) of the title compound.

$^1$H-NMR (DMSO-d6): δ=0.47 (2H), 0.63 (2H), 2.09 (3H), 2.68 (2H), 2.76 (1H), 3.59 (2H), 6.08 (1H), 6.83 (1H), 6.97 (1H), 7.05-7.17 (3H), 7.55 (1H), 7.62 (1H), 7.75 (1H), 7.90 (1H), 8.18 (1H), 9.53 (1H) ppm.

Example 281

N-cyclopropyl-4-{6-(3-fluorophenoxy)-8-[(tetrahydro-2H-thiopyran-4-ylmethyl)amino]imidazo[1,2-b]pyridazin-3-yl}-2-methylbenzamide

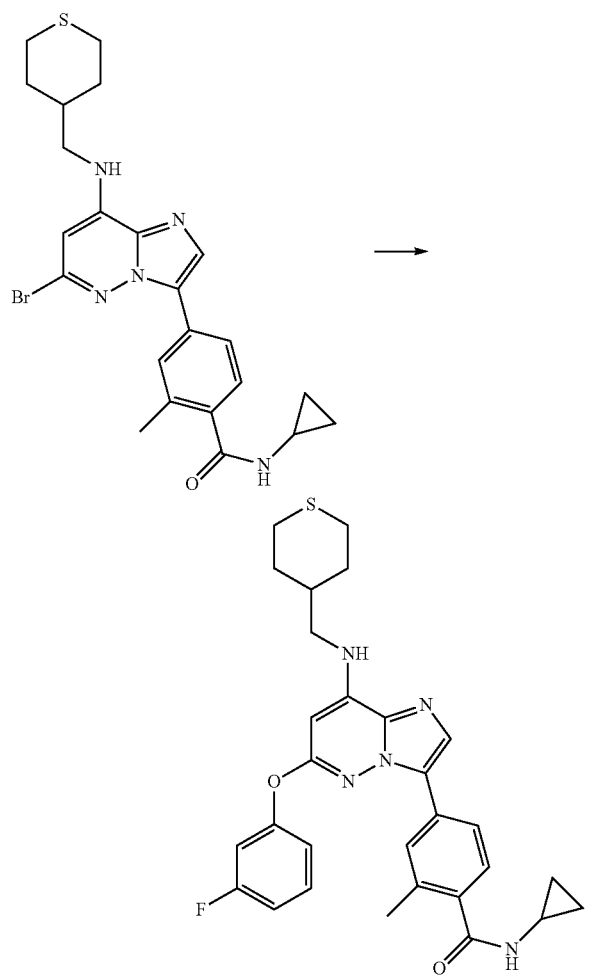

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 3-fluorophenol to give after working up and purification 33.7 mg (40%) of the title compound.

$^1$H-NMR (DMSO-d6): δ=0.50 (2H), 0.66 (2H), 1.32 (2H), 1.78 (1H), 2.04 (2H), 2.17 (3H), 2.59 (4H), 2.79 (1H), 3.22 (2H), 6.09 (1H), 7.15 (2H), 7.18 (1H), 7.27 (1H), 7.50 (1H), 7.68 (1H), 7.72 (1H), 7.78 (1H), 7.93 (1H), 8.22 (1H) ppm.

Intermediate Example 281a

4-{6-bromo-8-[(tetrahydro-2H-thiopyran-4-ylmethyl)amino]imidazo[1,2-b]pyridazin-3-yl}-N-cyclopropyl-2-methylbenzamide

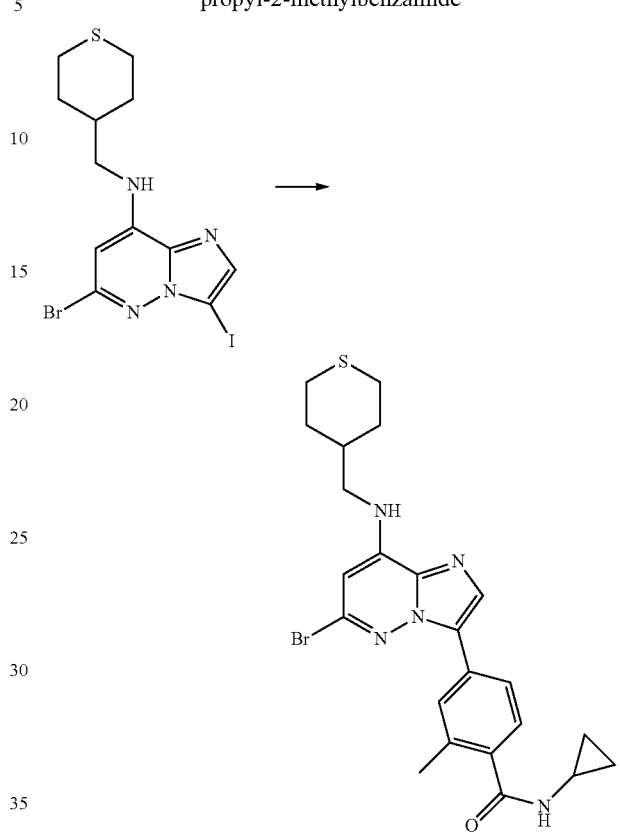

2.22 g (4.90 mmol) 6-bromo-3-iodo-N-(tetrahydro-2H-thiopyran-4-ylmethyl)imidazo[1,2-b]pyridazin-8-amine which was prepared according to intermediate example 281b were transformed in analogy to intermediate example 1a using N-cyclopropyl-2-methyl-4-(4,4,5,5-tetramethyl-1,3,2-dioxaborolan-2-yl)benzamide to give after working up and purification 1.49 g (55%) of the title compound.

Intermediate Example 281b 6-bromo-3-iodo-N-(tetrahydro-2H-thiopyran-4-ylmethyl)imidazo[1,2-b]pyridazin-8-amine

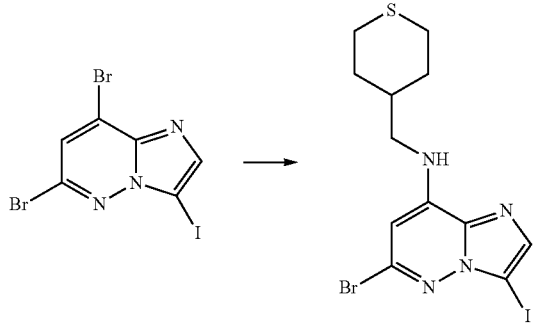 [SMILES: Brc1cc(Br)c2ncc(I)n2n1 ; Brc1cc(NCC2CCSCC2)c2ncc(I)n2n1]

2.31 g (5.75 mmol) 6,8-dibromo-3-iodoimidazo[1,2-b]pyridazine which was prepared according to intermediate example 96c were transformed in analogy to intermediate example 1b using 1-(tetrahydro-2H-thiopyran-4-yl)methanamine to give after working up and purification 2.23 g (81%) of the title compound.

405

Example 282

N-cyclopropyl-4-{6-(3-fluoro-5-methylphenoxy)-8-[(tetrahydro-2H-thiopyran-4-ylmethyl)amino]imidazo[1,2-b]pyridazin-3-yl}-2-methylbenzamide

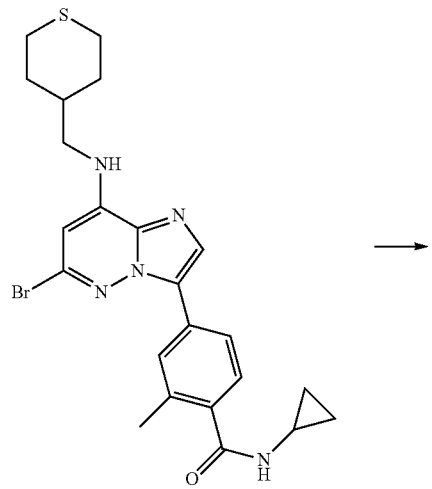

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 3-fluoro-5-methylphenol to give after working up and purification 14.1 mg (16%) of the title compound.

$^1$H-NMR (DMSO-d6): δ=0.50 (2H), 0.66 (2H), 1.32 (2H), 1.77 (1H), 2.04 (2H), 2.18 (3H), 2.34 (3H), 2.59 (4H), 2.79 (1H), 3.22 (2H), 6.07 (1H), 6.96 (1H), 6.97 (1H), 7.04 (1H), 7.20 (1H), 7.68-7.74 (2H), 7.80 (1H), 7.93 (1H), 8.23 (1H) ppm.

406

Example 283

N-cyclopropyl-4-{6-(2-fluorophenoxy)-8-[(tetrahydro-2H-thiopyran-4-ylmethyl)amino]imidazo[1,2-b]pyridazin-3-yl}-2-methylbenzamide

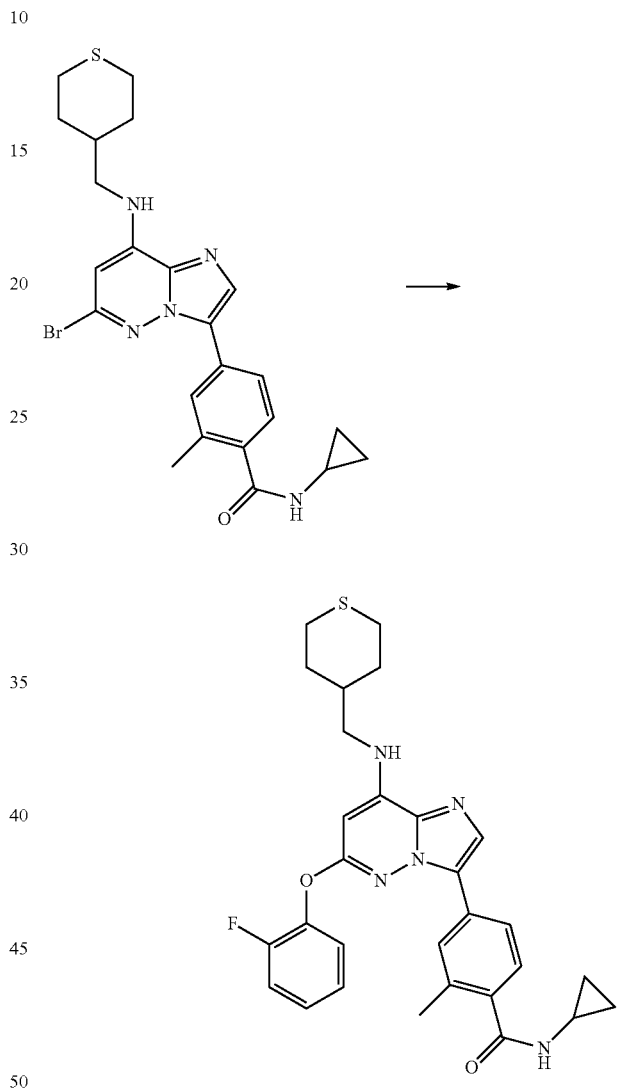

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 2-fluorophenol to give after working up and purification 26.6 mg (32%) of the title compound.

$^1$H-NMR (DMSO-d6): δ=0.49 (2H), 0.66 (2H), 1.33 (2H), 1.80 (1H), 2.06 (2H), 2.11 (3H), 2.60 (4H), 2.78 (1H), 3.23 (2H), 6.16 (1H), 7.13 (1H), 7.30 (1H), 7.37 (1H), 7.43 (1H), 7.47 (1H), 7.61 (1H), 7.69 (1H), 7.74 (1H), 7.93 (1H), 8.21 (1H) ppm.

407
Example 284

N-cyclopropyl-2-methyl-4-{6-(phenylsulfanyl)-8-[(tetrahydro-2H-thiopyran-4-ylmethyl)amino]imidazo[1,2-b]pyridazin-3-yl}benzamide

408
Example 285

N-cyclopropyl-4-{6-[(3-fluorophenyl)sulfanyl]-8-[(tetrahydro-2H-thiopyran-4-ylmethyl)amino]imidazo[1,2-b]pyridazin-3-yl}-2-methylbenzamide

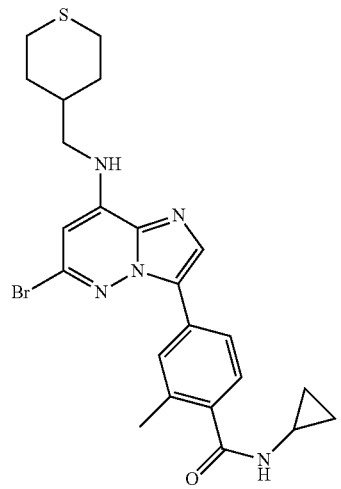

→

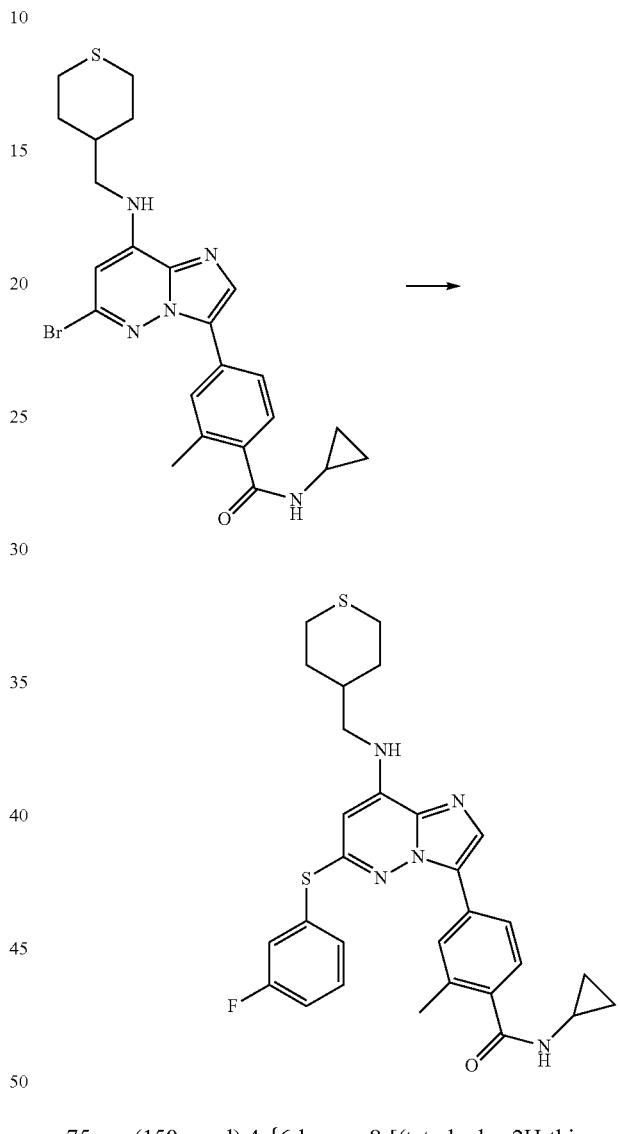

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using benzenethiol to give after working up and purification 45.3 mg (54%) of the title compound.

$^1$H-NMR (DMSO-d6): δ=0.48 (2H), 0.65 (2H), 1.22 (2H), 1.60 (1H), 1.91 (2H), 2.21 (3H), 2.52 (4H), 2.78 (1H), 3.08 (2H), 5.99 (1H), 7.10 (1H), 7.44-7.53 (3H), 7.59-7.73 (5H), 7.91 (1H), 8.24 (1H) ppm.

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 3-fluorobenzenethiol to give after working up and purification 9.8 mg (11%) of the title compound.

$^1$H-NMR (DMSO-d6): δ=0.49 (2H), 0.65 (2H), 1.23 (2H), 1.64 (1H), 1.93 (2H), 2.21 (3H), 2.53 (4H), 2.79 (1H), 3.11 (2H), 6.10 (1H), 7.13 (1H), 7.34 (1H), 7.44 (1H), 7.48-7.54 (2H), 7.68 (1H), 7.72 (1H), 7.74 (1H), 7.93 (1H), 8.25 (1H) ppm.

409

Example 286

N-cyclopropyl-4-{6-[(3-fluoro-5-methylphenyl)sul-
fanyl]-8-[(tetrahydro-2H-thiopyran-4-ylmethyl)
amino]imidazo[1,2-b]pyridazin-3-yl}-2-methylben-
zamide

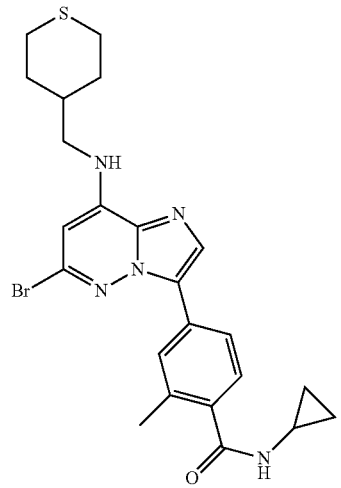

75 mg (150 μmol) 4-{6-bromo-8-[(tetrahydro-2H-thiopy-ran-4-ylmethyl)amino]imidazo[1,2-b]pyridazin-3-yl}-N-cyclopropyl-2-methylbenzamide which was prepared according to intermediate example 281a were transformed in analogy to example 51 using 3-fluoro-5-methylbenzenethiol to give after working up and purification 9.1 mg (10%) of the title compound.

$^1$H-NMR (DMSO-d6): δ=0.48 (2H), 0.65 (2H), 1.23 (2H), 1.62 (1H), 1.92 (2H), 2.21 (3H), 2.31 (3H), 2.52 (4H), 2.79 (1H), 3.11 (2H), 6.07 (1H), 7.14 (1H), 7.17 (1H), 7.26-7.32 (2H), 7.68-7.76 (3H), 7.93 (1H), 8.25 (1H) ppm.

410

Example 287

N-cyclopropyl-4-{6-[(3-hydroxyphenyl)sulfanyl]-8-
[(tetrahydro-2H-thiopyran-4-ylmethyl)amino]imi-
dazo[1,2-b]pyridazin-3-yl}-2-methylbenzamide

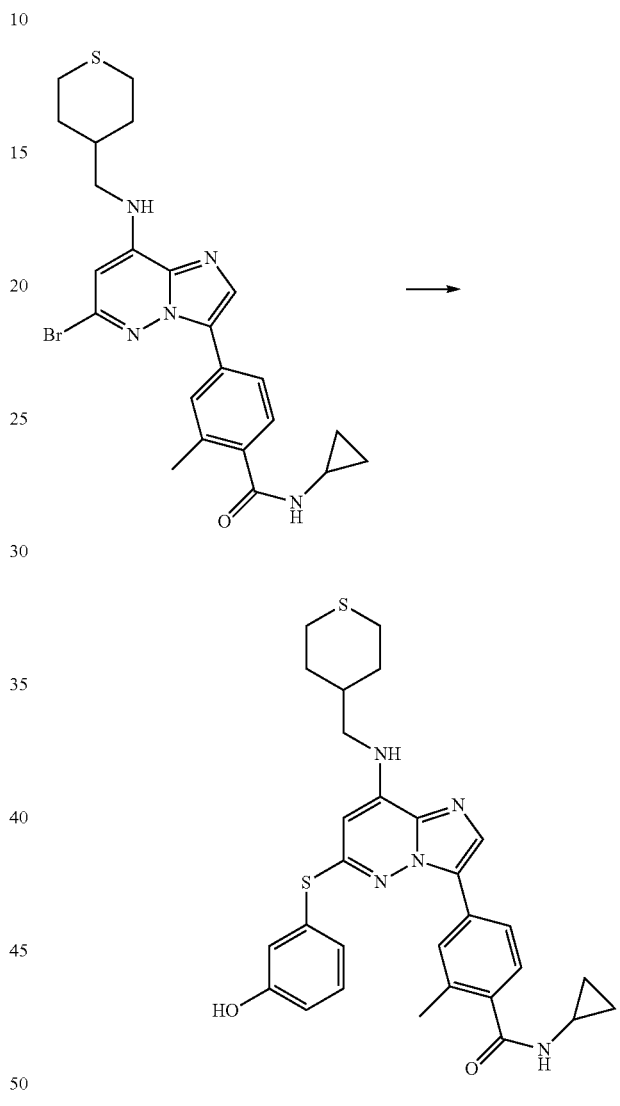

100 mg (200 μmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 3-methoxybenzenethiol to give after working up and purification 14 mg (12%) of the title compound.

$^1$H-NMR (DMSO-d6): δ=0.49 (2H), 0.65 (2H), 1.22 (2H), 1.58 (1H), 1.90 (2H), 2.24 (3H), 2.52 (4H), 2.79 (1H), 3.07 (2H), 5.95 (1H), 6.86 (1H), 6.96 (1H), 7.01 (1H), 7.17 (1H), 7.26 (1H), 7.69 (1H), 7.73-7.80 (2H), 7.92 (1H), 8.24 (1H), 9.76 (1H) ppm.

411

Example 288

N-cyclopropyl-2-methyl-4-{6-(pyridin-3-yloxy)-8-[(tetrahydro-2H-thiopyran-4-ylmethyl)amino]imidazo[1,2-b]pyridazin-3-yl}benzamide

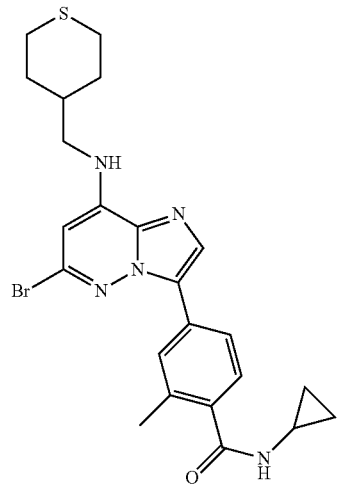

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using pyridin-3-ol to give after working up and purification 25.2 mg (31%) of the title compound.

$^1$H-NMR (DMSO-d6): δ=0.46 (2H), 0.63 (2H), 1.30 (2H), 1.76 (1H), 2.02 (2H), 2.12 (3H), 2.57 (4H), 2.76 (1H), 3.20 (2H), 6.13 (1H), 7.13 (1H), 7.51 (1H), 7.60 (1H), 7.68 (1H), 7.76 (1H), 7.80 (1H), 7.90 (1H), 8.21 (1H), 8.48 (1H), 8.57 (1H) ppm.

412

Example 289

N-cyclopropyl-4-{6-[(2-hydroxyphenyl)sulfanyl]-8-[(tetrahydro-2H-thiopyran-4-ylmethyl)amino]imidazo[1,2-b]pyridazin-3-yl}-2-methylbenzamide

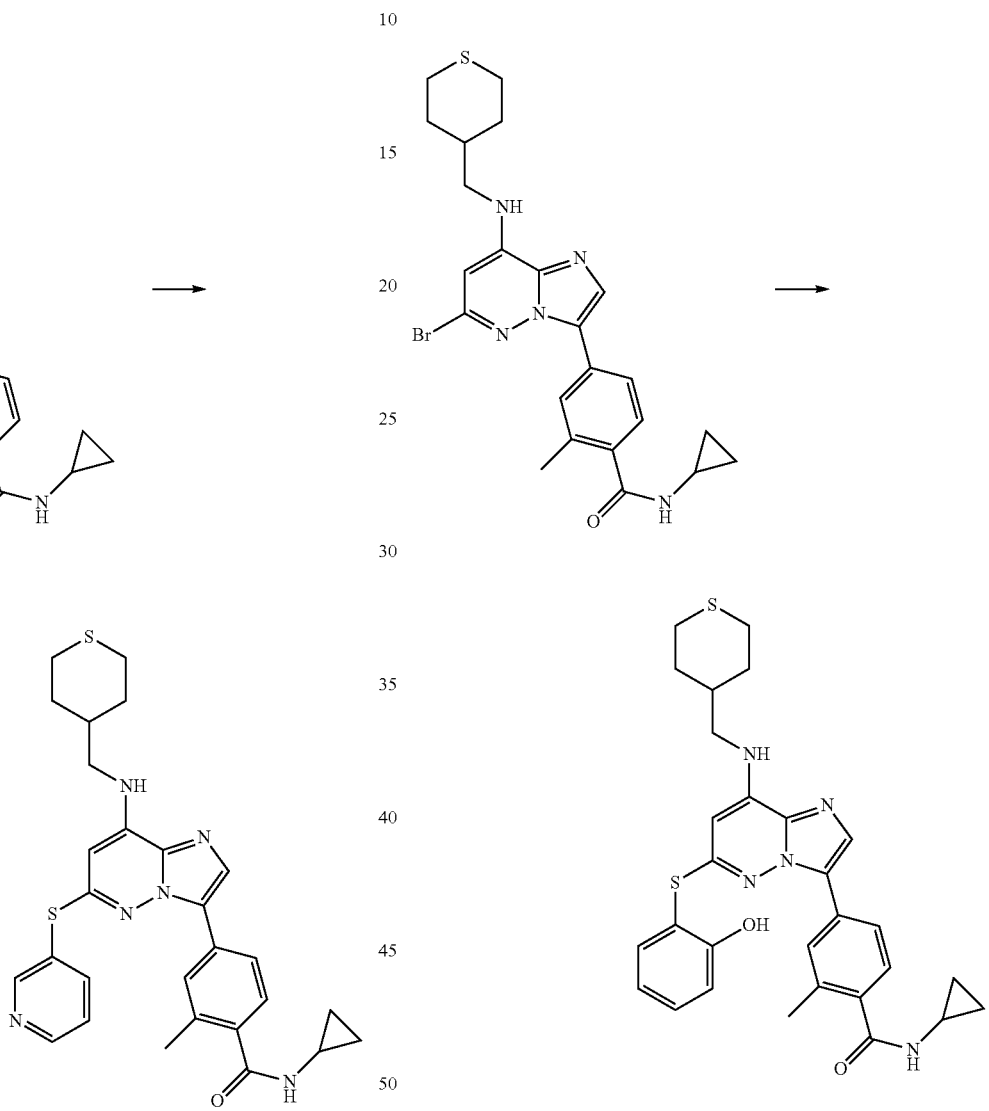

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 2-methoxybenzenethiol to give after working up and purification 40.9 mg (48%) of the title compound.

$^1$H-NMR (DMSO-d6): 0.5=0.49 (2H), 0.65 (2H), 1.20 (2H), 1.57 (1H), 1.88 (2H), 2.23 (3H), 2.52 (4H), 2.79 (1H), 3.03 (2H), 5.86 (1H), 6.87 (1H), 6.98 (1H), 7.12 (1H), 7.34 (1H), 7.46 (1H), 7.60 (1H), 7.72 (1H), 7.74 (1H), 7.90 (1H), 8.23 (1H), 10.01 (1H) ppm.

413

Example 290

N-cyclopropyl-4-{6-(4-fluorophenoxy)-8-[(tetrahydro-2H-thiopyran-4-ylmethyl)amino]imidazo[1,2-b]pyridazin-3-yl}-2-methylbenzamide

414

Example 291

4-{6-(4-chloro-3-fluorophenoxy)-8-[(tetrahydro-2H-thiopyran-4-ylmethyl)amino]imidazo[1,2-b]pyridazin-3-yl}-N-cyclopropyl-2-methylbenzamide

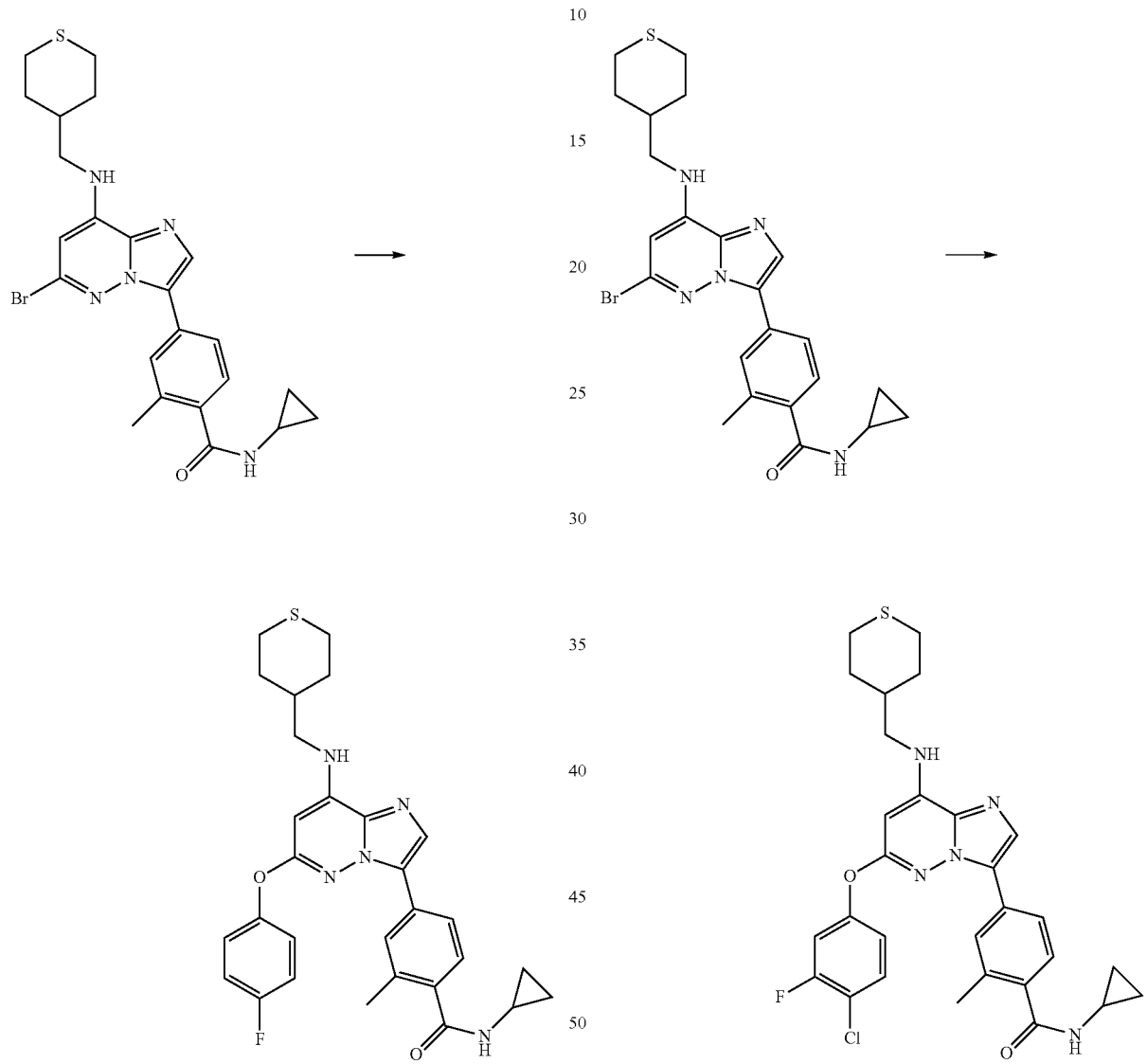

75 mg (150 μmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 4-fluorophenol to give after working up and purification 45.6 mg (54%) of the title compound.

$^1$H-NMR (DMSO-d6): δ=0.46 (2H), 0.63 (2H), 1.29 (2H), 1.75 (1H), 2.02 (2H), 2.12 (3H), 2.56 (4H), 2.76 (1H), 3.19 (2H), 6.06 (1H), 7.15 (1H), 7.23-7.35 (4H), 7.63 (1H), 7.68 (1H), 7.72 (1H), 7.90 (1H), 8.21 (1H) ppm.

75 mg (150 μmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 4-chloro-3-fluorophenol to give after working up and purification 5.4 mg (6%) of the title compound.

$^1$H-NMR (CDCl$_3$): δ=0.64 (2H), 0.91 (2H), 1.54 (2H), 1.80 (1H), 2.20 (2H), 2.37 (3H), 2.65-2.79 (4H), 2.93 (1H), 3.26 (2H), 5.86 (1H), 5.87 (1H), 5.97 (1H), 7.04 (1H), 7.16 (1H), 7.30 (1H), 7.46 (1H), 7.62 (1H), 7.74 (2H) ppm.

415
Example 292

4-{6-(4-chlorophenoxy)-8-[(tetrahydro-2H-thiopyran-4-ylmethyl)amino]imidazo[1,2-b]pyridazin-3-yl}-N-cyclopropyl-2-methylbenzamide

416
Example 293

N-cyclopropyl-4-{6-(2,3-difluorophenoxy)-8-[(tetrahydro-2H-thiopyran-4-ylmethyl)amino]imidazo[1,2-b]pyridazin-3-yl}-2-methylbenzamide


75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 51 using 4-chlorophenol to give after working up and purification 30.7 mg (36%) of the title compound.

$^1$H-NMR (DMSO-d6): δ=0.46 (2H), 0.63 (2H), 1.29 (2H), 1.75 (1H), 2.02 (2H), 2.12 (3H), 2.56 (4H), 2.77 (1H), 3.19 (2H), 6.07 (1H), 7.16 (1H), 7.31 (2H), 7.50 (2H), 7.62 (1H), 7.72 (2H), 7.90 (1H), 8.21 (1H) ppm.

75 mg (150 µmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy example 51 using 2,3-difluorophenol to give after working up and purification 19.1 mg (22%) of the title compound.

$^1$H-NMR (CDCl$_3$): δ=0.60 (2H), 0.88 (2H), 1.52 (2H), 1.79 (1H), 2.19 (2H), 2.30 (3H), 2.61-2.79 (4H), 2.89 (1H), 3.25 (2H), 5.82 (1H), 5.92 (2H), 7.05-7.17 (3H), 7.22 (1H), 7.54 (1H), 7.68 (1H), 7.70 (1H) ppm.

Example 294

4-[6-(4-chlorophenoxy)-8-{[(1,1-dioxidotetrahydro-2H-thiopyran-4-yl)methyl]amino}imidazo[1,2-b]pyridazin-3-yl]-N-cyclopropyl-2-methylbenzamide (A) and
4-[6-(4-chlorophenoxy)-8-({[(cis/trans)-1-oxidotetrahydro-2H-thiopyran-4-yl]methyl}amino)imidazo[1,2-b]pyridazin-3-yl]-N-cyclopropyl-2-methylbenzamide (B)

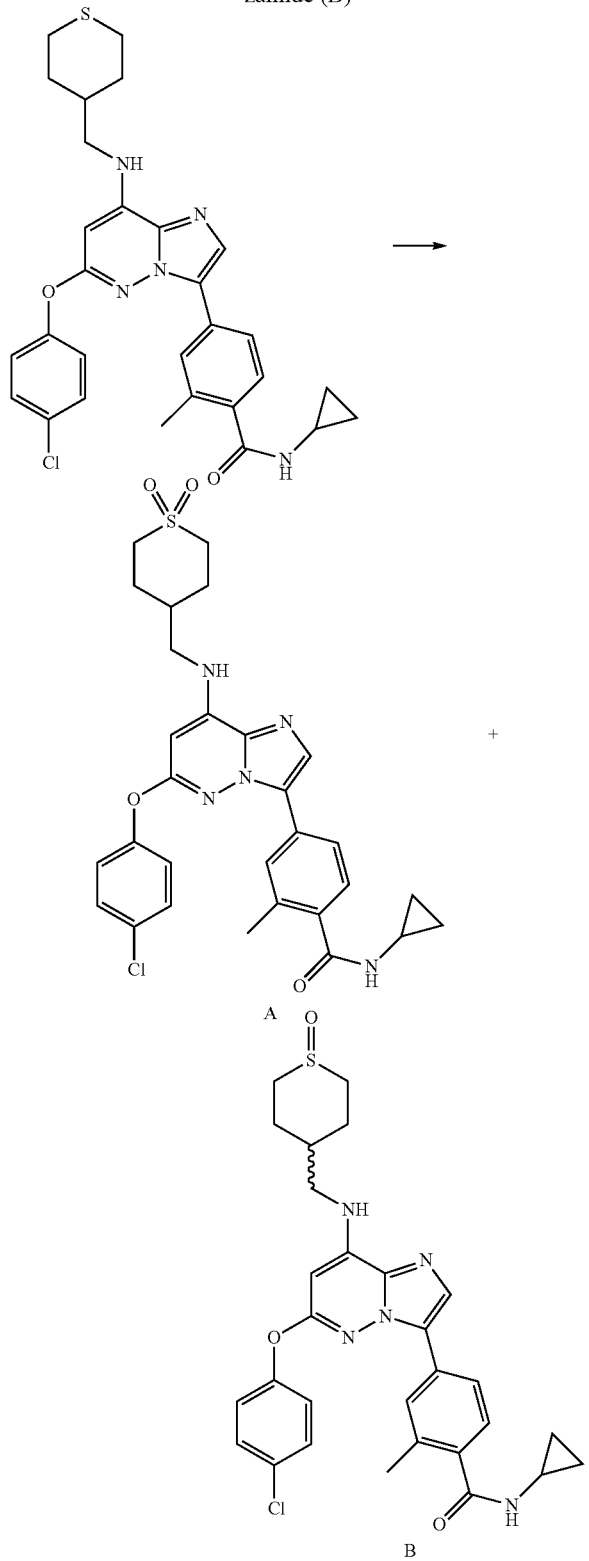

To a solution of 22.4 mg (41 µmol) 4-{6-(4-chlorophenoxy)-8-[(tetrahydro-2H-thiopyran-4-ylmethyl)amino]imidazo[1,2-b]pyridazin-3-yl}-N-cyclopropyl-2-methylbenzamide which was prepared according to example 292 in 327 µL trichloromethane were added 13.7 mg 3-chlorobenzenecarboperoxoic acid (77%) and the mixture was stirred at 23° C. for 40 minutes. Saturated sodium hydrogencarbonate solution was added and the solvents were removed. The residue was purified by chromatography to give 9.1 mg (38%) of the title compound A and 3.1 mg (13%) of a cis/trans-mixture of the title compounds B.

$^1$H-NMR (DMSO-d6) of A: δ=0.47 (2H), 0.63 (2H), 1.66 (2H), 1.98-2.15 (3H), 2.12 (3H), 2.77 (1H), 2.97-3.15 (4H), 3.25 (2H), 6.16 (1H), 7.17 (1H), 7.30 (2H), 7.50 (2H), 7.62 (1H), 7.72 (1H), 7.79 (1H), 7.91 (1H), 8.19 (1H) ppm.

$^1$H-NMR (DMSO-d6) of B: δ=0.46 (2H), 0.63 (2H), 1.65 (2H), 1.95-2.17 (3H), 2.12 (3H), 2.76 (1H), 2.96-3.16 (4H), 3.27 (2H), 6.17 (1H), 7.16 (1H), 7.30 (2H), 7.50 (2H), 7.62 (1H), 7.72 (1H), 7.82 (1H), 7.91 (1H), 8.22 (1H) ppm.

Example 295

N-cyclopropyl-4-[8-{[(1,1-dioxidotetrahydro-2H-thiopyran-4-yl)methyl]amino}-6-(4-fluorophenoxy)imidazo[1,2-b]pyridazin-3-yl]-2-methylbenzamide (A) and N-cyclopropyl-4-[6-(4-fluorophenoxy)-8-({[(cis/trans)-1-oxidotetrahydro-2H-thiopyran-4-yl]methyl}amino)imidazo[1,2-b]pyridazin-3-yl]-2-methylbenzamide (B)

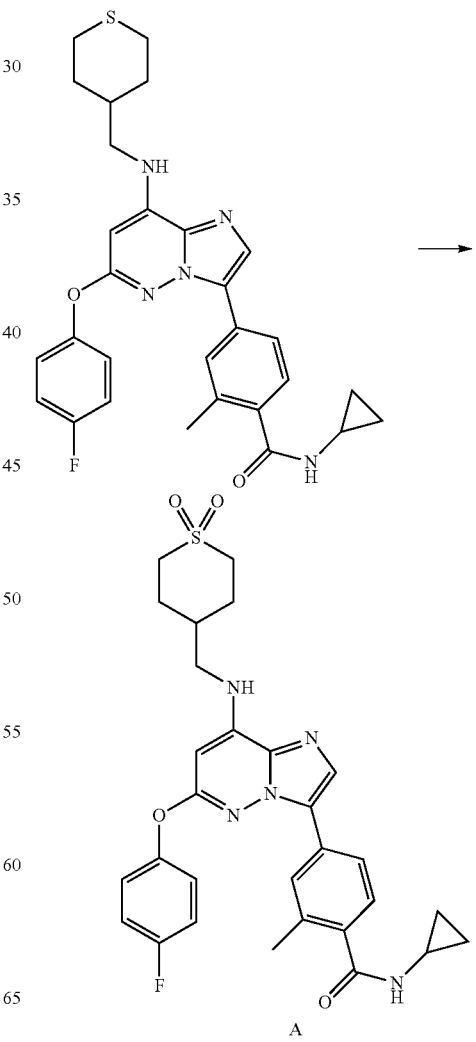

-continued

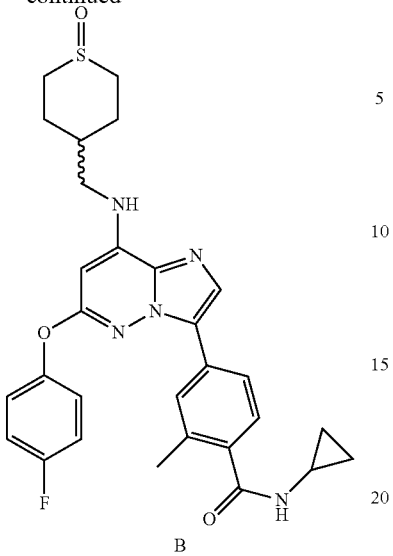

B 37 mg (70 µmol) N-cyclopropyl-4-{6-(4-fluorophenoxy)-8-[(tetrahydro-2H-thiopyran-4-ylmethyl)amino]imidazo[1,2-b]pyridazin-3-yl}-2-methylbenzamide which was prepared according to example 290 were transformed in analogy to example 294 to give after working up and purification 5.2 mg (13%) of the title compound A and 1.7 mg (4%) of a cis/trans-mixture of the title compounds B.

$^1$H-NMR (DMSO-d6) of A: δ=0.47 (2H), 0.63 (2H), 1.66 (2H), 1.95-2.17 (3H), 2.12 (3H), 2.76 (1H), 2.97-3.16 (4H), 3.22 (2H), 6.15 (1H), 7.15 (1H), 7.23-7.36 (4H), 7.63 (1H), 7.72 (1H), 7.76 (1H), 7.90 (1H), 8.19 (1H) ppm.

$^1$H-NMR (DMSO-d6) of B: δ=0.47 (2H), 0.63 (2H), 1.38 (1H), 1.64-2.26 (5H), 2.12 (3H), 2.57 (2H), 2.67-2.88 (2H), 3.19 (2H), 6.11 (1H), 7.15 (1H), 7.22-7.35 (4H), 7.63 (1H), 7.68-7.77 (2H), 7.90 (1H), 8.19 (1H) ppm.

Example 296
N-cyclopropyl-4-[8-{[(1,1-dioxidotetrahydro-2H-thiopyran-4-yl)methyl]amino}-6-(pyridin-3-yloxy)imidazo[1,2-b]pyridazin-3-yl]-2-methylbenzamide (A) and
N-cyclopropyl-2-methyl-4-[8-({[(cis)-1-oxidotetrahydro-2H-thiopyran-4-yl]methyl}amino)-6-(pyridin-3-yloxy)imidazo[1,2-b]pyridazin-3-yl]benzamide (B) and
N-cyclopropyl-2-methyl-4-[8-({[(trans)-1-oxidotetrahydro-2H-thiopyran-4-yl]methyl}amino)-6-(pyridin-3-yloxy)imidazo[1,2-b]pyridazin-3-yl]benzamide (C)

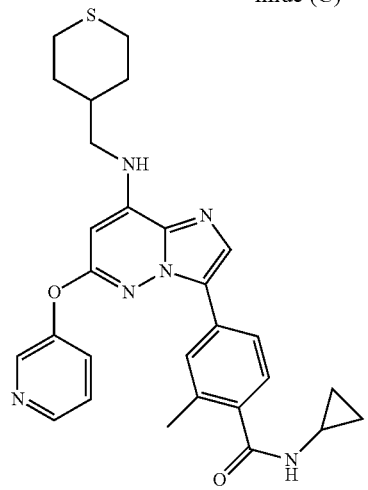

→

-continued

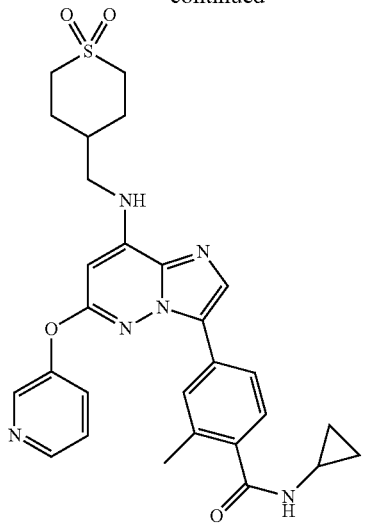

A

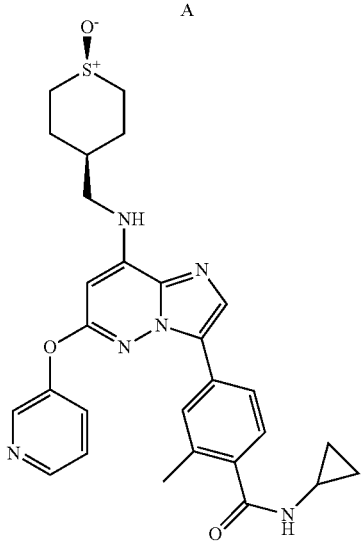

B

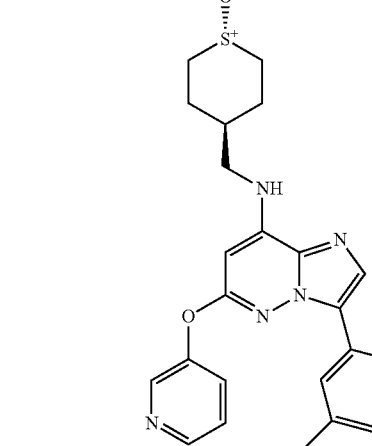

C 17.1 mg (33 µmol) N-cyclopropyl-2-methyl-4-{6-(pyridin-3-yloxy)-8-[(tetrahydro-2H-thiopyran-4-ylmeth yl)amino]imidazo[1,2-b]pyridazin-3-yl}benzamide which was prepared according to example 288 were transformed in analogy to example 294 to give after working up and purification 6.7 mg (37%) of the title compound A, 2.4 mg (12%) of the title compound B and 3.1 mg (16%) of the title compound C.

¹H-NMR (CDCl₃) of A: δ=0.61 (2H), 0.88 (2H), 1.96-2.11 (3H), 2.29 (2H), 2.32 (3H), 2.89 (1H), 3.04 (2H), 3.14 (2H), 3.37 (2H), 5.90 (1H), 5.92 (1H), 6.51 (1H), 7.24 (1H), 7.40 (1H), 7.55 (1H), 7.62 (1H), 7.64 (1H), 7.72 (1H), 8.54 (1H), 8.61 (1H) ppm.

¹H-NMR (CDCl₃) of B: δ=0.61 (2H), 0.88 (2H), 1.87-2.01 (3H), 2.24 (2H), 2.32 (3H), 2.48 (2H), 2.89 (1H), 3.10 (2H), 3.33 (2H), 5.89 (1H), 5.92 (1H), 6.02 (1H), 7.24 (1H), 7.39 (1H), 7.56 (1H), 7.62 (1H), 7.66 (1H), 7.71 (1H), 8.53 (1H), 8.60 (1H) ppm.

¹H-NMR (CDCl₃) of C: δ=0.61 (2H), 0.88 (2H), 1.57 (2H), 1.99 (1H), 2.29 (2H), 2.31 (3H), 2.68 (2H), 2.89 (1H), 3.30 (2H), 3.40 (2H), 5.87-5.92 (2H), 5.99 (1H), 7.23 (1H), 7.39 (1H), 7.55 (1H), 7.62 (1H), 7.65 (1H), 7.71 (1H), 8.53 (1H), 8.60 (1H) ppm.

Example 297

N-cyclopropyl-4-[8-{[(1,1-dioxidotetrahydro-2H-thiopyran-4-yl)methyl]amino}-6-(2-fluorophenoxy)imidazo[1,2-b]pyridazin-3-yl]-2-methylbenzamide 19.7 mg (37 µmol) N-cyclopropyl-4-{6-(2-fluorophenoxy)-8-[(tetrahydro-2H-thiopyran-4-ylmethyl)amino]imidazo[1,2-b]pyridazin-3-yl}-2-methylbenzamide which was prepared according to example 283 were transformed in analogy to example 294 to give after working up and purification 9.8 mg (47%) of the title compound.

¹H-NMR (CDCl₃): δ=0.60 (2H), 0.88 (2H), 1.94-2.08 (3H), 2.26 (3H), 2.28 (2H), 2.89 (1H), 3.02 (2H), 3.13 (2H), 3.36 (2H), 5.82 (1H), 5.94 (1H), 5.99 (1H), 7.17-7.33 (5H), 7.53 (1H), 7.68 (1H), 7.71 (1H) ppm.

Example 298

N-cyclopropyl-4-[8-{[(1,1-dioxidotetrahydro-2H-thiopyran-4-yl)methyl]amino}-6-(3-fluorophenoxy)imidazo[1,2-b]pyridazin-3-yl]-2-methylbenzamide (A) and N-cyclopropyl-4-[6-(3-fluorophenoxy)-8-({[(cis/trans)-1-oxidotetrahydro-2H-thiopyran-4-yl]methyl}amino)imidazo[1,2-b]pyridazin-3-yl]-2-methylbenzamide (B)

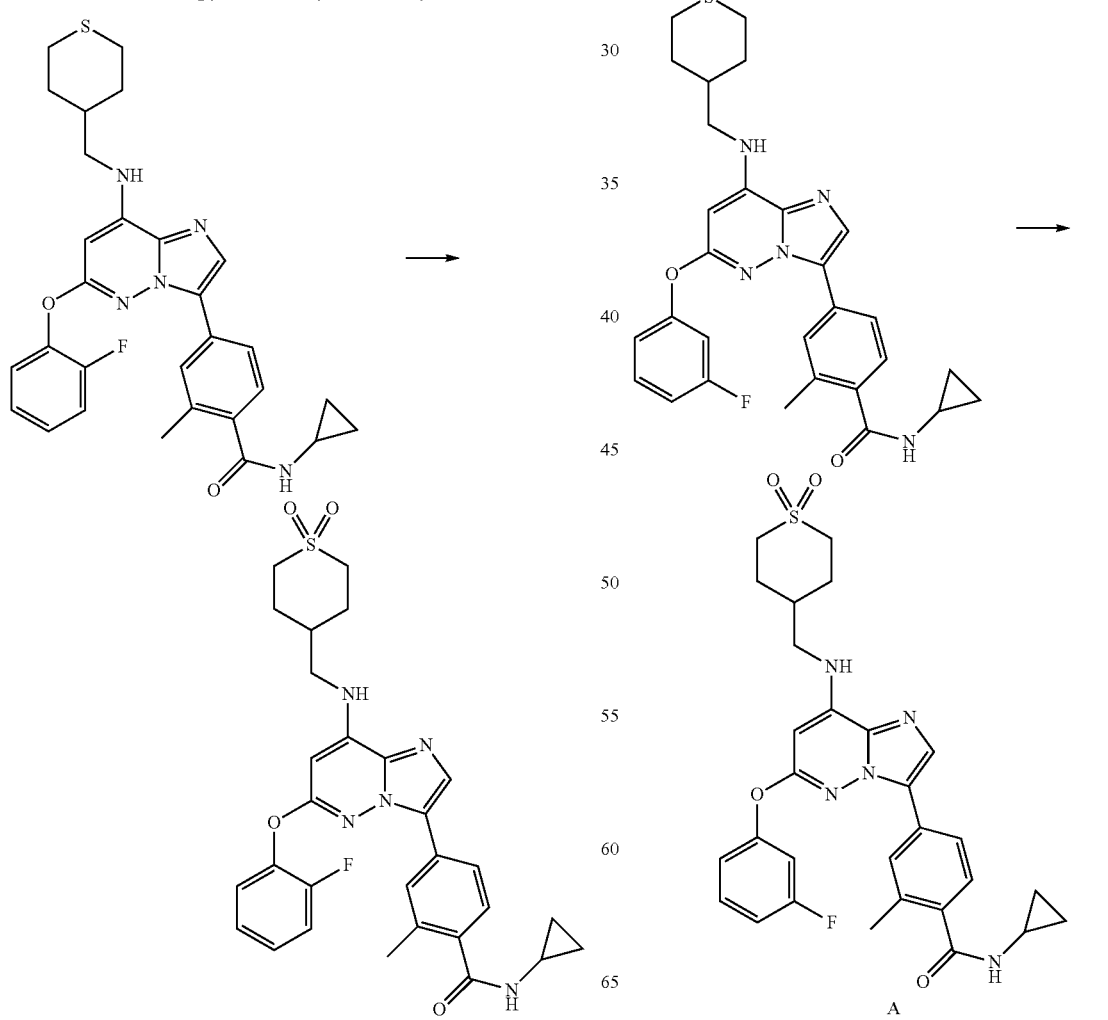

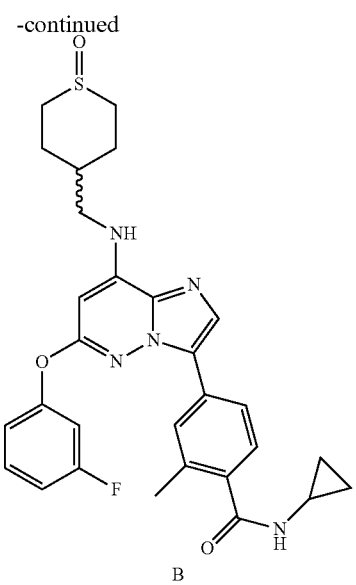

B 25.5 mg (48 μmol) N-cyclopropyl-4-{6-(3-fluorophenoxy)-8-[(tetrahydro-2H-thiopyran-4-ylmethyl)amino]imidazo[1,2-b]pyridazin-3-yl}-2-methylbenzamide which was prepared according to example 281 were transformed in analogy to example 294 to give after working up and purification 12.3 mg (43%) of the title compound A and 5.6 mg (21%) of a cis/trans-mixture of the title compounds B.

$^1$H-NMR (CDCl$_3$) of A: δ=0.61 (2H), 0.88 (2H), 1.93-2.08 (3H), 2.28 (2H), 2.33 (3H), 2.89 (1H), 3.02 (2H), 3.13 (2H), 3.35 (2H), 5.84 (1H), 5.86 (1H), 6.04 (1H), 6.95-7.09 (3H), 7.25 (1H), 7.39 (1H), 7.61 (1H), 7.72 (1H), 7.74 (1H) ppm.

$^1$H-NMR (CDCl$_3$) of B: δ=0.60 (2H), 0.88 (2H), 1.55 (1H), 1.89 (1H), 1.97 (1H), 2.15-2.31 (2H), 2.32 (3H), 2.47+2.67 (2H), 2.89 (1H), 3.08+3.39 (2H), 3.29 (2H), 5.84+5.87 (1H), 5.89 (1H), 6.13 (1H), 6.95-7.07 (3H), 7.25 (1H), 7.39 (1H), 7.61 (1H), 7.72 (1H), 7.74 (1H) ppm.

Example 299

N-cyclopropyl-4-{6-[4-fluoro-2-(hydroxymethyl)phenyl]-8-[(2-hydroxy-2-methylpropyl)amino]imidazo[1,2-b]pyridazin-3-yl}-2-methylbenzamide

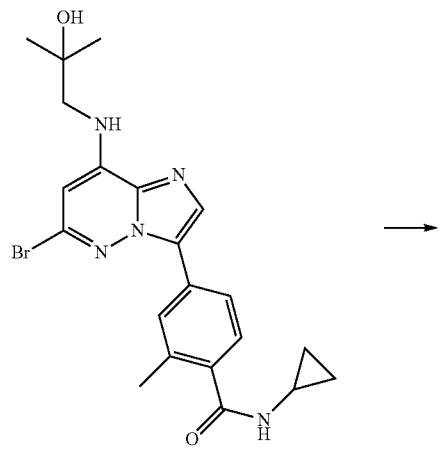

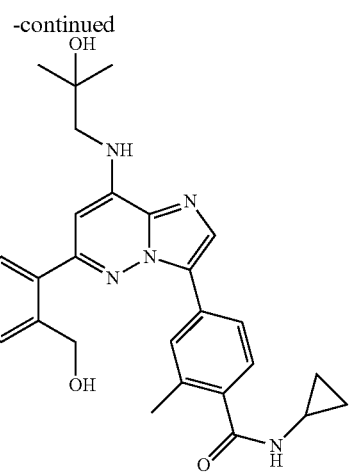

250 mg (545 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 1 using [4-fluoro-2-(hydroxymethyl)phenyl]boronic acid which was prepared according to intermediate example 299a to give after working up and purification 239 mg (87%) of the title compound.

$^1$H-NMR (DMSO-d6): δ=0.48 (2H), 0.64 (2H), 1.15 (6H), 2.34 (3H), 2.79 (1H), 3.28 (2H), 4.65 (2H), 4.73 (1H), 5.31 (1H), 6.41 (1H), 6.97 (1H), 7.19 (1H), 7.32 (1H), 7.40 (1H), 7.53 (1H), 7.91 (1H), 7.95 (1H), 7.99 (1H), 8.26 (1H) ppm.

Intermediate Example 299a

[4-fluoro-2-(hydroxymethyl)phenyl]boronic acid

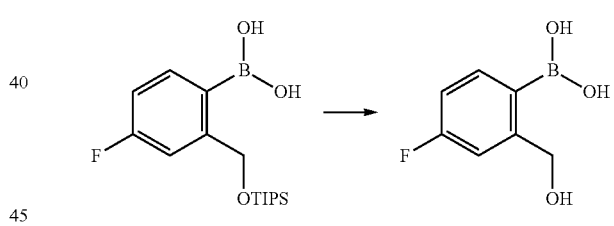

To a solution of 2.60 g (7.97 mmol) (4-fluoro-2-{[(triisopropylsilyl)oxy]methyl}phenyl)boronic acid which was prepared according to intermediate example 299b in 10 mL dichloromethane were added 6.14 mL trifluoroacetic acid and the mixture was stirred for 16 hours at 23° C. The solvent was removed and the residue crystallized from n-hexane to give 682 mg (50%) of the title compound.

Intermediate Example 299b (4-fluoro-2-{[(triisopropylsilyl)oxy]methyl}phenyl)boronic acid

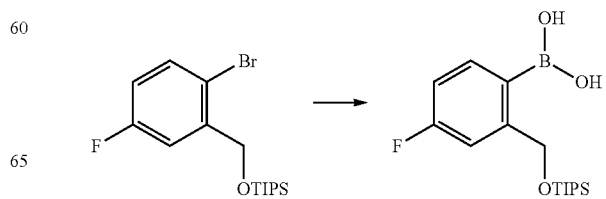

425

To a solution of 6.00 g (16.6 mmol) [(2-bromo-5-fluorobenzyl)oxy](triisopropyl)silane which was prepared according to intermediate example 299c in 60 mL tetrahydrofuran were added 7.31 mL n-butyllithium (2.5M in hexane) at −78° C. After 20 minutes of stirring 5.58 mL trimethyl borate were added and stirring was continued for additional 60 minutes. The mixture was allowed to warm to 23° C., poured into a saturated ammonium chloride solution and extracted with ethyl acetate. The organic layer was washed with brine and dried over sodium sulfate. After filtration and removal of the solvent the residue was purified by chromatography to give 3.16 g (58%) of the title compound.

Intermediate Example 299c

[(2-bromo-5-fluorobenzyl)oxy](triisopropyl)silane

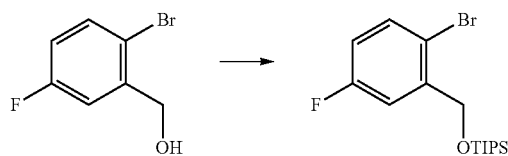

To a solution of 5.00 g (24.4 mmol) (2-bromo-5-fluorophenyl)methanol in 100 mL N,N-dimethylformamide were added 2.49 g imidazole, 6.20 mL chloro(triisopropyl)silane, 1.49 g N,N-dimethylpyridin-4-amine and the mixture was stirred at 23° C. for 2 days. Water was added and the mixture was extracted with ethyl acetate. The organic layer was washed with brine and dried over sodium sulfate. After filtration and removal of the solvent the residue was purified by chromatography to give 8.17 g (93%) of the title compound.

Example 300

N-cyclopropyl-4-{6-[(3,4-difluorophenyl)sulfanyl]-8-[(2-hydroxy-2-methylpropyl)amino]imidazo[1,2-b]pyridazin-3-yl}-2-methylbenzamide

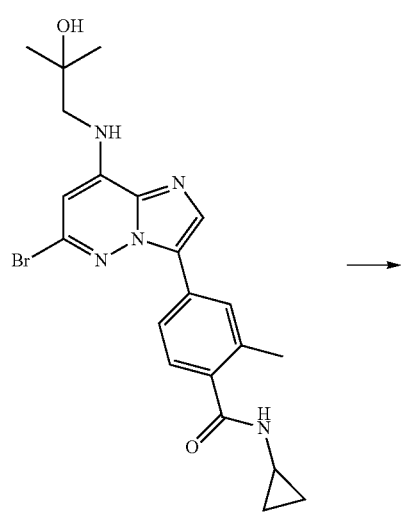

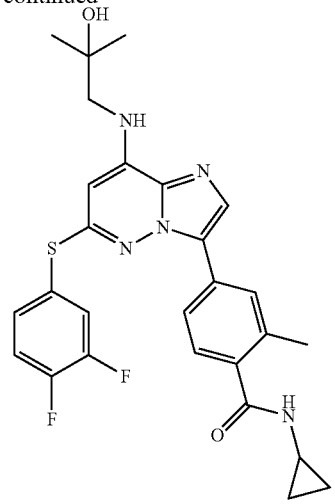

200 mg (436 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3,4-difluorobenzenethiol to give after working up and purification 5.8 mg (2%) of the title compound.

$^1$H-NMR (CDCl$_3$/CD$_3$OD): δ=0.62 (2H), 0.88 (2H), 1.33 (6H), 2.37 (3H), 2.89 (1H), 3.22 (2H), 5.95 (1H), 6.13 (1H), 6.42 (1H), 7.17 (1H), 7.21 (1H), 7.35 (1H), 7.47 (1H), 7.51 (1H), 7.52 (1H), 7.62 (1H) ppm.

Example 301

N-cyclopropyl-4-(8-{[(1,1-dioxidotetrahydro-2H-thiopyran-4-yl)methyl]amino}-6-[(3-fluorophenyl)sulfanyl]imidazo[1,2-b]pyridazin-3-yl)-2-methylbenzamide

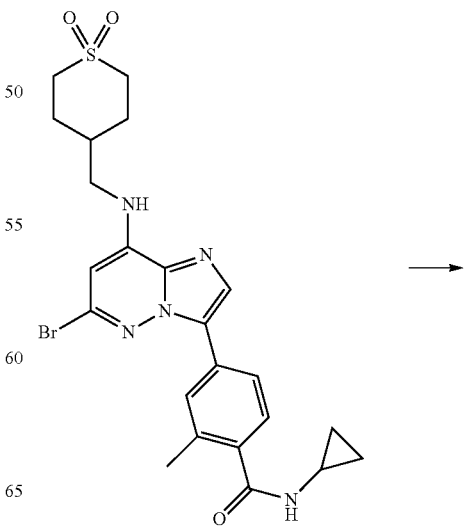

-continued

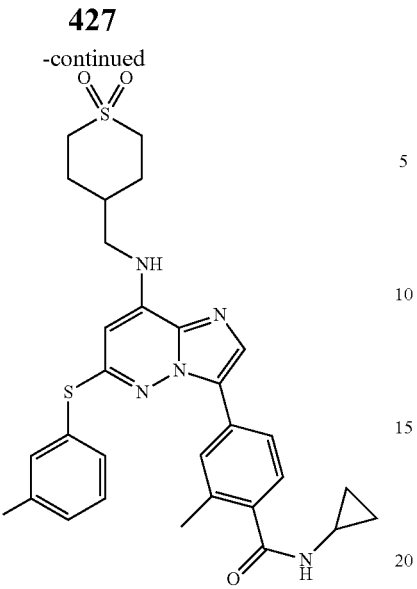

25 mg (47 μmol) 4-(6-bromo-8-{[(1,1-dioxidotetrahydro-2H-thiopyran-4-yl)methyl]amino}imidazo[1,2-b]pyridazin-3-yl)-N-cyclopropyl-2-methylbenzamide which was prepared according to intermediate example 301a were transformed in analogy to example 51 using 3-fluorobenzenethiol to give after working up and purification 13.0 mg (48%) of the title compound.

$^{1}$H-NMR (DMSO-d6): δ=0.48 (2H), 0.65 (2H), 1.62 (2H), 1.94 (1H), 2.01 (2H), 2.20 (3H), 2.79 (1H), 2.96-3.11 (4H), 3.23 (2H), 6.25 (1H), 7.11 (1H), 7.34 (1H), 7.44 (1H), 7.49 (1H), 7.54 (1H), 7.65 (1H), 7.70 (1H), 7.82 (1H), 7.94 (1H), 8.24 (1H) ppm.

Intermediate Example 301a 4-(6-bromo-8-{[(1,1-dioxidotetrahydro-2H-thiopyran-4-yl)methyl]amino}imidazo[1,2-b]pyridazin-3-yl)-N-cyclopropyl-2-methylbenzamide (A) and 4-(6-bromo-8-({[(cis/trans)-1-oxidotetrahydro-2H-thiopyran-4-yl]methyl}amino)imidazo[1,2-b]pyridazin-3-yl)-N-cyclopropyl-2-methylbenzamide (B)

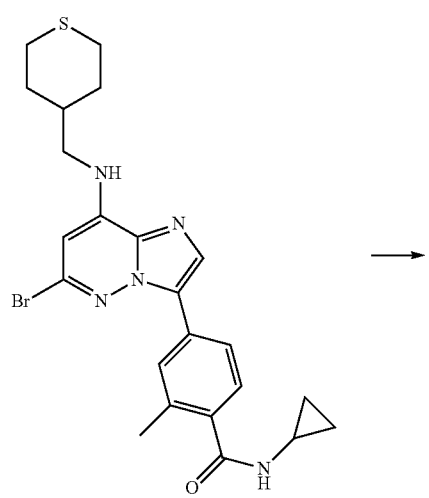

→

-continued

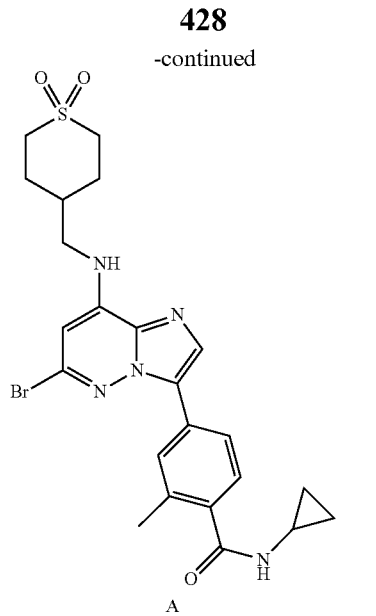

A

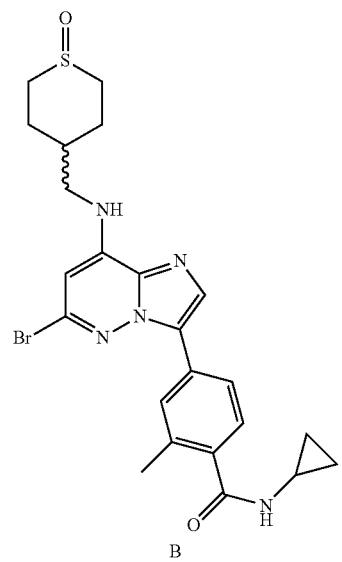

B 328 mg (655 μmol) 4-{6-bromo-8-[(tetrahydro-2H-thiopyran-4-ylmethyl)amino]imidazo[1,2-b]pyridazin-3-yl}-N-cyclopropyl-2-methylbenzamide which was prepared according to intermediate example 281a were transformed in analogy to example 294 to give after working up and purification 167 mg (48%) of the title compound A and 128 mg (38%) of the title compounds B.

Example 302

N-cyclopropyl-4-[8-{[(1,1-dioxidotetrahydro-2H-thiopyran-4-yl)methyl]amino}-6-(phenylsulfanyl)imidazo[1,2-b]pyridazin-3-yl]-2-methylbenzamide

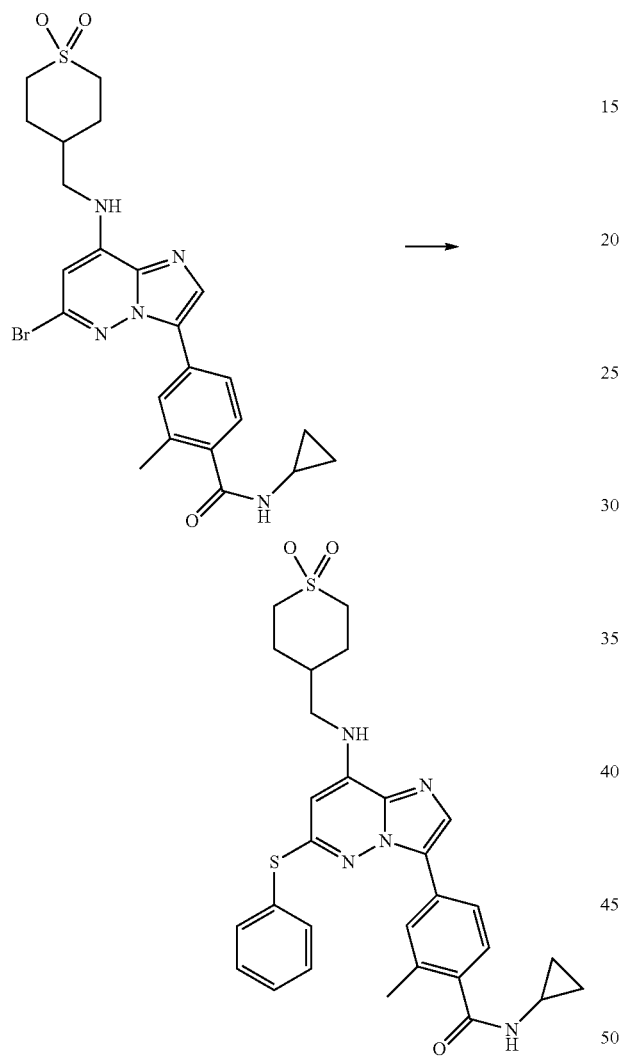

25 mg (47 μmol) 4-(6-bromo-8-{[(1,1-dioxidotetrahydro-2H-thiopyran-4-yl)methyl}amino]imidazo[1,2-b]pyridazin-3-yl)-N-cyclopropyl-2-methylbenzamide which was prepared according to intermediate example 301a were transformed in analogy to example 51 using benzenethiol to give after working up and purification 10.1 mg (26%) of the title compound.

¹H-NMR (DMSO-d6): δ=0.48 (2H), 0.65 (2H), 1.61 (2H), 1.91 (1H), 1.99 (2H), 2.19 (3H), 2.78 (1H), 2.96-3.12 (4H), 3.20 (2H), 6.15 (1H), 7.08 (1H), 7.44-7.53 (3H), 7.58-7.65 (3H), 7.69 (1H), 7.77 (1H), 7.93 (1H), 8.23 (1H) ppm.

Example 303

N-cyclopropyl-2-methyl-4-[8-({[(cis)-1-oxidotetrahydro-2H-thiopyran-4-yl]methyl}amino)-6-(phenylsulfanyl)imidazo[1,2-b]pyridazin-3-yl]benzamide (A) and N-cyclopropyl-2-methyl-4-[8-({[(trans)-1-oxidotetrahydro-2H-thiopyran-4-yl]methyl}amino)-6-(phenylsulfanyl)imidazo[1,2-b]pyridazin-3-yl]benzamide (B)

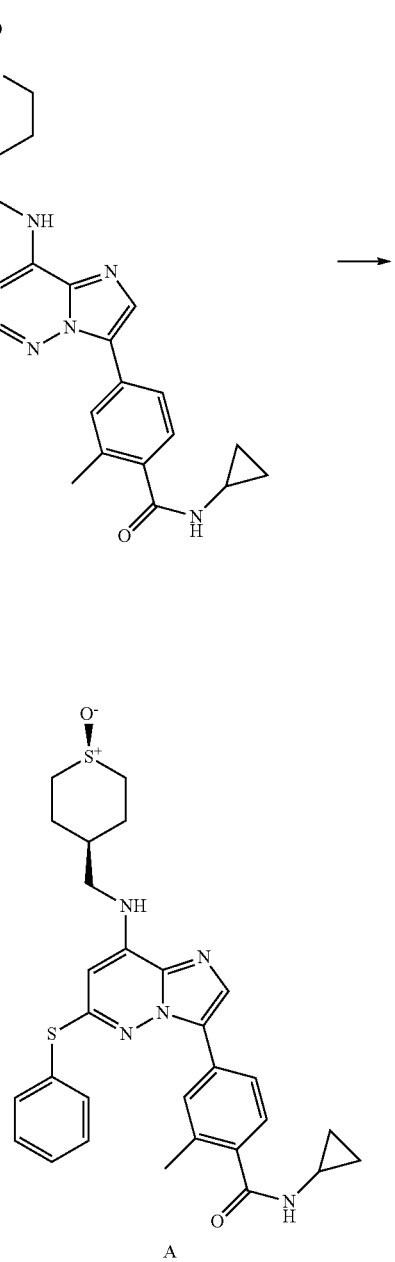

A

+

431

-continued

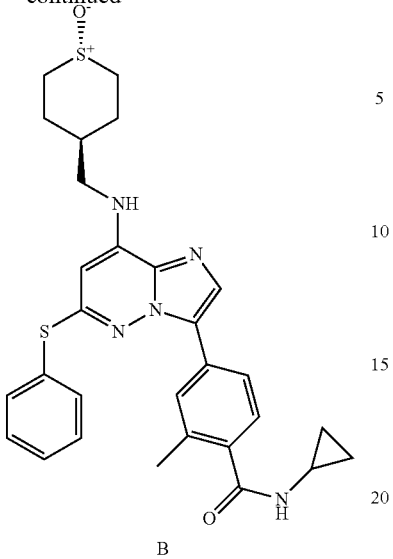

B 25 mg (48 μmol) 4-(6-bromo-8-({[(cis/trans)-1-oxidotetrahydro-2H-thiopyran-4-yl]methyl}amino)imidazo[1,2-b]pyridazin-3-yl)-N-cyclopropyl-2-methylbenzamide which was prepared according to intermediate example 301a were transformed in analogy to example 51 using benzenethiol to give after working up and purification 3.7 mg (14%) of the title compound A and 2.5 mg (9%) of the title compound B.

$^1$H-NMR (CDCl$_3$) of A: δ=0.62 (2H), 0.89 (2H), 1.75-1.88 (3H), 2.15 (2H), 2.38 (3H), 2.42 (2H), 2.91 (1H), 3.05 (2H), 3.19 (2H), 5.87 (1H), 5.89 (1H), 5.97 (1H), 7.20 (1H), 7.41-7.50 (3H), 7.61-7.686 (4H), 7.69 (1H) ppm.

$^1$H-NMR (CDCl$_3$) of B: δ=0.62 (2H), 0.89 (2H), 1.46 (2H), 1.83 (1H), 2.17 (2H), 2.39 (3H), 2.60 (2H), 2.92 (1H), 3.15 (2H), 3.34 (2H), 5.82 (1H), 5.85 (1H), 5.90 (1H), 7.21 (1H), 7.42-7.51 (3H), 7.61-7.68 (4H), 7.70 (1H) ppm.

Example 304

N-cyclopropyl-4-(6-[(3-fluorophenyl)sulfanyl]-8-({[(cis)-1-oxidotetrahydro-2H-thiopyran-4-yl]methyl}amino)imidazo[1,2-b]pyridazin-3-yl)-2-methylbenzamide (A) and N-cyclopropyl-4-(6-[(3-fluorophenyl)sulfanyl]-8-({[(trans)-1-oxidotetrahydro-2H-thiopyran-4-yl]methyl}amino)imidazo[1,2-b]pyridazin-3-yl)-2-methylbenzamide (B)

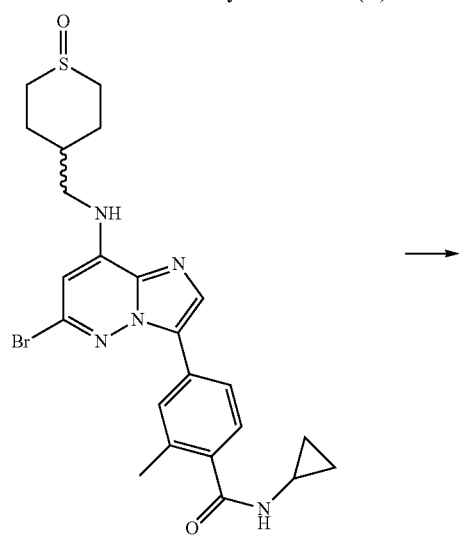

432

-continued

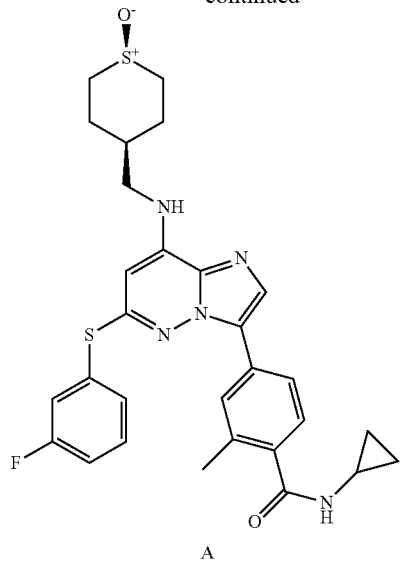

A

B 25 mg (48 μmol) 4-(6-bromo-8-({[(cis/trans)-1-oxidotetrahydro-2H-thiopyran-4-yl]methyl}amino)imidazo[1,2-b]pyridazin-3-yl)-N-cyclopropyl-2-methylbenzamide which was prepared according to intermediate example 301a were transformed in analogy to example 81 using 3-fluorobenzenethiol to give after working up and purification 7.4 mg (27%) of the title compound A and 4.8 mg (18%) of the title compound B.

$^1$H-NMR (CDCl$_3$) of A: δ=0.63 (2H), 0.89 (2H), 1.74-1.89 (3H), 2.17 (2H), 2.40 (3H), 2.43 (2H), 2.92 (1H), 3.06 (2H), 3.22 (2H), 5.90 (1H), 5.92 (1H), 5.98 (1H), 7.15 (1H), 7.23 (1H), 7.35-7.44 (3H), 7.63 (1H), 7.65 (1H), 7.69 (1H) ppm.

$^1$H-NMR (CDCl$_3$) of B: δ=0.62 (2H), 0.90 (2H), 1.49 (2H), 0.87 (1H), 2.20 (2H), 2.40 (3H), 2.62 (2H), 2.92 (1H), 3.19 (2H), 3.35 (2H), 5.87 (2H), 5.93 (1H), 7.15 (1H), 7.24 (1H), 7.35-7.44 (3H), 7.64 (1H), 7.65 (1H), 7.70 (1H) ppm.

433

Example 305

N-cyclopropyl-4-{6-[(4-fluorophenyl)amino]-8-[(2-hydroxy-2-methylpropyl)amino]imidazo[1,2-b]pyridazin-3-yl}-2-methylbenzamide

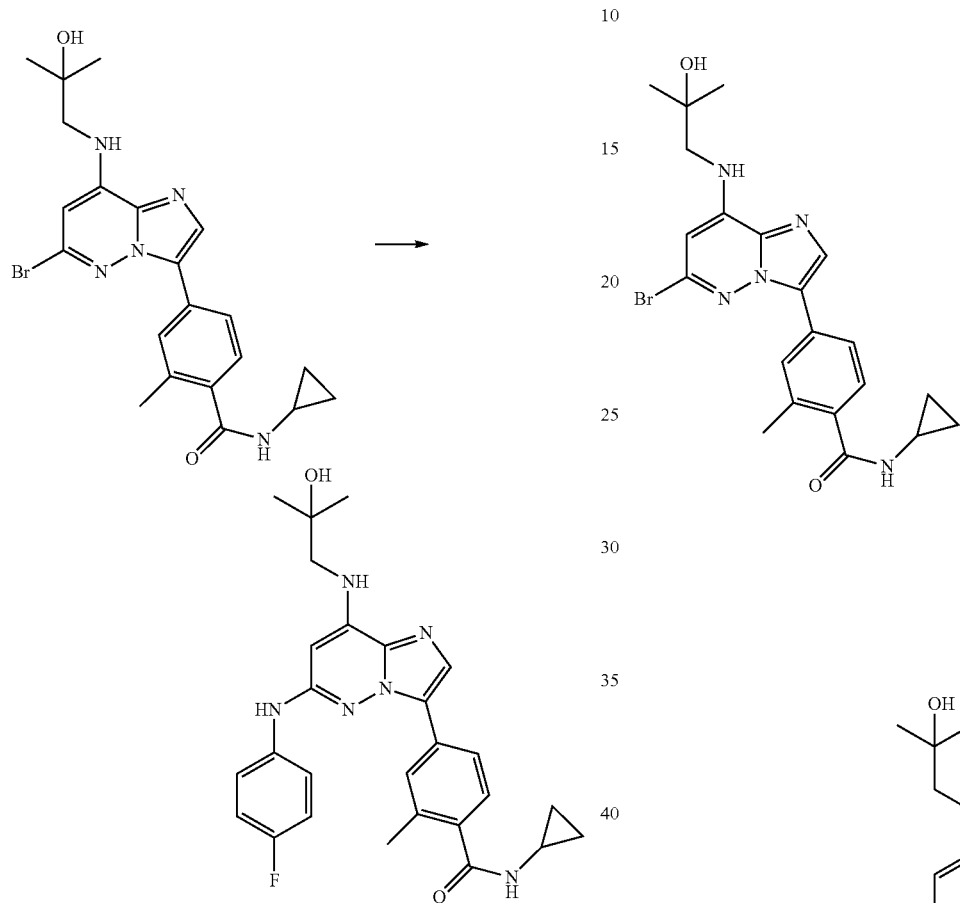

434

Example 306

4-{6-anilino-8-[(2-hydroxy-2-methylpropyl)amino]imidazo[1,2-b]pyridazin-3-yl}-N-cyclopropyl-2-methylbenzamide A mixture comprising 75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a, 3 mL dimethyl sulfoxide, 61.1 mg 1,1-binaphthalene-2,2'-diylbis(diphenylphosphine), 30.0 mg tris(dibenzylideneacetone)dipalladium (0) and 55 mg sodium 2-methylpropan-2-olate were heated to 160° C. under microwave irradiation for one hour. The reaction mixture was poured into water and extracted with dichloromethane. The combined organic phases were dried over sodium sulfate. After filtration and removal of solvent the residue was purified by chromatography to give 11.3 mg (14%) of the title compound.

$^1$H-NMR (DMSO-d6): δ=0.52 (2H), 0.66 (2H), 1.18 (6H), 2.37 (3H), 2.81 (1H), 3.15 (2H), 4.81 (1H), 5.85 (1H), 6.55 (1H), 7.10 (2H), 7.35 (1H), 7.65 (2H), 7.76 (1H), 7.84 (1H), 8.04 (1H), 8.29 (1H), 8.94 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using aniline to give after working up and purification 15.8 mg (21%) of the title compound.

$^1$H-NMR (DMSO-d6): δ=0.51 (2H), 0.66 (2H), 1.18 (6H), 2.38 (3H), 2.81 (1H), 3.16 (2H), 4.81 (1H), 5.89 (1H), 6.53 (1H), 6.90 (1H), 7.27 (2H), 7.34 (1H), 7.66 (2H), 7.77 (1H), 7.85 (1H), 8.12 (1H), 8.30 (1H), 8.92 (1H) ppm.

435

Example 307

N-cyclopropyl-4-{6-[(3,4-difluorophenyl)amino]-8-[(2-hydroxy-2-methylpropyl)amino]imidazo[1,2-b]pyridazin-3-yl}-2-methylbenzamide

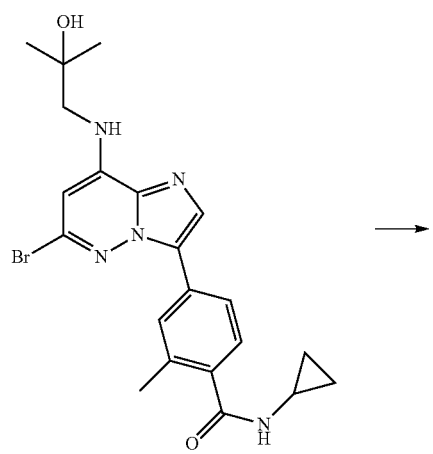

→

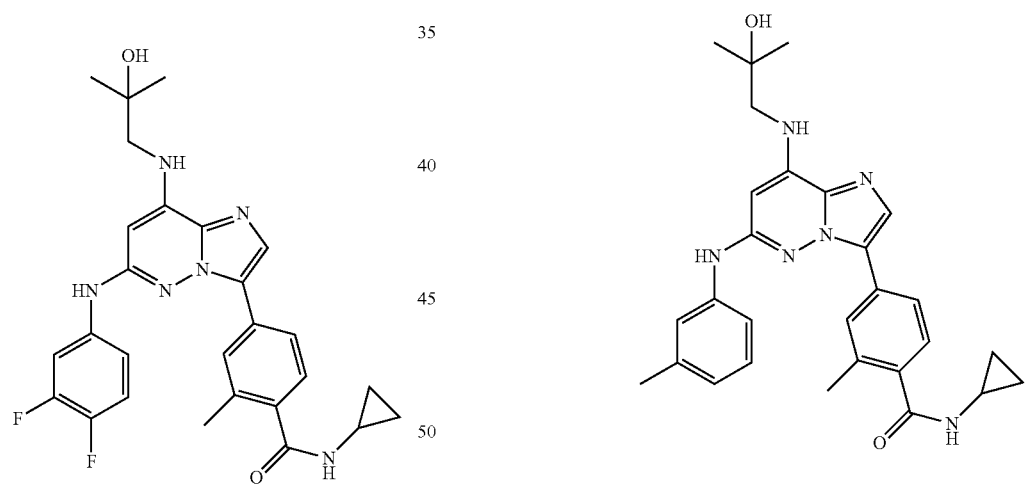

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3,4-difluoroaniline to give after working up and purification 8.3 mg (14%) of the title compound.

$^1$H-NMR (DMSO-d6): δ=0.51 (2H), 0.66 (2H), 1.18 (6H), 2.36 (3H), 2.81 (1H), 3.16 (2H), 4.80 (1H), 5.85 (1H), 6.65 (1H), 7.22 (1H), 7.31 (1H), 7.34 (1H), 7.76 (1H), 7.82 (1H), 7.91 (1H), 8.00 (1H), 8.30 (1H), 9.17 (1H) ppm.

436

Example 308

N-cyclopropyl-4-{8-[(2-hydroxy-2-methylpropyl)amino]-6-[(3-methylphenyl)amino]imidazo[1,2-b]pyridazin-3-yl}-2-methylbenzamide

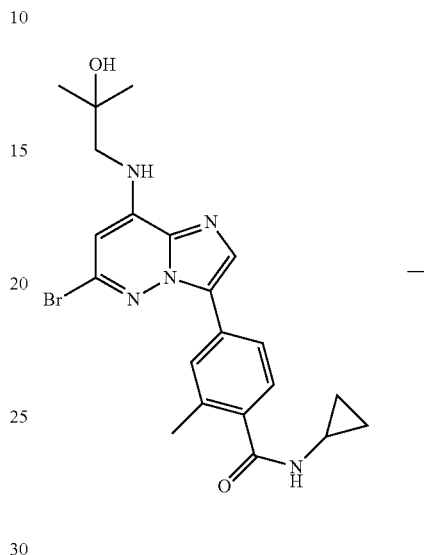

→

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using m-toluidine to give after working up and purification 8.3 mg (16%) of the title compound.

$^1$H-NMR (DMSO-d6): δ=0.50 (2H), 0.66 (2H), 1.18 (6H), 2.25 (3H), 2.36 (3H), 2.81 (1H), 3.15 (2H), 4.81 (1H), 5.89 (1H), 6.51 (1H), 6.71 (1H), 7.14 (1H), 7.33 (1H), 7.40 (1H), 7.51 (1H), 7.77 (1H), 7.95 (1H), 8.01 (1H), 8.29 (1H), 8.83 (1H) ppm.

Example 309

N-cyclopropyl-4-{6-[(5-fluoro-2-methylphenyl)amino]-8-[(2-hydroxy-2-methylpropyl)amino]imidazo[1,2-b]pyridazin-3-yl}-2-methylbenzamide e

Example 310

4-{6-[(4-chlorophenyl)amino]-8-[(2-hydroxy-2-methylpropyl)amino]imidazo[1,2-b]pyridazin-3-yl}-N-cyclopropyl-2-methylbenzamide

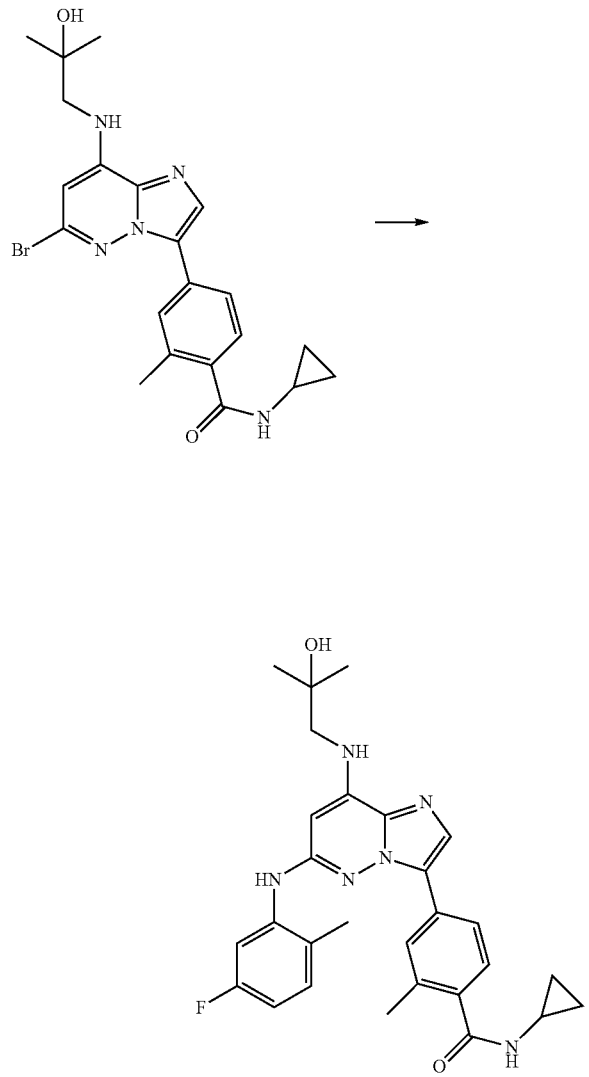 [SMILES: Cc1cc(-c2cnc3c(NCC(C)(C)O)cc(Br)nn23)ccc1C(=O)NC1CC1 ; Cc1ccc(F)cc1Nc1cc(NCC(C)(C)O)c2ncc(-c3ccc(C(=O)NC4CC4)c(C)c3)n2n1]

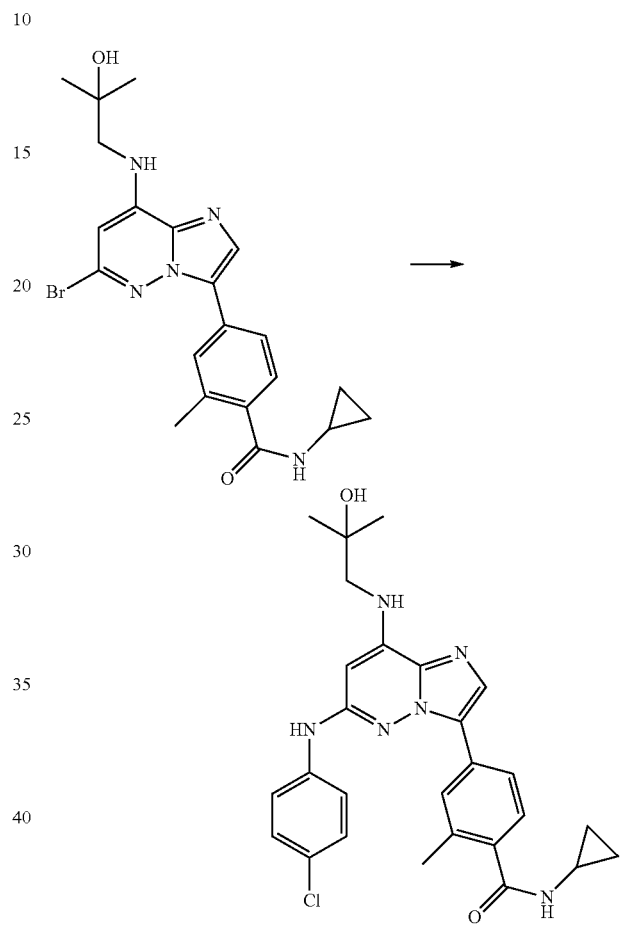

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 5-fluoro-2-methylaniline to give after working up and purification 5.9 mg (11%) of the title compound.

$^1$H-NMR (DMSO-d6): δ=0.49 (2H), 0.64 (2H), 1.19 (6H), 2.23 (3H), 2.26 (3H), 2.79 (1H), 3.17 (2H), 4.82 (1H), 6.15 (1H), 6.51 (1H), 6.74 (1H), 7.18 (1H), 7.23 (1H), 7.77-7.87 (3H), 7.95 (1H), 8.01 (1H), 8.25 (1H) ppm.

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-chloroaniline to give after working up and purification 8.1 mg (15%) of the title compound.

$^1$H-NMR (DMSO-d6): δ=0.52 (2H), 0.67 (2H), 1.18 (6H), 2.38 (3H), 2.81 (1H), 3.16 (2H), 4.80 (1H), 5.87 (1H), 6.60 (1H), 7.29 (2H), 7.37 (1H), 7.67 (2H), 7.77 (1H), 7.84 (1H), 8.02 (1H), 8.30 (1H), 9.08 (1H) ppm.

The following compound examples were prepared analogously to the procedure described for example 51 using the appropriate intermediate and the appropriate alcohols, thiols, or amines [LC-MS data such as retention time (RT in min) or observed mass peak were collected using LC-MS Method A unless explicitly stated]:

| Example | Structure | Name | Analytical Data |
|---|---|---|---|
| 311 | 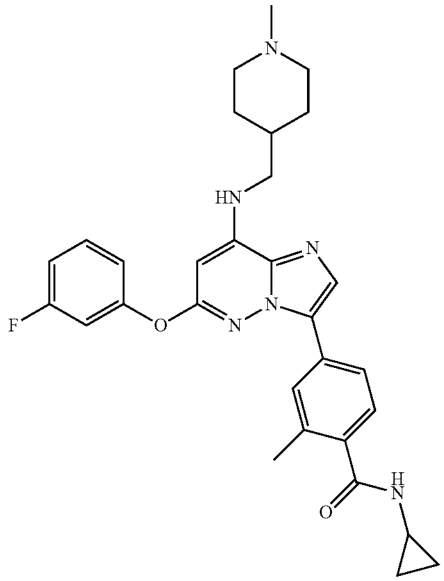 [SMILES: Cc1cc(-c2cnc3c(NCC4CCN(C)CC4)cc(Oc4cccc(F)c4)nn23)ccc1C(=O)NC1CC1] | N-cyclopropyl-4-[6-(3-fluorophenoxy)-8-{[(1-methylpiperidin-4-yl)methyl]amino}imidazo[1,2-b]pyridazin-3-yl]-2-methyl-benzamide | $^1$H-NMR (DMSO-d6): δ = 0.47 (2H), 0.63 (2H), 1.33 (2H), 1.77 (3H), 2.14 (3H), 2.37 (2H), 2.40 (3H), 2.77 (1H), 3.05 (2H), 3.23 (2H), 6.10 (1H), 7.09-7.14 (2H), 7.16 (1H), 7.25 (1H), 7.47 (1H), 7.65 (1H), 7.76 (1H), 7.78 (1H), 7.91 (1H), 8.23 (1H), 8.26 (1H) ppm<br>RT = 0.95<br>MW$_{found}$ = 529.6<br>MW$_{calc}$ = 528.6 |
| 312 | 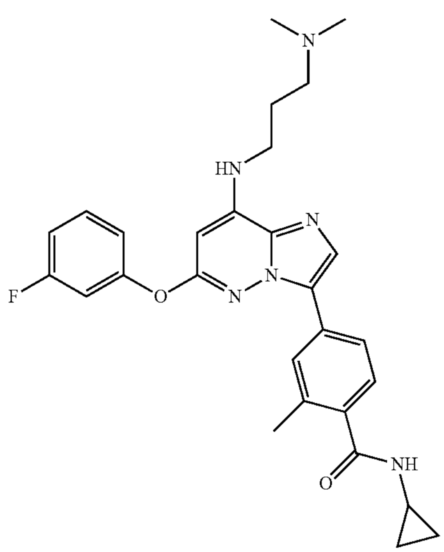 [SMILES: Cc1cc(-c2cnc3c(NCCCN(C)C)cc(Oc4cccc(F)c4)nn23)ccc1C(=O)NC1CC1] | N-cyclopropyl-4-[8-{[3-(dimethylamino)propyl]amino}-6-(3-fluorophenoxy)imidazo[1,2-b]pyridazin-3-yl]-2-methyl-benzamide | $^1$H-NMR (DMSO-d6): δ = 0.47 (2H), 0.62 (2H), 1.85 (2H), 2.14 (3H), 2.38 (6H), 2.63 (2H), 2.77 (1H), 3.37 (2H), 6.07 (1H), 7.08-7.15 (3H), 7.17 (1H), 7.24 (1H), 7.48 (1H), 7.66 (1H), 7.76 (1H), 7.78 (1H), 7.92 (1H) ppm<br>RT = 0.93<br>MW$_{found}$ = 503.6<br>MW$_{calc}$ = 502.6 |

-continued

| Example | Structure | Name | Analytical Data |
|---|---|---|---|
| 313 | 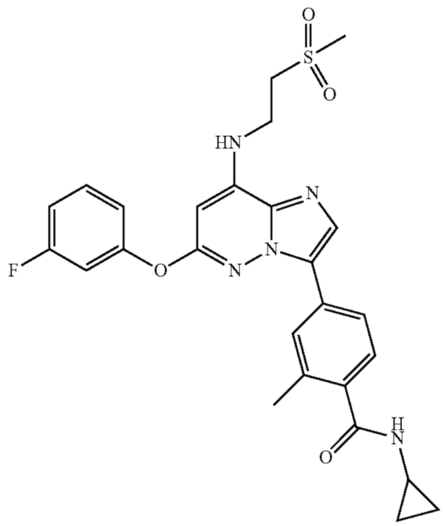 [SMILES: Cc1cc(-c2cnc3c(NCCS(C)(=O)=O)cc(Oc4cccc(F)c4)nn23)ccc1C(=O)NC1CC1] | N-cyclopropyl-4-[6-(3-fluorophenoxy)-8-{[2-(methylsulfonyl)ethyl]amino}imidazo[1,2-b]pyridazin-3-yl]-2-methyl-benzamide | RT = 1.12<br>$MW_{found}$ = 524.6<br>$MW_{calc}$ = 523.6 |
| 314 | 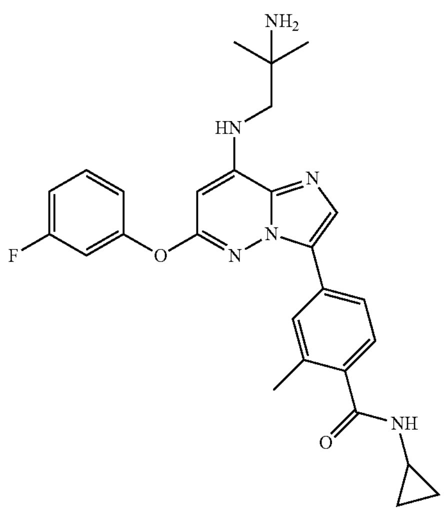 [SMILES: Cc1cc(-c2cnc3c(NCC(C)(C)N)cc(Oc4cccc(F)c4)nn23)ccc1C(=O)NC1CC1] | 4-{8-[(2-amino-2-methyl-propyl)amino]-6-(3-fluorophenoxy)imidazo[1,2-b]pyridazin-3-yl}-N-cyclopropyl-2-methyl-benzamide | $^1$H-NMR (DMSO-d6): δ = 0.47 (2H), 0.63 (2H), 1.25 (6H), 2.14 (3H), 2.76 (1H), 3.50 (2H), 6.31 (1H), 7.12 (2H), 7.17 (1H), 7.24 (1H), 7.48 (1H), 7.67 (1H), 7.77 (1H), 7.95 (1H), 8.24 (1H), 8.36 (1H) ppm<br>RT = 0.94<br>$MW_{found}$ = 489.6<br>$MW_{calc}$ = 488.6 |
| 315 | 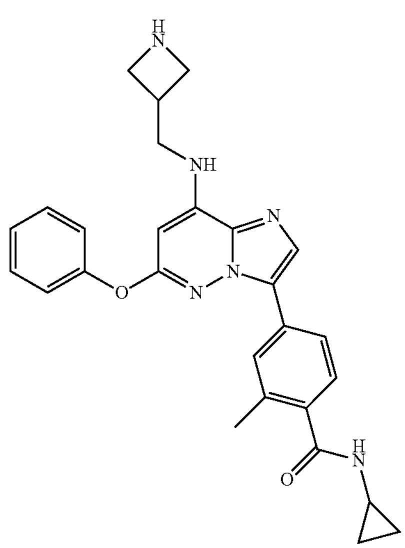 [SMILES: Cc1cc(-c2cnc3c(NCC4CNC4)cc(Oc4ccccc4)nn23)ccc1C(=O)NC1CC1] | 4-{8-[(azetidin-3-ylmethyl)amino]-6-phenoxy-imidazo[1,2-b]pyridazin-3-yl}-N-cyclopropyl-2-methylbenzamide | RT = 0.90<br>$MW_{found}$ = 469.6<br>$MW_{calc}$ = 468.6 |

| Example | Structure | Name | Analytical Data |
|---|---|---|---|
| 316 | 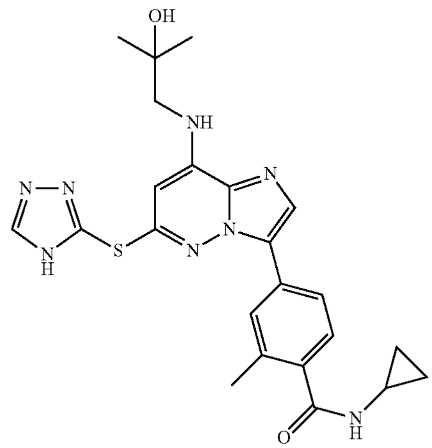 [SMILES: Cc1cc(-c2cnc3c(NCC(C)(C)O)cc(Sc4nnc[nH]4)nn23)ccc1C(=O)NC1CC1] | N-cyclopropyl-4-{8-[(2-hydroxy-2-methylpropyl)amino]-6-(4H-1,2,4-triazol-3-ylsulfanyl)imidazo[1,2-b]pyridazin-3-yl}-2-methylbenzamide | $^1$H-NMR (DMSO-d6): δ = 0.49 (2H), 0.65 (2H), 1.11 (6H), 2.28 (3H), 2.79 (1H), 3.21 (2H), 6.28 (1H), 7.06 (1H), 7.23 (1H), 7.41-7.59 (2H), 7.68 (2H), 7.95 (1H), 8.27 (1H), 8.82 (1H) ppm<br>RT = 0.85<br>MW$_{found}$ = 479.6<br>MW$_{calc}$ = 478.6 |
| 317 | 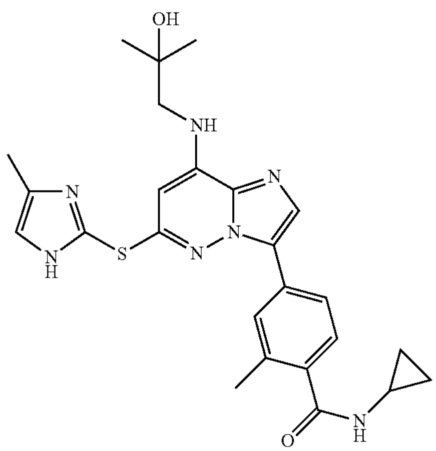 [SMILES: Cc1c[nH]c(Sc2cc(NCC(C)(C)O)c3ncc(-c4ccc(C(=O)NC5CC5)c(C)c4)n3n2)n1] | N-cyclopropyl-4-{8-[(2-hydroxy-2-methylpropyl)amino]-6-[(4-methyl-1H-imidazol-2-yl)sulfanyl]imidazo[1,2-b]pyridazin-3-yl}-2-methylbenzamide | RT = 0.71<br>MW$_{found}$ = 492.6<br>MW$_{calc}$ = 491.6 |
| 318 | 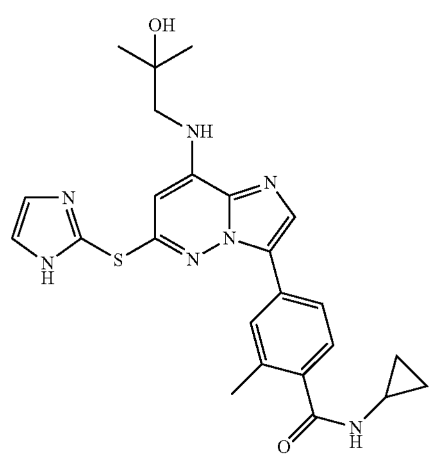 [SMILES: Cc1cc(-c2cnc3c(NCC(C)(C)O)cc(Sc4ncc[nH]4)nn23)ccc1C(=O)NC1CC1] | N-cyclopropyl-4-{8-[(2-hydroxy-2-methylpropyl)amino]-6-(1H-imidazol-2-ylsulfanyl)imidazo[1,2-b]pyridazin-3-yl}-2-methylbenzamide | $^1$H-NMR (DMSO-d6): δ = 0.50 (2H), 0.65 (2H), 1.11 (6H), 2.29 (3H), 2.79 (1H), 3.19 (2H), 6.13 (1H), 7.00 (1H), 7.20 (1H), 7.69 (1H), 7.74 (1H), 7.94 (1H), 8.10 (2H), 8.24 (1H) ppm<br>RT = 0.73<br>MW$_{found}$ = 478.6<br>MW$_{calc}$ = 477.6 |

| Example | Structure | Name | Analytical Data |
|---|---|---|---|
| 319 | 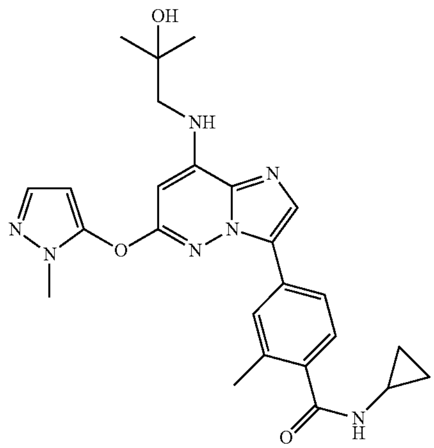 [SMILES: Cc1cc(-c2cnc3c(NCC(C)(C)O)cc(Oc4ccnn4C)nn23)ccc1C(=O)NC1CC1] | N-cyclopropyl-4-{8-[(2-hydroxy-2-methylpropyl)amino]-6-[(1-methyl-1H-pyrazol-5-yl)oxy]imidazo[1,2-b]pyridazin-3-yl}-2-methylbenzamide | RT = 0.97<br>$MW_{found} = 476.6$<br>$MW_{calc} = 475.6$ |
| 320 | 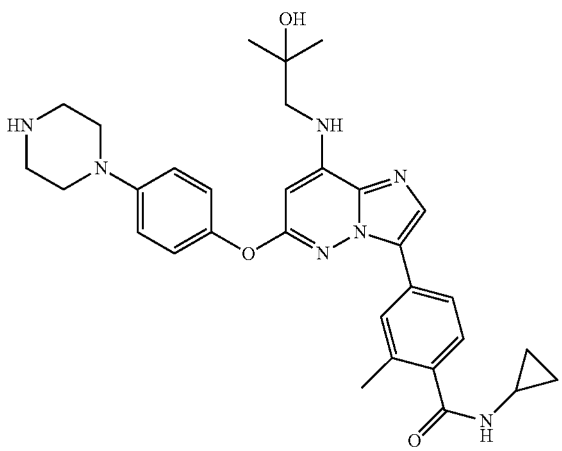 [SMILES: Cc1cc(-c2cnc3c(NCC(C)(C)O)cc(Oc4ccc(N5CCNCC5)cc4)nn23)ccc1C(=O)NC1CC1] | N-cyclopropyl-4-{8-[(2-hydroxy-2-methylpropyl)amino]-6-[4-(piperazin-1-yl)phenoxy]imidazo[1,2-b]pyridazin-3-yl}-2-methylbenzamide | RT = 0.81<br>$MW_{found} = 556.7$<br>$MW_{calc} = 555.7$ |
| 321 | 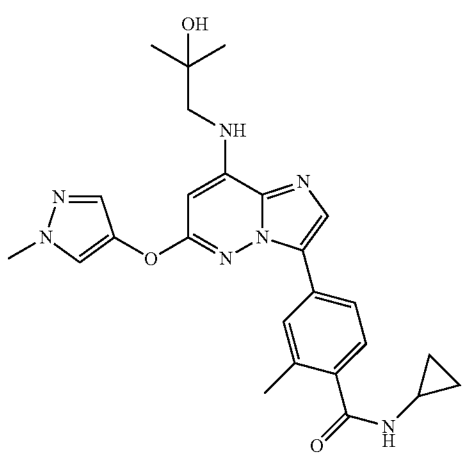 [SMILES: Cc1cc(-c2cnc3c(NCC(C)(C)O)cc(Oc4cnn(C)c4)nn23)ccc1C(=O)NC1CC1] | N-cyclopropyl-4-{8-[(2-hydroxy-2-methylpropyl)amino]-6-[(1-methyl-1H-pyrazol-4-yl)oxy]imidazo[1,2-b]pyridazin-3-yl}-2-methylbenzamide | $^1$H-NMR (DMSO-d6): δ = 0.55 (2H), 0.78 (2H), 1.30 (6H), 2.28 (3H), 2.82 (1H), 3.19 (2H), 3.75 (3H), 5.73 (1H), 6.36 (1H), 6.78 (1H), 7.18 (2H), 7.33 (2H), 7.44 (2H), 7.58 (1H), 8.06 (1H) ppm<br>RT = 0.96<br>$MW_{found} = 476.6$<br>$MW_{calc} = 475.6$ |

| Example | Structure | Name | Analytical Data |
|---|---|---|---|
| 322 | 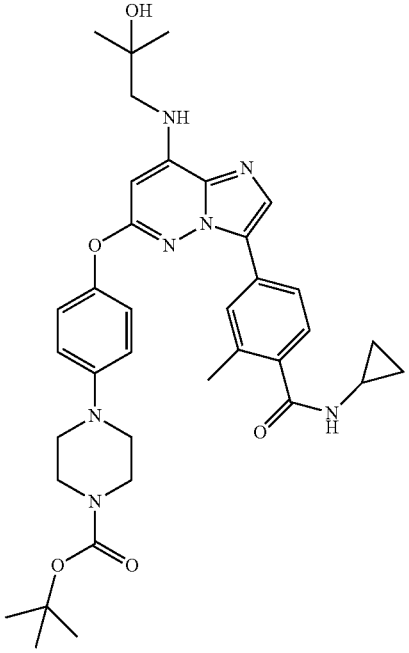 [SMILES: Cc1cc(-c2cnc3c(NCC(C)(C)O)cc(Oc4ccc(N5CCN(C(=O)OC(C)(C)C)CC5)cc4)nn23)ccc1C(=O)NC1CC1] | tert-butyl 4-[4-({3-[4-(cyclopropyl-carbamoyl)-3-methyl-phenyl]-8-[(2-hydroxy-2-methylpropyl)amino]imidazo[1,2-b]pyridazin-6-yl}oxy)phenyl]piperazine-1-carboxylate | RT = 1.36<br>$MW_{found}$ = 666.8<br>$MW_{calc}$ = 665.8 |
| 323 | 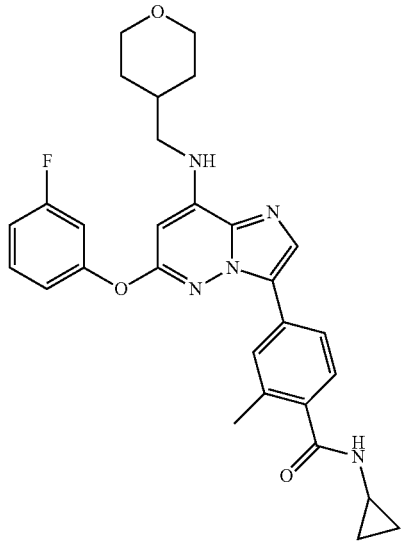 [SMILES: Cc1cc(-c2cnc3c(NCC4CCOCC4)cc(Oc4cccc(F)c4)nn23)ccc1C(=O)NC1CC1] | N-cyclopropyl-4-{6-(3-fluorophenoxy)-8-[(tetra-hydro-2H-pyran-4-yl-methyl)amino]imidazo[1,2-b]pyridazin-3-yl}-2-methylbenzamide | $^1$H-NMR (DMSO-d6): δ = 0.46 (2H), 0.64 (2H), 1.21 (2H), 1.60 (2H), 1.93 (1H), 2.14 (3H), 2.76 (1H), 3.23 (2H), 3.27 (2H), 3.82 (2H), 6.09 (1H), 7.07-7.19 (3H), 7.25 (1H), 7.47 (1H), 7.66 (1H), 7.73 (1H), 7.76 (1H), 7.91 (1H), 8.22 (1H) ppm<br>RT = 1.30<br>$MW_{found}$ = 516.9<br>$MW_{calc}$ = 515.9 |

-continued

| Example | Structure | Name | Analytical Data |
|---|---|---|---|
| 324 | 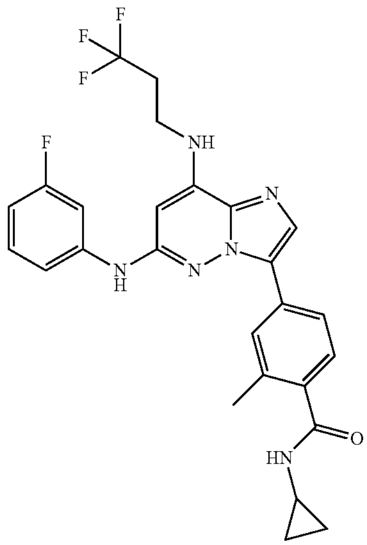 [SMILES: Cc1cc(-c2cnc3c(NCCC(F)(F)F)cc(Nc4cccc(F)c4)nn23)ccc1C(=O)NC1CC1] | N-cyclopropyl-4-{6-[(3-fluorophenyl)amino]-8-[(3,3,3-trifluoropropyl)amino]imidazo[1,2-b]pyridazin-3-yl}-2-methylbenzamide | $^1$H-NMR (DMSO-d6): δ = 0.49 (2H), 0.65 (2H), 2.35 (3H), 2.67 (2H), 2.80 (1H), 3.49 325(2H), 5.82 (1H), 6.70 (1H), 7.21-7.40 (4H), 7.72 (1H), 7.78 (1H), 7.82 (1H), 8.05 (1H), 8.30 (1H), 9.21 (1H) ppm<br>RT = 1.24<br>MW$_{found}$ = 513.5<br>MW$_{calc}$ = 512.5 |
| 325 | 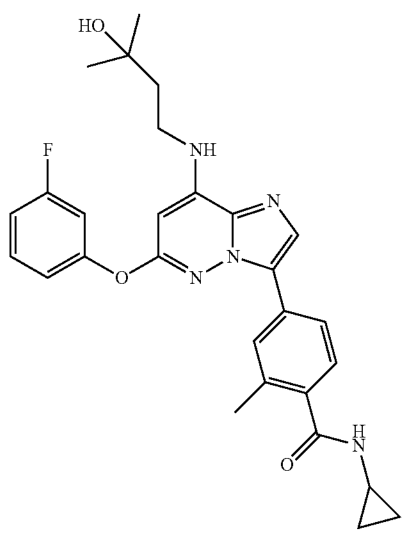 [SMILES: Cc1cc(-c2cnc3c(NCCC(C)(C)O)cc(Oc4cccc(F)c4)nn23)ccc1C(=O)NC1CC1] | N-cyclopropyl-4-{6-(3-fluorophenoxy)-8-[(3-hydroxy-3-methylbutyl)amino]imidazo[1,2-b]pyridazin-3-yl}-2-methylbenzamide | $^1$H-NMR (CDCl$_3$): δ = 0.60 (2H), 0.87 (2H), 1.35 (6H), 1.94 (2H), 2.31 (3H), 2.89 (1H), 3.50 (2H), 5.88 (2H), 6.72 (1H), 6.93-7.09 (3H), 7.23 (1H), 7.36 (1H), 7.60 (1H), 7.70 (2H) ppm<br>RT = 1.25<br>MW$_{found}$ = 504.6<br>MW$_{calc}$ = 505.6 |
| 326 | 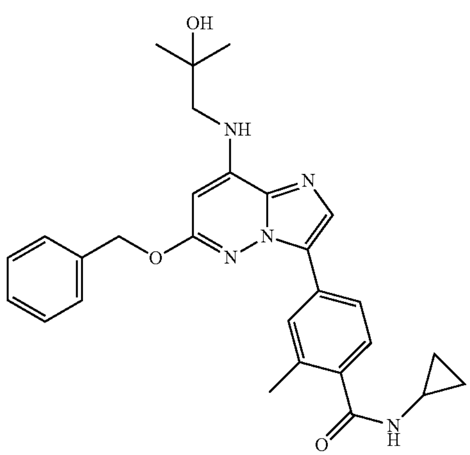 [SMILES: Cc1cc(-c2cnc3c(NCC(C)(C)O)cc(OCc4ccccc4)nn23)ccc1C(=O)NC1CC1] | 4-{6-(benzyloxy)-8-[(2-hydroxy-2-methylpropyl)amino]imidazo[1,2-b]pyridazin-3-yl}-N-cyclopropyl-2-methylbenzamide | 1H-NMR (CDCl3): δ = 0.63 (2H), 0.88 (2H), 1.39 (2H), 2.50 (3H), 2.93 (1H), 3.27 (2H), 5.35 (2H), 5.78 (1H), 5.95 (1H), 6.33 (1H), 7.32-7.51 (6H), 7.63 (1H), 7.84 (2H) ppm<br>RT = 1.19<br>MW$_{found}$ = 486.6<br>MW$_{calc}$ = 485.6 |

| Example | Structure | Name | Analytical Data |
|---|---|---|---|
| 327 | 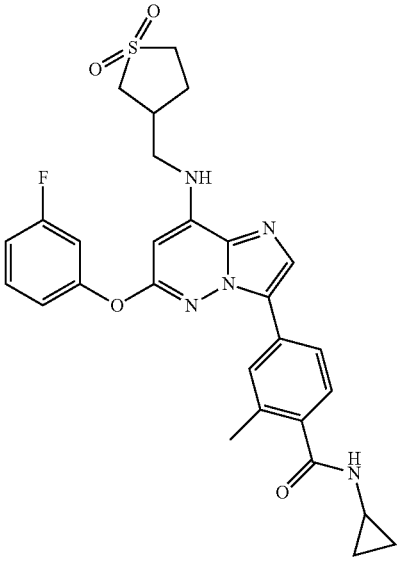 [SMILES: Cc1cc(-c2cnc3c(NCC4CCS(=O)(=O)C4)cc(Oc4cccc(F)c4)nn23)ccc1C(=O)NC1CC1] | N-cyclopropyl-4-[8-{[(1,1-dioxidotetrahydro-thiophen-3-yl)methyl]amino}-6-(3-fluorophenoxy)imidazo[1,2-b]pyridazin-3-yl]-2-methylbenzamide | RT = 1.16<br>MW$_{found}$ = 550.6<br>MW$_{calc}$ = 549.6 |
| 328 | 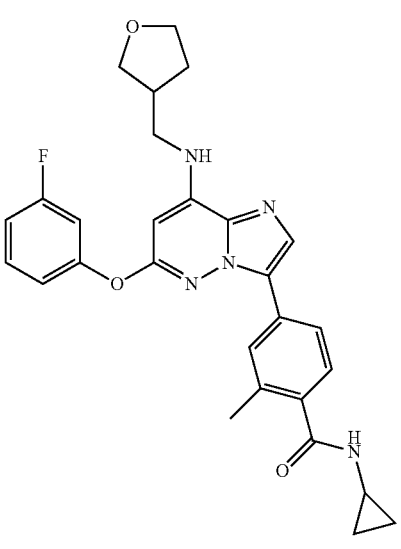 [SMILES: Cc1cc(-c2cnc3c(NCC4CCOC4)cc(Oc4cccc(F)c4)nn23)ccc1C(=O)NC1CC1] | N-cyclopropyl-4-{6-(3-fluorophenoxy)-8-[(tetrahydrofuran-3-ylmethyl)amino]imidazo[1,2-b]pyridazin-3-yl}-2-methylbenzamide | $^1$H-NMR (CDCl$_3$): δ = 0.61 (2H), 0.88 (2H), 1.69 (1H), 2.12 (1H), 2.32 (3H), 2.68 (1H), 2.90 (1H), 3.32 (2H), 3.72-4.00 (4H), ppm<br>RT = 1.25<br>MW$_{found}$ = 502.6<br>MW$_{calc}$ = 501.6 |

| Example | Structure | Name | Analytical Data |
|---|---|---|---|
| 329 | 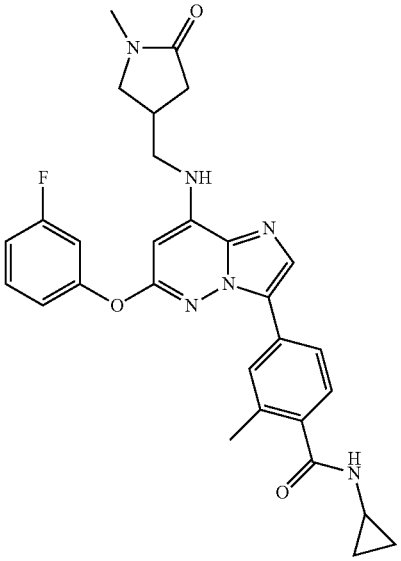 [SMILES: Cc1cc(-c2cnc3c(NCC4CC(=O)N(C)C4)cc(Oc4cccc(F)c4)nn23)ccc1C(=O)NC1CC1] | N-cyclopropyl-4-[6-(3-fluorophenoxy)-8-{[(1-methyl-5-oxopyrrolidin-3-yl)methyl]amino}imidazo[1,2-b]pyridazin-3-yl]-2-methylbenzamide | RT = 1.12<br>$MW_{found}$ = 529.6<br>$MW_{calc}$ = 528.6 |
| 330 | 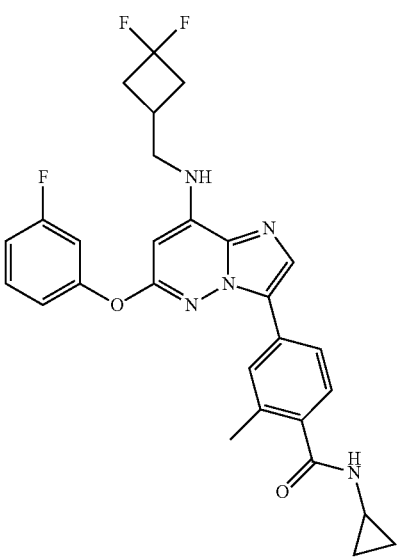 [SMILES: Cc1cc(-c2cnc3c(NCC4CC(F)(F)C4)cc(Oc4cccc(F)c4)nn23)ccc1C(=O)NC1CC1] | N-cyclopropyl-4-[8-{[(3,3-difluorocyclobutyl)methyl]amino}-6-(3-fluorophenoxy)imidazo[1,2-b]pyridazin-3-yl]-2-methylbenzamide | $^1$H-NMR (CDCl$_3$): δ = 0.60 (2H), 0.88 (2H), 2.33 (3H), 2.39 (2H), 2.61 (1H), 2.71-2.95 (3H), 3.48 (2H), 5.87 (1H), 5.91 (1H), 6.27 (1H), 6.97-7.07 (3H), 7.25 (1H), 7.38 (1H), 7.60 (1H), 7.72 (2H) ppm<br>RT = 1.38<br>$MW_{found}$ = 522.6<br>$MW_{calc}$ = 521.6 |

-continued

| Example | Structure | Name | Analytical Data |
|---|---|---|---|
| 331 | 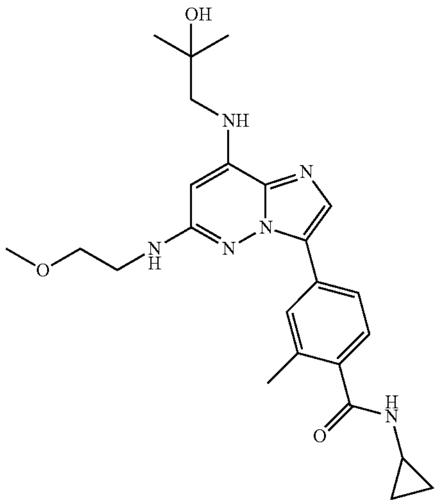 [SMILES: COCCNc1cc(NCC(C)(C)O)c2ncc(-c3ccc(C(=O)NC4CC4)c(C)c3)n2n1] | N-cyclopropyl-4-{8-[(2-hydroxy-2-methylpropyl)amino]-6-[(2-methoxyethyl)amino]imidazo[1,2-b]pyridazin-3-yl}-2-methylbenzamide | 1H-NMR (DMSO-d6): δ = 0.52 (2H), 0.77 (2H, (2H), 1.28 (6H), 2.38 (3H), 2.81 (1H), 3.11 (2H), 3.28 (3H), 3.41 (2H), 3.51 (2H), 5.37 (1H), 5.92 (1H), 6.28 (1H), 7.15 (2H), 7.26 (1H), 7.44 (1H), 7.77 (1H), 7.80 (1H) ppm<br>RT = 0.83<br>MWfound = 453.6<br>MWcalc = 452.6 |
| 332 | 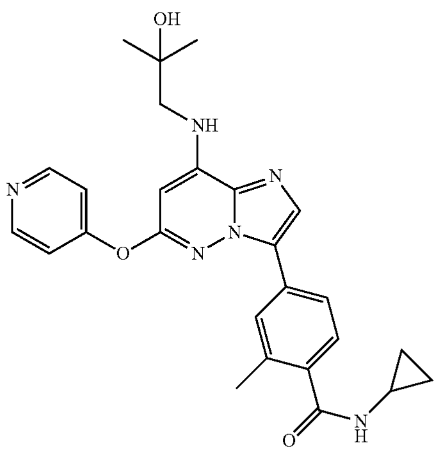 [SMILES: Cc1cc(-c2cnc3c(NCC(C)(C)O)cc(Oc4ccncc4)nn23)ccc1C(=O)NC1CC1] | N-cyclopropyl-4-{8-[(2-hydroxy-2-methylpropyl)amino]-6-(pyridin-4-yloxy)imidazo[1,2-b]pyridazin-3-yl}-2-methylbenzamide | $^1$H-NMR (DMSO-d6): δ = 0.56 (2H), 0.70 (2H), 1.22 (6H), 2.42 (3H), 2.85 (1H), 3.41 (2H), 4.82 (1H), 6.32 (2H), 6.69 (1H), 7.40 (1H), 7.42 (1H), 7.93 (1H), 8.01 (1H), 8.05 (1H), 8.32 (2H), 8.34 (1H) ppm<br>RT = 0.82<br>MW$_{found}$ = 473.6<br>MW$_{calc}$ = 472.6 |
| 333 | 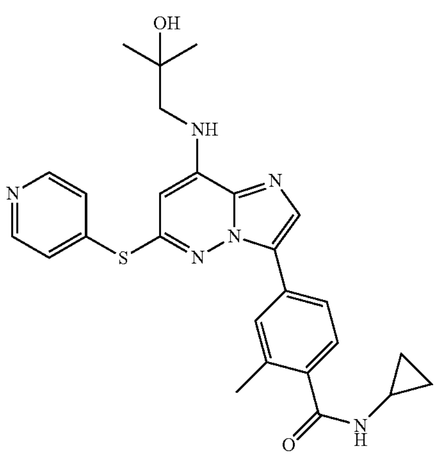 [SMILES: Cc1cc(-c2cnc3c(NCC(C)(C)O)cc(Sc4ccncc4)nn23)ccc1C(=O)NC1CC1] | N-cyclopropl-4-{8-[(2-hydroxy-2-methylpropyl)amino]-6-(pyridin-4-ylsulfanyl)imidazo[1,2-b]pyridazin-3-yl}-2-methyl-benzamide | RT = 87<br>MW$_{found}$ = 489.6<br>MW$_{calc}$ = 488.6 |

| Example | Structure | Name | Analytical Data |
|---|---|---|---|
| 334 | 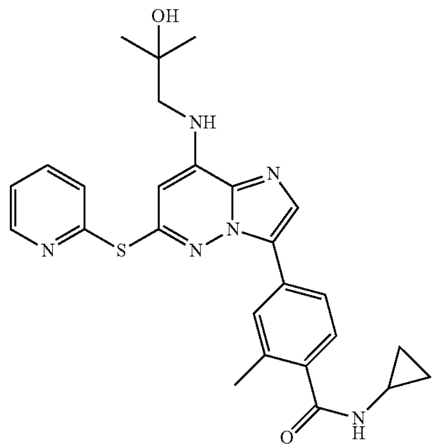 [SMILES: Cc1cc(-c2cnc3c(NCC(C)(C)O)cc(Sc4ccccn4)nn23)ccc1C(=O)NC1CC1] | N-cyclopropyl-4-{8-[(2-hydroxy-2-methylpropyl)amino]-6-(pyridin-2-ylsulfanyl)imidazo[1,2-b]pyridazin-3-yl}-2-methylbenzamide | RT = 1.05<br>MW$_{found}$ = 489.6<br>MW$_{calc}$ = 488.6 |
| 335 | 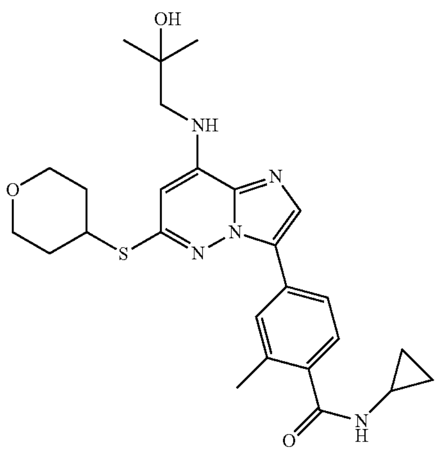 [SMILES: Cc1cc(-c2cnc3c(NCC(C)(C)O)cc(SC4CCOCC4)nn23)ccc1C(=O)NC1CC1] | N-cyclopropyl-4-{8-[(2-hydroxy-2-methylpropyl)amino]-6-(tetrahydro-2H-pyran-4-ylsulfanyl)imidazo[1,2-b]pyridazin-3-yl}-2-methylbenzamide | 1H-NMR (DMSO-d6): δ = 0.51 (2H), 0.65 (2H), 1.13 (6H), 1.65 (2H), 2.06 (2H), 2.38 (3H), 2.81 (1H), 3.22 (2H), 3.47 (2H), 3.97 (2H), 4.71 (1H), 6.14 (1H), 6.84 (1H)7.35 (1H), 7.92 (2H), 7.97 (1H), 8.28 (1H) ppm<br>RT = 1.09<br>MWfound = 496.7<br>MWcalc = 495.7 |
| 336 | 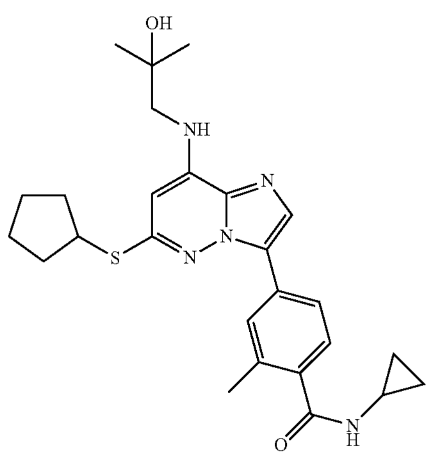 [SMILES: Cc1cc(-c2cnc3c(NCC(C)(C)O)cc(SC4CCCC4)nn23)ccc1C(=O)NC1CC1] | 4-{6-(cyclopentylsulfanyl)-8-[(2-hydroxy-2-methylpropyl)amino]imidazo[1,2-b]pyridazin-3-yl}-N-cyclopropyl-2-methylbenzamide | 1H-NMR (DMSO-d6): δ = 0.50 (2H), 0.65 (2H), 1.13 (6H), 1.52-1.76 (6H), 2.20 (2H), 2.35 (3H), 2.80 (1H), 3.21 (2H), 4.00 (1H), 4.71 (1H), 6.13 (1H), 6.78 (1H), 7.33 (1H), 7.90 (1H), 7.95 (1H), 8.05 (1H), 8.28 (1H) ppm<br>RT = 1.31<br>MWfound = 480.7<br>MWcalc = 479.7 |

| Example | Structure | Name | Analytical Data |
|---|---|---|---|
| 337 | 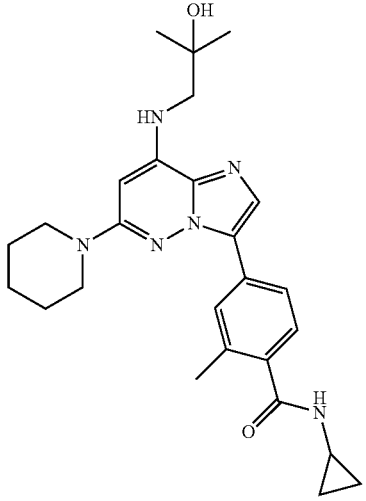 [SMILES: Cc1cc(-c2cnc3c(NCC(C)(C)O)cc(N4CCCCC4)nn23)ccc1C(=O)NC1CC1] | N-cyclopropyl-4-{8-[(2-hydroxy-2-methylpropyl)amino]-6-(piperidin-1-yl)imidazo[1,2-b]pyridazin-3-yl}-2-methyl-benzamide | 1H-NMR (DMSO-d6): δ = 0.50 (2H), 0.65 (2H), 1.15 (6H), 1.58 (6H), 2.27 (4H), 2.35 (3H), 2.78 (1H), 3.23 (2H), 4.75 (1H), 6.07 (1H), 6.40 (1H), 7.33 (1H), 7.86 (1H), 7.98 (1H), 8.03 (1H), 8.27 (1H) ppm<br>RT = 1.08<br>MWfound = 463.6<br>MWcalc = 462.6 |

The following compound examples were prepared analogously to the procedure described for example 101 using the appropriate intermediate and the appropriate boronic acid building block [LC-MS data such as retention time (RT in min) or observed mass peak were collected using LC-MS Method A unless explicitly stated]:

| Example | Structure | Name | Analytical Data |
|---|---|---|---|
| 338 | 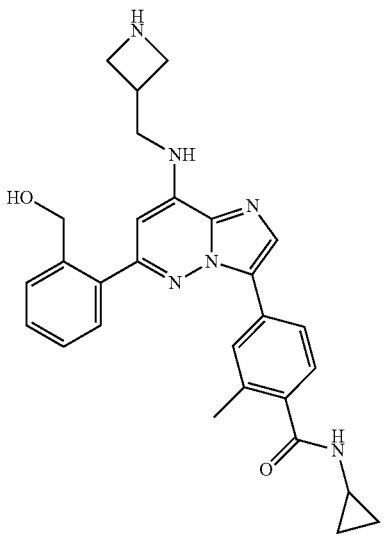 [SMILES: Cc1cc(-c2cnc3c(NCC4CNC4)cc(-c4ccccc4CO)nn23)ccc1C(=O)NC1CC1] | 4-{8-[(azetidin-3-ylmethyl)amino]-6-[2-(hydroxymethyl)phenyl]imidazo[1,2-b]pyridazin-3-yl}-N-cyclopropyl-2-methylbenzamide | RT = 0.77<br>MWfound = 483.6<br>MWcalc = 482.6 |

-continued
| Example | Structure | Name | Analytical Data |
|---|---|---|---|
| 339 | 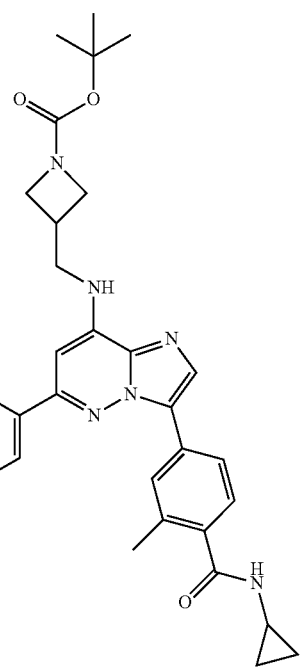 | tert-butyl 3-[({3-[4-(cyclopropylcarbamoyl)-3-methylphenyl]-6-[2-(hydroxymethyl)phenyl]imidazo[1,2-b]pyridazin-8-yl}amino)methyl]azetidine-1-carboxylate | RT = 1.24 MWfound = 583.7 MWcalc = 582.7 |
| 340 | 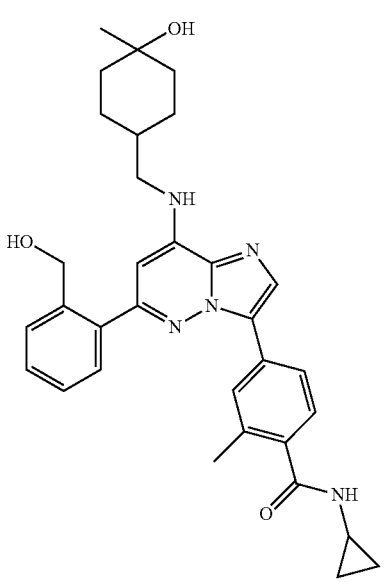 [SMILES: Cc1cc(-c2cnc3c(NCC4CCC(C)(O)CC4)cc(-c4ccccc4CO)nn23)ccc1C(=O)NC1CC1] | N-cyclopropyl-4-(8-{[(4-hydroxy-4-methylcyclohexyl)methyl]amino}-6-[2-(hydroxymethyl)phenyl]imidazo[1,2-b]pyridazin-3-yl)-2-methylbenzamide | RT = 1.13 MWfound = 540.7 MWcalc = 539.7 |

| Example | Structure | Name | Analytical Data |
|---|---|---|---|
| 341 | 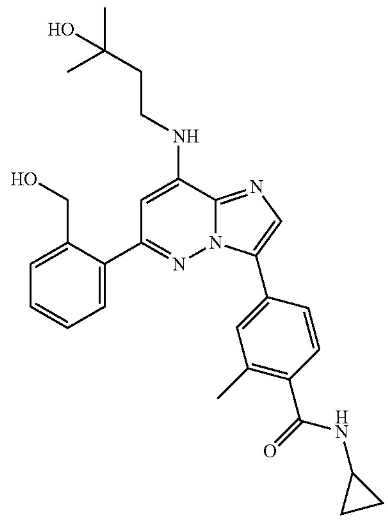 [SMILES: Cc1cc(-c2cnc3c(NCCC(C)(C)O)cc(-c4ccccc4CO)nn23)ccc1C(=O)NC1CC1] | N-cyclopropyl-4-{8-[(3-hydroxy-3-methylbutyl)amino]-6-[2-(hydroxymethyl)phenyl]imidazo[1,2-b]pyridazin-3-yl}-2-methylbenzamide | RT = 1.05<br>MWfound = 500.6<br>MWcalc = 499.6 |
| 342 | 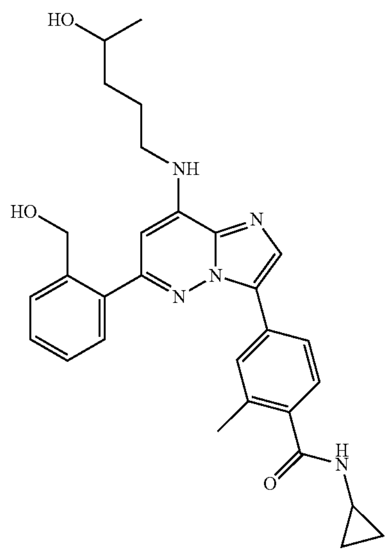 [SMILES: Cc1cc(-c2cnc3c(NCCCC(C)O)cc(-c4ccccc4CO)nn23)ccc1C(=O)NC1CC1] | (RS)-N-cyclopropyl-4-{6-[2-(hydroxymethyl)phenyl]-8-[(4-hydroxypentyl)amino]imidazo[1,2-b]pyridazin-3-yl}-2-methylbenzamide | RT = 1.03<br>MWfound = 500.6<br>MWcalc = 499.6 |
| 343 | 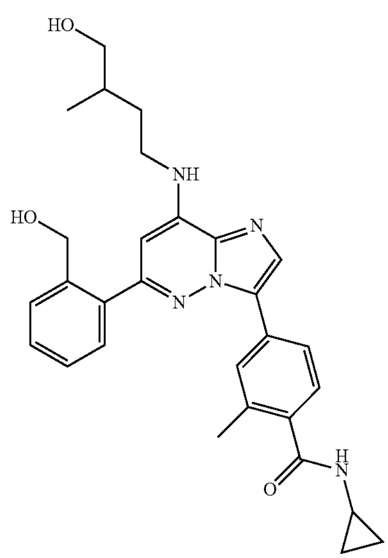 [SMILES: Cc1cc(-c2cnc3c(NCCC(C)CO)cc(-c4ccccc4CO)nn23)ccc1C(=O)NC1CC1] | (RS)-N-cyclopropyl-4-{8-[(4-hydroxy-3-methylbutyl)amino]-6-[2-(hydroxymethyl)phenyl]imidazo[1,2-b]pyridazin-3-yl}-2-methylbenzamide | RT = 1.04<br>MWfound = 500.6<br>MWcalc = 499.6 |

| Example | Structure | Name | Analytical Data |
|---|---|---|---|
| 344 | 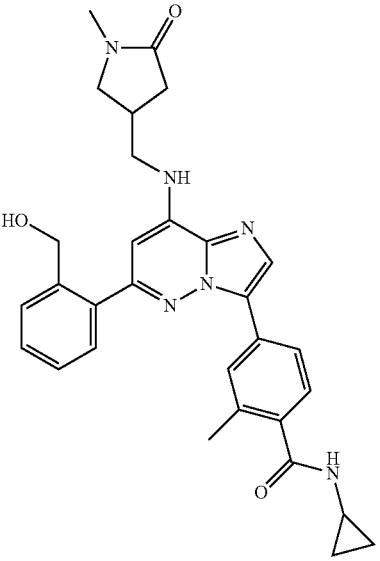 [SMILES: Cc1cc(-c2cnc3c(NCC4CC(=O)N(C)C4)cc(-c4ccccc4CO)nn23)ccc1C(=O)NC1CC1] | N-cyclopropyl-4-(6-[2-(hydroxy-methyl)phenyl]-8-{[(1-methyl-5-oxo-pyrrolidin-3-yl)methyl]amino}imidazo[1,2-b]pyridazin-3-yl)-2-methyl-benzamide | RT = 0.95 MWfound = 525.6 MWcalc = 524.6 |
| 345 | 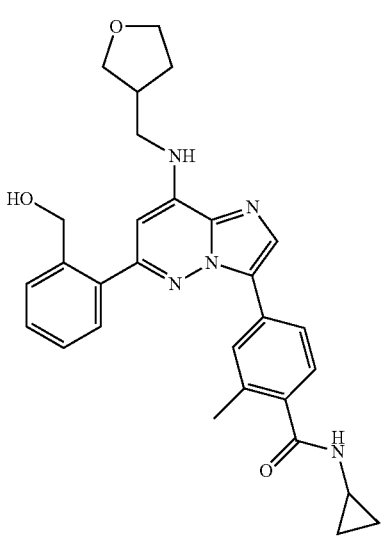 [SMILES: Cc1cc(-c2cnc3c(NCC4CCOC4)cc(-c4ccccc4CO)nn23)ccc1C(=O)NC1CC1] | (RS)-N-cyclopropyl-4-{6-[2-(hydroxy-methyl)phenyl]-8-[(tetrahydro-furan-3-ylmethyl)amino]imidazo[1,2-b]pyridazin-3-yl}-2-methyl-benzamide | RT = 1.06 MWfound = 498.6 MWcalc = 497.6 |

| Example | Structure | Name | Analytical Data |
|---|---|---|---|
| 346 | 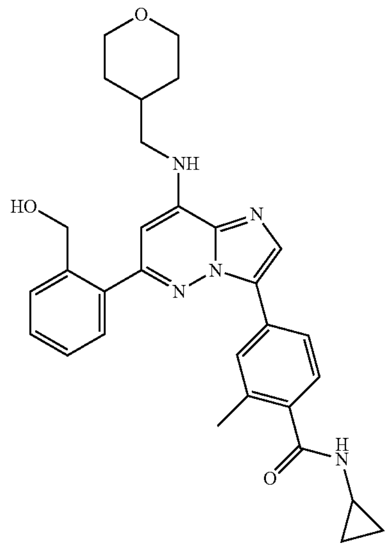 [SMILES: Cc1cc(-c2cnc3c(NCC4CCOCC4)cc(-c4ccccc4CO)nn23)ccc1C(=O)NC1CC1] | N-cyclopropyl-4-{6-[2-(hydroxy-methyl)phenyl]-8-[(tetrahydro-2H-pyran-4-ylmethyl)amino]imidazo[1,2-b]pyridazin-3-yl}-2-methyl-benzamide | 1H-NMR (DMSO-d6): δ = 0.59 (2H), 0.86 (2H), 1.44 (2H), 1.78 (2H), 2.02 (1H), 2.47 (3H), 2.89 (1H), 3.31 (2H), 3.41 (2H), 4.02 (2H), 4.40 (2H), 6.17 (1H), 6.22 (1H), 6.38 (1H), 7.26 (2H), 7.38 (1H), 7.48 (2H), 7.60 (2H), 7.69 (2H) ppm RT = 1.09 MWfound = 512.6 MWcalc = 511.6 |
| 347 | 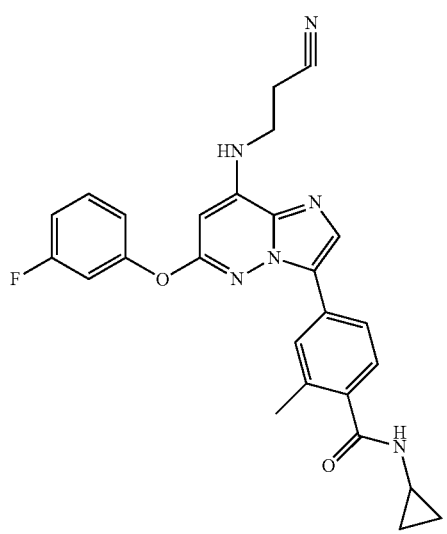 [SMILES: Cc1cc(-c2cnc3c(NCCC#N)cc(Oc4cccc(F)c4)nn23)ccc1C(=O)NC1CC1] | 4-{8-[(2-cyanoethyl)amino]-6-(3-fluorophenoxy)imidazo[1,2-b]pyridazin-3-yl}-N-cyclopropyl-2-methylbenzamide | RT = 1.18 MW$_{found}$ = 471.5 MW$_{calc}$ = 470.5 $^1$H-NMR (DMSO-d6): δ = 0.47 (2H), 0.63 (2H), 2.14 (3H), 2.76 (1H), 2.86 (2H), 3.65 (2H), 6.26 (1H), 7.07-7.20 (3H), 7.25 (1H), 7.49 (1H), 7.67 (1H), 7.76 (1H), 7.87 (1H), 7.94 (1H), 8.22 (1H) ppm. |

469
Example 348

4-{6-[(4-chloro-2-fluorophenyl)amino]-8-[(2-hydroxy-2-methylpropyl)amino]imidazo[1,2-b]pyridazin-3-yl}-N-cyclopropyl-2-methylbenzamide

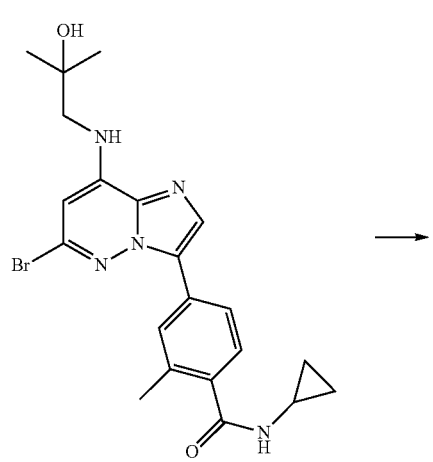

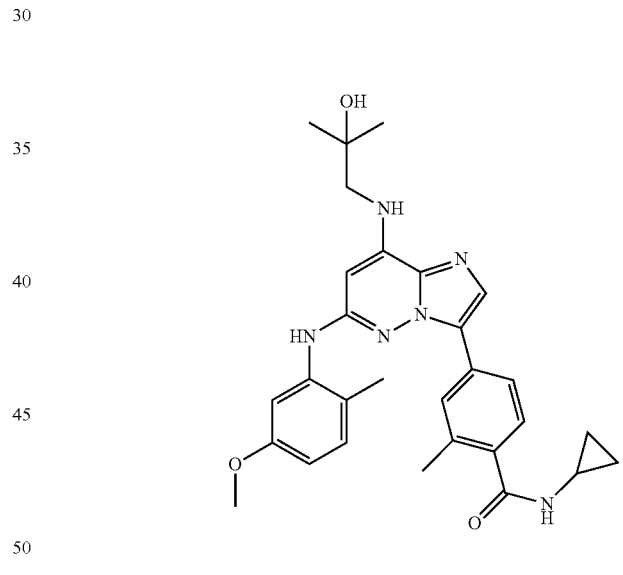

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-chloro-2-fluoroaniline to give after working up and purification 3.1 mg (3%) of the title compound.

¹H-NMR (DMSO-d6): δ=0.50 (2H), 0.65 (2H), 1.18 (6H), 2.31 (3H), 2.79 (1H), 3.16 (2H), 4.79 (1H), 6.15 (1H), 6.59 (1H), 7.19 (1H), 7.31 (1H), 7.43 (1H), 7.77 (1H), 7.79 (1H), 7.95 (1H), 8.15 (1H), 8.27 (1H), 8.63 (1H) ppm.

470
Example 349

N-cyclopropyl-4-{8-[(2-hydroxy-2-methylpropyl)amino]-6-[(5-methoxy-2-methylphenyl)amino]imidazo[1,2-b]pyridazin-3-yl}-2-methylbenzamide

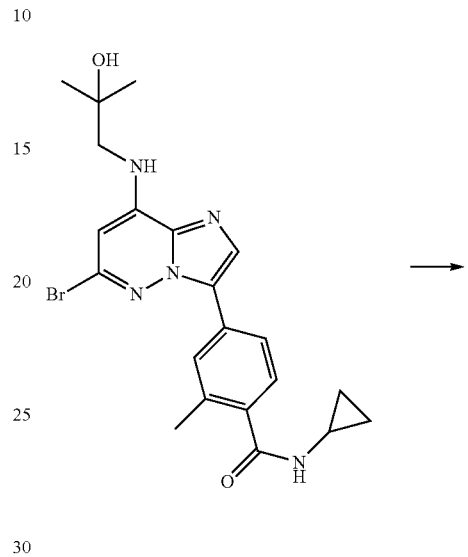

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 5-methoxy-2-methylaniline to give after working up and purification 9.1 mg (10%) of the title compound.

¹H-NMR (DMSO-d6): δ=0.48 (2H), 0.64 (2H), 1.18 (6H), 2.17 (3H), 2.22 (3H), 2.78 (1H), 3.16 (2H), 3.62 (3H), 4.81 (1H), 6.04 (1H), 6.43 (1H), 6.56 (1H), 7.08 (1H), 7.20 (1H), 7.34 (1H), 7.80 (1H), 7.85 (1H), 7.88 (1H), 8.02 (1H), 8.23 (1H) ppm.

Example 350

N-cyclopropyl-4-{6-[4-fluoro-2-(hydroxymethyl)phenyl]-8-[(3,3,3-trifluoropropyl)amino]imidazo[1,2-b]pyridazin-3-yl}-2-methylbenzamide

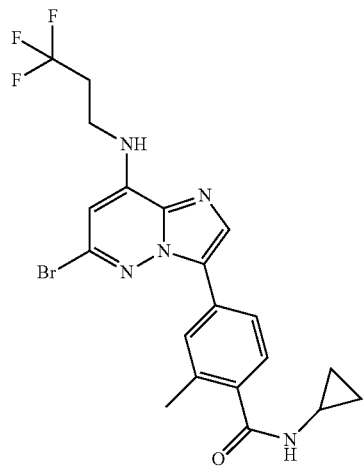

→

Example 351

N-cyclopropyl-4-{6-[(3,5-difluorophenyl)amino]-8-[(2-hydroxy-2-methylpropyl)amino]imidazo[1,2-b]pyridazin-3-yl}-2-methylbenzamide

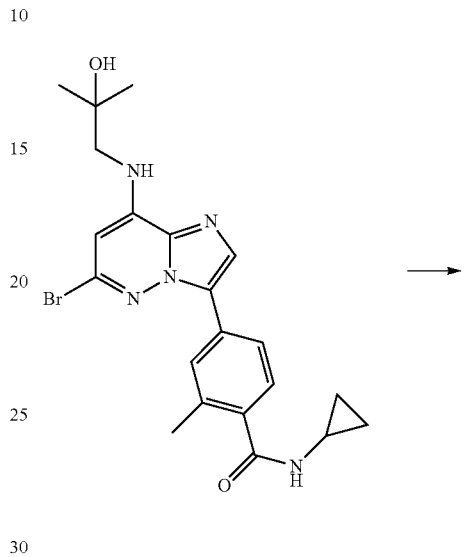

→

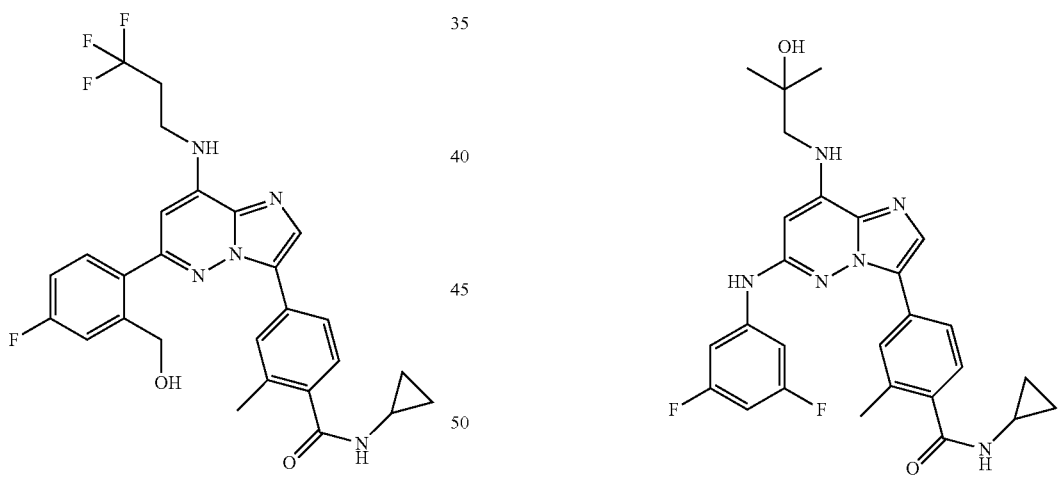

50 mg (104 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 1 using [4-fluoro-2-(hydroxymethyl)phenyl]boronic acid to give after working up and purification 10.4 mg (18%) of the title compound.

$^1$H-NMR (DMSO-d6): δ=0.48 (2H), 0.64 (2H), 2.34 (3H), 2.67 (2H), 2.79 (1H), 3.61 (2H), 4.65 (2H), 5.34 (1H), 6.36 (1H), 7.20 (1H), 7.33 (1H), 7.41 (1H), 7.59 (1H), 7.67 (1H), 7.91 (1H), 7.95 (1H), 8.01 (1H), 8.27 (1H) ppm.

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3,5-difluoroaniline to give after working up and purification 4.9 mg (6%) of the title compound.

$^1$H-NMR (DMSO-d6): δ=0.50 (2H), 0.66 (2H), 1.18 (6H), 2.35 (3H), 2.81 (1H), 3.17 (2H), 4.80 (1H), 5.87 (1H), 6.67 (1H), 6.73 (1H), 7.30-7.39 (3H), 7.77 (1H), 7.79 (1H), 8.01 (1H), 8.31 (1H), 9.40 (1H) ppm.

473
Example 352

N-cyclopropyl-4-{6-[(2,3-difluorophenyl)amino]-8-[(2-hydroxy-2-methylpropyl)amino]imidazo[1,2-b]pyridazin-3-yl}-2-methylbenzamide

474
Example 353

N-cyclopropyl-4-{6-[(3-fluoro-4-methoxyphenyl)amino]-8-[(2-hydroxy-2-methylpropyl)amino]imidazo[1,2-b]pyridazin-3-yl}-2-methylbenzamide

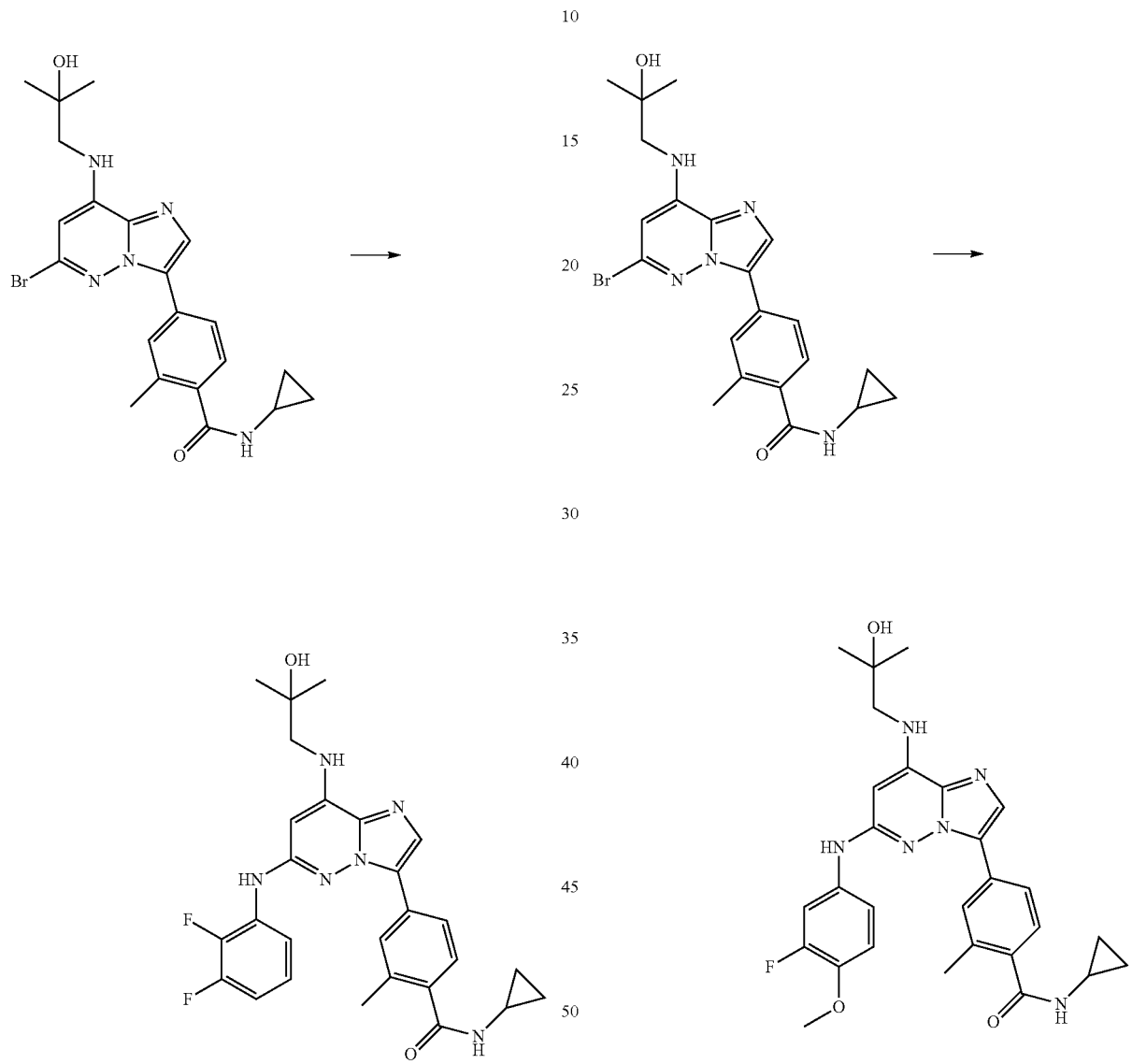

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2,3-difluoroaniline to give after working up and purification 4.3 mg (5%) of the title compound.

$^1$H-NMR (DMSO-d6): δ=0.49 (2H), 0.65 (2H), 1.18 (6H), 2.30 (3H), 2.79 (1H), 3.17 (2H), 4.80 (1H), 6.16 (1H), 6.62 (1H), 7.02 (1H), 7.12 (1H), 7.28 (1H), 7.80 (2H), 7.92 (1H), 8.00 (1H), 8.27 (1H), 8.77 (1H) ppm.

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3-fluoro-4-methoxyaniline to give after working up and purification 16.8 mg (19%) of the title compound.

$^1$H-NMR (DMSO-d6): δ=0.50 (2H), 0.66 (2H), 1.18 (6H), 2.35 (3H), 2.81 (1H), 3.15 (2H), 3.77 (3H), 4.80 (1H), 5.82 (1H), 6.55 (1H), 7.06 (1H), 7.21 (1H), 7.32 (1H), 7.70 (1H), 7.75 (1H), 7.83 (1H), 8.04 (1H), 8.29 (1H), 8.91 (1H) ppm.

475

Example 354

N-cyclopropyl-4-{8-[(2-hydroxy-2-methylpropyl)amino]-6-[(4-methoxyphenyl)amino]imidazo[1,2-b]pyridazin-3-yl}-2-methylbenzamide

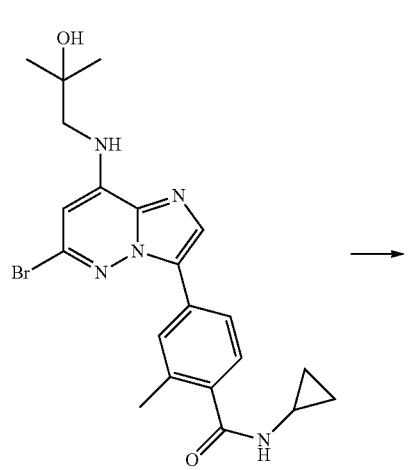

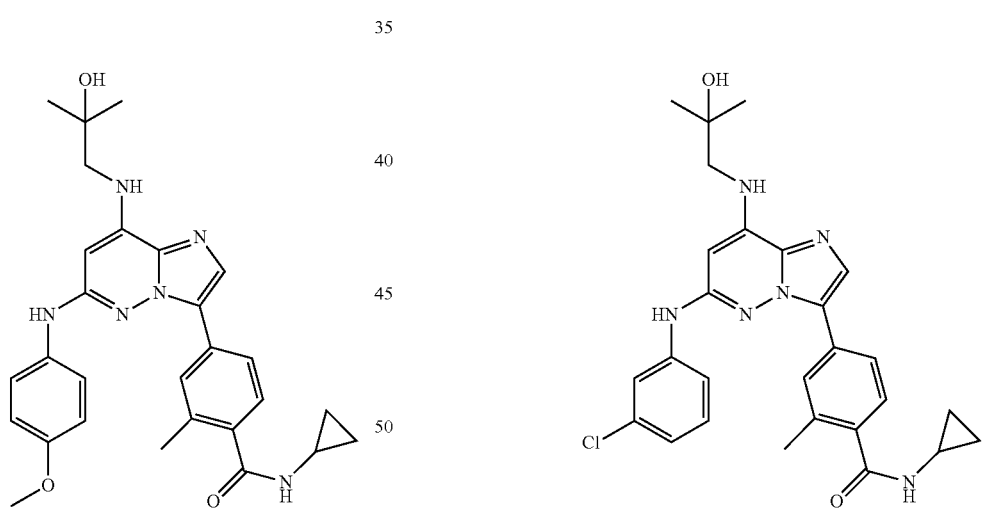

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-methoxyaniline to give after working up and purification 11.4 mg (13%) of the title compound.

$^1$H-NMR (DMSO-d6): δ=0.51 (2H), 0.66 (2H), 1.18 (6H), 2.37 (3H), 2.81 (1H), 3.14 (2H), 3.70 (3H), 4.80 (1H), 5.83 (1H), 6.46 (1H), 6.86 (2H), 7.33 (1H), 7.55 (2H), 7.75 (1H), 7.85 (1H), 8.10 (1H), 8.29 (1H), 8.71 (1H) ppm.

476

Example 355

4-{6-[(3-chlorophenyl)amino]-8-[(2-hydroxy-2-methylpropyl)amino]imidazo[1,2-b]pyridazin-3-yl}-N-cyclopropyl-2-methylbenzamide

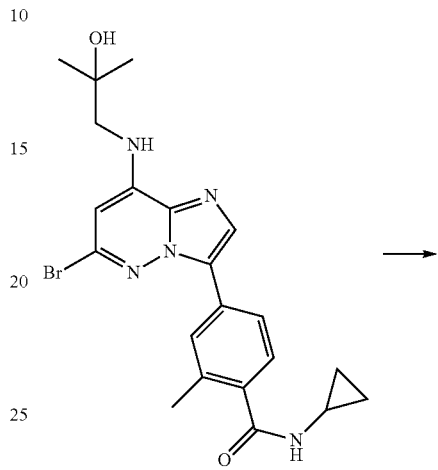

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3-chloroaniline to give after working up and purification 15.4 mg (18%) of the title compound.

$^1$H-NMR (DMSO-d6): δ=0.50 (2H), 0.66 (2H), 1.18 (6H), 2.36 (3H), 2.81 (1H), 3.16 (2H), 4.80 (1H), 5.88 (1H), 6.64 (1H), 6.92 (1H), 7.27 (1H), 7.36 (1H), 7.71 (1H), 7.58 (1H), 7.83 (1H), 7.93 (1H), 7.95 (1H), 8.28 (1H), 9.15 (1H) ppm.

477
Example 356

N-cyclopropyl-4-{6-[(2,4-difluorophenyl)amino]-8-[(2-hydroxy-2-methylpropyl)amino]imidazo[1,2-b]pyridazin-3-yl}-2-methylbenzamide

478
Example 357

N-cyclopropyl-4-{8-[(2-hydroxy-2-methylpropyl)amino]-6-(pyridin-2-ylamino) imidazo[1,2-b]pyridazin-3-yl}-2-methylbenzamide

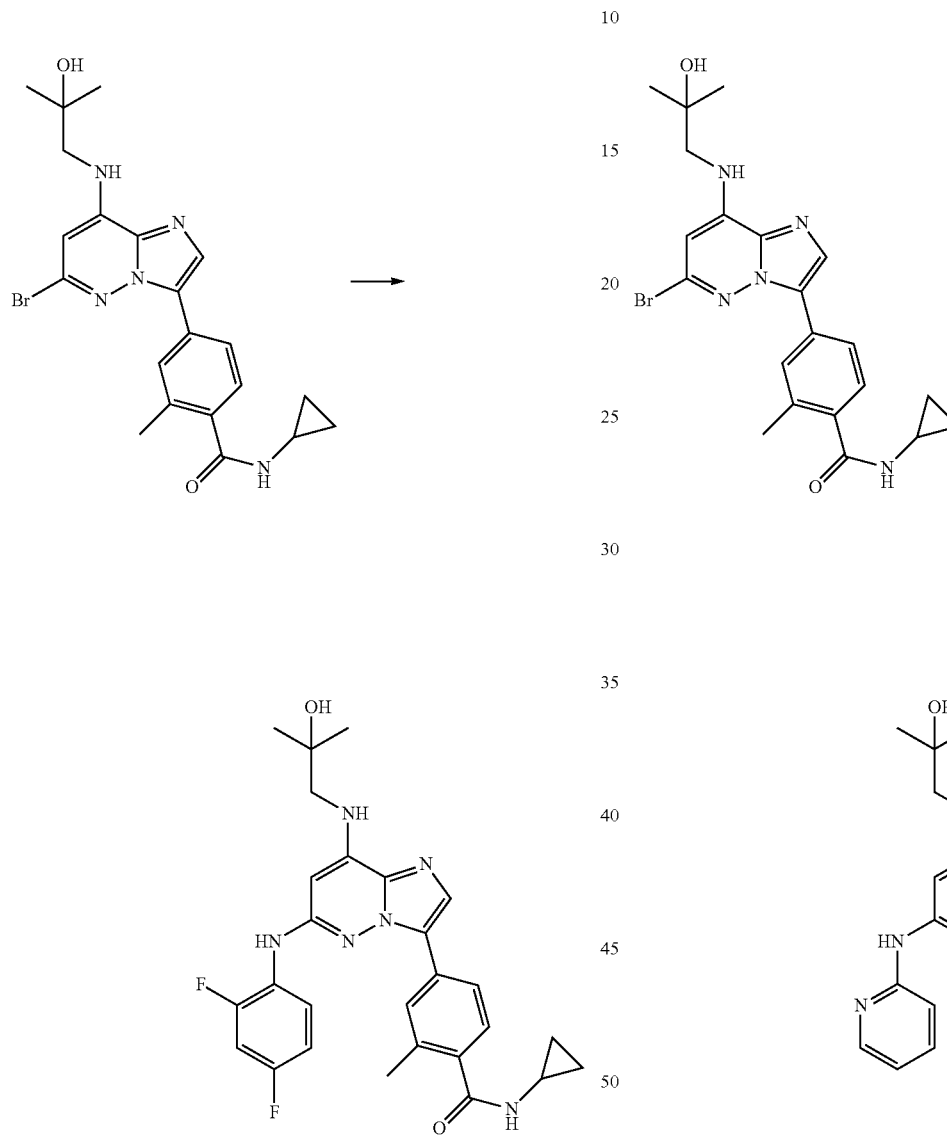

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2,4-difluoroaniline to give after working up and purification 5.0 mg (6%) of the title compound.

$^1$H-NMR (DMSO-d6): δ=0.50 (2H), 0.65 (2H), 1.18 (6H), 2.28 (3H), 2.79 (1H), 3.14 (2H), 4.80 (1H), 6.06 (1H), 6.54 (1H), 7.04 (1H), 7.27 (1H), 7.30 (1H), 7.78 (1H), 7.79 (1H), 7.94 (1H), 7.99 (1H), 8.25 (1H), 8.48 (1H) ppm.

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using pyridin-2-amine to give after working up and purification 10.1 mg (12%) of the title compound.

$^1$H-NMR (DMSO-d6): δ=0.51 (2H), 0.66 (2H), 1.18 (6H), 2.39 (3H), 2.81 (1H), 3.16 (2H), 4.80 (1H), 6.27 (1H), 6.60 (1H), 6.91 (1H), 7.36 (1H), 7.69 (1H), 7.80 (1H), 7.86 (1H), 8.01 (1H), 8.08 (1H), 8.23 (1H), 8.31 (1H), 9.48 (1H) ppm.

Example 358

N-cyclopropyl-4-{6-[(4-fluorophenyl)amino]-8-[(3,3,3-trifluoropropyl)amino]imidazo[1,2-b]pyridazin-3-yl}-2-methylbenzamide

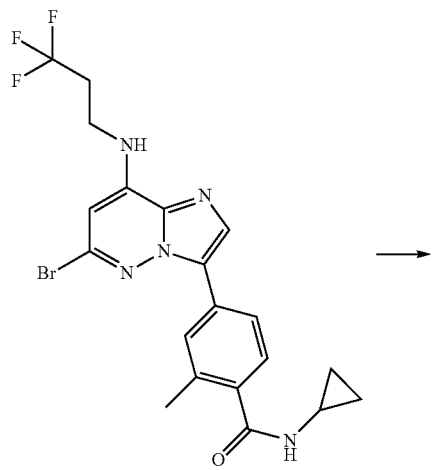

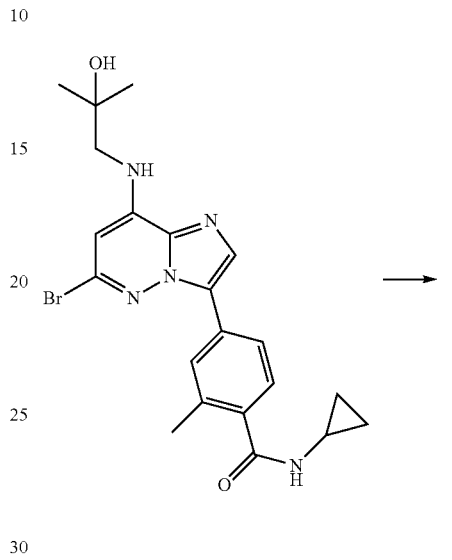

Example 359

N-cyclopropyl-4-{8-[(2-hydroxy-2-methylpropyl)amino]-6-(pyridin-3-ylamino) imidazo[1,2-b]pyridazin-3-yl}-2-methylbenzamide

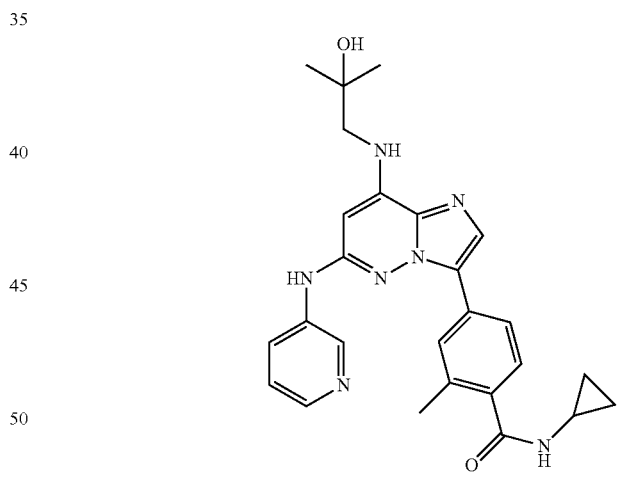

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-fluoroaniline to give after working up and purification 20.1 mg (24%) of the title compound.

$^1$H-NMR (DMSO-d6): δ=0.52 (2H), 0.66 (2H), 2.37 (3H), 2.68 (2H), 2.81 (1H), 3.49 (2H), 5.79 (1H), 7.11 (2H), 7.28 (1H), 7.35 (1H), 7.65 (2H), 7.77 (1H), 7.84 (1H), 8.04 (1H), 8.29 (1H), 8.98 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using pyridin-2-amine to give after working up and purification 12.6 mg (13%) of the title compound.

$^1$H-NMR (DMSO-d6): δ=0.51 (2H), 0.66 (2H), 1.19 (6H), 2.39 (3H), 2.81 (1H), 3.17 (2H), 4.82 (1H), 5.91 (1H), 6.66 (1H), 7.28 (1H), 7.34 (1H), 7.78 (1H), 7.81 (1H), 8.06 (1H), 8.11 (1H), 8.13 (1H), 8.31 (1H), 8.80 (1H), 9.13 (1H) ppm.

481

Example 360

N-cyclopropyl-4-{6-[(2-fluoro-4-methylphenyl)sulfanyl]-8-[(2-hydroxy-2-methylpropyl)amino]imidazo[1,2-b]pyridazin-3-yl}-2-methylbenzamide

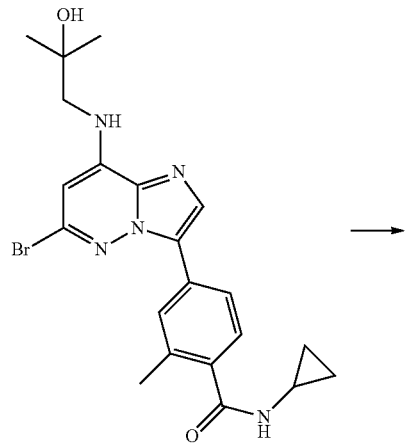

482

Example 361

N-cyclopropyl-4-{8-[(2-hydroxy-2-methylpropyl)amino]-6-(3-isopropoxyphenoxy)imidazo[1,2-b]pyridazin-3-yl}-2-methylbenzamide

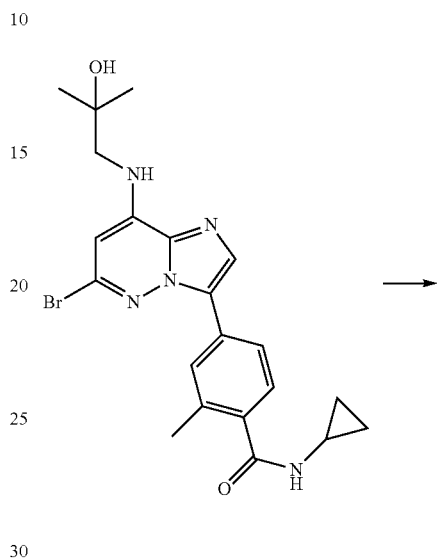

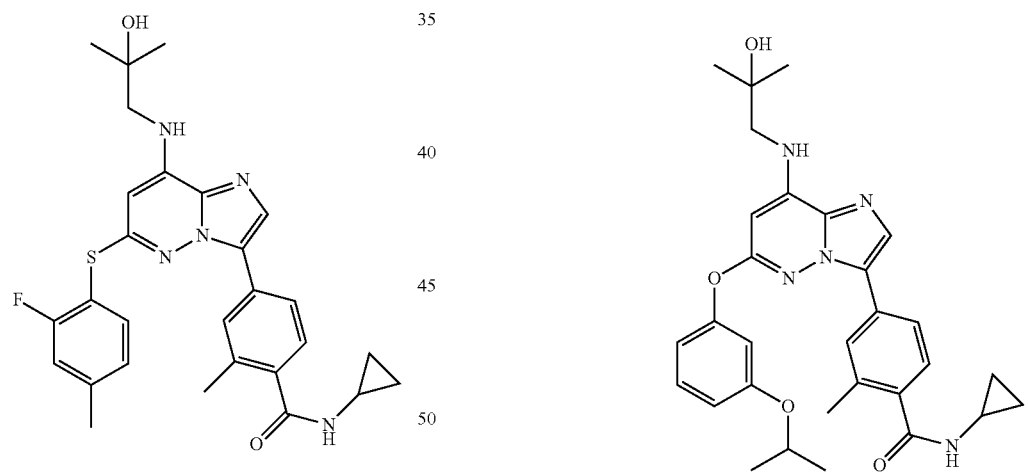

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 2-fluoro-4-methylbenzenethiol to give after working up and purification 43.2 mg (48%) of the title compound.

$^1$H-NMR (DMSO-d6): δ=0.48 (2H), 0.65 (2H), 1.13 (6H), 2.19 (3H), 2.39 (3H), 2.79 (1H), 3.24 (2H), 4.72 (1H), 6.29 (1H), 6.97 (1H), 7.00 (1H), 7.14 (1H), 7.25 (1H), 7.52 (1H), 7.57 (1H), 7.64 (1H), 7.93 (1H), 8.24 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 3-isopropoxyphenol to give after working up and purification 33.3 mg (37%) of the title compound.

$^1$H-NMR (DMSO-d6): δ=0.46 (2H), 0.63 (2H), 1.15 (6H), 1.20 (6H), 2.14 (3H), 2.76 (1H), 3.27 (2H), 4.58 (1H), 4.74 (1H), 6.14 (1H), 6.73-6.83 (3H), 6.96 (1H), 7.15 (1H), 7.30 (1H), 7.70 (1H), 7.80 (1H), 7.92 (1H), 8.21 (1H) ppm.

483
Example 362

N-cyclopropyl-4-{6-[(2-fluoro-4-methylphenyl)sulfanyl]-8-[(3,3,3-trifluoropropyl)amino]imidazo[1,2-b]pyridazin-3-yl}-2-methylbenzamide

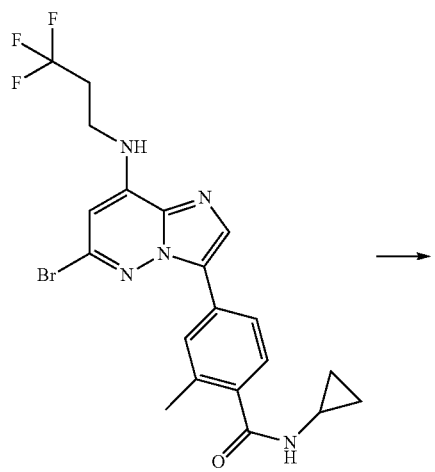

→

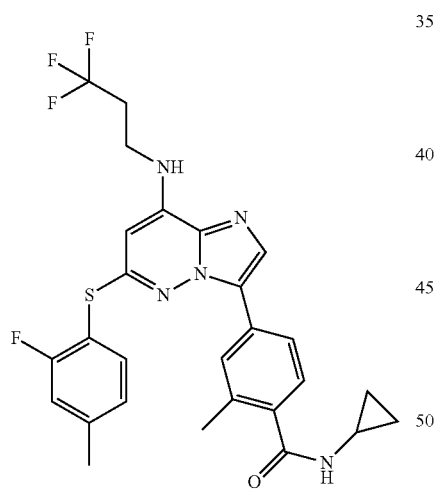

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-fluoro-4-methylbenzenethiol to give after working up and purification 30.3 mg (34%) of the title compound.

$^1$H-NMR (DMSO-d6): δ=0.48 (2H), 0.66 (2H), 2.19 (3H), 2.40 (3H), 2.64 (2H), 2.80 (1H), 3.55 (2H), 6.23 (1H), 7.01 (1H), 7.15 (1H), 7.26 (1H), 7.53 (1H), 7.57 (1H), 7.64 (1H), 7.66 (1H), 7.94 (1H), 8.25 (1H) ppm.

484
Example 363

4-{6-[4-chloro-2-(hydroxymethyl)phenyl]-8-[(2-hydroxy-2-methylpropyl)amino]imidazo[1,2-b]pyridazin-3-yl}-N-cyclopropyl-2-methylbenzamide

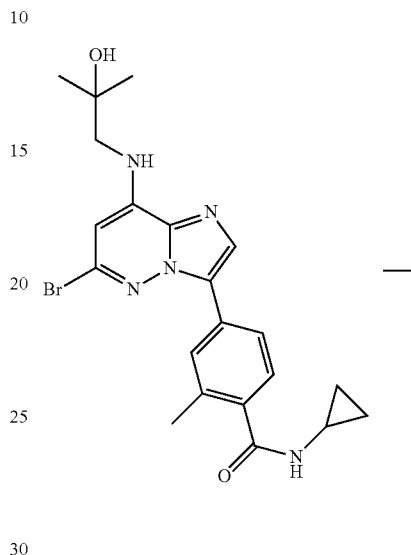

→

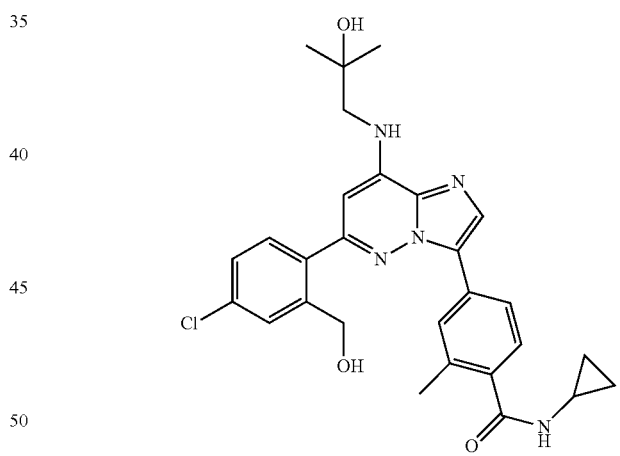

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 1 using [4-chloro-2-(hydroxymethyl)phenyl]boronic acid to give after working up and purification 22.5 mg (26%) of the title compound.

$^1$H-NMR (DMSO-d6): δ=0.48 (2H), 0.64 (2H), 1.15 (6H), 2.33 (3H), 2.79 (1H), 3.31 (2H), 4.64 (2H), 4.73 (1H), 5.32 (1H), 6.42 (1H), 7.00 (1H), 7.32 (1H), 7.43 (1H), 7.51 (1H), 7.65 (1H), 7.91 (1H), 7.95 (1H), 8.00 (1H), 8.26 (1H) ppm.

485
Example 364

4-{6-[4-chloro-2-(hydroxymethyl)phenyl]-8-[(3,3,3-trifluoropropyl)amino]imidazo[1,2-b]pyridazin-3-yl}-N-cyclopropyl-2-methylbenzamide

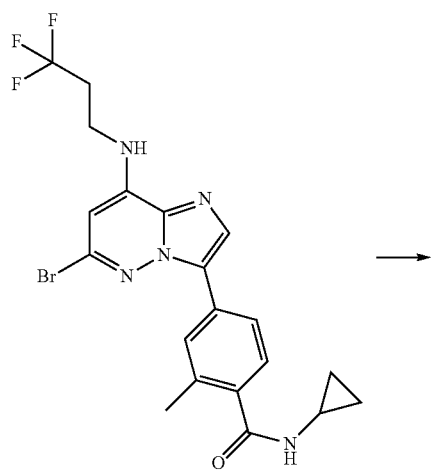

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 1 using [4-chloro-2-(hydroxymethyl)phenyl]boronic acid to give after working up and purification 15.6 mg (18%) of the title compound.

$^1$H-NMR (DMSO-d6): δ=0.48 (2H), 0.64 (2H), 2.33 (3H), 2.67 (2H), 2.79 (1H), 3.61 (2H), 4.64 (2H), 5.35 (1H), 6.37 (1H), 7.32 (1H), 7.43 (1H), 7.57 (1H), 7.65 (1H), 7.68 (1H), 7.91 (1H), 7.94 (1H), 8.01 (1H), 8.26 (1H) ppm.

486
Example 365

N-cyclopropyl-4-{8-[(2-hydroxy-2-methylpropyl)amino]-6-(pyridin-4-ylamino) imidazo[1,2-b]pyridazin-3-yl}-2-methylbenzamide

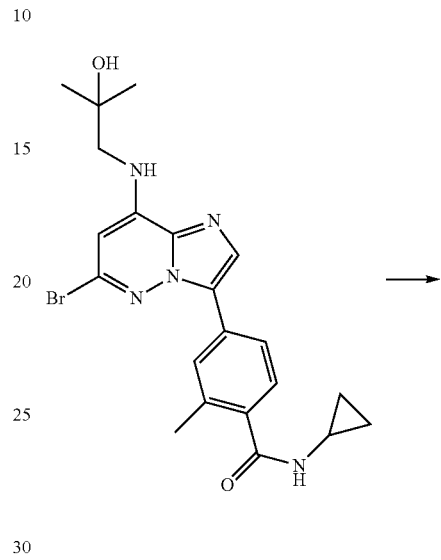

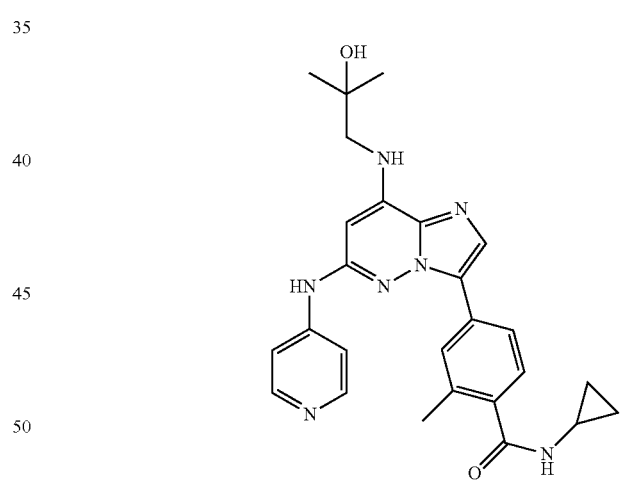

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using pyridin-4-amine to give after working up and purification 10.7 mg (14%) of the title compound.

$^1$H-NMR (DMSO-d6): δ=0.52 (2H), 0.67 (2H), 1.18 (6H), 2.40 (3H), 2.82 (1H), 3.18 (2H), 4.81 (1H), 5.95 (1H), 6.77 (1H), 7.38 (1H), 7.59 (2H), 7.81 (1H), 7.83 (1H), 8.06 (1H), 8.27-8.35 (3H), 9.45 (1H) ppm.

487

Example 366

N-cyclopropyl-4-{8-[(2-hydroxy-2-methylpropyl)
amino]-6-[(6-methoxypyridin-3-yl)-amino]imidazo
[1,2-b]pyridazin-3-yl}-2-methylbenzamide

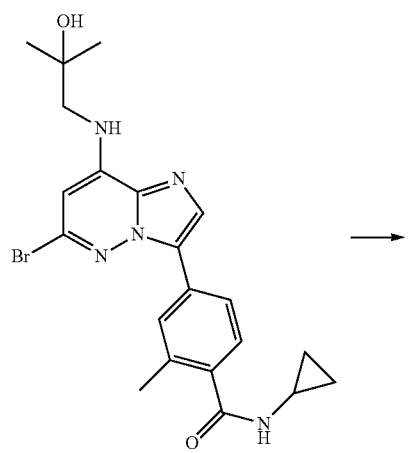

75 mg (164 µmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 305 using 4-methoxyaniline to give after working up and purification 27 mg (33%) of the title compound.

$^1$H-NMR (DMSO-d6): δ=0.50 (2H), 0.65 (2H), 1.18 (6H), 2.36 (3H), 2.80 (1H), 3.15 (2H), 3.79 (3H), 4.80 (1H), 5.83 (1H), 6.55 (1H), 6.77 (1H), 7.30 (1H), 7.76 (1H), 7.77 (1H), 7.92 (1H), 8.09 (1H), 8.28 (1H), 8.45 (1H), 8.82 (1H) ppm.

488

Example 367

N-cyclopropyl-4-{6-[(2-fluoro-5-methylphenyl)
amino]-8-[(3,3,3-trifluoropropyl)amino]imidazo[1,2-
b]pyridazin-3-yl}-2-methylbenzamide

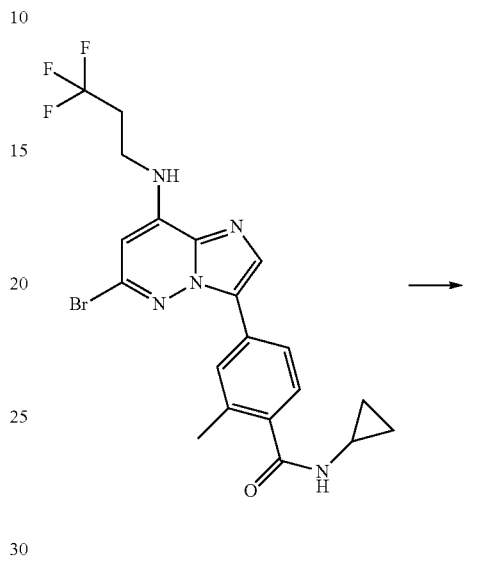

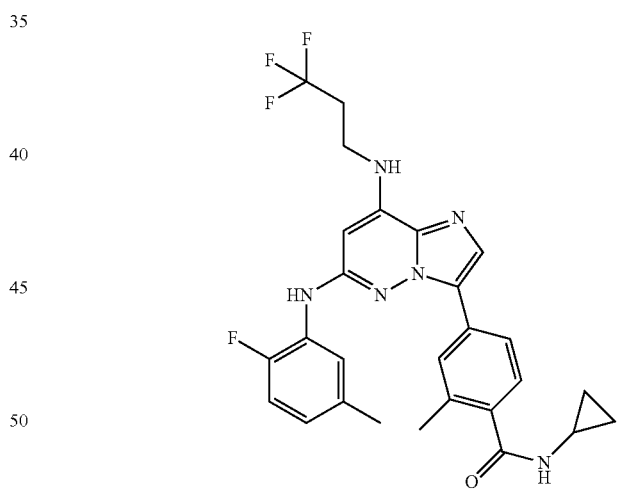

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 2-fluoro-5-methylaniline to give after working up and purification 18.7 mg (22%) of the title compound.

$^1$H-NMR (DMSO-d6): δ=0.48 (2H), 0.65 (2H), 2.23 (3H), 2.28 (2H), 2.68 (3H), 2.79 (1H), 3.48 (2H), 6.10 (1H), 6.79 (1H), 7.09 (1H), 7.24-7.32 (2H), 7.78 (1H), 7.87 (1H), 7.90 (1H), 7.94 (1H), 8.25 (1H), 8.47 (1H) ppm.

489

Example 368

4-{6-anilino-8-[(3,3,3-trifluoropropyl)amino]imidazo[1,2-b]pyridazin-3-yl}-N-cyclopropyl-2-methylbenzamide

490

Example 369

N-cyclopropyl-4-{6-[(2-fluorophenyl)amino]-8-[(3,3,3-trifluoropropyl)amino]imidazo[1,2-b]pyridazin-3-yl}-2-methylbenzamide

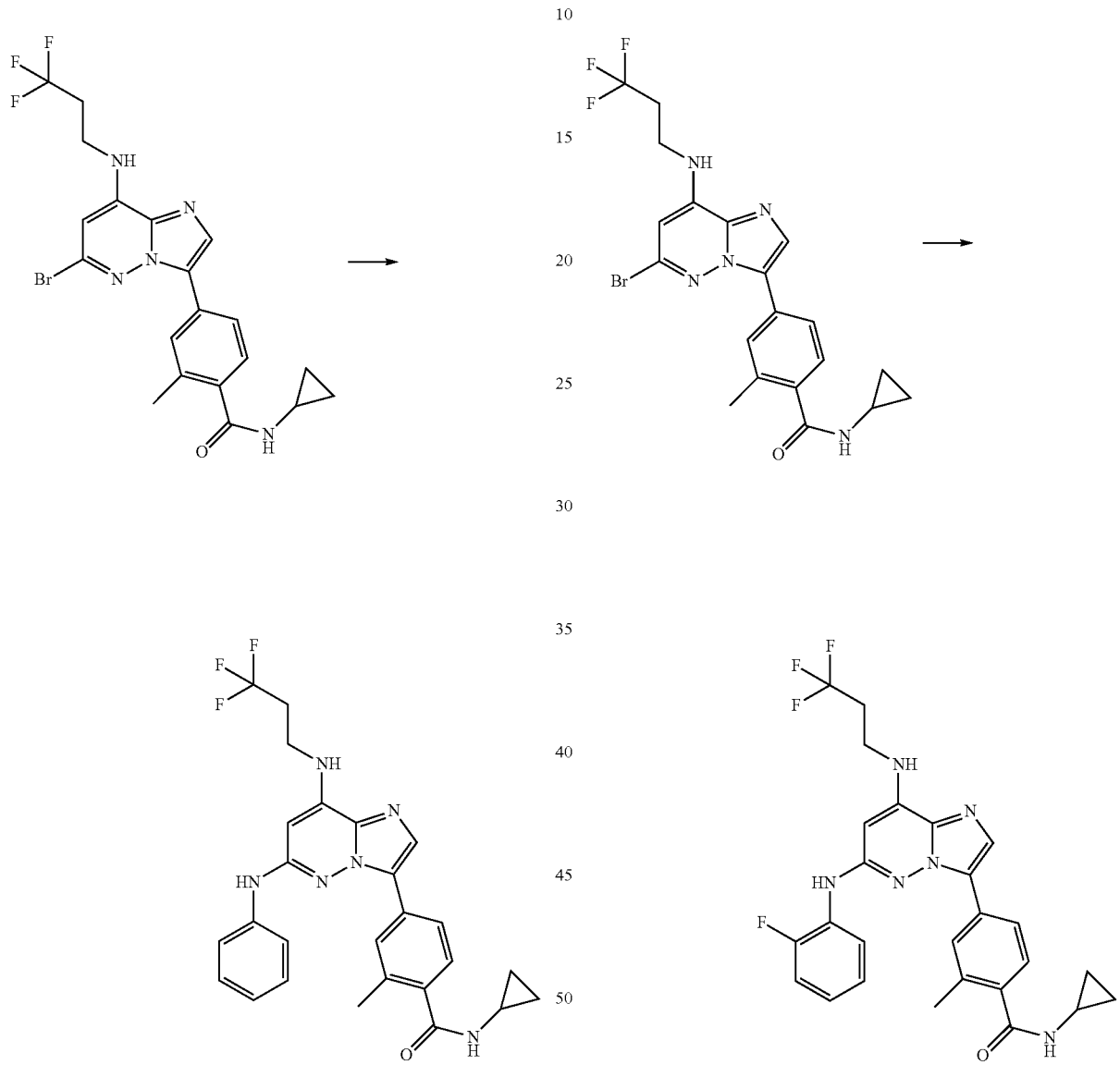

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using aniline to give after working up and purification 21.1 mg (26%) of the title compound.

$^1$H-NMR (DMSO-d6): δ=0.51 (2H), 0.66 (2H), 2.38 (3H), 2.68 (2H), 2.81 (1H), 3.49 (2H), 5.84 (1H), 6.90 (1H), 7.23-7.31 (3H), 7.34 (1H), 7.66 (2H), 7.78 (1H), 7.84 (1H), 8.12 (1H), 8.30 (1H), 8.96 (1H) ppm.

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 2-fluoroaniline to give after working up and purification 12.0 mg (14%) of the title compound.

$^1$H-NMR (DMSO-d6): δ=0.50 (2H), 0.65 (2H), 2.32 (3H), 2.68 (2H), 2.80 (1H), 3.49 (2H), 6.14 (1H), 7.00 (1H), 7.14 (1H), 7.23 (1H), 7.26-7.34 (2H), 7.79 (1H), 7.81 (1H), 8.02 (1H), 8.17 (1H), 8.27 (1H), 8.57 (1H) ppm.

491

Example 370

N-cyclopropyl-4-(6-{[2-(hydroxymethyl)phenyl]amino}-8-[(3,3,3-trifluoropropyl)amino]imidazo[1,2-b]pyridazin-3-O-2-methylbenzamide

492

Example 371

N-cyclopropyl-4-{6-[(3-fluoro-5-methylphenyl)amino]-8-[(3,3,3-trifluoropropyl)amino]imidazo[1,2-b]pyridazin-3-yl}-2-methylbenzamide

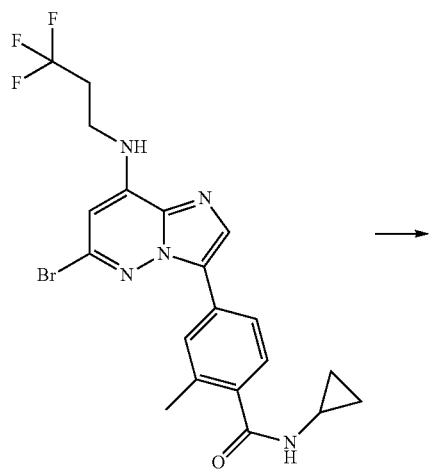

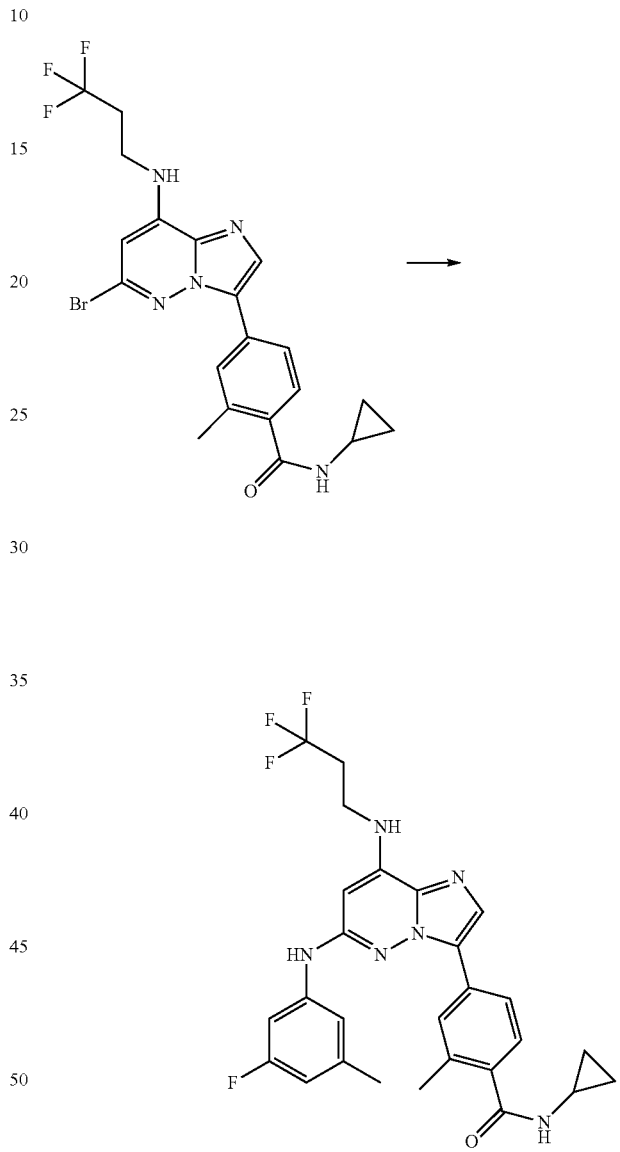

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using (2-aminophenyl)methanol to give after working up and purification 5.2 mg (6%) of the title compound.

$^1$H-NMR (DMSO-d6): δ=0.49 (2H), 0.64 (2H), 2.25 (3H), 2.69 (2H), 2.78 (1H), 3.50 (2H), 4.55 (2H), 5.30 (1H), 5.94 (1H), 7.05 (1H), 7.18-7.29 (3H), 7.38 (1H), 7.77-7.87 (3H), 8.01 (1H), 8.07 (1H), 8.24 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3-fluoro-5-methylaniline to give after working up and purification 20.2 mg (23%) of the title compound.

$^1$H-NMR (DMSO-d6): δ=0.50 (2H), 0.66 (2H), 2.25 (3H), 2.35 (3H), 2.68 (2H), 2.81 (1H), 3.49 (2H), 5.82 (1H), 6.53 (1H), 7.05 (1H), 7.29-7.39 (2H), 7.54 (1H), 7.77 (1H), 7.87 (1H), 7.98 (1H), 8.30 (1H), 9.12 (1H) ppm.

493

Example 372

4-{6-[(4-chloro-3-fluorophenyl)amino]-8-[(3,3,3-trifluoropropyl)amino]imidazo[1,2-b]pyridazin-3-yl}-N-cyclopropyl-2-methylbenzamide

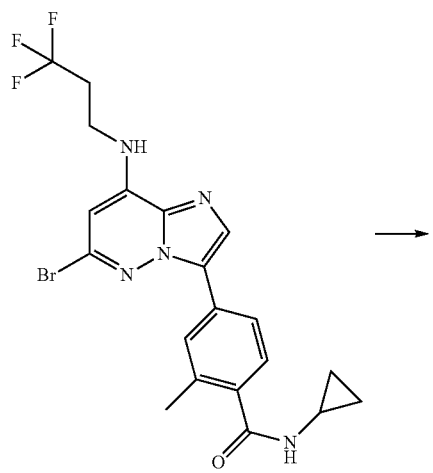

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-chloro-3-fluoroaniline to give after working up and purification 16.9 mg (19%) of the title compound.

¹H-NMR (DMSO-d6): δ=0.51 (2H), 0.66 (2H), 2.36 (3H), 2.68 (2H), 2.81 (1H), 3.50 (2H), 5.81 (1H), 7.26 (1H), 7.35 (1H), 7.39 (1H), 7.44 (1H), 7.77 (1H), 7.80 (1H), 7.95 (1H), 7.98 (1H), 8.31 (1H), 9.36 (1H) ppm.

494

Example 373

N-cyclopropyl-4-{6-[(3,4-difluorophenyl)amino]-8-[(3,3,3-trifluoropropyl)amino]imidazo[1,2-b]pyridazin-3-yl}-2-methylbenzamide

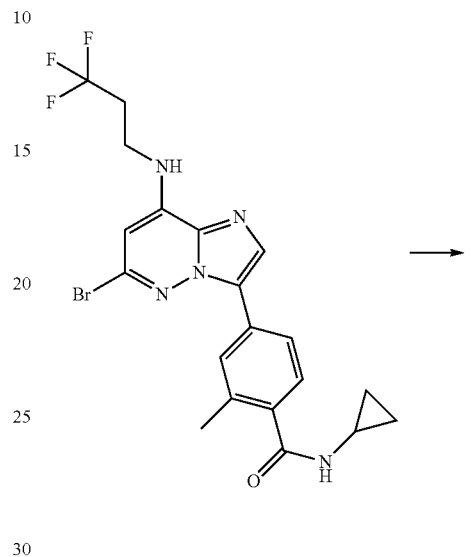

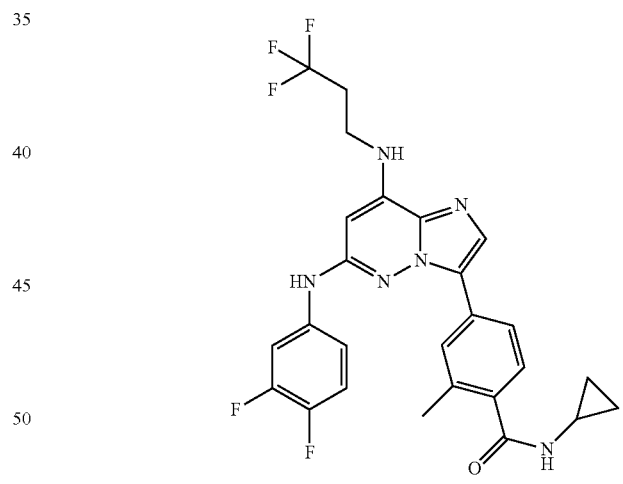

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3,4-difluoroaniline to give after working up and purification 11.9 mg (14%) of the title compound.

¹H-NMR (DMSO-d6): δ=0.51 (2H), 0.66 (2H), 2.36 (3H), 2.68 (2H), 2.81 (1H), 3.50 (2H), 5.79 (1H), 7.22 (1H), 7.28-7.39 (3H), 7.77 (1H), 7.81 (1H), 7.91 (1H), 8.00 (1H), 8.30 (1H), 9.20 (1H) ppm.

Example 374

4-{6-[(4-chlorophenyl)amino]-8-[(3,3,3-trifluoropropyl)amino]imidazo[1,2-b]pyridazin-3-yl}-N-cyclopropyl-2-methylbenzamide

Example 375

N-cyclopropyl-4-{6-[(5-fluoro-2-methylphenyl)amino]-8-[(3,3,3-trifluoropropyl)amino]imidazo[1,2-b]pyridazin-3-yl}-2-methylbenzamide

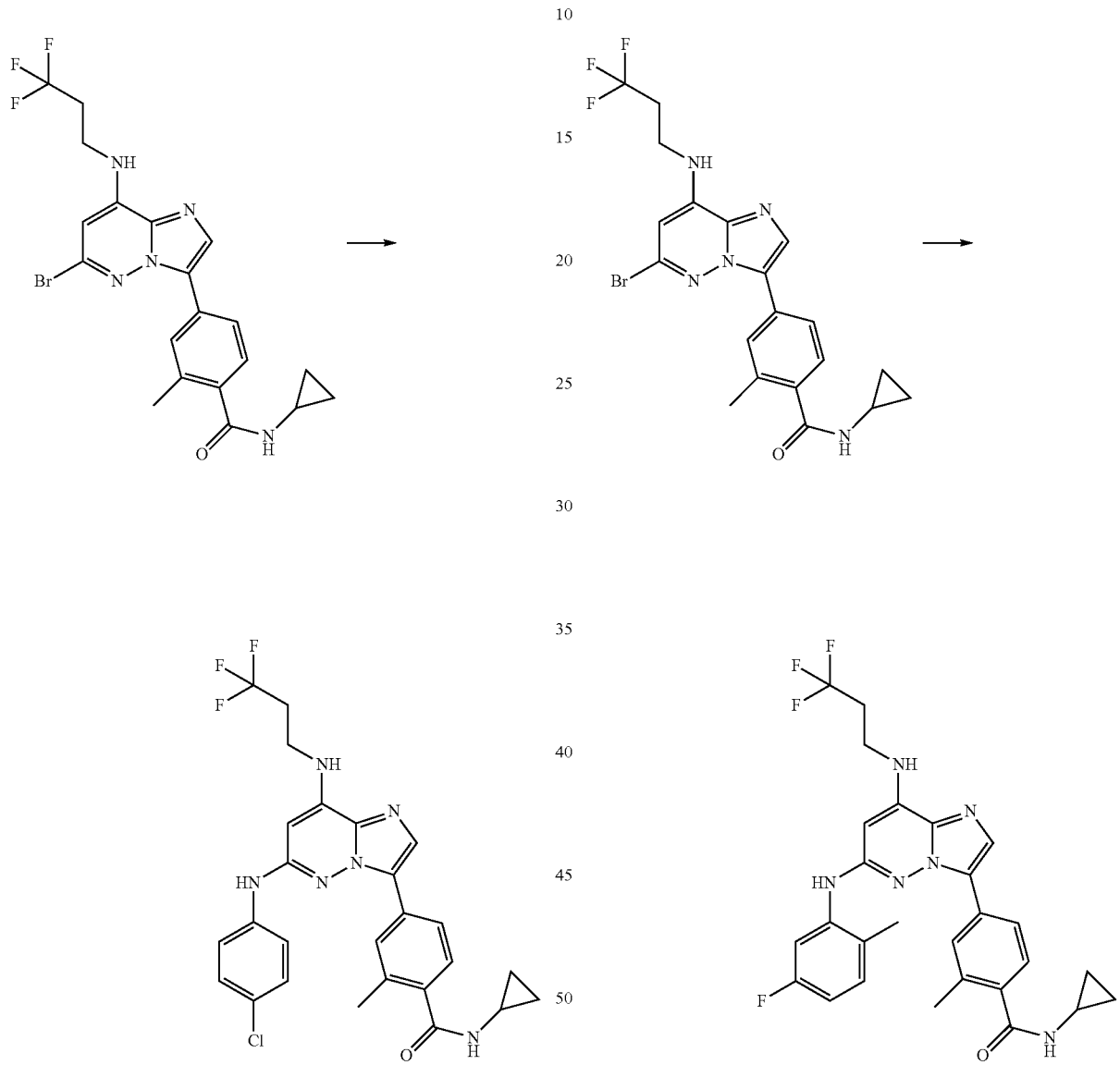

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-chloroaniline to give after working up and purification 14.3 mg (17%) of the title compound.

$^1$H-NMR (DMSO-d6): δ=0.52 (2H), 0.67 (2H), 2.38 (3H), 2.68 (2H), 2.81 (1H), 3.49 (2H), 5.82 (1H), 7.30 (2H), 7.33 (1H), 7.38 (1H), 7.68 (2H), 7.78 (1H), 7.84 (1H), 8.02 (1H), 8.30 (1H), 9.12 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 5-fluoro-2-methylaniline to give after working up and purification 6.6 mg (8%) of the title compound.

$^1$H-NMR (DMSO-d6): δ=0.49 (2H), 0.64 (2H), 2.24 (3H), 2.26 (3H), 2.63-2.85 (3H), 3.50 (2H), 6.11 (1H), 6.75 (1H), 7.19 (1H), 7.24 (1H), 7.29 (1H), 7.78-7.86 (3H), 7.96-8.03 (2H), 8.25 (1H) ppm.

497
Example 376

4-{6-[(4-chloro-2-fluorophenyl)amino]-8-[(3,3,3-trifluoropropyl)amino]imidazo[1,2-b]pyridazin-3-yl}-N-cyclopropyl-2-methylbenzamide

498
Example 377

4-{6-[(5-chloro-2-methylphenyl)amino]-8-[(3,3,3-trifluoropropyl)amino]imidazo[1,2-b]pyridazin-3-yl}-N-cyclopropyl-2-methylbenzamide

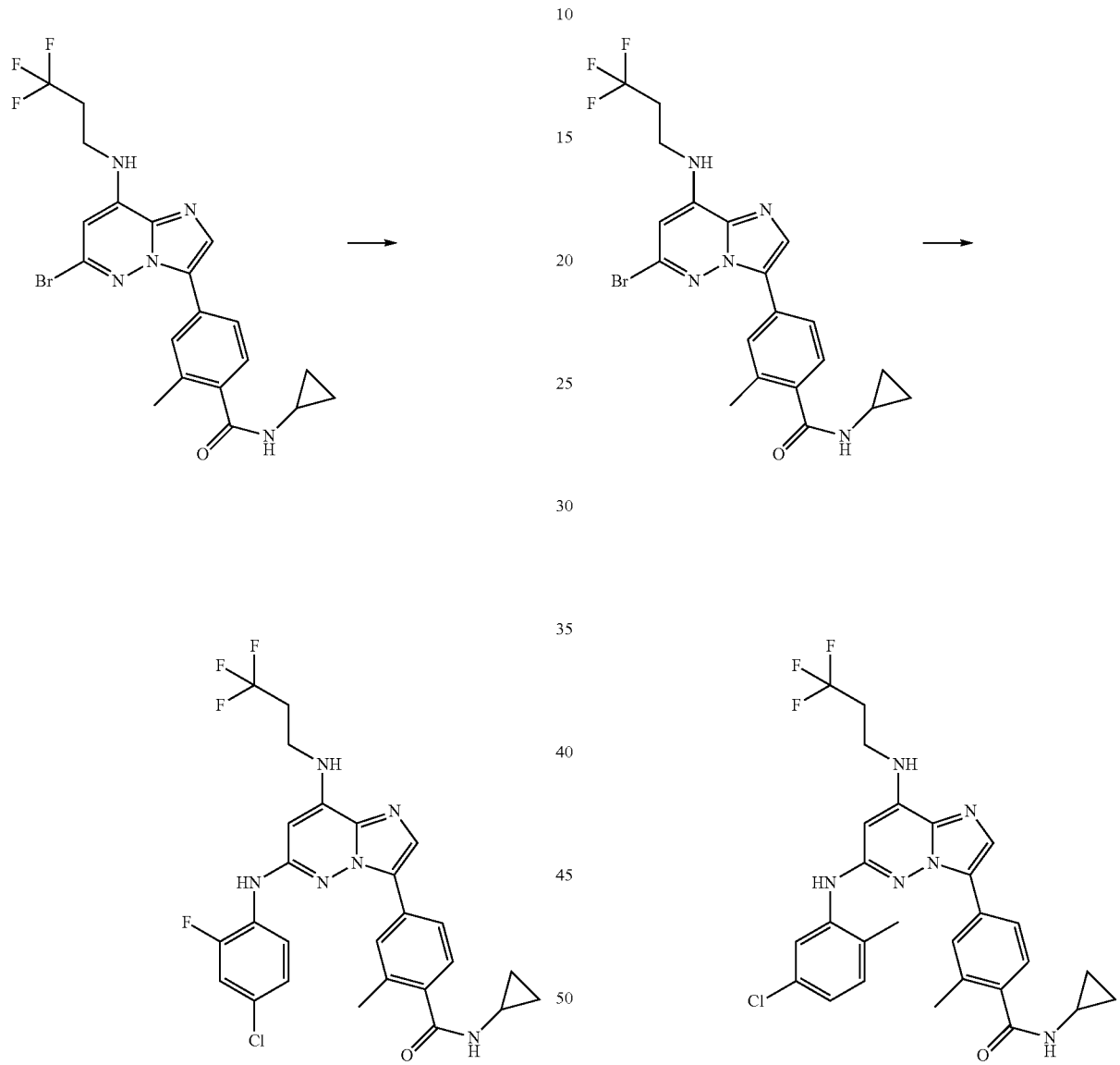

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-chloro-2-fluoroaniline to give after working up and purification 10.8 mg (12%) of the title compound.

$^1$H-NMR (DMSO-d6): δ=0.51 (2H), 0.66 (2H), 2.31 (3H), 2.68 (2H), 2.80 (1H), 3.49 (2H), 6.12 (1H), 7.21 (1H), 7.32 (1H), 7.35 (1H), 7.46 (1H), 7.79 (1H), 7.80 (1H), 7.96 (1H), 8.18 (1H), 8.28 (1H), 8.69 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 5-chloro-2-methylaniline to give after working up and purification 9.7 mg (11%) of the title compound.

$^1$H-NMR (DMSO-d6): δ=0.48 (2H), 0.64 (2H), 2.24 (3H), 2.26 (3H), 2.70 (2H), 2.78 (1H), 3.50 (2H), 6.06 (1H), 7.00 (1H), 7.21 (1H), 7.26 (1H), 7.29 (1H), 7.83 (1H), 7.89 (1H), 7.91-7.95 (2H), 8.04 (1H), 8.23 (1H) ppm.

Example 378

N-cyclopropyl-4-{6-[(3,5-difluorophenyl)amino]-8-[(3,3,3-trifluoropropyl)amino]imidazo[1,2-b]pyridazin-3-yl}-2-methylbenzamide

Example 379

4-{6-[(3-chlorophenyl)amino]-8-[(3,3,3-trifluoropropyl)amino]imidazo[1,2-b]pyridazin-3-yl}-N-cyclopropyl-2-methylbenzamide

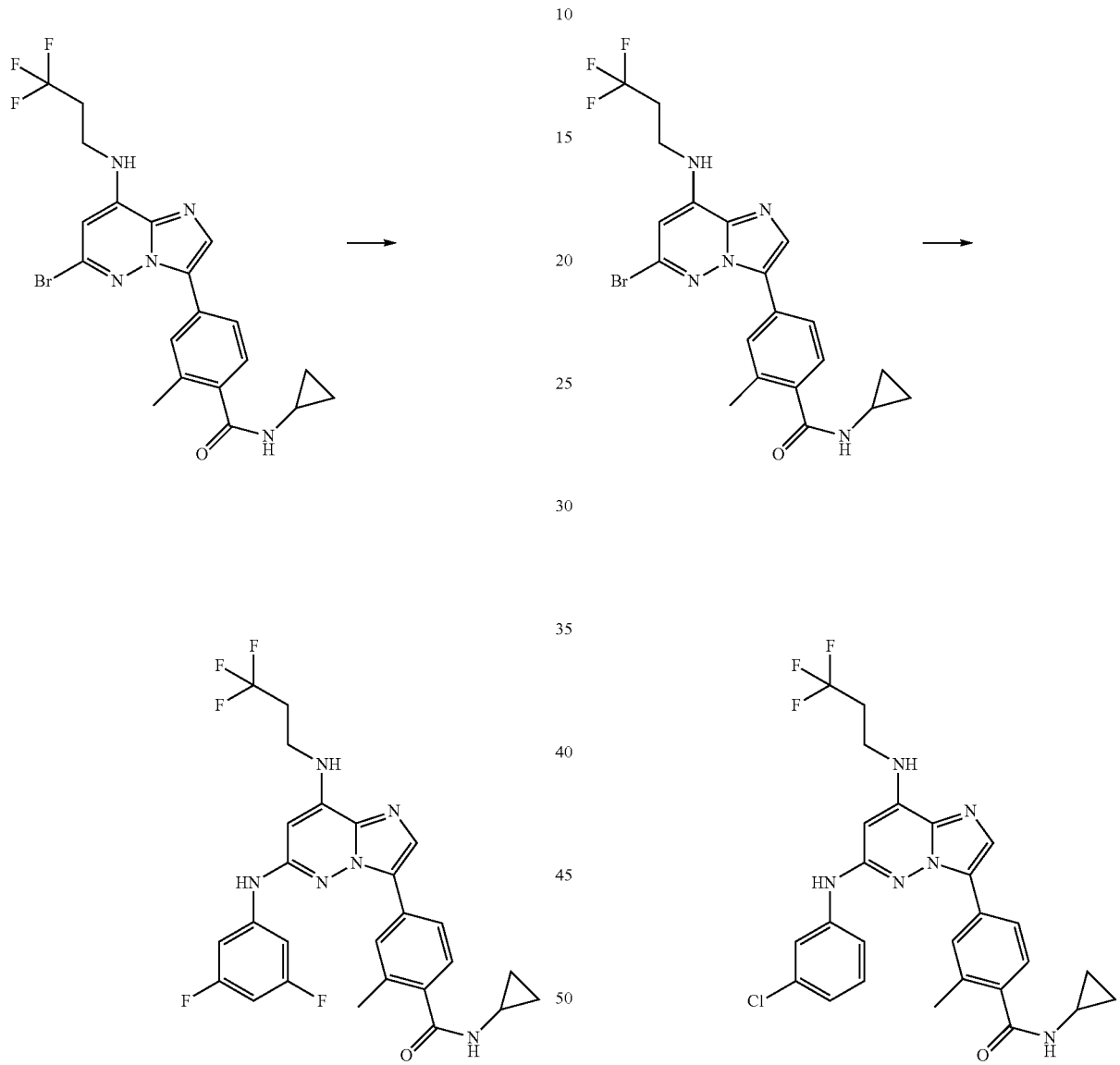

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3,5-difluoroaniline to give after working up and purification 14.7 mg (17%) of the title compound.

$^1$H-NMR (DMSO-d6): δ=0.50 (2H), 0.66 (2H), 2.35 (3H), 2.68 (2H), 2.81 (1H), 3.51 (2H), 5.80 (1H), 6.69 (1H), 7.31-7.38 (3H), 7.43 (1H), 7.78 (1H), 7.79 (1H), 8.00 (1H), 8.31 (1H), 9.43 (1H) ppm.

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3-chloroaniline to give after working up and purification 16.7 mg (19%) of the title compound.

$^1$H-NMR (DMSO-d6): δ=0.50 (2H), 0.66 (2H), 2.36 (3H), 2.68 (2H), 2.81 (1H), 3.50 (2H), 5.82 (1H), 6.93 (1H), 7.28 (1H), 7.32-7.39 (2H), 7.50 (1H), 7.79 (1H), 7.83 (1H), 7.92 (1H), 7.94 (1H), 8.28 (1H), 9.18 (1H) ppm.

501
Example 380

N-cyclopropyl-4-{6-[(2,3-difluorophenyl)amino]-8-[(3,3,3-trifluoropropyl)amino]imidazo[1,2-b]pyridazin-3-yl}-2-methylbenzamide

502
Example 381

N-cyclopropyl-2-methyl-4-{6-[3-(propan-2-yloxy)phenoxy]-8-[(3,3,3-trifluoropropyl)amino]imidazo[1,2-b]pyridazin-3-yl}benzamide

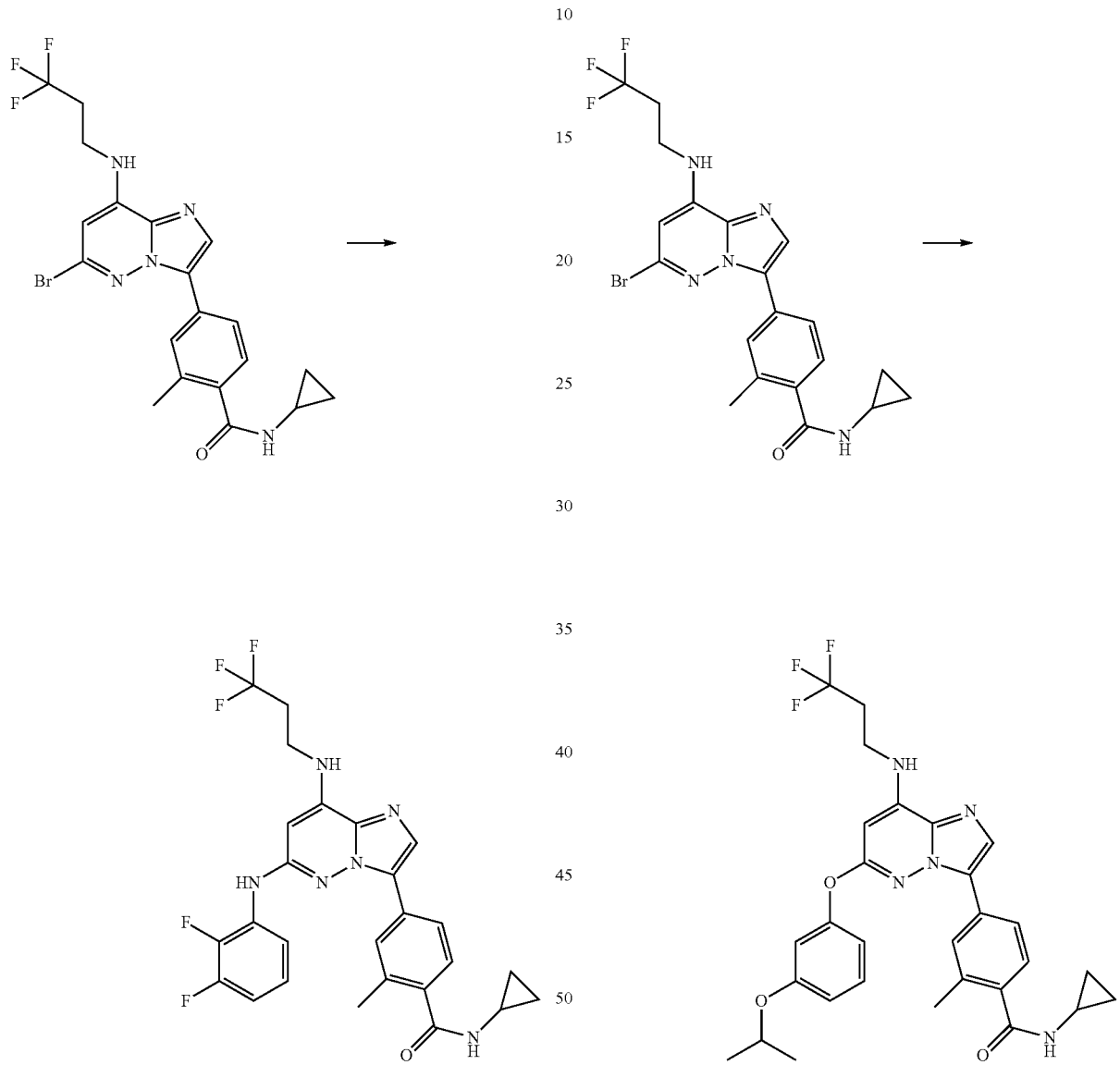

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 2,3-difluoroaniline to give after working up and purification 6.6 mg (8%) of the title compound.

$^1$H-NMR (DMSO-d6): δ=0.50 (2H), 0.65 (2H), 2.31 (3H), 2.68 (2H), 2.80 (1H), 3.50 (2H), 6.13 (1H), 7.02 (1H), 7.13 (1H), 7.28 (1H), 7.37 (1H), 7.79 (1H), 7.81 (1H), 7.95 (1H), 7.99 (1H), 8.28 (1H), 8.81 (1H) ppm.

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3-isopropoxyaniline to give after working up and purification 4.8 mg (5%) of the title compound.

$^1$H-NMR (DMSO-d6): δ=0.46 (2H), 0.63 (2H), 1.21 (6H), 2.14 (3H), 2.67 (2H), 2.76 (1H), 3.58 (2H), 4.58 (1H), 6.09 (1H), 6.75-6.84 (3H), 7.15 (1H), 7.31 (1H), 7.66 (1H), 7.70 (1H), 7.79 (1H), 7.93 (1H), 8.21 (1H) ppm.

503
Example 382

N-cyclopropyl-4-{6-[(4-fluoro-3-methylphenyl)amino]-8-[(2-hydroxy-2-methylpropyl)amino]imidazo[1,2-b]pyridazin-3-yl}-2-methylbenzamide

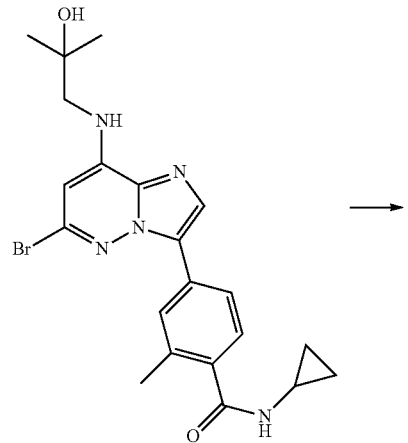

504
Example 383

N-cyclopropyl-4-{6-[(2-fluoro-5-methylphenyl)amino]-8-[(2-hydroxy-2-methylpropyl)amino]imidazo[1,2-b]pyridazin-3-yl}-2-methylbenzamide

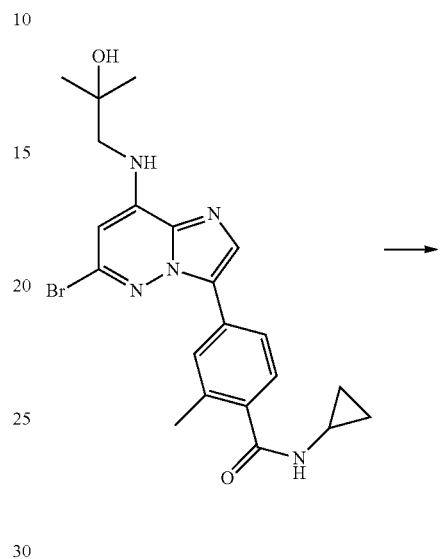

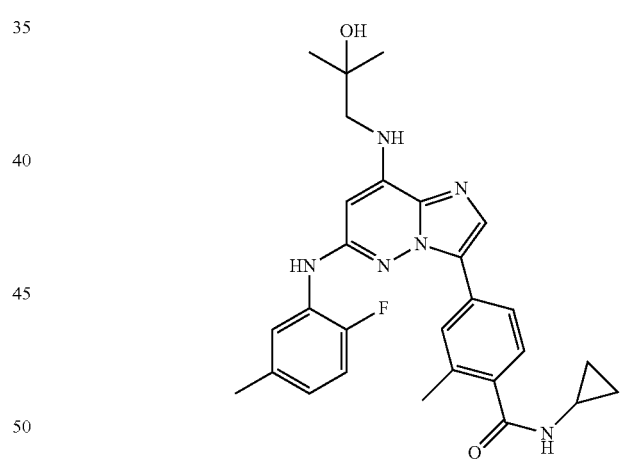

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-fluoro-3-methylaniline to give after working up and purification 16.5 mg (19%) of the title compound.

$^1$H-NMR (DMSO-d6): δ=0.50 (2H), 0.66 (2H), 1.18 (6H), 2.18 (3H), 2.34 (3H), 2.81 (1H), 3.15 (2H), 4.80 (1H), 5.84 (1H), 6.52 (1H), 7.02 (1H), 7.34 (1H), 7.44-7.51 (2H), 7.75 (1H), 7.92 (1H), 7.96 (1H), 8.27 (1H), 8.83 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2-fluoro-5-methylaniline to give after working up and purification 10.5 mg (12%) of the title compound.

$^1$H-NMR (DMSO-d6): δ=0.48 (2H), 0.65 (2H), 1.18 (6H), 2.23 (3H), 2.28 (3H), 2.79 (1H), 3.15 (2H), 4.79 (1H), 6.13 (1H), 6.52 (1H), 6.79 (1H), 7.09 (1H), 7.27 (1H), 7.78 (1H), 7.86 (1H), 7.88 (1H), 7.95 (1H), 8.25 (1H), 8.42 (1H) ppm.

505
Example 384

N-cyclopropyl-4-{6-[(2-fluorophenyl)amino]-8-[(2-hydroxy-2-methylpropyl)amino]imidazo[1,2-b]pyridazin-3-yl}-2-methylbenzamide

506
Example 385

N-cyclopropyl-4-{8-[(2-hydroxy-2-methylpropyl)amino]-6-[(3-isopropylphenyl)amino]imidazo[1,2-b]pyridazin-3-yl}-2-methylbenzamide

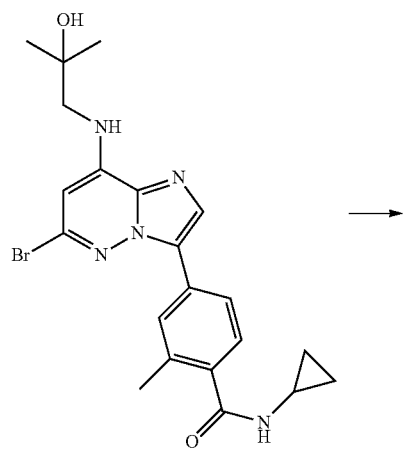

→

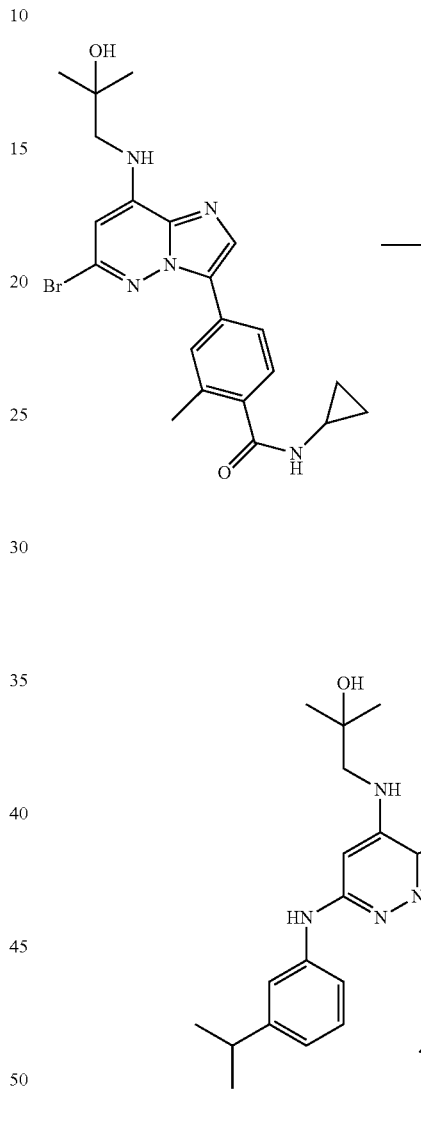

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2-fluoroaniline to give after working up and purification 8.3 mg (10%) of the title compound.

$^1$H-NMR (DMSO-d6): δ=0.50 (2H), 0.65 (2H), 1.18 (6H), 2.31 (3H), 2.80 (1H), 3.16 (2H), 4.79 (1H), 6.17 (1H), 6.54 (1H), 7.00 (1H), 7.14 (1H), 7.22 (1H), 7.28 (1H), 7.78 (1H), 7.81 (1H), 8.02 (1H), 8.14 (1H), 8.27 (1H), 8.52 (1H) ppm.

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3-isopropylaniline to give after working up and purification 11.6 mg (14%) of the title compound.

$^1$H-NMR (DMSO-d6): δ=0.50 (2H), 0.66 (2H), 1.16 (6H), 1.18 (6H), 2.37 (3H), 2.74-2.87 (2H), 3.15 (2H), 4.79 (1H), 5.89 (1H), 6.51 (1H), 6.79 (1H), 7.18 (1H), 7.26 (1H), 7.32 (1H), 7.68 (1H), 7.76 (1H), 7.93 (1H), 8.02 (1H), 8.28 (1H), 8.84 (1H) ppm.

Example 386

N-cyclopropyl-4-(6-{[4-(2-hydroxyethyl)phenyl]amino}-8-[(2-hydroxy-2-methylpropyl)amino]imidazo[1,2-b]pyridazin-3-yl)-2-methylbenzamide

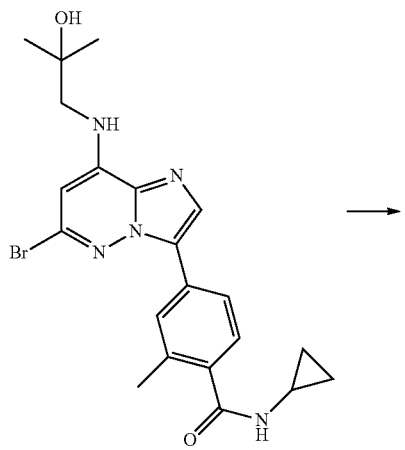

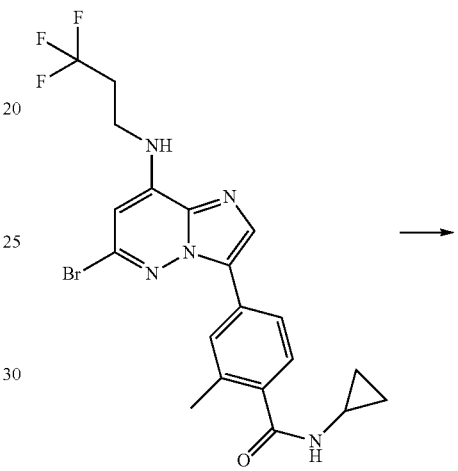

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2-(4-aminophenyl)ethanol to give after working up and purification 10.6 mg (13%) of the title compound.

¹H-NMR (DMSO-d6): δ=0.52 (2H), 0.66 (2H), 1.18 (6H), 2.38 (3H), 2.64 (2H), 2.81 (1H), 3.15 (2H), 3.54 (2H), 4.57 (1H), 4.80 (1H), 5.87 (1H), 6.49 (1H), 7.10 (2H), 7.34 (1H), 7.55 (2H), 7.76 (1H), 7.84 (1H), 8.12 (1H), 8.31 (1H), 8.82 (1H) ppm.

Example 387

N-cyclopropyl-4-{6-[(3-fluoro-2-methylphenyl)sulfanyl]-8-[(3,3,3-trifluoropropyl)amino]imidazo[1,2-b]pyridazin-3-yl}-2-methylbenzamide

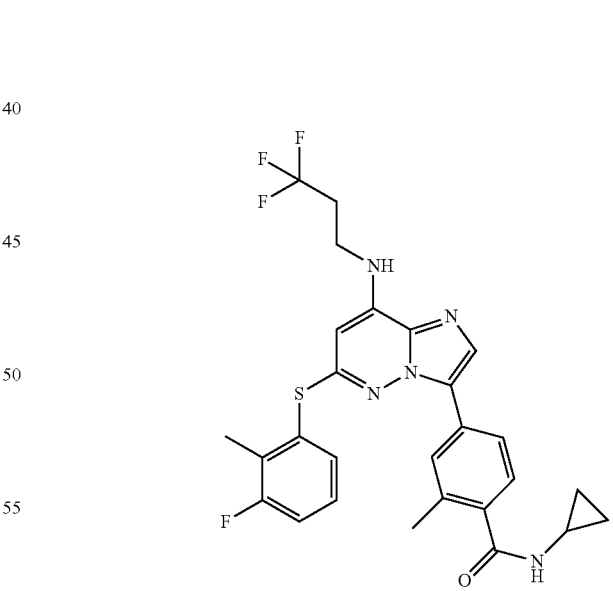

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3-fluoro-2-methylbenzenethiol to give after working up and purification 35.3 mg (42%) of the title compound.

509

¹H-NMR (DMSO-d6): δ=0.49 (2H), 0.65 (2H), 2.18 (3H), 2.27 (3H), 2.62 (2H), 2.79 (1H), 3.54 (2H), 6.19 (1H), 7.06 (1H), 7.30-7.42 (2H), 7.48 (1H), 7.55 (1H), 7.65 (1H), 7.68 (1H), 7.95 (1H), 8.24 (1H) ppm.

Example 388

N-cyclopropyl-4-{6-[(2-methoxyphenyl)amino]-8-[(3,3,3-trifluoropropyl)amino]imidazo[1,2-b]pyridazin-3-yl}-2-methylbenzamide

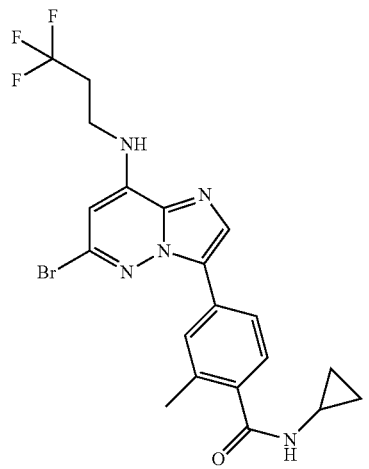

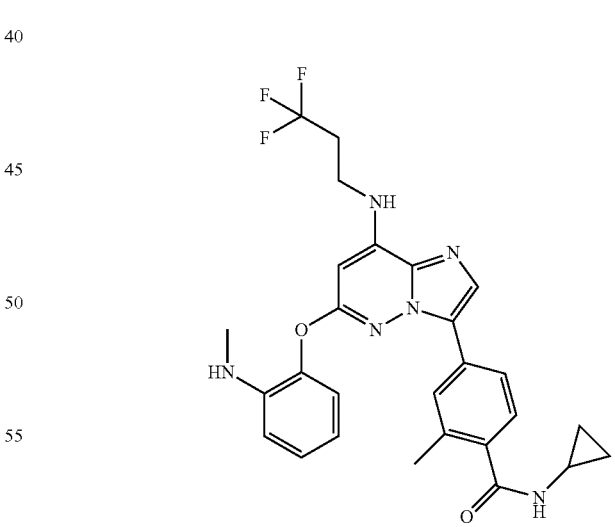

200 mg (415 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 2-methoxyaniline to give after working up and purification 68.3 mg (31%) of the title compound.

510

¹H-NMR (DMSO-d6): δ=0.51 (2H), 0.65 (2H), 2.35 (3H), 2.69 (2H), 2.80 (1H), 3.29 (3H), 3.49 (2H), 6.28 (1H), 6.87-7.05 (3H), 7.21 (1H), 7.31 (1H), 7.78 (1H), 7.84 (1H), 8.02 (1H), 8.09 (1H), 8.24-8.32 (2H) ppm.

Example 389

N-cyclopropyl-2-methyl-4-{6-[2-(methylamino)phenoxy]-8-[(3,3,3-trifluoropropyl)amino]imidazo[1,2-b]pyridazin-3-yl}benzamide

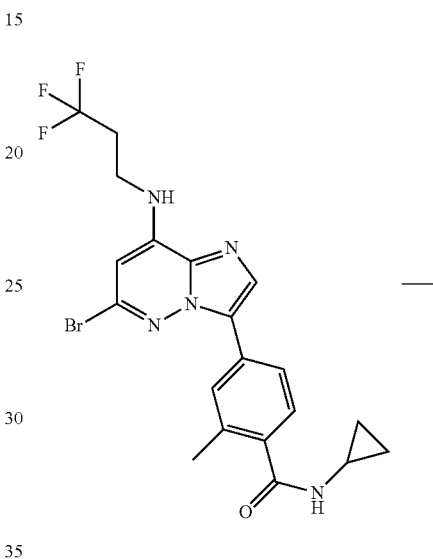

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-(methylamino)phenol to give after working up and purification 35.1 mg (43%) of the title compound.

511

¹H-NMR (DMSO-d6): δ=0.50 (2H), 0.65 (2H), 2.33 (3H), 2.46 (2H), 2.80 (1H), 3.25 (2H), 3.29 (3H), 5.21 (1H), 6.84 (1H), 6.95 (1H), 7.06 (1H), 7.14 (1H), 7.19 (1H), 7.31 (1H), 7.82 (1H), 8.04 (1H), 8.09 (1H), 8.26 (1H), 9.54 (1H) ppm.

Example 390

N-cyclopropyl-4-{6-(5-fluoro-2-methylphenoxy)-8-[(3,3,3-trifluoropropyl)amino]imidazo[1,2-b]pyridazin-3-yl}-2-methylbenzamide

512

¹H-NMR (DMSO-d6): δ=0.46 (2H), 0.63 (2H), 2.10 (6H), 2.69 (2H), 2.76 (1H), 3.60 (2H), 6.16 (1H), 7.07 (1H), 7.13 (1H), 7.18 (1H), 7.37 (1H), 7.60 (1H), 7.69 (1H), 7.72 (1H), 7.93 (1H), 8.21 (1H) ppm.

Example 391

N-cyclopropyl-4-{6-(5-fluoro-2-methylphenoxy)-8-[(2-hydroxy-2-methylpropyl)amino]imidazo[1,2-b]pyridazin-3-yl}-2-methylbenzamide

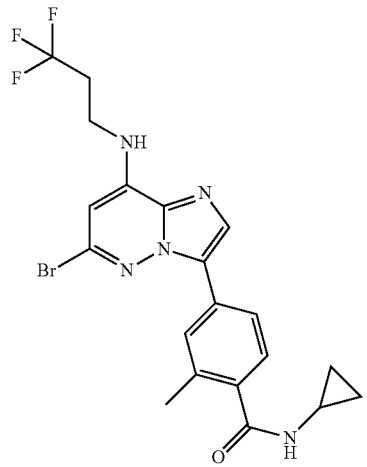

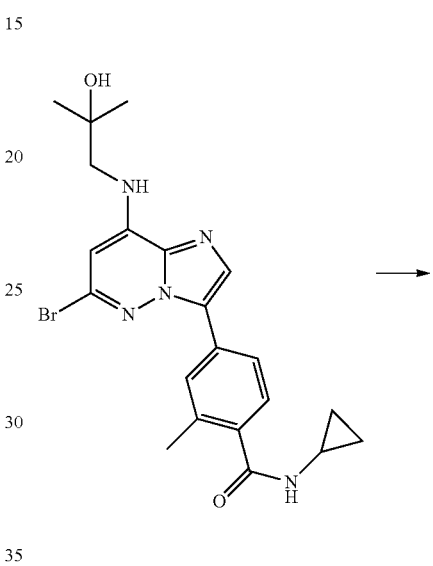

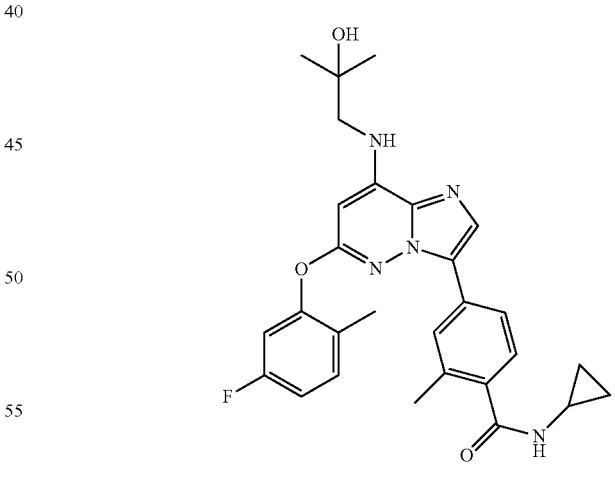

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 5-fluoro-2-methylphenol to give after working up and purification 31.5 mg (38%) of the title compound.

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 5-fluoro-2-methylphenol to give after working up and purification 29.4 mg (54%) of the title compound.

513

¹H-NMR (DMSO-d6): δ=0.46 (2H), 0.73 (2H), 1.17 (6H), 2.10 (6H), 2.76 (1H), 3.28 (2H), 4.76 (1H), 6.20 (1H), 6.98 (1H), 7.06 (1H), 7.13 (1H), 7.17 (1H), 7.36 (1H), 7.61 (1H), 7.71 (1H), 7.92 (1H), 8.21 (1H) ppm.

Example 392

4-(6-{[4-chloro-2-(hydroxymethyl)phenyl]sulfanyl}-8-[(3,3,3-trifluoropropyl)amino]imidazo[1,2-b]pyridazin-3-yl)-N-cyclopropyl-2-methylbenzamide

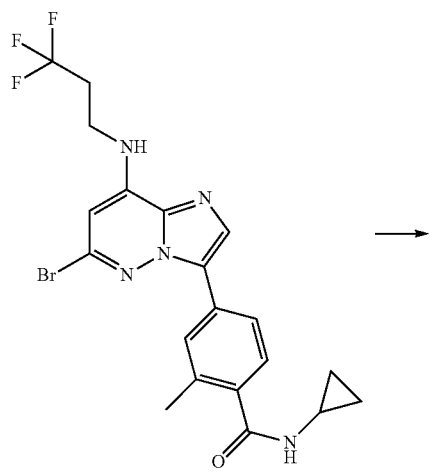

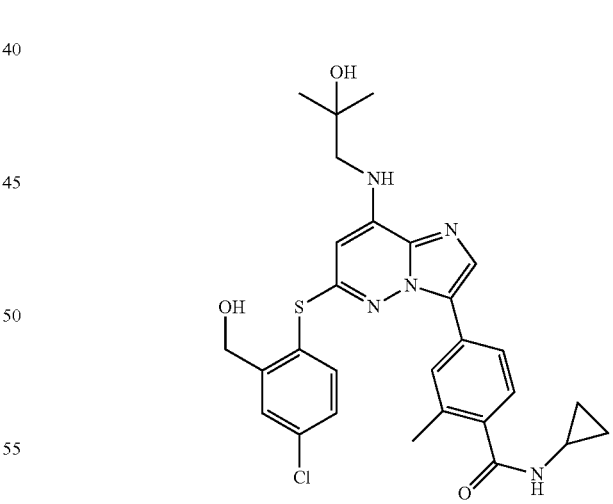

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using (5-chloro-2-sulfanylphenyl)methanol to give after working up and purification 49.0 mg (55%) of the title compound.

514

¹H-NMR (DMSO-d6): δ=0.48 (2H), 0.65 (2H), 2.19 (3H), 2.63 (2H), 2.79 (1H), 3.54 (2H), 4.58 (2H), 5.43 (1H), 6.21 (1H), 7.06 (1H), 7.42 (1H), 7.47 (1H), 7.58-7.70 (4H), 7.94 (1H), 8.24 (1H) ppm.

Example 393

4-(6-{[4-chloro-2-(hydroxymethyl)phenyl]sulfanyl}-8-[(2-hydroxy-2-methylpropyl)amino]imidazo[1,2-b]pyridazin-3-yl)-N-cyclopropyl-2-methylbenzamide

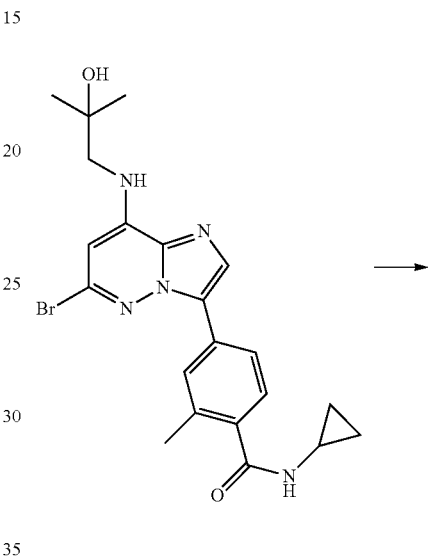

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using (5-chloro-2-sulfanylphenyl)methanol to give after working up and purification 57.0 mg (63%) of the title compound.

515

¹H-NMR (DMSO-d6): δ=0.48 (2H), 0.65 (2H), 1.13 (6H), 2.19 (3H), 2.79 (1H), 3.24 (2H), 4.57 (2H), 4.72 (1H), 5.42 (1H), 6.28 (1H), 6-98 (1H), 7.06 (1H), 7.41 (1H), 7.48 (1H), 7.59 (1H), 7.61 (1H), 7.64 (1H), 7.92 (1H), 8.23 (1H) ppm.

Example 394

N-cyclopropyl-4-{6-[(3-fluoro-5-methylphenyl)amino]-8-[(2-hydroxy-2-methylpropyl)amino]imidazo[1,2-b]pyridazin-3-yl}-2-methylbenzamide

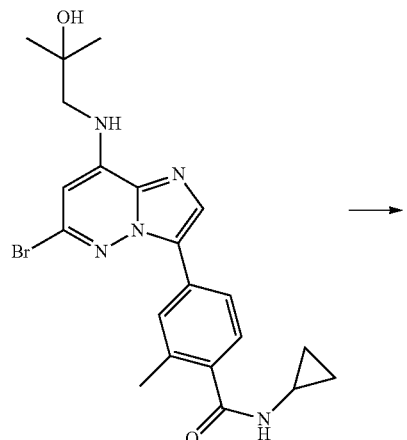

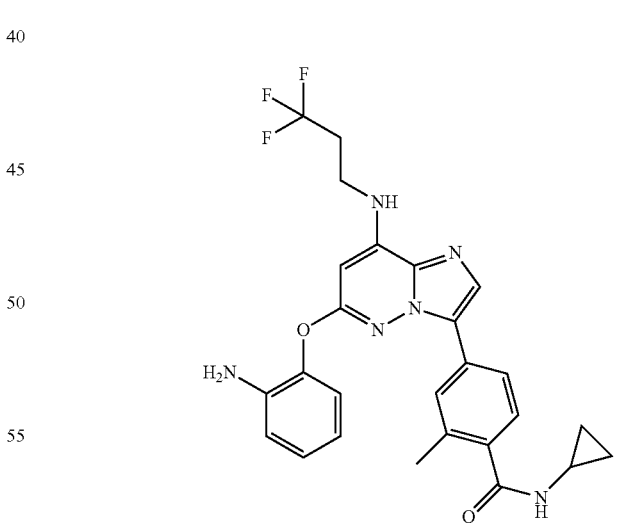

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3-fluoro-5-methylaniline to give after working up and purification 9.7 mg (11%) of the title compound.

516

¹H-NMR (DMSO-d6): δ=0.49 (2H), 0.65 (2H), 1.18 (6H), 2.24 (3H), 2.34 (3H), 2.81 (1H), 3.16 (2H), 4.81 (1H), 5.89 (1H), 6.52 (1H), 6.61 (1H), 7.05 (1H), 7.32 (1H), 7.53 (1H), 7.76 (1H), 7.88 (1H), 7.98 (1H), 8.29 (1H), 9.11 (1H) ppm.

Example 395

4-{6-(2-aminophenoxy)-8-[(3,3,3-trifluoropropyl)amino]imidazo[1,2-b]pyridazin-3-yl}-N-cyclopropyl-2-methylbenzamide

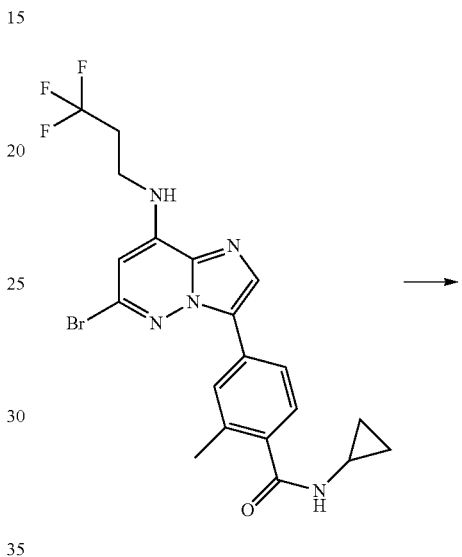

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-aminophenol to give after working up and purification 25.6 mg (32%) of the title compound.

¹H-NMR (DMSO-d6): δ=0.47 (2H), 0.63 (2H), 2.13 (3H), 2.69 (2H), 2.76 (1H), 3.58 (2H), 4.92 (2H), 6.08 (1H), 6.58 (1H), 6.79 (1H), 6.97 (1H), 7.03 (1H), 7.13 (1H), 7.59 (1H), 7.67 (1H), 7.83 (1H), 7.91 (1H), 8.20 (1H) ppm.

Example 396

4-{6-(2-amino-4-fluorophenoxy)-8-[(3,3,3-trifluoropropyl)amino]imidazo[1,2-b]pyridazin-3-yl}-N-cyclopropyl-2-methylbenzamide (A) and N-cyclopropyl-4-{6-[(4-fluoro-2-hydroxyphenyl)amino]-8-[(3,3,3-trifluoropropyl)amino]imidazo[1,2-b]pyridazin-3-yl}-2-methylbenzamide (B)

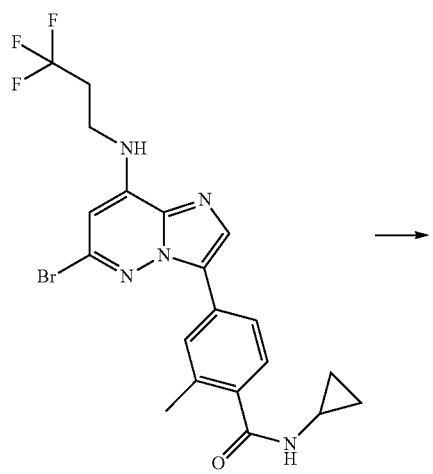

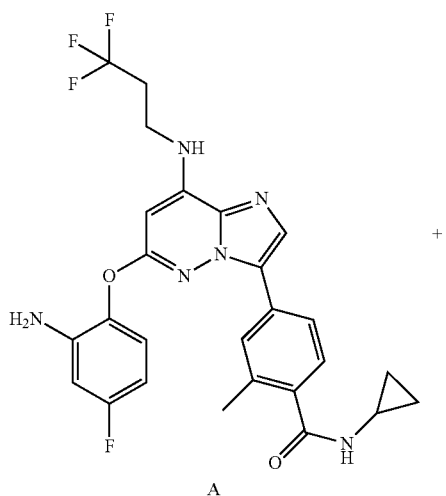

A

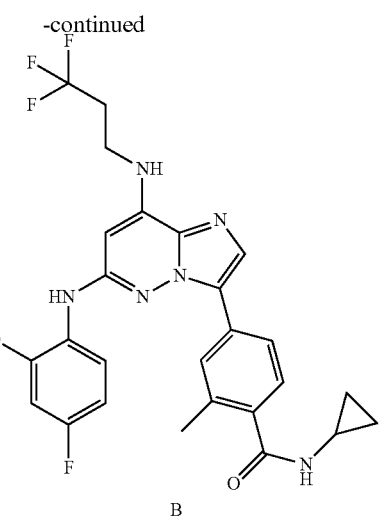

B 75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-amino-5-fluorophenol to give after working up and purification 14.8 mg (18%) of the title compound A and 12.6 mg (15%) of the title compound B.

¹H-NMR (DMSO-d6) of A: δ=0.47 (2H), 0.64 (2H), 2.15 (3H), 2.69 (2H), 2.77 (1H), 3.58 (2H), 5.27 (2H), 6.08 (1H), 6.34 (1H), 6.55 (1H), 7.03 (1H), 7.15 (1H), 7.60 (1H), 7.67 (1H), 7.83 (1H), 7.92 (1H), 8.22 (1H) ppm.

¹H-NMR (DMSO-d6) of B: δ=0.50 (2H), 0.66 (2H), 2.34 (3H), 2.68 (2H), 2.81 (1H), 3.49 (2H), 6.38 (1H), 6.55 (1H), 6.79 (1H), 7.26 (1H), 7.30 (1H), 7.76 (1H), 7.82 (1H), 8.04 (1H), 8.09 (1H), 8.14 (1H), 8.29 (1H), 9.86 (1H) ppm.

Example 397

4-{6-(2-chloro-3-fluorophenoxy)-8-[(2-hydroxy-2-methylpropyl)amino]imidazo[1,2-b]pyridazin-3-yl}-N-cyclopropyl-2-methylbenzamide

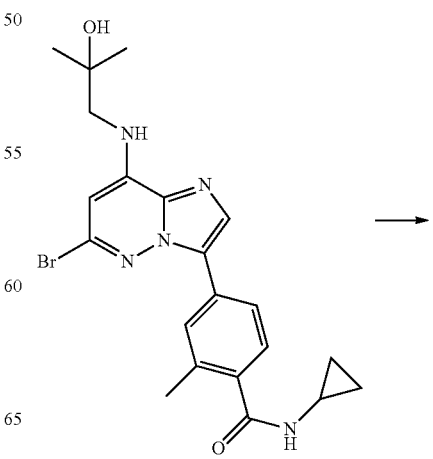

519

-continued

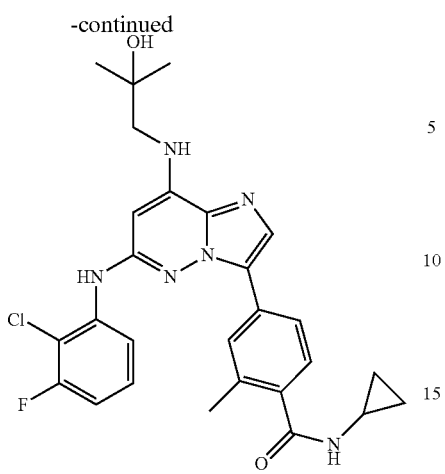

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2-chloro-3-fluoroaniline to give after working up and purification 6.0 mg (6%) of the title compound.

¹H-NMR (DMSO-d6): δ=0.51 (2H), 0.66 (2H), 1.17 (6H), 2.36 (3H), 2.81 (1H), 3.17 (2H), 4.83 (1H), 5.95 (1H), 6.68 (1H), 7.28 (1H), 7.35 (1H), 7.40 (1H), 7.76 (1H), 7.81 (1H), 7.95 (1H), 7.99 (1H), 8.31 (1H), 9.51 (1H) ppm.

520

-continued

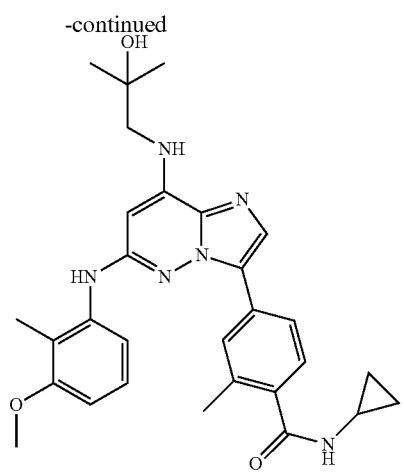

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 3-methoxy-2-methylaniline to give after working up and purification 16.7 mg (20%) of the title compound.

¹H-NMR (DMSO-d6): δ=0.48 (2H), 0.64 (2H), 1.18 (6H), 2.06 (3H), 2.21 (3H), 2.78 (1H), 3.15 (2H), 3.77 (3H), 4.81 (1H), 5.97 (1H), 6.40 (1H), 6.73 (1H), 7.13 (1H), 7.18 (1H), 7.24 (1H), 7.79 (2H), 8.01 (2H), 8.22 (1H) ppm.

Example 398

N-cyclopropyl-4-{8-[(2-hydroxy-2-methylpropyl)amino]-6-[(3-methoxy-2-methylphenyl)amino]imidazo[1,2-b]pyridazin-3-yl}-2-methylbenzamide

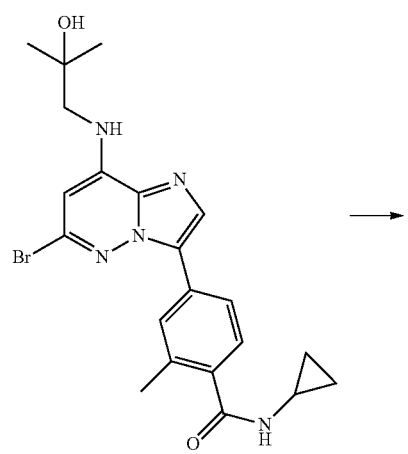

Example 399

N-cyclopropyl-4-{6-[(2-hydroxyphenyl)amino]-8-[(3,3,3-trifluoropropyl)amino]imidazo[1,2-b]pyridazin-3-yl}-2-methylbenzamide

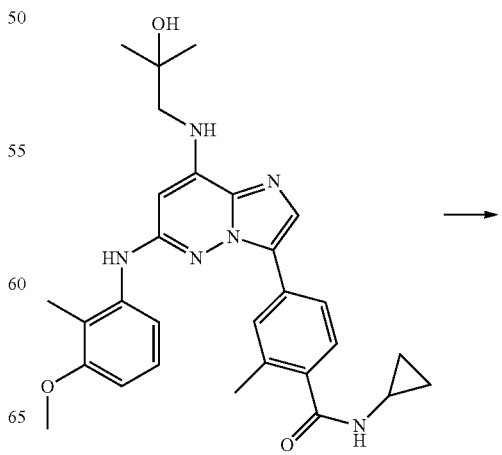

521
-continued

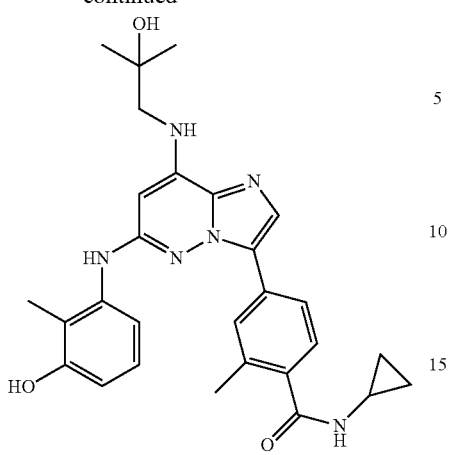

40 mg (76 μmol) N-cyclopropyl-4-{6-[(2-methoxyphenyl)amino]-8-[(3,3,3-trifluoropropyl)amino]imidazo[1,2-b]pyridazin-3-yl}-2-methylbenzamide which was prepared according to example 388 were transformed in analogy to intermediate example 280 to give after working up and purification 14.7 mg (36%) of the title compound.

$^1$H-NMR (DMSO-d6): δ=0.51 (2H), 0.66 (2H), 2.35 (3H), 2.68 (2H), 2.80 (1H), 3.48 (2H), 6.28 (1H), 6.73-6.88 (3H), 7.17 (1H), 7.30 (1H), 7.77 (1H), 7.83 (1H), 7.91 (1H), 8.10 (1H), 8.18 (1H), 8.28 (1H), 9.80 (1H) ppm.

522
-continued 75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to intermediate example 305 using 4-fluoro-3-methoxyaniline to give after working up and purification 20.3 mg (24%) of the title compound.

$^1$H-NMR (DMSO-d6): δ=0.51 (2H), 0.66 (2H), 1.18 (6H), 2.33 (3H), 2.81 (1H), 3.16 (2H), 3.67 (3H), 4.80 (1H), 5.85 (1H), 6.57 (1H), 7.08 (1H), 7.23 (1H), 7.28 (1H), 7.33 (1H), 7.75 (1H), 7.86 (1H), 7.99 (1H), 8.27 (1H), 8.91 (1H) ppm.

Example 400

N-cyclopropyl-4-{6-[(4-fluoro-3-methoxyphenyl)amino]-8-[(2-hydroxy-2-methylpropyl)amino]imidazo[1,2-b]pyridazin-3-yl}-2-methylbenzamide

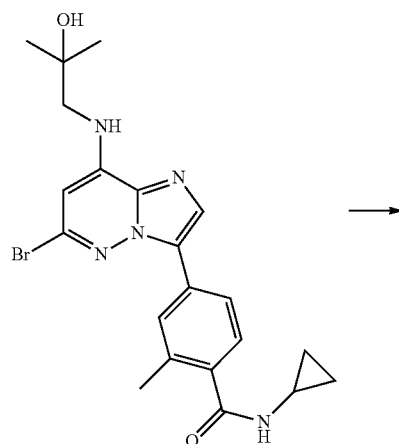

Example 401

4-{6-[(4-chloro-3-fluorophenyl)amino]-8-[(2-hydroxy-2-methylpropyl)amino]imidazo[1,2-b]pyridazin-3-yl}-N-cyclopropyl-2-methylbenzamide

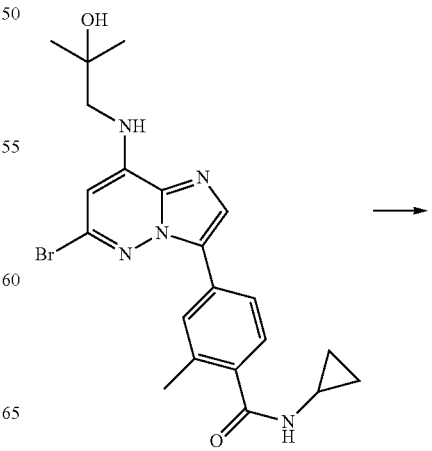

523

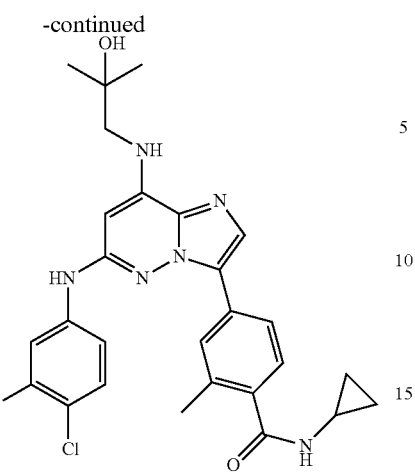

75 mg (164 µmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to intermediate example 305 using 4-chloro-3-fluoroaniline to give after working up and purification 5.6 mg (7%) of the title compound.

$^1$H-NMR (DMSO-d6): δ=0.52 (2H), 0.66 (2H), 1.18 (6H), 2.37 (3H), 2.82 (1H), 3.17 (2H), 4.81 (1H), 5.91 (1H), 6.69 (1H), 7.28 (1H), 7.35 (1H), 7.41 (1H), 7.76 (1H), 7.81 (1H), 7.95 (1H), 7.99 (1H), 8.31 (1H), 9.41 (1H) ppm.

524

50 mg (109 µmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 305 using 2-methoxyaniline to give after working up and purification 59.7 mg (35%) of the title compound.

$^1$H-NMR (DMSO-d6): δ=0.51 (2H), 0.66 (2H), 1.18 (6H), 2.35 (3H), 2.80 (1H), 3.17 (2H), 3.84 (3H), 4.78 (1H), 6.29 (1H), 6.43 (1H), 6.88-6.96 (2H), 7.00 (1H), 7.31 (1H), 7.77 (1H), 7.84 (1H), 7.92 (1H), 8.09 (1H), 8.25 (1H), 8.29 (1H) ppm.

Example 402

N-cyclopropyl-4-{8-[(2-hydroxy-2-methylpropyl)amino]-6-[(2-methoxyphenyl)amino]imidazo[1,2-b]pyridazin-3-yl}-2-methylbenzamide

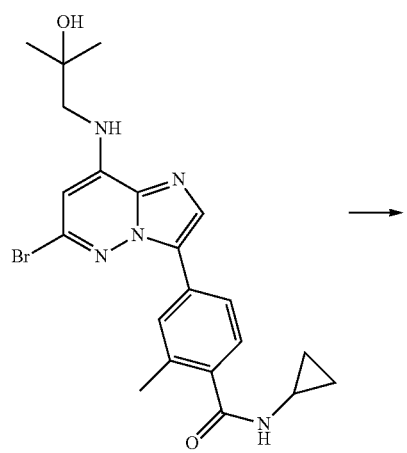

Example 403

N-cyclopropyl-4-{8-[(2-hydroxy-2-methylpropyl)amino]-6-[(3-methoxyphenyl)amino]imidazo[1,2-b]pyridazin-3-yl}-2-methylbenzamide

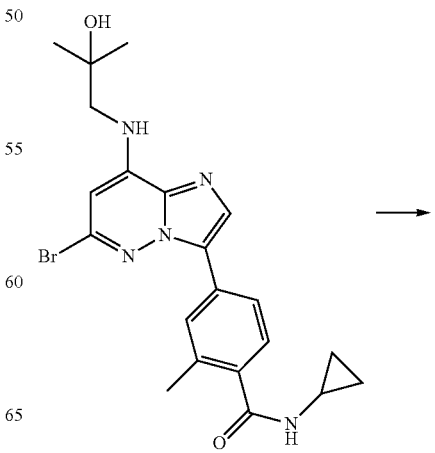

525
-continued

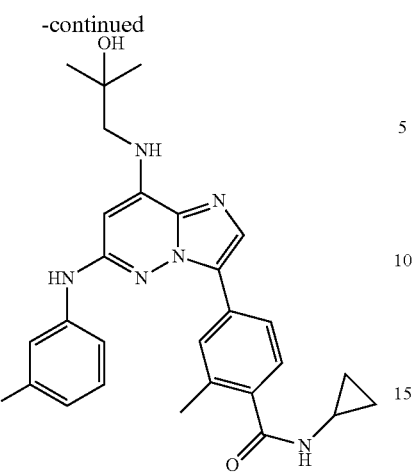

150 mg (327 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 305 using 3-methoxyaniline to give after working up and purification 44.4 mg (24%) of the title compound.

$^1$H-NMR (DMSO-d6): δ=0.51 (2H), 0.67 (2H), 1.18 (6H), 2.36 (3H), 2.81 (1H), 3.15 (2H), 3.66 (3H), 4.80 (1H), 5.88 (1H), 6.48 (1H), 6.55 (1H), 7.16 (1H), 7.20-7.28 (2H), 7.32 (1H), 7.77 (1H), 7.86 (1H), 8.08 (1H), 8.29 (1H), 8.90 (1H) ppm.

526
-continued

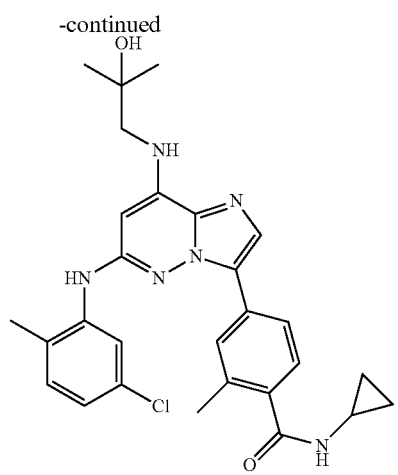

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 305 using 5-chloro-2-methylaniline to give after working up and purification 6.2 mg (7%) of the title compound.

$^1$H-NMR (DMSO-d6): δ=0.48 (2H), 0.64 (2H), 1.19 (6H), 2.23 (3H), 2.26 (3H), 2.78 (1H), 3.17 (2H), 4.82 (1H), 6.10 (1H), 6.52 (1H), 6.99 (1H), 7.20 (1H), 7.26 (1H), 7.82 (1H), 7.88-7.96 (3H), 8.01 (1H), 8.23 (1H) ppm.

Example 404

4-{6-[(5-chloro-2-methylphenyl)amino]-8-[(2-hydroxy-2-methylpropyl)amino]imidazo[1,2-b]pyridazin-3-yl}-N-cyclopropyl-2-methylbenzamide

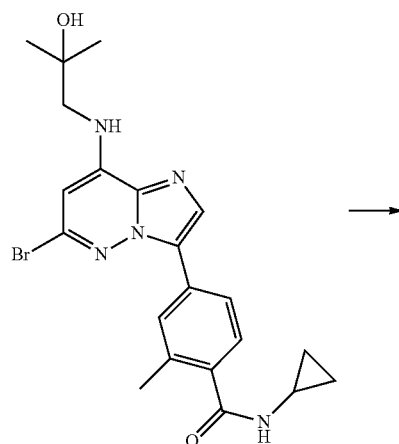

Example 405

4-{6-[(2-chloro-4-fluorophenyl)amino]-8-[(2-hydroxy-2-methylpropyl)amino]imidazo[1,2-b]pyridazin-3-yl}-N-cyclopropyl-2-methylbenzamide

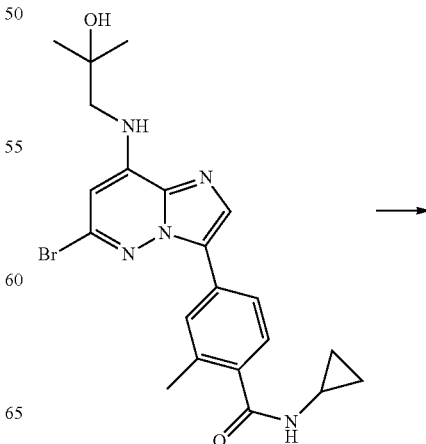

527
-continued

528
-continued

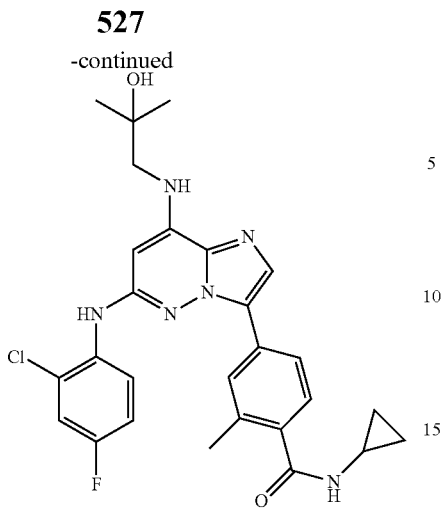

75 mg (164 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 2-chloro-4-fluoroaniline to give after working up and purification 7.3 mg (8%) of the title compound.

¹H-NMR (DMSO-d6): δ=0.49 (2H), 0.64 (2H), 1.18 (6H), 2.24 (3H), 2.78 (1H), 3.17 (2H), 4.80 (1H), 5.72 (1H), 6.09 (1H), 6.53 (1H), 7.23 (1H), 7.49 (1H), 7.76 (1H), 7.79 (1H), 7.90 (1H), 7.92 (1H), 8.23 (1H), 8.25 (1H) ppm.

50 mg (109 µmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 6-fluoropyridin-3-amine to give after working up and purification 9.9 mg (18%) of the title compound.

¹H-NMR (DMSO-d6): δ=0.51 (2H), 0.66 (2H), 1.18 (6H), 2.37 (3H), 2.81 (1H), 3.17 (2H), 4.80 (1H), 5.87 (1H), 6.67 (1H), 7.10 (1H), 7.34 (1H), 7.76 (1H), 7.78 (1H), 8.00 (1H), 8.16 (1H), 8.29 (1H), 8.50 (1H), 9.17 (1H) ppm.

Example 406

N-cyclopropyl-4-{6-[(6-fluoropyridin-3-yl)amino]-8-[(2-hydroxy-2-methylpropyl)amino]imidazo[1,2-b]pyridazin-3-yl}-2-methylbenzamide

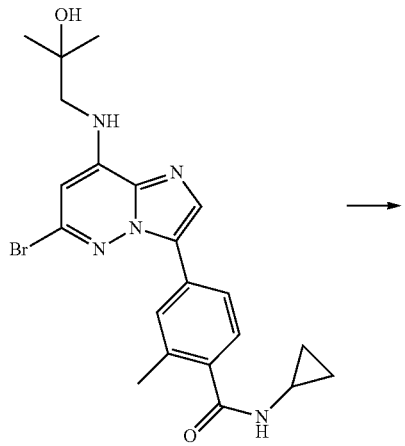

Example 407

4-{6-(cyclopentylamino)-8-[(2-hydroxy-2-methylpropyl)amino]imidazo[1,2-b]pyridazin-3-yl}-N-cyclopropyl-2-methylbenzamide

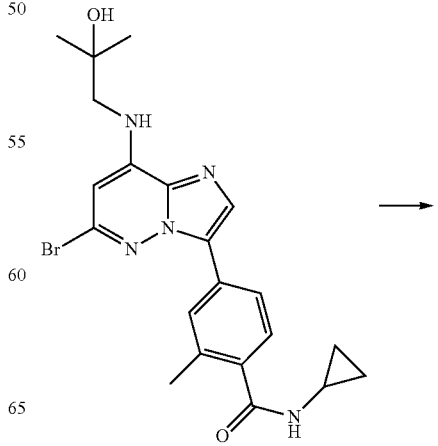

529

-continued

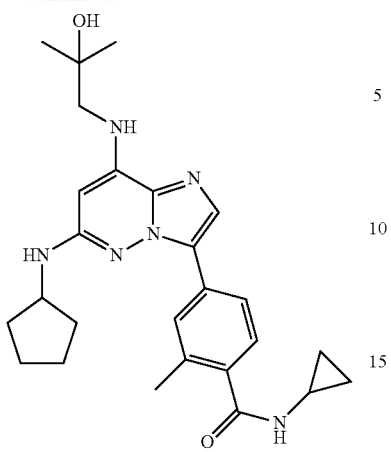

50 mg (109 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using cyclopentanamine to give after working up and purification 10.8 mg (20%) of the title compound.

$^1$H-NMR (DMSO-d6): δ=0.50 (2H), 0.64 (2H), 1.15 (6H), 1.43-1.72 (6H), 1.97 (2H), 2.34 (3H), 2.79 (1H), 3.06 (2H), 3.99 (1H), 4.76 (1H), 5.61 (1H), 6.17 (1H), 6.37 (1H), 7.29 (1H), 7.72 (1H), 7.99 (1H), 8.17 (1H), 8.24 (1H) ppm.

530

-continued

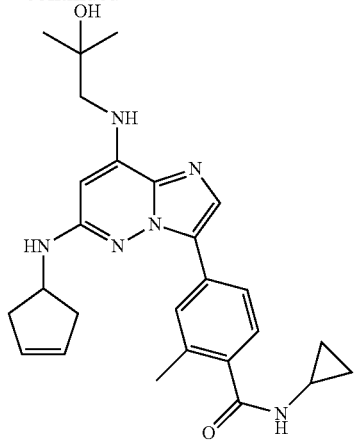

100 mg (218 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using cyclopent-3-en-1-amine to give after working up and purification 12.8 mg (12%) of the title compound.

$^1$H-NMR (DMSO-d6): δ=0.50 (2H), 0.64 (2H), 1.15 (6H), 2.25 (1H), 2.28 (1H), 2.34 (3H), 2.73-2.83 (3H), 3.07 (2H), 4.32 (1H), 4.76 (1H), 5.61 (1H), 5.73 (2H), 6.21 (1H), 6.57 (1H), 7.31 (1H), 7.73 (1H), 8.02 (1H), 8.13 (1H), 8.25 (1H) ppm.

Example 408

4-{6-(cyclopent-3-en-1-ylamino)-8-[(2-hydroxy-2-methylpropyl)amino]imidazo[1,2-b]pyridazin-3-yl}-N-cyclopropyl-2-methylbenzamide

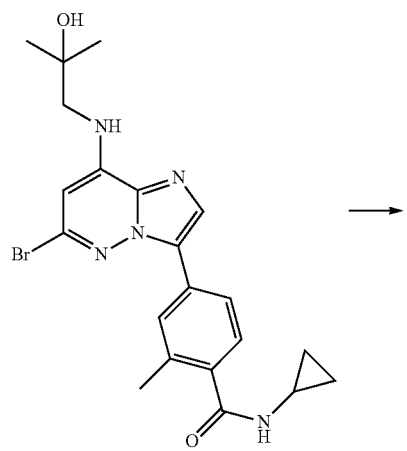

Example 409

N-cyclopropyl-4-{6-[(3-ethenylphenyl)amino]-8-[(2-hydroxy-2-methylpropyl)amino]imidazo[1,2-b]pyridazin-3-yl}-2-methylbenzamide

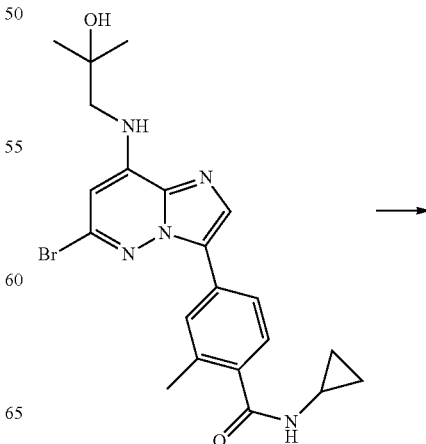

531
-continued

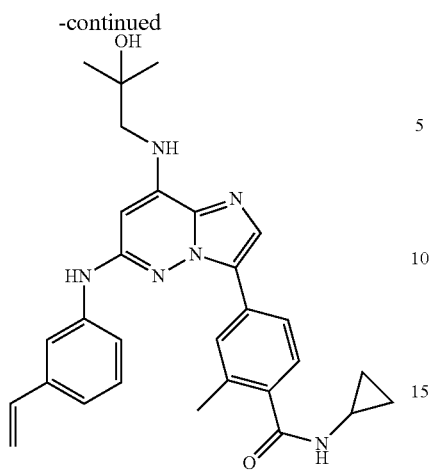

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 305 using 3-vinylaniline to give after working up and purification 28.0 mg (33%) of the title compound.

$^1$H-NMR (DMSO-d6): δ=0.51 (2H), 0.66 (2H), 1.18 (6H), 2.34 (3H), 2.81 (1H), 3.16 (2H), 4.81 (1H), 5.18 (1H), 5.67 (1H), 5.89 (1H), 6.56 (1H), 6.64 (1H), 7.03 (1H), 7.24 (1H), 7.31 (1H), 7.62 (1H), 7.63 (1H), 7.77 (1H), 7.91 (1H), 8.01 (1H), 8.29 (1H), 8.94 (1H) ppm.

532
-continued

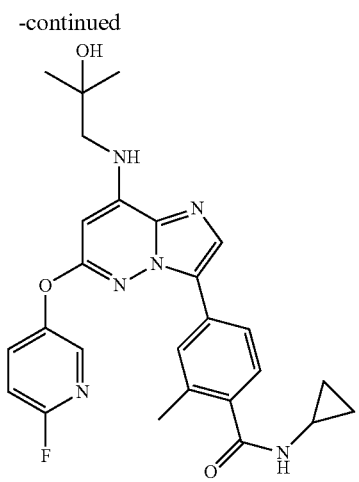

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using 6-fluoropyridin-3-ol to give after working up and purification 4.1 mg (5%) of the title compound.

$^1$H-NMR (DMSO-d6): δ=0.47 (2H), 0.64 (2H), 1.17 (6H), 2.14 (3H), 2.77 (1H), 3.28 (2H), 4.75 (1H), 6.24 (1H), 7.07 (1H), 7.17 (1H), 7.32 (1H), 7.61 (1H), 7.68 (1H), 7.92 (1H), 8.03 (1H), 8.23 (1H), 8.25 (1H) ppm.

Example 410

N-cyclopropyl-4-{6-[(6-fluoropyridin-3-yl)oxy]-8-[(2-hydroxy-2-methylpropyl)amino]imidazo[1,2-b]pyridazin-3-yl}-2-methylbenzamide

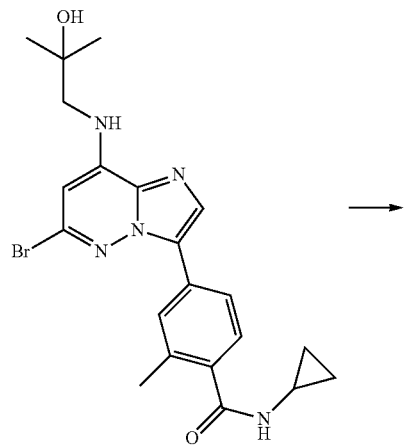

Example 411

5-({3-[4-(cyclopropylcarbamoyl)-3-methylphenyl]-8-[(2-hydroxy-2-methylpropyl)amino]imidazo[1,2-b]pyridazin-6-yl}oxy)nicotinamide

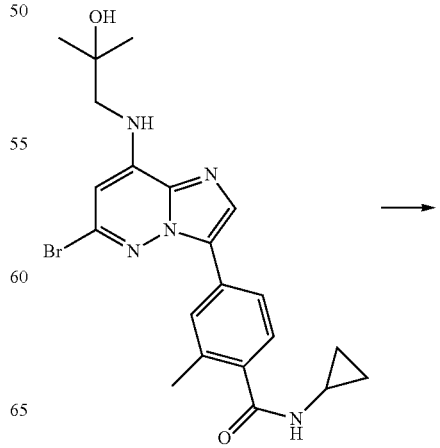

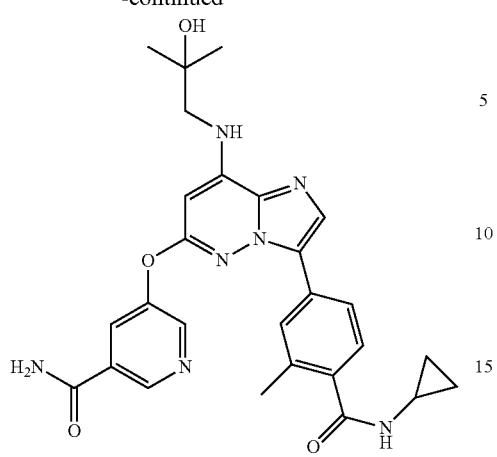

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using 5-hydroxynicotinamide to give after working up and purification 22.0 mg (25%) of the title compound.

$^1$H-NMR (DMSO-d6): δ=0.46 (2H), 0.63 (2H), 1.17 (6H), 2.09 (3H), 2.76 (1H), 3.13 (2H), 4.75 (1H), 6.27 (1H), 7.10 (1H), 7.13 (1H), 7.61 (1H), 7.64 (1H), 7.69 (1H), 7.92 (1H), 8.17-8.22 (3H), 8.72 (1H), 8.96 (1H) ppm.

75 mg (164 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using pyrazine-2-thiol to give after working up and purification 17.5 mg (21%) of the title compound.

$^1$H-NMR (DMSO-d6): δ=0.49 (2H), 0.65 (2H), 1.13 (6H), 2.23 (3H), 2.79 (1H), 3.25 (2H), 4.71 (1H), 6.48 (1H), 7.16 (1H), 7.19 (1H), 7.66 (1H), 7.71 (1H), 7.97 (1H), 8.25 (1H), 8.58 (1H), 8.61 (1H), 8.83 (1H) ppm.

Example 412

N-cyclopropyl-4-{8-[(2-hydroxy-2-methylpropyl)amino]-6-(pyrazin-2-ylsulfanyl) imidazo[1,2-b]pyridazin-3-yl}-2-methylbenzamide

Example 413

N-cyclopropyl-4-{8-[(2-hydroxy-2-methylpropyl)amino]-6-[(4-methyl-4H-1,2,4-triazol-3-yl)sulfanyl] imidazo[1,2-b]pyridazin-3-yl}-2-methylbenzamide

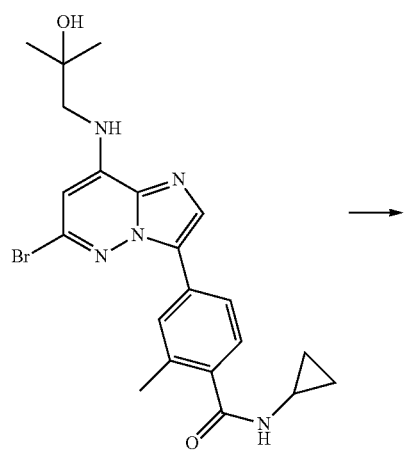

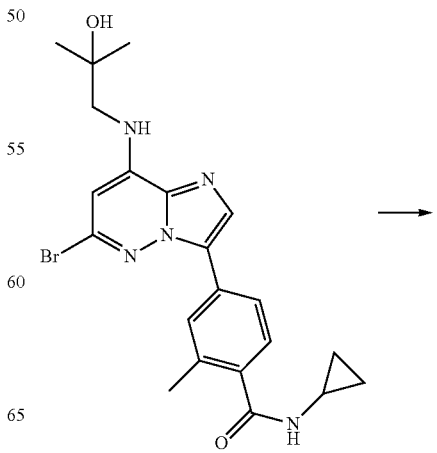

535
-continued

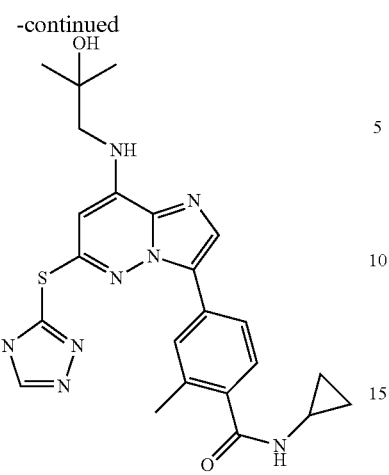

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 4-methyl-4H-1,2,4-triazole-3-thiol to give after working up and purification 17.5 mg (21%) of the title compound.

$^1$H-NMR (DMSO-d6): δ=0.51 (2H), 0.66 (2H), 1.14 (6H), 2.28 (3H), 2.80 (1H), 3.25 (2H), 3.61 (3H), 4.73 (1H), 6.38 (1H), 7.17 (1H), 7.21 (1H), 7.48 (1H), 7.60 (1H), 7.96 (1H), 8.28 (1H), 8.93 (1H) ppm.

536
-continued

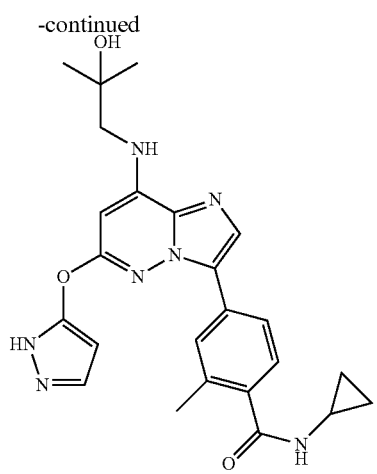

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 1H-pyrazol-5-ol to give after working up and purification 5.5 mg (7%) of the title compound.

$^1$H-NMR (DMSO-d6): δ=0.48 (2H), 0.64 (2H), 1.15 (6H), 2.25 (3H), 2.78 (1H), 3.26 (2H), 4.75 (1H), 6.13 (1H), 6.16 (1H), 6.98 (1H), 7.23 (1H), 7.73-7.80 (2H), 7.91 (1H), 7.93 (1H), 8.26 (1H), 12.45 (1H) ppm.

Example 414

N-cyclopropyl-4-{8-[(2-hydroxy-2-methylpropyl)amino]-6-(1H-pyrazol-5-yloxy) imidazo[1,2-b]pyridazin-3-yl}-2-methylbenzamide

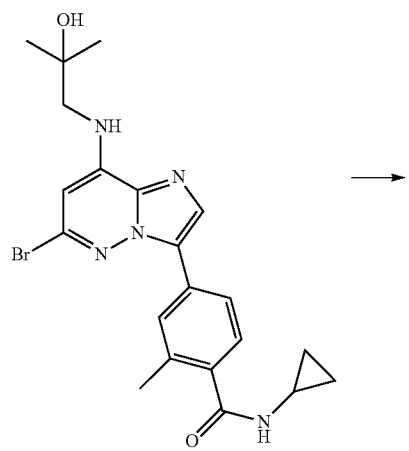

Example 415

N-cyclopropyl-4-{8-[(2-hydroxy-2-methylpropyl)amino]-6-[(5-methyl-1H-pyrazol-3-yl)oxy]imidazo[1,2-b]pyridazin-3-yl}-2-methylbenzamide

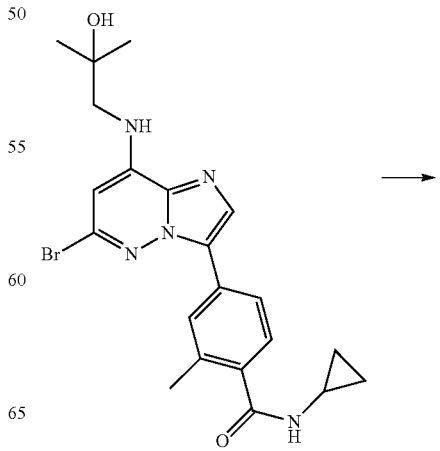

537

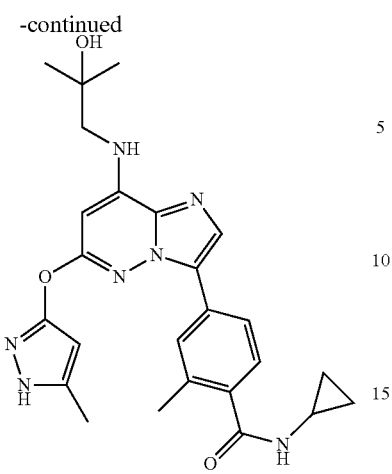

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 5-methyl-1H-pyrazol-3-ol to give after working up and purification 6.3 mg (8%) of the title compound.

$^1$H-NMR (DMSO-d6): δ=0.48 (2H), 0.64 (2H), 1.15 (6H), 2.23 (3H), 2.26 (3H), 2.79 (1H), 3.26 (2H), 4.74 (1H), 5.92 (1H), 6.11 (1H), 6.96 (1H), 7.24 (1H), 7.77 (1H), 7.90 (1H), 7.96 (1H), 8.26 (1H), 12.13 (1H) ppm.

538

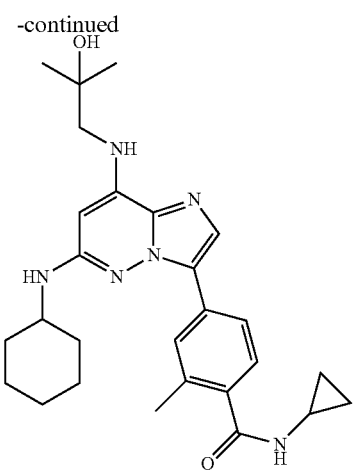

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using cyclohexanamine to give after working up and purification 7.8 mg (10%) of the title compound.

$^1$H-NMR (DMSO-d6): δ=0.50 (2H), 0.64 (2H), 1.11-1.42 (5H), 1.15 (6H), 1.60 (1H), 1.73 (2H), 2.03 (2H), 2.35 (3H), 2.79 (1H), 3.06 (2H), 3.56 (1H), 4.77 (1H), 5.61 (1H), 6.17 (1H), 6.25 (1H), 7.28 (1H), 7.72 (1H), 7.95 (1H), 8.16 (1H), 8.26 (1H) ppm.

Example 416

4-{6-(cyclohexylamino)-8-[(2-hydroxy-2-methylpropyl)amino]imidazo[1,2-b]pyridazin-3-yl}-N-cyclopropyl-2-methylbenzamide

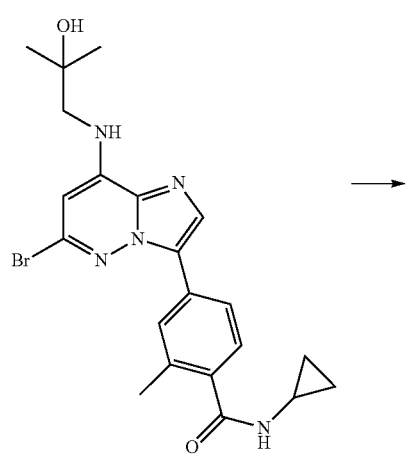

Example 417

4-{6-[(2-amino-4-fluorophenyl)sulfanyl]-8-[(3,3,3-trifluoropropyl)amino]imidazo[1,2-b]pyridazin-3-yl}-N-cyclopropyl-2-methylbenzamide

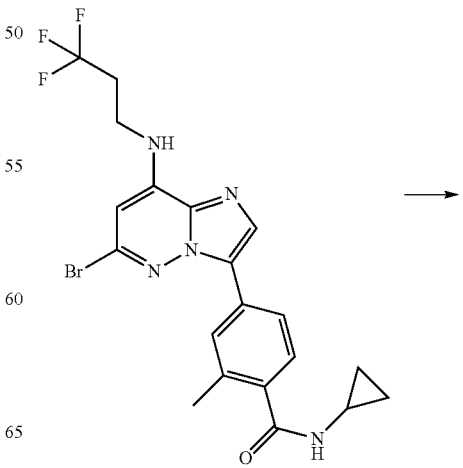

539
-continued

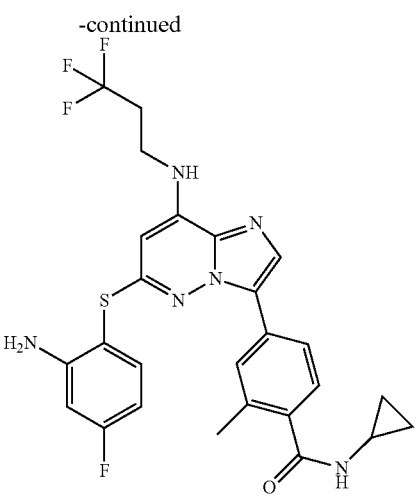

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-amino-4-fluorobenzenethiol to give after working up and purification 23.7 mg (27%) of the title compound.

$^1$H-NMR (DMSO-d6): δ=0.48 (2H), 0.65 (2H), 2.24 (3H), 2.60 (2H), 2.79 (1H), 3.49 (2H), 5.75 (2H), 6.02 (1H), 6.40 (1H), 6.58 (1H), 7.12 (1H), 7.38 (1H), 7.60 (1H), 7.74 (1H), 7.75 (1H), 7.93 (1H), 8.24 (1H) ppm.

540
-continued

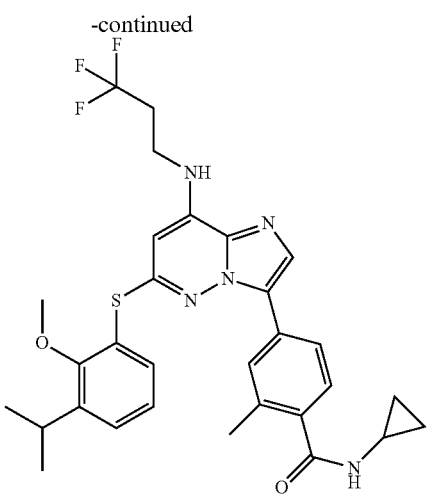

75 mg (156 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 3-isopropyl-2-methoxyphenol to give after working up and purification 45 mg (48%) of the title compound.

$^1$H-NMR (DMSO-d6): δ=0.45 (2H), 0.63 (2H), 1.16 (6H), 2.06 (3H), 2.60-2.80 (3H), 3.17-3.26 (1H), 3.60 (2H), 3.71 (3H), 6.17 (1H), 7.04-7.23 (4H), 7.61 (1H), 7.67 (1H), 7.71 (1H), 7.94 (1H), 8.19 (1H) ppm.

Example 418

N-cyclopropyl-4-{6-[2-methoxy-3-(propan-2-yl)phenoxy]-8-[(3,3,3-trifluoropropyl)amino]imidazo[1,2-b]pyridazin-3-yl}-2-methylbenzamide

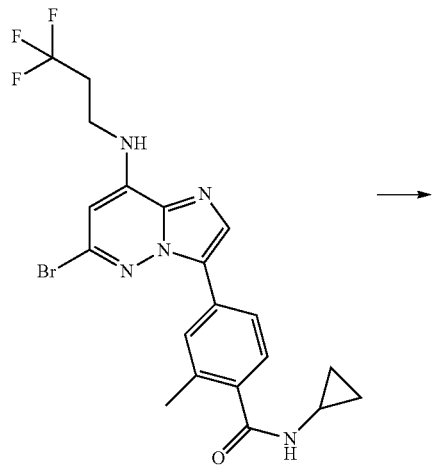

Example 419

N-cyclopropyl-2-methyl-4-{6-[(4-methyl-4H-1,2,4-triazol-3-yl)sulfanyl]-8-[(3,3,3-trifluoropropyl)amino]imidazo[1,2-b]pyridazin-3-yl}benzamide

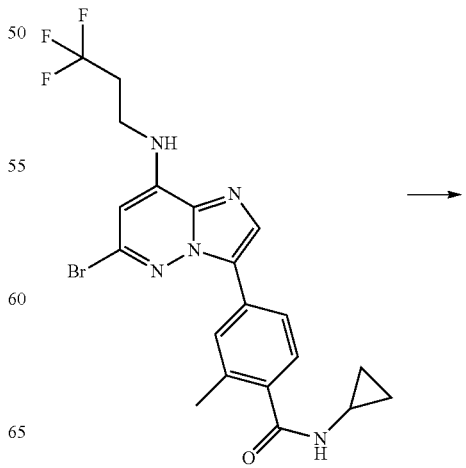

541

-continued

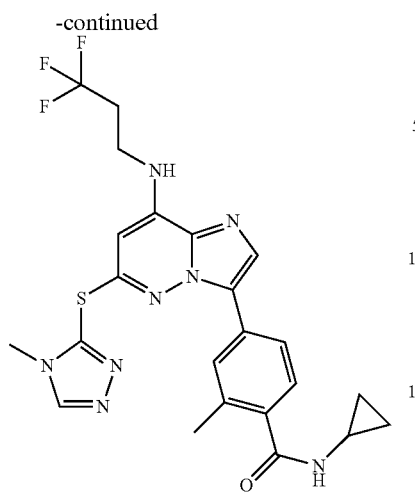

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 4-methyl-4H-1,2,4-triazole-3-thiol to give after working up and purification 29.4 mg (35%) of the title compound.

$^1$H-NMR (DMSO-d6): δ=0.51 (2H), 0.66 (2H), 2.28 (3H), 2.66 (2H), 2.80 (1H), 3.57 (2H), 3.61 (3H), 6.35 (1H), 7.20 (1H), 7.46 (1H), 7.59 (1H), 7.84 (1H), 7.96 (1H), 8.27 (1H), 8.93 (1H) ppm.

542

-continued

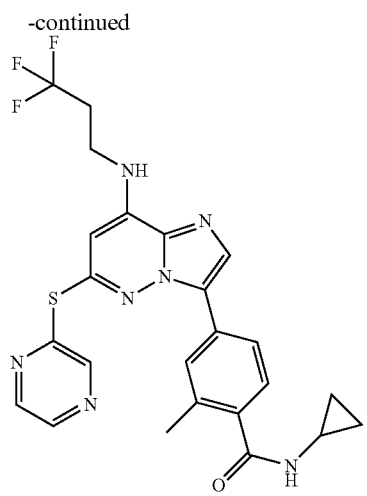

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using pyrazine-2-thiol to give after working up and purification 28.6 mg (34%) of the title compound.

$^1$H-NMR (DMSO-d6): δ=0.49 (2H), 0.64 (2H), 2.23 (3H), 2.64 (2H), 2.79 (1H), 3.57 (2H), 6.43 (1H), 7.18 (1H), 7.64 (1H), 7.69 (1H), 7.83 (1H), 7.97 (1H), 8.25 (1H), 8.57-8.62 (2H), 8.86 (1H) ppm.

Example 420

N-cyclopropyl-2-methyl-4-{6-(pyrazin-2-ylsulfanyl)-8-[(3,3,3-trifluoropropyl)amino]imidazo[1,2-b]pyridazin-3-yl}benzamide

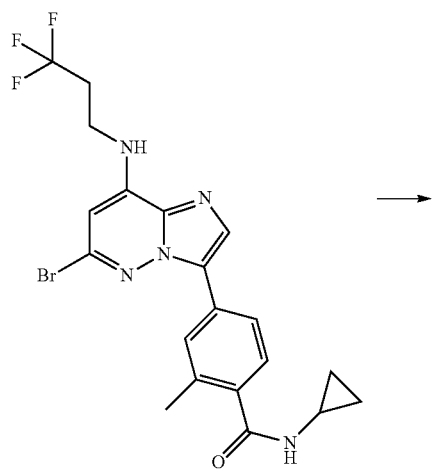

Example 421

N-cyclopropyl-4-(6-{[(1RS,2RS)-2-hydroxycyclohexyl]oxy}-8-[(2-hydroxy-2-methylpropyl)amino]imidazo[1,2-b]pyridazin-3-yl)-2-methylbenzamide

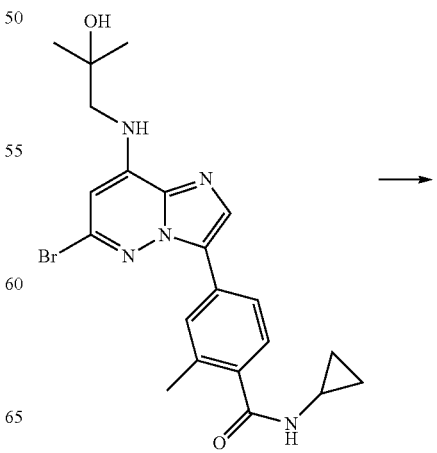

543

-continued

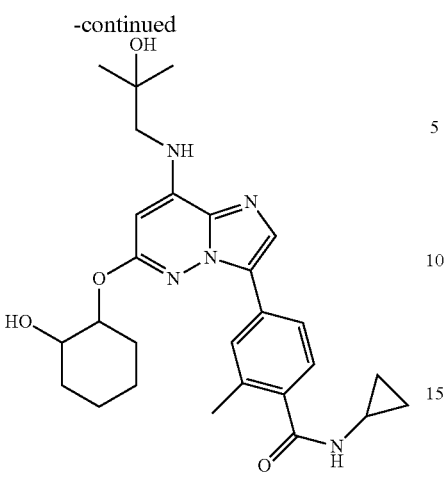

50 mg (109 μmol) 4-{6-bromo-8-[(2-hydroxy-2-methyl-propyl)amino]imidazo[1,2-b]pyridazin-3-yl}-N-cyclopropyl-2-methylbenzamide which was prepared according to intermediate example 96a were transformed in analogy to example 51 using (1RS,2RS)-cyclohexane-1,2-diol to give after working up and purification 2.8 mg (5%) of the title compound.

$^{1}$H-NMR (DMSO-d6): δ=0.50 (2H), 0.65 (2H), 1.13 (6H), 1.23-1.39 (4H), 1.66 (2H), 1.89 (1H), 2.36 (3H), 2.80 (1H), 3.19 (2H), 3.54 (1H), 4.65 (1H), 4.72 (1H), 4.82 (1H), 5.72 (1H), 5.84 (1H), 6.66 (1H), 7.33 (1H), 7.87 (1H), 7.91 (1H), 8.08 (1H), 8.29 (1H) ppm.

544

-continued

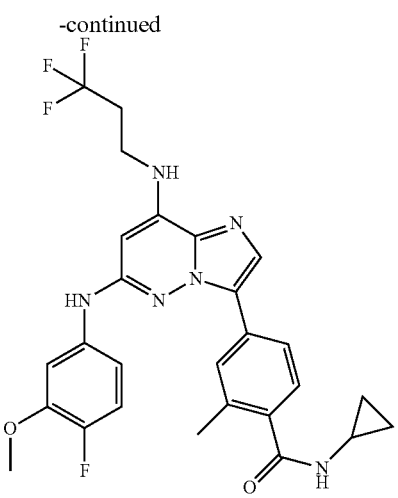

100 mg (207 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-fluoro-3-methoxyaniline to give after working up and purification 43.1 mg (38%) of the title compound.

$^{1}$H-NMR (DMSO-d6): δ=0.51 (2H), 0.66 (2H), 2.33 (3H), 2.67 (2H), 2.81 (1H), 3.49 (2H), 3.67 (3H), 5.78 (1H), 7.08 (1H), 7.19-7.37 (4H), 7.76 (1H), 7.85 (1H), 7.99 (1H), 8.27 (1H), 8.94 (1H) ppm.

Example 422

N-cyclopropyl-4-{6-[(4-fluoro-3-methoxyphenyl)amino]-8-[(3,3,3-trifluoropropyl)amino]imidazo[1,2-b]pyridazin-3-yl}-2-methylbenzamide

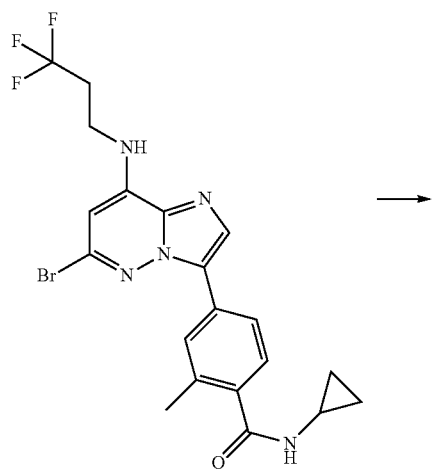

Example 423

N-cyclopropyl-2-methyl-4-{6-[(3-methylphenyl)amino]-8-[(3,3,3-trifluoropropyl)amino]imidazo[1,2-b]pyridazin-3-yl}benzamide

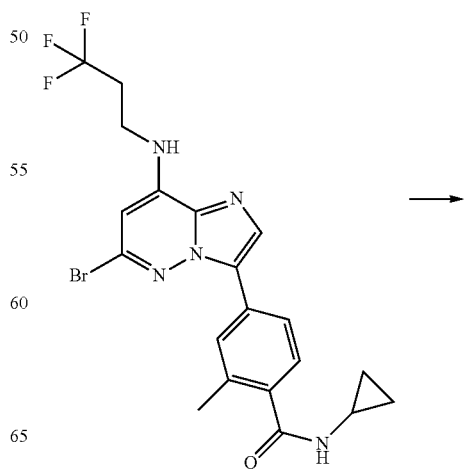

545
-continued

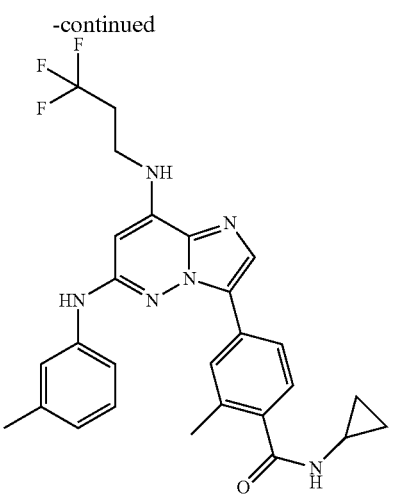

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using m-toluidine to give after working up and purification 14.5 mg (17%) of the title compound.

$^1$H-NMR (CDCl$_3$): δ=0.63 (2H), 0.90 (2H), 2.35 (3H), 2.43-2.58 (2H), 2.51 (3H), 2.61 (1H), 2.92 (1H), 3.59 (2H), 5.64 (1H), 5.78 (1H), 5.91 (1H), 6.25 (1H), 6.89 (1H), 7.22 (1H), 7.35 (1H), 7.40 (1H), 7.65 (1H), 7.90 (1H), 7.92 (1H) ppm.

546
-continued

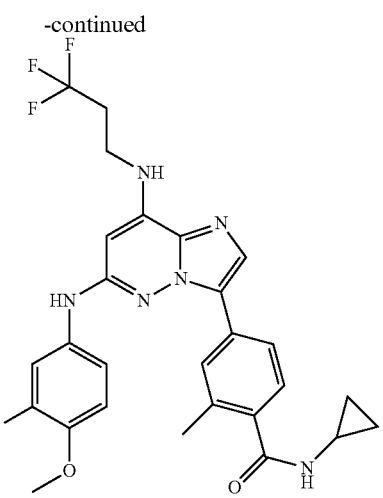

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3-fluoro-4-methoxyaniline to give after working up and purification 21.0 mg (24%) of the title compound.

$^1$H-NMR (CDCl$_3$): δ=0.64 (2H), 0.90 (2H), 2.44-2.60 (2H), 2.51 (3H), 2.92 (1H), 3.59 (2H), 3.89 (3H), 5.55 (1H), 5.78 (1H), 5.94 (1H), 6.20 (1H), 6.92 (1H), 7.06 (1H), 7.41 (1H), 7.55 (1H), 7.64 (1H), 7.83 (1H), 7.92 (1H) ppm.

Example 424

N-cyclopropyl-4-{6-[(3-fluoro-4-methoxyphenyl)amino]-8-[(3,3,3-trifluoropropyl)amino]imidazo[1,2-b]pyridazin-3-yl}-2-methylbenzamide

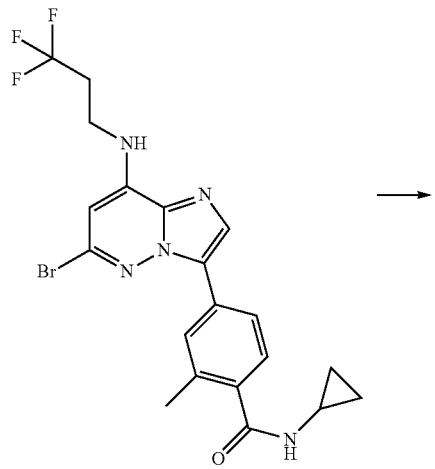

Example 425

N-cyclopropyl-4-{6-[(4-methoxyphenyl)amino]-8-[(3,3,3-trifluoropropyl)amino]imidazo[1,2-b]pyridazin-3-yl}-2-methylbenzamide

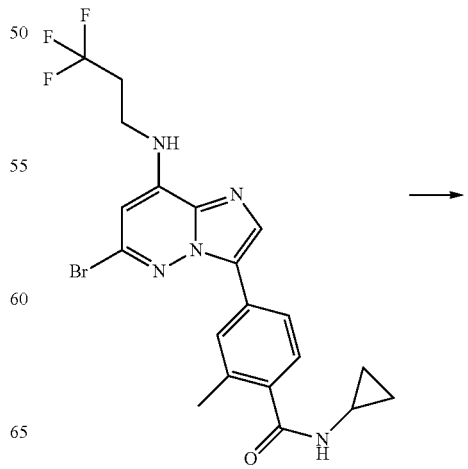

547

-continued

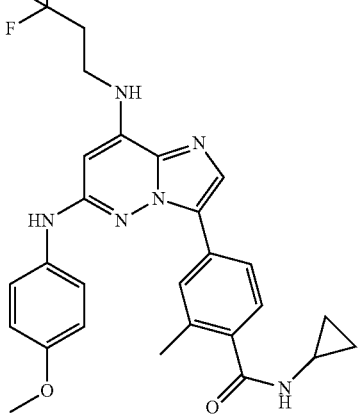

75 mg (156 μmol) 4-{6-bromo-8-[(3,3,3-trifluoropropyl) amino]imidazo[1,2-b]pyridazin-3-yl}-N-cyclopropyl-2-methylbenzamide which was prepared according to intermediate example 247a were transformed in analogy to example 305 using 4-methoxyaniline to give after working up and purification 17.8 mg (21%) of the title compound.

$^1$H-NMR (CDCl$_3$): δ=0.63 (2H), 0.90 (2H), 2.43-2.60 (2H), 2.51 (3H), 2.92 (1H), 3.57 (2H), 3.82 (3H), 5.56 (1H), 5.77 (1H), 5.91 (1H), 6.10 (1H), 6.91 (2H), 7.35-7.42 (3H), 7.64 (1H), 7.83 (1H), 7.98 (1H) ppm.

548

-continued 150 mg (311 μmol) 4-{6-bromo-8-[(3,3,3-trifluoropropyl) amino]imidazo[1,2-b]pyridazin-3-yl}-N-cyclopropyl-2-methylbenzamide which was prepared according to intermediate example 247a were transformed in analogy to example 305 using 3-methoxy-2-methylaniline to give after working up and purification 21.3 mg (12%) of the title compound.

$^1$H-NMR (CDCl$_3$): δ=0.62 (2H), 0.89 (2H), 2.20 (3H), 2.47 (3H), 2.50 (2H), 2.92 (1H), 3.55 (2H), 3.87 (3H), 5.63 (1H), 5.81 (1H), 5.89 (1H), 6.00 (1H), 6.72 (1H), 7.16-7.25 (2H), 7.36 (1H), 7.65 (1H), 7.84 (1H); 7.93 (1H) ppm.

Example 426

N-cyclopropyl-4-{6-[(3-methoxy-2-methylphenyl) amino]-8-[(3,3,3-trifluoropropyl)amino]imidazo[1,2-b]pyridazin-3-yl}-2-methylbenzamide

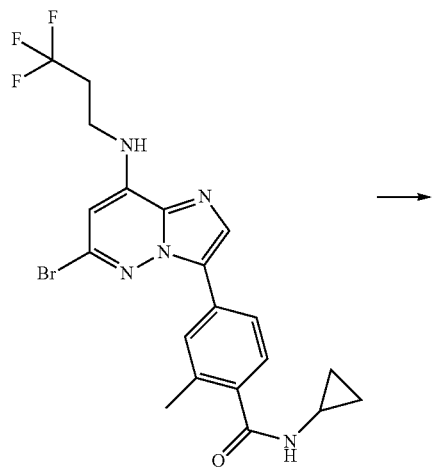

Example 427

N-cyclopropyl-4-(6-{[4-(2-hydroxyethyl)phenyl] amino}-8-[(3,3,3-trifluoropropyl)amino]imidazo[1,2-b]pyridazin-3-yl)-2-methylbenzamide

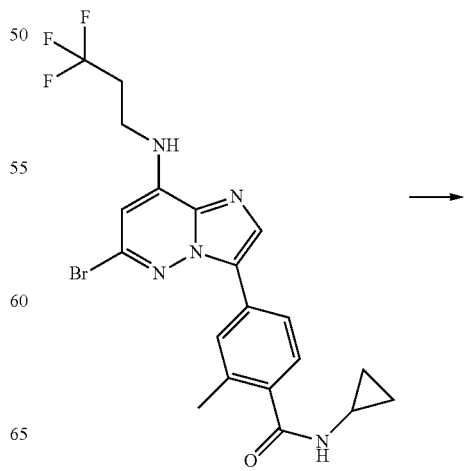

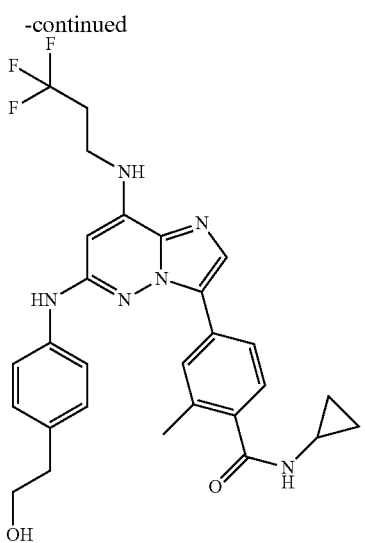

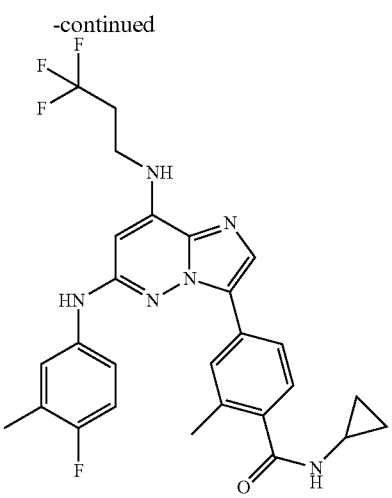

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 2-(4-aminophenyl)ethanol to give after working up and purification 9.2 mg (10%) of the title compound.

$^1$H-NMR (DMSO-d6): δ=0.52 (2H), 0.66 (2H), 2.38 (3H), 2.58-2.77 (4H), 2.82 (1H), 3.41-3.59 (4H), 4.59 (1H), 5.82 (1H), 7.11 (2H), 7.24 (1H), 7.34 (1H), 7.56 (2H), 7.77 (1H), 7.83 (1H), 8.12 (1H), 8.32 (1H), 8.86 (1H) ppm.

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 4-fluoro-3-methylaniline to give after working up and purification 11.9 mg (14%) of the title compound.

$^1$H-NMR (CDCl$_3$): δ=0.63 (2H), 0.89 (2H), 2.25 (3H), 2.42-2.56 (2H), 2.48 (3H), 2.92 (1H), 3.53 (2H), 5.57 (1H), 5.87 (1H), 5.99 (1H), 6.39 (1H), 6.95 (1H), 7.21-7.34 (2H), 7.36 (1H), 7.62 (1H), 7.85 (1H), 7.87 (1H) ppm.

Example 428

N-cyclopropyl-4-{6-[(4-fluoro-3-methylphenyl)amino]-8-[(3,3,3-trifluoropropyl)amino]imidazo[1,2-b]pyridazin-3-yl}-2-methylbenzamide Example 429

N-cyclopropyl-4-{6-[(6-methoxypyridin-3-yl)amino]-8-[(3,3,3-trifluoropropyl)amino]imidazo[1,2-b]pyridazin-3-yl}-2-methylbenzamide

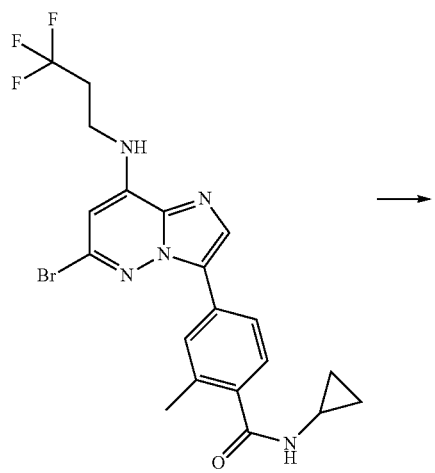

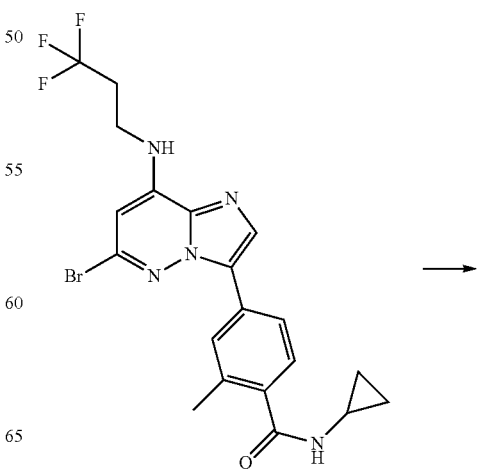

551

-continued

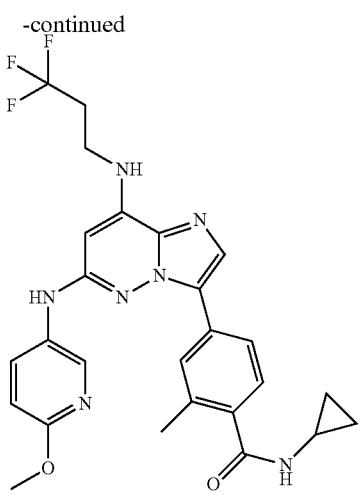

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 6-methoxypyridin-3-amine to give after working up and purification 8.7 mg (10%) of the title compound.

$^1$H-NMR (DMSO-d6): δ=0.50 (2H), 0.64 (2H), 2.37 (3H), 2.68 (2H), 2.80 (1H), 3.30 (3H), 3.49 (2H), 5.77 (1H), 6.78 (1H), 7.25-7.35 (2H), 7.77 (2H), 7.93 (1H), 8.09 (1H), 8.29 (1H), 8.46 (1H), 8.86 (1H) ppm.

552

-continued 150 mg (311 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 5-methoxy-2-methylaniline to give after working up and purification 15.5 mg (9%) of the title compound.

$^1$H-NMR (CDCl$_3$): δ=0.62 (2H), 0.89 (2H), 2.26 (3H), 2.48 (3H), 2.52 (2H), 2.92 (1H), 3.58 (2H), 3.73 (3H), 5.65 (1H), 5.79 (1H), 5.89 (1H), 5.96 (1H), 6.62 (1H), 7.14 (1H), 7.31 (1H), 7.38 (1H), 7.66 (1H), 7.87 (1H), 7.90 (1H) ppm.

Example 430

N-cyclopropyl-4-{6-[(5-methoxy-2-methylphenyl)amino]-8-[(3,3,3-trifluoropropyl)amino]imidazo[1,2-b]pyridazin-3-yl}-2-methylbenzamide

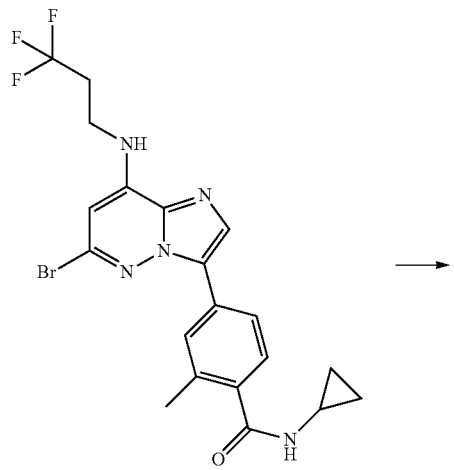

Example 431

N-cyclopropyl-4-{8-[(2-hydroxy-2-methylpropyl)amino]-6-[(2-hydroxyphenyl)amino]imidazo[1,2-b]pyridazin-3-yl}-2-methylbenzamide

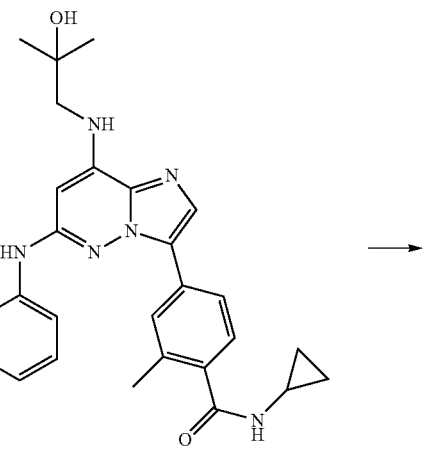

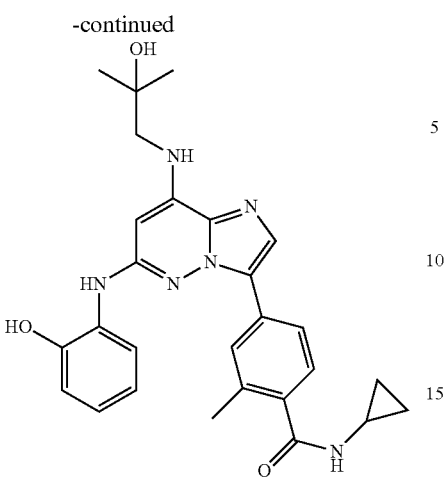

40 mg (80 μmol) N-cyclopropyl-4-{8-[(2-hydroxy-2-methylpropyl)amino]-6-[(2-methoxyphenyl)amino]imidazo[1,2-b]pyridazin-3-yl}-2-methylbenzamide which was prepared according to example 402 were transformed in analogy to example 280 to give after working up and purification 5.8 mg (13%) of the title compound.

$^1$H-NMR (DMSO-d6): δ=0.51 (2H), 0.66 (2H), 1.17 (6H), 2.36 (3H), 2.81 (1H), 3.17 (2H), 4.76 (1H), 6.28 (1H), 6.40 (1H), 6.71-6.89 (3H), 7.30 (1H), 7.76 (1H), 7.80-7.91 (2H), 8.11 (1H), 8.16 (1H), 8.29 (1H), 9.90 (1H) ppm.

150 mg (327 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-fluoro-2-methoxyaniline to give after working up and purification 12.2 mg (6%) of the title compound.

$^1$H-NMR (DMSO-d6): δ=0.51 (2H), 0.65 (2H), 1.18 (6H), 2.32 (3H), 2.80 (1H), 3.15 (2H), 3.84 (3H), 4.79 (1H), 6.21 (1H), 6.42 (1H), 6.72 (1H), 6.96 (1H), 7.30 (1H), 7.76 (1H), 7.82 (1H), 7.91 (1H), 8.01 (1H), 8.10 (1H), 8.27 (1H) ppm.

Example 432

N-cyclopropyl-4-{6-[(4-fluoro-2-methoxyphenyl)amino]-8-[(2-hydroxy-2-methylpropyl)amino]imidazo[1,2-b]pyridazin-3-yl}-2-methylbenzamide

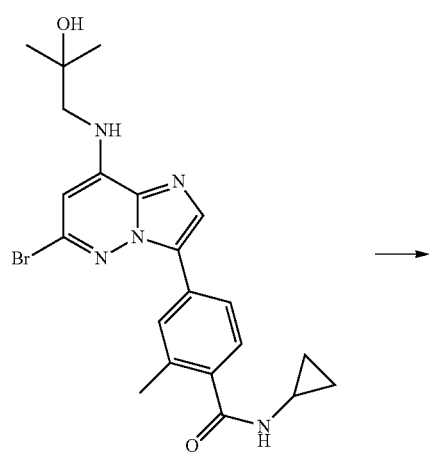

Example 433

N-cyclopropyl-2-methyl-4-(6-{[3-(propan-2-yl)phenyl]amino}-8-[(3,3,3-trifluoropropyl)amino]imidazo[1,2-b]pyridazin-3-yl)benzamide

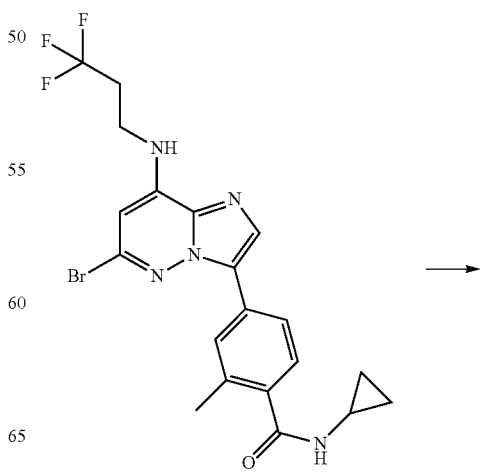

555

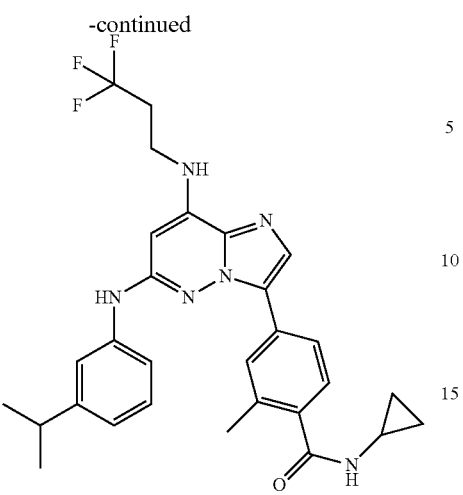

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 3-isopropylaniline to give after working up and purification 22.8 mg (26%) of the title compound.

$^1$H-NMR (DMSO-d6): δ=0.50 (2H), 0.66 (2H), 1.16 (6H), 2.37 (3H), 2.49-2.88 (4H), 3.49 (2H), 5.84 (1H), 6.79 (1H), 7.19 (1H), 7.23-7.29 (2H), 7.33 (1H), 7.70 (1H), 7.77 (1H), 7.92 (1H), 8.02 (1H), 8.29 (1H), 8.88 (1H) ppm.

556

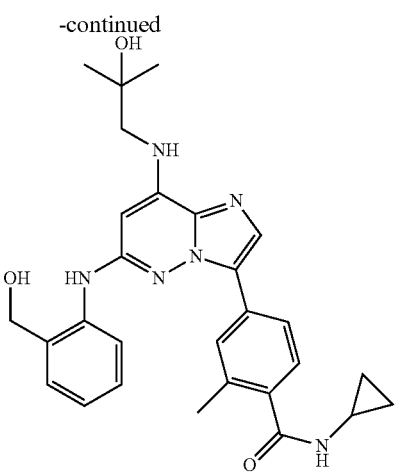

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using (2-aminophenyl)methanol to give after working up and purification 2.0 mg (2%) of the title compound.

$^1$H-NMR (DMSO-d6): δ=0.49 (2H), 0.64 (2H), 1.18 (6H), 2.26 (3H), 2.78 (1H), 3.18 (2H), 4.54 (2H), 4.80 (1H), 5.35 (1H), 5.96 (1H), 6.46 (1H), 7.03 (1H), 7.24 (2H), 7.36 (1H), 7.77-7.91 (3H), 8.02 (1H), 8.06 (1H), 8.24 (1H) ppm.

Example 434

N-cyclopropyl-4-(6-{[2-(hydroxymethyl)phenyl]amino}-8-[(2-hydroxy-2-methylpropyl)amino]imidazo[1,2-b]pyridazin-3-yl)-2-methylbenzamide

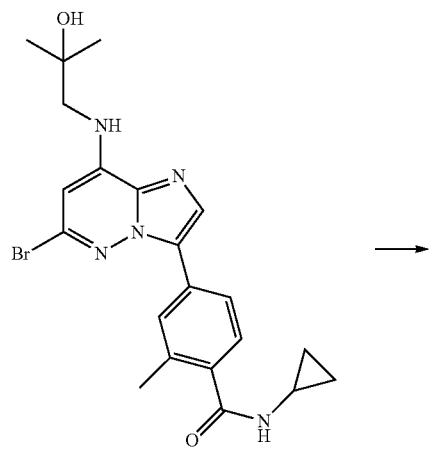

Example 435

4-(6-{[4-(2-aminoethyl)phenyl]amino}-8-[(2-hydroxy-2-methylpropyl)amino]imidazo[1,2-b]pyridazin-3-yl)-N-cyclopropyl-2-methylbenzamide

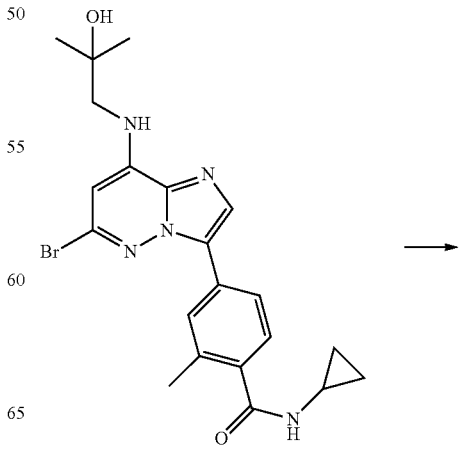

557

-continued

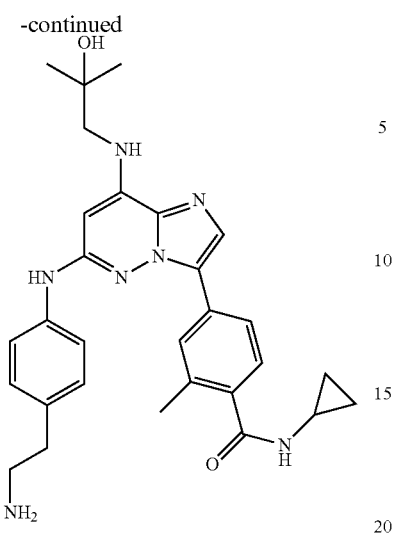

75 mg (164 μmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 305 using 4-(2-aminoethyl)aniline to give after working up and purification 11 mg (12%) of the title compound.

¹H-NMR (DMSO-d6): δ=0.51 (2H), 0.66 (2H), 1.18 (6H), 2.38 (3H), 2.59-2.65 (2H), 2.74-2.85 (3H), 3.15 (2H), 4.82 (1H), 5.88 (1H), 6.51 (1H), 7.10 (2H), 7.34 (1H), 7.58 (2H), 7.76 (1H), 7.84 (1H), 8.12 (1H), 8.32 (1H), 8.87 (1H) ppm.

Example 436

N-cyclopropyl-4-{6-[(6-fluoropyridin-3-yl)oxy]-8-[(3,3,3-trifluoropropyl)amino]imidazo[1,2-b]pyridazin-3-yl}-2-methylbenzamide

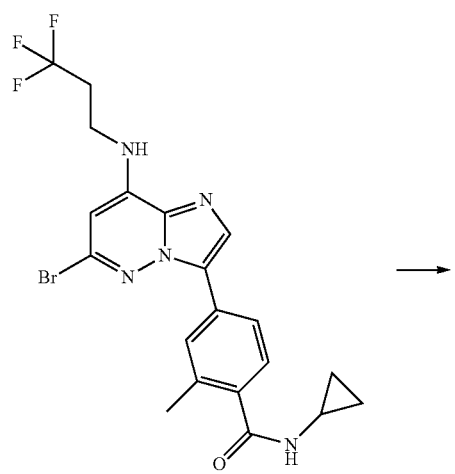

558

-continued

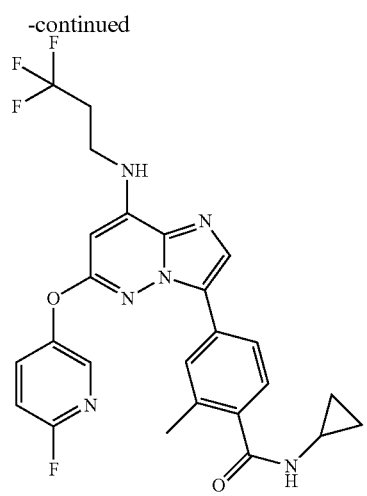

200 mg (415 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 6-fluoropyridin-3-ol to give after working up and purification 4.8 mg (2%) of the title compound.

¹H-NMR (DMSO-d6): δ=0.47 (2H), 0.64 (2H), 2.13 (3H), 2.60-2.80 (3H), 3.61 (2H), 6.19 (1H), 7.17 (1H), 7.32 (1H), 7.60 (1H), 7.67 (1H), 7.77 (1H), 7.93 (1H), 8.04 (1H), 8.22 (1H), 8.26 (1H) ppm.

Example 437

N-cyclopropyl-4-{6-(2-fluoro-4-methoxyphenoxy)-8-[(3,3,3-trifluoropropyl)amino]imidazo[1,2-b]pyridazin-3-yl}-2-methylbenzamide

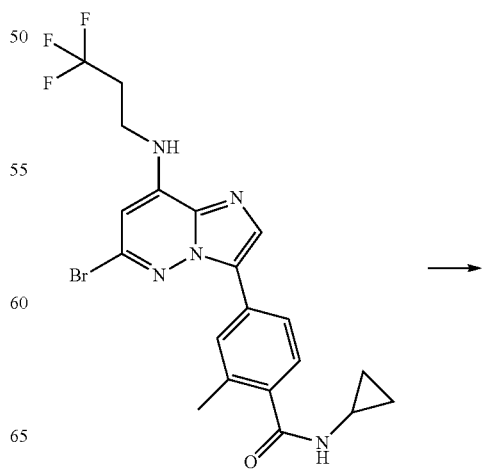

559

-continued

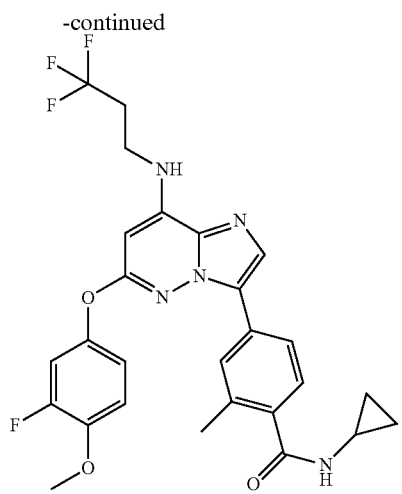

400 mg (829 µmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 2-fluoro-4-methoxyphenol to give after working up and purification 194 mg (41%) of the title compound.

$^1$H-NMR (DMSO-d6): δ=0.46 (2H), 0.64 (2H), 2.08 (3H), 2.60-2.80 (3H), 3.60 (2H), 3.78 (3H), 6.16 (1H), 6.84 (1H), 7.06 (1H), 7.15 (1H), 7.33 (1H), 7.61 (1H), 7.67-7.74 (2H), 7.94 (1H), 8.21 (1H) ppm.

Example 438

N-cyclopropyl-4-{6-(2-fluoro-4-methoxyphenoxy)-8-[(3,3,3-trifluoropropyl)amino]imidazo[1,2-b]pyridazin-3-yl}benzamide

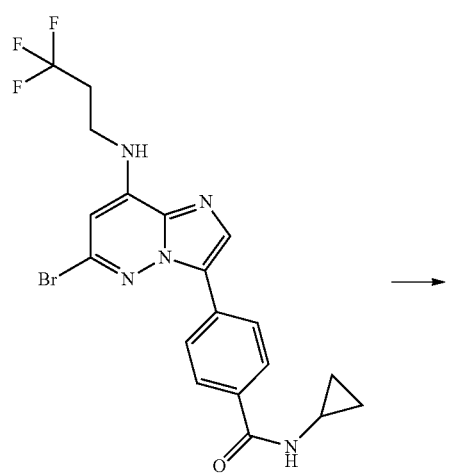

560

-continued

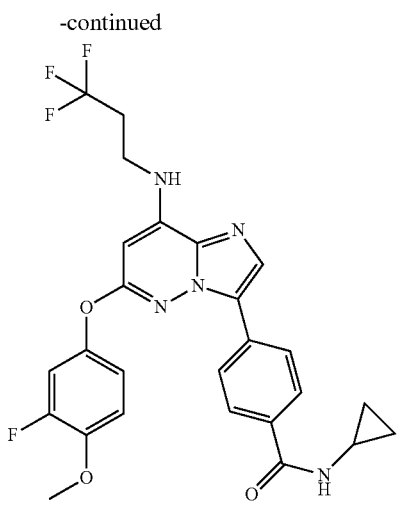

400 mg (854 µmol) 4-{6-bromo-8-[(3,3,3-trifluoropropyl)amino]imidazo[1,2-b]pyridazin-3-yl}-N-cyclopropylbenzamide which was prepared according to intermediate example 438a were transformed in analogy to example 51 using 2-fluoro-4-methoxyphenol to give after working up and purification 219 mg (46%) of the title compound.

$^1$H-NMR (DMSO-d6): δ=0.53 (2H), 0.66 (2H), 2.69 (2H), 2.79 (1H), 3.60 (2H), 3.81 (3H), 6.17 (1H), 6.85 (1H), 7.08 (1H), 7.34 (1H), 7.65 (2H), 7.74 (1H), 7.89 (2H), 8.01 (1H), 8.40 (1H) ppm.

Intermediate Example 438a

4-{6-bromo-8-[(3,3,3-trifluoropropyl)amino]imidazo[1,2-b]pyridazin-3-yl}-N-cyclopropylbenzamide

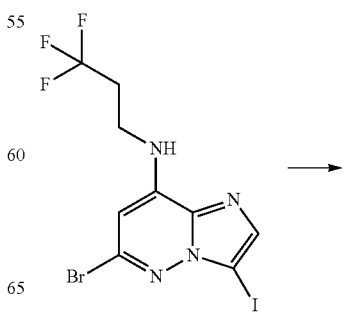

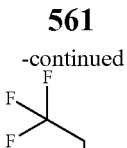

1.50 g (3.45 mmol) 6-bromo-3-iodo-N-(3,3,3-trifluoropropyl)imidazo[1,2-b]pyridazin-8-amine which was prepared according to intermediate example 247b were transformed in analogy to intermediate example 1a using [4-(cyclopropylcarbamoyl)phenyl]boronic acid to give after working up and purification 1.05 g (65%) of the title compound.

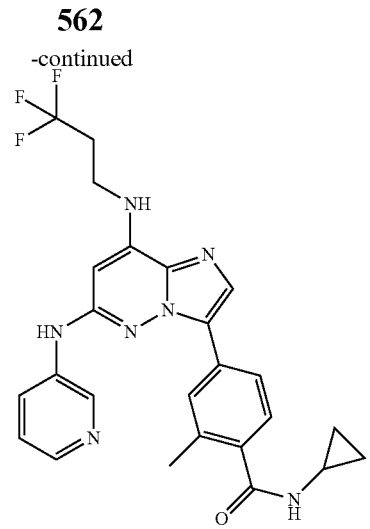

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using pyridin-3-amine to give after working up and purification 15.5 mg (19%) of the title compound.

$^1$H-NMR (DMSO-d6): δ=0.51 (2H), 0.66 (2H), 2.38 (3H), 2.68 (2H), 2.81 (1H), 3.51 (2H), 5.84 (1H), 7.29 (1H), 7.34 (1H), 7.38 (1H), 7.79 (1H), 7.80 (1H), 8.06 (1H), 8.10-8.16 (2H), 8.32 (1H), 8.80 (1H), 9.18 (1H) ppm.

Example 439

N-cyclopropyl-2-methyl-4-{6-(pyridin-3-ylamino)-8-[(3,3,3-trifluoropropyl)amino]imidazo[1,2-b]pyridazin-3-yl}benzamide

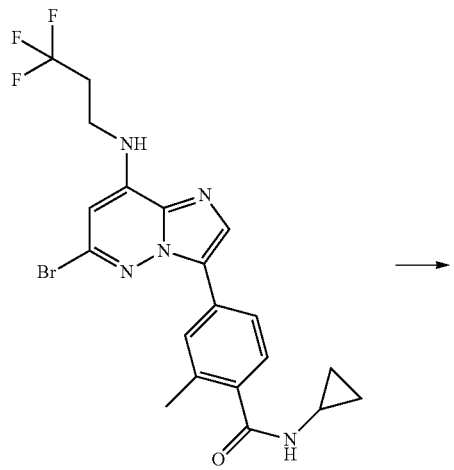

Example 440

N-cyclopropyl-4-{6-[(6-fluoropyridin-3-yl)-amino]-8-[(3,3,3-trifluoropropyl)amino]imidazo[1,2-b]pyridazin-3-yl}-2-methylbenzamide

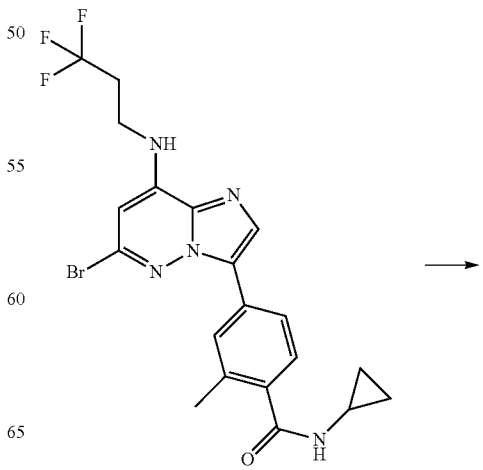

563

-continued

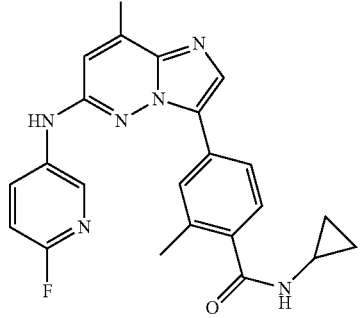

75 mg (156 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 305 using 6-fluoropyridin-3-amine to give after working up and purification 25.5 mg (30%) of the title compound.

$^1$H-NMR (DMSO-d6): δ=0.51 (2H), 0.66 (2H), 2.37 (3H), 2.68 (2H), 2.81 (1H), 3.50 (2H), 5.80 (1H), 7.12 (1H), 7.34 (1H), 7.39 (1H), 7.76-7.80 (2H), 8.00 (1H), 8.16 (1H), 8.31 (1H), 8.51 (1H), 9.21 (1H) ppm.

564

-continued

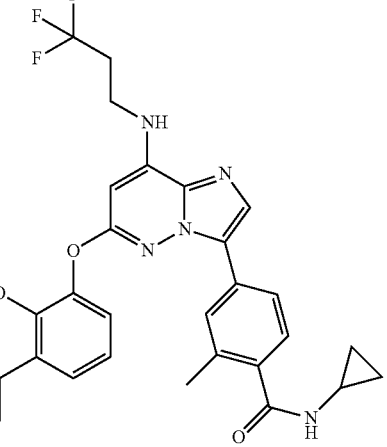

32 mg (56 μmol) N-cyclopropyl-4-{6-[2-methoxy-3-(propan-2-yl)phenoxy]-8-[(3,3,3-trifluoropropyl)amino]imidazo[1,2-b]pyridazin-3-yl}-2-methylbenzamide which was prepared according to example 418 were transformed in analogy to example 280 to give after working up and purification 8.2 mg (25%) of the title compound.

$^1$H-NMR (DMSO-d6): δ=0.46 (2H), 0.62 (2H), 1.07 (6H), 2.05 (3H), 2.69 (2H), 2.75 (1H), 3.04 (1H), 3.60 (2H), 6.14 (1H), 6.76 (1H), 6.82 (1H), 7.03-7.09 (2H), 7.56 (1H), 7.62 (1H), 7.77 (1H), 7.93 (1H), 8.19 (1H), 9.37 (1H) ppm.

Example 441

N-cyclopropyl-4-{6-[2-hydroxy-3-(propan-2-yl)phenoxy]-8-[(3,3,3-trifluoropropyl)amino]imidazo[1,2-b]pyridazin-3-yl}-2-methylbenzamide

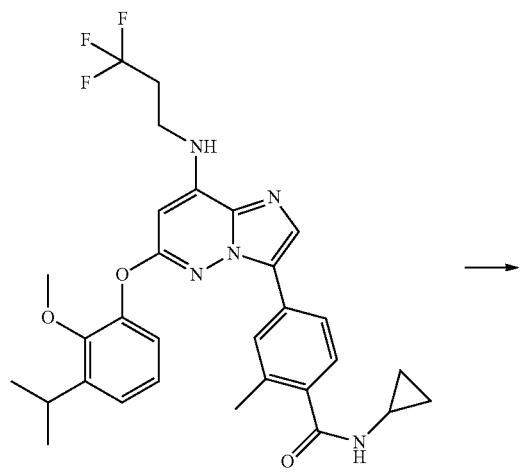

Example 442

N-cyclopropyl-4-{6-[(4-fluoro-3-hydroxyphenyl)amino]-8-[(3,3,3-trifluoropropyl)amino]imidazo[1,2-b]pyridazin-3-yl}-2-methylbenzamide

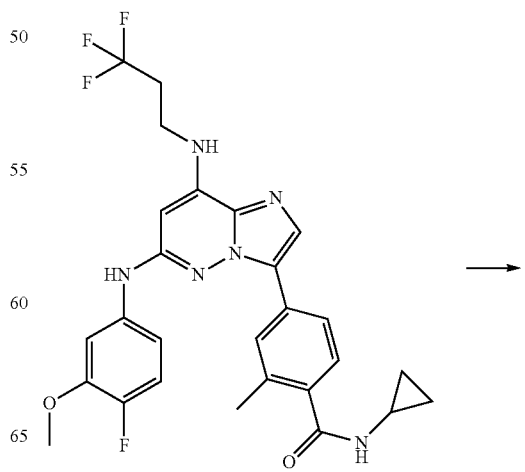

565
-continued

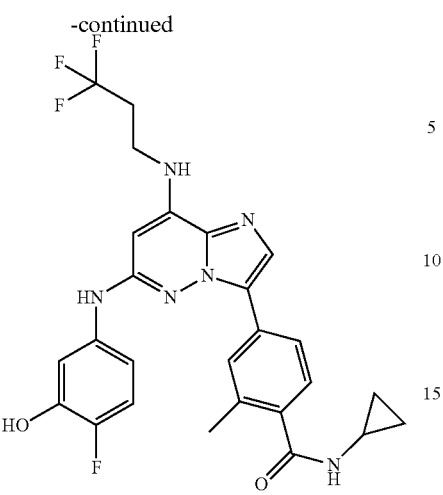

33 mg (61 μmol) N-cyclopropyl-4-{6-[(4-fluoro-3-methoxyphenyl)amino]-8-[(3,3,3-trifluoropropyl)amino]imidazo[1,2-b]pyridazin-3-yl}-2-methylbenzamide which was prepared according to example 422 were transformed in analogy to example 280 to give after working up and purification 9.3 mg (27%) of the title compound.

$^1$H-NMR (DMSO-d6): δ=0.51 (2H), 0.66 (2H), 2.36 (3H), 2.67 (2H), 2.81 (1H), 3.47 (2H), 5.78 (1H), 7.00 (1H), 7.05 (1H), 7.20-7.27 (2H), 7.33 (1H), 7.78 (1H), 7.87 (1H), 8.06 (1H), 8.28 (1H), 8.79 (1H), 9.71 (1H) ppm.

566
-continued

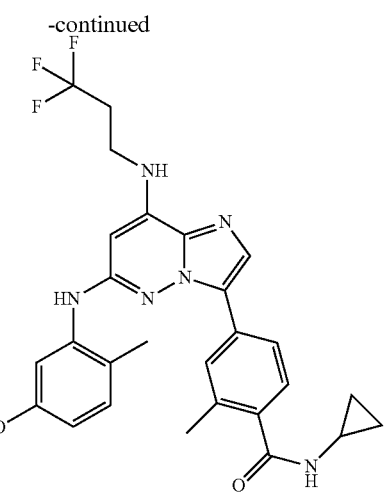

10.5 mg (19 μmol) N-cyclopropyl-4-{6-[(5-methoxy-2-methylphenyl)amino]-8-[(3,3,3-trifluoropropyl)amino]imidazo[1,2-b]pyridazin-3-yl}-2-methylbenzamide which was prepared according to example 430 were transformed in analogy to example 280 to give after working up and purification 2.0 mg (20%) of the title compound.

$^1$H-NMR (DMSO-d6): δ=0.47 (2H), 0.64 (2H), 2.11 (3H), 2.24 (3H), 2.69 (2H), 2.77 (1H), 3.48 (2H), 5.94 (1H), 6.42 (1H), 6.95 (1H), 7.10 (1H), 7.16 (1H), 7.20 (1H), 7.65-7.95 (3H), 8.01 (1H), 8.21 (1H), 9.06 (1H) ppm.

Example 443

N-cyclopropyl-4-{6-[(5-hydroxy-2-methylphenyl)amino]-8-[(3,3,3-trifluoropropyl)amino]imidazo[1,2-b]pyridazin-3-yl}-2-methylbenzamide

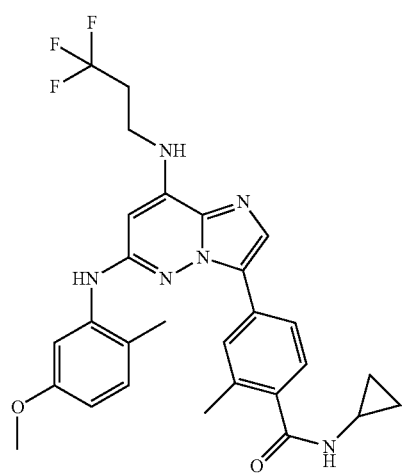

→

Example 444

N-cyclopropyl-4-{6-(2-fluoro-4-methoxyphenoxy)-8-[(tetrahydro-2H-pyran-4-ylmethyl)amino]imidazo[1,2-b]pyridazin-3-yl}benzamide

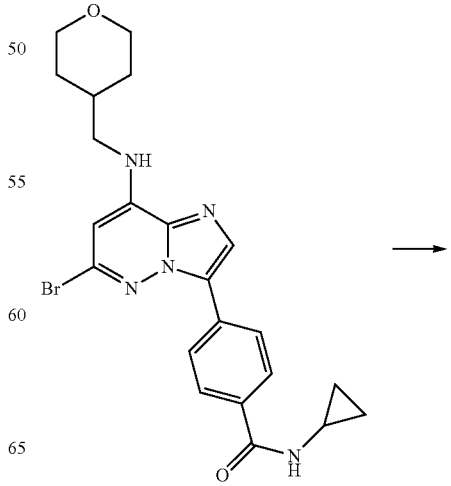

→

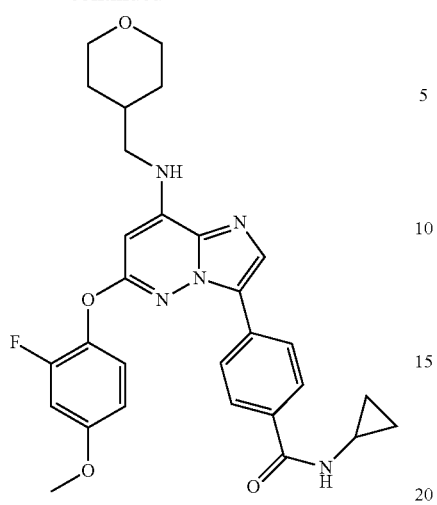

400 mg (850 µmol) 4-{6-bromo-8-[(tetrahydro-2H-pyran-4-ylmethyl)amino]imidazo[1,2-b]pyridazin-3-yl}-N-cyclopropylbenzamide which was prepared according to intermediate example 444a were transformed in analogy to example 51 using 2-fluoro-4-methoxyphenol to give after working up and purification 257 mg (54%) of the title compound.

$^{1}$H-NMR (DMSO-d6): δ=0.53 (2H), 0.66 (2H), 1.22 (2H), 1.62 (2H), 1.94 (1H), 2.80 (1H), 3.17-3.32 (4H), 3.81 (3H), 3.84 (2H), 6.12 (1H), 6.84 (1H), 7.07 (1H), 7.34 (1H), 7.64 (2H), 7.74 (1H), 7.89 (2H), 7.98 (1H), 8.39 (1H) ppm.

1.20 g (2.75 mmol) 6-bromo-3-iodo-N-(tetrahydro-2H-pyran-4-ylmethyl)imidazo[1,2-b]pyridazin-8-amine which was prepared according to intermediate example 444b were transformed in analogy to intermediate example 1a using [4-(cyclopropylcarbamoyl)phenyl]boronic acid to give after working up and purification 1.08 g (84%) of the title compound.

Intermediate Example 444b 6-bromo-3-iodo-N-(tetrahydro-2H-pyran-4-ylmethyl)imidazo[1,2-b]pyridazin-8-amine Intermediate Example 444a 4-{6-bromo-8-[(tetrahydro-2H-pyran-4-ylmethyl)amino]imidazo[1,2-b]pyridazin-3-yl}-N-cyclopropylbenzamide

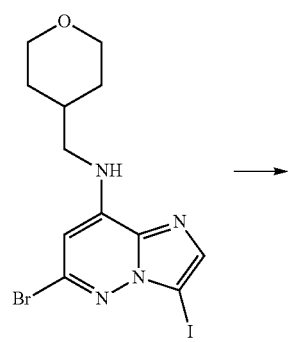

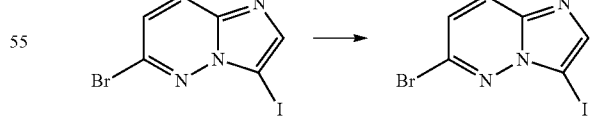

3.00 g (7.45 mmol) 6,8-dibromo-3-iodoimidazo[1,2-b]pyridazine which was prepared according to intermediate example 96c were transformed in analogy to intermediate example 1b using 1-(tetrahydro-2H-pyran-4-yl)methanamine to give after working up and purification 2.81 g (81%) of the title compound.

Example 445

N-cyclopropyl-4-{6-(2-fluoro-4-methoxyphenoxy)-8-[(tetrahydro-2H-pyran-4-ylmethyl)amino]imidazo[1,2-b]pyridazin-3-yl}-2-methylbenzamide

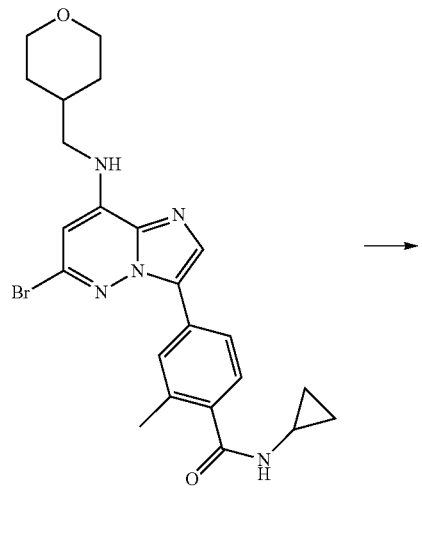

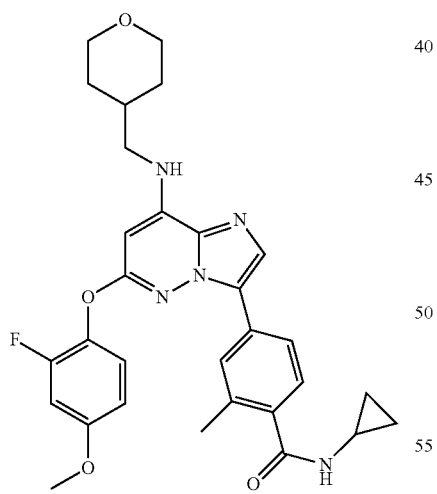

400 mg (826 μmol) 4-{6-bromo-8-[(tetrahydro-2H-pyran-4-ylmethyl)amino]imidazo[1,2-b]pyridazin-3-yl}-N-cyclopropyl-2-methylbenzamide which was prepared according to intermediate example 445a were transformed in analogy to example 51 using 2-fluoro-4-methoxyphenol to give after working up and purification 295 mg (65%) of the title compound.

¹H-NMR (DMSO-d6): δ=0.46 (2H), 0.63 (2H), 1.22 (2H), 1.62 (2H), 1.95 (1H), 2.08 (3H), 2.77 (1H), 3.19-3.27 (4H), 3.77 (3H), 3.83 (2H), 6.12 (1H), 6.83 (1H), 7.05 (1H), 7.14 (1H), 7.33 (1H), 7.61 (1H), 7.67-7.74 (2H), 7.91 (1H), 8.21 (1H) ppm.

Intermediate Example 445a

4-{6-bromo-8-[(tetrahydro-2H-pyran-4-ylmethyl)amino]imidazo[1,2-b]pyridazin-3-yl}-N-cyclopropyl-2-methylbenzamide

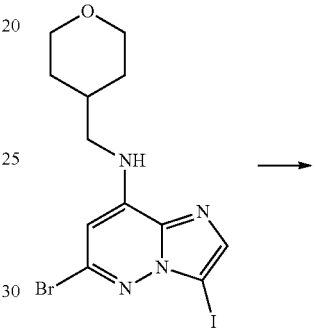

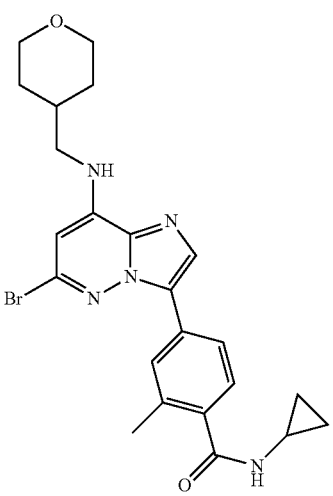

1.58 g (3.62 mmol) 6-bromo-3-iodo-N-(tetrahydro-2H-pyran-4-ylmethyl)imidazo[1,2-b]pyridazin-8-amine which was prepared according to intermediate example 444b were transformed in analogy to intermediate example 1a using N-cyclopropyl-2-methyl-4-(4,4,5,5-tetramethyl-1,3,2-dioxaborolan-2-yl)benzamide to give after working up and purification 1.05 g (57%) of the title compound.

571
Example 446

N-cyclopropyl-4-{8-[(2-hydroxy-2-methylpropyl)amino]-6-[(3-hydroxyphenyl) amino]imidazo[1,2-b]pyridazin-3-yl}-2-methylbenzamide

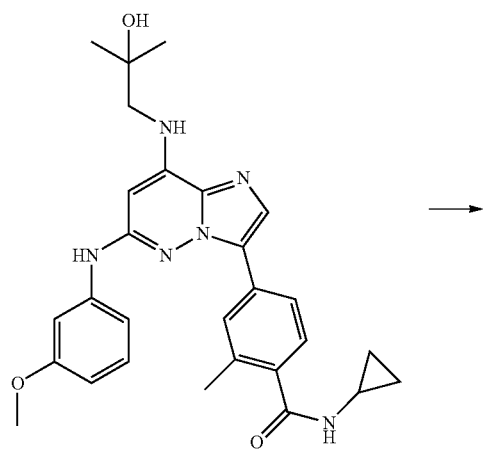

30 mg (60 µmol) N-cyclopropyl-4-{8-[(2-hydroxy-2-methylpropyl)amino]-6-[(3-methoxyphenyl)amino]imidazo[1,2-b]pyridazin-3-yl}-2-methylbenzamide which was prepared according to example 403 were transformed in analogy to example 280 to give after working up and purification 9.60 mg (31%) of the title compound.

$^1$H-NMR (DMSO-d6): δ=0.50 (2H), 0.65 (2H), 1.18 (6H), 2.37 (3H), 2.81 (1H), 3.14 (2H), 4.81 (1H), 5.88 (1H), 6.33 (1H), 6.49 (1H), 6.94 (1H), 7.03 (1H), 7.23 (1H), 7.32 (1H), 7.77 (1H), 7.89 (1H), 8.12 (1H), 8.29 (1H), 8.77 (1H), 9.25 (1H) ppm.

572
Example 447

N-cyclopropyl-4-{6-[(3,4-difluorophenyl)amino]-8-[(4,4,4-trifluorobutyl)amino]imidazo[1,2-b]pyridazin-3-yl}-2-methylbenzamide

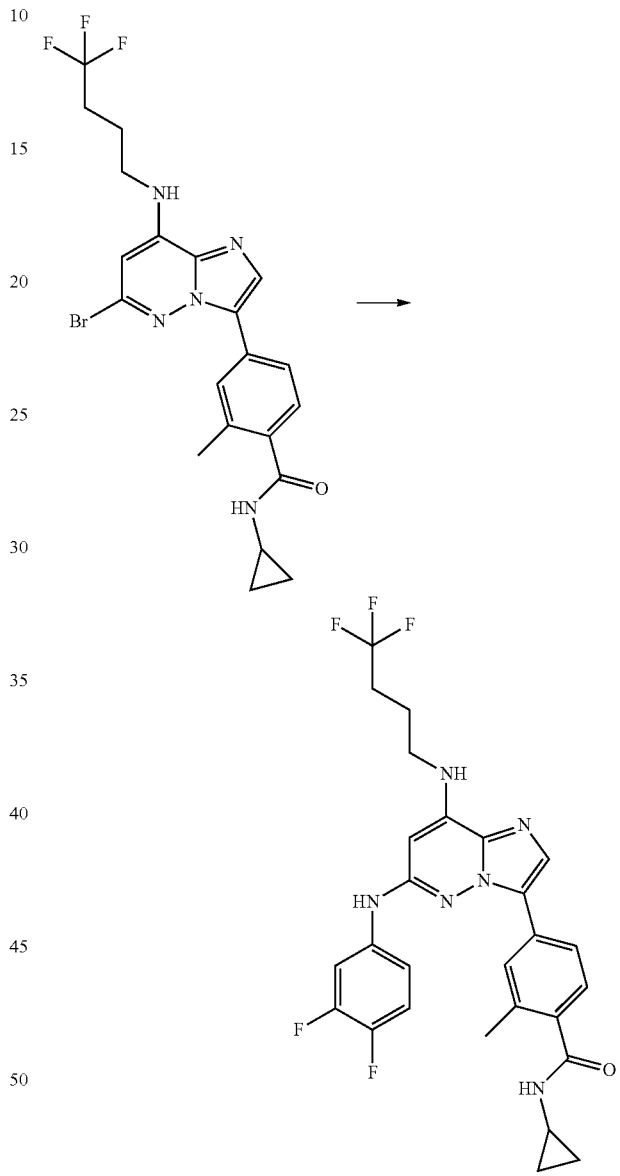

75 mg (151 µmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 305 using 3,4-difluoroaniline to give after working up and purification 6.3 mg (7%) of the title compound.

$^1$H-NMR (DMSO-d6): δ=0.51 (2H), 0.66 (2H), 1.86 (2H), 2.26-2.43 (2H), 2.36 (3H), 2.81 (1H), 3.32-3.38 (2H), 5.75 (1H), 7.20-7.39 (4H), 7.75 (1H), 7.81 (1H), 7.90 (1H), 7.99 (1H), 8.28 (1H), 9.14 (1H) ppm.

Intermediate Example 447a

4-{6-bromo-8-[(4,4,4-trifluorobutyl)amino]imidazo[1,2-b]pyridazin-3-yl}-N-cyclopropyl-2-methylbenzamide

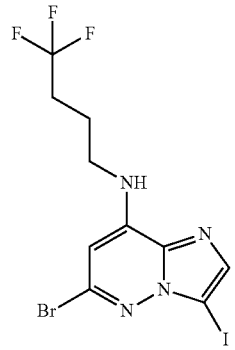

Intermediate Example 447b 6-bromo-3-iodo-N-(4,4,4-trifluorobutyl)imidazo[1,2-b]pyridazin-8-amine

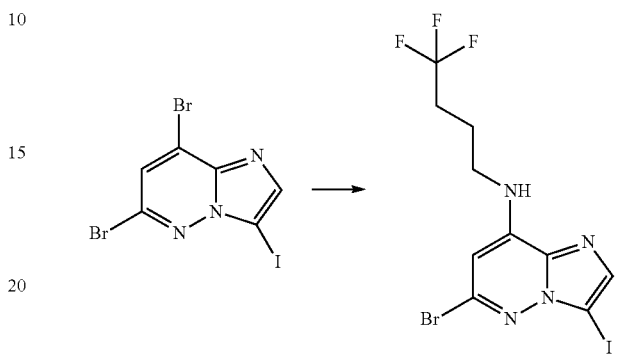

3.96 g (9.83 mmol) 6,8-dibromo-3-iodoimidazo[1,2-b]pyridazine which was prepared according to intermediate example 96c were transformed in analogy to intermediate example 1b using 4,4,4-trifluorobutan-1-amine to give after working up and purification 3.43 g (74%) of the title compound.

Example 448

N-cyclopropyl-4-{6-[(5-fluoro-2-methylphenyl)amino]-8-[(4,4,4-trifluorobutyl)amino]imidazo[1,2-b]pyridazin-3-yl}-2-methylbenzamide

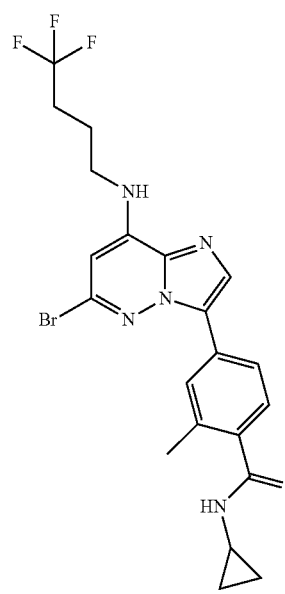

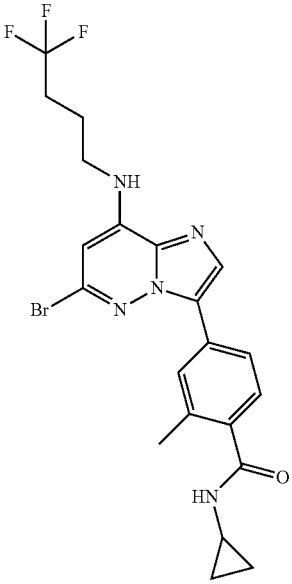

4.27 g (9.51 mmol) 6-bromo-3-iodo-N-(4,4,4-trifluorobutyl)imidazo[1,2-b]pyridazin-8-amine which was prepared according to intermediate example 447b were transformed in analogy to intermediate example 1a using N-cyclopropyl-2-methyl-4-(4,4,5,5-tetramethyl-1,3,2-dioxaborolan-2-yl)benzamide to give after working up and purification 2.37 g (50%) of the title compound.

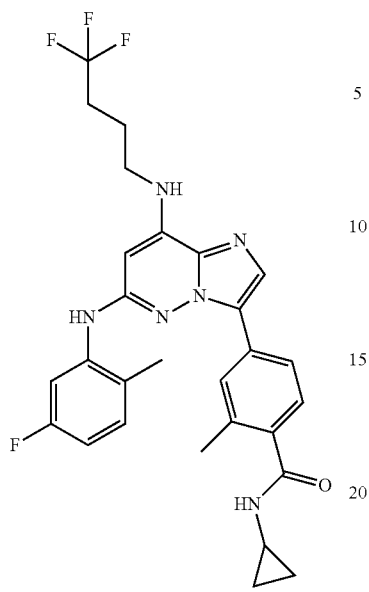

75 mg (151 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 305 using 5-fluoro-2-methylaniline to give after working up and purification 10.5 mg (12%) of the title compound.

¹H-NMR (CDCl₃): δ=0.63 (2H), 0.89 (2H), 2.00 (2H), 2.20-2.33 (2H), 2.30 (3H), 2.50 (3H), 2.92 (1H), 3.39 (2H), 5.62 (1H), 5.77 (1H), 5.92 (1H), 6.02 (1H), 6.70 (1H), 7.14 (1H), 7.40 (1H), 7.65 (1H), 7.76 (1H), 7.84 (1H), 7.87 (1H) ppm.

Example 449

N-cyclopropyl-4-{6-[(3-fluoro-5-methylphenyl)sulfanyl]-8-[(4,4,4-trifluorobutyl)amino]imidazo[1,2-b]pyridazin-3-yl}-2-methylbenzamide

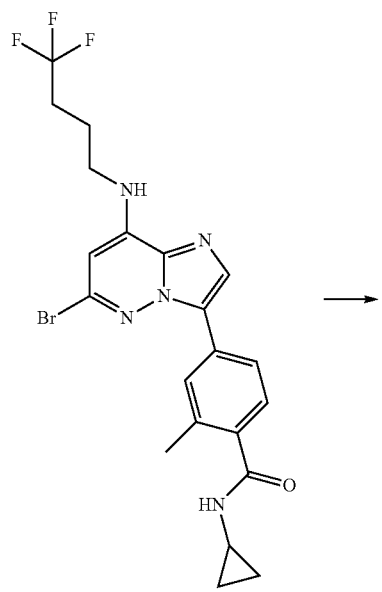

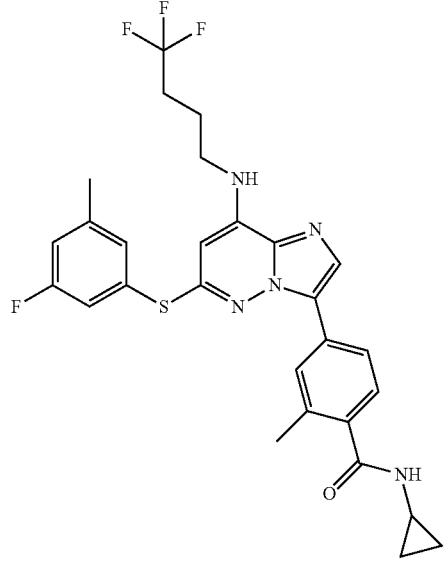

75 mg (151 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 51 using 3-fluoro-5-methylbenzenethiol to give after working up and purification 44.6 mg (50%) of the title compound.

¹H-NMR (CDCl₃): δ=0.63 (2H), 0.90 (2H), 1.97 (2H), 2.23 (2H), 2.36 (3H), 2.41 (3H), 2.92 (1H), 3.38 (2H), 5.79 (1H), 5.87 (1H), 5.91 (1H), 6.96 (1H), 7.17-7.29 (3H), 7.66 (1H), 7.69 (1H), 7.72 (1H) ppm.

Example 450

N-cyclopropyl-4-{6-[(2,3-difluorophenyl)amino]-8-[(4,4,4-trifluorobutyl)amino]imidazo[1,2-b]pyridazin-3-yl}-2-methylbenzamide

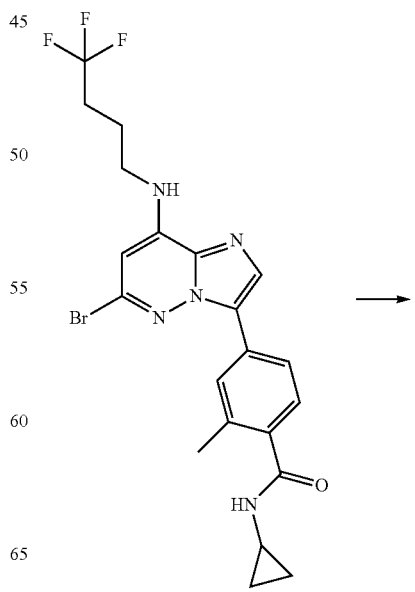

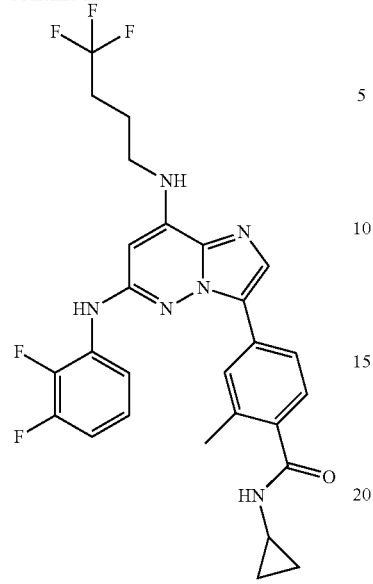

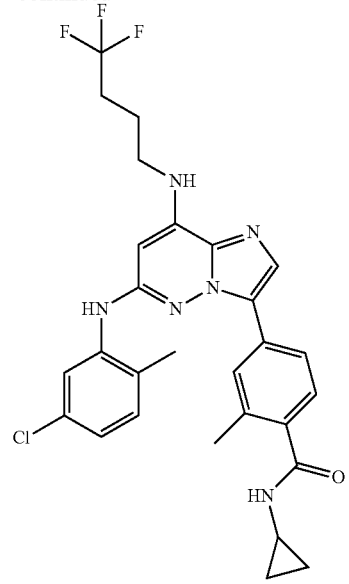

75 mg (151 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 305 using 2,3-difluoroaniline to give after working up and purification 10.6 mg (12%) of the title compound.

¹H-NMR (CDCl₃): δ=0.63 (2H), 0.90 (2H), 2.03 (2H), 2.28 (2H), 2.52 (3H), 2.93 (1H), 3.43 (2H), 5.64 (1H), 5.75 (1H), 5.91 (1H), 6.40 (1H), 6.81 (1H), 7.03 (1H), 7.40 (1H), 7.66 (1H), 7.78 (1H), 7.98 (1H), 8.07 (1H) ppm.

Example 451

4-{6-[(5-chloro-2-methylphenyl)amino]-8-[(4,4,4-trifluorobutyl)amino]imidazo[1,2-b]pyridazin-3-yl}-N-cyclopropyl-2-methylbenzamide 75 mg (151 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 305 using 5-chloro-2-methylaniline to give after working up and purification 12.7 mg (14%) of the title compound.

¹H-NMR (CDCl₃): δ=0.61 (2H), 0.88 (2H), 1.99 (2H), 2.17-2.38 (2H), 2.29 (3H), 2.48 (3H), 2.92 (1H), 3.38 (2H), 5.60 (1H), 5.73 (1H), 5.90 (1H), 5.98 (1H), 6.99 (1H), 7.13 (1H), 7.43 (1H), 7.65 (1H), 7.76 (1H), 7.91 (1H), 7.93 (1H) ppm.

Example 452

N-cyclopropyl-4-{6-(3-fluoro-5-methylphenoxy)-8-[(4,4,4-trifluorobutyl)amino]imidazo[1,2-b]pyridazin-3-yl}-2-methylbenzamide

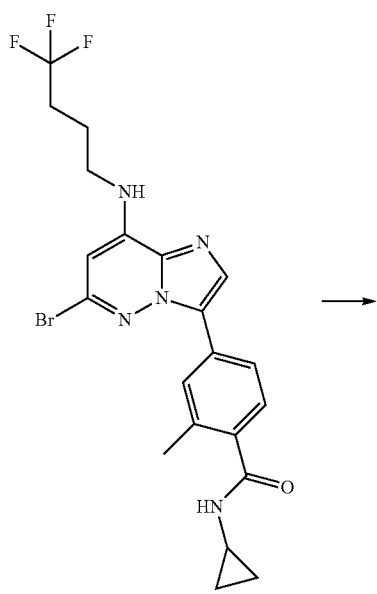

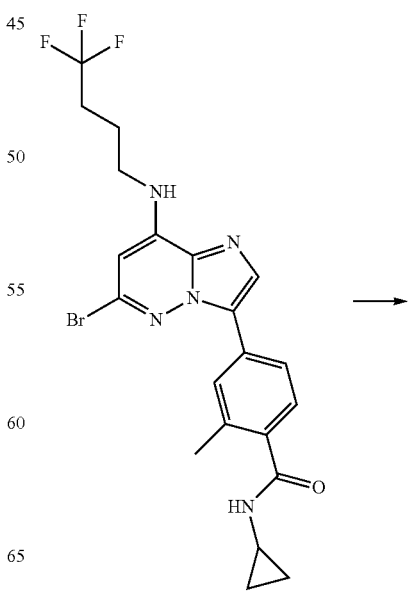

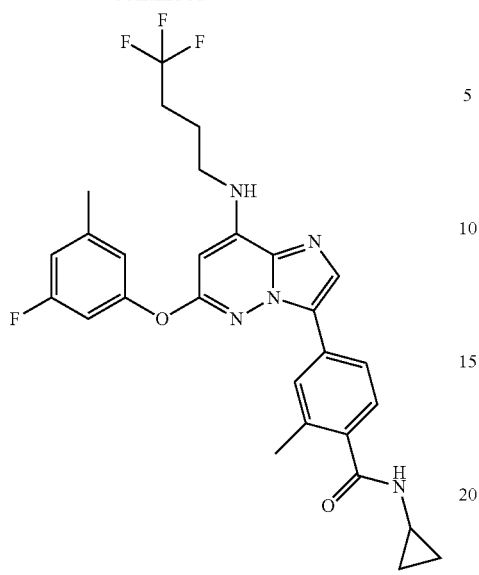

75 mg (151 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 51 using 3-fluoro-5-methylphenol to give after working up and purification 27.7 mg (32%) of the title compound.

$^1$H-NMR (CDCl$_3$): δ=0.60 (2H), 0.88 (2H), 2.04 (2H), 2.28 (2H), 2.34 (3H), 2.37 (3H), 2.90 (1H), 3.46 (2H), 5.81-5.89 (3H), 6.77-6.87 (3H), 7.27 (1H), 7.66 (1H), 7.73 (1H), 7.77 (1H) ppm.

Example 453

4-{6-(cyclopentylamino)-8-[(3,3,3-trifluoropropyl)amino]imidazo[1,2-b]pyridazin-3-yl}-N-cyclopropyl-2-methylbenzamide

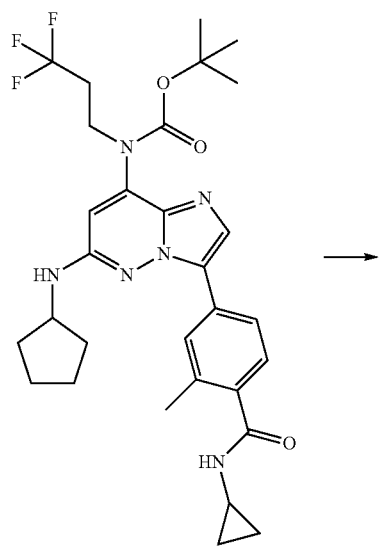

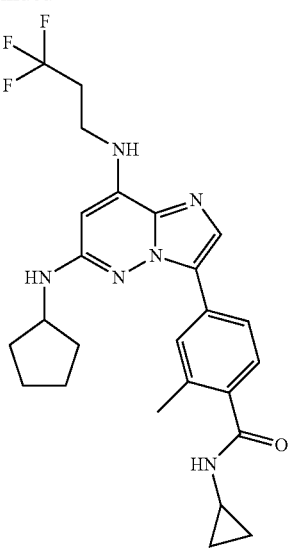

To a solution of 90 mg (153 μmol) ert-butyl {6-(cyclopentylamino)-3-[4-(cyclopropylcarbamoyl)-3-methylphenyl]imidazo[1,2-b]pyridazin-8-yl}(3,3,3-trifluoropropyl)carbamate which was prepared according to intermediate example 453a in 1 mL dichloromethane were added 177 μL trifluoroacetic acid and the mixture was stirred for 2 hours at 23° C. The mixture was poured into water and extracted with dichloromethane. The organic phase was washed with sodium hydrogencarbonate solution and dried over sodium sulfate. After filtration and removal of solvent the residue was purified by chromatography to give 64.1 mg (82%) of the title compound.

$^1$H-NMR (DMSO-d6): δ=0.50 (2H), 0.64 (2H), 1.44-1.72 (6H), 1.90-2.05 (2H), 2.34 (3H), 2.62 (2H), 2.79 (1H), 3.41 (2H), 3.99 (1H), 5.57 (1H), 6.43 (1H), 6.92 (1H), 7.30 (1H), 7.73 (1H), 7.98 (1H), 8.17 (1H), 8.24 (1H) ppm.

Intermediate Example 453a

4-{6-(cyclopentylamino)-8-[(3,3,3-trifluoropropyl)amino]imidazo[1,2-b]pyridazin-3-yl}-N-cyclopropyl-2-methylbenzamide

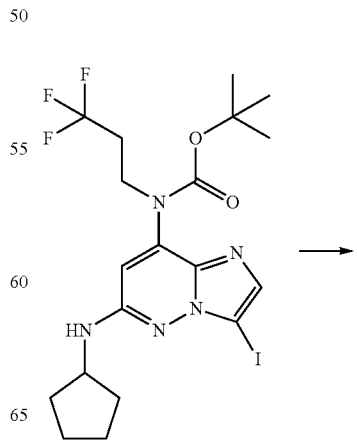

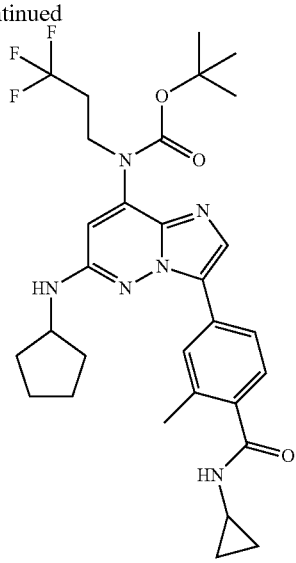

135 mg (250 μmol) tert-butyl [6-(cyclopentylamino)-3-iodoimidazo[1,2-b]pyridazin-8-yl](3,3,3-trifluoropropyl)carbamate which was prepared according to intermediate example 453b were transformed in analogy to intermediate example 1a using [4-(cyclopropylcarbamoyl)-3-methylphenyl]boronic acid to give after working up and purification 101 mg (65%) of the title compound.

Intermediate Example 453b tert-butyl[6-(cyclopentylamino)-3-iodoimidazo[1,2-b]pyridazin-8-yl](3,3,3-trifluoropropyl) carbamate

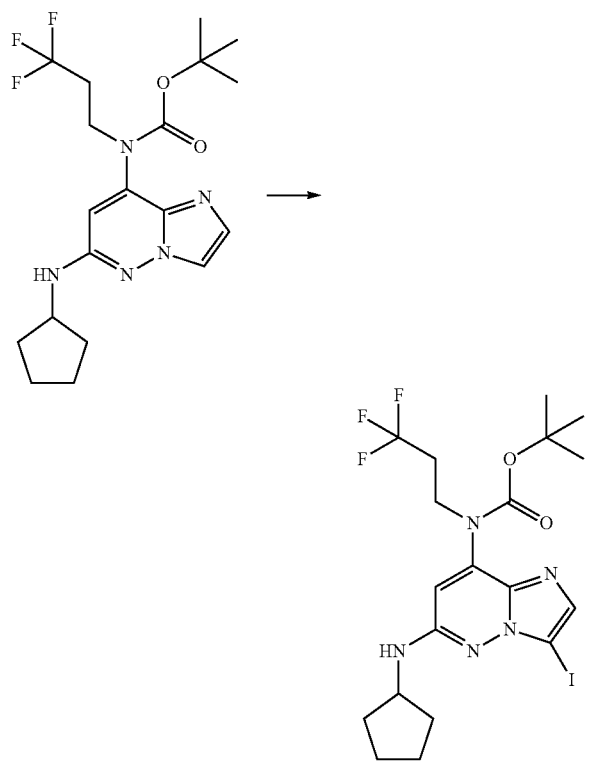

197 mg (405 μmol) tert-butyl [6-(cyclopentylamino)imidazo[1,2-b]pyridazin-8-yl](3,3,3-trifluoropropyl)carbamate which was prepared according to intermediate example 453c were transformed in analogy to intermediate example 96c to give after working up and purification 141 mg (58%) of the title compound.

Intermediate Example 453c tert-butyl[6-(cyclopentylamino)imidazo[1,2-b]pyridazin-8-yl](3,3,3-trifluoropropyl)carbamate

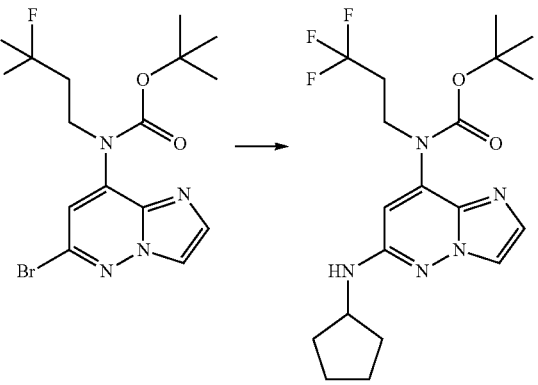

200 mg (489 μmol) tert-butyl (6-bromoimidazo[1,2-b]pyridazin-8-yl)(3,3,3-trifluoropropyl)carbamate which was prepared according to intermediate example 453d were transformed in analogy to intermediate example 305 using cyclopentanamine to give after working up and purification 205 mg (101%) of the title compound that contains some reagent.

Intermediate Example 453d tert-butyl (6-bromoimidazo[1,2-b]pyridazin-8-yl)(3,3,3-trifluoropropyl)carbamate

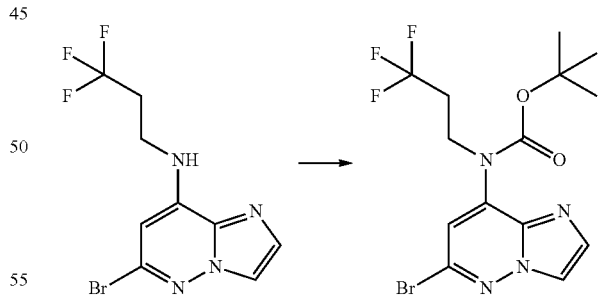

To a solution of 1.88 g (6.08 mmol) 6-bromo-N-(3,3,3-trifluoropropyl)imidazo[1,2-b]pyridazin-8-amine which was prepared according to intermediate example 453e in 7.0 mL tetrahydrofuran were added 2.92 g di-tert-butyl dicarbonate, 74.3 mg N,N-dimethylpyridin-4-amine and the mixture was heated for 2 hours at 55° C. Ethyl acetate was added and the organic phase was washed with saturated sodium hydrogencarbonate solution and dried over sodium sulfate. After filtration and removal of solvent the residue was purified by chromatography to give 2.15 g (82%) of the title compound.

Intermediate Example 453e 6-bromo-N-(3,3,3-trifluoropropyl)imidazo[1,2-b]pyridazin-8-amine

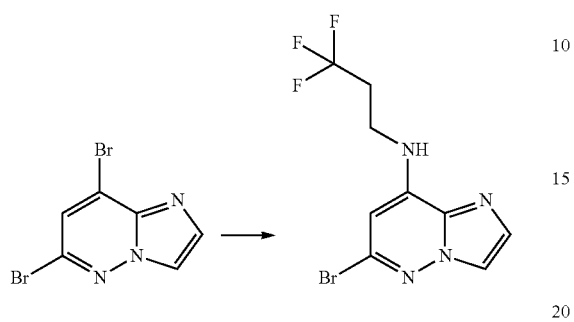

5.00 g (18.06 mmol) 6,8-dibromoimidazo[1,2-b]pyridazine which was prepared according to intermediate example 96d were transformed in analogy to intermediate example 1b using 3,3,3-trifluoropropan-1-amine to give after working up and purification 3.04 g (49%) of the title compound.

Example 454

N-cyclopropyl-4-{6-[(3-hydroxy-2-methylphenyl)amino]-8-[(3,3,3-trifluoropropyl)amino]imidazo[1,2-b]pyridazin-3-yl}-2-methylbenzamide

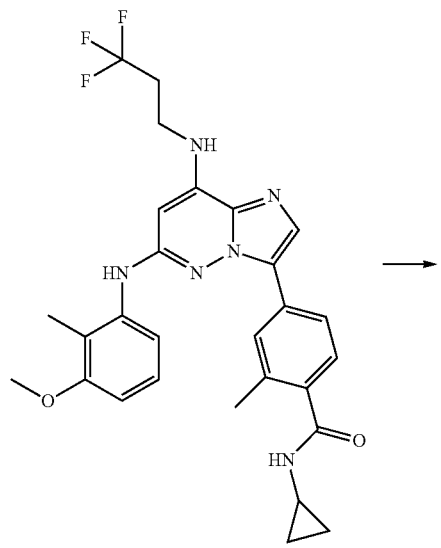

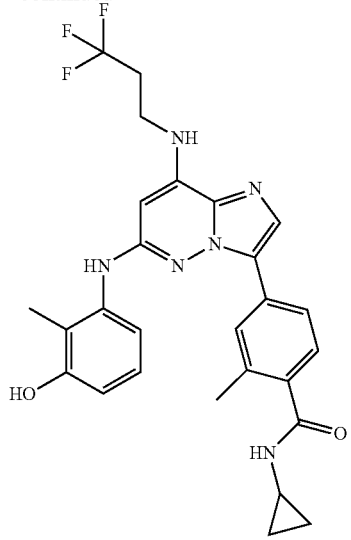

14.1 mg (26 µmol) N-cyclopropyl-4-{6-[(3-methoxy-2-methylphenyl)amino]-8-[(3,3,3-trifluoropropyl)amino]imidazo[1,2-b]pyridazin-3-yl}-2-methylbenzamide which was prepared according to example 426 were transformed in analogy to example 280 to give after working up and purification 4.7 mg (33%) of the title compound.

$^1$H-NMR (DMSO-d6): δ=0.48 (2H), 0.64 (2H), 2.04 (3H), 2.23 (3H), 2.60-2.82 (3H), 3.48 (2H), 5.94 (1H), 6.58 (1H), 6.95 (1H), 7.06-7.29 (3H), 7.79 (1H), 7.81 (1H), 7.93 (1H), 8.03 (1H), 8.22 (1H), 9.24 (1H) ppm.

Example 455

4-{6-(cyclopentyloxy)-8-[(3,3,3-trifluoropropyl)amino]imidazo[1,2-b]pyridazin-3-yl}-N-cyclopropyl-2-methylbenzamide

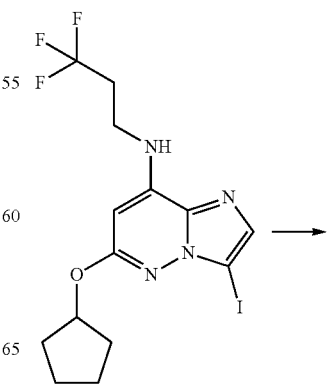

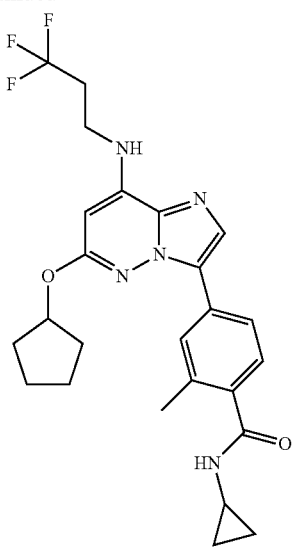

32 mg (73 μmol) 6-(cyclopentyloxy)-3-iodo-N-(3,3,3-trifluoropropyl)imidazo[1,2-b]pyridazin-8-amine which was prepared according to intermediate example 455a were transformed in analogy to intermediate example 1a using [4-(cyclopropylcarbamoyl)-3-methylphenyl]boronic acid to give after working up and purification 17.4 mg (47%) of the title compound.

$^1$H-NMR (CDCl$_3$): δ=0.65 (2H), 0.91 (2H), 1.50-1.73 (6H), 1.84 (2H), 2.40 (2H), 2.48 (3H), 2.94 (1H), 4.08 (2H), 4.82 (1H), 5.26 (1H), 5.93 (1H), 7.10 (1H), 7.13 (1H), 7.40 (1H), 7.45 (1H), 7.64 (1H) ppm.

Intermediate example 455a 6-(cyclopentyloxy)-3-iodo-N-(3,3,3-trifluoropropyl)imidazo[1,2-b]pyridazin-8-amine

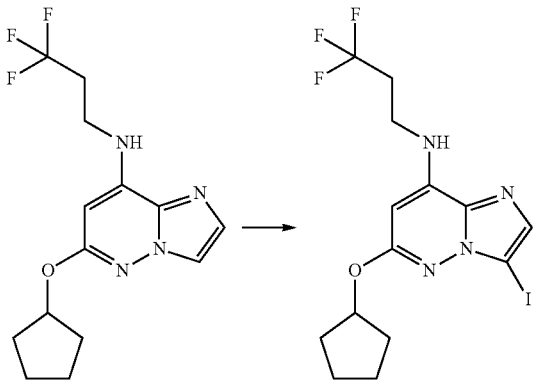 [SMILES: FC(F)(F)CCNc1cc(OC2CCCC2)nn2ccnc12 ; FC(F)(F)CCNc1cc(OC2CCCC2)nn2c(I)cnc12]

42 mg (134 μmol) 6-(cyclopentyloxy)-N-(3,3,3-trifluoropropyl)imidazo[1,2-b]pyridazin-8-amine which was prepared according to intermediate example 455b were transformed in analogy to intermediate example 96c to give after working up and purification 33 mg (56%) of the title compound.

Intermediate Example 455b 6-(cyclopentyloxy)-N-(3,3,3-trifluoropropyl)imidazo[1,2-b]pyridazin-8-amine

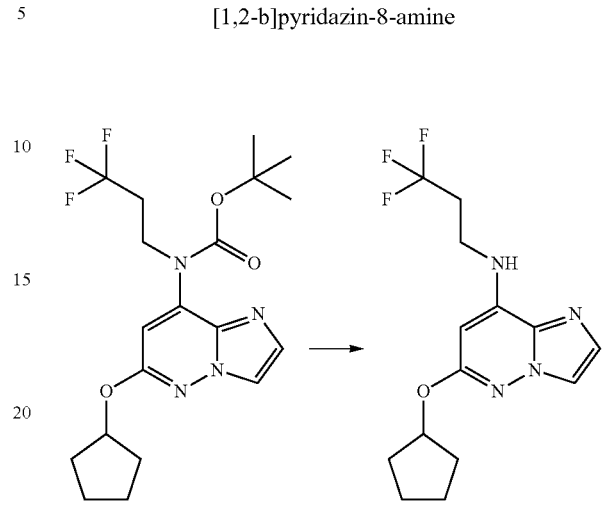

361 mg (max. 784 μmol) tert-butyl [6-(cyclopentyloxy)imidazo[1,2-b]pyridazin-8-yl](3,3,3-trifluoropropyl)carbamate which was prepared according to intermediate example 455c were transformed in analogy to example 453 to give after working up and purification 43 mg (17%) of the title compound.

Intermediate Example 455c tert-butyl[6-(cyclopentyloxy)imidazo[1,2-b]pyridazin-8-yl](3,3,3-trifluoropropyl)carbamate

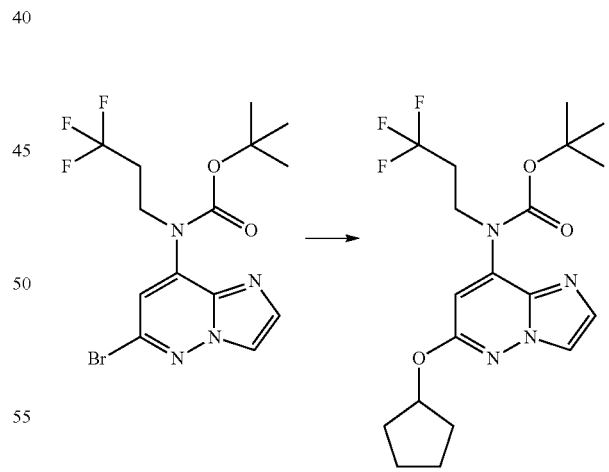

321 mg (784 μmol) tert-butyl (6-bromoimidazo[1,2-b]pyridazin-8-yl)(3,3,3-trifluoropropyl)carbamate which was prepared according to intermediate example 453d were transformed in analogy to intermediate example 51 using cyclopentanol to give after working up 361 mg of the title compound that contains starting material and products in which the carbanate was cleaved.

587

Example 456

N-cyclopropyl-4-{6-[(5-hydroxy-2-methylphenyl)amino]-8-[(3,3,3-trifluoropropyl)amino]imidazo[1,2-b]pyridazin-3-yl}-2-methylbenzamide

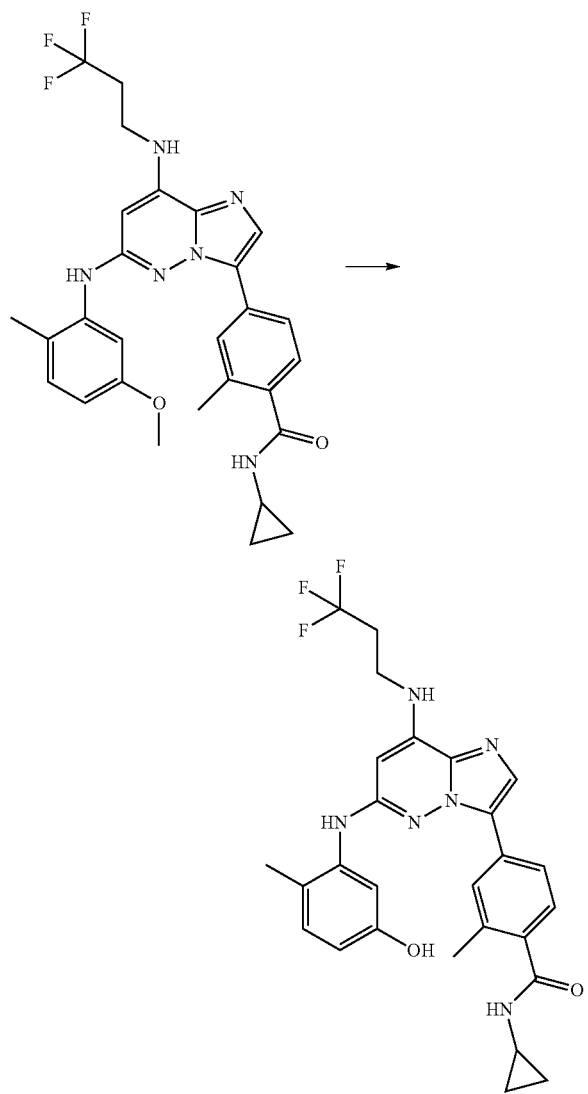

10.5 mg (19 μmol) N-cyclopropyl-4-{6-[(5-methoxy-2-methylphenyl)amino]-8-[(3,3,3-trifluoropropyl)amino]imidazo[1,2-b]pyridazin-3-yl}-2-methylbenzamide which was prepared according to example 430 were transformed in analogy to example 280 to give after working up and purification 2.0 mg (18%) of the title compound.

$^1$H-NMR (DMSO-d6): δ=0.48 (2H), 0.64 (2H), 2.21 (3H), 2.24 (3H), 2.60-2.83 (3H), 3.48 (2H), 5.94 (1H), 6.42 (1H), 6.95 (1H), 7.10 (1H), 7.16 (1H), 7.20 (1H), 7.79-7.90 (3H), 8.01 (1H), 8.21 (1H), 9.06 (1H) ppm.

588

Example 457

N-cyclopropyl-4-{6-[(4-fluoro-2-methoxyphenyl)amino]-8-[(4,4,4-trifluorobutyl)amino]imidazo[1,2-b]pyridazin-3-yl}-2-methylbenzamide

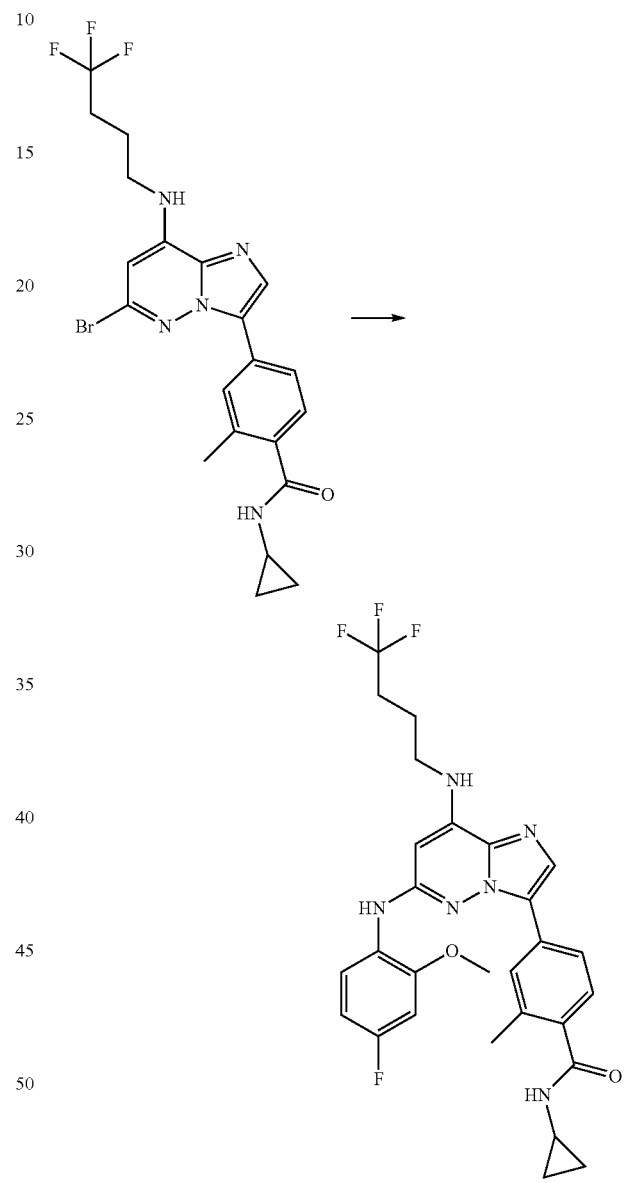

150 mg (302 μmol) 4-{6-bromo-8-[(4,4,4-trifluorobutyl)amino]imidazo[1,2-b]pyridazin-3-yl}-N-cyclopropyl-2-methylbenzamide which was prepared according to intermediate example 447a were transformed in analogy to example 305 using 4-fluoro-2-methoxyaniline to give after working up and purification 43.1 mg (24%) of the title compound.

$^1$H-NMR (CDCl$_3$): δ=0.65 (2H), 0.91 (2H), 2.02 (2H), 2.28 (2H), 2.54 (3H), 2.94 (1H), 3.42 (2H), 3.92 (3H), 5.58 (1H), 5.66 (1H), 5.93 (1H), 6.63-6.71 (3H), 7.41 (1H), 7.63 (1H), 7.81 (1H), 8.01 (1H), 8.28 (1H) ppm.

Example 458

N-cyclopropyl-4-{6-[2-fluoro-3-(methylsulfanyl)phenoxy]-8-[(2-hydroxy-2-methylpropyl)amino]imidazo[1,2-b]pyridazin-3-yl}-2-methylbenzamide

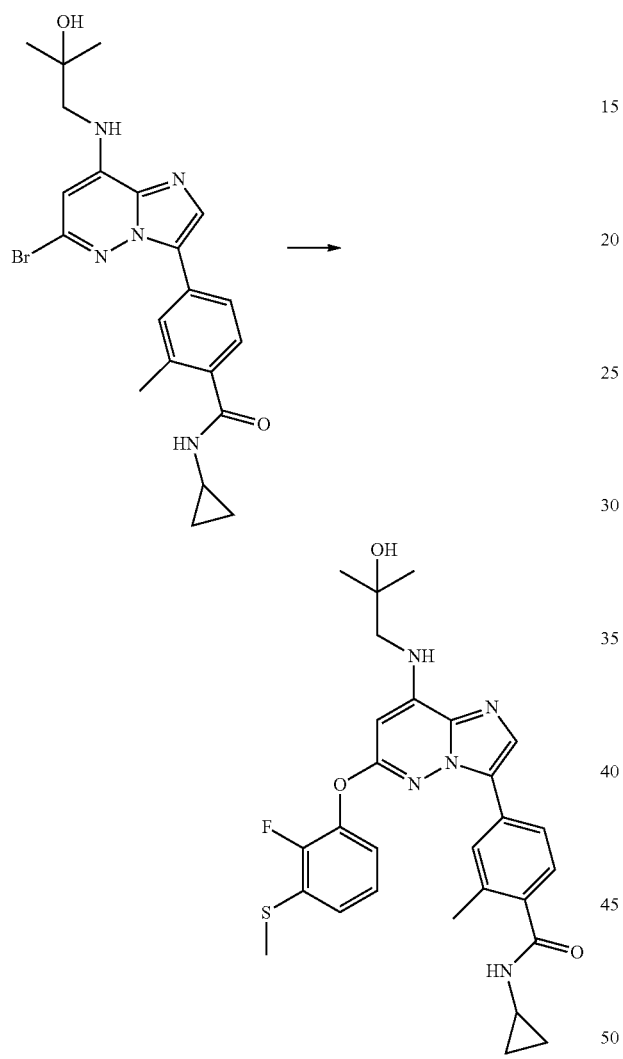

2.00 g (4.36 mmol) 4-{6-bromo-8-[(2-hydroxy-2-methylpropyl)amino]imidazo[1,2-b]pyridazin-3-yl}-N-cyclopropyl-2-methylbenzamide which was prepared according to intermediate example 96a were transformed in analogy to example 51 using 2,3-difluorophenol to give after working up and purification 4.6 mg (0.2%) of the title compound and 933 mg (42%) of the title compound described in example 92.

$^1$H-NMR (DMSO-d6): δ=0.50 (2H), 0.67 (2H), 1.21 (6H), 2.14 (3H), 2.52 (3H), 2.80 (1H), 3.33 (2H), 4.78 (1H), 6.27 (1H), 7.05 (1H), 7.17 (1H), 7.26 (1H), 7.28-7.34 (2H), 7.64 (1H), 7.70 (1H), 7.95 (1H), 8.23 (1H) ppm.

Example 459

4-{6-(3-fluorophenoxy)-8-[(3,3,3-trifluoropropyl)amino]imidazo[1,2-b]pyridazin-3-yl}-2-methyl-N-(1-methylcyclopropyl)benzamide

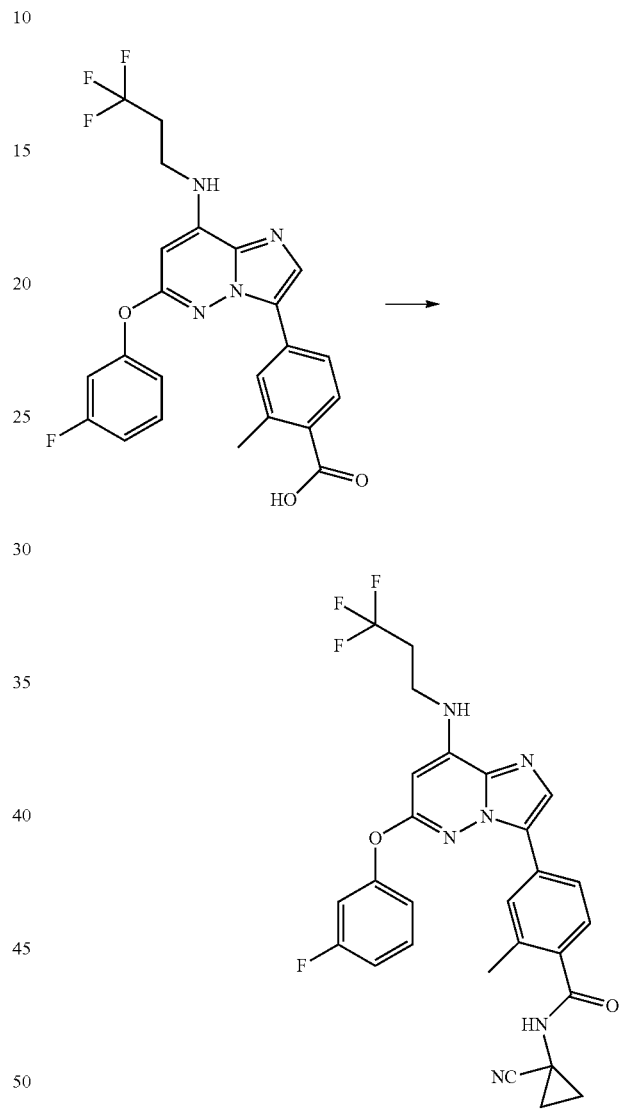

A mixture comprising 10.5 mg (22 µmol) 4-{6-(3-fluorophenoxy)-8-[(3,3,3-trifluoropropyl)amino]imidazo[1,2-b]pyridazin-3-yl}-2-methylbenzoic acid which was prepared according to intermediate example 459a, 3.94 mg 1-cyanocyclopropanaminium chloride, 12.6 mg N-[(dimethylamino)(3H-[1,2,3]triazolo[4,5-b]pyridin-3-yloxy)methylene]-N-methylmethanaminium hexafluorophosphate, 4.06 mg N,N-dimethylpyridin-4-amine and 0.5 mL N,N-dimethylformamide was stirred at 23° C. overnight. The solvent was removed and the residue purified by chromatography to give 4.5 mg (36%) of the title compound.

¹H-NMR (DMSO-d6): δ=1.21 (2H), 1.50 (2H), 2.16 (3H), 2.68 (2H), 3.60 (2H), 6.14 (1H), 7.14 (2H), 7.25 (2H), 7.49 (1H), 7.67-7.76 (2H), 7.81 (1H), 7.97 (1H), 9.09 (1H) ppm.

Intermediate Example 459a

4-{6-(3-fluorophenoxy)-8-[(3,3,3-trifluoropropyl)amino]imidazo[1,2-b]pyridazin-3-yl}-2-methylbenzoic acid

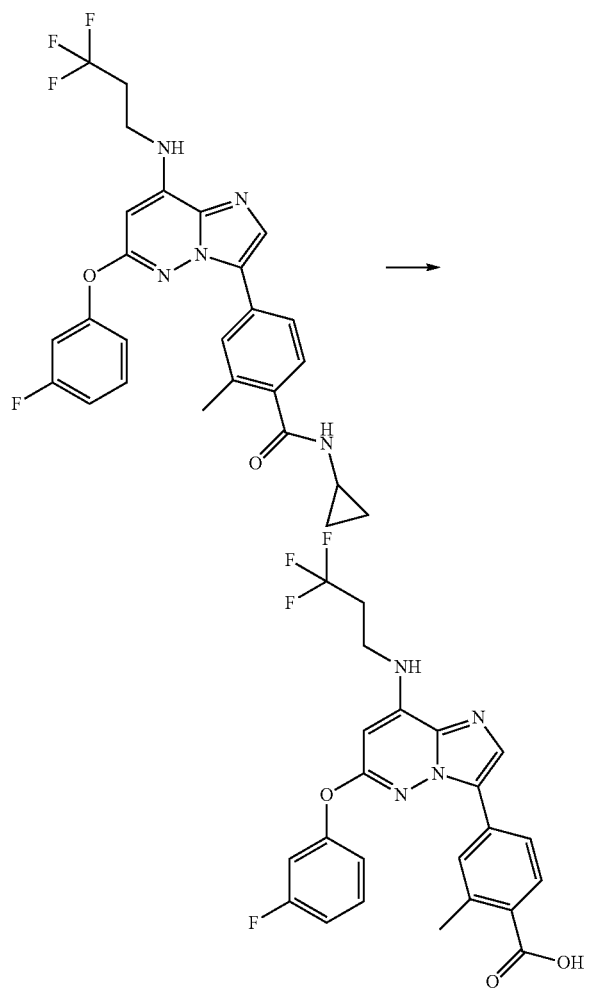

A mixture comprising 231.8 mg (451 μmol) N-cyclopropyl-4-{6-(3-fluorophenoxy)-8-[(3,3,3-trifluoropropyl)amino]imidazo[1,2-b]pyridazin-3-yl}-2-methylbenzamide which was prepared according to example 80 and 7.73 mL hydrobromic acid was heated at 120° C. for 10 hours. Water was added, the precipitate filtered off and purified by chromatography to give 74 mg (24%) of title compound that contained about 30% 4-{6-(3-fluorophenoxy)-8-[(3,3,3-trifluoropropyl)amino]imidazo[1,2-b]pyridazin-3-yl}-2-methylbenzamide.

Example 460

4-{6-(3-fluorophenoxy)-8-[(3,3,3-trifluoropropyl)amino]imidazo[1,2-b]pyridazin-3-yl}-N-(1-methoxycyclopropyl)-2-methylbenzamide

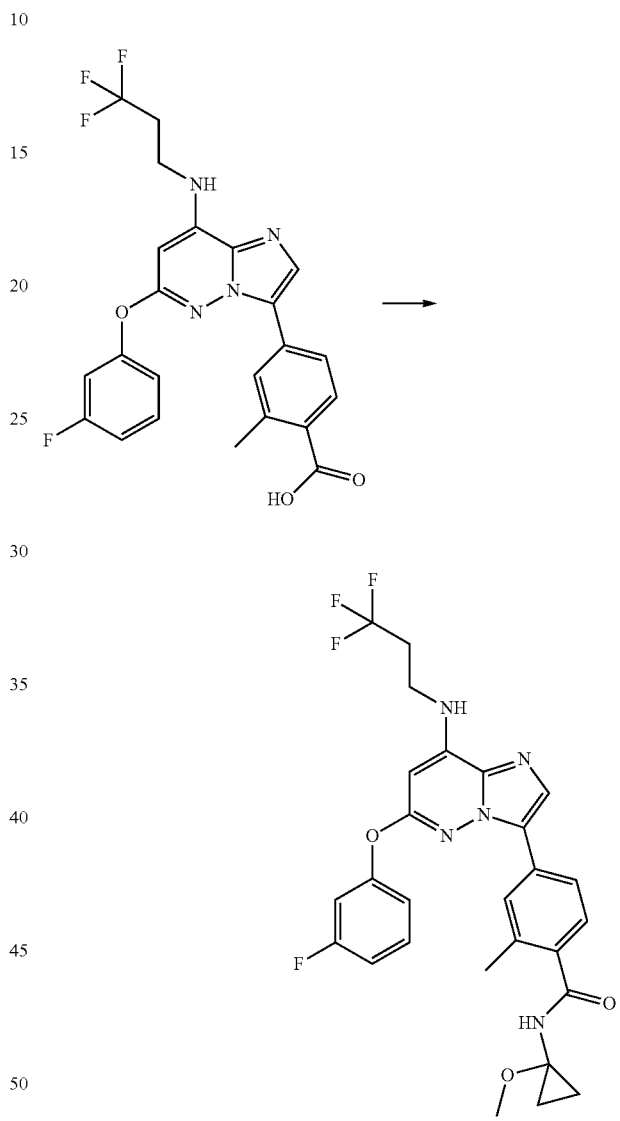

10.5 mg (22 μmol) 4-{6-(3-fluorophenoxy)-8-[(3,3,3-trifluoropropyl)amino]imidazo[1,2-b]pyridazin-3-yl}-2-methylbenzoic acid which was prepared according to intermediate example 459a were transformed in analogy to example 459 using 1-methoxycyclopropanaminium chloride to give after working up and purification 10.7 mg (85%) of the title compound.

¹H-NMR (DMSO-d6): δ=0.84 (2H), 0.97 (2H), 2.15 (3H), 2.68 (2H), 3.24 (3H), 3.60 (2H), 6.13 (1H), 7.09-7.16 (2H), 7.21 (1H), 7.25 (1H), 7.49 (1H), 7.67 (1H), 7.71 (1H), 7.78 (1H), 7.94 (1H), 9.04 (1H) ppm.

Example 461

4-{6-(3-fluorophenoxy)-8-[(3,3,3-trifluoropropyl)amino]imidazo[1,2-b]pyridazin-3-yl}-2-methyl-N-(1-methylcyclopropyl)benzamide

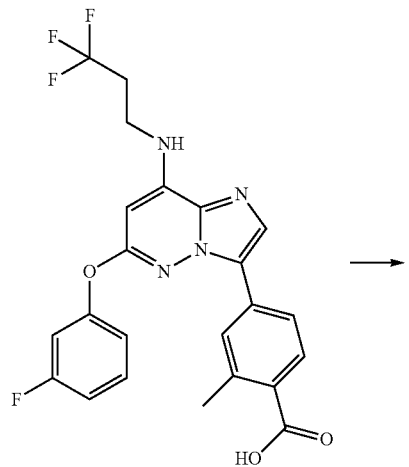

10.5 mg (22 µmol) 4-{6-(3-fluorophenoxy)-8-[(3,3,3-trifluoropropyl)amino]imidazo[1,2-b]pyridazin-3-yl}-2-methylbenzoic acid which was prepared according to intermediate example 459a were transformed in analogy to example 459 using 1-methylcyclopropanaminium chloride to give after working up and purification 12.0 mg (98%) of the title compound.

$^1$H-NMR (CDCl$_3$): δ=0.74 (2H), 0.85 (2H), 1.51 (3H), 2.31 (3H), 2.58 (2H), 3.68 (2H), 5.89 (1H), 5.99 (1H), 6.07 (1H), 6.94-7.09 (3H), 7.23 (1H), 7.39 (1H), 7.61 (1H), 7.73 (2H) ppm.

Example 462

3-(3-amino-1H-indazol-6-yl)-6-(3-fluorophenoxy)-N-(3,3,3-trifluoropropyl)imidazo[1,2-b]pyridazin-8-amine

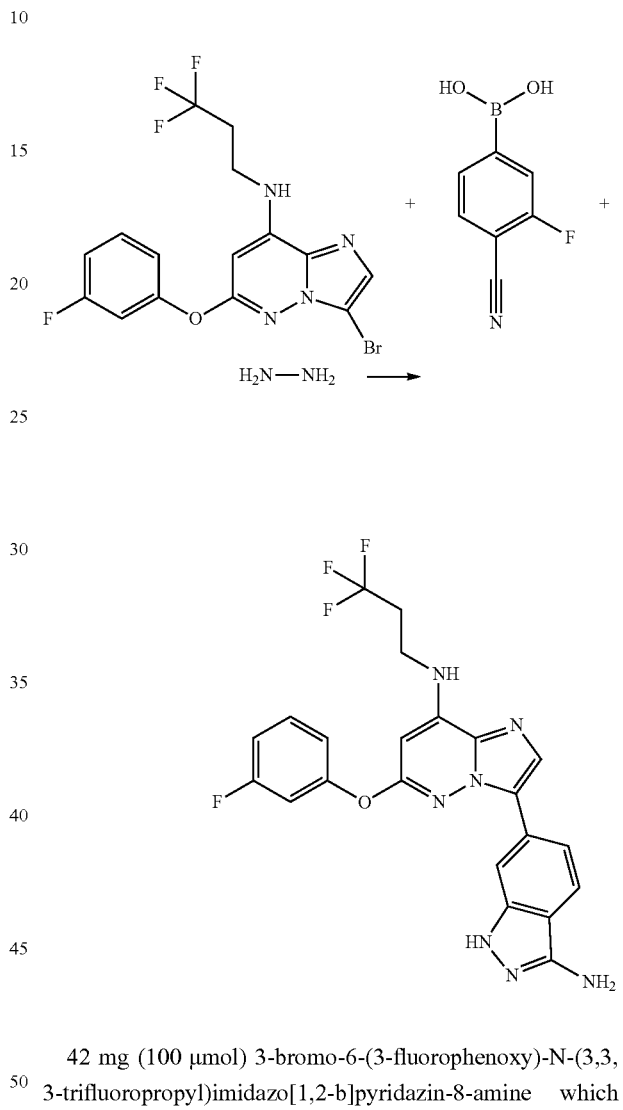

42 mg (100 µmol) 3-bromo-6-(3-fluorophenoxy)-N-(3,3,3-trifluoropropyl)imidazo[1,2-b]pyridazin-8-amine which was prepared according to intermediate example 462a were transformed in analogy to example 101 using (4-cyano-3-fluorophenyl)boronic acid to give 2-fluoro-4-[6-(3-fluorophenoxy)-8-(3,3,3-trifluoro-propylamino)-imidazo[1,2-b]pyridazin-3-yl]-benzonitrile. 62 µL (2 mmol) hydrazine hydrate were added and the mixture was heated at 80° C. overnight. After working up and purification 5.1 mg (11%) of the title compound were obtained.

UPLC-MS: RT=1.14, MWfound=472.4. MWcalc=471.4. 1H-NMR (300 MHz, DMSO-d6), δ [ppm]=2.65 (3H), 3.58 (3H), 5.32 (2H), 6.06 (1H), 7.00-7.21 (3H), 7.38 (1H), 7.49 (1H), 7.59 (1H), 7.73 (1H), 7.83 (1H), 7.91 (1H), 11.31 (1H)

Intermediate Example 462a 3-bromo-6-(3-fluorophenoxy)-N-(3,3,3-trifluoropropyl)imidazo[1,2-b]pyridazin-8-amine

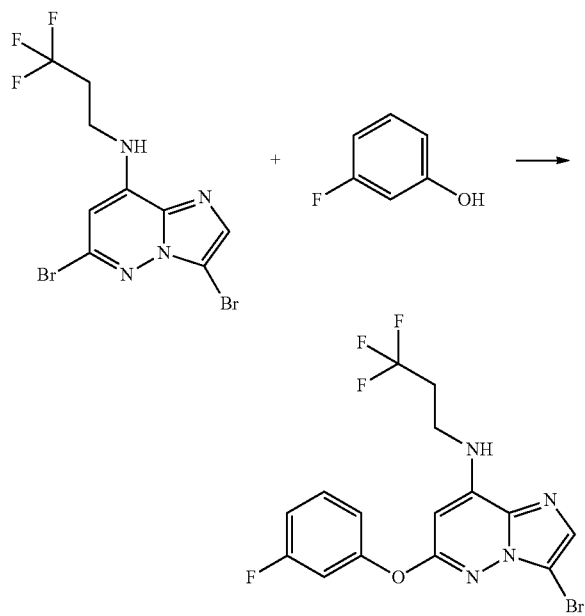

448.9 mg (1.16 mmol) 3,6-dibromo-N-(3,3,3-trifluoropropyl)imidazo[1,2-b]pyridazin-8-amine which was prepared according to intermediate example 462b were transformed in analogy to example 51 using 3-fluorophenol to give after working up and purification 105.7 mg (22%) of the title compound.

$^1$H-NMR (300 MHz, DMSO-d6), δ [ppm]=2.55-2.73 (2H), 3.55 (2H), 6.06 (1H), 7.00-7.09 (2H), 7.11-7.22 (1H), 7.33-7.49 (1H), 7.56 (1H), 7.82 (1H)

Intermediate Example 462b 3,6-dibromo-N-(3,3,3-trifluoropropyl)imidazo[1,2-b]pyridazin-8-amine

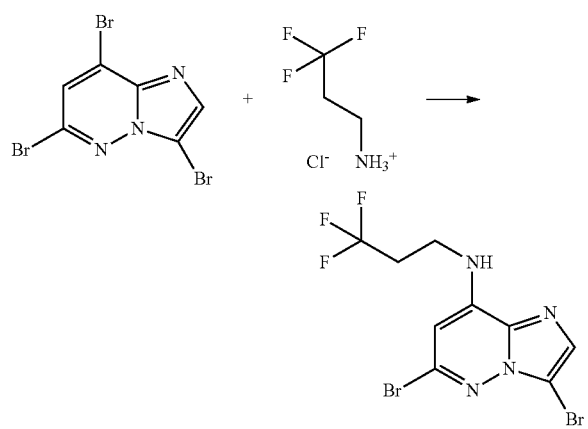

3,6-dibromo-N-(3,3,3-trifluoropropyl)imidazo[1,2-b]pyridazin-8-amine 3.00 g (8.43 mmol) 3,6,8-tribromoimidazo[1,2-b]pyridazine which was prepared according to intermediate example 462c were transformed in analogy to intermediate example 1b using 3,3,3-trifluoropropan-1-aminium chloride to give after working up and purification 2.97 g (91%) of the title compound.

$^1$H-NMR (300 MHz, DMSO-d$_6$), δ [ppm]=2.52-2.73 (2H), 3.56 (2H), 6.45 (1H), 7.61 (1H), 8.01 (1H)

Intermediate Example 462c 3,6,8-tribromoimidazo[1,2-b]pyridazine

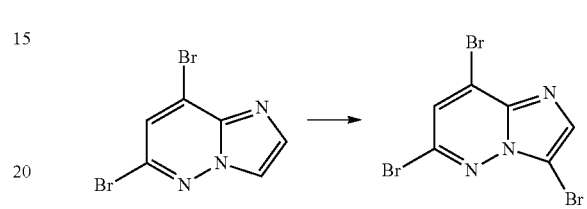

To a stirred suspension of 100.00 g (361.1 mmol) 6,8-dibromoimidazo[1,2-b]pyridazine, which was prepared according to intermediate example 96d, in 1.6 L acetic acid were added 69.2 g (433.3 mmol) bromine at it and the mixture was stirred for 1 h. The precipitate was filtered, washed with water and dissolved in 10 L DCM. The organic üphase was washed with saturated sodium hydrogen carbonate solution, dried over sodium sulfate, filtered and evaporated to give 81.99 g (64%) of the title compound.

$^1$H-NMR (400 MHz, DMSO-d$_6$), δ [ppm]=7.96 (1H), 8.04 (1H).

Example 463

N-cyclopropyl-4-{6-(3-fluorophenoxy)-8-[(3,3,3-trifluoropropyl)amino]imidazo[1,2-b]pyridazin-3-yl}benzamide

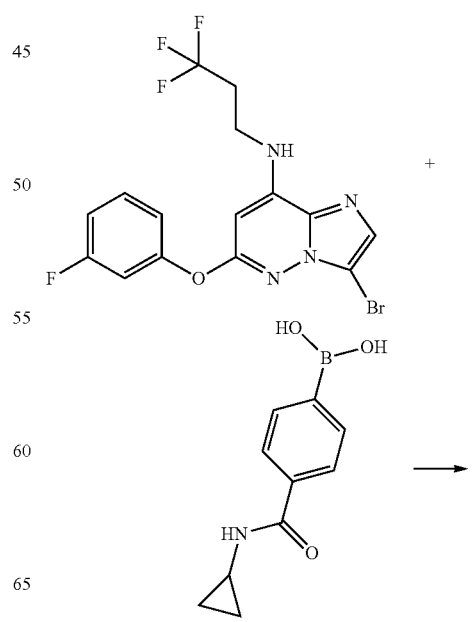

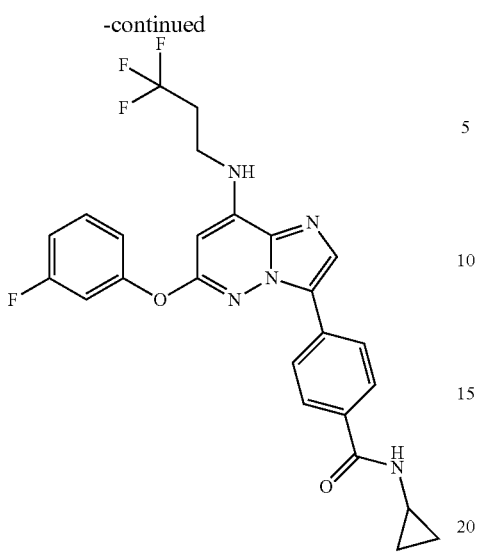

42 mg (100 μmol) 3-bromo-6-(3-fluorophenoxy)-N-(3,3,3-trifluoropropyl)imidazo[1,2-b]pyridazin-8-amine which was prepared according to intermediate example 462a were transformed in analogy to example 101 using [4-(cyclopropylcarbamoyl)phenyl]boronic acid to give after working up and purification 2.9 mg (5%) of the title compound.

UPLC-MS: RT=1.31, $MW_{found}$=500.5. $MW_{calc}$=499.5.
$^{1}$H-NMR (300 MHz, DMSO-d$_6$), δ [ppm]=0.52 (2H), 0.66 (2H), 2.67 (2H), 2.79 (1H), 3.59 (2H), 6.14 (1H), 7.08-7.17 (2H), 7.24 (1H), 7.33-7.60 (2H), 7.68 (1H), 7.77 (1H), 7.95 (1H), 8.01 (1H), 8.40 (1H).

Example 464

N-cyclopropyl-4-{6-[(5-fluoropyridin-3-yl)oxy]-8-[(3,3,3-trifluoropropyl)amino]imidazo[1,2-b]pyridazin-3-yl}-2-methylbenzamide

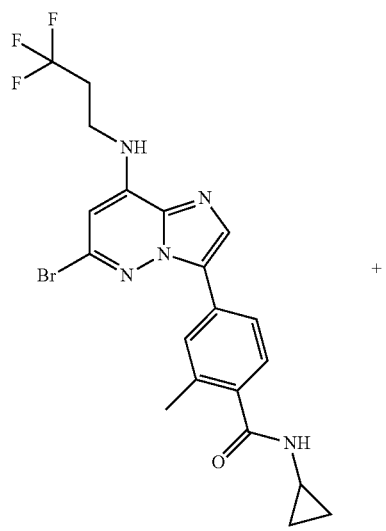

+

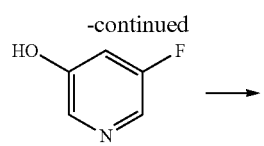

→

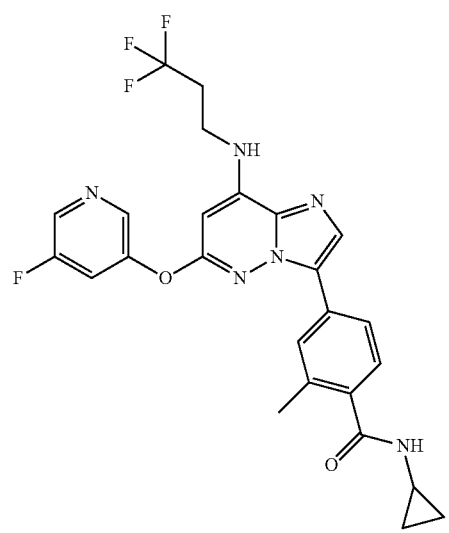

48 mg (100 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a were transformed in analogy to example 51 using 5-fluoropyridin-3-ol to give after working up and purification 8.1 mg (16%) of the title compound.

UPLC-MS: RT=1.19, $MW_{found}$=515.5. $MW_{calc}$=514.5.
$^{1}$H-NMR (300 MHz, DMSO-d$_6$), δ [ppm]=0.41-0.54 (2H), 0.58-0.71 (2H), 2.14 (3H), 2.59-2.85 (3H), 3.61 (2H), 6.21 (1H), 7.17 (1H), 7.61 (1H), 7.70 (1H), 7.81 (1H), 7.93 (1H), 7.95-8.06 (1H), 8.22 (1H), 8.46-8.63 (2H)

The following compound examples were prepared analogously to the procedure described for example 51 using the appropriate phenols or anilines [LC-MS data such as retention time (RT in min) or observed mass peak were collected using LC-MS Method A unless explicitly stated]:

| Example | Structure | Name | Analytical Data |
|---|---|---|---|
| 465 | 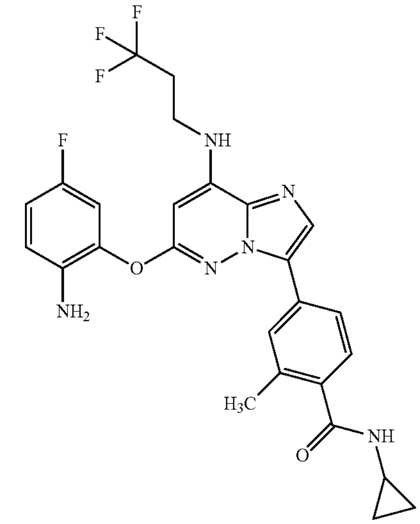 [SMILES: Cc1cc(-c2cnc3c(NCCC(F)(F)F)cc(Oc4cc(F)ccc4N)nn23)ccc1C(=O)NC1CC1] | 4-{6-(2-amino-5-fluoro-phenoxy)-8-[(3,3,3-trifluoropropyl)amino]imidazo[1,2-b]pyridazin-3-yl}-N-cyclopropyl-2-methylbenzamide | RT = 1.25 MW$_{found}$ = 529.5 MW$_{calc}$ = 528.5 $^1$H-NMR (300 MHz, DMSO-d$_6$), δ [ppm] = 0.43-0.51 (2H), 0.58-0.69 (2H), 2.15 (3H), 2.60-2.82 (3H), 3.59 (2H), 4.83 (2H), 6.10 (1H), 6.74-6.82 (1H), 6.85 (1H), 7.03 (1H), 7.15 (1H), 7.61-7.70 (2H), 7.84 (1H), 7.92 (1H), 8.22 (1H) |
| 466 | 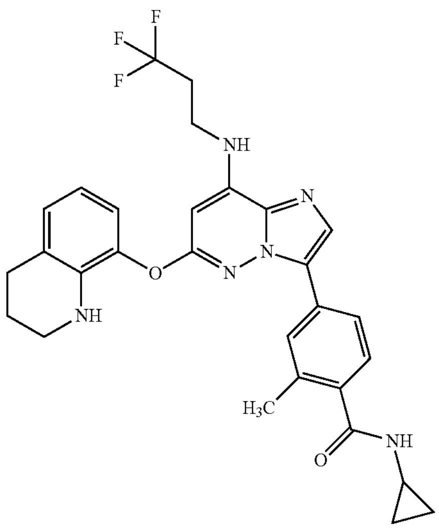 [SMILES: Cc1cc(-c2cnc3c(NCCC(F)(F)F)cc(Oc4cccc5c4NCCC5)nn23)ccc1C(=O)NC1CC1] | N-cyclopropyl-2-methyl-4-{6-(1,2,3,4-tetrahydro-quinolin-8-yloxy)-8-[(3,3,3-trifluoropropyl)amino]imidazo[1,2-b]pyridazin-3-yl}benzamide | RT = 1.36 MW$_{found}$ = 551.6 MW$_{calc}$ = 550.6 $^1$H-NMR (600 MHz, DMSO-d$_6$), δ [ppm] = 0.48-0.54 (2H), 0.63-0.70 (2H), 1.76-1.82 (2H), 2.19 (3H), 2.66-2.78 (4H), 2.80 (1H), 3.12-3.20 (2H), 3.61 (2H), 5.24 (1H), 6.08 (1H), 6.50 (1H), 6.82 (1H), 6.90 (1H), 7.18 (1H), 7.60 (1H), 7.72-7.77 (1H), 7.87 (1H), 7.95 (1H), 8.23 (1H) |
| 467 | 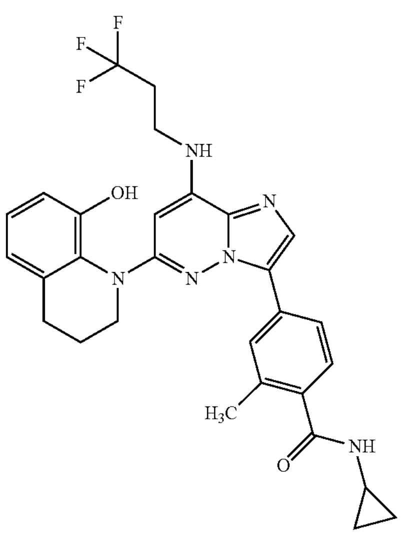 [SMILES: Cc1cc(-c2cnc3c(NCCC(F)(F)F)cc(N4CCCc5cccc(O)c54)nn23)ccc1C(=O)NC1CC1] | N-cyclopropyl-4-{6-(8-hydroxy-3,4-dihydro-quinolin-1(2H)-yl)-8-[(3,3,3-trifluoropropyl)amino]imidazo[1,2-b]pyridazin-3-yl}-2-methyl-benzamide | RT = 1.19 MW$_{found}$ = 551.6 MW$_{calc}$ = 550.6 $^1$H-NMR (600 MHz, DMSO-d$_6$), δ [ppm] = 0.50-0.56 (2H), 0.64-0.71 (2H), 1.88 (2H), 2.31 (3H), 2.62 (2H), 2.69 (2H), 2.83 (1H), 3.44 (2H), 3.84 (2H), 5.72 (1H), 6.66 (1H), 6.74 (1H), 6.90-6.94 (1H), 7.11 (1H), 7.27 (1H), 7.84 (1H), 7.92 (1H), 7.96 (1H), 8.25 (1H), 9.29 (1H) Isomer! |

-continued

| Example | Structure | Name | Analytical Data |
|---------|-----------|------|-----------------|
| 468 | 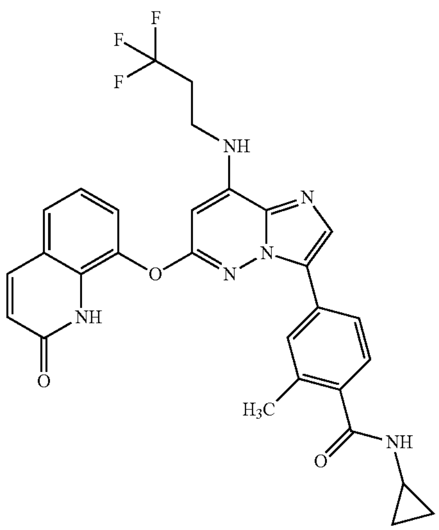 [SMILES: Cc1cc(-c2cnc3c(NCCC(F)(F)F)cc(Oc4cccc5ccc(=O)[nH]c45)nn23)ccc1C(=O)NC1CC1] | N-cyclopropyl-2-methyl-4-{6-[(2-oxo-1,2-dihydroquinolin-8-yl)oxy]-8-[(3,3,3-trifluoropropyl)amino]imidazo[1,2-b]pyridazin-3-yl}benzamide | RT = 1.01 MW$_{found}$ = 563.5 MW$_{calc}$ = 562.5 $^1$H-NMR (600 MHz, DMSO-d$_6$), δ [ppm] = 0.47-0.51 (2H), 0.64-0.69 (2H), 2.06 (3H), 2.71-2.82 (3H), 3.66 (2H), 6.25 (1H), 6.55 (1H), 7.08 (1H), 7.26 (1H), 7.54 (1H), 7.57 (1H), 7.62-7.65 (2H), 7.66-7.71 (1H), 7.93 (1H), 8.02 (1H), 8.20 (1H) |
| 469 | 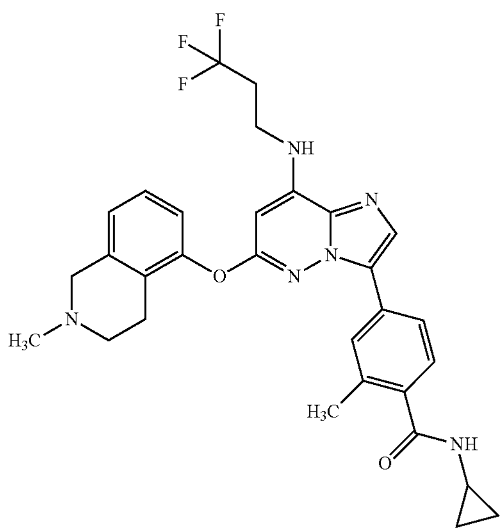 [SMILES: Cc1cc(-c2cnc3c(NCCC(F)(F)F)cc(Oc4cccc5c4CCN(C)C5)nn23)ccc1C(=O)NC1CC1] | N-cyclopropyl-2-methyl-4-{6-[(2-methyl-1,2,3,4-tetrahydroisoquinolin-5-yl)oxy]-8-[(3,3,3-trifluoropropyl)amino]imidazo[1,2-b]pyridazin-3-yl}benzamide | RT = 0.95 MW$_{found}$ = 565.6 MW$_{calc}$ = 564.6 $^1$H-NMR (300 MHz, DMSO-d$_6$), δ [ppm] = 0.42-0.50 (2H), 0.58-0.68 (2H), 2.09 (3H), 2.28 (3H), 2.53 (2H), 2.60-2.81 (5H), 3.51 (2H), 3.59 (2H), 6.11 (1H), 6.97-7.06 (2H), 7.12 (1H), 7.16-7.24 (1H), 7.58-7.67 (2H), 7.71 (1H), 7.91 (1H), 8.18 (1H) |
| 470 | 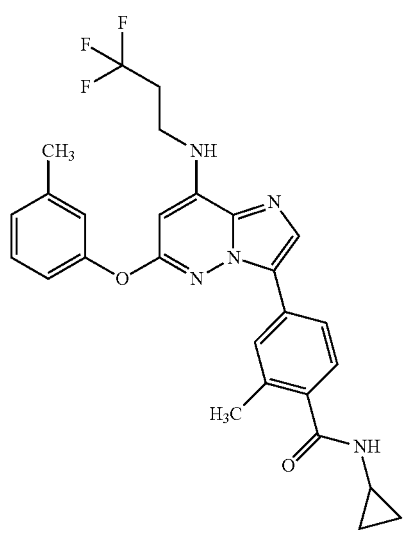 [SMILES: Cc1cccc(Oc2cc(NCCC(F)(F)F)c3ncc(-c4ccc(C(=O)NC5CC5)c(C)c4)n3n2)c1] | N-cyclopropyl-2-methyl-4-{6-(3-methylphenoxy)-8-[(3,3,3-trifluoropropyl)amino]imidazo[1,2-b]pyridazin-3-yl}benzamide | RT = 1.42 MW$_{found}$ = 510.5 MW$_{calc}$ = 509.5 |

| Example | Structure | Name | Analytical Data |
|---|---|---|---|
| 471 | 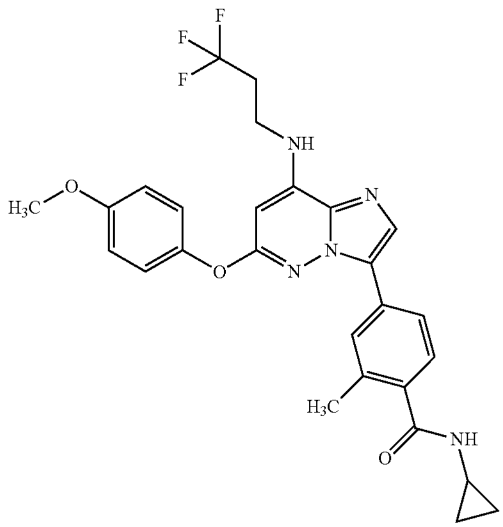 [SMILES: COc1ccc(Oc2cc(NCCC(F)(F)F)c3ncc(-c4ccc(C(=O)NC5CC5)c(C)c4)n3n2)cc1] | N-cyclopropyl-4-{6-(4-methoxyphenoxy)-8-[(3,3,3-trifluoropropyl)amino]imidazo[1,2-b]pyridazin-3-yl}-2-methylbenzamide | RT = 1.34 MW$_{found}$ = 526.5 MW$_{calc}$ = 525.5 $^1$H-NMR (400 MHz, DMSO-d$_6$), δ [ppm] = 0.43-0.50 (2H), 0.60-0.68 (2H), 2.11 (3H), 2.60-2.73 (2H), 2.77 (1H), 3.59 (2H), 3.75 (3H), 6.07 (1H), 6.99 (2H), 7.13-7.22 (3H), 7.58-7.67 (2H), 7.77 (1H), 7.91 (1H), 8.19 (1H) |
| 472 | 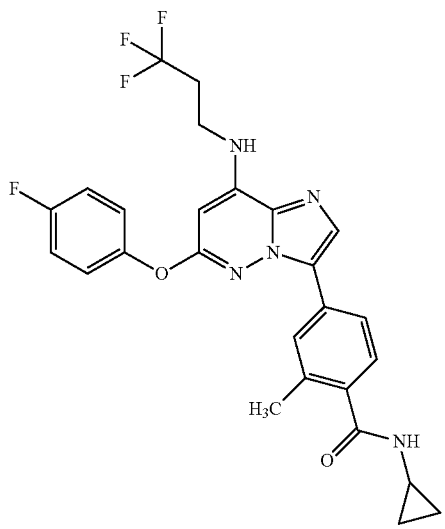 [SMILES: Cc1cc(-c2cnc3c(NCCC(F)(F)F)cc(Oc4ccc(F)cc4)nn23)ccc1C(=O)NC1CC1] | N-cyclopropyl-4-{6-(4-fluorophenoxy)-8-[(3,3,3-trifluoropropyl)amino]imidazo[1,2-b]pyridazin-3-yl}-2-methyl-benzamide | RT = 1.36 MW$_{found}$ = 514.5 MW$_{calc}$ = 513.5 $^1$H-NMR (400 MHz, DMSO-d$_6$), δ [ppm] = 0.47 (2H), 0.63 (2H), 2.13 (3H), 2.60-2.73 (2H), 2.73-2.82 (1H), 3.60 (2H), 6.11 (1H), 7.16 (1H), 7.23-7.36 (4H), 7.60-7.70 (2H), 7.72 (1H), 7.92 (1H), 8.20 (1H) |
| 473 | 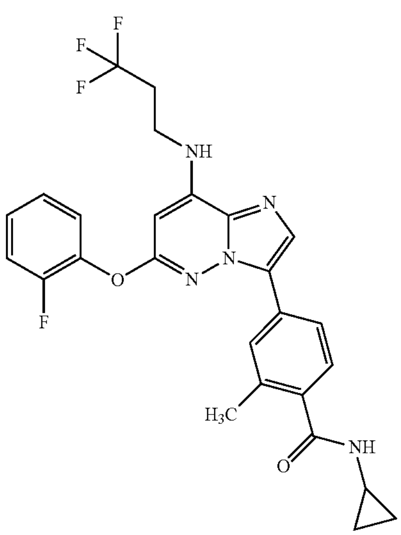 [SMILES: Cc1cc(-c2cnc3c(NCCC(F)(F)F)cc(Oc4ccccc4F)nn23)ccc1C(=O)NC1CC1] | N-cyclopropyl-4-{6-(2-fluorophenoxy)-8-[(3,3,3-trifluoropropyl)amino]imidazo[1,2-b]pyridazin-3-yl}-2-methyl-benzamide | RT = 1.36 MW$_{found}$ = 514.5 MW$_{calc}$ = 513.5 |

-continued

| Example | Structure | Name | Analytical Data |
|---|---|---|---|
| 474 | 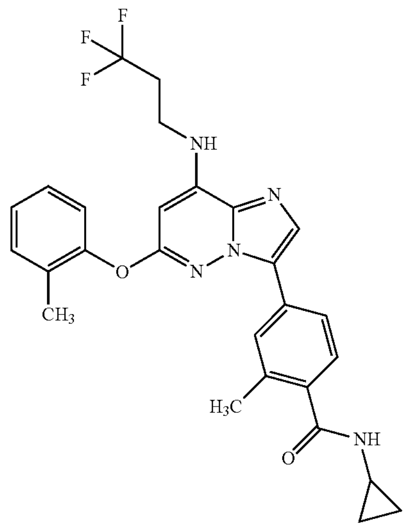 [SMILES: Cc1ccccc1Oc1cc(NCCC(F)(F)F)c2ncc(-c3ccc(C(=O)NC4CC4)c(C)c3)n2n1] | N-cyclopropyl-2-methyl-4-{6-(2-methylphenoxy)-8-[(3,3,3-trifluoropropyl)amino]imidazo[1,2-b]pyridazin-3-yl}benzamide | RT = 1.40 MW$_{found}$ = 510.5 MW$_{calc}$ = 509.5 |
| 475 | 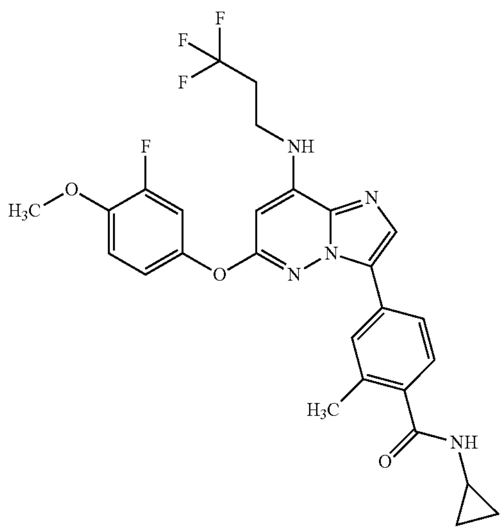 [SMILES: COc1ccc(Oc2cc(NCCC(F)(F)F)c3ncc(-c4ccc(C(=O)NC5CC5)c(C)c4)n3n2)cc1F] | N-cyclopropyl-4-{6-(3-fluoro-4-methoxyphenoxy)-8-[(3,3,3-trifluoropropyl)amino]imidazo[1,2-b]pyridazin-3-yl}-2-methylbenzamide | RT = 1.35 MW$_{found}$ = 544.5 MW$_{calc}$ = 543.5 |
| 476 | 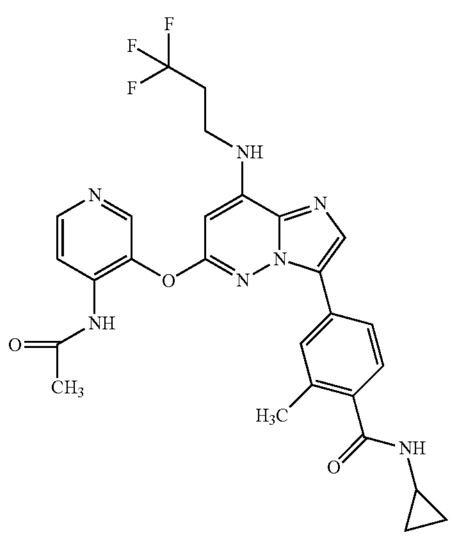 [SMILES: CC(=O)Nc1ccncc1Oc1cc(NCCC(F)(F)F)c2ncc(-c3ccc(C(=O)NC4CC4)c(C)c3)n2n1] | 4-(6-{[4-(acetylamino)pyridin-3-yl]oxy}-8-[(3,3,3-trifluoropropyl)amino]imidazo[1,2-b]pyridazin-3-yl)-N-cyclopropyl-2-methylbenzamide | RT = 0.89 MW$_{found}$ = 554.5 MW$_{calc}$ = 553.5 $^1$H-NMR (300 MHz, DMSO-d$_6$), δ [ppm] = 0.44-0.55 (2H), 0.60-0.69 (2H), 2.20-2.27 (3H), 2.36 (3H), 2.65-2.85 (3H), 3.69 (2H), 6.76 (1H), 7.38 (1H), 7.84-7.93 (2H), 7.95-8.04 (2H), 8.09 (1H), 8.23-8.34 (3H), 8.36 (1H) |

-continued

| Example | Structure | Name | Analytical Data |
|---|---|---|---|
| 477 | 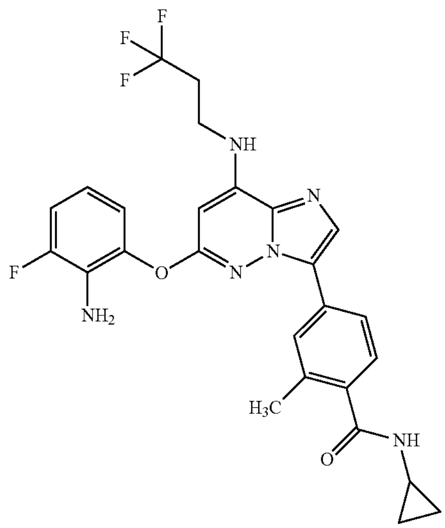 [SMILES: Cc1cc(-c2cnc3c(NCCC(F)(F)F)cc(Oc4cccc(F)c4N)nn23)ccc1C(=O)NC1CC1] | 4-{6-(2-amino-3-fluoro-phenoxy)-8-[(3,3,3-tri-fluoropropyl)amino]imidazo[1,2-b]pyridazin-3-yl}-N-cyclopropyl-2-methylbenzamide | RT = 1.28 MW$_{found}$ = 529.5 MW$_{calc}$ = 528.5 $^1$H-NMR (300 MHz, DMSO-d$_6$), δ [ppm] = 0.42-0.53 (2H), 0.58-0.69 (2H), 2.13 (3H), 2.59-2.85 (3H), 3.50-3.66 (2H), 4.98 (2H), 6.11 (1H), 6.53-6.63 (1H), 6.93 (1H), 6.96-7.03 (1H), 7.14 (1H), 7.60-7.68 (2H), 7.80 (1H), 7.89-7.95 (1H), 8.22 (1H) |
| 478 | 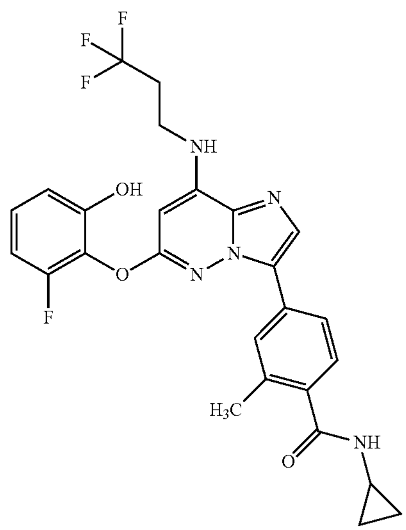 [SMILES: Cc1cc(-c2cnc3c(NCCC(F)(F)F)cc(Oc4c(O)cccc4F)nn23)ccc1C(=O)NC1CC1] | N-cyclopropyl-4-{6-[(2-fluoro-6-hydroxyphenyl)amino]-8-[(3,3,3-tri-fluoropropyl)amino]imidazo[1,2-b]pyridazin-3-yl}-2-methylbenzamide | RT = 1.10 MW$_{found}$ = 529.5 MW$_{calc}$ = 528.5 $^1$H-NMR (300 MHz, DMSO-d$_6$), δ [ppm] = 0.42-0.52 (2H), 0.59-0.69 (2H), 2.17 (3H), 2.58-2.82 (3H), 3.49 (2H), 5.89 (1H), 6.67-6.77 (2H), 6.99-7.10 (1H), 7.10-7.19 (2H), 7.68-7.75 (1H), 7.77 (1H), 7.92 (1H), 7.87 (1H), 8.21 (1H), 9.78 (1H) Isomer |
| 479 | 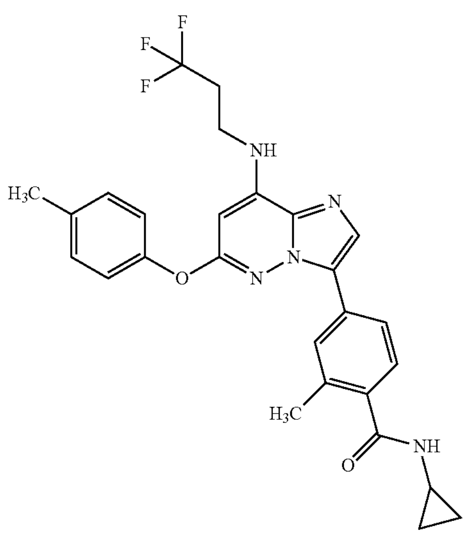 [SMILES: Cc1ccc(Oc2cc(NCCC(F)(F)F)c3ncc(-c4ccc(C(=O)NC5CC5)c(C)c4)n3n2)cc1] | N-cyclopropyl-2-methyl-4-{6-(4-methylphenoxy)-8-[(3,3,3-trifluoropropyl)amino]imidazo[1,2-b]pyridazin-3-yl}benzamide | RT = 1.41 MW$_{found}$ = 510.5 MW$_{calc}$ = 509.5 $^1$H-NMR (300 MHz, DMSO-d$_6$), δ [ppm] = 0.42-0.50 (2H), 0.59-0.67 (2H), 2.09 (3H), 2.31 (3H), 2.59-2.82 (3H), 3.58 (2H), 6.09 (1H), 7.15 (3H), 7.25 (2H), 7.60-7.68 (2H), 7.75 (1H), 7.92 (1H), 8.21 (1H) |

-continued

| Example | Structure | Name | Analytical Data |
|---|---|---|---|
| 480 | 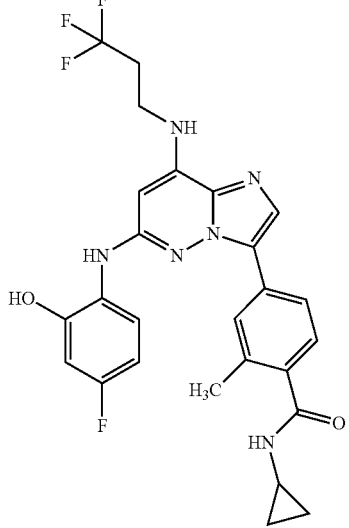 | N-cyclopropyl-4-{6-[(4-fluoro-2-hydroxyphenyl)amino]-8-[(3,3,3-trifluoropropyl)amino]imidazo[1,2-b]pyridazin-3-yl}-2-methylbenzamide | RT = 1.25 MW$_{found}$ = 529.5 MW$_{calc}$ = 528.5 $^1$H-NMR (300 MHz, DMSO-d$_6$), δ [ppm] = 0.45-0.55 (2H), 0.60-0.71 (2H), 2.33 (3H), 2.67 (2H), 2.80 (1H), 3.43-3.53 (2H), 6.21 (1H), 6.53-6.63 (1H), 6.67 (1H), 7.18 (1H), 7.30 (1H), 7.76 (1H), 7.78-7.86 (1H), 7.90 (1H), 7.98-8.14 (3H), 8.28 (1H), 10.28 (1H) |
| 481 | 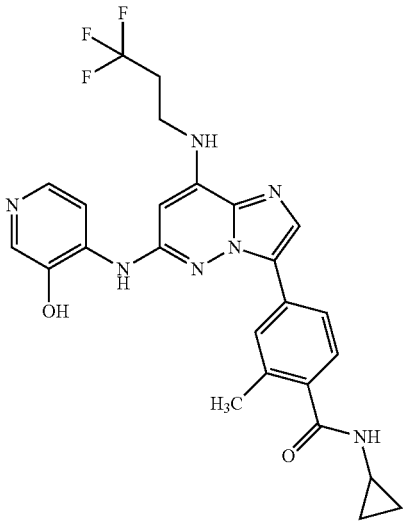 [SMILES: Cc1cc(-c2cnc3c(NCCC(F)(F)F)cc(Nc4ccncc4O)nn23)ccc1C(=O)NC1CC1] | N-cyclopropyl-4-{6-[(3-hydroxypyridin-4-yl)amino]-8-[(3,3,3-trifluoropropyl)amino]imidazo[1,2-b]pyridazin-3-yl}-2-methylbenzamide | RT = 0.84 MW$_{found}$ = 512.5 MW$_{calc}$ = 511.5 $^1$H-NMR (300 MHz, DMSO-d$_6$), δ [ppm] = 0.47-0.56 (2H), 0.62-0.71 (2H), 2.39 (3H), 2.68 (2H), 2.82 (1H), 3.45-3.56 (2H), 6.46 (1H), 7.32-7.42 (2H), 7.77-7.85 (2H), 7.88 (1H), 8.00 (1H), 8.06 (1H), 8.14 (2H), 8.29 (2H) |

Example 482

N-cyclopropyl-2-methyl-4-{6-(1-phenylethenyl)-8-[(3,3,3-trifluoropropyl)amino]imidazo[1,2-b]pyridazin-3-yl}benzamide

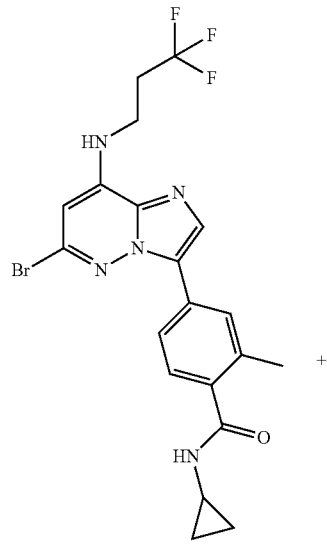

+

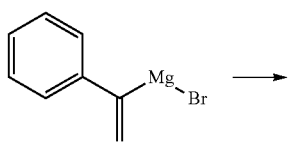

→

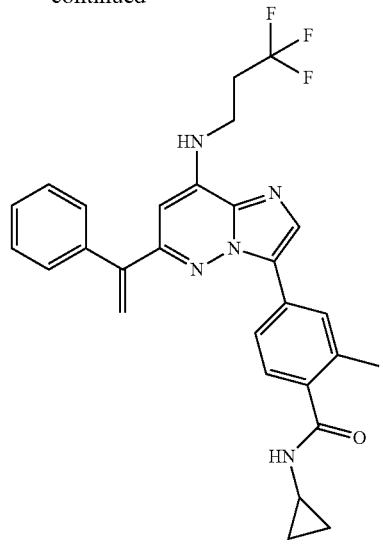

To a stirred solution of 24 mg (50 μmol) 4-{6-bromo-8-[(3,3,3-trifluoropropyl)amino]imidazo[1,2-b]pyridazin-3-yl}-N-cyclopropyl-2-methylbenzamide which was prepared according to intermediate example 247a in 1 mL THF is dropwise added 1.0 mL (0.5 mmol) of a 0.5 M solution of bromo(1-phenylethenyl)magnesium in THF at rt. After stirring overnight at rt, the mixture is heated at 50° C. and stirred for 3 more days to give after working up and purification 1.7 mg (5%) of the title compound.

UPLC-MS: RT=1.36, $MW_{found}$=506.5. $MW_{calc}$=505.5.
$^1$H-NMR (400 MHz, DMSO-$d_6$), δ [ppm]=0.42-0.50 (2H), 0.59-0.66 (2H), 2.15 (3H), 2.61-2.71 (2H), 2.77 (1H), 3.60 (2H), 5.74 (1H), 5.99 (1H), 6.36 (1H), 7.16-7.20 (2H), 7.34-7.45 (3H), 7.55 (2H), 7.79-7.84 (1H), 7.86 (1H), 8.01 (1H), 8.22 (1H)

The following compound examples were prepared analogously to the procedure described for example 482 using the appropriate Grignard reagents [LC-MS data such as retention time (RT in min) or observed mass peak were collected using LC-MS Method A unless explicitly stated]:

| Example | Structure | Name | Analytical Data |
|---|---|---|---|
| 483 | 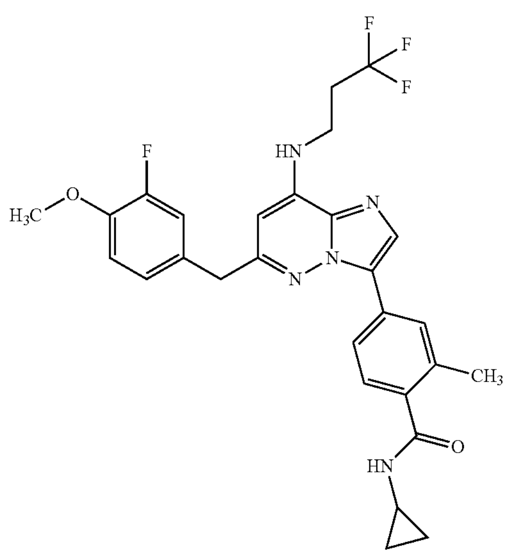 | N-cyclopropyl-4-{6-(3-fluoro-4-methoxybenzyl)-8-[(3,3,3-trifluoropropyl)amino]imidazo[1,2-b]pyridazin-3-yl}-2-methylbenzamide | RT = 1.33 $MW_{found}$ = 542.5 $MW_{calc}$ = 541.5 $^1$H-NMR (400 MHz, DMSO-$d_6$), δ [ppm] = 0.47-0.53 (2H), 0.62-0.69 (2H), 2.32 (3H), 2.64 (2H), 2.77-2.84 (1H), 3.53 (2H), 3.76 (3H), 3.96 (2H), 6.20 (1H), 7.04-7.12 (2H), 7.17-7.23 (1H), 7.30 (1H), 7.47 (1H), 7.93-7.98 (3H), 8.27 (1H) |

-continued

| Example | Structure | Name | Analytical Data |
|---|---|---|---|
| 484 | 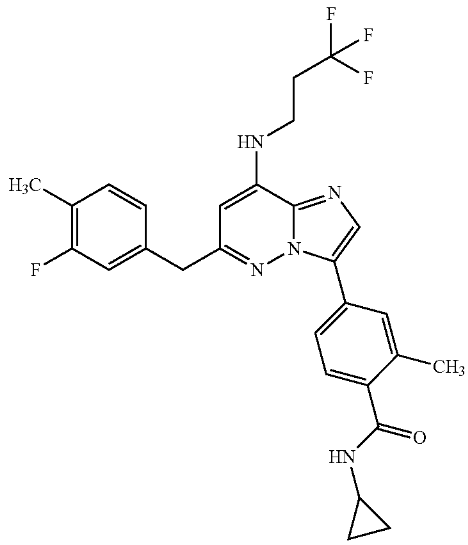 | N-cyclopropyl-4-{6-(3-fluoro-4-methylbenzyl)-8-[(3,3,3-trifluoropropyl)amino]imidazo[1,2-b]pyridazin-3-yl}-2-methylbenzamide | RT = 1.25 MW$_{found}$ = 526.5 MW$_{calc}$ = 525.5 $^1$H-NMR (400 MHz, DMSO-d$_6$), δ [ppm] = 0.47-0.53 (2H), 0.62-0.68 (2H), 2.14-2.17 (3H), 2.31 (3H), 2.59-2.71 (2H), 2.80 (1H), 3.53 (2H), 3.99 (2H), 6.21 (1H), 7.06 (1H), 7.13 (1H), 7.16-7.22 (1H), 7.30 (1H), 7.47 (1H), 7.92-7.99 (3H), 8.27 (1H) |

| Example | Structure | Name | Analytical Data |
|---|---|---|---|
| 485 | 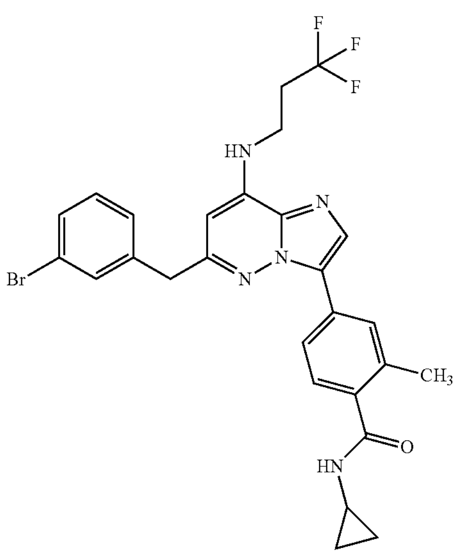 [SMILES: Cc1cc(-c2cnc3c(NCCC(F)(F)F)cc(Cc4cccc(Br)c4)nn23)ccc1C(=O)NC1CC1] | 4-{6-(3-bromobenzyl)-8-[(3,3,3-trifluoropropyl)amino]imidazo[1,2-b]pyridazin-3-yl}-N-cyclopropyl-2-methylbenzamide | RT = 1.44 MW$_{found}$ = 573.4 MW$_{calc}$ = 572.4 $^1$H-NMR (400 MHz, DMSO-d$_6$), δ [ppm] = 0.47-0.53 (2H), 0.62-0.68 (2H), 2.33 (3H), 2.58-2.70 (2H), 2.80 (1H), 3.54 (2H), 4.03 (2H), 6.24 (1H), 7.27 (1H), 7.31 (1H), 7.36 (1H), 7.39-7.44 (1H), 7.47-7.53 (1H), 7.57-7.61 (1H), 7.95 (3H), 8.27 (1H) |

615

Example 486

N-cyclopropyl-4-{6-(3-fluorophenoxy)-8-[(3,3,3-trifluoro-2-hydroxypropyl)amino]imidazo[1,2-b]pyridazin-3-yl}-2-methylbenzamide

616

Intermediate Example 486a

N-cyclopropyl-4-[6-(3-fluorophenoxy)-8-(methylsulfonyl)imidazo[1,2-b]pyridazin-3-yl]-2-methylbenzamide

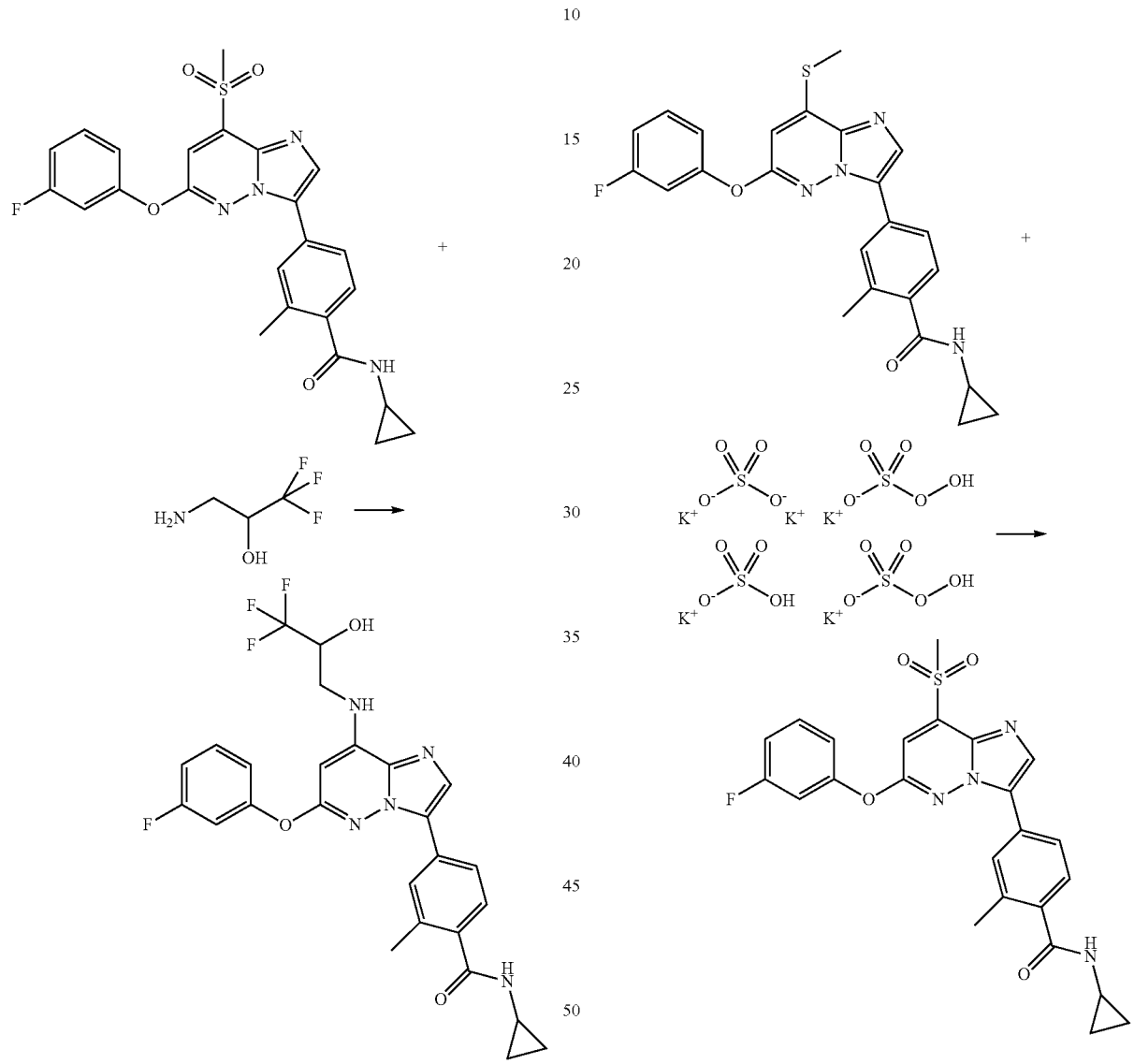

To a stirred solution of 96 mg (200 μmol) N-cyclopropyl-4-[6-(3-fluorophenoxy)-8-(methylsulfonyl)imidazo[1,2-b]pyridazin-3-yl]-2-methylbenzamide which was prepared according to intermediate example 486a in 2 mL NMP is added 77.5 mg (0.6 mmol) 3-amino-1,1,1-trifluoropropan-2-ol and 77.5 mg (0.6 mmol) DIPEA and the mixture is heated at 160° C. for 30 min in a microwave oven. After working up and purification 10.5 mg (9%) of the title compound are obtained.

UPLC-MS: RT=1.23, $MW_{found}$=530.5. $MW_{calc}$=529.5.

To a stirred solution of 4.96 g (11.06 mmol) N-cyclopropyl-4-[6-(3-fluorophenoxy)-8-(methylsulfanyl)imidazo[1,2-b]pyridazin-3-yl]-2-methylbenzamide which was prepared according to intermediate example 486b in DMF (250 mL) were added 20.4 g (33.18 mmol) oxone in one portion at rt. After reaction for 72 h, further 30 g (55 mmol) oxone are added and the mixture is heated at 70° C. for one hour. Extraction with ethyl acetate/water, filtration of the organic phase through a Whatman filter and evaporation of the organic phase yielded the crude product (4.96 g, 93%) which was used without further purification.

¹H-NMR (400 MHz, DMSO-d₆), δ [ppm]=0.44-0.50 (2H), 0.64 (2H), 2.73-2.82 (1H), 3.65 (3H), 7.19-7.24 (2H), 7.24-7.29 (1H), 7.39-7.45 (1H), 7.53-7.61 (2H), 7.68 (1H), 7.72 (1H), 8.28 (1H), 8.37 (1H)

Intermediate Example 486b

N-cyclopropyl-4-[6-(3-fluorophenoxy)-8-(methylsulfanyl)imidazo[1,2-b]pyridazin-3-yl]-2-methylbenzamide

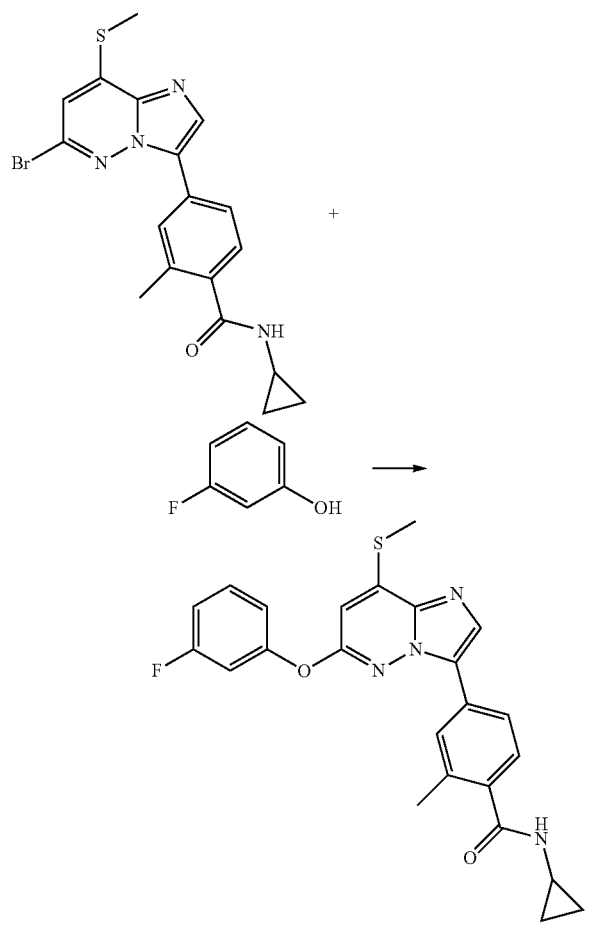

Intermediate Example 486c

4-[6-bromo-8-(methylsulfanyl)imidazo[1,2-b]pyridazin-3-yl]-N-cyclopropyl-2-methylbenzamide

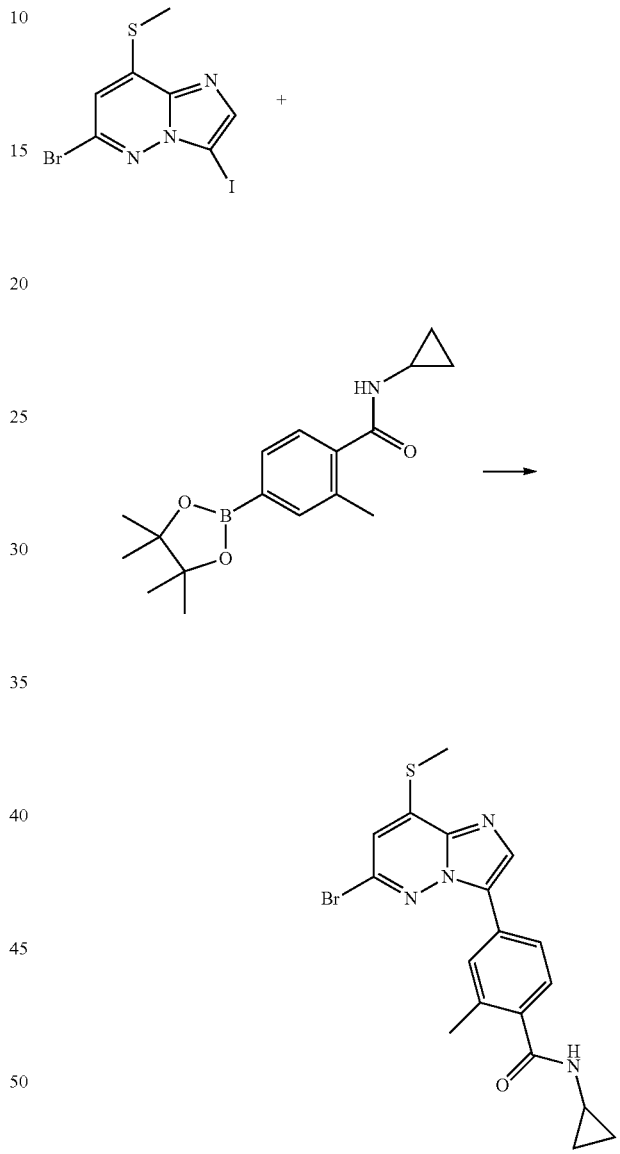

8 g (19.2 µmol) 4-[6-bromo-8-(methylsulfanyl)imidazo[1,2-b]pyridazin-3-yl]-N-cyclopropyl-2-methyl benzamide which was prepared according to intermediate example 486c were transformed in analogy to example 51 using 3-fluorophenol to give after working up and purification 4.96 g (46%) of the title compound.

¹H-NMR (400 MHz, DMSO-d₆), δ [ppm]=0.44-0.50 (2H), 0.60-0.67 (2H), 2.13 (3H), 2.65 (3H), 2.76 (1H), 6.99 (1H), 7.15-7.25 (3H), 7.37 (1H), 7.49-7.56 (1H), 7.65 (1H), 7.73 (1H), 8.06 (1H), 8.24 (1H)

42.1 g (113.9 mmol) 6-bromo-3-iodo-8-(methylsulfanyl)imidazo[1,2-b]pyridazine which was prepared according to intermediate example 486d were transformed in analogy to example 1a using N-cyclopropyl-2-methyl-4-(4,4,5,5-tetramethyl-1,3,2-dioxaborolan-2-yl)benzamide to give after working up and purification 17.78 g (34%) of the title compound.

¹H-NMR (300 MHz, DMSO-d₆), δ [ppm]=0.47-0.53 (2H), 0.62-0.70 (2H), 2.36 (4H), 2.64 (3H), 2.81 (1H), 7.19 (1H), 7.40 (1H), 7.86 (1H), 7.90 (1H), 8.12 (1H), 8.31 (1H)

Intermediate Example 486d

6-bromo-3-iodo-8-(methylsulfanyl)imidazo[1,2-b]pyridazine

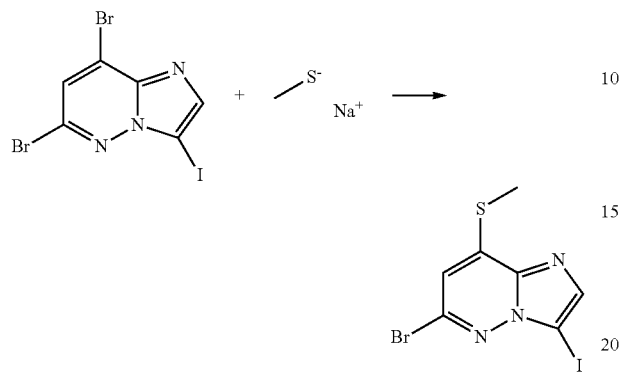

To a stirred solution of 51.2 g (146.8 mmol) 6,8-dibromo-3-iodoimidazo[1,2-b]pyridazine which was prepared according to intermediate example 96c in NMP (450 mL) are added 12.35 g (176.2 mmol) sodium methanethiolate in one portion at 0° C. After reaction for 15 min, 700 mL water are added and the precipitate is filtered off and dried. Trituration with ether, filtration and drying in vaccuo. yields 44.3 g (65%) of the title compound $^1$H-NMR (400 MHz, DMSO-d$_6$), δ [ppm]=2.62 (4H), 7.15 (1H), 7.75 (1H)

The following compound examples were prepared analogously to the procedure described for example 486 using the appropriate amine [LC-MS data such as retention time (RT in min) or observed mass peak were collected using LC-MS Method A unless explicitly stated]:

| Example | Structure | Name | Analytical Data |
|---|---|---|---|
| 549 | 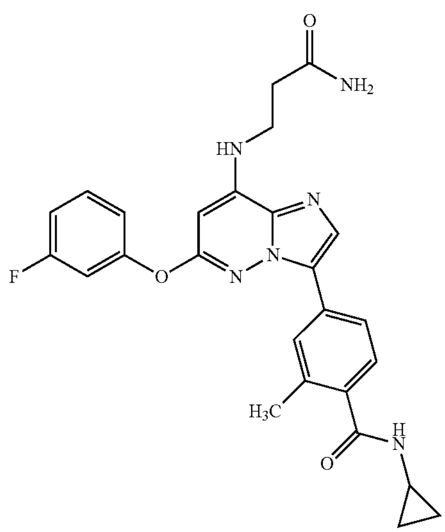 [SMILES: Cc1cc(-c2cnc3c(NCCC(N)=O)cc(Oc4cccc(F)c4)nn23)ccc1C(=O)NC1CC1] | 4-{8-[(3-amino-3-oxopropyl)amino]-6-(3-fluorophenoxy)imidazo[1,2-b]pyridazin-3-yl}-N-cyclopropyl-2-methyl-benzamide | RT = 1.01 MW$_{found}$ = 489.5 MW$_{calc}$ = 488.5 |
| 487 | 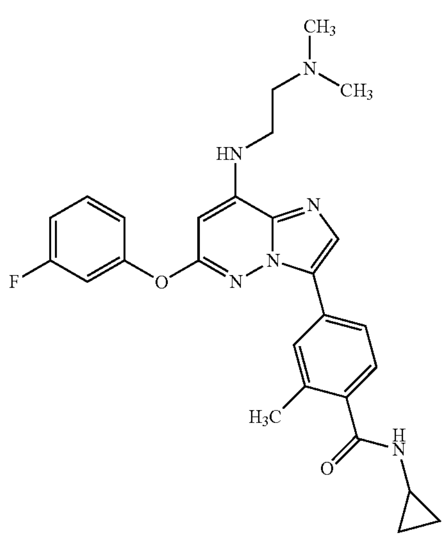 [SMILES: Cc1cc(-c2cnc3c(NCCN(C)C)cc(Oc4cccc(F)c4)nn23)ccc1C(=O)NC1CC1] | N-cyclopropyl-4-[8-{[2-(dimethylamino)ethyl]amino}-6-(3-fluorophenoxy)imidazo[1,2-b]pyridazin-3-yl]-2-methylbenzamide | RT = 0.88 MW$_{found}$ = 489.6 MW$_{calc}$ = 488.6 $^1$H-NMR (400 MHz, DMSO-d$_6$), δ [ppm] = 0.46 (2H), 0.63 (2H), 2.14 (3H), 2.19 (6H), 2.52 (2H), 2.76 (1H), 3.39 (2H), 6.06 (1H), 7.09-7.19 (4H), 7.24 (2H), 7.48 (1H), 7.66 (1H), 7.76 (1H), 7.90 (1H), 8.21 (1H) |

| Example | Structure | Name | Analytical Data |
|---|---|---|---|
| 488 | 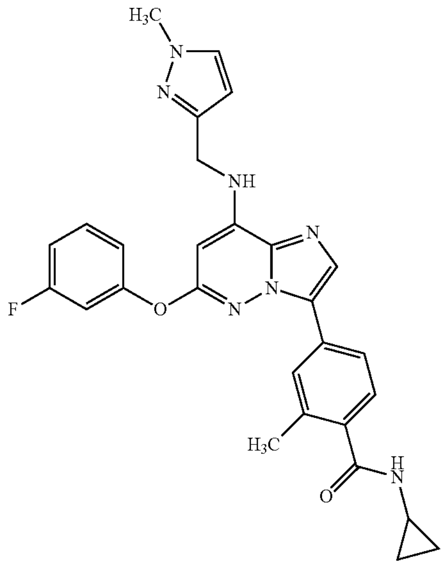 [SMILES: Cc1cc(-c2cnc3c(NCc4ccn(C)n4)cc(Oc4cccc(F)c4)nn23)ccc1C(=O)NC1CC1] | N-cyclopropyl-4-[6-(3-fluoro-phenoxy)-8-{[(1-methyl-1H-pyrazol-3-yl)methyl]amino}imidazo[1,2-b]pyridazin-3-yl]-2-methylbenzamide | RT = 1.17 MW$_{found}$ = 512.6 MW$_{calc}$ = 511.6 $^1$H-NMR (300 MHz, DMSO-d$_6$), δ [ppm] = 0.42-0.51 (2H), 0.58-0.68 (2H), 2.14 (3H), 2.76 (1H), 3.76 (3H), 4.45 (2H), 6.00 (1H), 6.15 (1H), 7.06-7.26 (5H), 7.46 (1H), 7.58 (1H), 7.66 (1H), 7.75 (1H), 7.92 (1H), 7.93-8.01 (1H), 8.21 (1H) |
| 489 | 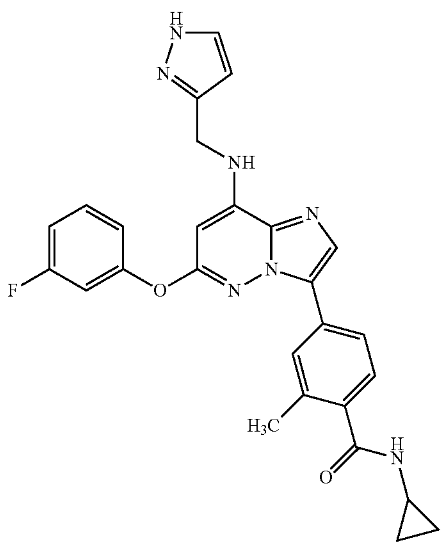 [SMILES: Cc1cc(-c2cnc3c(NCc4cc[nH]n4)cc(Oc4cccc(F)c4)nn23)ccc1C(=O)NC1CC1] | N-cyclopropyl-4-{6-(3-fluoro-phenoxy)-8-[(1H-pyrazol-3-ylmethyl)amino]imidazo[1,2-b]pyridazin-3-yl}-2-methylbenzamide | RT = 1.14 MW$_{found}$ = 498.5 MW$_{calc}$ = 497.5 $^1$H-NMR (400 MHz, DMSO-d$_6$), δ [ppm] = 0.43-0.50 (2H), 0.59-0.66 (2H), 2.13 (3H), 2.76 (1H), 4.51 (2H), 6.06 (1H), 6.19 (1H), 7.07-7.19 (4H), 7.23 (1H), 7.42-7.51 (2H), 7.65 (2H), 7.75 (1H), 7.87-7.95 (1H), 7.95-8.05 (1H), 8.21 (2H) |
| 490 | 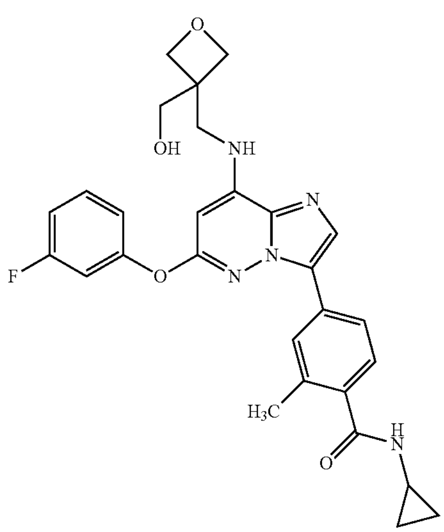 [SMILES: Cc1cc(-c2cnc3c(NCC4(CO)COC4)cc(Oc4cccc(F)c4)nn23)ccc1C(=O)NC1CC1] | N-cyclopropyl-4-[6-(3-fluoro-phenoxy)-8-({[3-(hydroxymethyl)oxetan-3-yl]methyl}amino)imidazo[1,2-b]pyridazin-3-yl]-2-methylbenzamide | RT = 1.08 MW$_{found}$ = 518.6 MW$_{calc}$ = 517.6 |

-continued

| Example | Structure | Name | Analytical Data |
|---|---|---|---|
| 491 | 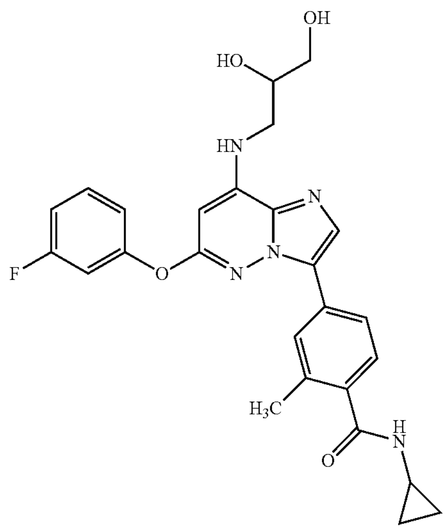 [SMILES: Cc1cc(-c2cnc3c(NCC(O)CO)cc(Oc4cccc(F)c4)nn23)ccc1C(=O)NC1CC1] | N-cyclopropyl-4-{8-[(2,3-dihydroxypropyl)amino]-6-(3-fluorophenoxy)imidazo[1,2-b]pyridazin-3-yl}-2-methylbenzamide | RT = 1.04 MW$_{found}$ = 492.5 MW$_{calc}$ = 491.5 $^1$H-NMR (300 MHz, DMSO-d$_6$), δ [ppm] = 0.39-0.51 (2H), 0.58-0.69 (2H), 2.14 (3H), 2.76 (1H), 3.39 (3H), 3.73 (1H), 4.70 (1H), 4.98 (1H), 6.08 (1H), 7.02-7.20 (3H), 7.20-7.37 (2H), 7.41-7.55 (1H), 7.66 (1H), 7.76 (1H), 7.91 (1H), 8.21 (1H) |
| 492 | 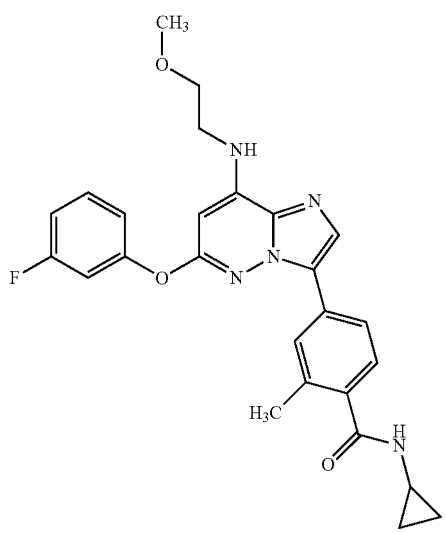 [SMILES: COCCNc1cc(Oc2cccc(F)c2)nn2c(-c3ccc(C(=O)NC4CC4)c(C)c3)cnc12] | N-cyclopropyl-4-{6-(3-fluorophenoxy)-8-[(2-methoxyethyl)amino]imidazo[1,2-b]pyridazin-3-yl}-2-methylbenzamide | RT = 1.26 MW$_{found}$ = 476.5 MW$_{calc}$ = 475.5 $^1$H-NMR (400 MHz, DMSO-d$_6$), δ [ppm] = 0.42-0.50 (2H), 0.60-0.67 (2H), 2.14 (3H), 2.77 (1H), 3.26 (3H), 3.51 (2H), 3.53-3.58 (2H), 6.10 (1H), 7.08-7.19 (3H), 7.25 (1H), 7.43-7.52 (2H), 7.66 (1H), 7.76 (1H), 7.92 (1H), 8.21 (1H) |
| 493 | 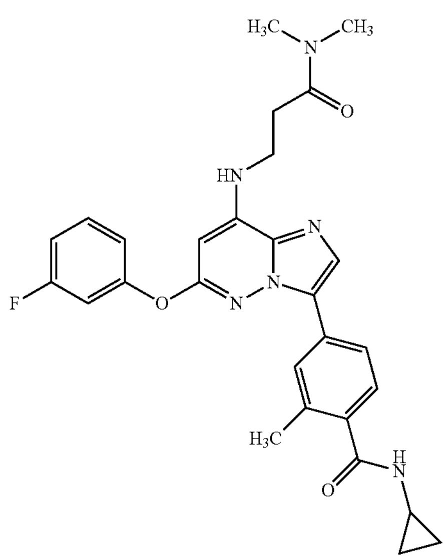 [SMILES: Cc1cc(-c2cnc3c(NCCC(=O)N(C)C)cc(Oc4cccc(F)c4)nn23)ccc1C(=O)NC1CC1] | N-cyclopropyl-4-[8-{[3-(dimethylamino)-3-oxopropyl]amino}-6-(3-fluorophenoxy)imidazo[1,2-b]pyridazin-3-yl]-2-methylbenzamide | RT = 1.26 MW$_{found}$ = 517.6 MW$_{calc}$ = 516.6 |

| Example | Structure | Name | Analytical Data |
|---|---|---|---|
| 494 | 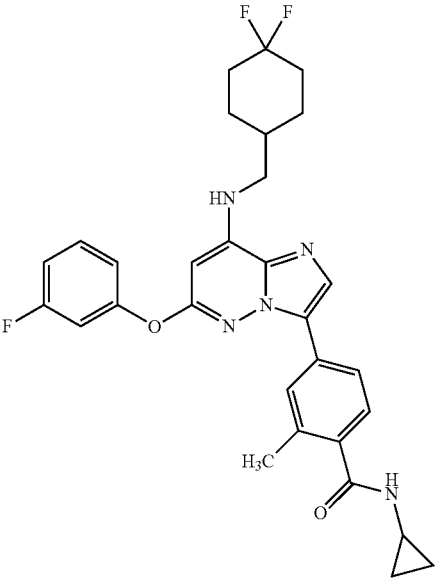 [SMILES: Cc1cc(-c2cnc3c(NCC4CCC(F)(F)CC4)cc(Oc4cccc(F)c4)nn23)ccc1C(=O)NC1CC1] | N-cyclopropyl-4-[8-{[(4,4-difluorocyclohexyl)methyl]amino}-6-(3-fluorophenoxy)imidazo[1,2-b]pyridazin-3-yl]-2-methylbenzamide | RT = 1.45 MW$_{found}$ = 550.6 MW$_{calc}$ = 549.6 |
| 495 | 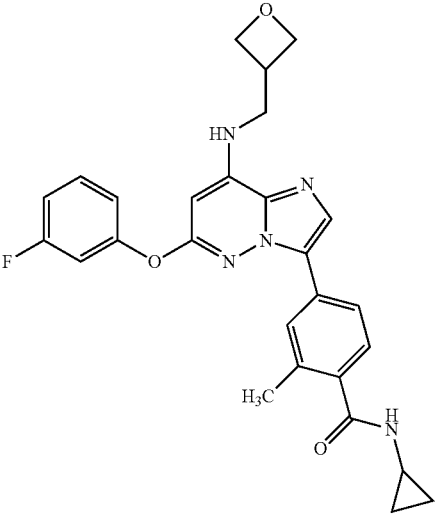 [SMILES: Cc1cc(-c2cnc3c(NCC4COC4)cc(Oc4cccc(F)c4)nn23)ccc1C(=O)NC1CC1] | N-cyclopropyl-4-{6-(3-fluorophenoxy)-8-[(oxetan-3-ylmethyl)amino]imidazo[1,2-b]pyridazin-3-yl}-2-methylbenzamide | RT = 1.17 MW$_{found}$ = 488.5 MW$_{calc}$ = 487.5 $^1$H-NMR (300 MHz, DMSO-d$_6$), δ [ppm] = 0.40-0.51 (2H), 0.56-0.69 (2H), 0.75-0.89 (1H), 2.13 (3H), 2.76 (1H), 3.61 (2H), 4.34 (2H), 4.63 (2H), 6.13 (1H), 7.05-7.20 (3H), 7.25 (1H), 7.41-7.54 (1H), 7.65 (1H), 7.75 (1H), 7.85-7.96 (2H), 8.21 (1H) |
| 496 | 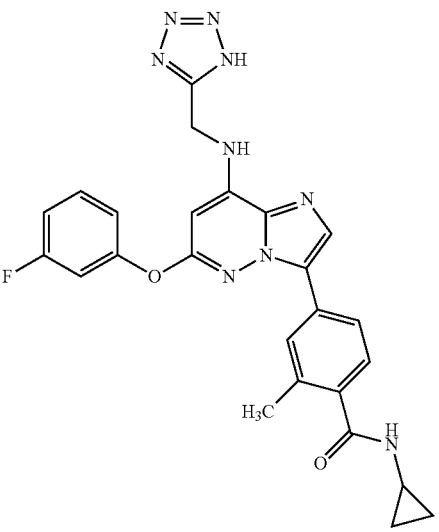 [SMILES: Cc1cc(-c2cnc3c(NCc4nnn[nH]4)cc(Oc4cccc(F)c4)nn23)ccc1C(=O)NC1CC1] | N-cyclopropyl-4-{6-(3-fluorophenoxy)-8-[(1H-tetrazol-5-ylmethyl)amino]imidazo[1,2-b]pyridazin-3-yl}-2-methylbenzamide | RT = 1.03 MW$_{found}$ = 500.5 MW$_{calc}$ = 499.5 |

| Example | Structure | Name | Analytical Data |
|---|---|---|---|
| 497 | 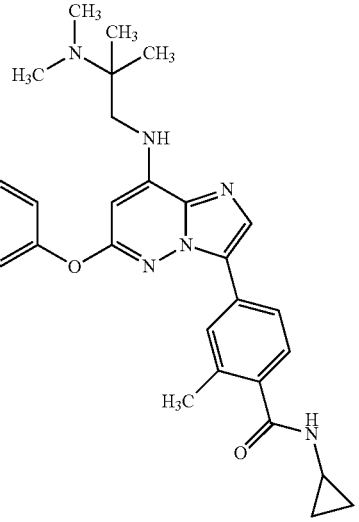 | N-cyclopropyl-4-[8-{[2-(dimethylamino)-2-methylpropyl]amino}-6-(3-fluorophenoxy)imidazo[1,2-b]pyridazin-3-yl]-2-methylbenzamide | RT = 0.97 MW$_{found}$ = 517.6 MW$_{calc}$ = 516.6 |
| 498 | 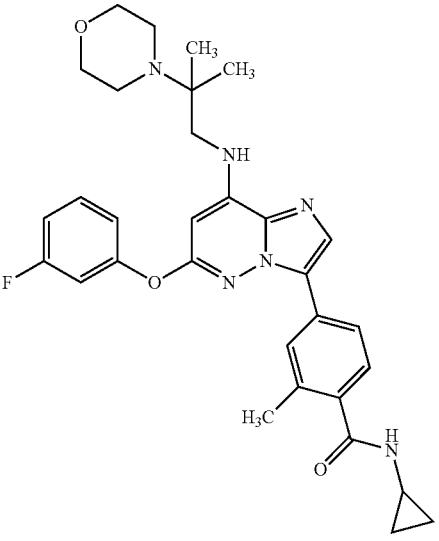 [SMILES: Cc1cc(-c2cnc3c(NCC(C)(C)N4CCOCC4)cc(Oc4cccc(F)c4)nn23)ccc1C(=O)NC1CC1] | N-cyclopropyl-4-[6-(3-fluorophenoxy)-8-{[2-methyl-2-(morpholin-4-yl)propyl]amino}imidazo[1,2-b]pyridazin-3-yl]-2-methylbenzamide | RT = 0.99 MW$_{found}$ = 559.6 MW$_{calc}$ = 558.6 |
| 499 | 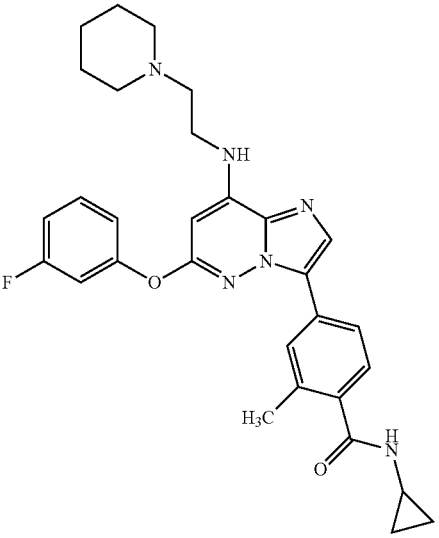 | N-cyclopropyl-4-[6-(3-fluorophenoxy)-8-{[2-(piperidin-1-yl)ethyl]amino}imidazo[1,2-b]pyridazin-3-yl]-2-methylbenzamide | RT = 0.98 MW$_{found}$ = 529.6 MW$_{calc}$ = 528.6 |

-continued

| Example | Structure | Name | Analytical Data |
|---|---|---|---|
| 500 | 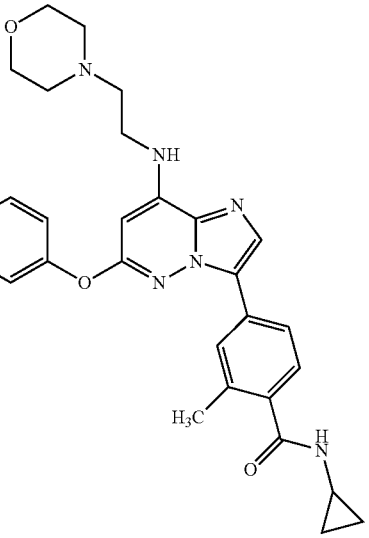 | N-cyclopropyl-4-[6-(3-fluoro-phenoxy)-8-{[2-(morpholin-4-yl)ethyl]amino}imidazo[1,2-b]pyridazin-3-yl]-2-methylbenzamide | RT = 0.93 $MW_{found}$ = 531.6 $MW_{calc}$ = 530.6 |
| 501 | 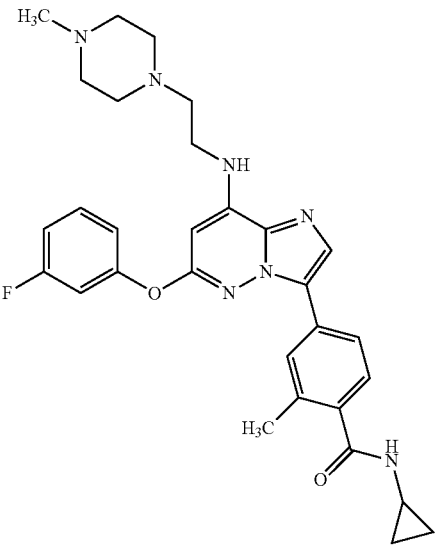 [SMILES: Cc1cc(-c2cnc3c(NCCN4CCN(C)CC4)cc(Oc4cccc(F)c4)nn23)ccc1C(=O)NC1CC1] | N-cyclopropyl-4-[6-(3-fluoro-phenoxy)-8-{[2-(4-methyl-piperazin-1-yl)ethyl]amino}imidazo[1,2-b]pyridazin-3-yl]-2-methylbenzamide | RT = 0.96 $MW_{found}$ = 544.6 $MW_{calc}$ = 543.6 |
| 502 | 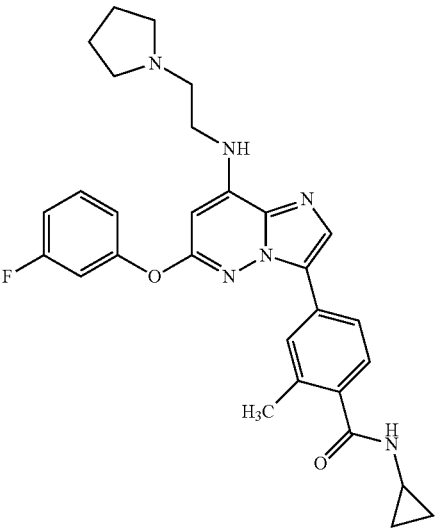 | N-cyclopropyl-4-[6-(3-fluoro-phenoxy)-8-{[2-(pyrrolidin-1-yl)ethyl]amino}imidazo[1,2-b]pyridazin-3-yl]-2-methyl-benzamide | RT = 0.96 $MW_{found}$ = 515.6 $MW_{calc}$ = 514.6 |

| Example | Structure | Name | Analytical Data |
|---|---|---|---|
| 503 | 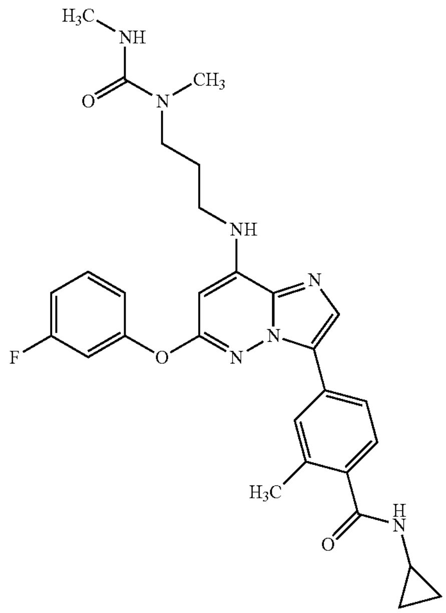 [SMILES: CNC(=O)N(C)CCCNc1cc(Oc2cccc(F)c2)nn2c(-c3ccc(C(=O)NC4CC4)c(C)c3)cnc12] | N-cyclopropyl-4-[6-(3-fluoro-phenoxy)-8-({3-[methyl(methyl-carbamoyl)amino]propyl}amino)imidazo[1,2-b]pyridazin-3-yl]-2-methylbenzamide | RT = 1.17 MW$_{found}$ = 546.6 MW$_{calc}$ = 545.6 |
| 504 | 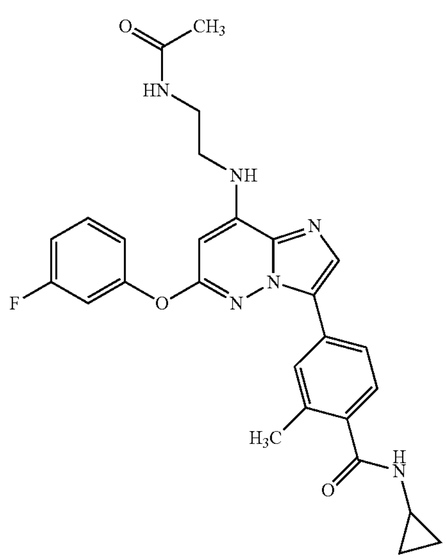 [SMILES: CC(=O)NCCNc1cc(Oc2cccc(F)c2)nn2c(-c3ccc(C(=O)NC4CC4)c(C)c3)cnc12] | 4-[8-{[2-(acetylamino)ethyl]amino}-6-(3-fluorophenoxy)imidazo[1,2-b]pyridazin-3-yl]-N-cyclopropyl-2-methyl-benzamide | RT = 1.10 MW$_{found}$ = 503.5 MW$_{calc}$ = 502.5 |

| Example | Structure | Name | Analytical Data |
|---|---|---|---|
| 505 | 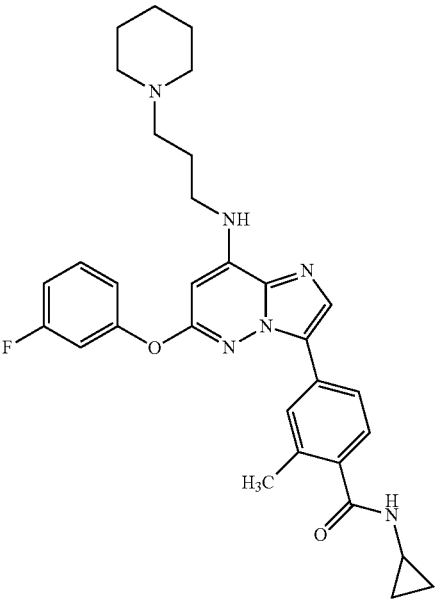 [SMILES: Cc1cc(-c2cnc3c(NCCCN4CCCCC4)cc(Oc4cccc(F)c4)nn23)ccc1C(=O)NC1CC1] | N-cyclopropyl-4-[6-(3-fluorophenoxy)-8-{[3-(piperidin-1-yl)propyl]amino}imidazo[1,2-b]pyridazin-3-yl]-2-methylbenzamide | RT = 1.01 MW$_{found}$ = 543.6 MW$_{calc}$ = 542.6 |
| 506 | 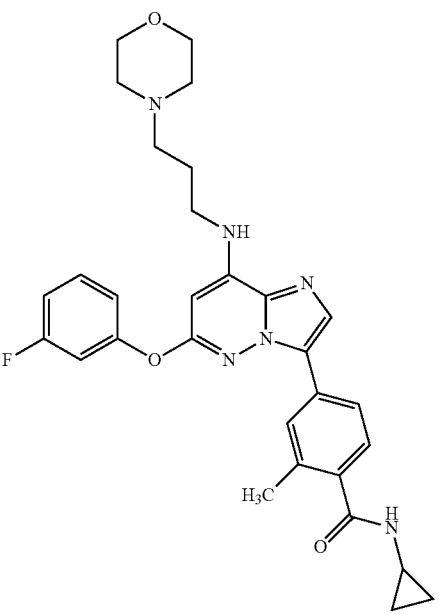 [SMILES: Cc1cc(-c2cnc3c(NCCCN4CCOCC4)cc(Oc4cccc(F)c4)nn23)ccc1C(=O)NC1CC1] | N-cyclopropyl-4-[6-(3-fluorophenoxy)-8-{[3-(morpholin-4-yl)propyl]amino}imidazo[1,2-b]pyridazin-3-yl]-2-methylbenzamide | RT = 0.96 MW$_{found}$ = 545.6 MW$_{calc}$ = 544.6 |

| Example | Structure | Name | Analytical Data |
|---|---|---|---|
| 507 | 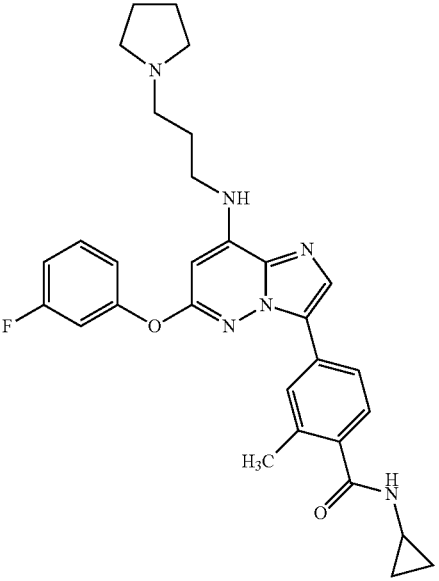 [SMILES: Cc1cc(-c2cnc3c(NCCCN4CCCC4)cc(Oc4cccc(F)c4)nn23)ccc1C(=O)NC1CC1] | N-cyclopropyl-4-[6-(3-fluorophenoxy)-8-{[3-(pyrrolidin-1-yl)propyl]amino}imidazo[1,2-b]pyridazin-3-yl]-2-methyl-benzamide | RT = 0.98 MW$_{found}$ = 529.6 MW$_{calc}$ = 528.6 $^1$H-NMR (300 MHz, DMSO-d$_6$), δ [ppm] = 0.43-0.50 (2H), 0.58-0.67 (2H), 1.68 (4H), 1.78 (2H), 2.14 (3H), 2.48-2.54 (2H), 2.76 (1H), 3.36 (6H), 6.04 (1H), 7.06-7.19 (4H), 7.23 (1H), 7.42-7.52 (1H), 7.62-7.70 (1H), 7.76 (1H), 7.82-7.92 (2H), 8.17-8.24 (1H) |
| 508 | 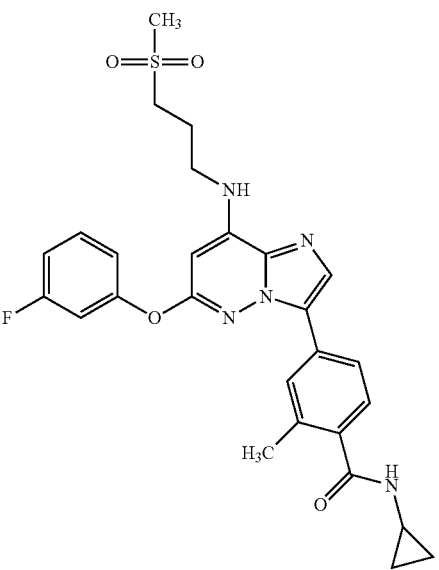 [SMILES: Cc1cc(-c2cnc3c(NCCCS(C)(=O)=O)cc(Oc4cccc(F)c4)nn23)ccc1C(=O)NC1CC1] | N-cyclopropyl-4-[6-(3-fluorophenoxy)-8-{[3-(methylsulfonyl)propyl]amino}imidazo[1,2-b]pyridazin-3-yl]-2-methyl-benzamide | RT = 1.15 MW$_{found}$ = 538.6 MW$_{calc}$ = 537.6 |

-continued

| Example | Structure | Name | Analytical Data |
|---|---|---|---|
| 509 | 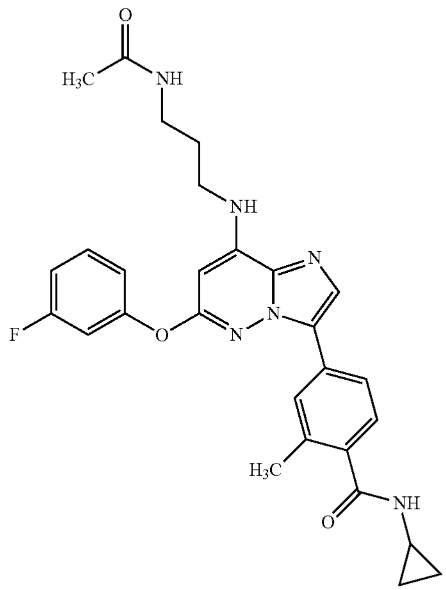 [SMILES: CC(=O)NCCCNc1cc(Oc2cccc(F)c2)nn2c(-c3ccc(C(=O)NC4CC4)c(C)c3)cnc12] | 4-[8-{[3-(acetylamino)propyl]amino}-6-(3-fluorophenoxy)imidazo[1,2-b]pyridazin-3-yl]-N-cyclopropyl-2-methyl-benzamide | RT = 1.12 MW$_{found}$ = 517.6 MW$_{calc}$ = 516.6 |
| 510 | 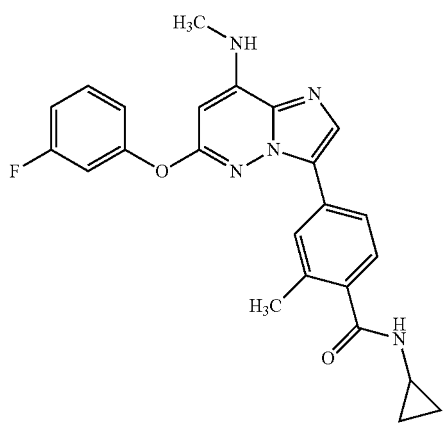 [SMILES: CNc1cc(Oc2cccc(F)c2)nn2c(-c3ccc(C(=O)NC4CC4)c(C)c3)cnc12] | N-cyclopropyl-4-[6-(3-fluoro-phenoxy)-8-(methylamino)imidazo[1,2-b]pyridazin-3-yl]-2-methylbenzamide | RT = 1.26 MW$_{found}$ = 432.5 MW$_{calc}$ = 431.5 $^1$H-NMR (300 MHz, DMSO-d$_6$), δ [ppm] = 0.40-0.52 (2H), 0.57-0.73 (2H), 2.20 (3H), 2.69-2.82 (1H), 2.90 (3H), 5.95 (1H), 7.04-7.20 (3H), 7.24 (1H), 7.41-7.55 (1H), 7.59-7.73 (2H), 7.76 (1H), 7.90 (1H), 8.21 (1H) |
| 511 | 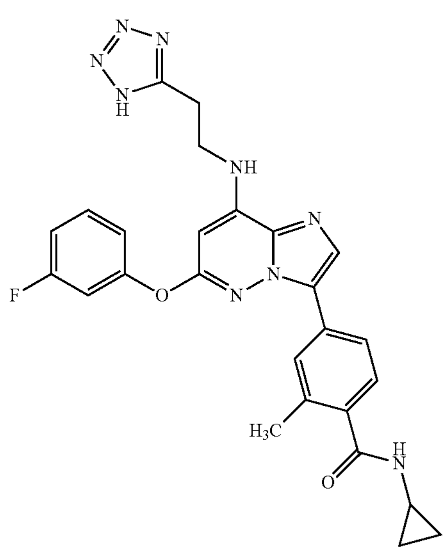 [SMILES: Cc1cc(-c2cnc3c(NCCc4nnn[nH]4)cc(Oc4cccc(F)c4)nn23)ccc1C(=O)NC1CC1] | N-cyclopropyl-4-[6-(3-fluoro-phenoxy)-8-{[2-(1H-tetrazol-5-yl)ethyl]amino}imidazo[1,2-b]pyridazin-3-yl]-2-methyl-benzamide | RT = 1.10 MW$_{found}$ = 514.5 MW$_{calc}$ = 513.5 |

| Example | Structure | Name | Analytical Data |
|---|---|---|---|
| 512 | 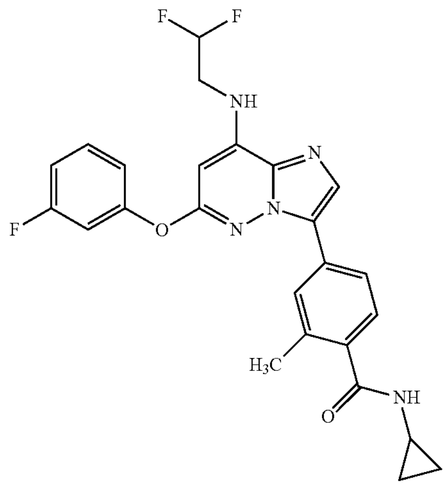 [SMILES: Cc1cc(-c2cnc3c(NCC(F)F)cc(Oc4cccc(F)c4)nn23)ccc1C(=O)NC1CC1] | N-cyclopropyl-4-{8-[(2,2-difluoro-ethyl)amino]-6-(3-fluoro-phenoxy)imidazo[1,2-b]pyridazin-3-yl}-2-methylbenzamide | RT = 1.28 MW$_{found}$ = 482.5 MW$_{calc}$ = 481.5 |
| 513 | 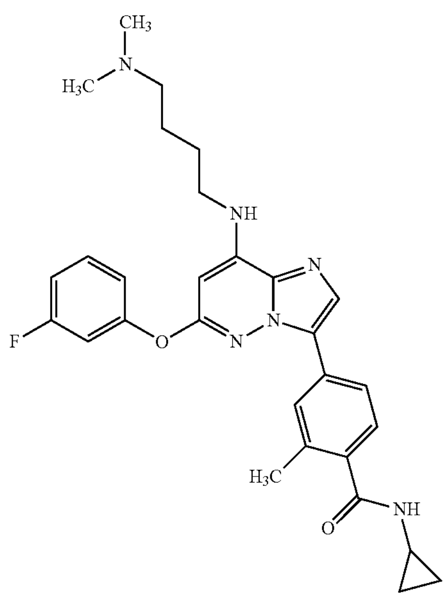 [SMILES: Cc1cc(-c2cnc3c(NCCCCN(C)C)cc(Oc4cccc(F)c4)nn23)ccc1C(=O)NC1CC1] | N-cyclopropyl-4-[8-{[4-(dimethyl-amino)butyl]amino}-6-(3-fluoro-phenoxy)imidazo[1,2-b]pyridazin-3-yl]-2-methylbenzamide | RT = 0.99 MW$_{found}$ = 517.6 MW$_{calc}$ = 516.6 |
| 514 | 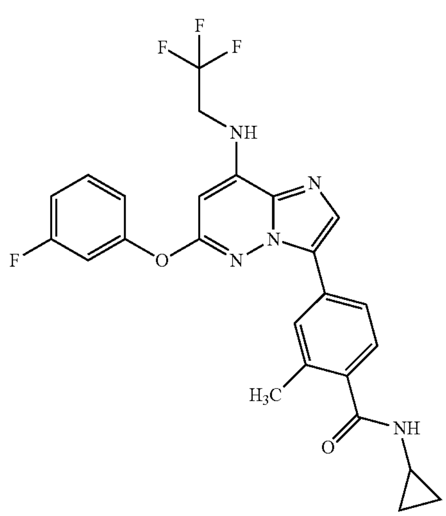 [SMILES: Cc1cc(-c2cnc3c(NCC(F)(F)F)cc(Oc4cccc(F)c4)nn23)ccc1C(=O)NC1CC1] | N-cyclopropyl-4-{6-(3-fluoro-phenoxy)-8-[(2,2,2-trifluoroethyl)amino]imidazo[1,2-b]pyridazin-3-yl}-2-methylbenzamide | RT = 1.06 MW$_{found}$ = 500.5 MW$_{calc}$ = 499.5 $^1$H-NMR (400 MHz, DMSO-d$_6$), δ [ppm] = 0.43-0.51 (2H), 0.59-0.69 (2H), 2.14 (3H), 2.72-2.81 (1H), 5.20 (2H), 6.96 (1H), 7.15-7.27 (4H), 7.39 (1H), 7.54 (1H), 7.67 (1H), 7.74 (1H), 8.17 (1H), 8.25 (1H) |

| Example | Structure | Name | Analytical Data |
|---|---|---|---|
| 515 | 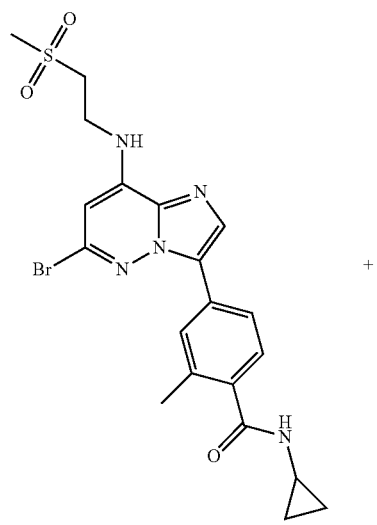 | N-cyclopropyl-4-[6-(3-fluoro-phenoxy)-8-{[2-(1H-pyrazol-1-yl)ethyl]amino}imidazo[1,2-b]pyridazin-3-yl]-2-methyl-benzamide | RT = 1.22 $MW_{found}$ = 512.6 $MW_{calc}$ = 511.6 |

Example 516

N-cyclopropyl-4-[6-(2,3-difluorophenoxy)-8-{[2-(methylsulfonyl)ethyl]amino}imidazo[1,2-b]pyridazin-3-yl]-2-methylbenzamide

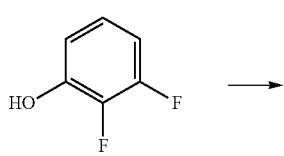

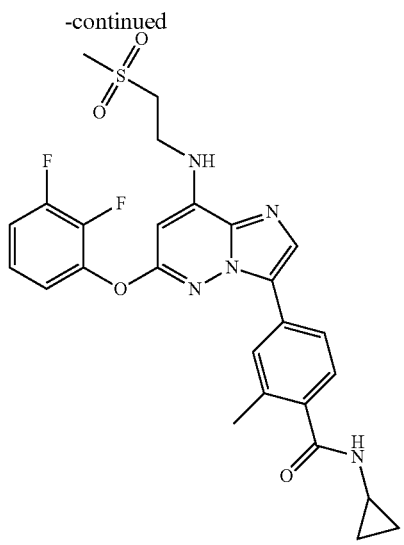

147 mg (300 μmol) 4-(6-bromo-8-{[2-(methylsulfonyl)ethyl]amino}imidazo[1,2-b]pyridazin-3-yl)-N-cyclopropyl-2-methylbenzamide which was prepared according to intermediate example 516a were transformed in analogy to example 51 using 2,3-difluorophenol to give after working up and purification 38 mg (21%) of the title compound.

UPLC-MS: RT=1.14, $MW_{found}$=542.6. $MW_{calc}$=541.6.

Intermediate Example 516a 4-(6-bromo-8-{[2-(methylsulfonyl)ethyl]amino}imidazo[1,2-b]pyridazin-3-yl)-N-cyclopropyl-2-methylbenzamide

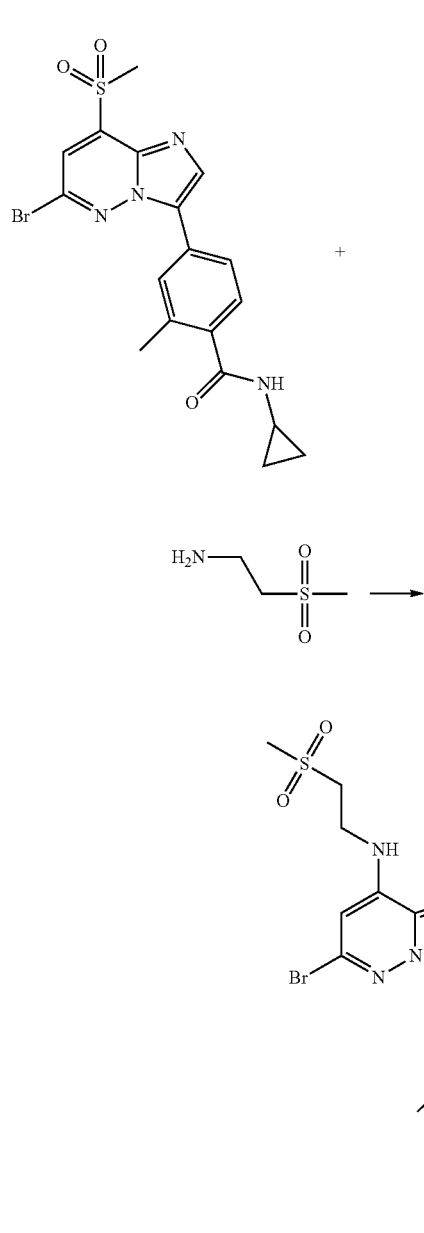

To a stirred solution of 1.12 g (2.5 mmol) 4-[6-bromo-8-(methylsulfonyl)imidazo[1,2-b]pyridazin-3-yl]-N-cyclopropyl-2-methyl benzamide which was prepared according to intermediate example 516b in 15 mL NMP is added 924 mg (7.5 mmol) 2-(methylsulfonyl)ethanamine and 1.94 g (15 mmol) DIPEA and the mixture is heated at 160° C. for 4 h in a heating block. After working up and without further purification 1.18 g (96%) of the title compound are obtained.

UPLC-MS: RT=0.95, MW$_{found}$=493.4. MW$_{calc}$=492.4.

Intermediate Example 516b

4-[6-bromo-8-(methylsulfonyl)imidazo[1,2-b]pyridazin-3-yl]-N-cyclopropyl-2-methylbenzamide

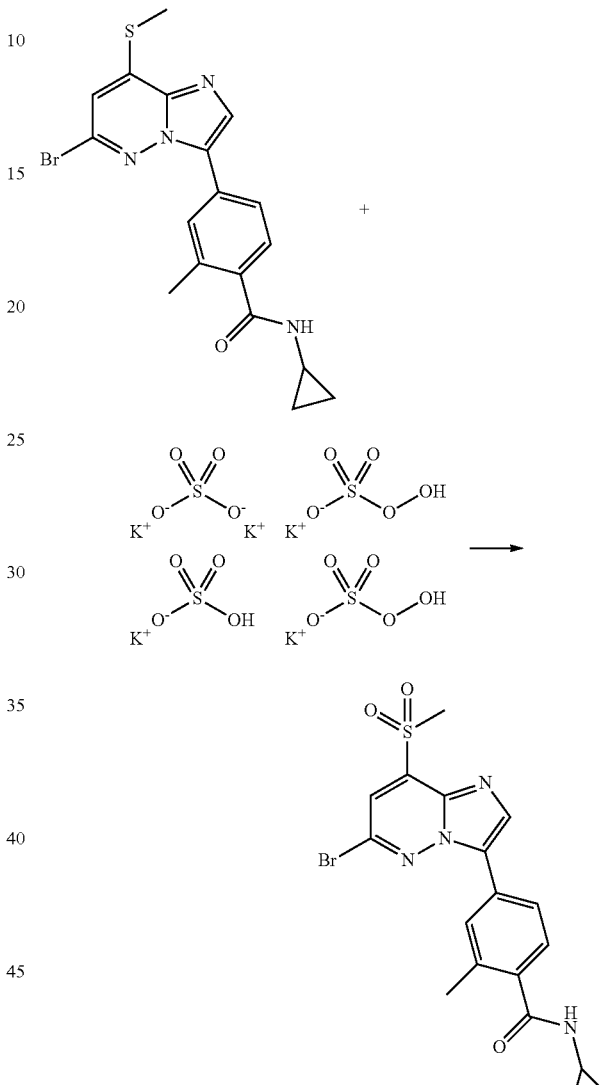

12 g (28.8 mmol) 4-[6-bromo-8-(methylsulfanyl)imidazo[1,2-b]pyridazin-3-yl]-N-cyclopropyl-2-methyl benzamide which was prepared according to intermediate example 486b were transformed in analogy to intermediate example 486a to give after working up and purification 8.61 g (59%) of the title compound.

UPLC-MS: RT=0.98, MW$_{found}$=450.4. MW$_{calc}$=449.4.

The following compound examples were prepared analogously to the procedure described for example 516 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 517 | 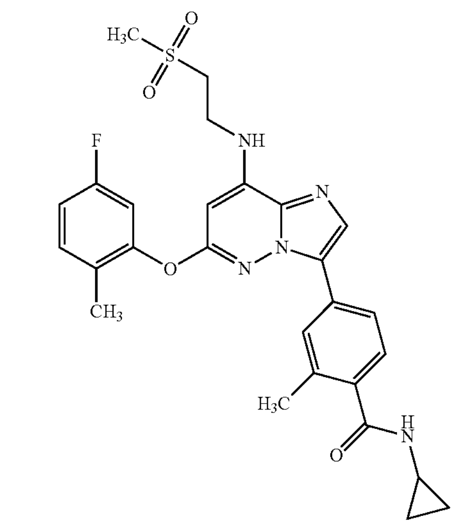 [SMILES: Cc1ccc(F)cc1Oc1cc(NCCS(C)(=O)=O)c2ncc(-c3ccc(C(=O)NC4CC4)c(C)c3)n2n1] | N-cyclopropyl-4-[6-(5-fluoro-2-methylphenoxy)-8-{[2-(methylsulfonyl)ethyl]amino}imidazo[1,2-b]pyridazin-3-yl]-2-methylbenzamide | RT = 1.17 MW$_{found}$ = 538.6 MW$_{calc}$ = 537.6 |
| 518 | 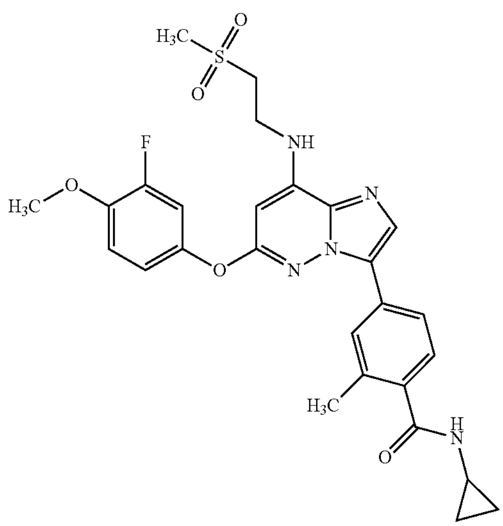 [SMILES: COc1ccc(Oc2cc(NCCS(C)(=O)=O)c3ncc(-c4ccc(C(=O)NC5CC5)c(C)c4)n3n2)cc1F] | N-cyclopropyl-4-[6-(3-fluoro-4-methoxyphenoxy)-8-{[2-(methylsulfonyl)ethyl]amino}imidazo[1,2-b]pyridazin-3-yl]-2-methylbenzamide | RT = 1.33 MW$_{found}$ = 554.6 MW$_{calc}$ = 553.6  $^1$H-NMR (300 MHz, DMSO-d$_6$), δ [ppm] = 0.43-0.51 (2H), 0.59-0.68 (2H), 2.12 (3H), 2.77 (1H), 3.05 (3H), 3.49 (2H), 3.73-3.81 (2H), 3.84 (3H), 6.13 (1H), 7.07 (1H), 7.17 (1H), 7.19-7.26 (1H), 7.30 (1H), 7.49-7.69 (2H), 7.77 (1H), 7.92 (1H), 8.20 (1H) |
| 519 | 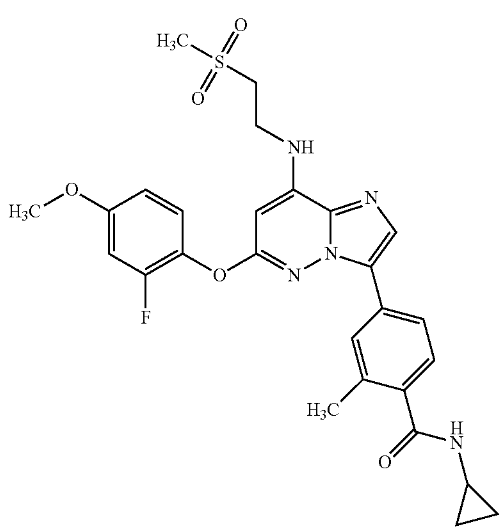 [SMILES: COc1ccc(Oc2cc(NCCS(C)(=O)=O)c3ncc(-c4ccc(C(=O)NC5CC5)c(C)c4)n3n2)c(F)c1] | N-cyclopropyl-4-[6-(2-fluoro-4-methoxyphenoxy)-8-{[2-(methylsulfonyl)ethyl]amino}imidazo[1,2-b]pyridazin-3-yl]-2-methylbenzamide | RT = 1.12 MW$_{found}$ = 554.6 MW$_{calc}$ = 553.6  $^1$H-NMR (500 MHz, DMSO-d$_6$), δ [ppm] = 0.49-0.53 (2H), 0.66-0.71 (2H), 2.13 (3H), 2.81 (1H), 3.11 (3H), 3.55 (2H), 3.82 (5H), 6.25 (1H), 6.89 (1H), 7.11 (1H), 7.19 (1H), 7.38 (1H), 7.66 (1H), 7.74-7.79 (2H), 7.99 (1H), 8.26 (1H) |

Example 520

4-{8-[(2-amino-2-methylpropyl)amino]-6-(3,4-difluorophenoxy)imidazo[1,2-b]pyridazin-3-yl}-N-cyclopropyl-2-methylbenzamide

Intermediate Example 520a

4-{8-[(2-amino-2-methylpropyl)amino]-6-bromoimidazo[1,2-b]pyridazin-3-yl}-N-cyclopropyl-2-methylbenzamide

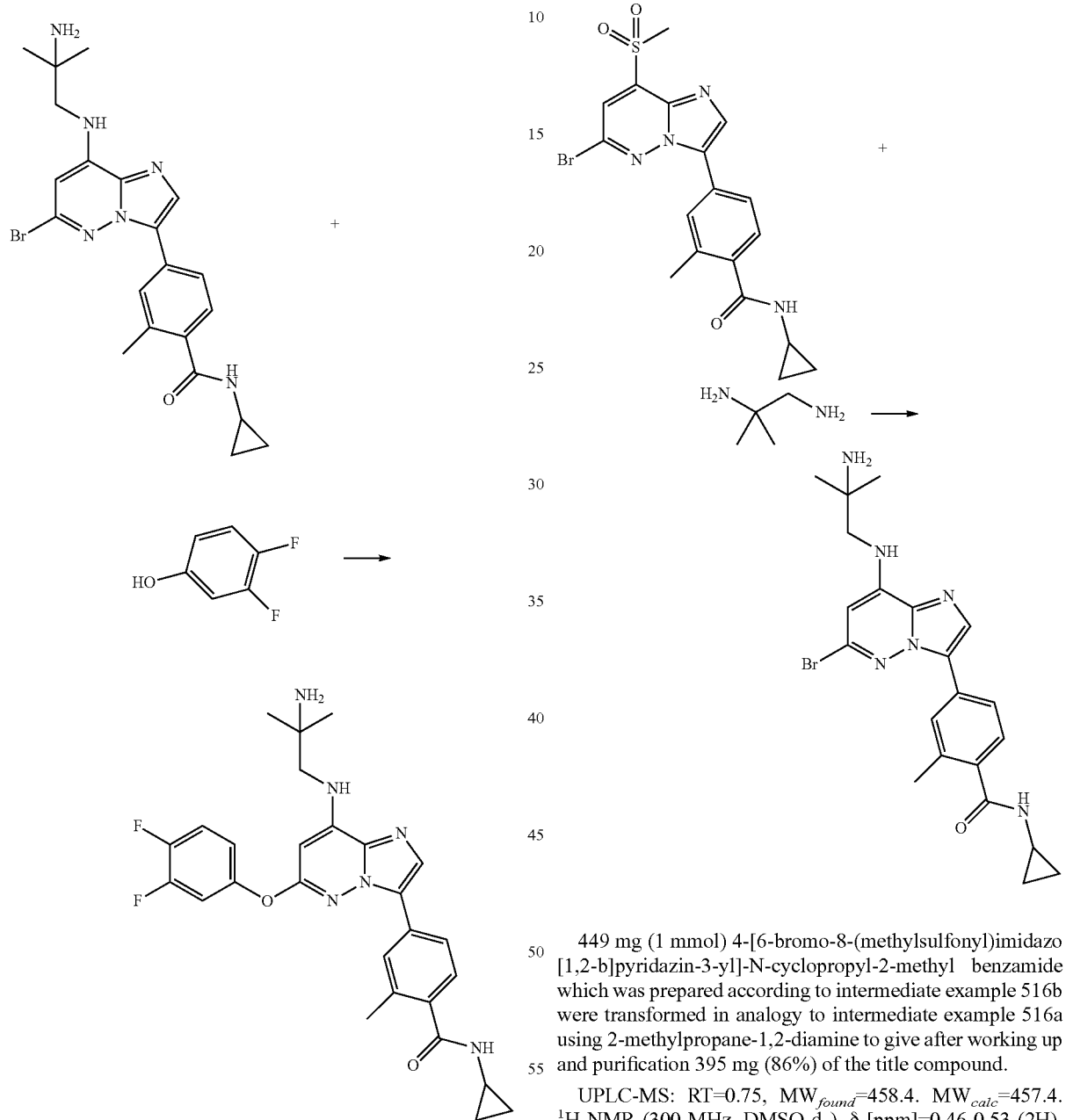

78 mg (171 µmol) 4-{8-[(2-amino-2-methylpropyl)amino]-6-bromoimidazo[1,2-b]pyridazin-3-yl}-N-cyclopropyl-2-methylbenzamide which was prepared according to intermediate example 520a were transformed in analogy to example 51 using 2,3-difluorophenol to give after working up and purification 8 mg (8%) of the title compound.

UPLC-MS: RT=0.97 MW$_{found}$=507.5 MW$_{calc}$=506.5.

449 mg (1 mmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to intermediate example 516a using 2-methylpropane-1,2-diamine to give after working up and purification 395 mg (86%) of the title compound.

UPLC-MS: RT=0.75, MW$_{found}$=458.4. MW$_{calc}$=457.4.
$^1$H-NMR (300 MHz, DMSO-d$_6$), δ [ppm]=0.46-0.53 (2H), 0.62-0.69 (2H), 1.07 (6H), 2.35 (3H), 2.80 (1H), 3.16 (2H), 6.50 (1H), 7.36 (1H), 7.85 (1H), 7.91 (1H), 7.93-7.96 (1H), 8.29 (1H)

The following compound examples were prepared analogously to the procedure described for example 520 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 521 | 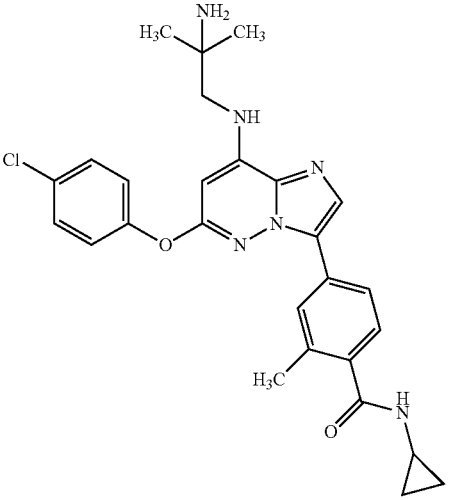 [SMILES: Cc1cc(-c2cnc3c(NCC(C)(C)N)cc(Oc4ccc(Cl)cc4)nn23)ccc1C(=O)NC1CC1] | 4-{8-[(2-amino-2-methyl-propyl)amino]-6-(4-chloro-phenoxy)imidazo[1,2-b]pyridazin-3-yl}-N-cyclopropyl-2-methylbenzamide | RT = 0.97 MW$_{found}$ = 506.0 MW$_{calc}$ = 505.0 $^1$H-NMR (300 MHz, DMSO-d$_6$), δ [ppm] = 0.44-0.52 (2H), 0.59-0.68 (2H), 1.12 (6H), 2.14 (3H), 2.77 (1H), 3.27 (3H), 6.20 (1H), 7.11-7.22 (3H), 7.34 (1H), 7.46-7.61 (2H), 7.62-7.68 (1H), 7.74 (1H), 7.92 (1H), 8.23 (1H) |
| 522 | 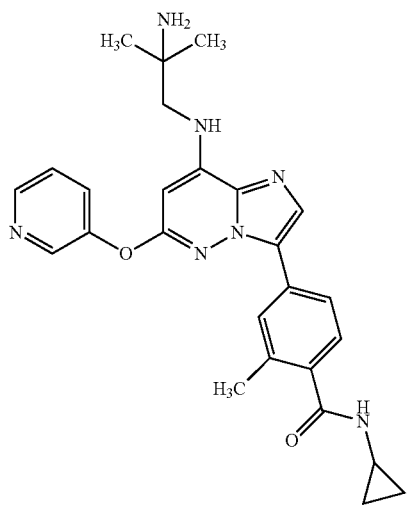 [SMILES: Cc1cc(-c2cnc3c(NCC(C)(C)N)cc(Oc4cccnc4)nn23)ccc1C(=O)NC1CC1] | 4-{8-[(2-amino-2-methyl-propyl)amino]-6-(pyridin-3-yloxy)imidazo[1,2-b]pyridazin-3-yl}-N-cyclopropyl-2-methylbenzamide | RT = 0.76 MW$_{found}$ = 472.6 MW$_{calc}$ = 471.6 $^1$H-NMR (300 MHz, DMSO-d$_6$), δ [ppm] = 0.43-0.50 (2H), 0.59-0.68 (2H), 1.14 (6H), 2.12 (3H), 2.76 (1H), 3.30 (3H), 6.27 (1H), 7.14 (1H), 7.40 (1H), 7.51 (1H), 7.58-7.64 (1H), 7.69 (1H), 7.76-7.82 (1H), 7.92 (1H), 8.21 (1H), 8.49 (1H), 8.57 (1H) |

Example 523

4-[6-(4-chlorophenoxy)-8-{[2-(dimethylamino)ethyl]amino}imidazo[1,2-b]pyridazin-3-yl]-N-cyclopropyl-2-methylbenzamide

Intermediate Example 523a 4-(6-bromo-8-{[2-(dimethylamino)ethyl]amino}imidazo[1,2-b]pyridazin-3-yl)-N-cyclopropyl-2-methylbenzamide

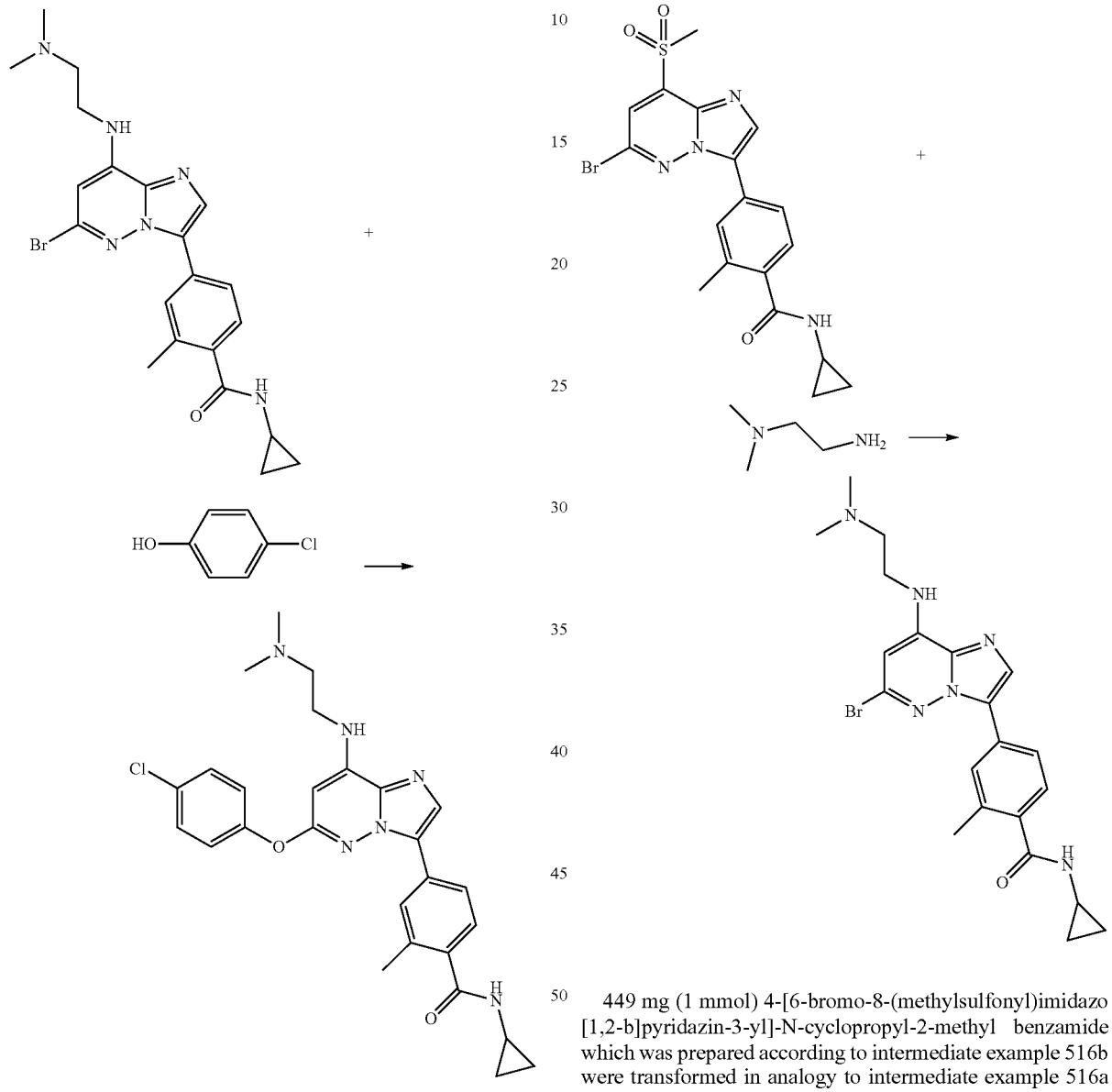

68 mg (150 μmol) 4-(6-bromo-8-{[2-(dimethylamino)ethyl]amino}imidazo[1,2-b]pyridazin-3-yl)-N-cyclopropyl-2-methylbenzamide which was prepared according to intermediate example 523a were transformed in analogy to example 51 using 4-chlorophenol to give after working up and purification 20 mg (27%) of the title compound.

UPLC-MS: RT=0.97, $MW_{found}$=506.0. $MW_{calc}$=505.0. $^1$H-NMR (300 MHz, DMSO-$d_6$), δ [ppm]=0.47 (2H), 0.59-0.68 (2H), 2.12 (3H), 2.18 (6H), 2.52 (2H), 2.76 (1H), 3.39 (2H), 6.06 (1H), 7.13-7.25 (2H), 7.27-7.35 (2H), 7.46-7.54 (2H), 7.63 (1H), 7.72 (1H), 7.90 (1H), 8.22 (1H)

449 mg (1 mmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to intermediate example 516a using N,N-dimethylethane-1,2-diamine to give after working up and purification 367 mg (80%) of the title compound.

UPLC-MS: RT=0.70, $MW_{found}$=458.4. $MW_{calc}$=457.4. $^1$H-NMR (300 MHz, DMSO-$d_6$), δ [ppm]=0.50 (2H), 0.65 (2H), 2.17 (6H), 2.35 (3H), 2.51 (2H), 2.80 (1H), 3.39 (2H), 6.38 (1H), 7.36 (1H), 7.44-7.50 (1H), 7.84 (1H), 7.91 (1H), 7.94 (1H), 8.28 (1H)

The following compound examples were prepared analogously to the procedure described for example 523 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 524 | 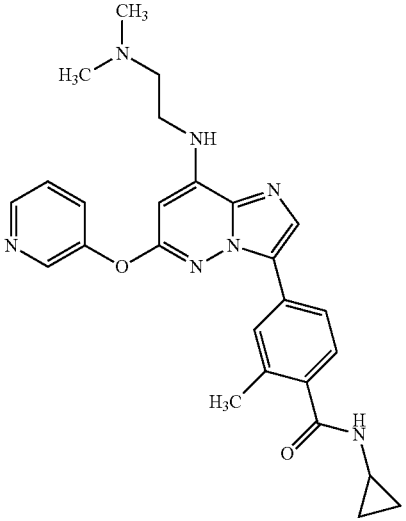 [SMILES: Cc1cc(-c2cnc3c(NCCN(C)C)cc(Oc4cccnc4)nn23)ccc1C(=O)NC1CC1] | N-cyclopropyl-4-[8-{[2-(dimethylamino)ethyl]amino}-6-(pyridin-3-yloxy)imidazo[1,2-b]pyridazin-3-yl]-2-methylbenzamide | RT = 0.74 MW$_{found}$ = 472.6 MW$_{calc}$ = 471.6 $^1$H-NMR (300 MHz, DMSO-d$_6$), δ [ppm] = 0.43-0.50 (2H), 0.59-0.67 (2H), 2.12 (3H), 2.20 (6H), 2.49-2.59 (2H), 2.76 (1H), 3.37-3.47 (2H), 6.11 (1H), 7.13 (1H), 7.26 (1H), 7.51 (1H), 7.57-7.64 (1H), 7.68 (1H), 7.80 (1H), 7.88-7.92 (1H), 8.21 (1H), 8.49 (1H), 8.57 (1H) |
| 525 | 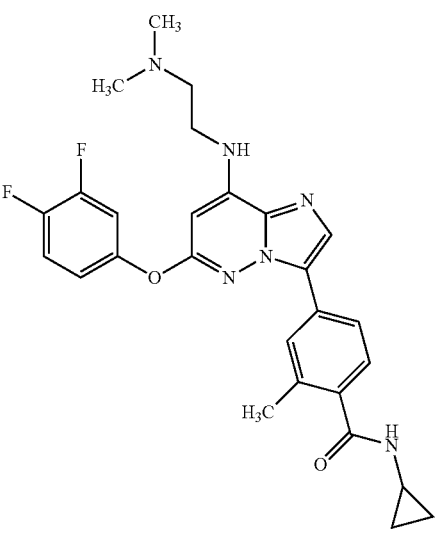 [SMILES: Cc1cc(-c2cnc3c(NCCN(C)C)cc(Oc4ccc(F)c(F)c4)nn23)ccc1C(=O)NC1CC1] | N-cyclopropyl-4-[6-(3,4-difluorophenoxy)-8-{[2-(dimethylamino)ethyl]amino}imidazo[1,2-b]pyridazin-3-yl]-2-methylbenzamide | RT = 0.95 MW$_{found}$ = 507.5 MW$_{calc}$ = 506.5 |

Example 526

N-cyclopropyl-4-[6-(2,3-difluorophenoxy)-8-{[(1-methylpiperidin-4-yl)-methyl]amino}imidazo[1,2-b]pyridazin-3-yl]-2-methylbenzamide

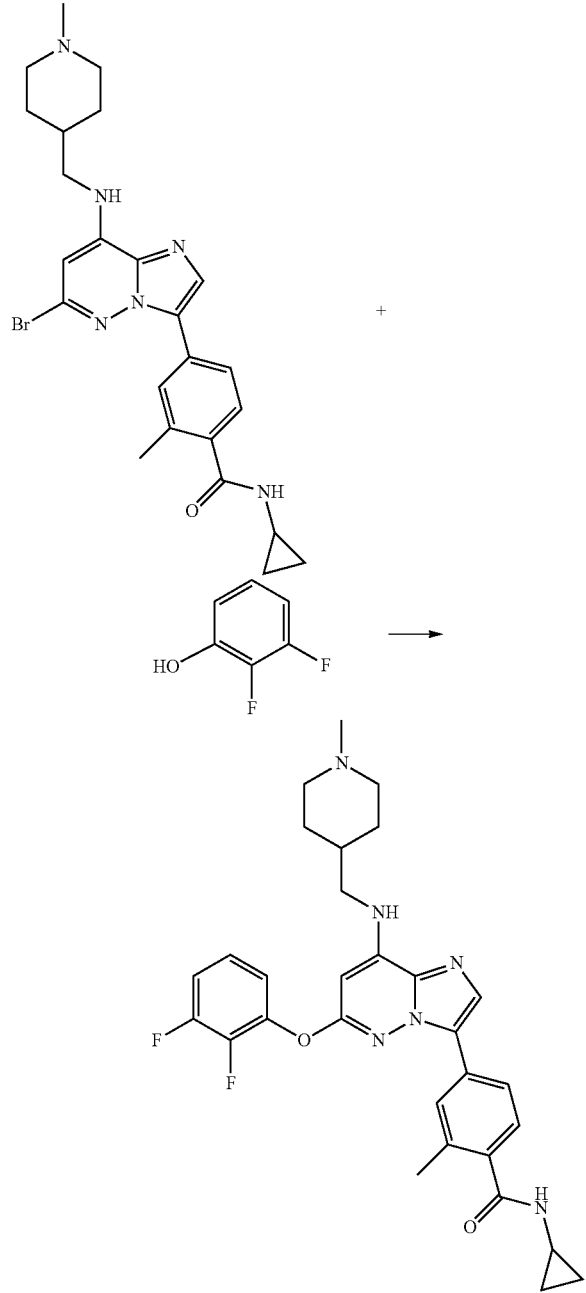

90 mg (181 μmol) 4-(6-bromo-8-{[(1-methylpiperidin-4-yl)methyl]amino}imidazo[1,2-b]pyridazin-3-yl)-N-cyclopropyl-2-methylbenzamide which was prepared according to intermediate example 526a were transformed in analogy to example 51 using 2,3-difluorophenol to give after working up and purification 16 mg (15%) of the title compound.

UPLC-MS: RT=0.97, $MW_{found}$=547.6. $MW_{calc}$=546.6.
$^1$H-NMR (300 MHz, DMSO-$d_6$), δ [ppm]=0.41-0.52 (2H), 0.58-0.69 (2H), 1.20 (2H), 1.67 (3H), 1.80 (2H), 2.11 (6H), 2.67-2.82 (3H), 3.22 (2H), 6.16 (1H), 6.69-6.81 (1H), 7.13 (1H), 7.26-7.34 (2H), 7.42 (1H), 7.59 (1H), 7.67 (1H), 7.79 (1H), 7.92 (1H), 8.22 (1H).

Intermediate Example 526a 4-(6-bromo-8-{[(1-methylpiperidin-4-yl)methyl]amino}imidazo[1,2-b]pyridazin-3-yl)-N-cyclopropyl-2-methylbenzamide

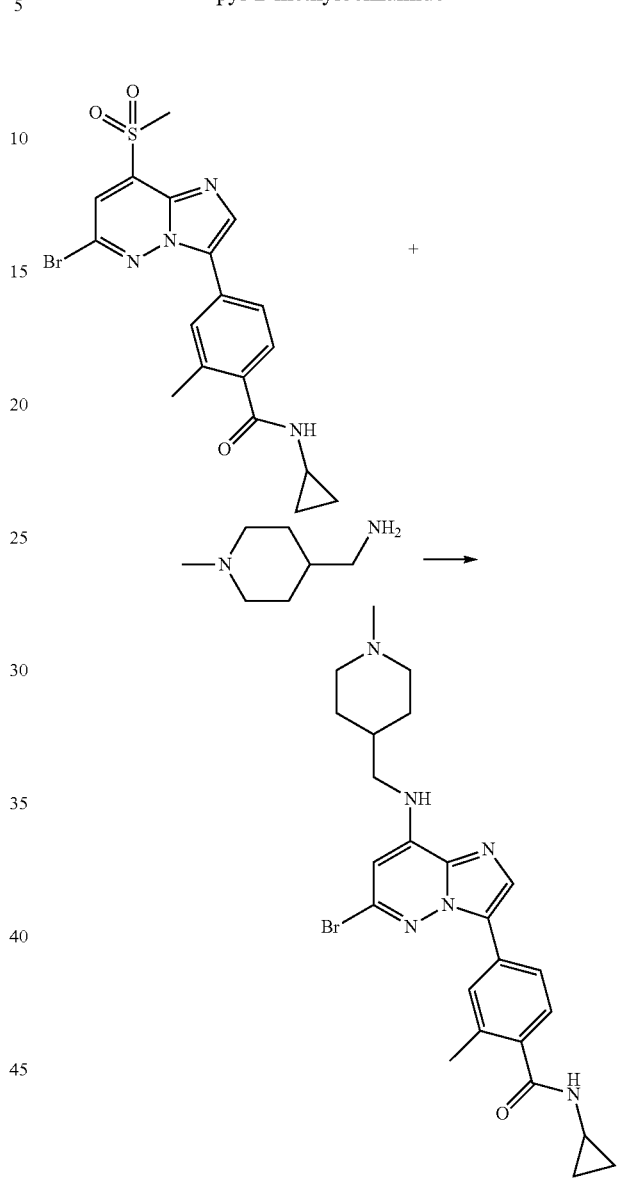

449 mg (1 mmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to intermediate example 516a using 1-(1-methylpiperidin-4-yl)methanamine to give after working up and purification 460 mg (92%) of the title compound.

UPLC-MS: RT=0.76, $MW_{found}$=498.5. $MW_{calc}$=497.5.
$^1$H-NMR (300 MHz, DMSO-$d_6$), δ [ppm]=0.46-0.53 (2H), 0.61-0.70 (2H), 1.18 (2H), 1.53-1.68 (3H), 1.75 (2H), 2.08 (3H), 2.34 (3H), 2.63-2.76 (2H), 2.80 (1H), 3.18 (2H), 6.38 (1H), 7.36 (1H), 7.84 (1H), 7.87-7.98 (3H), 8.28 (1H)

The following compound examples were prepared analogously to the procedure described for example 526 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 527 | 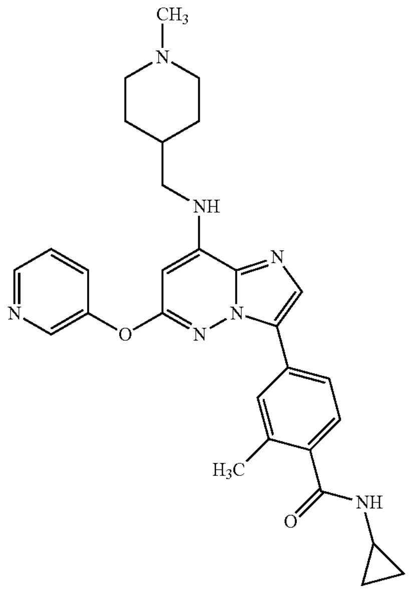 [SMILES: Cc1cc(-c2cnc3c(NCC4CCN(C)CC4)cc(Oc4cccnc4)nn23)ccc1C(=O)NC1CC1] | N-cyclopropyl-2-methyl-4-[8-{[(1-methylpiperidin-4-yl)methyl]amino}-6-(pyridin-3-yloxy)imidazo[1,2-b]pyridazin-3-yl]benzamide | RT = 0.77 MW$_{found}$ = 512.6 MW$_{calc}$ = 511.6 $^1$H-NMR (300 MHz, DMSO-d$_6$), δ [ppm] = 0.43-0.50 (2H), 0.59-0.68 (2H), 1.21 (2H), 1.67 (3H), 1.85 (2H), 2.12 (3H), 2.14 (3H), 2.70-2.81 (3H), 3.22 (2H), 6.11 (1H), 7.13 (1H), 7.51 (1H), 7.56-7.62 (1H), 7.68 (1H), 7.74 (1H), 7.78-7.83 (1H), 7.90 (1H), 8.18-8.23 (1H), 8.48 (1H), 8.57 (1H) |

Example 528
N-cyclopropyl-4-[6-(2,3-difluorophenoxy)-8-(methylamino)imidazo[1,2-b]pyridazin-3-yl]-2-methyl-benzamide

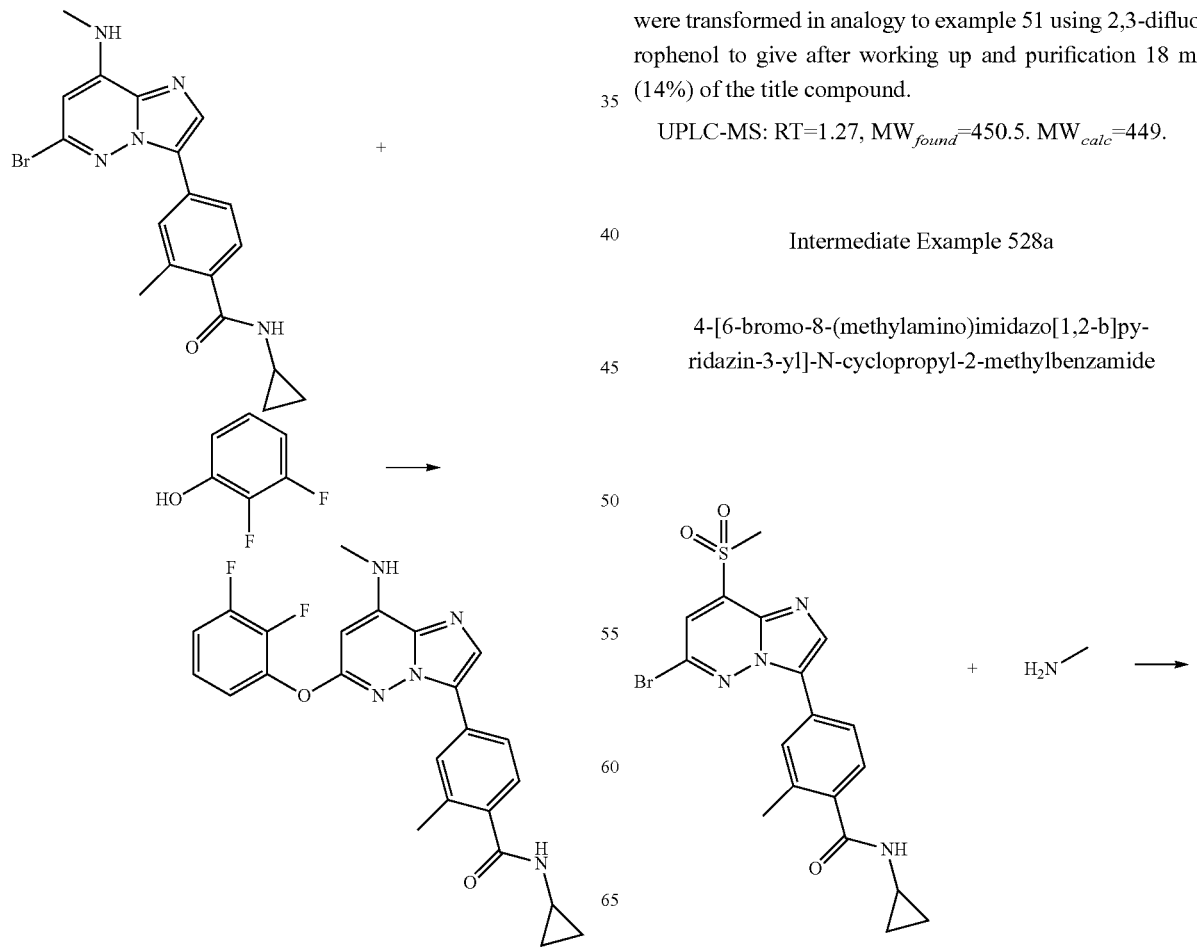

80 mg (200 μmol) 4-[6-bromo-8-(methylamino)imidazo[1,2-b]pyridazin-3-yl]-N-cyclopropyl-2-methylbenzamide which was prepared according to intermediate example 528a were transformed in analogy to example 51 using 2,3-difluorophenol to give after working up and purification 18 mg (14%) of the title compound.

UPLC-MS: RT=1.27, MW$_{found}$=450.5. MW$_{calc}$=449.

Intermediate Example 528a

4-[6-bromo-8-(methylamino)imidazo[1,2-b]pyridazin-3-yl]-N-cyclopropyl-2-methylbenzamide

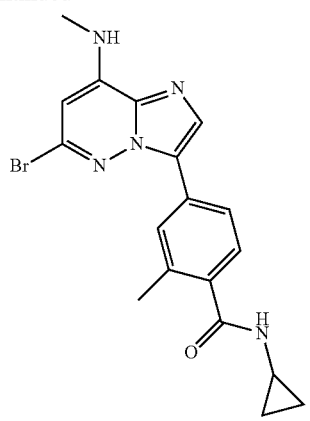

1123 mg (2.5 mmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to intermediate example 516a using methanamine to give after working up and purification 1000 mg (100%) of the title compound.

UPLC-MS: RT=1.08, $MW_{found}$=401.3. $MW_{calc}$=400.3.

The following compound examples were prepared analogously to the procedure described for example 528 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 529 | 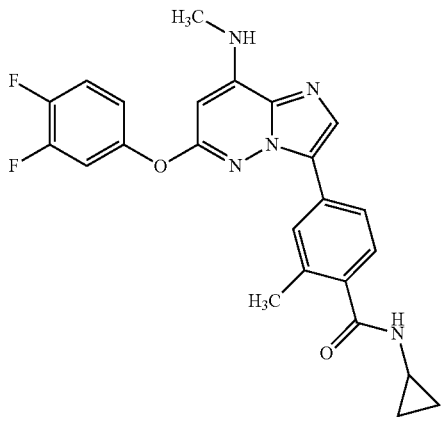 [SMILES: CNc1cc(Oc2ccc(F)c(F)c2)nn2c(-c3ccc(C(=O)NC4CC4)c(C)c3)cnc12] | N-cyclopropyl-4-[6-(3,4-difluorophenoxy)-8-(methylamino)imidazo[1,2-b]pyridazin-3-yl]-2-methylbenzamide | RT = 1.27 $MW_{found}$ = 450.5 $MW_{calc}$ = 449.5 |
| 530 | 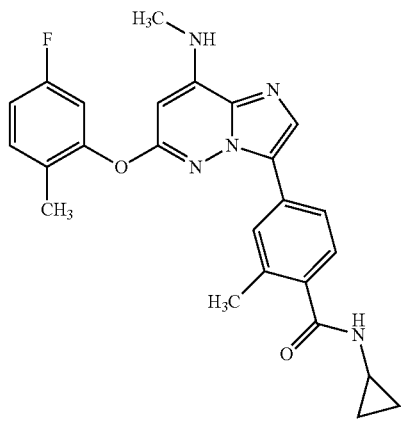 [SMILES: CNc1cc(Oc2cc(F)ccc2C)nn2c(-c3ccc(C(=O)NC4CC4)c(C)c3)cnc12] | N-cyclopropyl-4-[6-(5-fluoro-2-methylphenoxy)-8-(methylamino)imidazo[1,2-b]pyridazin-3-yl]-2-methylbenzamide | RT = 1.31 $MW_{found}$ = 446.5 $MW_{calc}$ = 445.5 |

-continued

| Example | Structure | Name | Analytical Data |
|---|---|---|---|
| 531 | 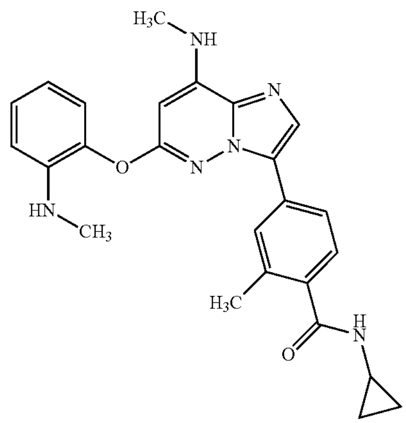 [SMILES: CNc1ccccc1Oc1cc(NC)c2ncc(-c3ccc(C(=O)NC4CC4)c(C)c3)n2n1] | N-cyclopropyl-2-methyl-4-{8-(methylamino)-6-[2-(methylamino)phenoxy]imidazo[1,2-b]pyridazin-3-yl}benzamide | RT = 0.97 MW$_{found}$ = 443.5 MW$_{calc}$ = 442.5 $^1$H-NMR (400 MHz, DMSO-d$_6$), δ [ppm] = 0.51-0.56 (2H), 0.65-0.70 (2H), 2.36 (3H), 2.61 (3H), 2.83 (1H), 3.29 (3H), 5.16 (1H), 6.84-6.90 (1H), 6.99 (2H), 7.15-7.23 (2H), 7.33 (1H), 7.82 (1H), 8.06 (1H), 8.12 (1H), 8.26 (1H) |
| 532 | 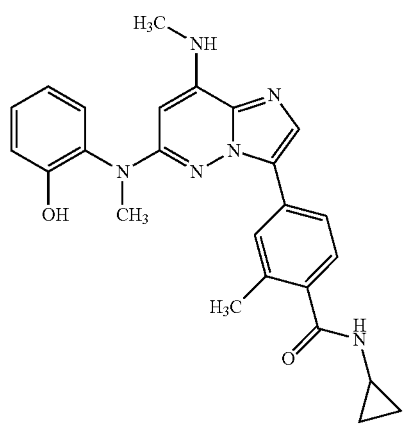 [SMILES: CNc1cc(N(C)c2ccccc2O)nn2c(-c3ccc(C(=O)NC4CC4)c(C)c3)cnc12] | N-cyclopropyl-4-{6-[(2-hydroxyphenyl)(methyl)amino]-8-(methylamino)imidazo[1,2-b]pyridazin-3-yl}-2-methylbenzamide | RT = 1.21 MW$_{found}$ = 443.5 MW$_{calc}$ = 442.5 |
| 533 | 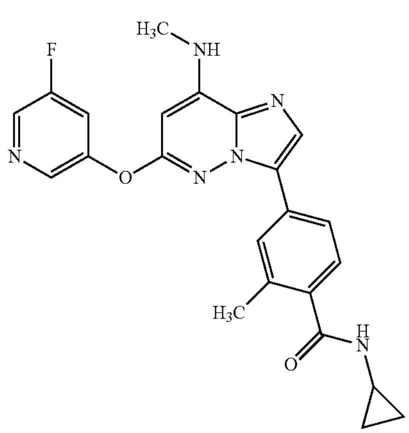 [SMILES: CNc1cc(Oc2cncc(F)c2)nn2c(-c3ccc(C(=O)NC4CC4)c(C)c3)cnc12] | N-cyclopropyl-4-{6-[(5-fluoropyridin-3-yl)oxy]-8-(methylamino)imidazo[1,2-b]pyridazin-3-yl}-2-methylbenzamide | RT = 1.06 MW$_{found}$ = 433.5 MW$_{calc}$ = 432.5 |

-continued

| Example | Structure | Name | Analytical Data |
|---|---|---|---|
| 534 | 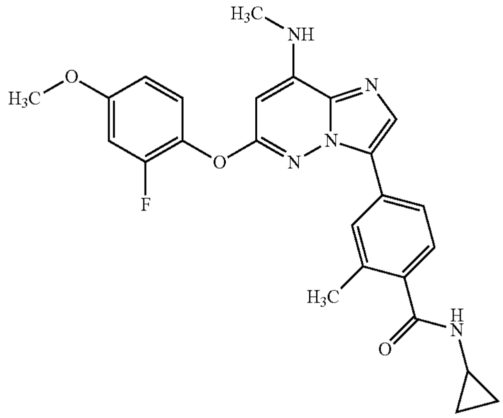 [SMILES: CNc1cc(Oc2ccc(OC)cc2F)nn2c(-c3ccc(C(=O)NC4CC4)c(C)c3)cnc12] | N-cyclopropyl-4-[6-(2-fluoro-4-methoxy-phenoxy)-8-(methyl-amino)imidazo[1,2-b]pyridazin-3-yl]-2-methylbenzamide | RT = 1.24 MW$_{found}$ = 462.5 MW$_{calc}$ = 461.5 |
| 535 | 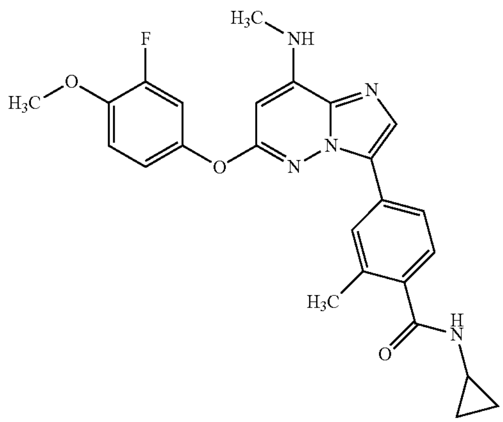 [SMILES: CNc1cc(Oc2ccc(OC)c(F)c2)nn2c(-c3ccc(C(=O)NC4CC4)c(C)c3)cnc12] | N-cyclopropyl-4-[6-(3-fluoro-4-methoxy-phenoxy)-8-(methyl-amino)imidazo[1,2-b]pyridazin-3-yl]-2-methylbenzamide | RT = 1.23 MW$_{found}$ = 462.5 MW$_{calc}$ = 461.5 $^1$H-NMR (400 MHz, DMSO-d$_6$), δ [ppm] = 0.44-0.50 (2H), 0.61-0.67 (2H), 2.12 (3H), 2.74-2.81 (1H), 2.90 (3H), 3.84 (3H), 5.91 (1H), 7.03-7.08 (1H), 7.17 (1H), 7.19-7.25 (1H), 7.29 (1H), 7.61 (1H), 7.65 (1H), 7.78 (1H), 7.89 (1H), 8.20 (1H) |

Example 536

N-cyclopropyl-4-[6-(2,3-difluorophenoxy)-8-{[2-(morpholin-4-yl)ethyl]amino}imidazo[1,2-b]pyridazin-3-yl]-2-methylbenzamide

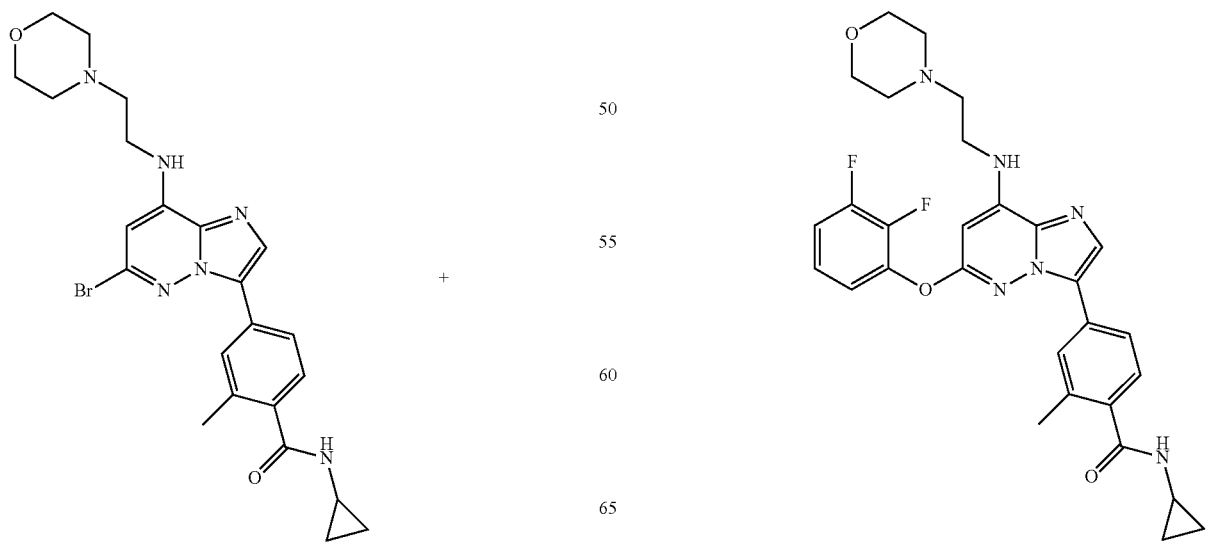

665

100 mg (200 μmol) 4-(6-bromo-8-{[2-(morpholin-4-yl)ethyl]amino}imidazo[1,2-b]pyridazin-3-yl)-N-cyclopropyl-2-methylbenzamide which was prepared according to intermediate example 536a were transformed in analogy to example 51 using 2,3-difluorophenol to give after working up and purification 25 mg (21%) of the title compound.

UPLC-MS: RT=0.93, MW$_{found}$=549.6. MW$_{calc}$=548.6.
$^1$H-NMR (400 MHz, DMSO-d$_6$), δ [ppm]=0.44-0.50 (2H), 0.60-0.67 (2H), 2.11 (3H), 2.46 (4H), 2.61 (2H), 2.77 (1H), 3.46 (2H), 3.57 (4H), 6.17 (1H), 7.14 (1H), 7.27-7.34 (2H), 7.39-7.46 (2H), 7.59 (1H), 7.67 (1H), 7.93 (1H), 8.11 (1H), 8.23 (1H)

Intermediate Example 536a 4-(6-bromo-8-{[2-(morpholin-4-yl)ethyl]amino}imidazo[1,2-b]pyridazin-3-yl)-N-cyclopropyl-2-methylbenzamide

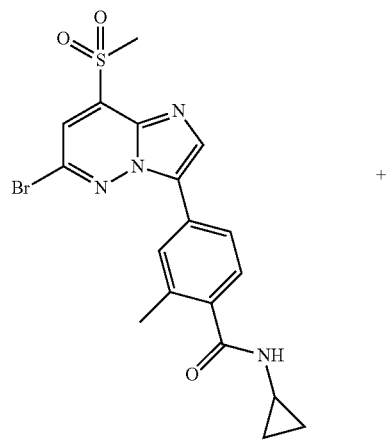

+

-continued

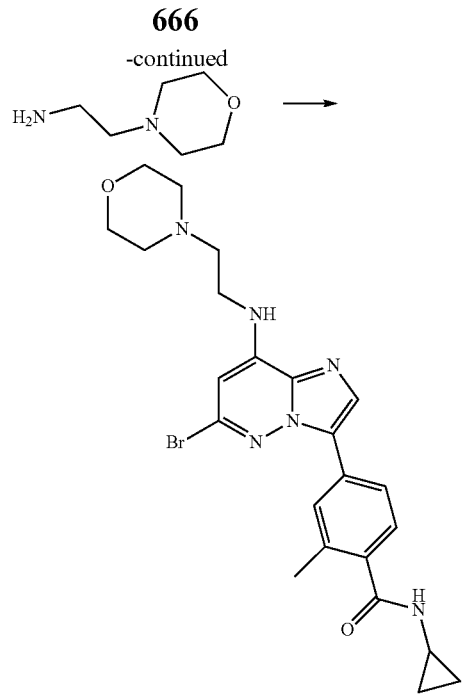

1123 mg (2.5 mmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to intermediate example 516a using 2-(morpholin-4-yl)ethanamine to give after working up and purification 1360 mg (108%) of the title compound.

UPLC-MS: RT=0.74, MW$_{found}$=500.4. MW$_{calc}$=499.4.

The following compound examples were prepared analogously to the procedure described for example 536 using the appropriate phenol or aniline building block [LC-MS data such as retention time (RT in min) or observed mass peak were collected using LC-MS Method A unless explicitly stated]:

| Example | Structure | Name | Analytical Data |
|---|---|---|---|
| 537 | (structure shown) | N-cyclopropyl-4-[6-(5-fluoro-2-methylphenoxy)-8-{[2-(morpholin-4-yl)ethyl]amino}imidazo[1,2-b]pyridazin-3-yl]-2-methylbenzamide | RT = 0.95 MW$_{found}$ = 545.6 MW$_{calc}$ = 544.6 $^1$H-NMR (300 MHz, DMSO-d$_6$), δ [ppm] = 0.44-0.51 (2H), 0.60-0.67 (2H), 2.11 (6H), 2.40-2.49 (4H), 2.59 (2H), 2.77 (1H), 3.38-3.49 (2H), 3.53-3.60 (4H), 6.09 (1H), 7.06 (1H), 7.11-7.20 (2H), 7.27 (1H), 7.32-7.39 (1H), 7.58-7.64 (1H), 7.71 (1H), 7.91 (1H), 8.20 (1H) |

| Example | Structure | Name | Analytical Data |
|---|---|---|---|
| 538 | 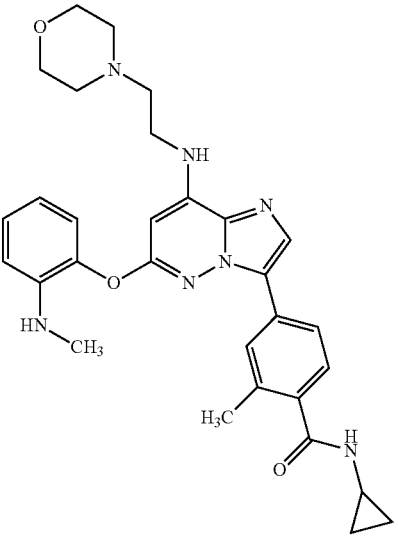 [SMILES: CNc1ccccc1Oc1cc(NCCN2CCOCC2)c2ncc(-c3ccc(C(=O)NC4CC4)c(C)c3)n2n1] | N-cyclopropyl-2-methyl-4-(6-[2-(methylamino)phenoxy]-8-{[2-(morpholin-4-yl)ethyl]amino}imidazo[1,2-b]pyridazin-3-yl)benzamide | RT = 0.85 MW$_{found}$ = 542.6 MW$_{calc}$ = 541.6 |
| 539 | 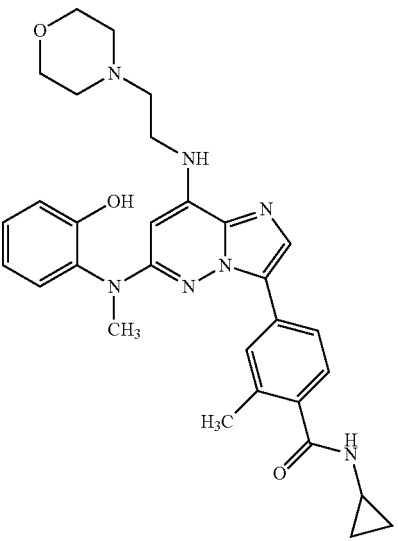 [SMILES: Cc1cc(-c2cnc3c(NCCN4CCOCC4)cc(N(C)c4ccccc4O)nn23)ccc1C(=O)NC1CC1] | N-cyclopropyl-4-(6-[(2-hydroxyphenyl)(methyl)amino]-8-{[2-(morpholin-4-yl)ethyl]amino}imidazo[1,2-b]pyridazin-3-yl)-2-methylbenzamide | RT = 0.81 MW$_{found}$ = 542.6 MW$_{calc}$ = 541.6 $^1$H-NMR (300 MHz, CDCl$_3$), δ [ppm] = 0.70 (2H), 0.89 (2H), 2.38 (7H), 2.52 (2H), 2.98 (3H), 3.30 (2H), 3.71 (4H), 5.06 (1H), 5.92 (1H), 6.42 (1H), 6.89-6.99 (1H), 7.10 (2H), 7.22 (3H), 7.65 (1H), 7.78 (1H), 7.90 (1H) |
| 540 | 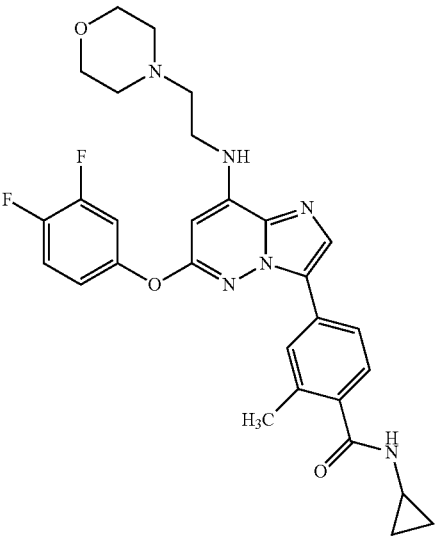 [SMILES: Cc1cc(-c2cnc3c(NCCN4CCOCC4)cc(Oc4ccc(F)c(F)c4)nn23)ccc1C(=O)NC1CC1] | N-cyclopropyl-4-[6-(3,4-difluorophenoxy)-8-{[2-(morpholin-4-yl)ethyl]amino}imidazo[1,2-b]pyridazin-3-yl]-2-methylbenzamide | RT = 0.94 MW$_{found}$ = 549.6 MW$_{calc}$ = 548.6 |

| Example | Structure | Name | Analytical Data |
|---|---|---|---|
| 541 | 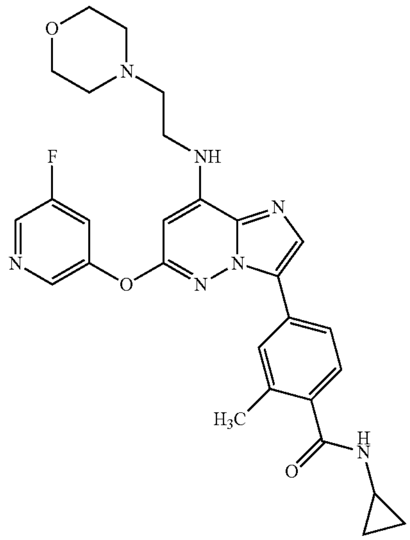 [SMILES: Cc1cc(-c2cnc3c(NCCN4CCOCC4)cc(Oc4cncc(F)c4)nn23)ccc1C(=O)NC1CC1] | N-cyclopropyl-4-(6-[(5-fluoro-pyridin-3-yl)oxy]-8-{[2-(morpholin-4-yl)ethyl]amino}imidazo[1,2-b]pyridazin-3-yl)-2-methylbenzamide | RT = 1.06 MW$_{found}$ = 532.6 MW$_{calc}$ = 531.6 $^1$H-NMR (300 MHz, DMSO-d$_6$), δ [ppm] = 0.44-0.52 (2H), 0.59-0.68 (2H), 2.14 (3H), 2.39-2.44 (4H), 2.58 (2H), 2.73-2.81 (1H), 3.45 (2H), 3.51-3.59 (4H), 6.14 (1H), 7.17 (1H), 7.41 (1H), 7.59-7.64 (1H), 7.70 (1H), 7.91 (1H), 7.98 (1H), 8.22 (1H), 8.50 (1H), 8.54 (1H) |

Example 542 tert-butyl 3-[({3-[4-(cyclopropylcarbamoyl)-3-methylphenyl]-6-(3-fluorophenoxy)imidazo[1,2-b]pyridazin-8-yl}amino)methyl]azetidine-1-carboxylate

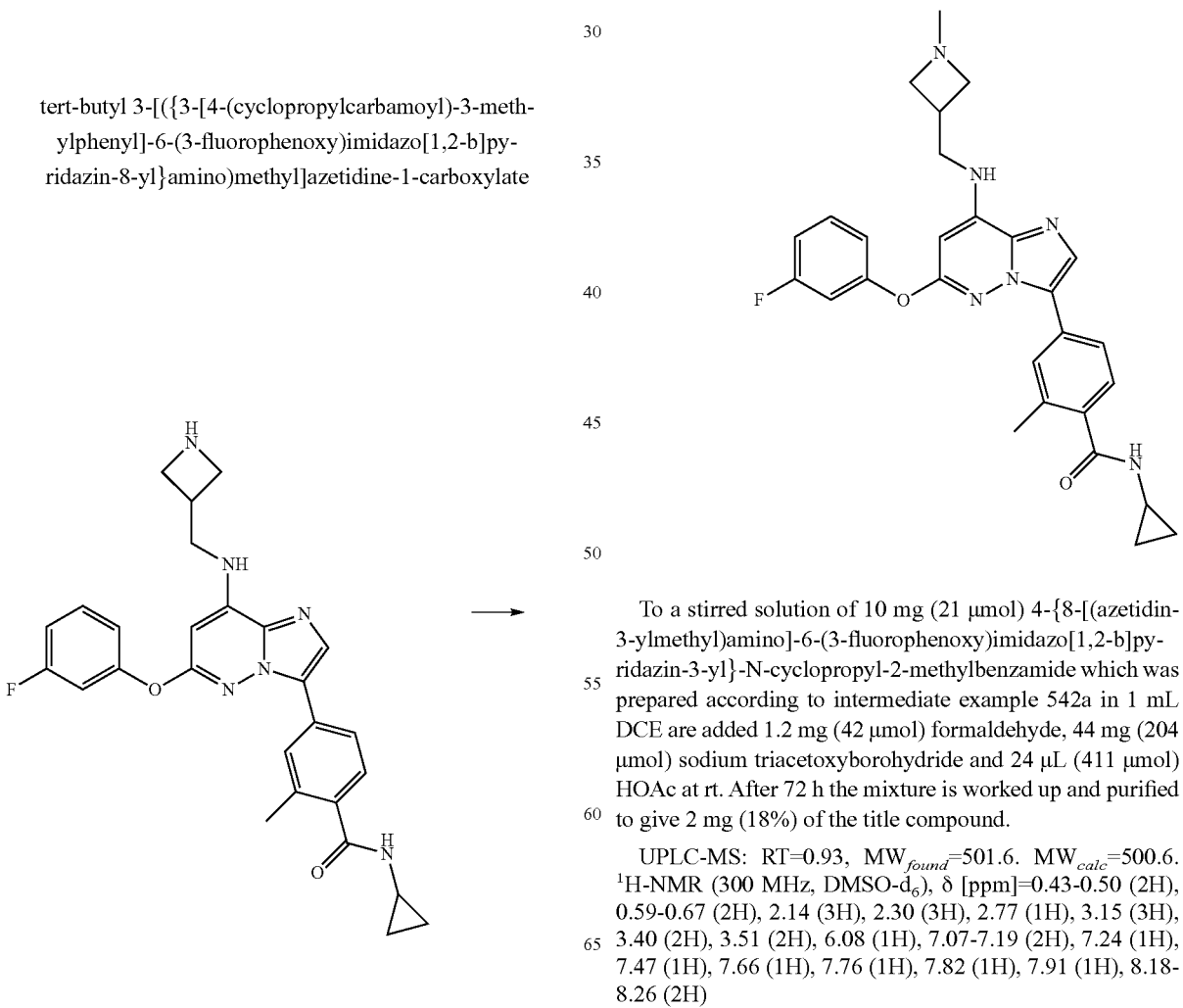

To a stirred solution of 10 mg (21 μmol) 4-{8-[(azetidin-3-ylmethyl)amino]-6-(3-fluorophenoxy)imidazo[1,2-b]pyridazin-3-yl}-N-cyclopropyl-2-methylbenzamide which was prepared according to intermediate example 542a in 1 mL DCE are added 1.2 mg (42 μmol) formaldehyde, 44 mg (204 μmol) sodium triacetoxyborohydride and 24 μL (411 μmol) HOAc at rt. After 72 h the mixture is worked up and purified to give 2 mg (18%) of the title compound.

UPLC-MS: RT=0.93, MW$_{found}$=501.6. MW$_{calc}$=500.6. $^1$H-NMR (300 MHz, DMSO-d$_6$), δ [ppm]=0.43-0.50 (2H), 0.59-0.67 (2H), 2.14 (3H), 2.30 (3H), 2.77 (1H), 3.15 (3H), 3.40 (2H), 3.51 (2H), 6.08 (1H), 7.07-7.19 (2H), 7.24 (1H), 7.47 (1H), 7.66 (1H), 7.76 (1H), 7.82 (1H), 7.91 (1H), 8.18-8.26 (2H)

671

Intermediate Example 542a tert-butyl 3-[({3-[4-(cyclopropylcarbamoyl)-3-methylphenyl]-6-(3-fluorophenoxy)imidazo[1,2-b]pyridazin-8-yl}amino)methyl]azetidine-1-carboxylate

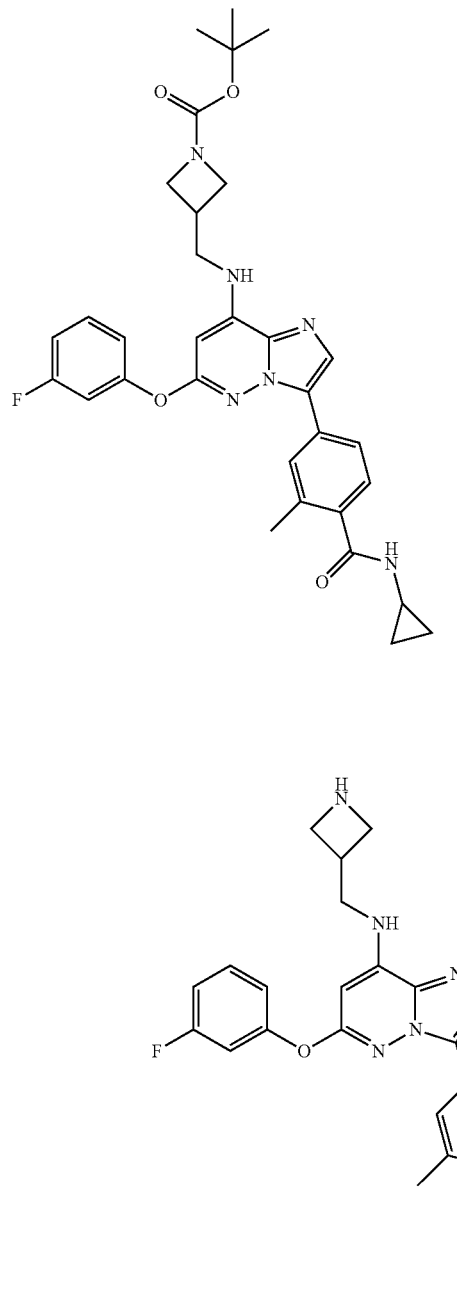

To a stirred solution of 43 mg (74 µmol) tert-butyl 3-[({3-[4-(cyclopropylcarbamoyl)-3-methylphenyl]-6-(3-fluorophenoxy)imidazo[1,2-b]pyridazin-8-yl}amino)methyl] azetidine-1-carboxylate which was prepared according to intermediate example 542b in 3 mL DCM are added 1 mL TFA and two drops of water at rt. After 1 h the mixture is worked up to give 34 mg (93%) of the title compound.

UPLC-MS: RT=0.82, $MW_{found}$=487.5. $MW_{calc}$=486.5.

672

Intermediate Example 542b tert-butyl-3-[({3-[4-(cyclopropylcarbamoyl)-3-methylphenyl]-6-(3-fluorophenoxy)imidazo[1,2-b]pyridazin-8-yl}amino)methyl]azetidine-1-carboxylate

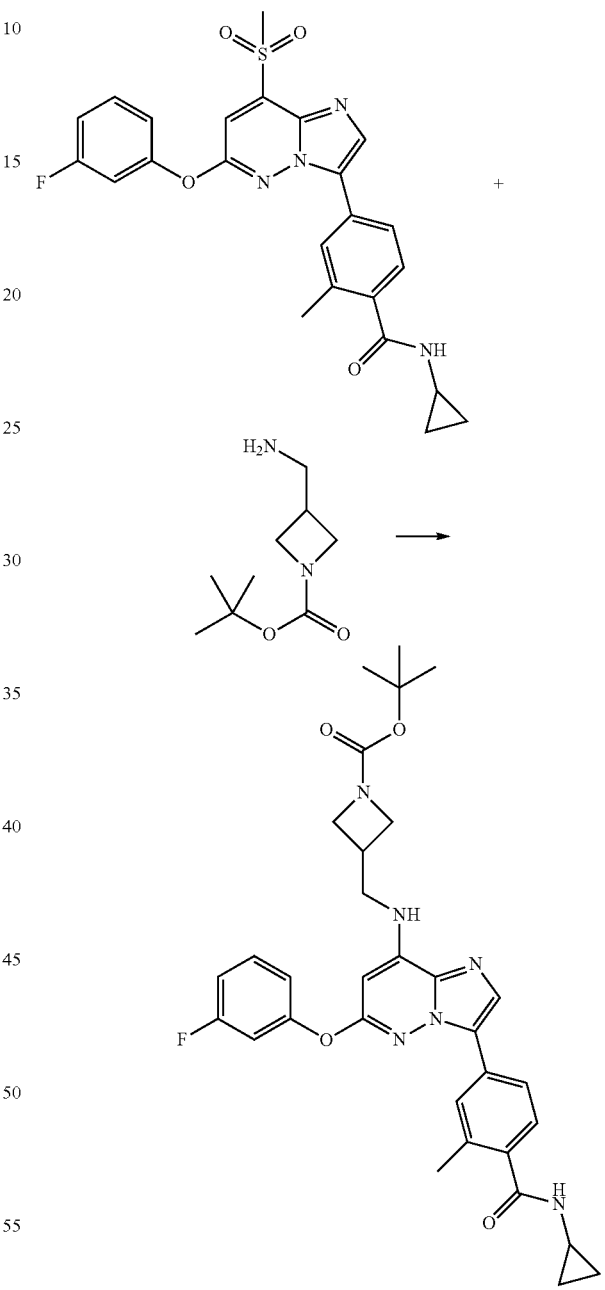

192 mg (400 µmol) N-cyclopropyl-4-[6-(3-fluorophenoxy)-8-(methylsulfonyl)imidazo[1,2-b]pyridazin-3-yl]-2-methylbenzamide which was prepared according to intermediate example 486a were transformed in analogy to example 486 using tert-butyl 3-(aminomethyl)azetidine-1-carboxylate to give after working up and purification 43 mg (18%) of the title compound.

UPLC-MS: RT=1.36, $MW_{found}$=587.7. $MW_{calc}$=586.7.

Example 543

N-cyclopropyl-4-[6-(2,3-difluorophenoxy)-8-{[(1-methylazetidin-3-yl)methyl]amino}imidazo[1,2-b]pyridazin-3-yl]-2-methylbenzamide

Intermediate Example 543a

4-{8-[(azetidin-3-ylmethyl)amino]-6-(2,3-difluorophenoxy)imidazo[1,2-b]pyridazin-3-yl}-N-cyclopropyl-2-methylbenzamide

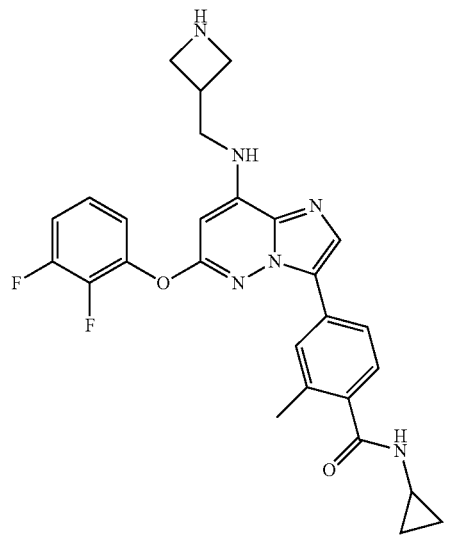

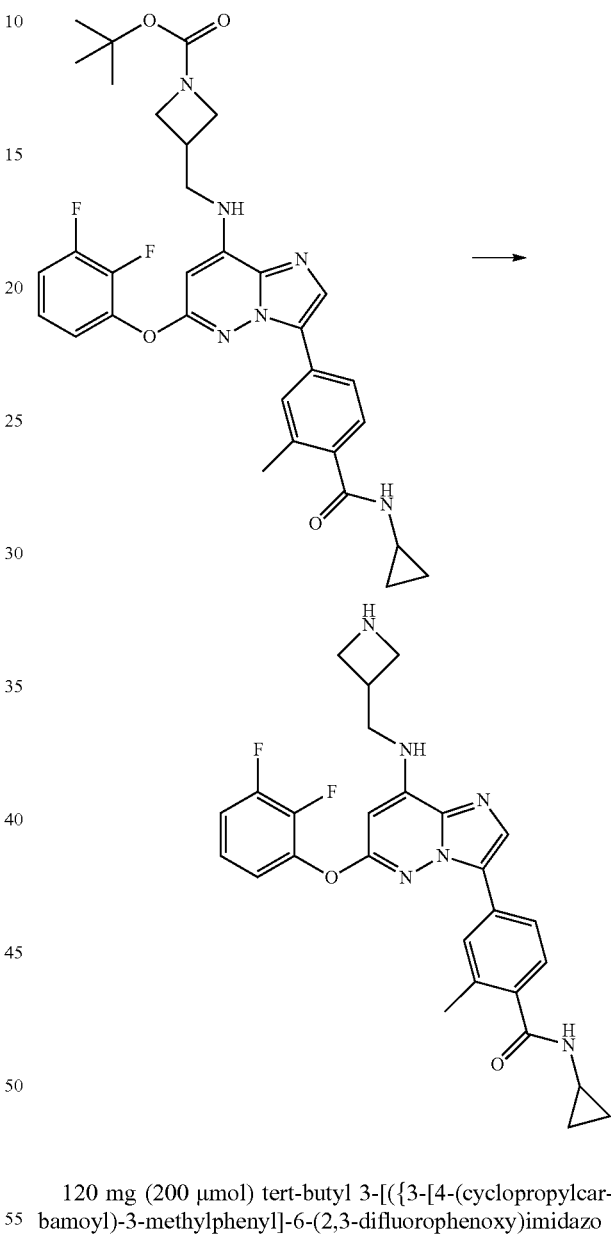

10 mg (21 µmol) 4-{8-[(azetidin-3-ylmethyl)amino]-6-(2,3-difluorophenoxy)imidazo[1,2-b]pyridazin-3-yl}-N-cyclopropyl-2-methylbenzamide which was prepared according to intermediate example 543a were transformed in analogy to example 542 to give after working up and purification 0.8 mg (6%) of the title compound.

UPLC-MS: RT=0.94, MW$_{found}$=519.6. MW$_{calc}$=518.6.

120 mg (200 µmol) tert-butyl 3-[({3-[4-(cyclopropylcarbamoyl)-3-methylphenyl]-6-(2,3-difluorophenoxy)imidazo[1,2-b]pyridazin-8-yl}amino)methyl]azetidine-1-carboxylate which was prepared according to intermediate example 543b were transformed in analogy to intermediate example 542a to give after working up and purification 13 mg (13%) of the title compound.

UPLC-MS: RT=0.92, MW$_{found}$=505.5. MW$_{calc}$=504.5.
$^1$H-NMR (400 MHz, DMSO-d$_6$), δ [ppm]=0.44-0.50 (2H), 0.60-0.68 (2H), 2.11 (3H), 2.72-2.81 (1H), 3.08-3.18 (1H), 3.59 (2H), 3.66-3.74 (2H), 3.91 (2H), 6.26 (1H), 6.74 (2H), 6.93 (1H), 7.14 (1H), 7.26-7.34 (1H), 7.43 (1H), 7.59 (1H), 7.67 (1H), 7.94 (1H), 7.99 (1H), 8.21 (1H)

Intermediate Example 543b tert-butyl-3-[({3-[4-(cyclopropylcarbamoyl)-3-methylphenyl]-6-(2,3-difluorophenoxy)imidazo[1,2-b]pyridazin-8-yl}amino)methyl]azetidine-1-carboxylate

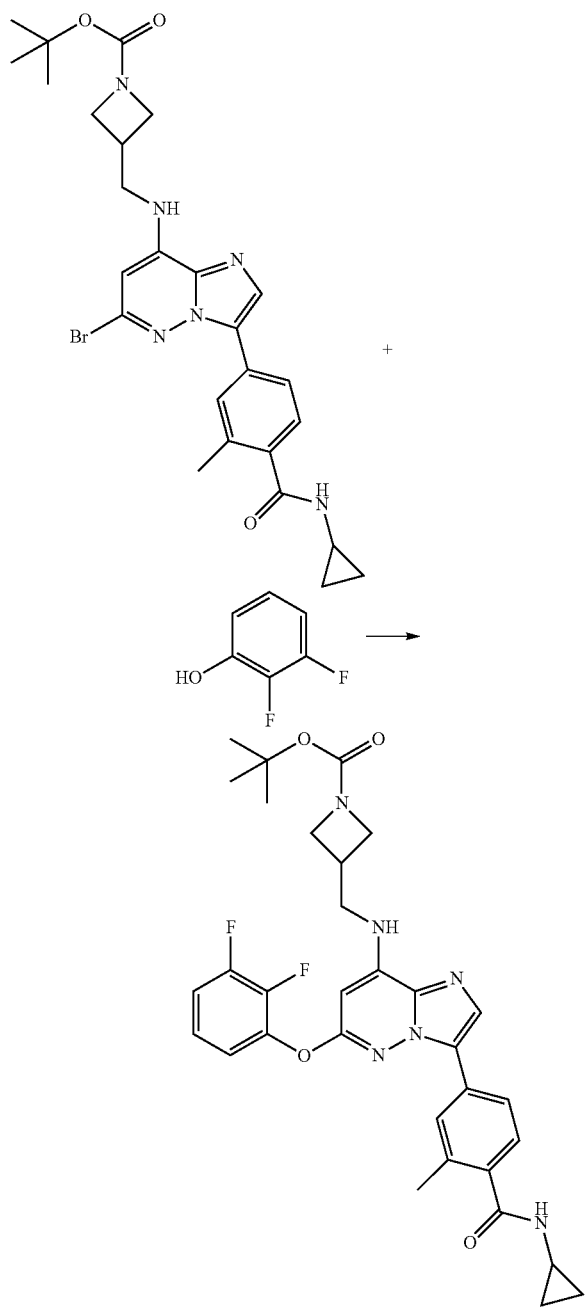

195 mg (200 µmol) tert-butyl 3-[({6-bromo-3-[4-(cyclopropylcarbamoyl)-3-methylphenyl]imidazo[1,2-b]pyridazin-8-yl}amino)methyl]azetidine-1-carboxylate which was prepared according to intermediate example 543c were transformed in analogy to example 51 using 2,3-difluorophenol and the product was used without working up in the next step.

UPLC-MS: RT=0.1.37, $MW_{found}$=605.7. $MW_{calc}$=605.7.

Intermediate Example 543c tert-butyl 3-[({6-bromo-3-[4-(cyclopropylcarbamoyl)-3-methylphenyl]imidazo[1,2-b]pyridazin-8-yl}amino)methyl]azetidine-1-carboxylate

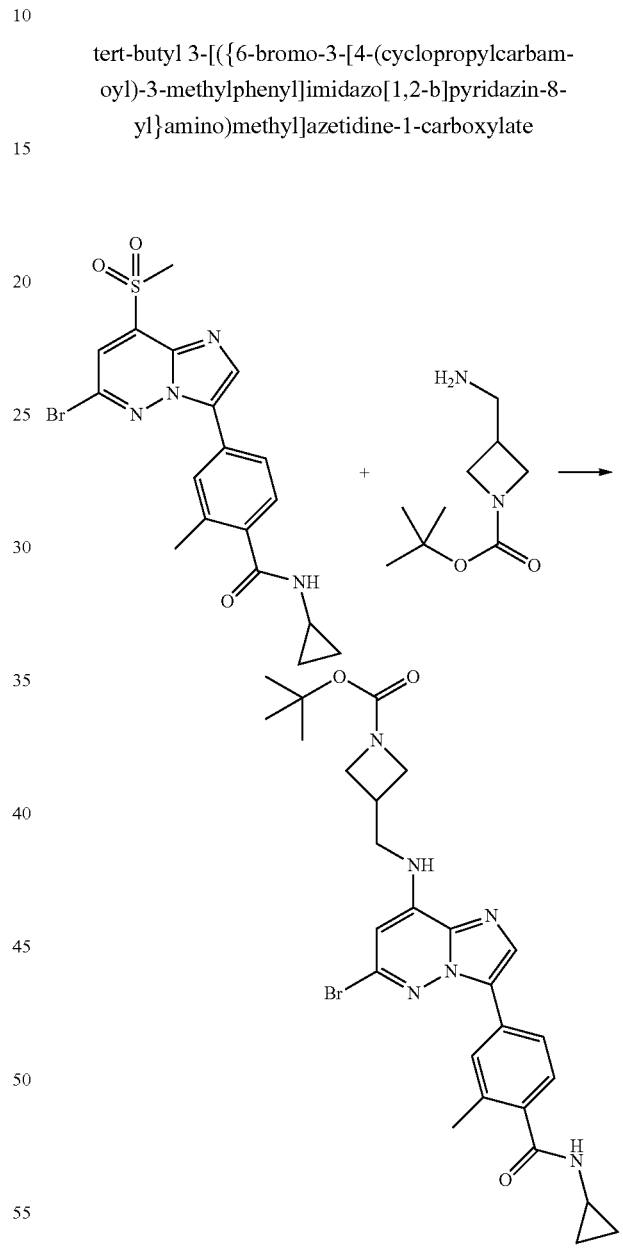

1348 mg (3 mmol) 4-[6-bromo-8-(methylsulfonyl)imidazo[1,2-b]pyridazin-3-yl]-N-cyclopropyl-2-methyl benzamide which was prepared according to intermediate example 516a were transformed in analogy to example 516 to give after working up and purification 1.67 g (100%) of the title compound.

UPLC-MS: RT=1.28, $MW_{found}$=556.5. $MW_{calc}$=555.5.

Example 544

4-{8-[(azetidin-3-ylmethyl)amino]-6-[(5-fluoropyridin-3-yl)oxy]imidazo[1,2-b]pyridazin-3-yl}-N-cyclopropyl-2-methylbenzamide

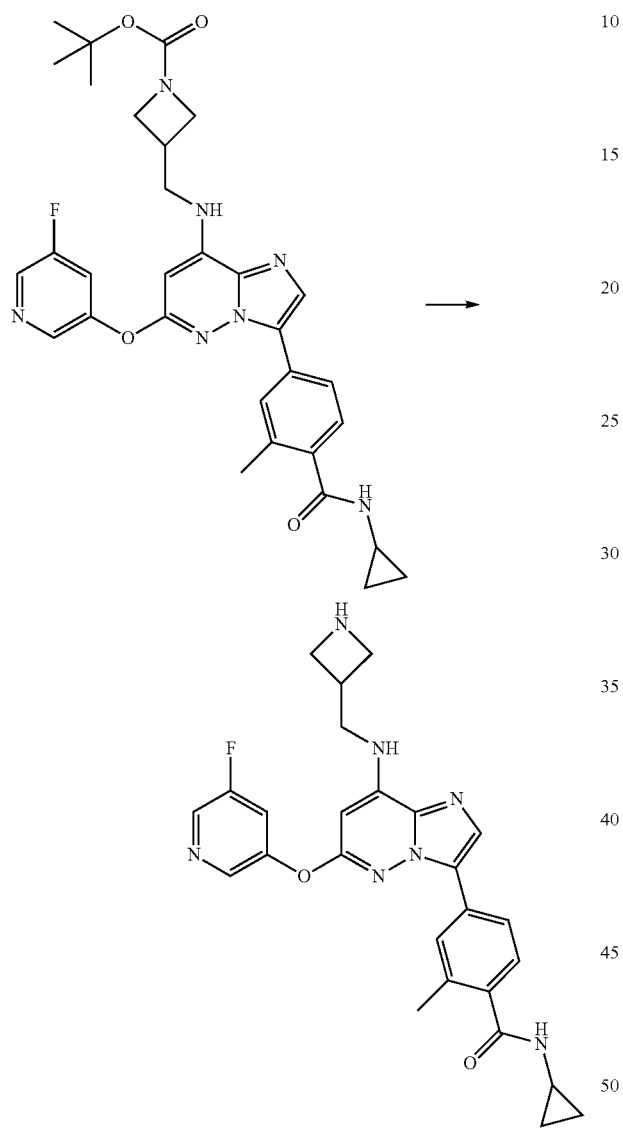

5 mg (8 μmol) tert-butyl 3-[({3-[4-(cyclopropylcarbamoyl)-3-methylphenyl]-6-[(5-fluoropyridin-3-yl)oxy]imidazo[1,2-b]pyridazin-8-yl}amino)methyl]azetidine-1-carboxylate which was prepared according to intermediate example 544a were transformed in analogy to intermediate example 542a to give after working up and purification 3.7 mg (99%) of the title compound.

RT=0.80, MW$_{found}$=488.5. MW$_{calc}$=487.5. $^1$H-NMR (300 MHz, DMSO-d$_6$), δ[ppm]=0.43-0.51 (2H), 0.59-0.69 (2H), 2.15 (3H), 2.77 (1H), 3.17 (1H), 3.59 (2H), 3.73-3.85 (2H), 3.92-4.04 (2H), 6.21-6.26 (1H), 7.17 (1H), 7.64 (1H), 7.70 (1H), 7.73 (1H), 7.92-8.01 (2H), 8.20 (1H), 8.33 (1H), 8.39 (1H), 8.55 (1H).

Intermediate Example 544a tert-butyl 3-[({3-[4-(cyclopropylcarbamoyl)-3-methylphenyl]-6-[(5-fluoropyridin-3-yl)oxy]imidazo[1,2-b]pyridazin-8-yl}amino)methyl]azetidine-1-carboxylate

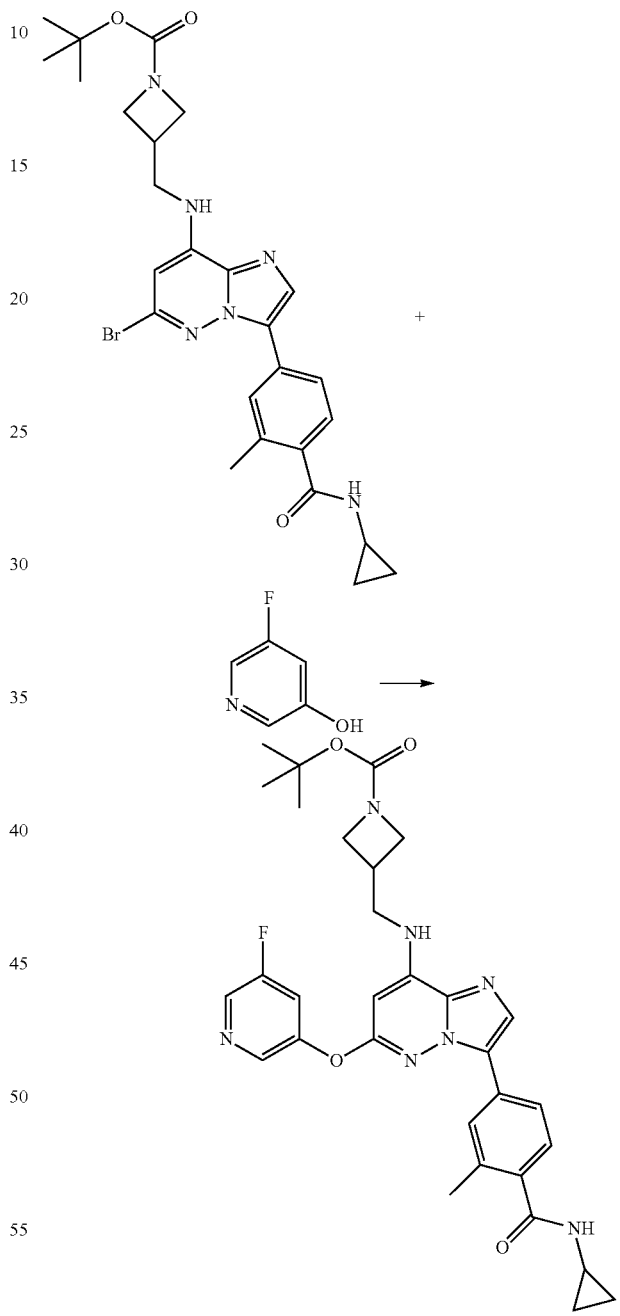

111 mg (200 μmol) tert-butyl 3-[({6-bromo-3-[4-(cyclopropylcarbamoyl)-3-methylphenyl]imidazo[1,2-b]pyridazin-8-yl}amino)methyl]azetidine-1-carboxylate which was prepared according to intermediate example 543c were transformed in analogy to example 51 using 5-fluoropyridin-3-ol to give after working up and purification 5 mg (4%) of the title compound.

UPLC-MS: RT=1.25, MW$_{found}$=588.7. MW$_{calc}$=587.7.

Example 545

4-{8-[(azetidin-3-ylmethyl)amino]-6-(5-fluoro-2-methylphenoxy)imidazo[1,2-b]pyridazin-3-yl}-N-cyclopropyl-2-methylbenzamide

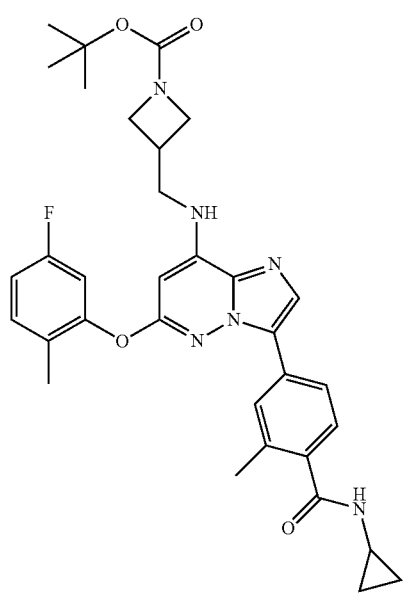

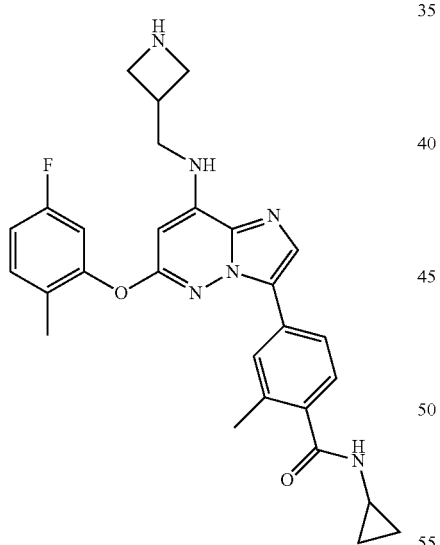

120 mg (200 µmol) tert-butyl 3-[({3-[4-(cyclopropylcarbamoyl)-3-methylphenyl]-6-(5-fluoro-2-methylphenoxy)imidazo[1,2-b]pyridazin-8-yl}amino)methyl]azetidine-1-carboxylate which was prepared according to intermediate example 545a were transformed in analogy to intermediate example 542a to give after working up and purification 13 mg (13%) of the title compound.

UPLC-MS: RT=0.94 MW$_{found}$=501.6 MW$_{calc}$=500.6.

Intermediate Example 545a tert-butyl 3-[({3-[4-(cyclopropylcarbamoyl)-3-methylphenyl]-6-(5-fluoro-2-methylphenoxy) imidazo[1,2-b]pyridazin-8-yl}amino)methyl]azetidine-1-carboxylate

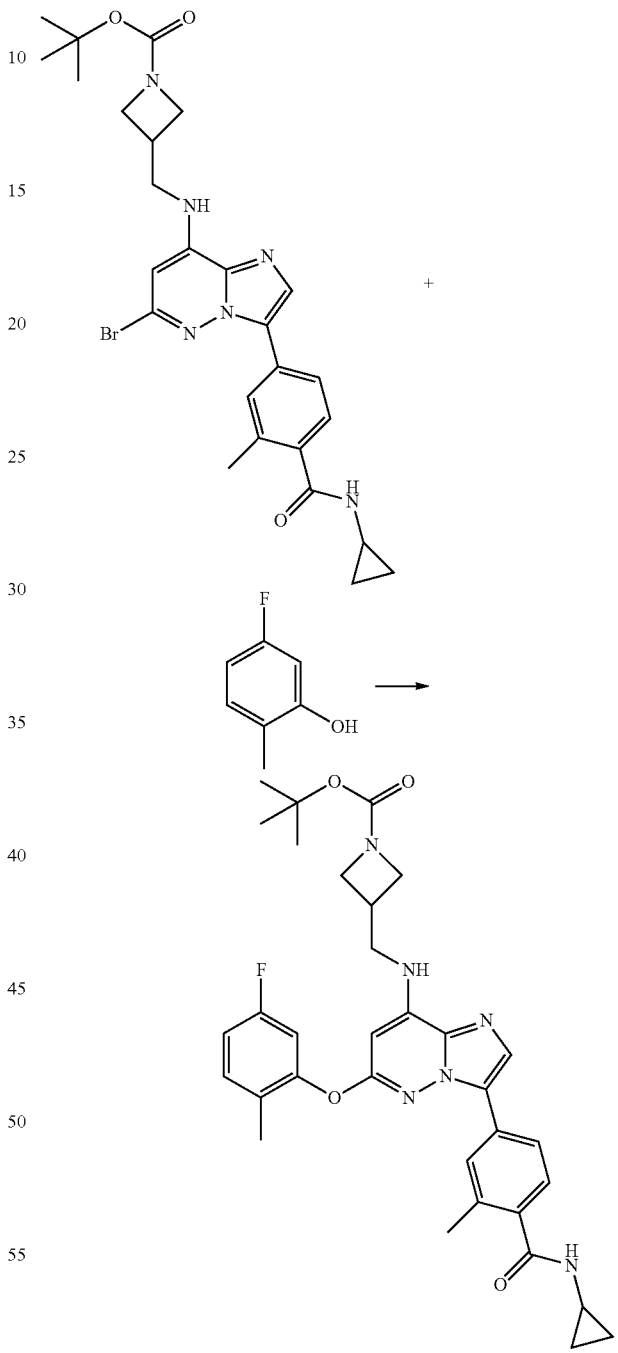

111 mg (200 µmol) tert-butyl 3-[({6-bromo-3-[4-(cyclopropylcarbamoyl)-3-methylphenyl]imidazo[1,2-b]pyridazin-8-yl}amino)methyl]azetidine-1-carboxylate which was prepared according to intermediate example 543c were transformed in analogy to example 51 using 2,3-difluorophenol and the product was used without working up in the next step.

UPLC-MS: RT=0.1.43, MW$_{found}$=601.7. MW$_{calc}$=600.7.

Example 546

4-{8-[(3-aminopropyl)amino]-6-(3-fluorophenoxy)imidazo[1,2-b]pyridazin-3-yl}-N-cyclopropyl-2-methylbenzamide

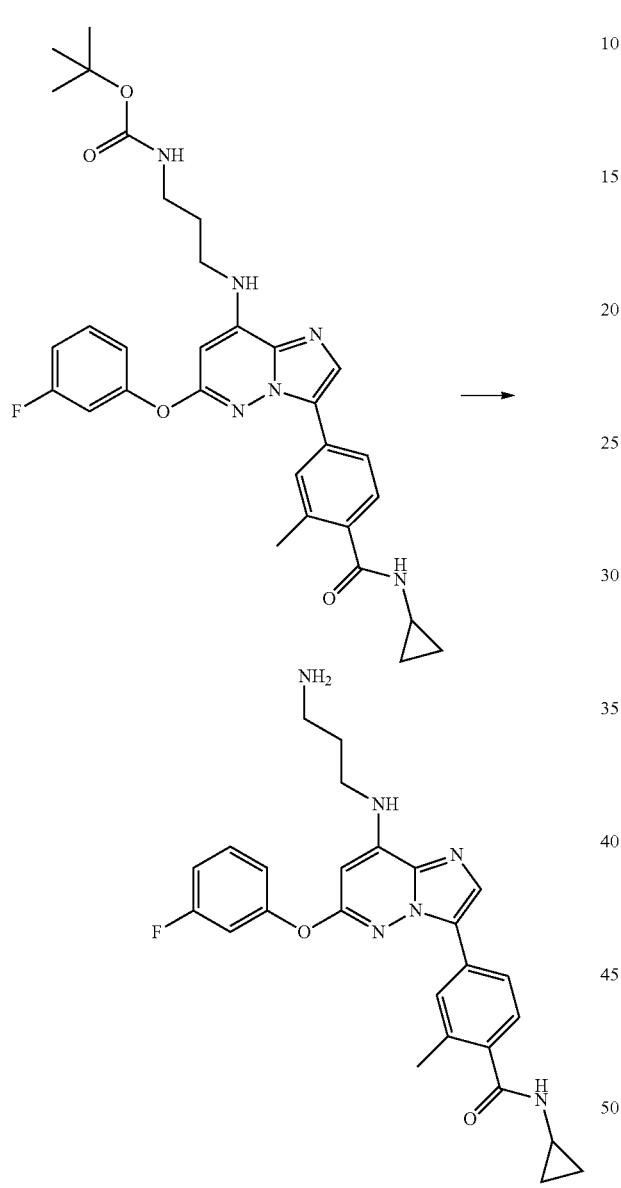

23 mg (40 µmol) tert-butyl [3-({3-[4-(cyclopropylcarbamoyl)-3-methylphenyl]-6-(3-fluorophenoxy)imidazo[1,2-b]pyridazin-8-yl}amino)propyl]carbamate which was prepared according to intermediate example 546a were transformed in analogy to intermediate example 542a to give after working up and purification 7 mg (36%) of the title compound.

UPLC-MS: RT=0.94, $MW_{found}$=475.5. $MW_{calc}$=474.5. $^1$H-NMR (300 MHz, DMSO-$d_6$), δ [ppm]=0.43-0.51 (2H), 0.59-0.68 (2H), 1.81-1.97 (2H), 2.14 (3H), 2.76 (1H), 2.87 (2H), 3.41 (2H), 6.14 (1H), 7.08-7.19 (4H), 7.19-7.28 (1H), 7.49 (1H), 7.60-7.73 (3H), 7.73-7.82 (2H), 7.93 (1H), 8.21 (1H)

Intermediate Example 546a

N-cyclopropyl-4-{6-(3-fluorophenoxy)-8-[(3,3,3-trifluoro-2-hydroxypropyl)amino]imidazo[1,2-b]pyridazin-3-yl}-2-methylbenzamide

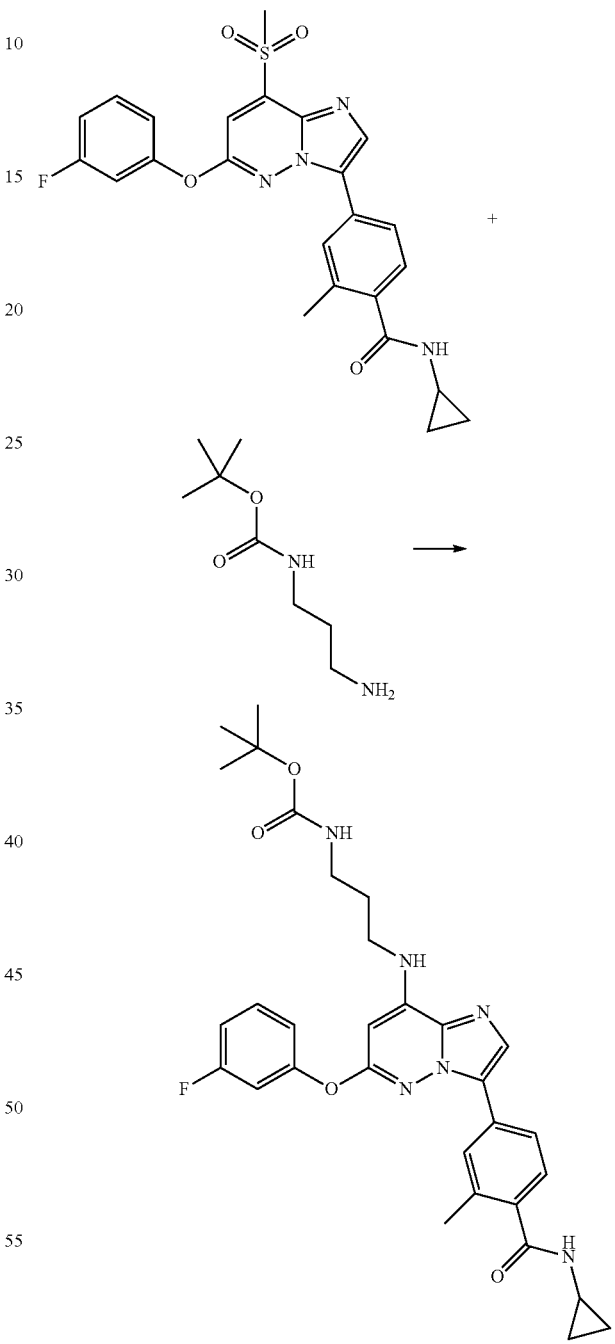

67 mg (140 µmol) N-cyclopropyl-4-[6-(3-fluorophenoxy)-8-(methylsulfonyl)imidazo[1,2-b]pyridazin-3-yl]-2-methylbenzamide which was prepared according to intermediate example 486a were transformed in analogy to example 486 to give after working up and purification 23 mg (29%) of the title compound.

UPLC-MS: RT=1.38, $MW_{found}$=575.7. $MW_{calc}$=574.7.

Example 547

3-({3-[4-(cyclopropylcarbamoyl)-3-methylphenyl]-6-(3-fluorophenoxy)imidazo[1,2-b]pyridazin-8-yl}amino)propane-1-sulfonic acid

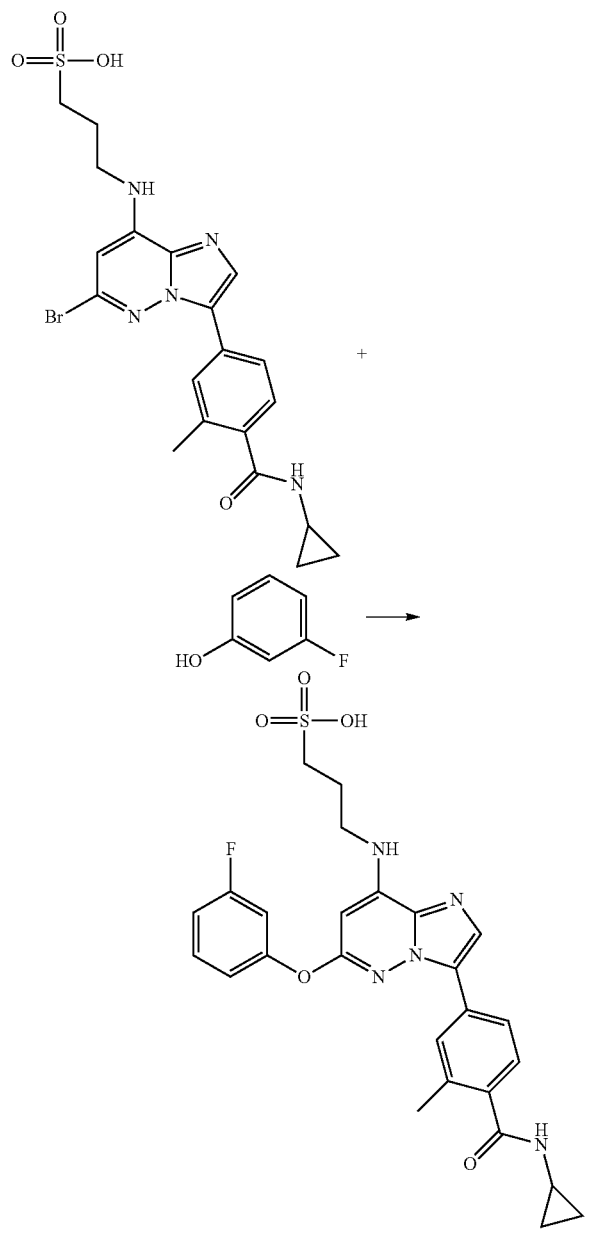

Intermediate Example 547a 3-({6-bromo-3-[4-(cyclopropylcarbamoyl)-3-methylphenyl]imidazo[1,2-b]pyridazin-8-yl}amino)propane-1-sulfonic acid

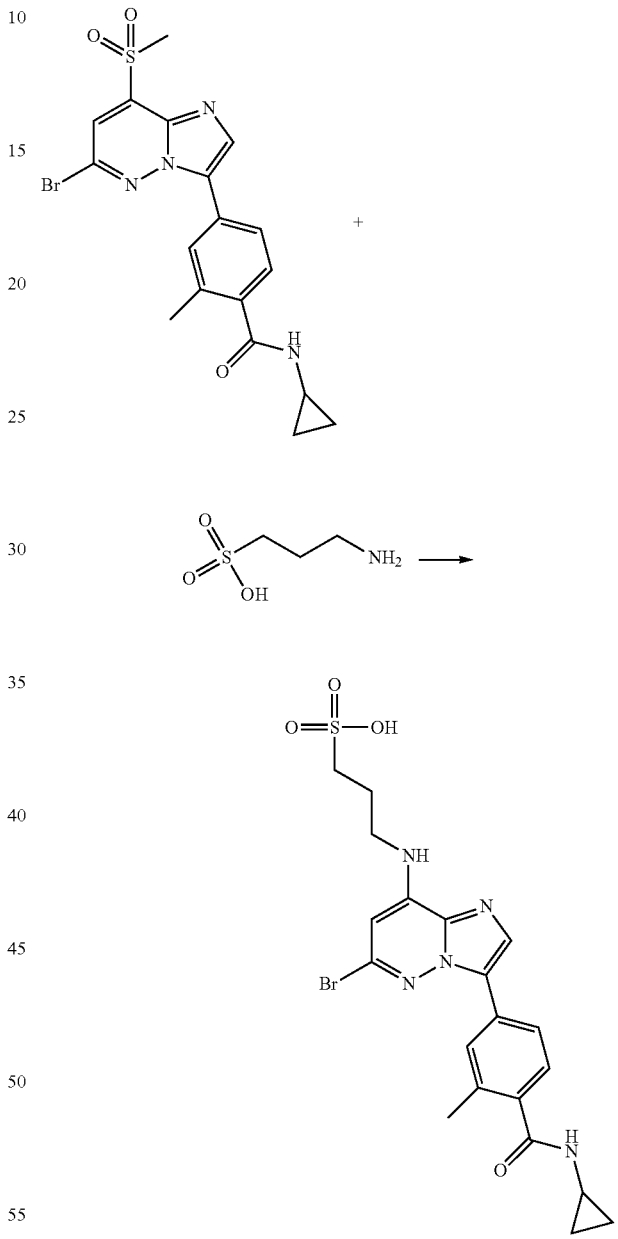

101 mg (200 µmol) 3-({6-bromo-3-[4-(cyclopropylcarbamoyl)-3-methylphenyl]imidazo[1,2-b]pyridazin-8-yl}amino)propane-1-sulfonic acid which was prepared according to intermediate example 547a were transformed in analogy to example 51 to give after working up and purification 12 mg (9%) of the title compound.

UPLC-MS: RT=0.98, $MW_{found}$=540.6. $MW_{calc}$=539.6.
$^1$H-NMR (300 MHz, DMSO-$d_6$), δ [ppm]=0.40-0.54 (2H), 0.58-0.70 (2H), 1.81-1.99 (2H), 2.14 (3H), 2.49-2.62 (2H), 2.77 (1H), 3.46 (2H), 6.29 (1H), 7.11-7.21 (3H), 7.27 (1H), 7.42-7.55 (1H), 7.64 (2H), 7.74 (2H), 8.11 (1H), 8.22 (1H)

To a stirred solution of 41 mg (300 µmol) 3-aminopropane-1-sulfonic acid in 2 mL DMSO is added 24 mg (600 µmol) sodium hydride at rt. After 30 min, 90 mg (200 µmol) 4-[6-bromo-8-(methylsulfonyl)imidazo[1,2-b]pyridazin-3-yl]-N-cyclopropyl-2-methyl benzamide are added which was prepared according to intermediate example 516b to give after stirring for 2 h, the crude title compound which was used after evaporation of the solvent without further workup.

UPLC-MS: RT=0.82, $MW_{found}$=509.4. $MW_{calc}$=508.4.

Example 548

2-({3-[4-(cyclopropylcarbamoyl)-3-methylphenyl]-6-(3-fluorophenoxy)imidazo[1,2-b]pyridazin-8-yl}amino)ethanesulfonic acid

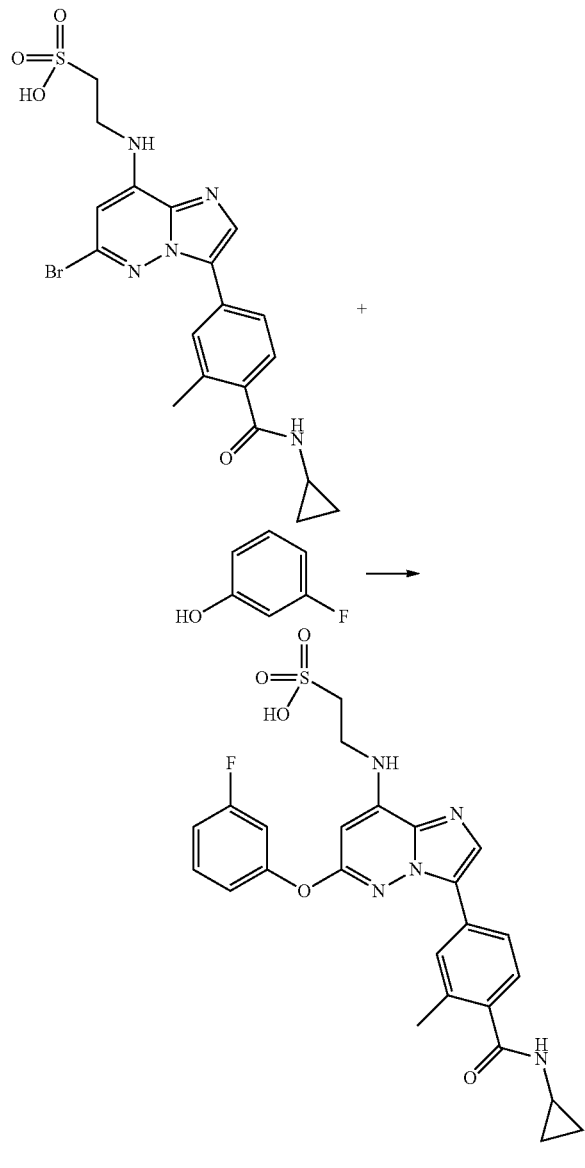

99 mg (200 µmol) 2-({6-bromo-3-[4-(cyclopropylcarbamoyl)-3-methylphenyl]imidazo[1,2-b]pyridazin-8-yl}amino)ethanesulfonic acid which was prepared according to intermediate example 548a were transformed in analogy to example 51 to give after working up and purification 9 mg (7%) of the title compound.

UPLC-MS: RT=0.97, $MW_{found}$=526.6. $MW_{calc}$=525.6. $^1$H-NMR (400 MHz, DMSO-$d_6$), δ [ppm]=0.44-0.54 (2H), 0.59-0.70 (2H), 2.14 (3H), 2.71-2.84 (3H), 3.59 (2H), 6.22 (1H), 7.09-7.21 (4H), 7.27 (1H), 7.49 (1H), 7.61-7.67 (1H), 7.73 (2H), 8.12 (1H), 8.23 (1H)

Intermediate Example 548a 2-({6-bromo-3-[4-(cyclopropylcarbamoyl)-3-methylphenyl]imidazo[1,2-b]pyridazin-8-yl}amino)ethanesulfonic acid

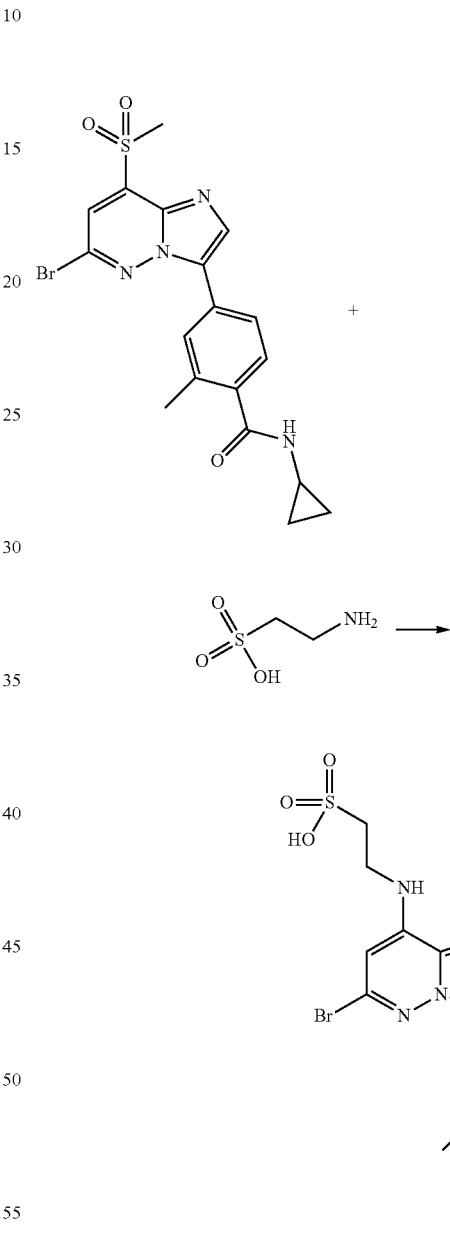

89 mg (200 µmol) 4-[6-bromo-8-(methylsulfonyl)imidazo[1,2-b]pyridazin-3-yl]-N-cyclopropyl-2-methyl benzamide which was prepared according to intermediate example 516b were transformed in analogy to example 547a to give the crude title compound that was used in the next step without further purification.

UPLC-MS: RT=0.84, $MW_{found}$=495.4. $MW_{calc}$=494.4.

Example 549

N-(1-cyanocyclopropyl)-4-{6-(3-fluorophenoxy)-8-[(3,3,3-trifluoropropyl)amino]imidazo[1,2-b]pyridazin-3-yl}-2-methylbenzamide

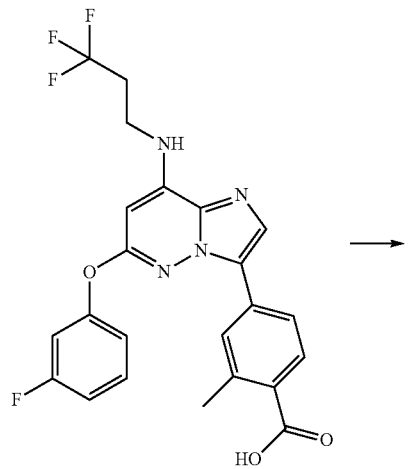

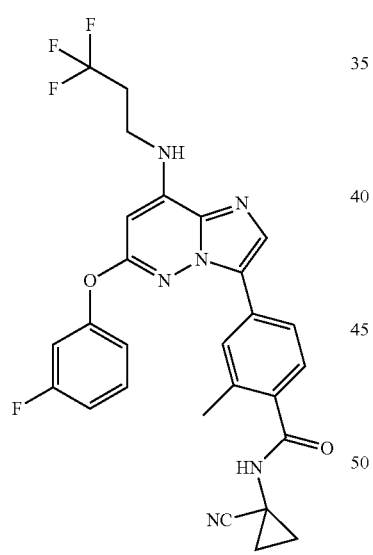

10.5 mg (22 µmol) 4-{6-(3-fluorophenoxy)-8-[(3,3,3-trifluoropropyl)amino]imidazo[1,2-b]pyridazin-3-yl}-2-methylbenzoic acid which was prepared according to intermediate example 459a were transformed in analogy to example 459 using 1-cyanocyclopropanaminium chloride to give after working up and purification 4.5 mg (36%) of the title compound.

$^1$H-NMR (DMSO-d6): δ=1.21 (2H), 1.50 (2H), 2.16 (3H), 2.61-2.76 (2H), 3.60 (2H), 6.14 (1H), 7.14 (2H), 7.25 (2H), 7.49 (1H), 7.66-7.76 (2H), 7.81 (1H), 7.97 (1H), 9.09 (1H) ppm.

Example 550

4-{6-(3-fluorophenoxy)-8-[(3,3,3-trifluoropropyl)amino]imidazo[1,2-b]pyridazin-3-yl}-2-methylbenzamide (A) and 4-{6-(3-fluorophenoxy)-8-[(3,3,3-trifluoropropyl)amino]imidazo[1,2-b]pyridazin-3-yl}-2-methylbenzoic acid (B)

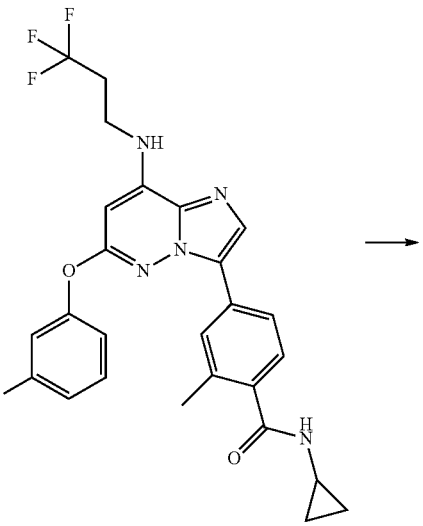

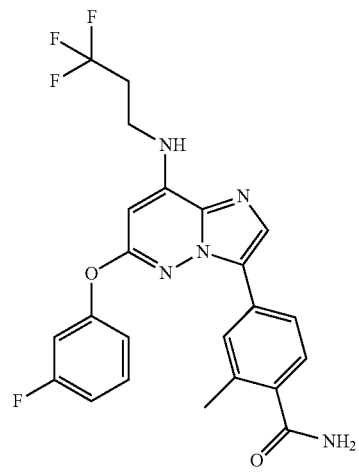

A

-continued

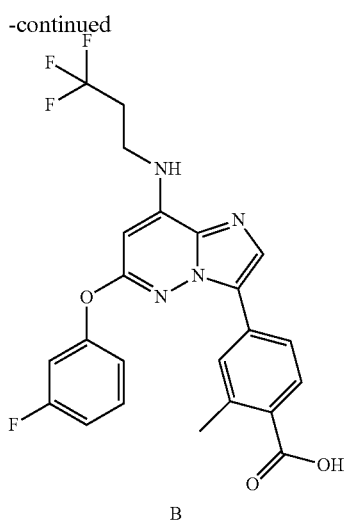

B

A mixture comprising 50 mg (97 µmol) N-cyclopropyl-4-{6-(3-fluorophenoxy)-8-[(3,3,3-trifluoropropyl)amino]imidazo[1,2-b]pyridazin-3-yl}-2-methylbenzamide and 0.5 mL hydrobromic acid was heated at 120° C. for 10 minutes under microwave irradiation. Water was added, the precipitate filtered off and purified by chromatography to give 30.0 mg (62%) of title compound A and 4.1 mg (9%) of title compound B.

$^1$H-NMR (DMSO-d6) of A: δ=2.20 (3H), 2.68 (2H), 3.60 (2H), 6.13 (1H), 7.13 (2H), 7.22-7.30 (3H), 7.48 (1H), 7.60-7.78 (4H), 7.93 (1H) ppm.

$^1$H-NMR (DMSO-d6) of B: δ=2.35 (3H), 2.68 (2H), 3.59 (2H), 6.15 (1H), 7.14 (2H), 7.26 (1H), 7.49 (1H), 7.64-7.77 (3H), 7.82 (1H), 7.99 (1H), 8.20 (1H) ppm.

Example 551

4-{6-(3-fluorophenoxy)-8-[(3,3,3-trifluoropropyl)amino]imidazo[1,2-b]pyridazin-3-yl}-N,2-dimethylbenzamide

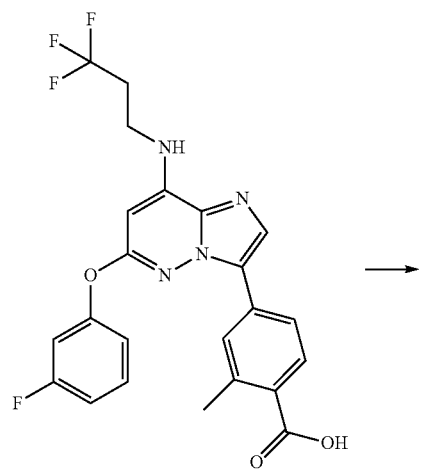

-continued

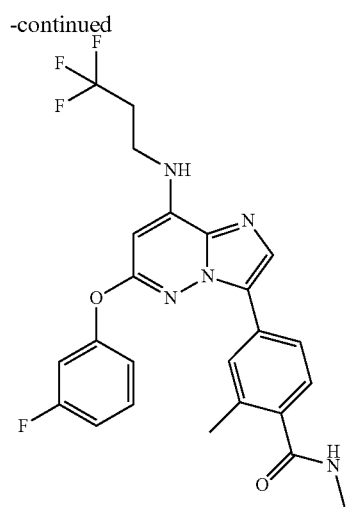

A mixture comprising 30 mg (63 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550, 2.94 mg methanamine, 36.1 mg N-[(dimethylamino)(3H-[1,2,3]triazolo[4,5-b]pyridin-3-yloxy)methylene]-N-methylmethanaminium hexafluorophosphate, 11.6 mg N,N-dimethylpyridin-4-amine and 1.5 mL N,N-dimethylformamide was stirred at 23° C. overnight. The solvent was removed and the residue purified by chromatography to give 30.0 mg (92%) of title compound.

$^1$H-NMR (DMSO-d6): δ=2.16 (3H), 2.49-2.76 (2H), 2.69 (3H), 3.60 (2H), 6.13 (1H), 7.13 (2H), 7.20 (1H), 7.25 (1H), 7.48 (1H), 7.63-7.74 (2H), 7.76 (1H), 7.93 (1H), 8.08 (1H) ppm.

Example 552

N-ethyl-4-{6-(3-fluorophenoxy)-8-[(3,3,3-trifluoropropyl)amino]imidazo[1,2-b]pyridazin-3-yl}-2-methylbenzamide

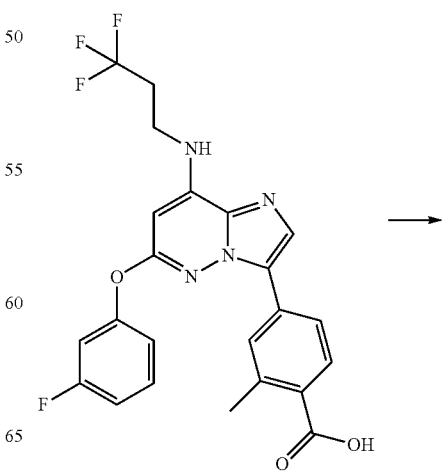

691

-continued

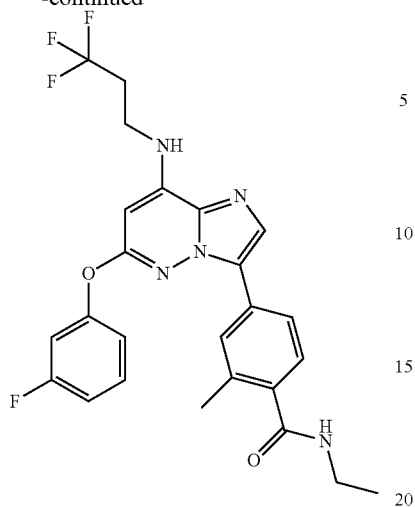

30 mg (63 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 2 using ethanamine to give after working up and purification 29.7 mg (89%) of the title compound.

$^1$H-NMR (DMSO-d6): δ=1.06 (3H), 2.16 (3H), 2.68 (2H), 3.19 (2H), 3.60 (2H), 6.13 (1H), 7.13 (2H), 7.19 (1H), 7.25 (1H), 7.48 (1H), 7.64-7.74 (2H), 7.76 (1H), 7.93 (1H), 8.15 (1H) ppm.

Example 553

4-{6-(3-fluorophenoxy)-8-[(3,3,3-trifluoropropyl)amino]imidazo[1,2-b]pyridazin-3-yl}-N-isopropyl-2-methylbenzamide

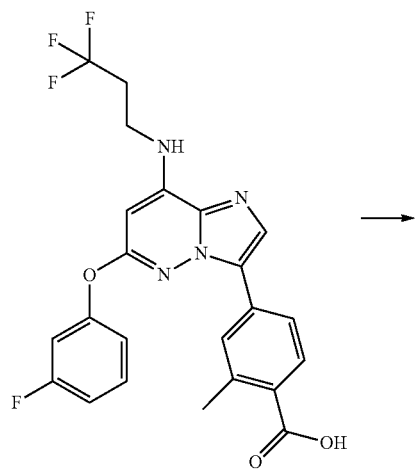

692

-continued

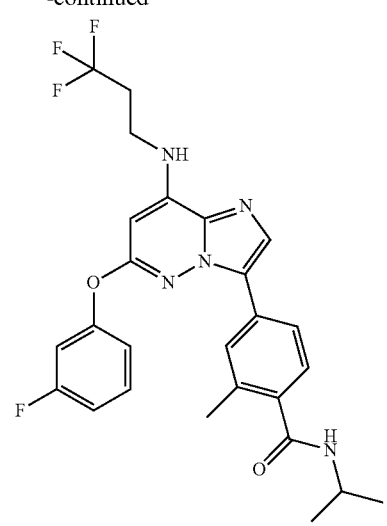

30 mg (63 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 2 using propan-2-amine to give after working up and purification 13.4 mg (39%) of the title compound.

$^1$H-NMR (DMSO-d6): δ=1.09 (6H), 2.14 (3H), 2.68 (2H), 3.60 (2H), 3.99 (1H), 6.13 (1H), 7.08-7.19 (3H), 7.26 (1H), 7.48 (1H), 7.66 (1H), 7.72 (1H), 7.77 (1H), 7.92 (1H), 8.03 (1H) ppm.

Example 554

4-{6-(3-fluorophenoxy)-8-[(3,3,3-trifluoropropyl)amino]imidazo[1,2-b]pyridazin-3-yl}-2-methyl-N-(3,3,3-trifluoropropyl)benzamide

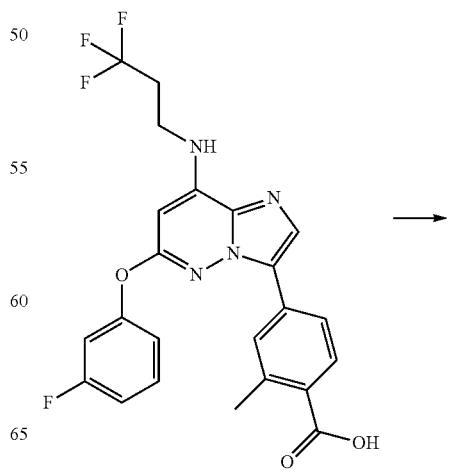

693

-continued

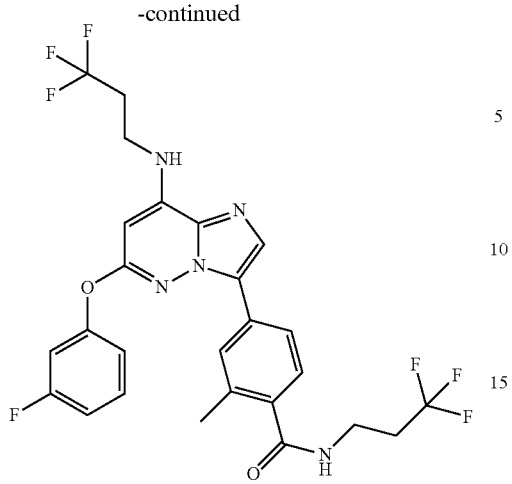

11.8 mg (25 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 2 using 3,3,3-trifluoropropan-1-amine to give after working up and purification 12.0 mg (83%) of the title compound.

$^1$H-NMR (CDCl$_3$): δ=2.34 (3H), 2.41-2.65 (4H), 3.69 (4H), 5.90 (1H), 5.97 (2H), 6.94-7.08 (3H), 7.28 (1H), 7.39 (1H), 7.65 (1H), 7.75 (1H), 7.77 (1H) ppm.

Example 555

4-{6-(3-fluorophenoxy)-8-[(3,3,3-trifluoropropyl)amino]imidazo[1,2-b]pyridazin-3-yl}-2-methyl-N-(2,2,3,3,3-pentafluoropropyl)benzamide

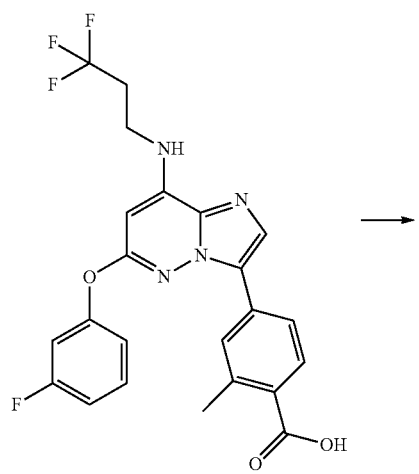

694

-continued

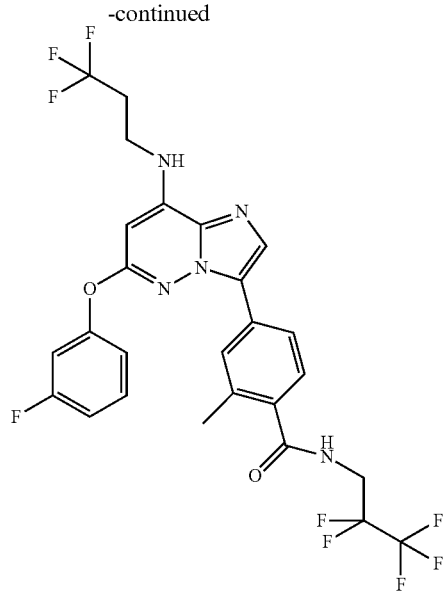

11.8 mg (25 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 552 using 2,2,3,3,3-pentafluoropropan-1-amine to give after working up and purification 12.5 mg (82%) of the title compound.

$^1$H-NMR (CDCl$_3$): δ=2.34 (3H), 2.50-2.65 (2H), 3.69 (2H), 4.16 (2H), 5.91 (1H), 5.96 (2H), 6.93-7.08 (3H), 7.32 (1H), 7.40 (1H), 7.67 (1H), 7.76 (1H), 7.80 (1H) ppm.

Example 556

N-(2,2-difluoroethyl)-4-{6-(3-fluorophenoxy)-8-[(3,3,3-trifluoropropyl)amino]imidazo[1,2-b]pyridazin-3-yl}-2-methylbenzamide

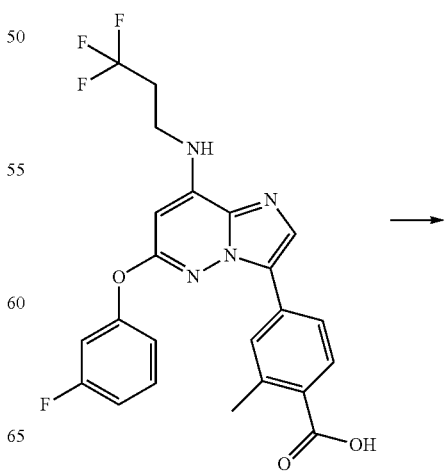

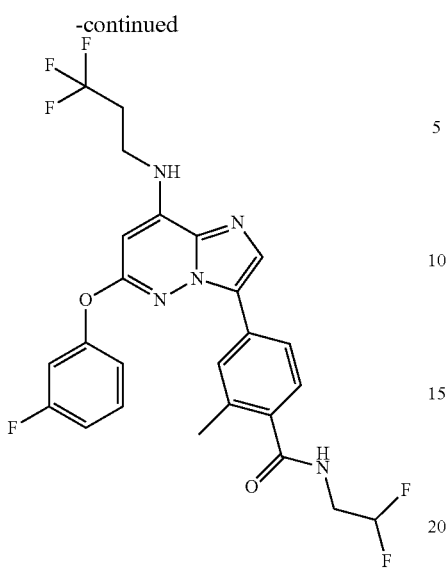

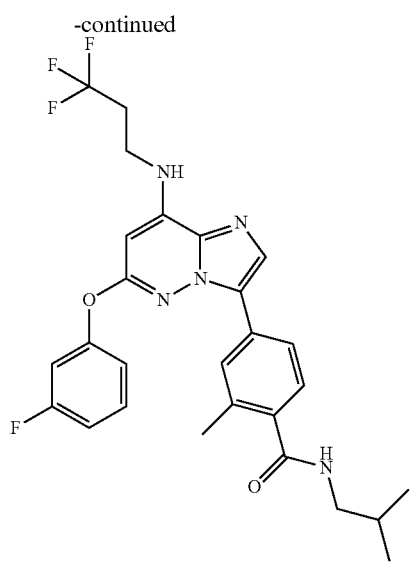

11.8 mg (25 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 551 using 2,2-difluoroethanamine to give after working up and purification 13.4 mg (93%) of the title compound.

¹H-NMR (CDCl₃): δ=2.35 (3H), 2.58 (2H), 3.69 (2H), 3.82 (2H), 5.90 (1H), 5.93-6.02 (2H), 5.99 (1H) 6.95-7.08 (3H), 7.33 (1H), 7.40 (1H), 7.66 (1H), 7.76 (1H), 7.79 (1H) ppm.

11.8 mg (25 µmol) 4-{6-(3-fluorophenoxy)-8-[(3,3,3-trifluoropropyl)amino]imidazo[1,2-b]pyridazin-3-yl}-2-methylbenzoic acid which was prepared according to example 550 were transformed in analogy to example 551 using 2-methylpropan-1-amine to give after working up and purification 12.8 mg (96%) of the title compound.

¹H-NMR (CDCl₃): δ=0.99 (6H), 1.89 (1H), 2.35 (3H), 2.58 (2H), 3.28 (2H), 3.68 (2H), 5.74 (1H), 5.89 (1H), 5.97 (1H), 6.92-7.08 (3H), 7.30 (1H), 7.39 (1H), 7.64 (1H), 7.74 (1H), 7.76 (1H) ppm.

Example 557

4-{6-(3-fluorophenoxy)-8-[(3,3,3-trifluoropropyl)amino]imidazo[1,2-b]pyridazin-3-yl}-N-isobutyl-2-methylbenzamide Example 558

4-{6-(4-chlorophenoxy)-8-[(3,3,3-trifluoropropyl)amino]imidazo[1,2-b]pyridazin-3-yl}-N, 2-dimethylbenzamide

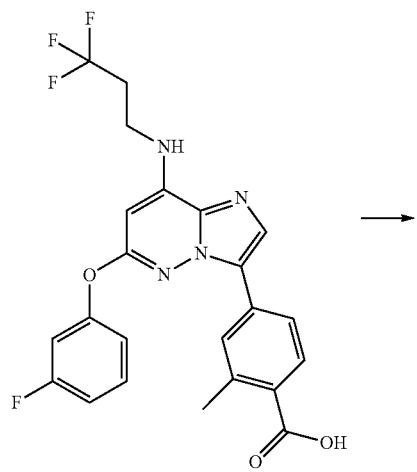 →

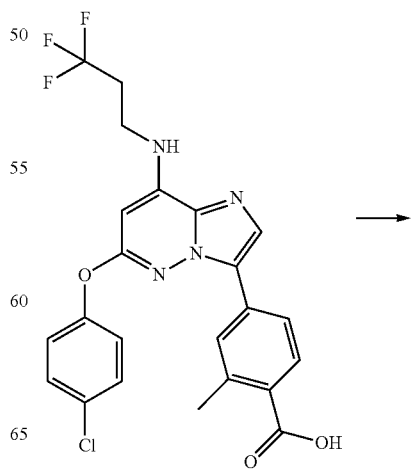 →

697

-continued

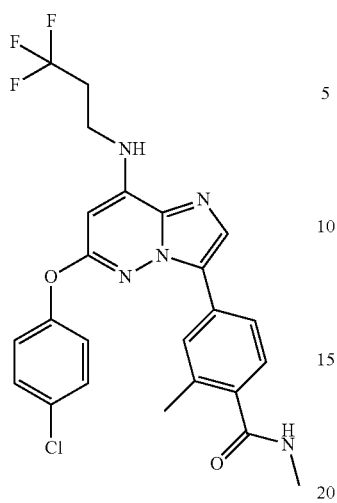

25 mg (51 µmol) 4-{6-(4-chlorophenoxy)-8-[(3,3,3-trifluoropropyl)amino]imidazo[1,2-b]pyridazin-3-yl}-2-methylbenzoic acid which was prepared according to intermediate example 558a were transformed in analogy to example 551 to give after working up and purification 11.1 mg (43%) of the title compound.

¹H-NMR (DMSO-d6): δ=2.15 (3H), 2.61-2.75 (2H), 2.70 (3H), 3.60 (2H), 6.13 (1H), 7.21 (1H), 7.32 (2H), 7.51 (2H), 7.64 (1H), 7.69 (1H), 7.74 (1H), 7.93 (1H), 8.09 (1H) ppm.

Intermediate Example 558a

4-{6-(4-chlorophenoxy)-8-[(3,3,3-trifluoropropyl)amino]imidazo[1,2-b]pyridazin-3-yl}-2-methylbenzoic acid

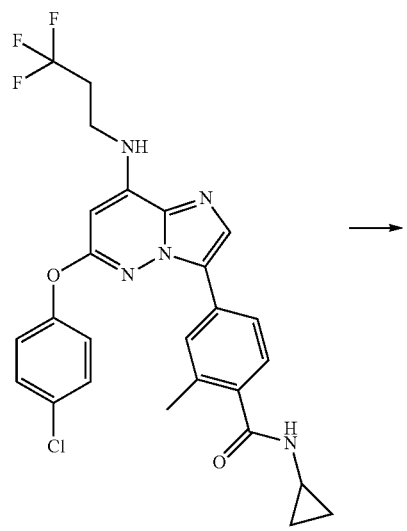

698

-continued

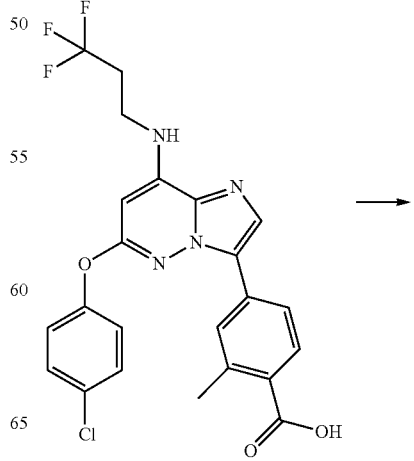

A mixture comprising 300 mg (566 µmol) 4-{6-(4-chlorophenoxy)-8-[(3,3,3-trifluoropropyl)amino]imidazo[1,2-b]pyridazin-3-yl}-N-cyclopropyl-2-methylbenzamide and 13.4 mL hydrobromic acid was heated at 120° C. for 2.5 days. Water was added, the precipitate filtered off to give the crude title compound that was used without further purification.

Example 559

4-{6-(4-chlorophenoxy)-8-[(3,3,3-trifluoropropyl)amino]imidazo[1,2-b]pyridazin-3-yl}-N-ethyl-2-methylbenzamide

699

-continued

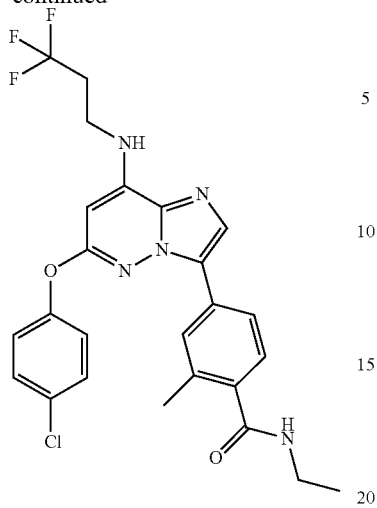

25 mg (51 µmol) 4-{6-(4-chlorophenoxy)-8-[(3,3,3-trifluoropropyl)amino]imidazo[1,2-b]pyridazin-3-yl}-2-methylbenzoic acid which was prepared according to intermediate example 558a were transformed in analogy to example 2 using ethanamine to give after working up and purification 10.4 mg (37%) of the title compound.

¹H-NMR (DMSO-d6): δ=1.07 (3H), 2.14 (3H), 2.62-2.75 (2H), 3.20 (2H), 3.60 (2H), 6.13 (1H), 7.20 (1H), 7.32 (2H), 7.51 (2H), 7.64 (1H), 7.69 (1H), 7.74 (1H), 7.93 (1H), 8.15 (1H) ppm.

Example 560

4-{6-(2-fluoro-4-hydroxyphenoxy)-8-[(3,3,3-trifluoropropyl)amino]imidazo[1,2-b]pyridazin-3-yl}-N,2-dimethylbenzamide

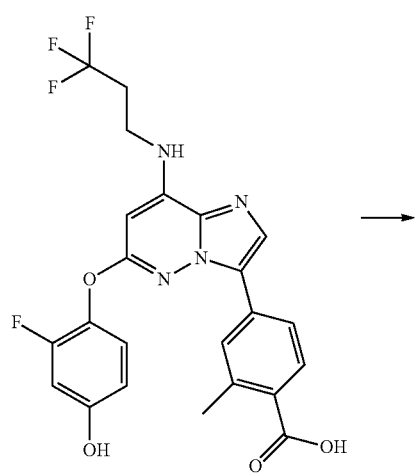

700

-continued

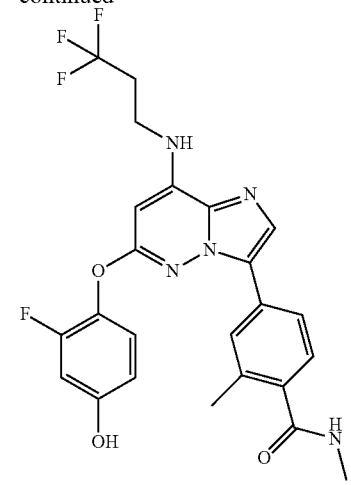

12.8 mg (26 µmol) 4-{6-(2-fluoro-4-hydroxyphenoxy)-8-[(3,3,3-trifluoropropyl)amino]imidazo[1,2-b]pyridazin-3-yl}-2-methylbenzoic acid which was prepared according to intermediate example 560a were transformed in analogy to example 551 to give after working up and purification 5.6 mg (43%) of the title compound.

¹H-NMR (DMSO-d6): 0.5=2.15 (3H), 2.61-2.79 (2H), 2.70 (3H), 3.60 (2H), 6.13 (1H), 6.64 (1H), 6.73 (1H), 7.13-7.25 (2H), 7.58-7.70 (2H), 7.75 (1H), 7.93 (1H), 8.09 (1H), 9.87 (1H) ppm.

Example 560a

4-{6-(2-fluoro-4-hydroxyphenoxy)-8-[(3,3,3-trifluoropropyl)amino]imidazo[1,2-b]pyridazin-3-yl}-2-methylbenzoic acid

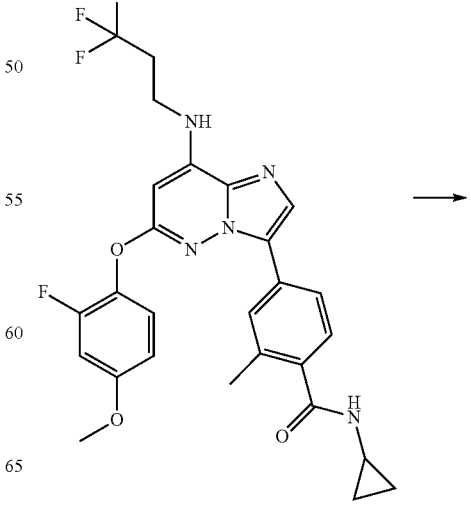

-continued

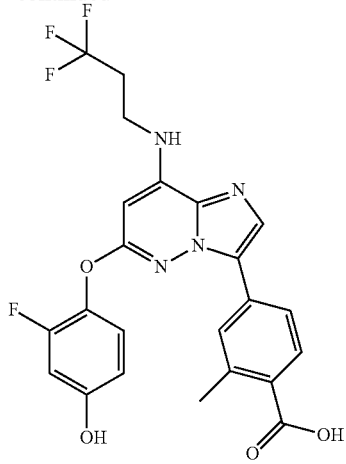

75 mg (138 µmol) N-cyclopropyl-4-{6-(2-fluoro-4-methoxyphenoxy)-8-[(3,3,3-trifluoropropyl)amino]imidazo[1,2-b]pyridazin-3-yl}-2-methylbenzamide were transformed in analogy to intermediate example 558a to give after working up 76.6 mg of the title compound with a purity of 85% that was used without further purification.

Example 561

N-ethyl-4-{6-(2-fluoro-4-hydroxyphenoxy)-8-[(3,3,3-trifluoropropyl)amino]imidazo[1,2-b]pyridazin-3-yl}-2-methylbenzamide

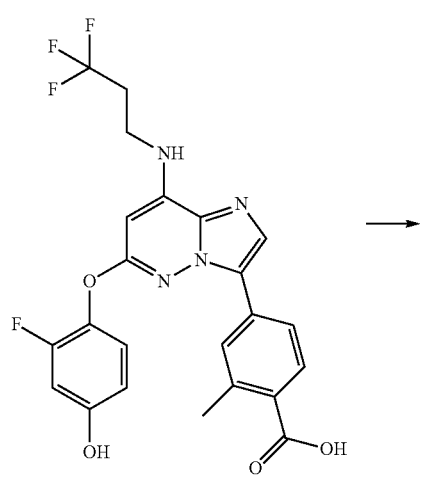

-continued

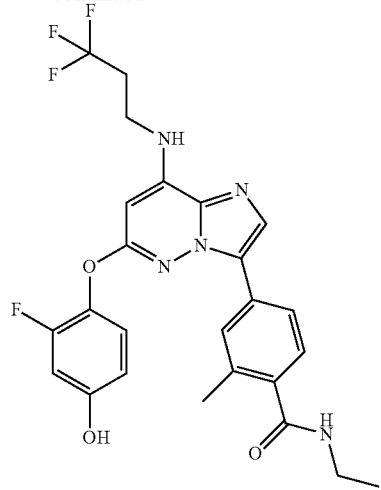

12.8 mg (26 µmol) 4-{6-(2-fluoro-4-hydroxyphenoxy)-8-[(3,3,3-trifluoropropyl)amino]imidazo[1,2-b]pyridazin-3-yl}-2-methylbenzoic acid which was prepared according to intermediate example 560a were transformed in analogy to example 551 using ethanamine to give after working up and purification 9.6 mg (713%) of the title compound.

$^1$H-NMR (DMSO-d6): δ=1.07 (3H), 2.15 (3H), 2.68 (2H), 3.20 (2H), 3.60 (2H), 6.13 (1H), 6.64 (1H), 6.74 (1H), 7.14-7.23 (2H), 7.60-7.70 (2H), 7.75 (1H), 7.92 (1H), 8.16 (1H), 9.86 (1H) ppm.

Example 562

4-[6-(3,4-difluorophenoxy)-8-{[2-(morpholin-4-yl)ethyl]amino}imidazo[1,2-b]pyridazin-3-yl]-N,2-dimethylbenzamide

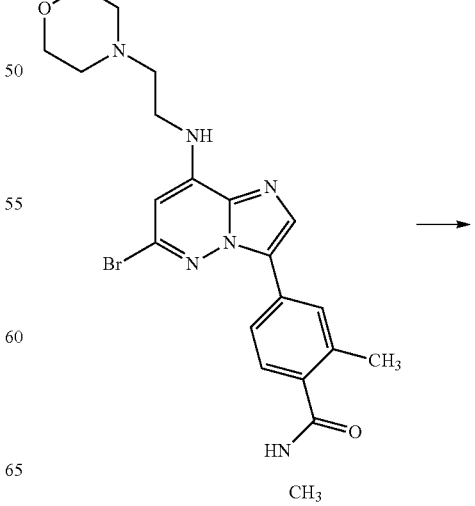

-continued

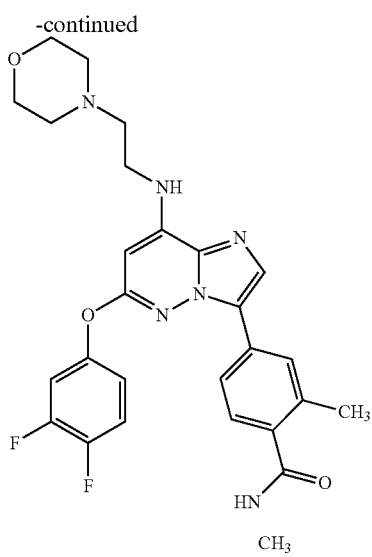

To a stirred solution of 48 mg (1200 μmol) sodium hydride in 1.2 mL DMSO were added 156 mg (1200 μmol) 3,4-difluorophenol in one portion at rt. After 1 h, 95 mg (200 μmol) 4-(6-bromo-8-{[2-(morpholin-4-yl)ethyl]amino}imidazo[1,2-b]pyridazin-3-yl)-N,2-dimethylbenzamide which was prepared according to intermediate example 562a in 1 mL DMSO were added and the mixture was heated for 8 h at 140° C. in a microwave oven. After working up and purification 7.42 mg (7%) of the title compound were obtained.

UPLC-MS: RT=0.82, MW$_{found}$=523.5. MW$_{calc}$=522.5. $^1$H-NMR (300 MHz, DMSO-d$_6$), [ppm]=2.16 (3H), 2.45-2.47 (3H), 2.59 (2H), 2.67-2.75 (4H), 3.44 (2H), 3.53-3.60 (4H), 6.07 (1H), 7.12-7.19 (1H), 7.22 (1H), 7.31 (1H), 7.47-7.60 (2H), 7.66 (1H), 7.74 (1H), 7.91 (1H), 8.09 (1H).

Intermediate Example 562a 4-(6-bromo-8-{[2-(morpholin-4-yl)ethyl]amino}imidazo[1,2-b]pyridazin-3-yl)-N,2-dimethyl-benzamide

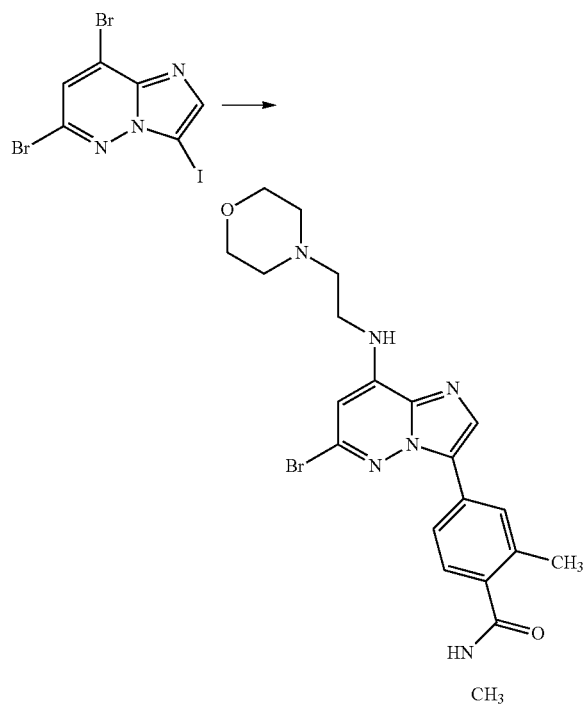

To a stirred solution of 2.01 g (5 mmol) 6,8-dibromo-3-iodoimidazo[1,2-b]pyridazine which was prepared according to intermediate example 96c in NMP (15 mL) were added 1.94 g (15 mmol) DIPEA and 1.30 g (10 mmol) 2-(morpholin-4-yl)ethanamine in one portion at rt. After heating for 2 h at 70° C., 100 mL DCM were added and the mixture was washed with water (3×100 mL). The organic phase was dried over sodium sulphate and evaporated to yield a brownish solid which was used without further purification in the next step. To a stirred solution of the remaining solid in 20 mL THF were added 1.16 g (6 mmol) [3-methyl-4-(methylcarbamoyl)phenyl]boronic acid which was prepared according to intermediate example 562b, 15 mL aqueous potassium carbonate solution (15 mmol, 1M), 816 mg Pd(dppf)Cl$_2$ (1 mmol) and the mixture was heated for 41 h at 70° C., to yield after working up and purification 2.35 g (99%) of the title compound.

UPLC-MS: RT=0.71, MW$_{found}$=474.4. MW$_{calc}$=473.4. $^1$H-NMR (400 MHz, DMSO-d$_6$), δ [ppm]=2.37 (3H), 2.42 (4H), 2.54 (2H), 2.73 (3H), 3.26 (2H), 3.49-3.59 (4H), 6.42 (1H), 7.40 (2H), 7.56-7.63 (1H), 7.86 (1H), 7.92 (1H), 7.96 (1H), 8.18 (1H)

Intermediate Example 562b

[3-methyl-4-(methylcarbamoyl)phenyl]boronic acid

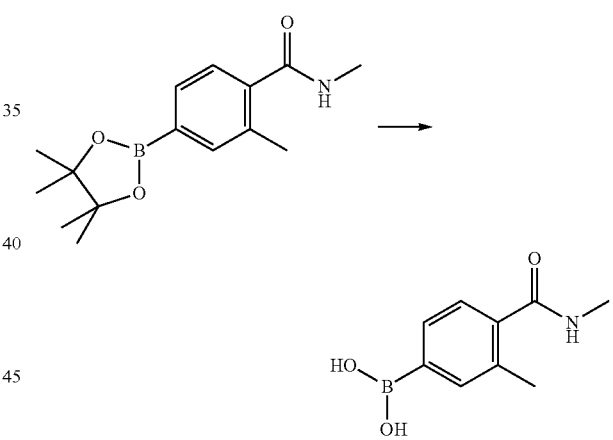

To a stirred solution of 20.22 g (67 mmol) N-cyclopropyl-2-methyl-4-(4,4,5,5-tetramethyl-1,3,2-dioxaborolan-2-yl)benzamide in acetone (300 mL) were added 43.08 g (201 mmol) sodium periodate 134 mL ammonium acetate (134 mmol, 1M in water) and the mixture was stirred for 3 h at rt and 2 h at 40° C. 4 N HCl was added (32 mL) and the organic phase was removed in vaccuo. The mixture was extracted with ethyl acetate, and the organic phase was washed with water, dried and removed in vaccuo to yield 14.59 g (94.2%) of the title compound. $^1$H-NMR (400 MHz, DMSO-d$_6$), δ [ppm]=0.44-0.52 (2H), 0.59-0.67 (2H), 2.26 (3H), 2.78 (1H), 7.18 (1H), 7.53-7.61 (2H), 8.01 (2H), 8.19 (1H).

The following compound examples were prepared analogously to the procedure described above for example 562 using the appropriate intermediate example and the appropriate phenol [LC-MS data such as retention time (RT in min) or observed mass peak were collected using LC-MS Method A unless explicitly stated]:

| Example | Structure | Name | Analytical Data |
|---|---|---|---|
| 563 | 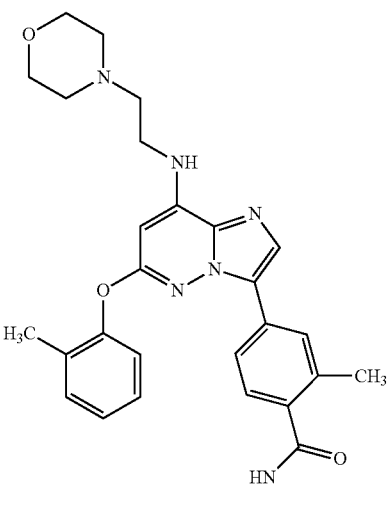 | N,2-dimethyl-4-[6-(2-methylphenoxy)-8-{[2-(morpholin-4-yl)ethyl]amino}imidazo[1,2-b]pyridazin-3-yl]benzamide | RT = 0.82<br>$MW_{found}$ = 501.6<br>$MW_{calc}$ = 500.6 |
| 564 | 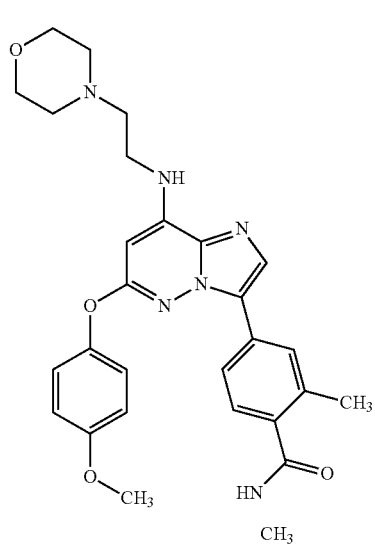 | 4-[6-(4-methoxyphenoxy)-8-{[2-(morpholin-4-yl)ethyl]amino}imidazo[1,2-b]pyridazin-3-yl]-N,2-dimethylbenzamide | RT = 0.78<br>$MW_{found}$ = 517.6<br>$MW_{calc}$ = 516.6 |
| 565 | 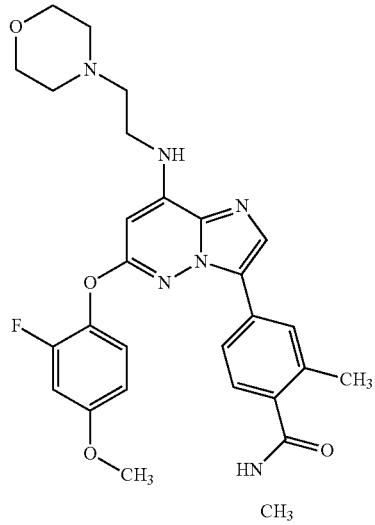 | 4-[6-(2-fluoro-4-methoxyphenoxy)-8-{[2-(morpholin-4-yl)ethyl]amino}imidazo[1,2-b]pyridazin-3-yl]-N,2-dimethylbenzamide | RT = 0.80<br>$MW_{found}$ = 535.6<br>$MW_{calc}$ = 534.6 |

| Example | Structure | Name | Analytical Data |
|---|---|---|---|
| 566 | 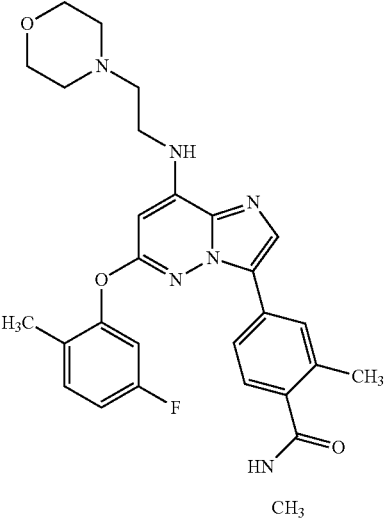 | 4-[6-(5-fluoro-2-methylphenoxy)-8-{[2-(morpholin-4-yl)ethyl]amino}imidazo[1,2-b]pyridazin-3-yl]-N,2-dimethylbenzamide | RT = 0.84<br>MW$_{found}$ = 519.6<br>MW$_{calc}$ = 518.6 |
| 567 | 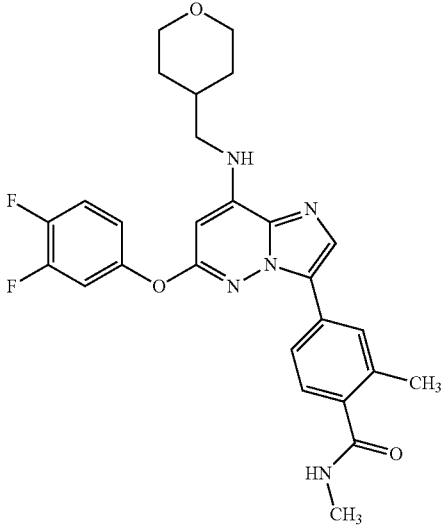 [SMILES: CNC(=O)c1ccc(-c2cnc3c(NCC4CCOCC4)cc(Oc4ccc(F)c(F)c4)nn23)cc1C] | 4-{6-(3,4-difluorophenoxy)-8-[(tetrahydro-2H-pyran-4-ylmethyl)amino]imidazo[1,2-b]pyridazin-3-yl}-N,2-dimethylbenzamide | RT = 1.22<br>MW$_{found}$ = 508.5<br>MW$_{calc}$ = 507.5 |
| 568 | 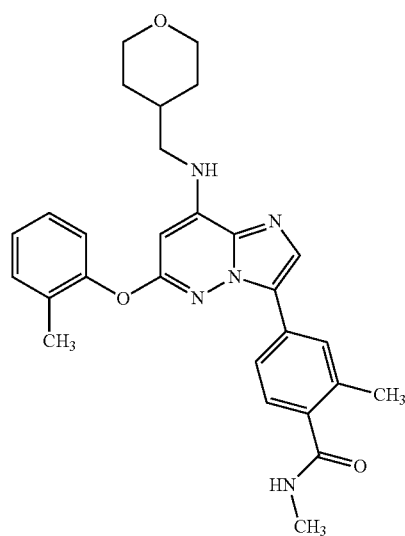 [SMILES: CNC(=O)c1ccc(-c2cnc3c(NCC4CCOCC4)cc(Oc4ccccc4C)nn23)cc1C] | N,2-dimethyl-4-{6-(2-methylphenoxy)-8-[(tetrahydro-2H-pyran-4-ylmethyl)amino]imidazo[1,2-b]pyridazin-3-yl}benzamide | RT = 1.22<br>MW$_{found}$ = 486.6<br>MW$_{calc}$ = 485.6<br>$^1$H-NMR (300 MHz, DMSO-d$_6$), δ [ppm] = 1.14-1.32 (2H), 1.63 (2H), 1.86-2.03 (1H), 2.50 (6H), 2.68 (3H), 3.22 (4H), 3.83 (2H), 6.08 (1H), 7.13 (1H), 7.15-7.23 (2H), 7.23-7.28 (1H), 7.33 (1H), 7.57-7.65 (2H), 7.69 (1H), 7.89 (1H), 8.05 (1H) |

| Example | Structure | Name | Analytical Data |
|---|---|---|---|
| 569 | 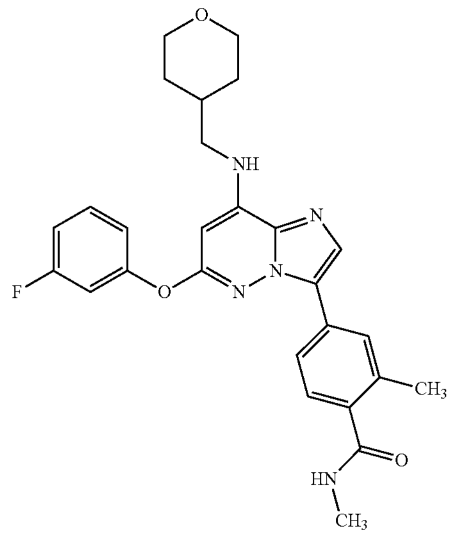 [SMILES: CNC(=O)c1ccc(-c2cnc3c(NCC4CCOCC4)cc(Oc4cccc(F)c4)nn23)cc1C] | 4-{6-(3-fluorophenoxy)-8-[(tetrahydro-2H-pyran-4-ylmethyl)amino]imidazo[1,2-b]pyridazin-3-yl}-N,2-dimethylbenzamide | RT = 1.20<br>$MW_{found}$ = 490.5<br>$MW_{calc}$ = 489.5 |
| 570 | 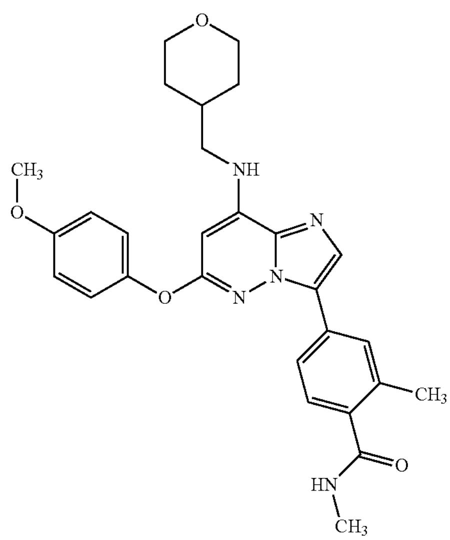 [SMILES: CNC(=O)c1ccc(-c2cnc3c(NCC4CCOCC4)cc(Oc4ccc(OC)cc4)nn23)cc1C] | 4-{6-(4-methoxyphenoxy)-8-[(tetrahydro-2H-pyran-4-ylmethyl)amino]imidazo[1,2-b]pyridazin-3-yl}-N,2-dimethylbenzamide | RT = 1.16<br>$MW_{found}$ = 502.6<br>$MW_{calc}$ = 501.6 |
| 571 | 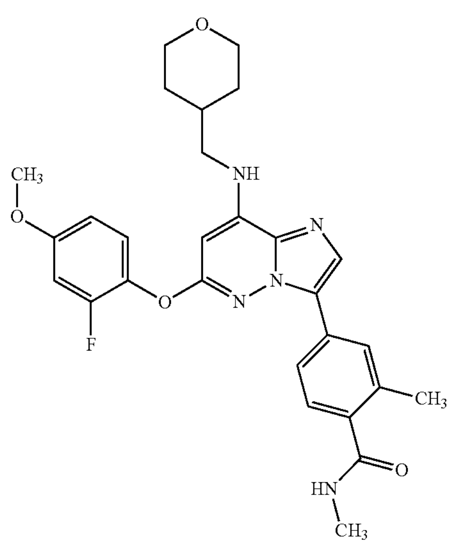 [SMILES: CNC(=O)c1ccc(-c2cnc3c(NCC4CCOCC4)cc(Oc4ccc(OC)cc4F)nn23)cc1C] | 4-{6-(2-fluoro-4-methoxyphenoxy)-8-[(tetrahydro-2H-pyran-4-ylmethyl)amino]imidazo[1,2-b]pyridazin-3-yl}-N,2-dimethylbenzamide | RT = 1.19<br>$MW_{found}$ = 520.6<br>$MW_{calc}$ = 519.6 |

| Example | Structure | Name | Analytical Data |
|---|---|---|---|
| 572 | 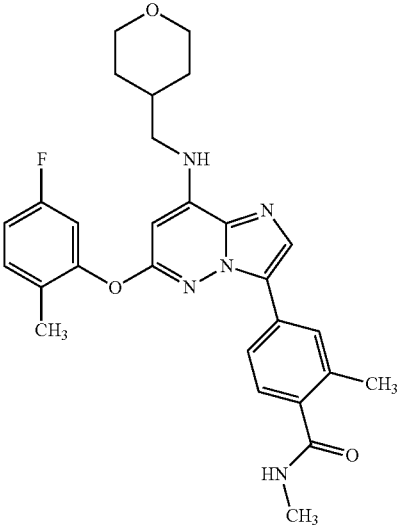 [SMILES: CNC(=O)c1ccc(-c2cnc3c(NCC4CCOCC4)cc(Oc4cc(F)ccc4C)nn23)cc1C] | 4-{6-(5-fluoro-2-methylphenoxy)-8-[(tetrahydro-2H-pyran-4-ylmethyl)amino]imidazo[1,2-b]pyridazin-3-yl}-N,2-dimethylbenzamide | RT = 1.24<br>$MW_{found}$ = 504.6<br>$MW_{calc}$ = 503.6 |
| 573 | 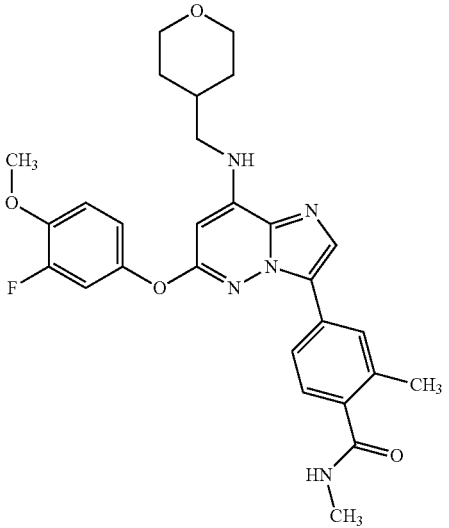 [SMILES: CNC(=O)c1ccc(-c2cnc3c(NCC4CCOCC4)cc(Oc4ccc(OC)c(F)c4)nn23)cc1C] | 4-{6-(3-fluoro-4-methoxyphenoxy)-8-[(tetrahydro-2H-pyran-4-ylmethyl)amino]imidazo[1,2-b]pyridazin-3-yl}-N,2-dimethylbenzamide | RT = 1.17<br>$MW_{found}$ = 520.6<br>$MW_{calc}$ = 519.6 |
| 574 | 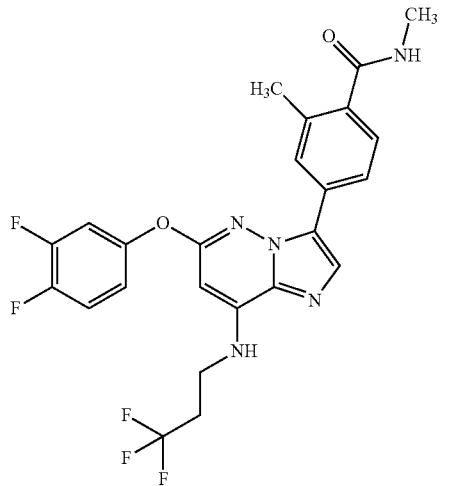 [SMILES: CNC(=O)c1ccc(-c2cnc3c(NCCC(F)(F)F)cc(Oc4ccc(F)c(F)c4)nn23)cc1C] | 4-{6-(3,4-difluorophenoxy)-8-[(3,3,3-trifluoropropyl)amino]imidazo[1,2-b]pyridazin-3-yl}-N,2-dimethylbenzamide | RT = 1.29<br>$MW_{found}$ = 506.4<br>$MW_{calc}$ = 505.4 |

| Example | Structure | Name | Analytical Data |
|---|---|---|---|
| 575 | 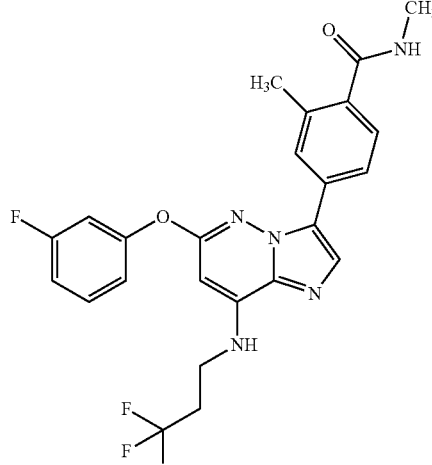 | 4-{6-(3-fluorophenoxy)-8-[(3,3,3-trifluoropropyl)amino]imidazo[1,2-b]pyridazin-3-yl}-N,2-dimethylbenzamide | RT = 1.29<br>$MW_{found}$ = 488.5<br>$MW_{calc}$ = 487.5<br>$^1$H-NMR (300 MHz, (DMSO-$d_6$), δ [ppm] = 2.16 (3H), 2.59-2.76 (5H), 3.54-3.66 (2H), 6.13 (1H), 7.13 (2H), 7.20 (1H), 7.25 (1H), 7.43-7.53 (1H), 7.64-7.74 (2H), 7.76 (1H), 7.93 (1H), 8.08 (1H) |
| 576 | 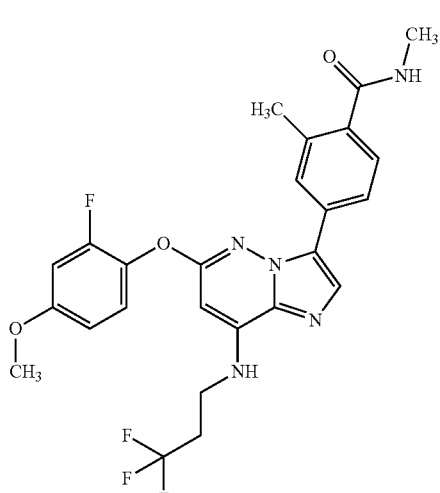 | 4-{6-(2-fluoro-4-methoxyphenoxy)-8-[(3,3,3-trifluoropropyl)amino]imidazo[1,2-b]pyridazin-3-yl}-N,2-dimethylbenzamide | RT = 1.26<br>$MW_{found}$ = 518.5<br>$MW_{calc}$ = 517.5 |
| 577 | 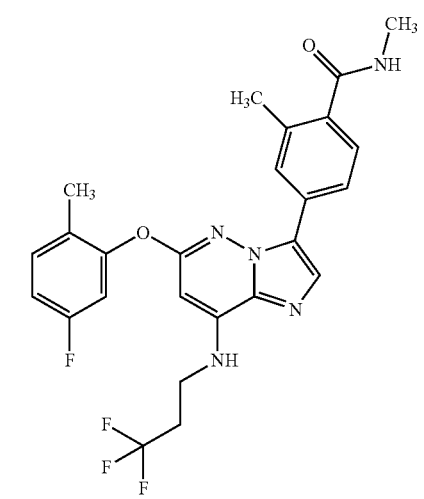 [SMILES: CNC(=O)c1ccc(-c2cnc3c(NCCC(F)(F)F)cc(Oc4cc(F)ccc4C)nn23)cc1C] | 4-{6-(5-fluoro-2-methylphenoxy)-8-[(3,3,3-trifluoropropyl)amino]imidazo[1,2-b]pyridazin-3-yl}-N,2-dimethylbenzamide | RT = 1.32<br>$MW_{found}$ = 502.5<br>$MW_{calc}$ = 501.5 |

| Example | Structure | Name | Analytical Data |
|---|---|---|---|
| 578 | 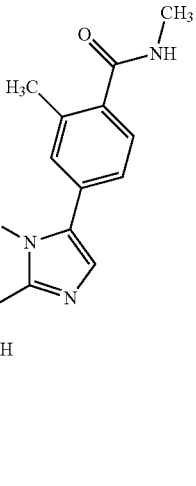 | 4-{6-(3-fluoro-4-methoxyphenoxy)-8-[(3,3,3-trifluoropropyl)amino]imidazo[1,2-b]pyridazin-3-yl}-N,2-dimethylbenzamide | RT = 1.25<br>MW$_{found}$ = 518.5<br>MW$_{calc}$ = 517.5 |
| 579 | 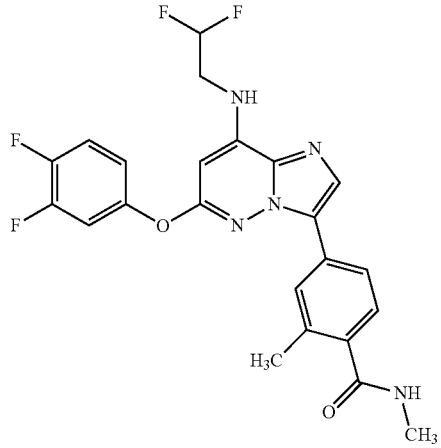 [SMILES: CNC(=O)c1ccc(-c2cnc3c(NCC(F)F)cc(Oc4ccc(F)c(F)c4)nn23)cc1C] | 4-{8-[(2,2-difluoroethyl)amino]-6-(3,4-difluorophenoxy)imidazo[1,2-b]pyridazin-3-yl}-N,2-dimethylbenzamide | RT = 1.17<br>MW$_{found}$ = 474.4<br>MW$_{calc}$ = 473.4 |
| 580 | 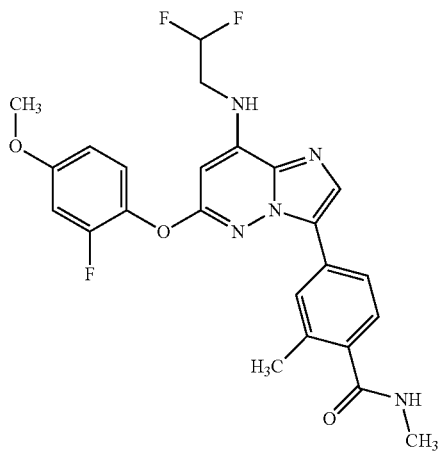 [SMILES: CNC(=O)c1ccc(-c2cnc3c(NCC(F)F)cc(Oc4ccc(OC)cc4F)nn23)cc1C] | 4-{8-[(2,2-difluoroethyl)amino]-6-(2-fluoro-4-methoxyphenoxy)imidazo[1,2-b]pyridazin-3-yl}-N,2-dimethylbenzamide | RT = 1.16<br>MW$_{found}$ = 486.5<br>MW$_{calc}$ = 485.5<br>$^1$H-NMR (300 MHz, DMSO-d$_6$), δ [ppm] = 2.10 (3H), 2.70 (3H), 3.78 (3H), 3.86 (3H), 6.23 (1H), 6.32 (1H), 6.84 (1H), 7.05 (1H), 7.19 (1H), 7.34 (1H), 7.62 (1H), 7.70-7.79 (1H), 7.97 (1H), 8.08 (1H) |

-continued

| Example | Structure | Name | Analytical Data |
|---|---|---|---|
| 581 | 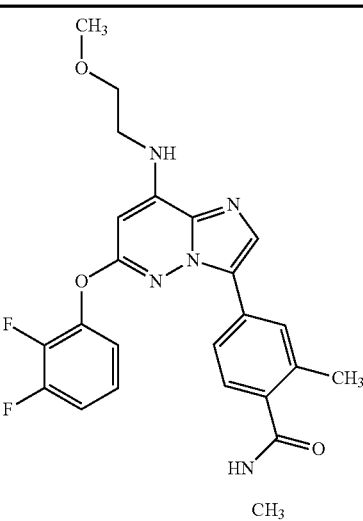 | 4-{6-(2,3-difluoro-phenoxy)-8-[(2-methoxyethyl)a-mino]imidazo[1,2-b]pyridazin-3-yl}-N,2-dimethylbenzamide | RT = 1.17<br>$MW_{found}$ = 468.5<br>$MW_{calc}$ = 467.5 |
| 582 | 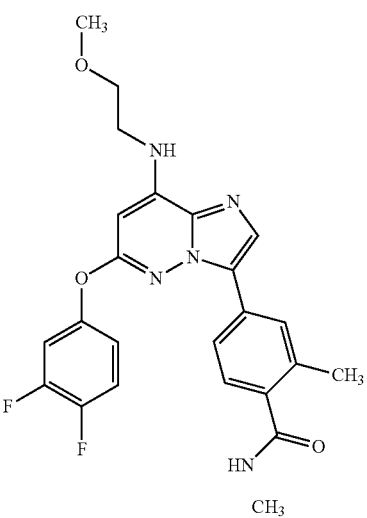 | 4-{6-(3,4-difluorophenoxy)-8-[(2-methoxyethyl)a-mino]imidazo[1,2-b]pyridazin-3-yl}-N,2-dimethylbenzamide | RT = 1.18<br>$MW_{found}$ = 468.5<br>$MW_{calc}$ = 467.5<br>$^1$H-NMR (400 MHz, DMSO-$d_6$), δ [ppm] = 2.16 (3H), 2.70 (3H), 3.27 (3H), 3.52 (2H), 3.54-3.59 (2H), 6.10 (1H), 7.13-7.19 (1H), 7.22 (1H), 7.45 (1H), 7.50-7.60 (2H), 7.66 (1H), 7.75 (1H), 7.92 (1H), 8.09 (1H) |
| 583 | 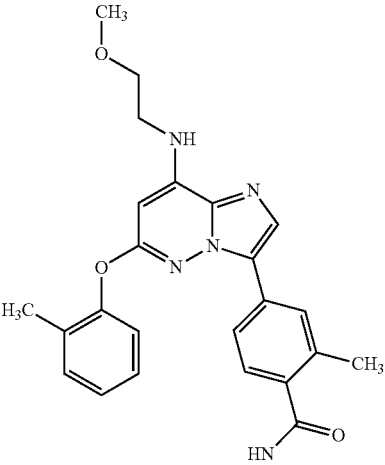 | 4-{8-[(2-methoxyethyl)amino]-6-(2-methylphenoxy)imidazo[1,2-b]pyridazin-3-yl}-N,2-dimethylbenzamide | RT = 1.18<br>$MW_{found}$ = 446.5<br>$MW_{calc}$ = 445.5 |

| Example | Structure | Name | Analytical Data |
|---|---|---|---|
| 584 | 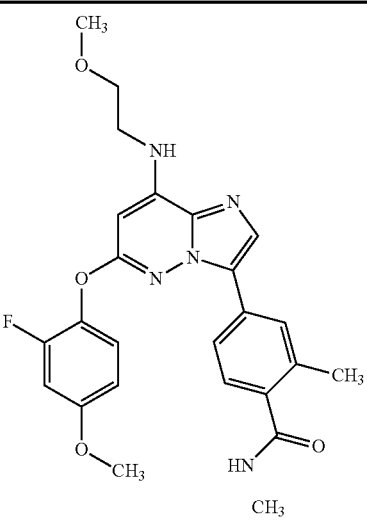 | 4-{6-(2-fluoro-4-methoxyphenoxy)-8-[(2-methoxyethyl)amino]imidazo[1,2-b]pyridazin-3-yl}-N,2-dimethylbenzamide | RT = 1.15<br>$MW_{found} = 480.5$<br>$MW_{calc} = 479.5$ |
| 585 | 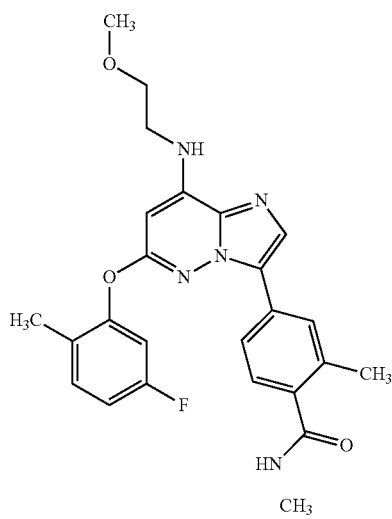 | 4-{6-(5-fluoro-2-methylphenoxy)-8-[(2-methoxyethyl)amino]imidazo[1,2-b]pyridazin-3-yl}-N,2-dimethylbenzamide | RT = 1.20<br>$MW_{found} = 464.5$<br>$MW_{calc} = 463.5$ |
| 586 | 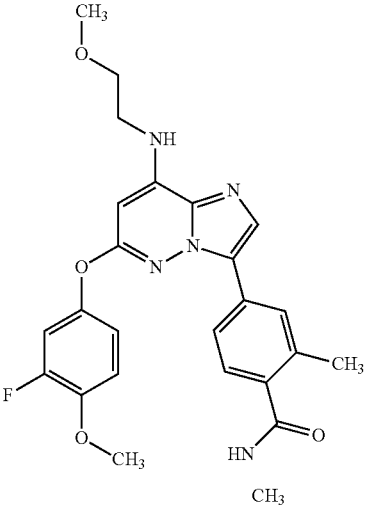 | 4-{6-(3-fluoro-4-methoxyphenoxy)-8-[(2-methoxyethyl)amino]imidazo[1,2-b]pyridazin-3-yl]-N,2-dimethylbenzamide | RT = 1.13<br>$MW_{found} = 480.5$<br>$MW_{calc} = 479.5$ |

-continued

| Example | Structure | Name | Analytical Data |
|---|---|---|---|
| 587 | 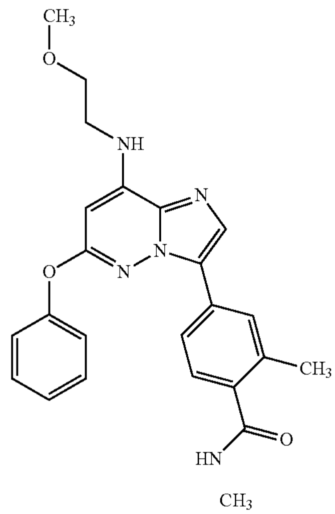 | 4-{8-[(2-methoxyethyl)amino]-6-phenoxyimidazo[1,2-b]pyridazin-3-yl}-N,2-dimethylbenzamide | RT = 1.14<br>$MW_{found}$ = 432.5<br>$MW_{calc}$ = 431.5<br>$^1$H-NMR (400 MHz, DMSO-$d_6$), δ [ppm] = 2.14 (3H), 2.69 (3H), 3.17-3.29 (3H), 3.51 (2H), 3.53-3.59 (2H), 6.08 (1H), 7.18 (1H), 7.24-7.29 (3H), 7.38 (1H), 7.41-7.48 (2H), 7.67 (1H), 7.75 (1H), 7.91 (1H), 8.09 (1H) |
| 588 | 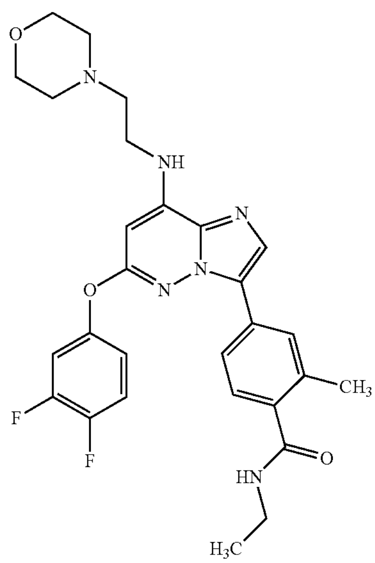 [SMILES: CCNC(=O)c1ccc(-c2cnc3c(NCCN4CCOCC4)cc(Oc4ccc(F)c(F)c4)nn23)cc1C] | 4-[6-(3,4-difluorophenoxy)-8-{[2-(morpholin-4-yl)ethyl]amino}imidazo[1,2-b]pyridazin-3-yl]-N-ethyl-2-methylbenzamide | RT = 0.88<br>$MW_{found}$ = 537.6<br>$MW_{calc}$ = 536.6 |
| 589 | 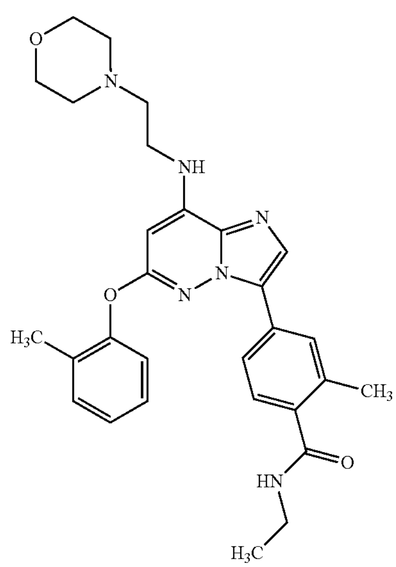 [SMILES: CCNC(=O)c1ccc(-c2cnc3c(NCCN4CCOCC4)cc(Oc4ccccc4C)nn23)cc1C] | N-ethyl-2-methyl-4-[6-(2-methylphenoxy)-8-{[2-(morpholin-4-yl)ethyl]amino}imidazo[1,2-b]pyridazin-3-yl]benzamide | RT = 0.88<br>$MW_{found}$ = 515.6<br>$MW_{calc}$ = 514.6 |

| Example | Structure | Name | Analytical Data |
|---|---|---|---|
| 590 | 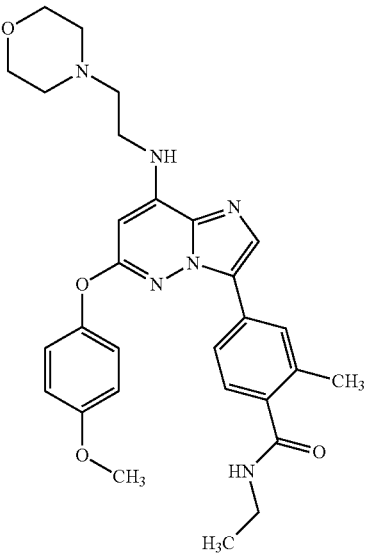 [SMILES: CCNC(=O)c1ccc(-c2cnc3c(NCCN4CCOCC4)cc(Oc4ccc(OC)cc4)nn23)cc1C] | N-ethyl-4-[6-(4-methoxyphenoxy)-8-{[2-(morpholin-4-yl)ethyl]amino}imidazo[1,2-b]pyridazin-3-yl]-2-methylbenzamide | RT = 0.83<br>MW$_{found}$ = 531.6<br>MW$_{calc}$ = 530.6 |
| 591 | 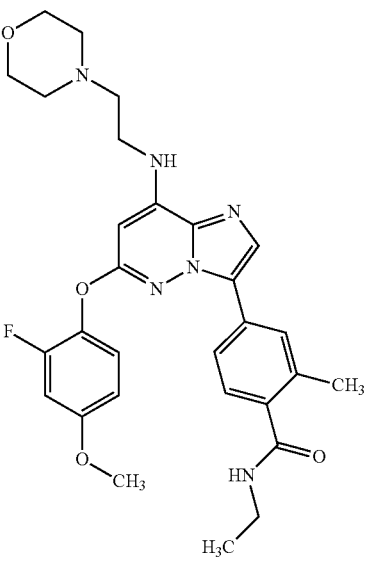 [SMILES: CCNC(=O)c1ccc(-c2cnc3c(NCCN4CCOCC4)cc(Oc4ccc(OC)cc4F)nn23)cc1C] | N-ethyl-4-[6-(2-fluoro-4-methoxyphenoxy)-8-{[2-(morpholin-4-yl)ethyl]amino}imidazo[1,2-b]pyridazin-3-yl]-2-methylbenzamide | RT = 0.86<br>MW$_{found}$ = 549.6<br>MW$_{calc}$ = 548.6<br>$^1$H-NMR (300 MHz, DMSO-d$_6$), δ [ppm] = 1.06 (3H), 2.10 (3H), 2.42 (4H), 2.59 (2H), 3.14-3.24 (2H), 3.44 (2H), 3.53-3.59 (4H), 3.77 (3H), 6.10 (1H), 6.54 (1H), 6.67-6.88 (1H), 7.05 (1H), 7.17 (1H), 7.25-7.32 (1H), 7.62 (1H), 7.72 (1H), 7.92 (1H), 8.16 (1H) |

-continued
| Example | Structure | Name | Analytical Data |
|---|---|---|---|
| 592 | 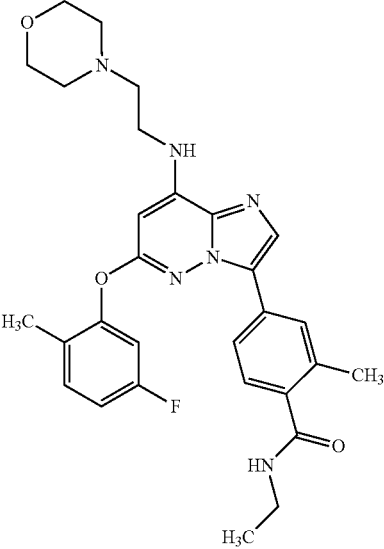 [SMILES: CCNC(=O)c1ccc(-c2cnc3c(NCCN4CCOCC4)cc(Oc4cc(F)ccc4C)nn23)cc1C] | N-ethyl-4-[6-(5-fluoro-2-methylphenoxy)-8-{[2-(morpholin-4-yl)ethyl]amino}imidazo[1,2-b]pyridazin-3-yl]-2-methylbenzamide | RT = 0.89<br>$MW_{found}$ = 533.6<br>$MW_{calc}$ = 532.6 |
| 593 | 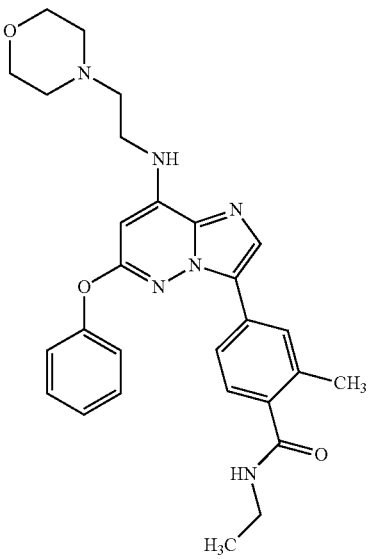 [SMILES: CCNC(=O)c1ccc(-c2cnc3c(NCCN4CCOCC4)cc(Oc4ccccc4)nn23)cc1C] | N-ethyl-2-methyl-4-(8-{[2-(morpholin-4-yl)ethyl]amino}-6-phenoxyimidazo[1,2-b]pyridazin-3-yl)benzamide | RT = 0.89<br>$MW_{found}$ = 501.6<br>$MW_{calc}$ = 500.6<br>$^1$H-NMR (400 MHz, DMSO-$d_6$), δ [ppm] = 1.06 (3H), 2.14 (3H), 2.59 (2H), 3.19 (4H), 3.43 (3H), 3.56 (5H), 6.05 (1H), 7.17 (1H), 7.26 (5H), 7.41-7.50 (2H), 7.66 (1H), 7.75 (1H), 7.90 (1H), 8.13 (2H) |

| Example | Structure | Name | Analytical Data |
|---|---|---|---|
| 594 | 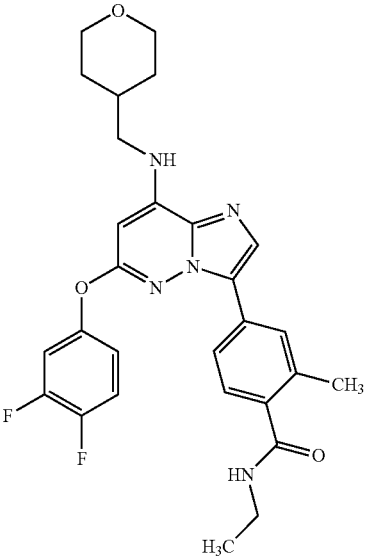 [SMILES: CCNC(=O)c1ccc(-c2cnc3c(NCC4CCOCC4)cc(Oc4ccc(F)c(F)c4)nn23)cc1C] | 4-{6-(3,4-difluorophenoxy)-8-[(tetrahydro-2H-pyran-4-ylmethyl)amino]imidazo[1,2-b]pyridazin-3-yl}-N-ethyl-2-methylbenzamide | RT = 1.28<br>$MW_{found}$ = 522.6<br>$MW_{calc}$ = 521.6<br>$^1$H-NMR (300 MHz, DMSO-$d_6$), δ [ppm] = 1.07 (3H), 1.14-1.32 (2H), 1.62 (2H), 1.86-2.01 (1H), 2.16 (3H), 3.14-3.25 (6H), 3.83 (2H), 6.09 (1H), 7.11-7.23 (2H), 7.46-7.60 (2H), 7.61-7.68 (1H), 7.68-7.77 (2H), 7.90 (1H), 8.15 (1H) |
| 595 | 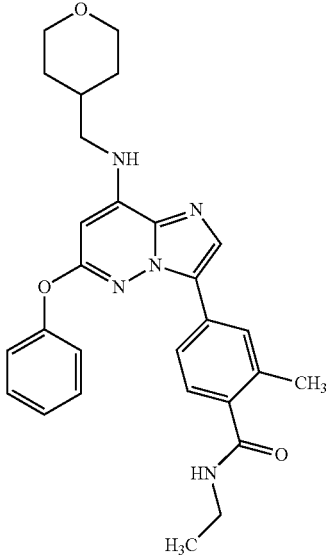 [SMILES: CCNC(=O)c1ccc(-c2cnc3c(NCC4CCOCC4)cc(Oc4ccccc4)nn23)cc1C] | N-ethyl-2-methyl-4-{6-phenoxy-8-[(tetrahydro-2H-pyran-4-ylmethyl)amino]imidazo[1,2-b]pyridazin-3-yl}benzamide | RT = 1.26<br>$MW_{found}$ = 486.6<br>$MW_{calc}$ = 485.6<br>$^1$H-NMR (400 MHz, DMSO-$d_6$), δ [ppm] = 1.06 (3H), 1.15-1.29 (4H), 1.62 (2H), 1.89-2.00 (1H), 2.13 (3H), 3.15-3.29 (4H), 3.83 (2H), 6.07 (1H), 7.16 (1H), 7.27 (3H), 7.41-7.48 (2H), 7.62-7.68 (2H), 7.75 (1H), 7.90 (1H), 8.10-8.18 (1H) |

| Example | Structure | Name | Analytical Data |
|---|---|---|---|
| 596 | 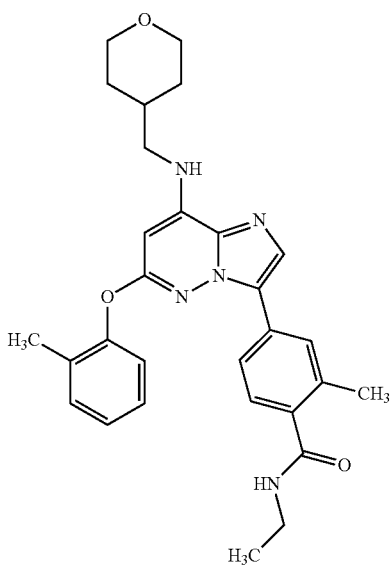 | N-ethyl-2-methyl-4-{6-(2-methylphenoxy)-8-[(tetrahydro-2H-pyran-4-ylmethyl)amino]imidazo[1,2-b]pyridazin-3-yl}benzamide | RT = 1.29<br>$MW_{found}$ = 500.6<br>$MW_{calc}$ = 499.6 |
| 597 | 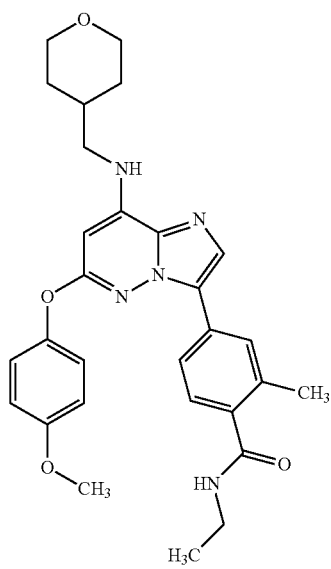 [SMILES: CCNC(=O)c1ccc(-c2cnc3c(NCC4CCOCC4)cc(Oc4ccc(OC)cc4)nn23)cc1C] | N-ethyl-4-{6-(4-methoxyphenoxy)-8-[(tetrahydro-2H-pyran-4-ylmethyl)amino]imidazo[1,2-b]pyridazin-3-yl}-2-methylbenzamide | RT = 1.22<br>$MW_{found}$ = 516.6<br>$MW_{calc}$ = 515.6 |

| Example | Structure | Name | Analytical Data |
|---|---|---|---|
| 598 | 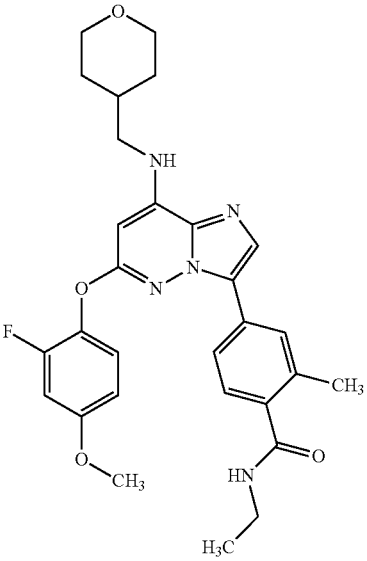 [SMILES: CCNC(=O)c1ccc(-c2cnc3c(NCC4CCOCC4)cc(Oc4ccc(OC)cc4F)nn23)cc1C] | N-ethyl-4-{6-(2-fluoro-4-methoxyphenoxy)-8-[(tetrahydro-2H-pyran-4-ylmethyl)amino]imidazo[1,2-b]pyridazin-3-yl}-2-methylbenzamide | RT = 1.24<br>$MW_{found}$ = 534.6<br>$MW_{calc}$ = 533.6 |
| 599 | 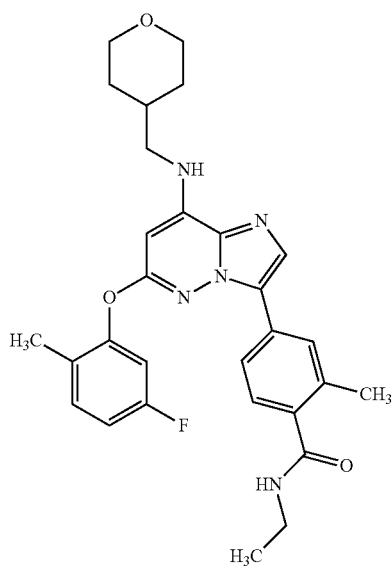 | N-ethyl-4-{6-(5-fluoro-2-methylphenoxy)-8-[(tetrahydro-2H-pyran-4-ylmethyl)amino]imidazo[1,2-b]pyridazin-3-yl}-2-methylbenzamide | RT = 1.31<br>$MW_{found}$ = 518.6<br>$MW_{calc}$ = 517.6 |

| Example | Structure | Name | Analytical Data |
|---|---|---|---|
| 600 | 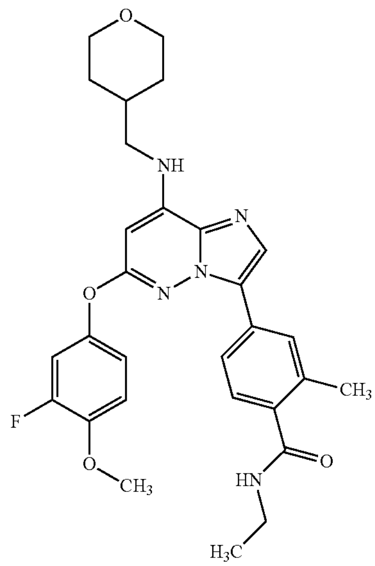 [SMILES: CCNC(=O)c1ccc(-c2cnc3c(NCC4CCOCC4)cc(Oc4ccc(OC)c(F)c4)nn23)cc1C] | N-ethyl-4-{6-(3-fluoro-4-methoxyphenoxy)-8-[(tetrahydro-2H-pyran-4-ylmethyl)amino]imidazo[1,2-b]pyridazin-3-yl}-2-methylbenzamide | RT = 1.25<br>$MW_{found}$ = 534.6<br>$MW_{calc}$ = 533.6<br>$^1$H-NMR (400 MHz, DMSO-$d_6$), δ [ppm] = 1.07 (3H), 1.15-1.29 (2H), 1.62 (2H), 1.94 (1H), 2.13 (3H), 3.15-3.26 (6H), 3.78-3.83 (2H), 3.84 (3H), 6.05 (1H), 7.03-7.09 (1H), 7.16-7.25 (2H), 7.30 (1H), 7.62-7.69 (2H), 7.78 (1H), 7.90 (1H), 8.15 (1H) |
| 601 | 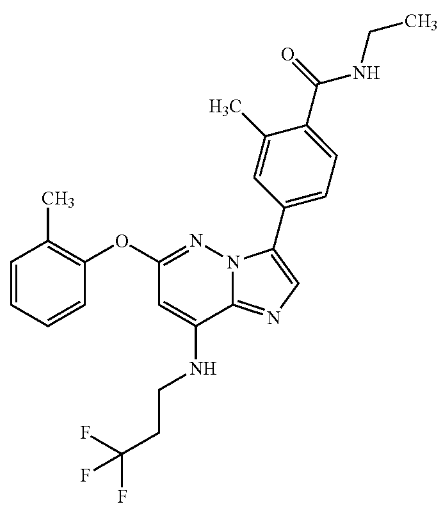 [SMILES: CCNC(=O)c1ccc(-c2cnc3c(NCCC(F)(F)F)cc(Oc4ccccc4C)nn23)cc1C] | N-ethyl-2-methyl-4-{6-(2-methylphenoxy)-8-[(3,3,3-trifluoropropyl)amino]imidazo[1,2-b]pyridazin-3-yl}benzamide | RT = 1.36<br>$MW_{found}$ = 498.5<br>$MW_{calc}$ = 497.5 |
| 602 | 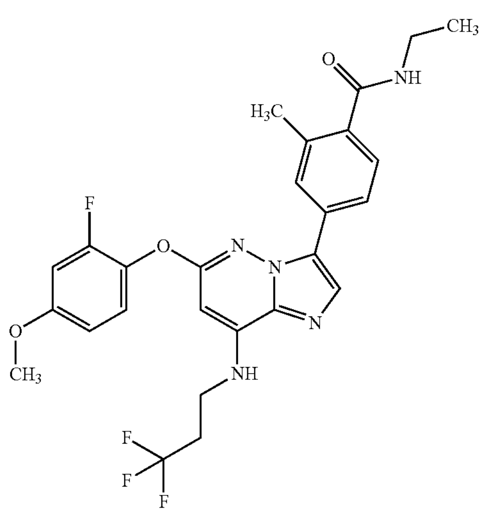 [SMILES: CCNC(=O)c1ccc(-c2cnc3c(NCCC(F)(F)F)cc(Oc4ccc(OC)cc4F)nn23)cc1C] | N-ethyl-4-{6-(2-fluoro-4-methoxyphenoxy)-8-[(3,3,3-trifluoropropyl)amino]imidazo[1,2-b]pyridazin-3-yl}-2-methylbenzamide | RT = 1.31<br>$MW_{found}$ = 532.5<br>$MW_{calc}$ = 531.5<br>$^1$H-NMR (300 MHz, DMSO-$d_6$), δ [ppm] = 1.06 (3H), 2.10 (3H), 2.69 (2H), 3.13-3.24 (2H), 3.61 (2H), 3.77 (3H), 6.16 (1H), 6.84 (1H), 7.06 (1H), 7.17 (1H), 7.34 (1H), 7.58-7.65 (1H), 7.68 (1H), 7.72 (1H), 7.93 (1H), 8.15 (1H) |

| Example | Structure | Name | Analytical Data |
|---|---|---|---|
| 603 | 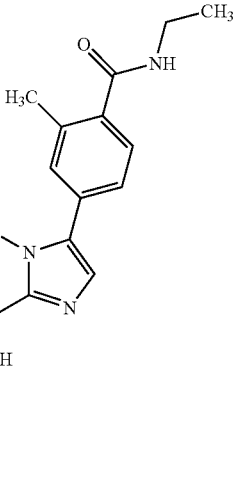 | N-ethyl-4-{6-(5-fluoro-2-methylphenoxy)-8-[(3,3,3-trifluoropropyl)amino]imidazo[1,2-b]pyridazin-3-yl}-2-methylbenzamide | RT = 1.37<br>$MW_{found}$ = 516.5<br>$MW_{calc}$ = 515.5 |
| 604 | 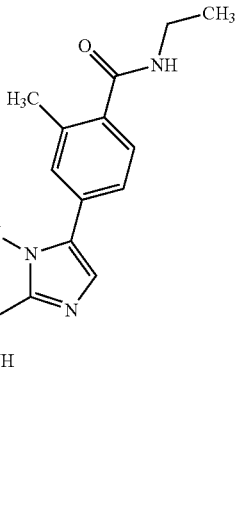 | N-ethyl-4-{6-(3-fluoro-4-methoxyphenoxy)-8-[(3,3,3-trifluoropropyl)amino]imidazo[1,2-b]pyridazin-3-yl}-2-methylbenzamide | RT = 1.32<br>$MW_{found}$ = 532.5<br>$MW_{calc}$ = 531.5<br>$^1$H-NMR (400 MHz, DMSO-$d_6$), δ [ppm] = 1.07 (3H), 2.13 (3H), 2.61-2.74 (2H), 3.20 (2H), 3.59 (2H), 3.84 (3H), 6.09 (1H), 7.04-7.09 (1H), 7.17-7.20 (1H), 7.20-7.25 (1H), 7.31 (1H), 7.63-7.68 (2H), 7.78 (1H), 7.93 (1H), 8.15 (1H) |
| 605 | 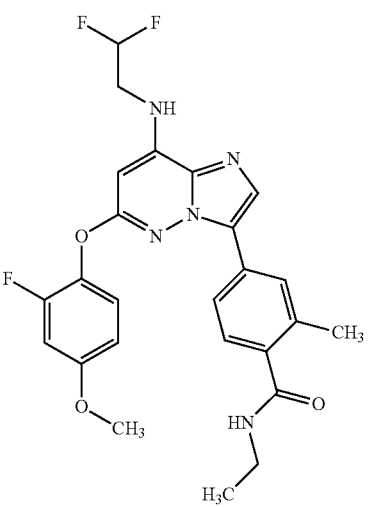 [SMILES: CCNC(=O)c1ccc(-c2cnc3c(NCC(F)F)cc(Oc4ccc(OC)cc4F)nn23)cc1C] | 4-{8-[(2,2-difluoroethyl)amino]-6-(2-fluoro-4-methoxyphenoxy)imidazo[1,2-b]pyridazin-3-yl}-N-ethyl-2-methylbenzamide | RT = 1.22<br>$MW_{found}$ = 500.5<br>$MW_{calc}$ = 499.5<br>$^1$H-NMR (300 MHz, DMSO-$d_6$), δ [ppm] = 1.06 (3H), 2.10 (3H), 3.19 (2H), 3.77 (2H), 3.86 (1H), 6.32 (1H), 6.84 (1H), 7.06 (1H), 7.17 (1H), 7.34 (1H), 7.59-7.65 (1H), 7.69-7.79 (2H), 7.96 (1H), 8.15 (1H) |

-continued

| Example | Structure | Name | Analytical Data |
|---|---|---|---|
| 606 | 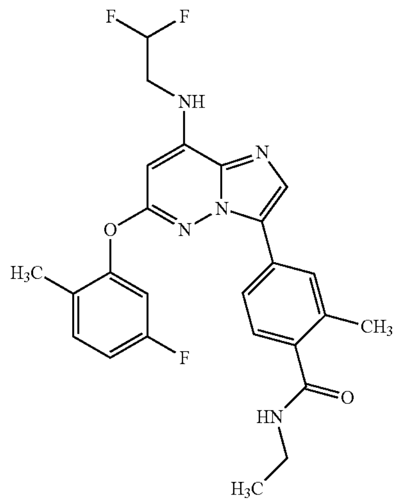 | 4-{8-[(2,2-difluoroethyl)amino]-6-(5-fluoro-2-methylphenoxy)imidazo[1,2-b]pyridazin-3-yl}-N-ethyl-2-methylbenzamide | RT = 1.28<br>$MW_{found}$ = 484.5<br>$MW_{calc}$ = 483.5 |
| 607 | 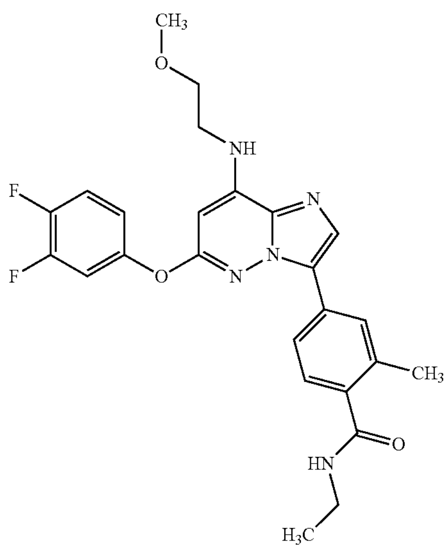 [SMILES: CCNC(=O)c1ccc(-c2cnc3c(NCCOC)cc(Oc4ccc(F)c(F)c4)nn23)cc1C] | 4-{6-(3,4-difluorophenoxy)-8-[(2-methoxyethyl)amino]imidazo[1,2-b]pyridazin-3-yl}-N-ethyl-2-methylbenzamide | RT = 1.24<br>$MW_{found}$ = 482.5<br>$MW_{calc}$ = 481.5 |
| 608 | 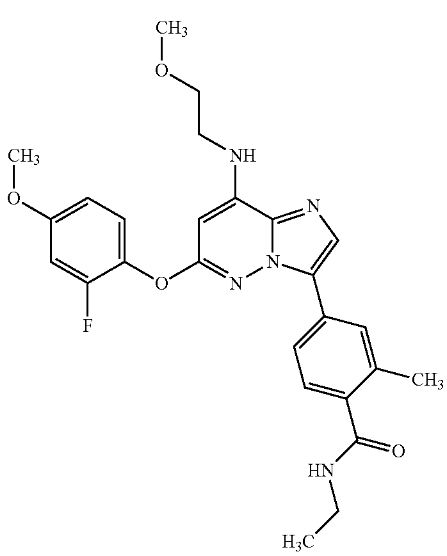 [SMILES: CCNC(=O)c1ccc(-c2cnc3c(NCCOC)cc(Oc4ccc(OC)cc4F)nn23)cc1C] | N-ethyl-4-{6-(2-fluoro-4-methoxyphenoxy)-8-[(2-methoxyethyl)amino]imidazo[1,2-b]pyridazin-3-yl}-2-methylbenzamide | RT = 1.21<br>$MW_{found}$ = 494.5<br>$MW_{calc}$ = 493.5 |

| Example | Structure | Name | Analytical Data |
|---|---|---|---|
| 609 | 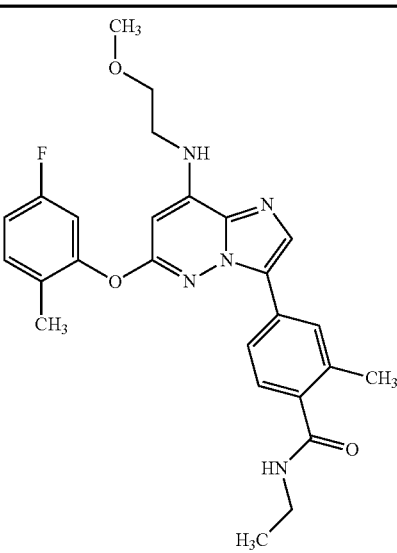 | N-ethyl-4-{6-(5-fluoro-2-methylphenoxy)-8-[(2-methoxyethyl)amino]imidazo[1,2-b]pyridazin-3-yl}-2-methylbenzamide | RT = 1.27<br>$MW_{found}$ = 478.5<br>$MW_{calc}$ = 477.5<br>$^1$H-NMR (300 MHz, DMSO-$d_6$), δ [ppm] = 1.06 (3H), 2.11 (3H), 2.12 (3H), 3.19 (4H), 3.46-3.61 (5H), 6.12 (1H), 7.06 (1H), 7.12-7.21 (2H), 7.32-7.44 (2H), 7.62 (1H), 7.71 (1H), 7.91 (1H), 8.14 (1H) |
| 610 | 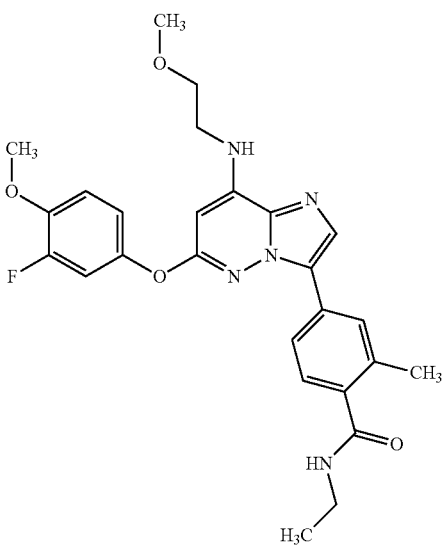 [SMILES: CCNC(=O)c1ccc(-c2cnc3c(NCCOC)cc(Oc4ccc(OC)c(F)c4)nn23)cc1C] | N-ethyl-4-{6-(3-fluoro-4-methoxyphenoxy)-8-[(2-methoxyethyl)amino]imidazo[1,2-b]pyridazin-3-yl}-2-methylbenzamide | RT = 1.19<br>$MW_{found}$ = 494.5<br>$MW_{calc}$ = 493.5 |

The following intermediate examples were prepared analogously to the procedure described above for example 562a using the appropriate amine and the appropriate boronic acid [LC-MS data such as retention time (RT in min) or observed mass peak were collected using LC-MS Method A unless explicitly stated]:

| Intermediate Example | Structure | Name | Analytical Data |
|---|---|---|---|
| 562a | 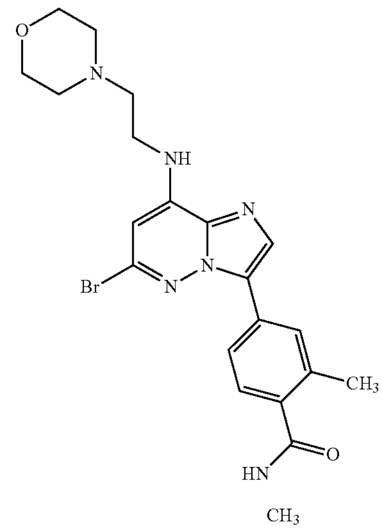 | 4-(6-bromo-8-{[2-(morpholin-4-yl)ethyl]amino}imidazo[1,2-b]pyridazin-3-yl)-N,2-dimethylbenzamide | RT = 0.71<br>MW$_{found}$ = 474.4<br>MW$_{calc}$ = 473.4<br>$^1$H-NMR (300 MHz, DMSO-d$_6$), δ [ppm] = 2.37 (3H), 2.42 (4H), 2.54 (2H), 2.73 (3H), 3.26 (2H), 3.49-3.59 (4H), 6.42 (1H), 7.40 (2H), 7.56-7.63 (1H), 7.86 (1H), 7.92 (1H), 7.96 (1H), 8.18 (1H) |
| 567a | 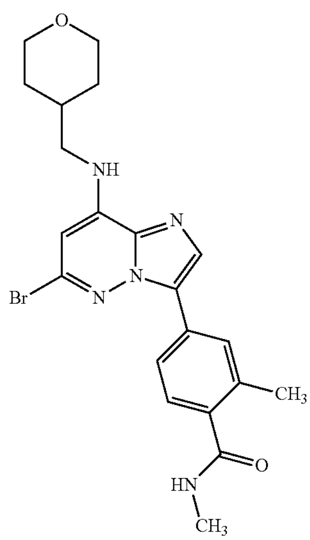 [SMILES: CNC(=O)c1ccc(-c2cnc3c(NCC4CCOCC4)cc(Br)nn23)cc1C] | 4-{6-bromo-8-[(tetrahydro-2H-pyran-4-ylmethyl)amino]imidazo[1,2-b]pyridazin-3-yl}-N,2-dimethylbenzamide | RT = 1.09<br>MW$_{found}$ = 459.4<br>MW$_{calc}$ = 458.4<br>$^1$H-NMR (300 MHz, DMSO-d$_6$), δ [ppm] = 1.11-1.31 (2H), 1.59 (2H), 1.83-1.98 (1H), 2.37 (3H), 2.69-2.78 (3H), 3.15-3.27 (4H), 3.81 (2H), 6.42 (1H), 7.40 (1H), 7.86 (1H), 7.89-8.00 (3H), 8.18 (1H) |
| 574a | 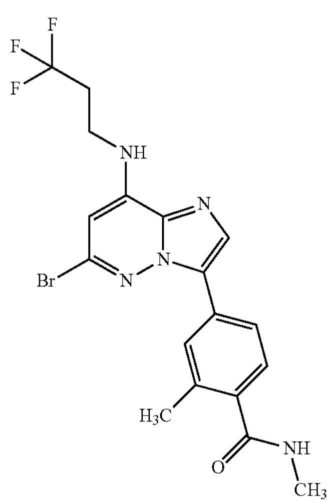 [SMILES: CNC(=O)c1ccc(-c2cnc3c(NCCC(F)(F)F)cc(Br)nn23)cc1C] | 4-{6-bromo-8-[(3,3,3-trifluoropropyl)amino]imidazo[1,2-b]pyridazin-3-yl}-N,2-dimethylbenzamide | RT = 1.18<br>MW$_{found}$ = 457.3<br>MW$_{calc}$ = 456.3<br>$^1$H-NMR (400 MHz, DMSO-d$_6$), δ [ppm] = 2.37 (3H), 2.59-2.71 (2H), 2.73 (3H), 3.59 (2H), 6.46 (1H), 7.41 (1H), 7.86 (1H), 7.89-7.96 (2H), 7.97 (1H), 8.17 (1H) |

-continued

| Intermediate Example | Structure | Name | Analytical Data |
|---|---|---|---|
| 579a | 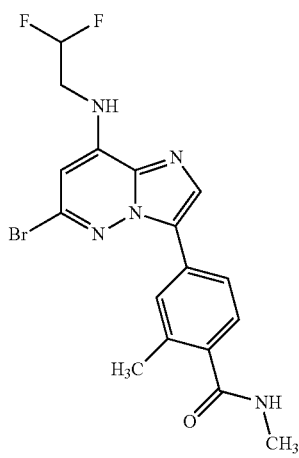 [SMILES: CNC(=O)c1ccc(-c2cnc3c(NCC(F)F)cc(Br)nn23)cc1C] | 4-{6-bromo-8-[(2,2-difluoroethyl)amino]imidazo[1,2-b]pyridazin-3-yl}-N,2-dimethylbenzamide | RT = 1.03<br>$MW_{found}$ = 425.3<br>$MW_{calc}$ = 424.3<br>$^1$H-NMR (400 MHz, DMSO-$d_6$), δ [ppm] = 2.37 (3H), 2.73 (3H), 3.25 (1H), 3.85 (2H), 6.62 (1H), 7.41 (1H), 7.87 (1H), 7.92 (1H), 7.97-8.03 (2H), 8.17 (1H) |
| 581a | 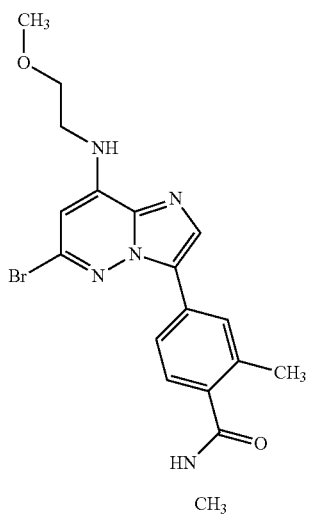 | 4-{6-bromo-8-[(2-methoxyethyl)amino]imidazo[1,2-b]pyridazin-3-yl}-N,2-dimethylbenzamide | RT = 1.02<br>$MW_{found}$ = 419.3<br>$MW_{calc}$ = 418.3<br>$^1$H-NMR (300 MHz, DMSO-$d_6$), δ [ppm] = 2.37 (3H), 2.73 (3H), 3.25 (3H), 3.53 (4H), 6.42 (1H), 7.41 (1H), 7.71 (1H), 7.86 (1H), 7.89-7.94 (1H), 7.95 (1H), 8.16 (1H) |
| 588a | 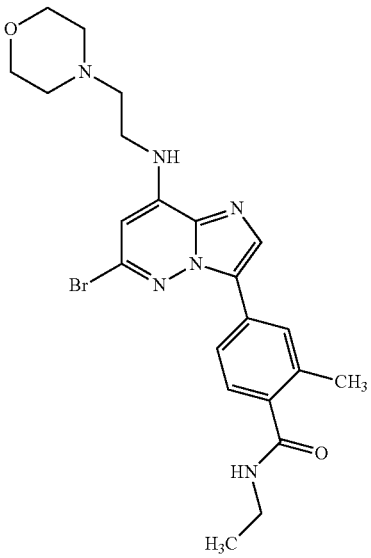 [SMILES: CCNC(=O)c1ccc(-c2cnc3c(NCCN4CCOCC4)cc(Br)nn23)cc1C] | 4-(6-bromo-8-{[2-(morpholin-4-yl)ethyl]amino}imidazo[1,2-b]pyridazin-3-yl)-N-ethyl-2-methylbenzamide | RT = 0.75<br>$MW_{found}$ = 488.4<br>$MW_{calc}$ = 487.4<br>$^1$H-NMR (400 MHz, DMSO-$d_6$), δ [ppm] = 1.06-1.12 (3H), 2.37 (3H), 2.42 (4H), 2.56 (2H), 3.18-3.26 (2H), 3.43 (2H), 3.52-3.58 (4H), 6.41 (1H), 7.39 (1H), 7.57 (1H), 7.85 (1H), 7.91 (1H), 7.95 (1H), 8.22 (1H) |

-continued

| Intermediate Example | Structure | Name | Analytical Data |
|---|---|---|---|
| 594a | 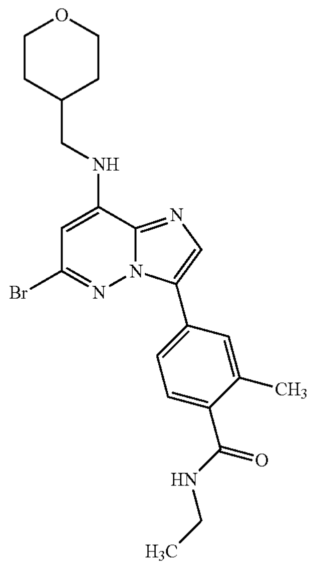 [SMILES: CCNC(=O)c1ccc(-c2cnc3c(NCC4CCOCC4)cc(Br)nn23)cc1C] | 4-{6-bromo-8-[(tetrahydro-2H-pyran-4-ylmethyl)amino]imidazo[1,2-b]pyridazin-3-yl}-N-ethyl-2-methylbenzamide | RT = 1.1.17<br>$MW_{found}$ = 473.4<br>$MW_{calc}$ = 472.4<br>$^1$H-NMR (300 MHz, DMSO-$d_6$), δ [ppm] = 1.05-1.12 (3H), 1.13-1.31 (2H), 1.59 (2H), 1.89 (1H), 2.37 (3H), 3.16-3.25 (6H), 3.81 (2H), 6.42 (1H), 7.39 (1H), 7.85 (1H), 7.88-7.98 (3H), 8.22 (1H) |
| 601a | 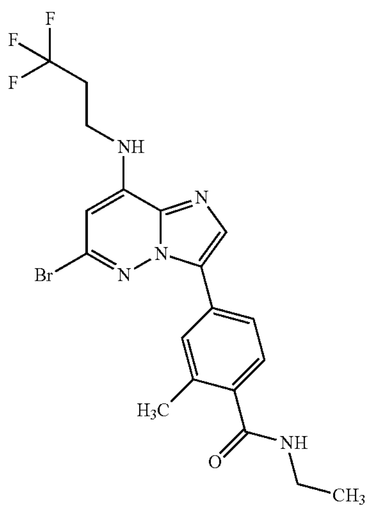 [SMILES: CCNC(=O)c1ccc(-c2cnc3c(NCCC(F)(F)F)cc(Br)nn23)cc1C] | 4-{6-bromo-8-[(3,3,3-trifluoropropyl)amino]imidazo[1,2-b]pyridazin-3-yl}-N-ethyl-2-methylbenzamide | RT = 1.25<br>$MW_{found}$ = 471.3<br>$MW_{calc}$ = 470.3<br>$^1$H-NMR (400 MHz, DMSO-$d_6$), δ [ppm] = 1.09 (3H), 2.37 (3H), 2.66 (2H), 3.18-3.26 (2H), 3.59 (2H), 6.46 (1H), 7.40 (1H), 7.85 (1H), 7.89-7.96 (2H), 7.96 (1H), 8.23 (1H) |
| 605a | 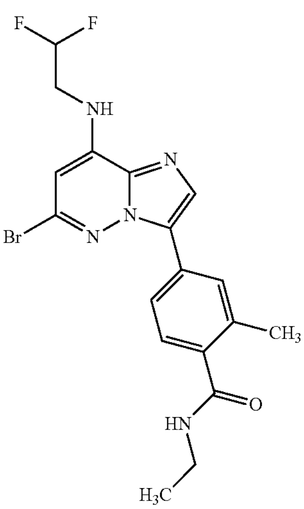 [SMILES: CCNC(=O)c1ccc(-c2cnc3c(NCC(F)F)cc(Br)nn23)cc1C] | 4-{6-bromo-8-[(2,2-difluoroethyl)amino]imidazo[1,2-b]pyridazin-3-yl}-N-ethyl-2-methylbenzamide | RT = 1.10<br>$MW_{found}$ = 439.3<br>$MW_{calc}$ = 438.3<br>$^1$H-NMR (300 MHz, DMSO-$d_6$), δ [ppm] = 1.09 (3H), 2.37 (3H), 3.18-3.26 (3H), 3.86 (2H), 6.61 (1H), 7.40 (1H), 7.86 (1H), 7.89-7.95 (1H), 7.99 (2H), 8.23 (1H) |

| Intermediate Example | Structure | Name | Analytical Data |
|---|---|---|---|
| 607a | 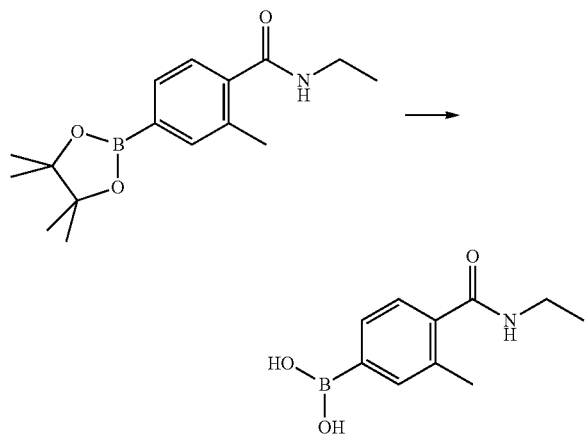 | 4-{6-bromo-8-[(2-methoxyethyl)amino]imidazo[1,2-b]pyridazin-3-yl}-N-ethyl-2-methylbenzamide | RT = 1.09<br>$MW_{found}$ = 433.3<br>$MW_{calc}$ = 432.3<br>$^1$H-NMR (300 MHz, DMSO-$d_6$), δ [ppm] = 1.09 (3H), 2.37 (3H), 3.18-3.27 (4H), 3.43-3.59 (5H), 6.43 (1H), 7.39 (2H), 7.75 (1H), 7.86 (1H), 7.92 (1H), 7.95 (1H), 8.24 (1H) |

Intermediate Example 582b

[4-(ethylcarbamoyl)-3-methylphenyl]boronic acid

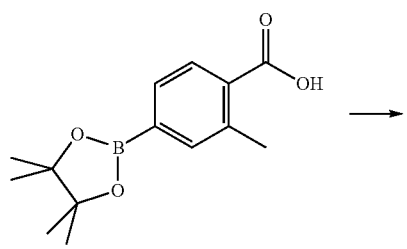 → 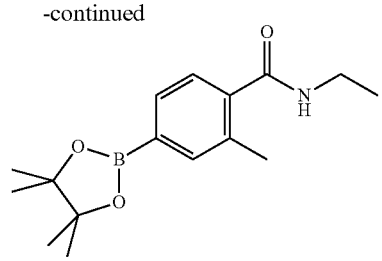

17.72 g (61.27 mmol) N-ethyl-2-methyl-4-(4,4,5,5-tetramethyl-1,3,2-dioxaborolan-2-yl)benzamide which was prepared according to intermediate example 582c were transformed in analogy to intermediate example 562b to give after working up and purification 8.75 g (70%) of the title compound.

Intermediate Example 582c

N-ethyl-2-methyl-4-(4,4,5,5-tetramethyl-1,3,2-dioxaborolan-2-yl)benzamide

To a stirred solution of 15 g (57 mmol) 2-methyl-4-(4,4,5,5-tetramethyl-1,3,2-dioxaborolan-2-yl)benzoic acid in NMP (20 mL) were added 85.84 mL (171.68 mmol) ethylamine and 72.8 mL 2,4,6-tripropyl-1,3,5,2,4,6-trioxatriphosphinane 2,4,6-trioxide (114.45 mmol, 2M in THF) and the mixture was stirred for 2 h at rt to give after working up and purification 16.00 g (96.7%) of the title compound.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science Et Technology 1998, 52(5), 238-311; Strickley, R. G "Parenteral Formulations of Small Molecule Therapeutics Marketed in the United States (1999)-Part-1" PDA Journal of Pharmaceutical Science Et Technology 1999, 53(6), 324-349; and Nema, S. et al., "Excipients and Their Use in Injectable Products" PDA Journal of Pharmaceutical Science Et Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FDC Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, topoisomerase inhibitors, biological response modifiers, or anti-hormones.

The additional pharmaceutical agent can be afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lapatinib, lentinan sulfate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, sunitinib, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib (BAY 43-9006), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, epothilone, an epothilone derivative, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylrnelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatunnunnab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

The compounds of the invention may also be combined with biological therapeutic agents, such as antibodies (e.g. avastin, rituxan, erbitux, herceptin), or recombinant proteins.

The compounds of the invention may also be in combination with antiangiogenesis agents, such as, for example, with avastin, axitinib, DAST, recentin, sorafenib or sunitinib. Combinations with inhibitors of proteasomes or mTOR inhibitors, or anti-hormones or steroidal metabolic enzyme inhibitors are also possible.

Generally, the use of cytotoxic and/or cytostatic agents in combination with a compound or composition of the present invention will serve to:

(1) yield better efficacy in reducing the growth of a tumour or even eliminate the tumour as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumour progression, and/or (8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula I, or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula I described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers. Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumour cells (MCF7, hormone dependent human mammary carcinoma cells, ATCCHTB22; NCl-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; B16F10 mouse melanoma cells, ATCC CRL-6475) were plated at a density of 5000 cells/well (MCF7, DU145, HeLa-MaTu-ADR), 3000 cells/well (NCl-H460, HeLa-MaTu, HeLa), or 1000 cells/well (B16F10) in a 96-well multititer plate in 200 μL of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.01-30 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 μm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 mL of a 100-fold concentrated solution of the test compound in DMSO was pipetted into a black low volume 384 well microtiter plate (Greiner Bio-One, Frickenhausen, Germany), 2 μl of a solution of Mps-1 in assay buffer [0.1 mM sodium-ortho-vanadate, 10 mM $MgCl_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 μl of a solution of 16.7 adenosine-tri-phosphate (ATP, 16.7 μM=>final conc. in the 5 μl assay volume is 10 μM) and peptide substrate (1.67 μM=>final conc. in the 5 μl assay volume is 1 μM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 μl assay volume). The reaction was stopped by the addition of 3 μl of a solution of HTRF detection reagents (100 mM Hepes pH 7.4, 0.1% BSA, 40 mM EDTA, 140 nM Streptavidin-XLent [#61GSTXLB, Fa. C is Biointernational, Marcoule, France], 1.5 nM anti-phospho (Ser/Thr)-Europium-antibody [#AD0180, Perkin Elmer LAS, Rodgau-Jügesheim, Germany].

The resulting mixture was incubated 1 h at 22° C. to allow the binding of the phosphorylated peptide to the anti-phospho (Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Rigesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

It was surprisingly found that the inhibitory activity of compounds of general formula I can be positively influenced by $R^3$ being an aryl-X— or heteroaryl-X— group. Therefore, compounds of general formula I, supra, in which $R^3$ represents an aryl-X— or heteroaryl-X— group are preferred.

TABLE 1

| Example | Mps1 IC50 [nM] |
|---|---|
| 1 | 61.1 |
| 2 | 90.5 |
| 3 | 13.7 |
| 4 | 20.6 |
| 5 | 13.3 |
| 6 | 43.6 |
| 7 | 1.2 |
| 8 | 111.0 |
| 9 | 25.0 |
| 10 | <1.0 |
| 11 | 2.4 |
| 12 | 3.2 |
| 13 | 1.8 |
| 14 | 1.2 |
| 15 | 21.5 |
| 16 | 27.3 |
| 17 | 3.2 |
| 18 | 228.0 |
| 19 | 1.6 |
| 20 | 1.2 |
| 21 | 3.7 |
| 22 | 35.7 |
| 23 | 2.4 |
| 24 | 23.8 |
| 25 | 13.1 |
| 26 | 4.1 |
| 27 | 33.2 |
| 28 | <1.0 |
| 29 | 80.2 |
| 30 | 2.1 |
| 31 | 1.1 |
| 32 | 4.3 |
| 33 | 1.5 |
| 34 | 2.4 |
| 35 | 2.5 |
| 36 | 3.0 |
| 37 | <1.0 |
| 38 | 10.3 |
| 39 | 3.7 |
| 40 | 111.0 |
| 41 | 7.1 |
| 42 | 7.8 |
| 43 | 21.1 |
| 44 | 2.6 |
| 45 | 1.1 |
| 46 | 1.1 |
| 47 | 2.0 |
| 48 | 1.4 |
| 49 | 11.9 |
| 50 | 84.8 |
| 51A | 58.0 |
| 51B | 1.2 |
| 52 | 3.2 |

TABLE 1-continued

| Example | Mps1 IC50 [nM] |
|---|---|
| 53 | 7.1 |
| 54 | 7.6 |
| 55 | 1.2 |
| 56 | <1.0 |
| 57 | 4.4 |
| 58 | 20.5 |
| 59 | 32.5 |
| 60A | 0.2 |
| 60B | <0.1 |
| 61A | 0.2 |
| 61B | 0.3 |
| 62A | 0.2 |
| 62B | 11.5 |
| 63 | <0.1 |
| 64 | 0.1 |
| 65 | 0.7 |
| 66 | 0.2 |
| 67 | 0.1 |
| 68 | <0.1 |
| 69 | 1.0 |
| 70 | 0.3 |
| 71 | 0.8 |
| 72 | 44.4 |
| 73A | <0.7 |
| 73B | 3.8 |
| 74 | <0.7 |
| 75 | <0.7 |
| 76 | <0.7 |
| 77 | <0.7 |
| 78 | 0.2 |
| 79 | 0.7 |
| 80 | 0.2 |
| 81 | 0.2 |
| 82 | 0.3 |
| 83A | 0.2 |
| 83B | 0.8 |
| 84 | 0.3 |
| 85 | 0.2 |
| 86 | 0.1 |
| 87 | 0.2 |
| 88 | 0.4 |
| 89 | 0.2 |
| 90 | 0.5 |
| 91 | 0.5 |
| 92 | 0.2 |
| 93 | 0.3 |
| 94 | 0.3 |
| 95 | 0.3 |
| 96 | 0.8 |
| 97 | 0.2 |
| 98 | 52.3 |
| 99 | 29.5 |
| 100 | 7.6 |
| 101 | 6.3 |
| 102 | 24.6 |
| 103 | <1.0 |
| 104 | <1.0 |
| 105 | 3.5 |
| 106 | 8.9 |
| 107 | 35.5 |
| 108 | 7.0 |
| 109 | 2.1 |
| 110 | 1.3 |
| 111 | 6.3 |
| 112 | 5.1 |
| 113 | 2.0 |
| 114 | <1.0 |
| 115 | 27.5 |
| 116 | 4.0 |
| 117 | 3.3 |
| 118 | 4.3 |
| 119 | <1.0 |
| 120 | 2.5 |
| 121 | 1.8 |
| 122 | 2.9 |
| 123 | 7.6 |
| 124 | 4.7 |

TABLE 1-continued

| Example | Mps1 IC50 [nM] |
|---|---|
| 125 | 3.8 |
| 126 | 2.0 |
| 127 | 40.0 |
| 128 | 2.7 |
| 129 | 3.3 |
| 130 | 5.9 |
| 131 | 10.0 |
| 132 | 1.5 |
| 133 | <1.0 |
| 134 | <1.0 |
| 135 | <1.0 |
| 136 | 4.0 |
| 137 | <1.0 |
| 138 | 2.0 |
| 139 | 3.7 |
| 140 | 3.9 |
| 141 | 2.4 |
| 142 | 1.4 |
| 143 | 4.7 |
| 144 | 2.3 |
| 145 | <1.0 |
| 146 | 3.8 |
| 147 | 2.2 |
| 148 | 1.5 |
| 149 | 2.2 |
| 150 | 3.7 |
| 151 | 3.1 |
| 152 | 3.3 |
| 153 | 3.6 |
| 154 | 25.0 |
| 155 | 3.6 |
| 156 | 5.1 |
| 157 | 12.0 |
| 158 | 6.4 |
| 159 | 14.8 |
| 160 | 13.6 |
| 161 | 6.2 |
| 162 | 64.9 |
| 163 | 30.5 |
| 164 | 6.3 |
| 165 | 1.8 |
| 166 | 5.3 |
| 167 | 2.3 |
| 168 | 0.3 |
| 169 | 0.1 |
| 170 | 0.7 |
| 171 | 0.8 |
| 172 | 0.8 |
| 173 | 0.4 |
| 174 | <0.1 |
| 175 | 7280.0 |
| 176 | 465.0 |
| 177 | 32.2 |
| 178 | 172.0 |
| 179 | 601.0 |
| 180 | 327.0 |
| 181 | 39.9 |
| 182 | Nt |
| 183 | 290.0 |
| 184 | 101.0 |
| 185 | Nt |
| 186 | 338.0 |
| 187 | 49.8 |
| 188 | Nt |
| 189 | Nt |
| 190 | 660.0 |
| 191 | 20000.0 |
| 192 | 21.5 |
| 193 | 1.3 |
| 194 | 2.5 |
| 195 | 3.2 |
| 196 | 2.7 |
| 197 | <1.0 |
| 198 | 2.6 |
| 199 | 6.9 |
| 200 | Nt |
| 201 | 2.3 |

TABLE 1-continued

| Example | Mps1 IC50 [nM] |
|---|---|
| 202 | 1.5 |
| 203 | 1.4 |
| 204 | <1.0 |
| 205 | 72.7 |
| 206 | 6.2 |
| 207 | <1.0 |
| 208 | 2.0 |
| 209 | 0.6 |
| 210 | 6.9 |
| 211 | 5.8 |
| 212 | <1.0 |
| 213 | <1.0 |
| 214 | <1.0 |
| 215 | 1.7 |
| 216 | <1.0 |
| 217 | 3.6 |
| 218 | 3.7 |
| 219 | Nt |
| 220 | Nt |
| 221 | 1.2 |
| 222 | 2.1 |
| 223 | 0.2 |
| 224 | <0.1 |
| 225 | 0.2 |
| 226 | 1.3 |
| 227 | 0.2 |
| 228 | 0.6 |
| 229 | 2.6 |
| 230 | 2.7 |
| 231 | 14.3 |
| 232 | 1.0 |
| 233 | 1.7 |
| 234 | 6.1 |
| 235 | 6.2 |
| 236 | Nt |
| 237 | 5.6 |
| 238 | <0.1 |
| 239 | 25.5 |
| 240 | 1.2 |
| 241A | Nt |
| 241B | 3.4 |
| 242 | 3.7 |
| 243 | 0.9 |
| 244 | 0.3 |
| 245 | 0.7 |
| 246 | 0.6 |
| 247 | 1.7 |
| 248 | 0.5 |
| 249 | 0.2 |
| 250 | 0.3 |
| 251 | 0.2 |
| 252 | 0.2 |
| 253 | 0.3 |
| 254 | 0.1 |
| 255 | 0.2 |
| 256 | 0.2 |
| 257 | 0.4 |
| 258 | 0.2 |
| 259 | 0.3 |
| 260 | 0.2 |
| 261 | 0.5 |
| 262 | 0.2 |
| 263 | 32.4 |
| 264 | 2.0 |
| 265 | 0.9 |
| 266 | 0.3 |
| 267 | 0.3 |
| 268 | 0.2 |
| 269 | 0.3 |
| 270 | 0.1 |
| 271 | 1.0 |
| 272 | 21.1 |
| 273 | 0.5 |
| 274 | 73.8 |
| 275 | 5.4 |
| 276 | 0.1 |
| 277 | <0.1 |
| 278A | 0.4 |
| 278B | 1.0 |
| 279 | 148.0 |
| 280 | 0.1 |
| 281 | 0.3 |
| 282 | 0.4 |
| 283 | 0.3 |
| 284 | 0.4 |
| 285 | 0.4 |
| 286 | 0.4 |
| 287 | 0.3 |
| 288 | 0.1 |
| 289 | 0.2 |
| 290 | 0.3 |
| 291 | 0.6 |
| 292 | 0.5 |
| 293 | 0.4 |
| 294A | 0.3 |
| 294B | 0.2 |
| 295A | 0.4 |
| 295B | 0.2 |
| 296A | 0.5 |
| 296B | 0.5 |
| 296C | 0.2 |
| 297 | 0.1 |
| 298A | <0.1 |
| 298B | 0.1 |
| 299 | 6.9 |
| 300 | 0.8 |
| 301 | 0.2 |
| 302 | 0.3 |
| 303A | Nt |
| 303B | 0.2 |
| 304A | <0.1 |
| 304B | 0.1 |
| 305 | 0.6 |
| 306 | 0.6 |
| 307 | 0.5 |
| 308 | 1.0 |
| 309 | Nt |
| 310 | Nt |
| 311 | 0.2 |
| 312 | 0.2 |
| 313 | 0.1 |
| 314 | 0.2 |
| 315 | 0.3 |
| 316 | 118.0 |
| 317 | 7.4 |
| 318 | 64.3 |
| 319 | 121.0 |
| 320 | 3.3 |
| 321 | 0.6 |
| 322 | 70.6 |
| 323 | 0.2 |
| 324 | 0.3 |
| 325 | 0.1 |
| 326 | 1.9 |
| 327 | 0.3 |
| 328 | 0.3 |
| 329 | <0.1 |
| 330 | 0.2 |
| 331 | 12.6 |
| 332 | 26.8 |
| 333 | 9.5 |
| 334 | 30.0 |
| 335 | 3.6 |
| 336 | 1.0 |
| 337 | 3.9 |
| 338 | 83.9 |
| 339 | 95.9 |
| 340 | 3.3 |
| 341 | 10.6 |
| 342 | 6.9 |
| 343 | 4.3 |
| 344 | 23.0 |
| 345 | 3.0 |
| 346 | 1.6 |

TABLE 1-continued

| Example | Mps1 IC50 [nM] |
|---|---|
| 347 | 0.1 |
| 348 | 1.5 |
| 349 | 0.4 |
| 351 | 1.0 |
| 352 | 0.2 |
| 353 | 0.4 |
| 354 | 0.4 |
| 355 | 0.9 |
| 356 | 0.6 |
| 357 | 4.4 |
| 358 | 0.1 |
| 359 | 1.2 |
| 360 | 0.9 |
| 361 | 0.3 |
| 362 | 0.2 |
| 365 | 4.4 |
| 366 | 1.1 |
| 367 | 0.1 |
| 368 | 0.1 |
| 369 | 0.1 |
| 370 | 0.1 |
| 371 | 0.2 |
| 372 | 0.2 |
| 373 | 0.2 |
| 374 | 0.3 |
| 375 | 0.1 |
| 376 | 0.2 |
| 377 | 0.3 |
| 378 | 0.2 |
| 379 | 0.2 |
| 380 | 0.1 |
| 381 | 0.6 |
| 382 | 1.2 |
| 383 | 0.3 |
| 384 | 0.4 |
| 385 | 0.9 |
| 386 | 1.5 |
| 387 | 0.3 |
| 388 | 0.4 |
| 389 | 0.1 |
| 390 | 0.1 |
| 391 | 0.1 |
| 392 | 0.4 |
| 393 | 2.3 |
| 394 | 0.2 |
| 395 | 0.3 |
| 396 | 0.1 |
| 396 | 0.3 |
| 397 | 1.0 |
| 398 | 0.4 |
| 399 | 0.1 |
| 400 | 3.1 |
| 401 | 1.0 |
| 402 | 3.4 |
| 403 | 1.0 |
| 404 | 0.3 |
| 405 | 0.2 |
| 406 | 0.4 |
| 409 | 0.7 |
| 410 | 0.5 |
| 411 | 4.8 |
| 412 | 19.2 |
| 413 | 45.7 |
| 414 | 6.7 |
| 415 | 8.2 |
| 417 | 0.2 |
| 418 | 1.2 |
| 419 | 3.5 |
| 420 | 2.8 |
| 422 | 0.4 |
| 423 | 0.3 |
| 424 | 0.2 |
| 425 | 0.1 |
| 426 | 0.2 |
| 427 | 0.2 |
| 428 | 0.4 |
| 429 | 0.1 |

TABLE 1-continued

| Example | Mps1 IC50 [nM] |
|---|---|
| 430 | 0.3 |
| 431 | 0.1 |
| 432 | 4.6 |
| 433 | 0.6 |
| 434 | 1.3 |
| 435 | 1.6 |
| 436 | 0.1 |
| 437 | 0.4 |
| 439 | 0.2 |
| 440 | 0.1 |
| 441 | 0.5 |
| 442 | 0.1 |
| 443 | 0.1 |
| 445 | 0.2 |
| 446 | 0.4 |
| 447 | 1.1 |
| 448 | 0.6 |
| 449 | 0.6 |
| 450 | 0.3 |
| 451 | 1.3 |
| 452 | 0.8 |
| 454 | 0.1 |
| 456 | nt |
| 457 | 5.4 |
| 458 | 1.1 |
| 459 | 0.4 |
| 460 | 0.3 |
| 461 | 0.2 |
| 464 | 0.1 |
| 465 | nt |
| 466 | 4.8 |
| 467 | 1.6 |
| 468 | 7.5 |
| 469 | 1.7 |
| 470 | 0.4 |
| 471 | 0.2 |
| 472 | 0.2 |
| 473 | 0.4 |
| 474 | 0.3 |
| 475 | 0.2 |
| 476 | 10.3 |
| 477 | 0.3 |
| 478 | 0.3 |
| 479 | 0.2 |
| 480 | nt |
| 481 | 3.1 |
| 482 | 0.6 |
| 483 | 0.1 |
| 484 | 0.3 |
| 485 | 0.4 |
| 486 | 0.1 |
| 487 | 0.1 |
| 488 | 0.1 |
| 489 | 0.2 |
| 490 | 1.5 |
| 491 | 0.1 |
| 492 | 0.1 |
| 493 | 0.3 |
| 494 | 0.3 |
| 495 | 0.1 |
| 496 | 8.9 |
| 497 | 0.2 |
| 498 | 0.3 |
| 499 | 0.2 |
| 500 | 0.1 |
| 501 | 0.1 |
| 502 | 0.2 |
| 503 | 0.2 |
| 504 | 0.2 |
| 505 | 0.2 |
| 506 | 0.1 |
| 507 | 0.2 |
| 508 | 0.2 |
| 509 | 0.1 |
| 510 | 0.1 |
| 511 | 0.3 |
| 512 | 0.1 |

TABLE 1-continued

| Example | Mps1 IC50 [nM] |
|---|---|
| 513 | 0.2 |
| 514 | 8.0 |
| 515 | 0.4 |
| 516 | 0.3 |
| 517 | 0.2 |
| 518 | 0.1 |
| 519 | 0.1 |
| 520 | 0.2 |
| 521 | 0.3 |
| 522 | 1.8 |
| 523 | 0.7 |
| 524 | 2.3 |
| 525 | 0.7 |
| 526 | 0.1 |
| 527 | 0.6 |
| 528 | 0.7 |
| 529 | 0.4 |
| 530 | 0.6 |
| 531 | 14.8 |
| 532 | 0.2 |
| 533 | 1.2 |
| 534 | 0.1 |
| 535 | 0.1 |
| 536 | 0.3 |
| 537 | 0.2 |
| 538 | 0.8 |
| 539 | 0.2 |
| 540 | 0.1 |
| 541 | 0.4 |
| 542 | 0.1 |
| 543 | 0.2 |
| 544 | 1.1 |
| 545 | 0.1 |
| 546 | 0.1 |
| 547 | 0.2 |
| 548 | 0.7 |
| 549 | 0.2 |
| 550 | 0.5 |
| 551 | 0.2 |
| 552 | 0.2 |
| 553 | 0.7 |
| 554 | 1.6 |
| 555 | 9.4 |
| 556 | 0.3 |
| 557 | 2.2 |
| 558 | 0.3 |
| 559 | 0.6 |
| 560 | 0.1 |
| 561 | 0.6 |
| 562 | 2.7 |
| 563 | 4.3 |
| 564 | Nt |
| 565 | 3.5 |
| 566 | 1.7 |
| 567 | <1.0 |
| 568 | <1.0 |
| 569 | <1.0 |
| 570 | <1.0 |
| 571 | <1.0 |
| 572 | <1.0 |
| 573 | <1.0 |
| 574 | Nt |
| 575 | <1.0 |
| 576 | <1.0 |
| 577 | 1.4 |
| 578 | Nt |
| 579 | Nt |
| 580 | <1.0 |
| 581 | <1.0 |
| 582 | 3.8 |
| 583 | 6.9 |
| 584 | 2.3 |
| 585 | 5.4 |
| 586 | 1.0 |
| 587 | 3.2 |
| 588 | 2.2 |
| 589 | 4.3 |
| 590 | Nt |
| 591 | 2.5 |
| 592 | 1.5 |
| 593 | 9.0 |
| 594 | <10 |
| 596 | 1.1 |
| 597 | 1.1 |
| 598 | <1.0 |
| 599 | 1.0 |
| 600 | <1.0 |
| 601 | <1.0 |
| 602 | <1.0 |
| 603 | <1.0 |
| 604 | <1.0 |
| 605 | 1.2 |
| 606 | Nt |
| 607 | 3.7 |
| 608 | 3.9 |
| 609 | 2.9 |
| 610 | <1.0 |

In the above Table, Nt = not tested

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumour cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2/M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/ml. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated. The following parameter values were used: Liver blood flow—4.2 L/h/kg rat; specific liver weight—32 g/kg rat body weight; liver cells in vivo—$1.1 \times 10^8$ cells/g liver, liver cells in vitro—$0.5 \times 10^6$/ml.

It was surprisingly found that the metabolic stability of compounds of general formula I can be positively influenced by at least one of the groups $R^{4b}$ and $R^{4c}$ being different from a hydrogen atom.

For example, the replacement of a hydrogen atom for $R^{4c}$ or $R^{4b}$ by a methyl group increases the metabolic stability by 700% (Table 2a) or by 177% (Table 2b), respectively.

Therefore, in a preferred embodiment, $R^{4a}$, $R^{4b}$, $R^{4c}$ and $R^{4d}$ represent, independently from each other, a hydrogen or halogen atom, or a —CN, $C_1$-$C_6$-alkyl-, $C_1$-$C_6$-alkoxy-, halo-$C_1$-$C_6$-alkyl-, halo-$C_1$-$C_6$-alkoxy-, $R^{6a}(R^{6b})$N—$C_1$-$C_6$-alkyl-, HO—$C_1$-$C_6$-alkyl-, NC—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-group; with the proviso that at least one of the groups $R^{4b}$ and $R^{4c}$ is not a hydrogen atom.

TABLE 2a

| Example | Structure | Fmax [%] |
|---|---|---|
| 463 | 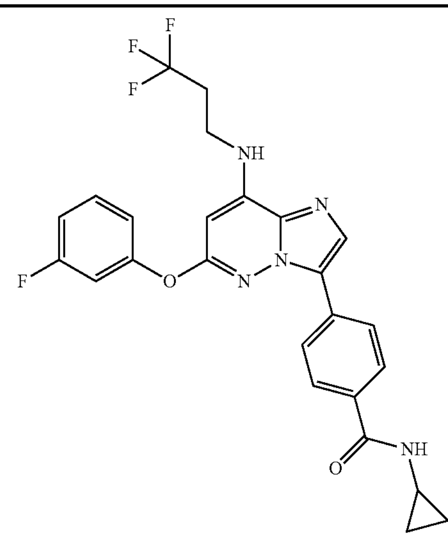 | 7 |
| 80 | 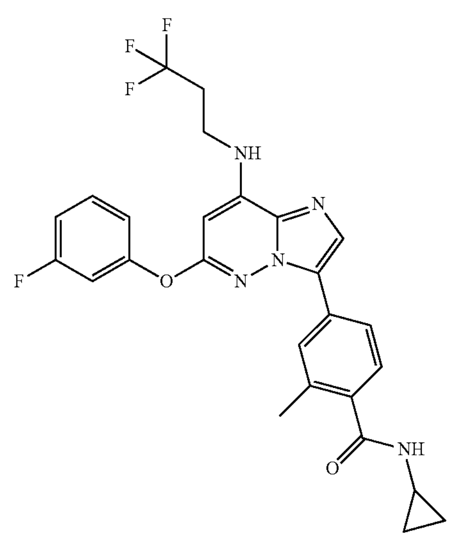 [SMILES: Cc1cc(-c2cnc3c(NCCC(F)(F)F)cc(Oc4cccc(F)c4)nn23)ccc1C(=O)NC1CC1] | 56 |

TABLE 2b

| Example | Structure | Fmax [%] |
|---|---|---|
| 444 | (structure) | 22 |
| 445 | (structure) | 61 |

TABLE 3a

| Example | Structure | Fmax [%] |
|---|---|---|
| 323 | (structure) | 31 |
| 80 | (structure) | 56 |
| 492 | (structure) | 42 |

It was surprisingly found that the metabolic stability of compounds of general formula I can be positively influenced by $R^5$ (Tables 3a, 3b, and 3c). For example, the replacement of a 4-tetrahydropyranyl-group for $R^5$ (compound of example 323) by a 1,1,1-trifluoroethyl group (compound of example 80) increases the metabolic stability by 81% (Table 3a).

TABLE 3a-continued
| Example | Structure | Fmax [%] |
|---|---|---|
| 500 | 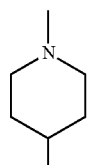 | 40 |
| 510 | 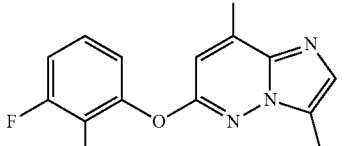 | 39 |
TABLE 3b
| Example | Structure | Fmax [%] |
|---|---|---|
| 516 | 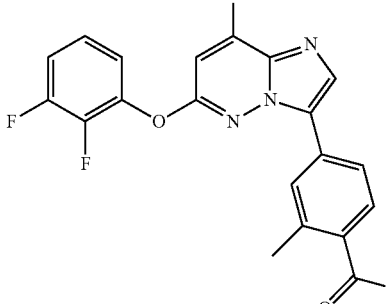 | 69 |
TABLE 3b-continued
| Example | Structure | Fmax [%] |
|---|---|---|
| 526 | 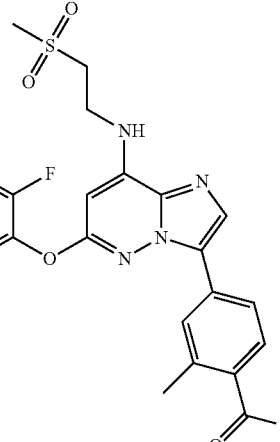 | 50 |
| 536 | 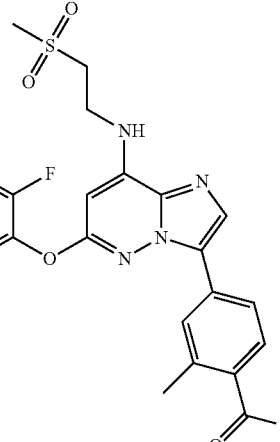 | 37 |

TABLE 3c

| Example | Structure | Fmax [%] |
|---|---|---|
| 390 | (structure) | 55 |
| 391 | (structure) | 47 |

TABLE 4

| Example | Structure | Fmax [%] |
|---|---|---|
| 80 | (structure) | 56 |
| 461 | (structure) | 75 |

It was surprisingly found that the metabolic stability of compounds of general formula I can be positively influenced by $R^2$.

For example, the replacement of a cylopropyl-group for $R^2$ by a substituted cylopropyl-group such as a 1-methylcyclopropyl group increases the metabolic stability by 34% (Table 4).

It was surprisingly found that the metabolic stability of compounds of general formula I can be positively influenced by $R^2$.

For example, the replacement of a cylopropyl-group for $R^2$ by a non-cyclic alkyl-group increases the metabolic stability significantly.

The invention claimed is:
1. A compound of general formula I:

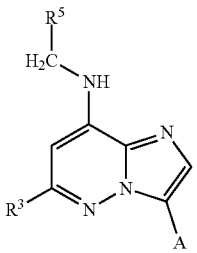

in which:
A represents a

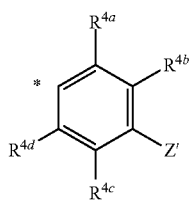

-group;
wherein * indicates the point of attachment of said groups with the rest of the molecule;
Z represents a —C(=O)N(H)R$^2$ or —C(=S)N(H)R$^2$ group, or a group selected from

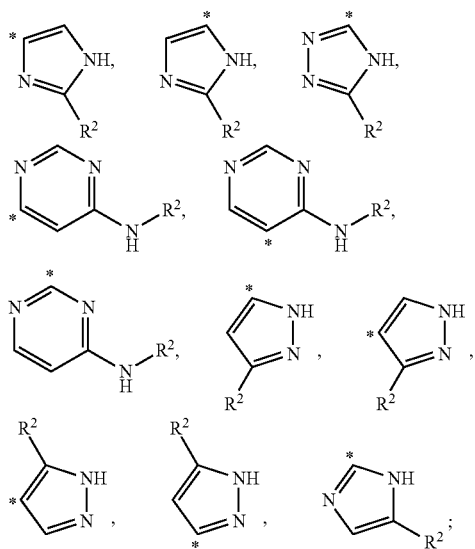

wherein * indicates the point of attachment of said groups with the rest of the molecule;
R$^2$ represents a hydrogen atom, or a C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl-, C$_2$-C$_6$-alkynyl- or C$_3$-C$_6$-cycloalkyl- group;
wherein said C$_3$-C$_6$-cycloalkyl- group is optionally substituted, identically or differently, with 1, 2, 3 or 4 groups selected from: halogen, —OH, —CN, C$_1$-C$_6$-alkyl-, C$_1$-C$_6$-alkoxy-, halo-C$_1$-C$_6$-alkyl-;
R$^3$ represents an aryl-X— or heteroaryl-X— group;
wherein said aryl-X— or heteroaryl-X— group is optionally substituted, identically or differently, with 1, 2, 3, 4 or 5 R$^7$ groups;
R$^{4a}$ represents hydrogen;
R$^{4d}$ represents hydrogen;
one of the groups R$^{4b}$ and R$^{4c}$ represents a hydrogen atom while the other one represents a group selected from: halo, CN, OH, C$_1$-C$_6$-alkyl- and C$_1$-C$_6$-alkoxy-;
R$^5$ represents a hydrogen atom, or a C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_2$-C$_6$-alkenyl-, C$_4$-C$_8$-cycloalkenyl-, C$_2$-C$_6$-alkynyl-, aryl- or heteroaryl- group;
wherein said C$_1$-C$_6$-alkyl-, —(CH$_2$)$_n$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, 3- to 7-membered heterocycloalkyl-, C$_4$-C$_8$-cycloalkenyl-, aryl- or heteroaryl- group is optionally substituted, identically or differently, with 1, 2, 3 or 4 R$^8$ groups;
R$^6$, R$^{6a}$, R$^{6b}$, R$^{6c}$,
represent, independently from each other, a hydrogen atom, or a C$_1$-C$_6$-alkyl-, HO—C$_1$-C$_6$-alkyl-, C$_3$-C$_6$-cycloalkyl-, C$_2$-C$_6$-alkenyl-, 3- to 7-membered heterocycloalkyl-, aryl-, heteroaryl-, aryl-C$_1$-C$_6$-alkyl- or heteroaryl-C$_1$-C$_6$-alkyl- group;
R$^7$ represents a hydrogen or halogen atom, or a HO—, —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl-, aryl-, heteroaryl-, —C(=O)R$^6$, —C(=O)N(H)R$^{6a}$, —C(=O)N(R$^{6a}$)R$^{6b}$, —C(=O)O—R$^6$, —N(R$^{6a}$)R$^{6b}$, NO$_2$, —N(H)C(=O)R$^6$, —N(R$^{6c}$)C(=O)R$^6$, —N(H)C(=O)N(R$^{6a}$)R$^{6b}$, —N(R$^{6c}$)C(=O)N(R$^{6a}$)R$^{6b}$, —N(H)C(=O)OR$^6$, —N(R$^{6c}$)C(=O)OR$^6$, —N(H)S(=O)R$^6$, —N(R$^{6c}$)S(=O)R$^6$, —N(H)S(=O)$_2$R$^6$, —N(R$^{6c}$)S(=O)$_2$R$^6$, —N=S(=O)(R$^{6a}$)R$^{6b}$, —OR$^6$, —O(C=O)R$^6$, —O(C=O)N(R$^{6a}$)R$^{6b}$, —O(C=O)OR$^6$, —SR$^6$, —S(=O)R$^6$, —S(=O)N(H)R$^6$, —S(=O)N(R$^{6a}$)R$^{6b}$, —S(=O)$_2$R$^6$, —S(=O)$_2$N(H)R$^6$, —S(=O)$_2$N(R$^{6a}$)R$^{6b}$ or —S(=O)(=NR$^{6c}$)R$^6$ group;
wherein said C$_1$-C$_6$-alkoxy-, aryl- or heteroaryl- group is optionally substituted, identically or differently, with 1, 2 or 3 C$_1$-C$_6$-alkyl-, C$_1$-C$_6$-alkoxy-, halo-C$_1$-C$_6$-alkoxy-, —C(=O)O—R$^6$ or —OH groups;
or
when 2 R$^7$ groups are present ortho to each other on an aryl- or heteroaryl-ring, said 2 R$^7$ groups together form a bridge:
*O(CH$_2$)$_2$O*, *O(CH$_2$)O*, *NH(C(=O))NH*,
wherein * represent the point of attachment to said aryl- or heteroaryl- ring;
R$^8$ represents a hydrogen or halogen atom, or a —CN, C$_1$-C$_6$-alkoxy-, C$_1$-C$_6$-alkyl-, halo-C$_1$-C$_6$-alkyl-, R$^{6a}$(R$^{6b}$)N—C$_1$-C$_6$-alkyl-, HO—C$_1$-C$_6$-alkyl-, C$_1$-C$_6$- alkoxy-$C_1$-$C_6$-alkyl-, halo-$C_1$-$C_6$-alkoxy-$C_1$-$C_6$-alkyl-, $C_2$-$C_6$-alkenyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2R^6$, —N($R^{6c}$)S(=O)$_2R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O)$_2R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;
wherein said 3- to 7-membered heterocycloalkyl- or heteroaryl- group is optionally substituted, identically or differently, with 1, 2, 3 or 4 $C_1$-$C_6$-alkyl- groups;
m is an integer of 0, 1, 2, 3, 4, 5 or 6;
n is an integer of 0, 1, 2, 3, 4 or 5;
X represents S(=O)$_p$, O, N$R^6$, C$R^{6a}R^{6b}$ or C=C$R^{6a}R^{6b}$;
p is an integer of 0, 1 or 2;
or a stereoisomer, a tautomer, or a salt thereof, or a mixture of same.

2. A compound according to claim 1, wherein
$R^2$ is selected from the groups consisting of:
$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-;
or a stereoisomer, a tautomer, or a salt thereof, or a mixture of same.

3. A compound according to claim 1, wherein
$R^5$ represents a hydrogen atom, or a $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, or heteroaryl- group;
said $C_1$-$C_6$-alkyl-, halo-$C_1$-$C_6$-alkyl-, HO—$C_1$-$C_6$-alkyl-, $C_3$-$C_6$-cycloalkyl-, 3- to 7-membered heterocycloalkyl, heteroaryl- group is optionally substituted, identically or differently, with 1, 2, 3, or 4 $R^8$ groups;
or a stereoisomer, a tautomer, or a salt thereof, or a mixture of same.

4. A compound according to claim 1, wherein
$R^7$ represents a halogen atom, or a HO—, —CN, $C_1$-$C_6$-alkoxy-, $C_1$-$C_6$-alkyl-, halo-$C_1$-$C_6$-alkyl-, HO—$C_1$-$C_6$-alkyl-, $H_2$N—$C_1$-$C_6$-alkyl-, $C_2$-$C_6$-alkenyl, 3- to 7-membered heterocycloalkyl, —C(=O)N(H)$R^{6a}$, —N($R^{6a}$)$R^{6b}$, —N(H)C(=O)$R^6$, or —S$R^6$ group;
wherein said $C_1$-$C_6$-alkoxy-, or 3- to 7-membered heterocycloalkyl- group is optionally substituted, identically or differently, with 1, 2, or 3 $C_1$-$C_6$-alkyl-, $C_1$-$C_6$-alkoxy-, halo-$C_1$-$C_6$-alkoxy-, —C(=O)O—$R^6$ or —OH groups;
or
when 2 $R^7$ groups are present ortho to each other on an aryl or heteroaryl ring, said 2 $R^7$ groups together form a bridge:
*CH$_2$(CH$_2$)$_2$NH*, *CH$_2$CH$_2$N($R^{6a}$)CH$_2$*, *C(H)=C(H)—C(=O)—N(H)*, wherein * represent the point of attachment to said aryl or heteroaryl ring;
or a stereoisomer, a tautomer, or a salt thereof, or a mixture of same.

5. A compound according to claim 1, wherein
$R^6$, $R^{6a}$, $R^{6b}$, and $R^{6c}$ represent, independently from each other, a hydrogen atom, or a $C_1$-$C_6$-alkyl- group;
or a stereoisomer, a tautomer, or a salt thereof, or a mixture of same.

6. A compound which is selected from the group consisting of:

N-cyclopropyl-4-{6-[(2-methoxyphenyl)sulfanyl]-8-[(3,3,3-trifluoropropyl)amino]imidazo[1,2-b]pyridazin-3-yl}-2-methylbenzamide, (RS)—N-cyclopropyl-2-methyl-4-[8-{[(4-methylmorpholin-2-yl)methyl]amino}-6-(phenylsulfanyl)imidazo[1,2-b]pyridazin-3-yl]benzamide, N-cyclopropyl-4-{8-[(2-hydroxy-2-methylpropyl)amino]-6-[(4-hydroxyphenyl)sulfanyl]imidazo[1,2-b]pyridazin-3-yl}-2-methylbenzamide, N-cyclopropyl-4-{8-[(2-hydroxy-2-methylpropyl)amino]-6-[(4-methoxyphenyl)sulfanyl]imidazo[1,2-b]pyridazin-3-yl}-2-methylbenzamide, N-cyclopropyl-4-{8-[(2-hydroxy-2-methylpropyl)amino]-6-[(3-hydroxyphenyl)sulfanyl]imidazo[1,2-b]pyridazin-3-yl}-2-methylbenzamide, N-cyclopropyl-4-{8-[(2-hydroxy-2-methylpropyl)amino]-6-[(3-methoxyphenyl)sulfanyl]imidazo[1,2-b]pyridazin-3-yl}-2-methylbenzamide, N-cyclopropyl-4-{6-[(4-hydroxy-3-methylphenyl)sulfanyl]-8-[(hydroxy-2-methylpropyl)amino]imidazo[1,2-b]pyridazin-3-yl}-2-methylbenzamide, N-cyclopropyl-4-{6-[(5-fluoro-2-methylphenyl)sulfanyl]-8-[(2-hydroxy-2-methylpropyl)amino]imidazo[1,2-b]pyridazin-3-yl}-2-methylbenzamide, N-cyclopropyl-4-{6-[(4-fluoro-3-methylphenyl)sulfanyl]-8-[(2-hydroxy-2-methylpropyl)amino]imidazo[1,2-b]pyridazin-3-yl}-2-methylbenzamide, N-cyclopropyl-4-{6-[(3-fluoro-4-methylphenyl)sulfanyl]-8-[(2-hydroxy-2-methylpropyl)amino]imidazo[1,2-b]pyridazin-3-yl}-2-methylbenzamide, N-cyclopropyl-4-{6-[(3-fluoro-5-methylphenyl)sulfanyl]-8-[(2-hydroxy-2-methylpropyl)amino]imidazo[1,2-b]pyridazin-3-yl}-2-methylbenzamide, N-cyclopropyl-4-{6-[(3,5-difluorophenyl)sulfanyl]-8-[(2-hydroxy-2-methylpropyl)amino]imidazo[1,2-b]pyridazin-3-yl}-2-methylbenzamide, N-cyclopropyl-4-{6-[(4-fluoro-2-methylphenyl)sulfanyl]-8-[(2-hydroxy-2-methylpropyl)amino]imidazo[1,2-b]pyridazin-3-yl}-2-methylbenzamide, N-cyclopropyl-4-{6-[(2-fluorophenyl)sulfanyl]-8-[(2-hydroxy-2-methylpropyl)amino]imidazo[1,2-b]pyridazin-3-yl}-2-methylbenzamide, N-cyclopropyl-4-{6-[(4-fluorophenyl)sulfanyl]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-[(2-hydroxyphenyl)sulfanyl]imidazo[1,2-b]pyridazin-3-yl}-2-methylbenzamide, N-cyclopropyl-4-{8-[(2-hydroxy-2-methylpropyl)amino]-6-[(2-methoxyphenyl)sulfanyl]imidazo[1,2-b]pyridazin-3-yl}-2-methylbenzamide, N-cyclopropyl-4-{6-(3-fluorophenoxy)-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-phenoxyimidazo[1,2-b]pyridazin-3-yl}-2-methylbenzamide, N-cyclopropyl-2-methyl-4-{6-phenoxy-8-[(3,3,3-trifluoropropyl)amino]imidazo[1,2-b]pyridazin-3-yl}benzamide, 4-{8-[(2-amino-2-methylpropyl)amino]-6-[(3-fluorophenyl)sulfanyl]imidazo[1,2-b]pyridazin-3-yl}-N-cyclopropyl-2-methylbenzamide, N-cyclopropyl-4-{6-[(3-fluoro-5-methylphenyl)sulfanyl]-8-[(3,3,3-trifluoropropyl)amino]imidazo[1,2-b]pyridazin-3-yl}-2-methylbenzamide,
N-cyclopropyl-4-{6-(3-fluorophenoxy)-8-[(3,3,3-trifluoropropyl)amino]imidazo[1,2-b]pyridazin-3-yl}-2-methylbenzamide,
N-cyclopropyl-4-{6-(2-fluoro-5-methylphenoxy)-8-[(2-hydroxy-2-methylpropyl)amino]imidazo[1,2-b]pyridazin-3-yl}-2-methylbenzamide,
4-{6-(3-cyanophenoxy)-8-[(2-hydroxy-2-methylpropy)amino]imidazo[1,2-b]pyridazin-3-yl}-N-cyclopropyl-2-methylbenzamide,
(RS)—N-cyclopropyl-4-{6-[(3-fluorophenyl)sulfinyl]-8-[(3,3,3-trifluoropropyl)amino]imidazo[1,2-b]pyridazin-3-yl}-2-methylbenzamide,
N-cyclopropyl-4-{6-[(3-fluorophenyl)sulfonyl]-8-[(3,3,3-trifluoropropyl)amino]imidazo[1,2-b]pyridazin-3-yl}-2-methylbenzamide,
N-cyclopropyl-2-methyl-4-{6-(phenylsulfanyl)-8-[(3,3,3-trifluoropropyl)amino]imidazo[1,2-b]pyridazin-3-yl}benzenecarbothioamide,
4-{6-(3-chlorophenoxy)-8-[(2-hydroxy-2-methylpropy)amino]imidazo[1,2-b]pyridazin-3-yl}-N-cyclopropyl-2-methylbenzamide,
N-cyclopropyl-4-{8-[(2-hydroxy-2-methylpropyl)amino]-6-(4-methoxyphenoxy)imidazo[1,2-b]pyridazin-3-yl}-2-methylbenzamide,
N-cyclopropyl-4-{6-(3-fluoro-5-methylphenoxy)-8-[(2-hydroxy-2-methylpropyl)amino]imidazo[1,2-b]pyridazin-3-yl}-2-methylbenzamide,
N-cyclopropyl-4-{6-(3-fluoro-5-methylphenoxy)-8-[(3,3,3-trifluoropropyl)amino]imidazo[1,2-b]pyridazin-3-yl}-2-methylbenzamide,
N-cyclopropyl-4-{6-[(3-fluorophenyl)sulfanyl]-8-[(2-hydroxy-2-methylpropyl)amino]imidazo[1,2-b]pyridazin-3-yl}-2-methylbenzamide
4-{6-(4-chlorophenoxy)-8-[(2-hydroxy-2-methylpropyl)amino]imidazo[1,2-b]pyridazin-3-yl}-N-cyclopropyl-2-methylbenzamide,
4-{6-(3-chloro-4-fluorophenoxy)-8-[(2-hydroxy-2-methylpropyl)amino]imidazo[1,2-b]pyridazin-3-yl}-N-cyclopropyl-2-methylbenzamide,
N-cyclopropyl-4-{6-(2,3-difluorophenoxy)-8-[(2-hydroxy-2-methylpropyl)amino]imidazo[1,2-b]pyridazin-3-yl}-2-methylbenzamide,
N-cyclopropyl-4-{6-(2-fluorophenoxy)-8-[(2-hydroxy-2-methylpropyl)amino]imidazo[1,2-b]pyridazin-3-yl}-2-methylbenzamide,
N-cyclopropyl-4-{8-[(2-hydroxy-2-methylpropyl)amino]-6-(3-isopropylphenoxy)imidazo[1,2-b]pyridazin-3-yl}-2-methylbenzamide,
4-{6-(4-chloro-3-fluorophenoxy)-8-[(2-hydroxy-2-methylpropyl)amino]imidazo[1,2-b]pyridazin-3-yl}-N-cyclopropyl-2-methylbenzamide,
N-cyclopropyl-4-{6-(3,5-dimethylphenoxy)-8-[(2-hydroxy-2-methylpropyl)amino]imidazo[1,2-b]pyridazin-3-yl}-2-methylbenzamide,
N-cyclopropyl-4-{8-[(2-hydroxy-2-methylpropyl)amino]-6-(3-methylphenoxy)imidazo[1,2-b]pyridazin-3-yl}-2-methylbenzamide,
N-cyclopropyl-4-{8-[(2-hydroxy-2-methylpropyl)amino]-6-(quinolin-5-yloxy)imidazo[1,2-b]pyridazin-3-yl}-2-methylbenzamide,
N-cyclopropyl-4-{8-[(2-hydroxy-2-methylpropyl)amino]-6-(quinolin-6-yloxy)imidazo[1,2-b]pyridazin-3-yl}-2-methylbenzamide,
N-cyclopropyl-2-methyl-4-{6-(quinolin-6-yloxy)-8-[(3,3,3-trifluoropropyl)amino]imidazo[1,2-b]pyridazin-3-yl}benzamide,
N-cyclopropyl-2-methyl-4-{6-(quinolin-5-yloxy)-8-[(3,3,3-trifluoropropyl)amino]imidazo[1,2-b]pyridazin-3-yl}benzamide,
N-cyclopropyl-4-{8-[(2-hydroxy-2-methylpropyl)amino]-6-(pyridin-3-yloxy)imidazo[1,2-b]pyridazin-3-yl}-2-methylbenzamide,
N-cyclopropyl-2-methyl-4-{6-(pyridin-3-yloxy)-8-[(3,3,3-trifluoropropyl)amino]imidazo[1,2-b]pyridazin-3-yl}benzamide,
N-cyclopropyl-2-methyl-4-{8-[(2-methylpropyl)amino]-6-(phenylsulfanyl)imidazo[1,2-b]pyridazin-3-yl}benzamide,
N-cyclopropyl-2-methyl-4-{8-[(2-methylpropyl)amino]-6-(phenylsulfonyl)imidazo[1,2-b]pyridazin-3-yl}benzamide,
N-cyclopropyl-2-methyl-4-{6-(phenylsulfanyl)-8-[(3,3,3-trifluoropropyl)amino]imidazo[1,2-b]pyridazin-3-yl}benzamide,
N-cyclopropyl-4-{6-[(3-fluorophenyl)sulfanyl]-8-[(3,3,3-trifluoropropyl)amino]imidazo[1,2-b]pyridazin-3-yl}-2-methylbenzamide,
N-cyclopropyl-2-methyl-4-{6-(phenylsulfonyl)-8-[(3,3,3-trifluoropropyl)amino]imidazo[1,2-b]pyridazin-3-yl}benzamide,
N-cyclopropyl-4-{8-[(2-hydroxy-2-methylpropyl)amino]-6-(phenylsulfanyl)imidazo[1,2-b]pyridazin-3-yl}-2-methylbenzamide,
N-cyclopropyl-4-{6-[(3-fluorophenyl)sulfanyl]-8-[(3,3,3-trifluoro-2-hydroxypropyl)amino]imidazo[1,2-b]pyridazin-3-yl}-2-methylbenzamide,
N-cyclopropyl-4-{6-[(2,6-difluorophenyl)sulfanyl]-8-[(2-hydroxy-2-methylpropyl)amino]imidazo[1,2-b]pyridazin-3-yl}-2-methylbenzamide,
N-cyclopropyl-4-{6-(2-methoxyphenoxy)-8-[(3,3,3-trifluoropropyl)amino]imidazo[1,2-b]pyridazin-3-yl}-2-methylbenzamide,
N-cyclopropyl-4-{6-[(2-hydroxyphenyl)sulfanyl]-8-[(3,3,3-trifluoropropyl)amino]imidazo[1,2-b]pyridazin-3-yl}-2-methylbenzamide,
N-cyclopropyl-4-{6-(3-methoxyphenoxy)-8-[(3,3,3-trifluoropropyl)amino]imidazo[1,2-b]pyridazin-3-yl}-2-methylbenzamide,
N-cyclopropyl-4-{6-[(4-methoxyphenyl)sulfanyl]-8-[(3,3,3-trifluoropropyl)amino]imidazo[1,2-b]pyridazin-3-yl}-2-methylbenzamide,
N-cyclopropyl-4-{6-[(3-hydroxyphenyl)sulfanyl]-8-[(3,3,3-trifluoropropyl)amino]imidazo[1,2-b]pyridazin-3-yl}-2-methylbenzamide,
N-cyclopropyl-4-(8-[(2-hydroxy-2-methylpropyl)amino]-6-{[4-(trifluoromethyl)phenyl]sulfanyl}imidazo[1,2-b]pyridazin-3-yl)-2-methylbenzamide,
N-cyclopropyl-4-{8-[(2-hydroxy-2-methylpropyl)amino]-6-phenoxyimidazo[1,2-b]pyridazin-3-yl}benzenecarbothioamide,
N-cyclopropyl-4-{6-(3-fluorophenoxy)-8-[(2-hydroxy-2-methylpropyl)amino]imidazo[1,2-b]pyridazin-3-yl}benzenecarbothioamide,
N-cyclopropyl-4-{8-[(2-hydroxy-2-methylpropyl)amino]-6-(phenylsulfanyl)imidazo[1,2-b]pyridazin-3-yl}benzenecarbothioamide,
N-cyclopropyl-4-{6-[(3-fluorophenyl)sulfanyl]-8-[(2-hydroxy-2-methylpropyl)amino]imidazo[1,2-b]pyridazin-3-yl}benzenecarbothioamide, N-cyclopropyl-2-methyl-4-(6-{[4-(trifluoromethyl)phenyl]sulfanyl}-8-[(3,3,3-trifluoropropyl)amino]imidazo[1,2-b]pyridazin-3-yl)benzamide,
N-cyclopropyl-4-{6-[(2,5-difluorophenyl)sulfanyl]-8-[(2-hydroxy-2-methylpropyl)amino]imidazo[1,2-b]pyridazin-3-yl}-2-methylbenzamide,
N-cyclopropyl-4-{6-[(3,4-difluorophenyl)sulfanyl]-8-[(3,3,3-trifluoropropyl)amino]imidazo[1,2-b]pyridazin-3-yl}-2-methylbenzamide,
N-cyclopropyl-4-{6-[(4-fluorophenyl)sulfanyl]-8-[(3,3,3-trifluoropropyl)amino]imidazo[1,2-b]pyridazin-3-yl}-2-methylbenzamide,
N-cyclopropyl-4-{6-[(3,5-difluorophenyl)sulfanyl]-8-[(3,3,3-trifluoropropyl)amino]imidazo[1,2-b]pyridazin-3-yl}-2-methylbenzamide,
N-cyclopropyl-4-{6-[(2,3-difluorophenyl)sulfanyl]-8-[(3,3,3-trifluoropropyl)amino]imidazo[1,2-b]pyridazin-3-yl}-2-methylbenzamide,
N-cyclopropyl-4-{6-(4-fluorophenoxy)-8-[(2-hydroxy-2-methylpropyl)amino]imidazo[1,2-b]pyridazin-3-yl}-2-methylbenzamide,
N-cyclopropyl-4-{6-(3,4-difluorophenoxy)-8-[(2-hydroxy-2-methylpropyl)amino]imidazo[1,2-b]pyridazin-3-yl}-2-methylbenzamide,
N-cyclopropyl-4-{6-[(2,5-difluorophenyl)sulfanyl]-8-[(3,3,3-trifluoropropyl)amino]imidazo[1,2-b]pyridazin-3-yl}-2-methylbenzamide,
N-cyclopropyl-4-{8-[(2-hydroxy-2-methylpropyl)amino]-6-(4-isopropoxyphenoxy)imidazo[1,2-b]pyridazin-3-yl}-2-methylbenzamide,
N-cyclopropyl-4-{6-(4-isopropoxyphenoxy)-8-[(3,3,3-trifluoropropyl)amino]imidazo[1,2-b]pyridazin-3-yl}-2-methylbenzamide,
N-cyclopropyl-4-{6-(2,3-difluorophenoxy)-8-[(3,3,3-trifluoropropyl)amino]imidazo[1,2-b]pyridazin-3-yl}-2-methylbenzamide,
N-cyclopropyl-4-{6-(2-fluoro-5-methylphenoxy)-8-[(3,3,3-trifluoropropyl)amino]imidazo[1,2-b]pyridazin-3-yl}-2-methylbenzamide,
N-cyclopropyl-4-{6-(3,4-difluorophenoxy)-8-[(3,3,3-trifluoropropyl)amino]imidazo[1,2-b]pyridazin-3-yl}-2-methylbenzamide,
N-cyclopropyl-4-{8-[(2-hydroxy-2-methylpropyl)amino]-6-(2-thienylsulfanyl)imidazo[1,2-b]pyridazin-3-yl}-2-methylbenzamide,
N-cyclopropyl-4-{6-(3,5-di fluorophenoxy)-8-[(2-hydroxy-2-methylpropyl)amino]imidazo[1,2-b]pyridazin-3-yl}-2-methylbenzamide,
N-cyclopropyl-4-{8-[(2-hydroxy-2-methylpropyl)amino]-6-[(6-methylpyridin-3-yl)oxy]imidazo[1,2-b]pyridazin-3-yl}-2-methylbenzamide,
N-cyclopropyl-4-{8-[(2-hydroxy-2-methylpropyl)amino]-6-(pyrimidin-5-yloxy)imidazo[1,2-b]pyridazin-3-yl}-2-methylbenzamide,
4-{6-(3-chlorophenoxy)-8-[(3,3,3-trifluoropropyl)amino]imidazo[1,2-b]pyridazin-3-yl}-N-cyclopropyl-2-methylbenzamide,
4-{6-(4-chlorophenoxy)-8-[(3,3,3-trifluoropropyl)amino]imidazo[1,2-b]pyridazin-3-yl}-N-cyclopropyl-2-methylbenzamide,
N-cyclopropyl-4-{6-[(2-fluorophenyl)sulfanyl]-8-[(3,3,3-trifluoropropyl)amino]imidazo[1,2-b]pyridazin-3-yl}-2-methylbenzamide,
N-cyclopropyl-4-{6-[(5-fluoro-2-methylphenyl)sulfanyl]-8-[(3,3,3-trifluoropropyl)amino]imidazo[1,2-b]pyridazin-3-yl}-2-methylbenzamide,
N-cyclopropyl-4-(6-{[2-(hydroxymethyl)phenyl]sulfanyl}-8-[(3,3,3-trifluoropropyl)amino]imidazo[1,2-b]pyridazin-3-yl)-2-methylbenzamide,
N-cyclopropyl-4-{8-[(2-hydroxy-2-methylpropyl)amino]-6-[(3-methoxy-phenyl)sulfanyl]imidazo[1,2-b]pyridazin-3-yl}-2-methylbenzamide,
N-cyclopropyl-4-{8-[(2-hydroxy-2-methylpropyl)amino]-6-[(3-isopropyl-phenyl)sulfanyl]imidazo[1,2-b]pyridazin-3-yl}-2-methylbenzamide,
N-cyclopropyl-4-{8-[(2-hydroxy-2-methylpropyl)amino]-6-(pyridin-2-yloxy)imidazo[1,2-b]pyridazin-3-yl}-2-methylbenzamide,
N-cyclopropyl-4-{6-[3-(2-hydroxy-2-methylpropoxy)phenoxy]-8-[(2-hydroxy-2-methylpropyl)amino]imidazo[1,2-b]pyridazin-3-yl}-2-methylbenzamide,
N-cyclopropyl-4-{6-[(3-fluorophenyl)sulfanyl]-8-[(2-hydroxy-ethyl)amino]imidazo[1,2-b]pyridazin-3-yl}-2-methylbenzamide,
N-cyclopropyl-4-{6-(3-fluorophenoxy)-8-[(2-hydroxy-ethyl)amino]imidazo[1,2-b]pyridazin-3-yl}-2-methylbenzamide,
N-cyclopropyl-4-{6-(2-hydroxyphenoxy)-8-[(3,3,3-trifluoropropyl)amino]imidazo[1,2-b]pyridazin-3-yl}-2-methylbenzamide,
N-cyclopropyl-4-{6-(3-fluorophenoxy)-8-[(tetrahydro-2H-thiopyran-4-ylmethyl)amino]imidazo[1,2-b]pyridazin-3-yl}-2-methylbenzamide,
N-cyclopropyl-4-{6-(3-fluoro-5-methylphenoxy)-8-[(tetrahydro-2H-thiopyran-4-ylmethyl)amino]imidazo[1,2-b]pyridazin-3-yl}-2-methylbenzamide,
N-cyclopropyl-4-{6-(2-fluorophenoxy)-8-[(tetrahydro-2H-thiopyran-4-ylmethyl)amino]imidazo[1,2-b]pyridazin-3-yl}-2-methylbenzamide,
N-cyclopropyl-2-methyl-4-{6-(phenylsulfanyl)-8-[(tetrahydro-2H-thiopyran-4-ylmethyl)amino]imidazo[1,2-b]pyridazin-3-yl}benzamide,
N-cyclopropyl-4-{6-[(3-fluorophenyl)sulfanyl]-8-[(tetrahydro-2H-thiopyran-4-ylmethyl)amino]imidazo[1,2-b]pyridazin-3-yl}-2-methylbenzamide,
N-cyclopropyl-4-{6-[(3-fluoro-5-methylphenyl)sulfanyl]-8-[(tetrahydro-2H-thiopyran-4-ylmethyl)amino]imidazo[1,2-b]pyridazin-3-yl}-2-methylbenzamide,
N-cyclopropyl-4-{6-[(3-hydroxyphenyl)sulfanyl]-8-[(tetrahydro-2H-thiopyran-4-ylmethyl)amino]imidazo[1,2-b]pyridazin-3-yl}-2-methylbenzamide,
N-cyclopropyl-2-methyl-4-{6-(pyridin-3-yloxy)-8-[(tetrahydro-2H-thiopyran-4-ylmethyl)amino]imidazo[1,2-b]pyridazin-3-yl}benzamide,
N-cyclopropyl-4-{6-[(2-hydroxyphenyl)sulfanyl]-8-[(tetrahydro-2H-thiopyran-4-ylmethyl)amino]imidazo[1,2-b]pyridazin-3-yl}-2-methylbenzamide,
N-cyclopropyl-4-{6-(4-fluorophenoxy)-8-[(tetrahydro-2H-thiopyran-4-ylmethyl)amino]imidazo[1,2-b]pyridazin-3-yl}-2-methylbenzamide
4-{6-(4-chloro-3-fluorophenoxy)-8-[(tetrahydro-2H-thiopyran-4-ylmethyl)amino]imidazo[1,2-b]pyridazin-3-yl}-N-cyclopropyl-2-methylbenzamide,
4-{6-(4-chlorophenoxy)-8-[(tetrahydro-2H-thiopyran-4-ylmethyl)amino]imidazo[1,2-b]pyridazin-3-yl}-N-cyclopropyl-2-methylbenzamide,
N-cyclopropyl-4-{6-(2,3-difluorophenoxy)-8-[(tetrahydro-2H-thiopyran-4-ylmethyl)amino]imidazo[1,2-b]pyridazin-3-yl}-2-methylbenzamide,
4-[6-(4-chlorophenoxy)-8-({[(cis/trans)-1-oxidotetrahydro-2H-thiopyran-4-yl]methyl}amino)imidazo[1,2-b]pyridazin-3-yl]-N-cyclopropyl-2-methylbenzamide, 4-[6-(4-chlorophenoxy)-8-{[(1,1-dioxidotetrahydro-2H-thiopyran-4-yl)methyl]amino}imidazo[1,2-b]pyridazin-3-yl]-N-cyclopropyl-2-methylbenzamide, N-cyclopropyl-4-[6-(4-fluorophenoxy)-8-({[(cis/trans)-1-oxidotetrahydro-2H-thiopyran-4-yl]methyl}amino)imidazo[1,2-b]pyridazin-3-yl]-2-methylbenzamide, N-cyclopropyl-4-[8-{[(1,1-dioxidotetrahydro-2H-thiopyran-4-yl)methyl]amino}-6-(4-fluorophenoxy)imidazo[1,2-b]pyridazin-3-yl]-2-methylbenzamide, N-cyclopropyl-2-methyl-4-[8-({[(cis)-1-oxidotetrahydro-2H-thiopyran-4-yl]methyl}amino)-6-(pyridin-3-yloxy)imidazo[1,2-b]pyridazin-3-yl]benzamide, N-cyclopropyl-2-methyl-4-[8-({[(trans)-1-oxidotetrahydro-2H-thiopyran-4-yl]methyl}amino)-6-(pyridin-3-yloxy)imidazo[1,2-b]pyridazin-3-yl]benzamide, N-cyclopropyl-4-[8-{[(1,1-dioxidotetrahydro-2H-thiopyran-4-yl)methyl]amino}-6-(pyridin-3-yloxy)imidazo[1,2-b]pyridazin-3-yl]-2-methylbenzamide, N-cyclopropyl-4-[8-{[(1,1-dioxidotetrahydro-2H-thiopyran-4-yl)methyl]amino}-6-(2-fluorophenoxy)imidazo[1,2-b]pyridazin-3-yl]-2-methylbenzamide, N-cyclopropyl-4-[6-(3-fluorophenoxy)-8-({[(cis/trans)-1-oxidotetrahydro-2H-thiopyran-4-yl]methyl}amino)imidazo[1,2-b]pyridazin-3-yl]-2-methylbenzamide, N-cyclopropyl-4-[8-{[(1,1-dioxidotetrahydro-2H-thiopyran-4-yl)methyl]amino}-6-(3-fluorophenoxy)imidazo[1,2-b]pyridazin-3-yl]-2-methylbenzamide, N-cyclopropyl-4-{6-[(3,4-difluorophenyl)sulfanyl]-8-[(2-hydroxy-2-methylpropyl)amino]imidazo[1,2-b]pyridazin-3-yl}-2-methylbenzamide, N-cyclopropyl-4-(8-{[(1,1-dioxidotetrahydro-2H-thiopyran-4-yl)methyl]amino}-6-[(3-fluorophenyl)sulfanyl]imidazo[1,2-b]pyridazin-3-yl)-2-methylbenzamide, N-cyclopropyl-4-[8-{[(1,1-dioxidotetrahydro-2H-thiopyran-4-yl)methyl]amino}-6-(phenylsulfanyl)imidazo[1,2-b]pyridazin-3-yl]-2-methylbenzamide, N-cyclopropyl-2-methyl-4-[8-({[(cis)-1-oxidotetrahydro-2H-thiopyran-4-yl]methyl}amino)-6-(phenylsulfanyl)imidazo[1,2-b]pyridazin-3-yl]benzamide, N-cyclopropyl-2-methyl-4-[8-({[(trans)-1-oxidotetrahydro-2H-thiopyran-4-yl]methyl}amino)-6-(phenylsulfanyl)imidazo[1,2-b]pyridazin-3-yl]benzamide, N-cyclopropyl-4-(6-[(3-fluorophenyl)sulfanyl]-8-({[(cis)-1-oxidotetrahydro-2H-thiopyran-4-yl]methyl}amino)imidazo[1,2-b]pyridazin-3-yl)-2-methylbenzamide, N-cyclopropyl-4-(6-[(3-fluorophenyl)sulfanyl]-8-({[(trans)-1-oxidotetrahydro-2H-thiopyran-4-yl]methyl}amino)imidazo[1,2-b]pyridazin-3-yl)-2-methylbenzamide, N-cyclopropyl-4-{6-[(4-fluorophenyl)amino]-8-[(2-hydroxy-2-methylpropyl)amino]imidazo[1,2-b]pyridazin-3-yl}-2-methylbenzamide, 4-{6-anilino-8-[(2-hydroxy-2-methylpropyl)amino]imidazo[1,2-b]pyridazin-3-yl}-N-cyclopropyl-2-methylbenzamide, N-cyclopropyl-4-{6-[(3,4-difluorophenyl)amino]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-[(3-methylphenyl)amino]imidazo[1,2-b]pyridazin-3-yl}-2-methylbenzamide, N-cyclopropyl-4-{6-[(5-fluoro-2-methylphenyl)amino]-8-[(2-hydroxy-2-methylpropyl)amino]imidazo[1,2-b]pyridazin-3-yl}-2-methylbenzamide, 4-{6-[(4-chlorophenyl)amino]-8-[(2-hydroxy-2-methylpropyl)amino]imidazo[1,2-b]pyridazin-3-yl}-N-cyclopropyl-2-methylbenzamide, N-cyclopropyl-4-[6-(3-fluorophenoxy)-8-{[(1-methylpiperidin-4-yl)methyl]amino}imidazo[1,2-b]pyridazin-3-yl]-2-methylbenzamide, N-cyclopropyl-4-[8-{[3-(dimethylamino)propyl]amino}-6-(3-fluorophenoxy)imidazo[1,2-b]pyridazin-3-yl]-2-methylbenzamide, N-cyclopropyl-4-[6-(3-fluorophenoxy)-8-{[2-(methylsulfonyl)ethyl]amino}imidazo[1,2-b]pyridazin-3-yl]-2-methylbenzamide, 4-{8-[(2-amino-2-methylpropyl)amino]-6-(3-fluorophenoxy)imidazo[1,2-b]pyridazin-3-yl}-N-cyclopropyl-2-methylbenzamide, 4-{8-[(azetidin-3-ylmethyl)amino]-6-phenoxyimidazo[1,2-b]pyridazin-3-yl}-N-cyclopropyl-2-methylbenzamide, N-cyclopropyl-4-{8-[(2-hydroxy-2-methylpropyl)amino]-6-(4H-1,2,4-triazol-3-ylsulfanyl)imidazo[1,2-b]pyridazin-3-yl}-2-methylbenzamide, N-cyclopropyl-4-{8-[(2-hydroxy-2-methylpropyl)amino]-6-[(4-methyl-1H-imidazol-2-yl)sulfanyl]imidazo[1,2-b]pyridazin-3-yl}-2-methylbenzamide, N-cyclopropyl-4-{8-[(2-hydroxy-2-methylpropyl)amino]-6-(1H-imidazol-2-ylsulfanyl)imidazo[1,2-b]pyridazin-3-yl}-2-methylbenzamide, N-cyclopropyl-4-{8-[(2-hydroxy-2-methylpropyl)amino]-6-[(1-methyl-1H-pyrazol-5-yl)oxy]imidazo[1,2-b]pyridazin-3-yl}-2-methylbenzamide, N-cyclopropyl-4-{8-[(2-hydroxy-2-methylpropyl)amino]-6-[4-(piperazin-1-yl)phenoxy]imidazo[1,2-b]pyridazin-3-yl}-2-methylbenzamide, N-cyclopropyl-4-{8-[(2-hydroxy-2-methylpropyl)amino]-6-[(1-methyl-1H-pyrazol-4-yl)oxy]imidazo[1,2-b]pyridazin-3-yl}-2-methylbenzamide, tert-butyl 4-[4-({3-[4-(cyclopropylcarbamoyl)-3-methylphenyl]-8-[(2-hydroxy-2-methylpropyl)amino]imidazo[1,2-b]pyridazin-6-yl}oxy)phenyl]piperazine-1-carboxylate, N-cyclopropyl-4-{6-(3-fluorophenoxy)-8-[(tetrahydro-2H-pyran-4-ylmethyl)amino]imidazo[1,2-b]pyridazin-3-yl}-2-methylbenzamide, N-cyclopropyl-4-{6-[(3-fluorophenyl)amino]-8-[(3,3,3-trifluoropropyl)amino]imidazo[1,2-b]pyridazin-3-yl}-2-methylbenzamide, N-cyclopropyl-4-{6-(3-fluorophenoxy)-8-[(3-hydroxy-3-methylbutyl)amino]imidazo[1,2-b]pyridazin-3-yl}-2-methylbenzamide, N-cyclopropyl-4-[8-{[(1,1-dioxidotetrahydrothiophen-3-yl)methyl]amino}-6-(3-fluorophenoxy)imidazo[1,2-b]pyridazin-3-yl]-2-methylbenzamide, N-cyclopropyl-4-{6-(3-fluorophenoxy)-8-[(tetrahydrofuran-3-ylmethyl)amino]imidazo[1,2-b]pyridazin-3-yl}-2-methylbenzamide, N-cyclopropyl-4-[6-(3-fluorophenoxy)-8-{[(1-methyl-5-oxopyrrolidin-3-yl)methyl]amino}imidazo[1,2-b]pyridazin-3-yl]-2-methylbenzamide, N-cyclopropyl-4-[8-{[(3,3-difluorocyclobutyl)methyl]amino}-6-(3-fluorophenoxy)imidazo[1,2-b]pyridazin-3-yl]-2-methylbenzamide, N-cyclopropyl-4-{8-[(2-hydroxy-2-methylpropyl)amino]-6-(pyridin-4-yloxy)imidazo[1,2-b]pyridazin-3-yl}-2-methylbenzamide, N-cyclopropyl-4-{8-[(2-hydroxy-2-methylpropyl)amino]-6-(pyridin-4-ylsulfanyl)imidazo[1,2-b]pyridazin-3-yl}-2-methylbenzamide, N-cyclopropyl-4-{8-[(2-hydroxy-2-methylpropyl)amino]-6-(pyridin-2-ylsulfanyl)imidazo[1,2-b]pyridazin-3-yl}-2-methylbenzamide, 4-{8-[(2-cyanoethyl)amino]-6-(3-fluorophenoxy)imidazo[1,2-b]pyridazin-3-yl}-N-cyclopropyl-2-methylbenzamide, 4-{6-[(4-chloro-2-fluorophenyl)amino]-8-[(2-hydroxy-2-methylpropyl)amino]imidazo[1,2-b]pyridazin-3-yl}-N-cyclopropyl-2-methylbenzamide, N-cyclopropyl-4-{8-[(2-hydroxy-2-methylpropyl)amino]-6-[(5-methoxy-2-methylphenyl)amino]imidazo[1,2-b]pyridazin-3-yl}-2-methylbenzamide, N-cyclopropyl-4-{6-[(3,5-difluorophenyl)amino]-8-[(2-hydroxy-2-methylpropyl)amino]imidazo[1,2-b]pyridazin-3-yl}-2-methylbenzamide, N-cyclopropyl-4-{6-[(2,3-difluorophenyl)amino]-8-[(2-hydroxy-2-methylpropyl)amino]imidazo[1,2-b]pyridazin-3-yl}-2-methylbenzamide, N-cyclopropyl-4-{6-[(3-fluoro-4-methoxyphenyl)amino]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-[(4-methoxyphenyl)amino]imidazo[1,2-b]pyridazin-3-yl}-2-methylbenzamide, 4-{6-[(3-chlorophenyl)amino]-8-[(2-hydroxy-2-methylpropyl)amino]imidazo[1,2-b]pyridazin-3-yl}-N-cyclopropyl-2-methylbenzamide, N-cyclopropyl-4-{6-[(2,4-difluorophenyl)amino]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-(pyridin-2-ylamino)imidazo[1,2-b]pyridazin-3-yl}-2-methylbenzamide, N-cyclopropyl-4-{6-[(4-fluorophenyl)amino]-8-[(3,3,3-trifluoropropyl)amino]imidazo[1,2-b]pyridazin-3-yl}-2-methylbenzamide, N-cyclopropyl-4-{8-[(2-hydroxy-2-methylpropyl)amino]-6-(pyridin-3-ylamino)imidazo[1,2-b]pyridazin-3-yl}-2-methylbenzamide, N-cyclopropyl-4-{6-[(2-fluoro-4-methylphenyl)sulfanyl]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-(3-isopropoxyphenoxy)imidazo[1,2-b]pyridazin-3-yl}-2-methylbenzamide, N-cyclopropyl-4-{6-[(2-fluoro-4-methylphenyl)sulfanyl]-8-[(3,3,3-trifluoropropyl)amino]imidazo[1,2-b]pyridazin-3-yl}-2-methylbenzamide N-cyclopropyl-4-{8-[(2-hydroxy-2-methylpropyl)amino]-6-(pyridin-4-ylamino)imidazo[1,2-b]pyridazin-3-yl}-2-methylbenzamide, N-cyclopropyl-4-{8-[(2-hydroxy-2-methylpropyl)amino]-6-[(6-methoxypyridin-3-yl)amino]imidazo[1,2-b]pyridazin-3-yl}-2-methylbenzamide, N-cyclopropyl-4-{6-[(2-fluoro-5-methylphenyl)amino]-8-[(3,3,3-trifluoropropyl)amino]imidazo[1,2-b]pyridazin-3-yl}-2-methylbenzamide, 4-{6-anilino-8-[(3,3,3-trifluoropropyl)amino]imidazo[1,2-b]pyridazin-3-yl}-N-cyclopropyl-2-methylbenzamide, N-cyclopropyl-4-{6-[(2-fluorophenyl)amino]-8-[(3,3,3-trifluoropropyl)amino]imidazo[1,2-b]pyridazin-3-yl}-2-methylbenzamide, N-cyclopropyl-4-(6-{[2-(hydroxymethyl)phenyl]amino}-8-[(3,3,3-trifluoropropyl)amino]imidazo[1,2-b]pyridazin-3-yl)-2-methylbenzamide, N-cyclopropyl-4-{6-[(3-fluoro-5-methylphenyl)amino]-8-[(3,3,3-trifluoropropyl)amino]imidazo[1,2-b]pyridazin-3-yl}-2-methylbenzamide, 4-{6-[(4-chloro-3-fluorophenyl)amino]-8-[(3,3,3-trifluoropropyl)amino]imidazo[1,2-b]pyridazin-3-yl}-N-cyclopropyl-2-methylbenzamide, N-cyclopropyl-4-{6-[(3,4-difluorophenyl)amino]-8-[(3,3,3-trifluoropropyl)amino]imidazo[1,2-b]pyridazin-3-yl}-2-methylbenzamide, 4-{6-[(4-chlorophenyl)amino]-8-[(3,3,3-trifluoropropyl)amino]imidazo[1,2-b]pyridazin-3-yl}-N-cyclopropyl-2-methylbenzamide, N-cyclopropyl-4-{6-[(5-fluoro-2-methylphenyl)amino]-8-[(3,3,3-trifluoropropyl)amino]imidazo[1,2-b]pyridazin-3-yl}-2-methylbenzamide, 4-{6-[(4-chloro-2-fluorophenyl)amino]-8-[(3,3,3-trifluoropropyl)amino]imidazo[1,2-b]pyridazin-3-yl}-N-cyclopropyl-2-methylbenzamide, 4-{6-[(5-chloro-2-methylphenyl)amino]-8-[(3,3,3-trifluoropropyl)amino]imidazo[1,2-b]pyridazin-3-yl}-N-cyclopropyl-2-methylbenzamide, N-cyclopropyl-4-{6-[(3,5-difluorophenyl)amino]-8-[(3,3,3-trifluoropropyl)amino]imidazo[1,2-b]pyridazin-3-yl}-2-methylbenzamide, 4-{6-[(3-chlorophenyl)amino]-8-[(3,3,3-trifluoropropyl)amino]imidazo[1,2-b]pyridazin-3-yl}-N-cyclopropyl-2-methylbenzamide, N-cyclopropyl-4-{6-[(2,3-difluorophenyl)amino]-8-[(3,3,3-trifluoropropyl)amino]imidazo[1,2-b]pyridazin-3-yl}-2-methylbenzamide, N-cyclopropyl-2-methyl-4-{6-[3-(propan-2-yloxy)phenoxy]-8-[(3,3,3-trifluoropropyl)amino]imidazo[1,2-b]pyridazin-3-yl}benzamide, N-cyclopropyl-4-{6-[(4-fluoro-3-methylphenyl)amino]-8-[(2-hydroxy-2-methylpropyl)amino]imidazo[1,2-b]pyridazin-3-yl}-2-methylbenzamide, N-cyclopropyl-4-{6-[(2-fluoro-5-methylphenyl)amino]-8-[(2-hydroxy-2-methylpropyl)amino]imidazo[1,2-b]pyridazin-3-yl}-2-methylbenzamide, N-cyclopropyl-4-{6-[(2-fluorophenyl)amino]-8-[(2-hydroxy-2-methylpropyl)amino]imidazo[1,2-b]pyridazin-3-yl}-2-methylbenzamide, N-cyclopropyl-4-{8-[(2-hydroxy-2-methylpropyl)amino]-6-[(3-isopropylphenyl)amino]imidazo[1,2-b]pyridazin-3-yl}-2-methylbenzamide, N-cyclopropyl-4-(6-{[4-(2-hydroxyethyl)phenyl]amino}-8-[(2-hydroxy-2-methylpropyl)amino]imidazo[1,2-b]pyridazin-3-yl)-2-methylbenzamide, N-cyclopropyl-4-{6-[(3-fluoro-2-methylphenyl)sulfanyl]-8-[(3,3,3-trifluoropropyl)amino]imidazo[1,2-b]pyridazin-3-yl}-2-methylbenzamide, N-cyclopropyl-4-{6-[(2-methoxyphenyl)amino]-8-[(3,3,3-trifluoropropyl)amino]imidazo[1,2-b]pyridazin-3-yl}-2-methylbenzamide, N-cyclopropyl-2-methyl-4-{6-[2-(methylamino)phenoxy]-8-[(3,3,3-trifluoropropyl)amino]imidazo[1,2-b]pyridazin-3-yl}benzamide, N-cyclopropyl-4-{6-(5-fluoro-2-methylphenoxy)-8-[(3,3,3-trifluoropropyl)amino]imidazo[1,2-b]pyridazin-3-yl}-2-methylbenzamide, N-cyclopropyl-4-{6-(5-fluoro-2-methylphenoxy)-8-[(2-hydroxy-2-methylpropyl)amino]imidazo[1,2-b]pyridazin-3-yl}-2-methylbenzamide, 4-(6-{[4-chloro-2-(hydroxymethyl)phenyl]sulfanyl}-8-[(3,3,3-trifluoropropyl)amino]imidazo[1,2-b]pyridazin-3-yl)-N-cyclopropyl-2-methylbenzamide, 4-(6-{[4-chloro-2-(hydroxymethyl)phenyl]sulfanyl}-8-[(2-hydroxy-2-methylpropyl)amino]imidazo[1,2-b]pyridazin-3-yl)-N-cyclopropyl-2-methylbenzamide, N-cyclopropyl-4-{6-[(3-fluoro-5-methylphenyl)amino]-8-[(2-hydroxy-2-methylpropyl)amino]imidazo[1,2-b]pyridazin-3-yl}-2-methylbenzamide, 4-{6-(2-aminophenoxy)-8-[(3,3,3-trifluoropropyl)amino]imidazo[1,2-b]pyridazin-3-yl}-N-cyclopropyl-2-methylbenzamide, 4-{6-(2-amino-4-fluorophenoxy)-8-[(3,3,3-trifluoropropyl)amino]imidazo[1,2-b]pyridazin-3-yl}-N-cyclopropyl-2-methylbenzamide, N-cyclopropyl-4-{6-[(4-fluoro-2-hydroxyphenyl)amino]-8-[(3,3,3-trifluoropropyl)amino]imidazo[1,2-b]pyridazin-3-yl}-2-methylbenzamide, 4-{6-(2-chloro-3-fluorophenoxy)-8-[(2-hydroxy-2-methylpropyl)amino]imidazo[1,2-b]pyridazin-3-yl}-N-cyclopropyl-2-methylbenzamide, N-cyclopropyl-4-{8-[(2-hydroxy-2-methylpropyl)amino]-6-[(3-methoxy-2-methylphenyl)amino]imidazo[1,2-b]pyridazin-3-yl}-2-methylbenzamide, N-cyclopropyl-4-{6-[(2-hydroxyphenyl)amino]-8-[(3,3,3-trifluoropropyl)amino]imidazo[1,2-b]pyridazin-3-yl}-2-methylbenzamide, N-cyclopropyl-4-{6-[(4-fluoro-3-methoxyphenyl)amino]-8-[(2-hydroxy-2-methylpropyl)amino]imidazo[1,2-b]pyridazin-3-yl}-2-methylbenzamide, 4-{6-[(4-chloro-3-fluorophenyl)amino]-8-[(2-hydroxy-2-methylpropyl)amino]imidazo[1,2-b]pyridazin-3-yl}-N-cyclopropyl-2-methylbenzamide, N-cyclopropyl-4-{8-[(2-hydroxy-2-methylpropyl)amino]-6-[(2-methoxyphenyl)amino]imidazo[1,2-b]pyridazin-3-yl}-2-methylbenzamide N-cyclopropyl-4-{8-[(2-hydroxy-2-methylpropyl)amino]-6-[(3-methoxyphenyl)amino]imidazo[1,2-b]pyridazin-3-yl}-2-methylbenzamide, 4-{6-[(5-chloro-2-methylphenyl)amino]-8-[(2-hydroxy-2-methylpropyl)amino]imidazo[1,2-b]pyridazin-3-yl}-N-cyclopropyl-2-methylbenzamide, 4-{6-[(2-chloro-4-fluorophenyl)amino]-8-[(2-hydroxy-2-methylpropyl)amino]imidazo[1,2-b]pyridazin-3-yl}-N-cyclopropyl-2-methylbenzamide, N-cyclopropyl-4-{6-[(6-fluoropyridin-3-yl)amino]-8-[(2-hydroxy-2-methylpropyl)amino]imidazo[1,2-b]pyridazin-3-yl}-2-methylbenzamide, N-cyclopropyl-4-{6-[(3-ethenylphenyl)amino]-8-[(2-hydroxy-2-methylpropyl)amino]imidazo[1,2-b]pyridazin-3-yl}-2-methylbenzamide, N-cyclopropyl-4-{6-[(6-fluoropyridin-3-yl)oxy]-8-[(2-hydroxy-2-methylpropyl)amino]imidazo[1,2-b]pyridazin-3-yl}-2-methylbenzamide, 5-({3-[4-(cyclopropylcarbamoyl)-3-methylphenyl]-8-[(2-hydroxy-2-methylpropyl)amino]imidazo[1,2-b]pyridazin-6-yl}oxy)nicotinamide, N-cyclopropyl-4-{8-[(2-hydroxy-2-methylpropyl)amino]-6-(pyrazin-2-ylsulfanyl)imidazo[1,2-b]pyridazin-3-yl}-2-methylbenzamide, N-cyclopropyl-4-{8-[(2-hydroxy-2-methylpropyl)amino]-6-[(4-methyl-4H-1,2,4-triazol-3-yl)sulfanyl]imidazo[1,2-b]pyridazin-3-yl}-2-methylbenzamide, N-cyclopropyl-4-{8-[(2-hydroxy-2-methylpropyl)amino]-6-(1H-pyrazol-5-yloxy)imidazo[1,2-b]pyridazin-3-yl}-2-methylbenzamide, N-cyclopropyl-4-{8-[(2-hydroxy-2-methylpropyl)amino]-6-[(5-methyl-1H-pyrazol-3-yl)oxy]imidazo[1,2-b]pyridazin-3-yl}-2-methylbenzamide, 4-{6-[(2-amino-4-fluorophenyl)sulfanyl]-8-[(3,3,3-trifluoropropyl)amino]imidazo[1,2-b]pyridazin-3-yl}-N-cyclopropyl-2-methylbenzamide, N-cyclopropyl-4-{6-[2-methoxy-3-(propan-2-yl)phenoxy]-8-[(3,3,3-trifluoropropyl)amino]imidazo[1,2-b]pyridazin-3-yl}-2-methylbenzamide, N-cyclopropyl-2-methyl-4-{6-[(4-methyl-4H-1,2,4-triazol-3-yl)sulfanyl]-8-[(3,3,3-trifluoropropyl)amino]imidazo[1,2-b]pyridazin-3-yl}benzamide, N-cyclopropyl-2-methyl-4-{6-(pyrazin-2-ylsulfanyl)-8-[(3,3,3-trifluoropropyl)amino]imidazo[1,2-b]pyridazin-3-yl}benzamide, N-cyclopropyl-4-{6-[(4-fluoro-3-methoxyphenyl)amino]-8-[(3,3,3-trifluoropropyl)amino]imidazo[1,2-b]pyridazin-3-yl}-2-methylbenzamide, N-cyclopropyl-2-methyl-4-{6-[(3-methylphenyl)amino]-8-[(3,3,3-trifluoropropyl)amino]imidazo[1,2-b]pyridazin-3-yl}benzamide, N-cyclopropyl-4-{6-[(3-fluoro-4-methoxyphenyl)amino]-8-[(3,3,3-trifluoropropyl)amino]imidazo[1,2-b]pyridazin-3-yl}-2-methylbenzamide, N-cyclopropyl-4-{6-[(4-methoxyphenyl)amino]-8-[(3,3,3-trifluoropropyl)amino]imidazo[1,2-b]pyridazin-3-yl}-2-methylbenzamide, N-cyclopropyl-4-{6-[(3-methoxy-2-methylphenyl)amino]-8-[(3,3,3-trifluoropropyl)amino]imidazo[1,2-b]pyridazin-3-yl}-2-methylbenzamide, N-cyclopropyl-4-(6-{[4-(2-hydroxyethyl)phenyl]amino}-8-[(3,3,3-trifluoropropyl)amino]imidazo[1,2-b]pyridazin-3-yl)-2-methylbenzamide, N-cyclopropyl-4-{6-[(4-fluoro-3-methylphenyl)amino]-8-[(3,3,3-trifluoropropyl)amino]imidazo[1,2-b]pyridazin-3-yl}-2-methylbenzamide, N-cyclopropyl-4-{6-[(6-methoxypyridin-3-yl)amino]-8-[(3,3,3-trifluoropropyl)amino]imidazo[1,2-b]pyridazin-3-yl}-2-methylbenzamide, N-cyclopropyl-4-{6-[(5-methoxy-2-methylphenyl)amino]-8-[(3,3,3-trifluoropropyl)amino]imidazo[1,2-b]pyridazin-3-yl}-2-methylbenzamide, N-cyclopropyl-4-{8-[(2-hydroxy-2-methylpropyl)amino]-6-[(2-hydroxyphenyl)amino]imidazo[1,2-b]pyridazin-3-yl}-2-methylbenzamide, N-cyclopropyl-4-{6-[(4-fluoro-2-methoxyphenyl)amino]-8-[(2-hydroxy-2-methylpropyl)amino]imidazo[1,2-b]pyridazin-3-yl}-2-methylbenzamide, N-cyclopropyl-4-(6-{[2-(hydroxymethyl)phenyl]amino}-8-[(2-hydroxy-2-methylpropyl)amino]imidazo[1,2-b]pyridazin-3-yl)-2-methylbenzamide, 4-(6-{[4-(2-aminoethyl)phenyl]amino}-8-[(2-hydroxy-2-methylpropyl)amino]imidazo[1,2-b]pyridazin-3-yl)-N-cyclopropyl-2-methylbenzamide, N-cyclopropyl-4-{6-[(6-fluoropyridin-3-yl)oxy]-8-[(3,3,3-trifluoropropyl)amino]imidazo[1,2-b]pyridazin-3-yl}-2-methylbenzamide, N-cyclopropyl-4-{6-(2-fluoro-4-methoxyphenoxy)-8-[(3,3,3-trifluoropropyl)amino]imidazo[1,2-b]pyridazin-3-yl}-2-methylbenzamide, N-cyclopropyl-4-{6-[(6-fluoropyridin-3-yl)amino]-8-[(3,3,3-trifluoropropyl)amino]imidazo[1,2-b]pyridazin-3-yl}-2-methylbenzamide, N-cyclopropyl-4-{6-[2-hydroxy-3-(propan-2-yl)phenoxy]-8-[(3,3,3-trifluoropropyl)amino]imidazo[1,2-b]pyridazin-3-yl}-2-methylbenzamide, N-cyclopropyl-4-{6-[(4-fluoro-3-hydroxyphenyl)amino]-8-[(3,3,3-trifluoropropyl)amino]imidazo[1,2-b]pyridazin-3-yl}-2-methylbenzamide, N-cyclopropyl-4-{6-[(5-hydroxy-2-methylphenyl)amino]-8-[(3,3,3-trifluoropropyl)amino]imidazo[1,2-b]pyridazin-3-yl}-2-methylbenzamide, N-cyclopropyl-4-{6-(2-fluoro-4-methoxyphenoxy)-8-[(tetrahydro-2H-pyran-4-ylmethyl)amino]imidazo[1,2-b]pyridazin-3-yl}-2-methylbenzamide, N-cyclopropyl-4-{8-[(2-hydroxy-2-methylpropyl)amino]-6-[(3-hydroxyphenyl)amino]imidazo[1,2-b]pyridazin-3-yl}-2-methylbenzamide, N-cyclopropyl-4-{6-[(3,4-difluorophenyl)amino]-8-[(4,4,4-trifluorobutyl)amino]imidazo[1,2-b]pyridazin-3-yl}-2-methylbenzamide, N-cyclopropyl-4-{6-[(5-fluoro-2-methylphenyl)amino]-8-[(4,4,4-trifluorobutyl)amino]imidazo[1,2-b]pyridazin-3-yl}-2-methylbenzamide, N-cyclopropyl-4-{6-[(3-fluoro-5-methylphenyl)sulfanyl]-8-[(4,4,4-trifluorobutyl)amino]imidazo[1,2-b]pyridazin-3-yl}-2-methylbenzamide, N-cyclopropyl-4-{6-[(2,3-difluorophenyl)amino]-8-[(4,4,4-trifluorobutyl)amino]imidazo[1,2-b]pyridazin-3-yl}-2-methylbenzamide, 4-{6-[(5-chloro-2-methylphenyl)amino]-8-[(4,4,4-trifluorobutyl)amino]imidazo[1,2-b]pyridazin-3-yl}-N-cyclopropyl-2-methylbenzamide, N-cyclopropyl-4-{6-(3-fluoro-5-methylphenoxy)-8-[(4,4,4-trifluorobutyl)amino]imidazo[1,2-b]pyridazin-3-yl}-2-methylbenzamide, 4-{6-(cyclopentylamino)-8-[(3,3,3-trifluoropropyl)amino]imidazo[1,2-b]pyridazin-3-yl}-N-cyclopropyl-2-methylbenzamide, N-cyclopropyl-4-{6-[(3-hydroxy-2-methylphenyl)amino]-8-[(3,3,3-trifluoropropyl)amino]imidazo[1,2-b]pyridazin-3-yl}-2-methylbenzamide, 4-{6-(cyclopentyloxy)-8-[(3,3,3-trifluoropropyl)amino]imidazo[1,2-b]pyridazin-3-yl}-N-cyclopropyl-2-methylbenzamide, N-cyclopropyl-4-{6-[(5-hydroxy-2-methylphenyl)amino]-8-[(3,3,3-trifluoropropyl)amino]imidazo[1,2-b]pyridazin-3-yl}-2-methylbenzamide, N-cyclopropyl-4-{6-[(4-fluoro-2-methoxyphenyl)amino]-8-[(4,4,4-trifluorobutyl)amino]imidazo[1,2-b]pyridazin-3-yl}-2-methylbenzamide, N-cyclopropyl-4-{6-[2-fluoro-3-(methylsulfanyl)phenoxy]-8-[(2-hydroxy-2-methylpropyl)amino]imidazo[1,2-b]pyridazin-3-yl}-2-methylbenzamide, 4-{6-(3-fluorophenoxy)-8-[(3,3,3-trifluoropropyl)amino]imidazo[1,2-b]pyridazin-3-yl}-2-methyl-N-(1-methylcyclopropyl)benzamide, 4-{6-(3-fluorophenoxy)-8-[(3,3,3-trifluoropropyl)amino]imidazo[1,2-b]pyridazin-3-yl}-N-(1-methoxycyclopropyl)-2-methylbenzamide, N-(1-cyanocyclopropyl)-4-{6-(3-fluorophenoxy)-8-[(3,3,3-trifluoropropyl)amino]imidazo[1,2-b]pyridazin-3-yl}-2-methylbenzamide, N-cyclopropyl-4-{6-[(5-fluoropyridin-3-yl)oxy]-8-[(3,3,3-trifluoropropyl)amino]imidazo[1,2-b]pyridazin-3-yl}-2-methylbenzamide, 4-{6-(2-amino-5-fluorophenoxy)-8-[(3,3,3-trifluoropropyl)amino]imidazo[1,2-b]pyridazin-3-yl}-N-cyclopropyl-2-methylbenzamide, N-cyclopropyl-2-methyl-4-{6-(1,2,3,4-tetrahydroquinolin-8-yloxy)-8-[(3,3,3-trifluoropropyl)amino]imidazo[1,2-b]pyridazin-3-yl}benzamide, N-cyclopropyl-4-{6-(8-hydroxy-3,4-dihydroquinolin-1(2H)-yl)-8-[(3,3,3-trifluoropropyl)amino]imidazo[1,2-b]pyridazin-3-yl}-2-methylbenzamide, N-cyclopropyl-2-methyl-4-{6-[(2-oxo-1,2-dihydroquinolin-8-yl)oxy]-8-[(3,3,3-trifluoropropyl)amino]imidazo[1,2-b]pyridazin-3-yl}benzamide, N-cyclopropyl-2-methyl-4-{6-[(2-methyl-1,2,3,4-tetrahydroisoquinolin-5-yl)oxy]-8-[(3,3,3-trifluoropropyl)amino]imidazo[1,2-b]pyridazin-3-yl}benzamide, N-cyclopropyl-2-methyl-4-{6-(3-methylphenoxy)-8-[(3,3,3-trifluoropropyl)amino]imidazo[1,2-b]pyridazin-3-yl}benzamide, N-cyclopropyl-4-{6-(4-methoxyphenoxy)-8-[(3,3,3-trifluoropropyl)amino]imidazo[1,2-b]pyridazin-3-yl}-2-methylbenzamide, N-cyclopropyl-4-{6-(4-fluorophenoxy)-8-[(3,3,3-trifluoropropyl)amino]imidazo[1,2-b]pyridazin-3-yl}-2-methylbenzamide, N-cyclopropyl-4-{6-(2-fluorophenoxy)-8-[(3,3,3-trifluoropropyl)amino]imidazo[1,2-b]pyridazin-3-yl}-2-methylbenzamide, N-cyclopropyl-2-methyl-4-{6-(2-methylphenoxy)-8-[(3,3,3-trifluoropropyl)amino]imidazo[1,2-b]pyridazin-3-yl}benzamide, N-cyclopropyl-4-{6-(3-fluoro-4-methoxyphenoxy)-8-[(3,3,3-trifluoropropyl)amino]imidazo[1,2-b]pyridazin-3-yl}-2-methylbenzamide, 4-(6-{[4-(acetylamino)pyridin-3-yl]oxy}-8-[(3,3,3-trifluoropropyl)amino]imidazo[1,2-b]pyridazin-3-yl)-N-cyclopropyl-2-methylbenzamide, 4-{6-(2-amino-3-fluorophenoxy)-8-[(3,3,3-trifluoropropyl)amino]imidazo[1,2-b]pyridazin-3-yl}-N-cyclopropyl-2-methylbenzamide, N-cyclopropyl-4-{6-[(2-fluoro-6-hydroxyphenyl)amino]-8-[(3,3,3-trifluoropropyl)amino]imidazo[1,2-b]pyridazin-3-yl}-2-methylbenzamide, N-cyclopropyl-2-methyl-4-{6-(4-methylphenoxy)-8-[(3,3,3-trifluoropropyl)amino]imidazo[1,2-b]pyridazin-3-yl}benzamide, N-cyclopropyl-4-{6-[(4-fluoro-2-hydroxyphenyl)amino]-8-[(3,3,3-trifluoropropyl)amino]imidazo[1,2-b]pyridazin-3-yl}-2-methylbenzamide, N-cyclopropyl-4-{6-[(3-hydroxypyridin-4-yl)amino]-8-[(3,3,3-trifluoropropyl)amino]imidazo[1,2-b]pyridazin-3-yl}-2-methylbenzamide, N-cyclopropyl-2-methyl-4-{6-(1-phenylethenyl)-8-[(3,3,3-trifluoropropyl)amino]imidazo[1,2-b]pyridazin-3-yl}benzamide, N-cyclopropyl-4-{6-(3-fluoro-4-methoxybenzyl)-8-[(3,3,3-trifluoropropyl)amino]imidazo[1,2-b]pyridazin-3-yl}-2-methylbenzamide, N-cyclopropyl-4-{6-(3-fluoro-4-methylbenzyl)-8-[(3,3,3-trifluoropropyl)amino]imidazo[1,2-b]pyridazin-3-yl}-2-methylbenzamide, 4-{6-(3-bromobenzyl)-8-[(3,3,3-trifluoropropyl)amino]imidazo[1,2-b]pyridazin-3-yl}-N-cyclopropyl-2-methylbenzamide, N-cyclopropyl-4-{6-(3-fluorophenoxy)-8-[(3,3,3-trifluoro-2-hydroxypropyl)amino]imidazo[1,2-b]pyridazin-3-yl}-2-methylbenzamide, N-cyclopropyl-4-{8-{[2-(dimethylamino)ethyl]amino}-6-(3-fluorophenoxy)imidazo[1,2-b]pyridazin-3-yl]-2-methylbenzamide, N-cyclopropyl-4-[6-(3-fluorophenoxy)-8-{[(1-methyl-1H-pyrazol-3-yl)methyl]amino}imidazo[1,2-b]pyridazin-3-yl]-2-methylbenzamide, N-cyclopropyl-4-{6-(3-fluorophenoxy)-8-[(1H-pyrazol-3-ylmethyl)amino]imidazo[1,2-b]pyridazin-3-yl}-2-methylbenzamide, N-cyclopropyl-4-[6-(3-fluorophenoxy)-8-({[3-(hydroxymethyl)oxetan-3-yl]methyl}amino)imidazo[1,2-b]pyridazin-3-yl]-2-methylbenzamide,
N-cyclopropyl-4-{8-[(2,3-dihydroxypropyl)amino]-6-(3-fluorophenoxy)imidazo[1,2-b]pyridazin-3-yl}-2-methylbenzamide,
N-cyclopropyl-4-{6-(3-fluorophenoxy)-8-[(2-methoxyethyl)amino]imidazo[1,2-b]pyridazin-3-yl}-2-methylbenzamide,
N-cyclopropyl-4-[8-{[3-(dimethylamino)-3-oxopropyl]amino}-6-(3-fluorophenoxy)imidazo[1,2-b]pyridazin-3-yl]-2-methylbenzamide,
N-cyclopropyl-4-[8-{[(4,4-difluorocyclohexyl)methyl]amino}-6-(3-fluorophenoxy)imidazo[1,2-b]pyridazin-3-yl]-2-methylbenzamide,
N-cyclopropyl-4-{6-(3-fluorophenoxy)-8-[(oxetan-3-ylmethyl)amino]imidazo[1,2-b]pyridazin-3-yl}-2-methylbenzamide,
N-cyclopropyl-4-{6-(3-fluorophenoxy)-8-[(1H-tetrazol-5-ylmethyl)amino]imidazo[1,2-b]pyridazin-3-yl}-2-methylbenzamide,
N-cyclopropyl-4-[8-{[2-(dimethylamino)-2-methylpropyl]amino}-6-(3-fluorophenoxy)imidazo[1,2-b]pyridazin-3-yl]-2-methylbenzamide,
N-cyclopropyl-4-[6-(3-fluorophenoxy)-8-{[2-methyl-2-(morpholin-4-yl)propyl]amino}imidazo[1,2-b]pyridazin-3-yl]-2-methylbenzamide,
N-cyclopropyl-4-[6-(3-fluorophenoxy)-8-{[2-(piperidin-1-yl)ethyl]amino}imidazo[1,2-b]pyridazin-3-yl]-2-methylbenzamide,
N-cyclopropyl-4-[6-(3-fluorophenoxy)-8-{[2-(morpholin-4-yl)ethyl]amino}imidazo[1,2-b]pyridazin-3-yl]-2-methylbenzamide,
N-cyclopropyl-4-[6-(3-fluorophenoxy)-8-{[2-(4-methylpiperazin-1-yl)ethyl]amino}imidazo[1,2-b]pyridazin-3-yl]-2-methylbenzamide,
N-cyclopropyl-4-[6-(3-fluorophenoxy)-8-{[2-(pyrrolidin-1-yl)ethyl]amino}imidazo[1,2-b]pyridazin-3-yl]-2-methylbenzamide,
N-cyclopropyl-4-[6-(3-fluorophenoxy)-8-({3-[methyl(methylcarbamoyl)amino]propy}amino)imidazo[1,2-b]pyridazin-3-yl]-2-methylbenzamide,
4-[8-{[2-(acetylamino)ethyl]amino}-6-(3-fluorophenoxy)imidazo[1,2-b]pyridazin-3-yl]-N-cyclopropyl-2-methylbenzamide,
N-cyclopropyl-4-[6-(3-fluorophenoxy)-8-{[3-(piperidin-1-yl)propyl]amino}imidazo[1,2-b]pyridazin-3-yl]-2-methylbenzamide,
N-cyclopropyl-4-[6-(3-fluorophenoxy)-8-{[3-(morpholin-4-yl)propyl]amino}imidazo[1,2-b]pyridazin-3-yl]-2-methylbenzamide,
N-cyclopropyl-4-[6-(3-fluorophenoxy)-8-{[3-(pyrrolidin-1-yl)propyl]amino}imidazo[1,2-b]pyridazin-3-yl]-2-methylbenzamide,
N-cyclopropyl-4-[6-(3-fluorophenoxy)-8-{[3-(methylsulfonyl)propyl]amino}imidazo[1,2-b]pyridazin-3-yl]-2-methylbenzamide,
4-[8-{[3-(acetylamino)propyl]amino}-6-(3-fluorophenoxy)imidazo[1,2-b]pyridazin-3-yl]-N-cyclopropyl-2-methylbenzamide,
N-cyclopropyl-4-[6-(3-fluorophenoxy)-8-(methylamino)imidazo[1,2-b]pyridazin-3-yl]-2-methylbenzamide,
N-cyclopropyl-4-[6-(3-fluorophenoxy)-8-{[2-(1H-tetrazol-5-yl)ethyl]amino}imidazo[1,2-b]pyridazin-3-yl]-2-methylbenzamide,
N-cyclopropyl-4-{8-[(2,2-difluoroethyl)amino]-6-(3-fluorophenoxy)imidazo[1,2-b]pyridazin-3-yl}-2-methylbenzamide,
N-cyclopropyl-4-[8-{[4-(dimethylamino)butyl]amino}-6-(3-fluorophenoxy)imidazo[1,2-b]pyridazin-3-yl]-2-methylbenzamide,
N-cyclopropyl-4-{6-(3-fluorophenoxy)-8-[(2,2,2-trifluoroethyl)amino]imidazo[1,2-b]pyridazin-3-yl}-2-methylbenzamide,
N-cyclopropyl-4-[6-(3-fluorophenoxy)-8-{[2-(1H-pyrazol-1-yl)ethyl]amino}imidazo[1,2-b]pyridazin-3-yl]-2-methylbenzamide,
N-cyclopropyl-4-[6-(2,3-difluorophenoxy)-8-{[2-(methylsulfonyl)ethyl]amino}imidazo[1,2-b]pyridazin-3-yl]-2-methylbenzamide,
N-cyclopropyl-4-[6-(5-fluoro-2-methylphenoxy)-8-{[2-(methylsulfonyl)ethyl]amino}imidazo[1,2-b]pyridazin-3-yl]-2-methylbenzamide,
N-cyclopropyl-4-[6-(3-fluoro-4-methoxyphenoxy)-8-{[2-(methylsulfonyl)ethyl]amino}imidazo[1,2-b]pyridazin-3-yl]-2-methylbenzamide,
N-cyclopropyl-4-[6-(2-fluoro-4-methoxyphenoxy)-8-{[2-(methylsulfonyl)ethyl]amino}imidazo[1,2-b]pyridazin-3-yl]-2-methylbenzamide,
4-{8-[(2-amino-2-methylpropyl)amino]-6-(3,4-difluorophenoxy)imidazo[1,2-b]pyridazin-3-yl}-N-cyclopropyl-2-methylbenzamide,
4-{8-[(2-amino-2-methylpropyl)amino]-6-(4-chlorophenoxy)imidazo[1,2-b]pyridazin-3-yl}-N-cyclopropyl-2-methylbenzamide
4-{8-[(2-amino-2-methylpropyl)amino]-6-(pyridin-3-yloxy)imidazo[1,2-b]pyridazin-3-yl}-N-cyclopropyl-2-methylbenzamide,
4-[6-(4-chlorophenoxy)-8-{[2-(dimethylamino)ethyl]amino}imidazo[1,2-b]pyridazin-3-yl]-N-cyclopropyl-2-methylbenzamide,
N-cyclopropyl-4-[8-{[2-(dimethylamino)ethyl]amino}-6-(pyridin-3-yloxy)imidazo[1,2-b]pyridazin-3-yl]-2-methylbenzamide,
N-cyclopropyl-4-[6-(3,4-difluorophenoxy)-8-{[2-(dimethylamino)ethyl]amino}imidazo[1,2-b]pyridazin-3-yl]-2-methylbenzamide,
N-cyclopropyl-4-[6-(2,3-difluorophenoxy)-8-{[(1-methylpiperidin-4-yl)methyl]amino}imidazo[1,2-b]pyridazin-3-yl]-2-methylbenzamide,
N-cyclopropyl-2-methyl-4-[8-{[(1-methylpiperidin-4-yl)methyl]amino}-6-(pyridin-3-yloxy)imidazo[1,2-b]pyridazin-3-yl]benzamide,
N-cyclopropyl-4-[6-(2,3-difluorophenoxy)-8-(methylamino)imidazo[1,2-b]pyridazin-3-yl]-2-methylbenzamide,
N-cyclopropyl-4-[6-(3,4-difluorophenoxy)-8-(methylamino)imidazo[1,2-b]pyridazin-3-yl]-2-methylbenzamide,
N-cyclopropyl-4-[6-(5-fluoro-2-methylphenoxy)-8-(methylamino)imidazo[1,2-b]pyridazin-3-yl]-2-methylbenzamide,
N-cyclopropyl-2-methyl-4-{8-(methylamino)-6-[2-(methylamino)phenoxy]imidazo[1,2-b]pyridazin-3-yl}benzamide,
N-cyclopropyl-4-{6-[(2-hydroxyphenyl)(methyl)amino]-8-(methylamino)imidazo[1,2-b]pyridazin-3-yl}-2-methylbenzamide,
N-cyclopropyl-4-{6-[(5-fluoropyridin-3-yl)oxy]-8-(methylamino)imidazo[1,2-b]pyridazin-3-yl}-2-methylbenzamide, N-cyclopropyl-4-[6-(2-fluoro-4-methoxyphenoxy)-8-(methylamino)imidazo[1,2-b]pyridazin-3-yl]-2-methylbenzamide,
N-cyclopropyl-4-[6-(3-fluoro-4-methoxyphenoxy)-8-(methylamino)imidazo[1,2-b]pyridazin-3-yl]-2-methylbenzamide,
N-cyclopropyl-4-[6-(2,3-difluorophenoxy)-8-{[2-(morpholin-4-yl)ethyl]amino}imidazo[1,2-b]pyridazin-3-yl]-2-methylbenzamide,
N-cyclopropyl-4-[6-(5-fluoro-2-methylphenoxy)-8-{[2-(morpholin-4-yl)ethyl]amino}imidazo[1,2-b]pyridazin-3-yl]-2-methylbenzamide,
N-cyclopropyl-2-methyl-4-(6-[2-(methylamino)phenoxy]-8-{[2-(morpholin-4-yl)ethyl]amino}imidazo[1,2-b]pyridazin-3-yl)benzamide,
N-cyclopropyl-4-(6-[(2-hydroxyphenyl)(methyl)amino]-8-{[2-(morpholin-4-yl)ethyl]amino}imidazo[1,2-b]pyridazin-3-yl)-2-methylbenzamide,
N-cyclopropyl-4-[6-(3,4-difluorophenoxy)-8-{[2-(morpholin-4-yl)ethyl]amino}imidazo[1,2-b]pyridazin-3-yl]-2-methylbenzamide,
N-cyclopropyl-4-(6-[(5-fluoropyridin-3-yl)oxy]-8-{[2-(morpholin-4-yl)ethyl]amino}imidazo[1,2-b]pyridazin-3-yl)-2-methylbenzamide,
N-cyclopropyl-4-[6-(3-fluorophenoxy)-8-{[(1-methylazetidin-3-yl)methyl]amino}imidazo[1,2-b]pyridazin-3-yl]-2-methylbenzamide,
4-{8-[(azetidin-3-ylmethyl)amino]-6-(3-fluorophenoxy)imidazo[1,2-b]pyridazin-3-yl}-N-cyclopropyl-2-methylbenzamide,
N-cyclopropyl-4-[6-(2,3-difluorophenoxy)-8-{[(1-methylazetidin-3-yl)methyl]amino}imidazo[1,2-b]pyridazin-3-yl]-2-methylbenzamide,
4-{8-[(azetidin-3-ylmethyl)amino]-6-(2,3-difluorophenoxy)imidazo[1,2-b]pyridazin-3-yl}-N-cyclopropyl-2-methylbenzamide,
4-{8-[(azetidin-3-ylmethyl)amino]-6-[(5-fluoropyridin-3-yl)oxy]imidazo[1,2-b]pyridazin-3-yl}-N-cyclopropyl-2-methylbenzamide,
4-{8-[(azetidin-3-ylmethyl)amino]-6-(5-fluoro-2-methylphenoxy)imidazo[1,2-b]pyridazin-3-yl}-N-cyclopropyl-2-methylbenzamide,
4-{8-[(3-aminopropyl)amino]-6-(3-fluorophenoxy)imidazo[1,2-b]pyridazin-3-yl}-N-cyclopropyl-2-methylbenzamide,
3-({3-[4-(cyclopropylcarbamoyl)-3-methylphenyl]-6-(3-fluorophenoxy)imidazo[1,2-b]pyridazin-8-yl}amino)propane-1-sulfonic acid,
2-({3-[4-(cyclopropylcarbamoyl)-3-methylphenyl]-6-(3-fluorophenoxy)imidazo[1,2-b]pyridazin-8-yl}amino)ethanesulfonic acid,
N-(1-cyanocyclopropyl)-4-{6-(3-fluorophenoxy)-8-[(3,3,3-trifluoropropyl)amino]imidazo[1,2-b]pyridazin-3-yl}-2-methylbenzamide,
4-{6-(3-fluorophenoxy)-8-[(3,3,3-trifluoropropyl)amino]imidazo[1,2-b]pyridazin-3-yl}-2-methylbenzamide,
4-{6-(3-fluorophenoxy)-8-[(3,3,3-trifluoropropyl)amino]imidazo[1,2-b]pyridazin-3-yl}-N,2-dimethylbenzamide,
N-ethyl-4-{6-(3-fluorophenoxy)-8-[(3,3,3-trifluoropropyl)amino]imidazo[1,2-b]pyridazin-3-yl}-2-methylbenzamide,
4-{6-(3-fluorophenoxy)-8-[(3,3,3-trifluoropropyl)amino]imidazo[1,2-b]pyridazin-3-yl}-N-isopropyl-2-methylbenzamide,
4-{6-(3-fluorophenoxy)-8-[(3,3,3-trifluoropropyl)amino]imidazo[1,2-b]pyridazin-3-yl}-2-methyl-N-(3,3,3-trifluoropropyl)benzamide,
4-{6-(3-fluorophenoxy)-8-[(3,3,3-trifluoropropyl)amino]imidazo[1,2-b]pyridazin-3-yl}-2-methyl-N-(2,2,3,3,3-pentafluoropropyl)benzamide,
N-(2,2-difluoroethyl)-4-{6-(3-fluorophenoxy)-8-[(3,3,3-trifluoropropyl)amino]imidazo[1,2-b]pyridazin-3-yl}-2-methylbenzamide,
-{6-(3-fluorophenoxy)-8-[(3,3,3-trifluoropropyl)amino]imidazo[1,2-b]pyridazin-3-yl}-N-isobutyl-2-methylbenzamide,
4-{6-(4-chlorophenoxy)-8-[(3,3,3-trifluoropropyl)amino]imidazo[1,2-b]pyridazin-3-yl}-N,2-dimethylbenzamide,
4-{6-(4-chlorophenoxy)-8-[(3,3,3-trifluoropropyl)amino]imidazo[1,2-b]pyridazin-3-yl}-N-ethyl-2-methylbenzamide,
4-{6-(2-fluoro-4-hydroxyphenoxy)-8-[(3,3,3-trifluoropropyl)amino]imidazo[1,2-b]pyridazin-3-yl}-N,2-dimethylbenzamide,
N-ethyl-4-{6-(2-fluoro-4-hydroxyphenoxy)-8-[(3,3,3-trifluoropropyl)amino]imidazo[1,2-b]pyridazin-3-yl}-2-methylbenzamide,
4-[6-(3,4-difluorophenoxy)-8-{[2-(morpholin-4-yl)ethyl]amino}imidazo[1,2-b]pyridazin-3-yl]-N,2-dimethylbenzamide,
N,2-dimethyl-4-[6-(2-methylphenoxy)-8-{[2-(morpholin-4-yl)ethyl]amino}imidazo[1,2-b]pyridazin-3-yl]benzamide,
4-[6-(4-methoxyphenoxy)-8-{[2-(morpholin-4-yl)ethyl]amino}imidazo[1,2-b]pyridazin-3-yl]-N,2-dimethylbenzamide,
4-[6-(2-fluoro-4-methoxyphenoxy)-8-{[2-(morpholin-4-yl)ethyl]amino}imidazo[1,2-b]pyridazin-3-yl]-N,2-dimethylbenzamide,
4-[6-(5-fluoro-2-methylphenoxy)-8-{[2-(morpholin-4-yl)ethyl]amino}imidazo[1,2-b]pyridazin-3-yl]-N,2-dimethylbenzamide,
4-{6-(3,4-difluorophenoxy)-8-[(tetrahydro-2H-pyran-4-ylmethyl)amino]imidazo[1,2-b]pyridazin-3-yl}-N,2-dimethylbenzamide,
N,2-dimethyl-4-{6-(2-methylphenoxy)-8-[(tetrahydro-2H-pyran-4-ylmethyl)amino]imidazo[1,2-b]pyridazin-3-yl}benzamide,
4-{6-(3-fluorophenoxy)-8-[(tetrahydro-2H-pyran-4-ylmethyl)amino]imidazo[1,2-b]pyridazin-3-yl}-N,2-dimethylbenzamide,
4-{6-(4-methoxyphenoxy)-8-[(tetrahydro-2H-pyran-4-ylmethyl)amino]imidazo[1,2-b]pyridazin-3-yl}-N,2-dimethylbenzamide,
4-{6-(2-fluoro-4-methoxyphenoxy)-8-[(tetrahydro-2H-pyran-4-ylmethyl)amino]imidazo[1,2-b]pyridazin-3-yl}-N,2-dimethylbenzamide,
4-{6-(5-fluoro-2-methylphenoxy)-8-[(tetrahydro-2H-pyran-4-ylmethyl)amino]imidazo[1,2-b]pyridazin-3-yl}-N,2-dimethylbenzamide,
4-{6-(3-fluoro-4-methoxyphenoxy)-8-[(tetrahydro-2H-pyran-4-ylmethyl)amino]imidazo[1,2-b]pyridazin-3-yl}-N,2-dimethylbenzamide,
4-{6-(3,4-difluorophenoxy)-8-[(3,3,3-trifluoropropyl)amino]imidazo[1,2-b]pyridazin-3-yl}-N,2-dimethylbenzamide,
4-{6-(3-fluorophenoxy)-8-[(3,3,3-trifluoropropyl)amino]imidazo[1,2-b]pyridazin-3-yl}-N, 2-dimethylbenzamide, 4-{6-(2-fluoro-4-methoxyphenoxy)-8-[(3,3,3-trifluoropropyl)amino]imidazo[1,2-b]pyridazin-3-yl}-N,2-dimethylbenzamide,
4-{6-(5-fluoro-2-methylphenoxy)-8-[(3,3,3-trifluoropropyl)amino]imidazo[1,2-b]pyridazin-3-yl}-N,2-dimethylbenzamide,
4-{6-(3-fluoro-4-methoxyphenoxy)-8-[(3,3,3-trifluoropropyl)amino]imidazo[1,2-b]pyridazin-3-yl}-N,2-dimethylbenzamide,
4-{8-[(2,2-difluoroethyl)amino]-6-(3,4-difluorophenoxy)imidazo[1,2-b]pyridazin-3-yl}-N,2-dimethylbenzamide,
4-{8-[(2,2-difluoroethyl)amino]-6-(2-fluoro-4-methoxyphenoxy)imidazo[1,2-b]pyridazin-3-yl}-N,2-dimethylbenzamide,
4-{6-(2,3-difluorophenoxy)-8-[(2-methoxyethyl)amino]imidazo[1,2-b]pyridazin-3-yl}-N,2-dimethylbenzamide,
4-{6-(3,4-difluorophenoxy)-8-[(2-methoxyethyl)amino]imidazo[1,2-b]pyridazin-3-yl}-N, 2-dimethylbenzamide,
4-{8-[(2-methoxyethyl)amino]-6-(2-methylphenoxy)imidazo[1,2-b]pyridazin-3-yl}-N,2-dimethylbenzamide,
4-{6-(2-fluoro-4-methoxyphenoxy)-8-[(2-methoxyethyl)amino]imidazo[1,2-b]pyridazin-3-yl}-N,2-dimethylbenzamide,
4-{6-(5-fluoro-2-methylphenoxy)-8-[(2-methoxyethyl)amino]imidazo[1,2-b]pyridazin-3-yl}-N, 2-dimethylbenzamide,
4-{6-(3-fluoro-4-methoxyphenoxy)-8-[(2-methoxyethyl)amino]imidazo[1,2-b]pyridazin-3-yl}-N, 2-dimethylbenzamide,
4-{8-[(2-methoxyethyl)amino]-6-phenoxyimidazo[1,2-b]pyridazin-3-yl}-N,2-dimethylbenzamide,
4-[6-(3,4-difluorophenoxy)-8-{[2-(morpholin-4-yl)ethyl]amino}imidazo[1,2-b]pyridazin-3-yl]-N-ethyl-2-methylbenzamide,
N-ethyl-2-methyl-4-[6-(2-methylphenoxy)-8-{[2-(morpholin-4-yl)ethyl]amino}imidazo[1,2-b]pyridazin-3-yl]benzamide,
N-ethyl-4-[6-(4-methoxyphenoxy)-8-{[2-(morpholin-4-yl)ethyl]amino}imidazo[1,2-b]pyridazin-3-yl]-2-methylbenzamide,
N-ethyl-4-[6-(2-fluoro-4-methoxyphenoxy)-8-{[2-(morpholin-4-yl)ethyl]amino}imidazo[1,2-b]pyridazin-3-yl]-2-methylbenzamide,
N-ethyl-4-[6-(5-fluoro-2-methylphenoxy)-8-{[2-(morpholin-4-yl)ethyl]amino}imidazo[1,2-b]pyridazin-3-yl]-2-methylbenzamide,
N-ethyl-2-methyl-4-(8-{[2-(morpholin-4-yl)ethyl]amino}-6-phenoxyimidazo[1,2-b]pyridazin-3-yl)benzamide,
4-{6-(3,4-difluorophenoxy)-8-[(tetrahydro-2H-pyran-4-ylmethyl)amino]imidazo[1,2-b]pyridazin-3-yl}-N-ethyl-2-methylbenzamide,
N-ethyl-2-methyl-4-{6-(2-methylphenoxy)-8-[(tetrahydro-2H-pyran-4-ylmethyl)amino]imidazo[1,2-b]pyridazin-3-yl}benzamide,
N-ethyl-4-{6-(4-methoxyphenoxy)-8-[(tetrahydro-2H-pyran-4-ylmethyl)amino]imidazo[1,2-b]pyridazin-3-yl}-2-methylbenzamide,
N-ethyl-4-{6-(2-fluoro-4-methoxyphenoxy)-8-[(tetrahydro-2H-pyran-4-ylmethyl)amino]imidazo[1,2-b]pyridazin-3-yl}-2-methylbenzamide,
N-ethyl-4-{6-(5-fluoro-2-methylphenoxy)-8-[(tetrahydro-2H-pyran-4-ylmethyl)amino]imidazo[1,2-b]pyridazin-3-yl}-2-methylbenzamide,
N-ethyl-4-{6-(3-fluoro-4-methoxyphenoxy)-8-[(tetrahydro-2H-pyran-4-ylmethyl)amino]imidazo[1,2-b]pyridazin-3-yl}-2-methylbenzamide,
N-ethyl-2-methyl-4-{6-(2-methylphenoxy)-8-[(3,3,3-trifluoropropyl)amino]imidazo[1,2-b]pyridazin-3-yl}benzamide,
N-ethyl-4-{6-(2-fluoro-4-methoxyphenoxy)-8-[(3,3,3-trifluoropropyl)amino]imidazo[1,2-b]pyridazin-3-yl}-2-methylbenzamide,
N-ethyl-4-{6-(5-fluoro-2-methylphenoxy)-8-[(3,3,3-trifluoropropyl)amino]imidazo[1,2-b]pyridazin-3-yl}-2-methylbenzamide,
N-ethyl-4-{6-(3-fluoro-4-methoxyphenoxy)-8-[(3,3,3-trifluoropropyl)amino]imidazo[1,2-b]pyridazin-3-yl}-2-methylbenzamide,
4-{8-[(2,2-difluoroethyl)amino]-6-(2-fluoro-4-methoxyphenoxy)imidazo[1,2-b]pyridazin-3-yl}-N-ethyl-2-methylbenzamide,
4-{8-[(2,2-difluoroethyl)amino]-6-(5-fluoro-2-methylphenoxy)imidazo[1,2-b]pyridazin-3-yl}-N-ethyl-2-methylbenzamide,
4-{6-(3,4-difluorophenoxy)-8-[(2-methoxyethyl)amino]imidazo[1,2-b]pyridazin-3-yl}-N-ethyl-2-methylbenzamide,
N-ethyl-4-{6-(2-fluoro-4-methoxyphenoxy)-8-[(2-methoxyethyl)amino]imidazo[1,2-b]pyridazin-3-yl}-2-methylbenzamide,
N-ethyl-4-{6-(5-fluoro-2-methylphenoxy)-8-[(2-methoxyethyl)amino]imidazo[1,2-b]pyridazin-3-yl}-2-methylbenzamide,
N-ethyl-4-{6-(3-fluoro-4-methoxyphenoxy)-8-[(2-methoxyethyl)amino]imidazo[1,2-b]pyridazin-3-yl}-2-methylbenzamide, or a stereoisomer, a tautomer, or a salt thereof, or a mixture of same.

7. A compound of general formula Ia:

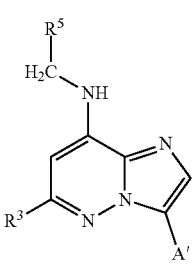

Ia in which $R^3$ and $R^5$ are as defined in claim 1, and A' is

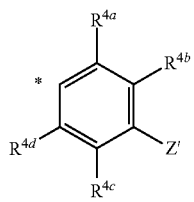

wherein * indicates the point of attachment of said group with the rest of the molecule; $R^{4a}$, $R^{4b}$, $R^{4c}$ and $R^{4d}$ are as defined in claim 1, and Z' represents a group selected from:
—C(=O)OH, —C(=S)OH, —C(=O)O—($C_1$-$C_6$-alkyl) or —C(=S)O—($C_1$-$C_6$-alkyl).

8. A compound of general formula IV:

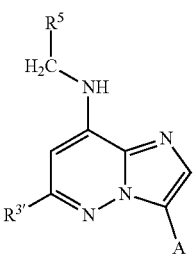

IV in which A, and $R^5$ are as defined in claim 1, and $R^{3'}$ is a leaving group.

9. A compound of general formula VII:

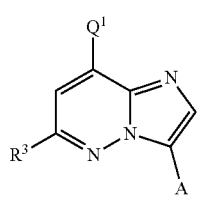

VII in which A, and $R^3$ are as defined in claim 1, and $Q^1$ represents an optionally protected $NH_2$-group or a leaving group.

10. A pharmaceutical composition comprising a compound according to claim 1, or a stereoisomer, a tautomer, or a pharmaceutically acceptable salt thereof, or a mixture of same, and a pharmaceutically acceptable diluent or carrier.

11. A pharmaceutical combination comprising:
one or more compounds according to claim 1, or a stereoisomer, a tautomer, or a pharmaceutically acceptable salt thereof, or a mixture of same;
and
one or more agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, such as Flutamide, Cyproterone acetate, or Bicalutamide; Bortezomib; a platinum derivative, such as Cisplatin, or Carboplatin; Chlorambucil; Methotrexate; and Rituximab.

12. A method of preparing a compound according to claim 1, said method comprising the step of allowing an intermediate compound of general formula IV:

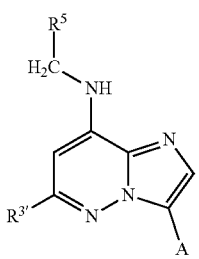

IV in which A, and $R^5$ are as defined in claim 1, and $R^{3'}$ is a leaving group;

to react with a compound of general formula IVa:

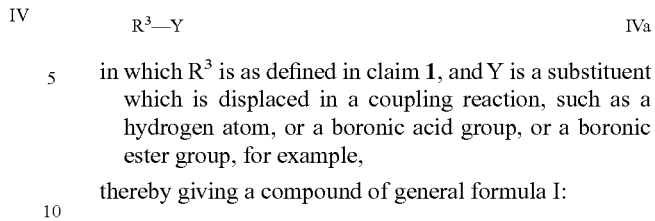

IVa in which $R^3$ is as defined in claim 1, and Y is a substituent which is displaced in a coupling reaction, such as a hydrogen atom, or a boronic acid group, or a boronic ester group, for example, thereby giving a compound of general formula I:

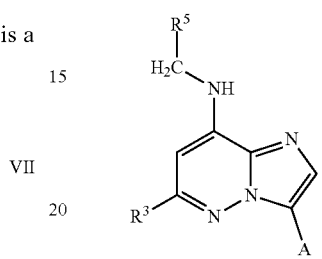

I in which A, $R^3$, and $R^5$ are as defined in claim 1.

13. A method of preparing a compound according to claim 1, said method comprising the step of allowing an intermediate compound of general formula Ia:

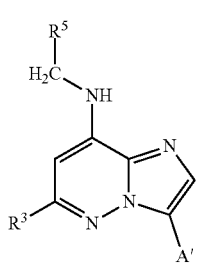

Ia in which $R^3$ and $R^5$ are as defined in claim 1;
and A' is

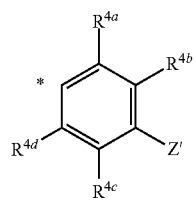

wherein * indicates the point of attachment of said group with the rest of the molecule; $R^{4a}$, $R^{4b}$, $R^{4c}$ and $R^{4d}$ are as defined in claim 1, and Z' represents a group selected from:

—C(=O)OH, —C(=S)OH, —C(=O)O—($C_1$-$C_6$-alkyl) or —C(=S)O—($C_1$-$C_6$-alkyl);

to react with a compound of general formula Ib:

Ib $H_2NR^2$ in which $R^2$ is as defined in claim 1, thereby giving, upon optional deprotection, a compound of general formula I:

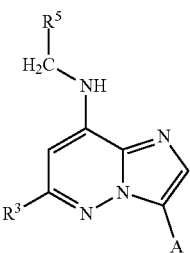

I in which $R^3$, $R^5$ and A are as defined in claim 1.

14. A method of preparing a compound according to claim 1, said method comprising the step of allowing an intermediate compound of general formula VII:

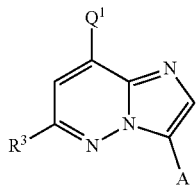

VII in which $R^3$ and A are as defined in claim 1, and $Q^1$ is a leaving group, to react with a compound of general formula VIIa:

$$R^5\text{—}CH_2\text{—}NH_2 \qquad \text{VIIa}$$

in which $R^5$ is as defined in claim 1, thereby giving, upon optional deprotection, a compound of general formula I:

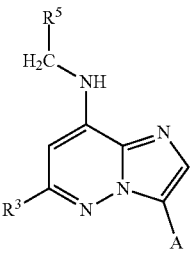

I in which $R^3$, $R^5$ and A are as defined in claim 1.

* * * * *